(12) United States Patent
Wiles et al.

(10) Patent No.: US 11,814,391 B2
(45) Date of Patent: *Nov. 14, 2023

(54) MACROCYCLIC COMPOUNDS FOR THE TREATMENT OF MEDICAL DISORDERS

(71) Applicant: Achillion Pharmaceuticals, Inc., Blue Bell, PA (US)

(72) Inventors: Jason Allan Wiles, Madison, CT (US); Venkat Rao Gadhachanda, Hamden, CT (US); Kyle J. Eastman, Wallingford, CT (US); Godwin Pais, Hamden, CT (US)

(73) Assignee: Achillion Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/272,923

(22) PCT Filed: Sep. 6, 2019

(86) PCT No.: PCT/US2019/050065
§ 371 (c)(1),
(2) Date: Mar. 2, 2021

(87) PCT Pub. No.: WO2020/051532
PCT Pub. Date: Mar. 12, 2020

(65) Prior Publication Data
US 2022/0380380 A1      Dec. 1, 2022

Related U.S. Application Data

(60) Provisional application No. 62/727,857, filed on Sep. 6, 2018.

(51) Int. Cl.
| | | |
|---|---|---|
| *C07D 471/16* | (2006.01) | |
| *C07D 487/08* | (2006.01) | |
| *C07D 487/18* | (2006.01) | |
| *C07D 498/18* | (2006.01) | |
| *C07D 519/00* | (2006.01) | |
| *A61K 31/4162* | (2006.01) | |
| *A61P 1/16* | (2006.01) | |
| *A61P 37/00* | (2006.01) | |

(52) U.S. Cl.
CPC ......... *C07D 487/18* (2013.01); *C07D 471/16* (2013.01); *C07D 487/08* (2013.01); *C07D 498/18* (2013.01); *C07D 519/00* (2013.01)

(58) Field of Classification Search
CPC .. C07D 471/16; C07D 487/08; C07D 487/18; C07D 498/18; C07D 519/00; A61K 31/4162; A61P 1/16; A61P 37/00
See application file for complete search history.

(56) References Cited

U.S. PATENT DOCUMENTS

| | | |
|---|---|---|
| 5,628,984 A | 5/1997 | Boucher, Jr. |
| 6,319,897 B1 | 11/2001 | Lambris et al. |
| 6,489,476 B1 | 12/2002 | Dang et al. |
| 6,653,340 B1 | 11/2003 | Babu et al. |
| 7,629,340 B2 | 12/2009 | Schmitz et al. |
| 7,888,323 B2 | 2/2011 | Lambris et al. |
| 7,989,589 B2 | 8/2011 | Lambris |
| 7,999,081 B2 | 8/2011 | Tedesco et al. |
| 8,168,584 B2 | 5/2012 | Deschatelets et al. |
| 8,241,628 B2 | 8/2012 | Diefenbach-Streiber et al. |
| 8,524,716 B2 | 9/2013 | Raboisson et al. |
| 8,580,735 B2 | 11/2013 | Francois et al. |
| 8,883,158 B2 | 11/2014 | Diefenbach-Streiber et al. |
| 8,946,145 B2 | 2/2015 | Lambris et al. |
| 9,056,076 B2 | 6/2015 | Deschatelets et al. |
| 9,085,555 B2 | 7/2015 | Altmann et al. |
| 9,169,307 B2 | 10/2015 | Lambris et al. |
| 9,291,622 B2 | 3/2016 | Zhang et al. |
| 9,371,365 B2 | 6/2016 | Lambris et al. |
| 9,421,240 B2 | 8/2016 | Francois et al. |
| 9,468,661 B2 | 10/2016 | Altmann et al. |
| 9,598,446 B2 | 3/2017 | Gadhachanda et al. |
| 9,643,986 B2 | 5/2017 | Wiles et al. |
| 9,663,543 B2 | 5/2017 | Wiles et al. |
| 9,695,205 B2 | 7/2017 | Wiles et al. |
| 9,732,103 B2 | 8/2017 | Wiles et al. |
| 9,732,104 B2 | 8/2017 | Gadhachanda et al. |
| 9,758,537 B2 | 9/2017 | Wiles et al. |
| 9,796,741 B2 | 10/2017 | Gadhachanda et al. |
| 9,828,396 B2 | 11/2017 | Wiles et al. |
| 10,000,516 B2 | 6/2018 | Wiles et al. |

(Continued)

FOREIGN PATENT DOCUMENTS

| | | |
|---|---|---|
| CN | 103402996 A | 11/2013 |
| EA | 201890594 A1 | 8/2018 |

(Continued)

OTHER PUBLICATIONS

"Are There Any Treatments for ALS?" WebMD, <https://www.webmd.com/brain/understanding-als-treatment#1>, retrieved on May 3, 2019 (8 pages).
"Arteriosclerosis/atherosclerosis," Mayo Clinic, <https://www.mayoclinic.org/diseases-conditions/arteriosclerosis-atherosclerosis/diagnosis-treatment/drc-20350575>, retrieved on Apr. 24, 2018 (10 pages).
"Cancer," MedLine Plus, <http://www.nlm.nih.gov/medlineplus/cancer.html>, retrieved Jul. 6, 2007 (10 pages).
"Dermatomyositis," Mayo Clinic, <https://www.mayoclinic.org/diseases-conditions/dermatomyositis/diagnosis-treatment/drc-20353192>, retrieved on Aug. 1, 2017 (7 pages).

(Continued)

*Primary Examiner* — Brenda L Coleman
(74) *Attorney, Agent, or Firm* — Clark & Elbing LLP

(57) ABSTRACT

Compounds, methods of use, and processes for making inhibitors of complement factor D or a pharmaceutically acceptable salt or composition thereof are provided. The inhibitors described herein target factor D and inhibit or regulate the complement cascade. The inhibitors of factor D described herein reduce excessive activation of complement.

17 Claims, No Drawings

(56) References Cited

U.S. PATENT DOCUMENTS

| | | |
|---|---|---|
| 10,005,802 B2 | 6/2018 | Wiles et al. |
| 10,011,612 B2 | 7/2018 | Wiles et al. |
| 10,081,645 B2 | 9/2018 | Wiles et al. |
| 10,087,203 B2 | 10/2018 | Wiles et al. |
| 10,092,547 B2 | 10/2018 | Wiles et al. |
| 10,092,584 B2 | 10/2018 | Wiles et al. |
| 10,100,072 B2 | 10/2018 | Wiles et al. |
| 10,106,563 B2 | 10/2018 | Wiles et al. |
| 10,138,225 B2 | 11/2018 | Wiles et al. |
| 10,189,869 B2 | 1/2019 | Gadhachanda et al. |
| 10,253,053 B2 | 4/2019 | Wiles et al. |
| 10,287,301 B2 | 5/2019 | Wiles et al. |
| 10,301,336 B2 | 5/2019 | Wiles et al. |
| 10,370,394 B2 | 8/2019 | Wiles et al. |
| 10,385,097 B2 | 8/2019 | Wiles et al. |
| 10,428,094 B2 | 10/2019 | Wiles et al. |
| 10,428,095 B2 | 10/2019 | Wiles et al. |
| 10,464,956 B2 | 11/2019 | Wiles et al. |
| 10,550,140 B2 | 2/2020 | Wiles et al. |
| 10,660,876 B2 | 5/2020 | Wiles et al. |
| 10,662,175 B2 | 5/2020 | Wiles et al. |
| 10,807,952 B2 | 10/2020 | Wiles et al. |
| 10,822,352 B2 | 11/2020 | Wiles et al. |
| 10,906,887 B2 | 2/2021 | Wiles et al. |
| 10,919,884 B2 | 2/2021 | Wiles et al. |
| 11,001,600 B2 | 5/2021 | Wiles et al. |
| 11,053,253 B2 | 7/2021 | Wiles et al. |
| 11,084,800 B2 | 8/2021 | Wiles et al. |
| 11,407,738 B2 | 8/2022 | Wiles et al. |
| 11,447,465 B2 | 9/2022 | Wiles et al. |
| 2002/0133004 A1 | 9/2002 | Sekiyama et al. |
| 2005/0228000 A1 | 10/2005 | Smallheer et al. |
| 2005/0267108 A1 | 12/2005 | Hsieh et al. |
| 2006/0004000 A1 | 1/2006 | D'Orchymont et al. |
| 2007/0155712 A1 | 7/2007 | Zahn et al. |
| 2008/0075720 A1 | 3/2008 | Holers et al. |
| 2008/0075728 A1 | 3/2008 | Newman |
| 2008/0108691 A1 | 5/2008 | Hamann et al. |
| 2010/0041628 A1 | 2/2010 | Enomoto et al. |
| 2011/0280808 A1 | 11/2011 | Kroth et al. |
| 2012/0231471 A1 | 9/2012 | Sato et al. |
| 2012/0237515 A1 | 9/2012 | Bell et al. |
| 2012/0295884 A1 | 11/2012 | Altmann et al. |
| 2013/0029912 A1 | 1/2013 | Holers et al. |
| 2013/0035392 A1 | 2/2013 | McGeer et al. |
| 2013/0296377 A1 | 11/2013 | Adams et al. |
| 2013/0324482 A1 | 12/2013 | Francois et al. |
| 2013/0344073 A1 | 12/2013 | Schwaeble et al. |
| 2014/0050739 A1 | 2/2014 | Francois et al. |
| 2014/0323407 A1 | 10/2014 | Francois et al. |
| 2014/0371133 A1 | 12/2014 | Francois et al. |
| 2015/0141455 A1 | 5/2015 | Altmann et al. |
| 2015/0148374 A1 | 5/2015 | Hommel et al. |
| 2015/0158915 A1 | 6/2015 | Lambris et al. |
| 2015/0191462 A1 | 7/2015 | Hommel et al. |
| 2015/0239837 A1 | 8/2015 | Wiles et al. |
| 2015/0239838 A1 | 8/2015 | Phadke et al. |
| 2015/0239868 A1 | 8/2015 | Pais et al. |
| 2015/0239893 A1 | 8/2015 | Wang et al. |
| 2015/0239894 A1 | 8/2015 | Gadhachanda et al. |
| 2015/0239895 A1 | 8/2015 | Gadhachanda et al. |
| 2015/0239919 A1 | 8/2015 | Gadhachanda et al. |
| 2015/0239920 A1 | 8/2015 | Gadhachanda et al. |
| 2015/0239921 A1 | 8/2015 | Wiles et al. |
| 2015/0269868 A1 | 9/2015 | Carney et al. |
| 2015/0322060 A1 | 11/2015 | Flohr et al. |
| 2015/0368271 A1 | 12/2015 | Su et al. |
| 2016/0015810 A1 | 1/2016 | Deschatelets et al. |
| 2016/0024079 A1 | 1/2016 | Adams et al. |
| 2016/0060297 A1 | 3/2016 | Deschatelets et al. |
| 2016/0194359 A1 | 7/2016 | Francois et al. |
| 2016/0215020 A1 | 7/2016 | Francois et al. |
| 2016/0215022 A1 | 7/2016 | Francois et al. |
| 2016/0361329 A1 | 12/2016 | Wiles et al. |
| 2016/0362398 A1 | 12/2016 | Wiles et al. |
| 2016/0362399 A1 | 12/2016 | Wiles et al. |
| 2016/0362432 A1 | 12/2016 | Wiles et al. |
| 2016/0362433 A1 | 12/2016 | Wiles et al. |
| 2017/0056428 A1 | 3/2017 | Wiles et al. |
| 2017/0057950 A1 | 3/2017 | Wiles et al. |
| 2017/0057983 A1 | 3/2017 | Wiles et al. |
| 2017/0057993 A1 | 3/2017 | Wiles et al. |
| 2017/0066783 A1 | 3/2017 | Wiles et al. |
| 2017/0189410 A1 | 7/2017 | Gadhachanda et al. |
| 2017/0202821 A1 | 7/2017 | Bekker |
| 2017/0202935 A1 | 7/2017 | Lambris et al. |
| 2017/0226142 A1 | 8/2017 | Wiles et al. |
| 2017/0260219 A1 | 9/2017 | Wiles et al. |
| 2017/0298084 A1 | 10/2017 | Wiles et al. |
| 2017/0298085 A1 | 10/2017 | Wiles et al. |
| 2018/0022766 A1 | 1/2018 | Wiles et al. |
| 2018/0022767 A1 | 1/2018 | Wiles et al. |
| 2018/0030075 A1 | 2/2018 | Wiles et al. |
| 2018/0072762 A1 | 3/2018 | Wiles et al. |
| 2018/0177761 A1 | 6/2018 | Wiles et al. |
| 2018/0179185 A1 | 6/2018 | Wiles et al. |
| 2018/0179186 A1 | 6/2018 | Wiles et al. |
| 2018/0179236 A1 | 6/2018 | Wiles et al. |
| 2018/0186782 A1 | 7/2018 | Wiles et al. |
| 2018/0201580 A1 | 7/2018 | Wiles et al. |
| 2018/0305375 A1 | 10/2018 | Wiles et al. |
| 2019/0023729 A1 | 1/2019 | Wiles et al. |
| 2019/0031692 A1 | 1/2019 | Wiles et al. |
| 2019/0038623 A1 | 2/2019 | Huang et al. |
| 2019/0048033 A1 | 2/2019 | Wiles et al. |
| 2019/0085005 A1 | 3/2019 | Wiles et al. |
| 2019/0144473 A1 | 5/2019 | Gadhachanda et al. |
| 2019/0211033 A1 | 7/2019 | Wiles et al. |
| 2019/0359645 A1 | 11/2019 | Birkus et al. |
| 2019/0382376 A1 | 12/2019 | Wiles et al. |
| 2020/0002347 A1 | 1/2020 | Wiles et al. |
| 2020/0062790 A1 | 2/2020 | Wiles et al. |
| 2020/0071301 A1 | 3/2020 | Wiles et al. |
| 2020/0101071 A1 | 4/2020 | Huang et al. |
| 2020/0262818 A1 | 8/2020 | Wiles et al. |
| 2021/0332026 A1 | 10/2021 | Phadke et al. |
| 2022/0079943 A1 | 3/2022 | Huang et al. |

FOREIGN PATENT DOCUMENTS

| | | |
|---|---|---|
| JP | 2014-506877 A | 3/2014 |
| JP | 2015-522005 A | 8/2015 |
| JP | 2015-522006 A | 8/2015 |
| JP | 2015-522007 A | 8/2015 |
| JP | 2017-511815 A | 4/2017 |
| JP | 6400738 B2 | 10/2018 |
| JP | 2018-199714 A | 12/2018 |
| JP | 6537532 B2 | 7/2019 |
| JP | 6688352 B2 | 4/2020 |
| JP | 6877406 B2 | 5/2021 |
| WO | WO-93/20099 A2 | 10/1993 |
| WO | WO-95/29697 A1 | 11/1995 |
| WO | WO-99/48492 A1 | 9/1999 |
| WO | WO-2004/007501 A1 | 1/2004 |
| WO | WO-2004/045518 A2 | 6/2004 |
| WO | WO-2004/111041 A1 | 12/2004 |
| WO | WO-2008/047831 A1 | 4/2008 |
| WO | WO-2009/091826 A2 | 7/2009 |
| WO | WO-2012/093101 A1 | 7/2012 |
| WO | WO-2012/177782 A1 | 12/2012 |
| WO | WO-2013/166436 A1 | 11/2013 |
| WO | WO-2013/192345 A1 | 12/2013 |
| WO | WO-2014/002051 A2 | 1/2014 |
| WO | WO-2014/002052 A1 | 1/2014 |
| WO | WO-2014/002053 A1 | 1/2014 |
| WO | WO-2014/002054 A1 | 1/2014 |
| WO | WO-2014/002057 A1 | 1/2014 |
| WO | WO-2014/002058 A2 | 1/2014 |
| WO | WO-2014/002059 A1 | 1/2014 |
| WO | WO-2014/002067 A2 | 1/2014 |
| WO | WO-2014/005150 A1 | 1/2014 |
| WO | WO-2014/009833 A2 | 1/2014 |
| WO | WO-2014/037480 A1 | 3/2014 |
| WO | WO-2014/116880 A1 | 7/2014 |

(56) References Cited

FOREIGN PATENT DOCUMENTS

| | | |
|---|---|---|
| WO | WO-2015/008861 A1 | 1/2015 |
| WO | WO-2015/021166 A2 | 2/2015 |
| WO | WO-2015/054569 A1 | 4/2015 |
| WO | WO-2015/130784 A1 | 9/2015 |
| WO | WO-2015/130795 A1 | 9/2015 |
| WO | WO-2015/130806 A1 | 9/2015 |
| WO | WO-2015/130830 A1 | 9/2015 |
| WO | WO-2015/130838 A1 | 9/2015 |
| WO | WO-2015/130842 A2 | 9/2015 |
| WO | WO-2015/130845 A1 | 9/2015 |
| WO | WO-2015/130854 A1 | 9/2015 |
| WO | WO-2017/035348 A1 | 3/2017 |
| WO | WO-2017/035349 A1 | 3/2017 |
| WO | WO-2017/035351 A1 | 3/2017 |
| WO | WO-2017/035352 A1 | 3/2017 |
| WO | WO-2017/035353 A1 | 3/2017 |
| WO | WO-2017/035355 A1 | 3/2017 |
| WO | WO-2017/035357 A1 | 3/2017 |
| WO | WO-2017/035360 A1 | 3/2017 |
| WO | WO-2017/035361 A1 | 3/2017 |
| WO | WO-2017/035362 A1 | 3/2017 |
| WO | WO-2017/035401 A1 | 3/2017 |
| WO | WO-2017/035405 A1 | 3/2017 |
| WO | WO-2017/035408 A1 | 3/2017 |
| WO | WO-2017/035409 A1 | 3/2017 |
| WO | WO-2017/035411 A1 | 3/2017 |
| WO | WO-2017/035413 A2 | 3/2017 |
| WO | WO-2017/035415 A1 | 3/2017 |
| WO | WO-2017/035417 A1 | 3/2017 |
| WO | WO-2017/035418 A1 | 3/2017 |
| WO | WO-2017/098328 A2 | 6/2017 |
| WO | WO-2017/127761 A1 | 7/2017 |
| WO | WO-2017/136395 A1 | 8/2017 |
| WO | WO-2018/005552 A1 | 1/2018 |
| WO | WO-2018/026722 A1 | 2/2018 |
| WO | WO-2018/160889 A1 | 9/2018 |
| WO | WO-2018/160891 A1 | 9/2018 |
| WO | WO-2018/160892 A1 | 9/2018 |
| WO | WO-2019/070714 A1 | 4/2019 |

OTHER PUBLICATIONS

"History of Changes for Study: NCT03053102—A Treatment Study of ACH-0144471 in Patients With Paroxysmal Nocturnal Hemoglobinuria (PNH)," U.S. National Library of Medicine, available at: <https://clinicaltrials.gov/ct2/history/NCT03053102?V_4=View#StudyPageTop>, submitted Jun. 6, 2017, retrieved Mar. 9, 2021 (3 pages).
"NCT03472885—A Treatment Study of ACH-0144471 in Patients With Paroxysmal Nocturnal Hemoglobinuria (PNH) With Inadequate Response to Eculizumab (PNH)," U.S. National Library of Medicine, available at: <https://clinicaltrials.gov/ct2/show/NCT03472885>, first posted Mar. 21, 2018, last update posted Dec. 3, 2019, retrieved Mar. 27, 2020 (7 pages).
"Reperfusion injury," Wikipedia, <https://en.wikipedia.org/wiki/Reperfusion_injury>, retrieved Apr. 30, 2020 (8 pages).
"Treatment for Multiple Sclerosis," WebMD, <https://www.webmd.com/multiple-sclerosis/ms-treatment#1>, retrieved on May 3, 2019 (24 pages).
"What Are the Treatments for Cirrhosis?," WebMD, <https://www.webmd.com/digestive-disorders/understanding-cirrhosis-treatment#1>, retrieved May 3, 2019 (15 pages).
"What is Cardiovascular Disease?" American Heart Association, <https://www.heart.org/en/health-topics/consumer-healthcare/what-is-cardiovascular-disease>, last reviewed May 31, 2017 (4 pages).
"What is Dementia?" Alzheimer's Association, <https://www.alz.org/alzheimers-dementia/what-is-dementia>, retrieved on Nov. 17, 2020 (6 pages).
Airey et al., "A Convenient Preparation of Thieno[3,2-c]pyrazole," Synthesis. 46: 96-100 (2014).
Armand, "Fatty liver disease: What it is and what to do about it," Harvard Health Publishing, <https://www.health.harvard.edu/blog/fatty-liver-disease-what-it-is-and-what-to-do-about-it-2019011015746>, dated Jan. 10, 2019, retrieved May 2, 2019 (3 pages).
Babiker et al., "Transfer of prostasomal CD59 to CD59-deficient red blood cells results in protection against complement-mediated hemolysis," Am J Reprod Immunol. 47(3): 183-92 (2002) (Abstract Only).
Barraclough et al., "Synthesis of (2S,3R)- and (2S,3S)-[3-$^2$H$_1$]-proline via highly selective hydrolysis of a silyl enol ether," Tetrahedron Letters. 46(1): 4653-4655 (2005).
Barraclough et al., "Two separate and distinct syntheses of stereospecifically deuteriated samples of (2S)-proline," Org Biomol Chem. 4(8):1483-1491 (2006).
Borowitz et al., "Guidelines for the Diagnosis and Monitoring of Paroxysmal Nocturnal Hemoglobinuria and Related Disorders by Flow Cytometry," Cytometry B Clin Cytom. 78B(4): 211-230 (2010).
Brodsky, "Eculizumab: another breakthrough," Blood. 129(8):922-3 (2017).
Carter, "Complement Activation: An Emerging Player in the Pathogenesis of Cardiovascular Disease," Scientifica. 2012:402783 (2012) (14 pages).
CAS RN 1236228-05-9, dated Aug. 16, 2010 (1 page).
CAS RN 1236251-51-6, dated Aug. 17, 2010 (2 pages).
CAS RN 1270608-88-2, dated 2019 (1 page).
CAS RN 1277041-86-7, dated Apr. 8, 2011 (2 pages).
Cofiell et al., "Eculizumab reduces complement activation, inflammation, endothelial damage, thrombosis, and renal injury markers in aHUS," Blood. 125(21):3253-62 (2015).
Cole et al. "Structure of 3,4-Dichloroisocoumarin-Inhibited Factor D," Acta Crystallogr D Biol Crystallogr. 54(Pt 5): 711-717 (1998).
Compound Summary for CID 1129904, PubChem. <https://pubchem.ncbi.nlm.nih.gov/compound/1129904> retrieved Jul. 14, 2020, created Jul. 10, 2005 (10 pages).
Compound Summary for CID 118324207, PubChem, <https://pubchem.ncbi.nlm.nih.gov/compound/118324207>, created Feb. 23, 2016, retrieved on Jul. 14, 2020 (8 pages).
Compound Summary for CID 123543544, PubChem, <https://pubchem.ncbi.nlm.nih.gov/compound/123543544>, created on Jan. 25, 2017, retrieved on Jul. 13, 2020 (8 pages).
Compound Summary for CID 134222466, PubChem, <https://pubchem.ncbi.nlm.nih.gov/compound/134222466>, created on Jun. 23, 2018, retrieved on Jul. 14, 2020 (11 pages).
Compound Summary for CID 59912842, PubChem, <https://pubchem.ncbi.nlm.nih.gov/compound/59912842>, created Aug. 20, 2012, retrieved Jul. 14, 2020 (9 pages).
Damasio, "Alzheimer's disease and related dementias," Cecil Textbook of Medicine, 20th Edition, vol. 2. Bennet and Plum, 1992-6 (1996).
Database Registry Chemical Abstracts Service, Columbus, Ohio, Accession No. RN1236248-20-6, Entered STN: Aug. 16, 2010 (1 page).
Database Registry Chemical Abstracts Service, Columbus, Ohio, Accession No. RN1380849-41-1, Entered STN: Jul. 3, 2012 (2 pages).
De Luca et al., "HIV-1 integrase strand-transfer inhibitors: Design, synthesis and molecular modeling investigation," Eur J Med Chem. 46(2): 756-764 (2011).
DeZern et al., "Paroxysmal nocturnal hemoglobinuria: a complement-mediated hemolytic anemia," available in PMC Dec. 30, 2015, published in final edited form as: Hematol Oncol Clin North Am. 29(3):479-94 (2015) (18 pages).
Donthiri et al., "Copper-Catalyzed C—H Functionalization of Pyridines and Isoquinolines with Vinyl Azides: Synthesis of Imidazo Heterocycles," J Org Chem. 79(22): 11277-11284 (2014).
Dormoy et al., "Synthesis of N-t-Butoxycarbonyl-4,4-dideuterio-L-proline," Synthesis. 1: 81-82 (1986).
Ellis-Pegler et al., "An Orally Administered Small Molecule Factor D Inhibitor (ACH-4471) For Treatment of PNH and Complement Diseases: Preliminary Phase 1 Results In Healthy Volunteers," European Hematology Association. Abstract LB2250, available

(56) References Cited

OTHER PUBLICATIONS

<https://library.ehaweb.org/eha/2016/21st/135361/roderick.b.ellis-pegler.an.orally.administered.small.molecule.factor.d.html> (2016) (2 pages).
Ellis-Pegler et al., "An Orally Administered Small Molecule Factor D Inhibitor (ACH-4471) For Treatment of PNH, C3G and Complement—Mediated Diseases: Interim Phase 1 Results In Healthy Volunteers," European Hematology Association, Copenhagen 21st Congress, Jun. 9-12, Abstract ID: EHA-4145 (2016).
Gadhachanda et al., CAplus Database Summary Sheet for Document No. 164:507515, Accession No. 2016:627420, CAplus on STN. (2016) (6 pages).
Gavrillaki et al., "275 Small Molecule Factor D Inhibitors Block Complement Activation in Paroxysmal Nocturnal Hemoglobinuria and Atypical Hemolytic Uremic Syndrome," ASH 57th Annual Meeting & Exposition, Session: 101. Dec. 6, 2015 (2 pages).
Golub et al., "Molecular classification of cancer: class discovery and class prediction by gene expression monitoring," Science. 286(5439):531-537 (1999) (8 pages).
Gura, "Systems for identifying new drugs are often faulty," Science. 278(5340):1041-2 (1997).
Haddrill, "Stargardt's Disease (Fundus Flavimaculatus)," All About Vision, <https://www.allaboutvision.com/conditions/stargardts.htm#article-section-2>, retrieved May 3, 2019 (5 pages).
Harder et al., "Incomplete inhibition by eculizumab: mechanistic evidence for residual C5 activity during strong complement activation," Blood.129(8):970-80 (2017).
Hartmann et al., "Diagnostic Specificity of Sucrose Hemolysis Test for Paroxysmal Nocturnal Hemoglobinuria," Blood. 35(4):462-475 (1970).
Hecker et al., "Liver-Targeted Prodrugs of 2'-C-Methyladenosine for Therapy of Hepatitis C Virus Infection," J Med Chem. 50(16): 3891-3896 (2007).
Hruby et al., "$^{13}$C Nuclear Magnetic Resonance Studies of the Peptide Hormones Oxytocin, Arginine Vasopressin, Isotocin, Mesotocin, Glumitocin, Aspartocin, Related Analogues, and Diastereoisomers. Use of Specifically Deuterated Hormone Derivatives for Assignments and Effects of Structural Changes on $^{13}$C NMR Chemical Shifts in Peptides," J Am Chem Soc. 101(1): 202-212 (1979).
International Search Report and Written Opinion for International Application No. PCT/US2015/017523, dated May 14, 2015 (7 pages).
International Search Report and Written Opinion for International Application No. PCT/US2015/017538, dated May 14, 2015 (8 pages).
International Search Report and Written Opinion for International Application No. PCT/US2015/017554, dated May 14, 2015 (7 pages).
International Search Report and Written Opinion for International Application No. PCT/US2015/017583, dated May 27, 2015 (12 pages).
International Search Report and Written Opinion for International Application No. PCT/US2015/017593, dated Jun. 16, 2015 (6 pages).
International Search Report and Written Opinion for International Application No. PCT/US2015/017597, dated Jan. 29, 2016 (10 pages).
International Search Report and Written Opinion for International Application No. PCT/US2015/017600, dated May 27, 2015 (12 pages).
International Search Report and Written Opinion for International Application No. PCT/US2015/017609, dated May 29, 2015 (6 pages).
International Search Report and Written Opinion for International Application No. PCT/US2016/048688, dated Dec. 28, 2016 (11 pages).
International Search Report and Written Opinion for International Application No. PCT/US2016/048690, dated Dec. 28, 2016 (11 pages).
International Search Report and Written Opinion for International Application No. PCT/US2016/048693, dated Jan. 13, 2017 (11 pages).
International Search Report and Written Opinion for International Application No. PCT/US2016/048695, dated Dec. 30, 2016 (10 pages).
International Search Report and Written Opinion for International Application No. PCT/US2016/048696, dated Jan. 5, 2017 (10 pages).
International Search Report and Written Opinion for International Application No. PCT/US2016/048701, dated Jan. 10, 2017 (10 pages).
International Search Report and Written Opinion for International Application No. PCT/US2016/048704, dated Dec. 27, 2016 (7 pages).
International Search Report and Written Opinion for International Application No. PCT/US2016/048707, dated Jan. 5, 2017 (10 pages).
International Search Report and Written Opinion for International Application No. PCT/US2016/048709, dated Jan. 17, 2017 (9 pages).
International Search Report and Written Opinion for International Application No. PCT/US2016/048710, dated Jan. 5, 2017 (8 pages).
International Search Report and Written Opinion for International Application No. PCT/US2016/048779, dated Dec. 27, 2016 (8 pages).
International Search Report and Written Opinion for International Application No. PCT/US2016/048783, dated Feb. 3, 2017 (8 pages).
International Search Report and Written Opinion for International Application No. PCT/US2016/048787, dated Jan. 5, 2017 (13 pages).
International Search Report and Written Opinion for International Application No. PCT/US2016/048788, dated Jan. 5, 2017 (12 pages).
International Search Report and Written Opinion for International Application No. PCT/US2016/048793, dated Dec. 28, 2016 (8 pages).
International Search Report and Written Opinion for International Application No. PCT/US2016/048795, dated Feb. 17, 2017 (12 pages).
International Search Report and Written Opinion for International Application No. PCT/US2016/048797, dated Jan. 5, 2017 (12 pages).
International Search Report and Written Opinion for International Application No. PCT/US2016/048799, dated Nov. 15, 2016 (7 pages).
International Search Report and Written Opinion for International Application No. PCT/US2016/048800, dated Jan. 5, 2017 (12 pages).
International Search Report for International Application No. PCT/US18/20530, dated Jun. 25, 2018 (3 pages).
International Search Report for International Application No. PCT/US2018/020528, dated Apr. 24, 2018 (3 pages).
International Search Report for International Application No. PCT/US2018/045057, dated Nov. 15, 2018 (5 pages).
International Search Report for International Application No. PCT/US2018/20531, dated May 15, 2018 (3 pages).
International Search Report for International Application No. PCT/US2019/034210, dated Sep. 13, 2019 (4 pages).
International Search Report for International Application No. PCT/US2019/047252, dated Dec. 17, 2019 (4 pages).
International Search Report for International Application No. PCT/US2019/050065, dated Feb. 25, 2020 (4 pages).
International Search Report for International Application No. PCT/US2019/050073, dated Nov. 21, 2019 (3 pages).
International Search Report for International Application No. PCT/US2019/053012, dated Jan. 28, 2020 (4 pages).
International Search Report for International Application No. PCT/US2019/066999, dated Feb. 12, 2020 (3 pages).
Johnson et al., "Relationships between drug activity in NCI preclinical in vitro and in vivo models and early clinical trials," Br J Cancer. 84(10):1424-31 (2001).

(56) References Cited

OTHER PUBLICATIONS

Józsi, "Anti-Complement Autoantibodies in Membranoproliferative Glomerulonephritis and Dense Deposit Disease", *An Update on Glomerulopathies—Etiology and Pathogenesis*. Prof. Sharma Prabhakar, 31-46 (2011) (18 pages).
Kathuria, "Membranoproliferative Glomerulonephritis Medication," Medscape, <https://emedicine.medscape.com/article/240056-medication>, updated Jun. 23, 2016, retrieved May 3, 2019, (1 page).
Kinman, "COPD Drugs: A List of Medications to Help Relieve Your Symptoms," Healthline, <https://www.healthline.com/health/copd/drugs>, retrieved on May 3, 2019 (12 pages).
Komiya et al., CAplus Database Summary Sheet for Document No. 162:229476, Accession No. 2015:126147, CAplus on STN. (2015) (2 pages).
Krauss, "Laboratory Diagnosis of Paroxysmal Nocturnal Hemoglobinuria," Annals of Clinical & Laboratory Science. 33(4):401-406 (2003).
Kuang et al., "Synthesis of (Z)-1-bromo-1-alkenes and terminal alkynes from anti-2,3-dibromoalkanoic acids by microwave-induced reaction," Tetrahedron. 61(16):4043-4052 (2005).
Lala et al., "Role of nitric oxide in tumor progression: lessons from experimental tumors," Cancer Metastasis Rev. 17(1):91-106 (1998).
Lassmann, "What drives disease in multiple sclerosis: Inflammation or neurodegeneration?" Clinical and Experimental Neuroimmunology. 1:2-11 (2010).
Layzer, "Degenerative Diseases of the Nervous System," *Cecil Textbook of Medicine, 20th Edition*, vol. 2. J. Claude Bennett and Fred Plum, p. 2050-2057 (1996).
Le et al., "A mechanistic pharmacokinetic/pharmacodynamic model of factor D inhibition in cynomolgus monkeys by lampalizumab for the treatment of geographic atrophy," J Pharmacol Exp Ther. 355(2):288-96 (2015).
MacKay et al., "Rapid Synthesis of the N-Methylwelwitindolinone Skeleton," Org Lett. 7(16):3421-4 (2005).
Mastellos et al., "Complement in paroxysmal nocturnal hemoglobinuria: exploiting our current knowledge to improve the treatment landscape," available in PMC Apr. 2, 2015, published in final edited form as: Expert Rev Hematol. 7(5):583-98 (2014) (26 pages).
Noris et al., "Overview of Complement Activation and Regulation," Semin Nephrol. 33:479-492 (2013).
Office Action issued for Eurasian Patent Application No. 201992005, dated Oct. 23, 2020 (6 pages).
Okutani et al., "Conversion of Bromoalkenes into Alkynes by Wet Tetra-n-butylammonium Fluoride," J Org Chem. 74(1):442-444 (2009).
Oseini et al., "Therapies in Non-Alcoholic Steatohepatitis (NASH)," available in PMC Jan. 1, 2018, published in final edited form as: Liver Int. 37(Suppl 1):97-103 (2017) (15 pages).
Pandya et al., "Complement System in Lung Disease," Am J Respir Cell Mol Biol. 51(4):467-473 (2014).
Parker, "Update on the diagnosis and management of paroxysmal nocturnal hemoglobinuria," Hematology Am Soc Hemtol Educ Program. 2016(1):208-16 (2016).
Partial Supplementary European Search Report for European Application No. 18761960.6, dated Nov. 27, 2020 (12 pages).
Patel et al., "In Vitro Combination Studies of ACH-4471 with Eculizumab to Assess a Potential 'Switch' Treatment Approach for Paroxysmal Nocturnal Hemoglobinuria" 59th American Society of Hematology Annual Meeting and Exposition, Dec. 9-12, Atlanta, Georgia, Poster Abstract 2198 (2017).
Pearce et al., "Failure modes in anticancer drug discovery and development," Cancer Drug Design and Discovery Edited by Stephen Neidle, Chapter 18, pp. 424-435 (2008).
Peifer et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors," J Med Chem. 51(13):3814-3824 (2008).
Pugsley et al., "Inhibitors of the complement system currently in development for cardiovascular disease," Cardiovasc Toxicol. 3(1):43-69 (2003).
Qu et al., "Recent Developments in Low Molecular Weight Complement Inhibitors," available in PMC, Dec. 1, 2010, published in final edited form as: Mol Immunol. 47(2-3):185-195 (2009) (25 pages).
Quesada et al., "One-pot conversion of activated alcohols into terminal alkynes using manganese dioxide in combination with the Bestmann—Ohira reagent," Tetrahedron Letters. 46:6473-6476 (2005).
Ricklin et al., "Complement in immune and inflammatory disorders: pathophysiological mechanisms," J Immunol. 190(8):3831-3838 (2013).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Peptide inhibitors of C3 activation as a novel strategy of complement inhibition for the treatment of paroxysmal nocturnal hemoglobinuria," Blood. 123(13):2094-101 (2014).
Risitano et al., "Safety and Pharmacokinetics of the Complement Inhibitor TT30 in a Phase I Trial for Untreated PNH Patients" Blood. 126(23): 2137 (2015) (Abstract Only) (7 pages).
Risitano et al., "Toward complement inhibition 2.0: Next generation anticomplement agents for paroxysmal nocturnal hemoglobinuria," Am J Hematol. 93(4):564-77 (2018).
Risitano, "Anti-Complement Treatment in Paroxysmal Nocturnal Hemoglobinuria: Where we Stand and Where we are Going," Transl Med UniSa. 8:43-52 (2014).
Risitano, "Paroxysmal nocturnal hemoglobinuria in the era of complement inhibition," Am J Hematol. 91(4):359-60 (2016).
Rohrer et al., "Eliminating complement factor D reduces photoreceptor susceptibility to light-induced damage," Invest Ophthalmol Vis Sci. 48(11):5282-9 (2007).
Roth et al., "Further Improvements of the Synthesis of Alkynes from Aldehydes," Synthesis. 1:59-62 (2004).
Ruiz-Gómez et al., "Structure-Activity Relationships for Substrate-Based Inhibitors of Human Complement Factor B," J Med Chem. 52(19):6042-6052 (2009).
Salifu, "Chronic Glomerulonephritis Medication," Medscape, <https://emedicine.medscape.com/article/239392-medication>, updated Feb. 1, 2017, retrieved on May 2, 2019 (1 page).
Segers et al., "Complement Alternative Pathway Activation in Human Nonalcoholic Steatohepatitis," PLOS One. 9(10):e110053 (2014) (9 pages).
Sica et al., "Eculizumab treatment: stochastic occurrence of C3 binding to individual PNH erythrocytes," J Hematol Oncol. 10(1):126 (2017) (10 pages).
Simone, "Oncology: Introduction," Cecil Textbook of Medicine, 20th Edition, vol. 1, pp. 1004-1010, (1996).
Stanton et al., "Complement Factor D in Age-Related Macular Degeneration," Invest Ophthalmol Vis Sci. 52(12):8828-8834 (2011) (15 pages).
Strobel et al., "Anti-factor B autoantibody in dense deposit disease," Mol Immunol. 47:1476-1483 (2010).
Tandon et al., "Substrate specificity of human prolyl-4-hydroxylase," Bioorg Med Chem Lett. 8(10):1139-1144 (1998).
Tang et al., "Palladium-Catalyzed Carbonylative Sonogashira Coupling of Aryl Bromides via tert-Butyl Isocyanide Insertion," J Org Chem. 78(7):3170-3175 (2013).
Wehling et al., "Monitoring of complement activation biomarkers and eculizumab in complement-mediated renal disorders," Clin Exp Immunol. 187(2):304-15 (2017).
Written Opinion for International Application No. PCT/US18/20528, dated Apr. 24, 2018 (6 pages).
Written Opinion for International Application No. PCT/US18/20530, dated Jun. 25, 2018 (6 pages).
Written Opinion for International Application No. PCT/US18/20531, dated May 15, 2018 (7 pages).
Written Opinion for International Application No. PCT/US19/47252, dated Dec. 17, 2019 (6 pages).
Written Opinion for International Application No. PCT/US19/50065, dated Feb. 25, 2020 (7 pages).

(56) References Cited

OTHER PUBLICATIONS

Written Opinion for International Application No. PCT/US19/53012, dated Jan. 28, 2020 (5 pages).
Written Opinion for International Application No. PCT/US19/66999, dated Feb. 12, 2020 (7 pages).
Written Opinion for International Application No. PCT/US2018/045057, dated Nov. 15, 2018 (7 pages).
Written Opinion for International Application No. PCT/US2019/034210, dated Sep. 13, 2019 (17 pages).
Written Opinion for International Application No. PCT/US2019/050073, dated Nov. 21, 2019 (4 pages).
Yonemoto-Kobayashi et al., "Carboxylation of alkynylsilanes with carbon dioxide mediated by cesium fluoride in DMSO," Org Biomol Chem. 11(23):3773-5 (2013).
Yuan et al., "Small-molecule Factor D Inhibitors Selectively Block the Alternative Pathway of Complement in Paroxysmal Nocturnal Hemoglobinuria and Atypical Hemolytic Uremic Syndrome," Haematologica. 102(3):466-75 (2017).
Partial Supplementary European Search Report for European Application No. 19857913.8, dated Apr. 13, 2022 (17 pages).
Iatropoulos et al., "Cluster Analysis Identifies Distinct Pathogenetic Patterns in C3 Glomerulopathies/Immune Complex-Mediated Membranoproliferative GN," J Am Soc Nephrol. 29(1):283-94 (Jan. 2018) (36 pages).
Marinozzi et al., "C5 nephritic factors drive the biological phenotype of C3 glomerulopathies," Kidney Int. 92(5):1232-41 (Nov. 2017).
Michels et al., "Long-term follow-up including extensive complement analysis of a pediatric C3 glomerulopathy cohort," Pediatr Nephrol. 37(3):601-12 (Mar. 2022).
Zhang et al., "Defining the complement biomarker profile of C3 glomerulopathy," Clin J Am Soc Nephrol. 9(11):1876-82 (Nov. 7, 2014) (10 pages).

MACROCYCLIC COMPOUNDS FOR THE TREATMENT OF MEDICAL DISORDERS

CROSS-REFERENCE TO RELATED APPLICATIONS

This application claims the benefit of priority to U.S. Application No. 62/727,857, filed Sep. 6, 2018, which is incorporated by reference herein for all purposes.

FIELD OF THE INVENTION

This invention provides macrocycles to treat medical disorders, such as complement-mediated disorders, including Complement Factor D mediated disorders

BACKGROUND OF THE INVENTION

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells), and agglutination (clustering and binding of pathogens together).

The complement system has three pathways: classical, alternative, and lectin. Complement Factor D plays an early and central role in activation of the alternative pathway of the complement cascade. Activation of the alternative complement pathway is initiated by spontaneous hydrolysis of a thioester bond within the C3 protein to produce $C3(H_2O)$, which associates with Factor B to form the $C3(H_2O)B$ complex. Complement Factor D acts to cleave Factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

BioCryst Pharmaceuticals Inc. U.S. Pat. No. 6,653,340 titled "Compounds useful in the complement, coagulate and kallikrein pathways and method for their preparation" describes fused bicyclic ring compounds that are inhibitors of Factor D. US Patent Application 2019-0142802 assigned to BioCryst Pharmaceuticals describes benzopyrazole compounds for the treatment of aberrant complement disorders. Additional patents assigned to BioCryst for the treatment and prevention of complement disorders include granted U.S. Pat. No. 10,125,102 and US Applications US2018-0362458. Development of BioCryst's Factor D inhibitor BCX1470 was discontinued due to lack of specificity and short half-life of the compound.

Novartis PCT patent publication WO2012/093101 titled "Indole compounds or analogues thereof useful for the treatment of age-related macular degeneration" describes certain Factor D inhibitors. Additional Factor D inhibitors are described in Novartis PCT patent publications WO2012093101, WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, WO2015/066241, and WO2016088082.

Lifesci Pharmaceuticals PCT patent publication WO2017/098328 titled "Therapeutic Inhibitory Compounds" describes various Factor inhibitors with variations in the central core heterocyclic ring. PCT patent publication WO2018/015818 is also titled "Therapeutic Inhibitory Compounds" and describes Factor D inhibitors without a cyclic central core.

Bristol-Myers Squibb PCT patent publication WO2004/045518 titled "Open chain prolyl urea-related modulators of androgen receptor function" describes open chain prolyl urea and thiourea related compounds for the treatment of androgen receptor-associated conditions, such as age-related diseases, for example, sarcopenia.

Additional complement factor D inhibitors are described in U.S. Pat. Nos. 9,598,446; 9,643,986; 9,663,543; 9,695,205; 9,732,103; 9,732,104; 9,758,537; 9,796,741; 9,828,396; 10,000,516; 10,005,802; 10,011,612; 10,081,645; 10,087,203; 10,092,584; 10,100,072; 10,138,225; 10,189,869; 10,106,563; 10,301,336; and 10,287,301; International Publication Nos. WO2019/028284; WO2018/160889; WO2018/160891; WO2018/160892; WO2017/035348; WO2017/035349; WO 2017/035351; WO 2017/035352; WO 2017/035353; WO 2017/035355; WO2017/035357; WO2017/035360; WO2017/035361; WO2017/035362; WO2017/035415; WO2017/035401; WO2017/035405; WO2017/035413; WO2017/035409; WO2017/035411; WO2017/035417; WO2017/035408 WO2015/130784; WO2015/130795; WO2015/130806; WO2015/130830; WO2015/130838; WO2015/130842; WO2015/130845; and WO2015/130854; and U.S. Patent Publication Nos. US 2016-0361329; US 2016-0362432; US 2016-0362433; US 2016-0362399; US 2017-0056428; US 2017-0057950; US 2017-0057993; US 2017-0189410; US 2017-0226142; US 2017-0260219; US 2017-0298084; US 2017-0298085; US 2018-0022766; US 2018-0022767; US 2018-0072762; US 2018-0030075; US 2018-0169109; US 2018-0177761; US 2018-0179185; US 2018-0179186; US 2018-0179236; US 2018-0186782; US 2018-0201580; US 2019-0031692; US 2019-0048033; US 2019-0144473; and US 2019-0211033 all owned by Achillion Pharmaceuticals, Inc.

Given the wide variety of medical disorders that are caused by detrimental immune or inflammatory responses, new compounds are needed for medical treatment.

SUMMARY

This invention includes a compound of Formula I, Formula II, Formula III, Formula IV, Formula V, Formula VI, Formula VII, Formula VIII, or Formula IX or a pharmaceutically acceptable salt, prodrug, isotopic analog, N-oxide, or isolated isomer thereof, optionally in a pharmaceutically acceptable composition. In one embodiment, the compound or its salt or composition, as described herein is used to treat a medical disorder which is an inflammatory or immune condition, a disorder mediated by the complement cascade (including a dysfunctional cascade), a disorder or abnormality of a cell that adversely affects the ability of the cell to engage in or respond to normal complement activity including the alternative complement pathway, or an undesired complement-mediated response to a medical treatment, such as surgery or other medical procedure or a pharmaceutical or biopharmaceutical drug administration, a blood transfusion, or other allogenic tissue or fluid administration.

These compounds can be used to treat medical conditions in a host in need thereof, typically a human. The active compound may act as an inhibitor of the complement factor D cascade. In one embodiment, a method for the treatment of such a disorder is provided that includes the administration of an effective amount of a compound of Formula I, Formula II, Formula III, Formula IV, Formula V, Formula VI, Formula VII, Formula VIII or Formula IX or a pharmaceutically acceptable salt, prodrug, isotopic analog, N-oxide, or isolated isomer thereof, optionally in a pharmaceutically acceptable composition, as described in more detail below.

In certain embodiments, compounds are provided that have minimal effect on BSEP (bile salt export pump protein) (e.g., with an $IC_{50}$ of greater than about 20, 30, 40, 50, 60, 75 or 100 µM or greater), or with a therapeutic index of BSEP relative to complement D inhibition (e.g., $IC_{50}$ inhibition of BSEP/$IC_{50}$ inhibition of complement D inhibitor), of about at least 50, 100, 200, 300, 400, 500, 750 or 1000 or greater). BSEP inhibition correlates with cholestatic drug-induced liver injury.

In some embodiments, the compounds of the present invention exhibit reduced hydrolysis of the amide bond between the C ring and the B ring in vivo, for example, by including a proline that has a cis-substituent relative to the proline-carbonyl bond directed toward the B-ring. In certain embodiments, the cis-substituent is in the Q3 position or the Q2 position or is a group that bridges Q3 and Q2.

A B-ring substituent in the position ortho to the amide (for example 2-(L1)-3-methyl-6-substituted-pyridine or 2-(L1)-3-cyclopropyl-6-substituted-pyridine) may decrease the potential for formation of reactive metabolites.

In one embodiment, the disorder is associated with the alternative complement cascade pathway. In yet another embodiment, the disorder is associated with the complement classical pathway. In a further embodiment, the disorder is associated with the complement lectin pathway. Alternatively, the active compound or its salt or prodrug may act through a different mechanism of action than the complement cascade to treat the disorder described herein.

In another embodiment, a method is provided for treating a host, typically a human, with a disorder mediated by the complement system, that includes administration of a prophylactic antibiotic or vaccine to reduce the possibility of a bacterial infection during the treatment using one of the compounds described herein. In certain embodiments, the host, typically a human, is given a prophylactic vaccine prior to, during or after treatment with one of the compounds described herein. In certain embodiments, the host, typically a human, is given a prophylactic antibiotic prior to, during or after treatment with one of the compounds described herein. In some embodiments, the infection is a meningococcal infection (e.g., septicemia and/or meningitis), an *Aspergillus* infection, or an infection due to an encapsulated organism, for example, *Streptococcus pneumoniae* or *Haemophilus* influenza type b (Hib), especially in children. In other embodiments, the vaccine or antibiotic is administered to the patient after contracting an infection due to, or concommitent with inhibition of the complement system.

The disclosure provides a compound of Formula I:

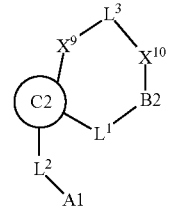

Formula I or a pharmaceutically acceptable salt, isotopic analog, prodrug, N-oxide, or isolated isomer thereof, optionally in a pharmaceutically acceptable carrier;

wherein:

C2 is

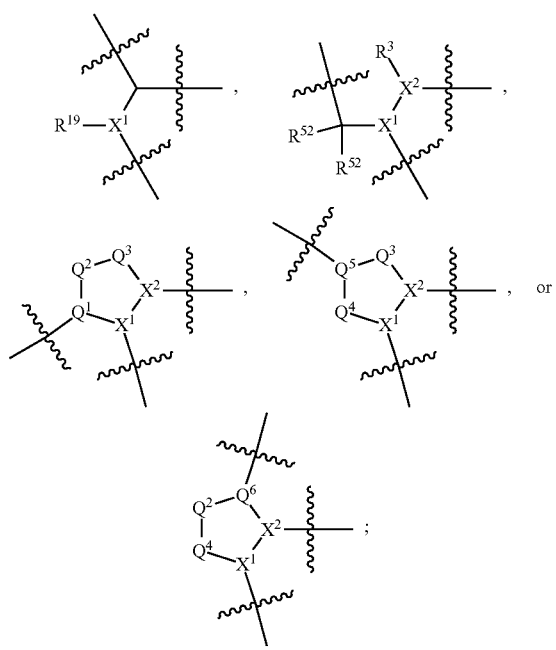

$Q^1$ is $C(R^1)$, wherein $Q^1$ is directly bound to $X^9$;
$Q^2$ is $C(R^2R^{2'})$;
$Q^3$ is $C(R^3R^{3'})$;
$Q^4$ is $C(R^1R^{1'})$;
$Q^5$ is $C(R^2)$, wherein $Q^5$ is directly bound to $X^9$;
$Q^6$ is $C(R^3)$, wherein $Q^6$ is directly bound to $X^9$;

$X^1$ is nitrogen, wherein $X^1$ is directly bound to $L^2$;
$X^2$ is CH, wherein $X^2$ is directly bound to $L^1$;
wherein $Q^1$, $Q^2$, $Q^3$, $Q^4$, $Q^5$, $Q^6$, $X^1$, and $X^2$ are selected such that a stable compound results;
$R^1$, $R^{1'}$, $R^2$, $R^{2'}$, $R^3$, and $R^{3'}$ are independently selected at each occurrence, as appropriate, and only where a stable compound results, from hydrogen, —$C_0$-$C_4$alkyl$NR^9R^{16}$, —$C_0$-$C_4$alkyl$OR^{16}$, $C_1$-$C_6$haloalkyl, —$SO_2R^{15}$, halogen, hydroxyl, and $C_1$-$C_6$alkyl;
or $R^1$ and $R^2$ are taken together to form a 3- to 6-membered carbocyclic ring;
or $R^2$ and $R^3$ are taken together to form a 3- to 6-membered carbocyclic ring;
or $R^1$ and $R^2$ are taken together to form a double bond;
or $R^2$ and $R^3$ are taken together to form a double bond;
$R^{19}$ is selected at each occurrence, as appropriate, and only where a stable compound results, from hydrogen, —$C_1$-$C_4$alkyl$NR^9R^{16}$, —$C_1$-$C_4$alkyl$OR^{16}$, $C_1$-$C_6$haloalkyl, —$SO_2R^{15}$, and $C_1$-$C_6$alkyl;
A1 is selected from:

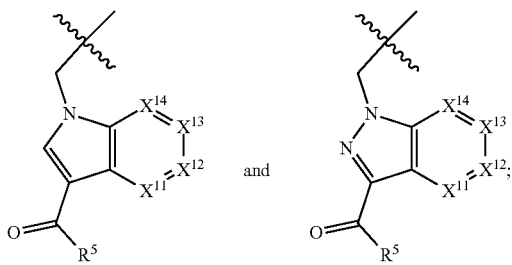

In an alternative embodiment A1 is selected from:

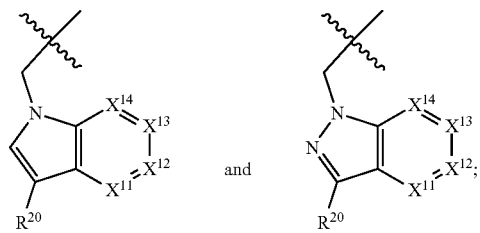

$L^1$ is

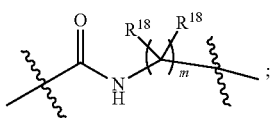

m is 0, 1, or 3;
$L^2$ is —C(O)—;
$L^3$ is

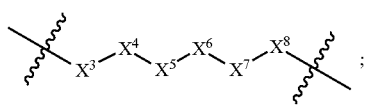

$X^3$, $X^4$, $X^5$, $X^6$, $X^7$ and $X^8$ are each independently selected from bond, —$C(R^{52})_2$—, —$C(R^{52})_2C(R^{52})_2$—, —$C(R^{52})_2C(R^{52})_2C(R^{52})_2$—, —C(O)—, —C(S)—, —P(O)$OR^{16}$—, —S(O)—, —$S(O)_2$—, N=$S(O)_2$($R^{52}$)—, —$S(O)_2(R^{52})$=N—, —$S(O)_2$-heteroaryl-, -heteroaryl-$S(O)_2$—, —O—, —S—, alkylene, alkenylene, alkynylene, heterocycle, aryl, heteroaryl, cycloalkyl, and —$NR^{16}$—, each of which moieties are used in any order that results in a stable compound each of which is considered independently disclosed;
$X^9$ and $X^{10}$ are independently selected from alkylene, —$C(R^{52})_2$—, —$C(R^{52})_2O$—, —$C(R^{52})_2NR^9$—, —$C(R^{52})_2OC(O)$—, —$C(R^{52})_2NR^9C(O)$—, —O—, —S—, —C(O)—, —C(S)—, —P(O)$OR^{16}$—, —S(O)—, —$S(O)_2$—, alkenylene, alkynylene, —$CH_2O$—, —$CH_2N(H)$—, —$CH_2OC(O)$—, —$CH_2N(H)C(O)$—, —$CH_2N(CH_3)$—, $CH_2N(CH_3)C(O)$—, $R^{32}$ in a divalent state, and —$NR^{16}$—;
$X^{11}$ is N or $CR^{11}$;
$X^{12}$ is N or $CR^{12}$;
$X^{13}$ is N or $CR^{13}$;
$X^{14}$ is N or $CR^{14}$;
wherein no more than 2 of $X^{11}$, $X^{12}$, $X^{13}$, and $X^{14}$ are N;
$R^5$ is selected from $C_1$-$C_3$alkyl, —$C_1$-$C_3$alkyl-$OR^{16}$, and —$NR^9R^{10}$;
in an alternative embodiment $R^5$ is selected from hydrogen, $C_1$-$C_3$alkyl, —$C_1$-$C_3$alkyl-$OR^{16}$, and —$NR^9R^{10}$;
each $R^9$ and $R^{10}$ are independently selected from hydrogen, aryl, heteroaryl, and $C_1$-$C_6$alkyl;
$R^{11}$, $R^{12}$, $R^{13}$, and $R^{14}$ are independently selected at each occurrence from hydrogen, —$C_0$-$C_4$alkyl$NR^9R^{16}$, —$C_0$-$C_4$alkyl$OR^{16}$, $C_1$-$C_6$haloalkyl, —$SO_2R^{15}$, halogen, hydroxyl, nitro, cyano, —O(PO)($OR^{16}$)$_2$, —(PO)($OR^{16}$)$_2$, $C_2$-$C_6$alkenyl, $C_2$-$C_6$alkynyl, $C_2$-$C_6$alkynyl, $C_2$-$C_6$alkanoyl, $C_1$-$C_6$alkoxy, $C_1$-$C_6$thioalkyl, —$C_0$-$C_4$alkyl($C_3$-$C_7$cycloalkyl), $C_1$-$C_6$haloalkyl, $C_1$-$C_6$haloalkoxy, amino, —$COOR^{15}$, —C(O)$NR^9R^{10}$, —OC(O)$R^9$, —C($NR^9$)$NR^9R^{10}$, and $R^{32}$, each of which $R^{11}$, $R^{12}$, $R^{13}$, and $R^{14}$ other than hydrogen, halogen, hydroxyl, nitro, cyano, haloalkyl, and haloalkoxy is optionally substituted with one or more substituents independently selected from halogen, hydroxyl, nitro, cyano, amino, —COOH, —$CONH_2$, $C_1$-$C_6$haloalkyl, $C_1$-$C_6$haloalkoxy, phenyl, and 4- to 7-membered heterocycle containing 1, 2, or 3 heteroatoms independently selected from N, O, and S;
each $R^{15}$ is independently selected from hydrogen, $C_1$-$C_3$alkyl, —$OR^9$, —$NR^{24}R^{25a}$ and —$NR^9R^{10}$;
each $R^{16}$ is independently selected from hydrogen, aryl, heteroaryl, $C_1$-$C_3$alkyl, and —C(O)$R^{15}$;
each $R^{18}$ is independently selected from hydrogen and $C_1$-$C_6$alkyl;
$R^{20}$ is selected from heterocycle, heteroaryl, imine, oxetane, and oxime, wherein each $R^{20}$ is optionally substituted with 1, 2, or 3 substituents independently selected from $C_1$-$C_3$alkyl, halogen, —$OR^9$, and —$NR^9R^{10}$;
$R^{21}$ and $R^{22}$ are independently selected from hydrogen, hydroxyl, cyano, amino, $C_1$-$C_6$alkyl, $C_1$-$C_6$haloalkyl, $C_1$-$C_6$alkoxy, —$C_0$-$C_4$alkyl-aryl, —$C_0$-$C_4$alkyl-heteroaryl, and —$C_0$-$C_4$alkyl-(4- to 7-membered heterocycle having 1, 2, or 3 heteroatoms independently selected from N, O, and S);
or $R^{21}$ and $R^{22}$ can be taken together to form a carbocyclic or heterocyclic ring;
$R^{24}$ and $R^{25a}$ are taken together with the nitrogen to which they are attached to form a 4- to 7-membered monocyclic heterocycloalkyl group, or a 6- to 10-membered bicyclic heterocyclic group having fused, spiro, or bridged rings;

$R^{32}$ is independently selected from $C_1$-$C_6$alkyl, $C_1$-$C_6$haloalkyl, aryl, heteroaryl, saturated heterocycle, partially unsaturated heterocycle, $C_2$-$C_6$alkynyl, —C(O)NR$^9$R$^{16}$, —C(O)OR$^{16}$, —NR$^9$C(O)R$^{15}$, —OC(O)R$^{15}$, —C(O)R$^{15}$, —NR$^9$R$^{16}$, —NR$^9$SO$_2$R$^{16}$, —O(CH$_2$)$_{1-4}$P(O)R$^{23b}$R$^{23b}$, and —P(O)R$^{75}$R$^{75}$ wherein each $R^{32}$ is optionally substituted with 1, 2, 3, or 4 substituents selected from halogen, —SO$_2$R$^{15}$, $C_1$-$C_6$haloalkyl, aryl, 5- or 6-membered heterocycle having 1, 2, or 3 heteroatoms independently selected from N, O, and S, 5- or 6-membered heteroaryl, —C(O)R$^{15}$, $C_2$-$C_6$alkanoyl, —B(OH)$_2$, —C(O)(CH$_2$)$_{1-4}$S(O)R$^{21}$, —P(O)(OR$^{21}$)(OR$^{22}$), —P(O)(OR$^{21}$)R$^{22}$, —P(O)R$^{21}$R$^{22}$, —NR$^9$P(O)(NHR$^{21}$)(NHR$^{22}$), —NR$^9$P(O)(OR$^{21}$)(NHR$^{22}$), —NR$^9$P(O)(OR$^{21}$)(OR$^{22}$), —C(S)R$^{21}$, —NR$^{21}$SO$_2$R$^{22}$, —NR$^9$S(O)NR$^{10}$R$^{22}$, —NR$^9$SO$_2$NR$^{10}$R$^{22}$, —SO$_2$NR$^9$COR$^{22}$, —SO$_2$NR$^9$CONR$^{21}$R$^{22}$, —NR$^{21}$SO$_2$R$^{22}$, —C(O)NR$^{21}$SO$_2$R$^{22}$, —C(NH$_2$)NR$^9$R$^{22}$, —C(NH$_2$)NR$^9$S(O)$_2$R$^{22}$, —NR$^9$C(O)OR$^{10}$, —NR$^{21}$OC(O)R$^{22}$, —(CH$_2$)$_{1-4}$C(O)NR$^{21}$R$^{22}$, —C(O)R$^{24}$R$^{25a}$, —NR$^9$C(O)R$^{21}$, —C(O)R$^{21}$, —NR$^9$C(O)NR$^9$R$^{10}$, —NR$^9$C(O)NR$^{24}$R$^{25a}$, and —(CH$_2$)$_{1-4}$OC(O)R$^{21}$;

$R^{23b}$ is independently selected at each occurrence from hydroxyl, OR$^{16}$, $C_1$-$C_6$alkoxy, $C_1$-$C_6$alkyl, an N-linked amino acid and an N-linked amino acid ester;

$R^{75}$ is independently selected at each occurrence from hydroxyl, $C_1$-$C_6$alkoxy, $C_1$-$C_6$haloalkoxy, $C_1$-$C_6$alkyl, —$C_0$-$C_4$alkyl-aryl, —O—$C_0$-$C_4$alkyl-aryl, —$C_0$-$C_4$alkyl-heteroaryl, —O—$C_0$-$C_4$alkyl-heteroaryl, —$C_0$-$C_4$alkyl-(4- to 7-membered heterocycle having 1, 2, or 3 heteroatoms independently selected from N, O, and S), or —NR$^9$R$^{16}$;

B2 is $C_1$-$C_6$alkyl, $C_2$-$C_6$alkenyl, $C_2$-$C_6$alkynyl, heteroaryl, heterocycle, aryl, or a monocyclic or bicyclic carbocycle; wherein B2 is directly bound to both L$^1$ and X$^{10}$ at two independent positions; and wherein, each of which B2 is optionally substituted with 1, 3, or 4 substituents independently selected from aryl, heteroaryl, heterocycle, halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{16}$, —$C_0$-$C_4$alkylOR$^{16}$, —SO$_2$R$^{15}$, $C_1$-$C_6$haloalkyl, and $C_1$-$C_6$haloalkoxy;

each $R^{52}$ is independently selected from halogen, hydrogen, $C_1$-$C_6$alkyl, amino, hydroxyl, aminoalkyl, alkenyl, alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), alkanoyl, $C_1$-$C_6$alkoxy, $C_1$-$C_6$thioalkyl, —$C_0$-$C_4$alkylNR$^9$R$^{16}$, haloalkyl, haloalkoxy, —COOH, $C_2$-$C_6$alkenyloxy, —C(O)OR$^{16}$, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and N(R$^9$)C(O)R$^{10}$;

or two $R^{52}$ groups can be taken together to form a 3- to 6-membered carbocyclic ring or a 3- to 6-membered heterocyclic spiro ring containing 1 or 2 heteroatoms independently selected from N, O, or S;

or two $R^{52}$ groups on the same carbon can be taken together with the carbon to which they are attached to form an oxo or alkene group

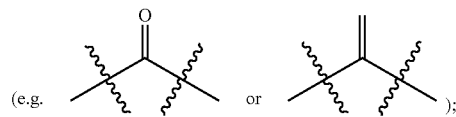

(e.g. or );

and where any of these groups may be further optionally substituted as that term is defined in the Terminology Section below, if desired to achieve the target effect, results in a stable compound, and the group is not redundant (i.e., as known in the art, alkyl substituted with alkyl is redundant; however, for example, alkoxy substituted with alkoxy is not redundant).

In an alternative embodiment C2 is

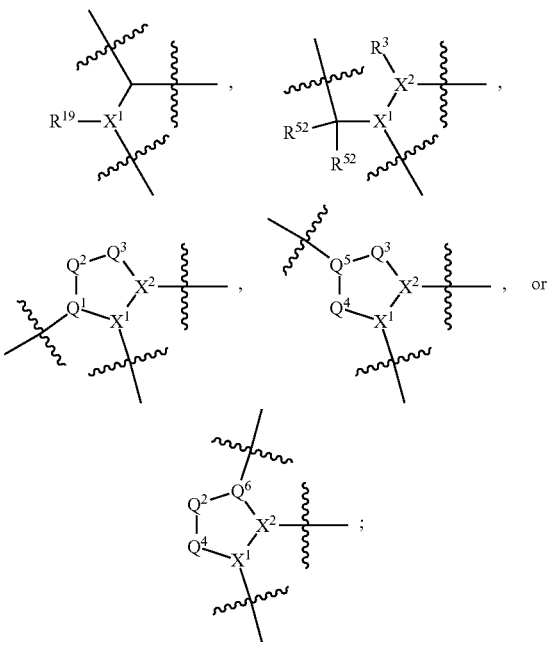

wherein
Q$^1$ is N or C(R$^1$), wherein Q$^1$ is directly bound to X$^9$;
Q$^2$ is O, S, NR$^9$, or C(R$^2$R$^{2'}$);
Q$^3$ is O, S, NR$^9$, or C(R$^3$R$^{3'}$);
Q$^4$ is N(R$^9$) or C(R$^1$R$^{1'}$);
Q$^5$ is N or C(R$^2$), wherein Q$^5$ is directly bound to X$^9$;
Q$^6$ is N or C(R$^3$), wherein Q$^6$ is directly bound to X$^9$;
X$^1$ is CH or nitrogen, wherein X$^1$ is directly bound to L$^2$;
X$^2$ is CH or N, wherein X$^2$ is directly bound to L$^1$;
wherein Q$^1$, Q$^2$, Q$^3$, Q$^4$, Q$^5$, Q$^6$, X$^1$, and X$^2$ are selected such that a stable compound results.

In one embodiment the compound of Formula I is selected from:

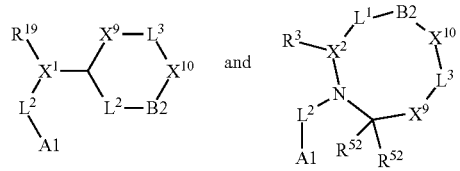

or a pharmaceutically acceptable salt, isotopic analog, prodrug, N-oxide, or isolated isomer thereof, optionally in a pharmaceutically acceptable carrier.

In one embodiment of any formula described herein C2 is

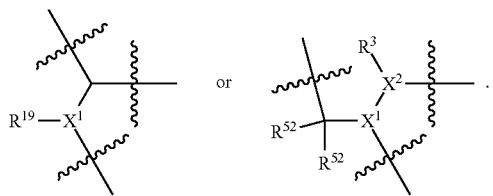

In one embodiment of any formula described herein C2 is

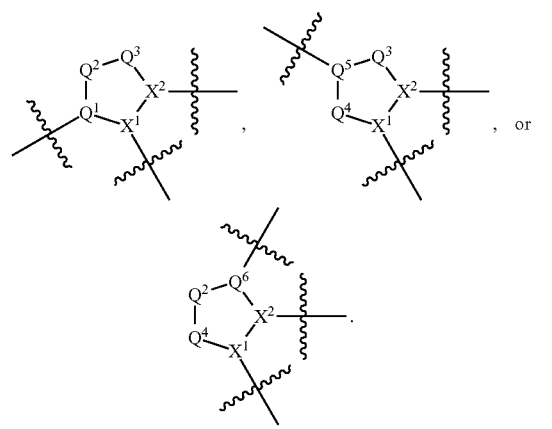

The disclosure also provides a compound of Formula II:

Formula II

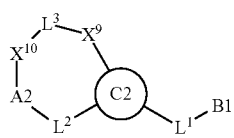

or a pharmaceutically acceptable salt, isotopic analog, prodrug, N-oxide, or isolated isomer thereof, optionally in a pharmaceutically acceptable carrier;
wherein:
A2 is selected from:

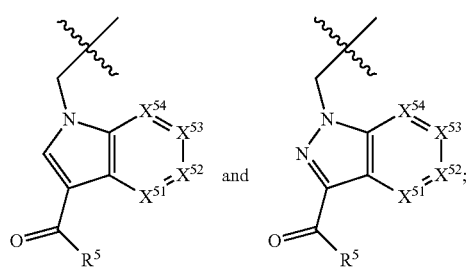

wherein $X^{51}$, $X^{52}$, $X^{53}$ and $X^{54}$ are selected from N, $CR^{13}$, and a carbon directly bound to $X^{10}$, and wherein one and only one of $X^{51}$, $X^{52}$, $X^{53}$ and $X^{54}$ is a carbon directly bound to $X^{10}$;

in and alternative embodiment A2 is selected from:

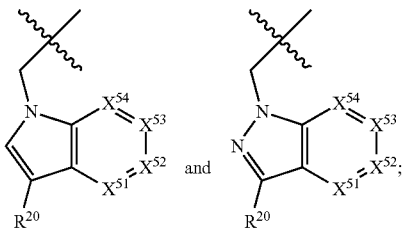

wherein $X^{51}$, $X^{52}$, $X^{53}$ and $X^{54}$ are selected from N, $CR^{13}$, and a carbon directly bound to $X^{10}$, and wherein one and only one of $X^{51}$, $X^{52}$, $X^{53}$ and $X^{54}$ is a carbon directly bound to $X^{10}$;

B1 is $C_1$-$C_6$alkyl, $C_2$-$C_6$alkenyl, $C_2$-$C_6$alkynyl, heteroaryl, heterocycle, aryl, or a monocyclic or bicyclic carbocycle; each of which B1 is optionally substituted with 1, 2, 3, or 4 substituents independently selected from aryl, heteroaryl, heterocycle, halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{16}$, —$C_0$-$C_4$alkylOR$^{16}$, —$SO_2R^{15}$, $C_1$-$C_6$haloalkyl, and $C_1$-$C_6$haloalkoxy; and wherein each other variable is as defined herein.

In one embodiment the compound of Formula II is selected from:

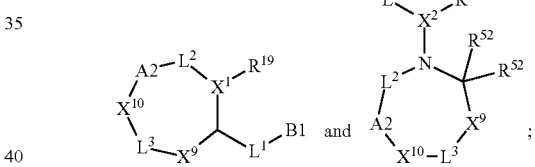

or a pharmaceutically acceptable salt, isotopic analog, prodrug, N-oxide, or isolated isomer thereof, optionally in a pharmaceutically acceptable carrier.

The disclosure provides a compound of Formula III:

Formula III

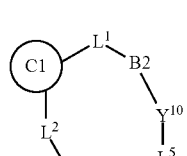

or a pharmaceutically acceptable salt, isotopic analog, prodrug, N-oxide, or isolated isomer thereof, optionally in a pharmaceutically acceptable carrier;
wherein:
A2 is as defined in Formula II except A2 is directly bound to $Y^9$ instead of $X^{10}$;
B2 is as defined in Formula I except B2 is directly bound to $Y^{10}$ instead of $X^{10}$;
$L^5$ is selected from $L^3$ and $L^4$;
$Y^9$ is selected from $X^9$ and $Z^9$;
$Y^{10}$ is selected from $X^{10}$ and $Z^{10}$;

C1 is

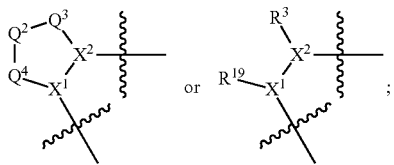

$Z^9$ is —CO—, —S(O)$_2$—, or —S(O)—;
$Z^{10}$ is —CO— or —S(O)—;
$L^4$ is

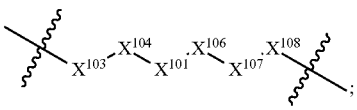

$X^{101}$ is selected from —CR$^{52a}$R$^{52}$—, —C(O)—, —C(S)—, —P(O)OR$^{16}$—, —S(O)—, —S(O)$_2$—, —O—, —S—, alkenylene, alkynylene, heterocycle, heteroalkylene, heteroalkynylene, heteroalkenylene, arylalkyl, heterocycloalkyl, heterocycloalkyl, heteroarylalkyl, aryl, heteroaryl, cycloalkyl, and —NR$^{16}$—, which moieties are used in any order that results in a stable compound each of which is considered independently disclosed;

$X^{103}$, $X^{104}$, $X^{106}$, $X^{107}$, and $X^{108}$ are each independently selected from bond, —C(R$^{52}$)$_2$—, —C(O)—, —C(S)—, —P(O)OR$^{16}$—, —S(O)—, —S(O)$_2$—, —S—, alkenylene, alkynylene, heterocycle, heteroalkylene, heteroalkynylene, heteroalkenylene, arylalkyl, heterocycloalkyl, heterocycloalkyl, heteroarylalkyl, aryl, heteroaryl, cycloalkyl, and —NR$^{16}$—, which moieties are used in any order that results in a stable compound each of which is considered independently disclosed; or in an alternative embodiment, $L^4$ is

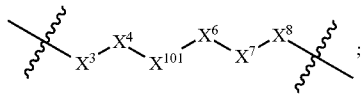

$R^{52a}$ is independently selected from halogen, hydroxyl, nitro, cyano, —O(PO)(OR$^{16}$)$_2$, —(PO)(OR$^{16}$)$_2$, $C_1$-$C_6$alkyl, $C_2$-$C_6$alkenyl, $C_2$-$C_6$alkynyl, $C_2$-$C_6$alkanoyl, $C_1$-$C_6$alkoxy, $C_1$-$C_6$thioalkyl, —$C_0$-$C_4$alkylNR$^9$R$^{16}$, —$C_0$-$C_4$alkyl($C_3$-$C_7$cycloalkyl), —$C_0$-$C_4$alkoxy($C_3$-$C_7$cycloalkyl), $C_1$-$C_6$haloalkyl, $C_1$-$C_6$haloalkoxy, amino, —COOH, —$C_0$-$C_4$alkyl($C_3$-$C_7$cycloalkyl), $C_2$-$C_6$alkenyloxy, —C(O)OR$^{16}$, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$;

or $R^{52a}$ and $R^{52}$ can be taken together to form a 3- to 6-membered carbocyclic spiro ring or a 3- to 6-membered heterocyclic spiro ring containing 1 or 2 heteroatoms independently selected from N, O, and S;

or $R^{52a}$ and $R^{52}$ are taken together to form an oxo or alkenyl group;

wherein all remaining variables are as defined herein;
and wherein for compounds of Formula III at least one of the following is true:

$L^5$ is $L^4$;
$Y^9$ is $Z^9$;
$Y^{10}$ is $Z^{10}$; or
C1 is

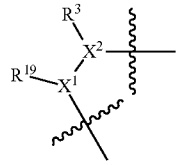

In an alternative embodiment C1 is

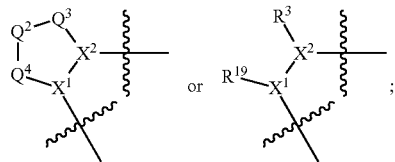

wherein
$Q^2$ is O, S, NR$^9$, or C(R$^2$R$^{2'}$);
$Q^3$ is O, S, NR$^9$, or C(R$^3$R$^{3'}$);
$Q^4$ is N(R$^9$) or C(R$^1$R$^{1'}$);
$X^1$ is CH or nitrogen, wherein $X^1$ is directly bound to $L^2$;
$X^2$ is CH or N, wherein $X^2$ is directly bound to $L^1$;
wherein $Q^1$, $Q^2$, $Q^3$, $Q^4$, $X^1$, and $X^2$ are selected such that a stable compound results.

In one embodiment of any formula described herein C1 is

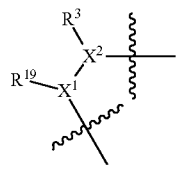

In one embodiment of any formula described herein C1 is

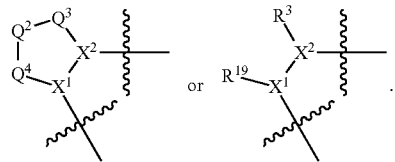

In one embodiment the compound of Formula III is:

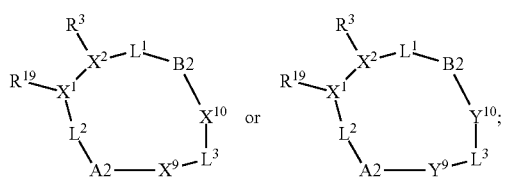

or a pharmaceutically acceptable salt, isotopic analog, prodrug, N-oxide, or isolated isomer thereof, optionally in a pharmaceutically acceptable carrier.

The disclosure also provides a compound of Formula IV:

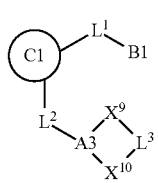

Formula IV or a pharmaceutically acceptable salt, isotopic analog, prodrug, N-oxide, or isolated isomer thereof, optionally in a pharmaceutically acceptable carrier;
wherein:
A3 is selected from:

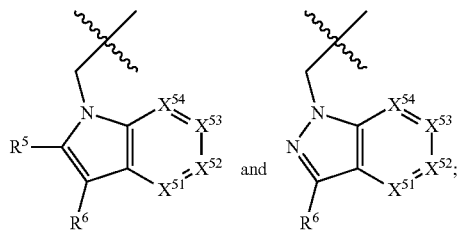

wherein $X^{51}$, $X^{52}$, $X^{53}$ and $X^{54}$ are selected from N, $CR^{13}$, a carbon directly bound to $X^9$, and a carbon directly bound to $X^{10}$, and wherein one and only one of $X^{51}$, $X^{52}$, $X^{53}$ and $X^{54}$ is a carbon directly bound to $X^9$, and wherein one and only one of $X^{51}$, $X^{52}$, $X^{53}$ and $X^{54}$ is a carbon directly bound to $X^{10}$, and wherein $X^9$ and $X^{10}$ are linked to $L^3$;
in an alternative embodiment A3 is selected from:

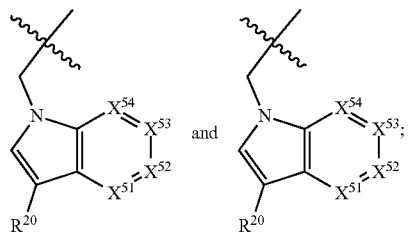

wherein $X^{51}$, $X^{52}$, $X^{53}$ and $X^{54}$ are selected from N, $CR^{13}$, a carbon directly bound to $X^9$, and a carbon directly bound to $X^{10}$, and wherein one and only one of $X^{51}$, $X^{52}$, $X^{53}$ and $X^{54}$ is a carbon directly bound to $X^9$, and wherein one and only one of $X^{51}$, $X^{52}$, $X^{53}$ and $X^{54}$ is a carbon directly bound to $X^{10}$, and wherein $X^9$ and $X^{10}$ are linked to $L^3$;
$R^6$ is selected from $C(O)CH_3$ and $C(O)NR^9R^{10}$; and wherein each other variable is as defined herein.
In one embodiment the compound of Formula IV is:

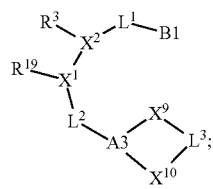

or a pharmaceutically acceptable salt, isotopic analog, prodrug, N-oxide, or isolated isomer thereof, optionally in a pharmaceutically acceptable carrier.

The disclosure also provides a compound of Formula V:

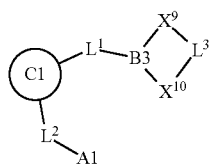

Formula V or a pharmaceutically acceptable salt, isotopic analog, prodrug, N-oxide, or isolated isomer thereof, optionally in a pharmaceutically acceptable carrier;
wherein:
B3 is $C_2$-$C_6$alkenyl, $C_2$-$C_6$alkynyl, heteroaryl, heterocycle, aryl, or a monocyclic or bicyclic carbocycle; wherein B3 is bound to $L^1$, $X^9$ and $X^{10}$ at three independent positions;
and wherein, each of which B3 is optionally substituted with 1, 2, 3, or 4 substituents independently selected from aryl, heteroaryl, heterocycle, halogen, hydroxyl, —COOH, cyano, $C_1$-$C_6$alkyl, $C_2$-$C_6$alkanoyl, $C_1$-$C_6$alkoxy, —$C_0$-$C_4$alkyl$NR^9R^{16}$, —$C_0$-$C_4$alkyl$OR^{16}$, —$SO_2R^{15}$, $C_1$-$C_6$haloalkyl, and $C_1$-$C_6$haloalkoxy;
wherein each other variable is as defined herein.
In one embodiment the compound of Formula V is:

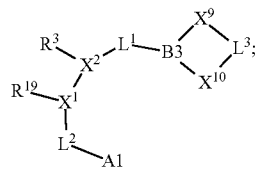

or a pharmaceutically acceptable salt, isotopic analog, prodrug, N-oxide, or isolated isomer thereof, optionally in a pharmaceutically acceptable carrier.

The disclosure also provides a compound of Formula VI:

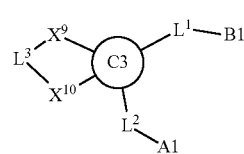

Formula VI or a pharmaceutically acceptable salt, isotopic analog, prodrug, N-oxide, or isolated isomer thereof, optionally in a pharmaceutically acceptable carrier;

wherein:

C3 is

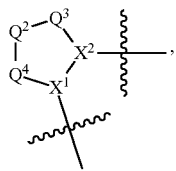

wherein one of $R^1$, $R^2$, $R^3$, $R^{1'}$, $R^{2'}$, or $R^{3'}$ is replaced with a direct bond to $X^9$, and wherein one of $R^1$, $R^2$, $R^3$, $R^{1'}$, $R^{2'}$, or $R^{3'}$ is replaced with a direct bond to $X^{10}$; or C3 is C4; C4 is

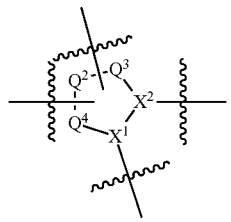

wherein C4 is directly bound to $X^9$, $X^{10}$, $L^1$, and $L^2$, wherein $X^9$ and/or $X^{10}$ can be directly bound to C4 (e.g. $Q^4$ is $CH_2$ and one H is replaced with a bond to $X^9$ or $X^{10}$), or $X^9$ and/or $X^{10}$ can be bound to a ring resulting from the cyclization of $R^1$, $R^2$, $R^3$, $R^{1'}$, $R^{2'}$, or $R^{3'}$, as defined herein; and wherein each other variable is as defined herein.

In an alternative embodiment C3 is

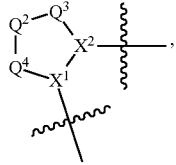

wherein one of $R^1$, $R^2$, $R^3$, $R^{1'}$, $R^{2'}$, or $R^{3'}$ is replaced with a direct bond to $X^9$, and wherein one of $R^1$, $R^2$, $R^3$, $R^{1'}$, $R^{2'}$, or $R^{3'}$ is replaced with a direct bond to $X^{10}$;

$Q^2$ is O, S, $NR^9$, or $C(R^2R^{2'})$;

$Q^3$ is O, S, $NR^9$, or $C(R^3R^{3'})$, $Q^4$ is $N(R^9)$ or $C(R^1R^{1'})$;

$X^1$ is CH or nitrogen, wherein $X^1$ is directly bound to $L^2$;

$X^2$ is CH or N, wherein $X^2$ is directly bound to $L^1$;

wherein $Q^2$, $Q^3$, $Q^4$, $X^1$, and $X^2$ are selected such that a stable compound results.

The disclosure also provides a compound of Formula VII:

Formula VII

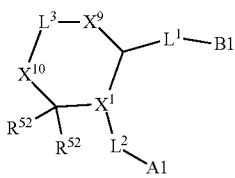

or a pharmaceutically acceptable salt, isotopic analog, prodrug, N-oxide, or isolated isomer thereof, optionally in a pharmaceutically acceptable carrier;

wherein each variable is as defined herein.

The disclosure also provide a compound of Formula VIII:

Formula VIII

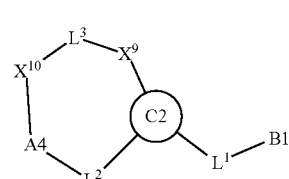

or a pharmaceutically acceptable salt, isotopic analog, prodrug, N-oxide, or isolated isomer thereof, optionally in a pharmaceutically acceptable carrier;

wherein:

A4 is selected from:

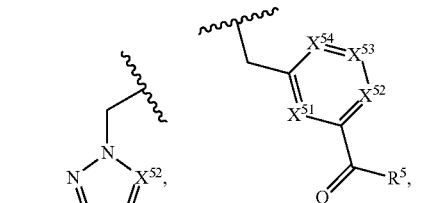

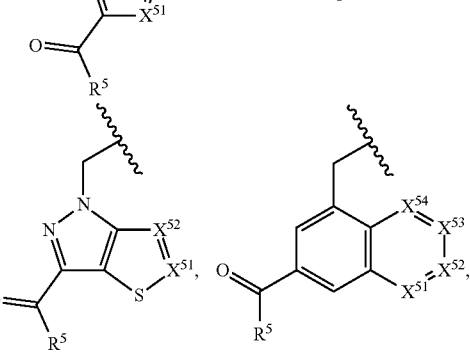

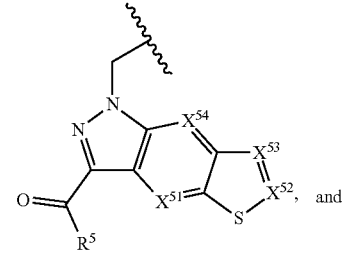

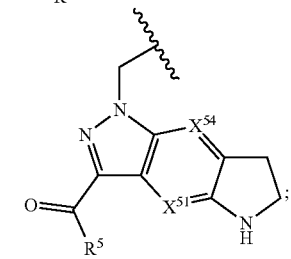

wherein $X^{51}$, $X^{52}$, $X^{53}$, and $X^{54}$ are selected from N, $CR^{13}$, and a carbon directly bound to $X^{10}$; and for clarity every A4 is selected such that there is a carbon directly bound to $X^{10}$;

in an alternative embodiment A4 is selected from:

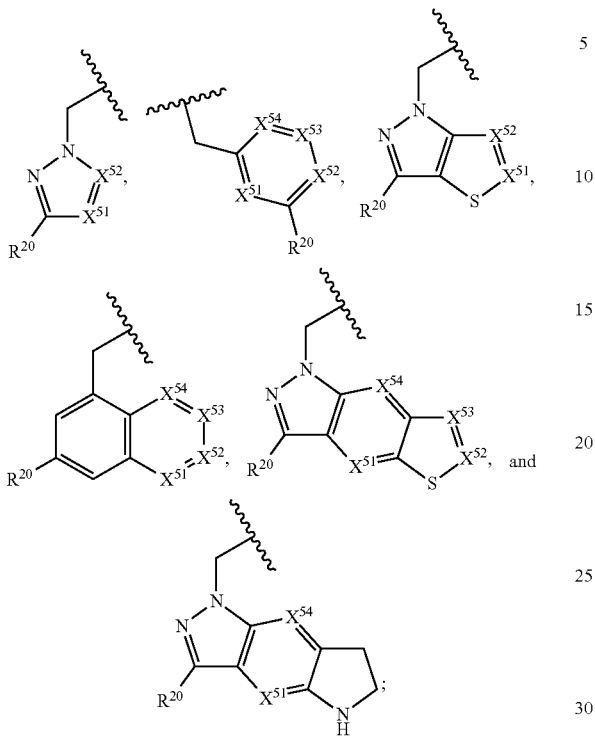

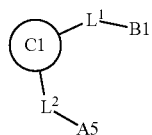

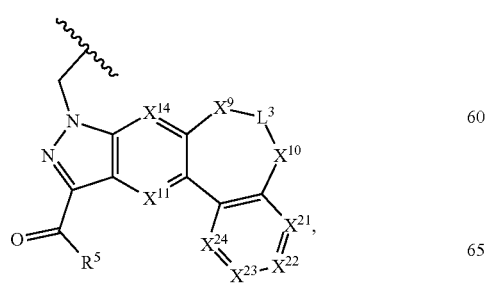

wherein $X^{51}$, $X^{52}$, $X^{53}$, and $X^{54}$ are selected from N, $CR^{13}$, and a carbon directly bound to $X^{10}$; and for clarity every A4 is selected such that there is a carbon directly bound to $X^{10}$;

wherein all other variables are as defined herein.

The disclosure also provides a compound of Formula IX:

Formula IX or a pharmaceutically acceptable salt, isotopic analog, prodrug, N-oxide, or isolated isomer thereof, optionally in a pharmaceutically acceptable carrier;

wherein:

A5 is selected from

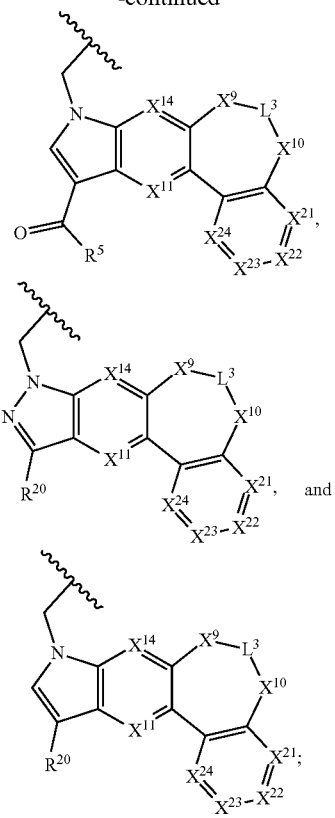

$X^{21}$ is N or $CR^{11}$;
$X^{22}$ is N or $CR^{12}$;
$X^{23}$ is N or $CR^{13}$;
$X^{24}$ is N or $CR^{14}$;
wherein no more than 2 of $X^{21}$, $X^{22}$, $X^{23}$, and $X^{24}$ are N; and
wherein all other variables are as defined herein.

In certain embodiments, A5 is selected from:

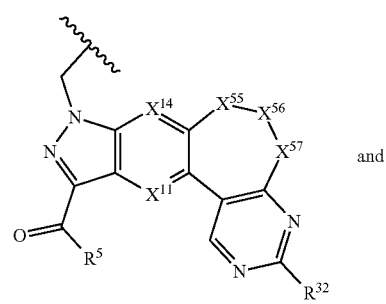

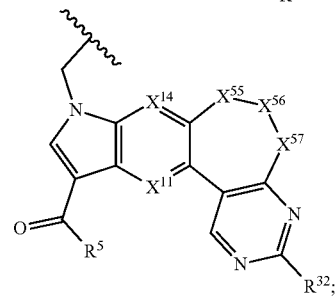

wherein $X^{55}$, $X^{56}$, and $X^{57}$ are selected from $NR^{16}$, S, O, and $CR^{52}R^{52}$ each of which moieties are used in any order that results in a stable compound each of which is considered independently disclosed.

Pharmaceutical compositions comprising a compound or salt of Formula I, Formula II, Formula III, Formula IV, Formula V, Formula VI, Formula VII Formula VIII, or Formula IX together with a pharmaceutically acceptable carrier are also disclosed.

The present invention thus includes at least the following features:

a. a compound of the present invention or a pharmaceutically acceptable salt, prodrug, isotopic analog, N-oxide, or isolated isomer thereof, optionally in a pharmaceutically acceptable composition, b. a compound of the present invention or a pharmaceutically acceptable salt, prodrug, isotopic analog, N-oxide, or isolated isomer thereof, optionally in a pharmaceutically acceptable composition, for use in treating or preventing a disorder including but not limited to the development of fatty liver and conditions stemming from fatty liver, such as nonalcoholic steatohepatitis (NASH), liver inflammation, cirrhosis, or liver failure; dermatomyositis; amyotrophic lateral sclerosis; cytokine or inflammatory reactions in response to biotherapeutics (e.g. CAR T-cell therapy); paroxysmal nocturnal hemoglobinuria (PNH), C3 glomerulonephritis, dense deposit disease, C3 glomerulopathy, rheumatoid arthritis, multiple sclerosis, age-related macular degeneration (AMD), retinal degeneration, other ophthalmic diseases (e.g., geographic atrophy), a respiratory disease or a cardiovascular disease;

c. a pharmaceutically acceptable composition of a compound of the present invention or its pharmaceutically acceptable salt, prodrug, isotopic analog, N-oxide, or isolated isomer thereof in a pharmaceutically acceptable carrier;

d. a compound of the present invention or a pharmaceutically acceptable salt, prodrug, isotopic analog, N-oxide, or isolated isomer thereof, optionally in a pharmaceutically acceptable composition, for use in treating or preventing a disorder mediated by the complement pathway, and for example, cascade Factor D;

e. use of a compound of the present invention as described herein, or a pharmaceutically acceptable salt, prodrug, isotopic analog, N-oxide, or isolated isomer thereof, optionally in a pharmaceutically acceptable composition, in the manufacture of a medicament for treating or preventing a disorder, including but not limited to the development of fatty liver and conditions stemming from fatty liver, such as nonalcoholic steatohepatitis (NASH), liver inflammation, cirrhosis, liver failure; dermatomyositis; amyotrophic lateral sclerosis; cytokine or inflammatory reactions in response to biotherapeutics (e.g. CAR T-cell therapy); paroxysmal nocturnal hemoglobinuria (PNH), C3 glomerulonephritis, dense deposit disease, C3 glomerulopathy, rheumatoid arthritis, multiple sclerosis, age-related macular degeneration (AMD), retinal degeneration, other ophthalmic diseases (e.g., geographic atrophy), a respiratory disease or a cardiovascular disease;

f. a process for manufacturing a medicament intended for the therapeutic use for treating or preventing a disorder, or generally for treating or preventing disorders mediated by complement cascade Factor D, characterized in that a compound of the present invention or an embodiment of the active compound is used in the manufacture;

g. a compound of the present invention or a salt thereof as described herein in substantially pure form (e.g., at least 90, 95, or 98%):

h. a compound of the present invention as described herein, or a pharmaceutically acceptable salt, prodrug, isotopic analog, N-oxide, or isolated isomer thereof, optionally in a carrier to form a pharmaceutically acceptable composition, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

i. For each of (a) through (h) above, and otherwise herein, each assembly of moieties and each active compound made therefrom or its use is considered and deemed specifically and individually disclosed, as such depiction is for convenience of space only and not intended to describe a only a genus or even a subgenus for such indication.

DETAILED DESCRIPTION

Terminology

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, tautomers, racemates and other isomers, such as rotamers, as if each is specifically described, unless otherwise indicated or otherwise excluded by context.

The terms "a" and "an" do not denote a limitation of quantity, but rather denote the presence of at least one of the referenced items. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula I, Formula II, Formula III, Formula IV, Formula V, Formula VI, Formula VII Formula VIII, or Formula IX with at least one desired isotopic substitution of an atom, at an amount above the natural abundance of the isotope, i.e., enriched.

Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$, and $^{125}I$ respectively. In one embodiment, isotopically labelled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}H$) and tritium ($^{3}H$) may optionally be used anywhere in described structures that achieves the desired result. Alternatively or in addition, isotopes of carbon, e.g., $^{13}C$ and $^{14}C$, may be used. In one embodiment, the isotopic substitution is replacing hydrogen with a deuterium at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 80, 85, 90, 95 or 99% or more enriched in an isotope at any location of interest. In one embodiments deuterium is 80, 85, 90, 95 or 99% enriched at a desired location. Unless otherwise stated, the enrichment at any point is above natural abundance, and in an embodiment is enough to alter a detectable property of the drug in a human.

In one embodiment, the substitution of a hydrogen atom for a deuterium atom can be provided in any of A1, A2, A3, A4, A5, B1, B2, B3, C1, C2, C4, $L^1$, $L^3$, $L^4$, $L^5$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{21}$, $X^{22}$, $X^{23}$, $X^{24}$, $X^{51}$, $X^{52}$, $X^{53}$, $X^{54}$, $X^{101}$, $X^{103}$, $X^{104}$, $X^{106}$, $X^{107}$, $X^{108}$, $X^{300}$, $Y^9$, and $Y^{10}$. In one embodiment, the substitution of a hydrogen atom for a deuterium atom occurs within any R group. In one embodiment the R group is selected from any of R, $R^1$, $R^{1'}$, $R^2$, $R^{2'}$, $R^3$, $R^{3'}$, $R^5$, $R^6$, $R^9$, $R^{10}$, $R^{11}$, $R^{12}$, $R^{13}$, $R^{14}$, $R^{15}$, $R^{16}$, $R^{17}$, $R^{18}$, $R^{20}$, $R^{21}$, $R^{22}$, $R^{23b}$, $R^{24}$, $R^{25}$, $R^{26}$, $R^{27}$, $R^{28}$, $R^{32}$, $R^{52}$, $R^{52a}$, $R^{75}$, $R^{201}$, $R^{301}$, $R^{302}$, $R^{303}$, $R^{304}$, $R^{305}$, $R^{306}$, $R^{307}$, $R^{308}$, and $R^{309}$. For example, when any of R groups are, or contain for example through substitution, methyl, ethyl, or methoxy, the alkyl residue may be deuterated (in nonlimiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, $OCDH_2$, $OCD_2H$, or $OCD_3$ etc.). In certain other embodiments, an R group has a "'" or an "a" designation, which in one embodiment can be deuterated. In certain other embodiments, when two substituents of the central core ring are combined to form a cyclopropyl ring, the unsubstituted methylene carbon may be deuterated.

The compound of the present invention may form a solvate with solvents (including water). Therefore, in one embodiment, the invention includes a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A dash ("—") that is not between two letters or symbols is used to indicate a point of attachment for a substituent. For example, —(C=O)NH$_2$ is attached through carbon of the keto (C=O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., =O) then two hydrogens on the atom are replaced. For example a pyridyl group substituted by oxo is a pyridone. Combinations of substituents and/or variables are permissible only if such combinations result in stable compounds or useful synthetic intermediates.

A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Nonlimiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, alkyl including C$_1$-C$_6$alkyl, alkenyl including C$_2$-C$_6$alkenyl, alkynyl including C$_2$-C$_6$alkynyl, —C$_1$-C$_6$alkoxy, alkanoyl including C$_2$-C$_6$alkanoyl, (mono- and di-C$_1$-C$_6$alkylamino)C$_0$-C$_2$alkyl, haloalkyl including C$_1$-C$_6$haloalkyl, hydroxyC$_1$-C$_6$alkyl, ester, carbamate, urea, sulfonamide, —C$_1$-C$_6$alkyl (heterocyclo), C$_1$-C$_6$alkyl(heteroaryl), —C$_1$-C$_6$alkyl(C$_3$-C$_7$cycloalkyl), O—C$_1$-C$_6$alkyl(C$_3$-C$_7$cycloalkyl), B(OH)$_2$, phosphate, phosphonate and haloalkoxy including C$_1$-C$_6$haloalkoxy.

"Alkyl" is a branched or straight chain saturated aliphatic hydrocarbon group. In one embodiment, the alkyl contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is C$_1$-C$_2$, C$_1$-C$_3$, C$_1$-C$_4$, C$_1$-C$_5$ or C$_1$-C$_6$. The specified ranges as used herein indicate an alkyl group having each member of the range described as an independent species. For example, the term C$_1$-C$_6$ alkyl as used herein indicates a straight or branched alkyl group having from 1, 2, 3, 4, 5, or 6 carbon atoms and is intended to mean that each of these is described as an independent species. For example, the term C$_1$-C$_4$alkyl as used herein indicates a straight or branched alkyl group having from 1, 2, 3, or 4 carbon atoms and is intended to mean that each of these is described as an independent species. When C$_0$-C$_n$ alkyl is used herein in conjunction with another group, for example, (C$_3$-C$_7$cycloalkyl)C$_0$-C$_4$ alkyl, or —C$_0$-C$_4$alkyl(C$_3$-C$_7$cycloalkyl), the indicated group, in this case cycloalkyl, is either directly bound by a single covalent bond (C$_0$alkyl), or attached by an alkyl chain in this case 1, 2, 3, or 4 carbon atoms. Alkyls can also be attached via other groups such as heteroatoms as in —O—C$_0$-C$_4$alkyl (C$_3$-C$_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, 2,3-dimethylbutane, and hexyl.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is C$_1$-C$_2$, C$_1$-C$_3$, C$_1$-C$_4$, C$_1$-C$_5$ or C$_1$-C$_6$. The specified ranges as used herein indicate an aliphatic group having each member of the range described as an independent species. For example, the term C$_1$-C$_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term C$_1$-C$_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycle, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc. When a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenloxy, haloalkyl, etc. can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Nonlimiting examples are C$_2$-C$_8$alkenyl, C$_2$-C$_7$alkenyl, C$_2$-C$_6$alkenyl, C$_2$-C$_5$alkenyl and C$_2$-C$_4$alkenyl. The specified ranges as used herein indicate an alkenyl group having each member of the range described as an independent species, as described above for the alkyl moiety. Examples of alkenyl include, but are not limited to, ethenyl and propenyl.

"Alkynyl" is a branched or straight chain aliphatic hydrocarbon group having one or more carbon-carbon triple bonds that may occur at any stable point along the chain, for example, C$_2$-C$_8$alkynyl or C$_2$-C$_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Alkanoyl" is an alkyl group as defined above covalently bound through a carbonyl (C=O) bridge. The carbonyl carbon is included in the number of carbons, that is C$_2$alkanoyl is a CH$_3$(C=O)— group. In one embodiment, the alkanoyl group is optionally substituted as described "Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Halo" or "halogen" indicates independently, any of fluoro, chloro, bromo or iodo.

"Aryl" indicates an aromatic group containing only carbon in the aromatic ring or rings. In one embodiment, the aryl group contains 1 to 3 separate or fused rings and is 6 to 14 or 18 ring atoms, without heteroatoms as ring members. When indicated, such aryl groups may be further substituted with carbon or non-carbon atoms or groups. Such substitution may include fusion to a 4 to 7 or a 5 to 7-membered saturated or partially unsaturated cyclic group that optionally contains 1, 2 or 3 heteroatoms independently selected from N, O, B, P, Si and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group.

The term "heterocycle" refers to saturated and partially saturated heteroatom-containing ring radicals, where the heteroatoms may be selected from N, S, and O. The term "heterocycle" includes monocyclic 3-12 membered rings, as well as bicyclic 5-16 membered ring systems (which can include fused, bridged, or spino, bicyclic ring systems). It does not include rings containing —O—O—, —O—S—, or —S—S— portions. Examples of saturated heterocycle groups include saturated 4- to 7-membered monocyclic groups containing 1 to 4 nitrogen atoms [e.g. pyrrolidinyl, imidazolidinyl, piperidinyl, pyrrolinyl, azetidinyl, piperazinyl, and pyrazolidinyl]; saturated 4 to 6-membered monocyclic groups containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocycle radicals include but are not limited to, dihydrothienyl, dihydropyranyl, dihydrofuryl, and dihydrothiazolyl. Examples of partially saturated and saturated heterocycle groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydroquinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl. "Bicyclic heterocycle" includes groups wherein the heterocyclic radical is fused with an aryl radical wherein the point of attachment is the heterocycle ring. "Bicyclic heterocycle" also includes heterocyclic radicals that are fused with a carbocycle radical. For example partially unsaturated condensed heterocyclic group containing 1 to 5 nitrogen atoms, for example, indoline, isoindoline, partially unsaturated condensed heterocyclic group containing 1 to 2 oxygen atoms and 1 to 3 nitrogen atoms, partially unsaturated condensed heterocyclic group containing 1 to 2 sulfur atoms and 1 to 3 nitrogen atoms, and saturated condensed heterocyclic group containing 1 to 2 oxygen or sulfur atoms.

Non-limiting examples of bicyclic heterocycles include:

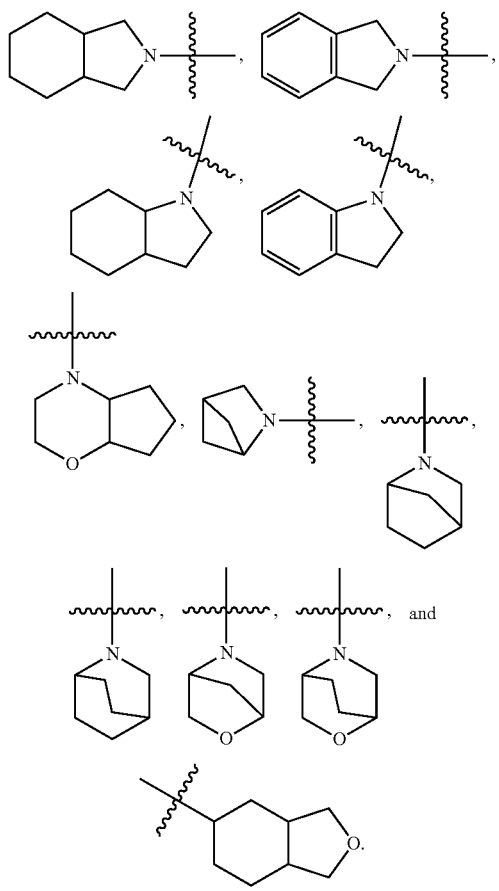

Unless otherwise drawn or clear from the context, the term "bicyclic heterocycle" includes cis and trans diastereomers. Non-limiting examples of chiral bicyclic heterocycles include:

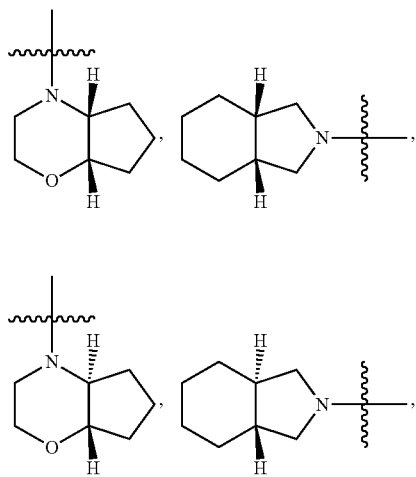

-continued

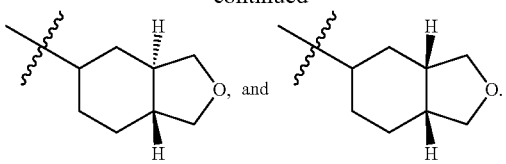

"Heteroaryl" refers to a stable monocyclic, bicyclic, or multicyclic aromatic ring which contains from 1 to 3, or in some embodiments from 1, 2, or 3 heteroatoms selected from N, O, S, B, and P (and typically selected from N, O, and S) with remaining ring atoms being carbon, or a stable bicyclic or tricyclic system containing at least one 5, 6, or 7 membered aromatic ring which contains from 1 to 3, or in some embodiments from 1 to 2, heteroatoms selected from N, O, S, B or P with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 or 6 ring atoms. In some embodiments bicyclic heteroaryl groups are 8- to 10-membered heteroaryl groups, that is, groups containing 8 or 10 ring atoms in which one 5, 6, or 7 member aromatic ring is fused to a second aromatic or non-aromatic ring wherein the point of attachment is the aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein. "Heteroaryloxy" is a heteroaryl group as described bound to the group it substituted via an oxygen, —O—, linker.

"Heterocycloalkyl" is a fully saturated heterocycle as defined herein. It may, for example, include 1, 2, 3, or 4 heteroatoms independently selected from N, S, O, Si and B with the remaining ring atoms being carbon. In a typical embodiment, nitrogen is the heteroatom. Monocyclic heterocycloalkyl groups typically have from 3 to about 8 ring atoms or from 4 to 6 ring atoms.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" is a derivative of the disclosed compound in which the parent compound is modified by making inorganic and organic, pharmaceutically acceptable, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include salts which are acceptable for human consumption and the quaternary ammonium salts of the parent compound formed, for example, from inorganic or organic acids. Examples of such salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_{1-4}$—COOH, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, acceptable for human consumption, and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, including but not limited to by modulation of the complement Factor D pathway or with a condition that is treatable with one of the compounds described herein. Typically the host is a human. A "patient" or "host" or "subject" also refers to for example, a mammal, primate (e.g., human), cows, sheep, goat, horse, dog, cat, rabbit, rat, mice, bird and the like.

A "prodrug" as used herein, means a compound which when administered to a host in vivo is converted into a parent drug. As used herein, the term "parent drug" means any of the presently described chemical compounds herein.

Prodrugs can be used to achieve any desired effect, including to enhance properties of the parent drug or to improve the pharmaceutic or pharmacokinetic properties of the parent, including to increase the half-life of the drug in vivo. Prodrug strategies provide choices in modulating the conditions for in vivo generation of the parent drug. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others. In certain embodiments, the prodrug renders the parent compound more lipophilic. In certain embodiments, a prodrug can be provided that has several prodrug moieties in linear, branched or cyclic manner. For example, nonlimiting embodiments include the use of a divalent linker moiety such as a dicarboxylic acid, amino acid, diamine, hydroxycarboxylic acid, hydroxyamine, dihydroxy compound, or other compound that has at least two functional groups that can link the parent molecule with another prodrug moiety, and is typically biodegradable in vivo. In some embodiments, 2, 3, 4, or 5 prodrug biodegradable moieties are covalently bound in sequence, branched or cyclic fashion to the parent compound. Nonlimiting examples of prodrugs according to the present invention are formed with:

i. a carboxylic acid on the parent drug and a hydroxylated prodrug moiety to form an ester;
ii. a carboxylic acid on the parent drug and an amine prodrug to form an amide;
iii. an amino on the parent drug and a carboxylic acid prodrug moiety to form an amide,
iv. an amino on the parent drug and a sulfonic acid to form a sulfonamide;
v. a sulfonic acid on the parent drug and an amino on the prodrug moiety to form a sulfonamide;
vi. a hydroxyl group on the parent drug and a carboxylic acid on the prodrug moiety to form an ester;
vii. a hydroxyl on the parent drug and a hydroxylated prodrug moiety to form an ether;
viii. a phosphonate on the parent drug and a hydroxylated prodrug moiety to form a phosphonate ester;
ix. a phosphoric acid on the parent drug and a hydroxylated prodrug moiety to form a phosphate ester;
x. a hydroxyl on the parent drug and a phosphonate on the prodrug to form a phosphonate ester;
xi. a hydroxyl on the parent drug and a phosphoric acid prodrug moiety to form a phosphate ester;
xii. a carboxylic acid on the parent drug and a prodrug of the structure HO—$(CH_2)_2$—O—($C_{2-24}$ aliphatic group), for example, HO—$(CH_2)_2$—O—($C_{2-24}$ alkyl group) to form an ester;
xiii. a carboxylic acid on the parent drug and a prodrug of the structure HO—$(CH_2)_2$—S—($C_{2-24}$ aliphatic group), for example, HO—$(CH_2)_2$—S—($C_{2-24}$ alkyl group) to form a thioester;
xiv. a hydroxyl on the parent drug and a prodrug of the structure HO—$(CH_2)_2$—O—($C_{2-24}$ aliphatic group), for example, HO—$(CH_2)_2$—O—($C_{2-24}$ alkyl group) to form an ether;
xv. a carboxylic acid on the parent drug and a prodrug of the structure HO—$(CH_2)_2$—S—($C_{2-24}$ aliphatic group), for example, HO—$(CH_2)_2$—S—($C_{2-24}$ alkyl group), to form a thioether; and
xvi. a carboxylic acid, oxime, hydrazide, hydrazone, amine or hydroxyl on the parent compound and a prodrug moiety that is a biodegradable polymer or oligomer including but not limited to polylactic acid, polylactide-co-glycolide, polyglycolide, polyethylene glycol, polyanhydride, polyester, polyimide or a peptide. An exemplary synthesis of Oxime linkages is provided in the paper published by Jin et. al. titled "Oxime Linkage: A Robust Tool for the Design of PH-Sensitive Polymeric Drug Carriers" in BioMacromolecules, 2011, 12(10), 3460-3468.

In one embodiment, a prodrug is provided by attaching a natural or non-natural amino acid to an appropriate functional moiety on the parent compound, for example, oxygen, nitrogen, or sulfur, and typically oxygen or nitrogen, usually in a manner such that the amino acid can be cleaved in vivo to provide the parent drug. The amino acid can be used alone or covalently linked (straight, branched or cyclic) to one or more other prodrug moieties to modify the parent drug to achieve the desired performance, such as increased half-life, lipophilicity, or other drug delivery or pharmacokinetic properties. The amino acid can be any compound with an amino group and a carboxylic acid, which includes an aliphatic amino acid, alkyl amino acid, aromatic amino acid, heteroaliphatic amino acid, heteroalkyl amino acid, or heterocyclic amino acid or heteroaryl amino acid.

"Providing a compound with at least one additional active agent," for example, in one embodiment can mean that the compound and the additional active agent(s) are provided simultaneously in a single dosage form, provided concomitantly in separate dosage forms, or provided in separate dosage forms for administration. In one embodiment, the compound administrations are separated by some amount of time that is within the time in which both the compound and the at least one additional active agent are within the blood stream of a patient. In certain embodiments the compound and the additional active agent need not be prescribed for a patient by the same medical care worker. In certain embodiments the additional active agent or agents need not require a prescription. Administration of the compound or the at least one additional active agent can occur via any appropriate route, for example, oral tablets, oral capsules, oral liquids, inhalation, injection, suppositories, parenteral, sublingual, buccal, intravenous, intraaortal, transdermal, polymeric controlled delivery, non-polymeric controlled delivery, nano or microparticles, liposomes, and/or topical contact. In one embodiment, the instructions for administration in a form of combination therapy is provided in the drug labeling.

A "therapeutically effective amount" of a pharmaceutical composition/combination of this invention means an amount effective, when administered to a host, provides a therapeutic benefit such as an amelioration of symptoms or reduction or diminution of the disease itself. In one embodiment, a therapeutically effective amount is an amount sufficient to prevent a significant increase or will significantly reduce the detectable level of complement Factor D in the patient's blood, serum, or tissues.

N-Oxides

In certain embodiments, any of the active compounds can be provided in its N-oxide form to a patient in need thereof. In one embodiment, an N-oxide of an active compound or a precursor of the active compound is used in a manufacturing scheme. In yet another embodiment, the N-oxide is a metabolite of administration of one of the active compounds herein, and may have independent activity. The N-oxide can be formed by treating the compound of interest with an oxidizing agent, for example a suitable peroxyacid or peroxide, to generate an N-oxide compound. For example, a heteroaryl group, for example a pyridyl group, can be treated with an oxidizing agent such as sodium percarbonate in the presence of a rhenium-based catalyst under mild reaction conditions to generate an N-oxide compound. A person skilled in the art will understand that appropriate protecting groups may be necessary to carry out the chemistry, See, Jain, S. L. et al., "Rhenium-Catalyzed Highly Efficient Oxidations of Tertiary Nitrogen Compounds to N-Oxides Using Sodium Percarbonate as Oxygen Source, Synlett, 2261-2663, 2006.

In one embodiment the N-oxide is in the A-Ring. In one embodiment the N-oxide is in the B-Ring. In one embodiment the N-oxide is on the $R^{32}$ group.

In other aspects of the present invention, any of the active compounds with a sulfur can be provided in its sulfoxide or sulfone form to a patient in need thereof. In a different embodiment, a sulfoxide or sulfone of one of the active compounds or a precursor of the active compound is used in a manufacturing scheme. A sulfur atom in a selected compound as described herein can be oxidized to form a sulfoxide

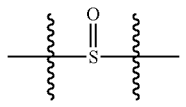 [SMILES: *S(*)=O]

or a sulfone

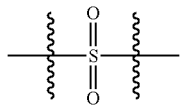 [SMILES: *S(*)(=O)=O]

using known methods. For example, the compound 1,3,5-triazo-2,4,6-triphosphorine-2,2,4,4,6,6-tetrachloride (TAPC) is an efficient promoter for the oxidation of sulfides to sulfoxides. See, Bahrami, M. et al., "TAPC-Promoted Oxidation of sulfides and Deoxygenation of Sulfoxides", J. Org. Chem., 75, 6208-6213 (2010). Oxidation of sulfides with 30% hydrogen peroxide catalyzed by tantalum carbide provides sulfoxides in high yields, see, Kirihara, A., et al., "Tantalum Carbide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Sulfides can be oxidized to sulfones using, for example, niobium carbide as the catalyst, see, Kirihara, A., et al., "Tantalum Cardide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Urea-hydrogen peroxide adduct is a stable inexpensive and easily handled reagent for the oxidation of sulfides to sulfones, see Varma, R. S. and Naicker, K. P., "The Urea-Hydrogen Peroxide Complex: Solid-State Oxidative Protocols for Hydroxylated Aldehydes and Ketones (Dakin Reaction), Nitriles, Sulfides, and Nitrogen Heterocycles", Org. Lett, 1, 189-191 (1999). One skilled in the art will appreciate that other heteroatoms, such as nitrogen, may need to be protected and then deprotected while carrying out the oxidation of a sulfur atom to produce the desired compound.

Embodiments of Formula I

In one embodiment, the compound of Formula I is selected from:

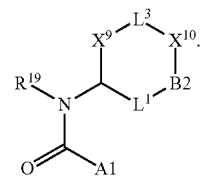

In one embodiment, the compound of Formula I is selected from:

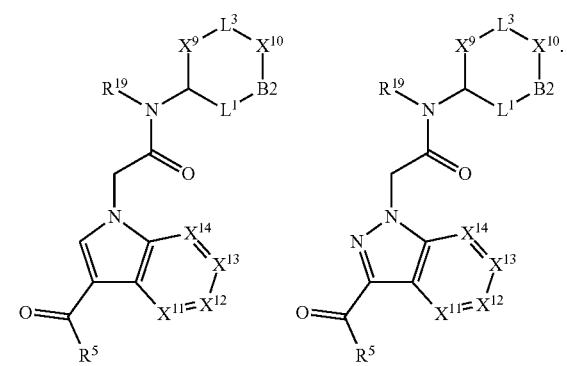

and

In one embodiment, the compound of Formula I selected from:

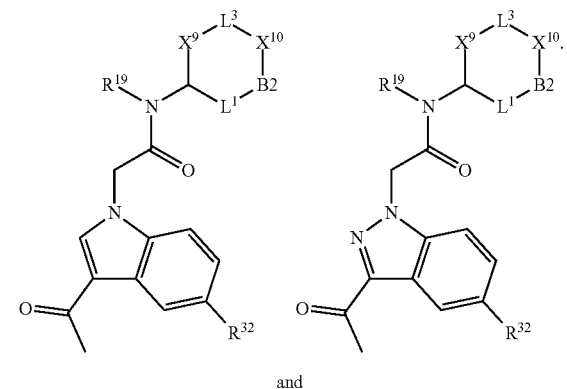

and

In one embodiment, the compound of Formula I is selected from:

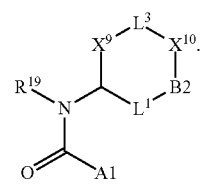

In one embodiment, the compound of Formula I selected from:
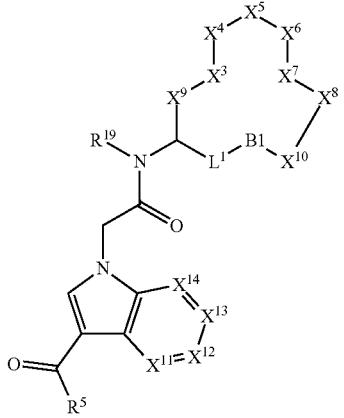
and
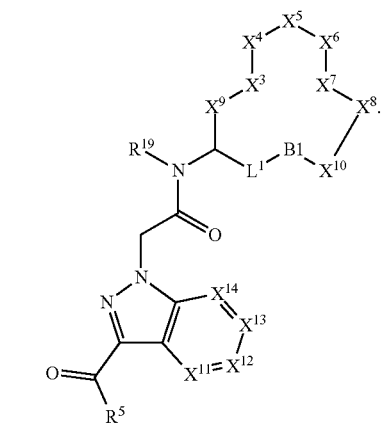
In one embodiment, the compound of Formula I selected from:
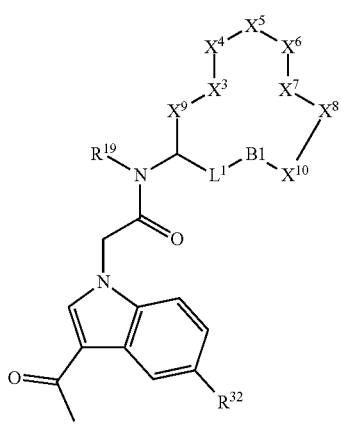
and
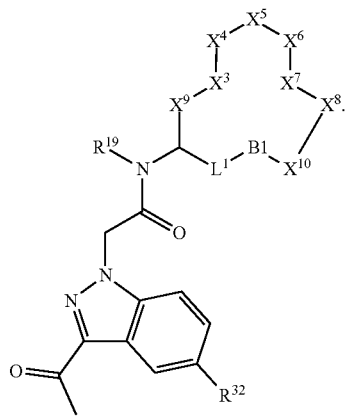
In certain embodiments, the compound of Formula I is selected from:
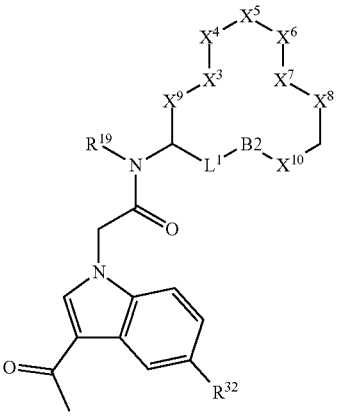
and
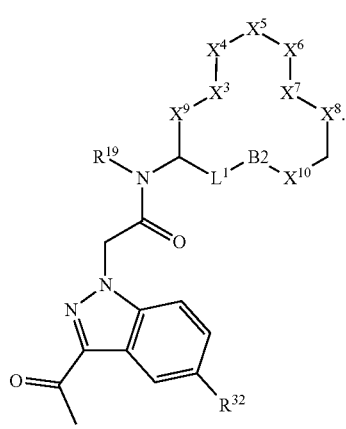
In one embodiment, the compound of Formula I is selected from:

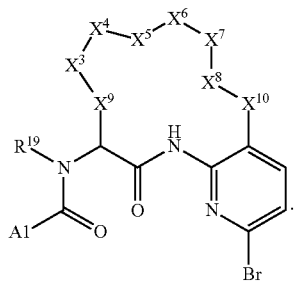
In one embodiment, the compound of Formula I is selected from:
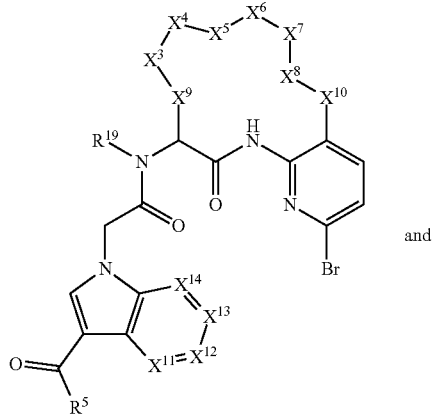
In one embodiment, the compound of Formula I is selected from:
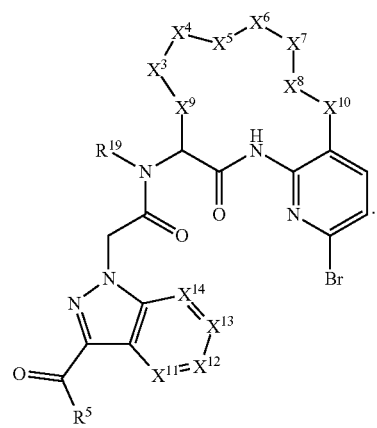
In one embodiment, the compound of Formula I is selected from:
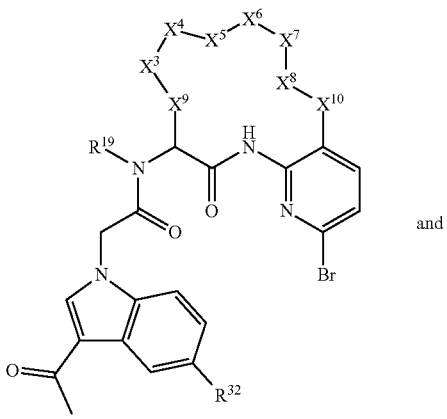
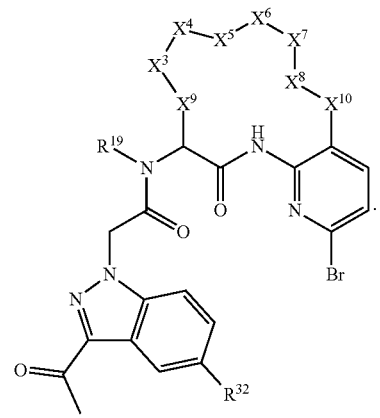
In one embodiment, the compound of Formula I is selected from:
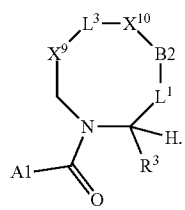
In one embodiment, the compound of Formula I is selected from:
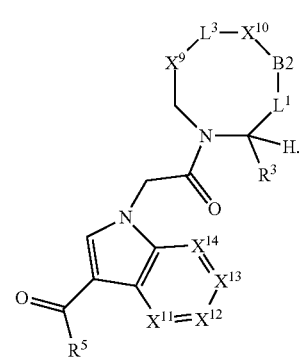

-continued
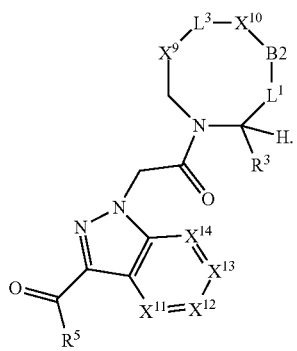
In one embodiment, the compound of Formula I is selected from:
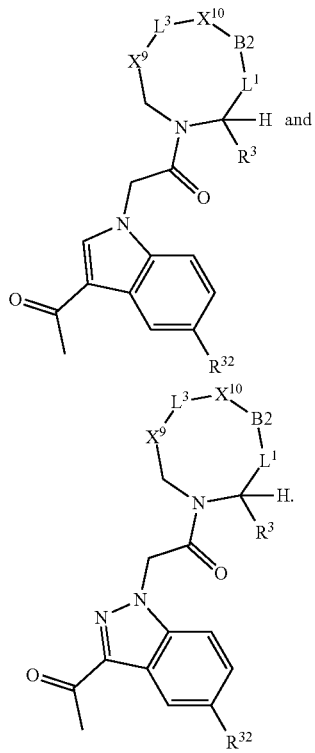
In one embodiment, the compound of Formula I is selected from:
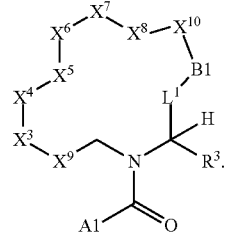
In an alternate embodiment, the compound of Formula I selected from:
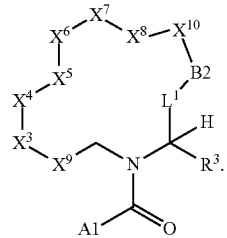
In one embodiment, the compound of Formula I is selected from:
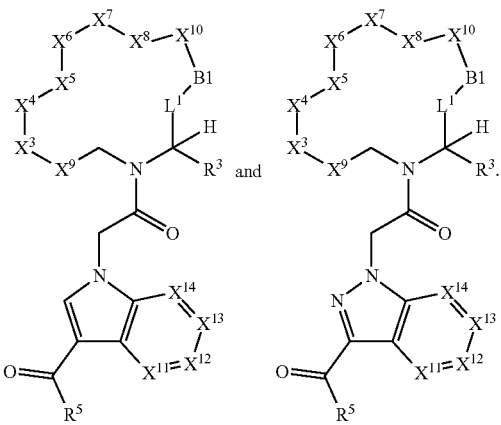
In one embodiment, the compound of Formula I is selected from:
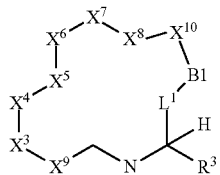
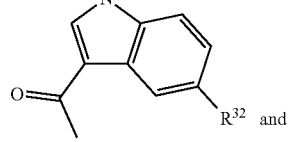

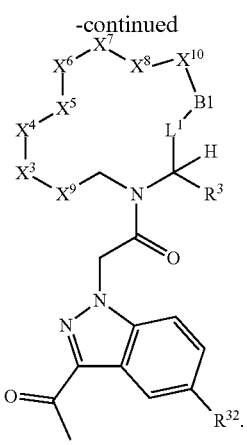
In certain embodiments, the compound of Formula I is selected from:
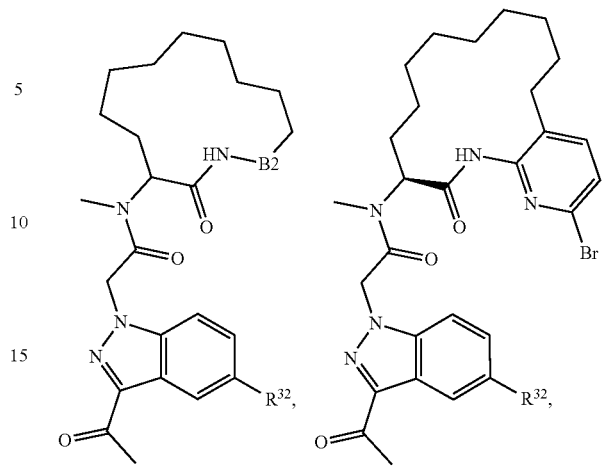
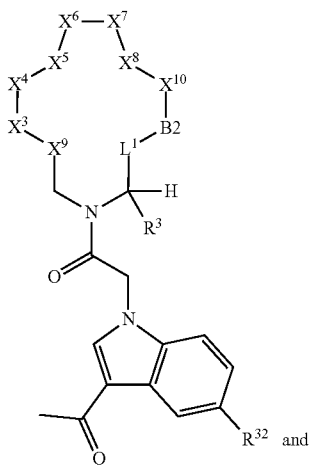
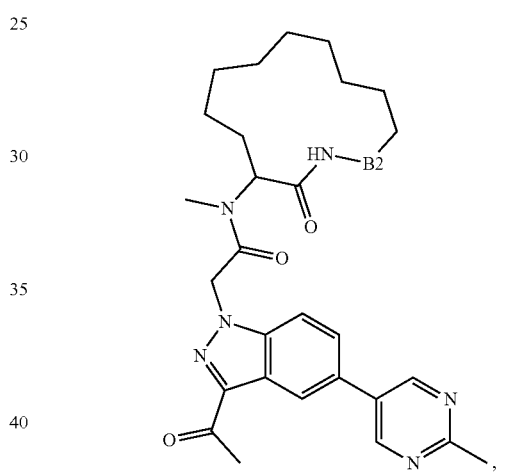
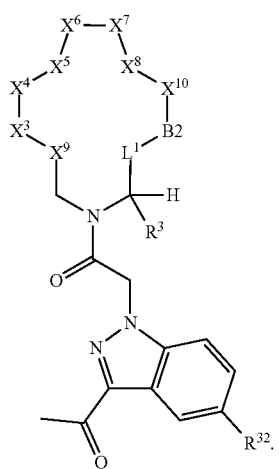
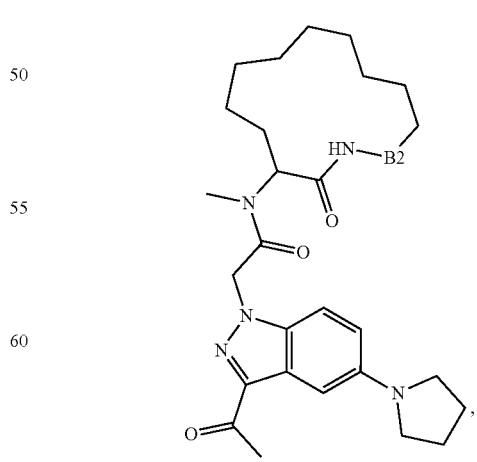
In one embodiment, the compound of Formula I is selected from:

41
-continued
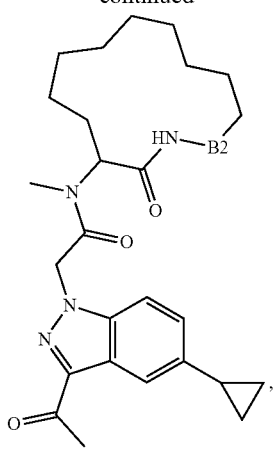
42
-continued
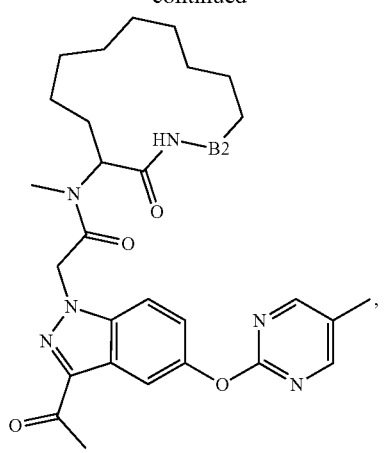
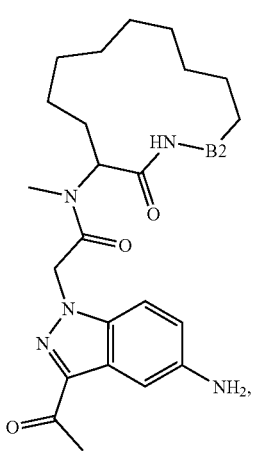
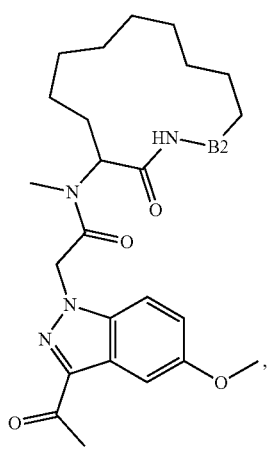
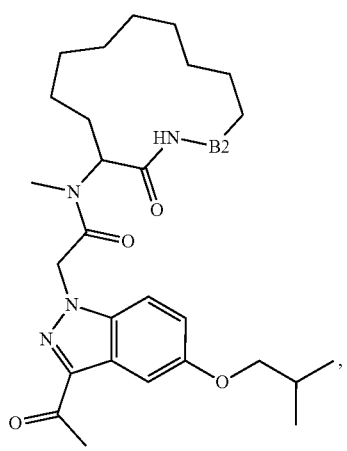

-continued
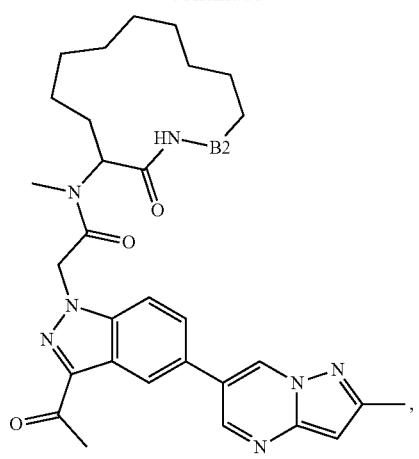
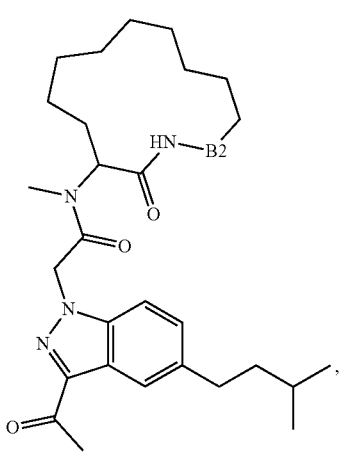
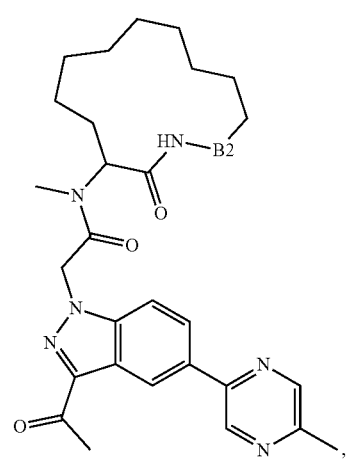
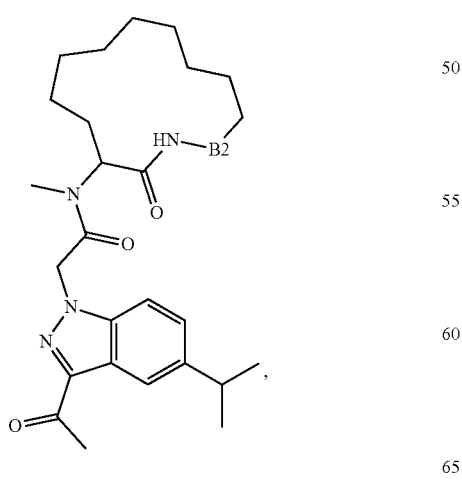
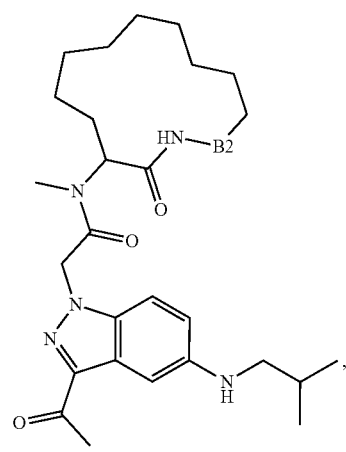

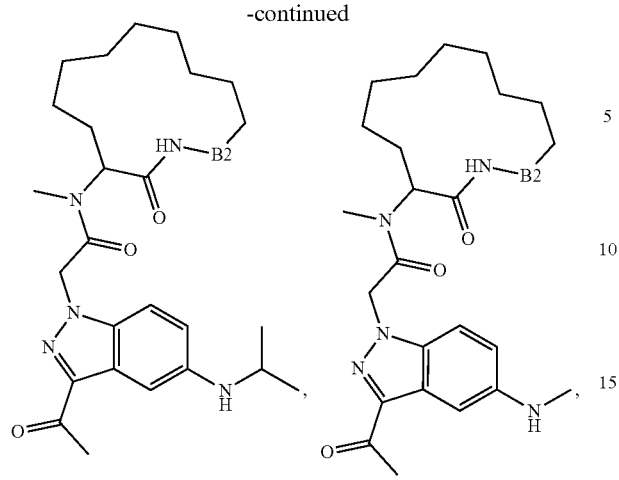
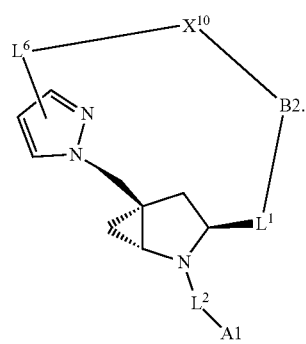
In one embodiment the compound of Formula I is selected from:
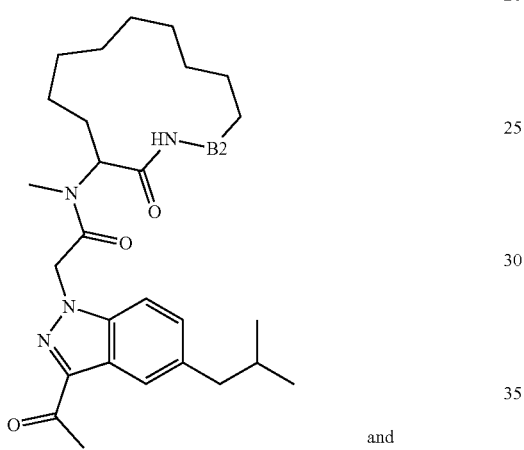
and
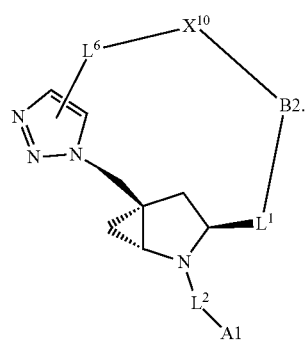
In one embodiment the compound of Formula I is selected from:
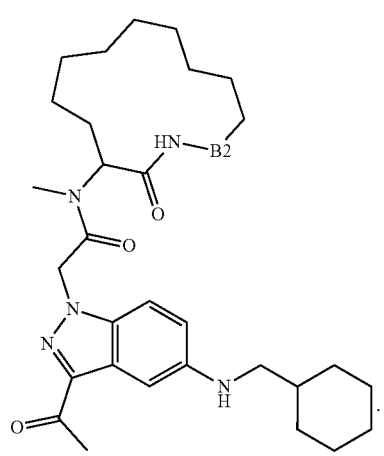
In the below embodiments $L^6$ is
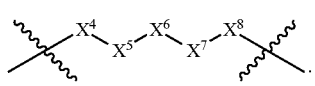
In one embodiment the compound of Formula I is selected from:
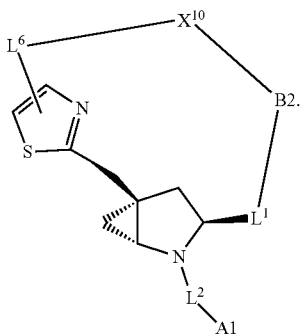
In one embodiment the compound of Formula I is selected from:

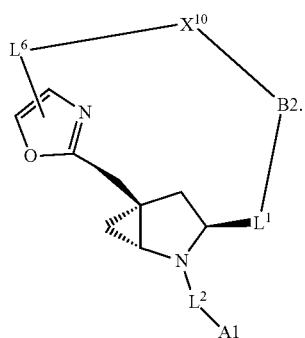
In one embodiment the compound of Formula I is selected from:
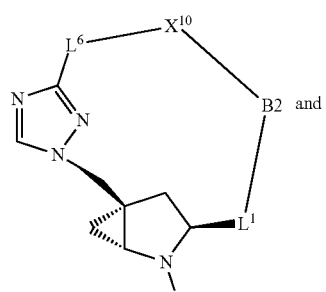
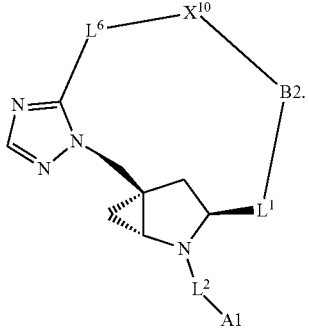
In one embodiment the compound of Formula I is selected from:
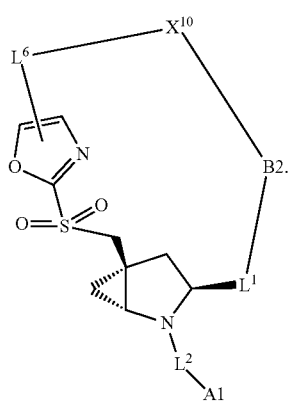
In one embodiment the compound of Formula I is selected from:
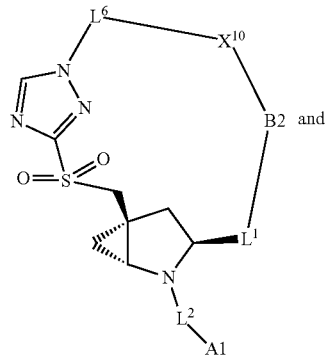
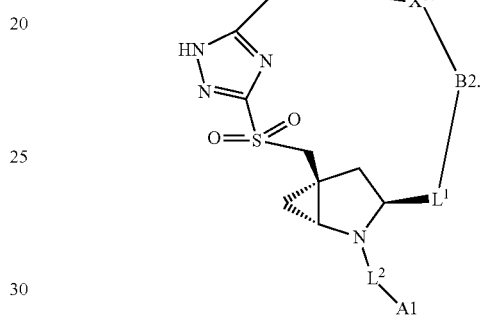
In one embodiment the compound of Formula I is selected from:
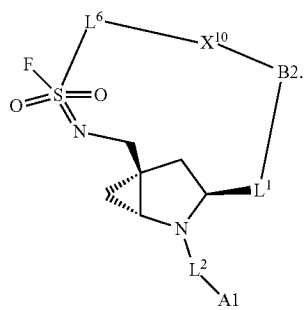
In one embodiment the compound of Formula I is selected from:
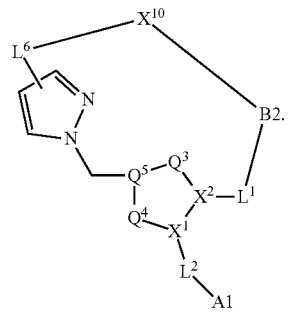

In one embodiment the compound of Formula I is selected from:

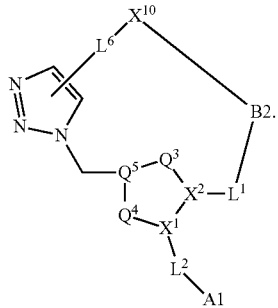

In one embodiment the compound of Formula I is selected from:

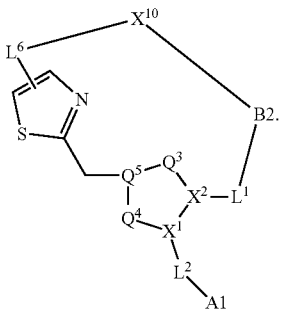

In one embodiment the compound of Formula I is selected from:

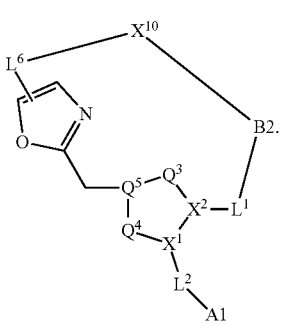

In one embodiment the compound of Formula I is selected from:

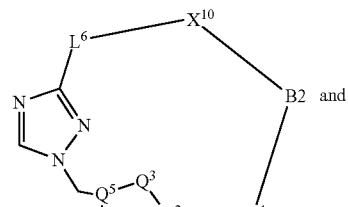

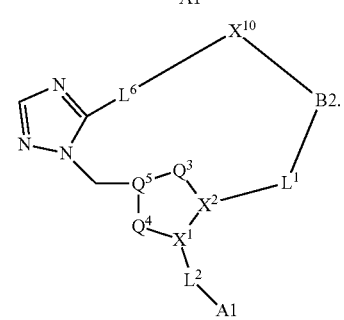

In one embodiment the compound of Formula I is selected from:

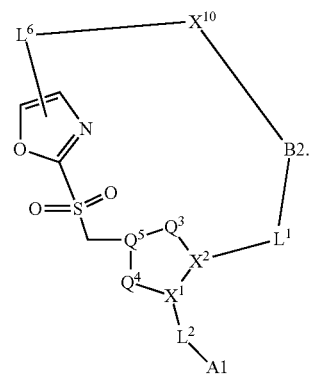

In one embodiment the compound of Formula I is selected from:

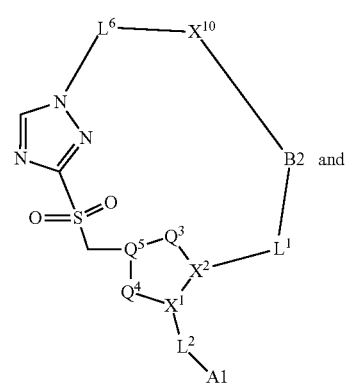

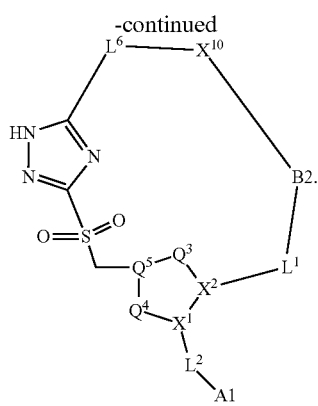

In one embodiment the compound of Formula I is selected from:

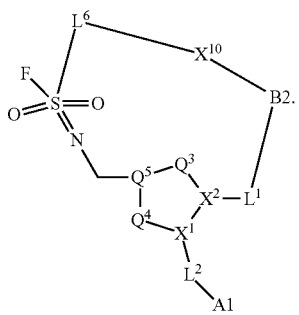

In one embodiment the compound of Formula I is selected from:

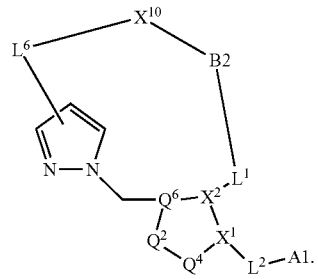

In one embodiment the compound of Formula I is selected from:

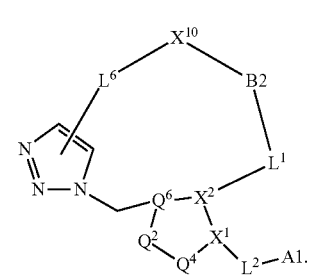

In one embodiment the compound of Formula I is selected from:

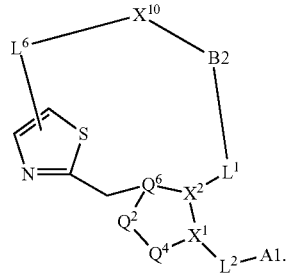

In one embodiment the compound of Formula I is selected from:

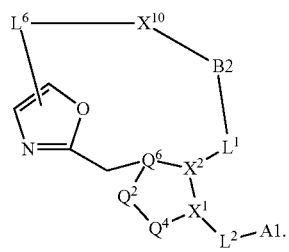

In one embodiment the compound of Formula I is selected from:

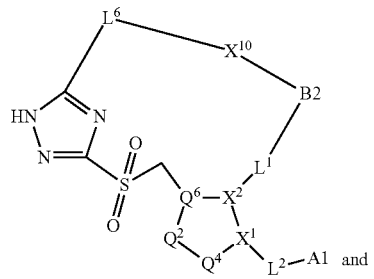

In one embodiment the compound of Formula I is selected from:

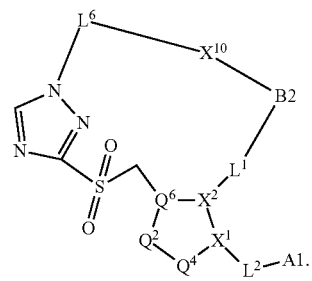

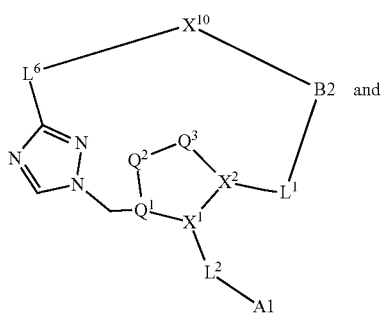

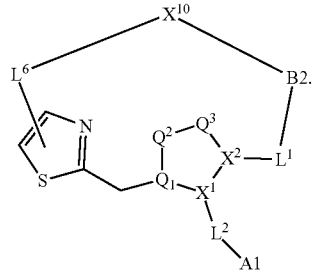

In one embodiment the compound of Formula I is selected from:

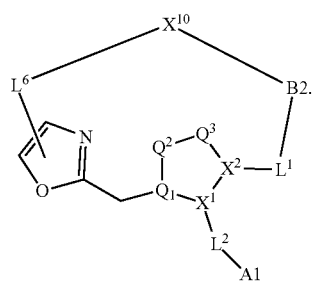

In one embodiment the compound of Formula I is selected from:

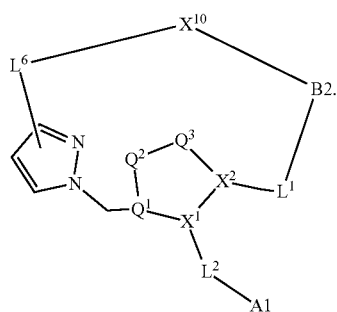

In one embodiment the compound of Formula I is selected from:

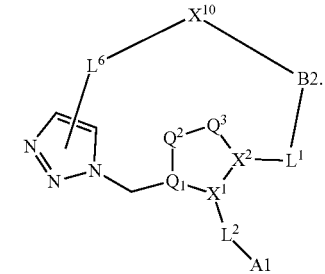

In one embodiment the compound of Formula I is selected from:

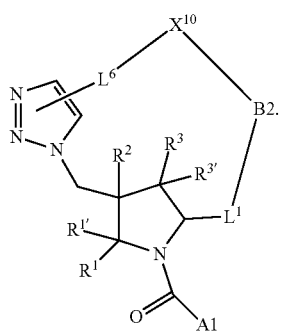

In one embodiment the compound of Formula I is selected from:


In one embodiment the compound of Formula I is selected from:

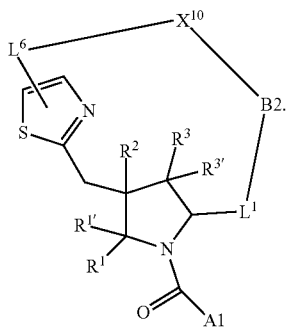
In one embodiment the compound of Formula I is selected from:
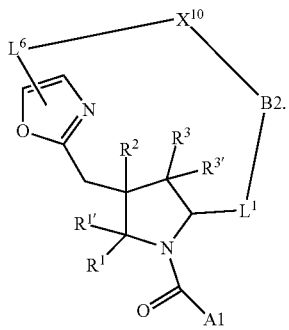
In one embodiment the compound of Formula I is selected from:
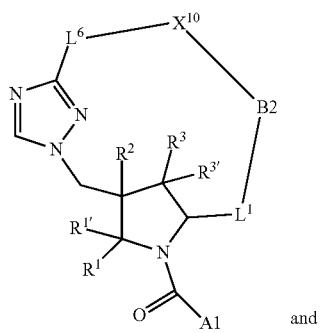
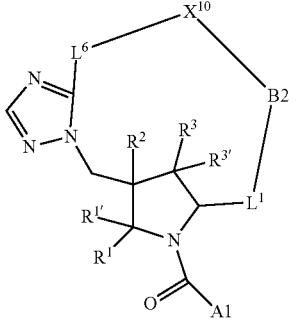
In one embodiment the compound of Formula I is selected from:
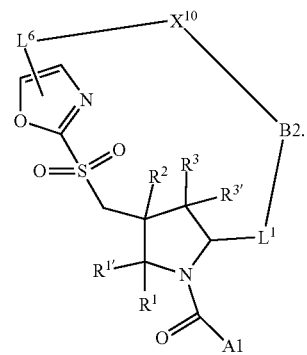
In one embodiment the compound of Formula I is selected from:
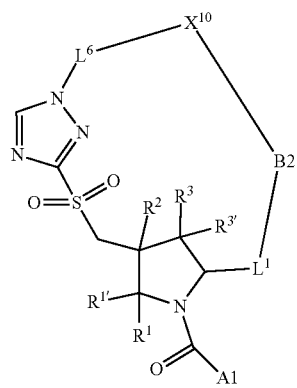  and
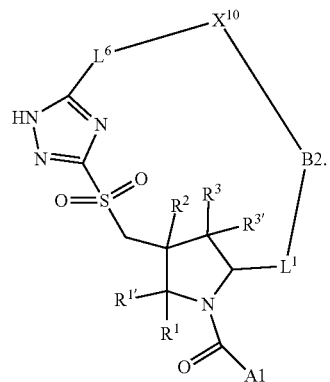
In one embodiment the compound of Formula I is selected from:

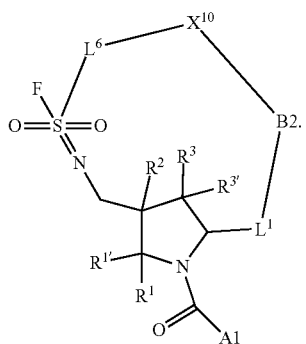

Embodiments of Formula II

In one embodiment, the compound of Formula II is selected from:

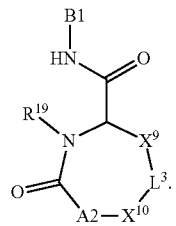

In one embodiment, the compound of Formula II is selected from:

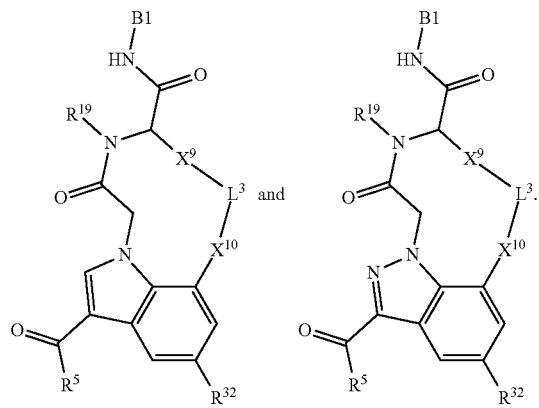

In one embodiment, the compound of Formula II is selected from:

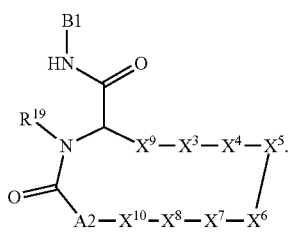

In one embodiment, the compound of Formula II is selected from:

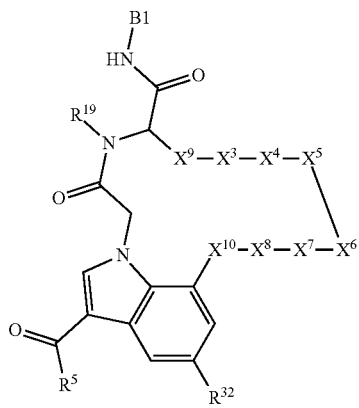

In one embodiment, the compound of Formula II is selected from:

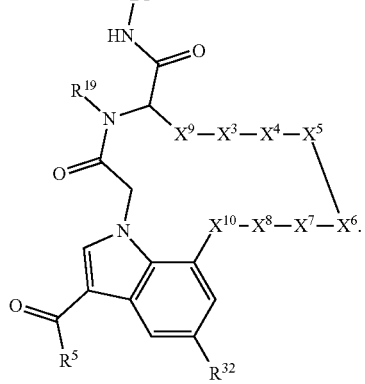

In one embodiment, the compound of Formula II is selected from:

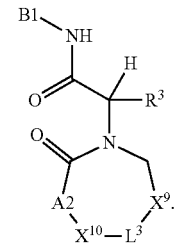

In one embodiment, the compound of Formula II is selected from:

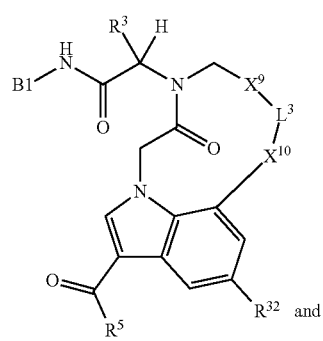

and

-continued
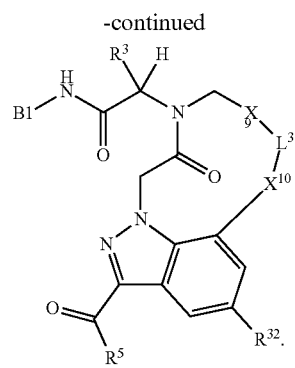
In one embodiment, the compound of Formula II is selected from:
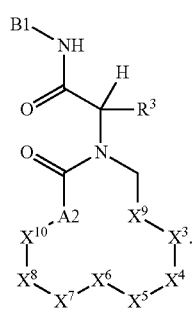
In one embodiment, the compound of Formula II is selected from:
In one embodiment, the compound of Formula II is selected from:
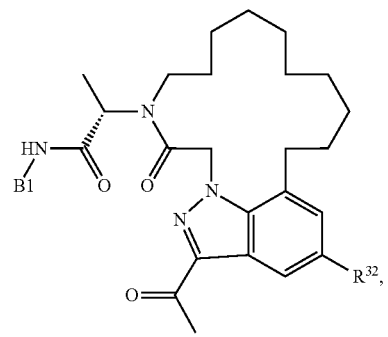
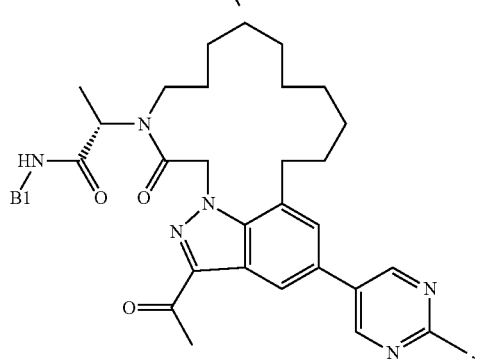
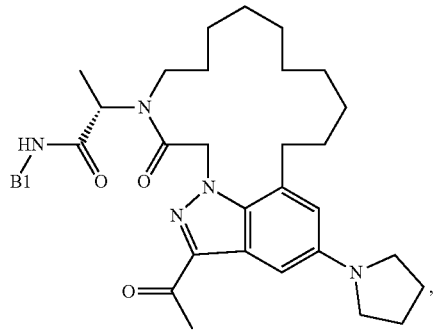
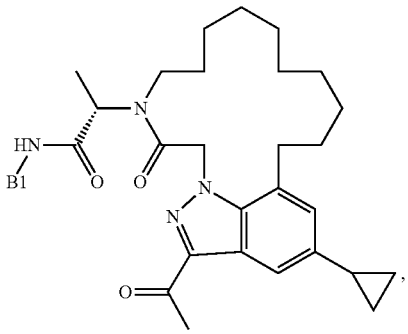
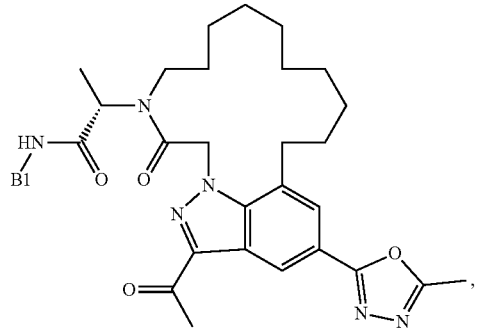

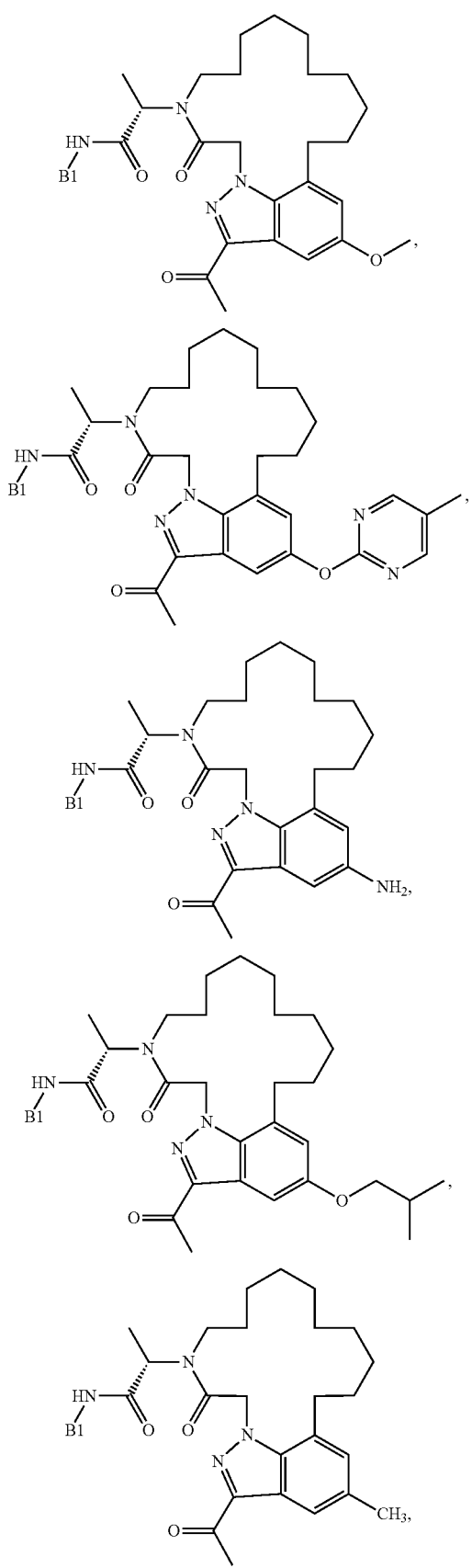
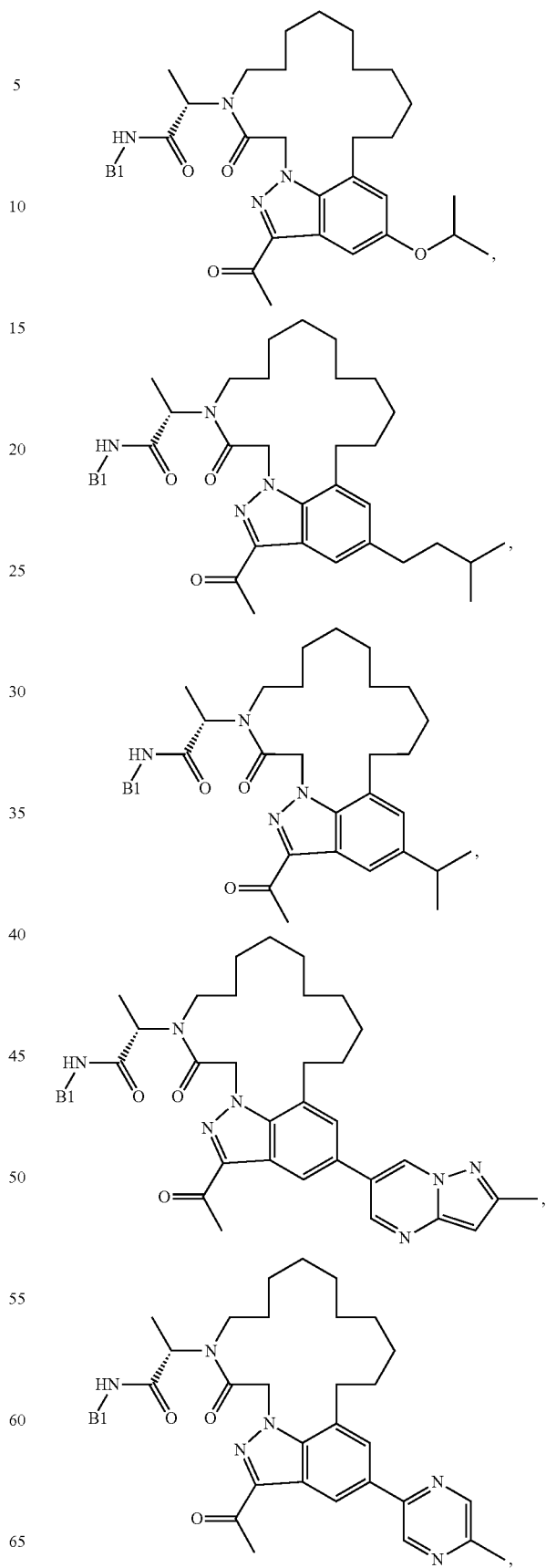

63
-continued
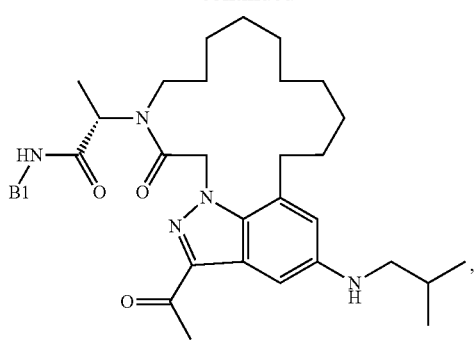
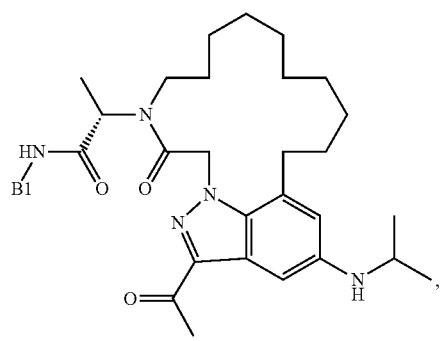
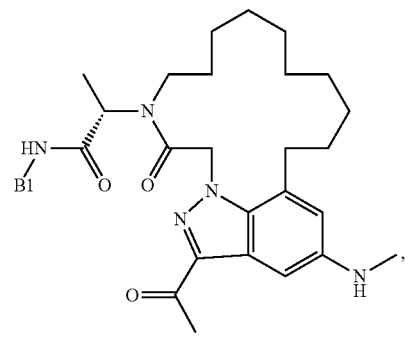
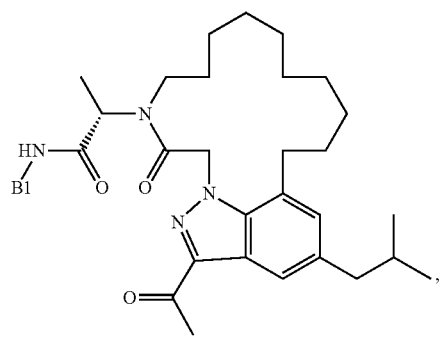
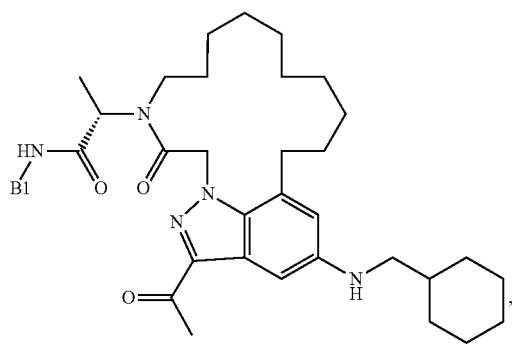
64
-continued
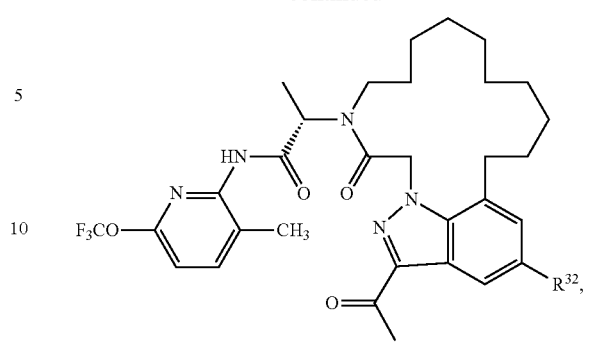
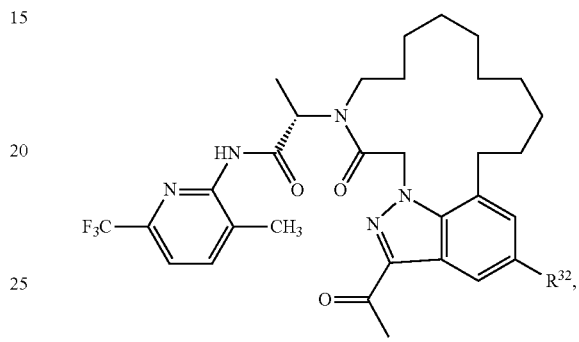
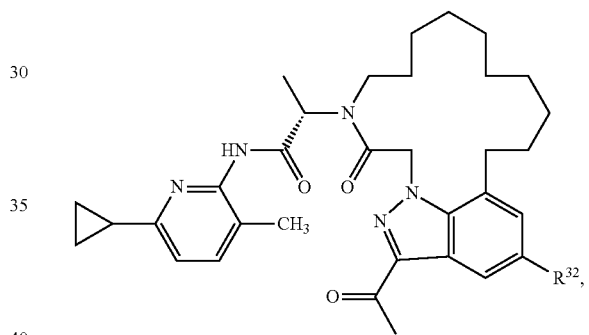
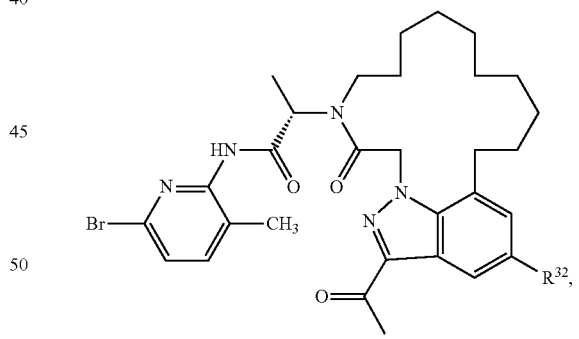
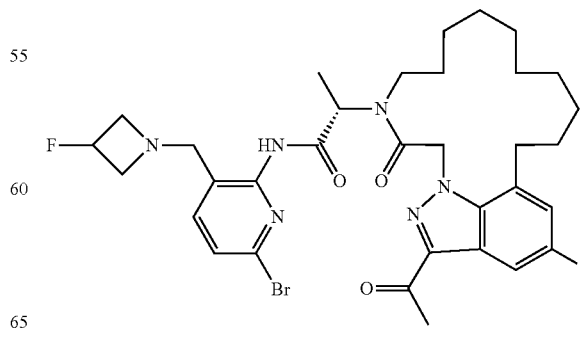

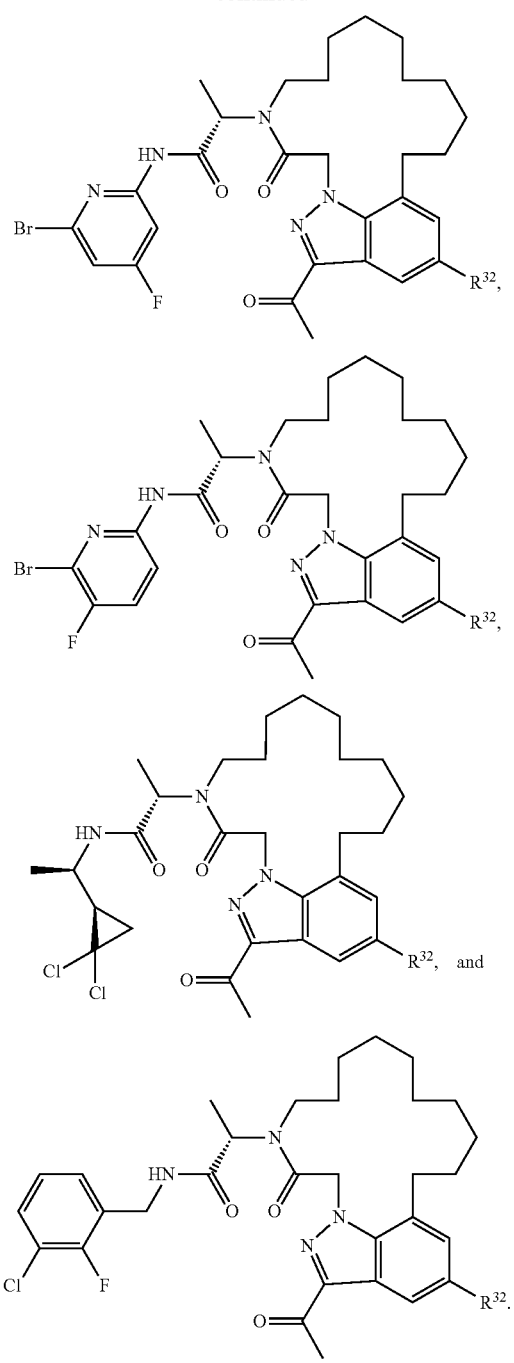
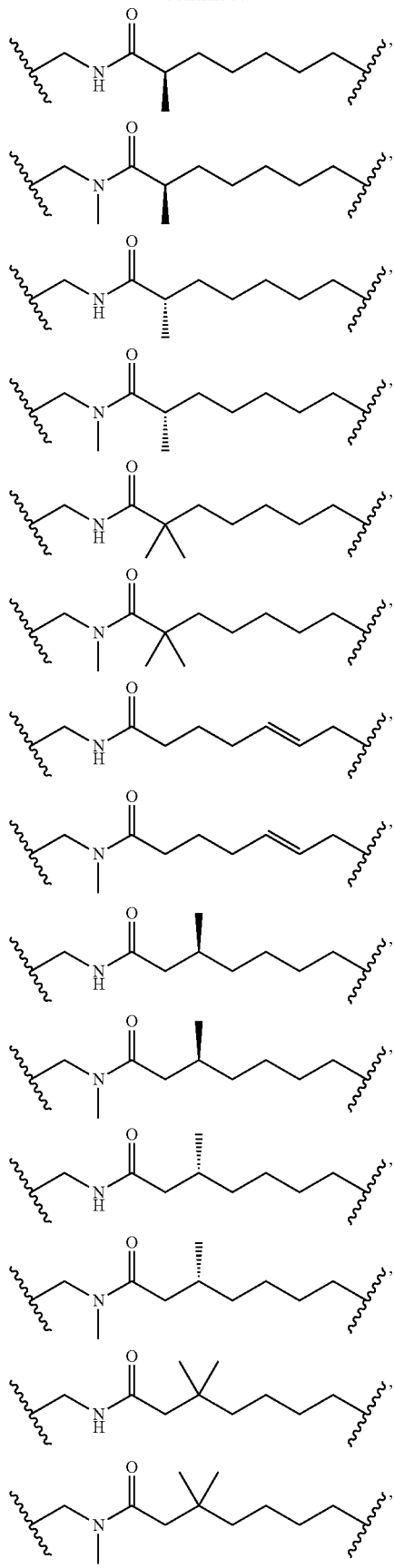
In one embodiment, —X⁹-L³-X¹⁰— is selected from:

-continued
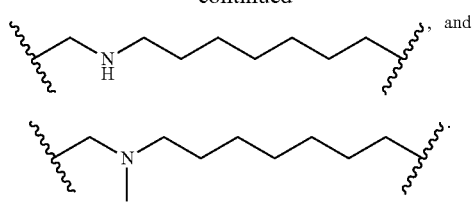
In one embodiment, —X⁹-L³-X¹⁰— is selected from:
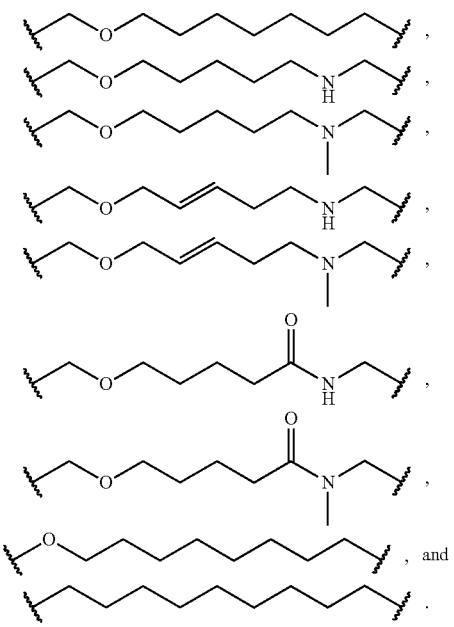
In one embodiment, R³² is selected from:
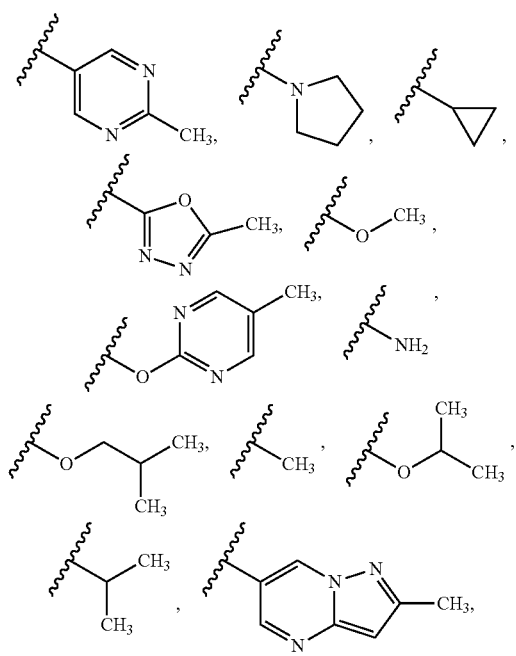
-continued
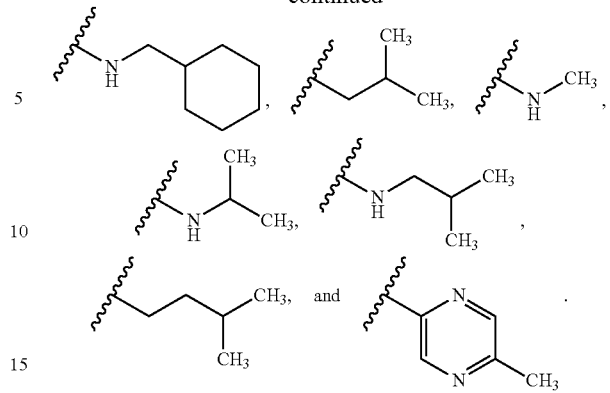
In one embodiment, B1 is selected from:
In one embodiment, the compound of Formula II is selected from:

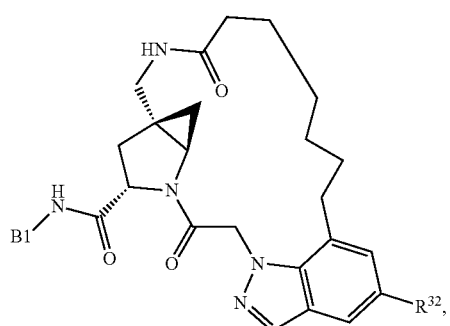
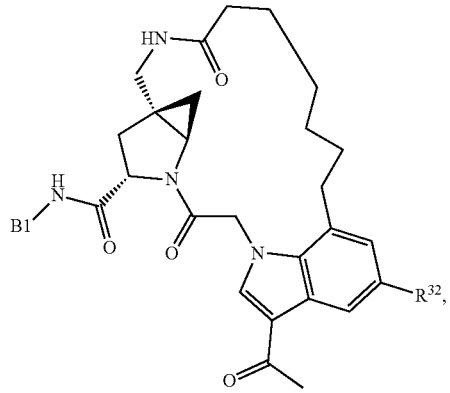
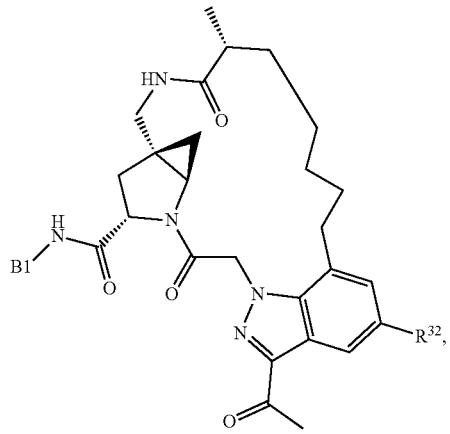
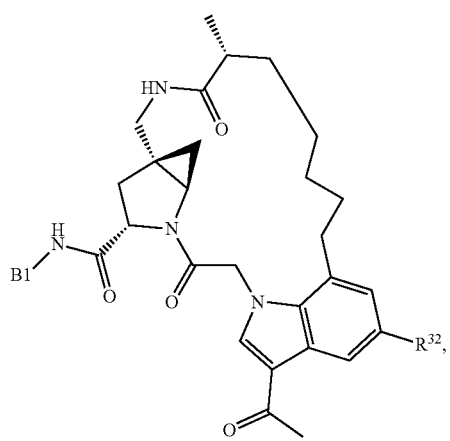
-continued
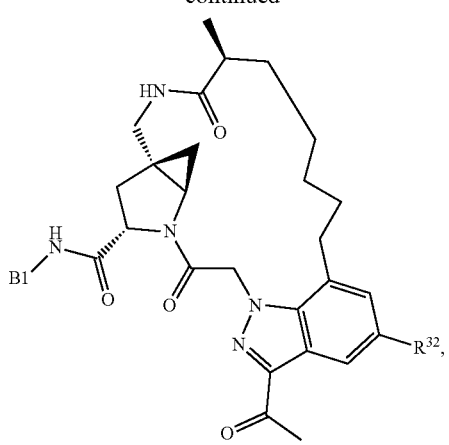
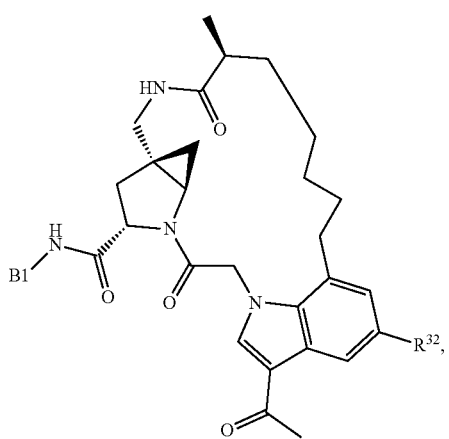
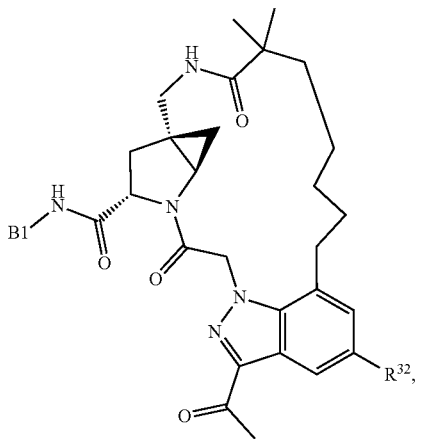

71
-continued
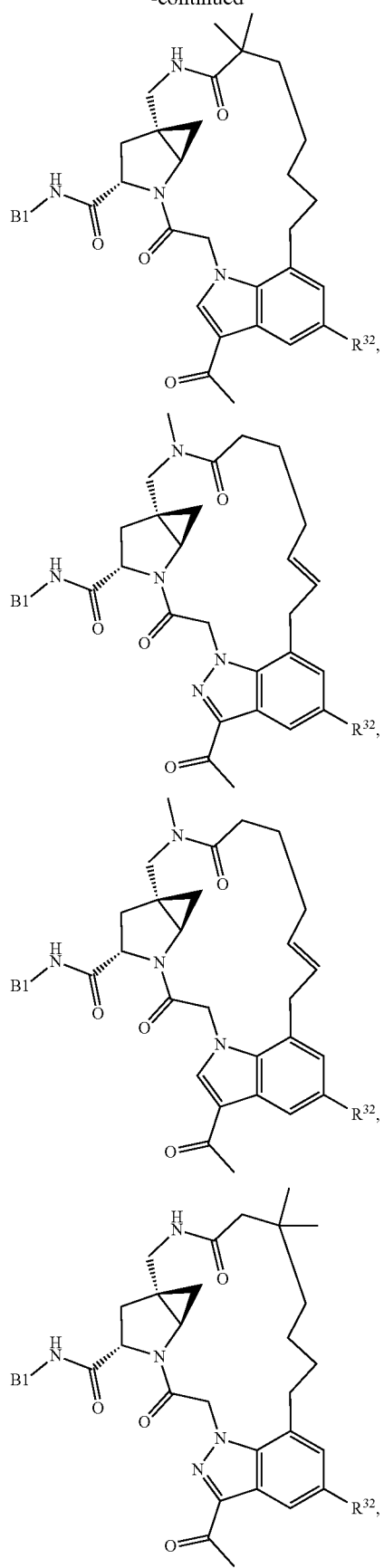
72
-continued
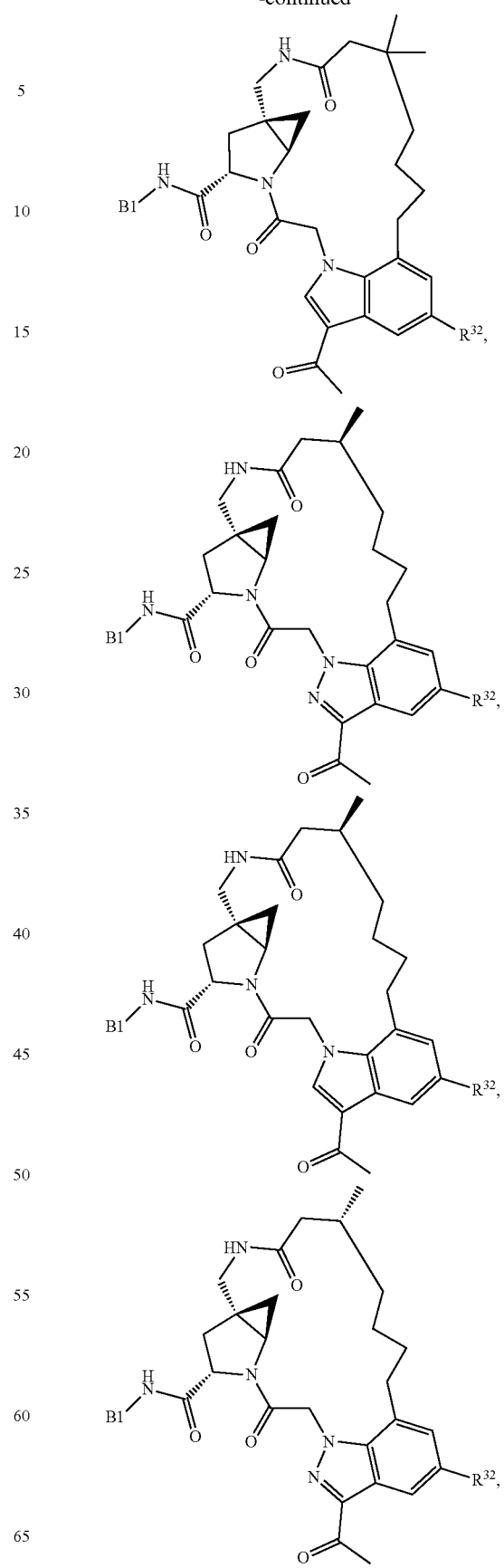

-continued
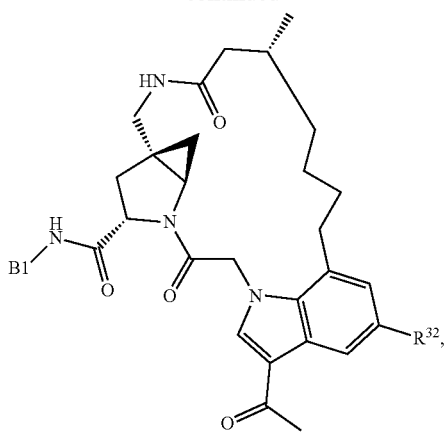
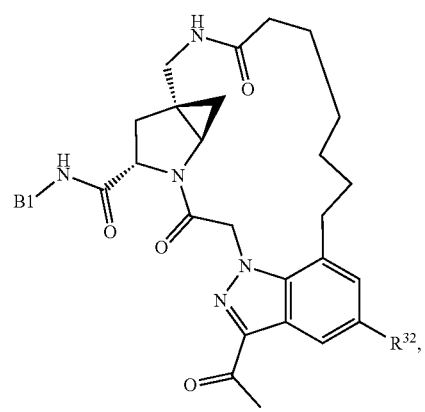
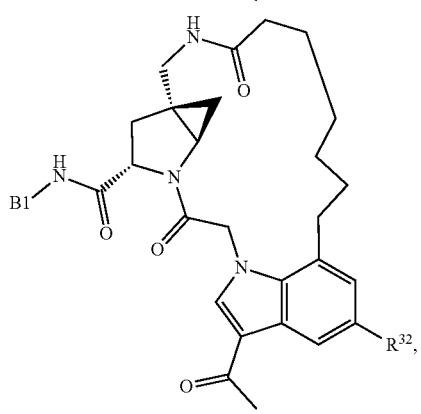
-continued
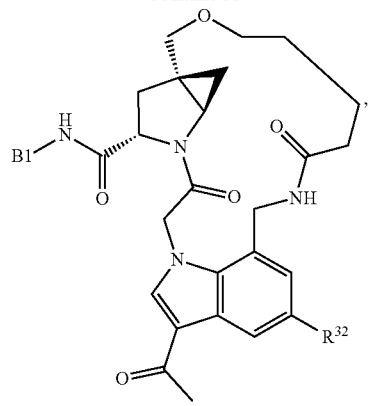
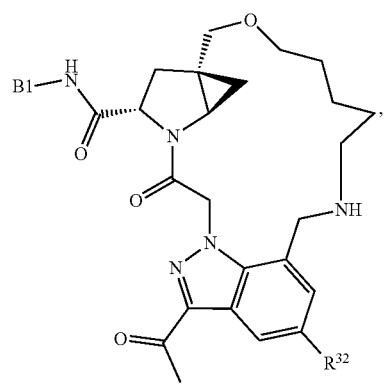
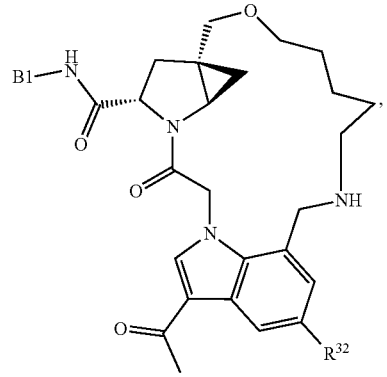
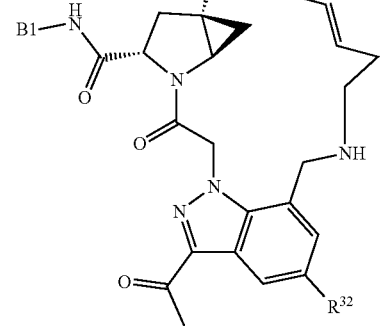

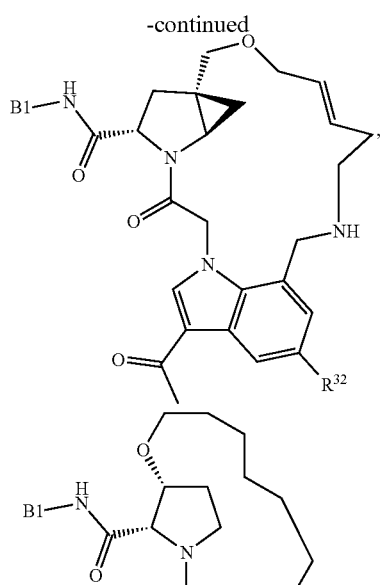
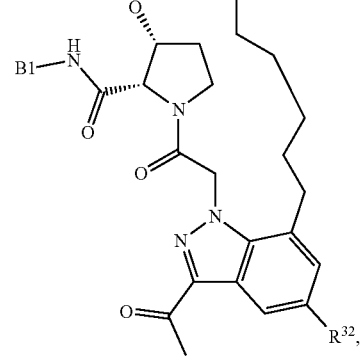
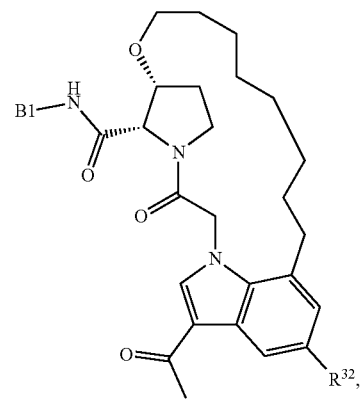
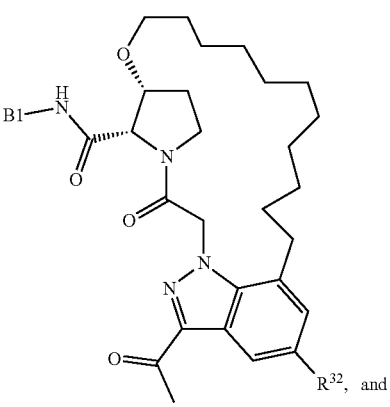
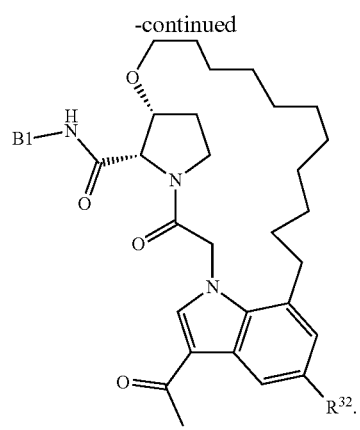
In one embodiment, the compound of Formula II is selected from:
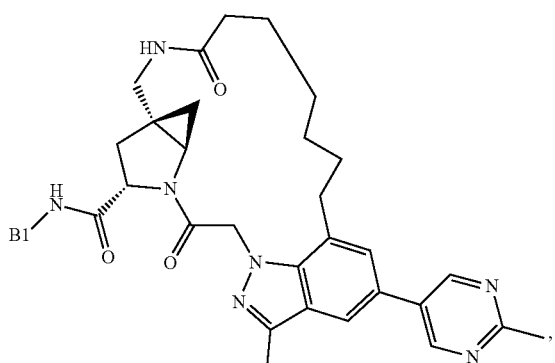
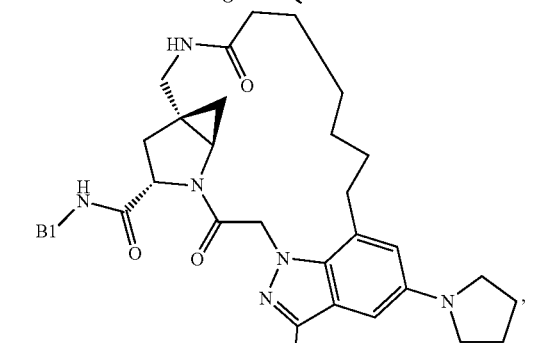
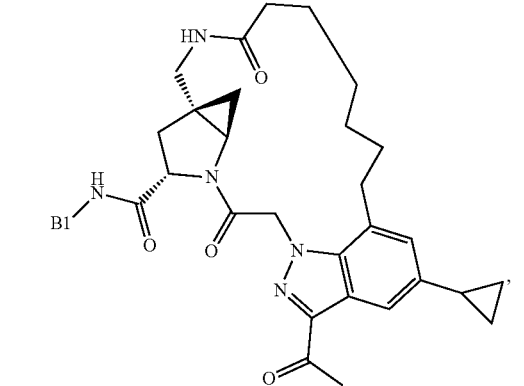

-continued
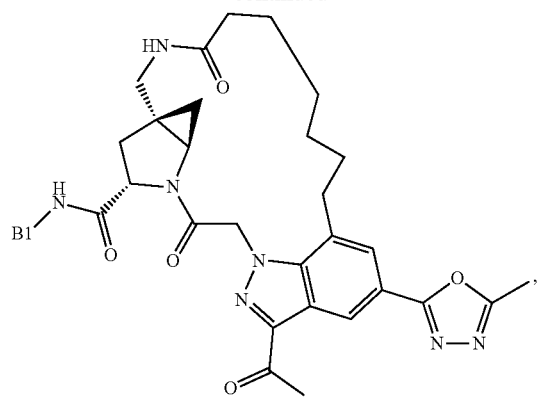
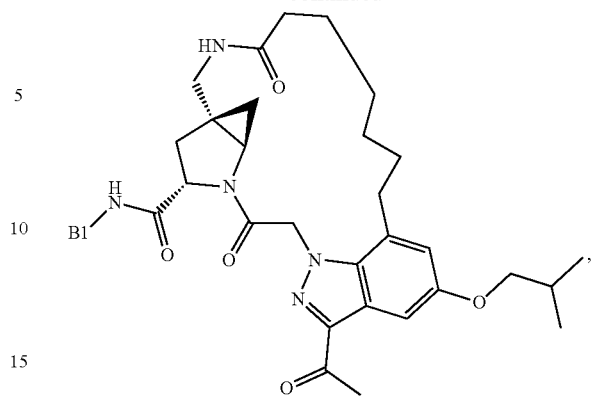
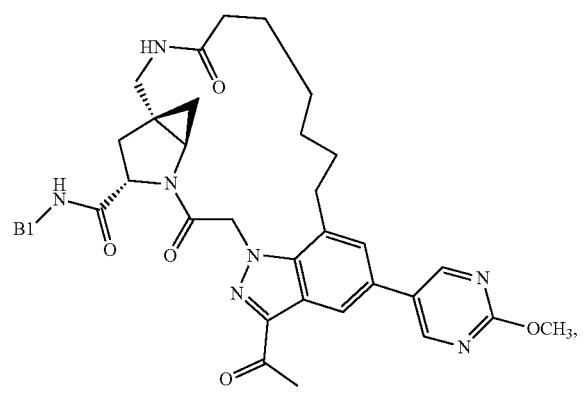
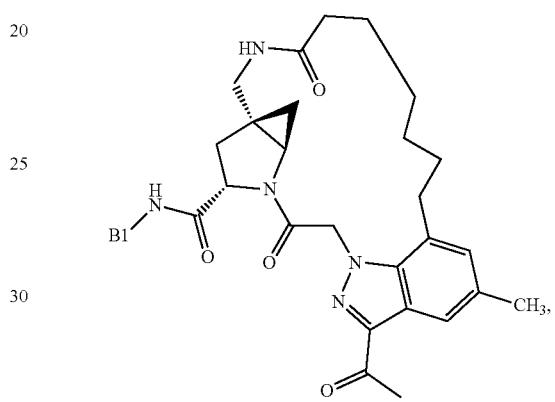
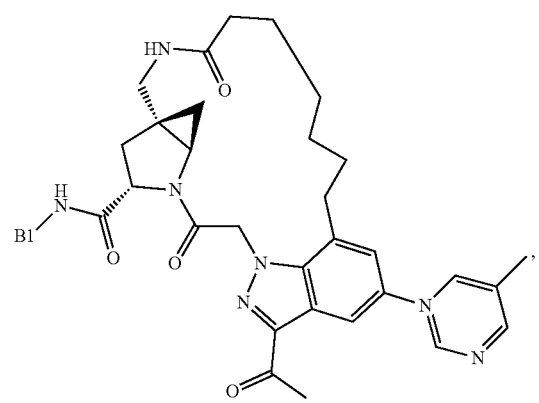
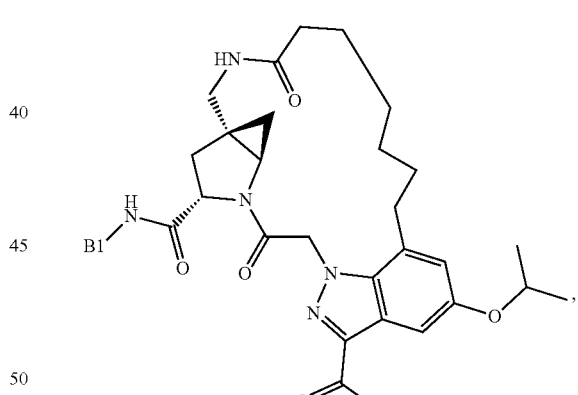
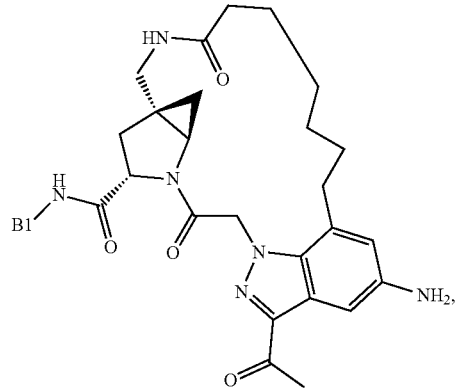
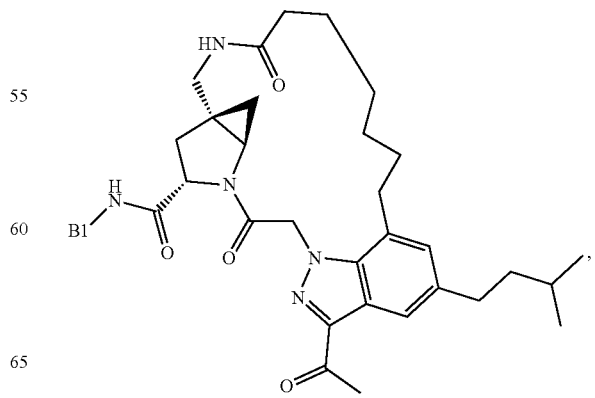

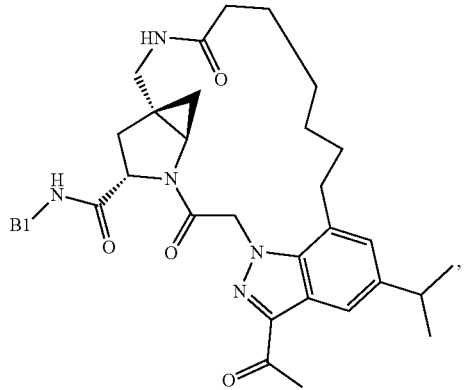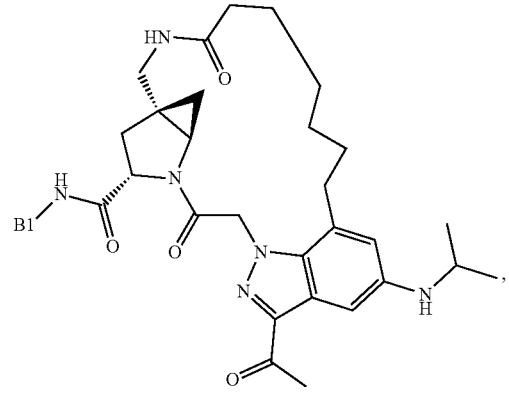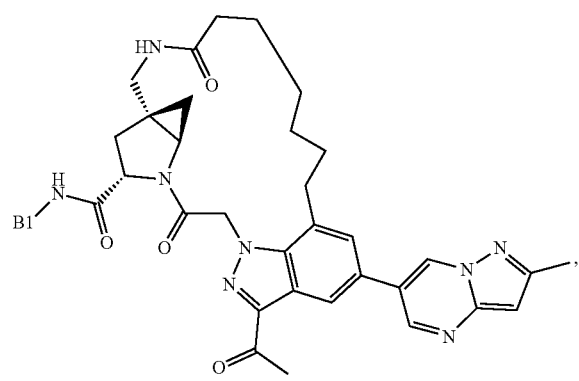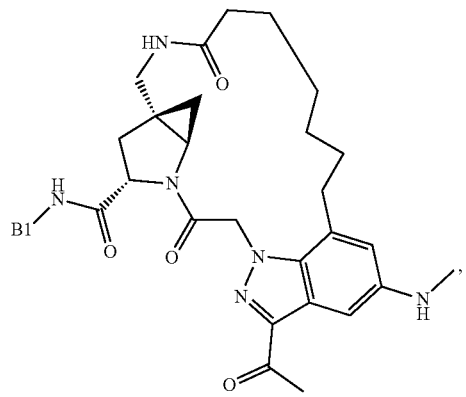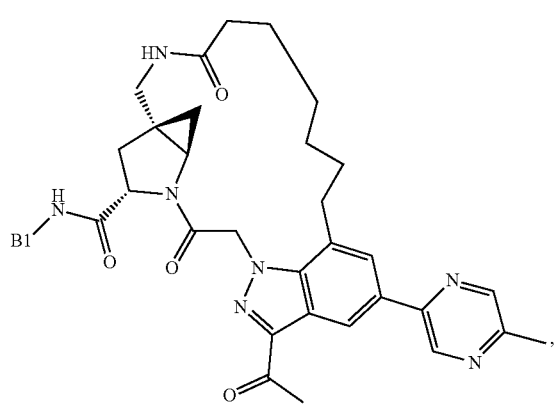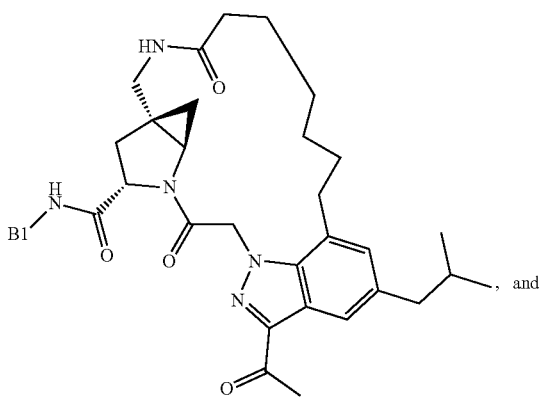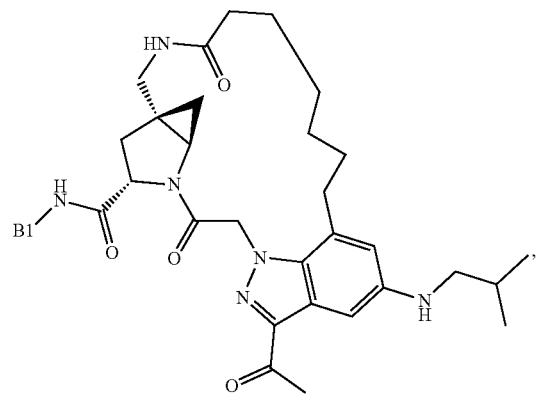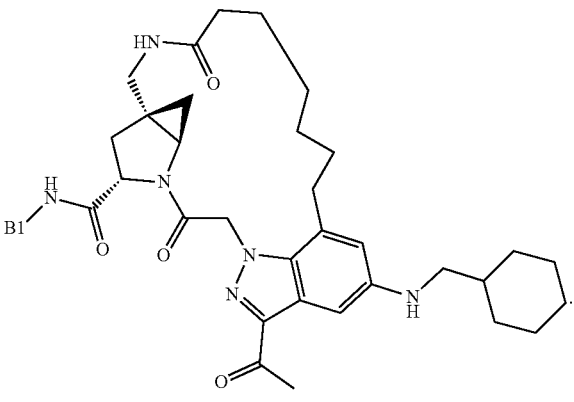
In one embodiment, the compound of Formula II is selected from:

81
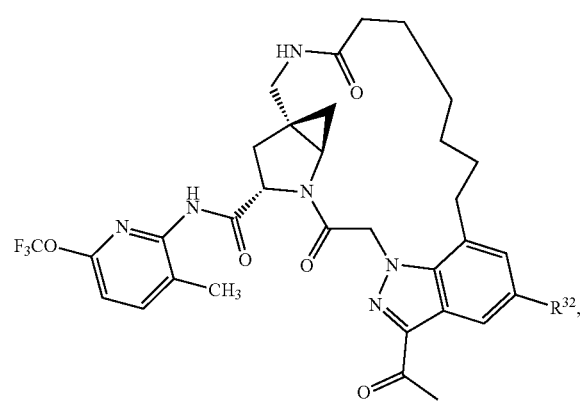
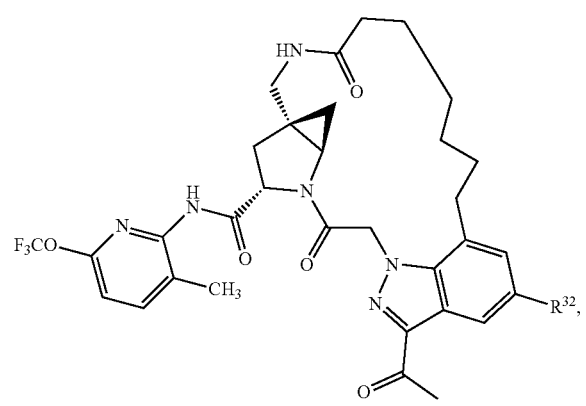
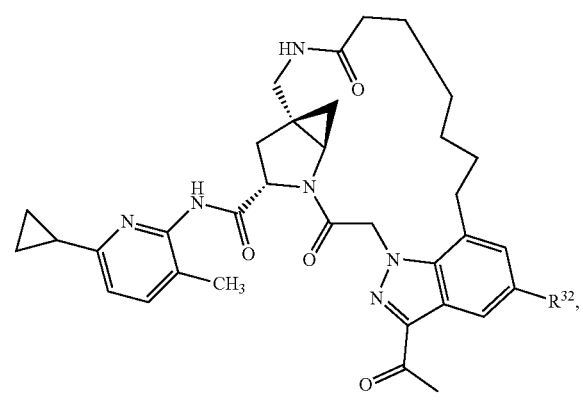
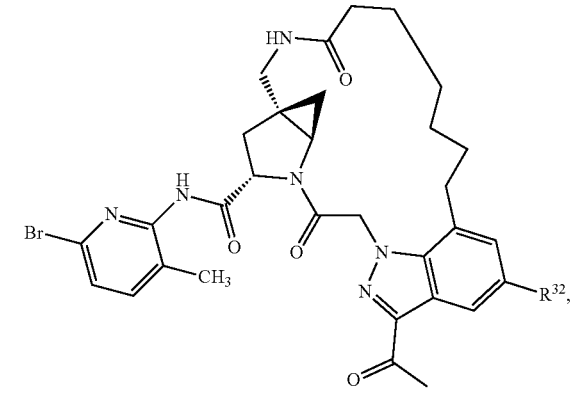
82
-continued
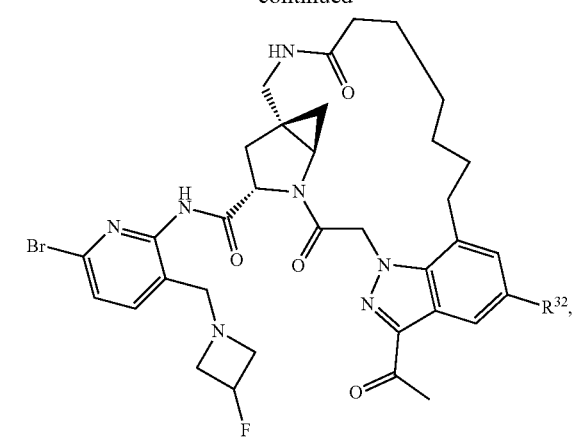
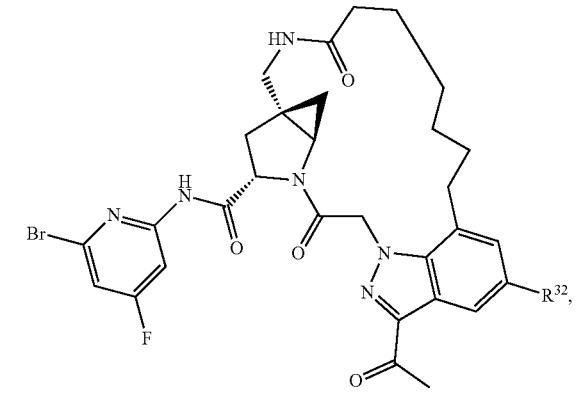
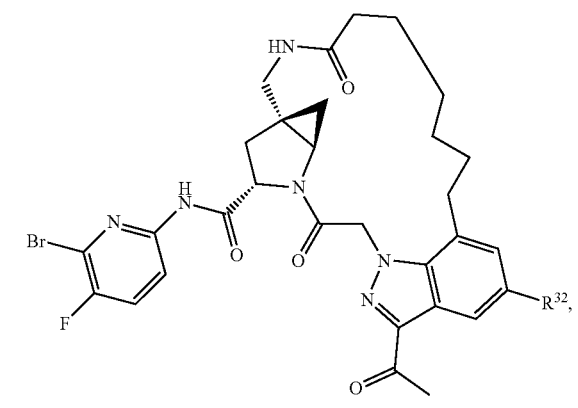
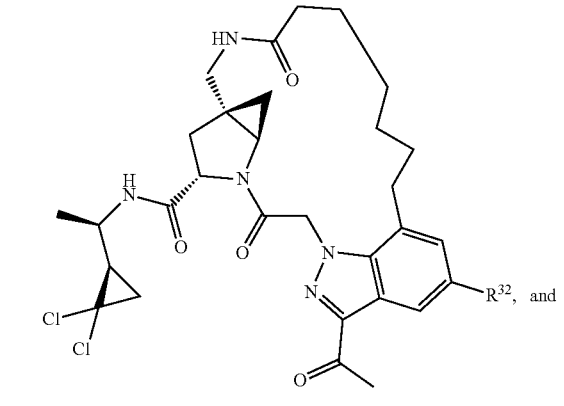

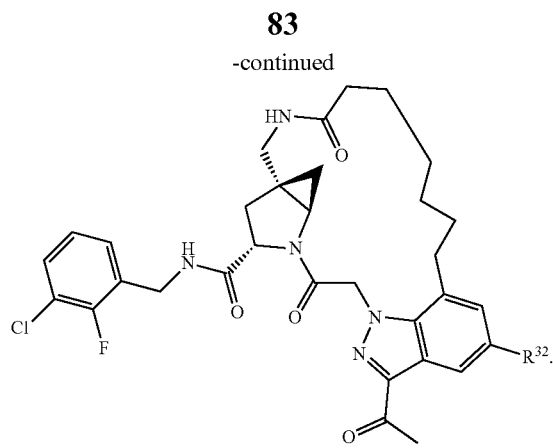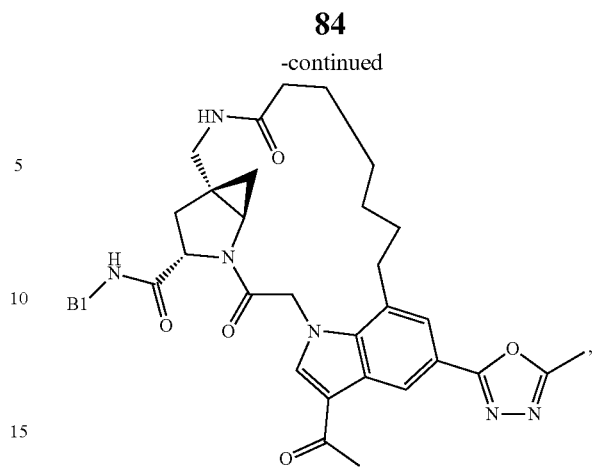
In one embodiment, the compound of Formula II is selected from:
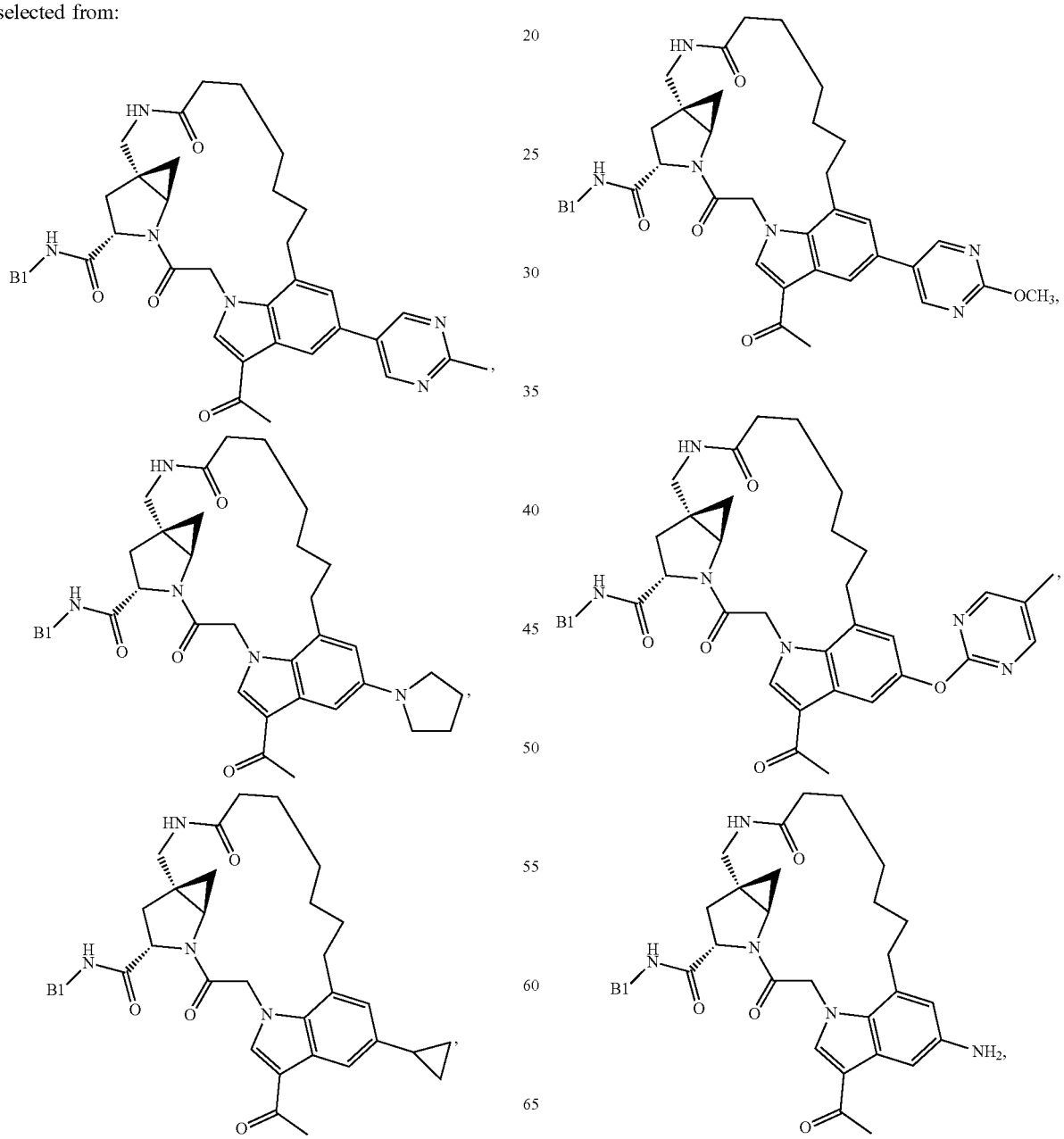

85
-continued
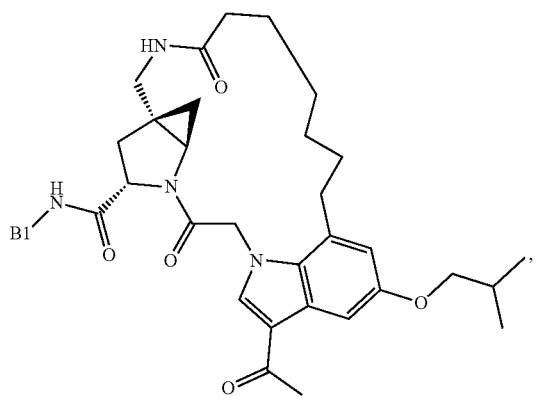
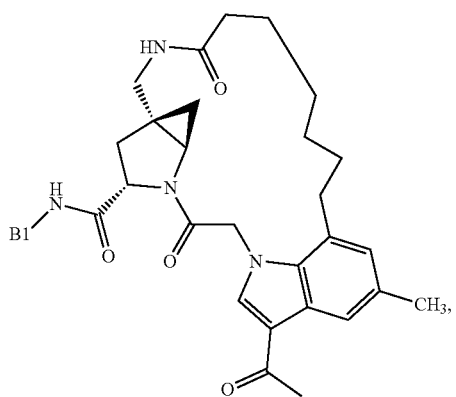
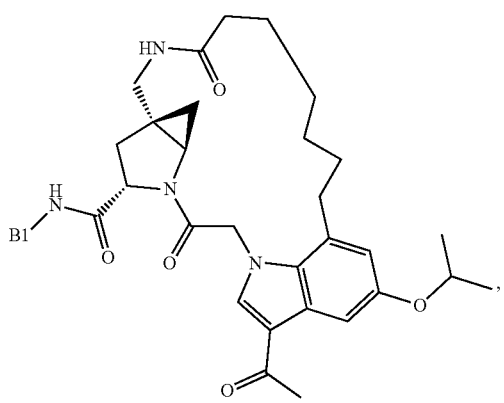
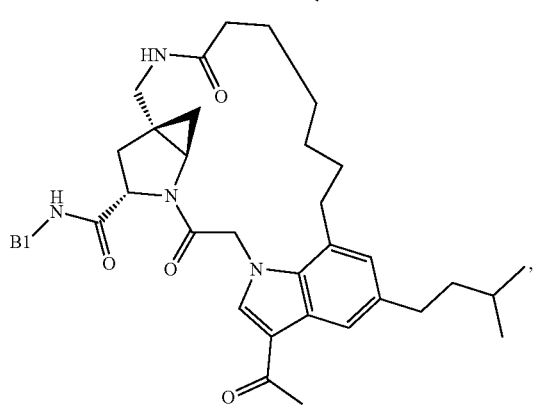
86
-continued
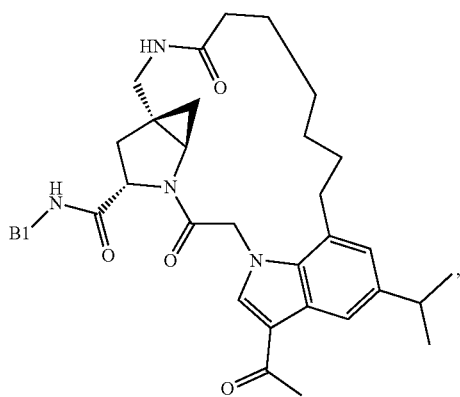
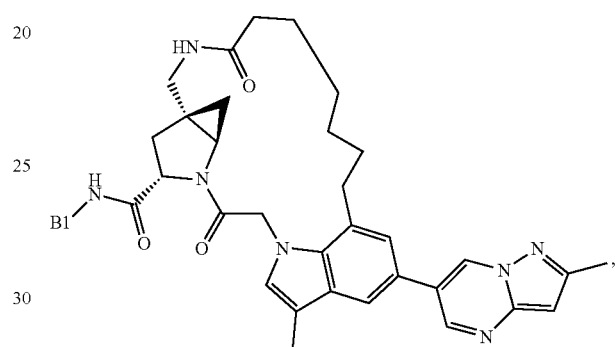
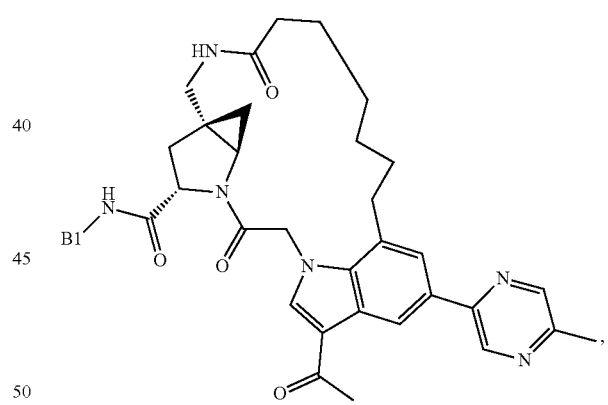
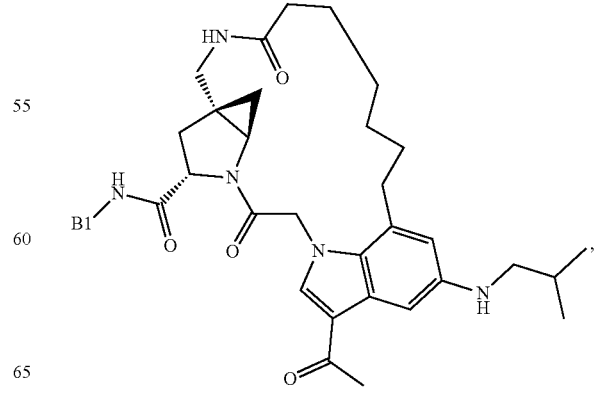

87
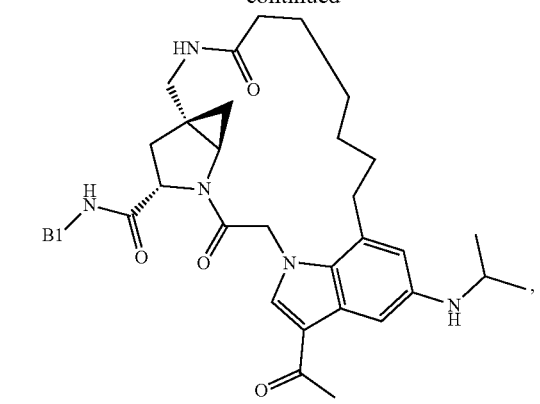
88
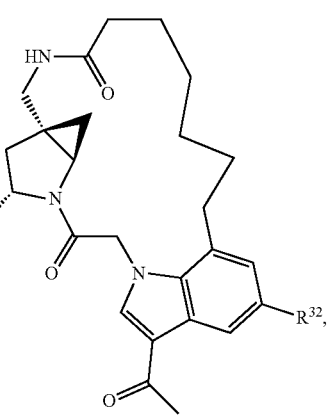
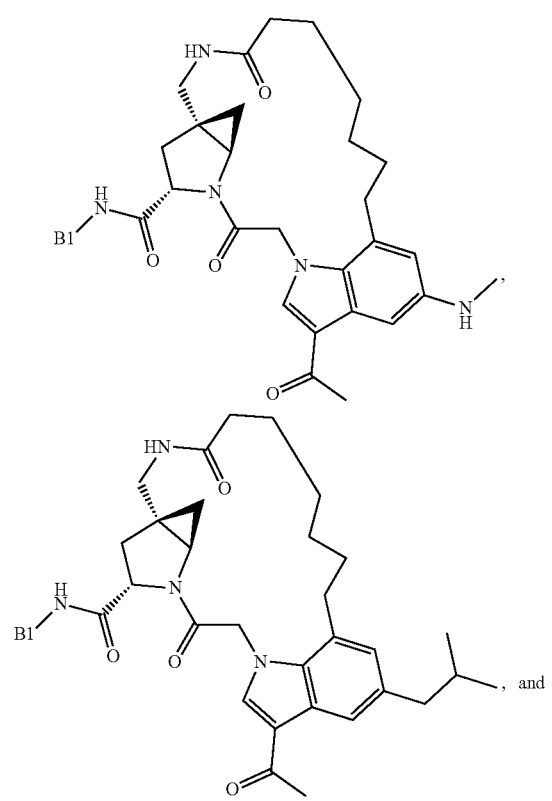
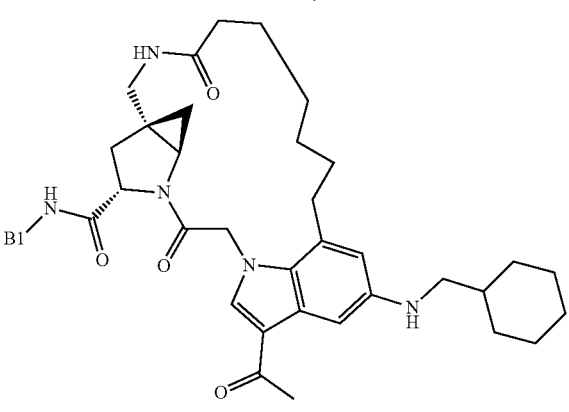
In one embodiment, the compound of Formula II is selected from:

89
-continued
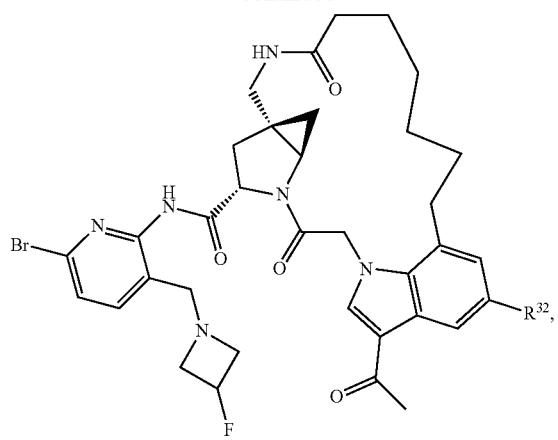
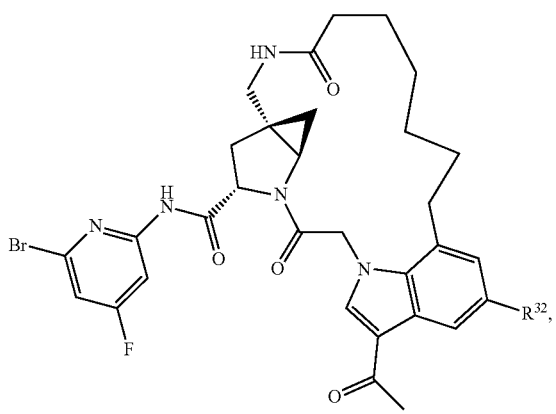
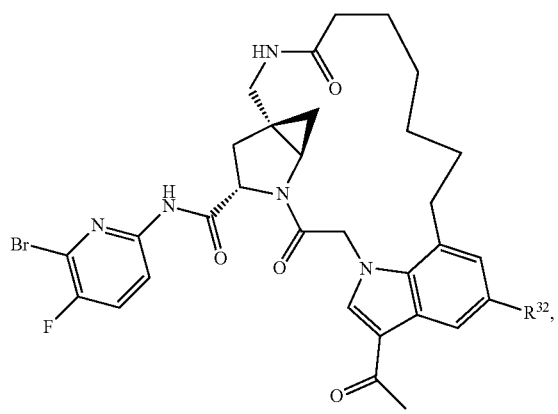
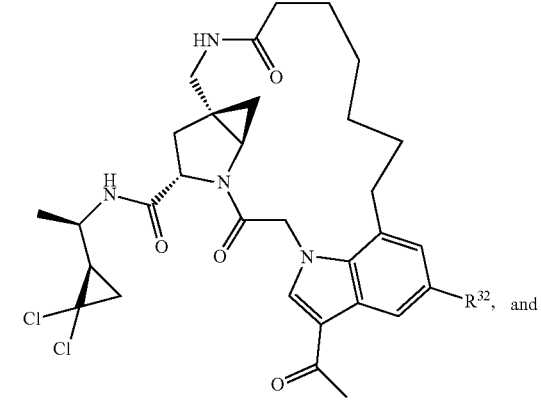
90
-continued
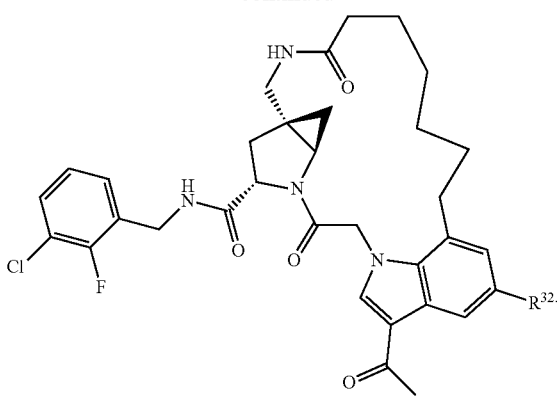
In one embodiments, the compound of Formula II is selected from:
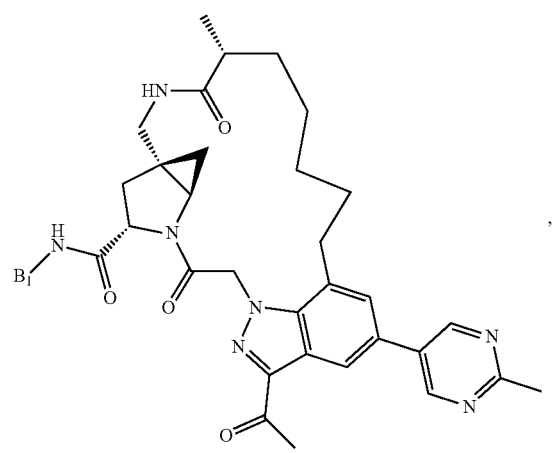
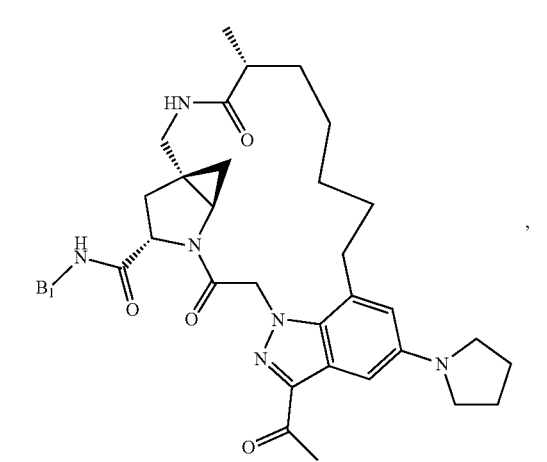

91
-continued
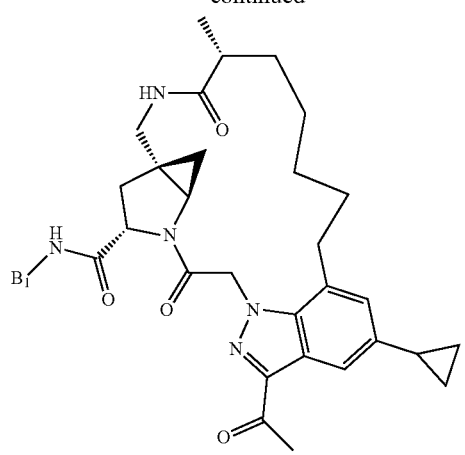
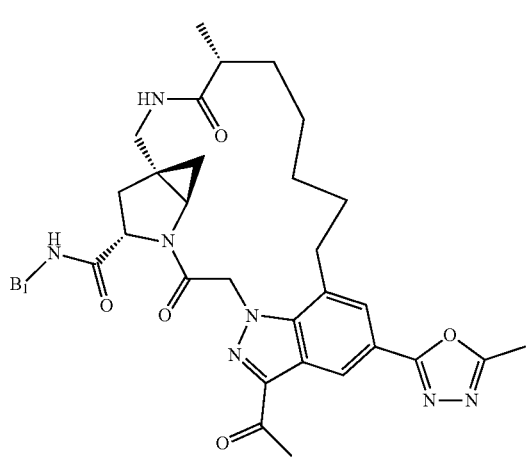
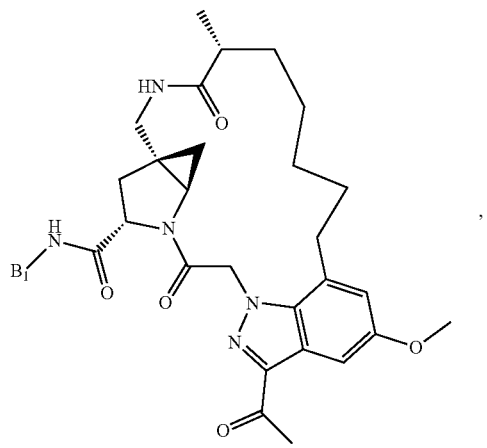
92
-continued
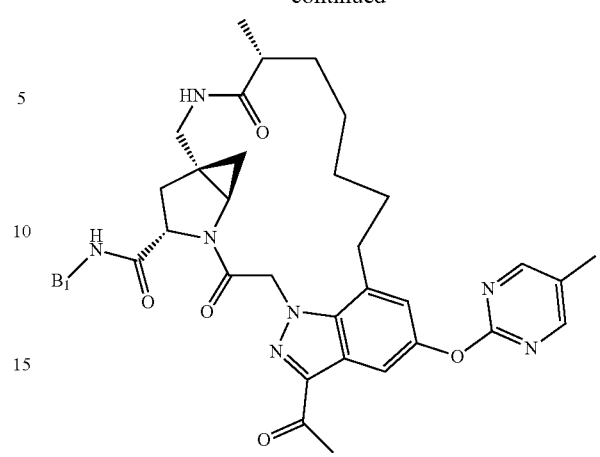
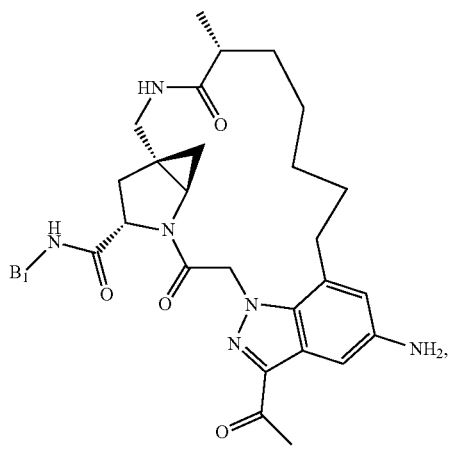
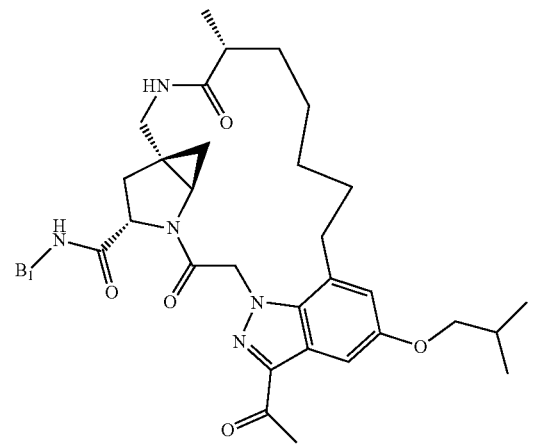

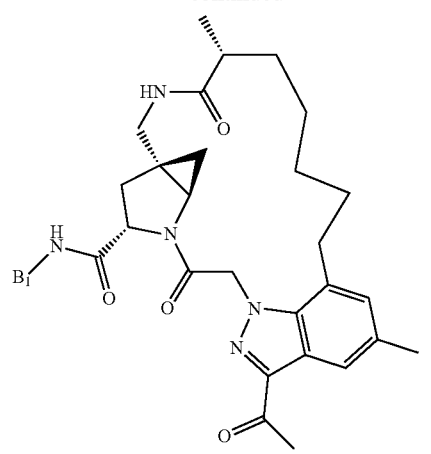
,
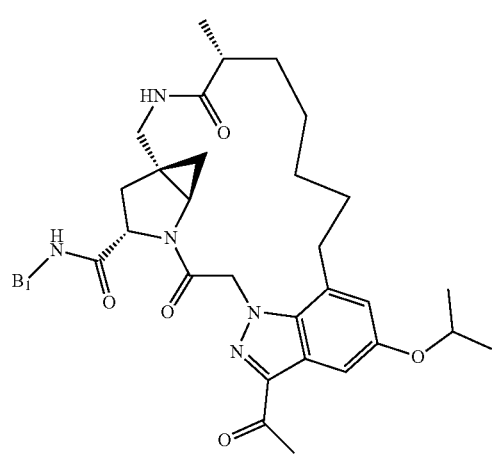
,
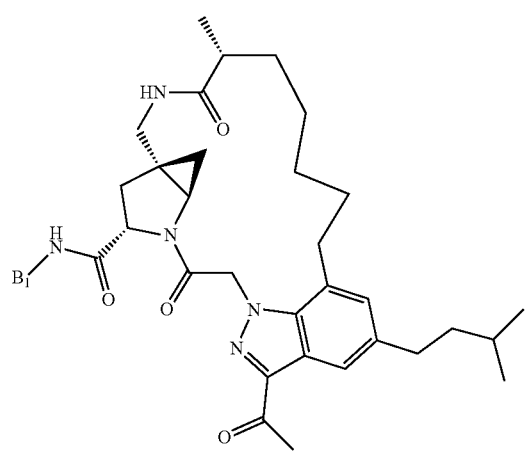
,
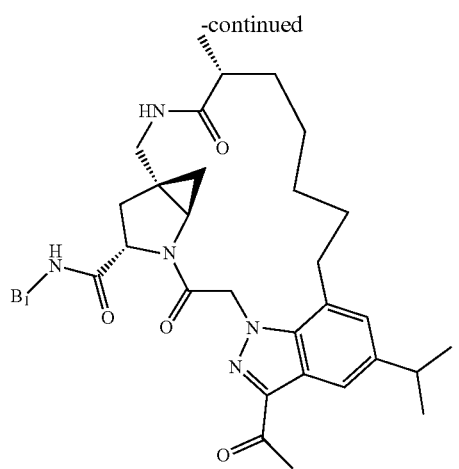
,
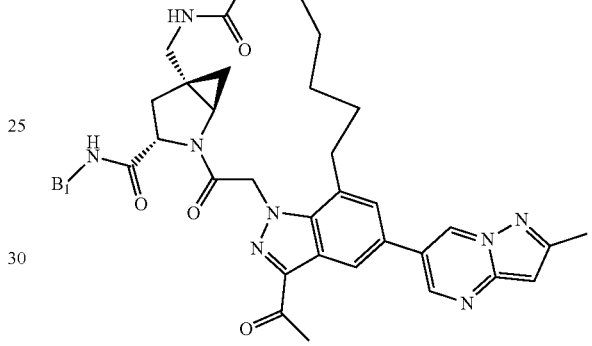
,
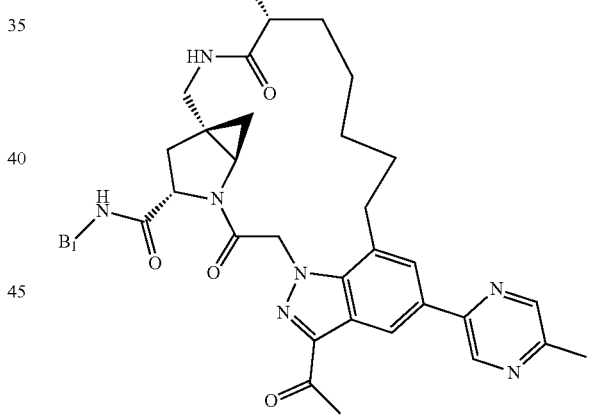
, 95
-continued

,

,
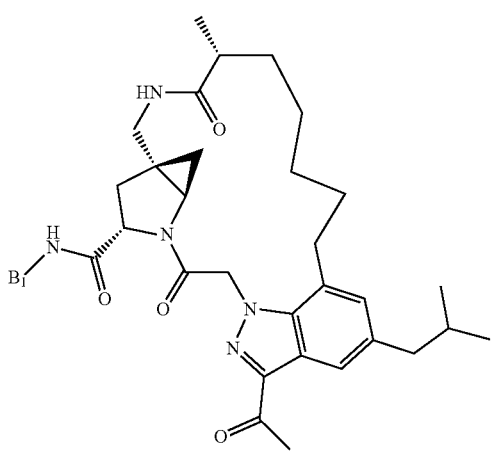
, and
96
-continued

.
In one embodiment, the compound of Formula II is selected from:
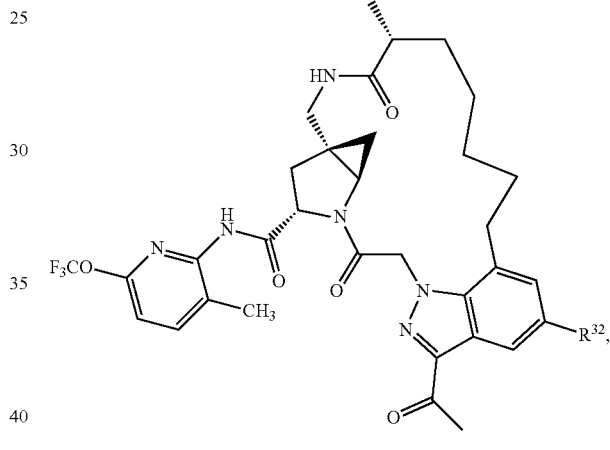
,
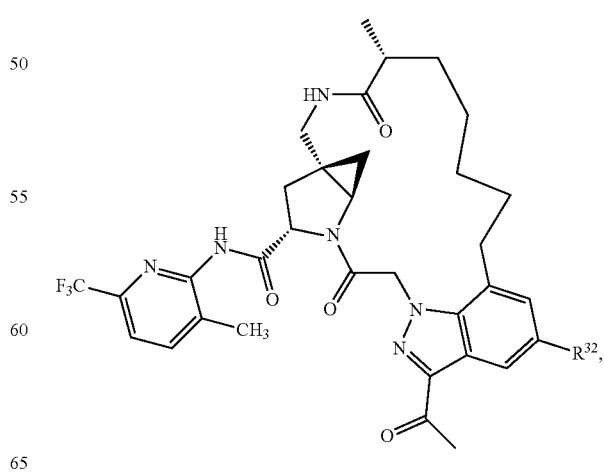
, 97
-continued
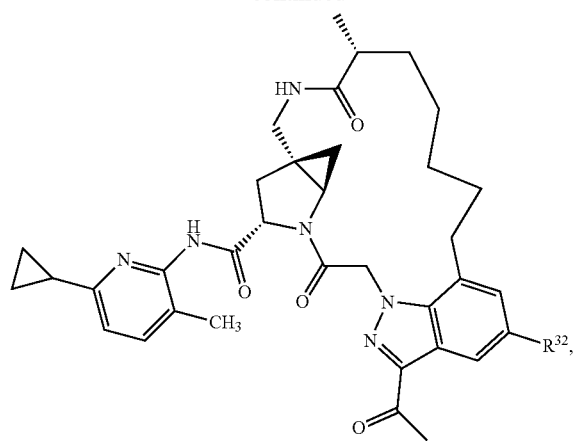
98
-continued
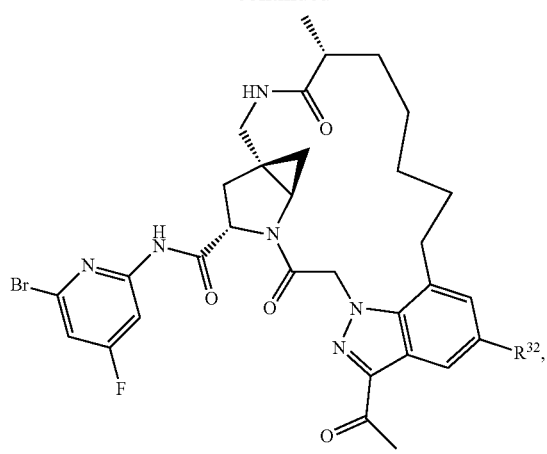
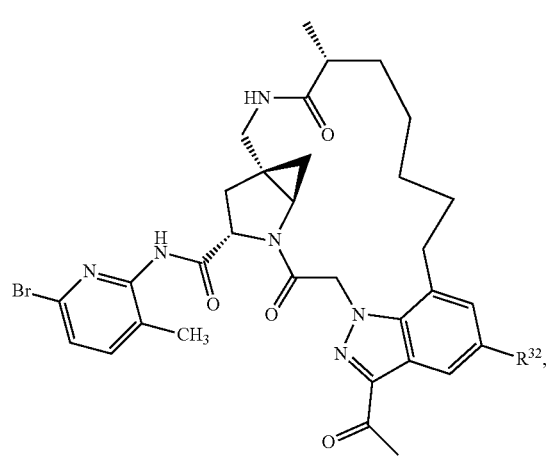
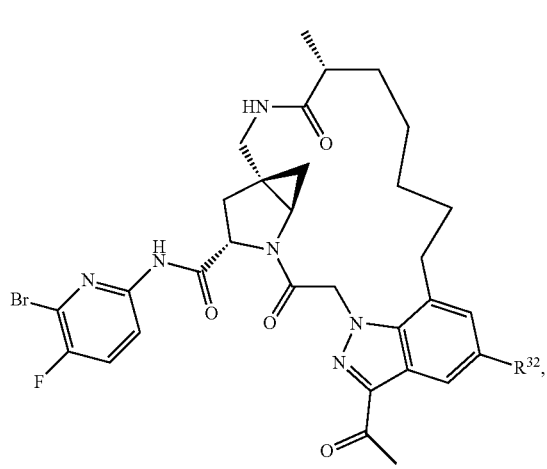
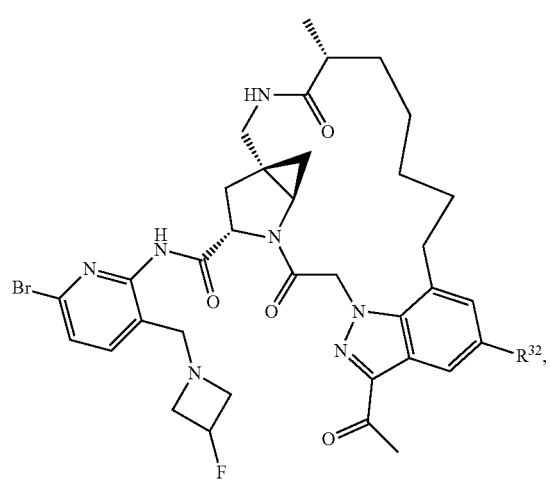
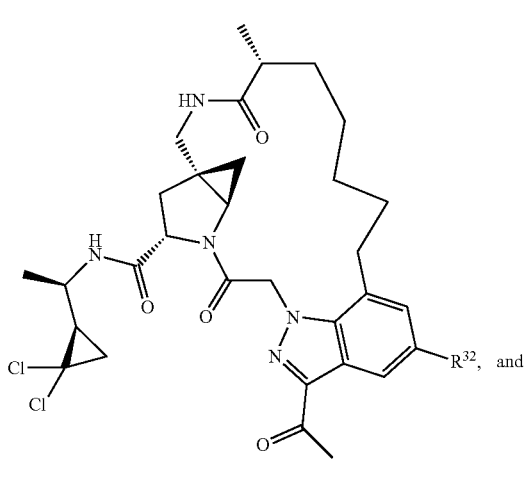, and 99
-continued
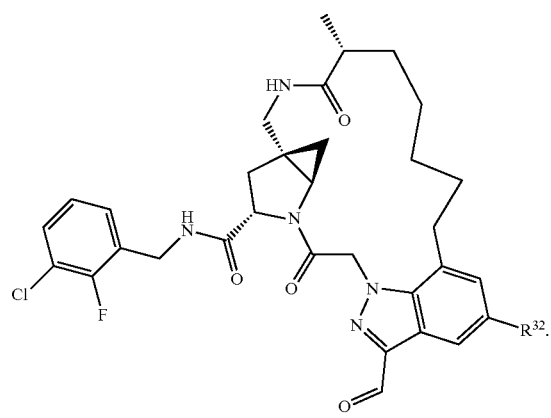
In one embodiments, the compound of Formula II is selected from:
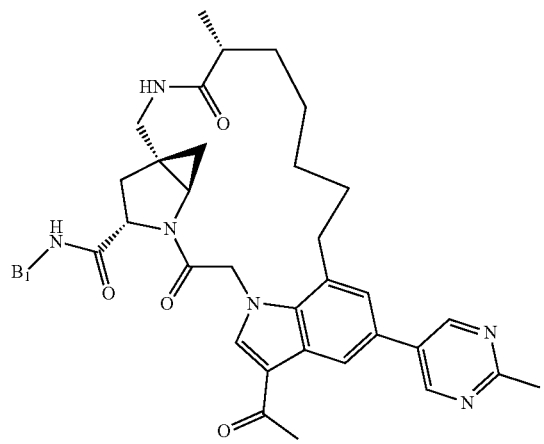
,
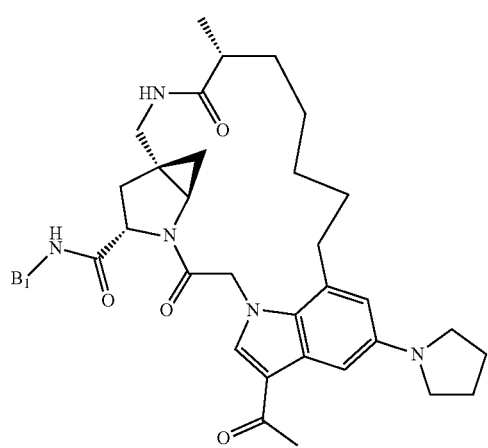
,
100
-continued
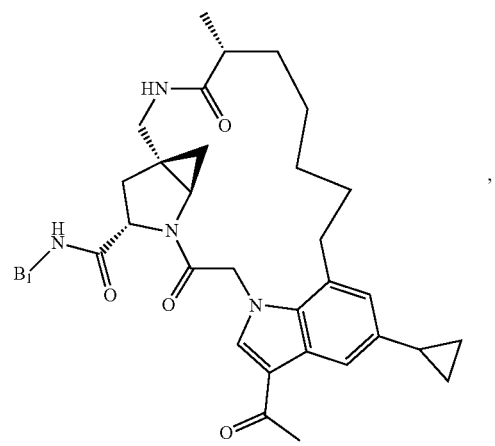
,
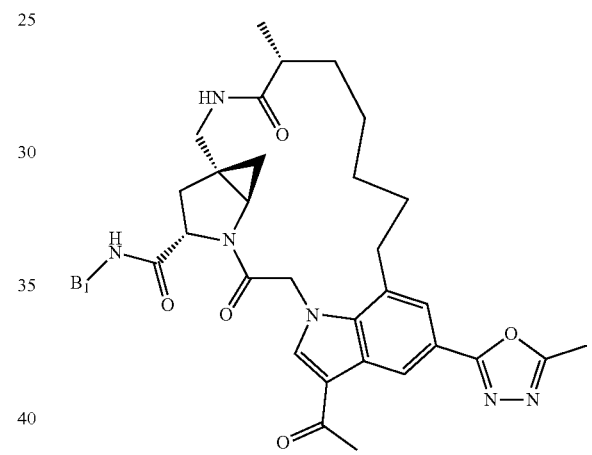
,
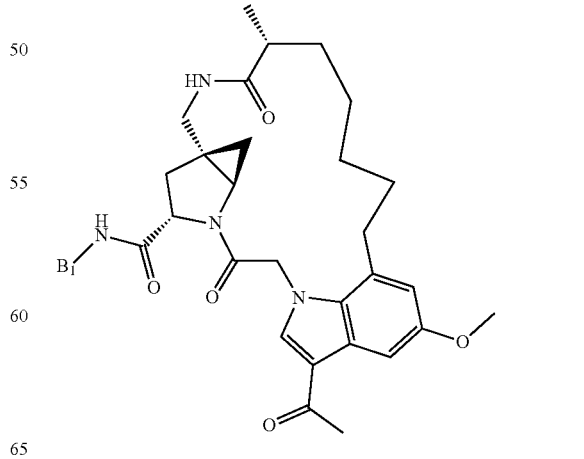
, 101
-continued
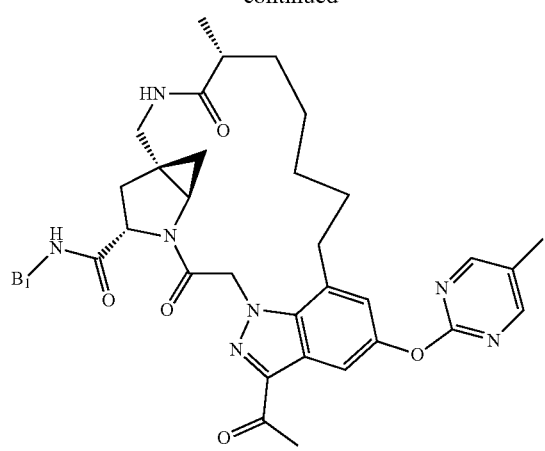
102
-continued
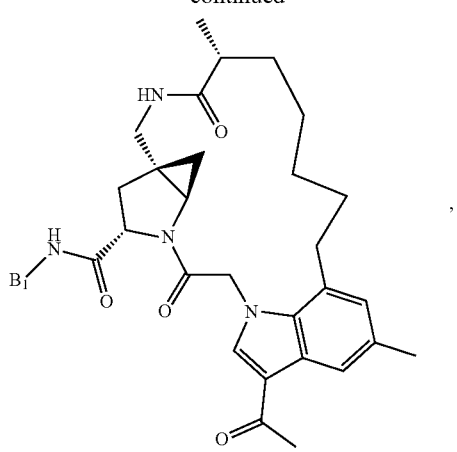
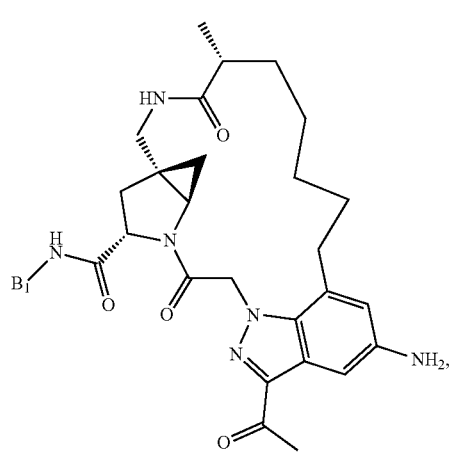
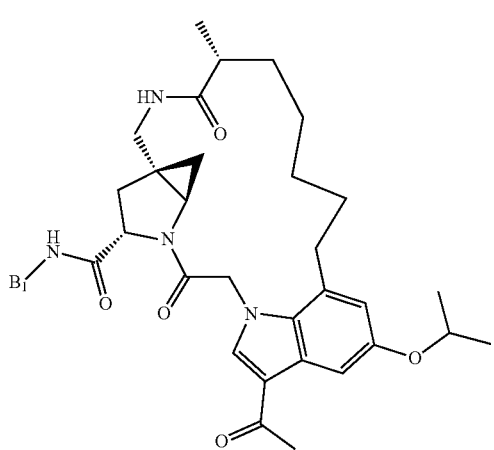
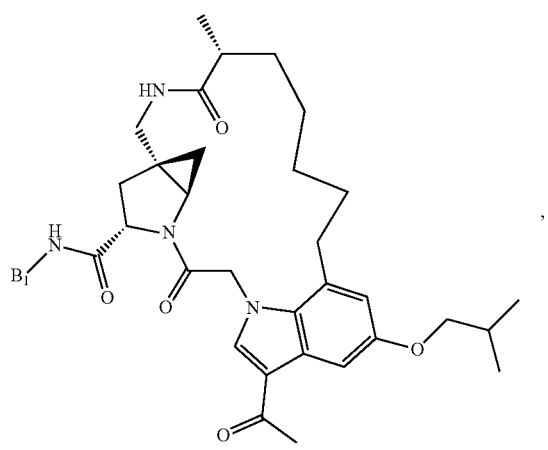
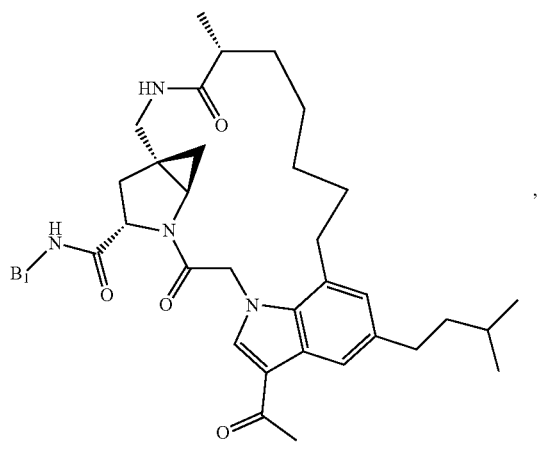

103
-continued
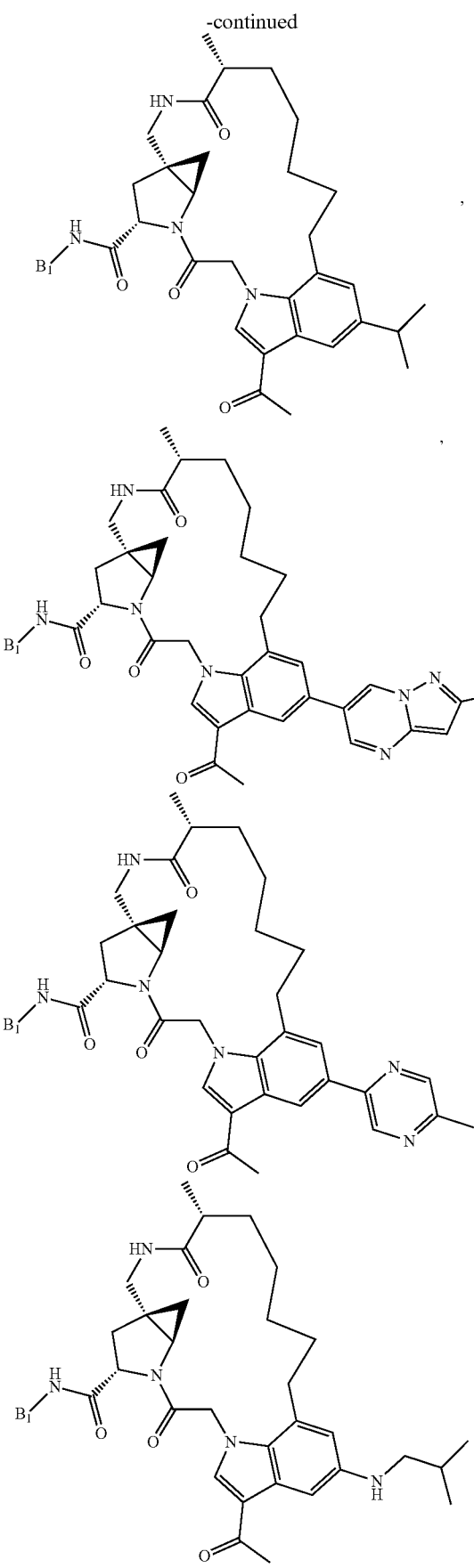
104
-continued
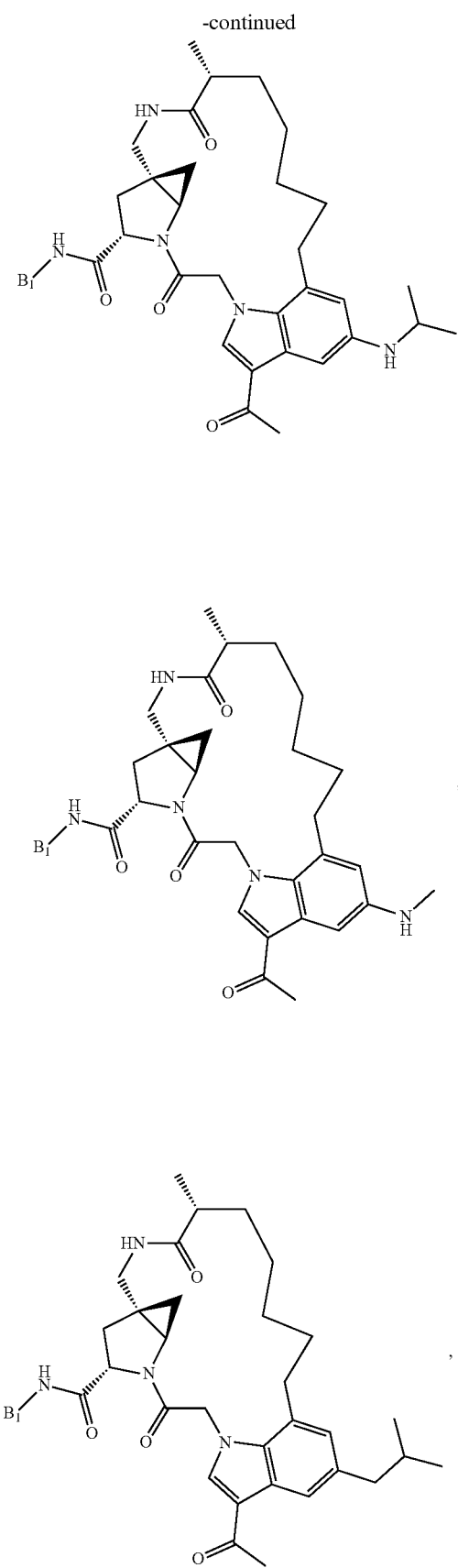
, and

105
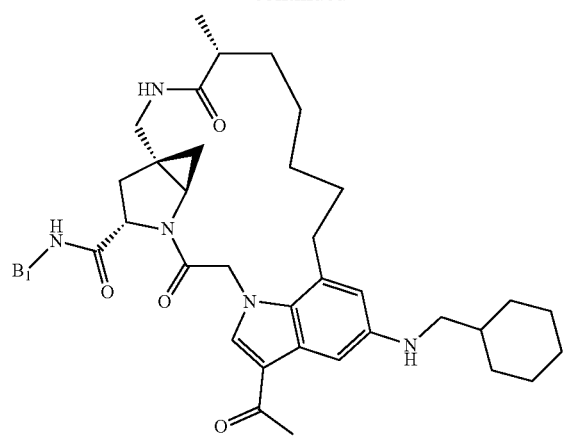
106
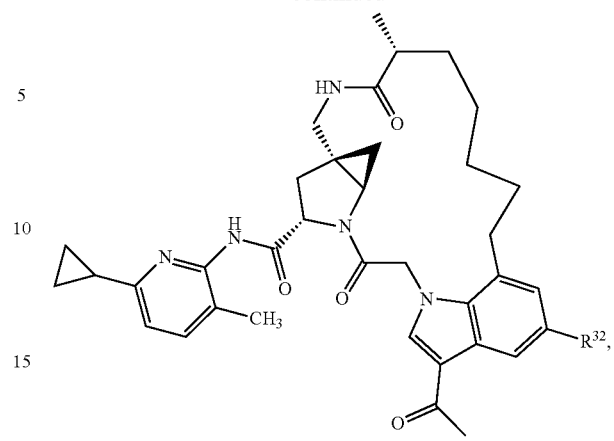
In one embodiment, the compound of Formula II is selected from:
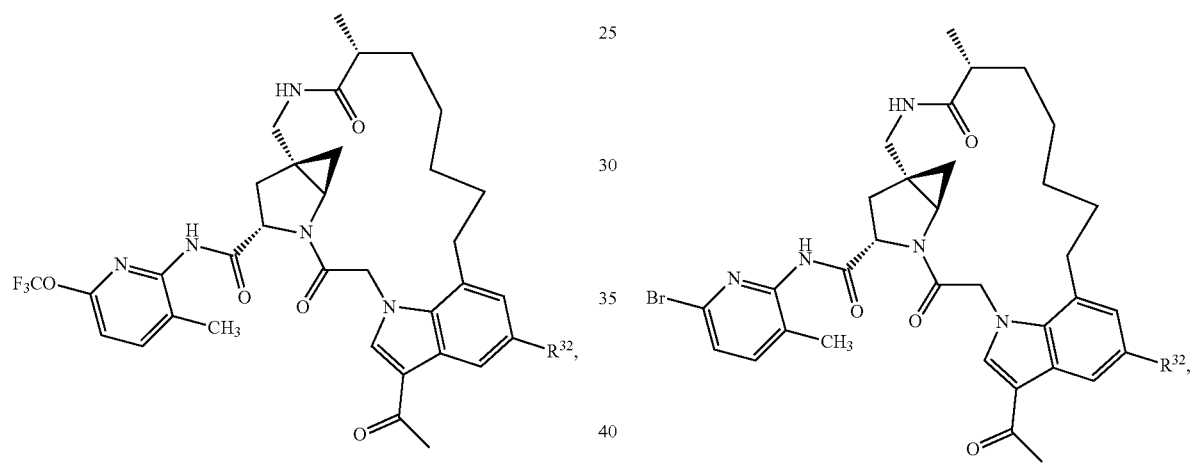
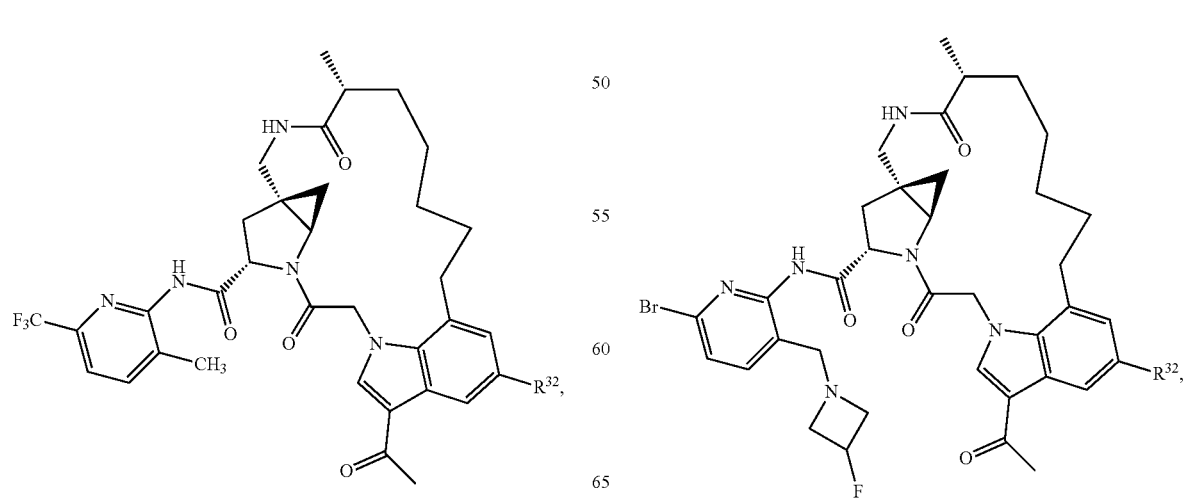

107
-continued
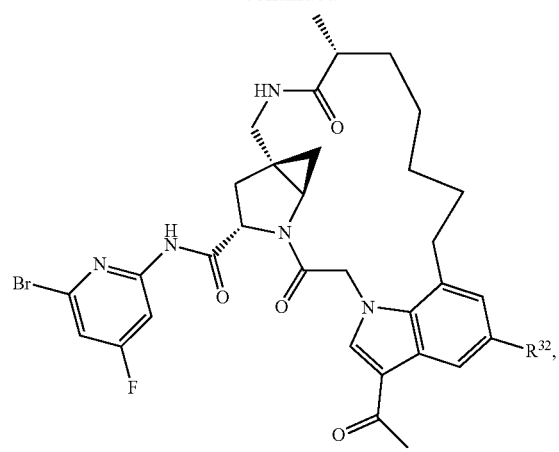
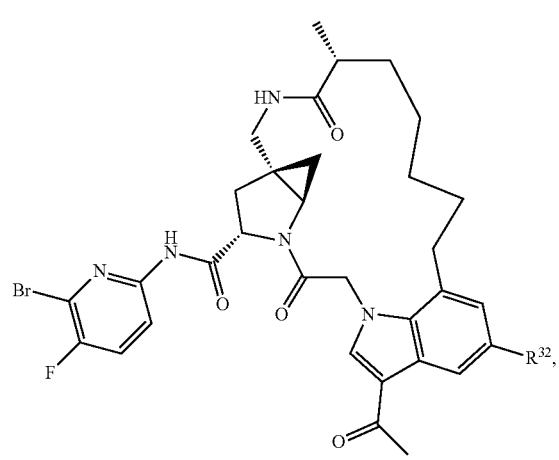
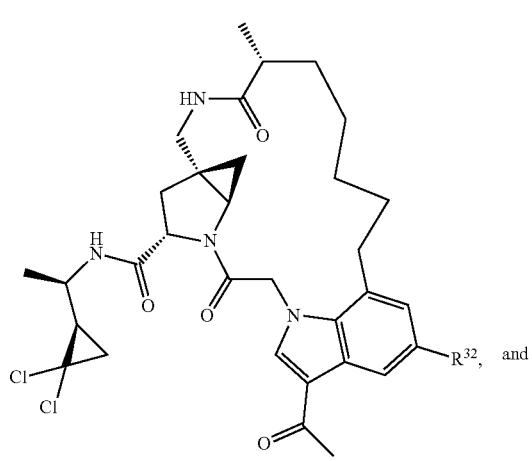
108
-continued
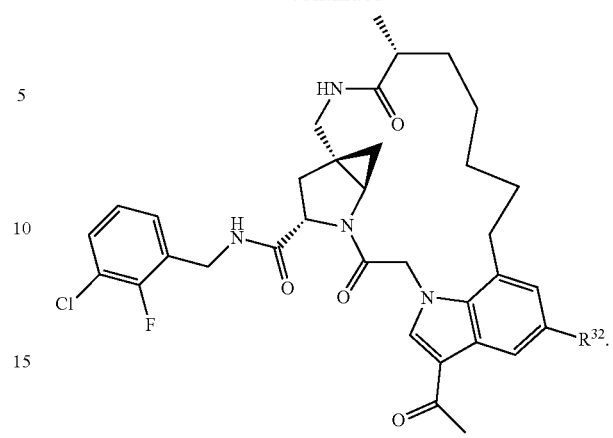
In one embodiments, the compound of Formula II is selected from:
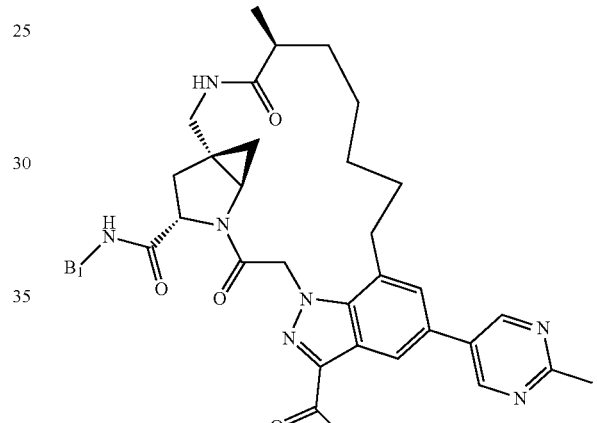
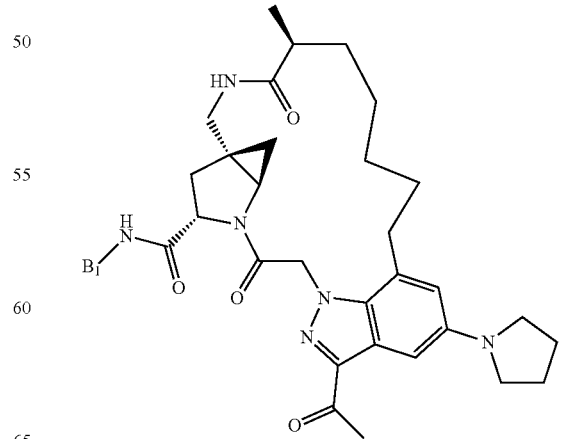

109 110
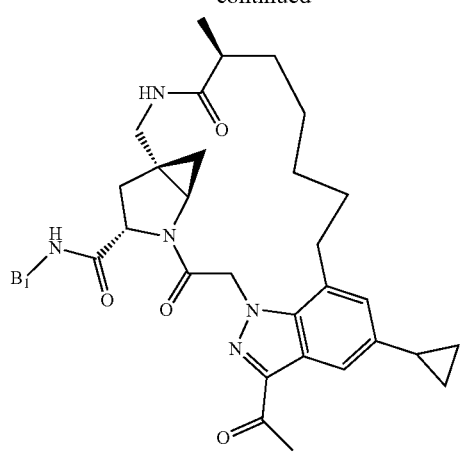 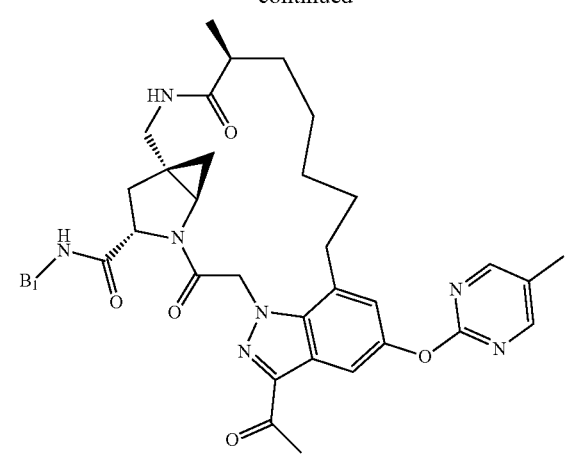
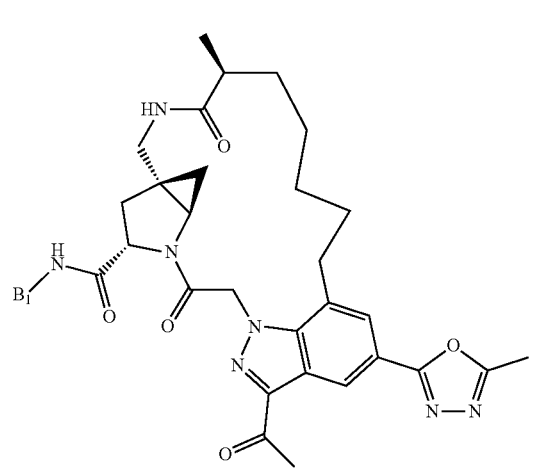 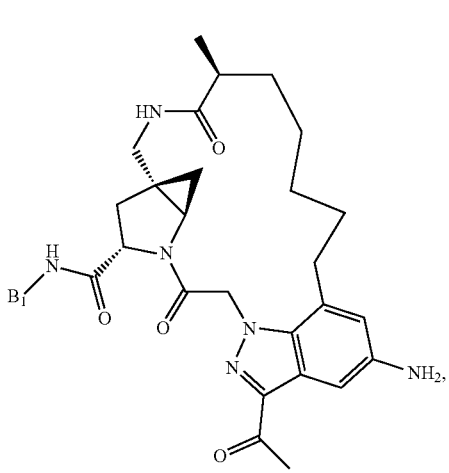
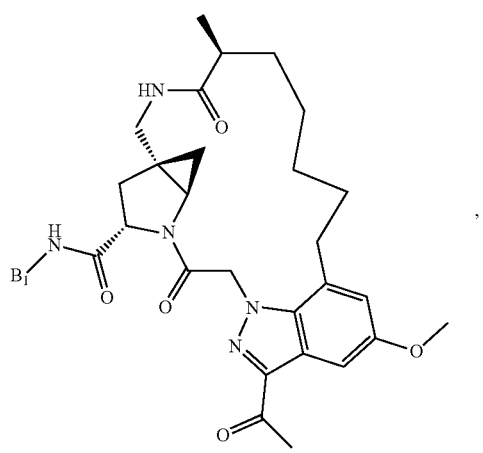 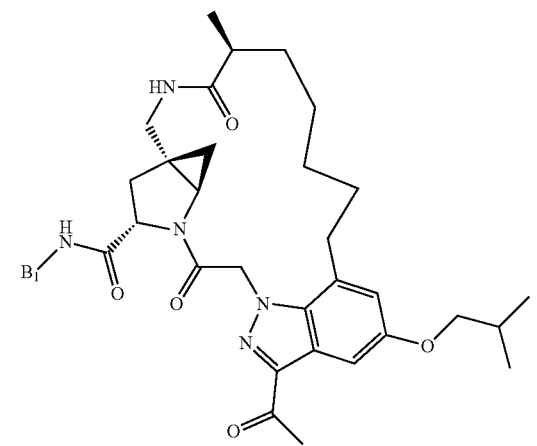

111
-continued
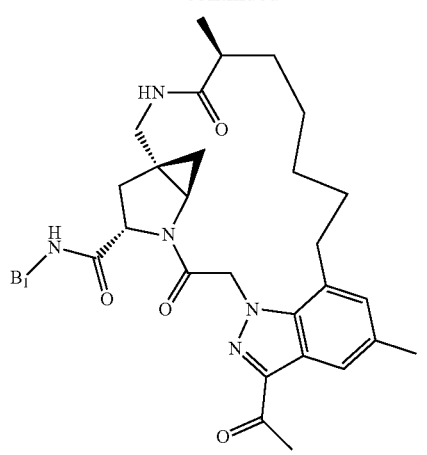
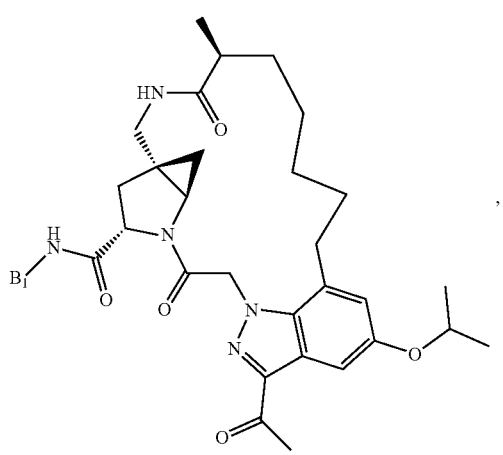
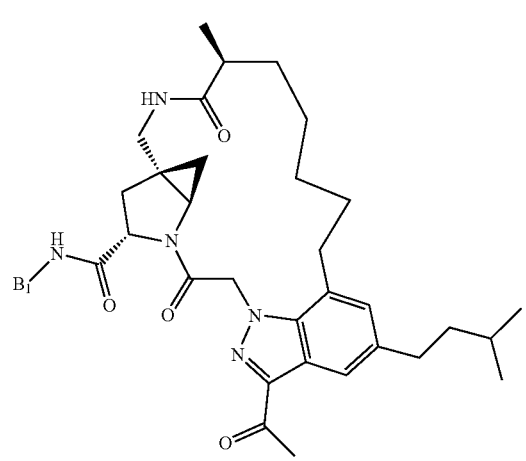
112
-continued
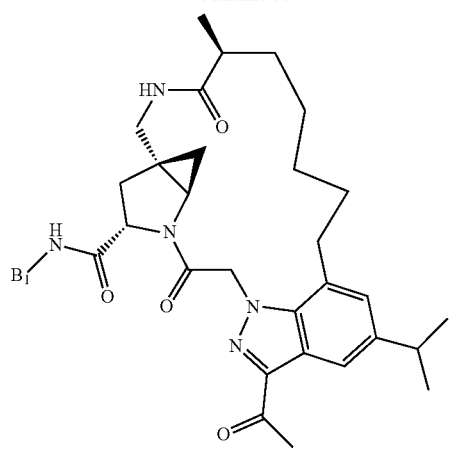
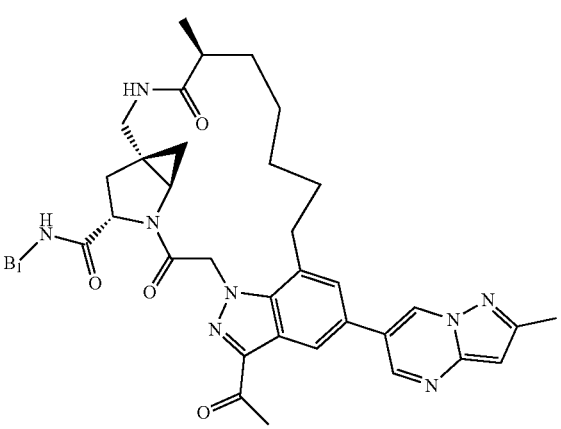
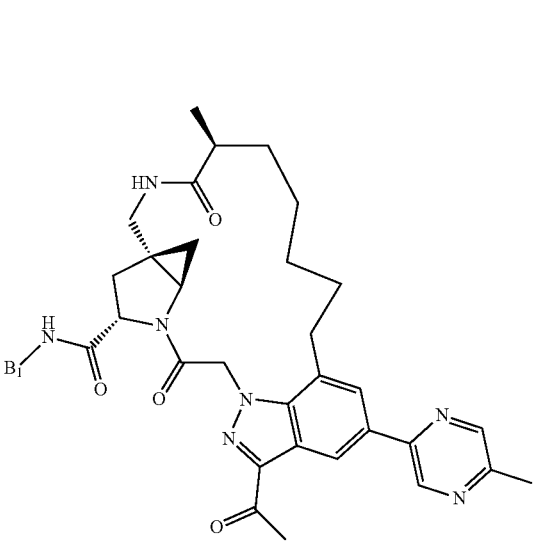

113
-continued
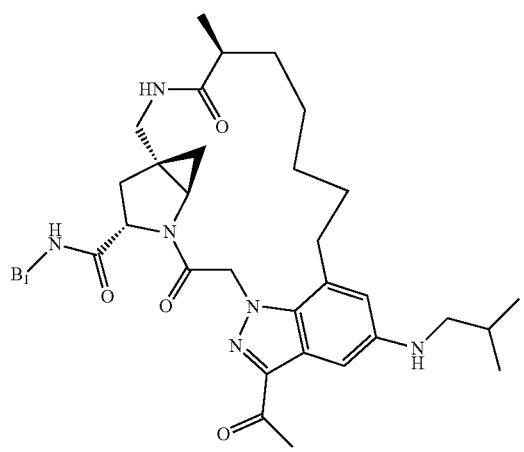
,
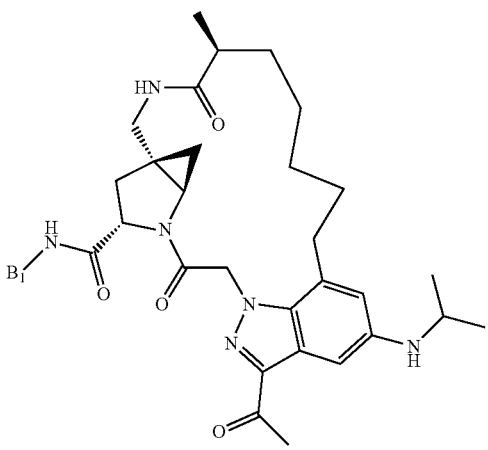
,
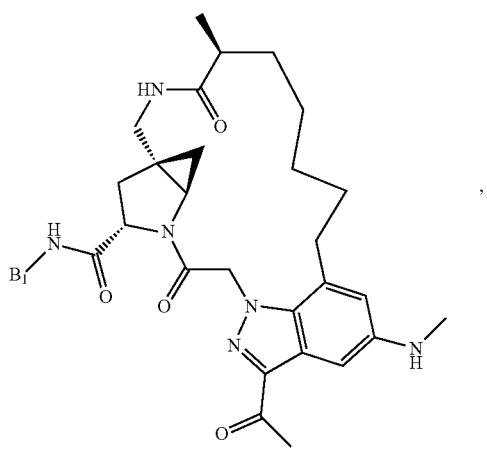
,
114
-continued
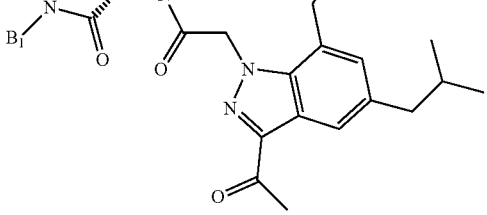
, and
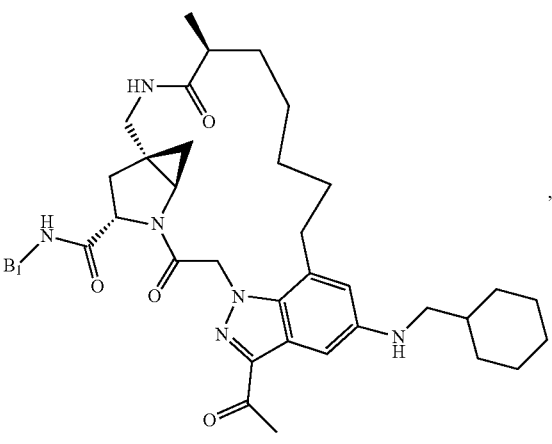
,
In one embodiment, the compound of Formula II is selected from:
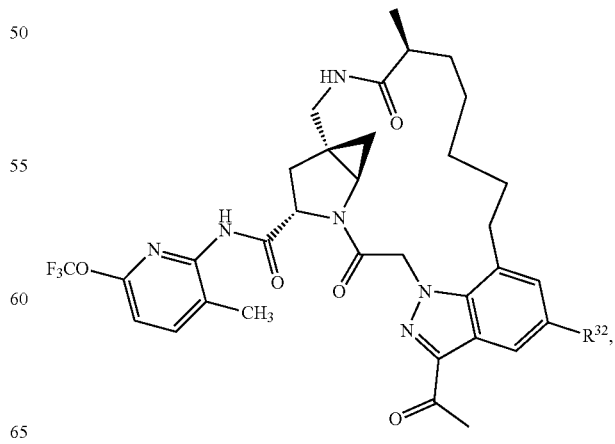

115
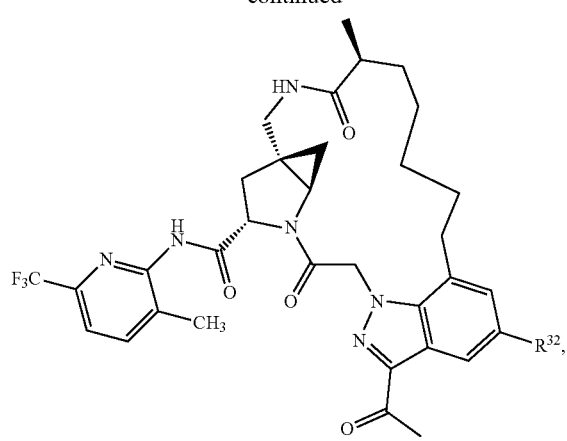
116
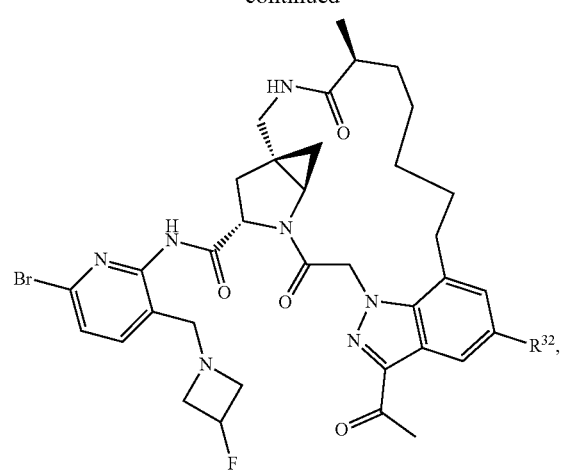
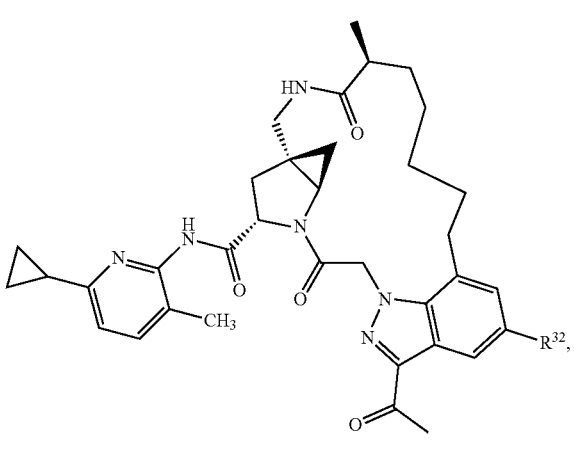
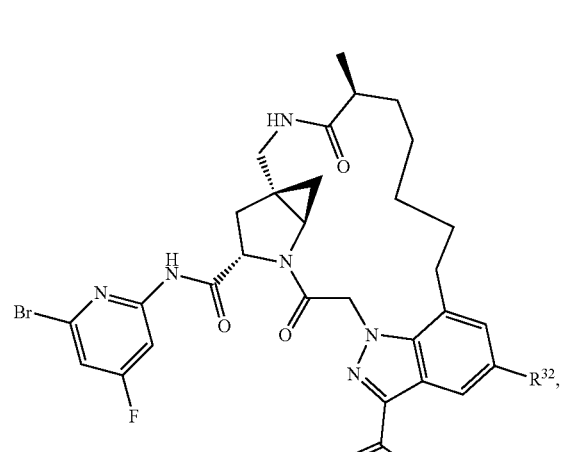
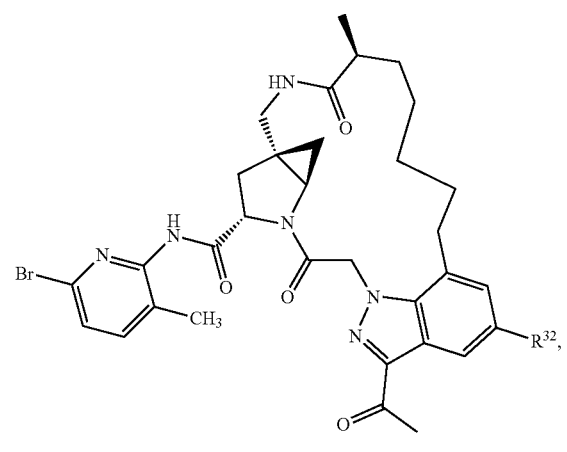
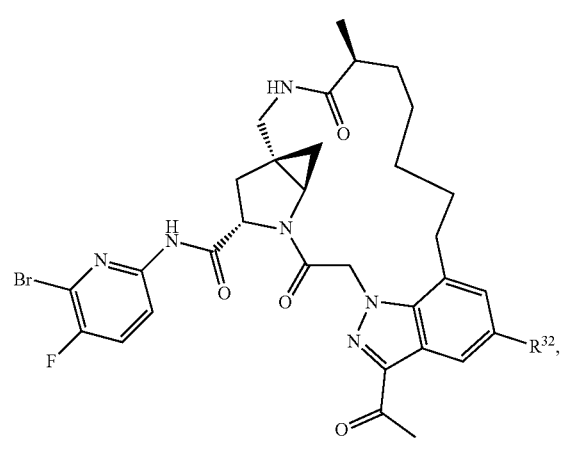

117
-continued
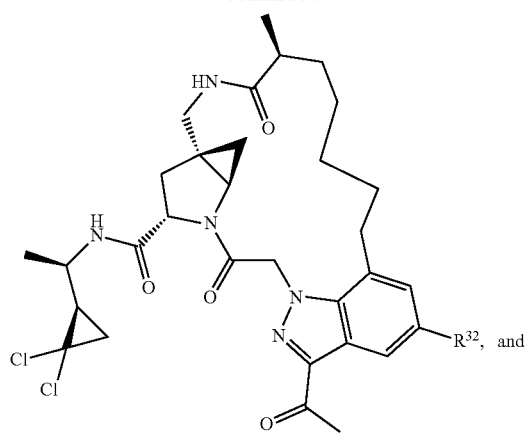
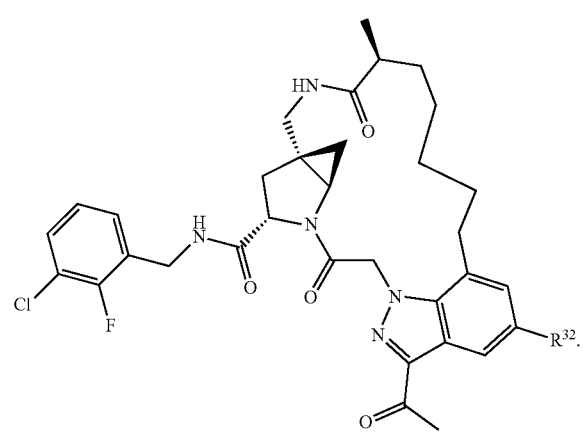
In one embodiments, the compound of Formula II is selected from:
118
-continued
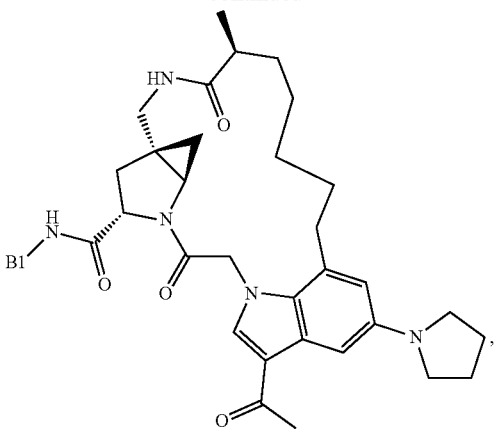
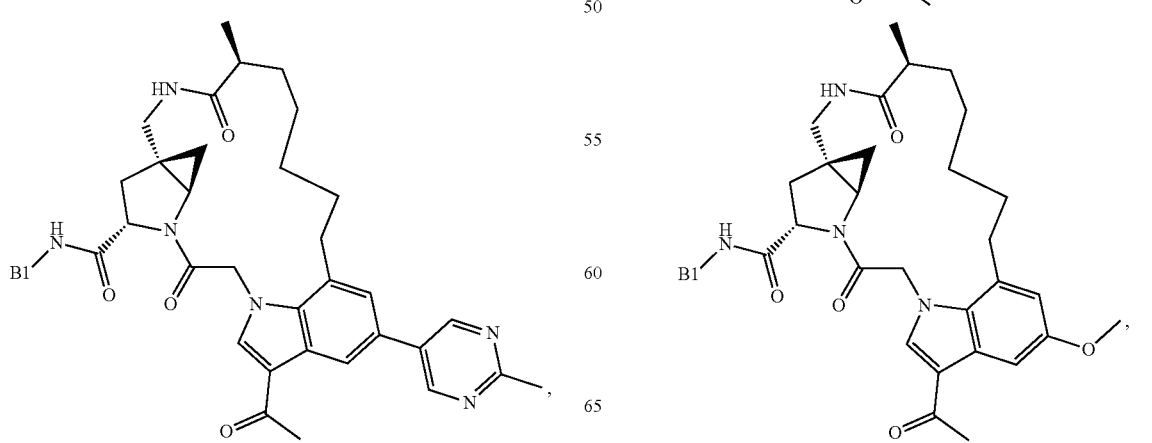

119
-continued
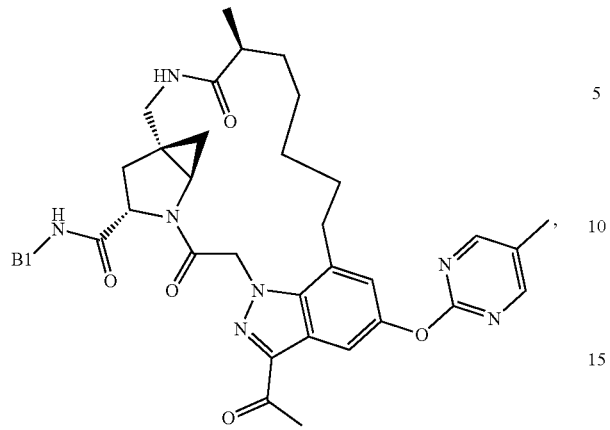
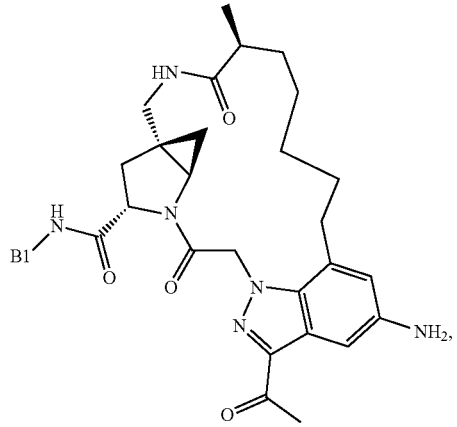
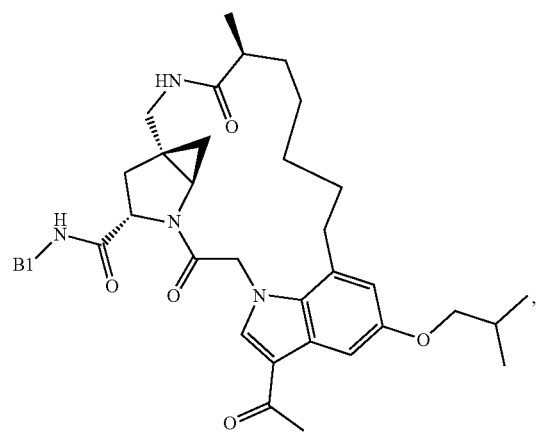
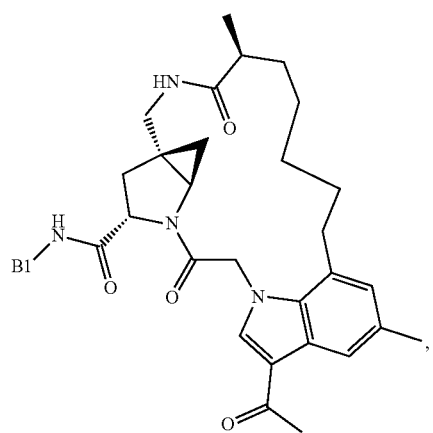
120
-continued
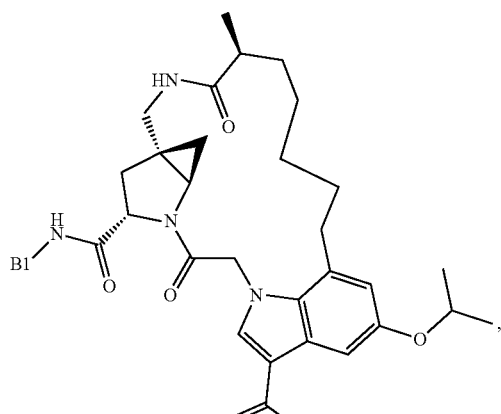
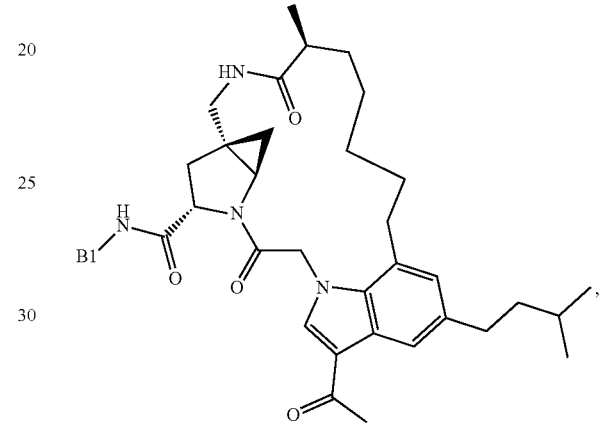
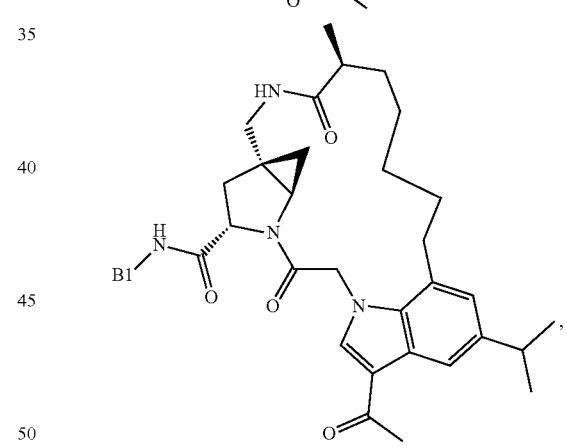
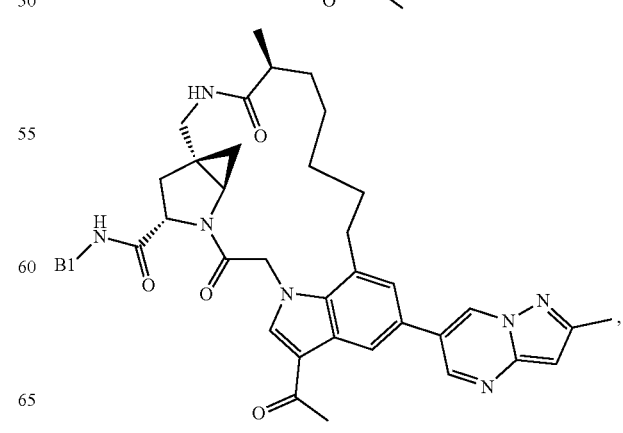

121
-continued

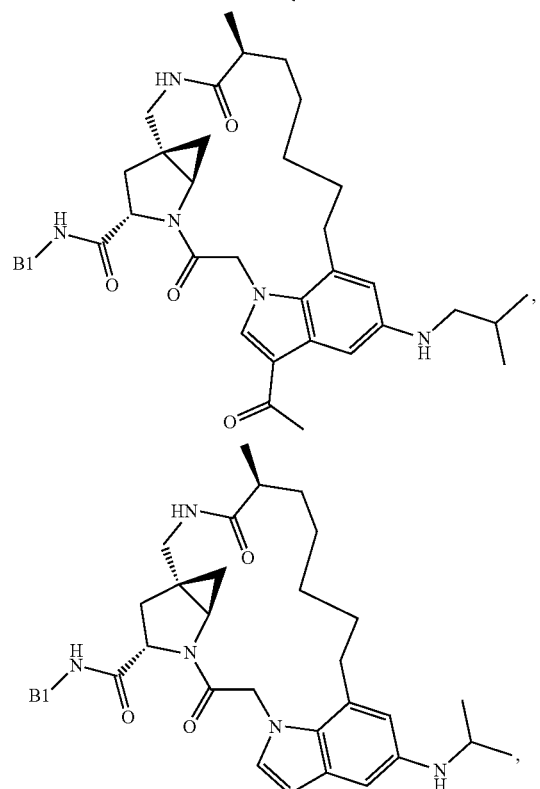
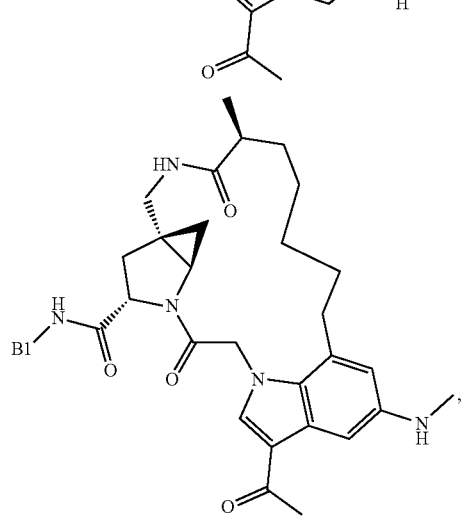
122
-continued
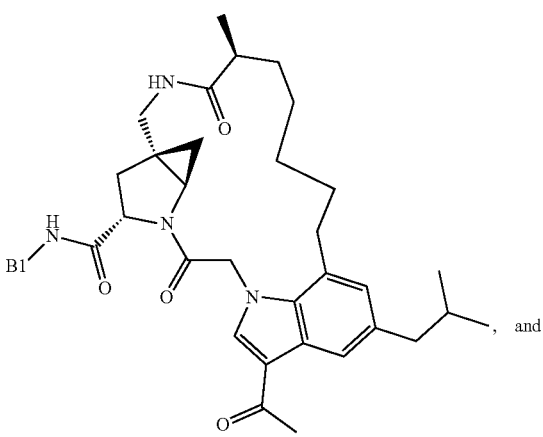
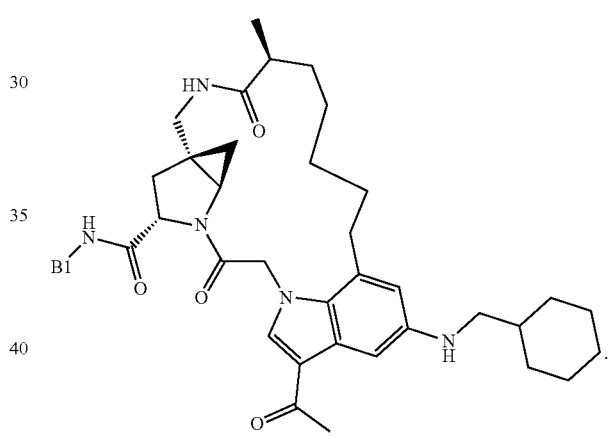
In one embodiment, the compound of Formula II is selected from:
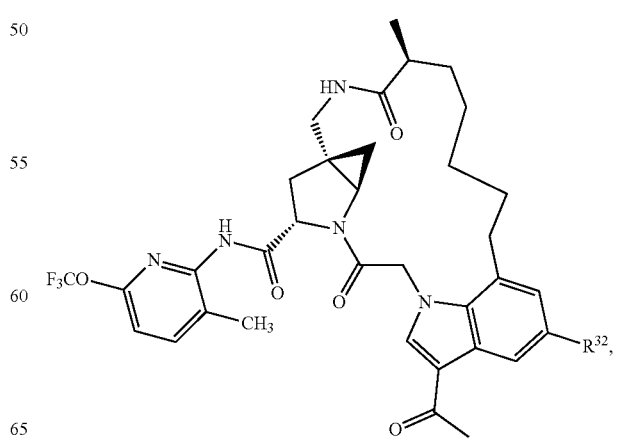

123
-continued
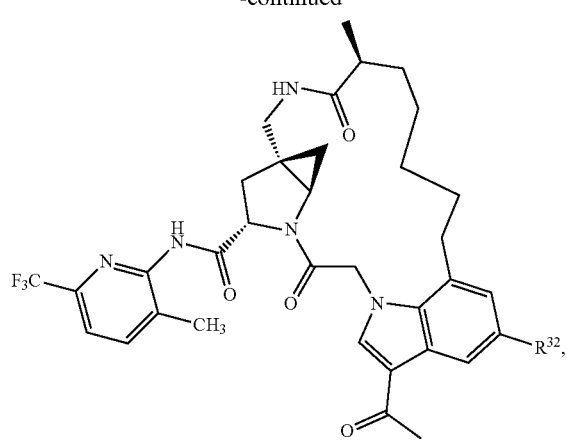
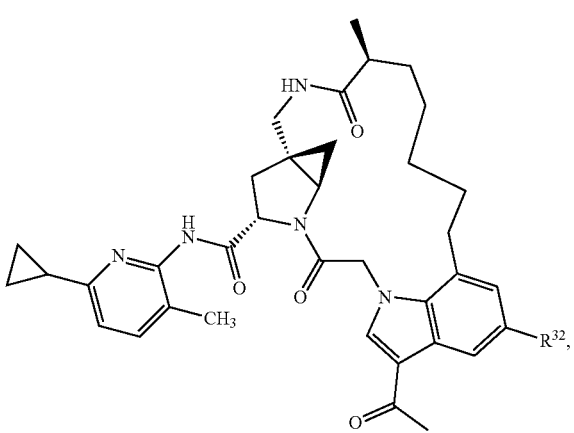
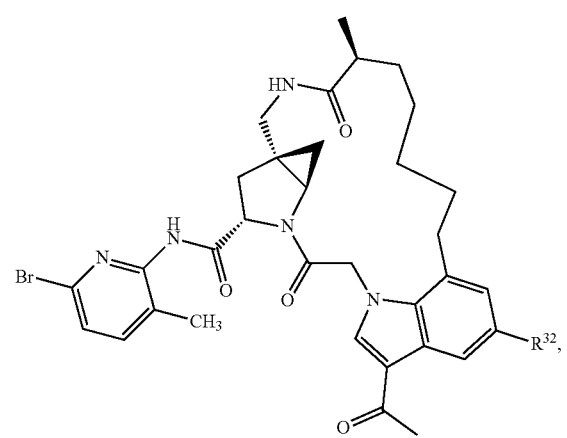
124
-continued
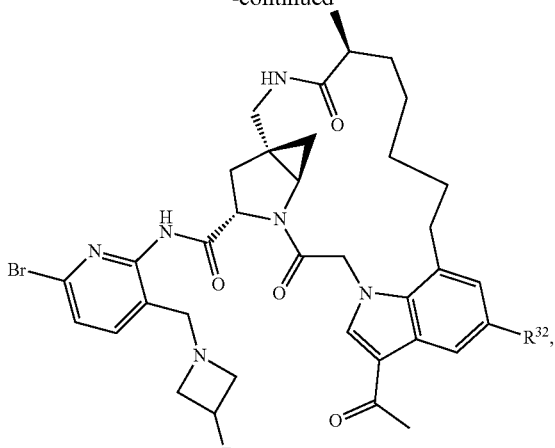
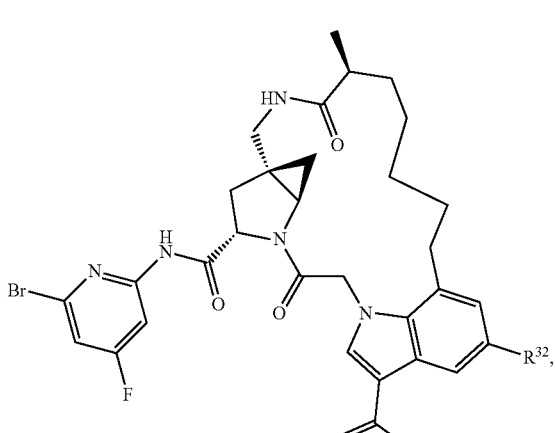

125
-continued
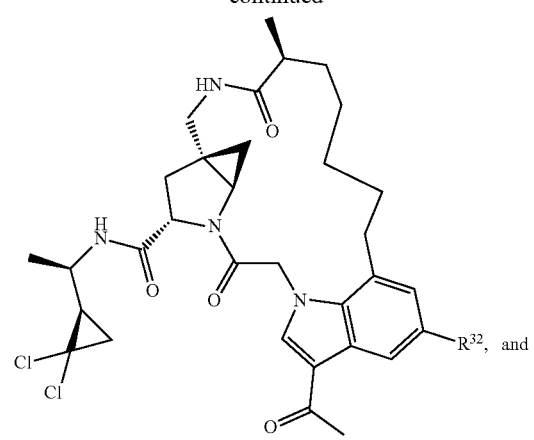
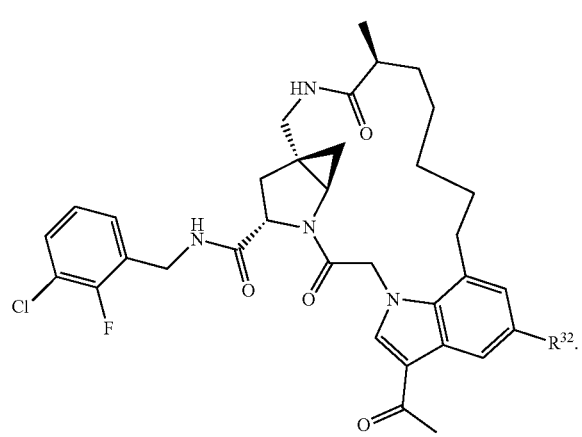
In one embodiment, the compound of Formula II is selected from:
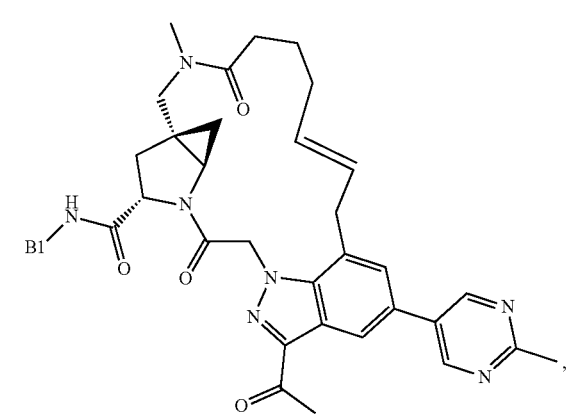
126
-continued
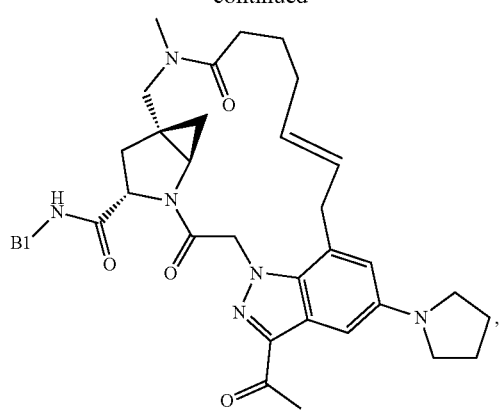
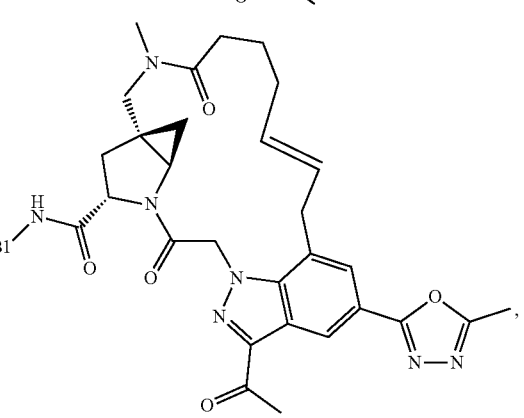
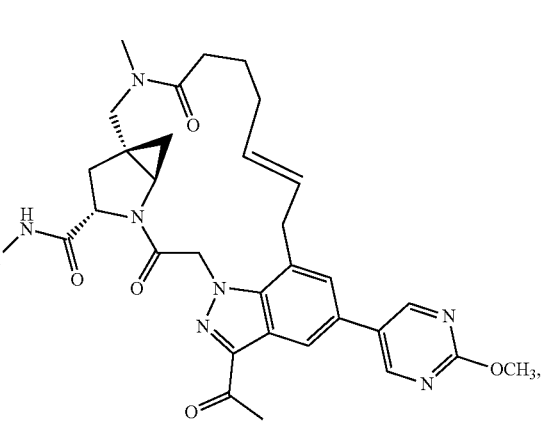

127
-continued
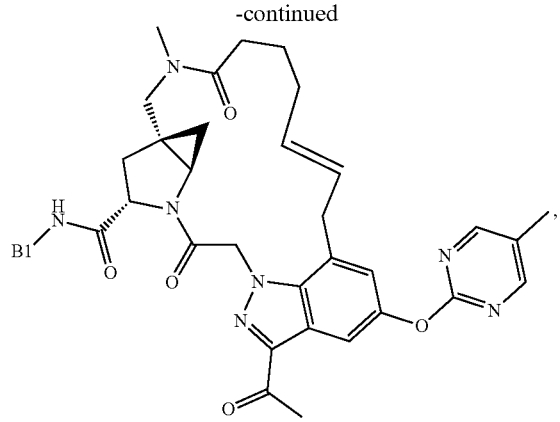
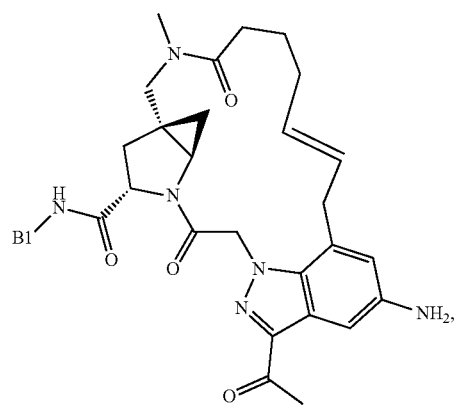
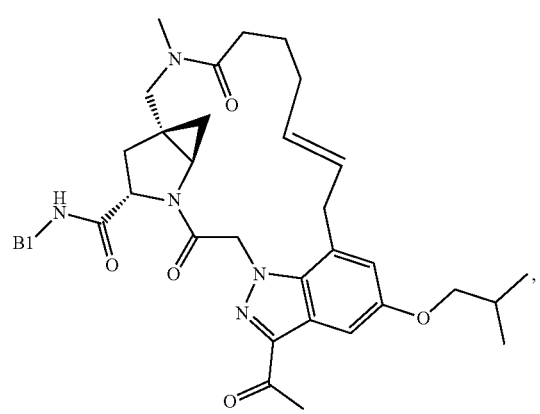
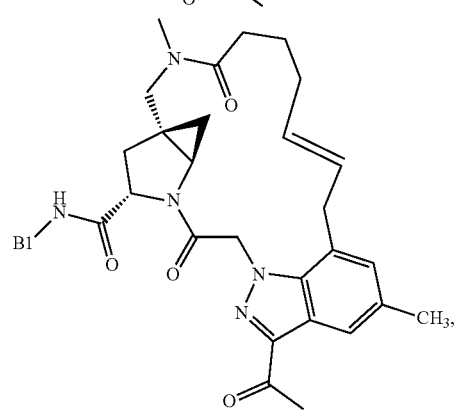
128
-continued
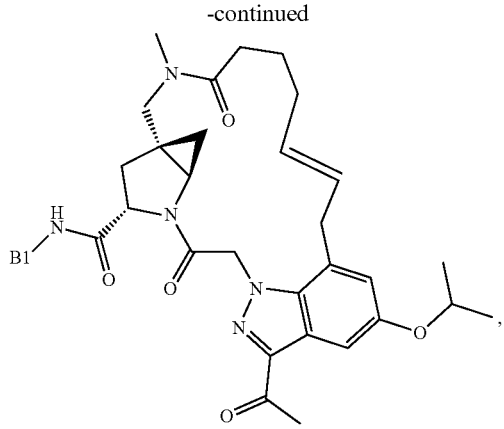
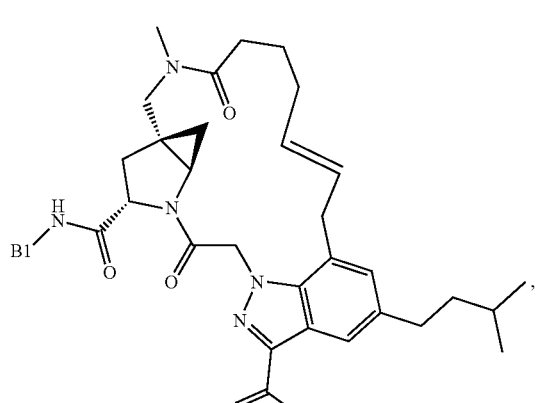
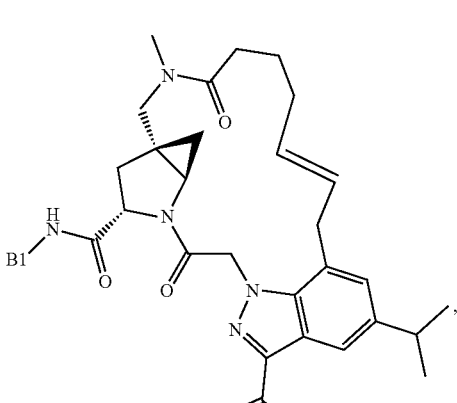
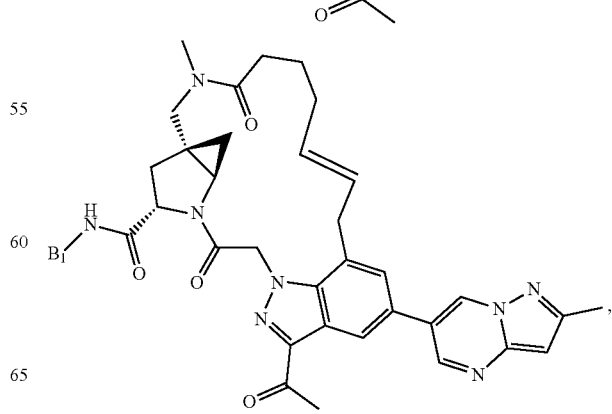

129
-continued
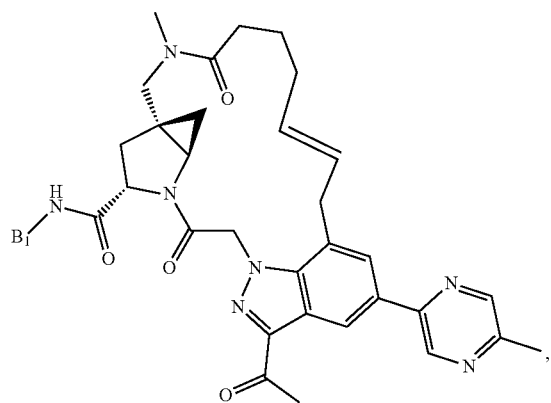
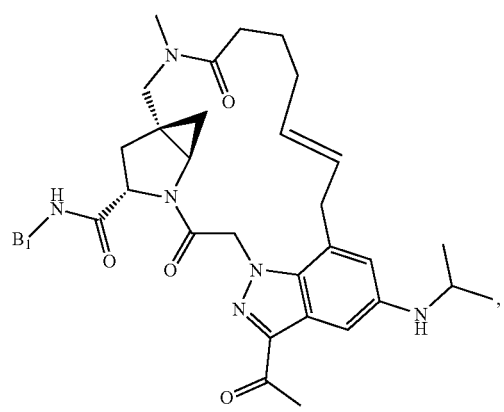
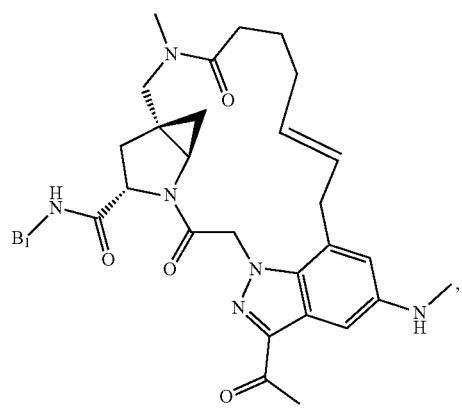
130
-continued
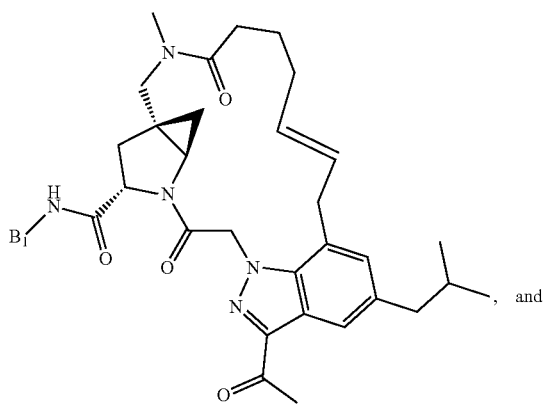, and
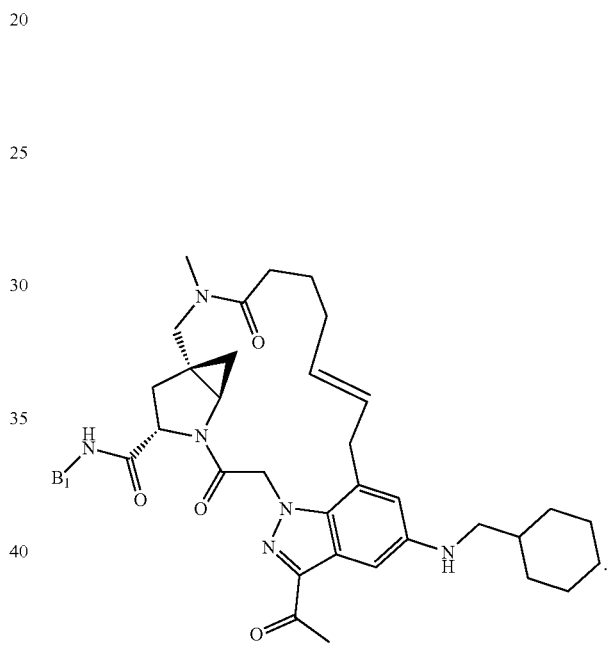.
In one embodiment, the compound of Formula II is selected from:
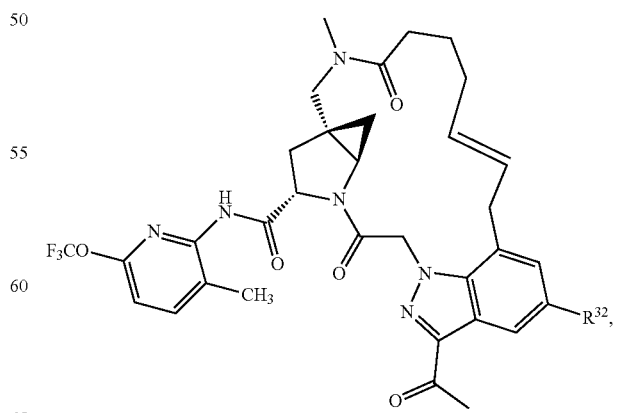

131
-continued
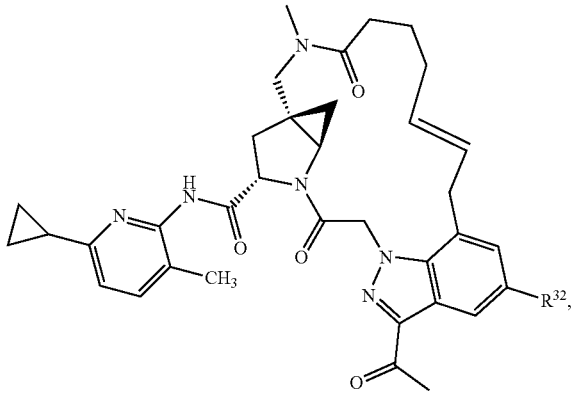
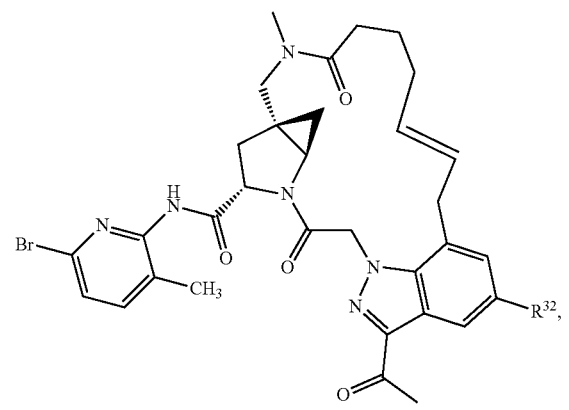
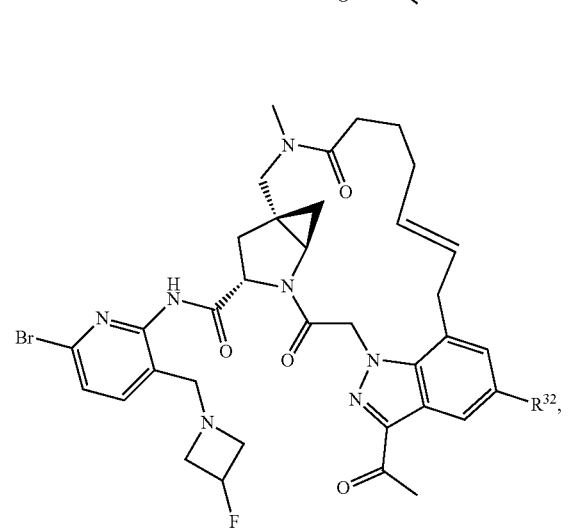
132
-continued
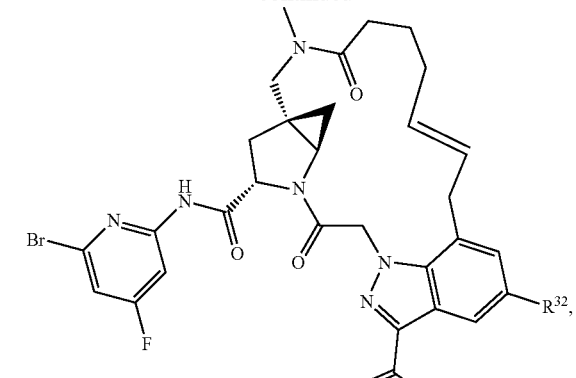
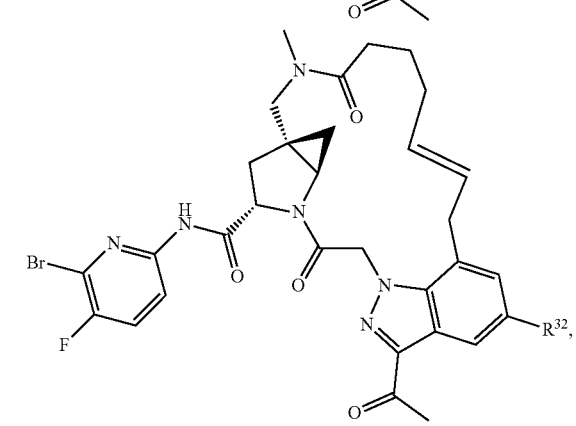
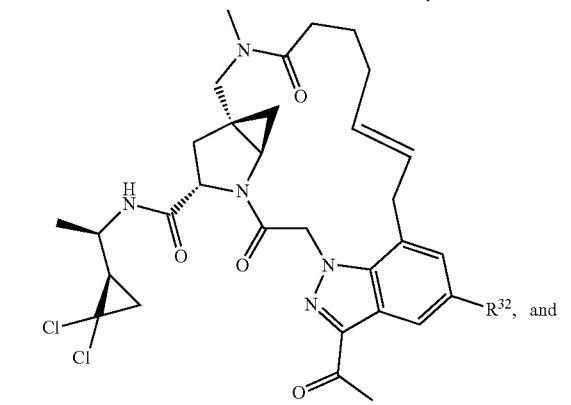
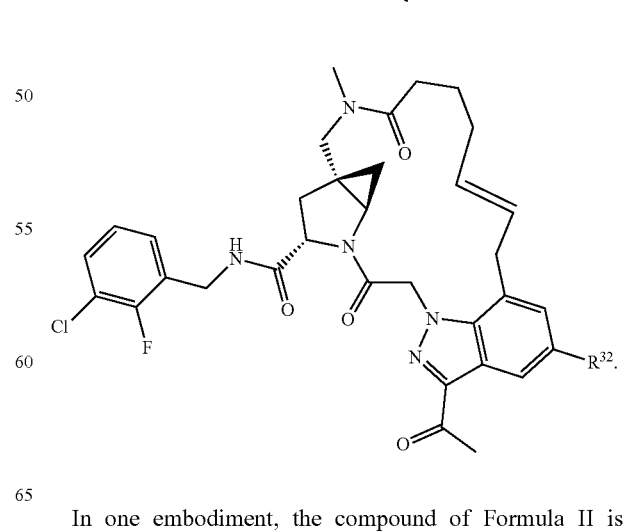
In one embodiment, the compound of Formula II is selected from:

133
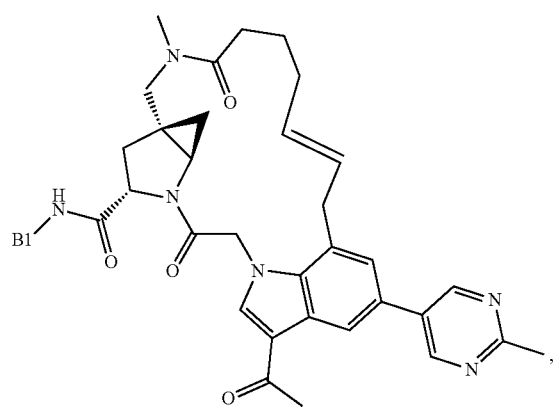
134
-continued
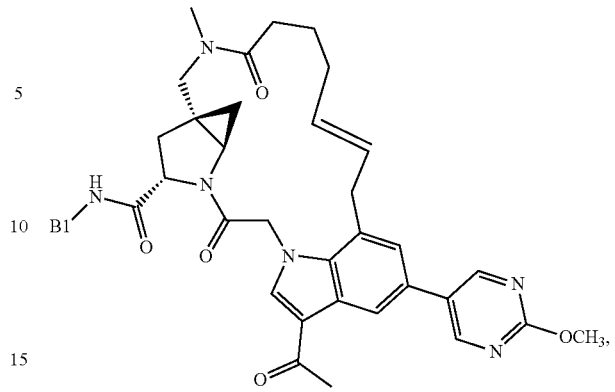
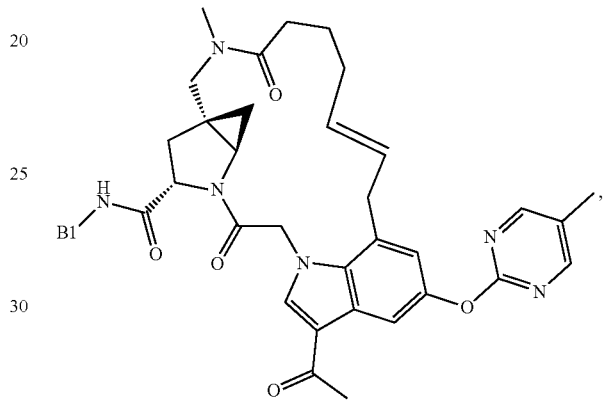
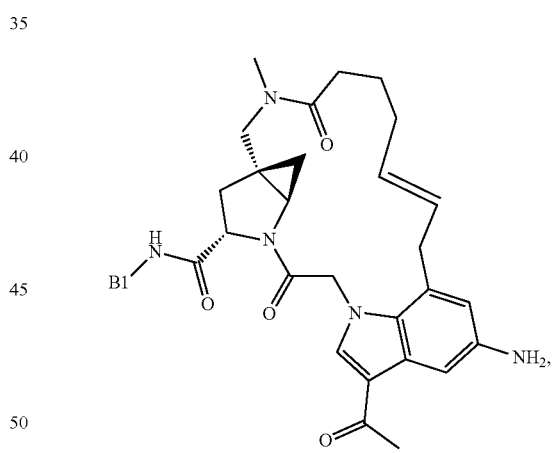
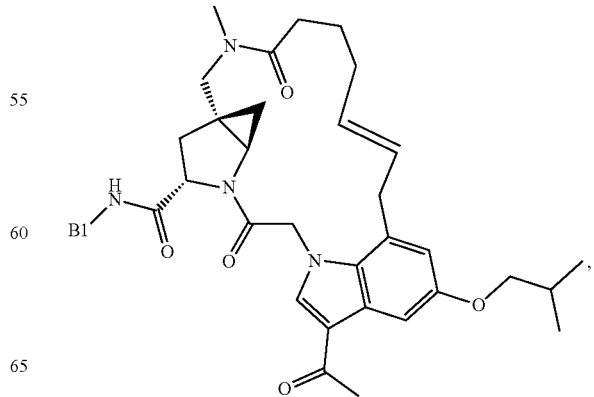

135 -continued
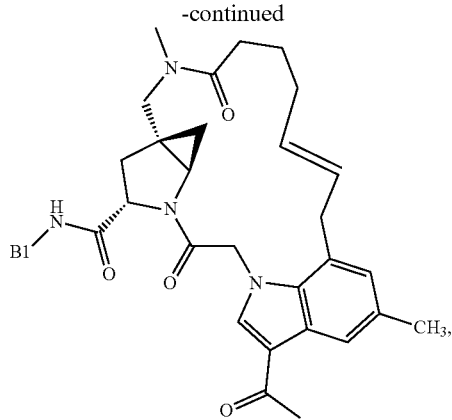
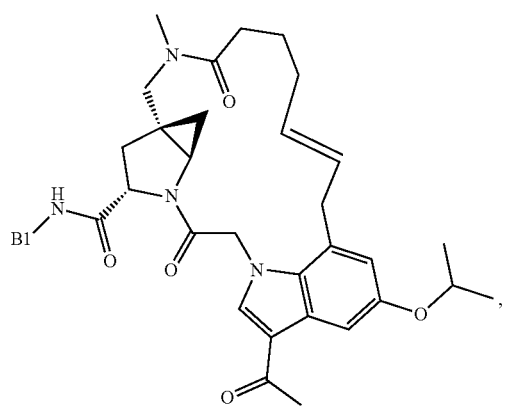
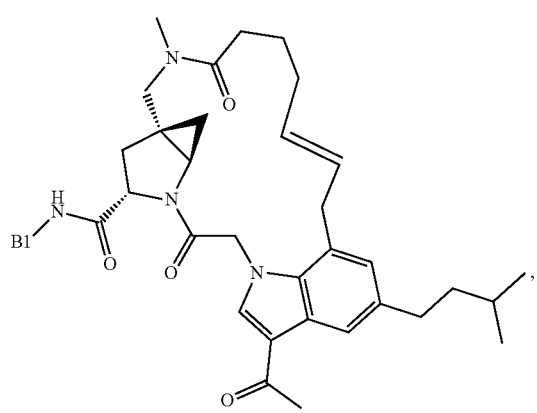
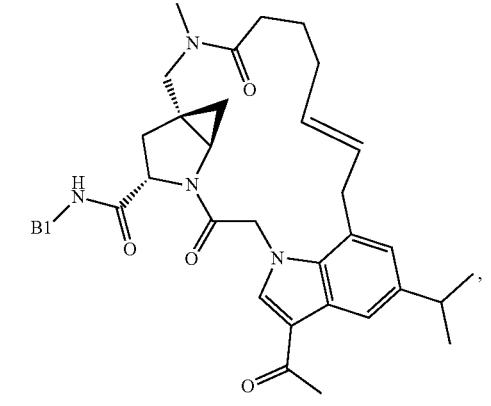
136 -continued
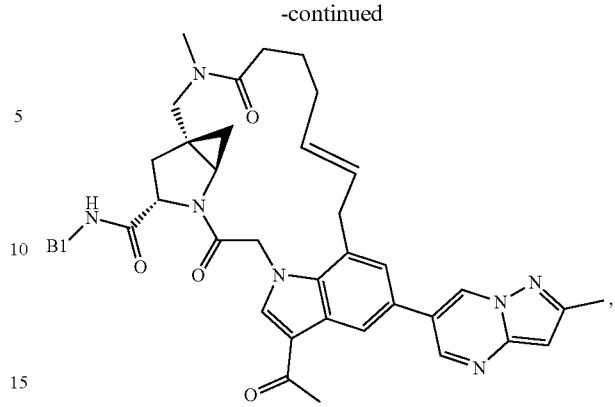
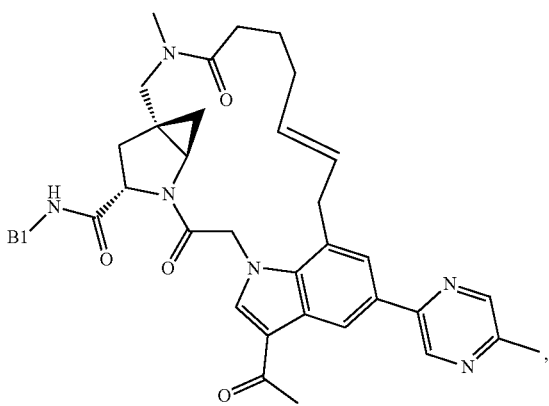
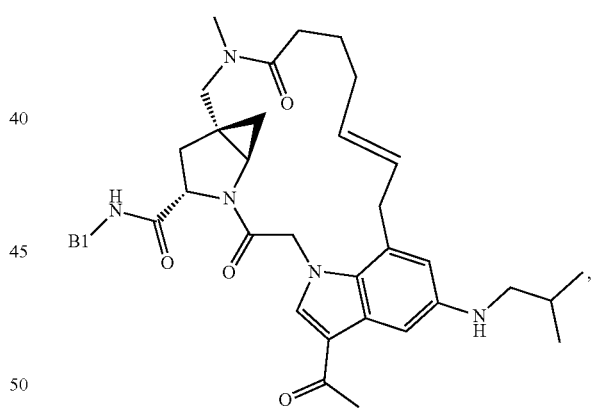
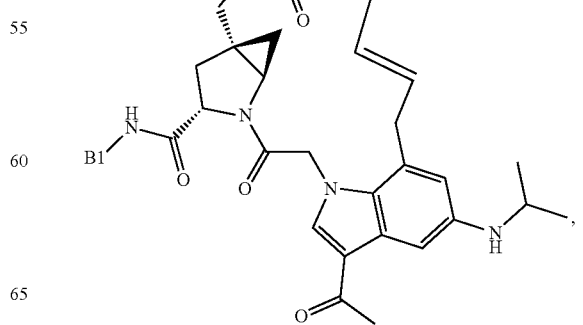

137
-continued
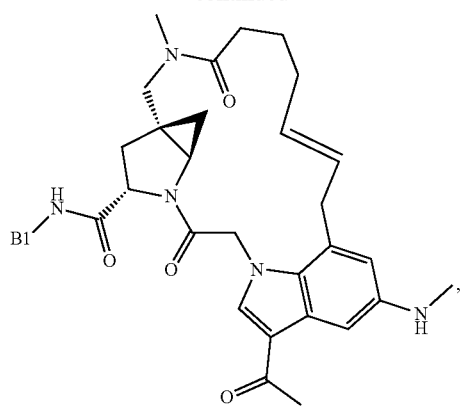
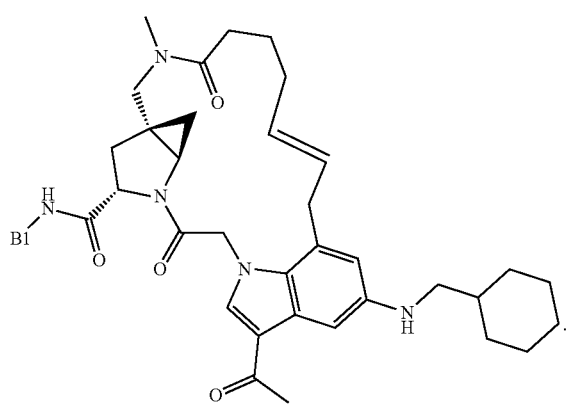
In one embodiment, the compound of Formula II is selected from:
138
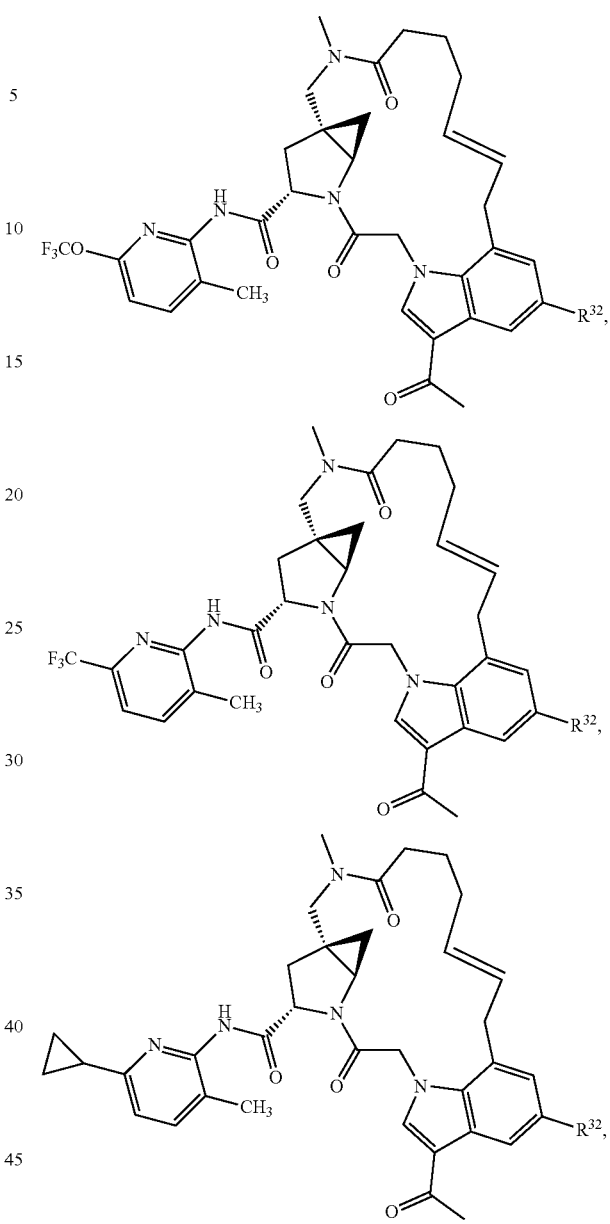
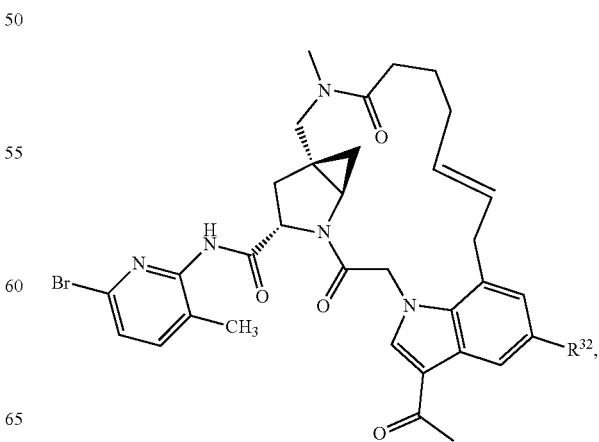

-continued
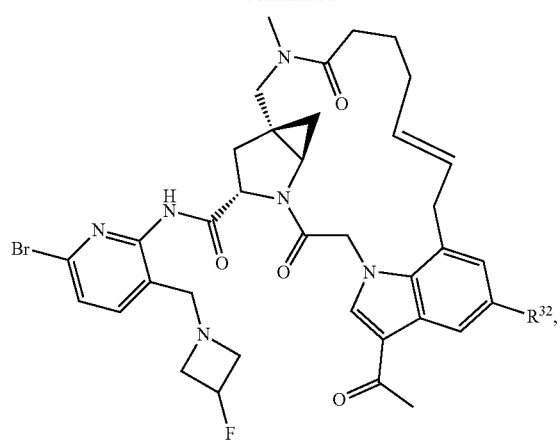
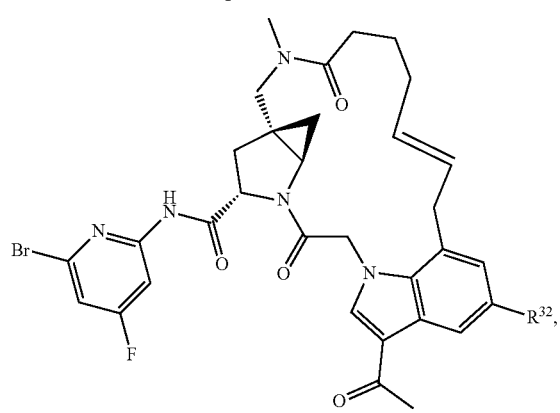
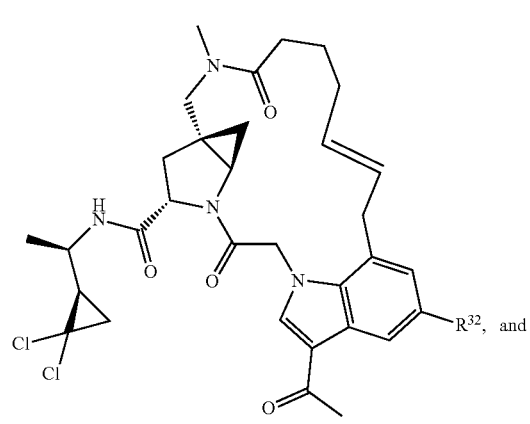
-continued
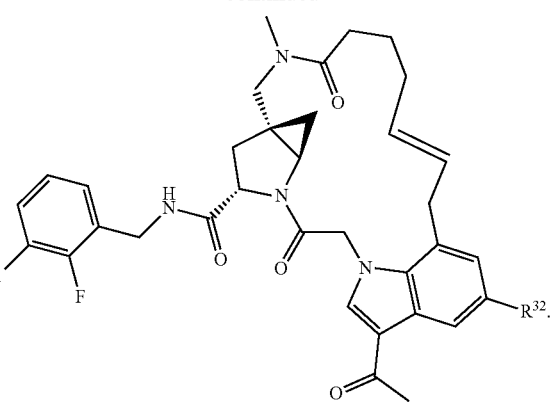
In one embodiment, the compound of Formula II is selected from:
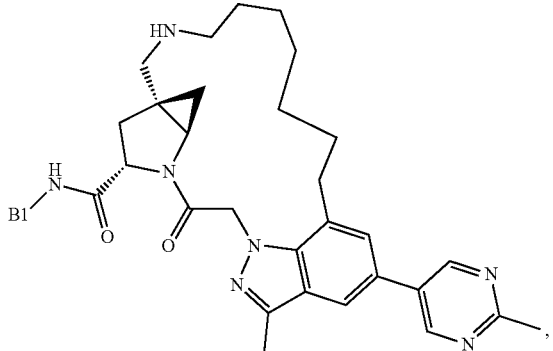
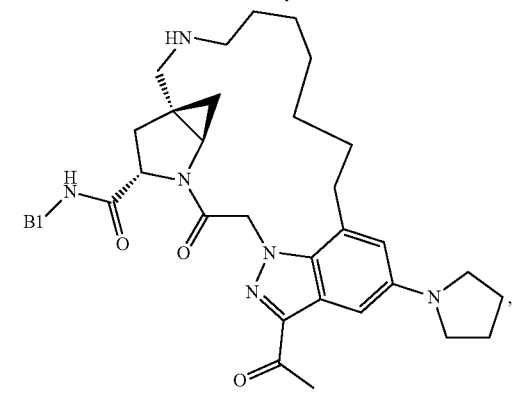
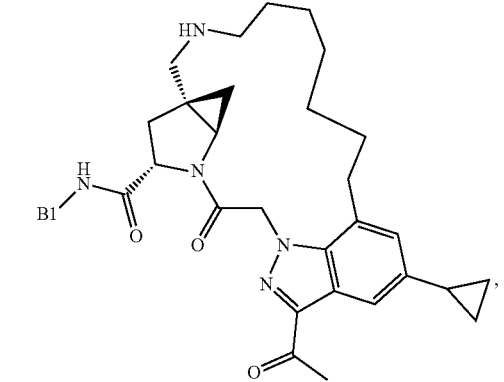

-continued
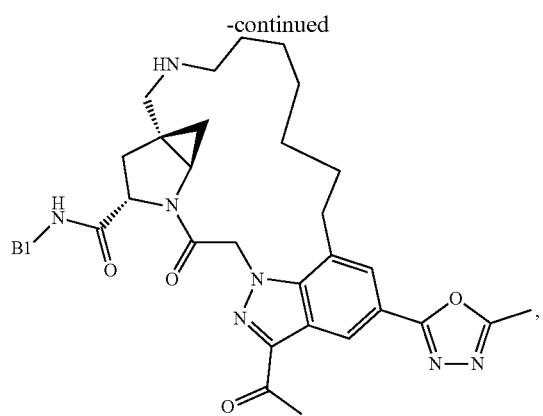
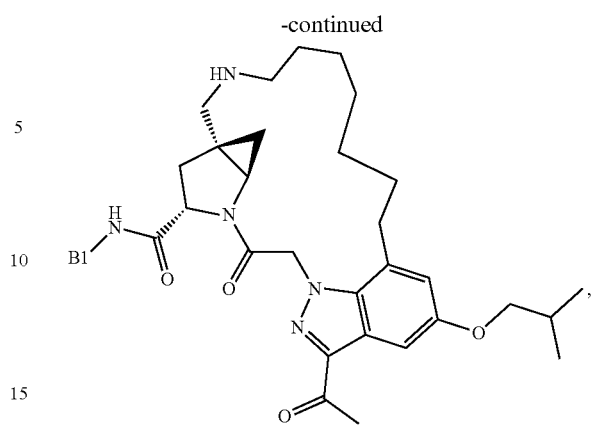
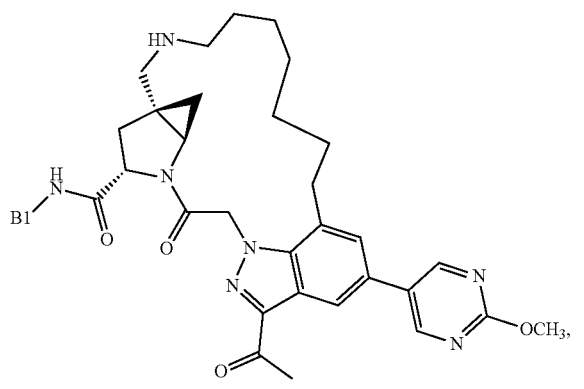
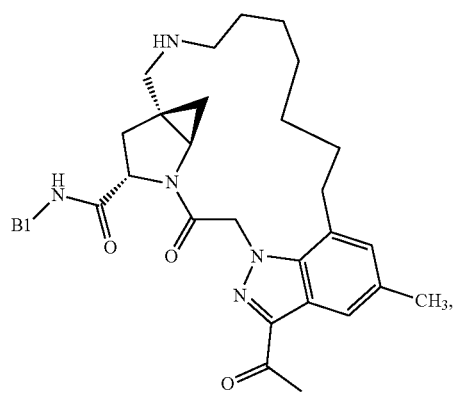
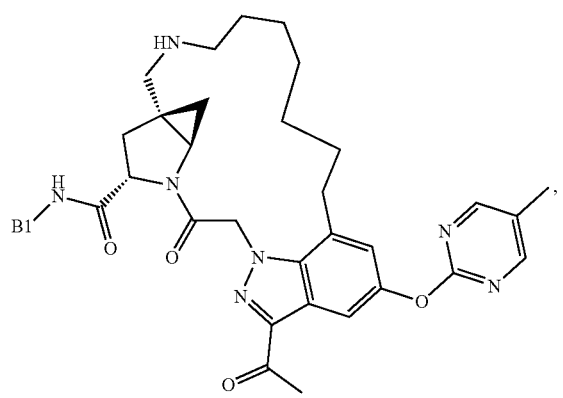
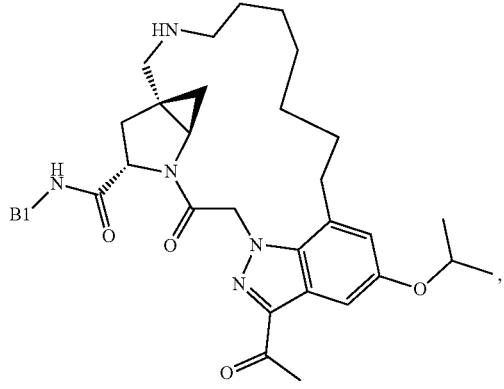
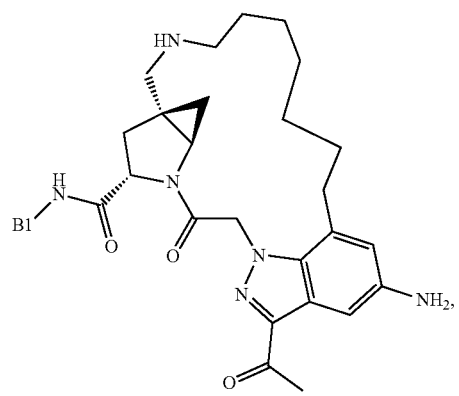
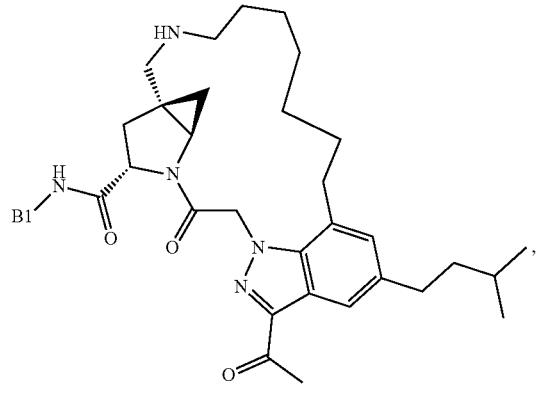

-continued
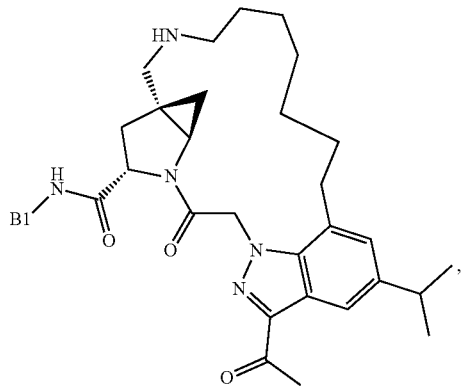,
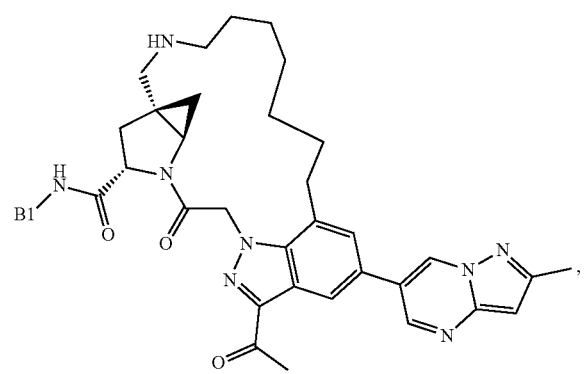,
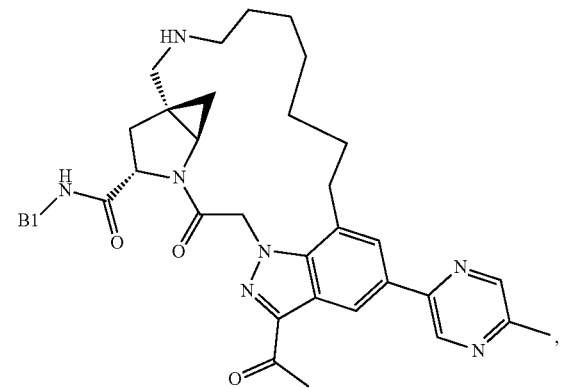,
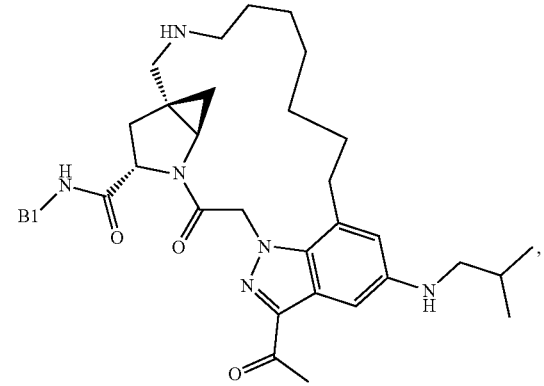,
-continued
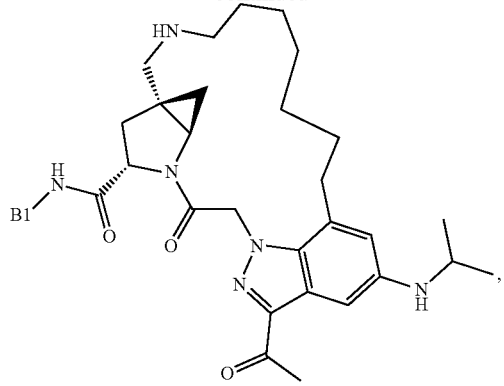,
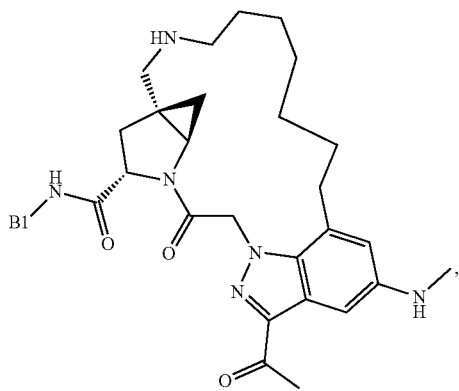,
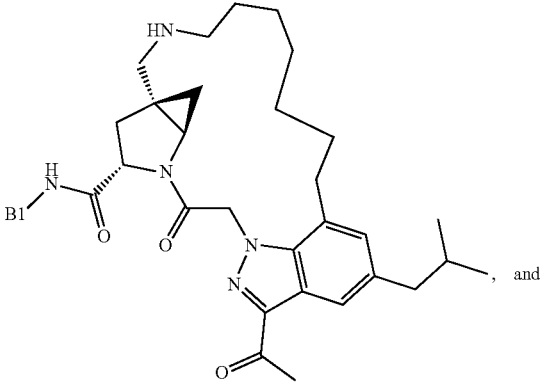, and
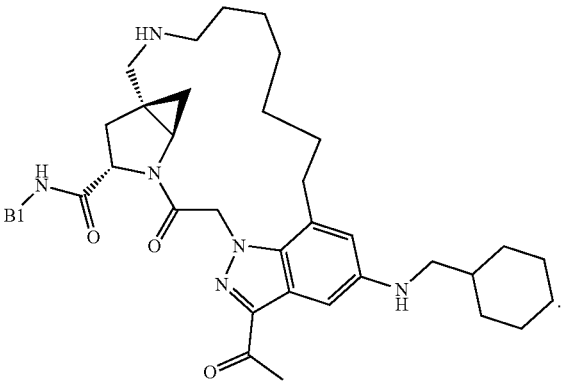.
In one embodiment, the compound of Formula II is selected from:

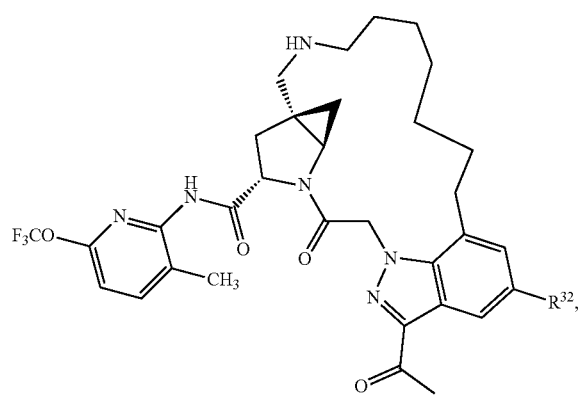
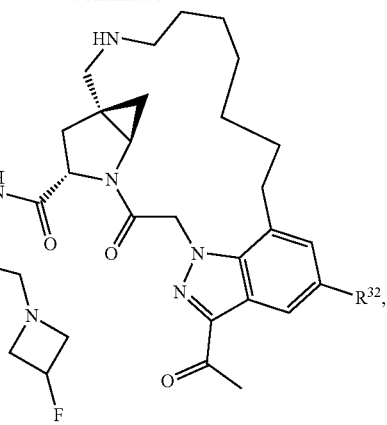
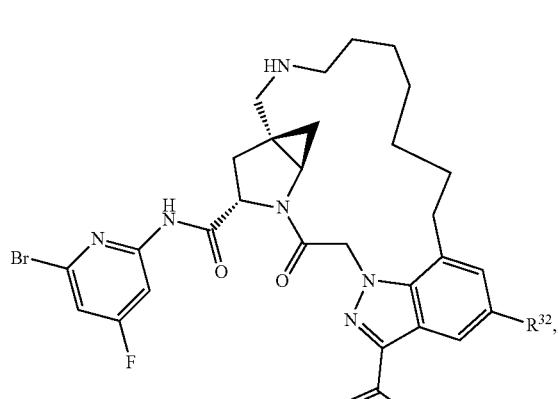
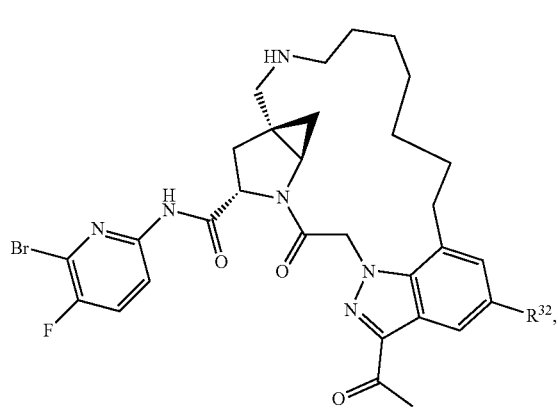
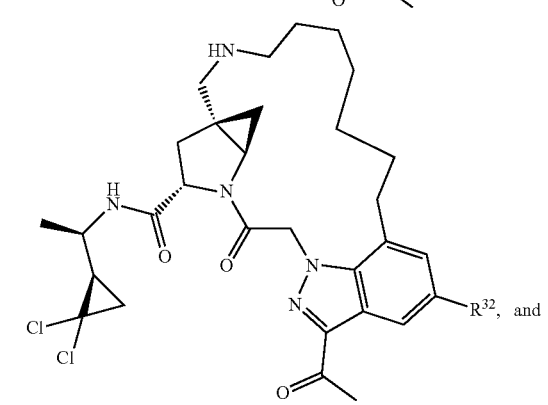

147
-continued
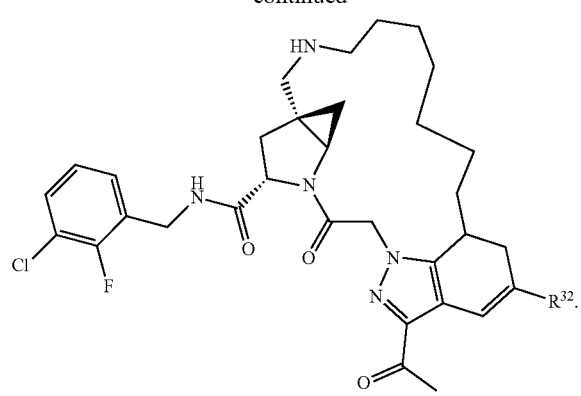
In one embodiment, the compound of Formula II is selected from:
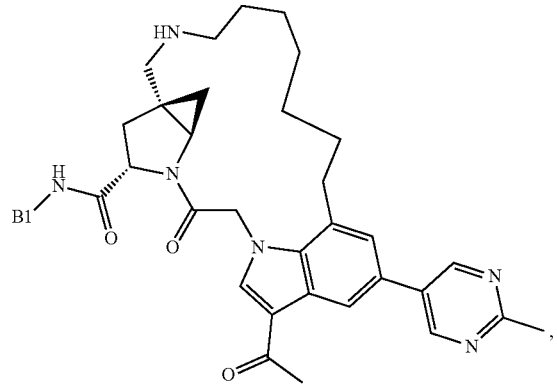
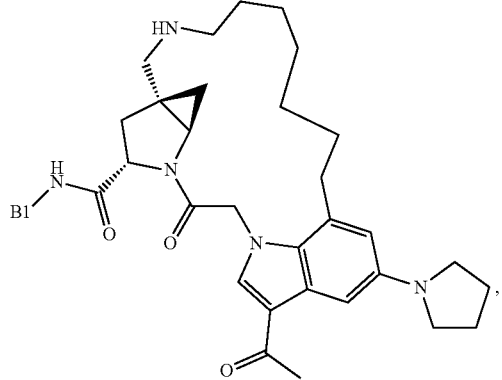
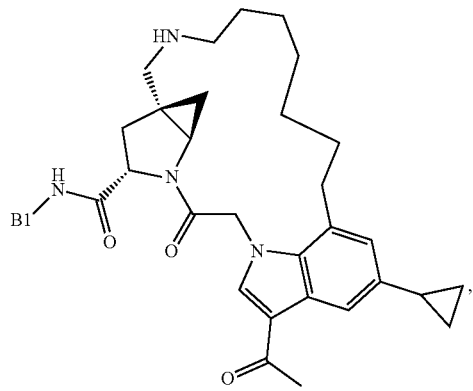
148
-continued
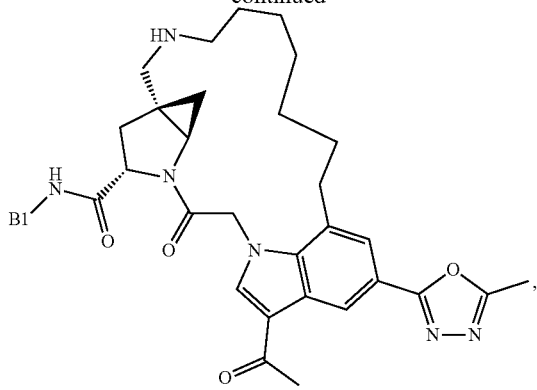
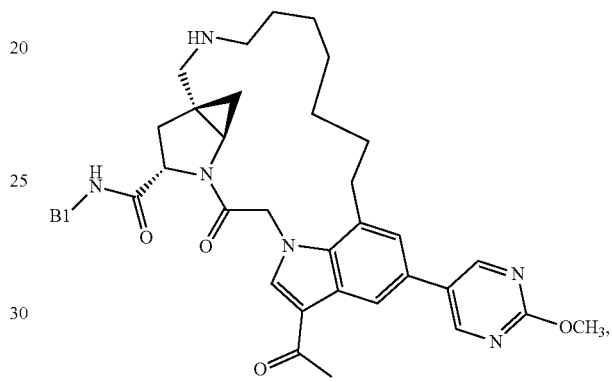
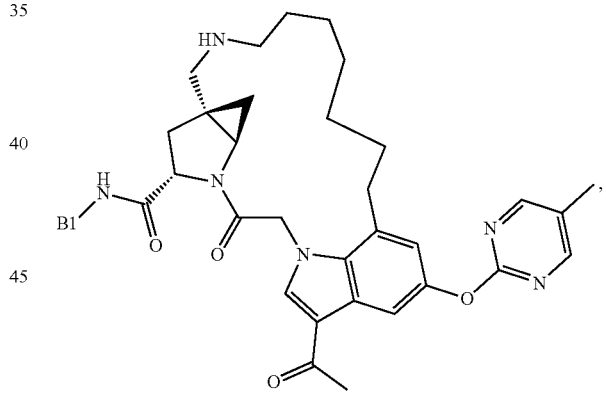
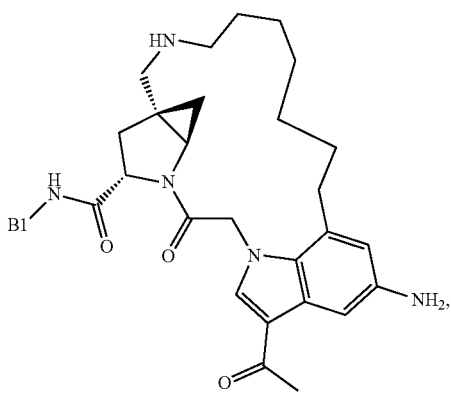

149
-continued
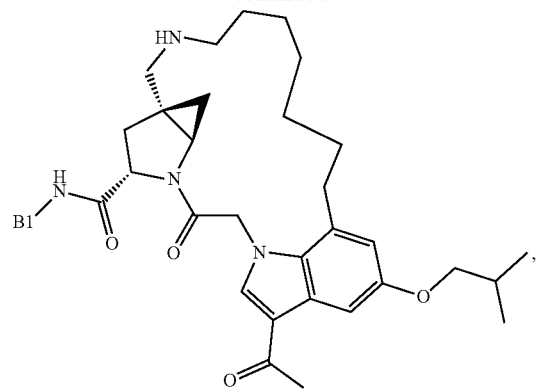
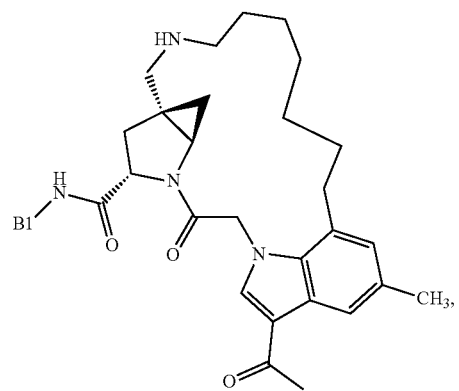
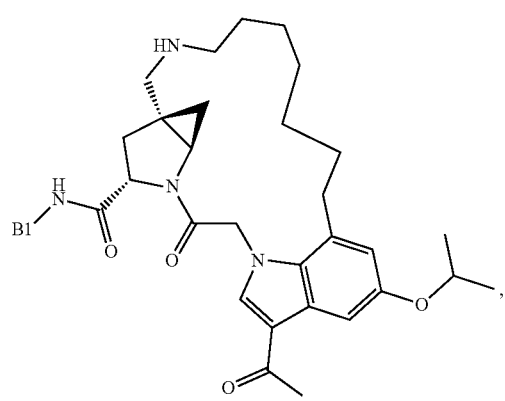
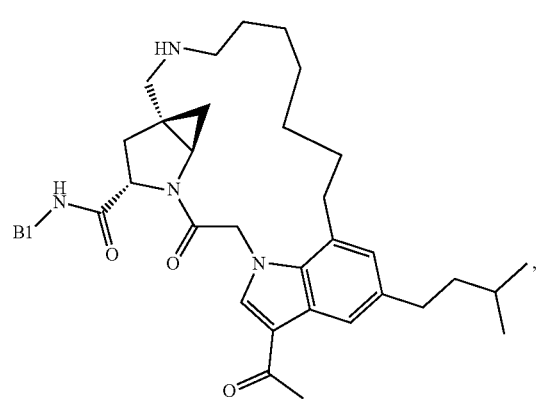
150
-continued
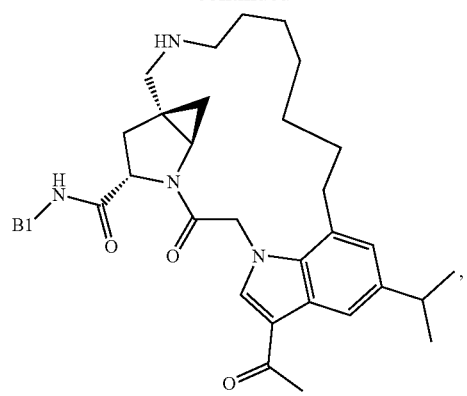
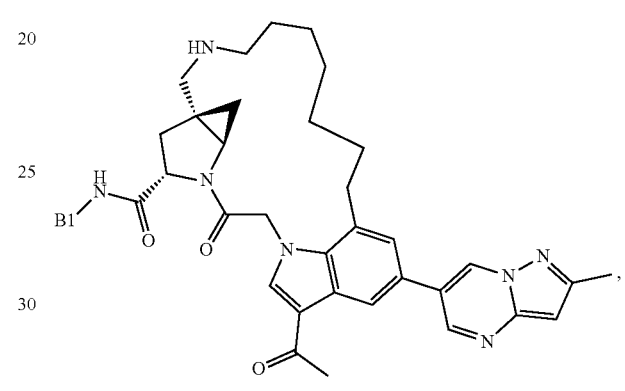
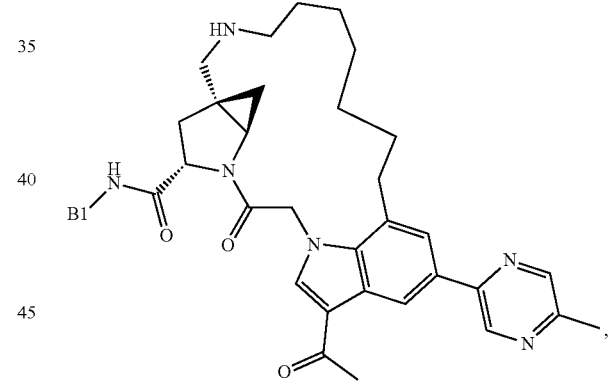
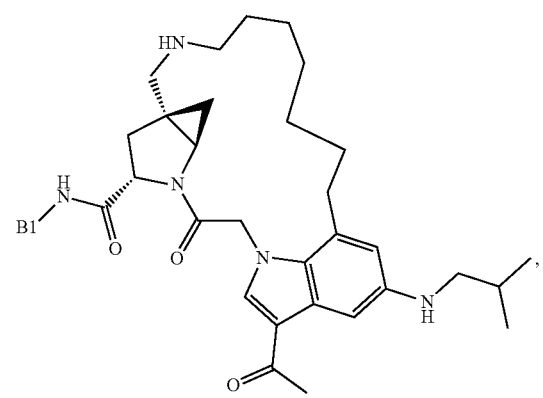

151
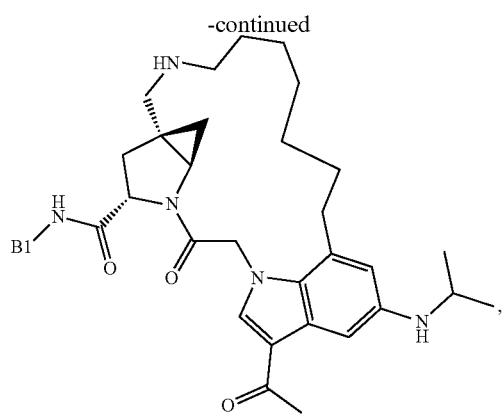
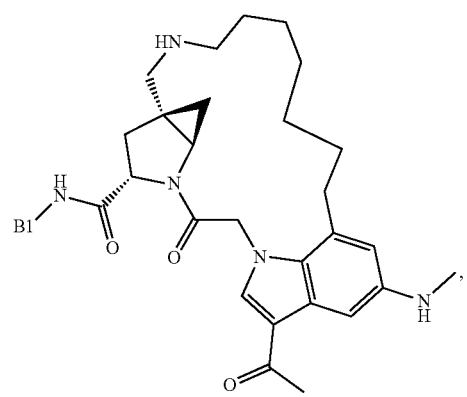
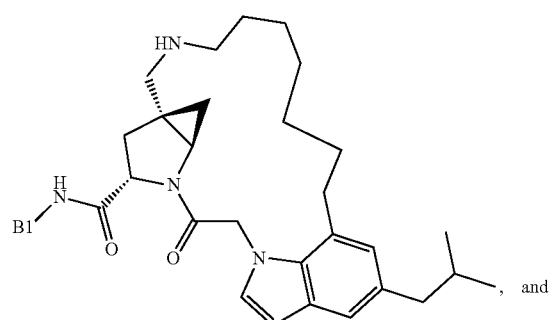, and
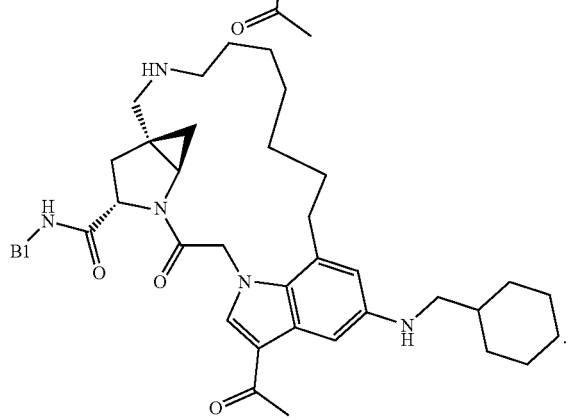.
In one embodiment, the compound of Formula II is selected from:
152
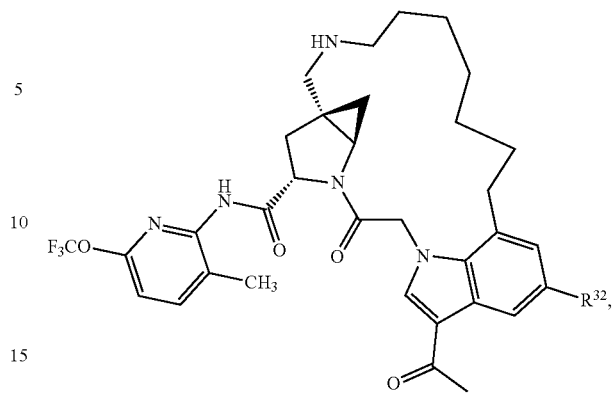
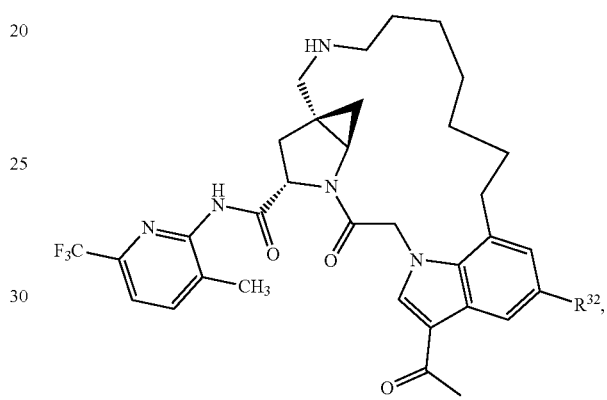
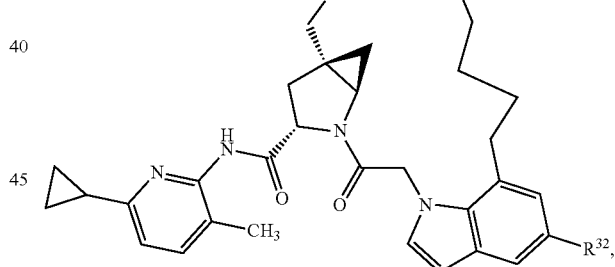
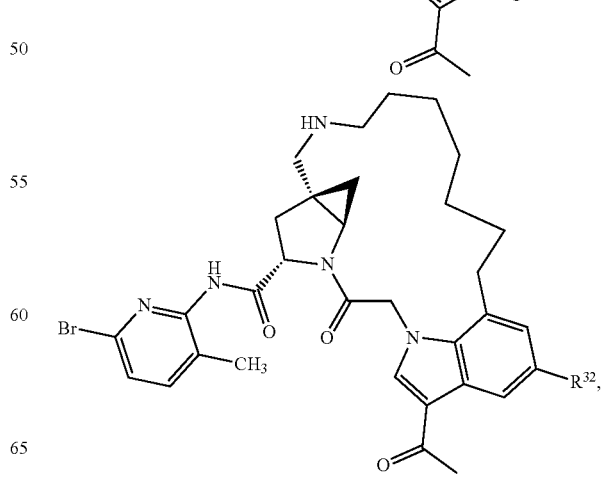

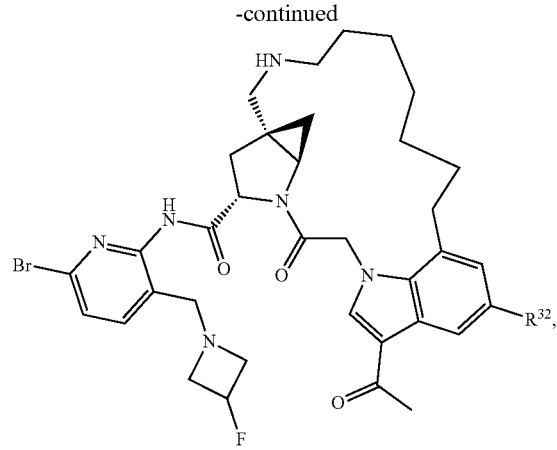
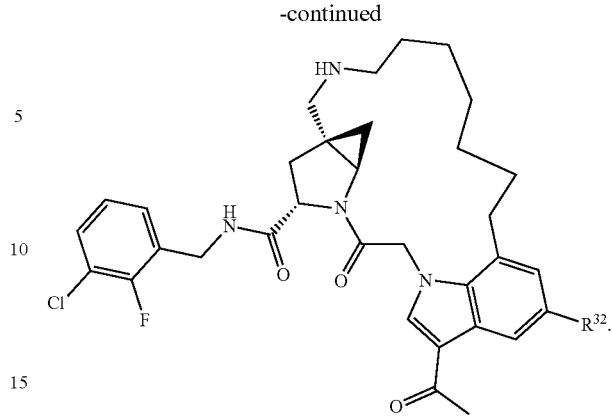
In one embodiment, the compound of Formula II is selected from:
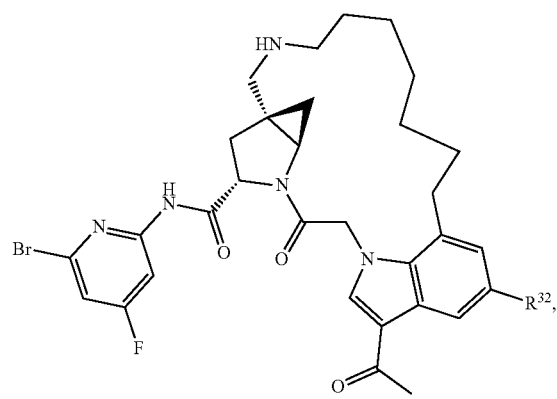
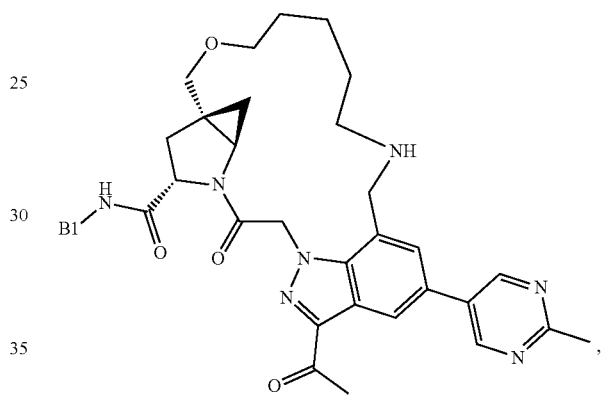
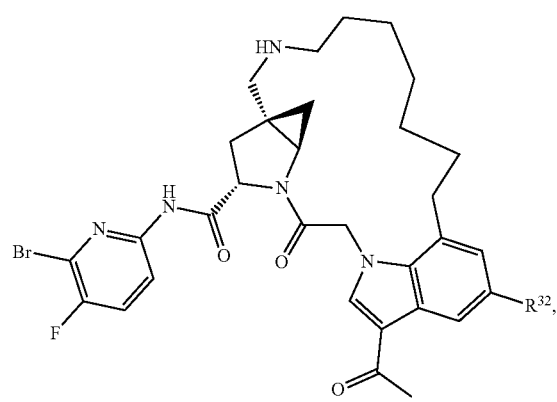
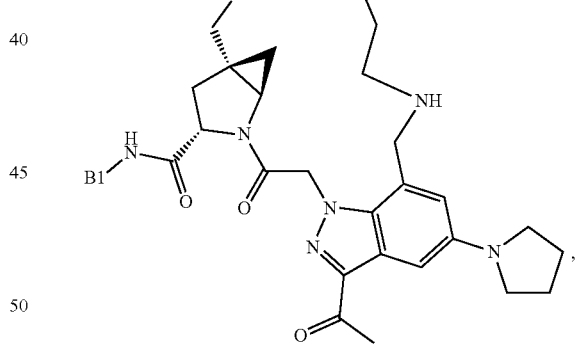
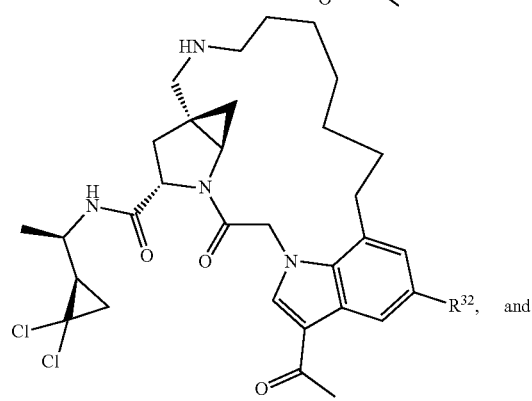
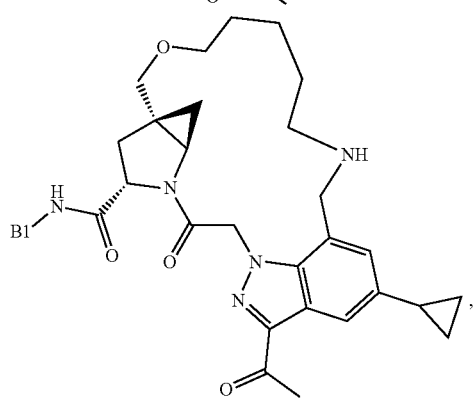

155
-continued
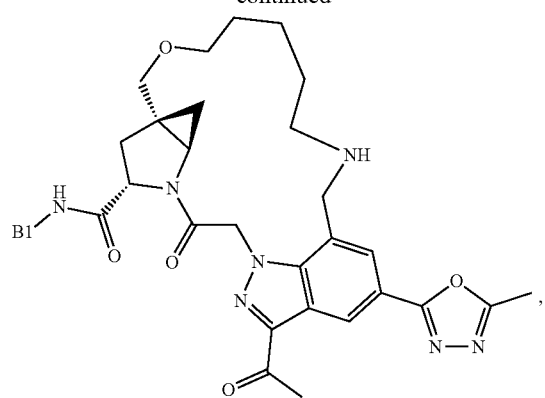
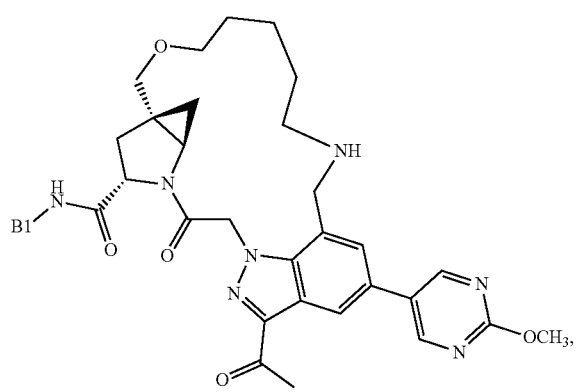
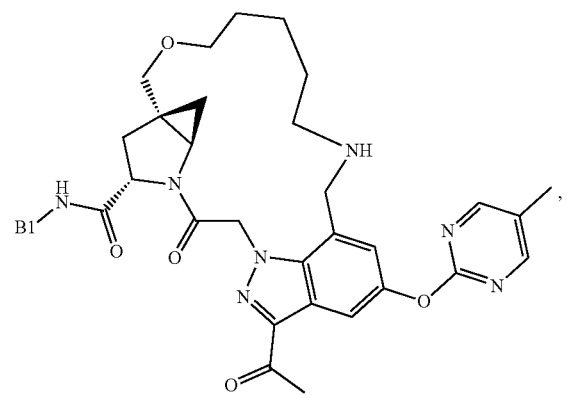
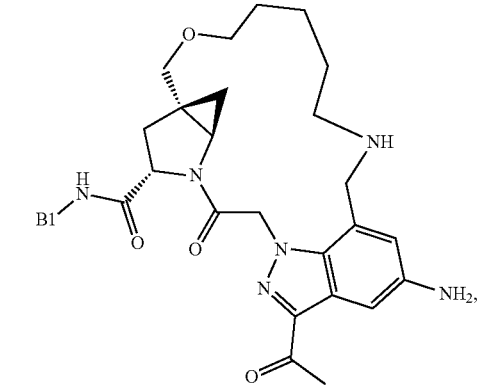
156
-continued
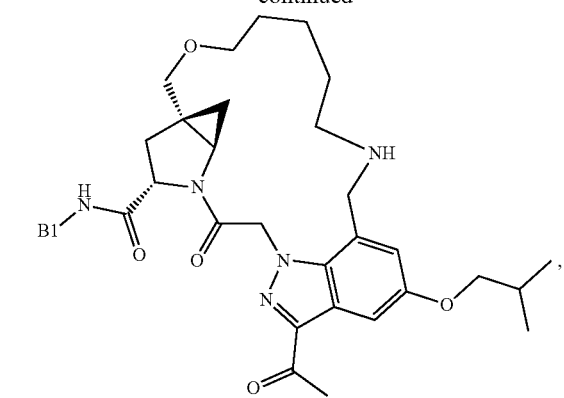
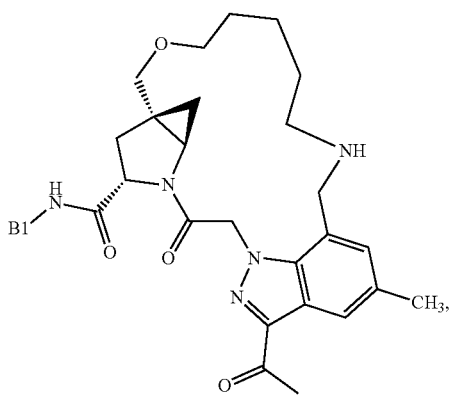
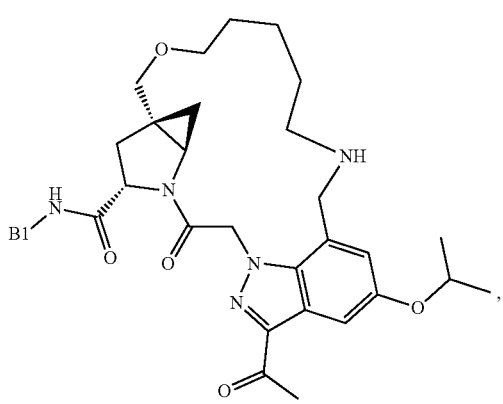
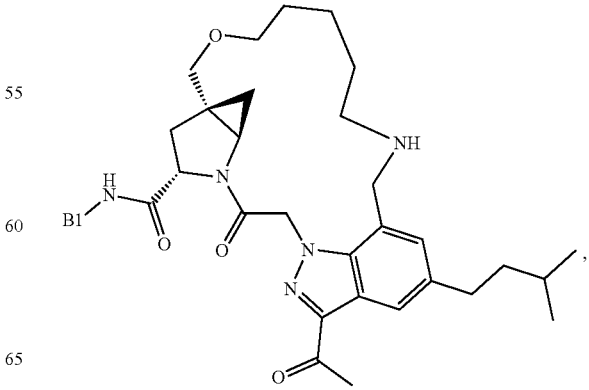

157
-continued
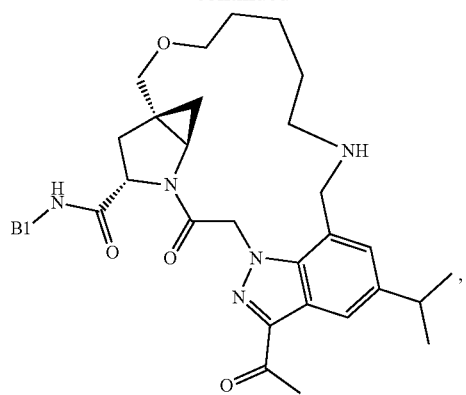
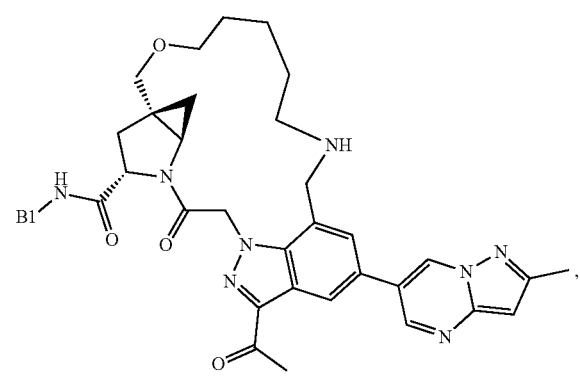
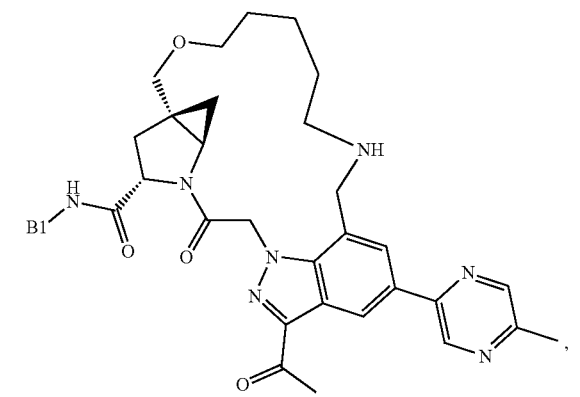
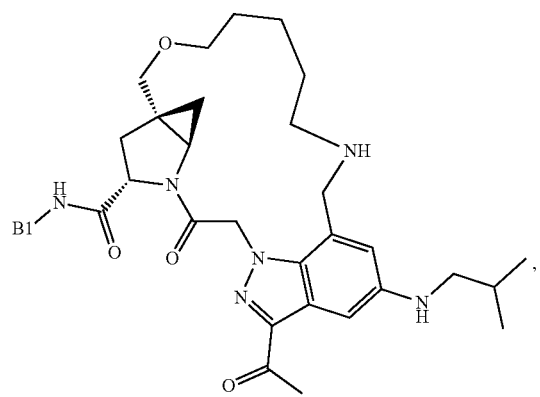
158
-continued
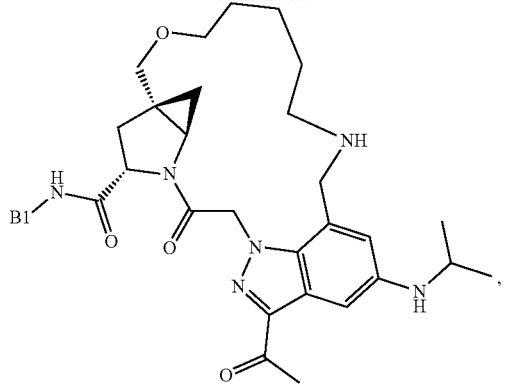
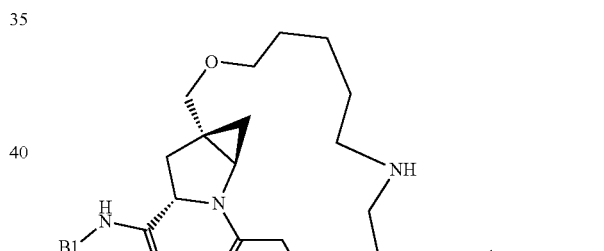
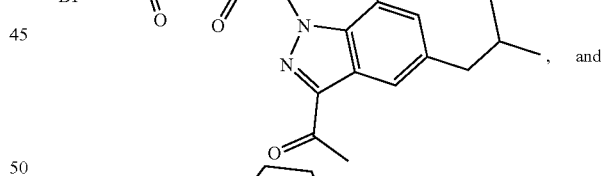
, and
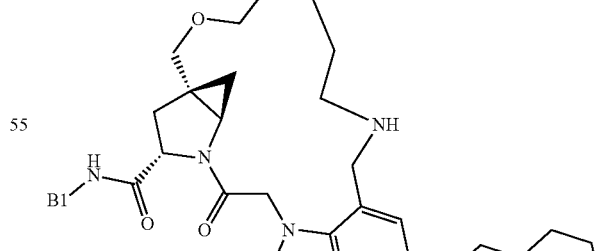
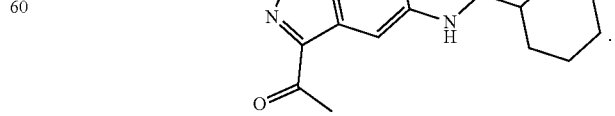
.
In one embodiment, the compound of Formula II is selected from:

159
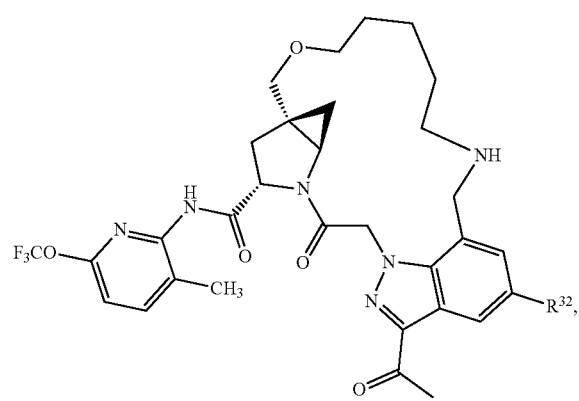
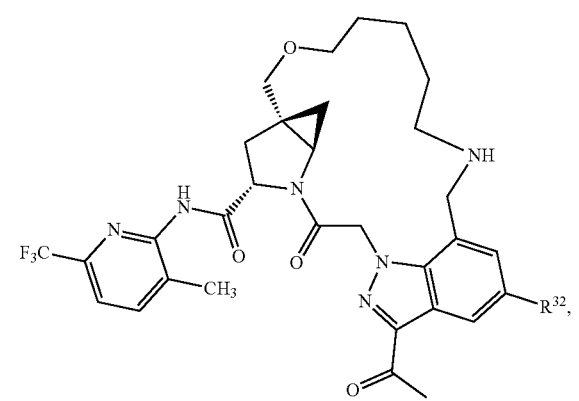
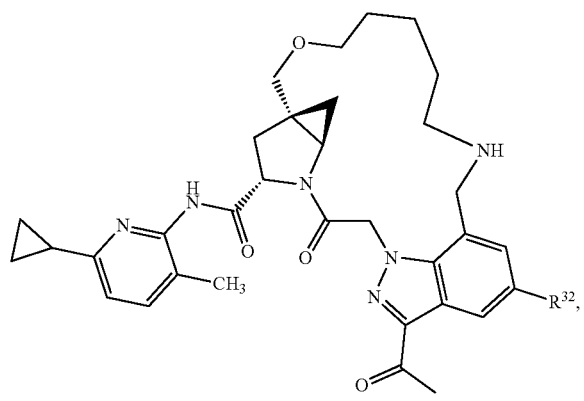
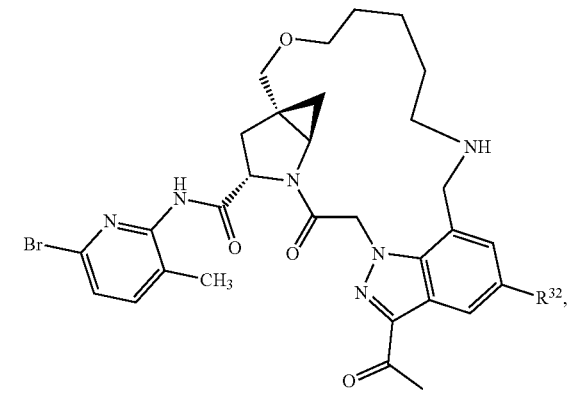
160
-continued
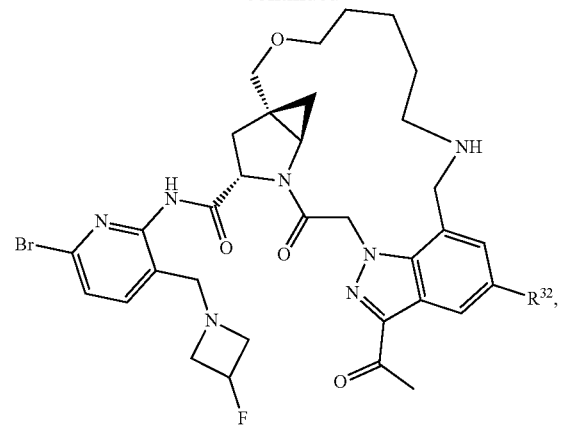
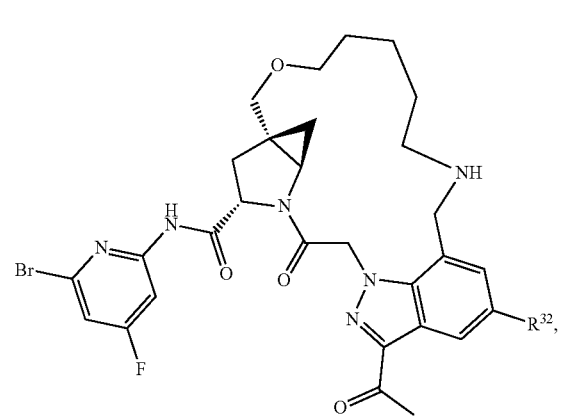
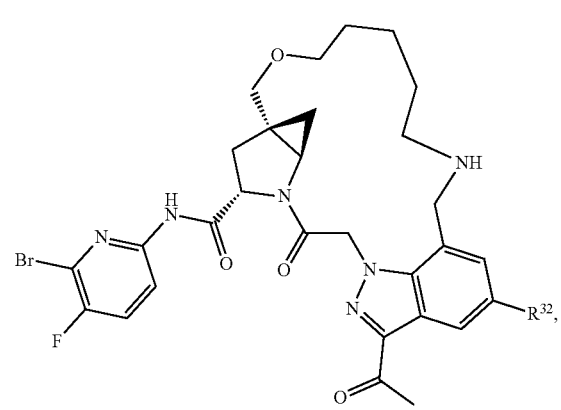
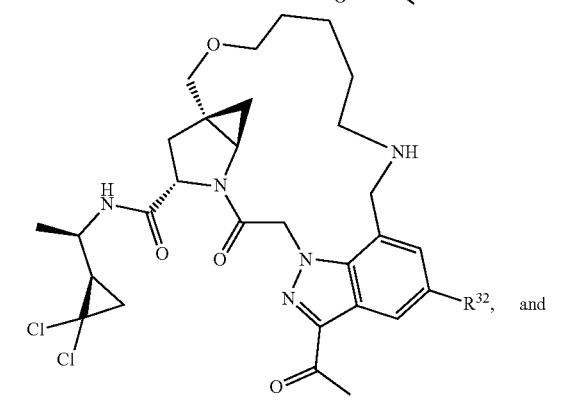, and

161
-continued
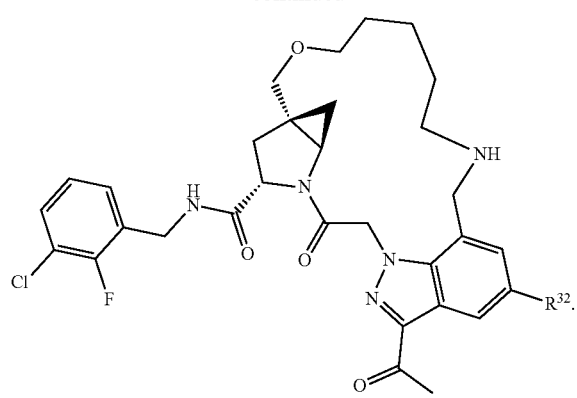
In one embodiment, the compound of Formula II is selected from:
162
-continued
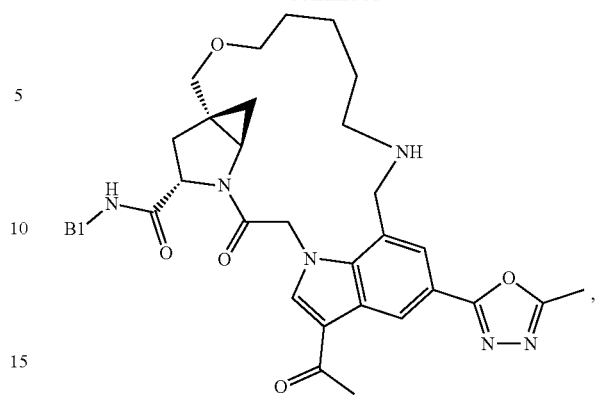
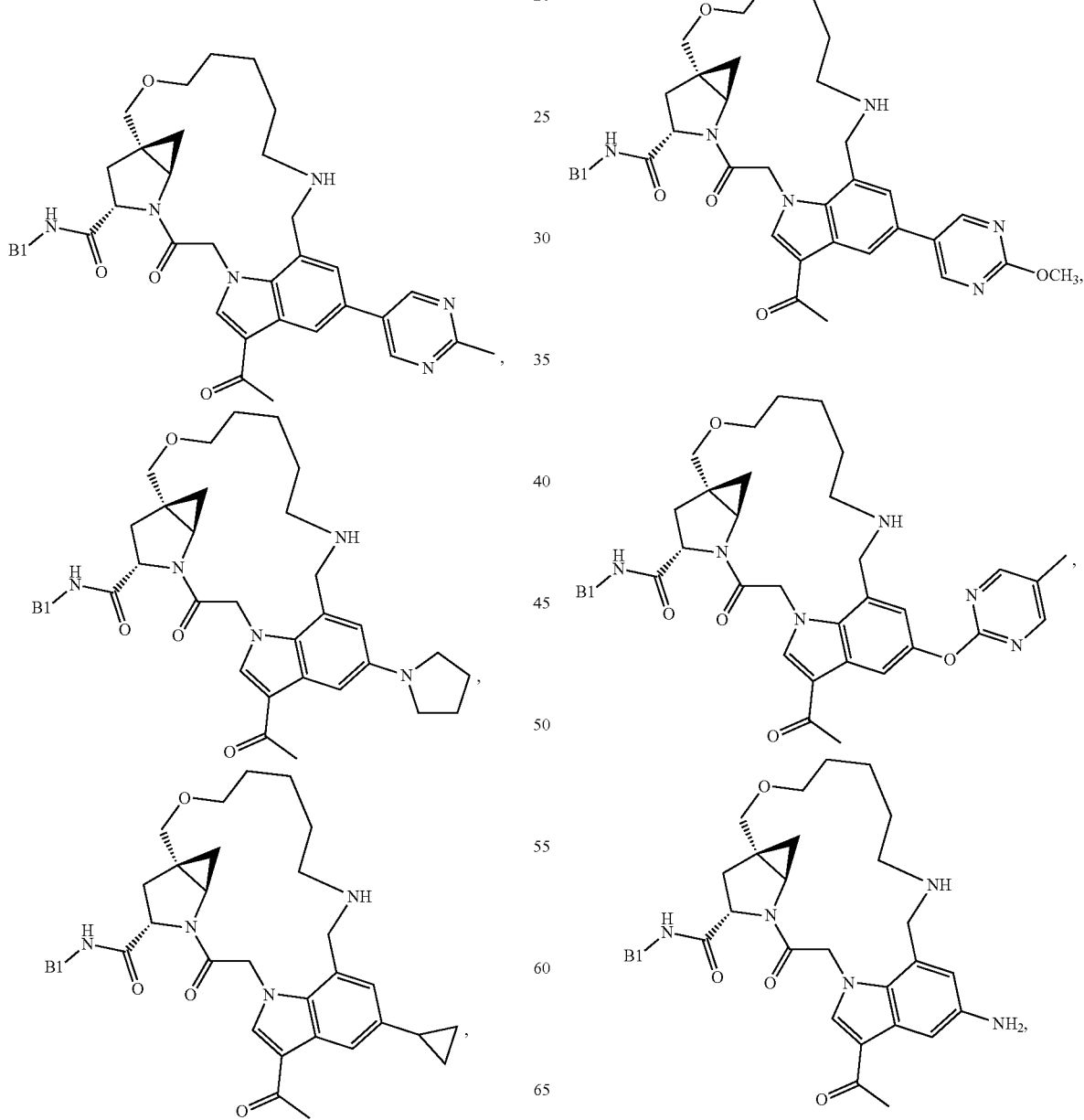

163
-continued
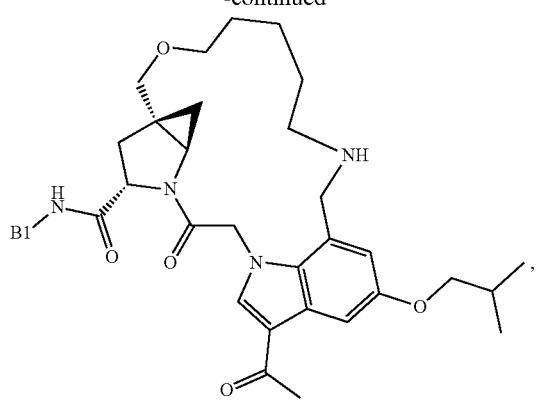
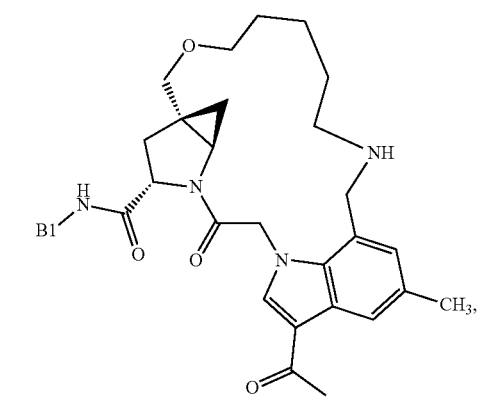
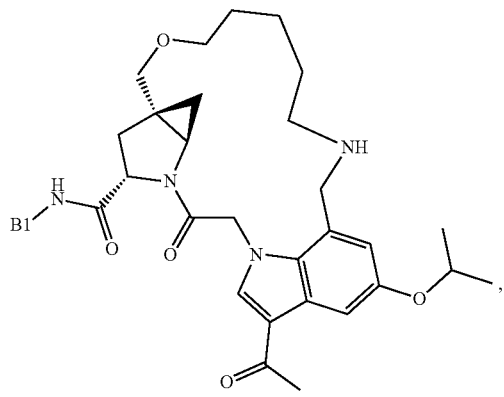
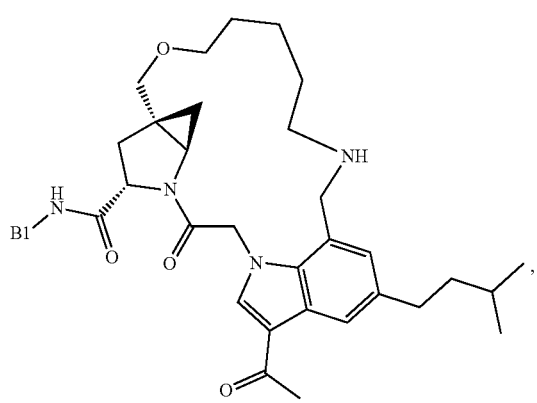
164
-continued
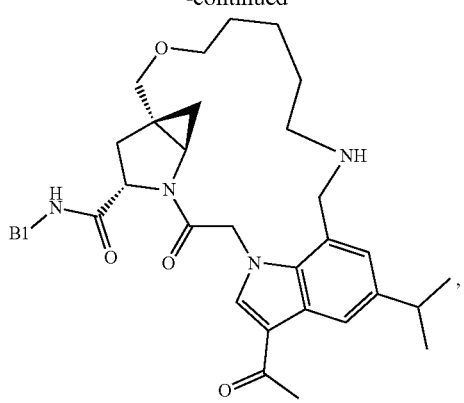
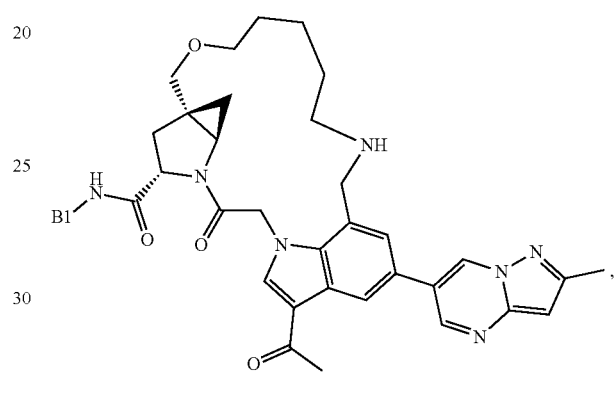
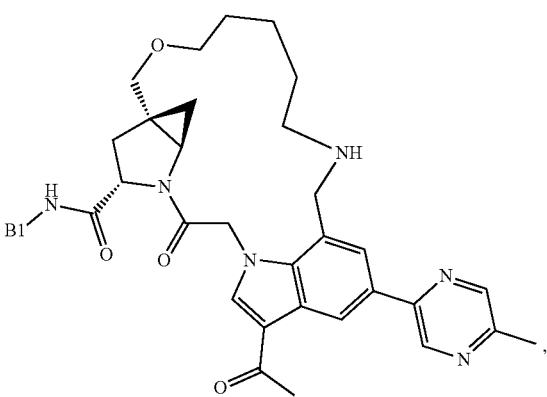
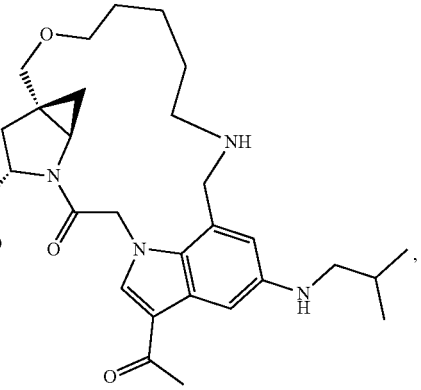

-continued
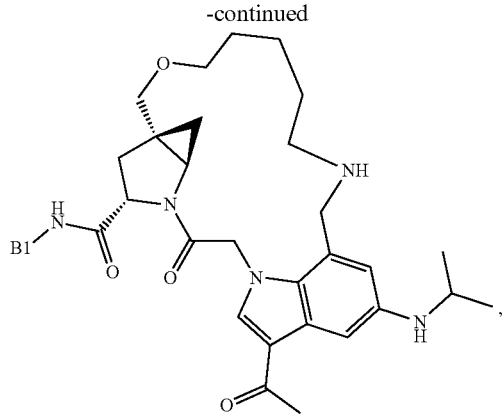
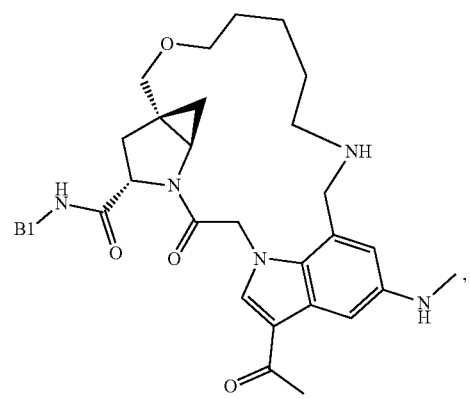
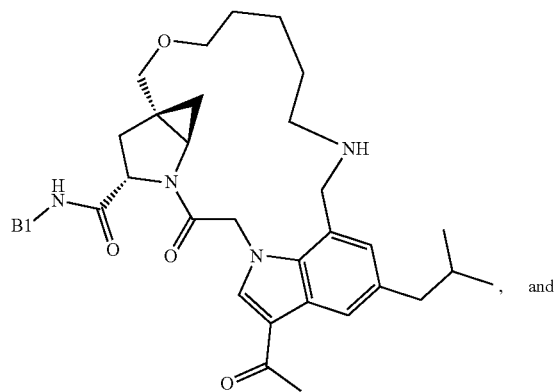
, and
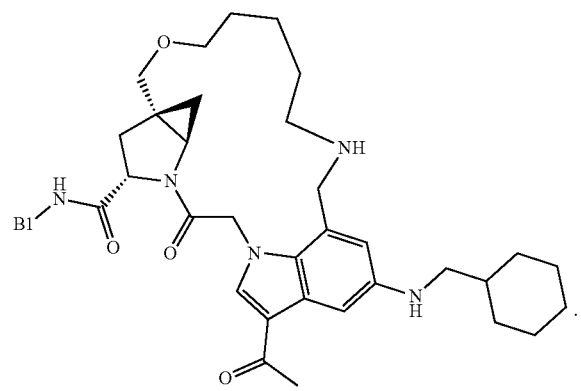
In one embodiment, the compound of Formula II is selected from:
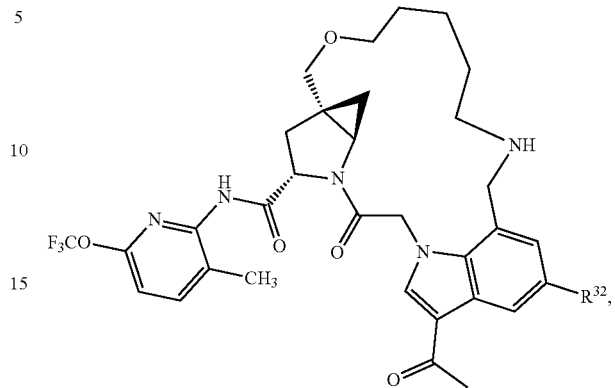
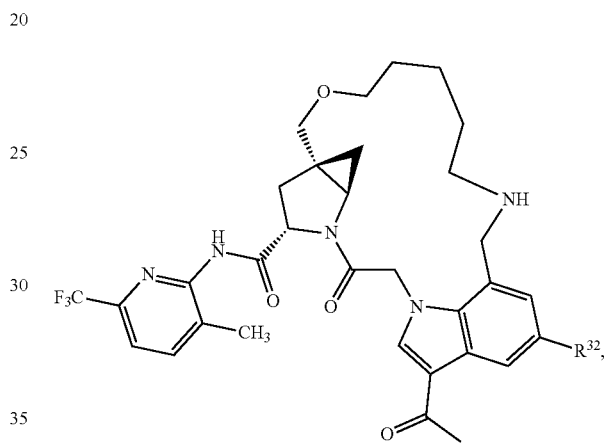
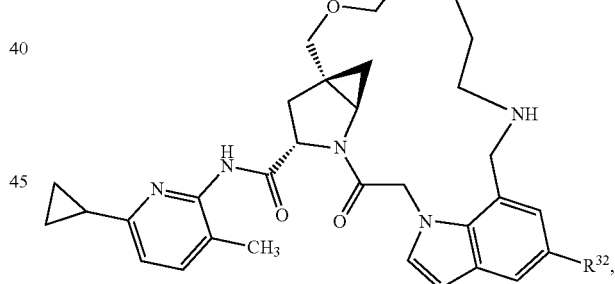
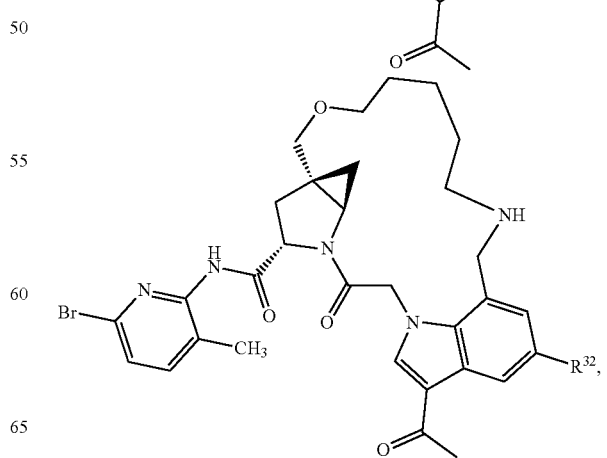

167
-continued
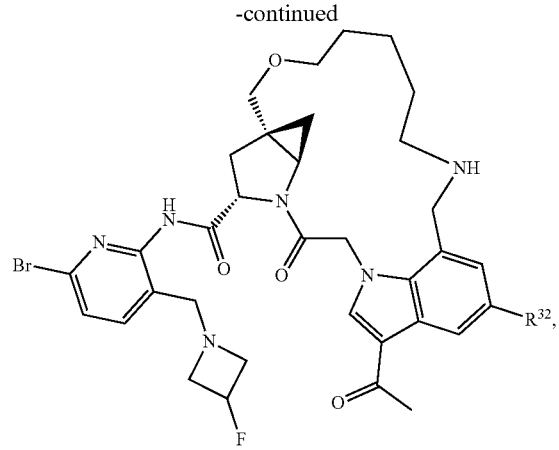
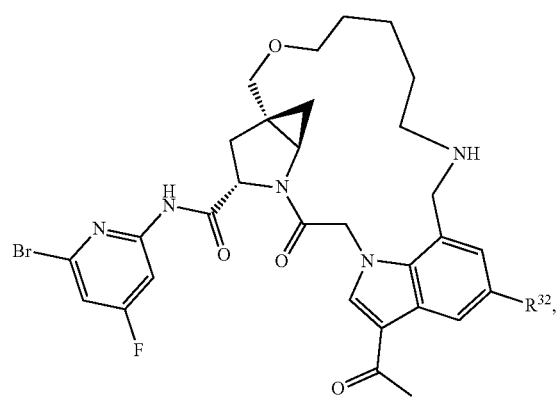
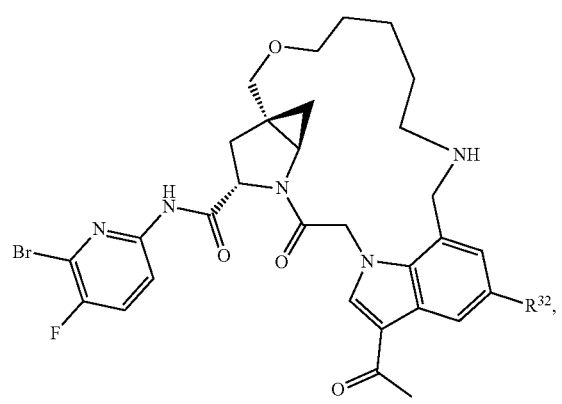
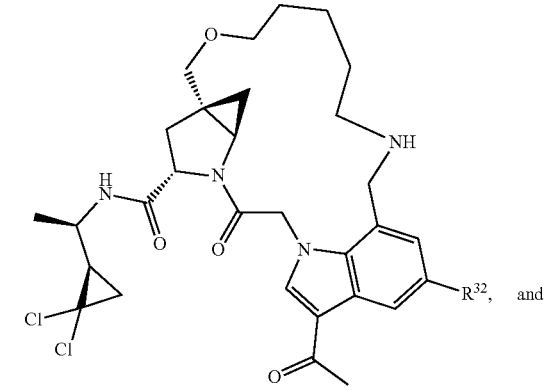
168
-continued
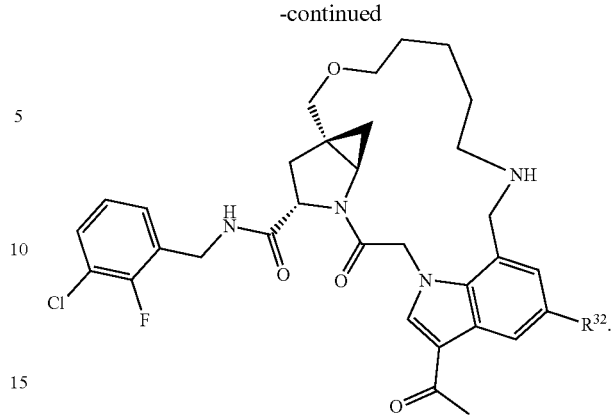
In one embodiment, the compound of Formula II is selected from:

169
-continued
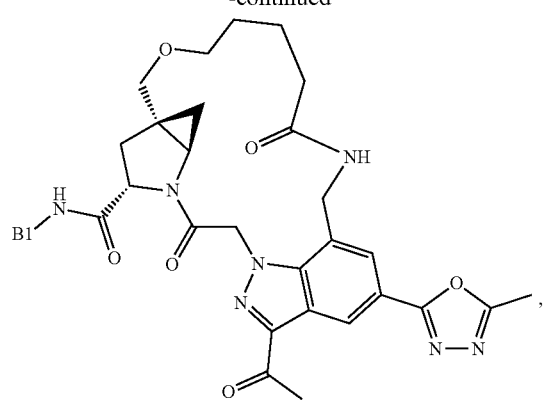
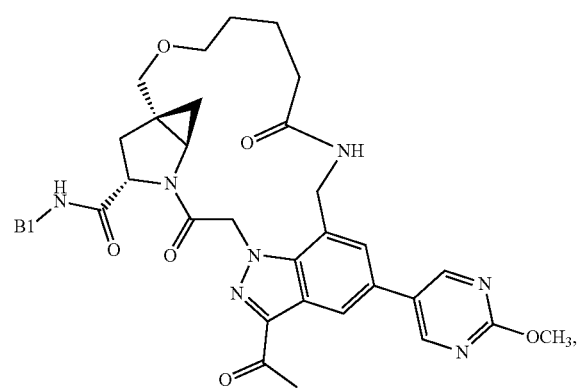
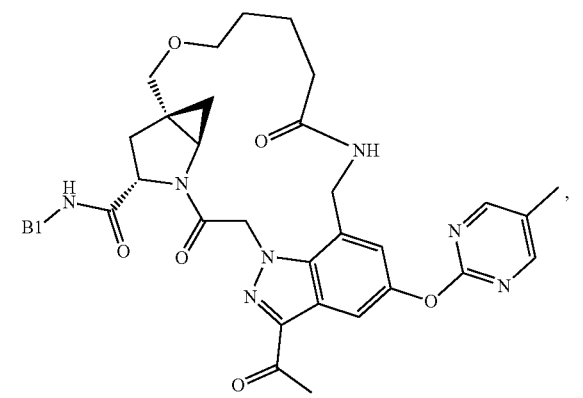
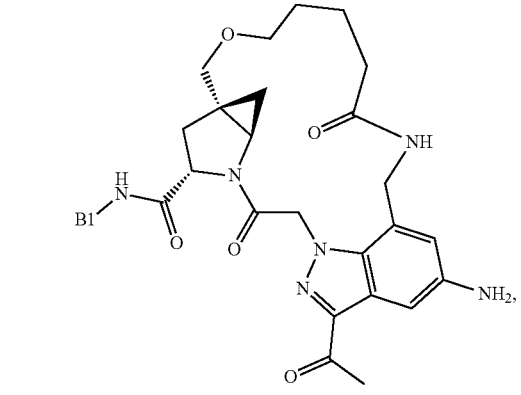
170
-continued
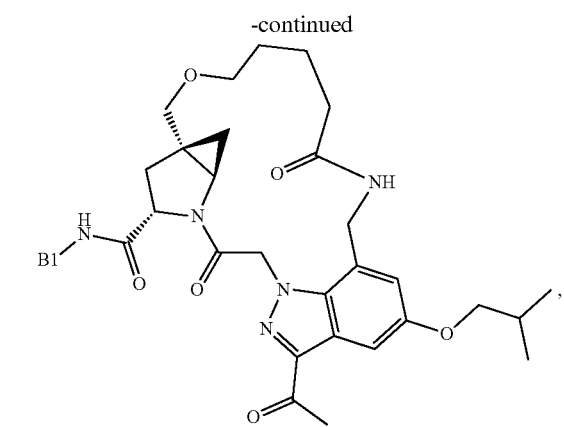
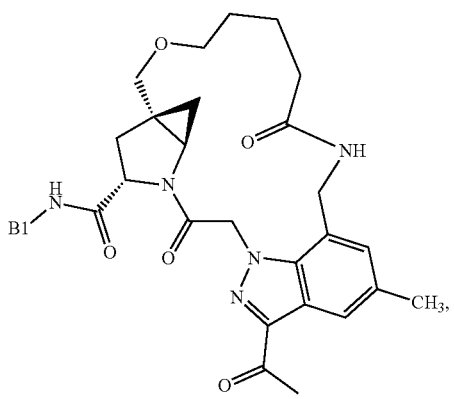
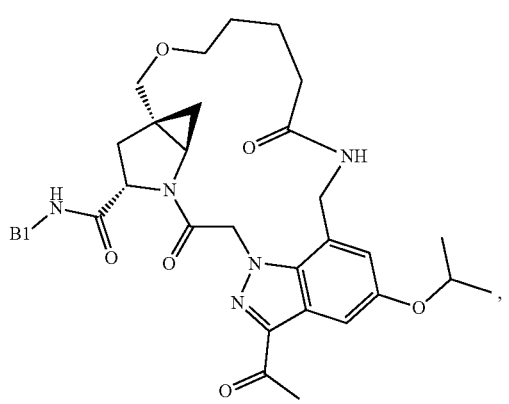
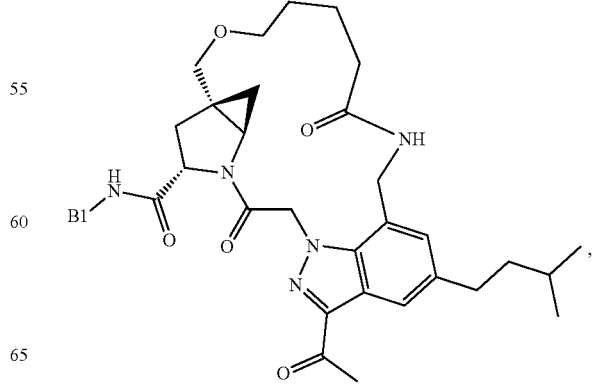

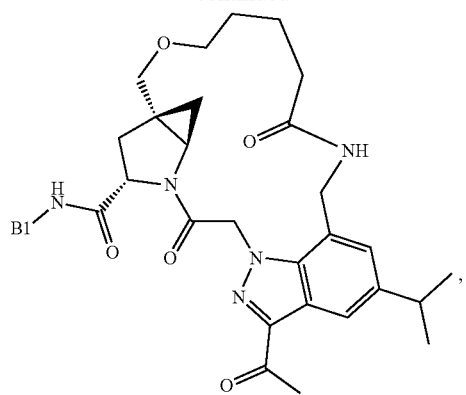
,
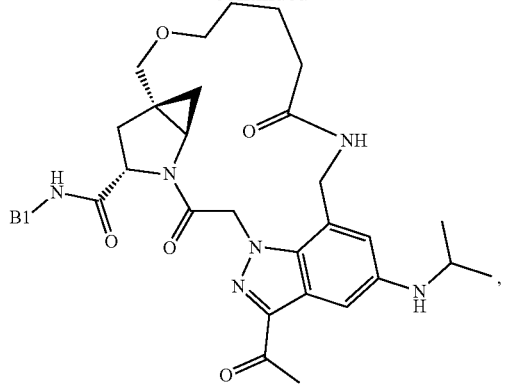
,
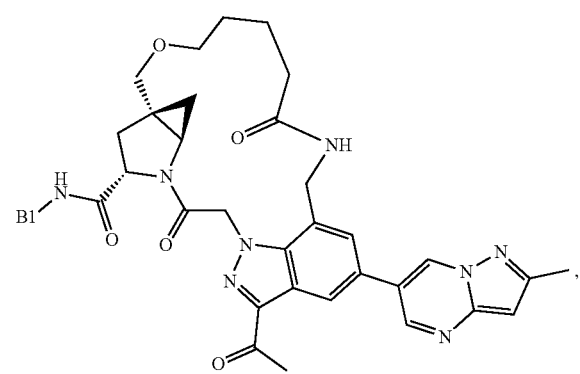
,
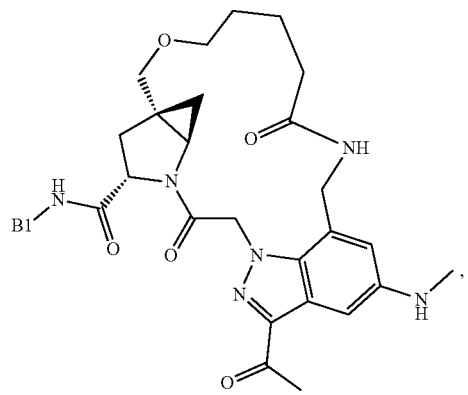
,
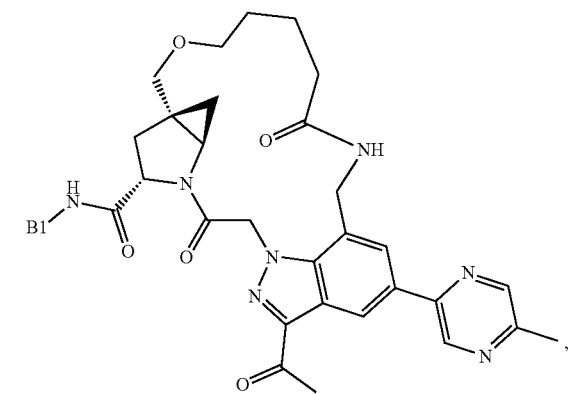
,
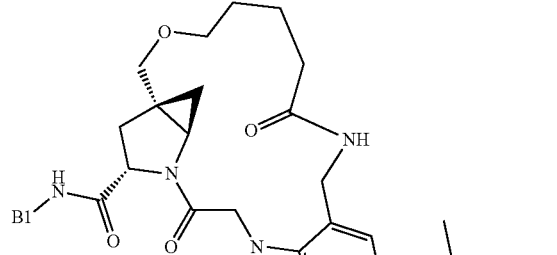
, and
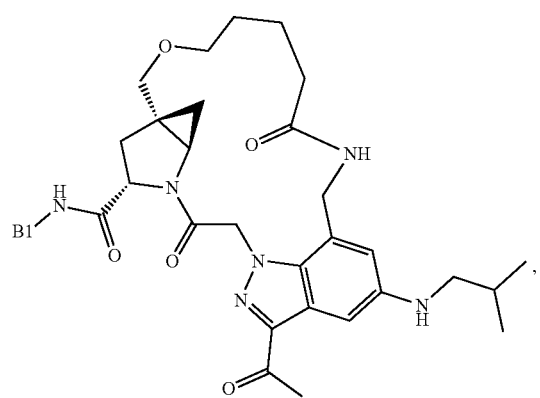
,
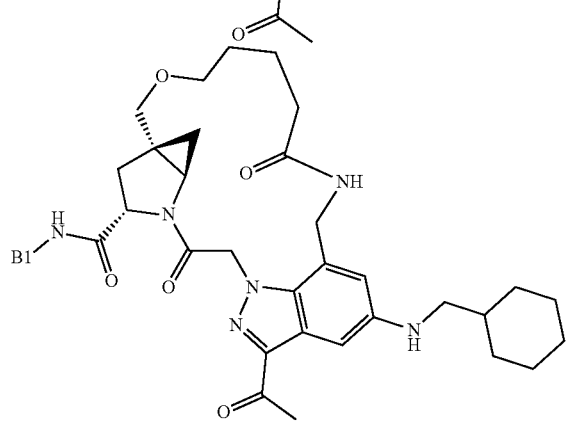
.
In one embodiment, the compound of Formula II is selected from:

173
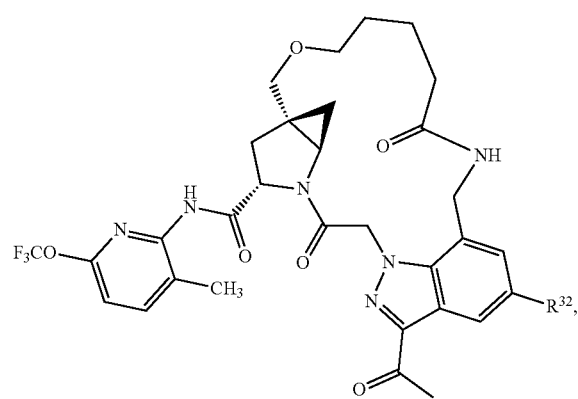
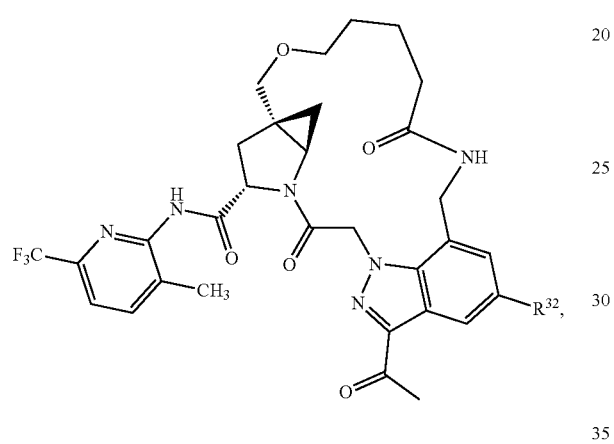
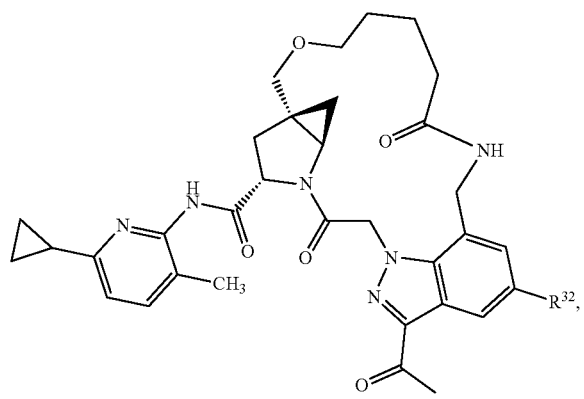
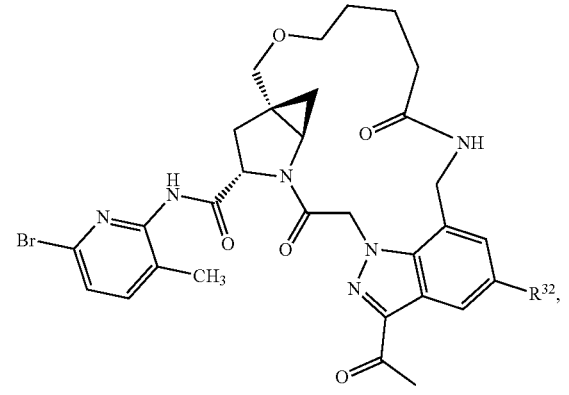
174
-continued
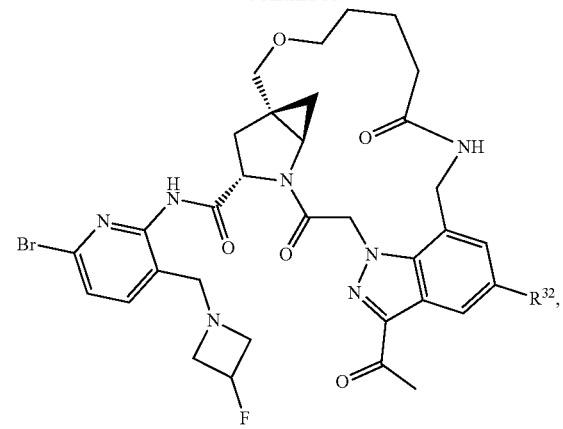
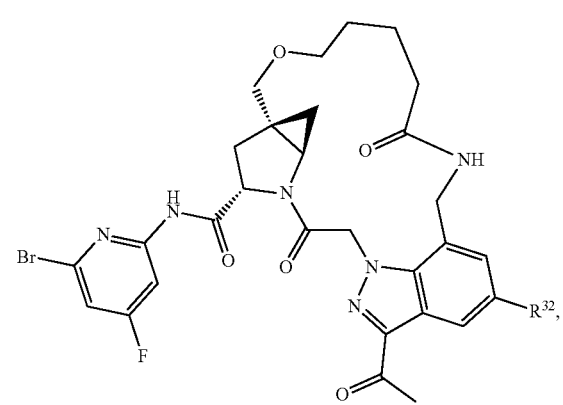
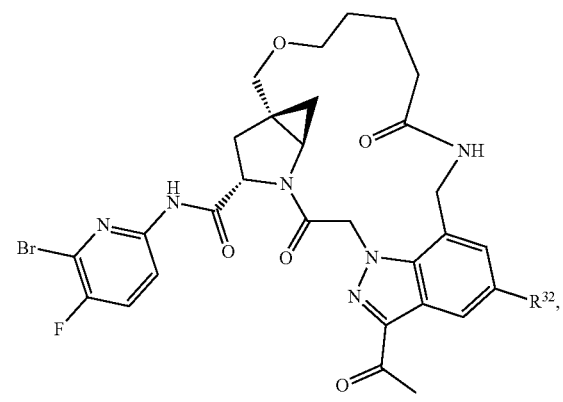
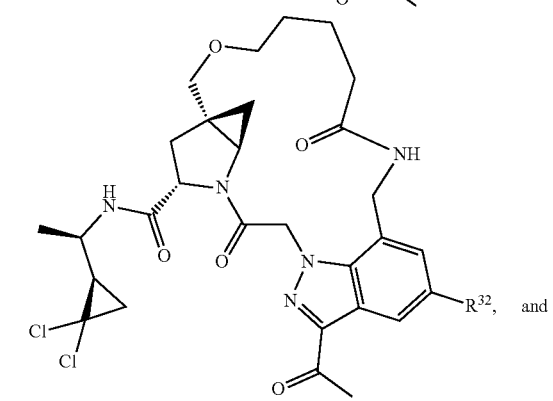, and -continued
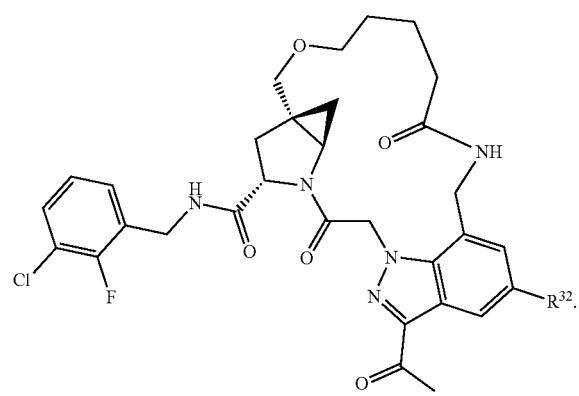
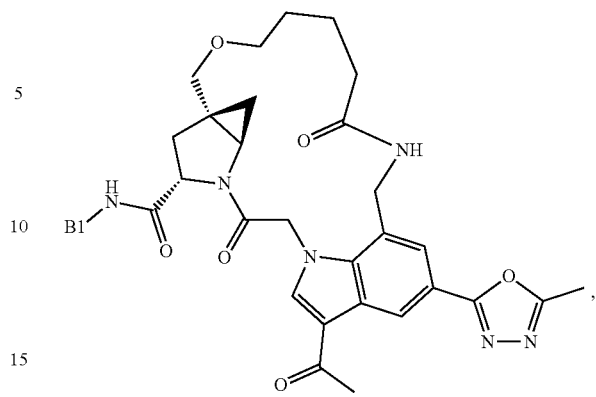
In one embodiment, the compound of Formula II is selected from:
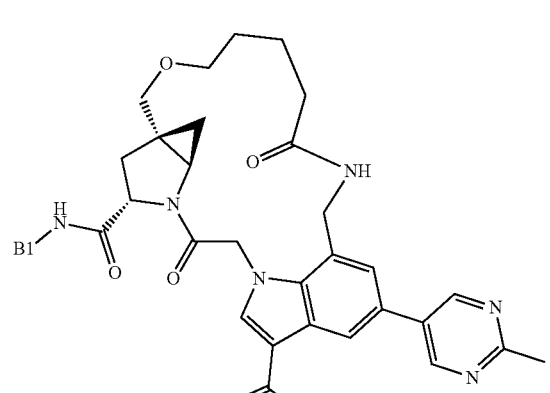
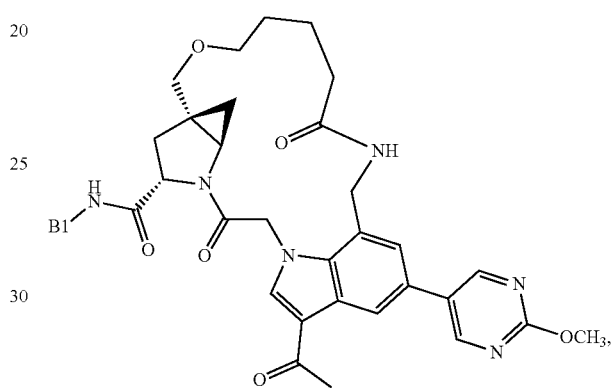
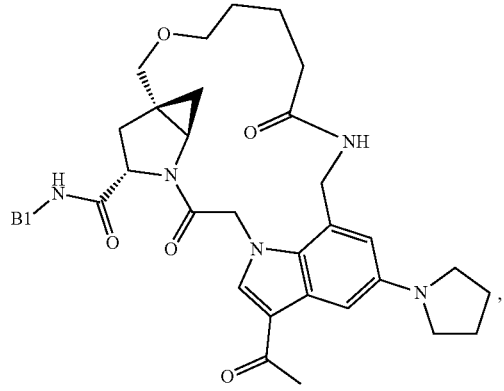
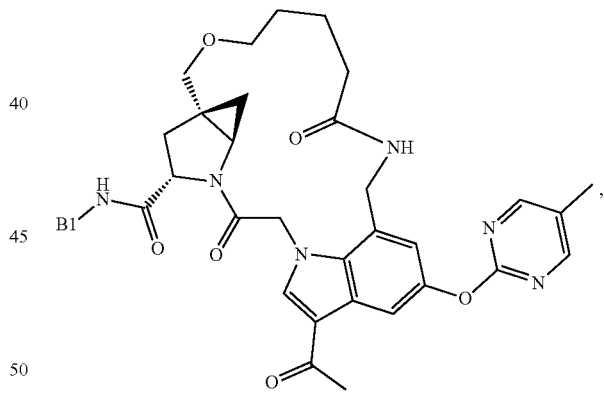
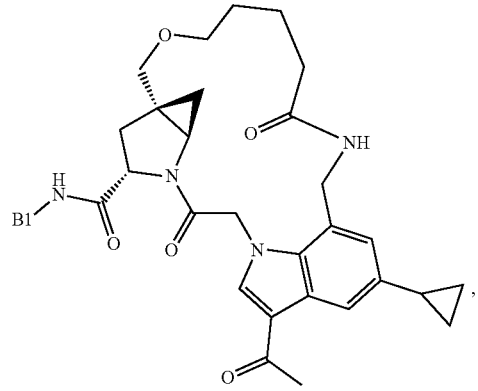
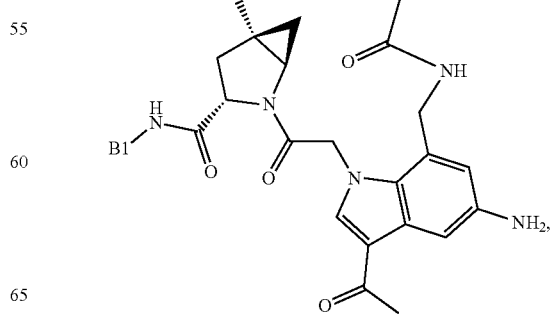

177
-continued
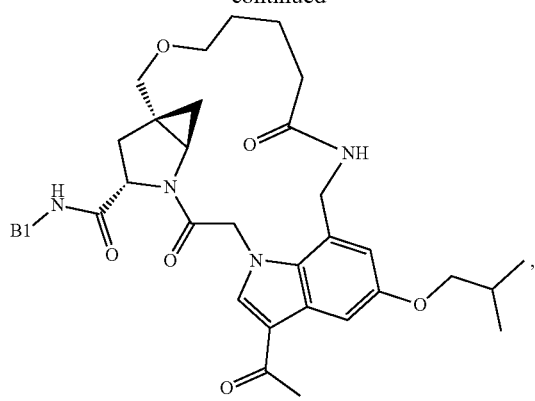
,
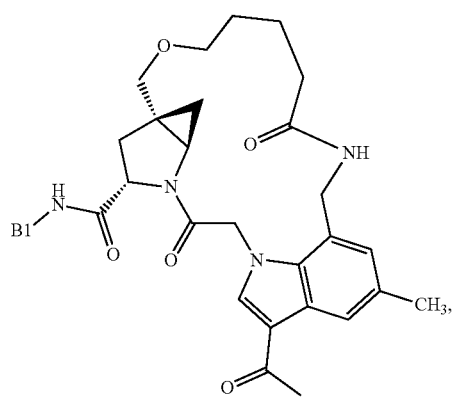
,
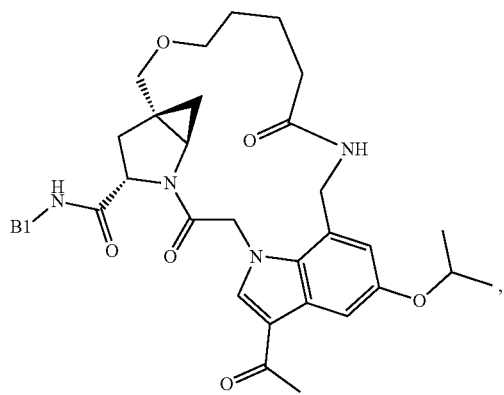
,
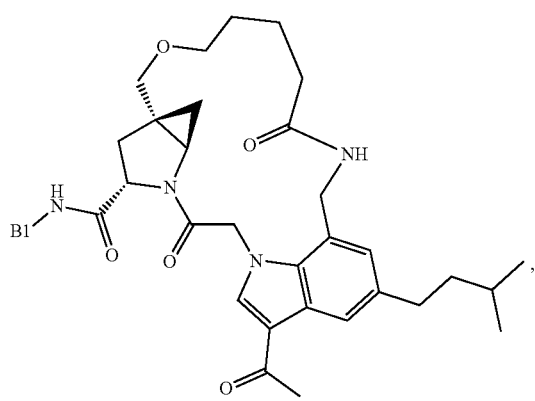
,
178
-continued
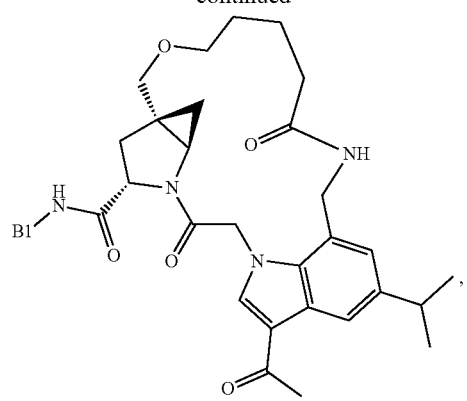
,
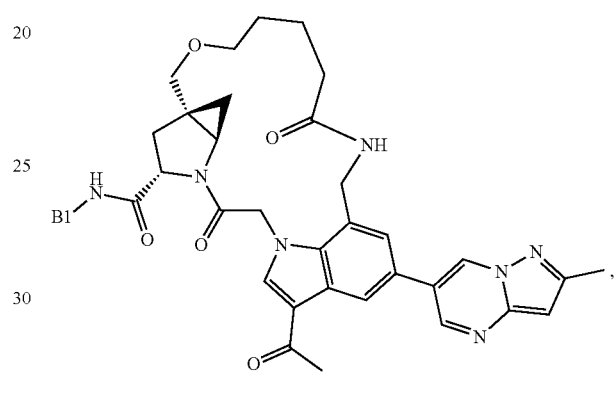
,
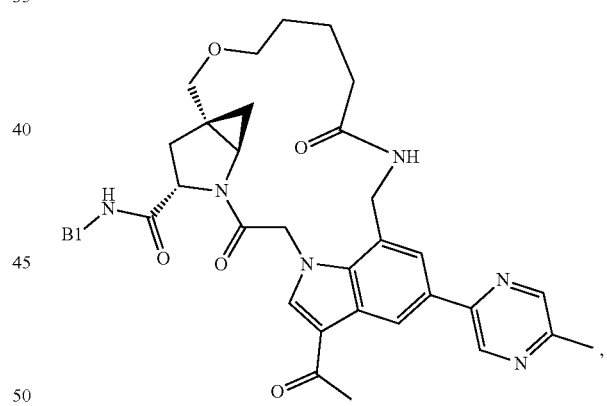
,
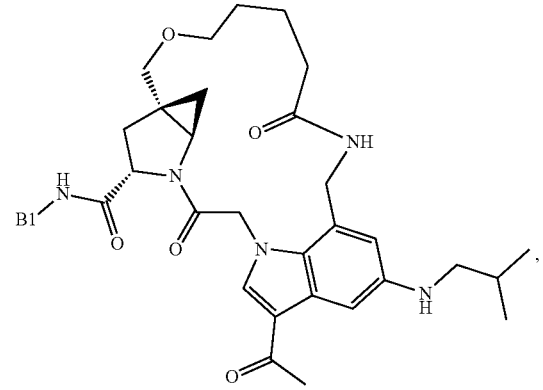
, -continued
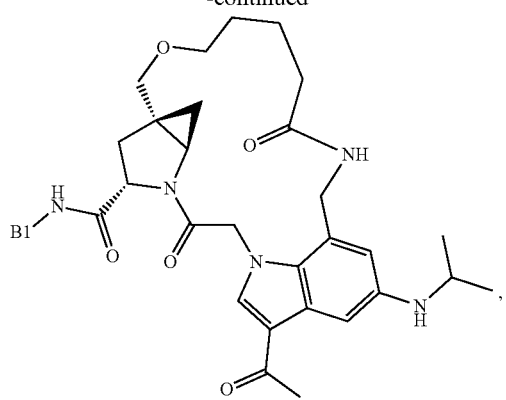
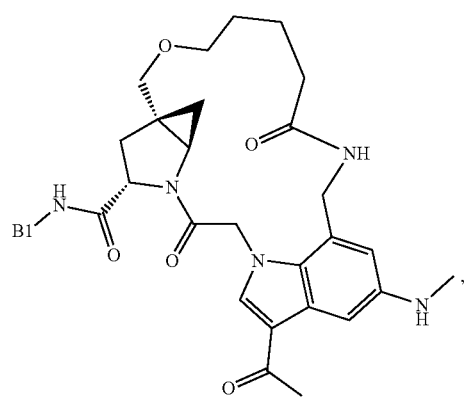
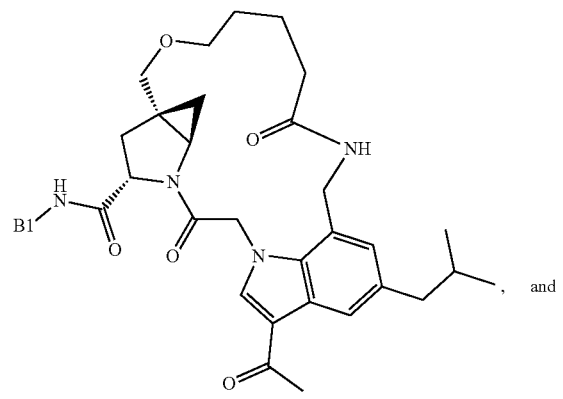, and
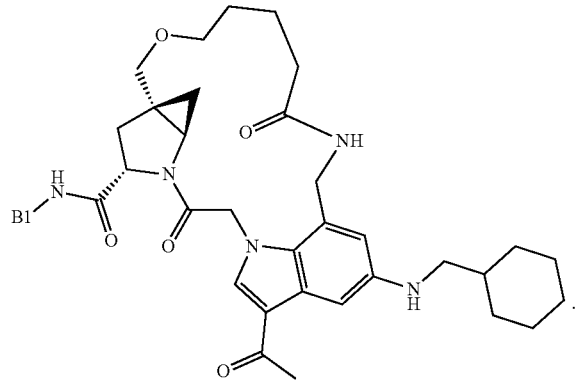
In one embodiment, the compound of Formula II is selected from:
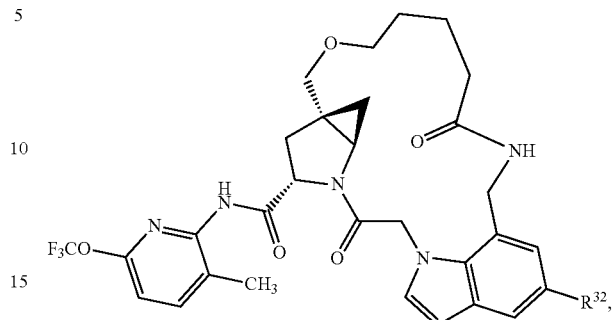
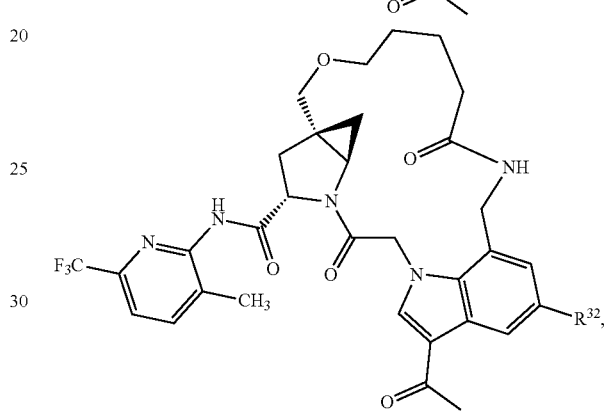
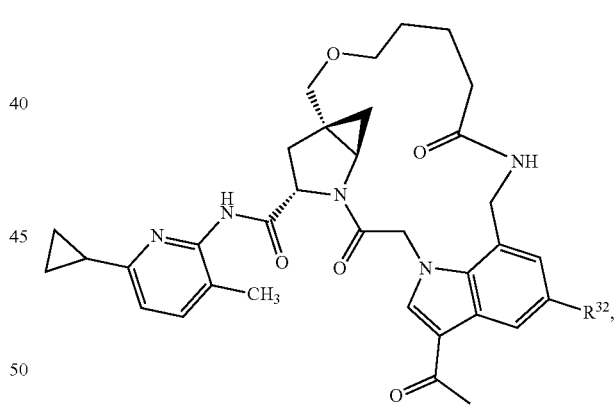
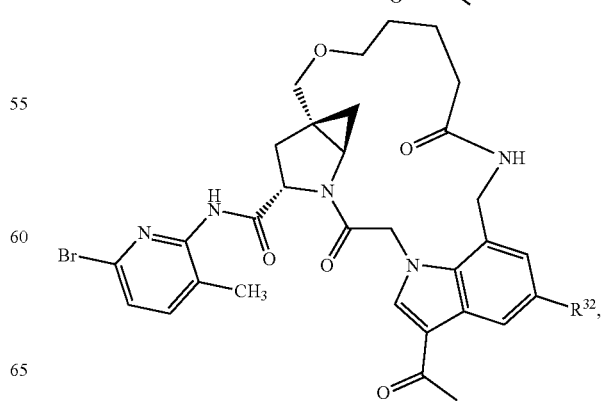

181
-continued
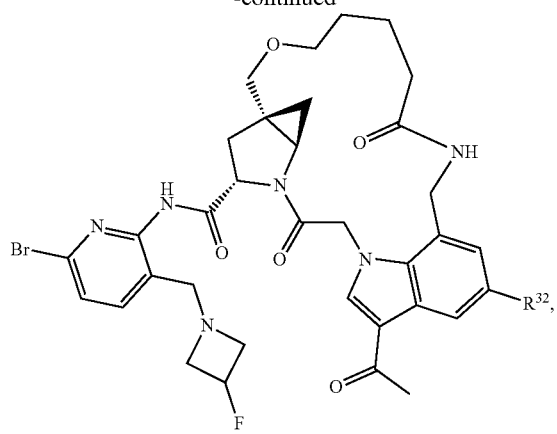
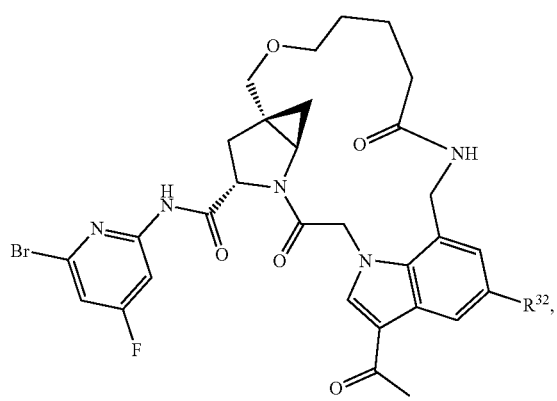
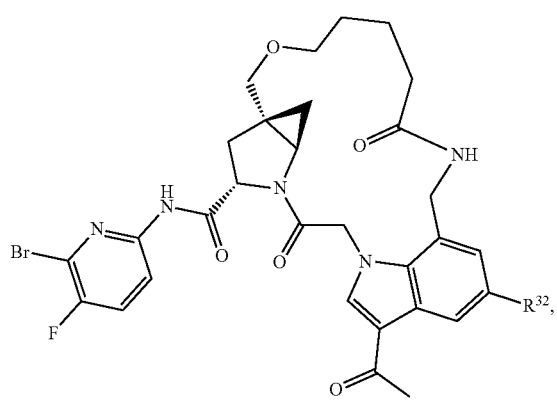
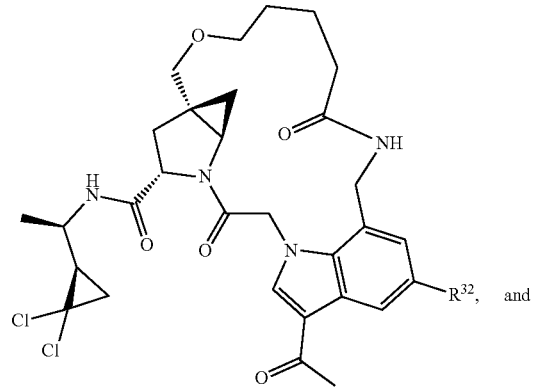
182
-continued
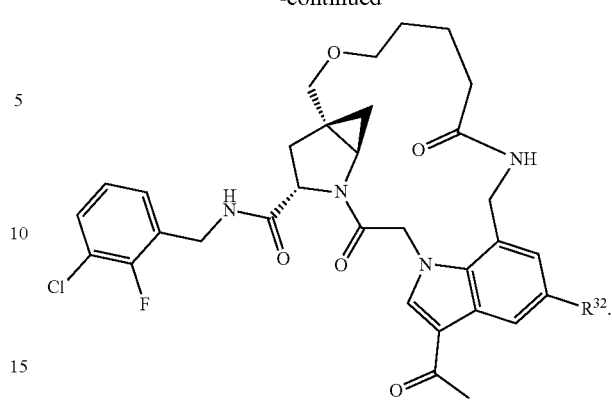
In one embodiment, the compound of Formula II is selected from:
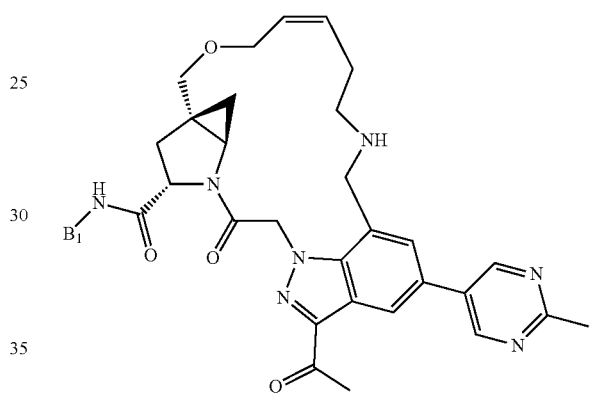
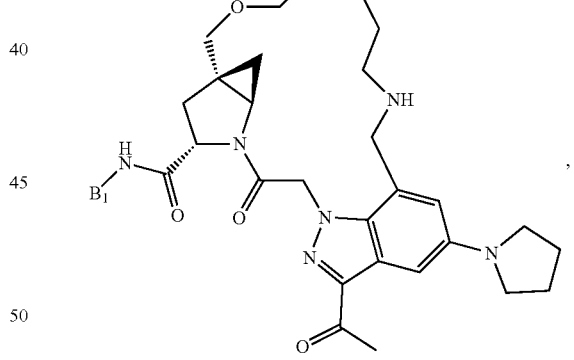
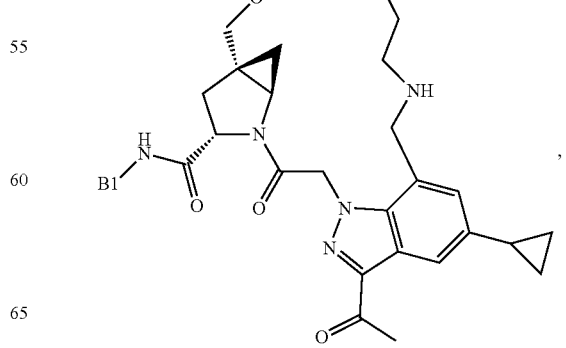

-continued
183
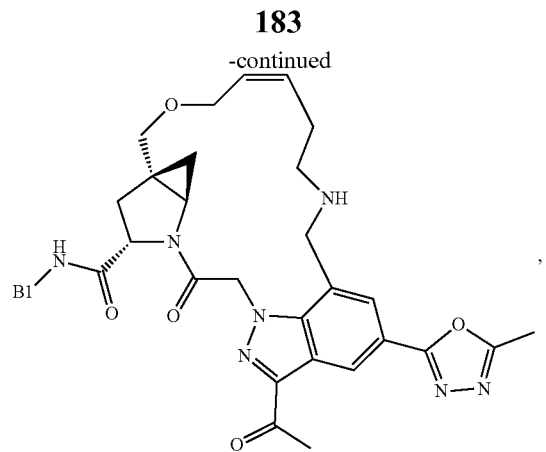
,
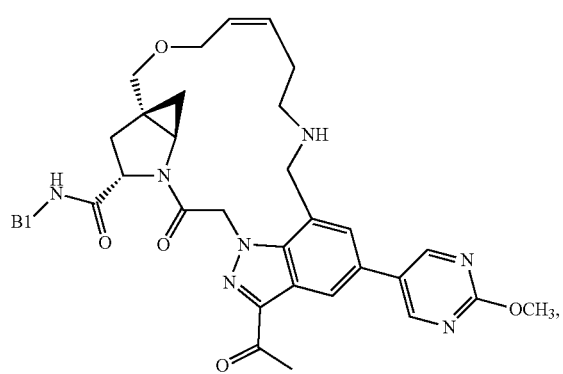
,
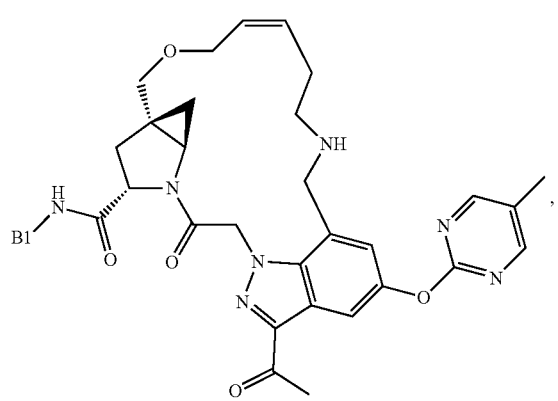
,
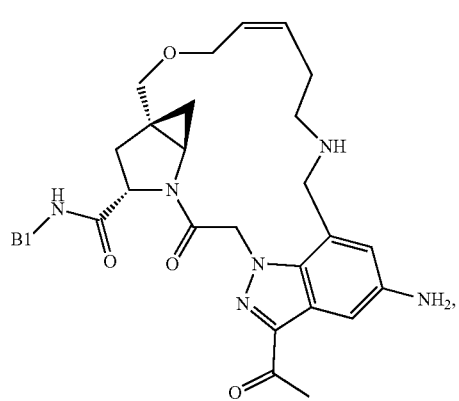
,
184
-continued
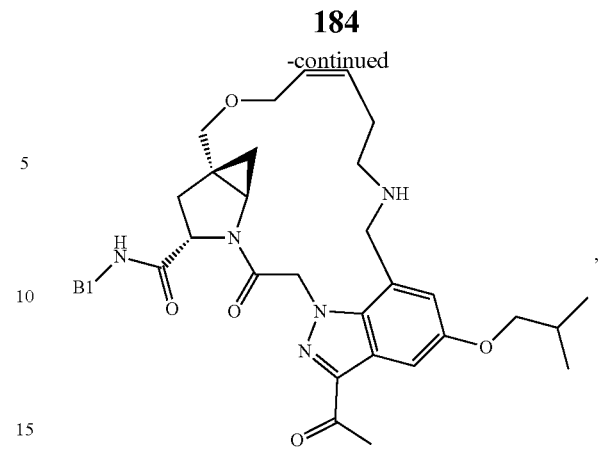
,
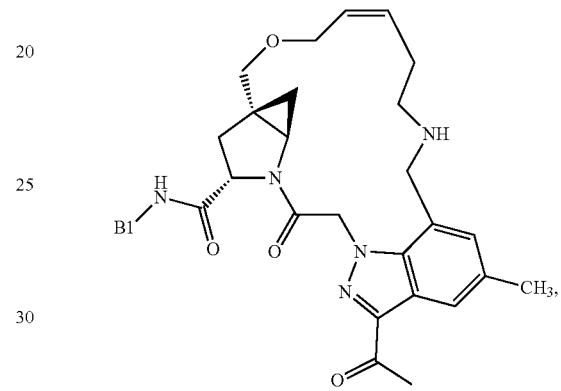
,
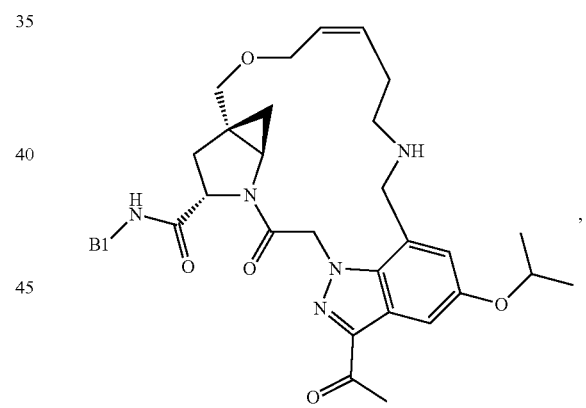
,
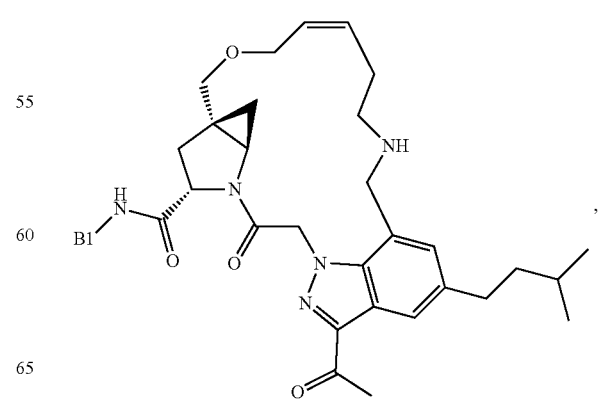
, -continued
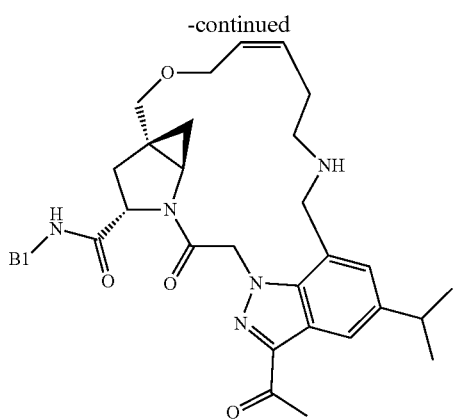
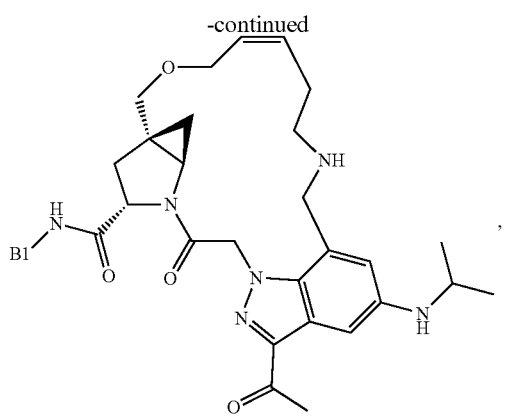
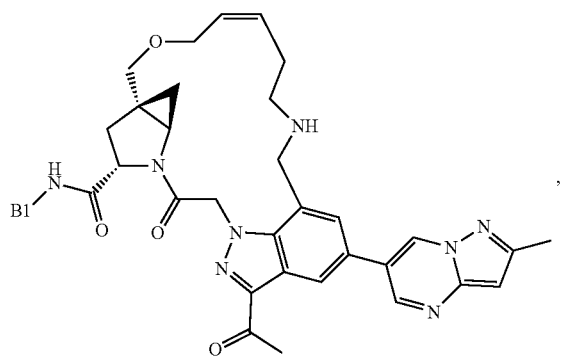
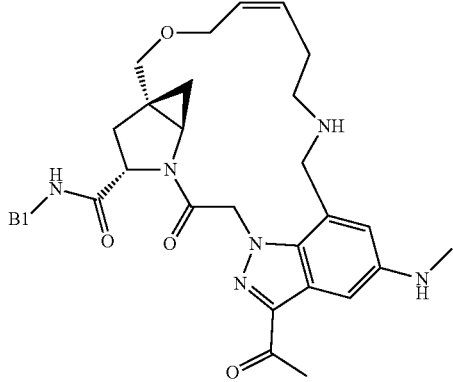
,
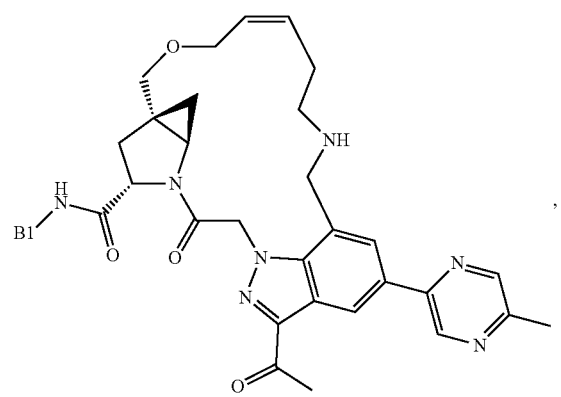
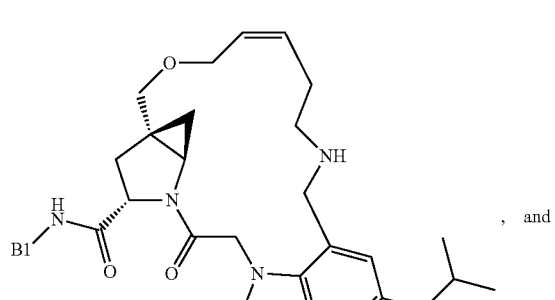
, and
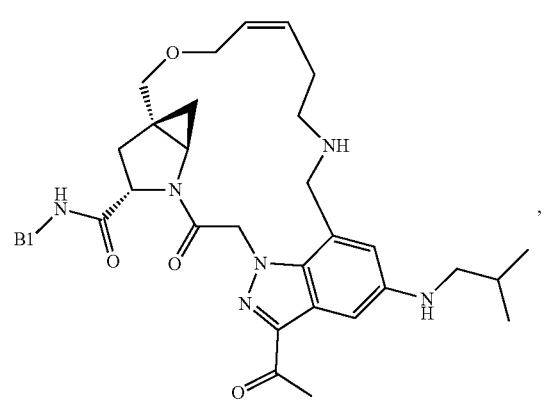
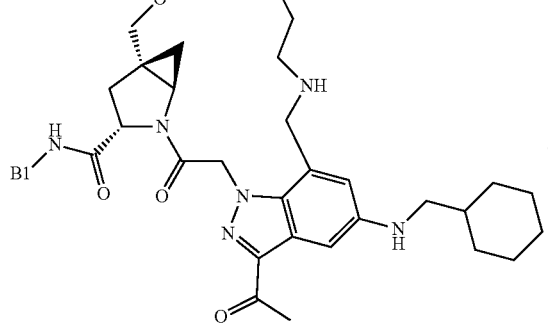
In one embodiment, the compound of Formula II is selected from:

187
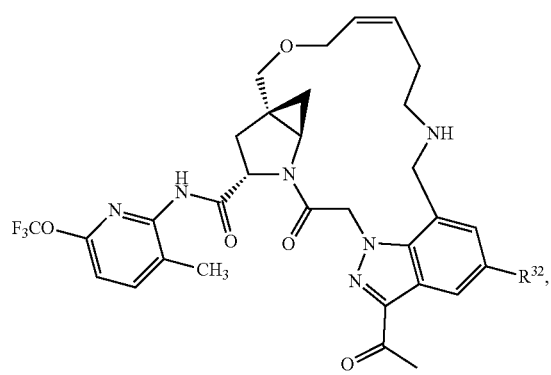
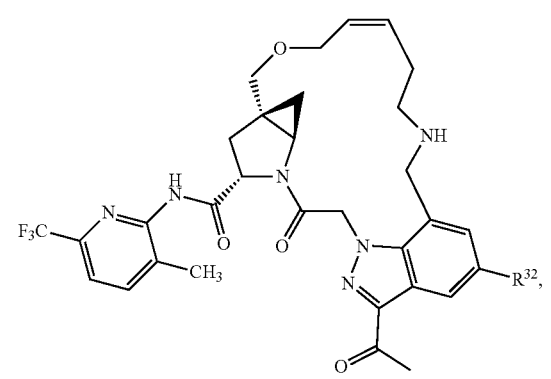
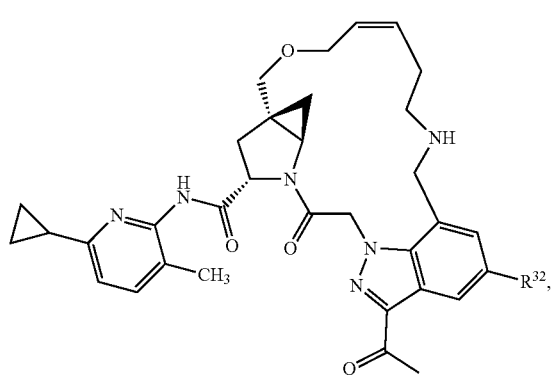
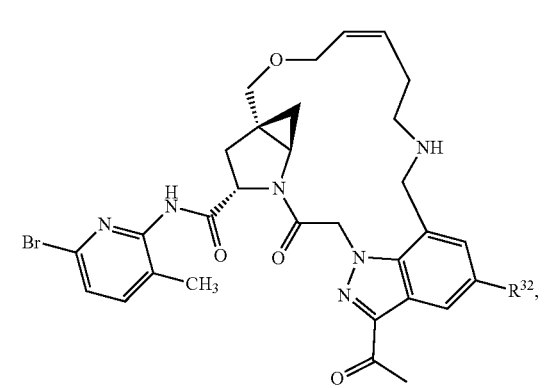
188
-continued
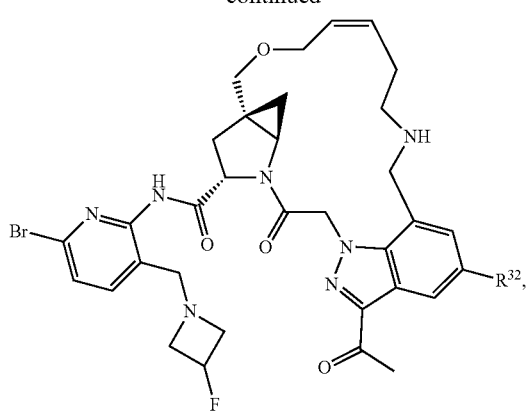
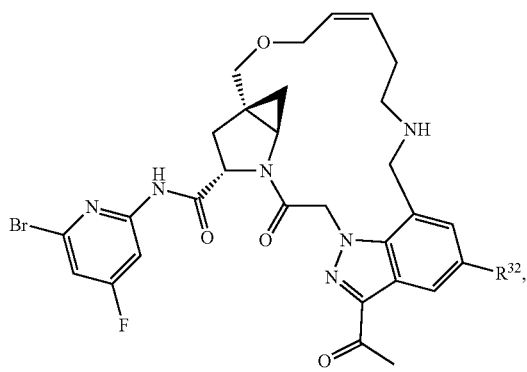
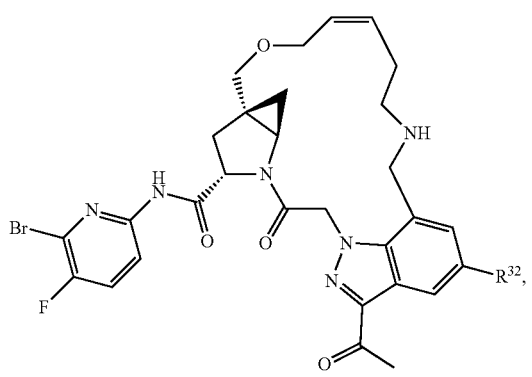
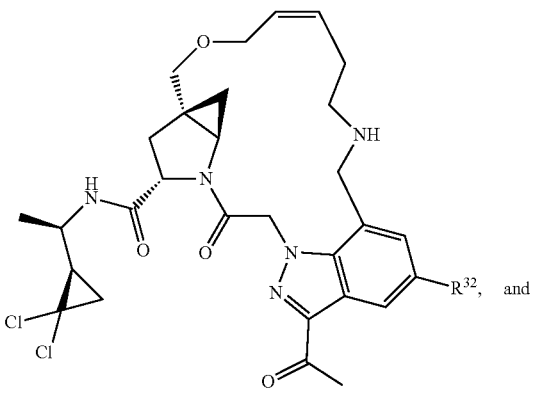
and 189
-continued
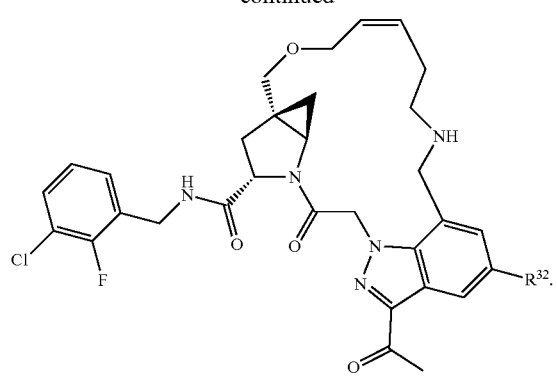
In one embodiment, the compound of Formula II is selected from:
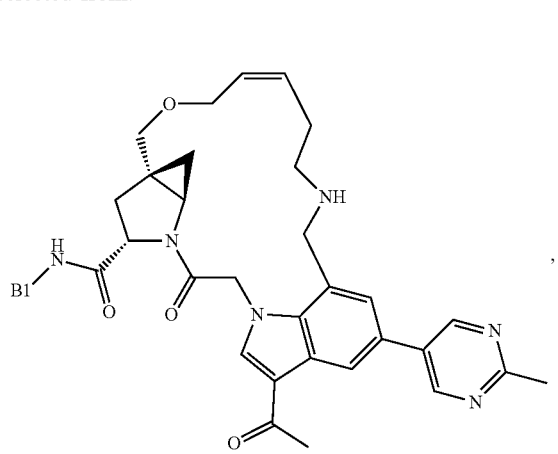
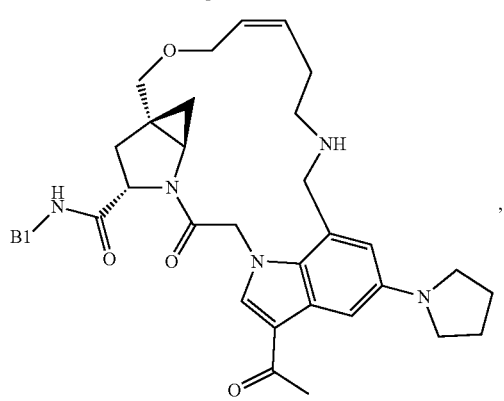
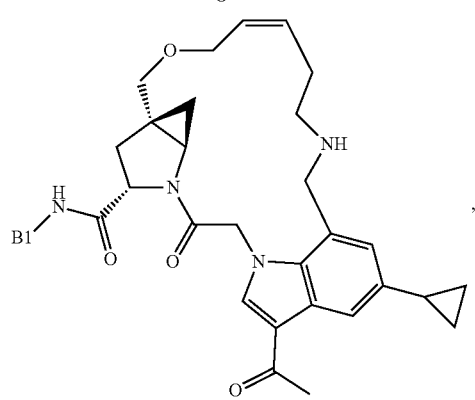
190
-continued
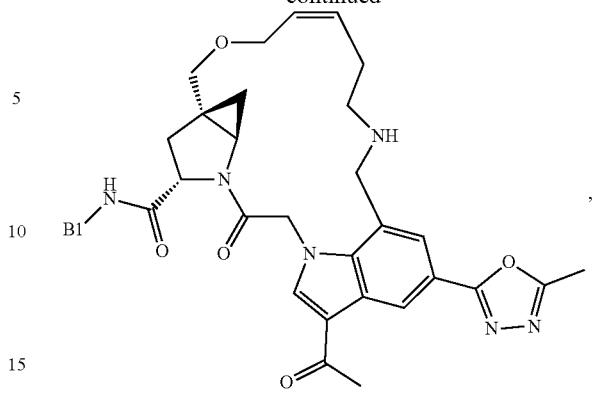
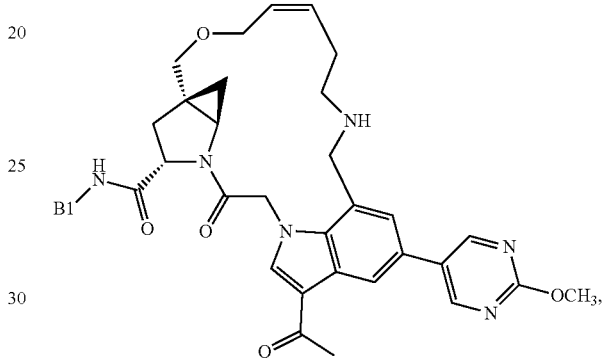
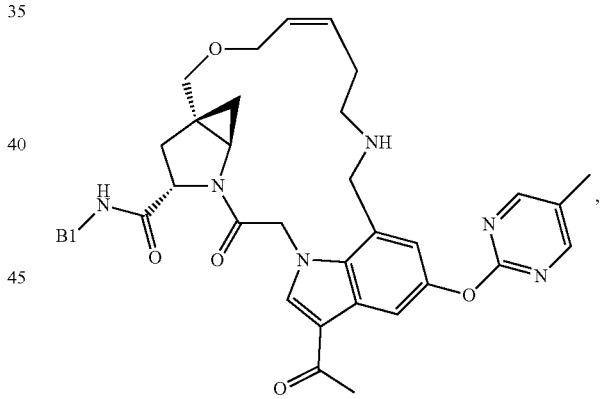
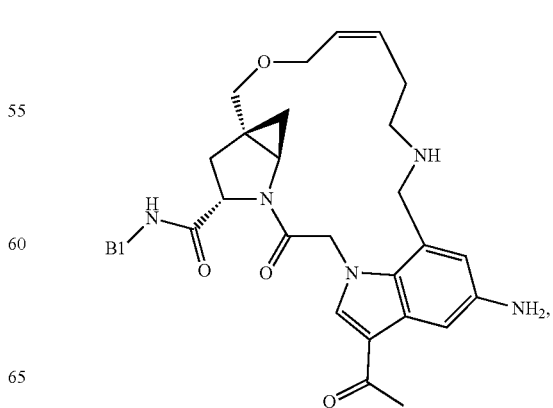

191
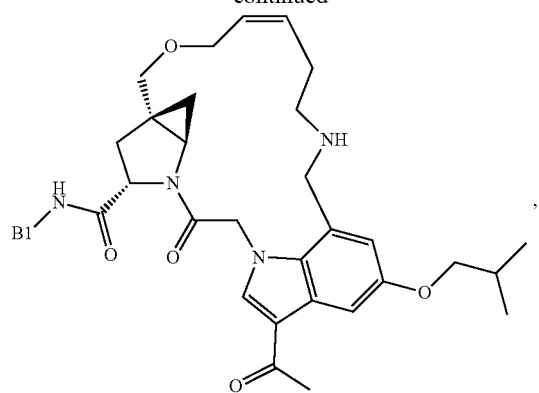
,
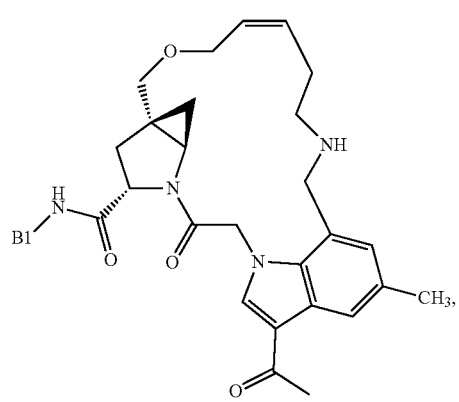
,
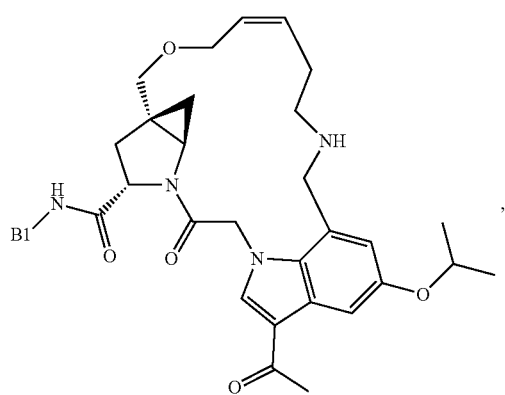
,
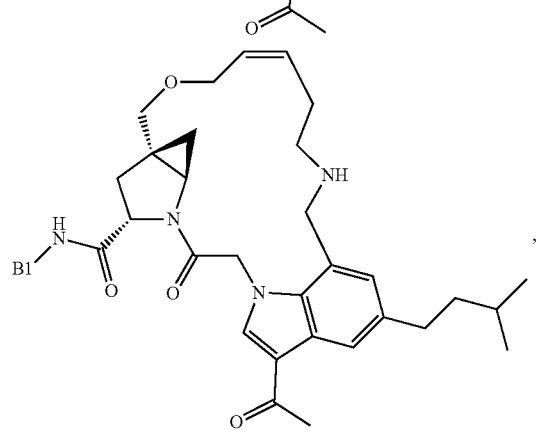
,
192
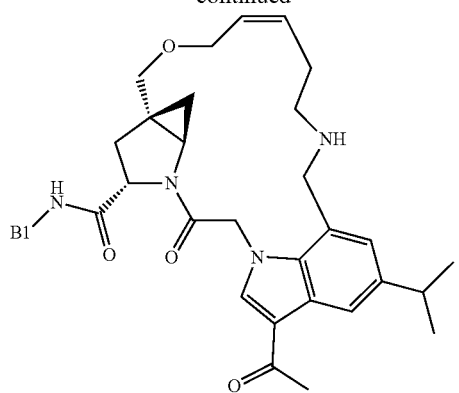
,
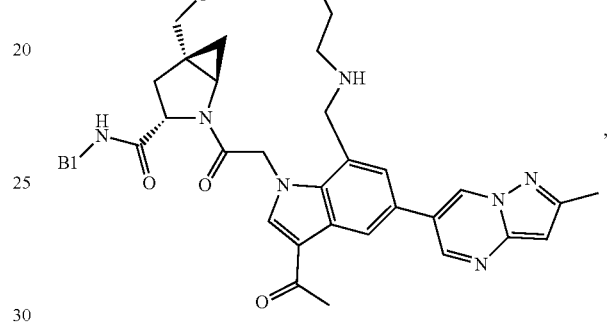
,
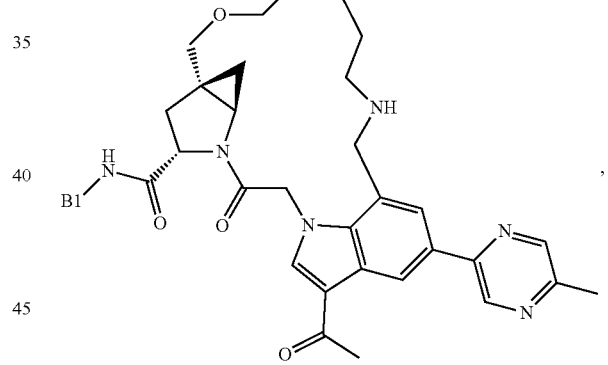
,
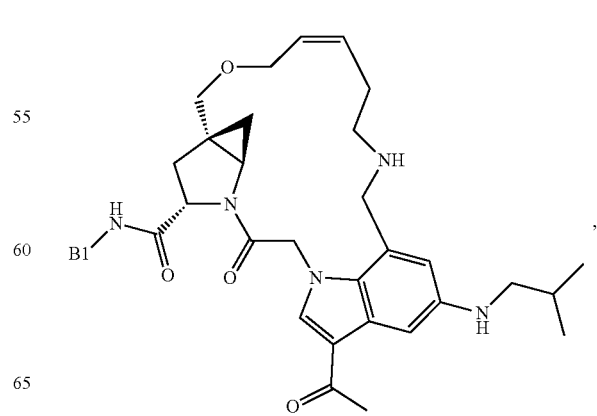
,

193
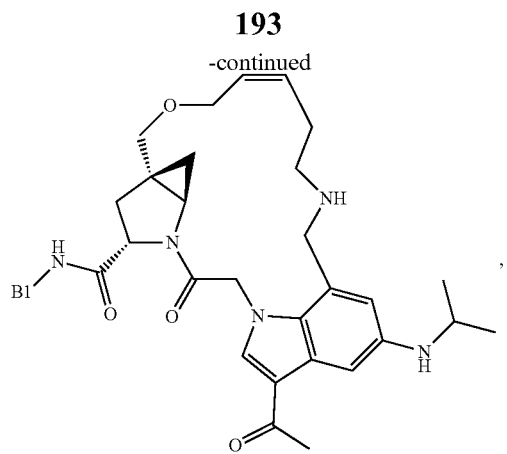
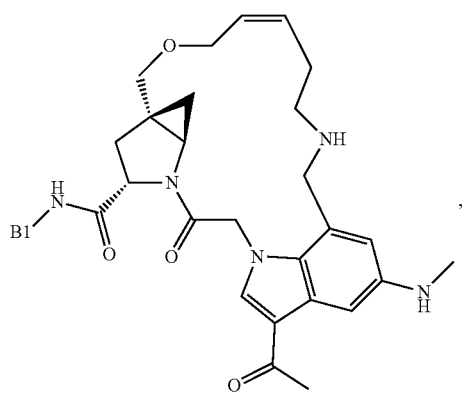
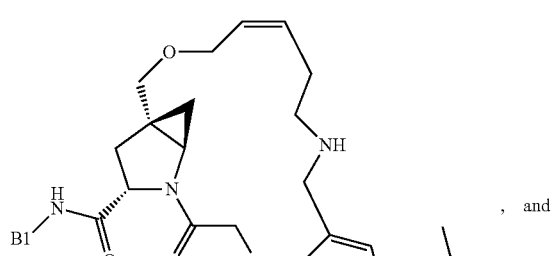
, and
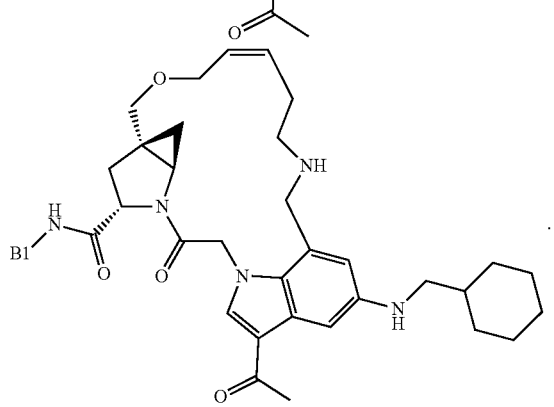
In one embodiment, the compound of Formula II is selected from:
194
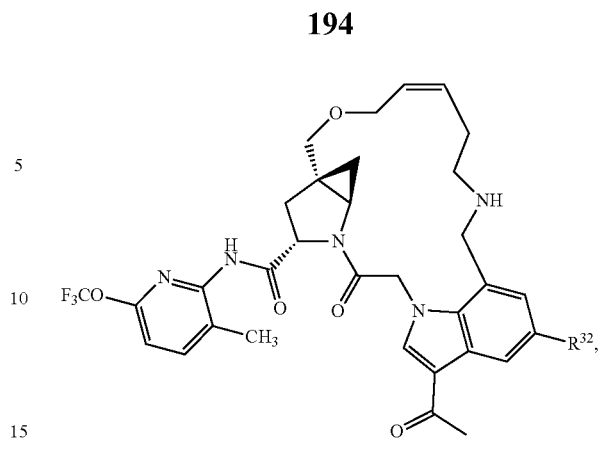
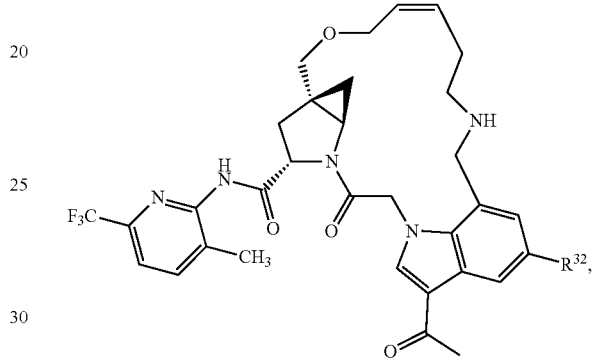
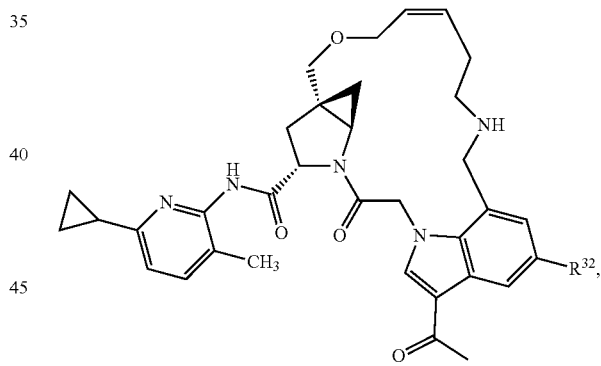
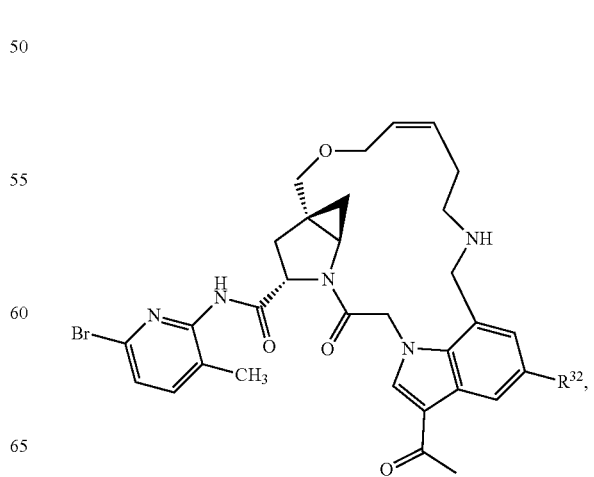

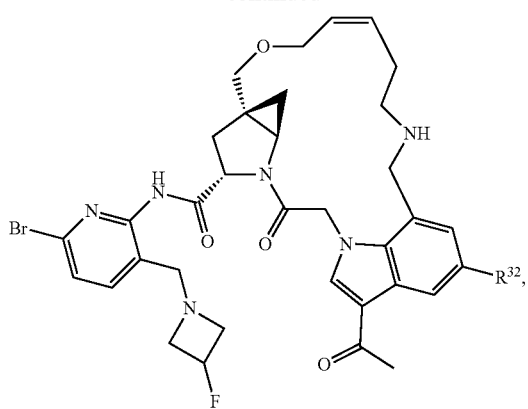
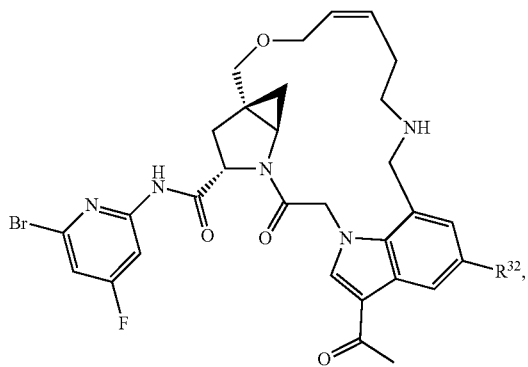
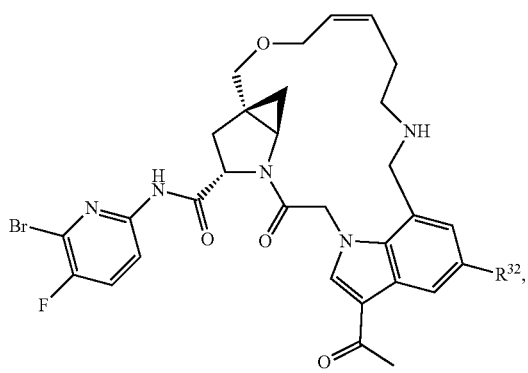
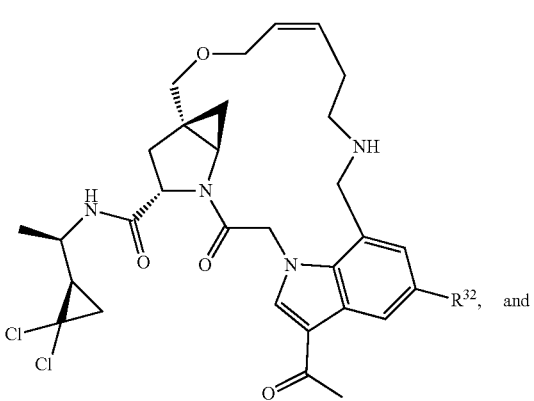
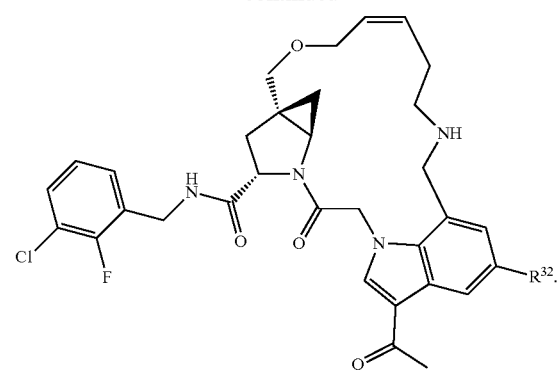
In one embodiment, the compound of Formula II is selected from:
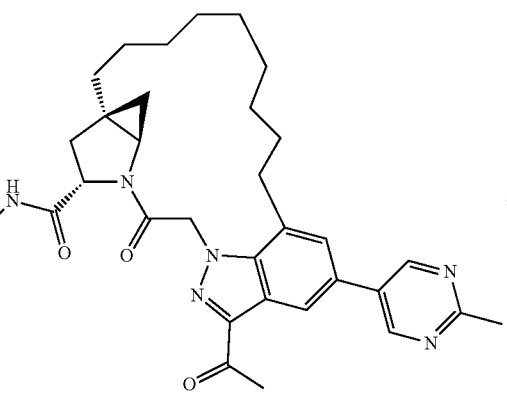
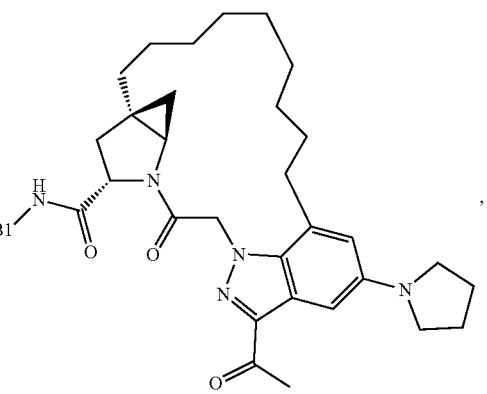
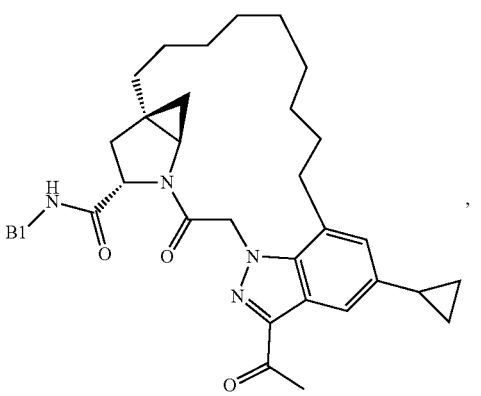

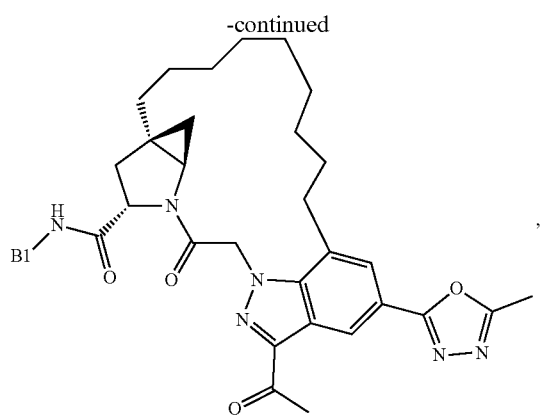
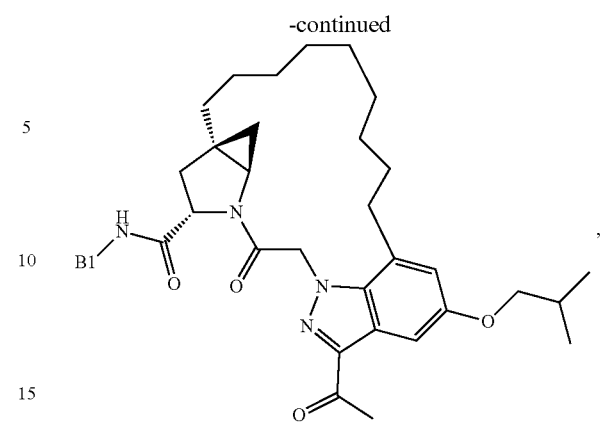
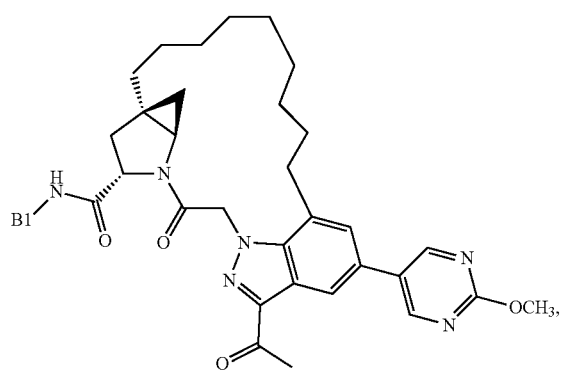
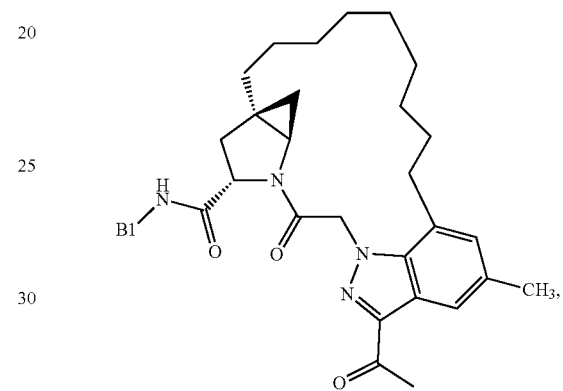
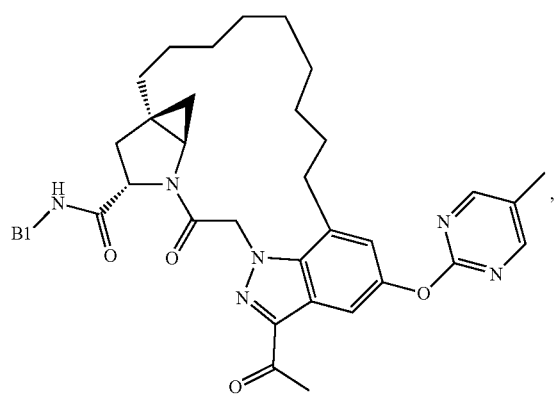
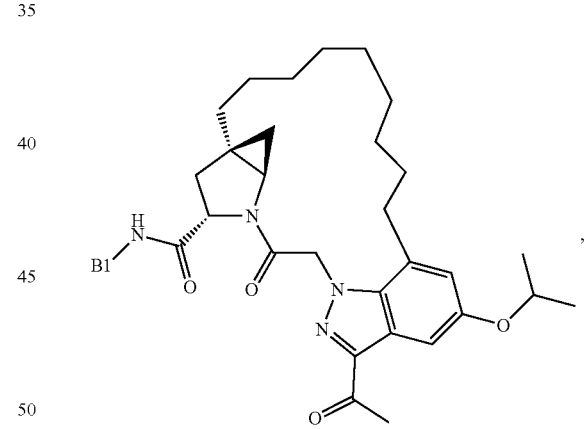
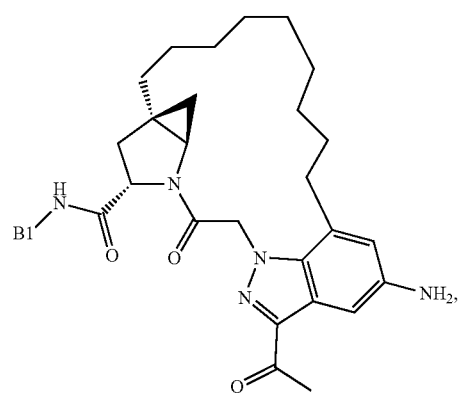
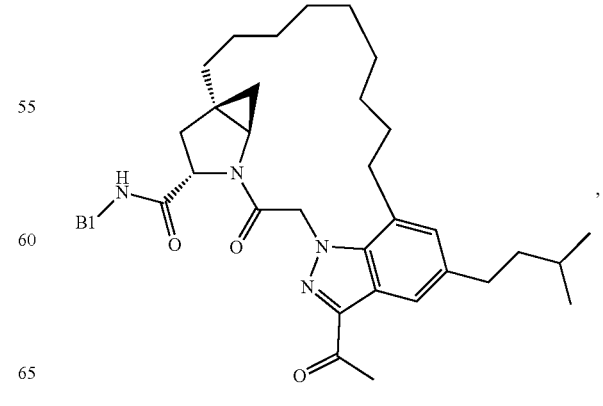

In one embodiment, the compound of Formula II is selected from:

201
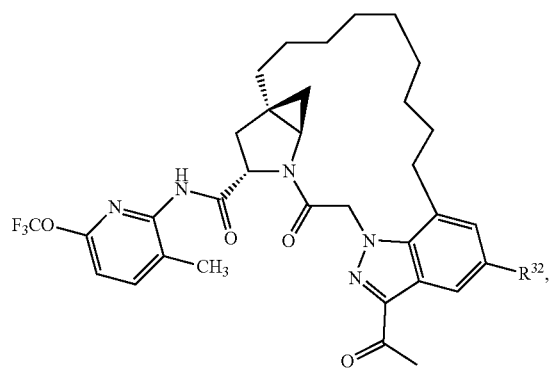
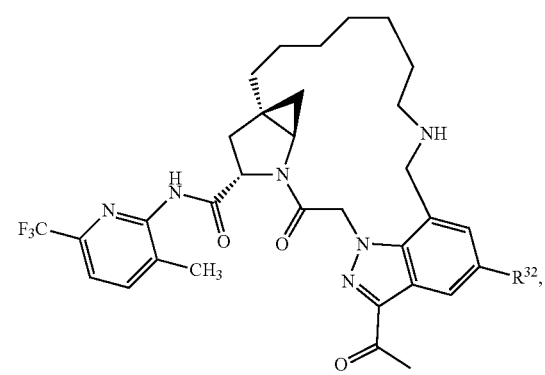
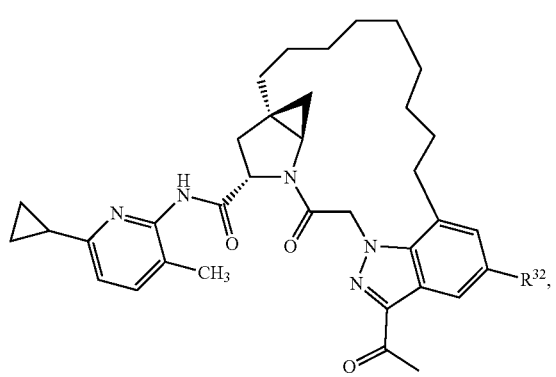
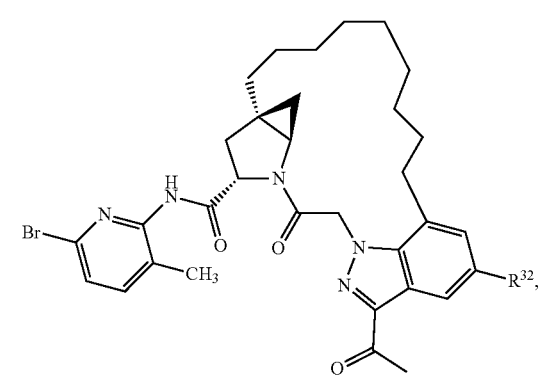
202
-continued
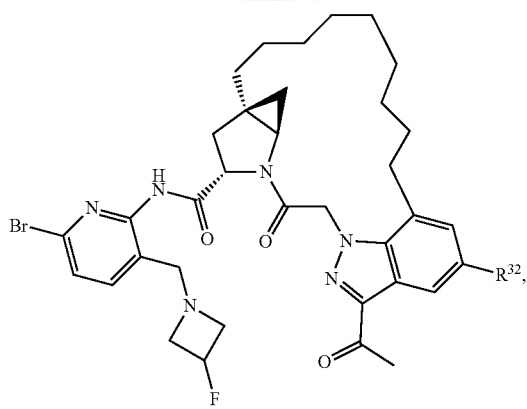
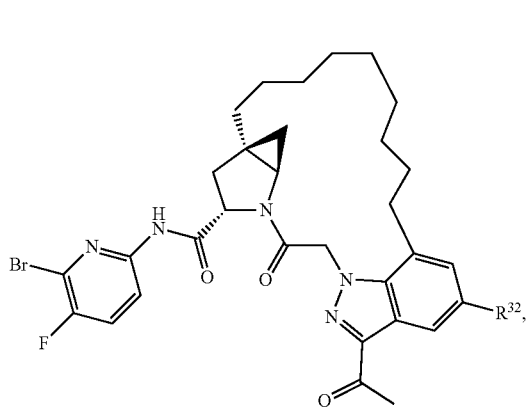
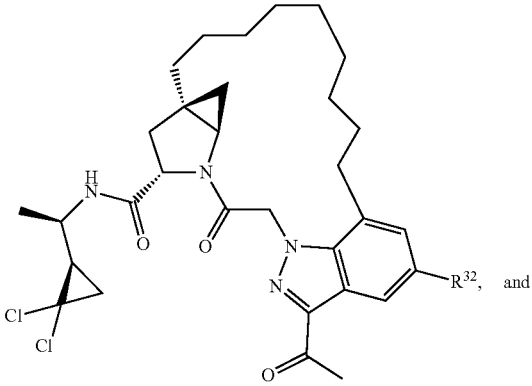

203
-continued
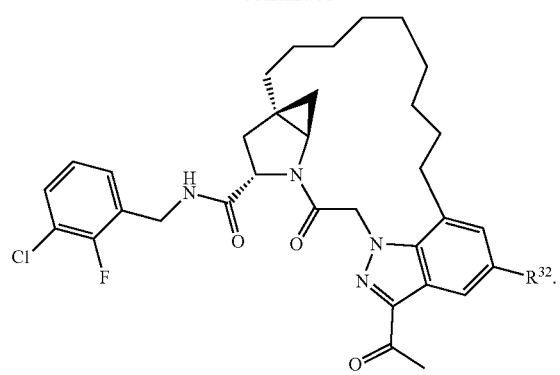
204
-continued
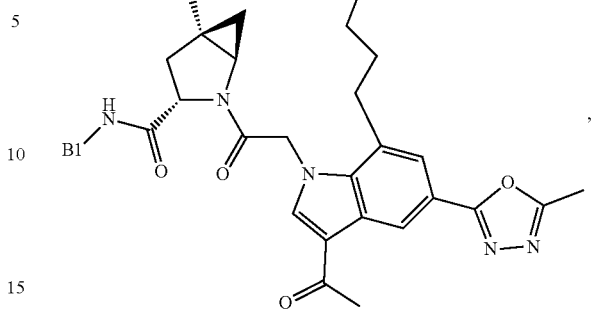
In one embodiment, the compound of Formula II is selected from:
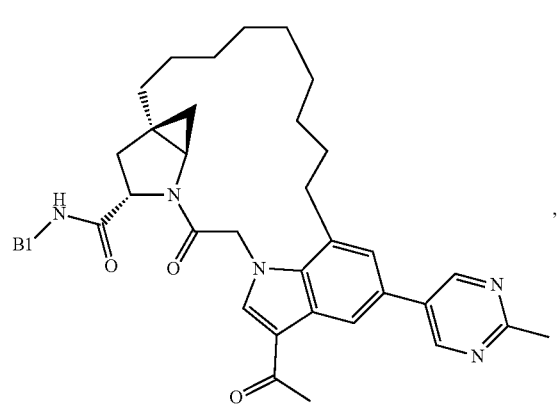
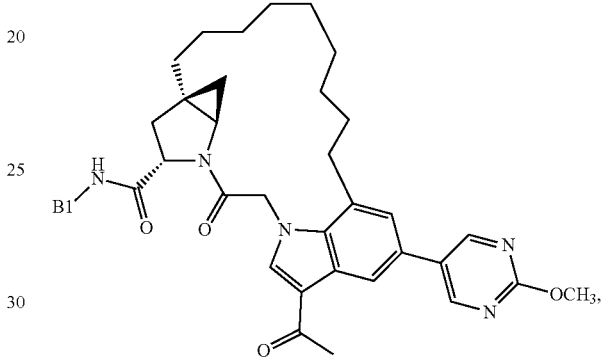
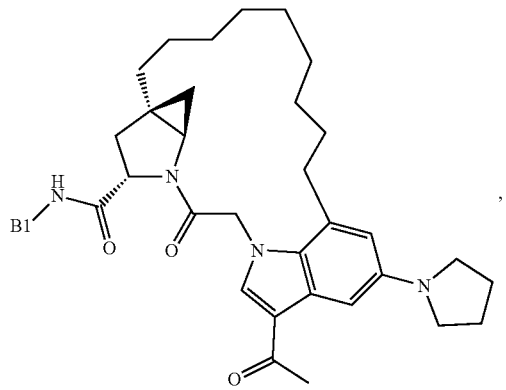
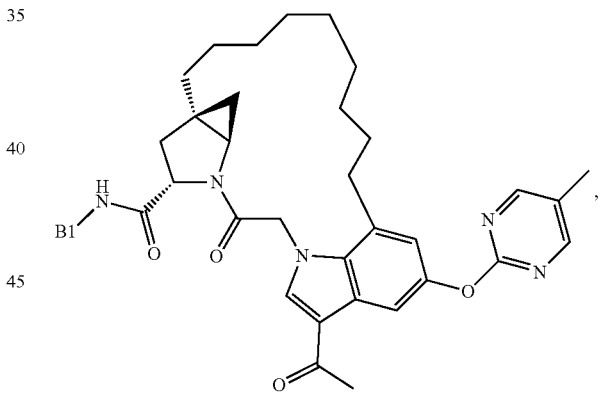
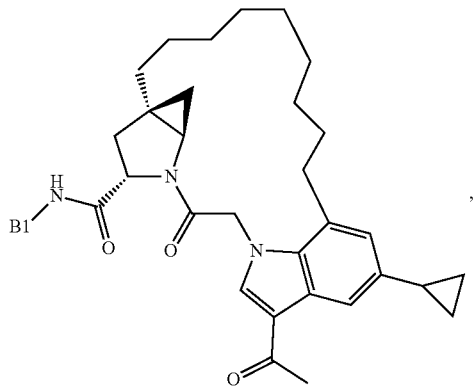
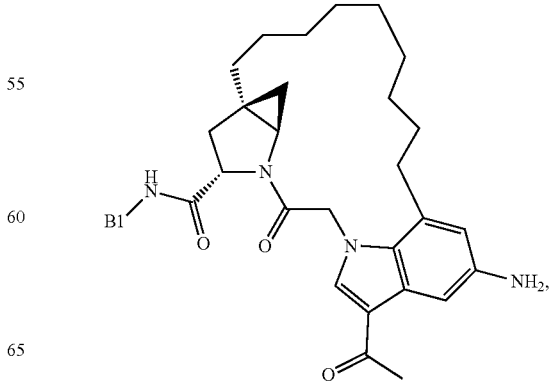

205
-continued
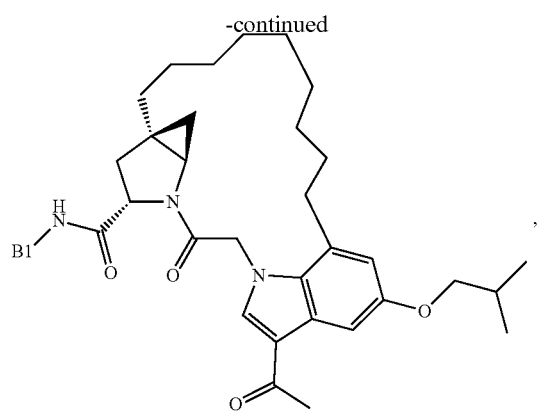
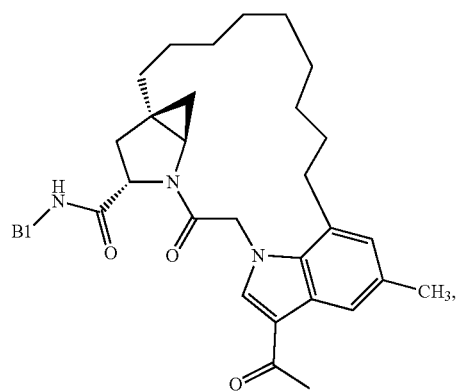
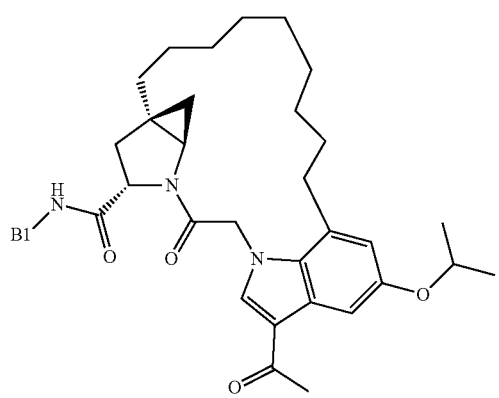
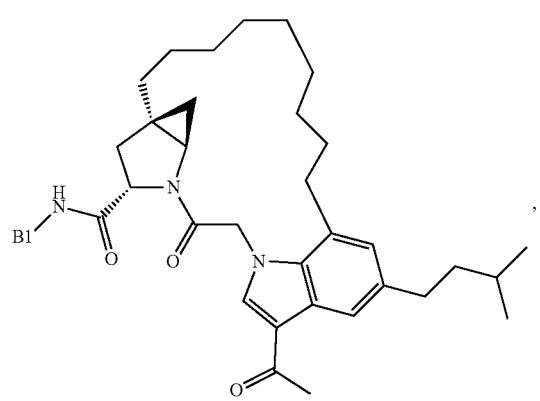
206
-continued
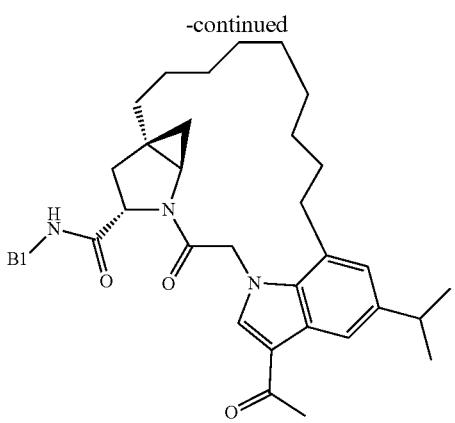
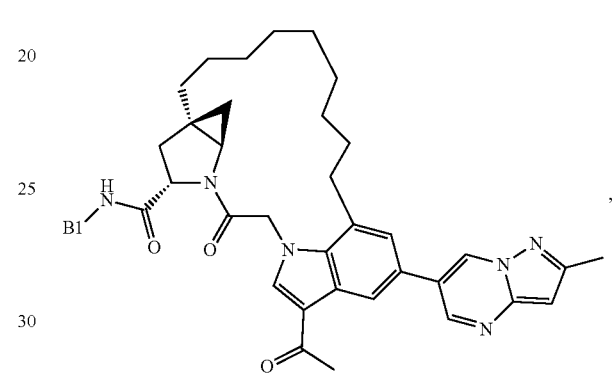
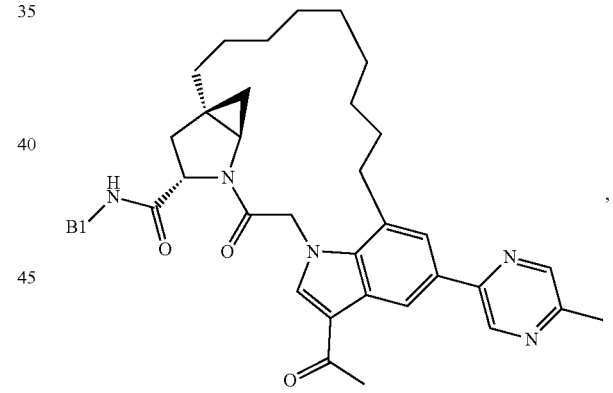
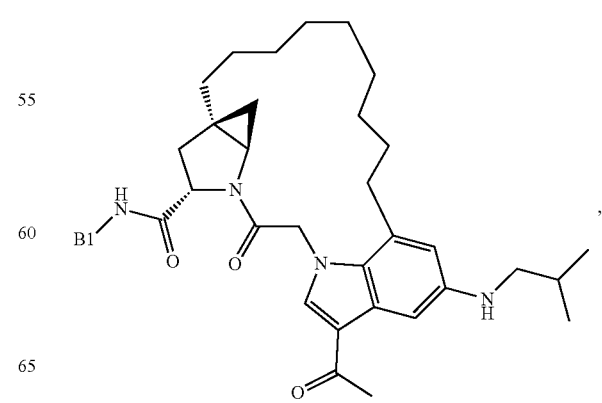

207
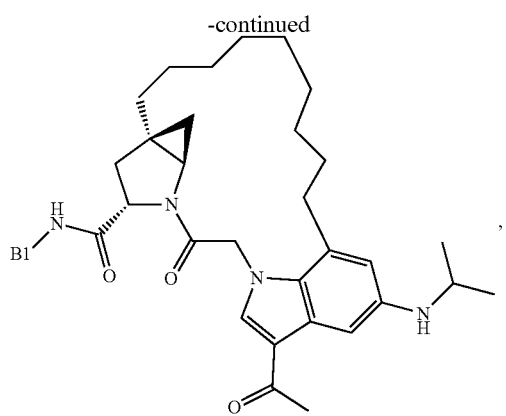
208
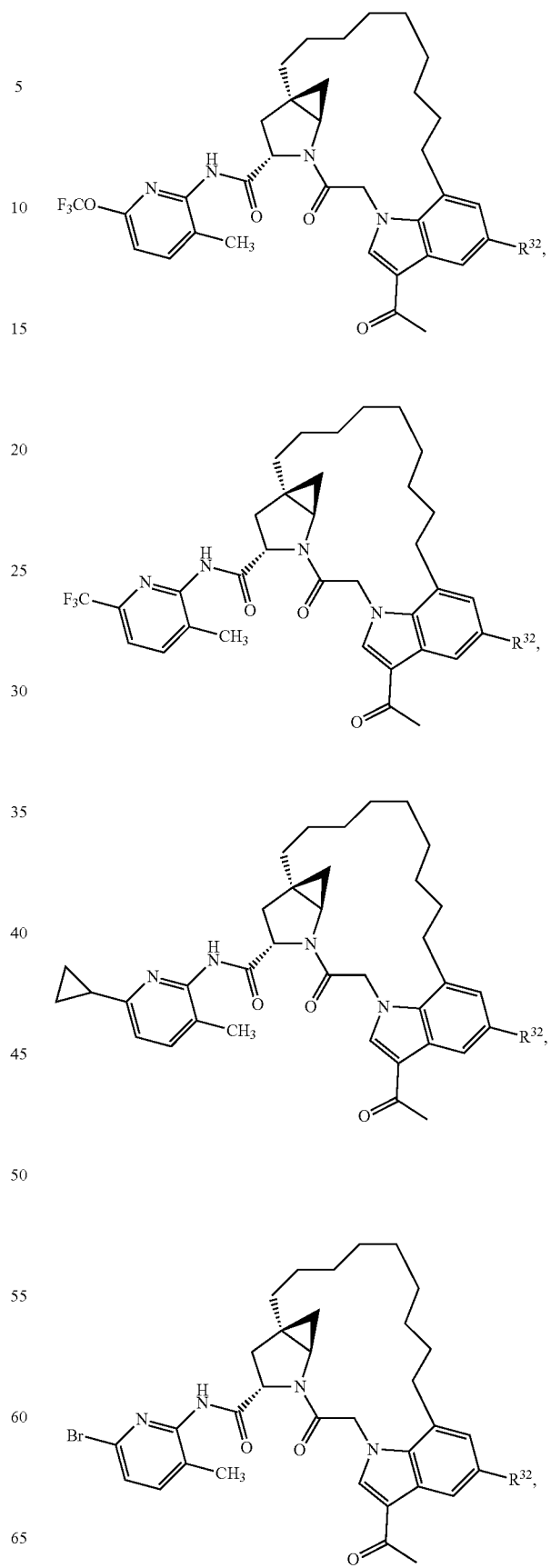
In one embodiment, the compound of Formula II is selected from:

209
-continued
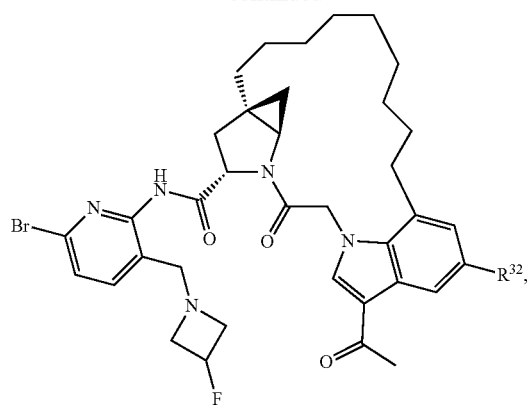
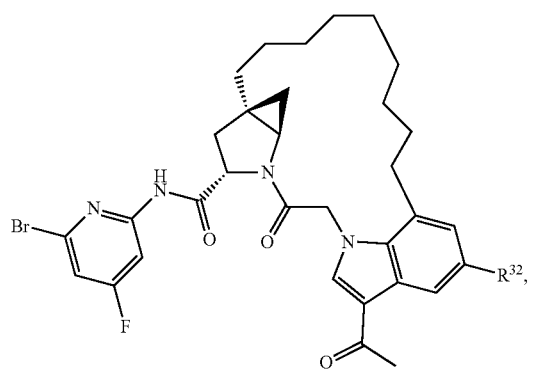
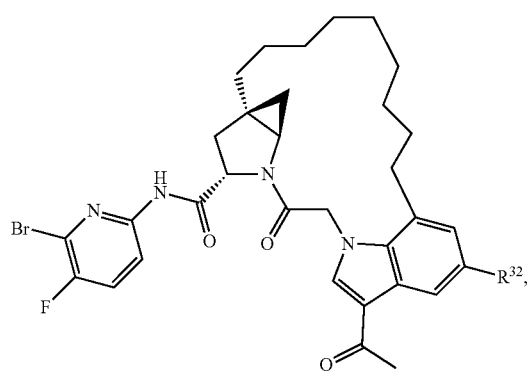
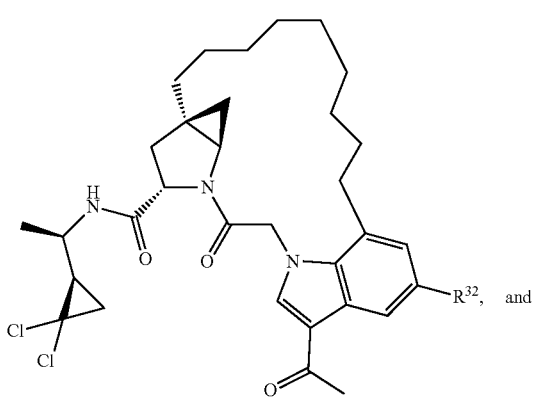
210
-continued
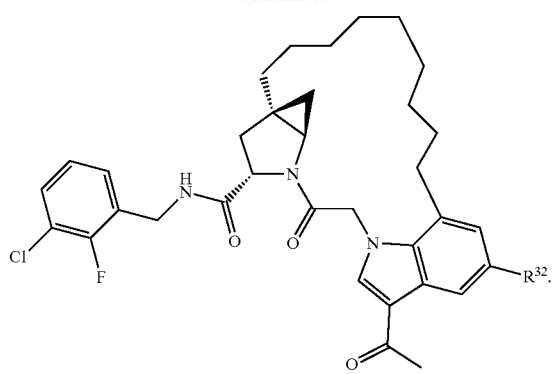
In one embodiment, the compound of Formula II is selected from:
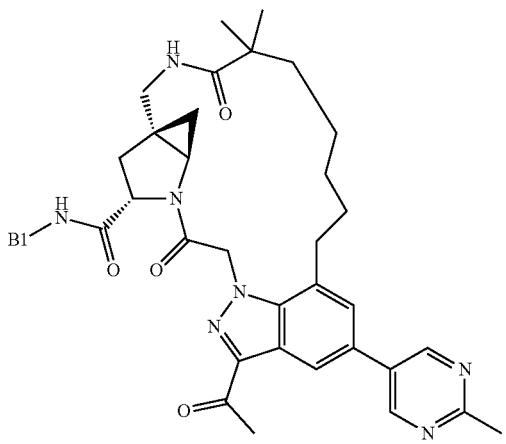
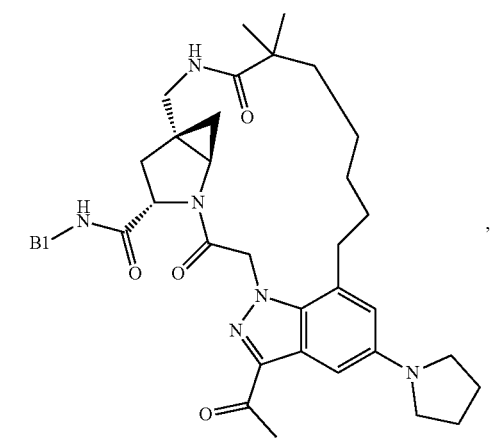

211
-continued
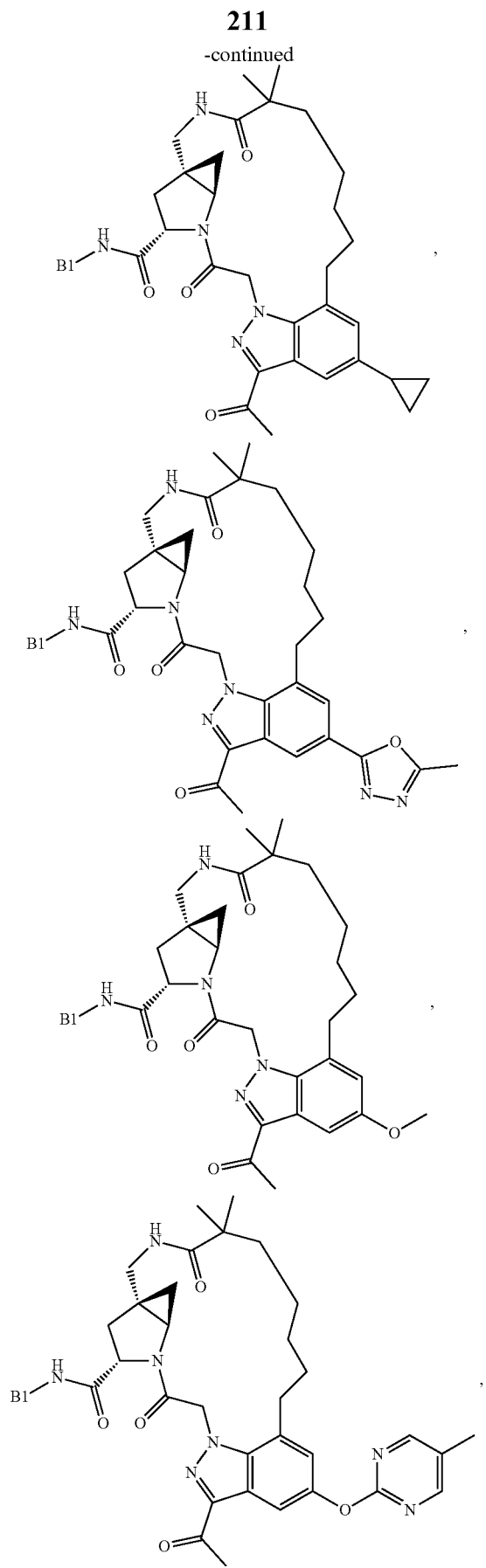
212
-continued
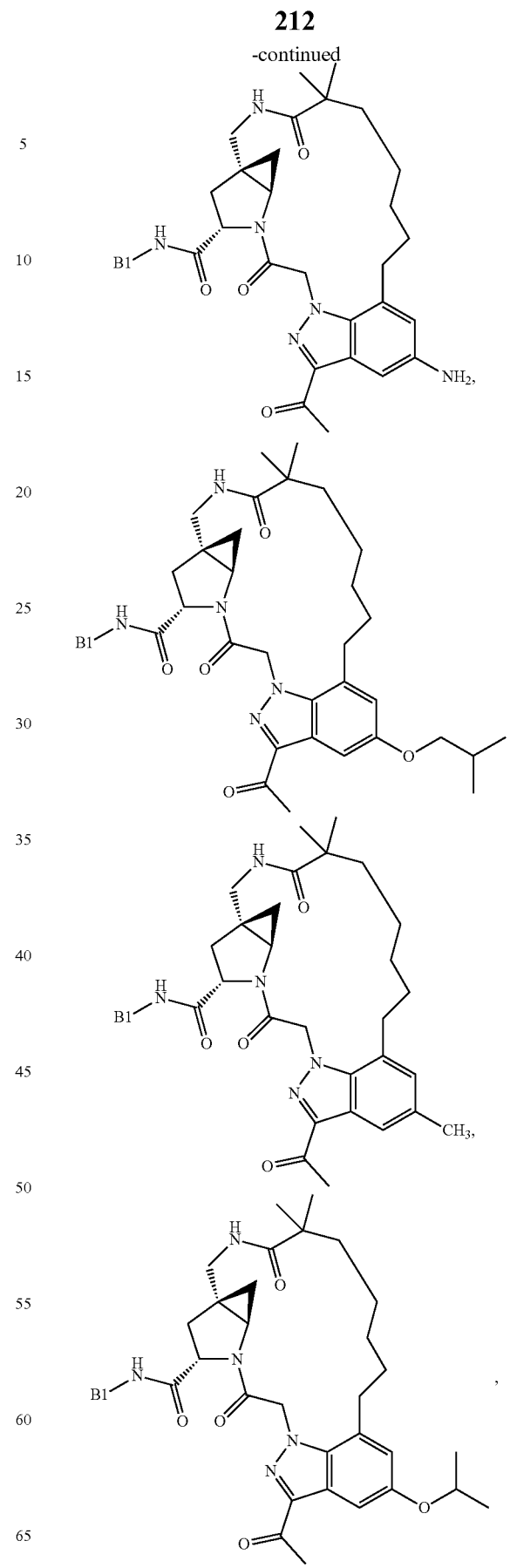

213
-continued
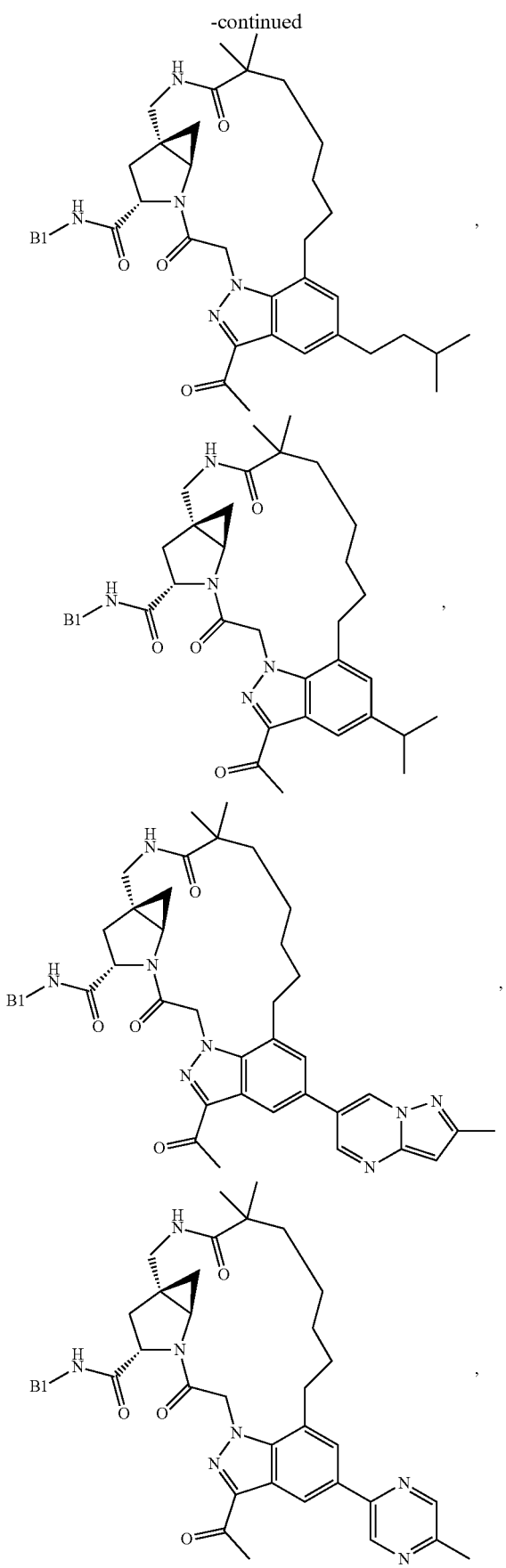
214
-continued
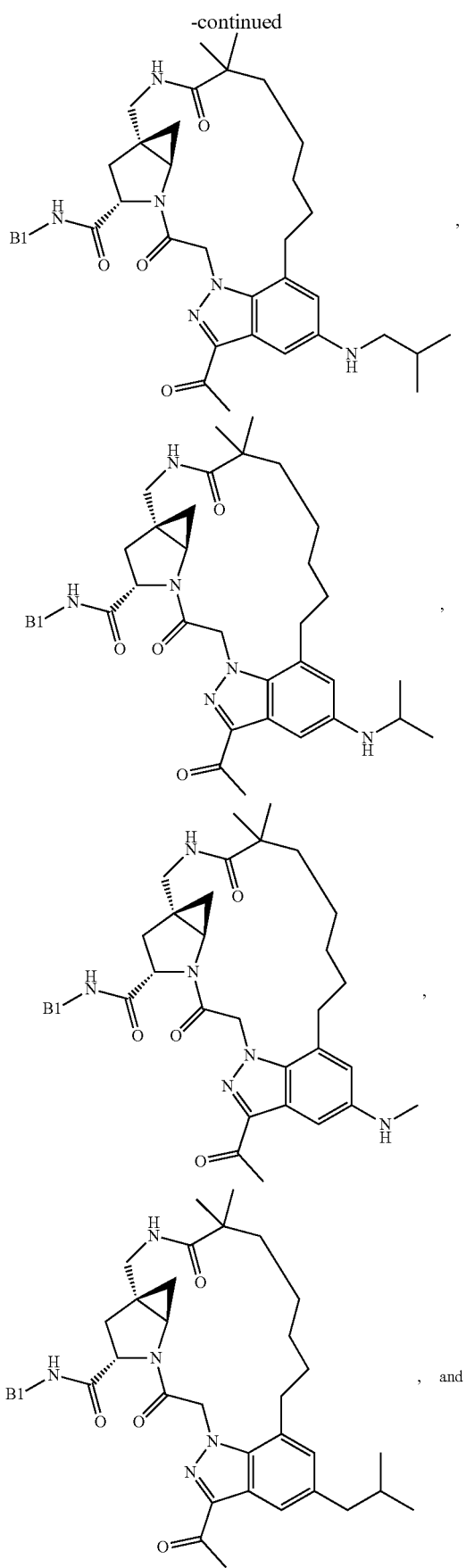
, and

215
-continued
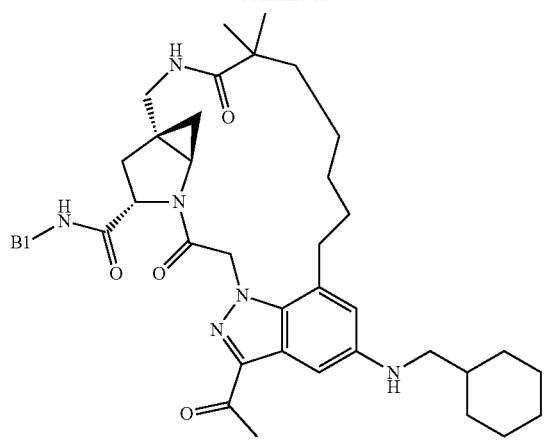
216
-continued
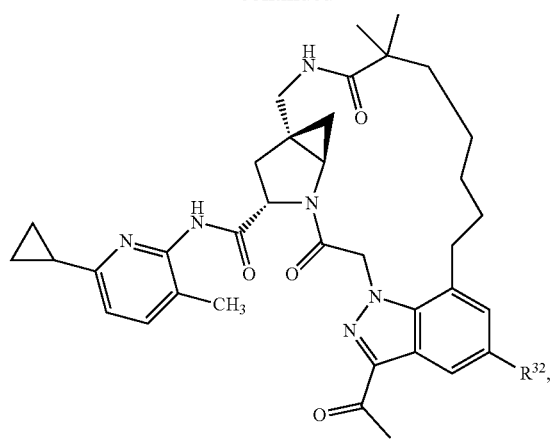
In one embodiment, the compound of Formula II is selected from:
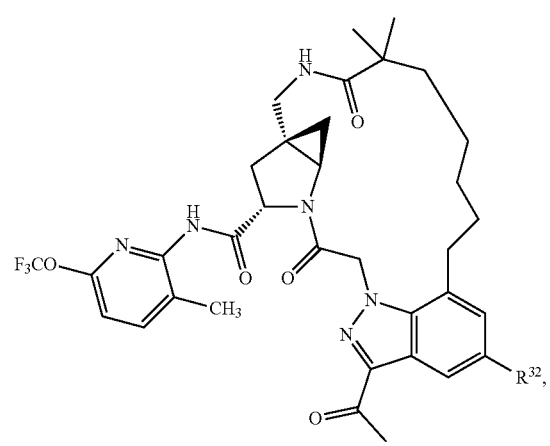
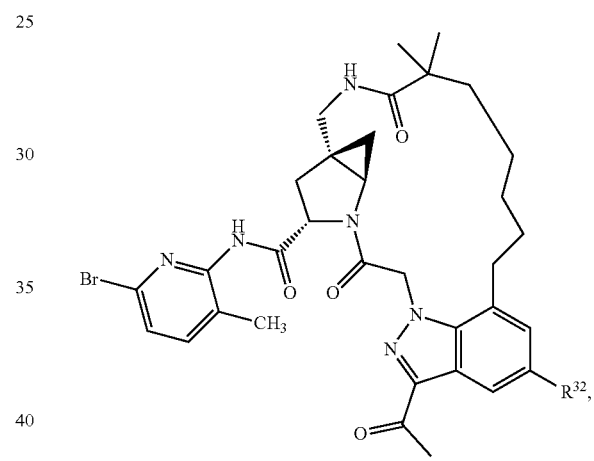
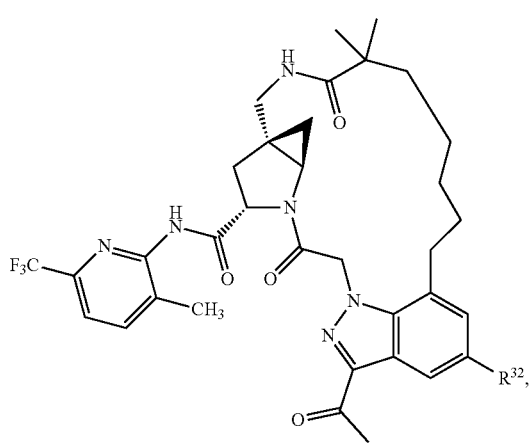
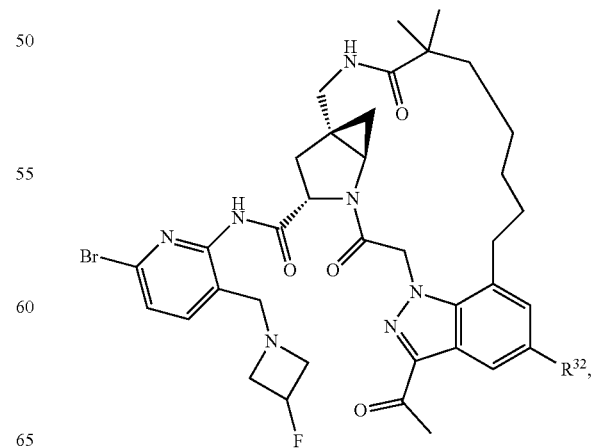

217
-continued
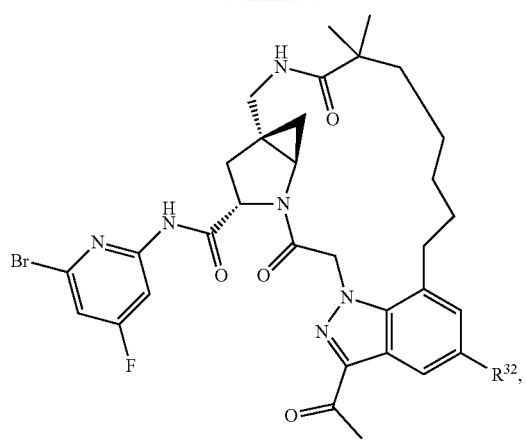
218
-continued
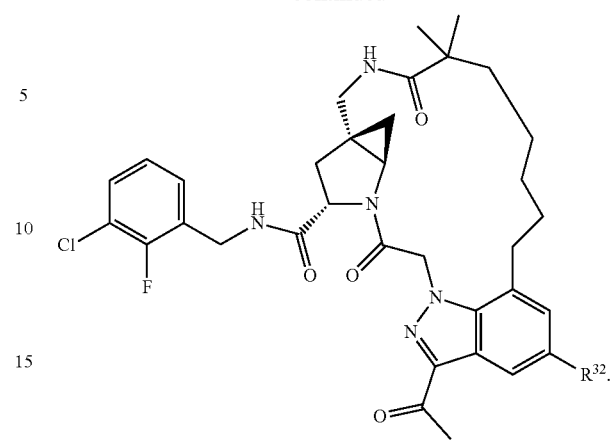
In one embodiment, the compound of Formula II is selected from:
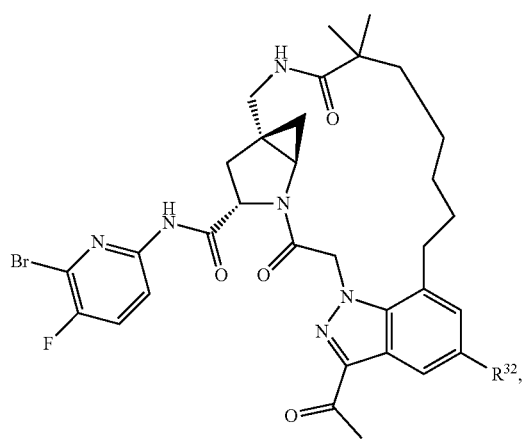
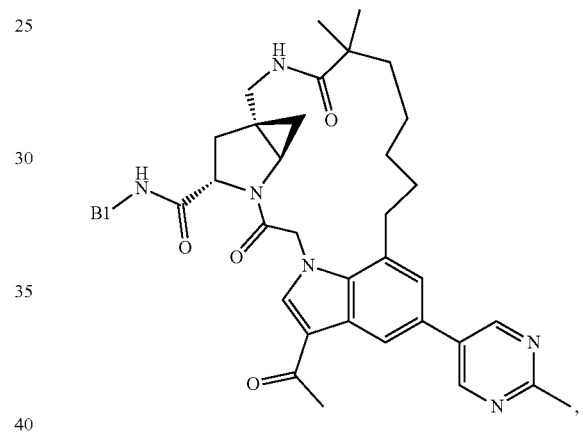
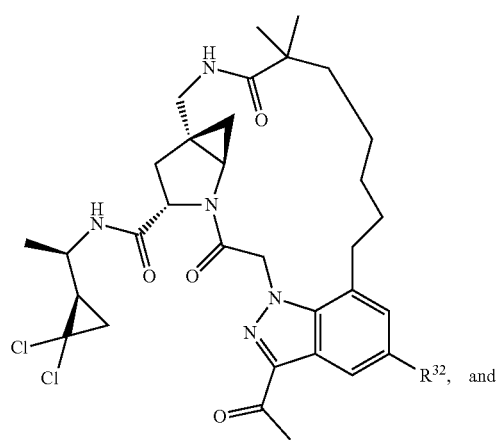, and
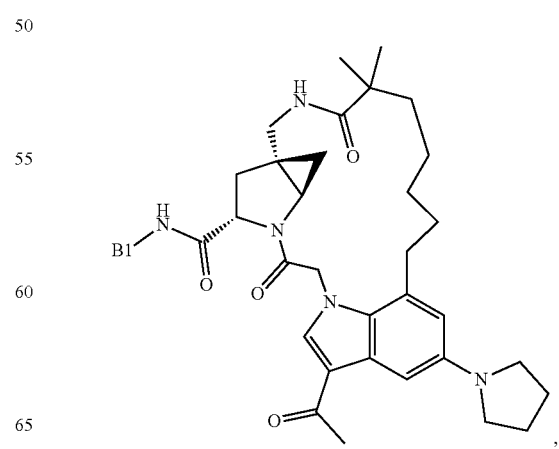

219
-continued
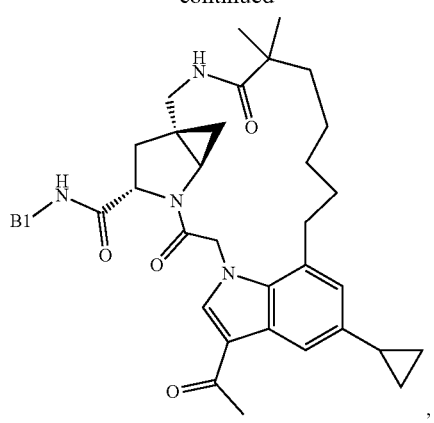
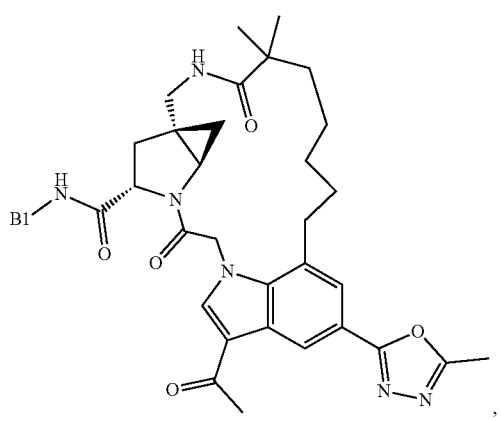
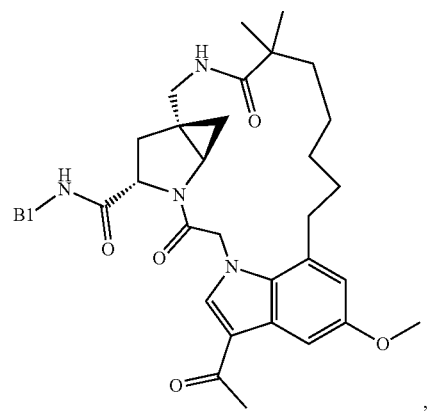
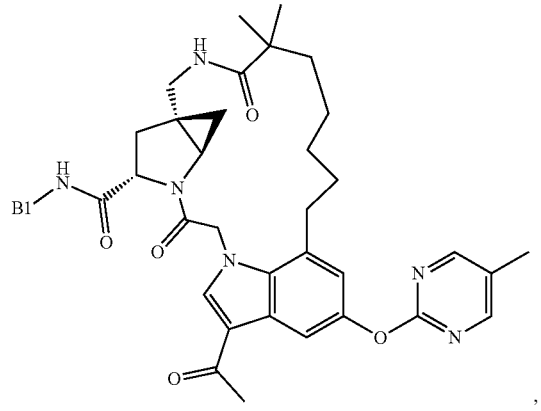
220
-continued
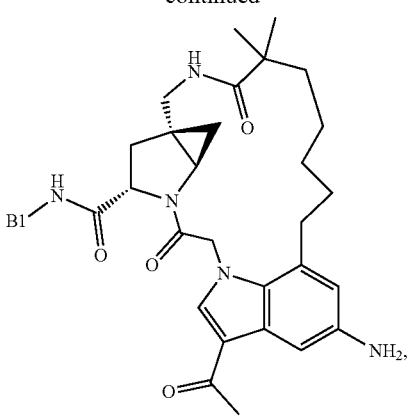
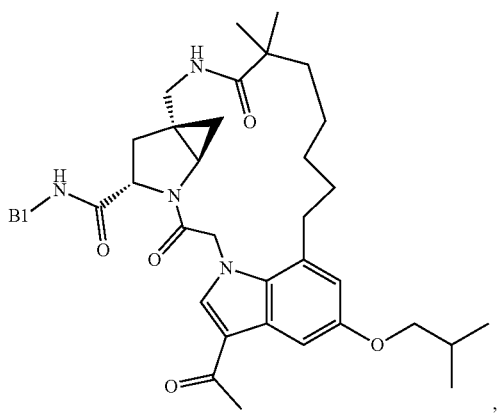
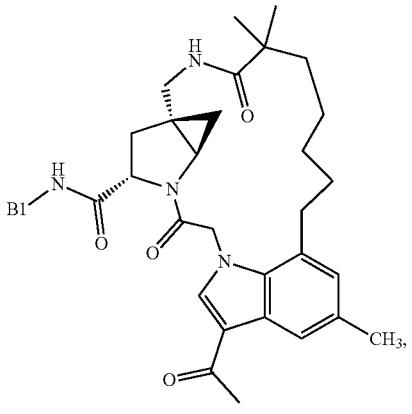
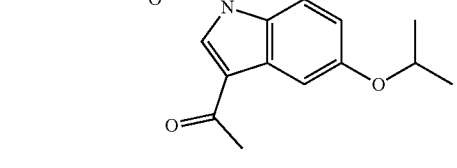

221
-continued
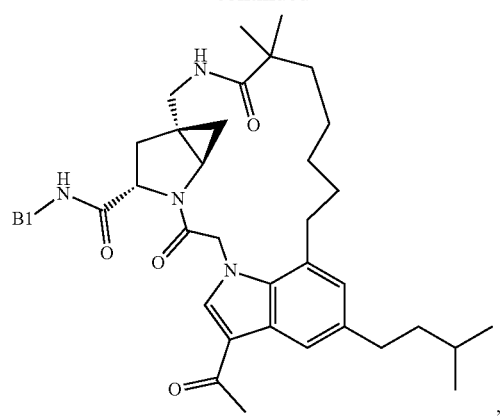
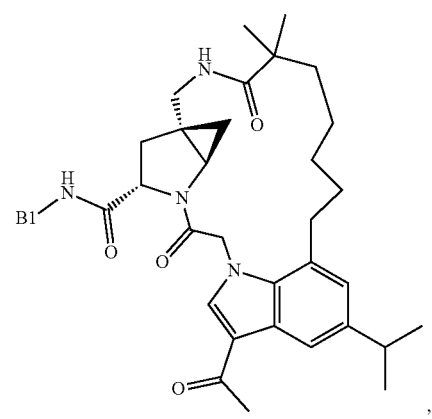
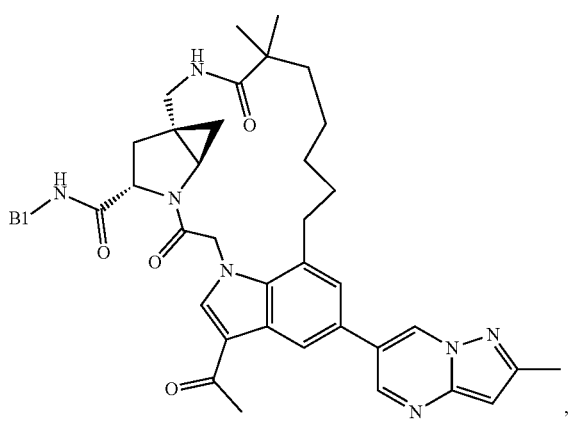
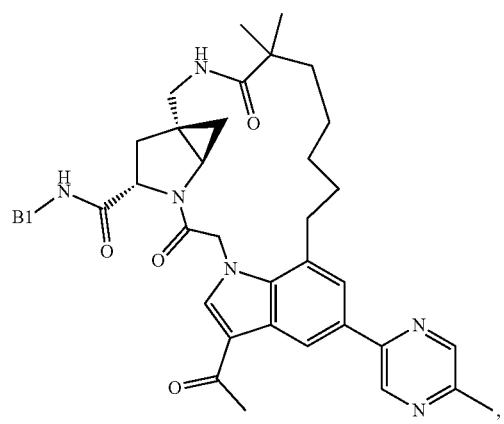
222
-continued
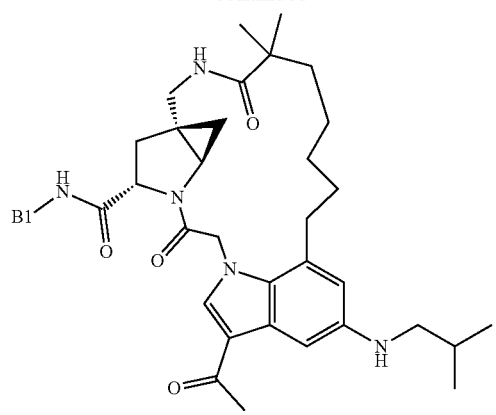
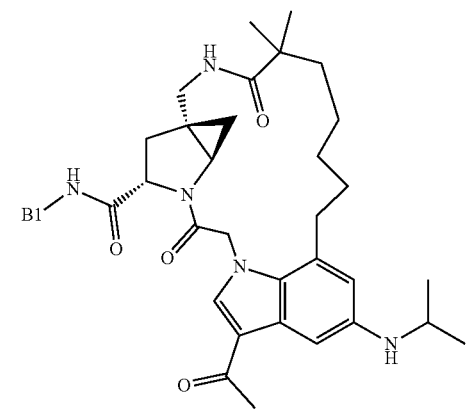
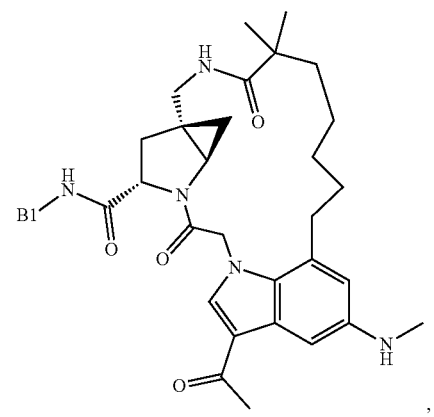
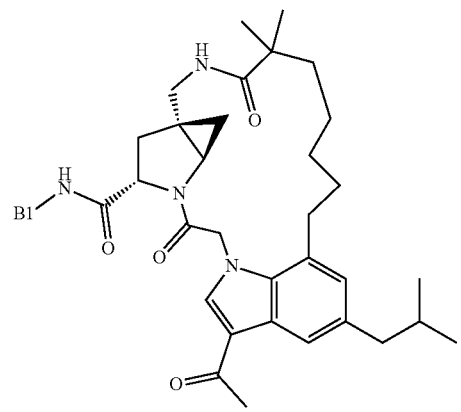
, and

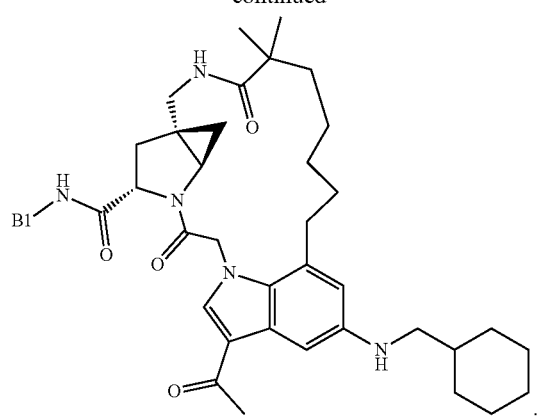
In one embodiment, the compound of Formula II is selected from:
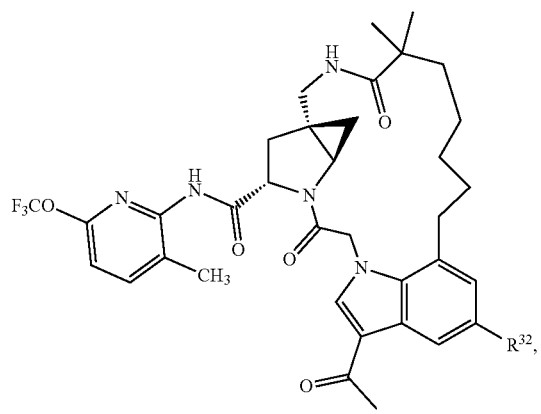
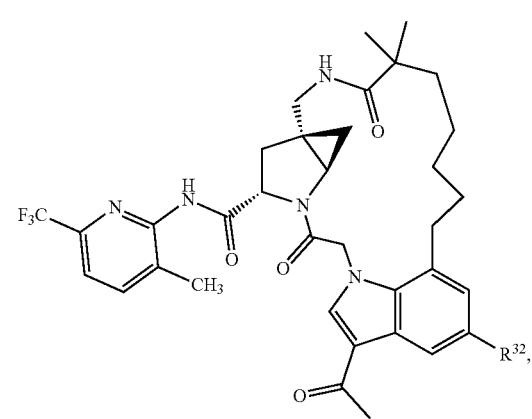
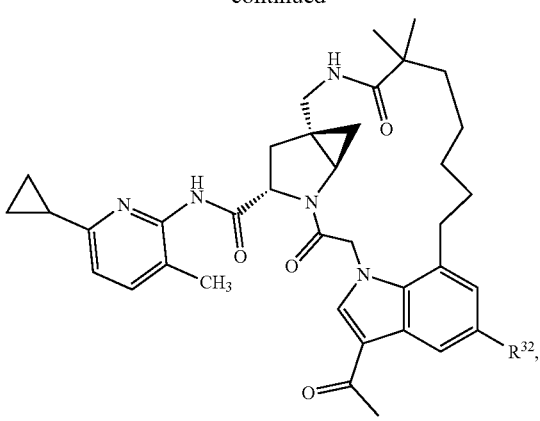
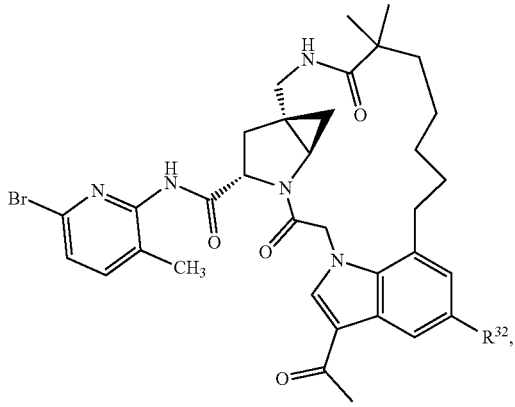
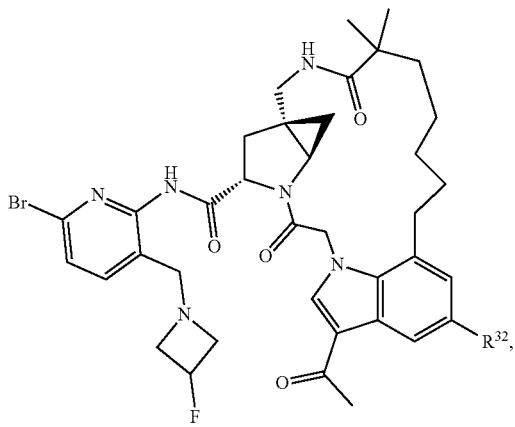
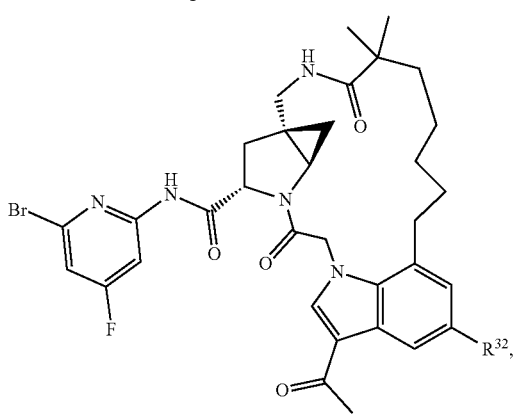

225
-continued
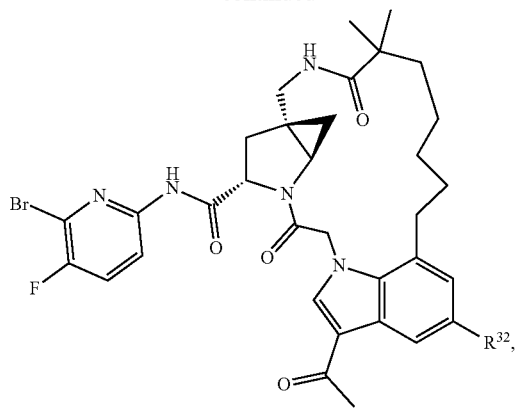
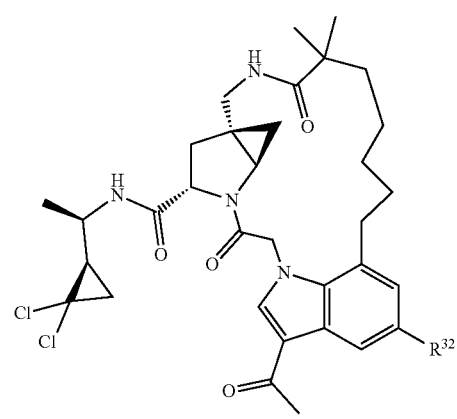
, and
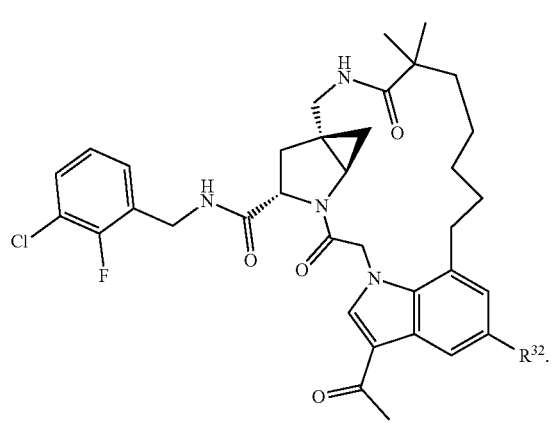
226
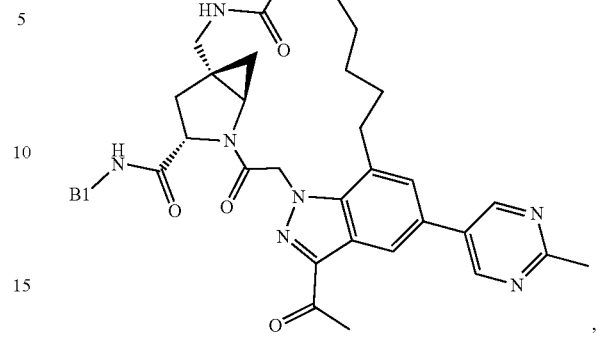
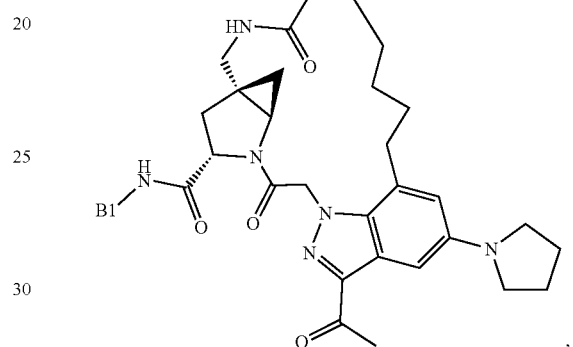
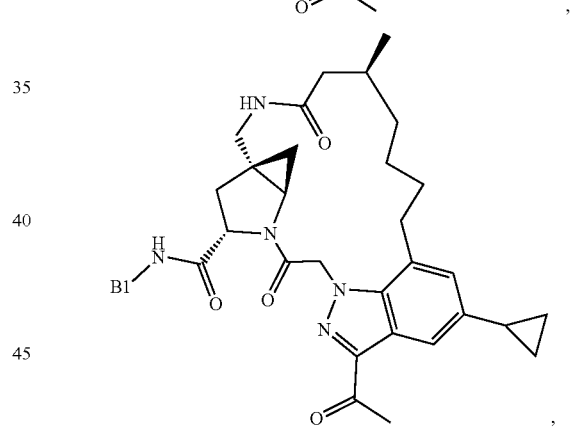
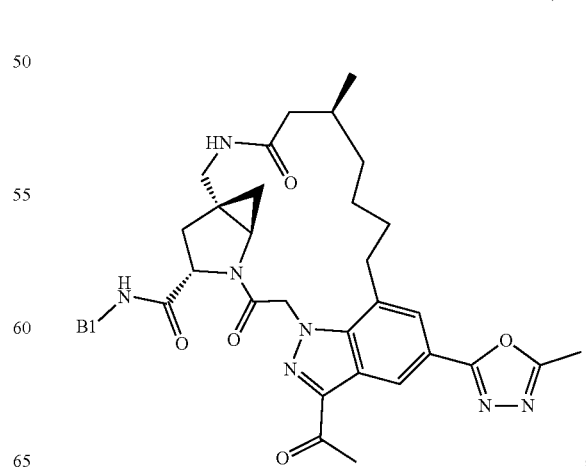
In one embodiment, the compound of Formula II is selected from:

227
-continued
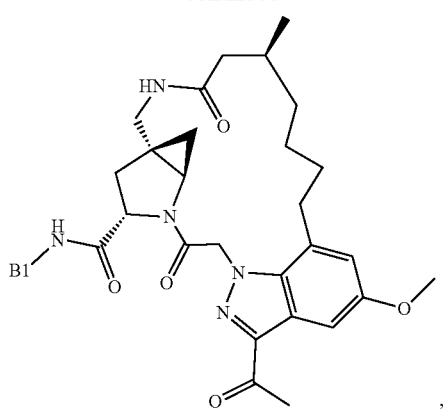
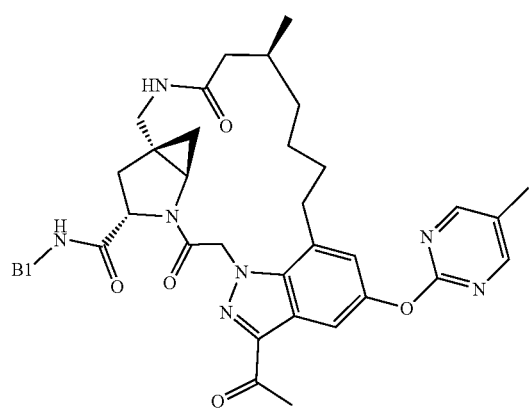
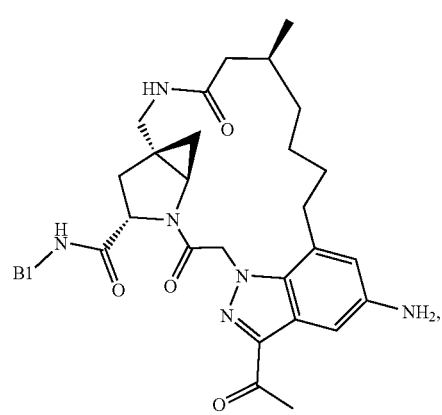
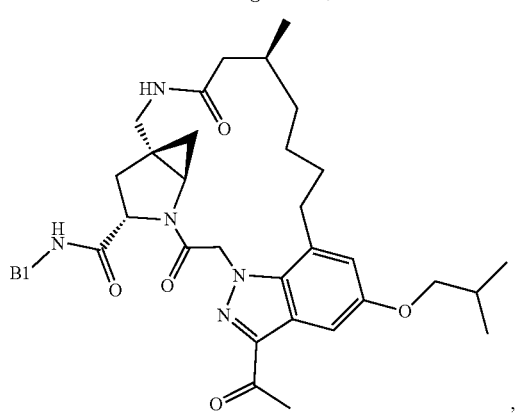
,
228
-continued
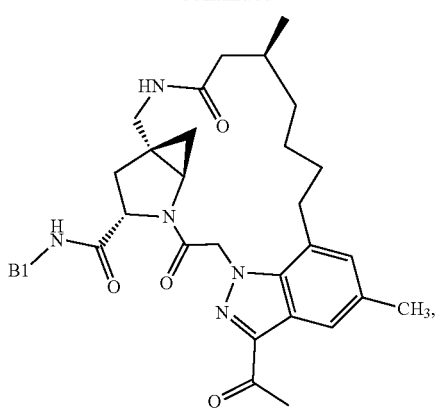
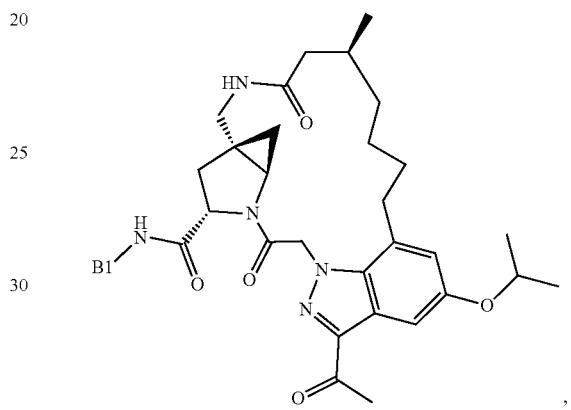
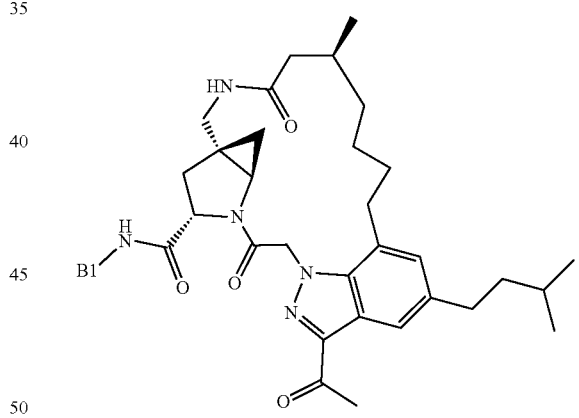
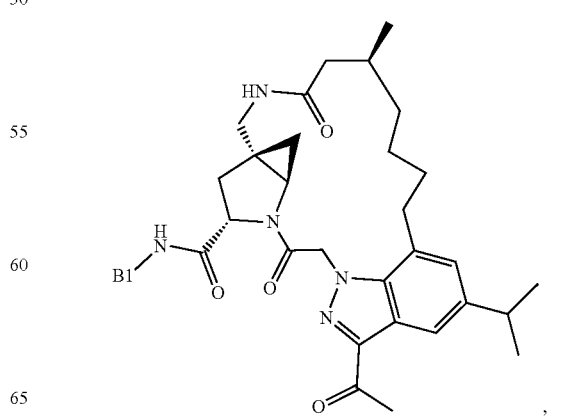
, 229
-continued
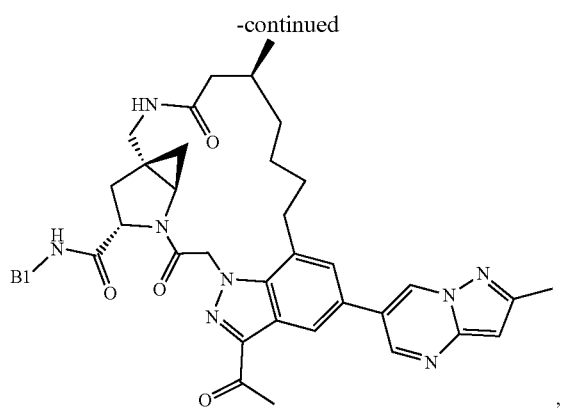
,
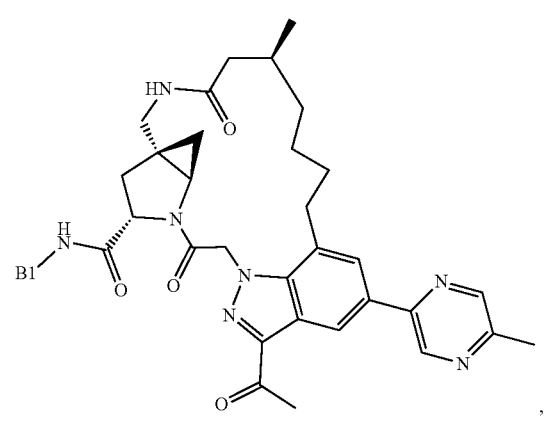
,
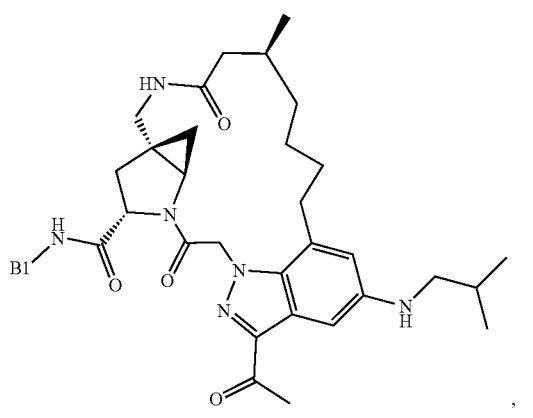
,
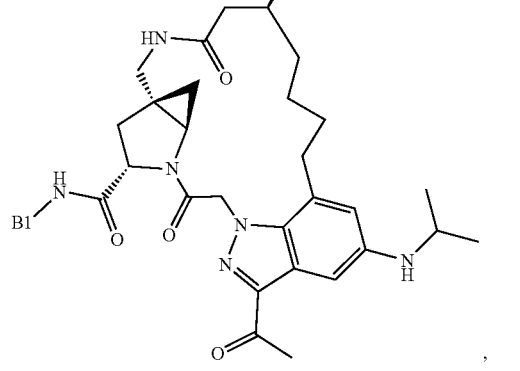
,
230
-continued
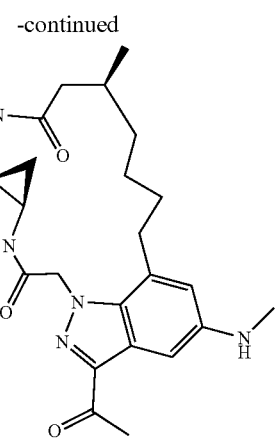
,
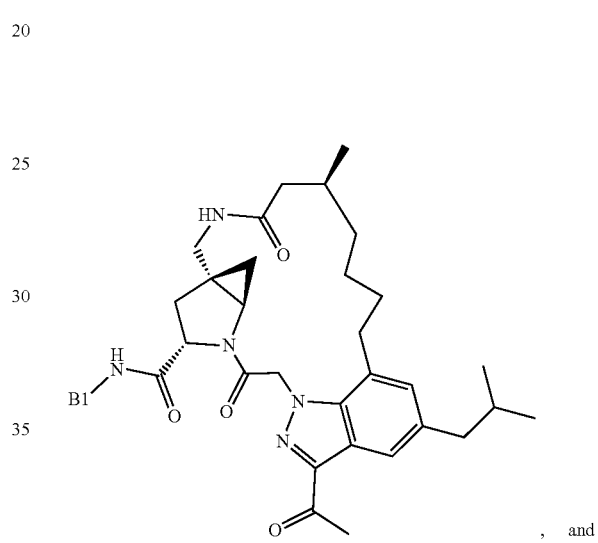
, and
In one embodiment, the compound of Formula II is selected from:

231
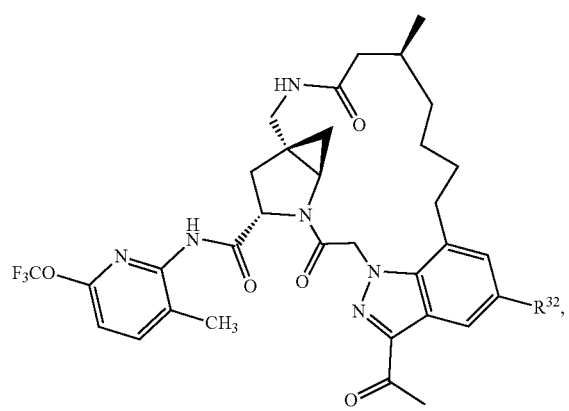
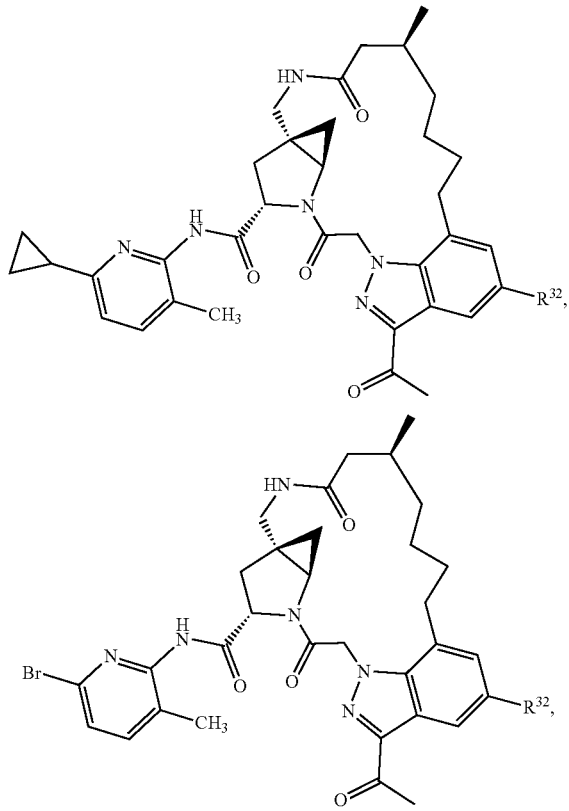
232
-continued
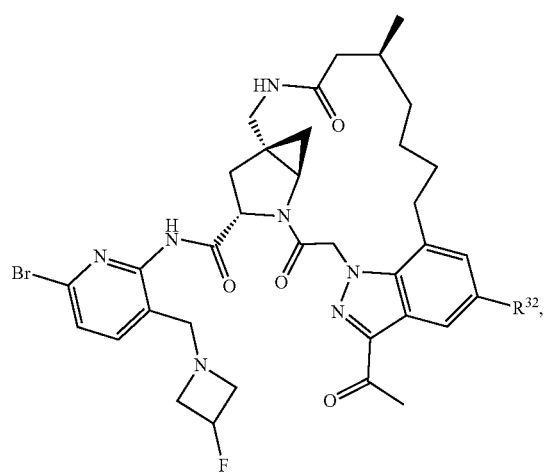
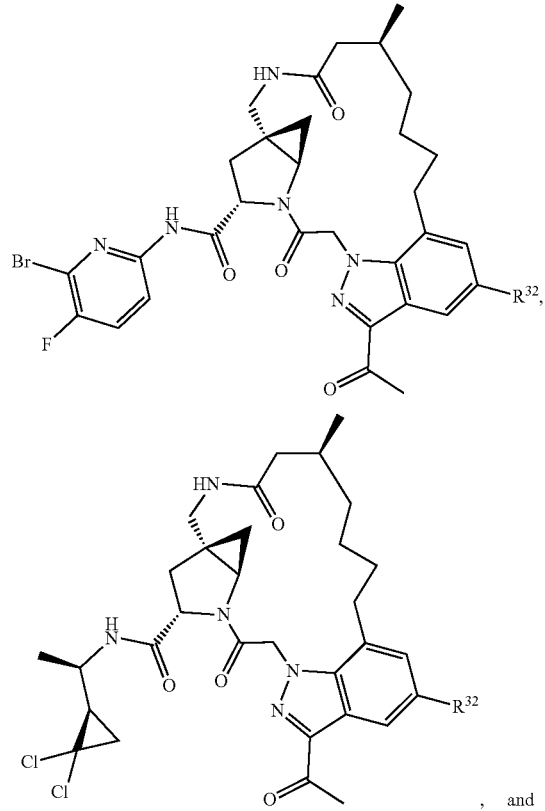
, and

233
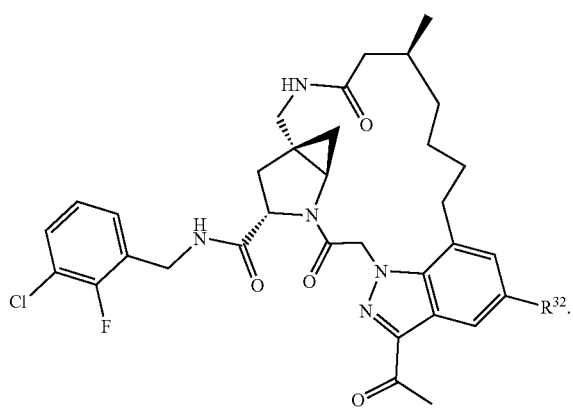
In one embodiment, the compound of Formula II is selected from:
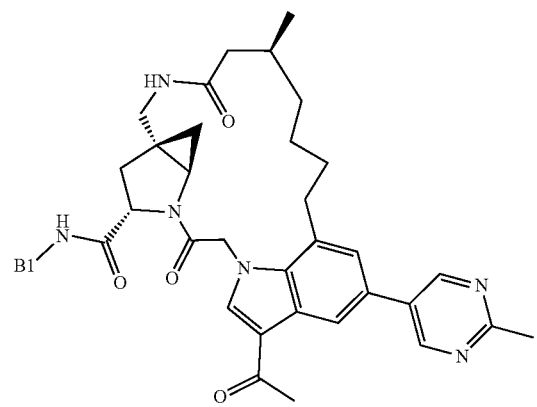
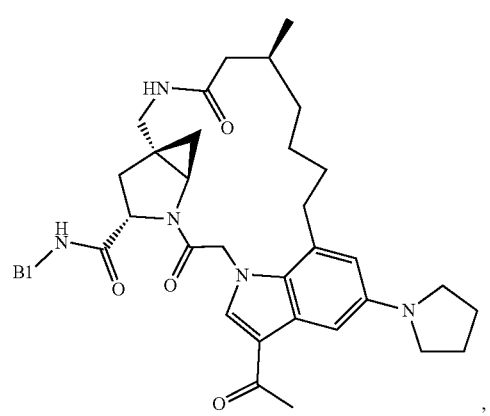
234
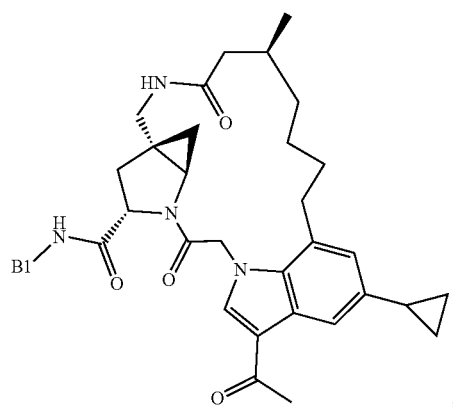
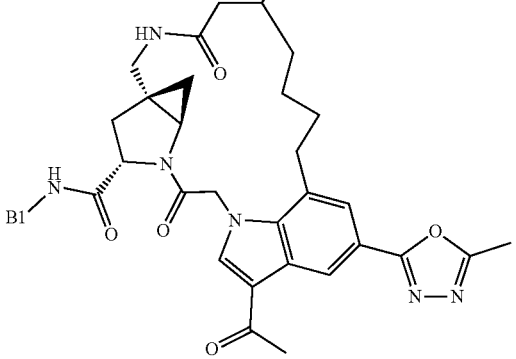
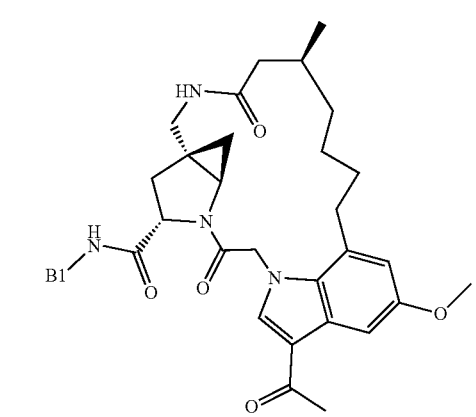
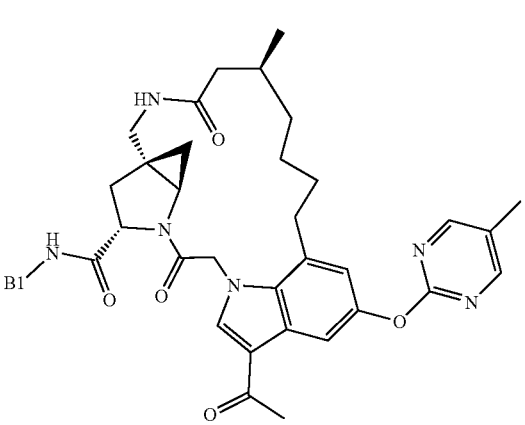

235
-continued
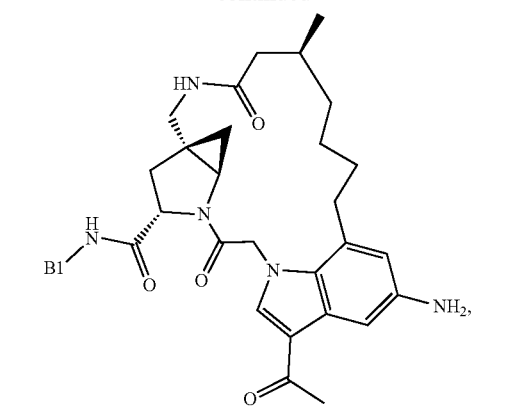
,
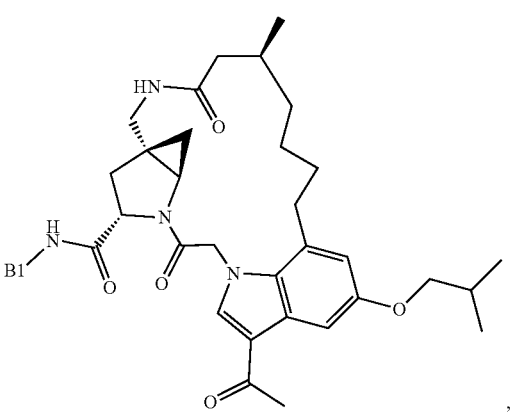
,
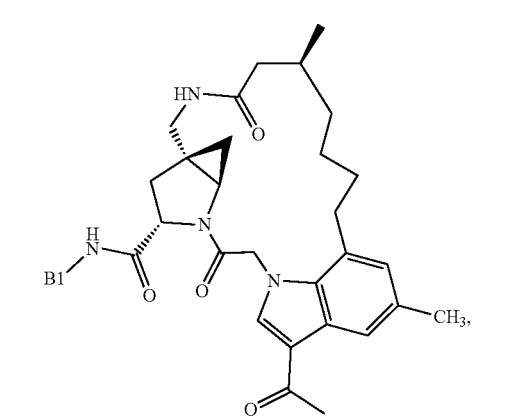
,
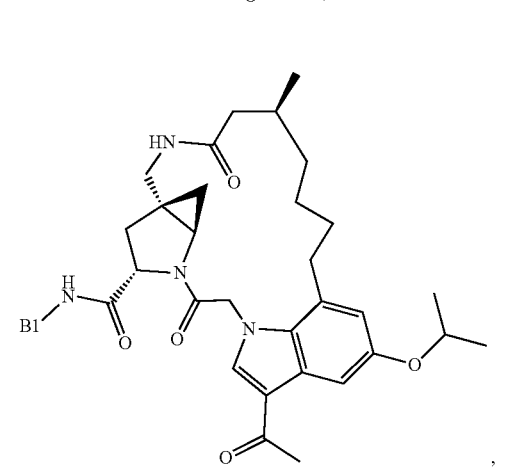
,
236
-continued
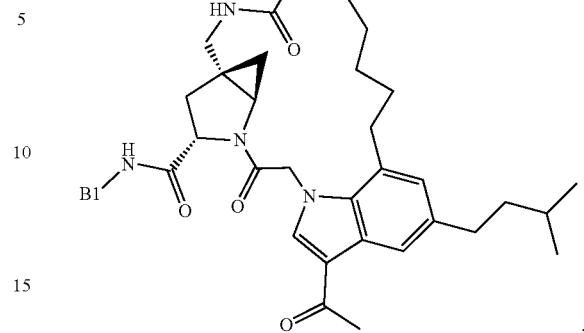
,
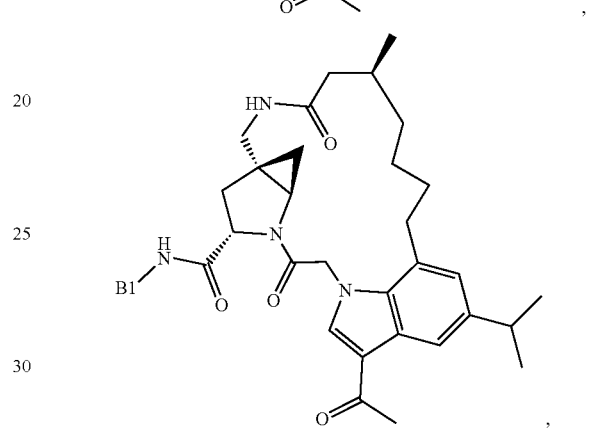
,
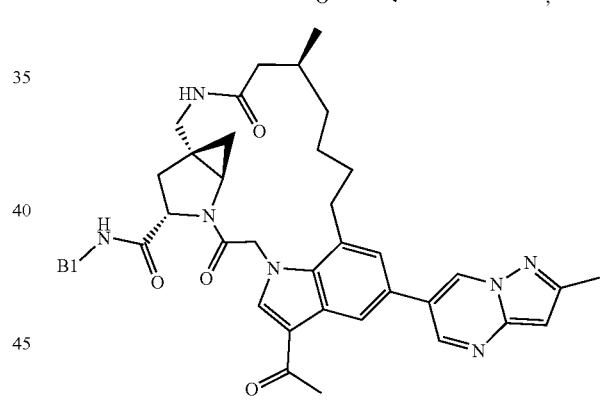
,
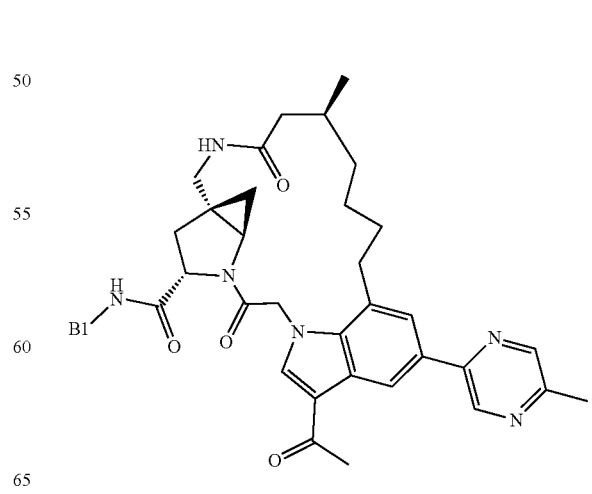
, 237
-continued
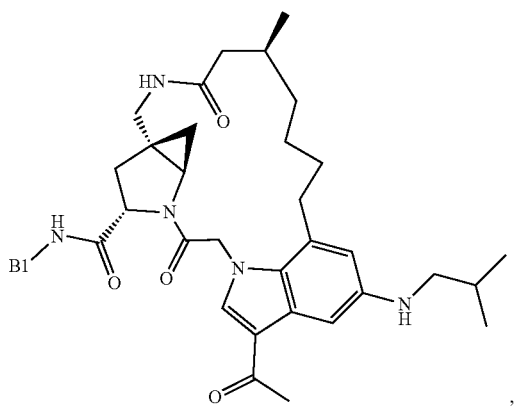
,
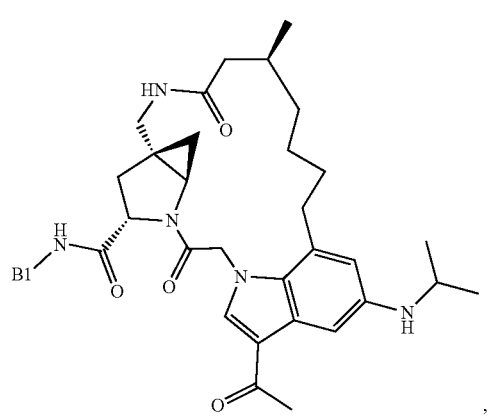
,
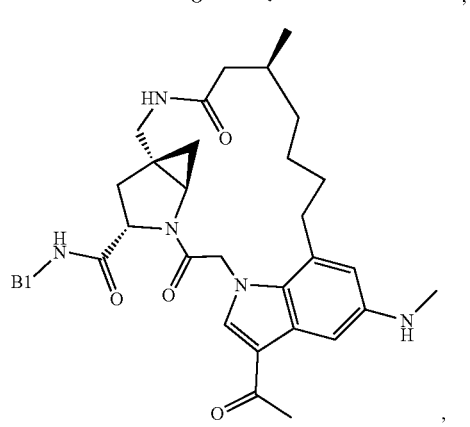
,
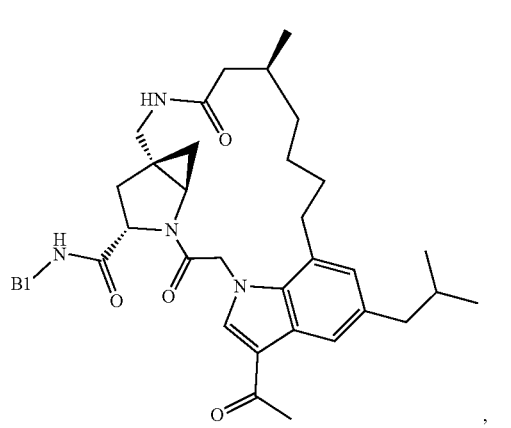
, and
238
-continued
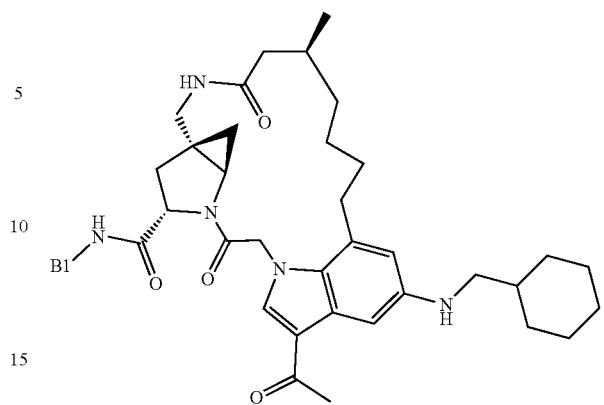
.
In one embodiment, the compound of Formula II is selected from:
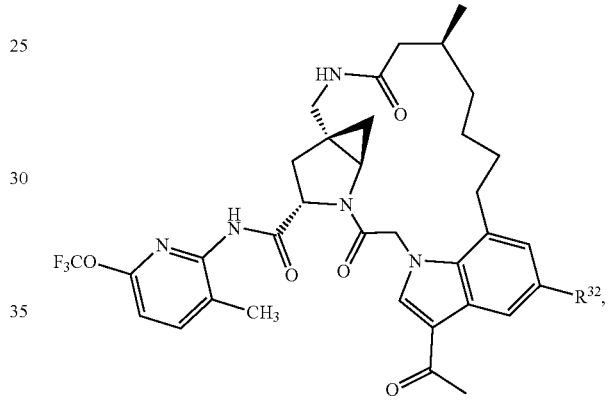
,
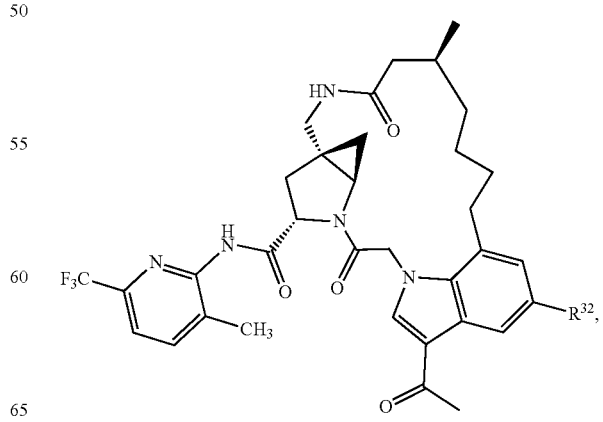
,

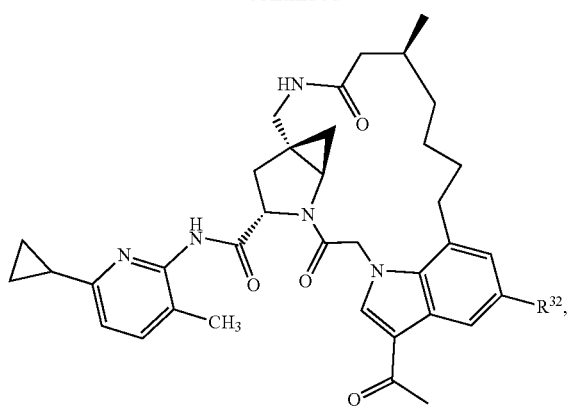
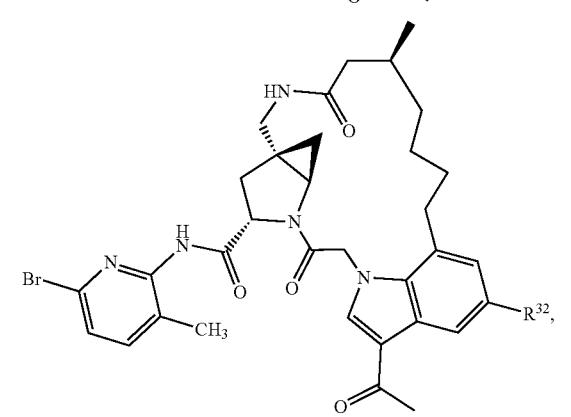
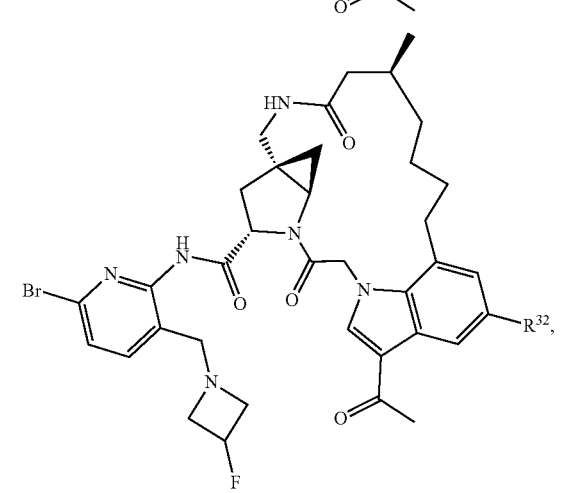
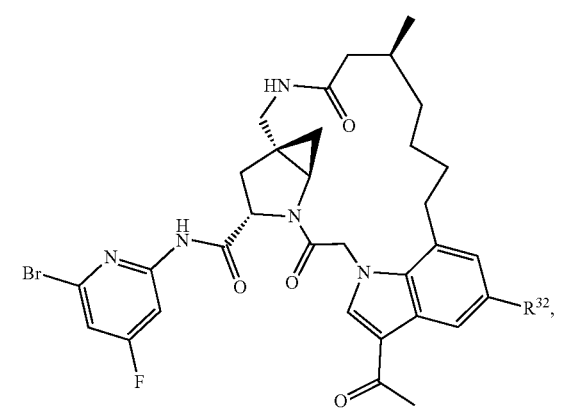
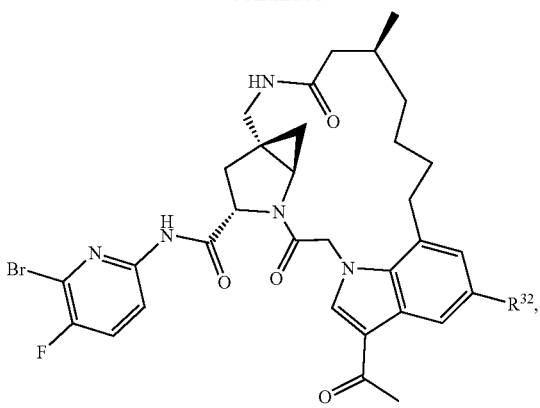
In one embodiment, the compound of Formula II is selected from:

241
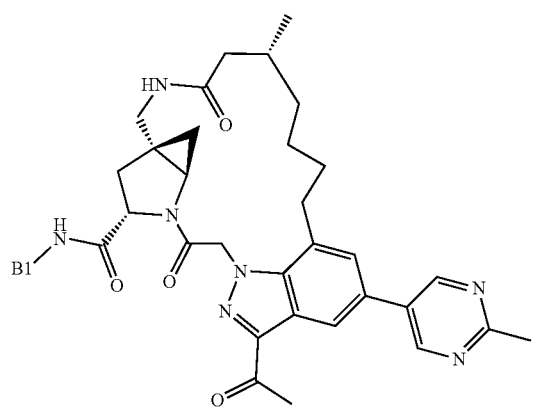
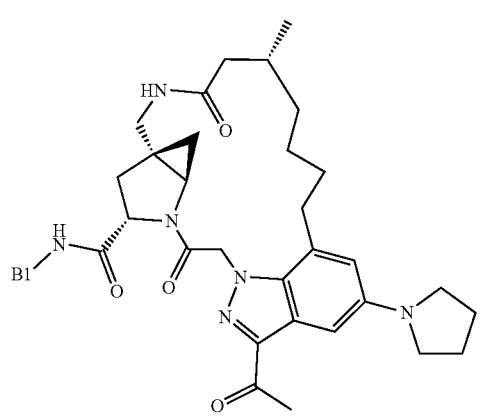
242
-continued
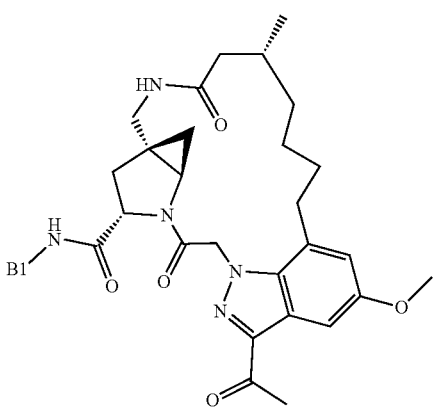
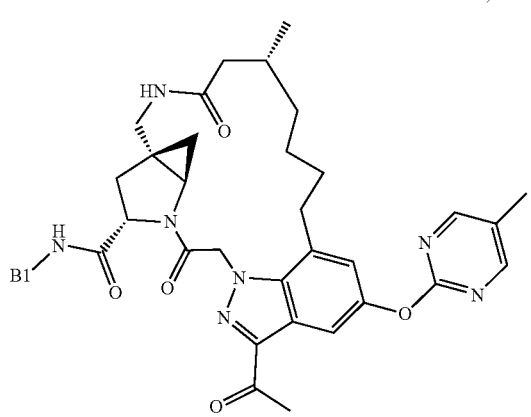
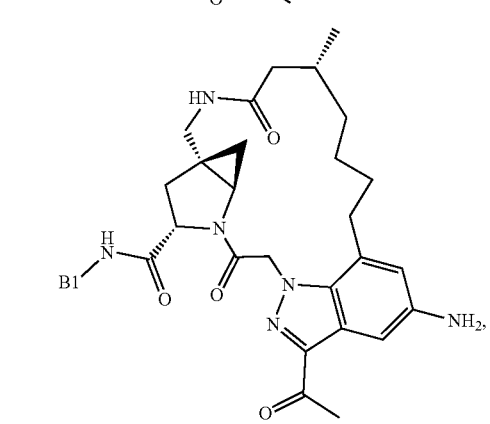
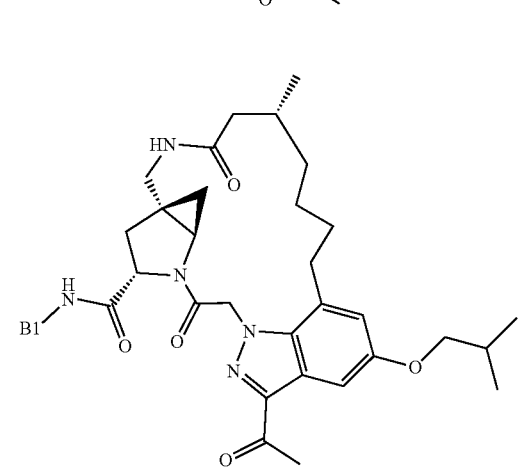

243
-continued
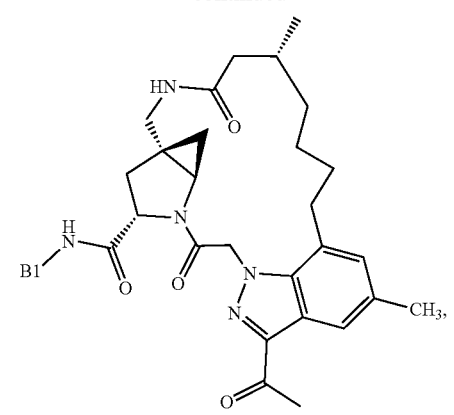
,
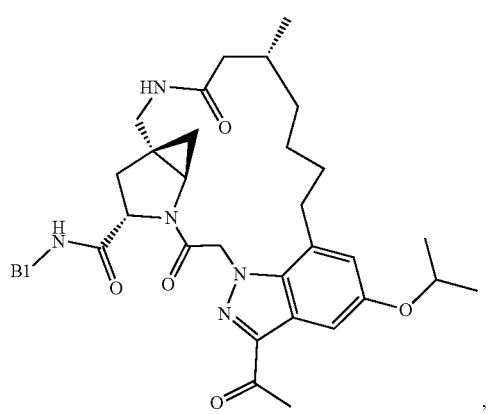
,
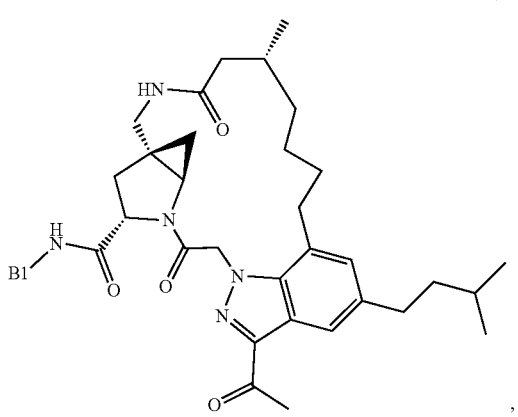
,
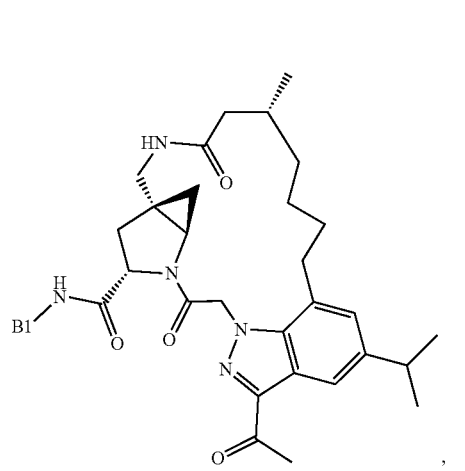
,
244
-continued
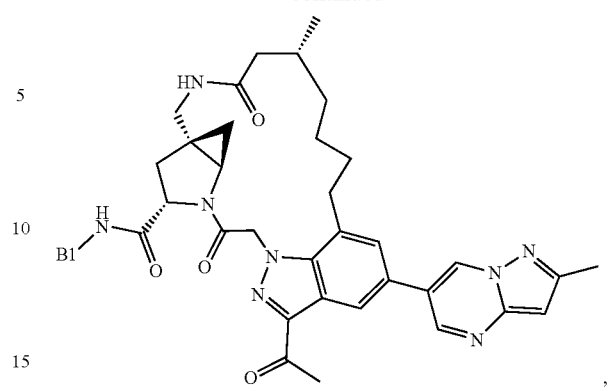
,
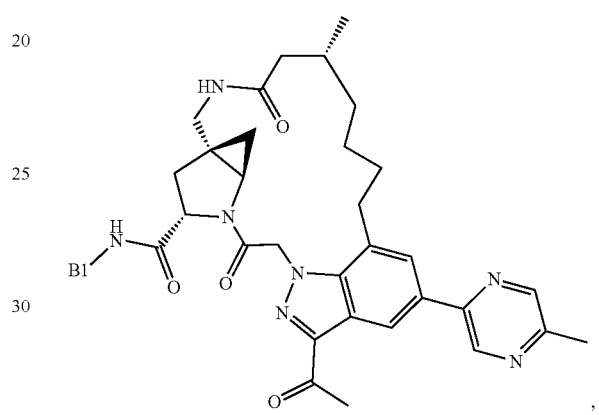
,
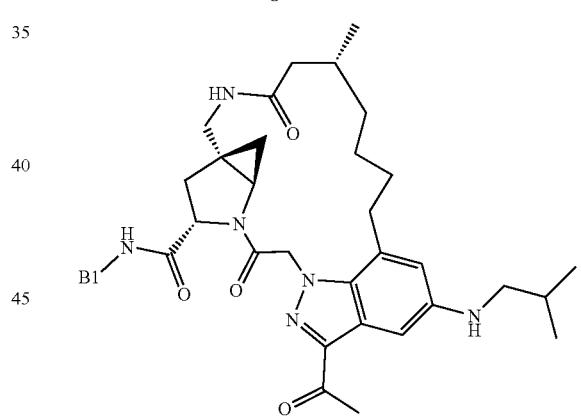
,
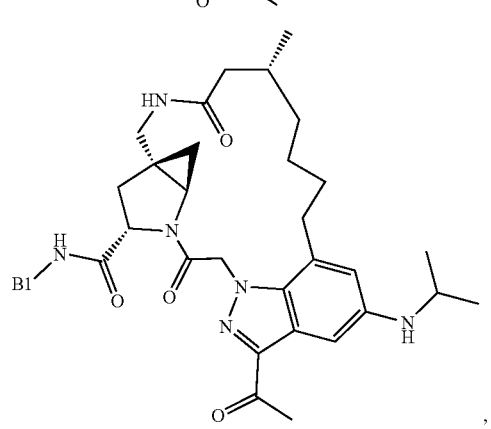
,

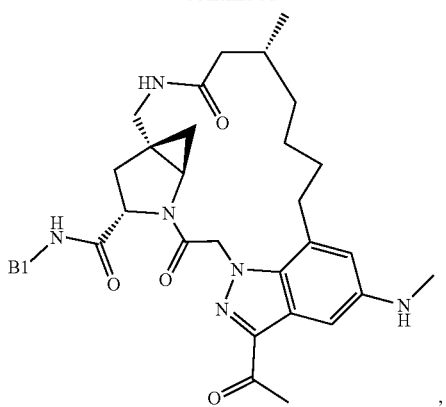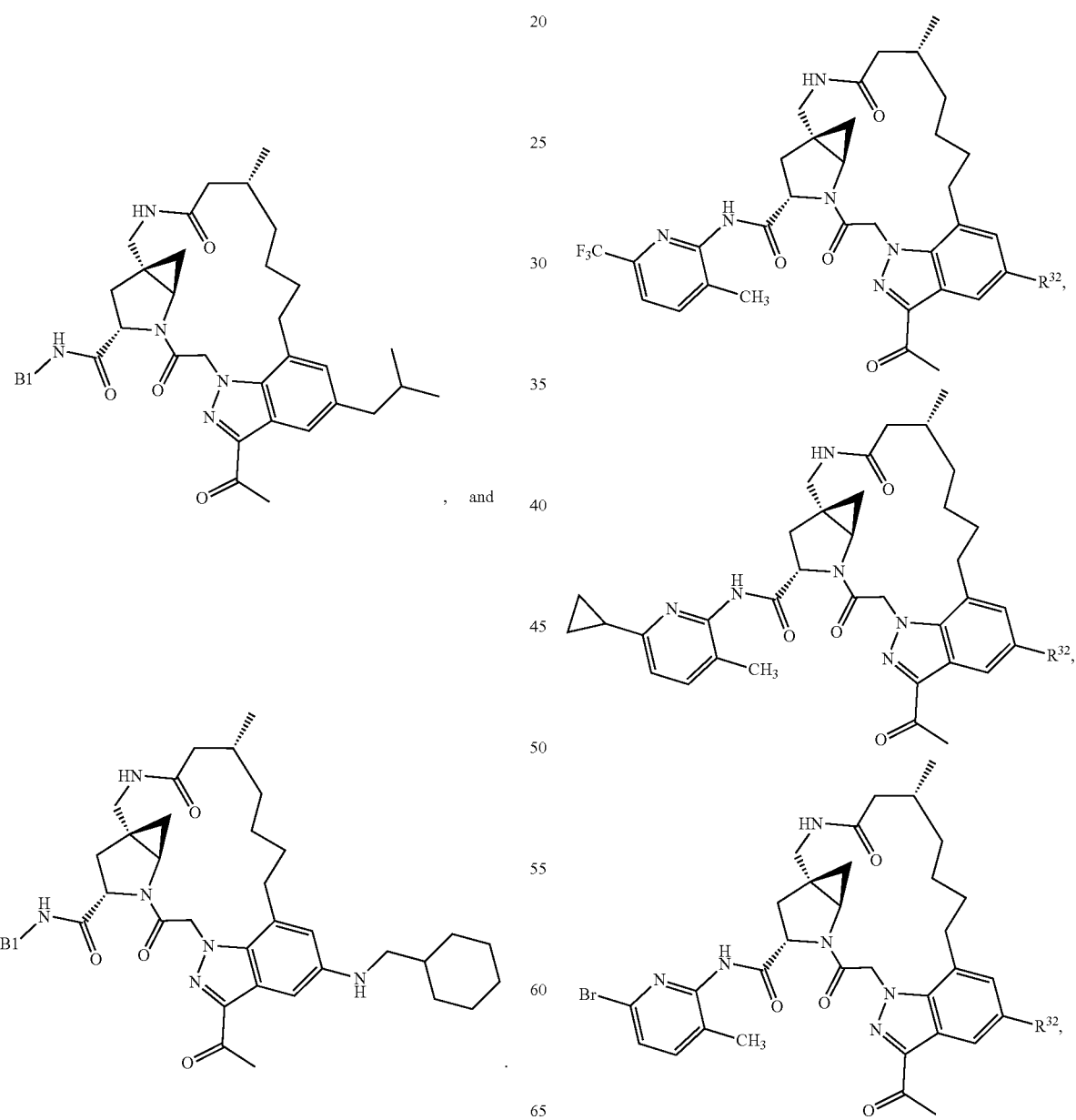
In one embodiment, the compound of Formula II is selected from:

247
-continued
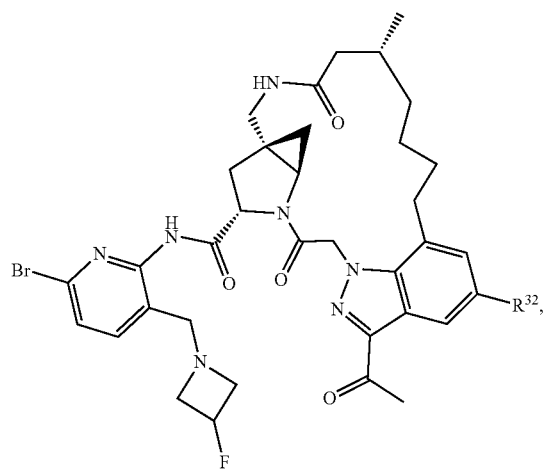
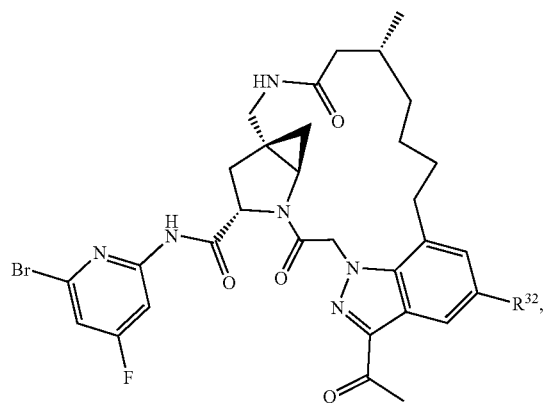
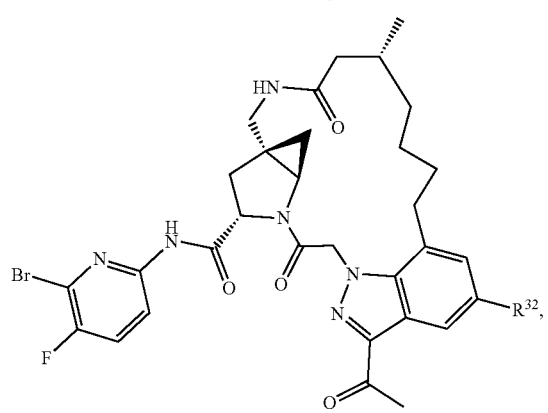
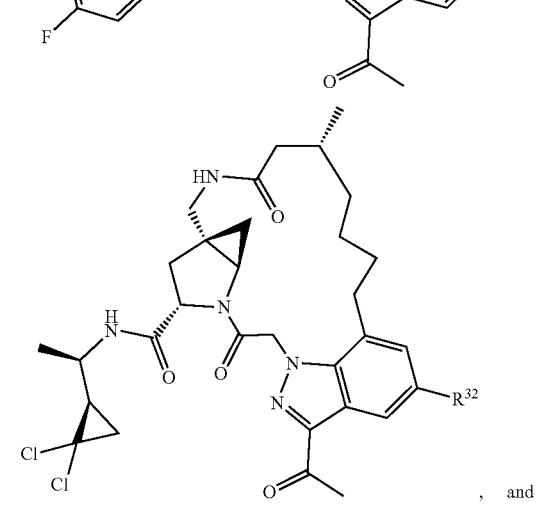
, and
248
-continued
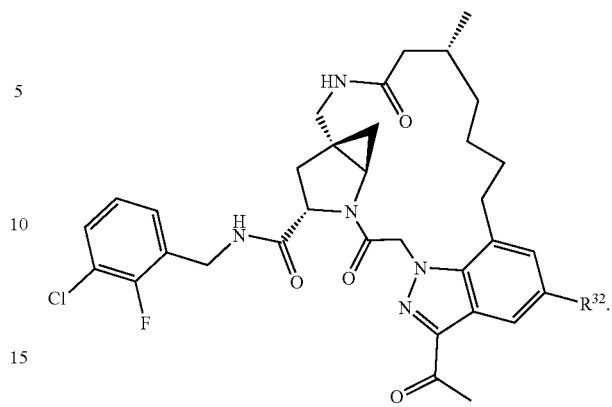
In one embodiment, the compound of Formula II is selected from:
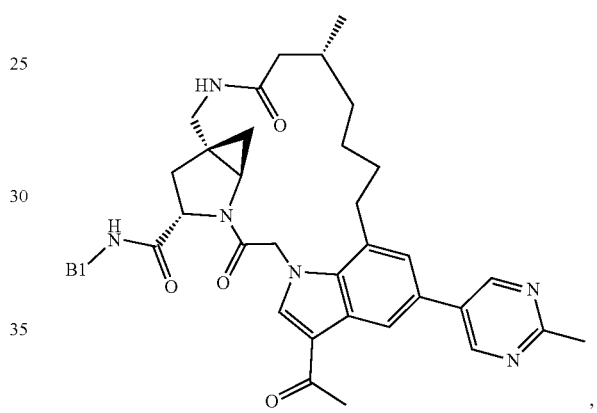
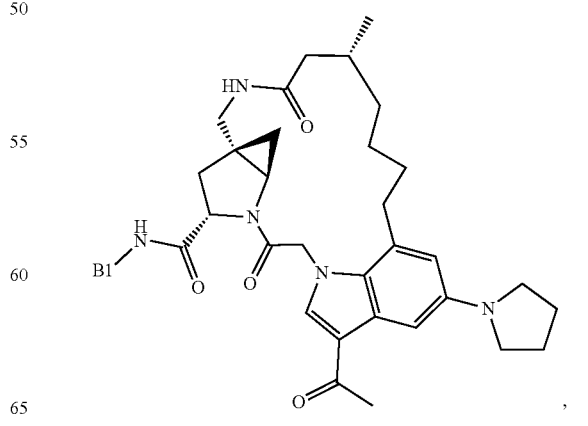
, 249
-continued
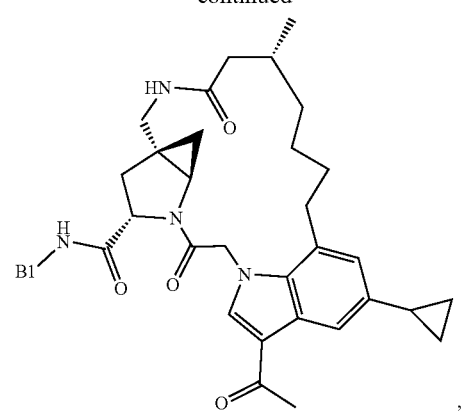
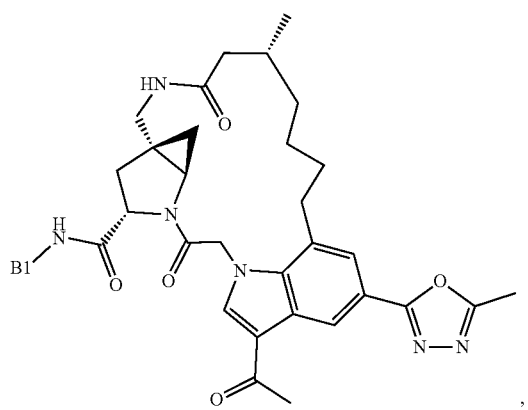
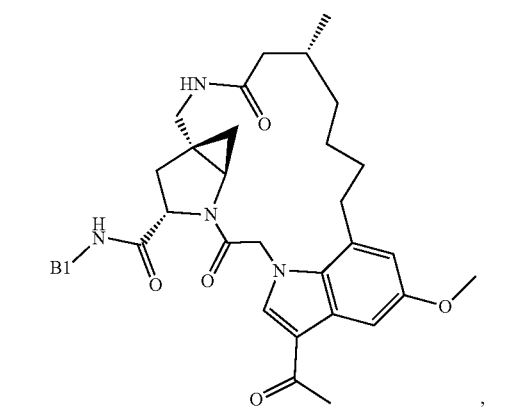
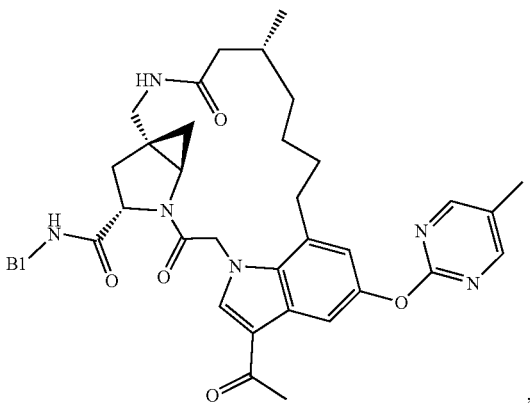
250
-continued
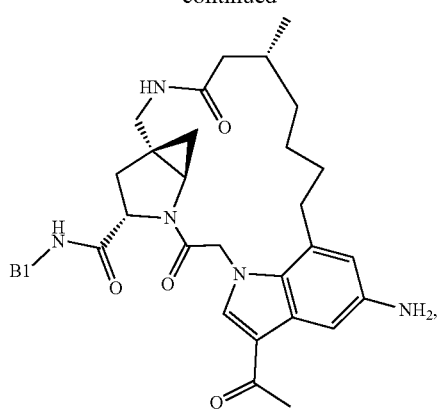
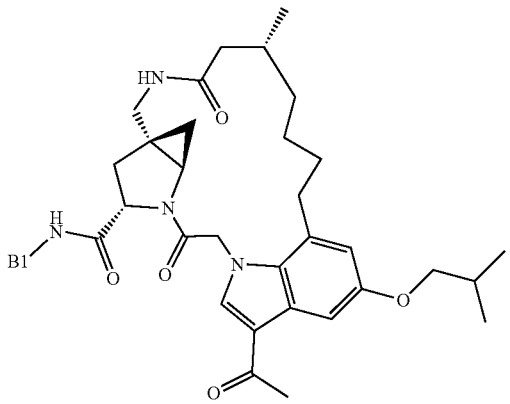
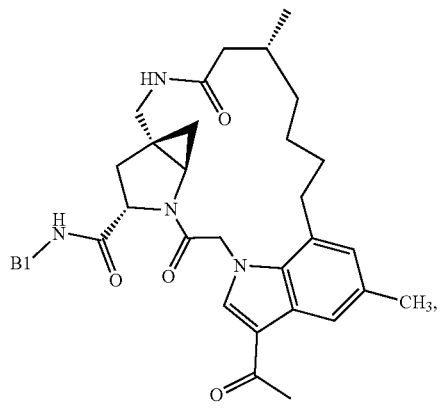
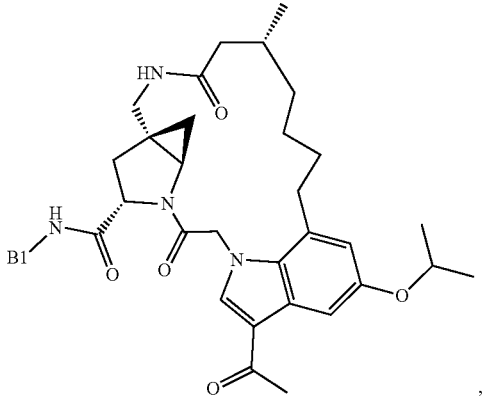

-continued
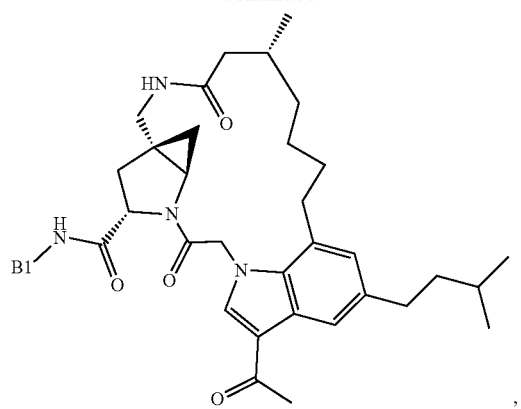
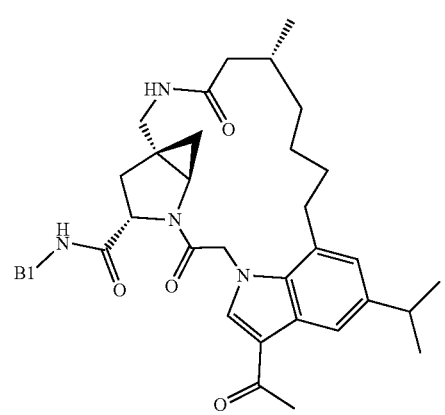
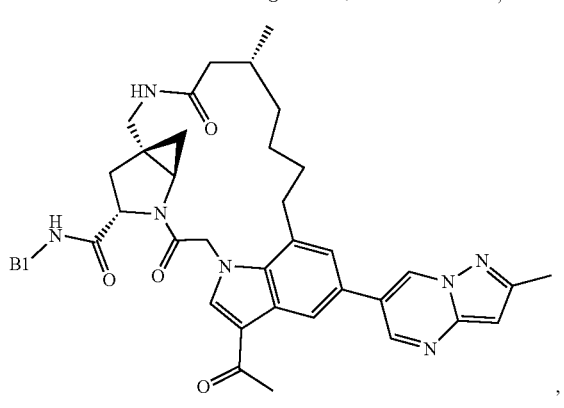
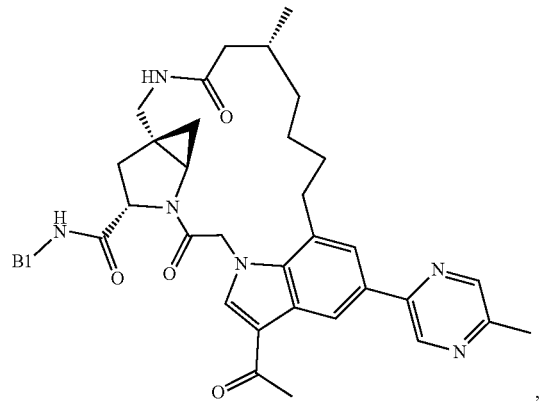
-continued
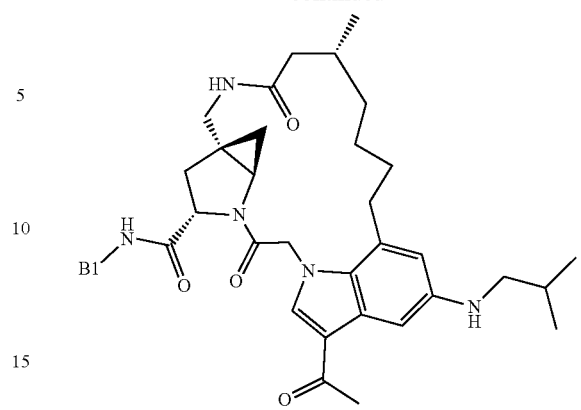
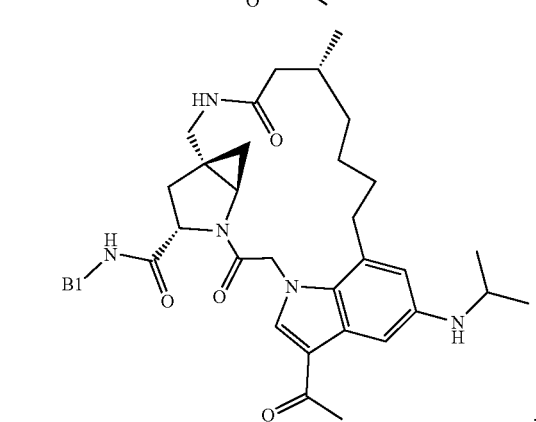
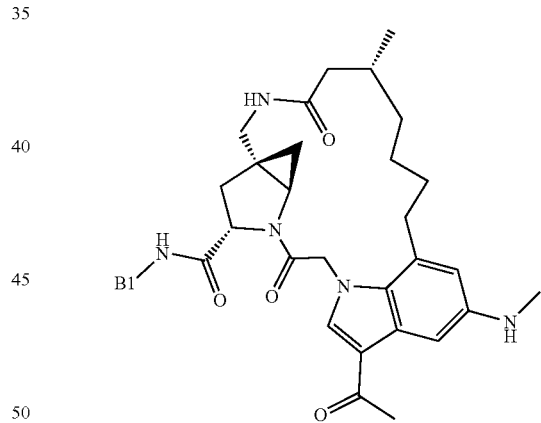
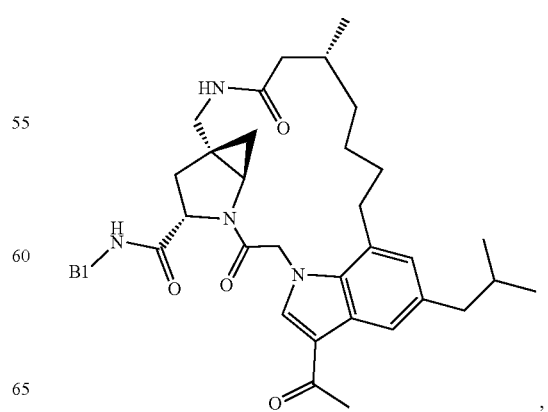
, and 253
-continued
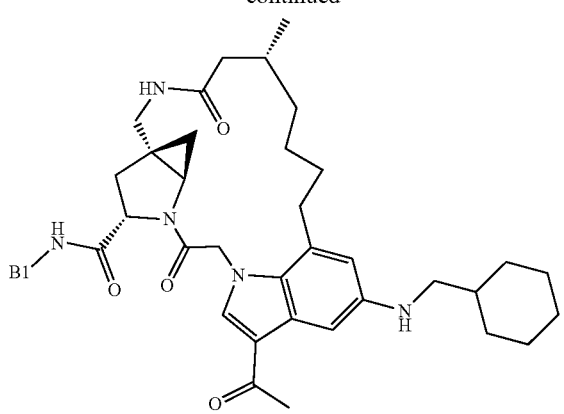
In one embodiment, the compound of Formula II is selected from:
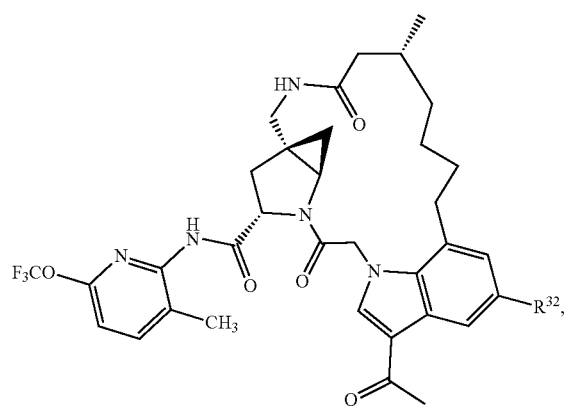
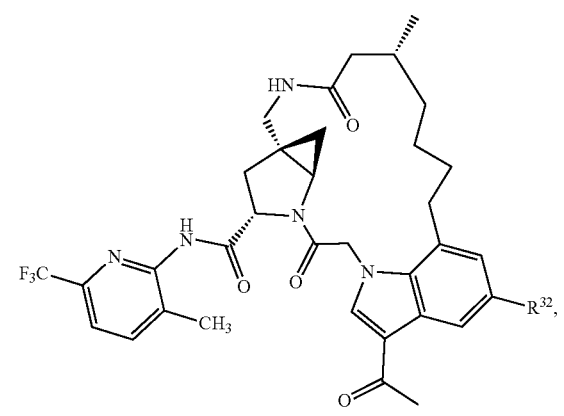
254
-continued
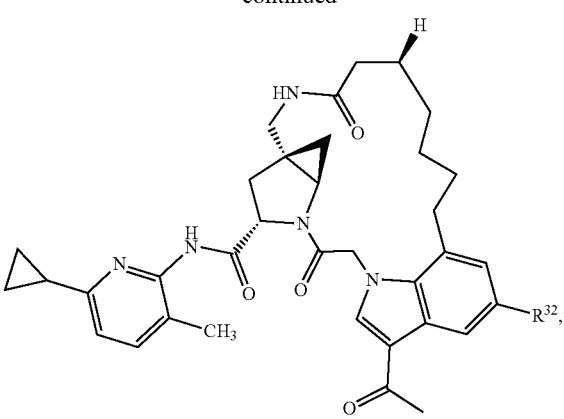
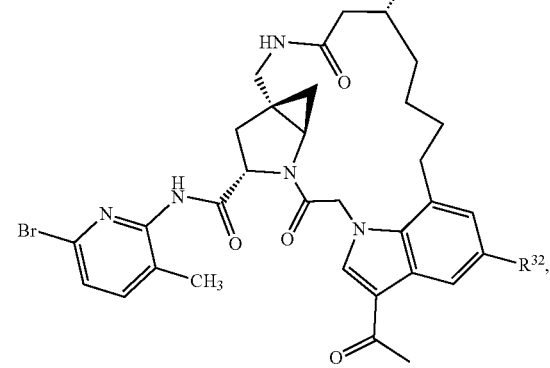
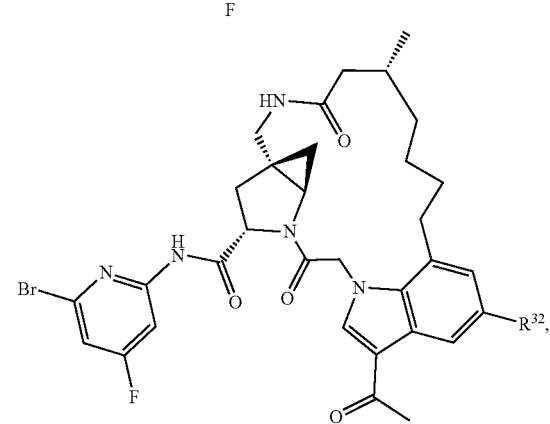

255
-continued
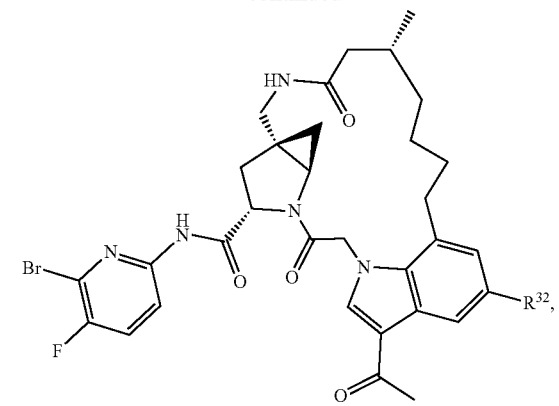
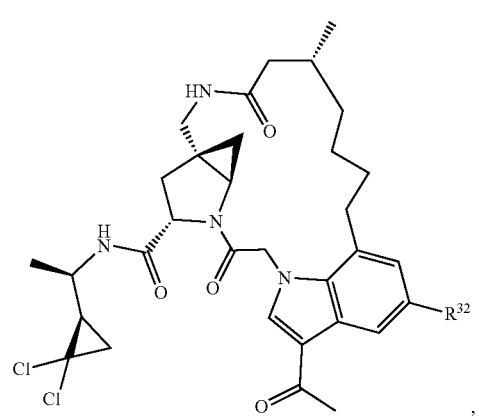
, and
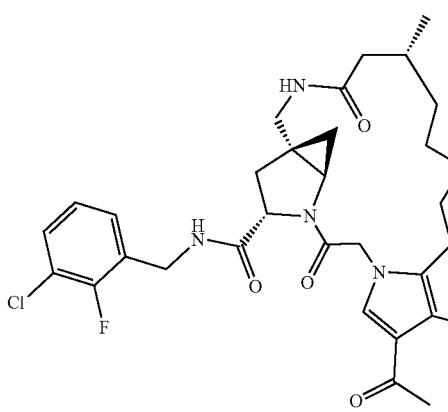
In one embodiment, the compound of Formula II is selected from:
256
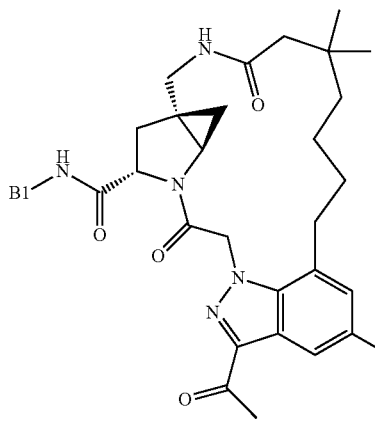
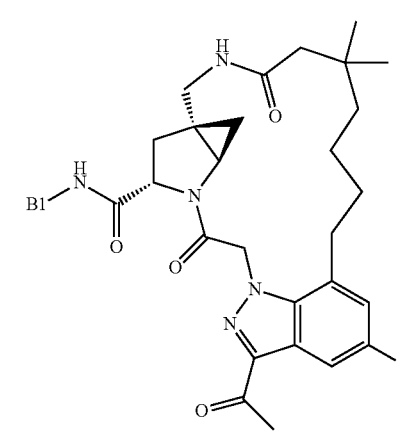
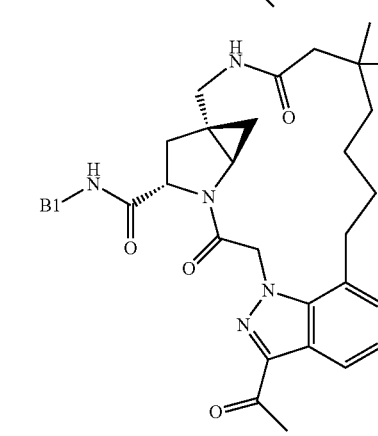
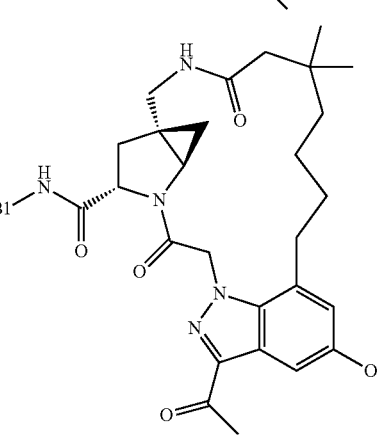

257
-continued
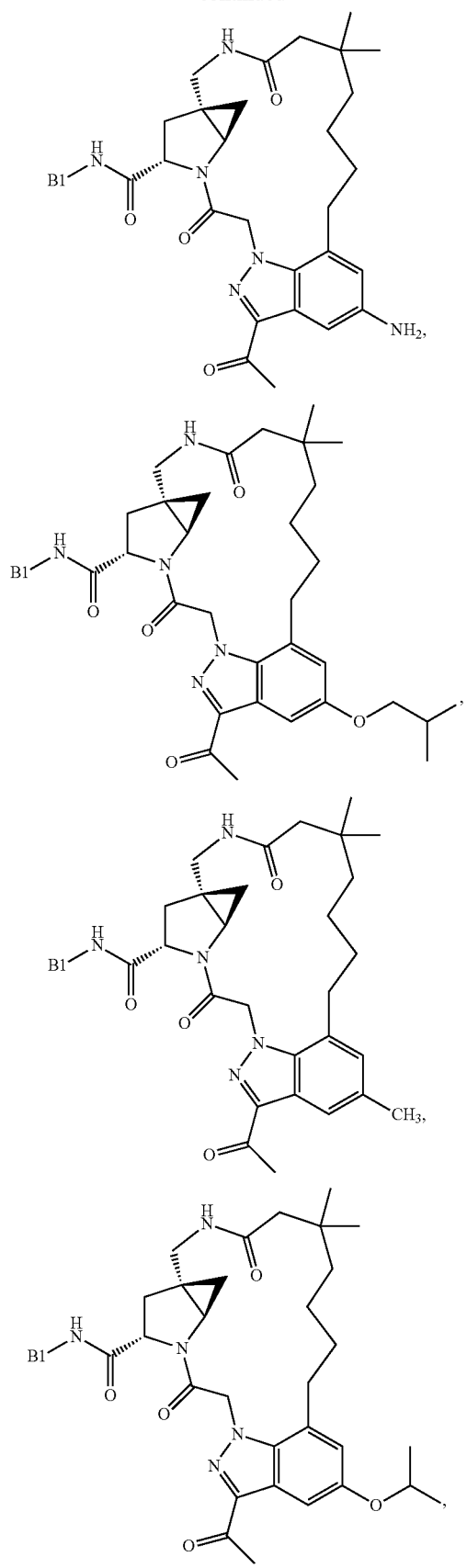
258
-continued
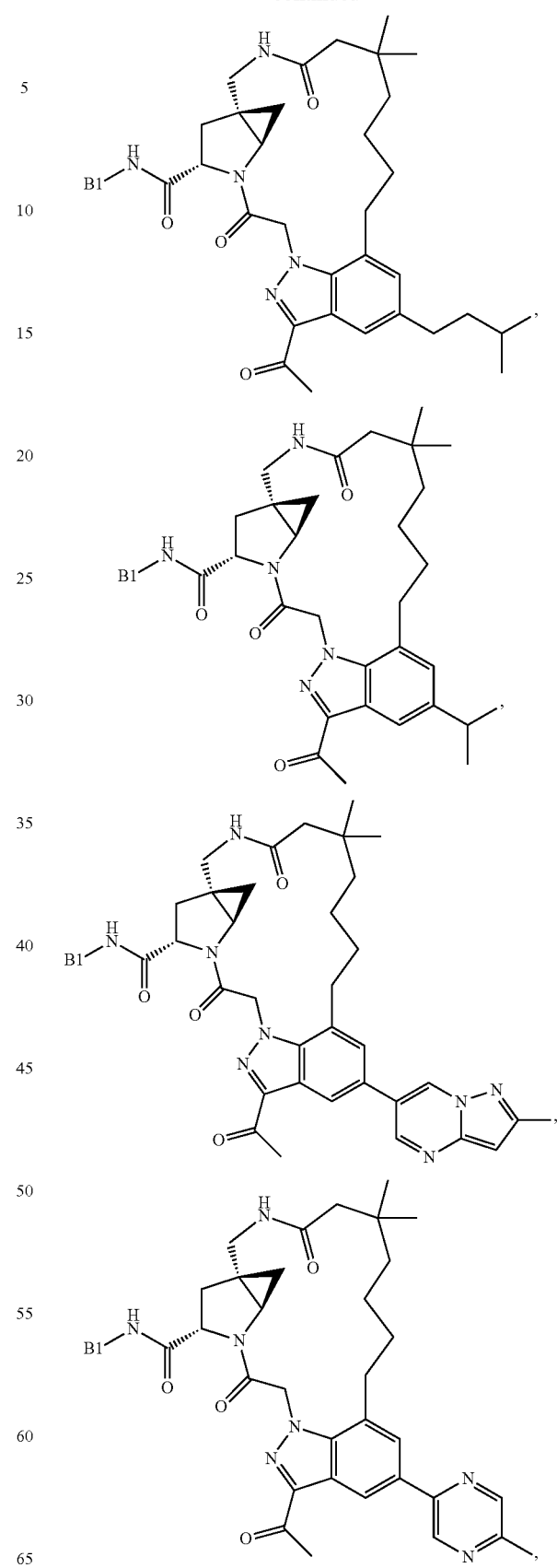

259
-continued
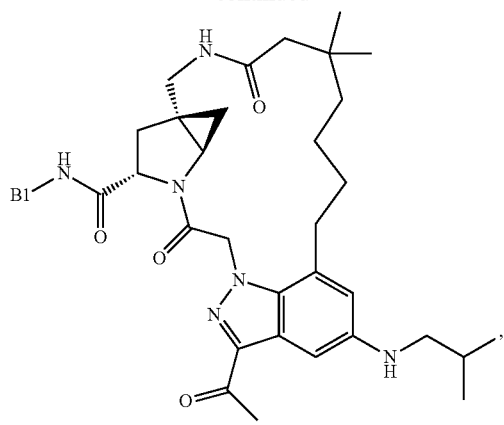
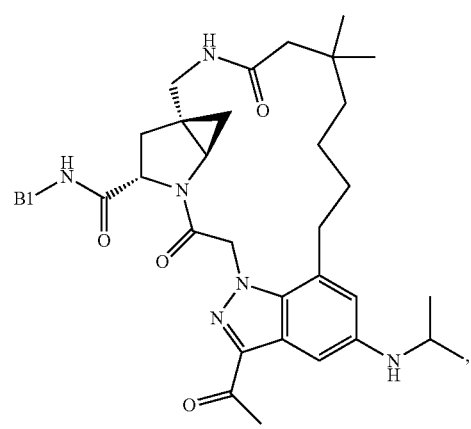
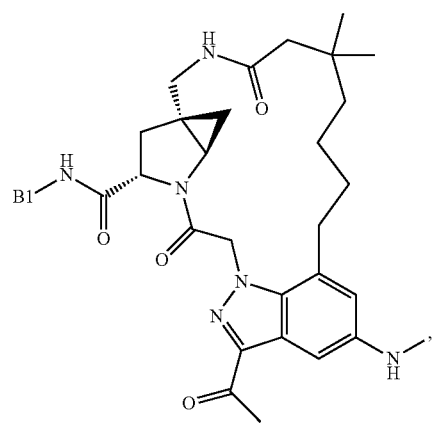
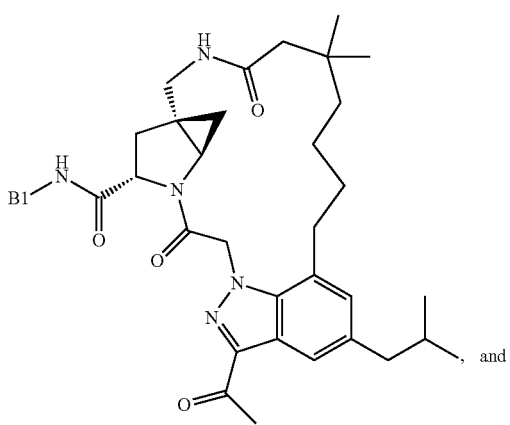
260
-continued
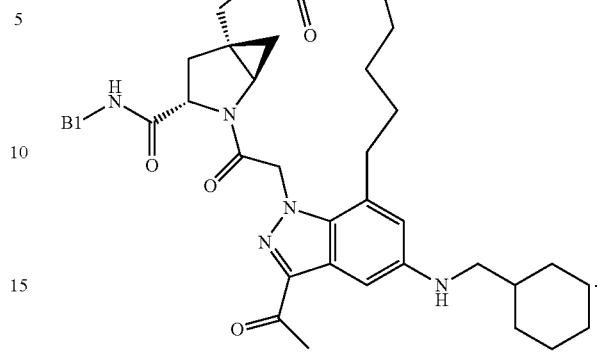
In one embodiment, the compound of Formula II is selected from:
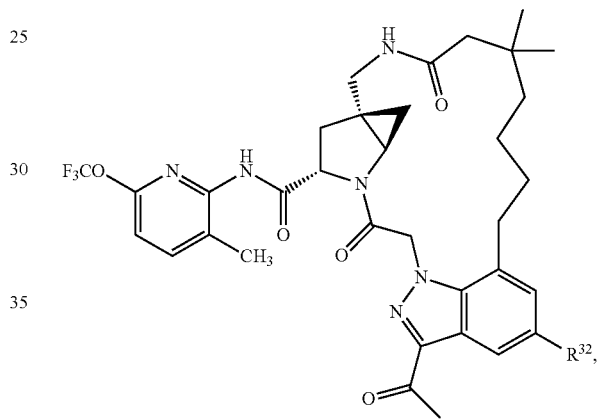
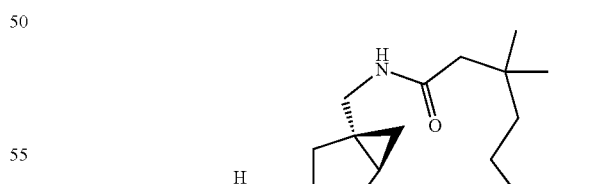

261
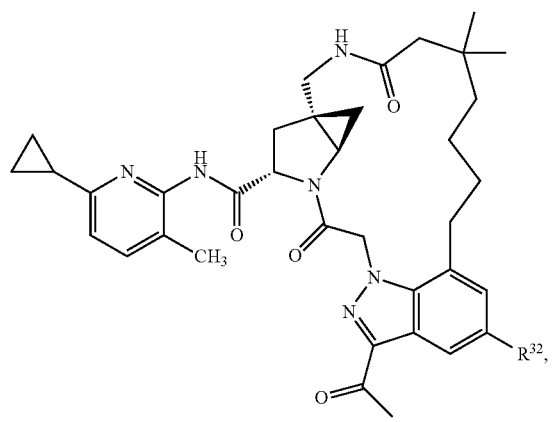
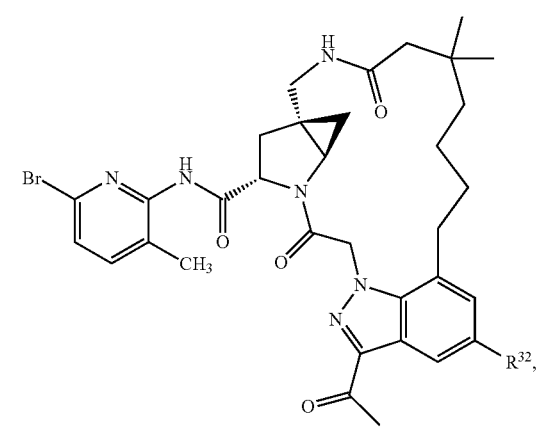
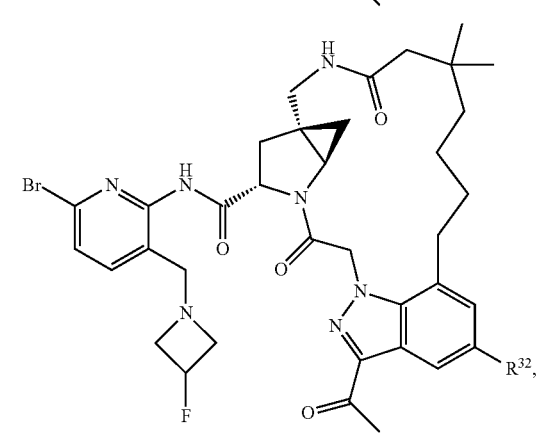
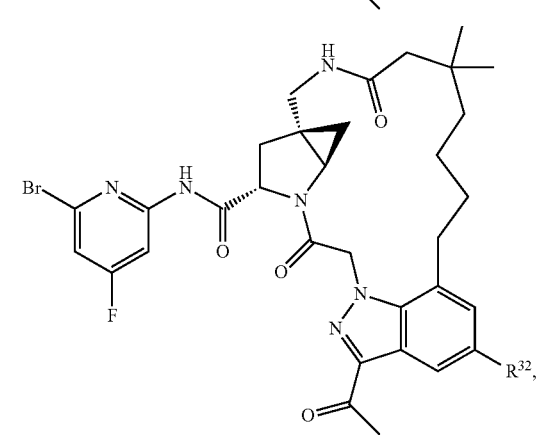
262
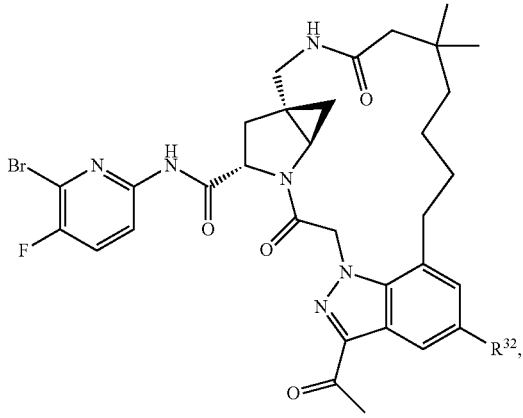
In one embodiment, the compound of Formula II is selected from:

263
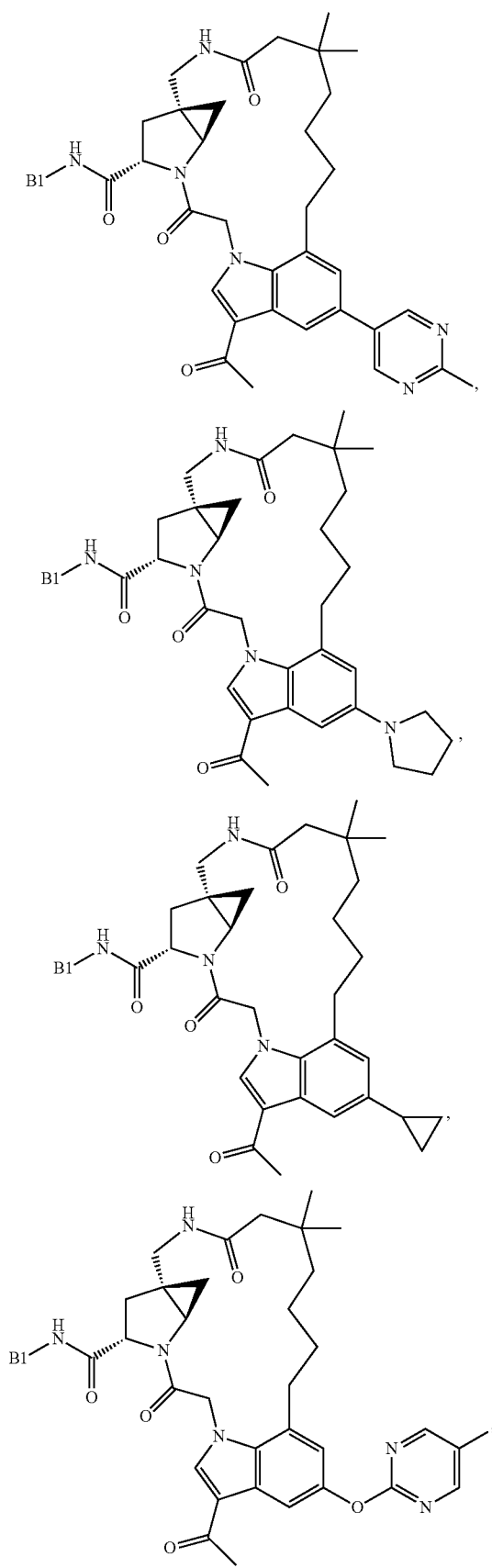
264
-continued
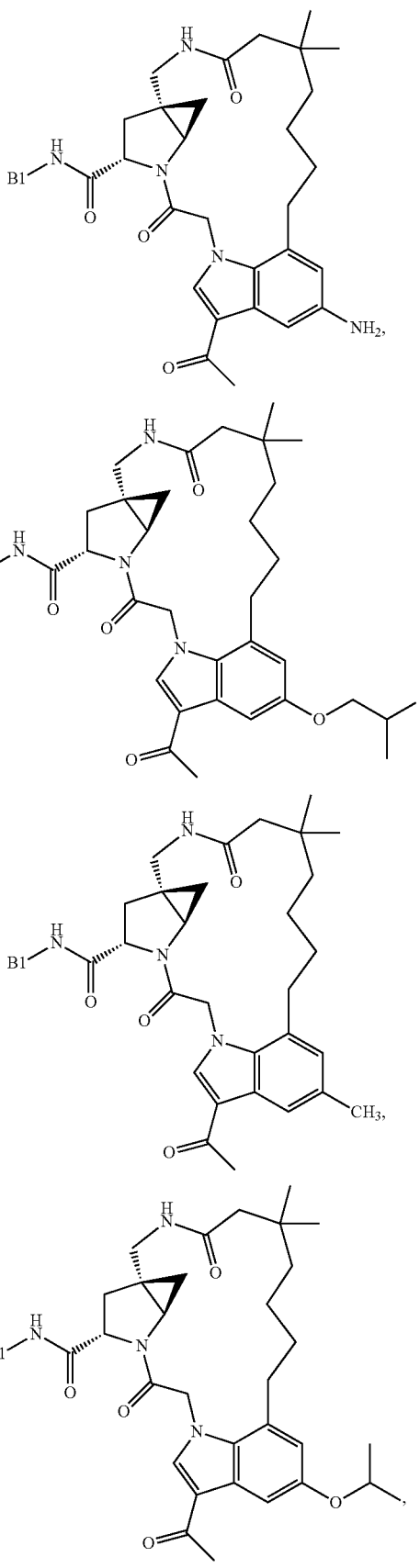

265
-continued
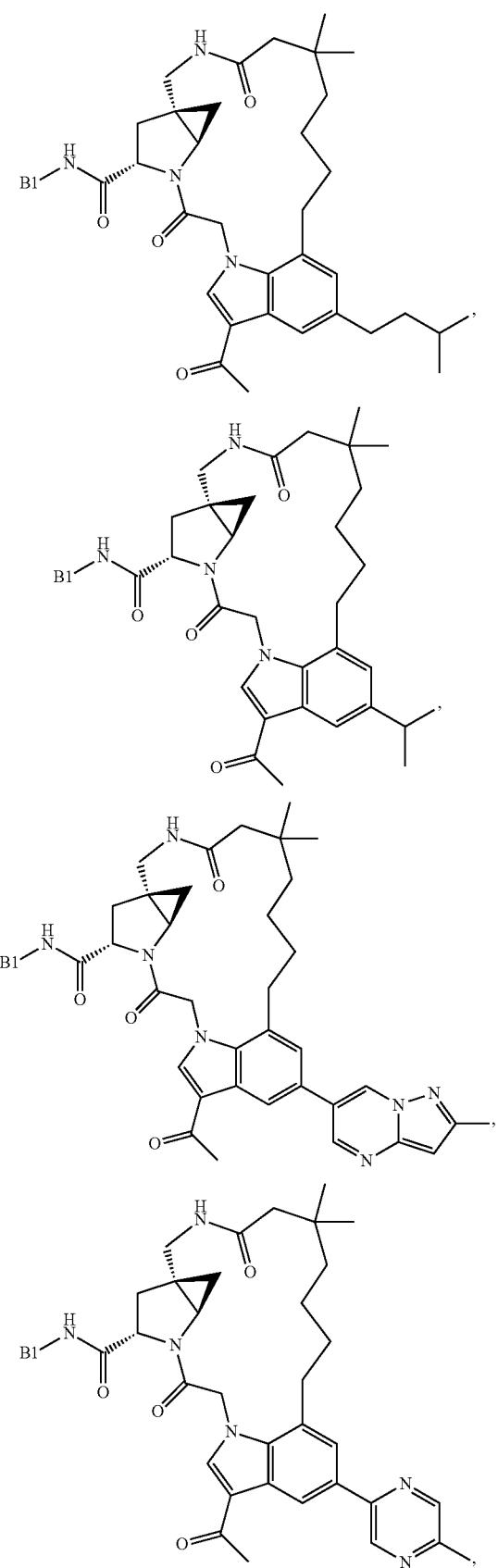
266
-continued
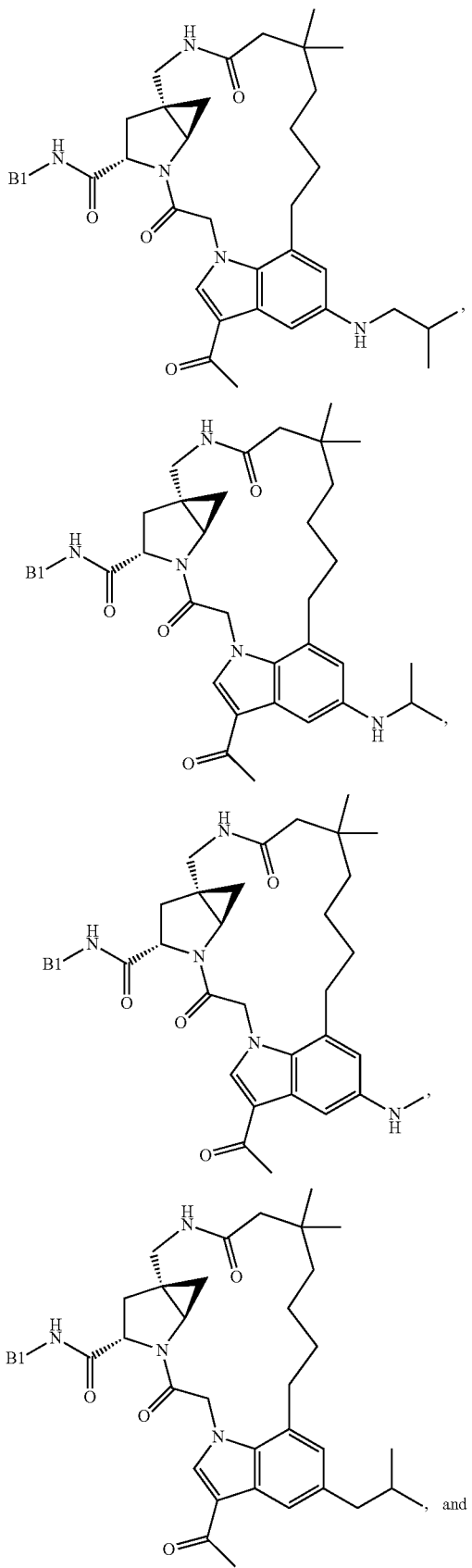

267
-continued
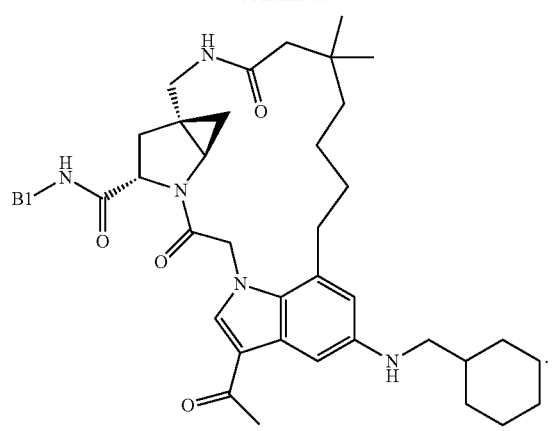
In one embodiment, the compound of Formula II is selected from:
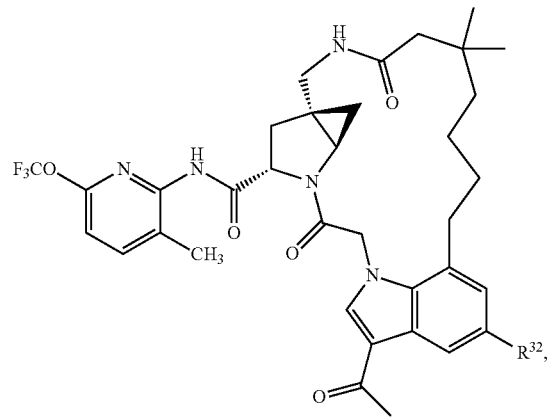
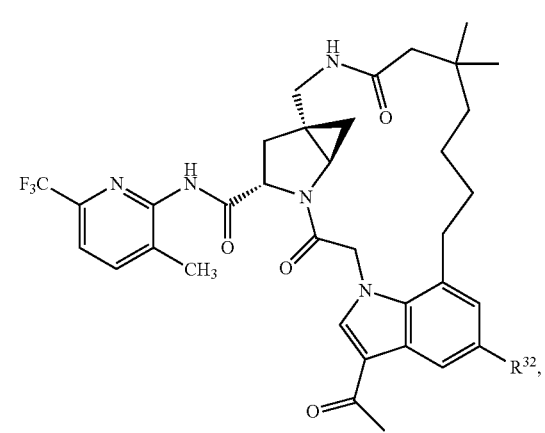
268
-continued
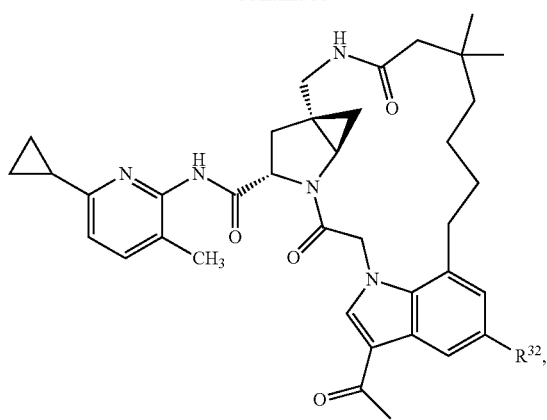
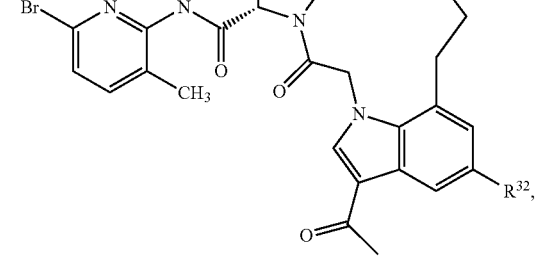
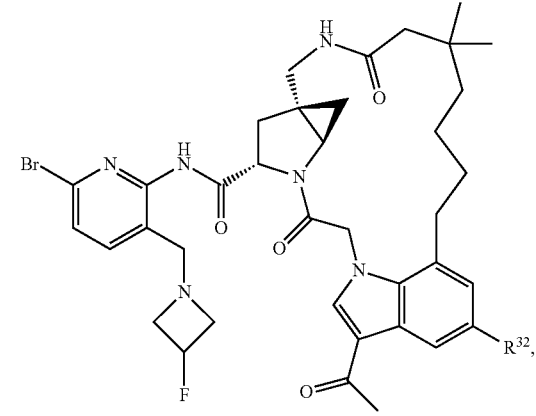
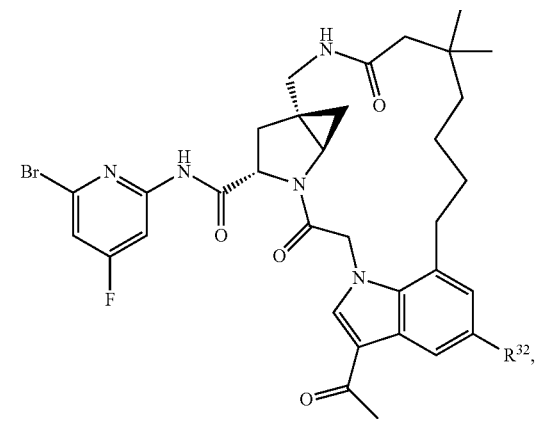

269
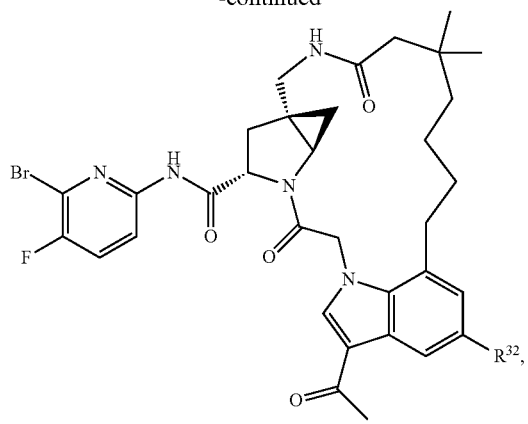
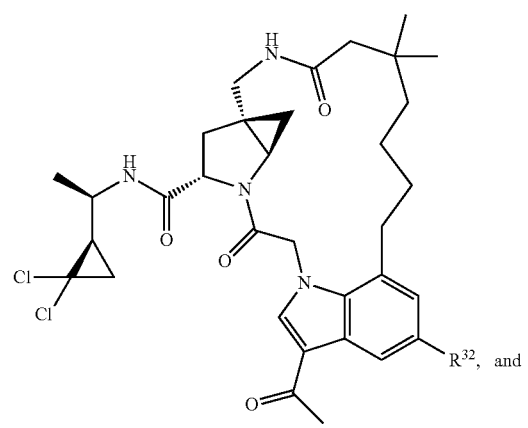
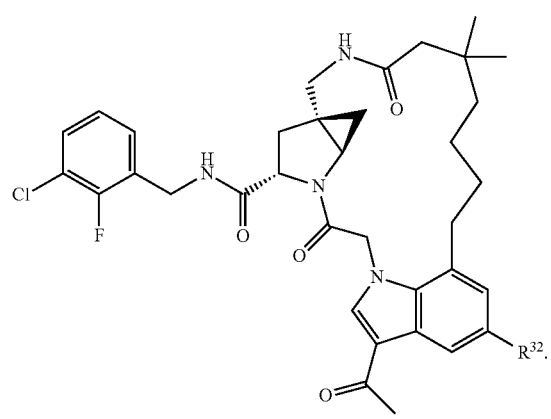
In one embodiment, the compound of Formula II is selected from:
270
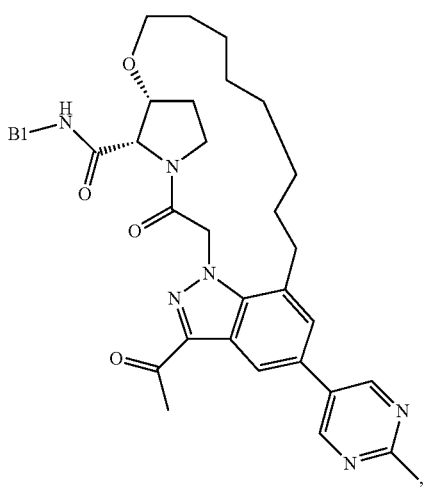
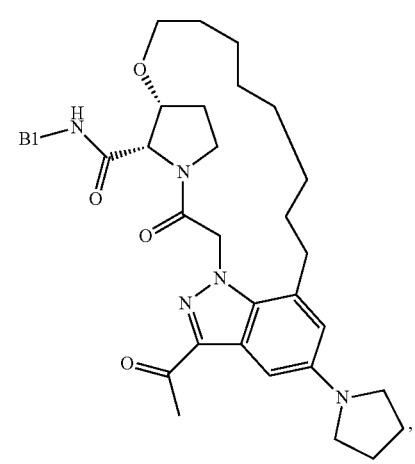
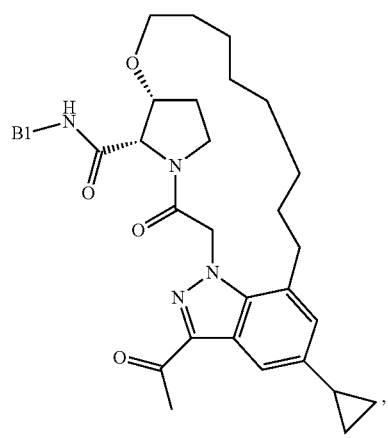

271
-continued
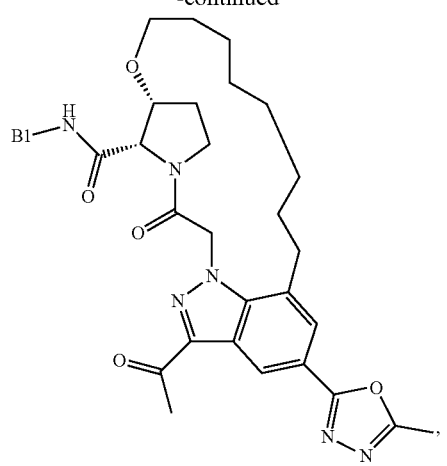
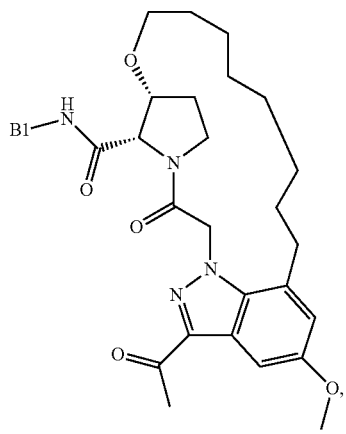
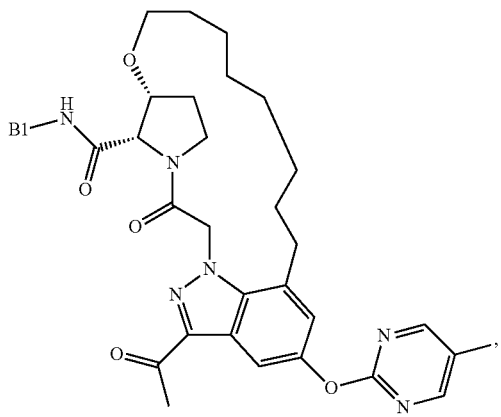
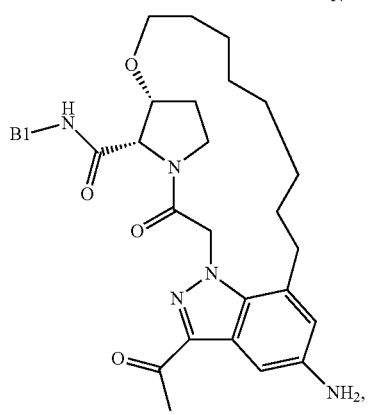
272
-continued
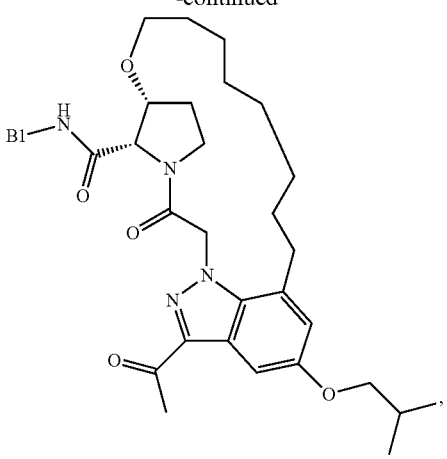
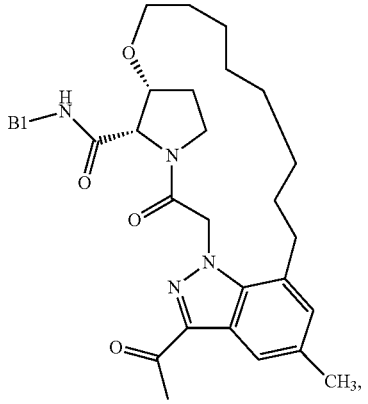
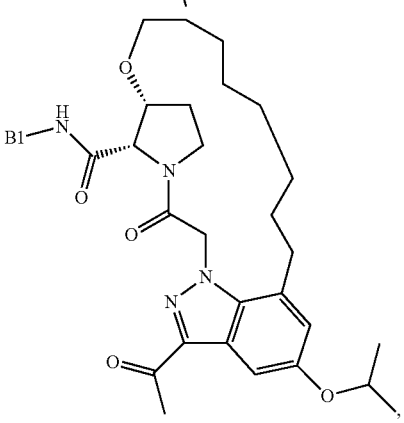
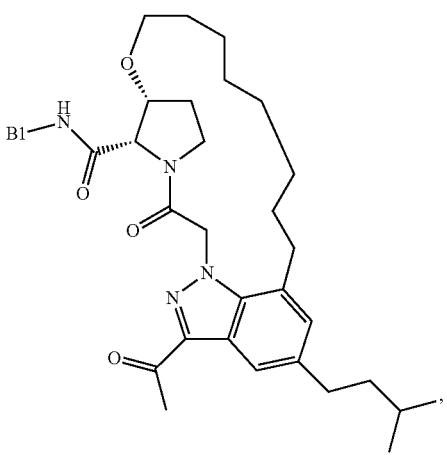

273
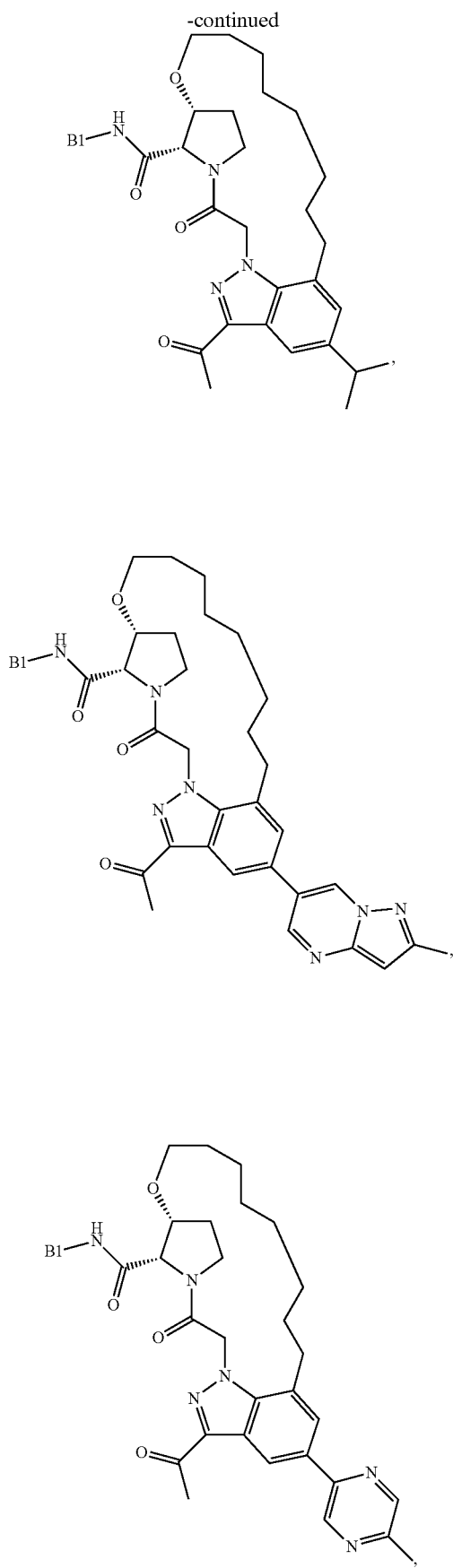
274
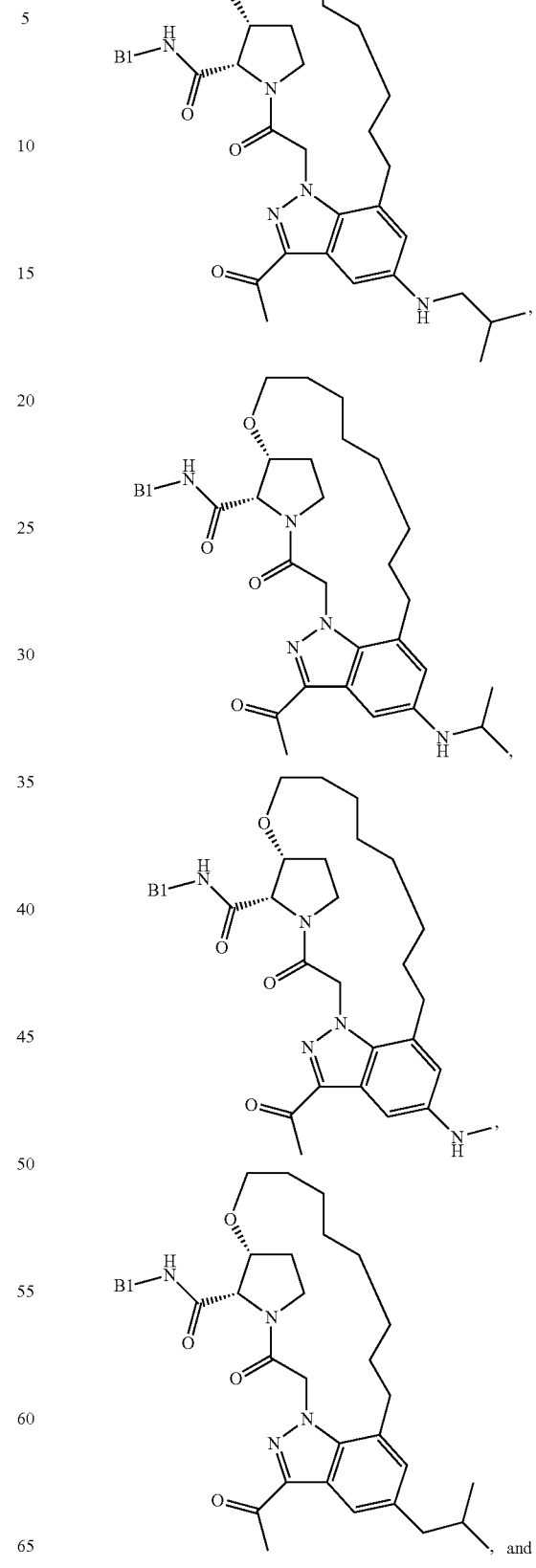

275
-continued
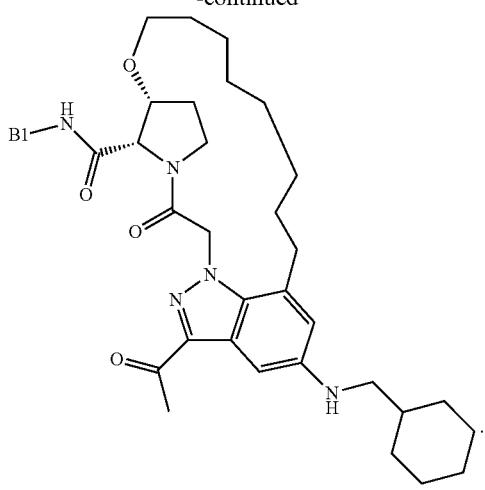
In one embodiment, the compound of Formula II is selected from:
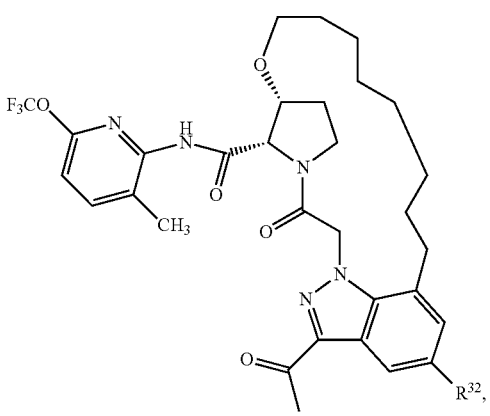
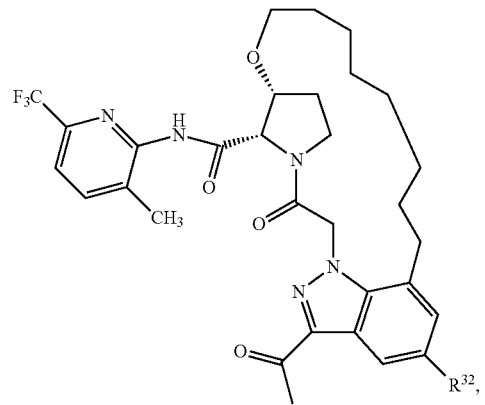
276
-continued
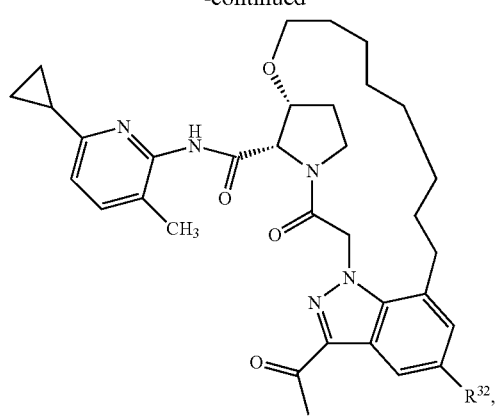
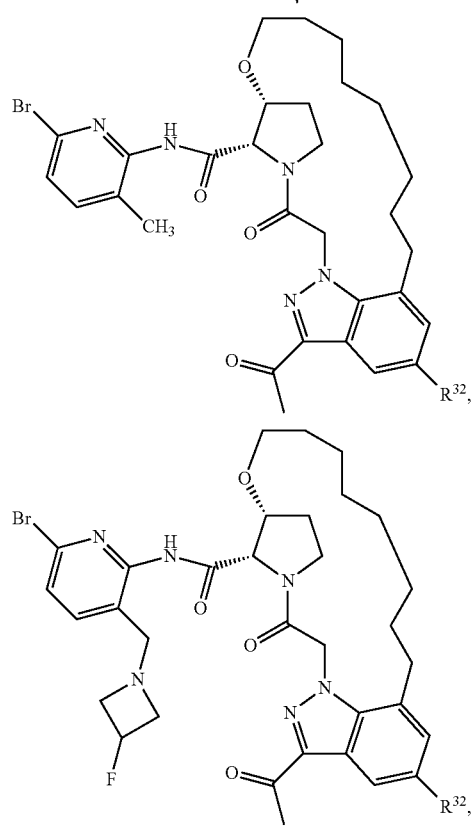
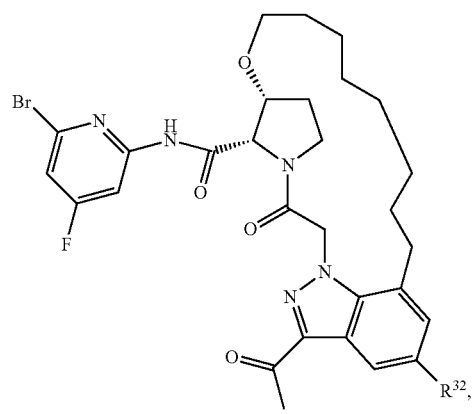

277
-continued
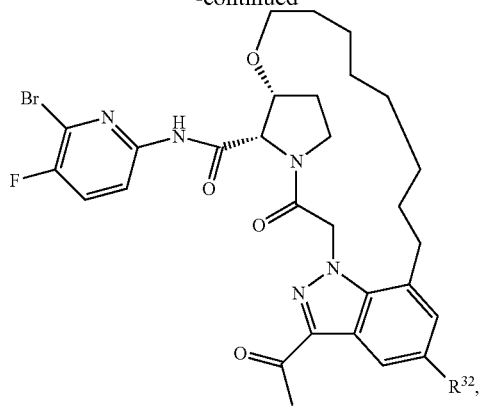
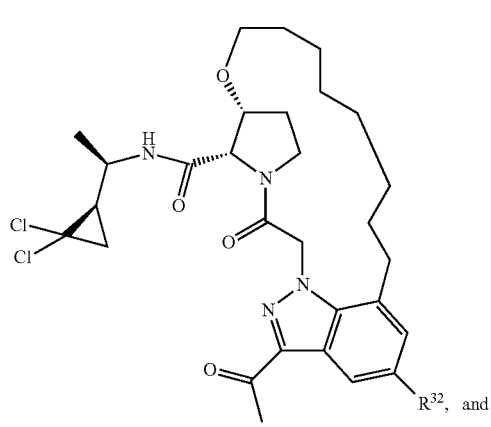
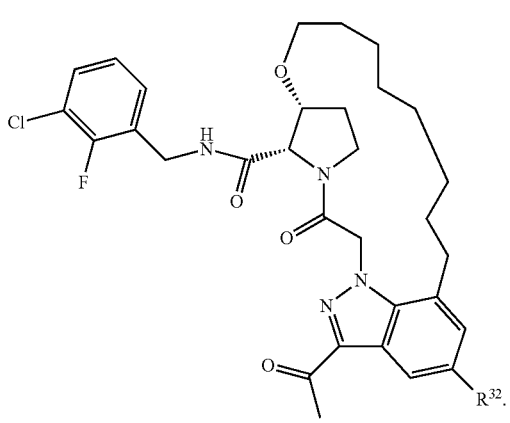
In one embodiment, the compound of Formula II is selected from:
278
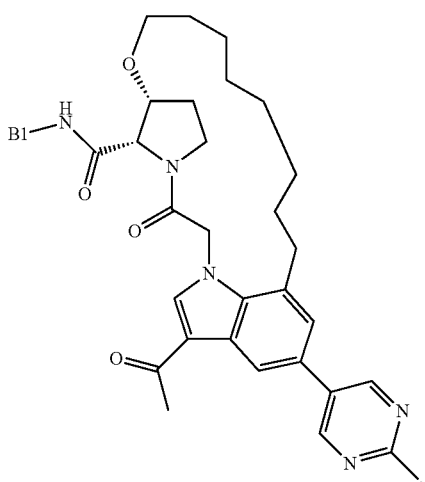
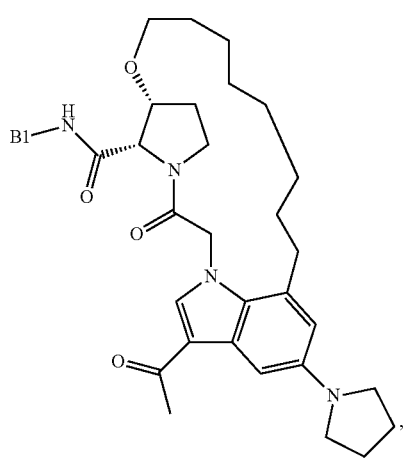
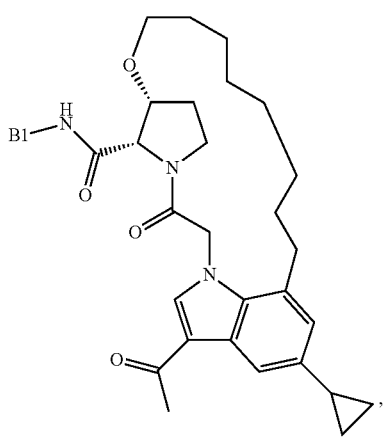

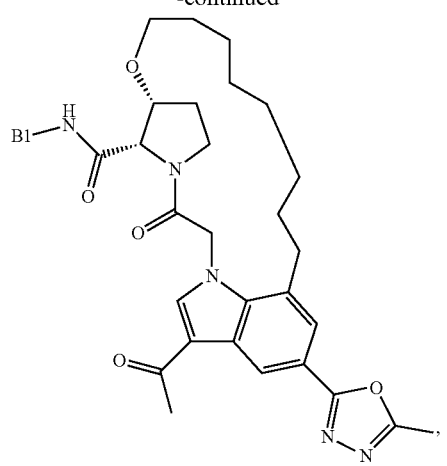
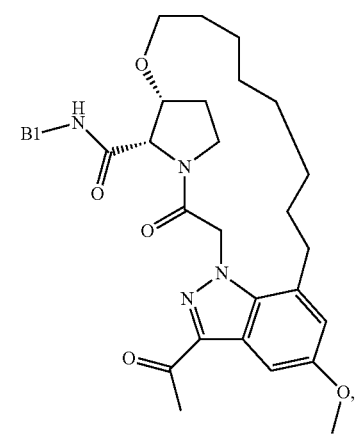
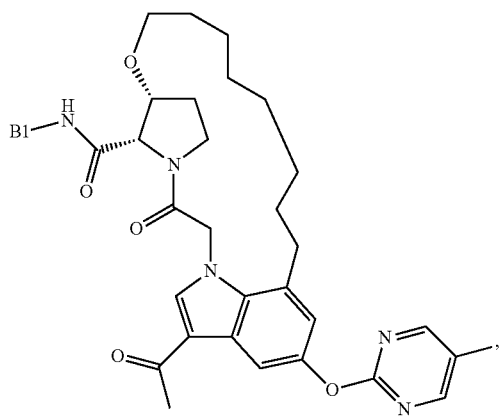
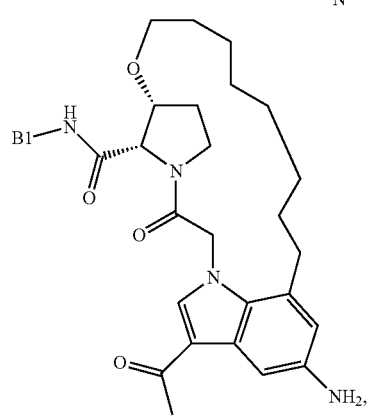

-continued
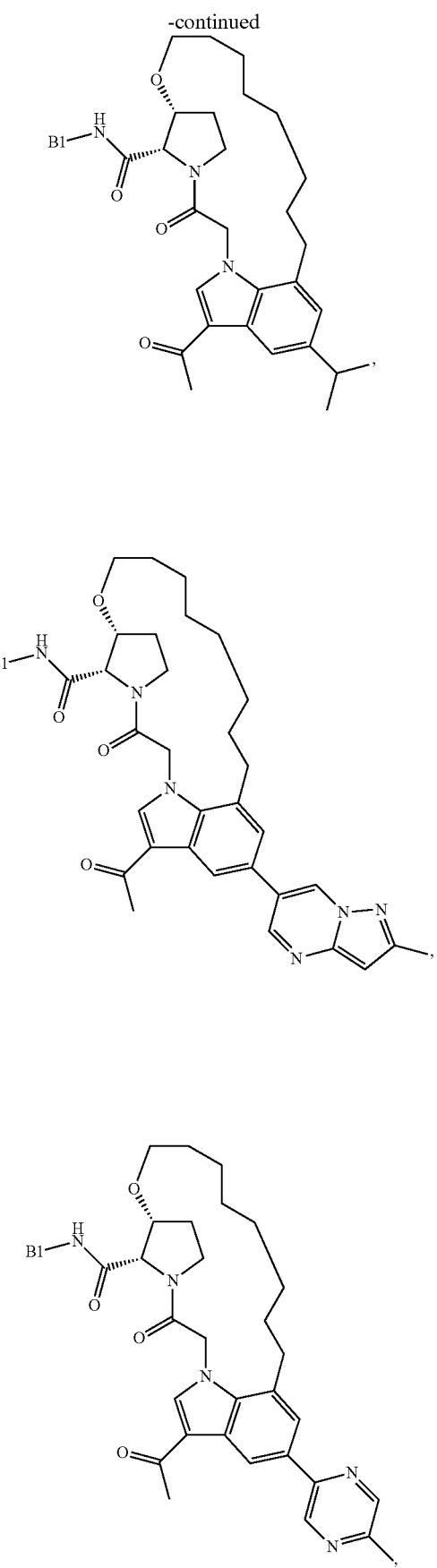
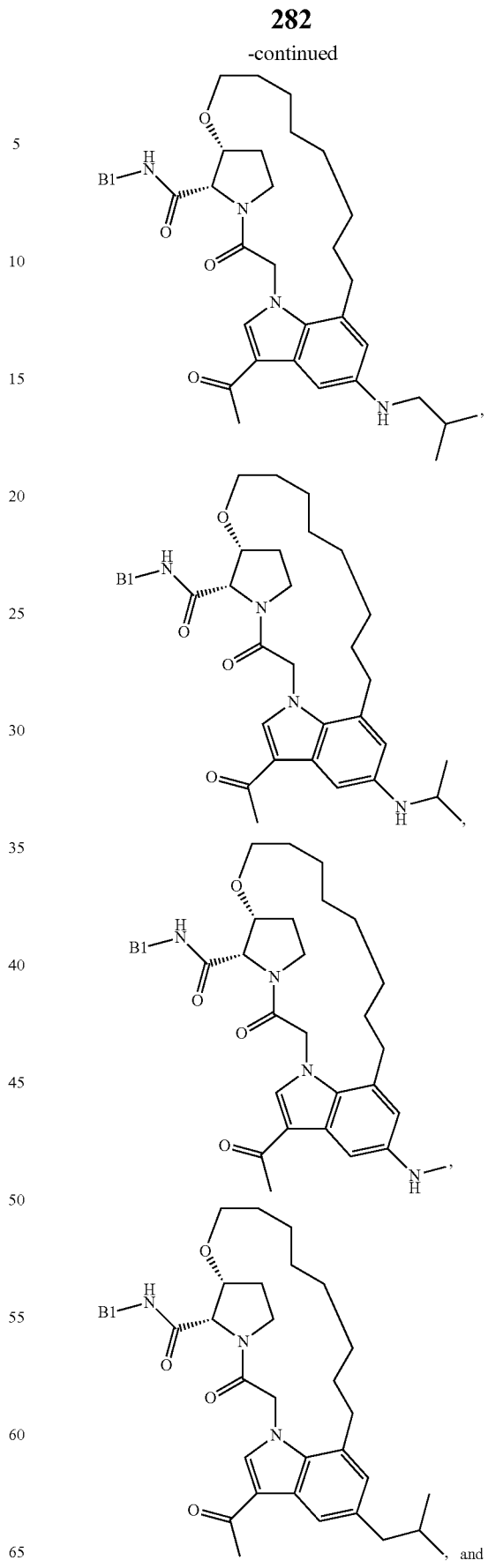

283
-continued
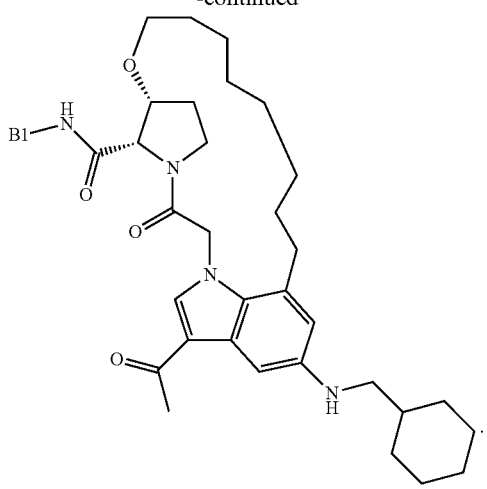
In one embodiment, the compound of Formula II is selected from:
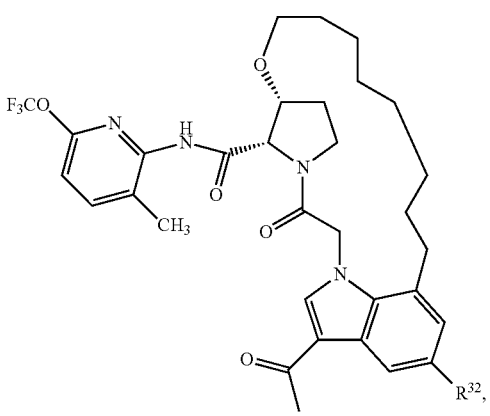
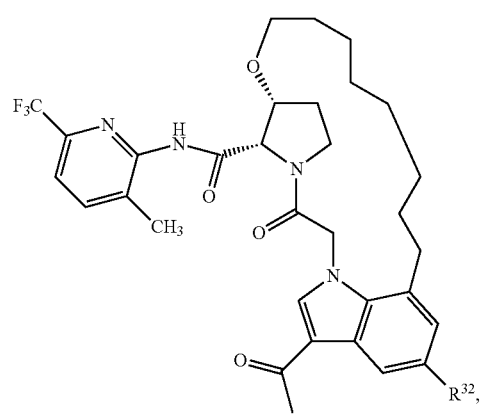
284
-continued
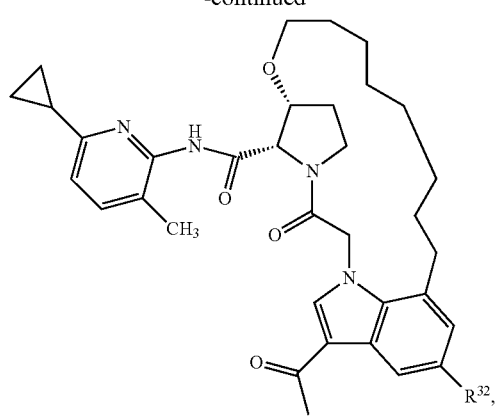
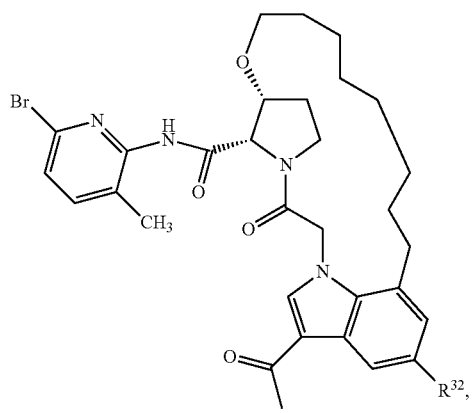
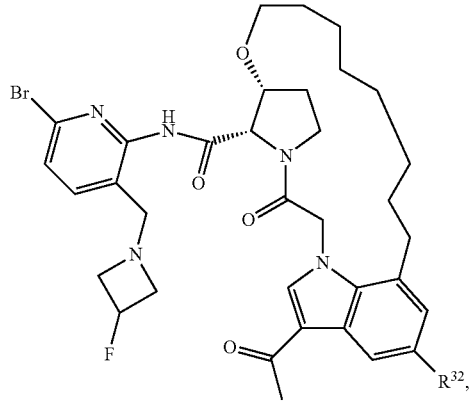

285
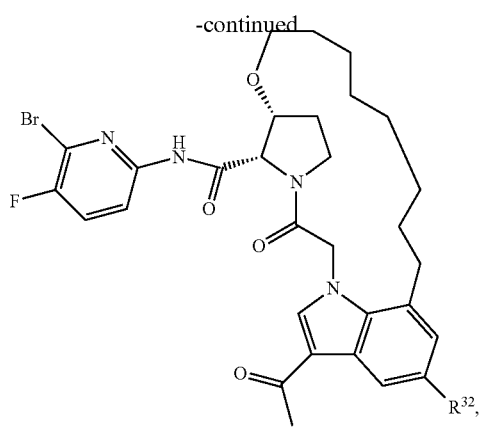
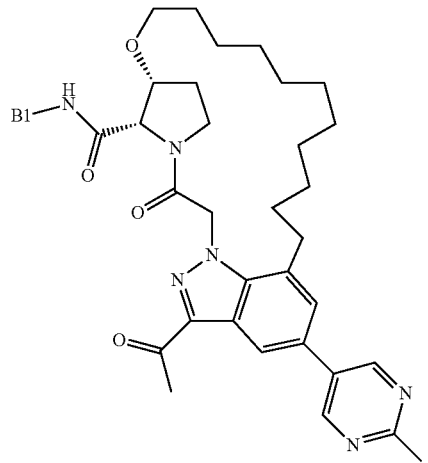
286
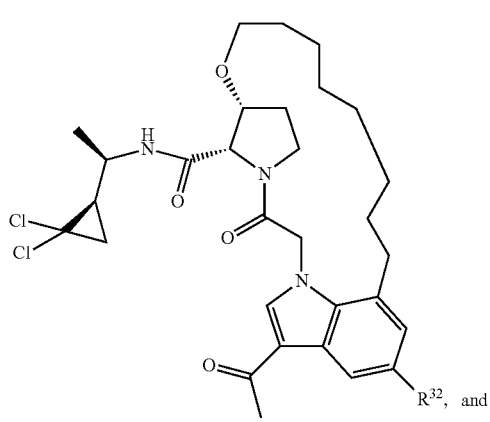
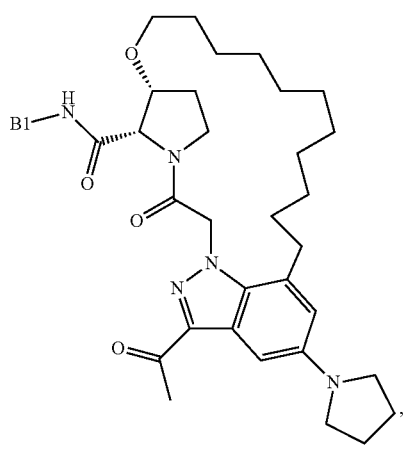
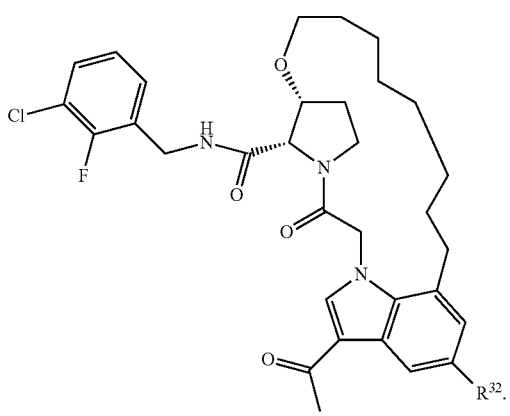
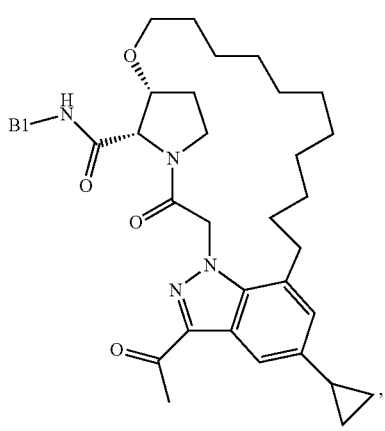
In one embodiment, the compound of Formula II is selected from:

287
-continued
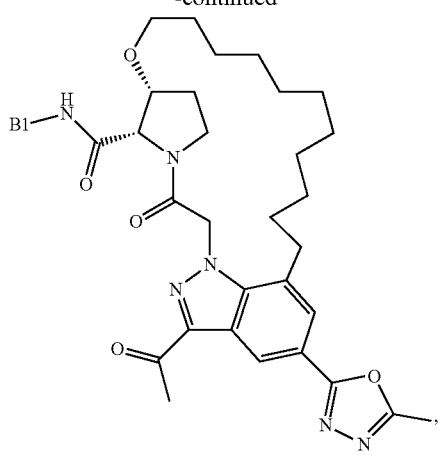
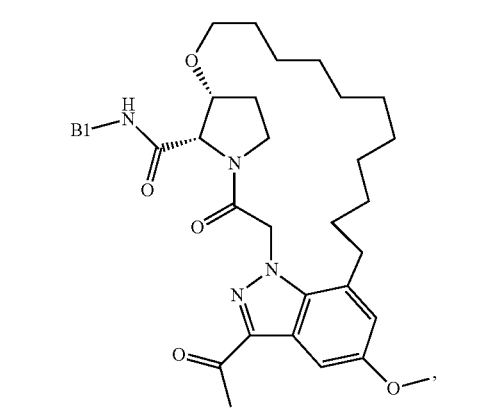
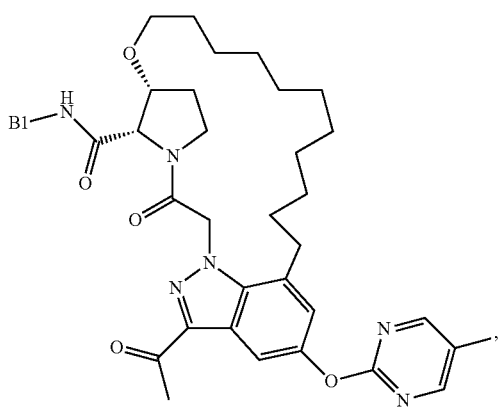
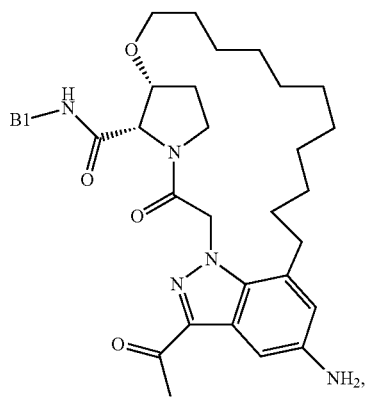
288
-continued
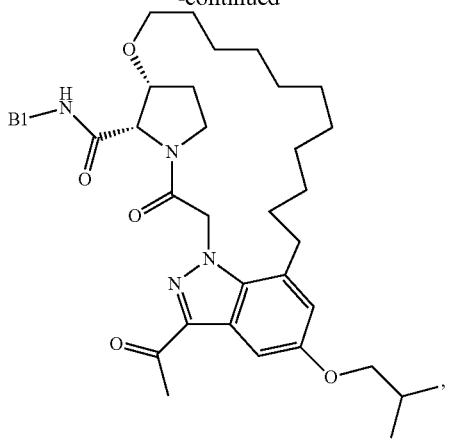
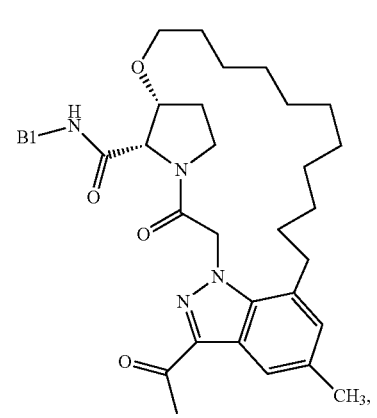
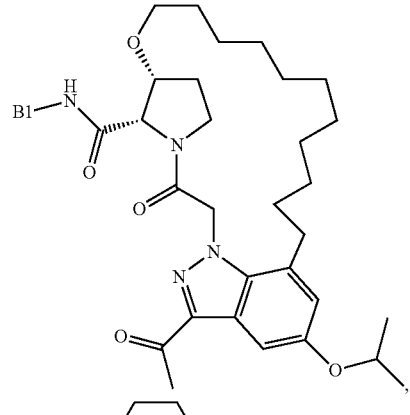
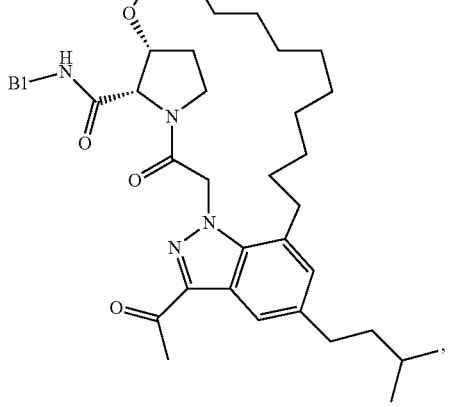

289
-continued
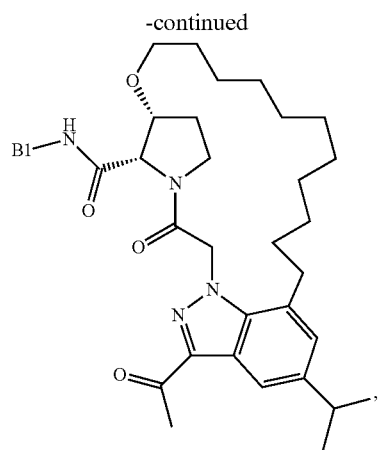
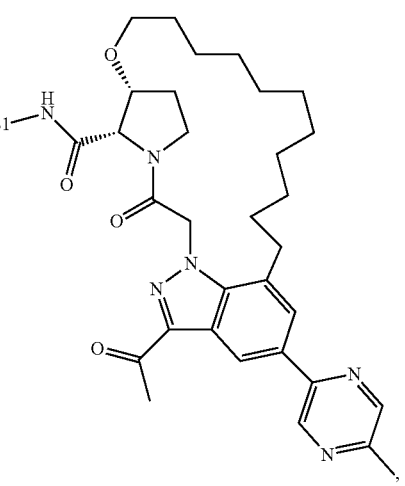
290
-continued
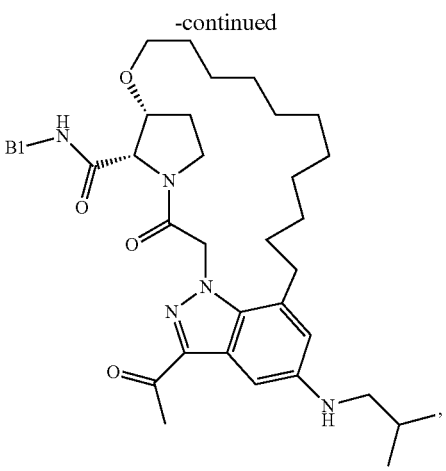
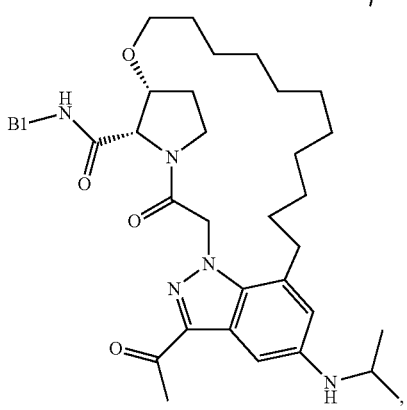
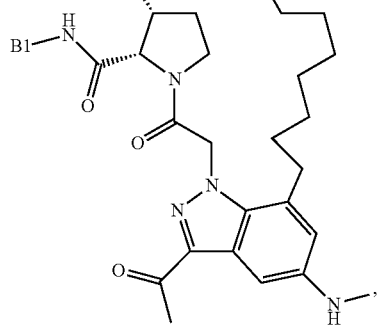
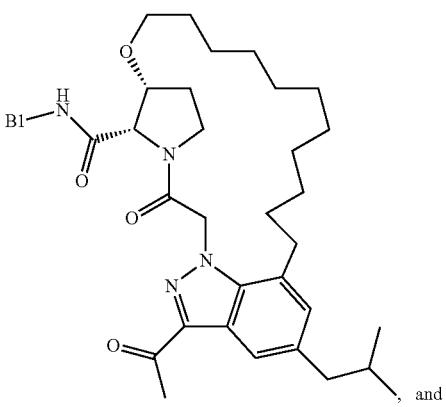

291
-continued
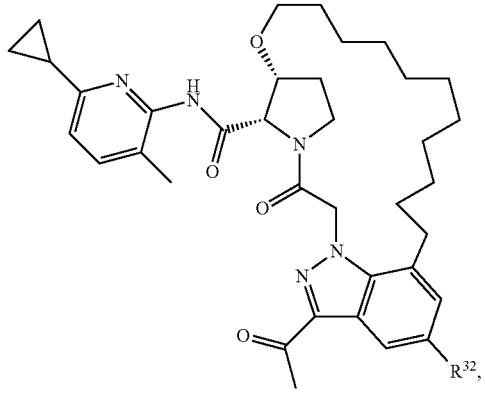
292
-continued
In one embodiment, the compound of Formula II is selected from:
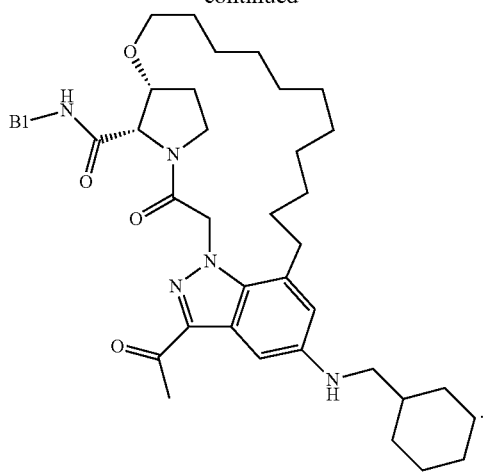
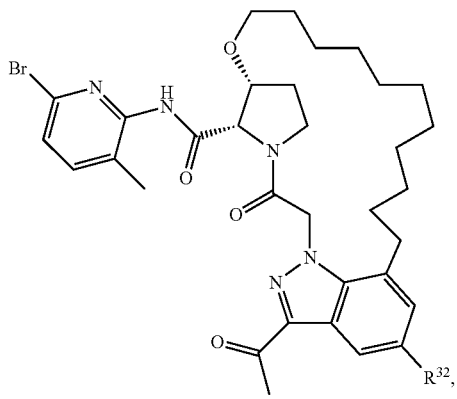
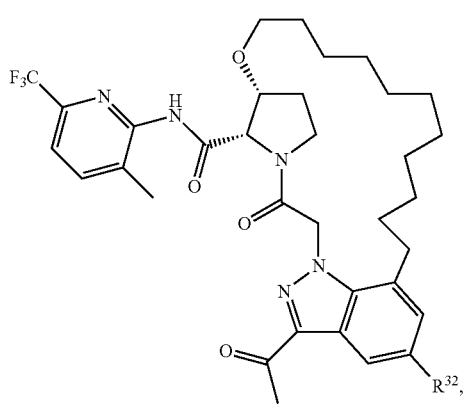
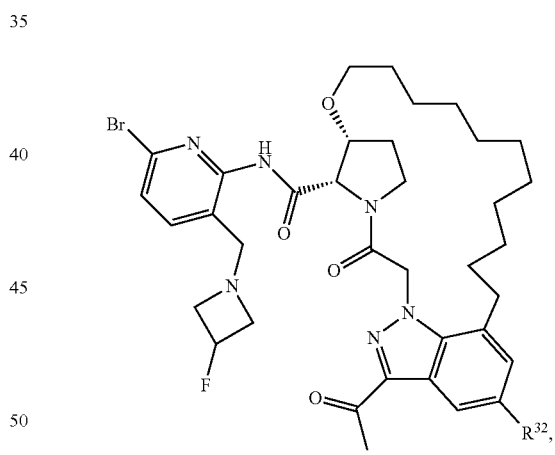

293
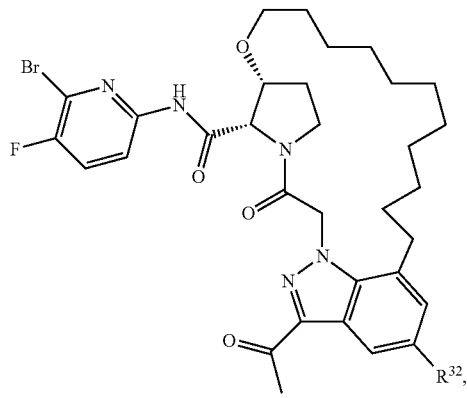
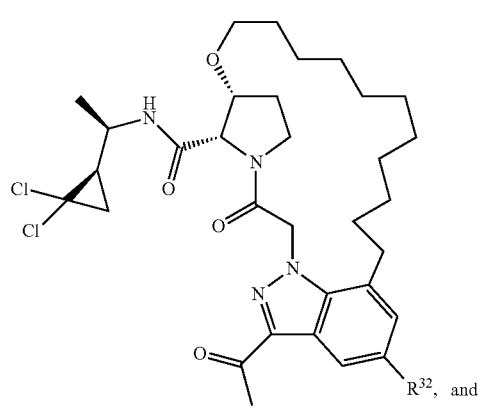
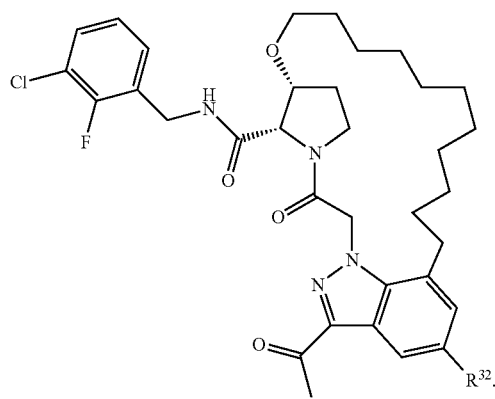
294
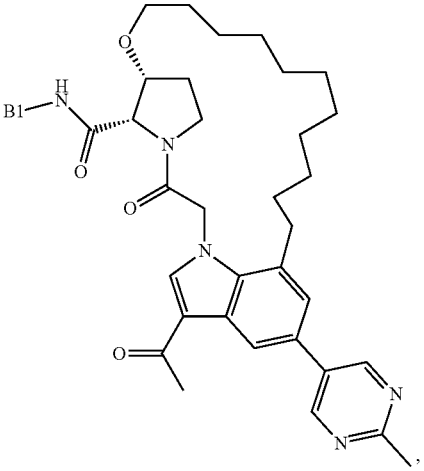
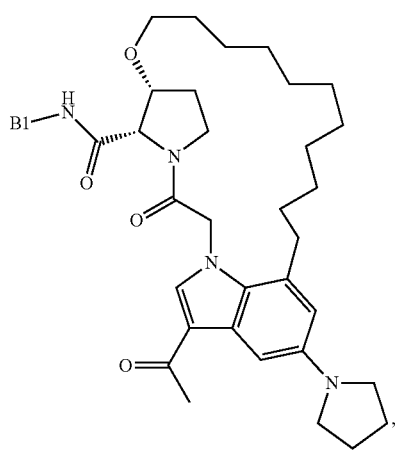
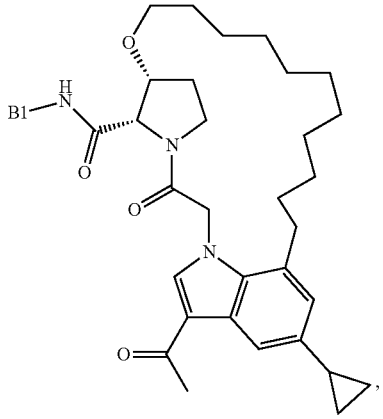
In one embodiment, the compound of Formula II is selected from:

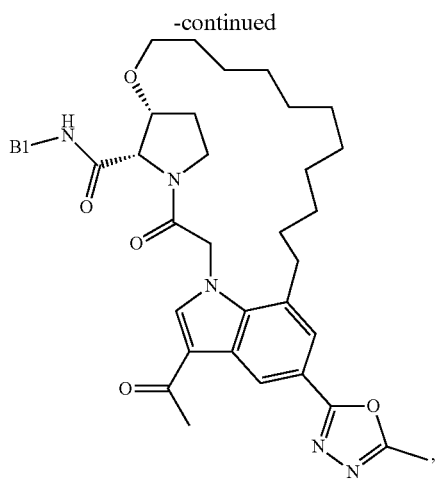
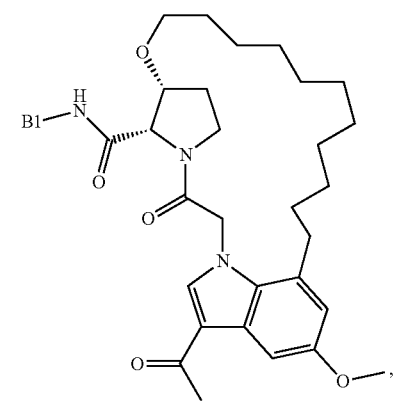
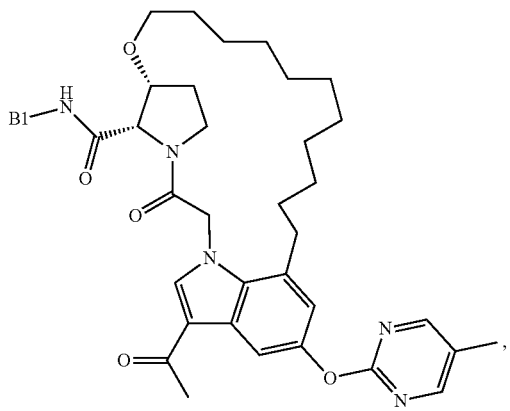
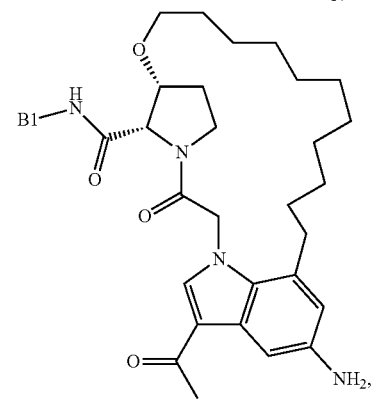
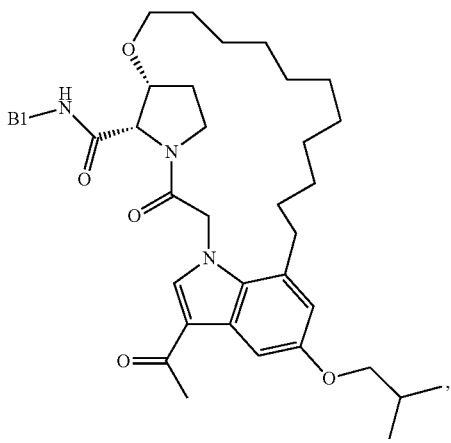
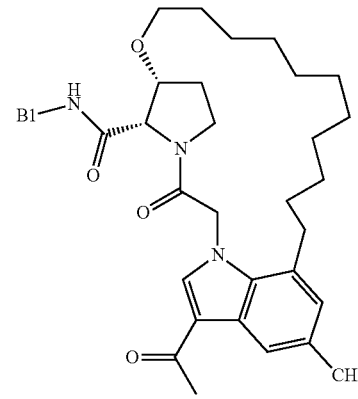
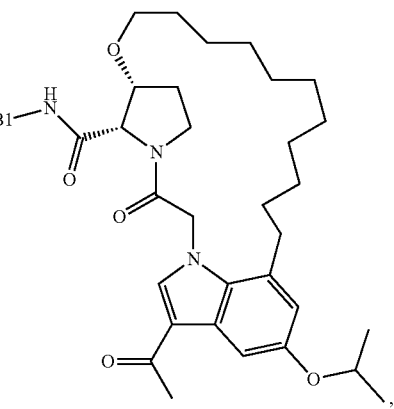
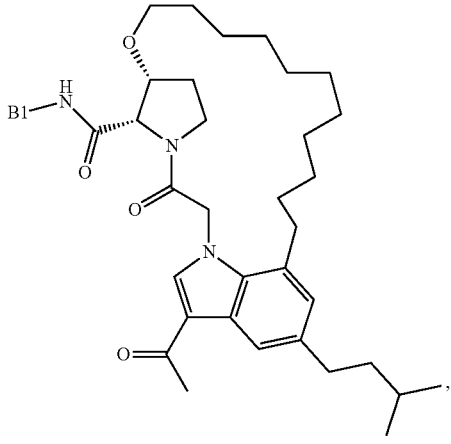

297
-continued
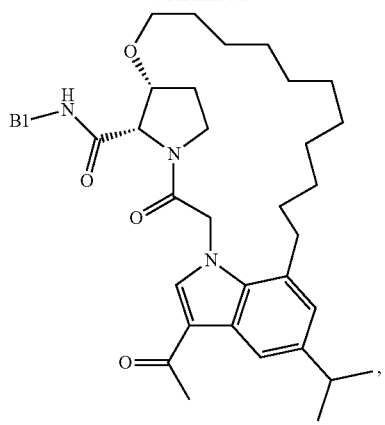
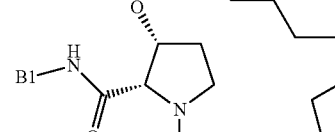
298
-continued
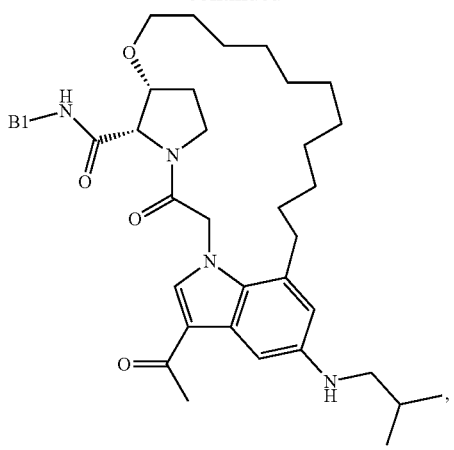
, and

299
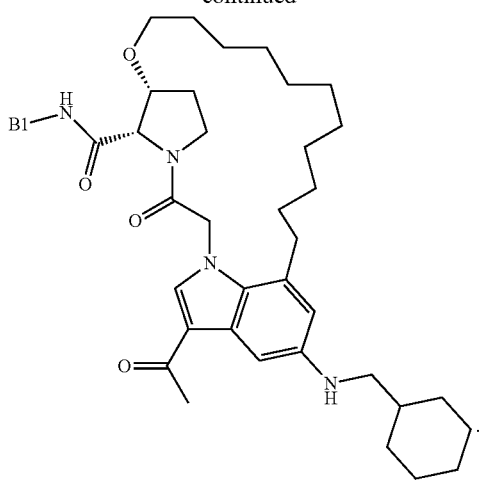
In one embodiment, the compound of Formula II is selected from:
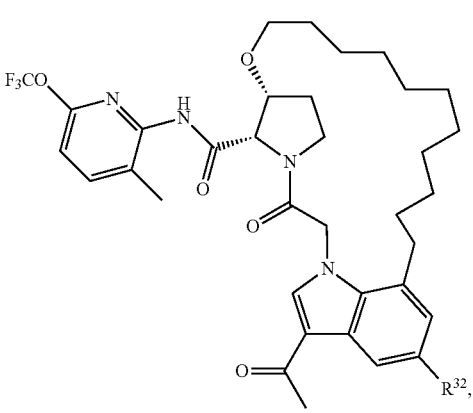
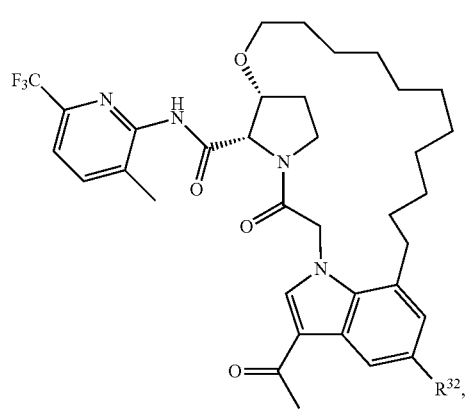
300
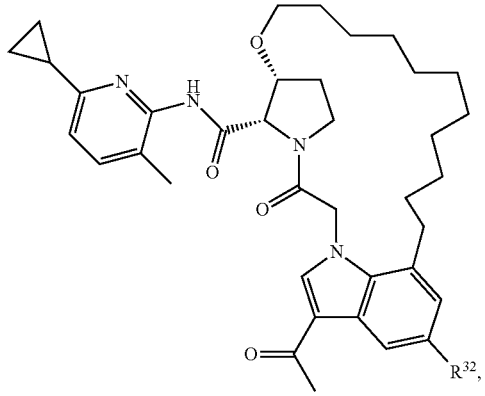
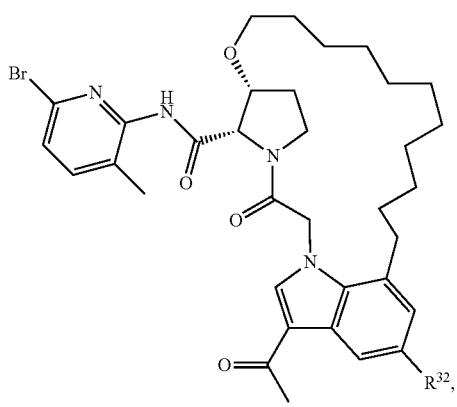
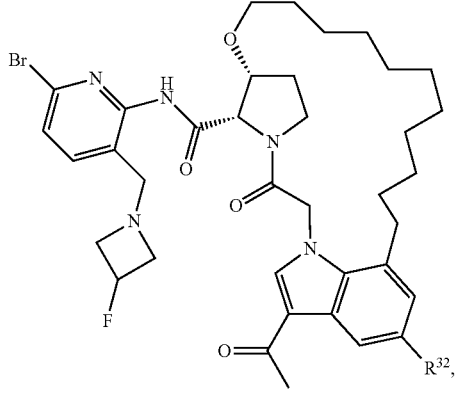

301
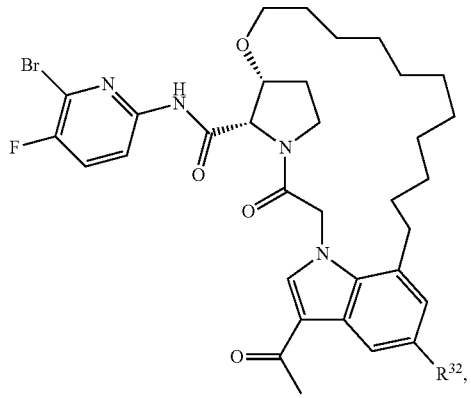
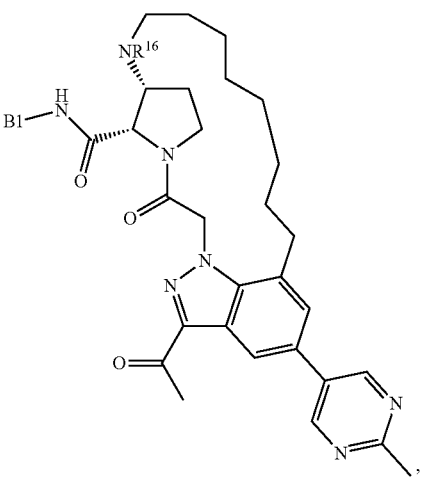
302
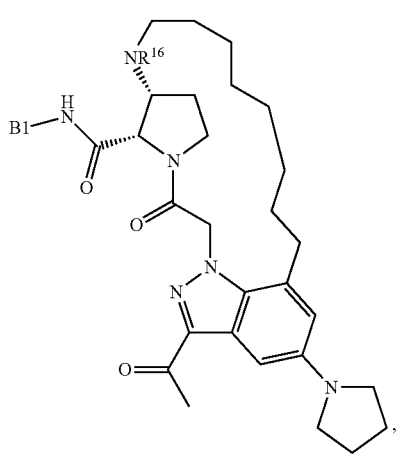
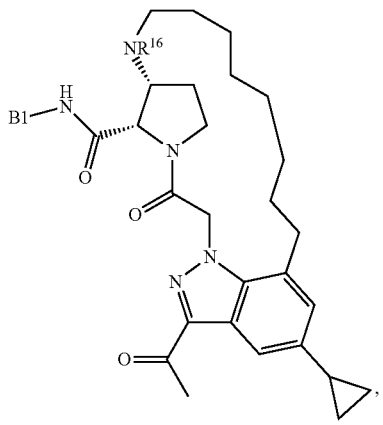
In one embodiment, the compound of Formula II is selected from:

303
-continued
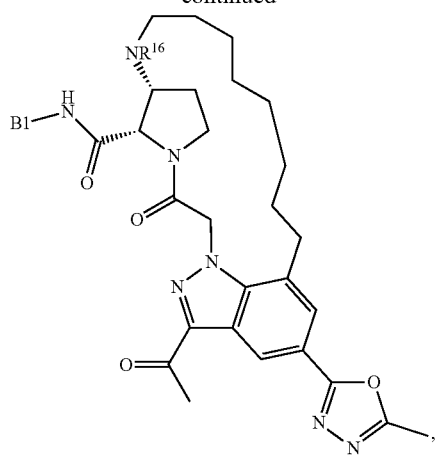
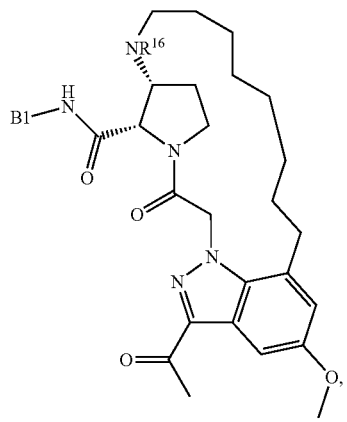
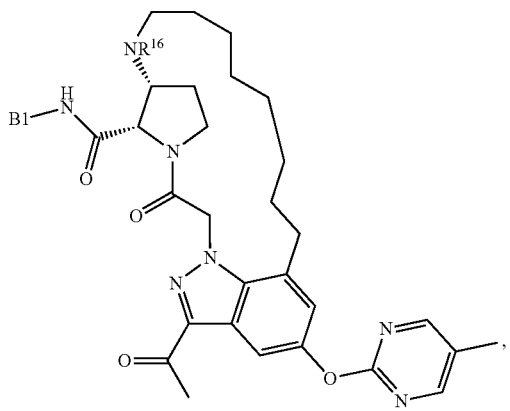
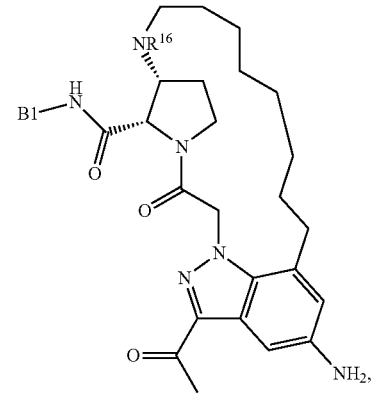
304
-continued
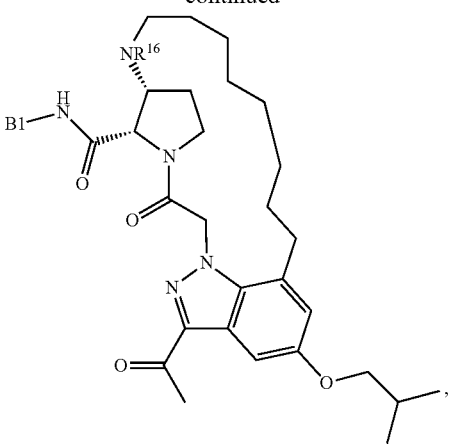
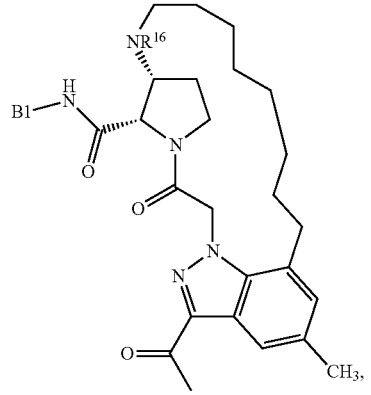
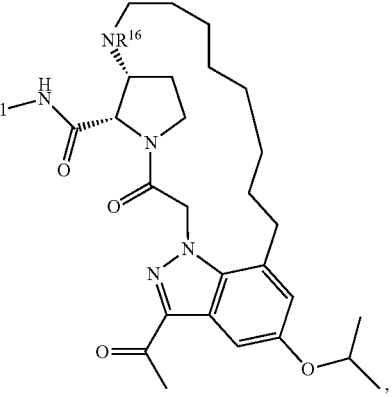
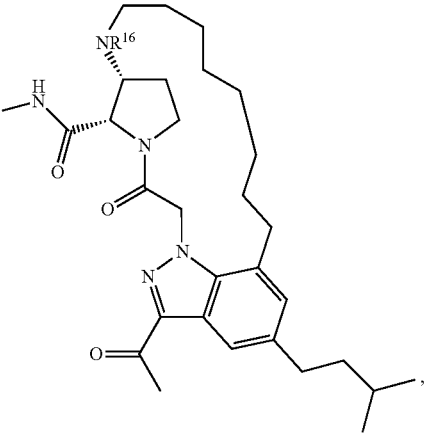

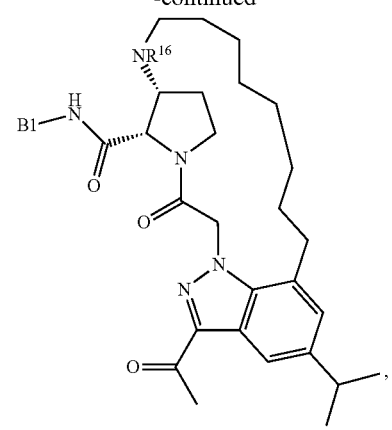
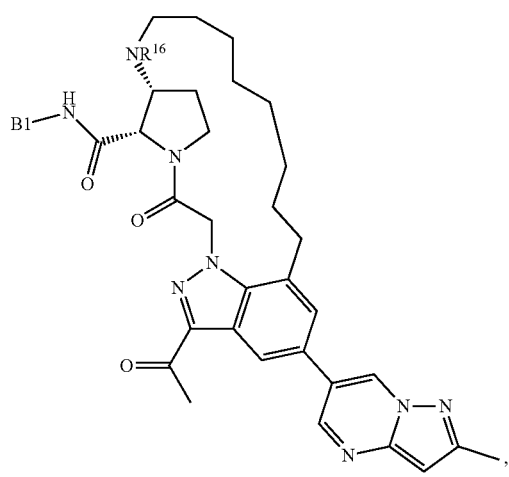
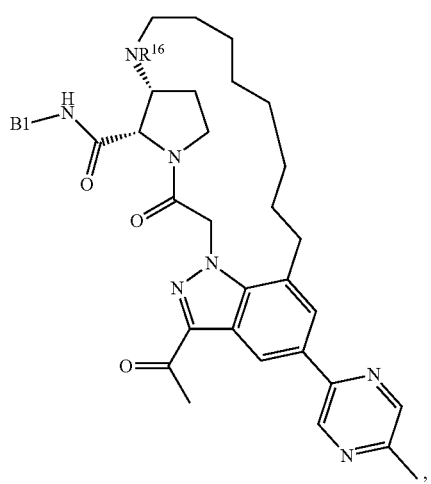
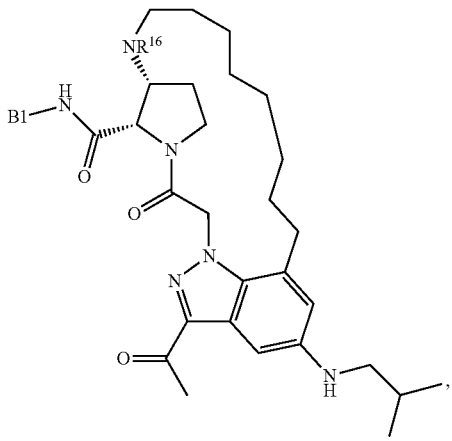
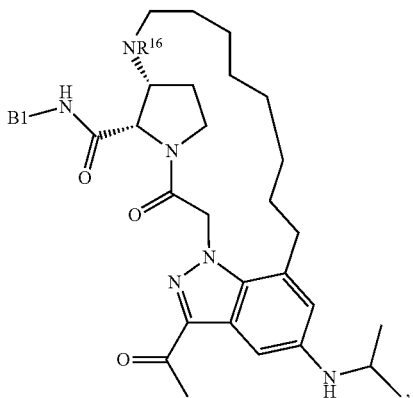
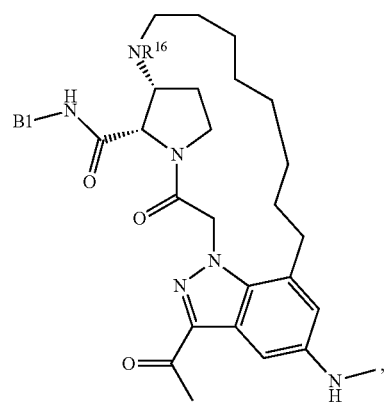
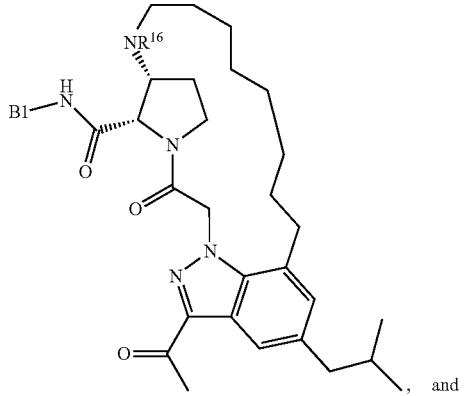

307
-continued
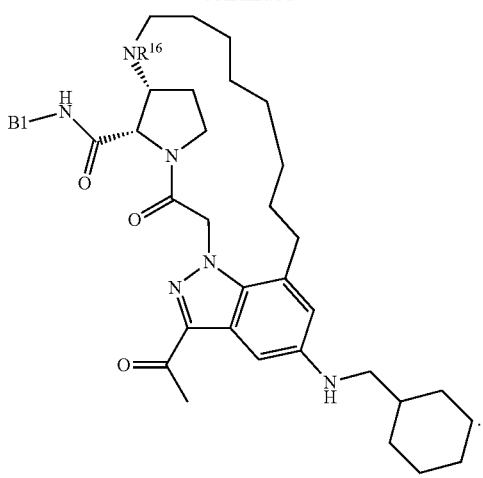
In one embodiment, the compound of Formula II is selected from:
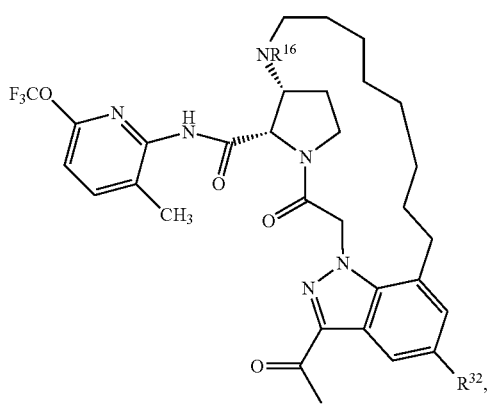
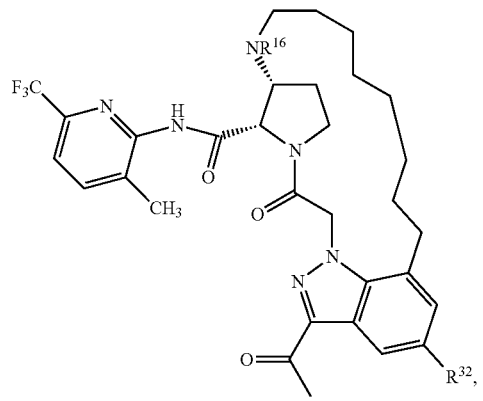
308
-continued
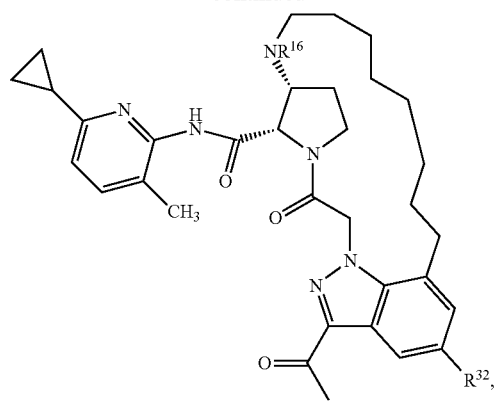
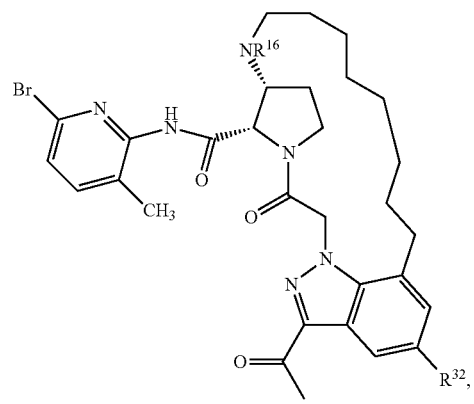
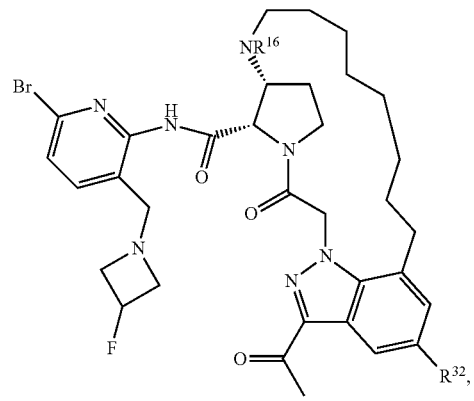

309
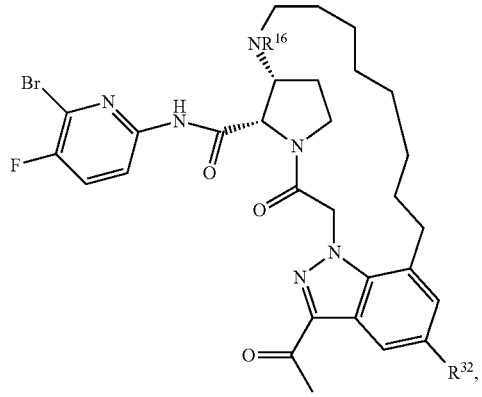
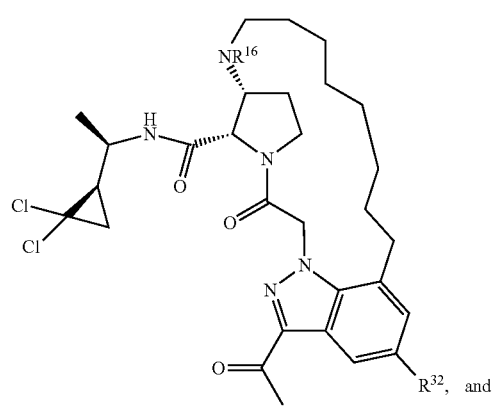
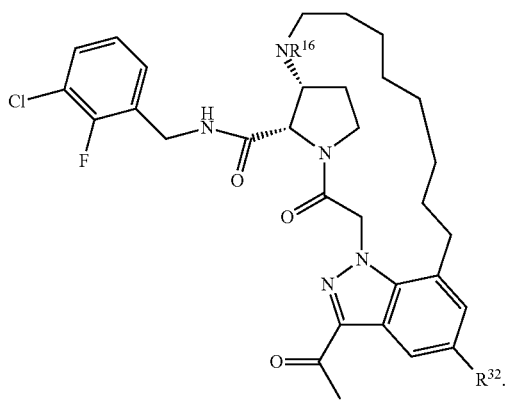
In one embodiment, the compound of Formula II is selected from:
310
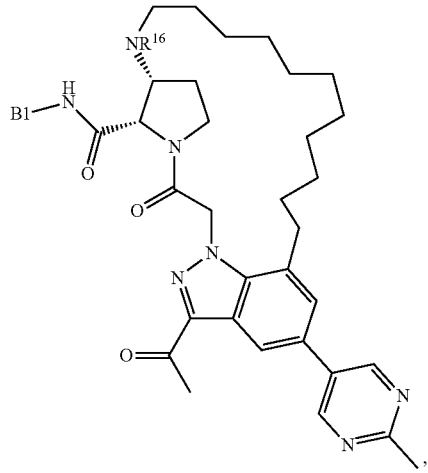
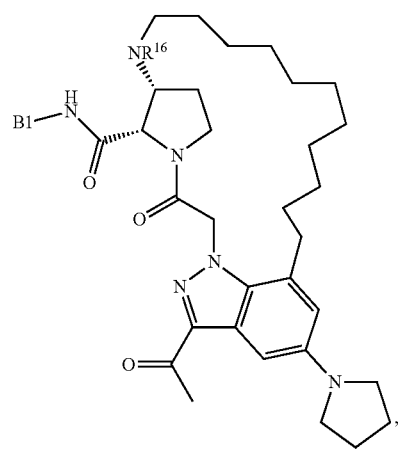
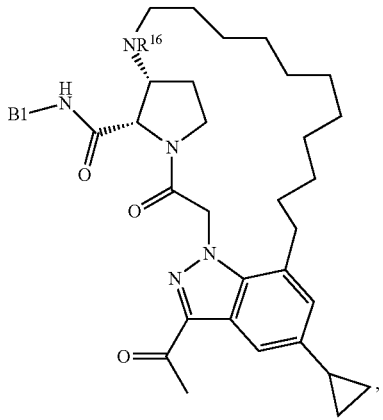

311
-continued
312
-continued
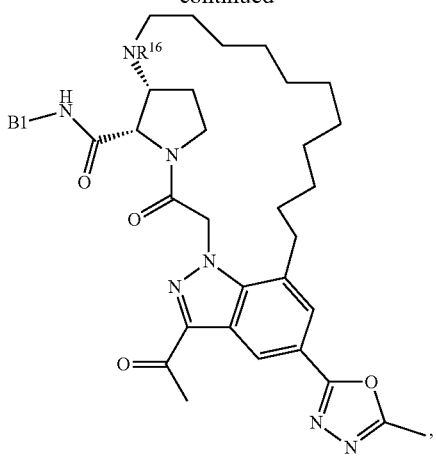
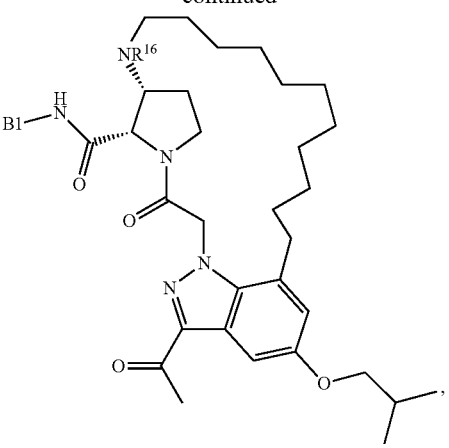
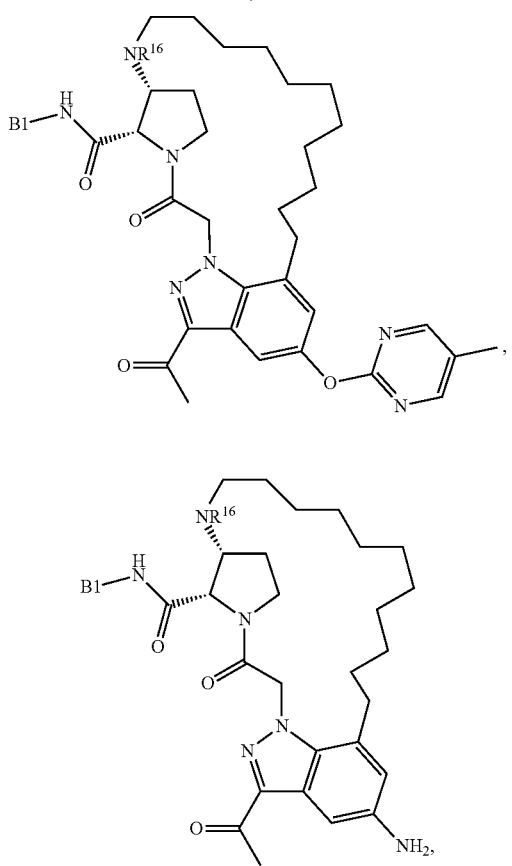

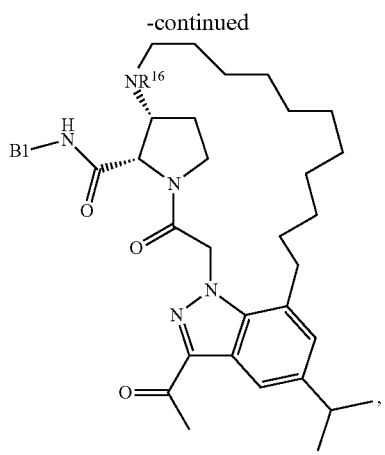
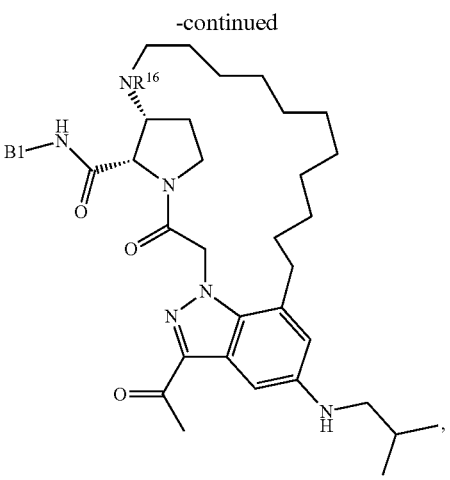

315
-continued
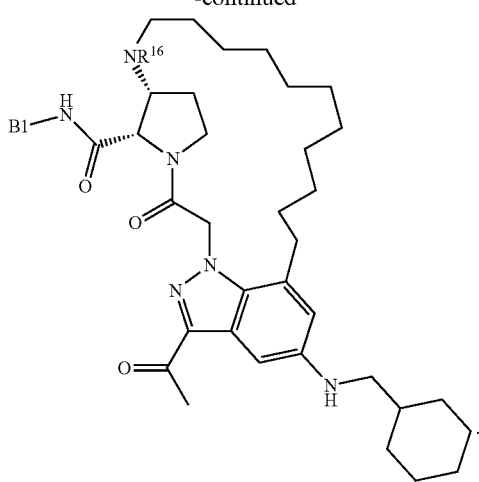
In one embodiment, the compound of Formula II is selected from:
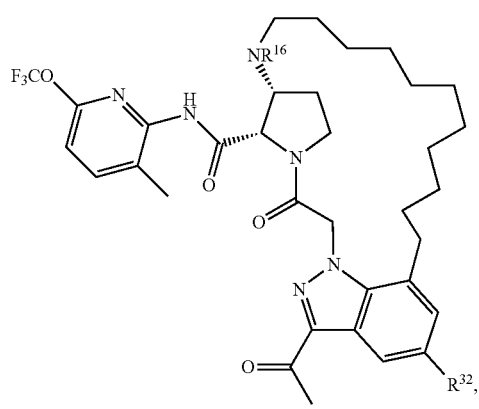
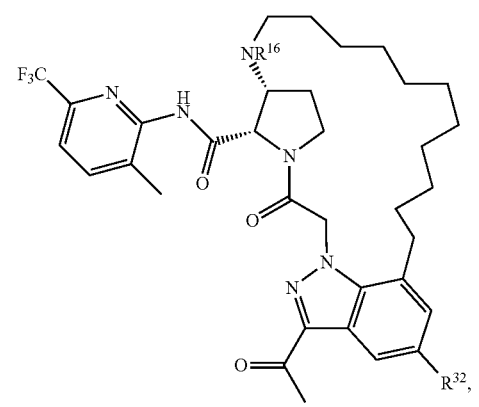
316
-continued
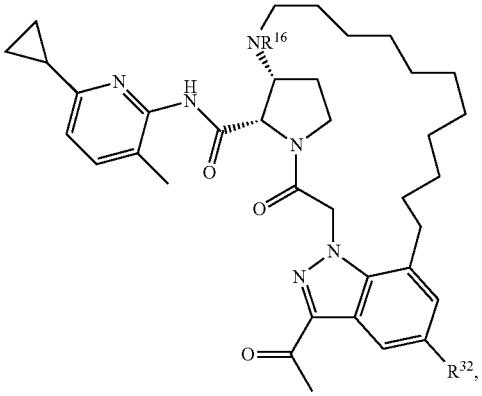
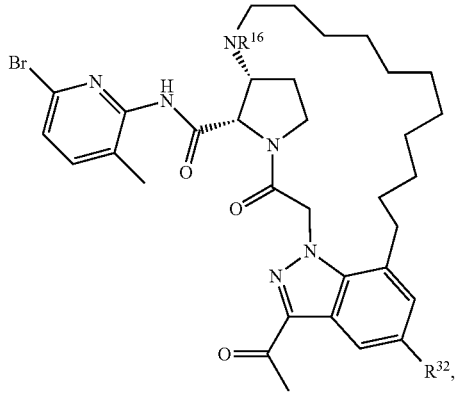
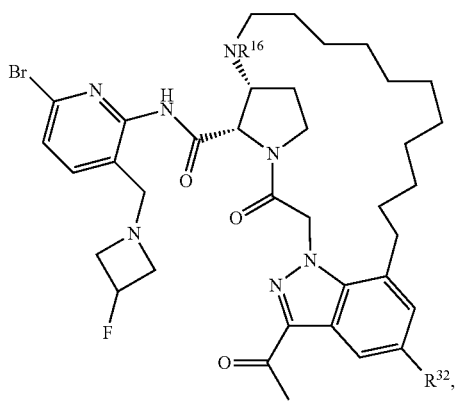
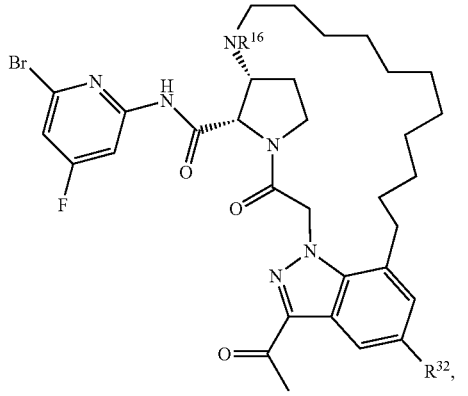

317
-continued
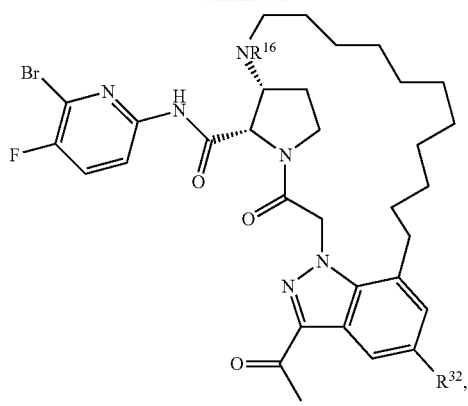
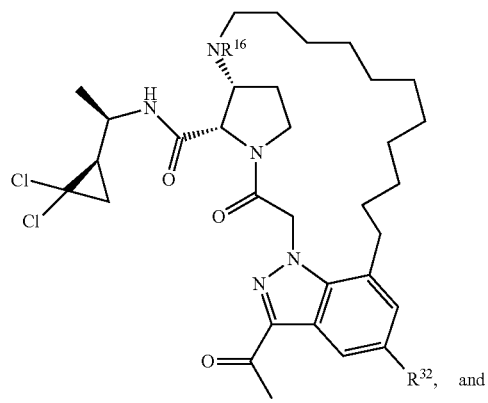
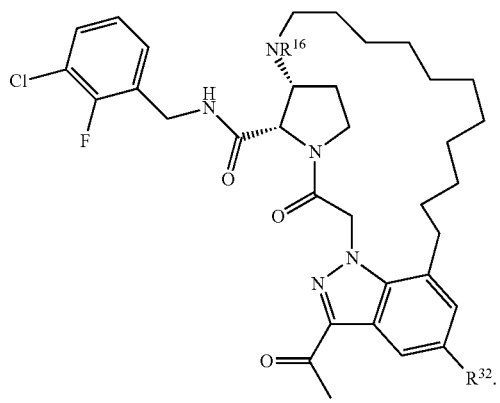
Embodiments of Formula III
In one embodiment, the compound of Formula III is selected from:
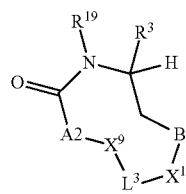 and 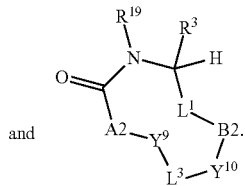
In one embodiment, the compound of Formula III is selected from:
318
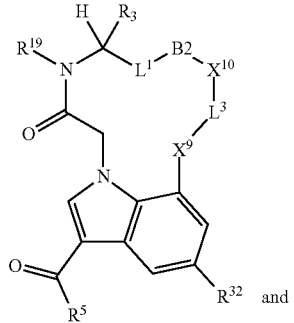
and
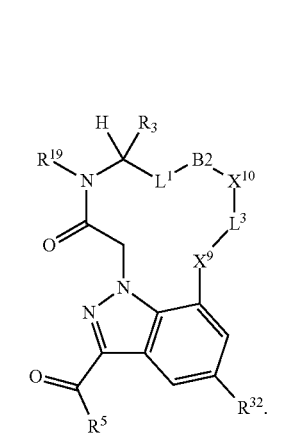
In one embodiment, the compound of Formula III is selected from:
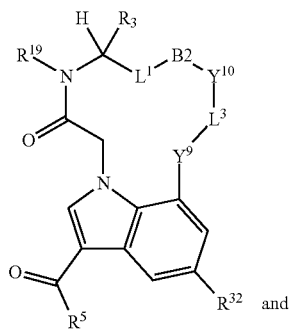
and
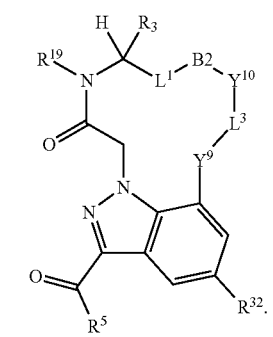
In one embodiment, the compound of Formula III is selected from:

319
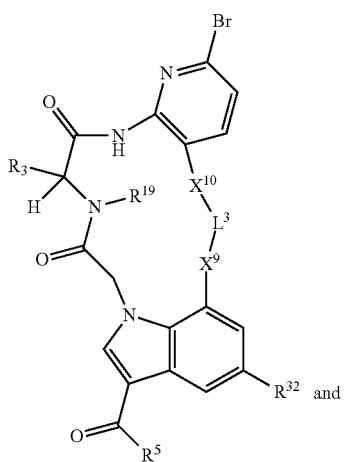
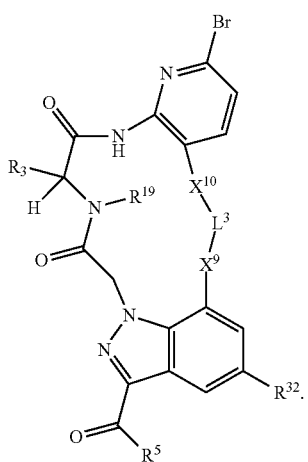
In one embodiment, the compound of Formula III is selected from:
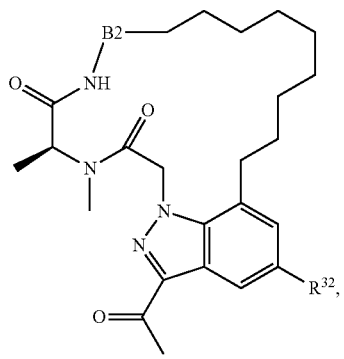
320
-continued
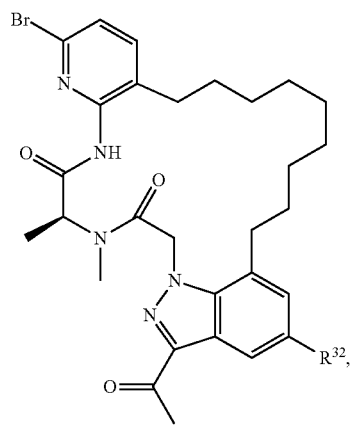
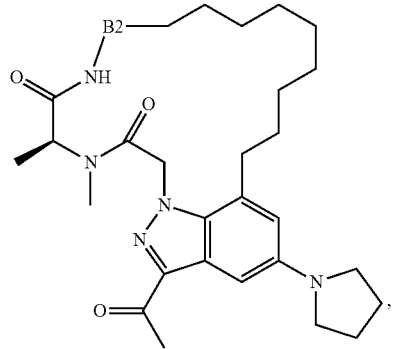
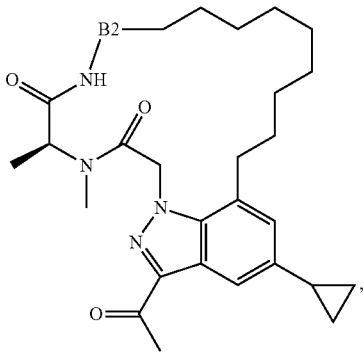

321
-continued
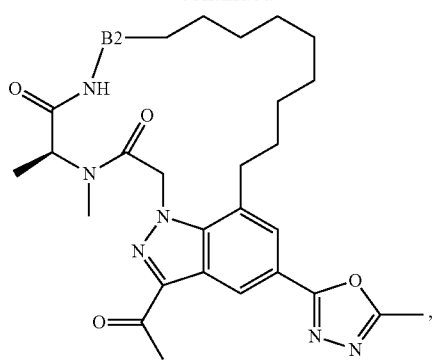
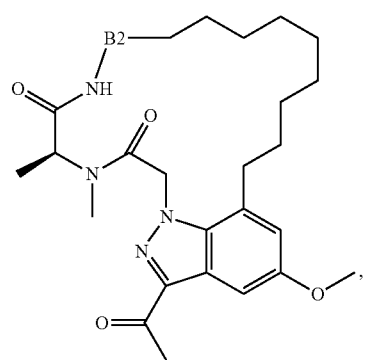
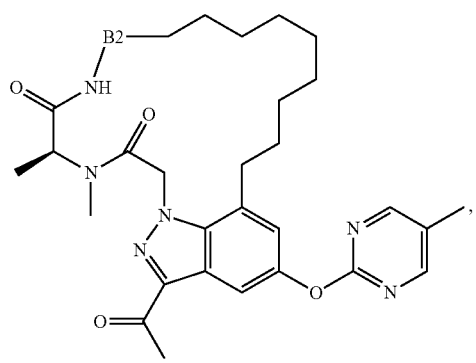
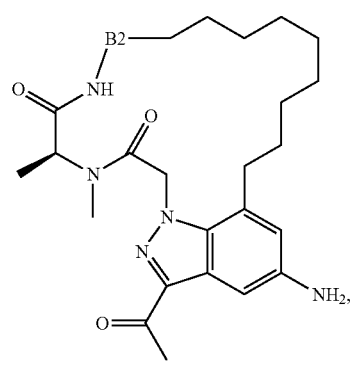
322
-continued
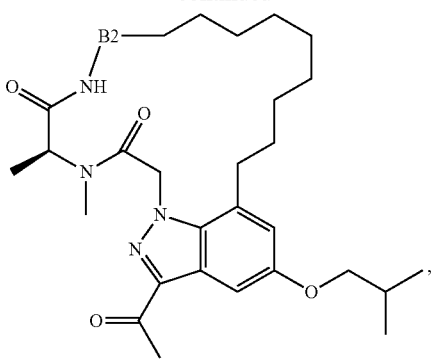
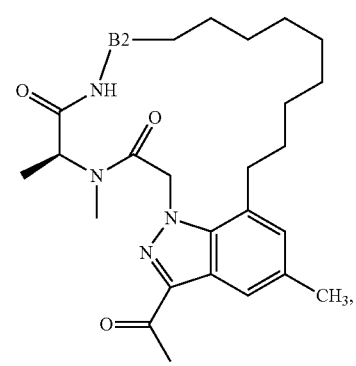
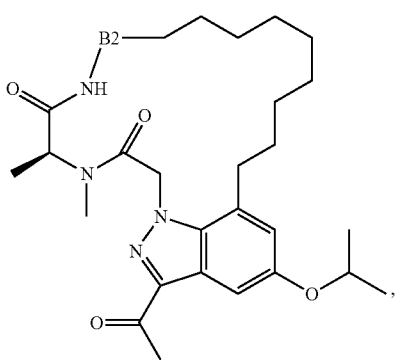
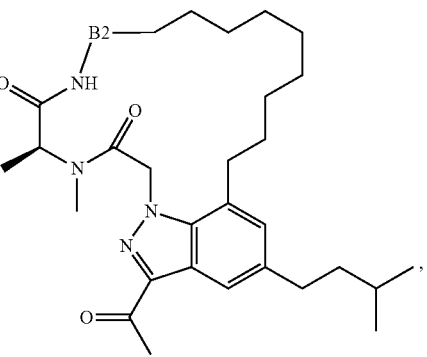

323
-continued
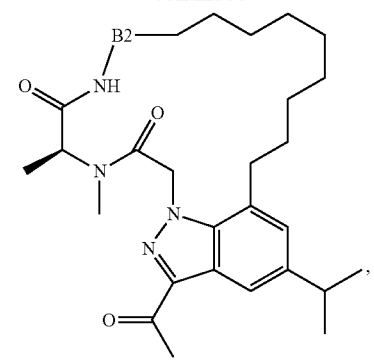
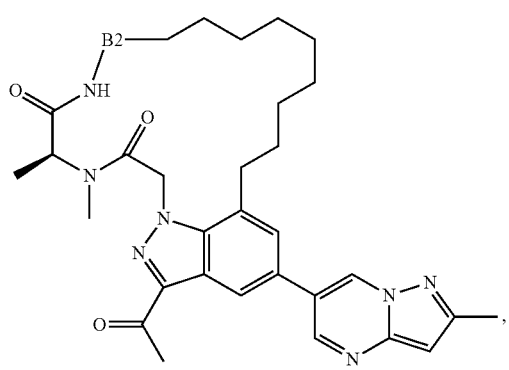
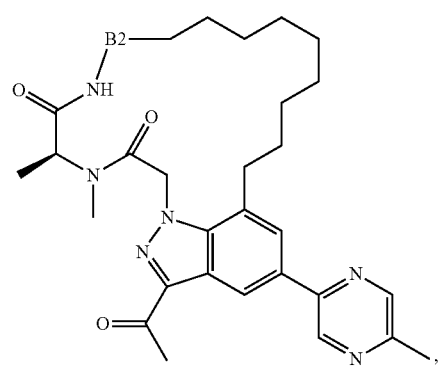
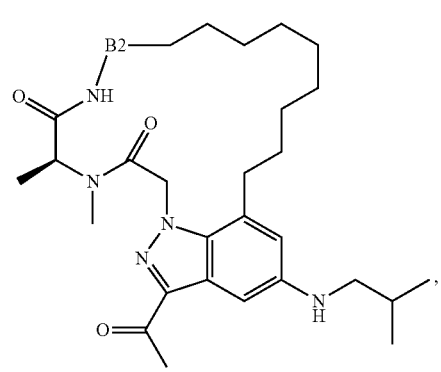
324
-continued
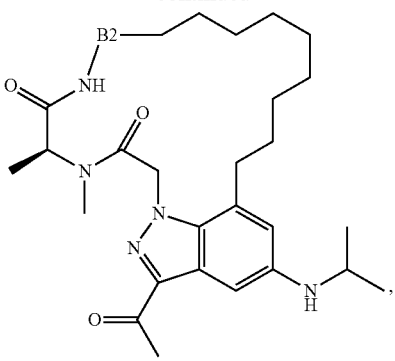
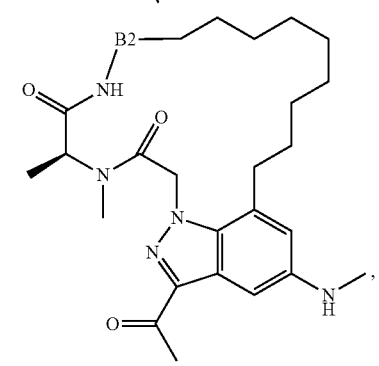
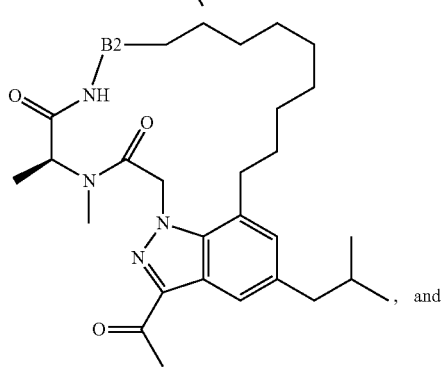
, and
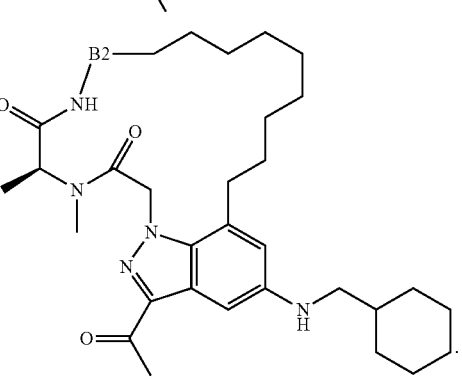
Additional Compounds of the Present Invention
In the below embodiments $L^6$ is
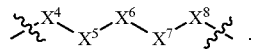
In one embodiment the compound of the present invention is selected from:

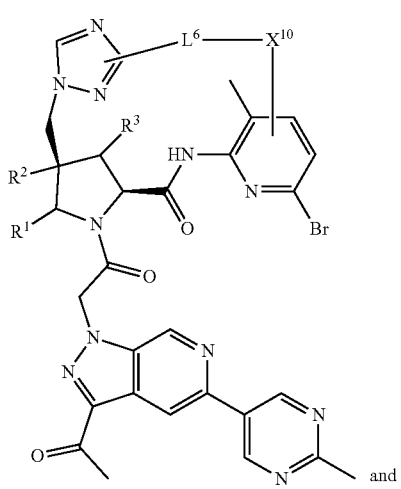
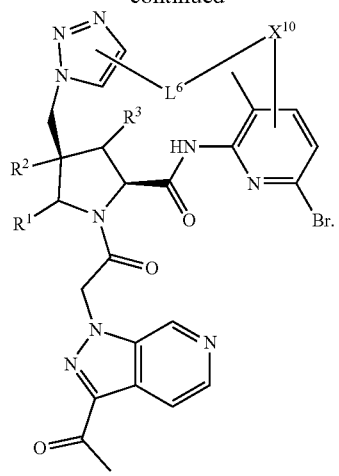
In one embodiment the compound of the present invention is selected from:
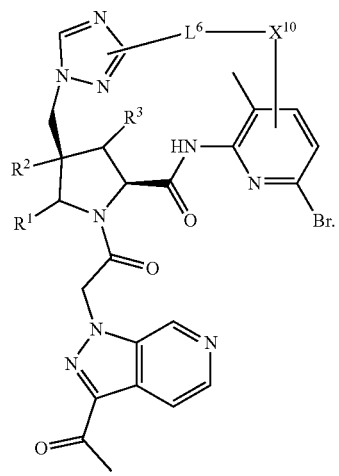
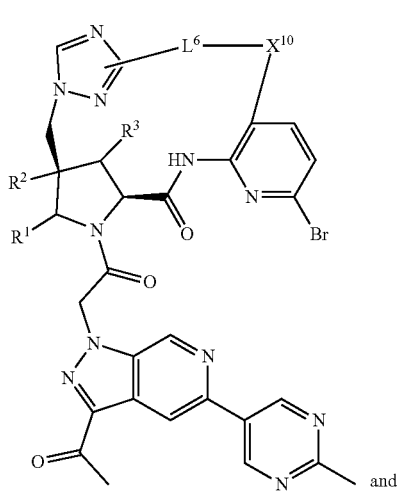
and
In one embodiment the compound of the present invention is selected from:
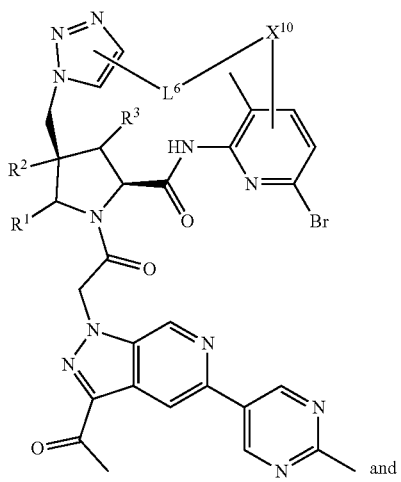
and
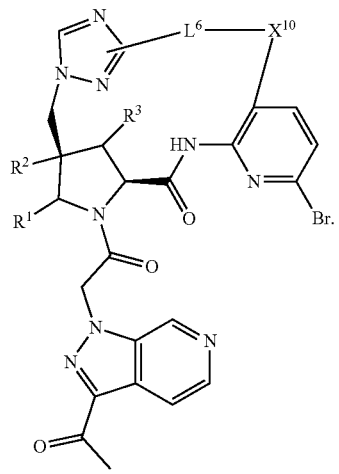
In one embodiment the compound of the present invention is selected from:

327
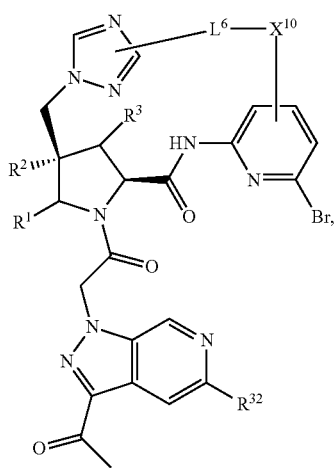
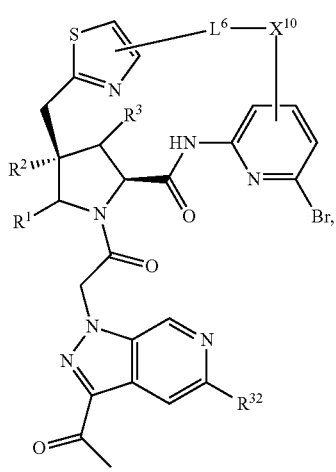
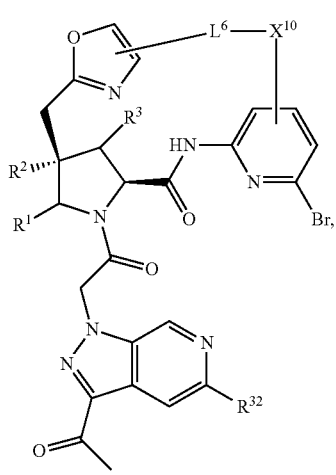
328
-continued
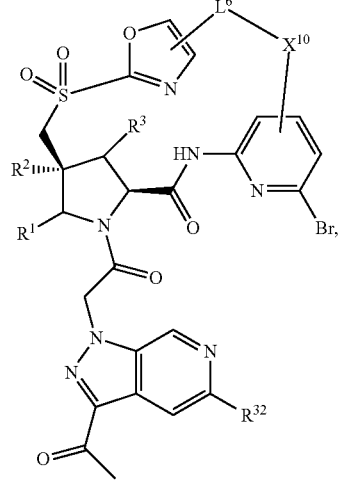
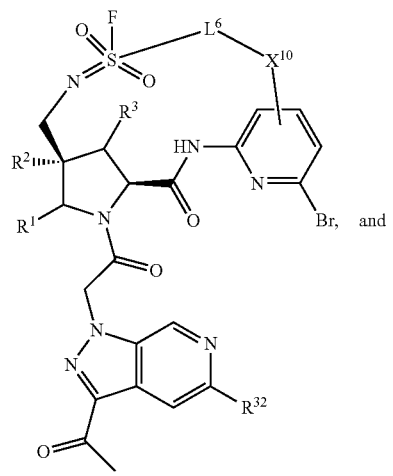
and
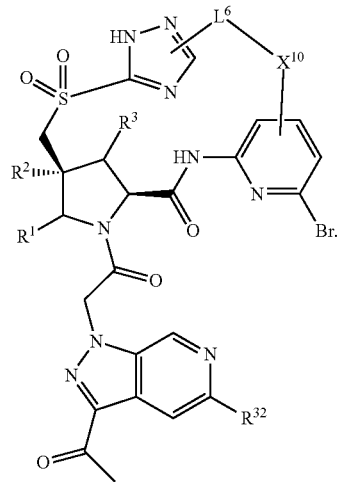
In one embodiment the compound of the present invention is selected from:

329
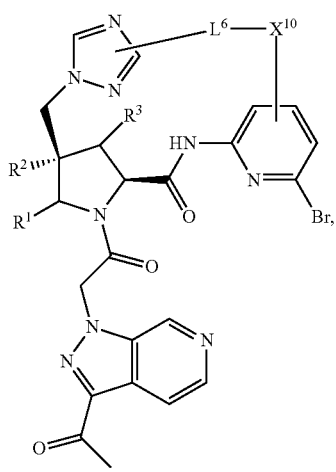
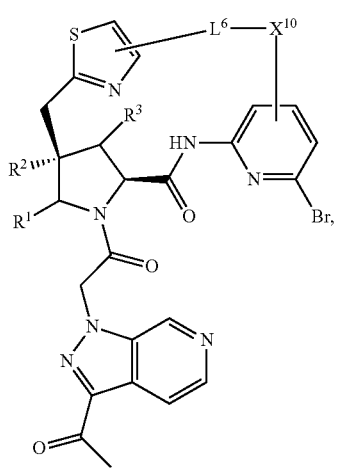
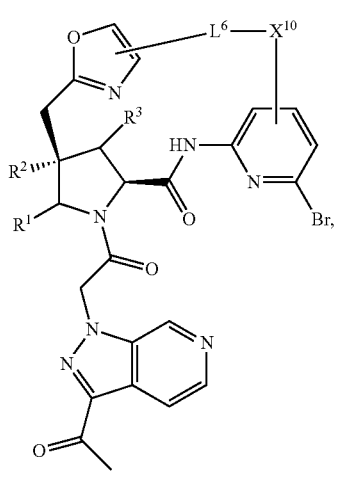
330
-continued
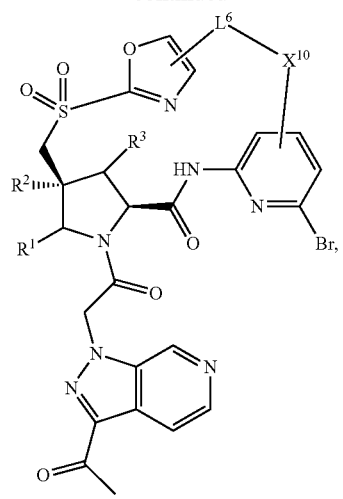
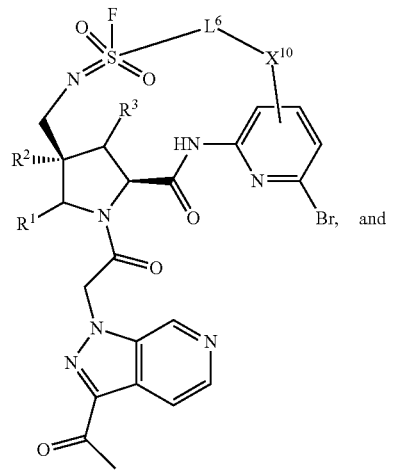
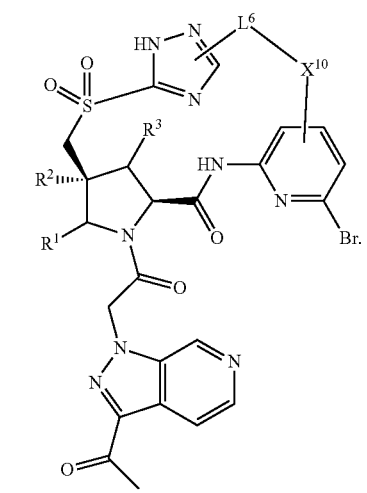
Additional Formulas of the Present Invention
Representative examples of compounds Formula I include:

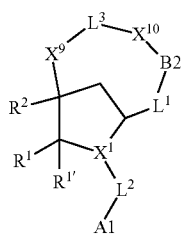
Formula I-1
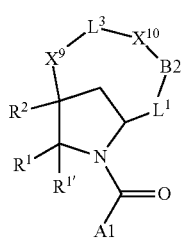
Formula I-2
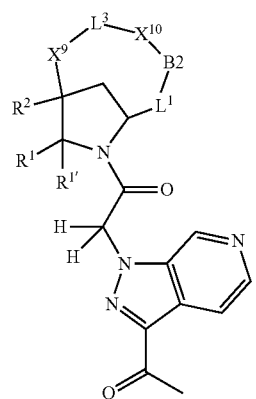
Formula I-11
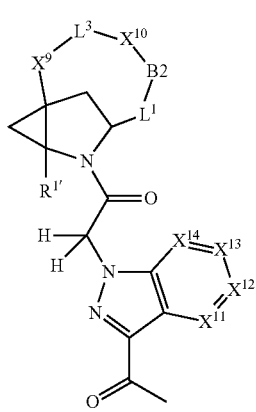
Formula I-15
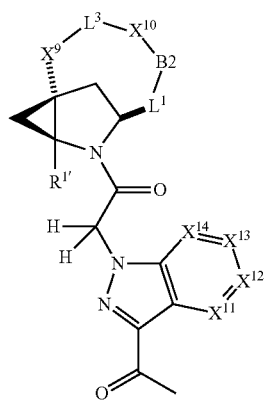
Formula I-17
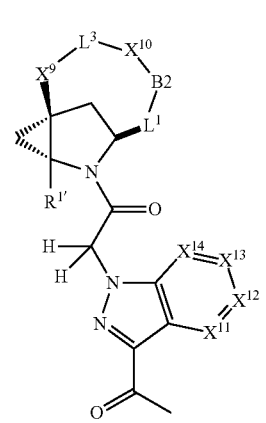
Formula I-19
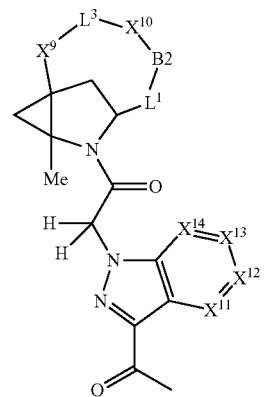
Formula I-21
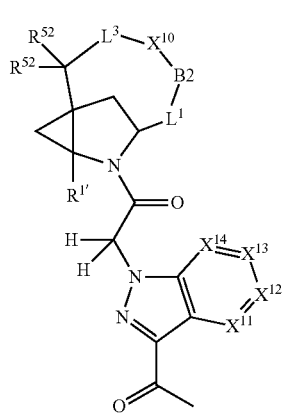
Formula I-23

333
-continued
Formula I-25
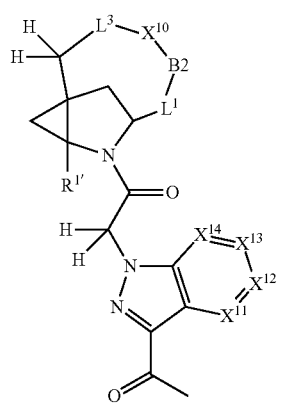
Formula I-27

Formula I-29
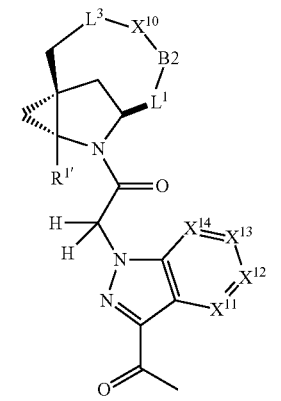
Formula I-31
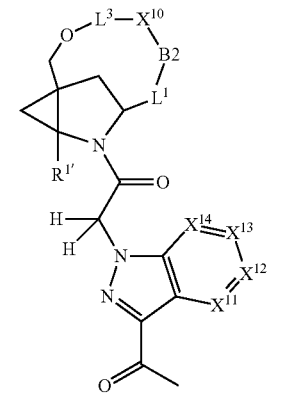
334
-continued
Formula I-33
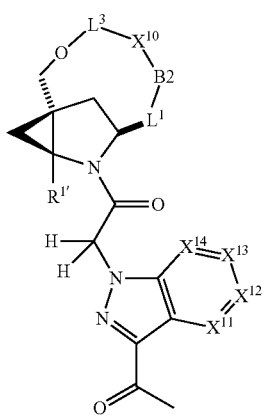
Formula I-35
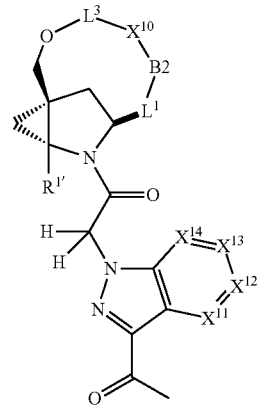
Formula I-36
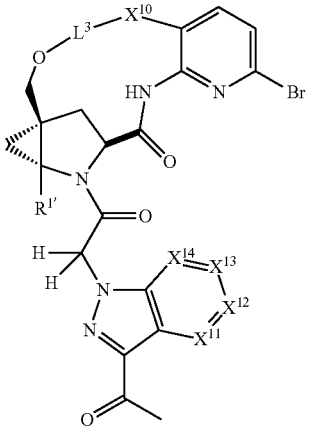

Formula I-37
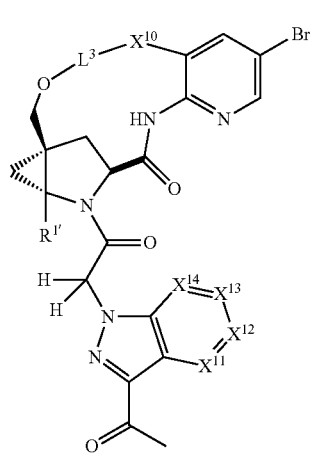
Formula I-38
Formula I-39
Formula I-40
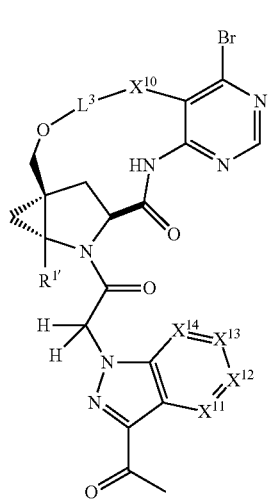
Formula I-41
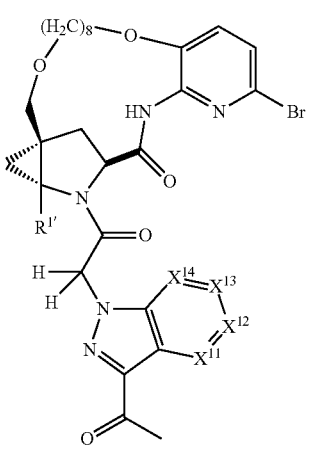
Formula I-42
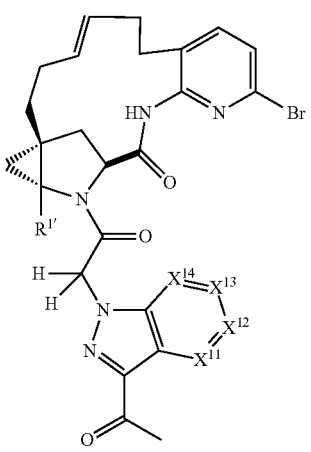

Formula I-43
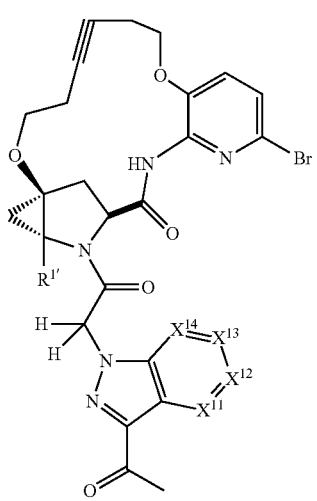
Formula I-44
Formula I-45
Formula II-1
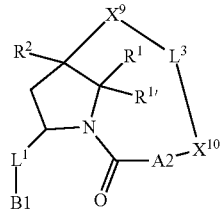
Formula II-2
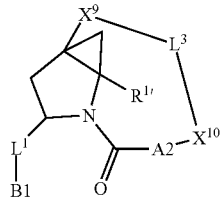
Formula II-3
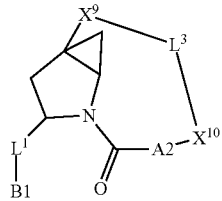
Formula II-11
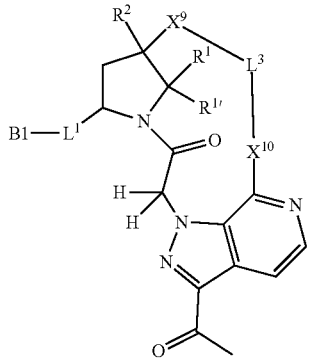
Formula II-15
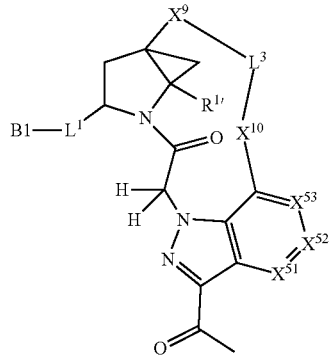
Representative examples of compound Formula II include:

-continued
Formula II-17
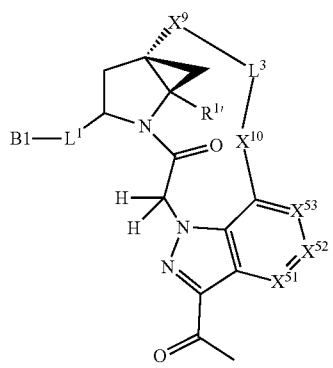
Formula II-19
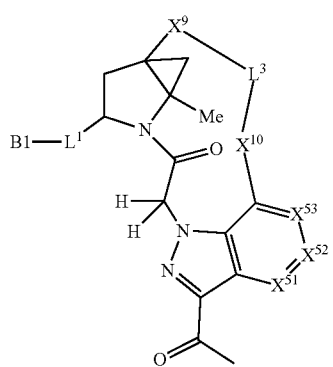
Formula II-21
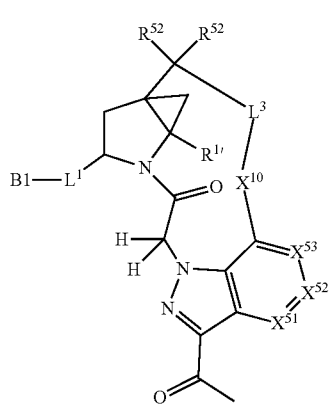
Formula II-23
Formula II-24
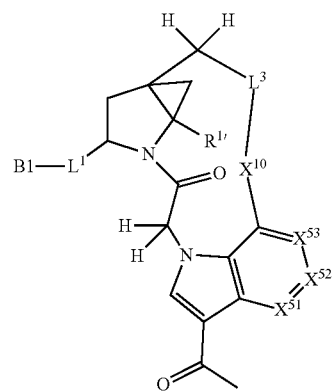
Formula II-25
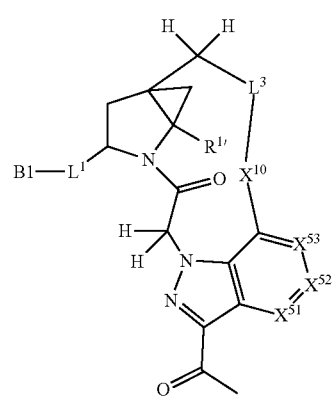
Formula II-27
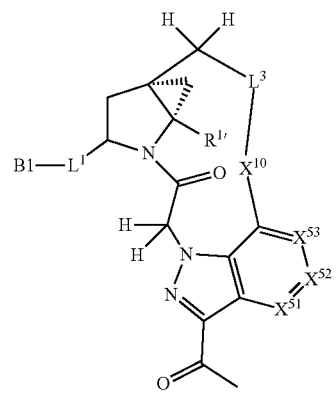
Formula II-29
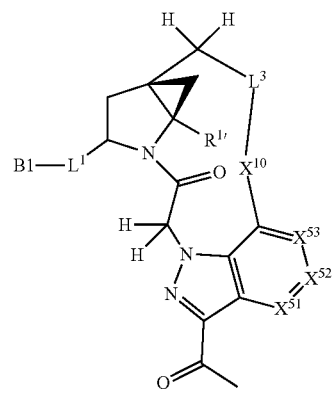

Formula II-30
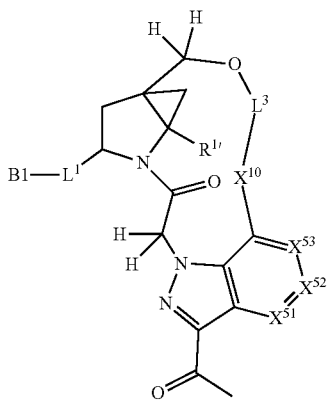
Formula II-36
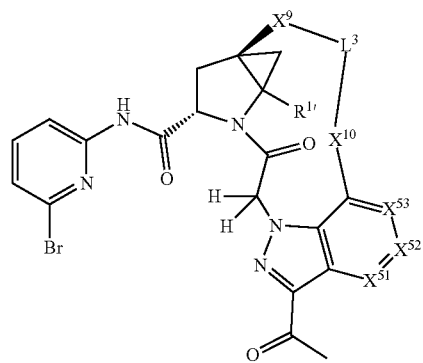
Formula II-31
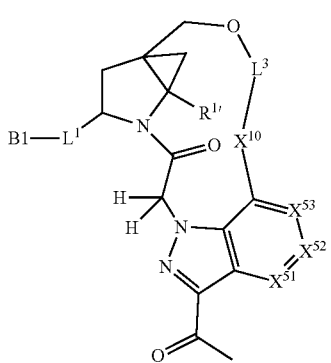
Formula II-39
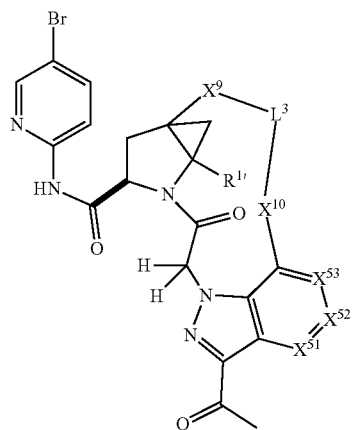
Formula II-33
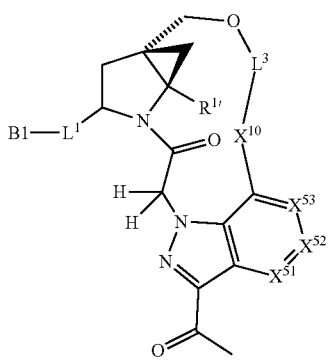
Formula II-40
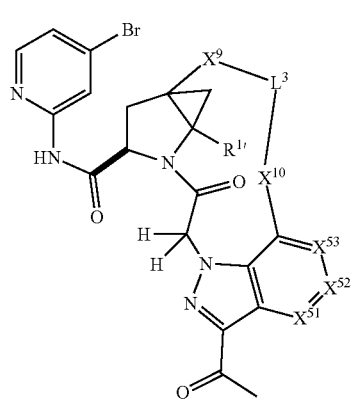
Formula II-35
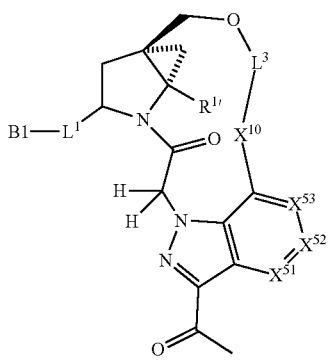
Formula II-42
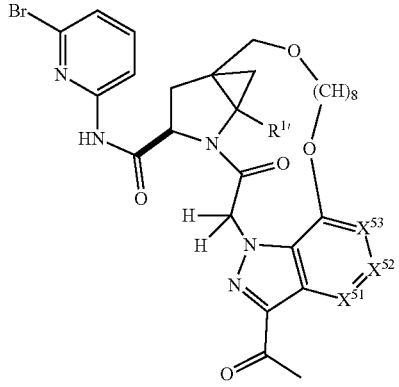

Formula II-43
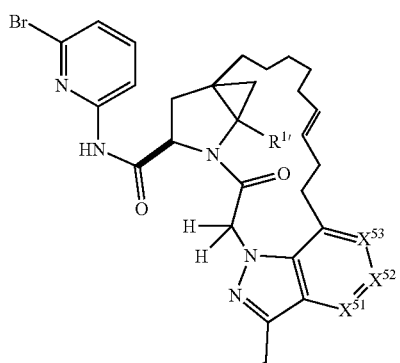
Formula II-46
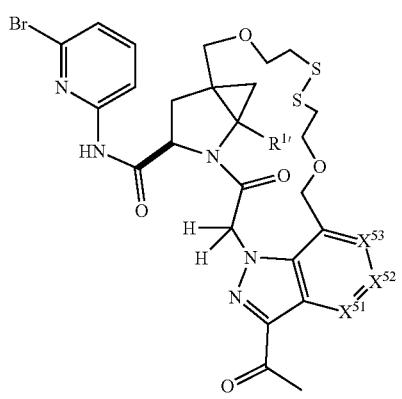
Formula II-47
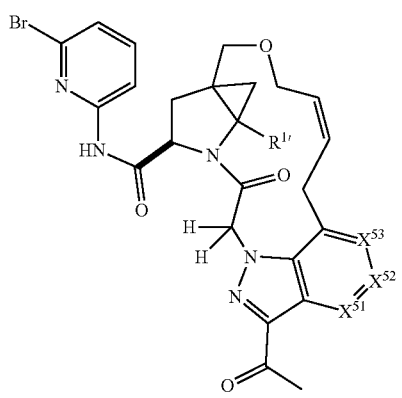
Formula II-48
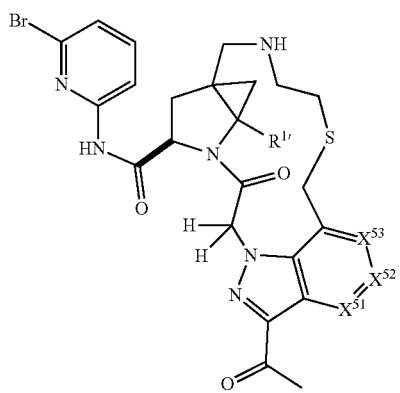
Representative examples of compounds of Formula III include:
Formula III-1
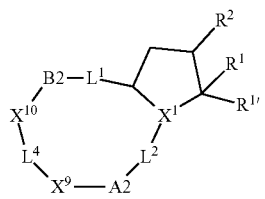
Formula III-2
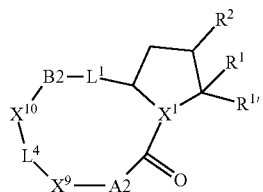
Formula III-11
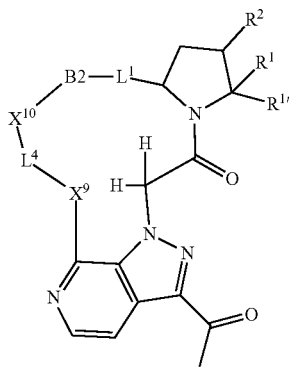
Formula III-15
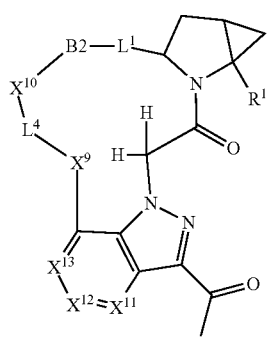
Formula III-17
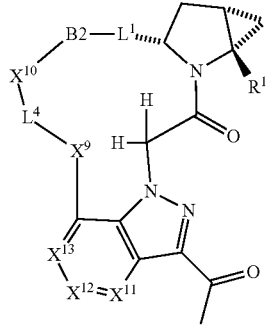

Formula III-19
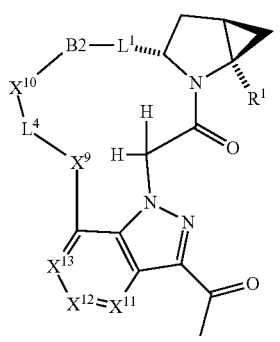
Formula III-21
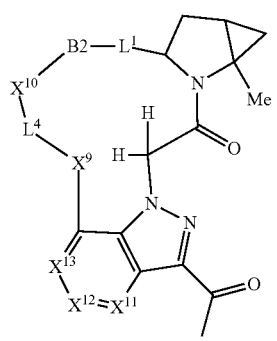
Formula III-23
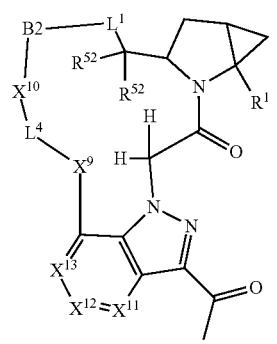
Representative examples of compound of Formula IV include:
Formula IV-1
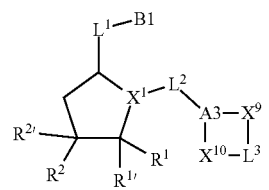
Formula IV-2
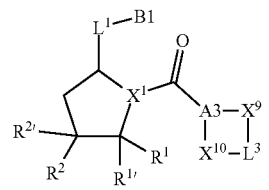
Formula IV-10
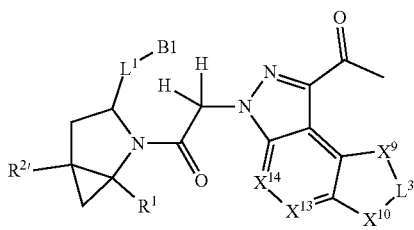
Formula IV-12
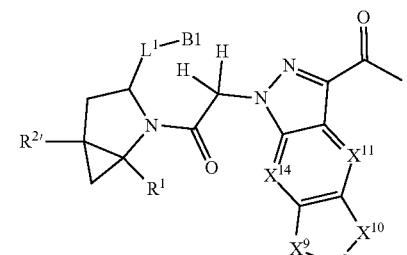
Formula IV-13
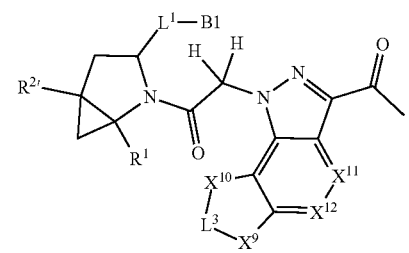
Formula IV-16
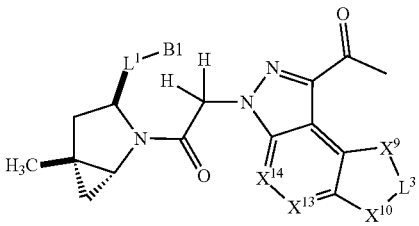
Formula IV-18
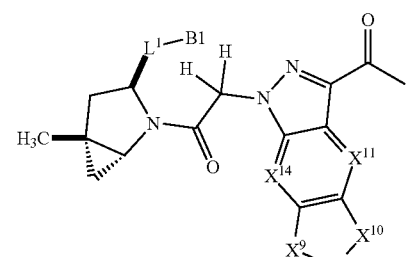
Formula IV-19
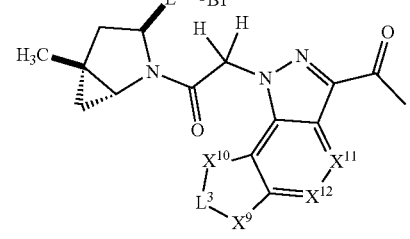

Formula IV-22
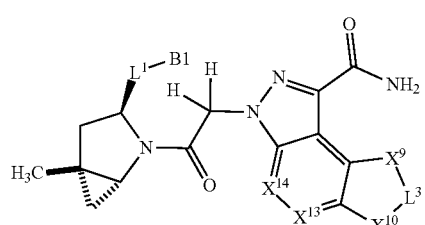
Formula IV-24
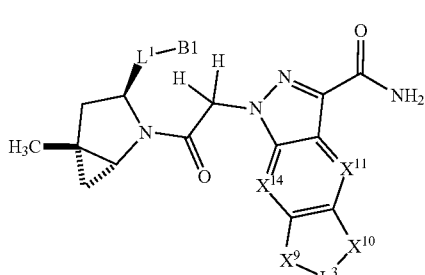
Formula IV-25
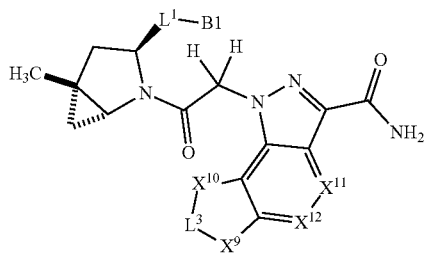
Representative examples of compound of Formula V include:
Formula V-1
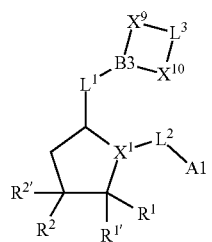
Formula V-4
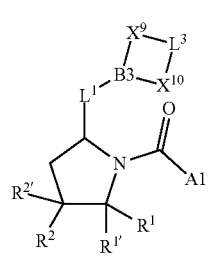
Formula V-11
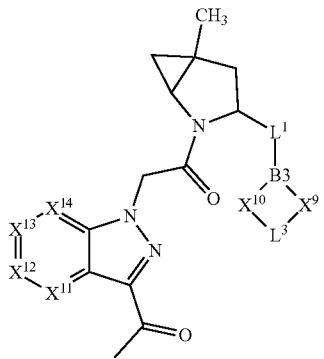
Formula V-14
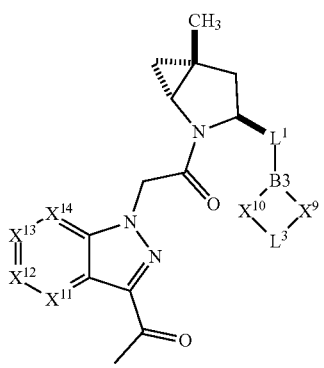
Formula V-18
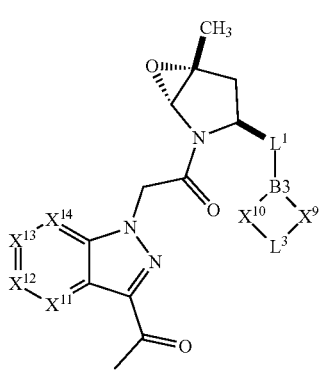
Formula V-28
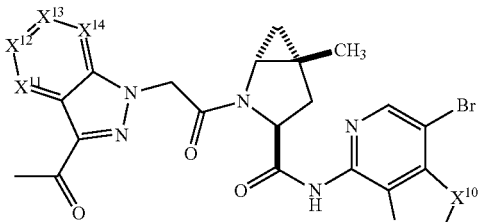
Formula V-29
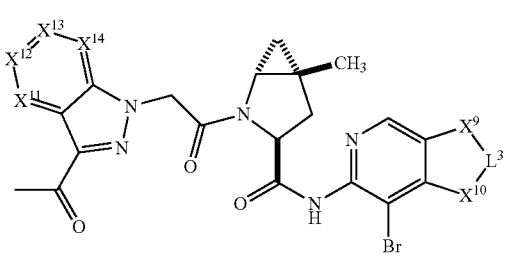

Formula V-30
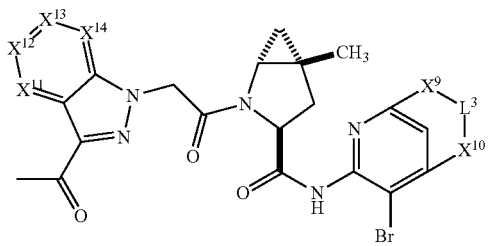
Formula V-31
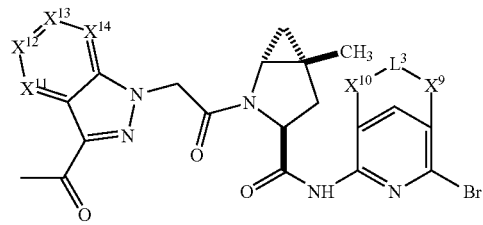
Formula V-32
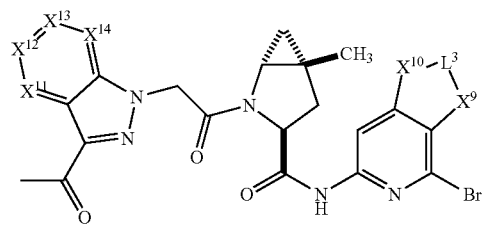
Formula V-33
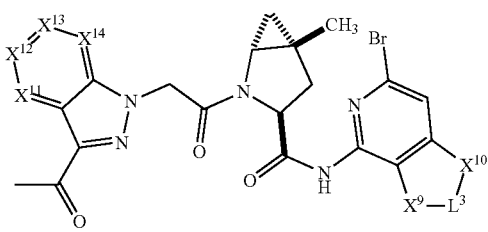
Formula V-34
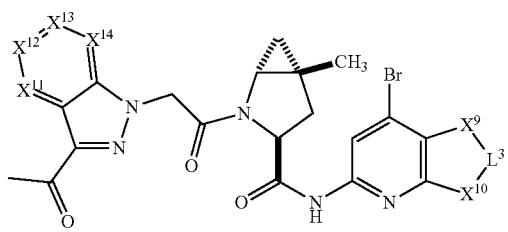
Formula V-35
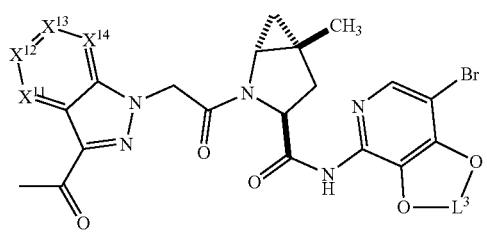
Formula V-36
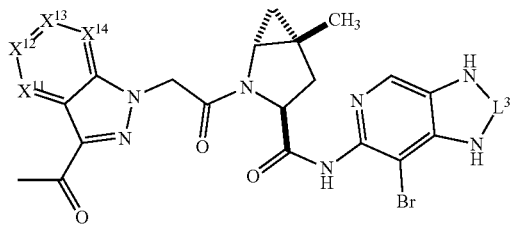
Formula V-37
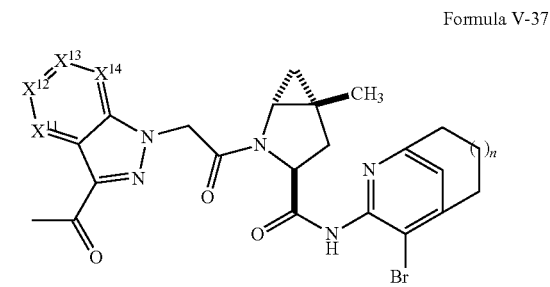
Formula V-38
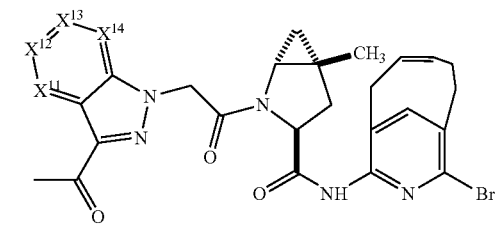
Formula V-39
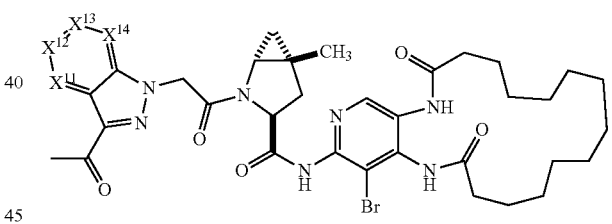
Representative examples of compounds of Formula VI include:
Formula VI-1
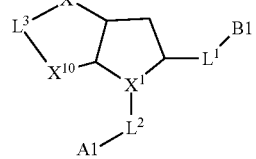
Formula VI-2
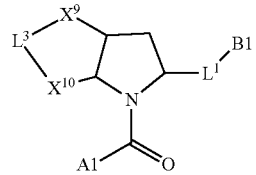

-continued
Formula VI-11
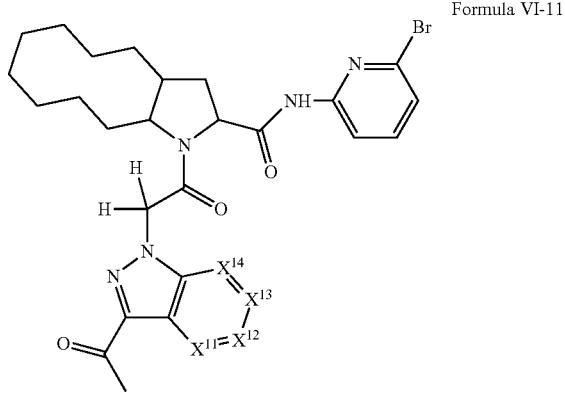
Additional Embodiments
In another embodiment $X^9$-$L^3$-$X^{10}$ or $X^{10}$-$L^3$-$X^9$ is selected from:
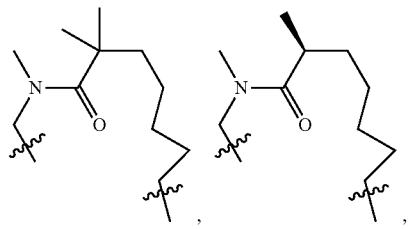
,
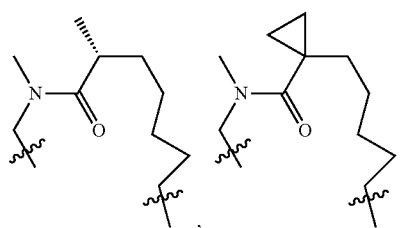
,
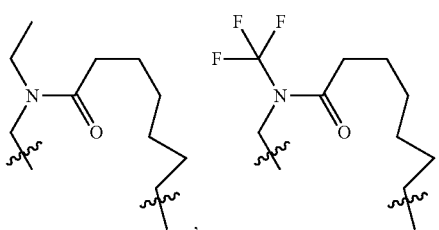
,

, and
-continued
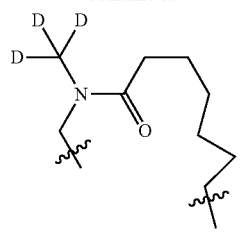
.
In another embodiment or $X^9$-$L^3$-$X^{10}$ or $X^{10}$-$L^3$-$X^9$ is
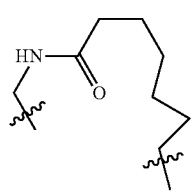
.
In another embodiment $X^9$-$L^3$-$X^{10}$ or $X^{10}$-$L^3$-$X^9$ is selected from:
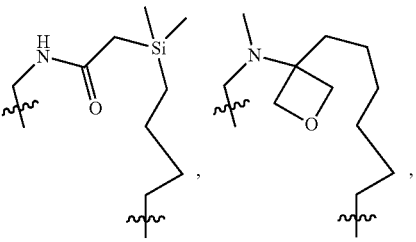
,
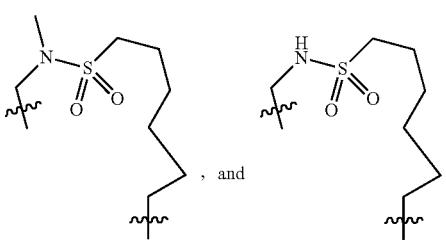
, and .
In another embodiment $X^9$-$L^3$-$X^{10}$ or $X^{10}$-$L^3$-$X^9$ is selected from:
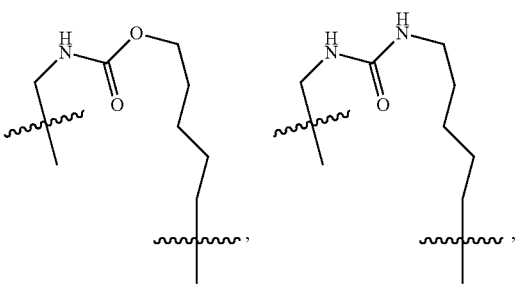
,

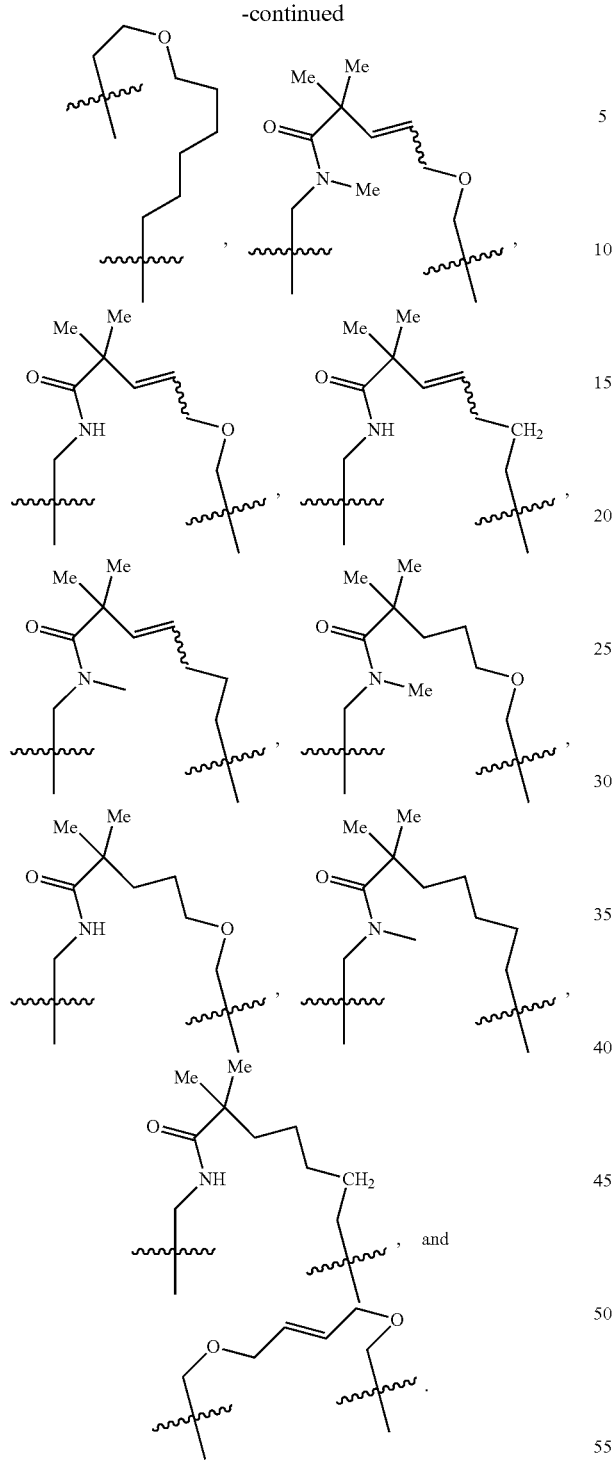
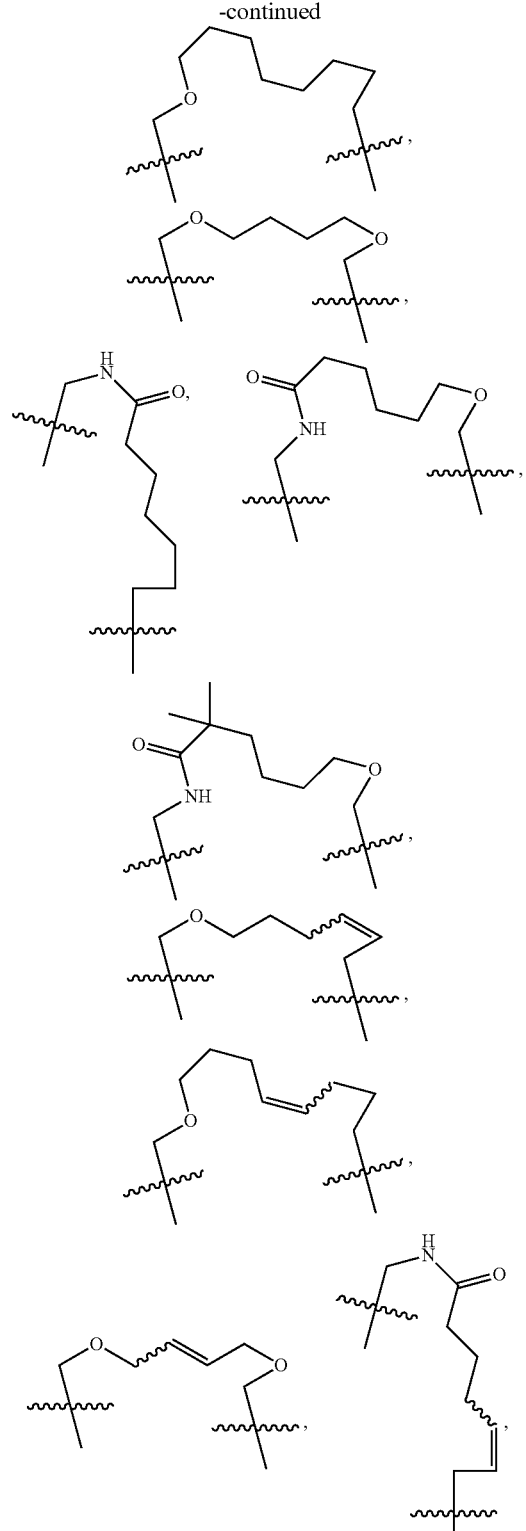
In another embodiment $X^9$-$L^3$-$X^{10}$ or $X^{10}$-$L^3$-$X^9$ is selected from:
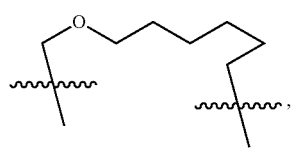
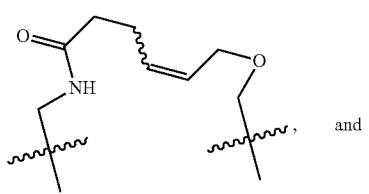

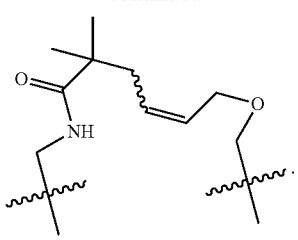
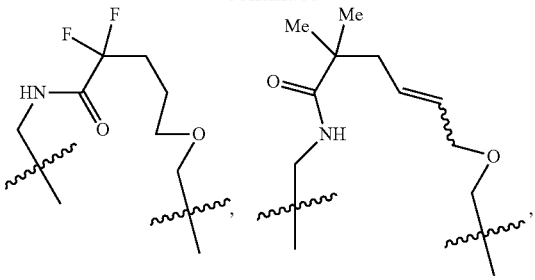
In another embodiment $X^9$-$L^3$-$X^{10}$ or $X^{10}$-$L^3$-$X^9$ is selected from:
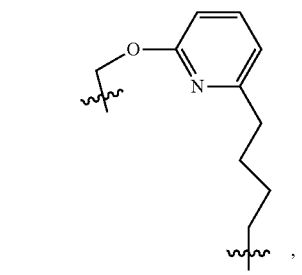
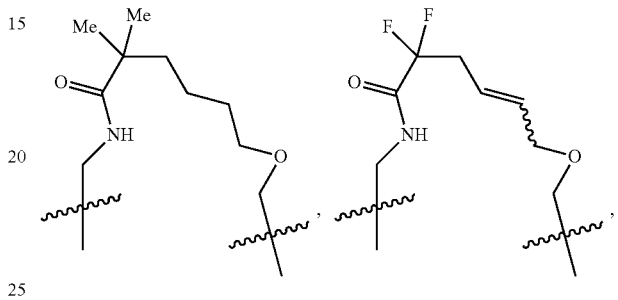
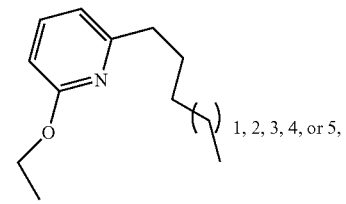, 1, 2, 3, 4, or 5,
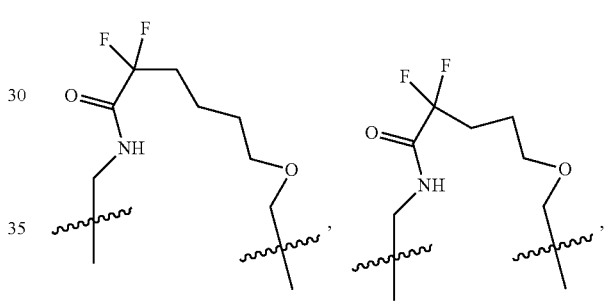
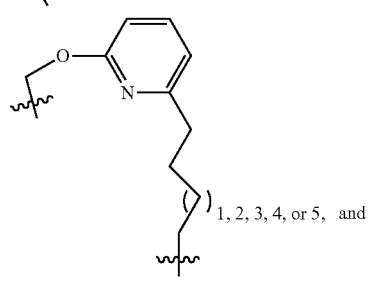, 1, 2, 3, 4, or 5, and
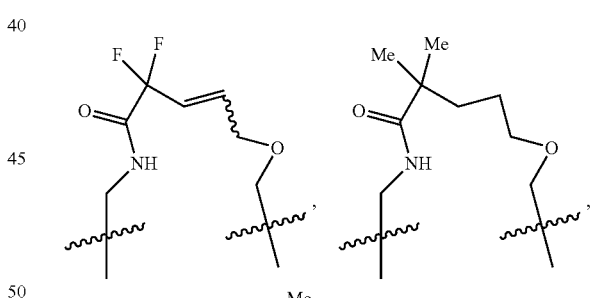
In another embodiment $X^9$-$L^3$-$X^{10}$ or $X^{10}$-$L^3$-$X^9$ is selected from:
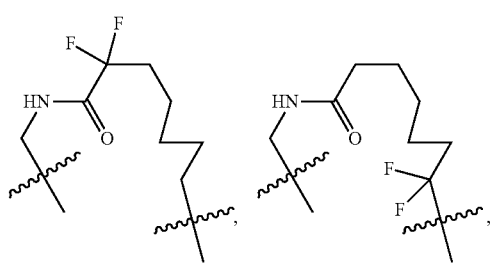
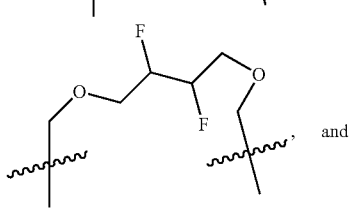 and -continued
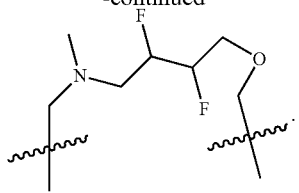
In another embodiment $X^9$-$L^3$-$X^{10}$ or $X^{10}$-$L^3$-$X^9$ is selected from:
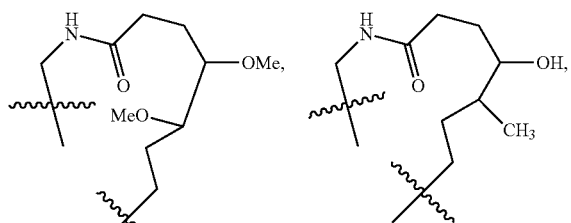
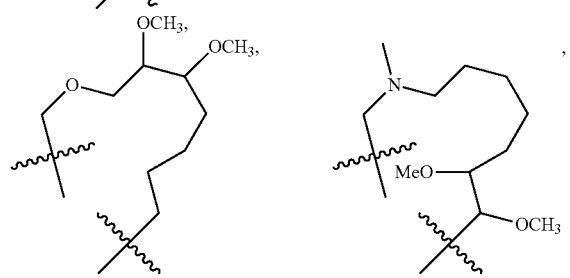
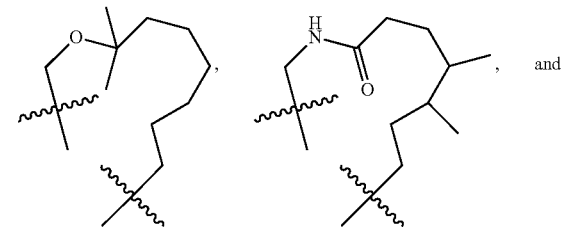
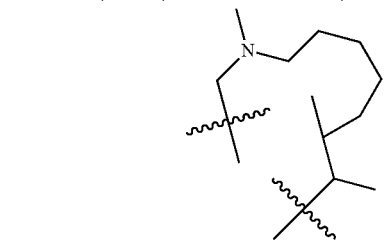
In another embodiment $X^9$-$L^3$-$X^{10}$ or $X^{10}$-$L^3$-$X^9$ is selected from:
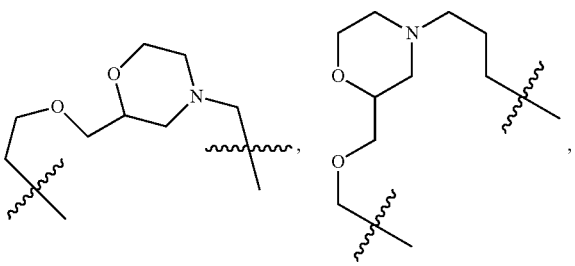
-continued
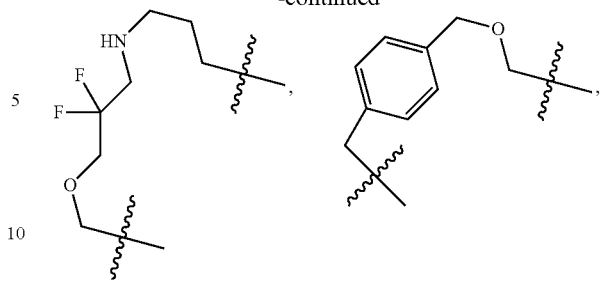
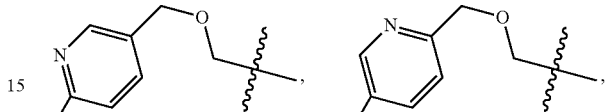
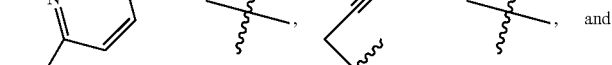, and
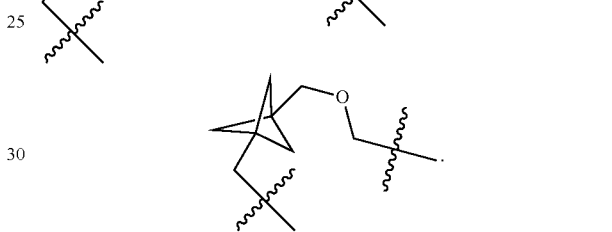
In another embodiment $X^9$-$L^3$-$X^{10}$ or $X^{10}$-$L^3$-$X^9$ is selected from:
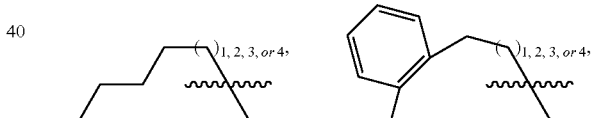
In another embodiment $X^9$-$L^3$-$X^{10}$ or $X^{10}$-$L^3$-$X^9$ is selected from:
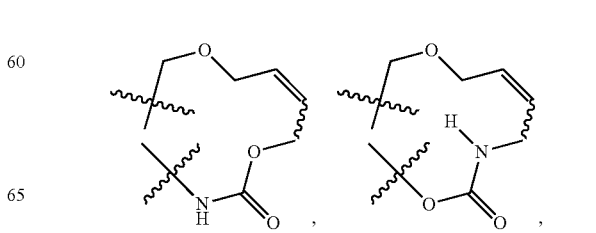

-continued
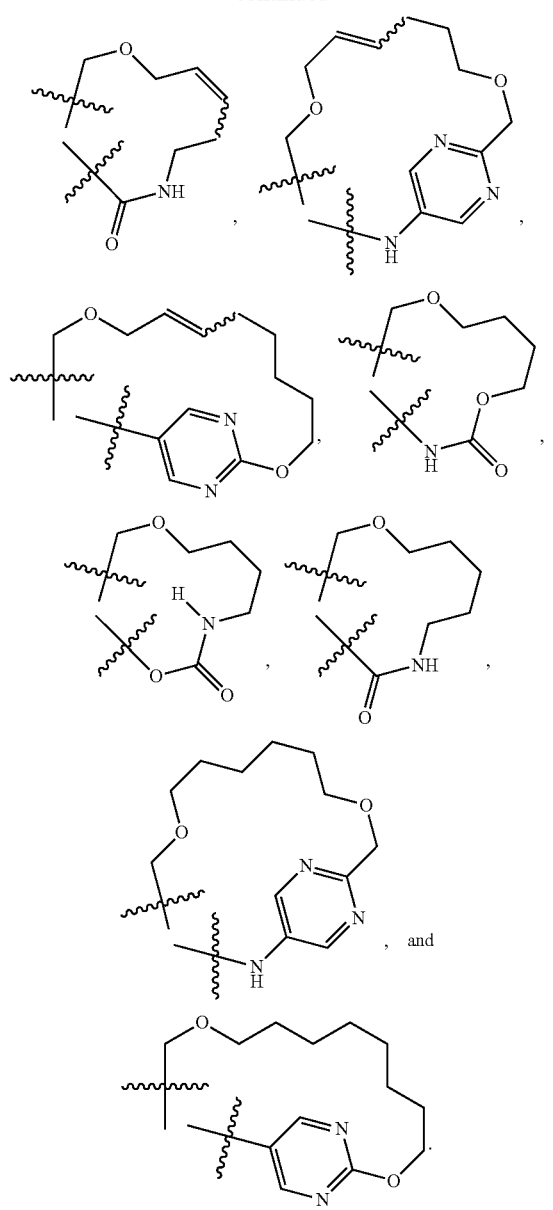
In another embodiment $X^9$-$L^3$-$X^{10}$ or $X^{10}$-$L^3$-$X^9$ is selected from:
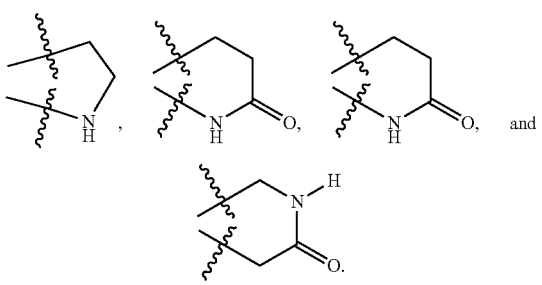
In another embodiment $X^9$-$L^3$-$X^{10}$ or $X^{10}$-$L^3$-$X^9$ is selected from:
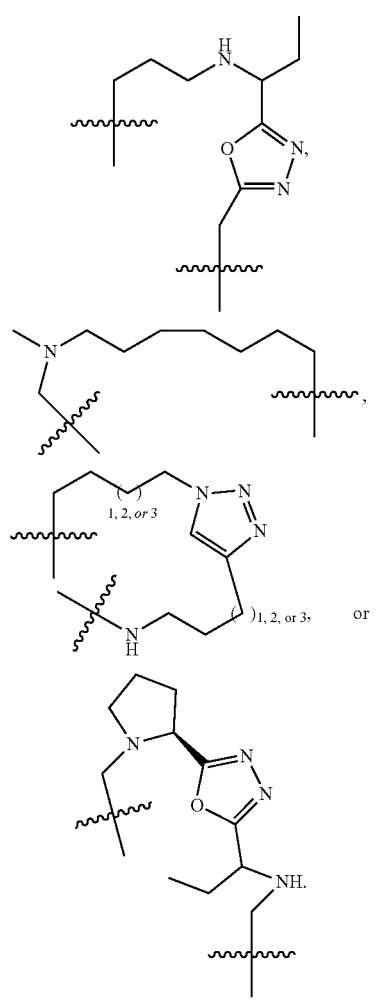
In one embodiment $R^{32}$ is selected from:
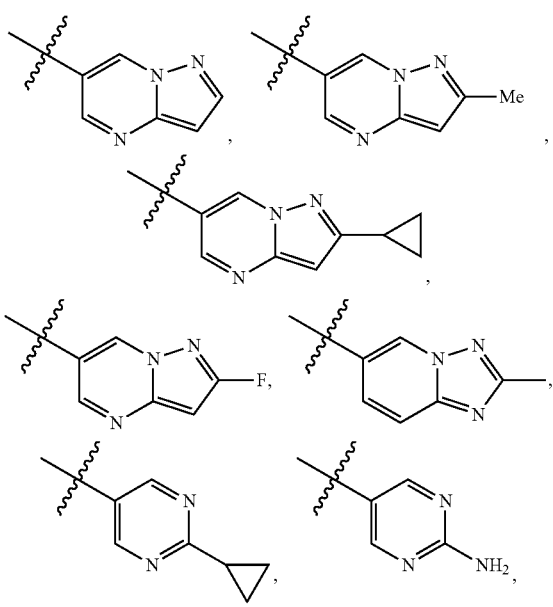

361

-continued

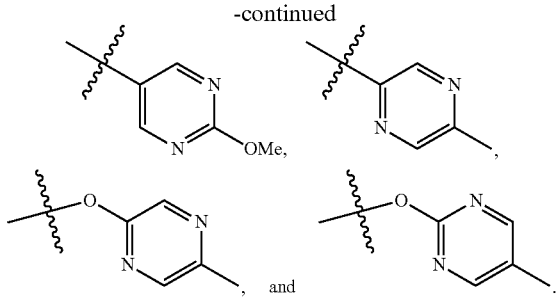

In an alternative embodiment R³² is selected from:

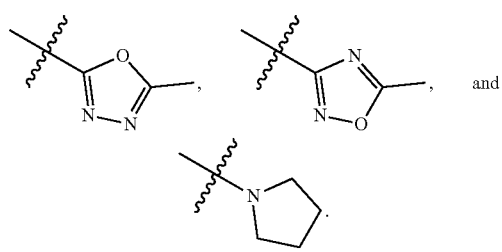

In an alternative embodiment R¹¹, R¹², R¹³, R¹⁴, or R¹⁵ is -alkyl-R³² or —O-alkyl-R³².

In an alternative embodiment R¹¹, R¹², R¹³, R¹⁴, or R¹⁵ is

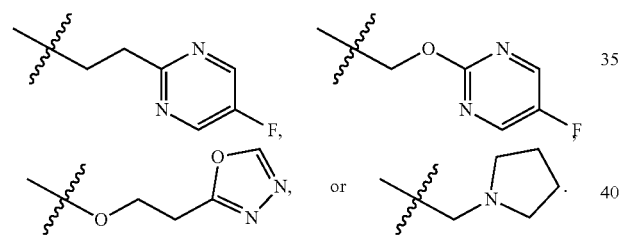

In one embodiment R¹¹, R¹², R¹³, R¹⁴, or R¹⁵ is

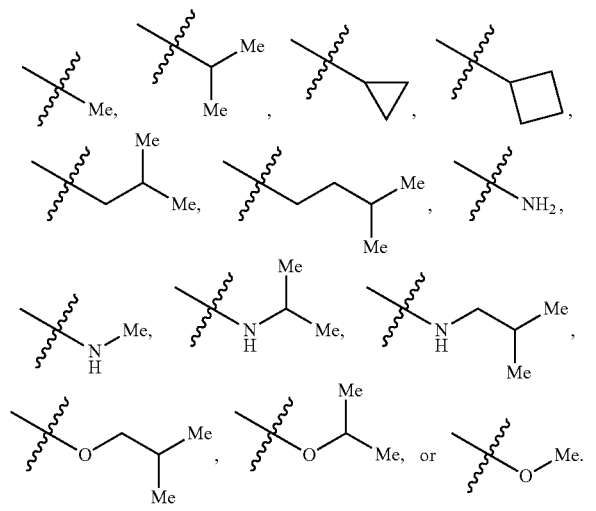

362

In one embodiment a compound of Formula:

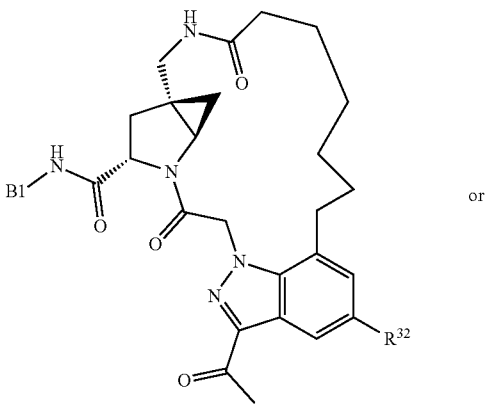

or

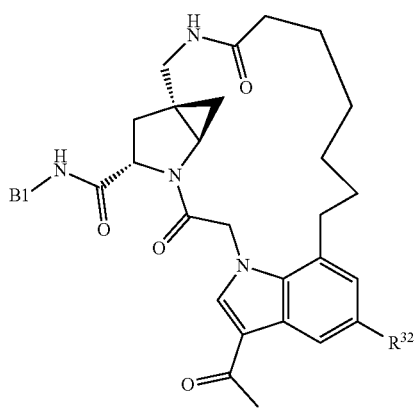

is provided, wherein B1 and R³² are as defined above.

In another embodiment a compound of Formula:

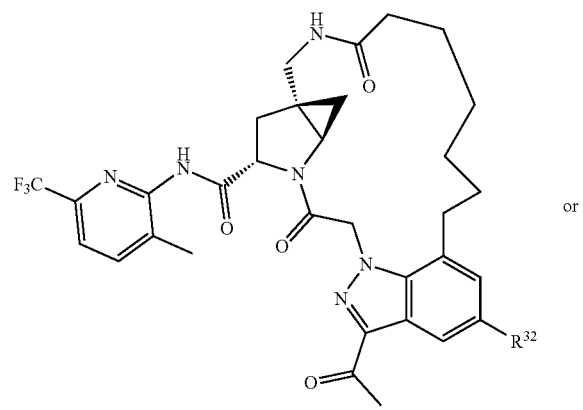

or

363
-continued
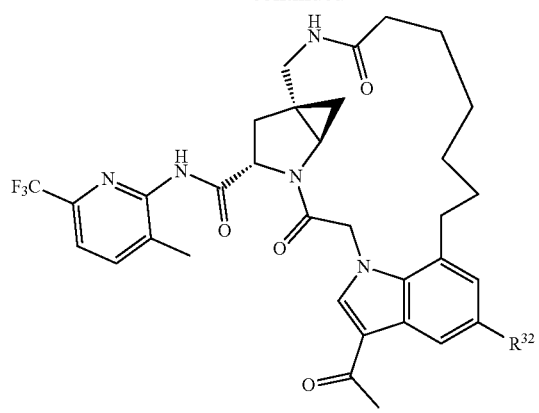
is provided, wherein R³² is as defined above.
In another embodiment a compound of Formula:
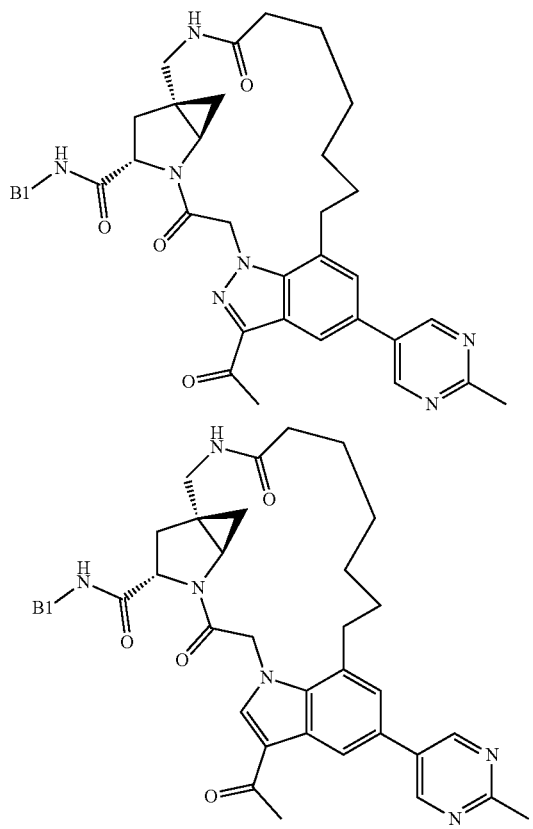
is provided, wherein B1 is as defined above.
In another embodiment, B1 is selected from:
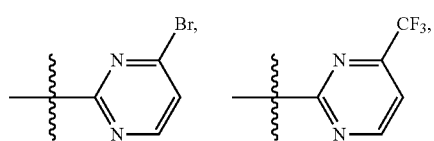
364
-continued
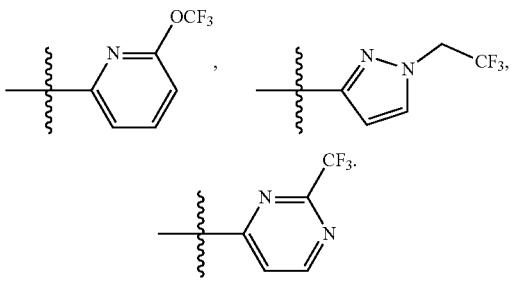
In another embodiment, provided is a compound of formula:

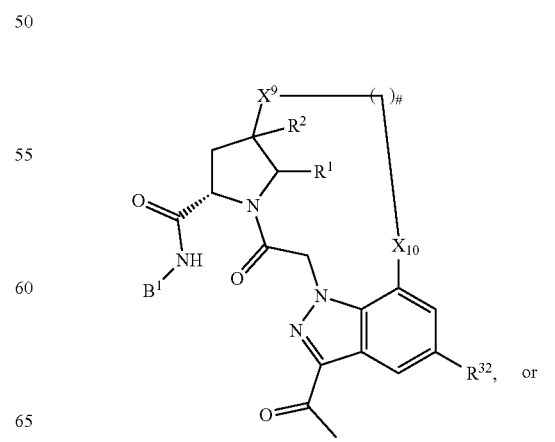

365
-continued
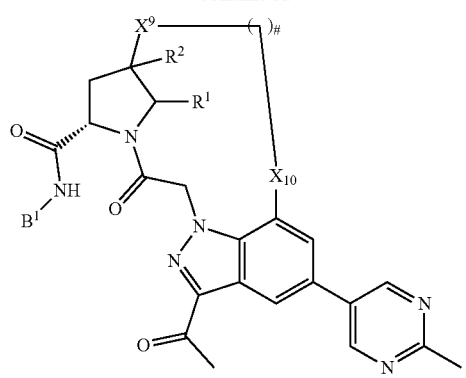
or a pharmaceutically acceptable salt, isotopic analog, prodrug, or isolated isomer thereof; wherein # is 3, 4, 5, 6, 7, 8, 9, or 10 and all other variables are as defined herein.
Non-limiting examples of compounds Formula II include:
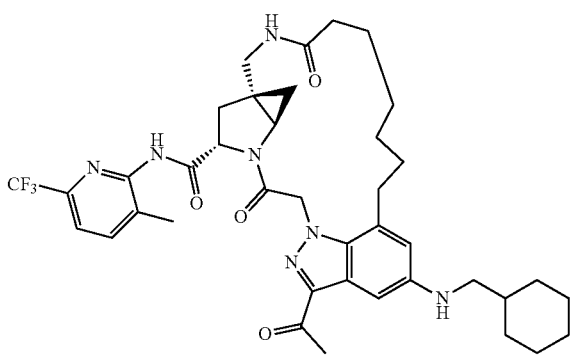
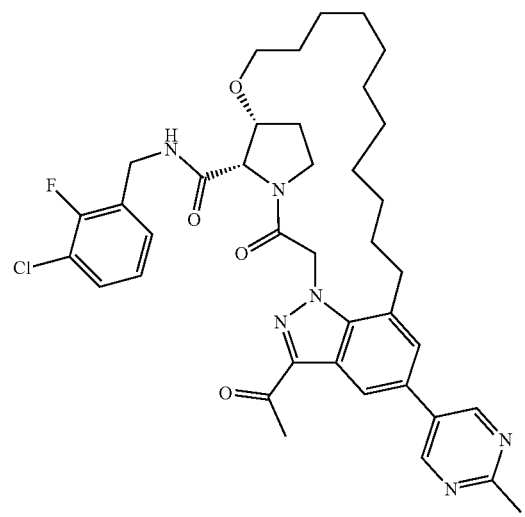
366
-continued
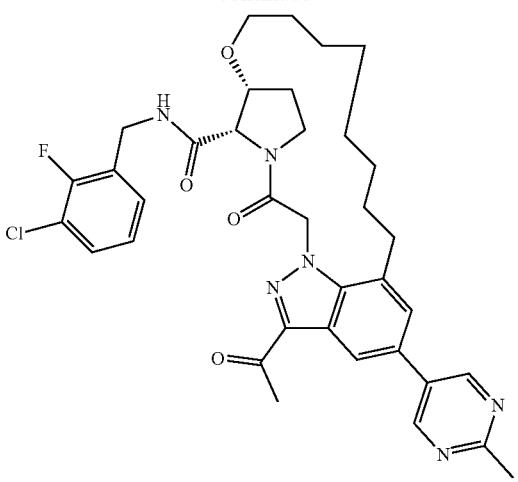
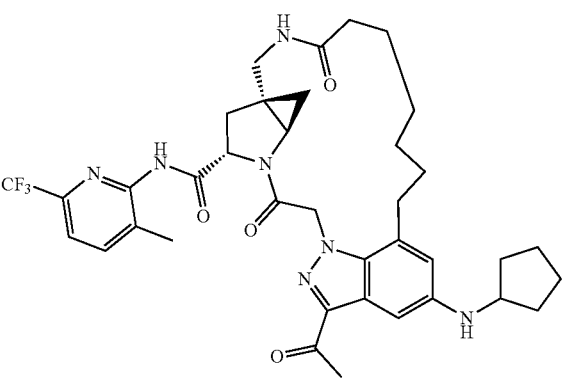
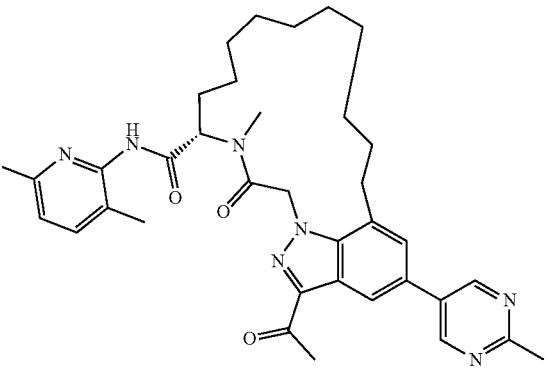
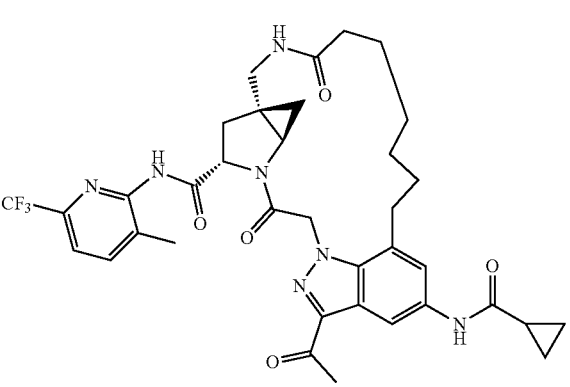

367
-continued
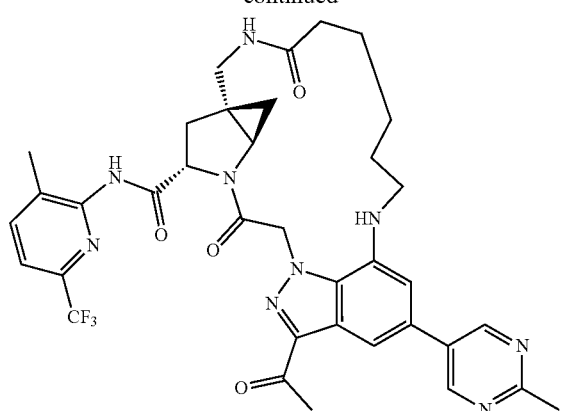
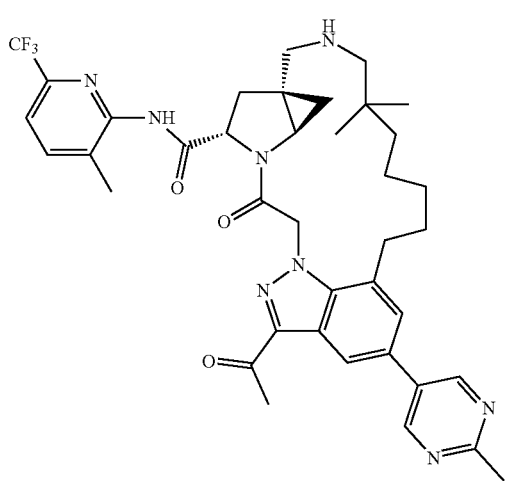
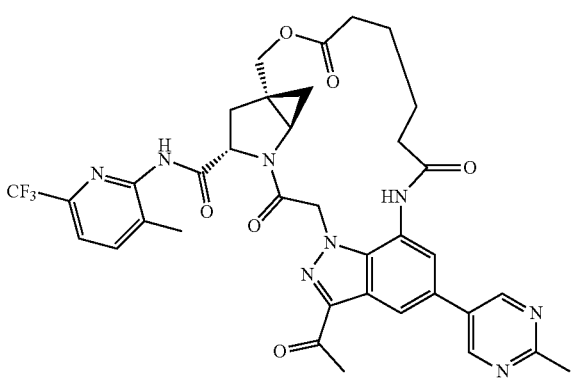
368
-continued
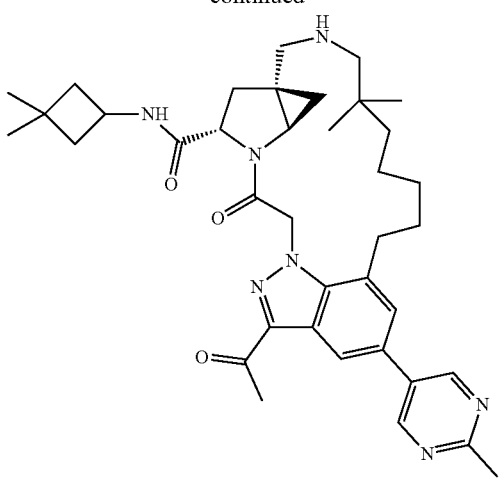
In certain embodiments, the compound of Formula II is selected from
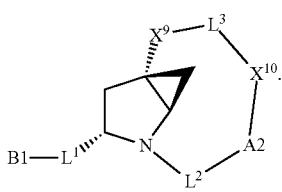
In certain embodiments, the compound of Formula II is selected from
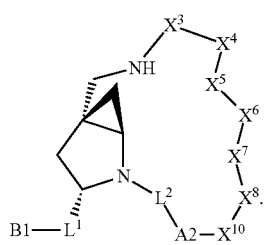
In certain embodiments, the compound of Formula II is selected from

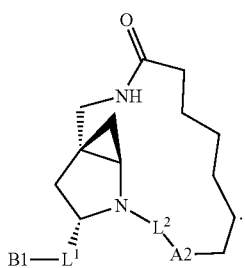
In certain embodiments, the compound of Formula II is selected from
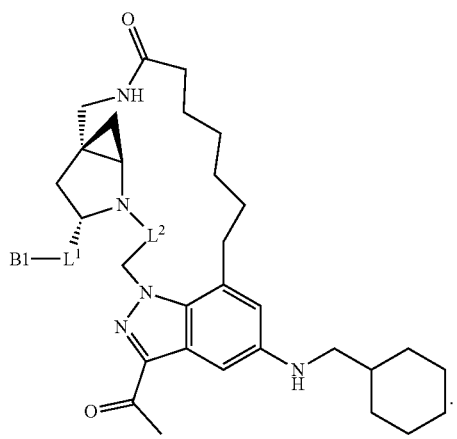
In certain embodiments, the compound of Formula II is selected from
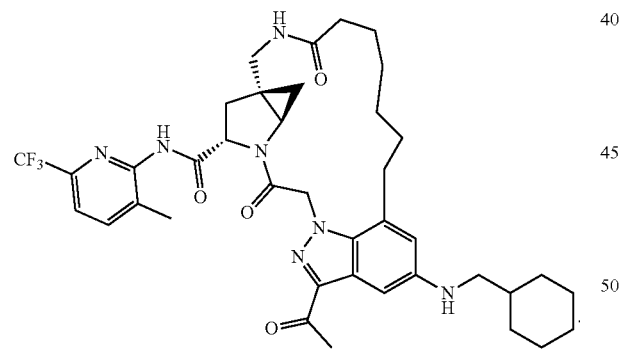
In certain embodiments, C2 is selected from
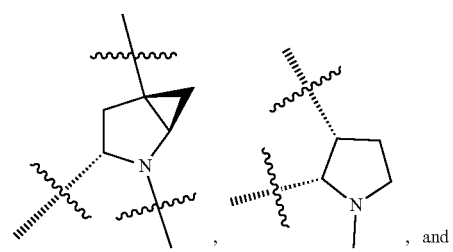
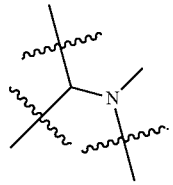
In certain embodiments, B1 is selected from
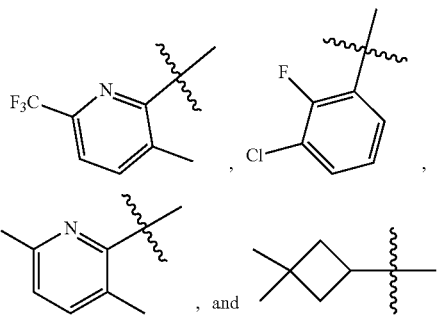
, and
In certain embodiments, A2 is selected from
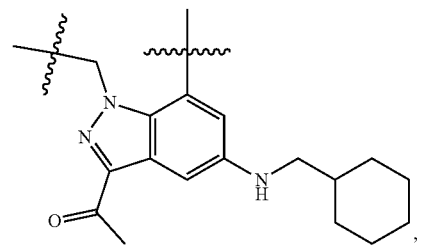
,
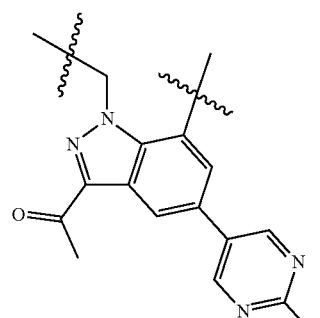
,
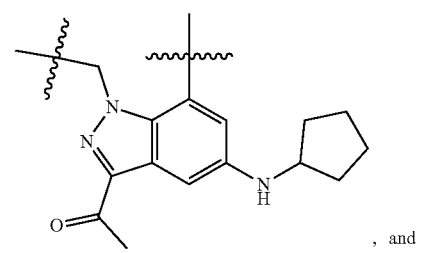
, and

371

-continued

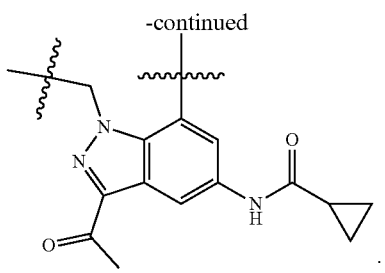

Non-limiting examples of compounds of Formula III include:

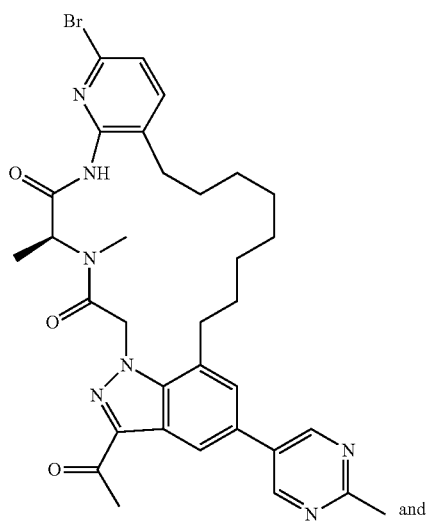
and

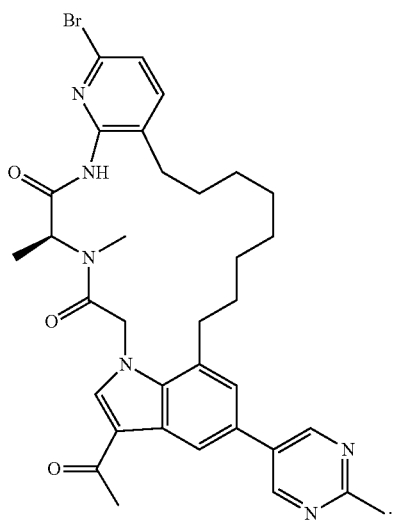

In certain embodiments, the compound of Formula III is selected from:

372

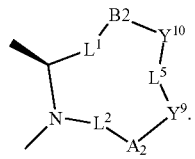

In certain embodiments, the compound of Formula III is selected from:

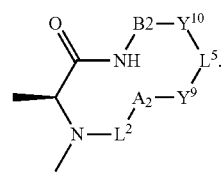

In certain embodiments, the compound of Formula III is selected from:

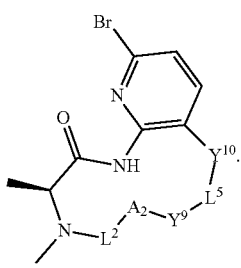

In certain embodiments, the compound of Formula III is selected from:

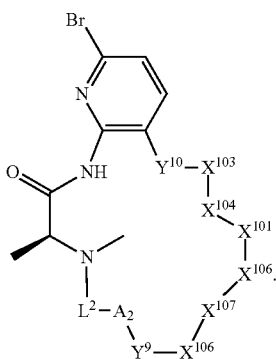

In certain embodiments, the compound of Formula III is selected from:

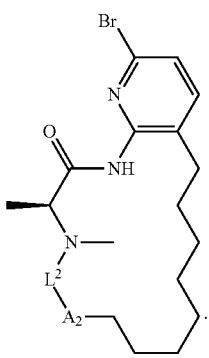

In certain embodiments, the compound of Formula III is selected from:

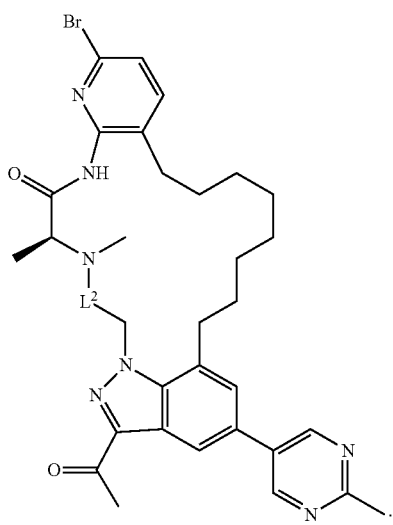

In certain embodiments, the compound of Formula III is selected from:

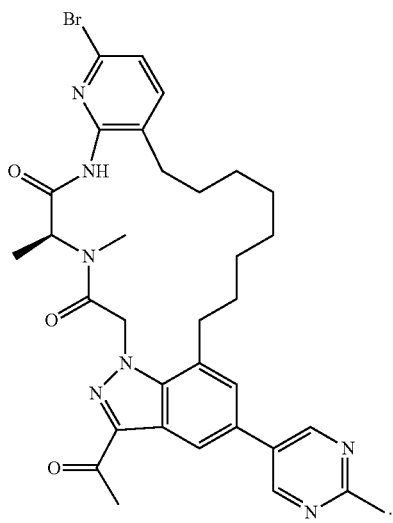 [SMILES: CC(=O)c1nn2c3c(cc(-c4cnc(C)nc4)cc13)CCCCCCCCc1ccc(Br)nc1NC(=O)[C@H](C)N(C)C(=O)C2]

In certain embodiments, C1 is

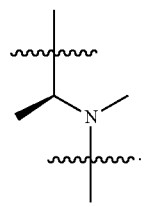 [SMILES: *[C@H](C)N(*)C]

In certain embodiments, B2 is

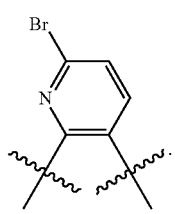 [SMILES: *c1ccc(Br)nc1*]

In certain embodiments, A2 is

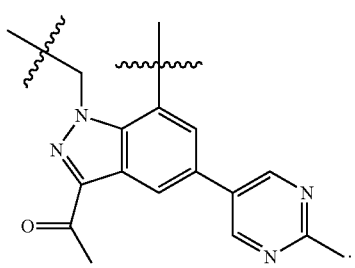 [SMILES: *Cn1nc(C(C)=O)c2cc(-c3cnc(C)nc3)cc(*)c21]

Embodiments of "Alkyl"

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In an alternative embodiment the "alkyl" group is optionally substituted.

In an alternative embodiment the "alkenyl" group is optionally substituted.

In an alternative embodiment the "alkynyl" group is optionally substituted.

Embodiments of "Haloalkyl"

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.

In one embodiment "haloalkyl" has one carbon and one halogen.

In one embodiment "haloalkyl" has one carbon and two halogens.

In one embodiment "haloalkyl" has one carbon and three halogens.

In one embodiment "haloalkyl" has two carbons.
In one embodiment "haloalkyl" has three carbons.
In one embodiment "haloalkyl" has four carbons.
In one embodiment "haloalkyl" has five carbons.
In one embodiment "haloalkyl" has six carbons.
Non-limiting examples of "haloalkyl" include:

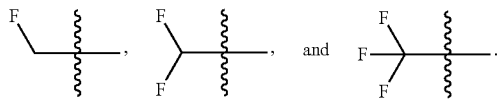

Additional non-limiting examples of "haloalkyl" include:

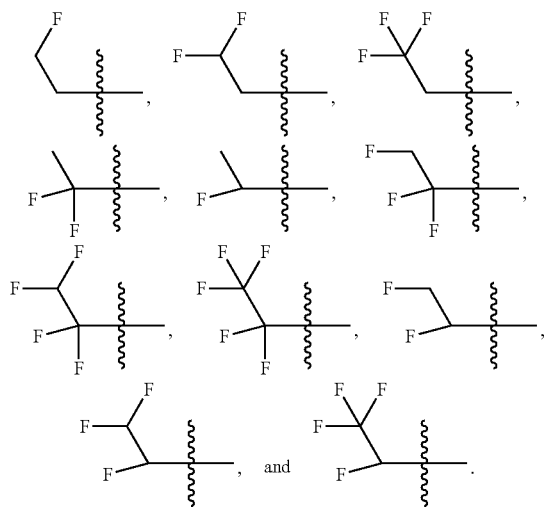

Additional non-limiting examples of "haloalkyl" include:

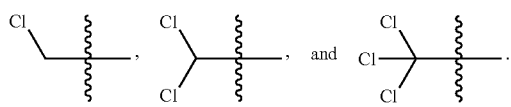

Additional non-limiting examples of "haloalkyl" include:

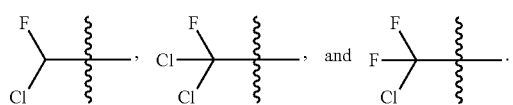

Embodiments of "Aryl"

In one embodiment "aryl" is a 6 carbon aromatic group (phenyl)

In one embodiment "aryl" is a 10 carbon aromatic group (napthyl)

In one embodiment "aryl" is "substituted aryl".

In an alternative embodiment the "aryl" group is optionally substituted.

Embodiments of "Heteroaryl"

In one embodiment "heteroaryl" is a 5 membered aromatic group containing 1, 2, or 3, nitrogen atoms.

Non-limiting examples of 5 membered "heteroaryl" groups include pyrrole, furan, thiophene, pyrazole, imidazole, triazole, isoxazole, oxazole, oxadiazole, oxatriazole, isothiazole, thiazole, thiadiazole, and thiatriazole.

Additional non-limiting examples of 5 membered "heteroaryl" groups include:

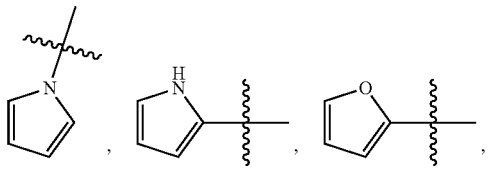
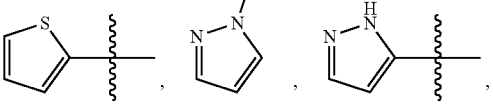
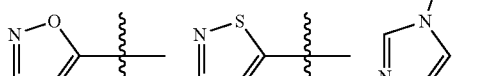
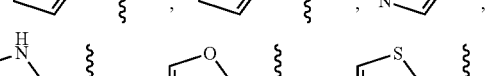
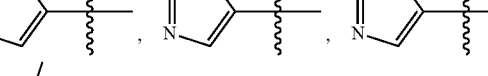
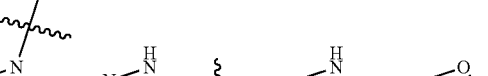
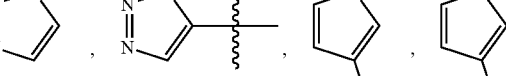
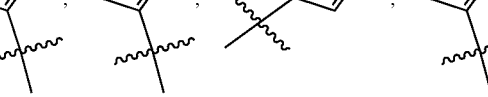

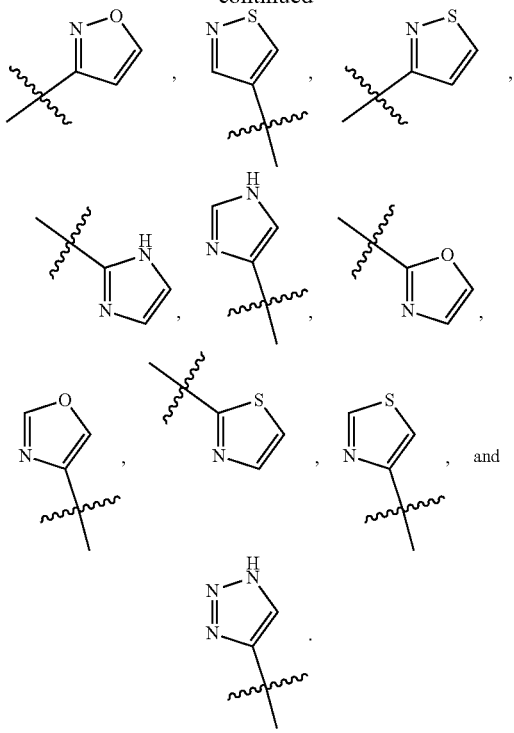

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

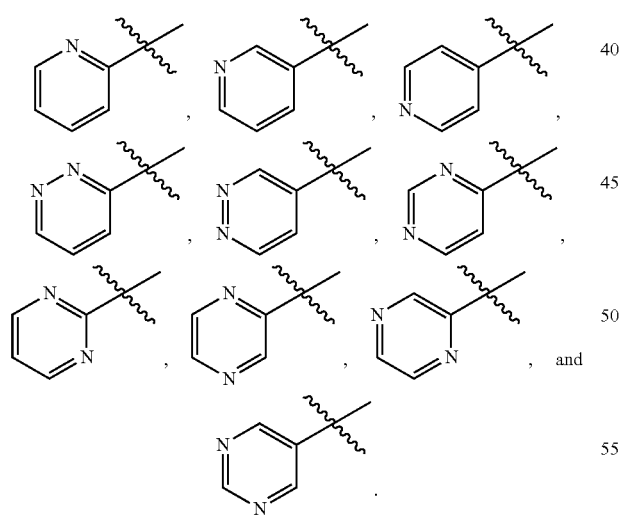

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

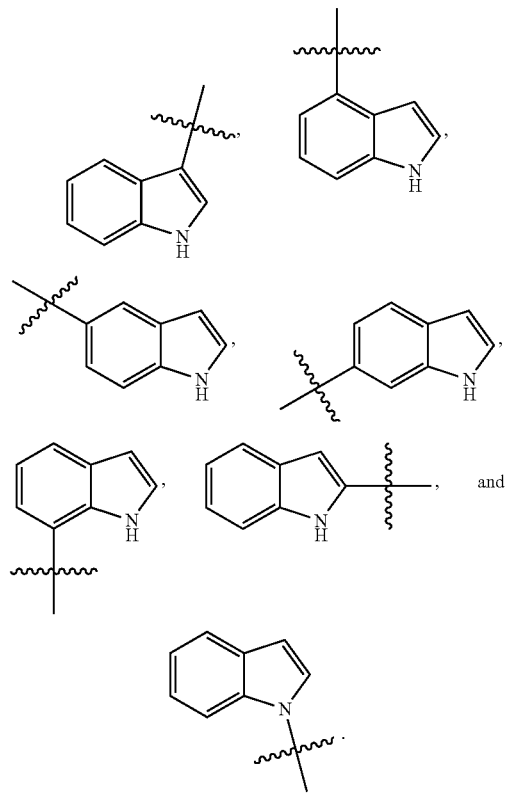

Additional non-limiting examples of "heteroaryl" groups that are bicyclic include:

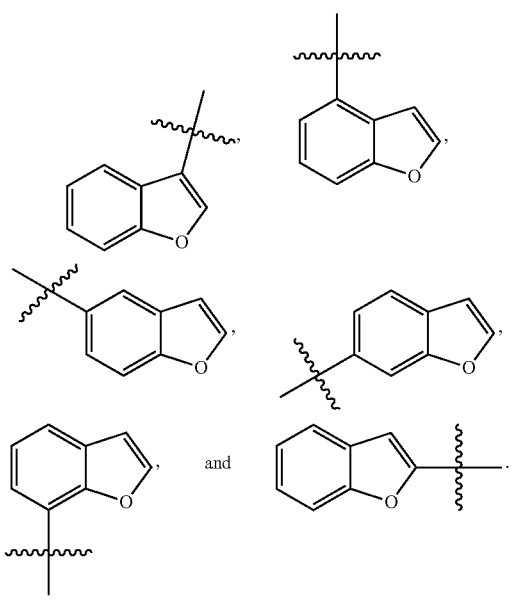

Additional non-limiting examples of "heteroaryl" groups that are bicyclic include:

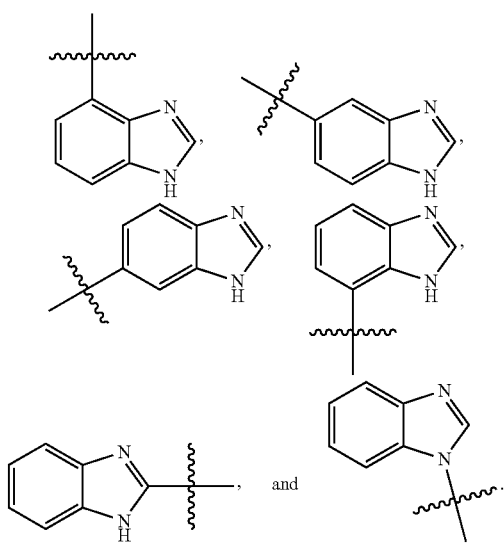

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

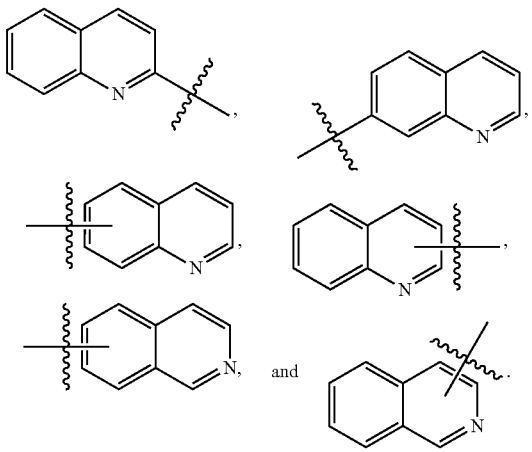

In an alternative embodiment heteroaryl is tetrazole.
In an alternative embodiment the "heteroaryl" group is optionally substituted.

Embodiments of "Cycloalkyl"

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.
In one embodiment "cycloalkyl" has four carbons.
In one embodiment "cycloalkyl" has five carbons.
In one embodiment "cycloalkyl" has six carbons.
In one embodiment "cycloalkyl" has seven carbons.
In one embodiment "cycloalkyl" has eight carbons.
In one embodiment "cycloalkyl" has nine carbons.
In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

In an alternative embodiment the "cycloalkyl" group is optionally substituted.

Embodiments of "Heterocycle"

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Non-limiting examples of "heterocycle" also include:

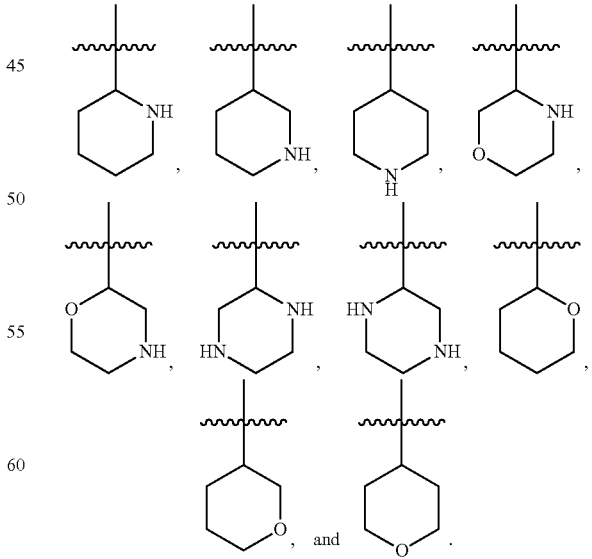

Additional non-limiting examples of "heterocycle" include:

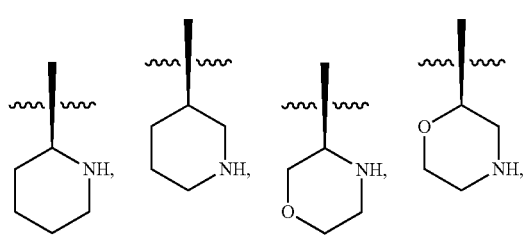

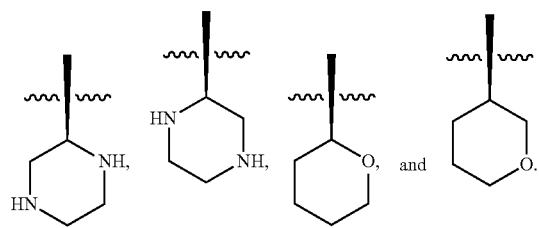

Additional non-limiting examples of "heterocycle" include:

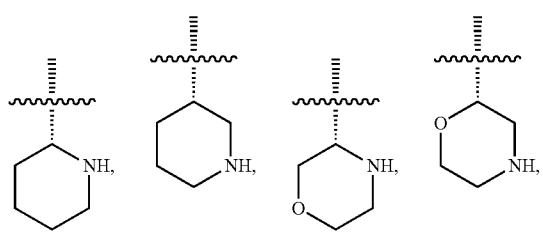

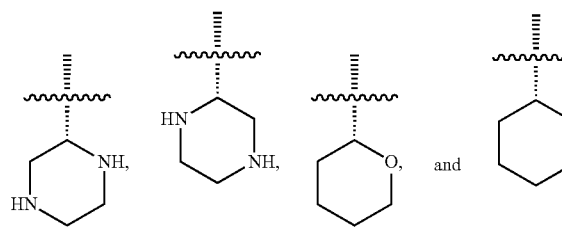

Non-limiting examples of "heterocycle" also include:

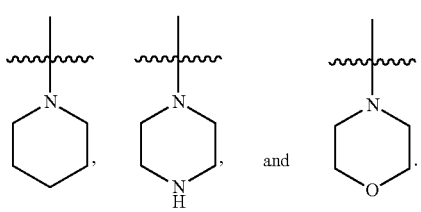

Non-limiting examples of "heterocycle" also include:

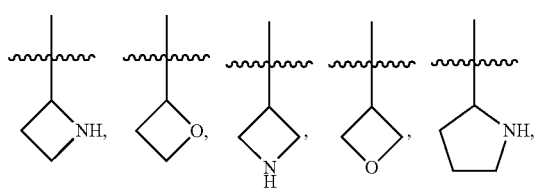

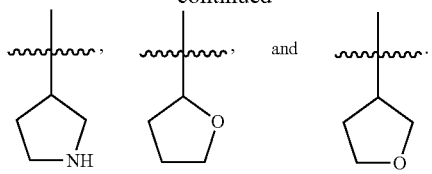

Additional non-limiting examples of "heterocycle" include:

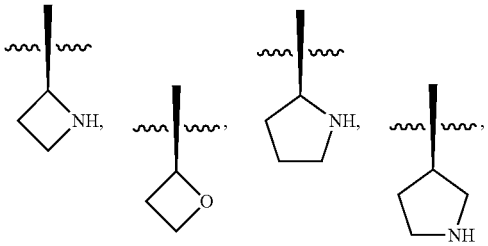

Additional non-limiting examples of "heterocycle" include:

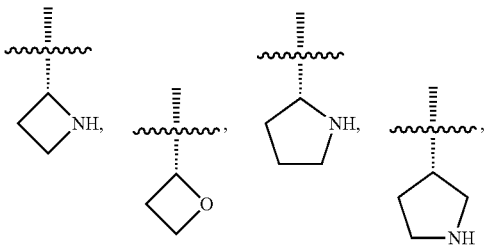

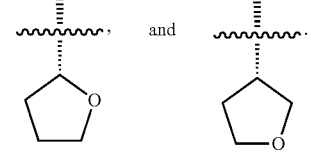

In an alternative embodiment the "heterocycle" group is optional substituted.

Additional Embodiments of Formula I, Formula II, Formula III, Formula IV, Formula V, Formula VI, Formula VII, Formula VIII and Formula IX Embodiments of $R^{201}$ In one aspect of the present invention a compound of: Formula I, Formula II, Formula III, Formula IV, Formula V, Formula VI, Formula VII, Formula VIII, or Formula IX is provided wherein a single C—H bond is replaced with a $R^{201}$ group, wherein:

$R^{201}$ is selected from $C_0$-$C_3$alkyl-$NR^9R^{15}$, $C_0$-$C_3$alkyl-$OR^{15}$, $C_0$-$C_3$alkyl-$SR^{15}$; $C_0$-$C_3$alkyl-heterocycle, -aliphatic-OR$^{15}$, -aliphatic-SR$^{15}$, and -aliphatic-NR$^9$R$^{15}$; and wherein R$^{201}$ can be optionally substituted with R$^{301}$, which can be directly linked to R$^{201}$ or can be linked to R$^{201}$ through an amino, hydroxyl, thio, carboxylic acid, phosphate, phosphonate, or sulfonate linkage;

each R$^9$ and R$^{10}$ are independently selected from hydrogen and C$_1$-C$_4$alkyl;

each R$^{11}$ is independently selected from C$_1$-C$_3$alkyl, —OR$^9$, and —NR$^9$R$^{10}$;

each R$^{12}$ is independently selected from hydrogen, C$_1$-C$_3$alkyl, and —C(O)R$^{11}$;

each R$^{14}$ is independently selected from C$_1$-C$_4$alkyl, C$_2$-C$_4$alkenyl, C$_2$-C$_4$alkynyl, —OR$^9$, and —NR$^9$R$^{10}$;

R$^{15}$ is selected from hydrogen, C$_1$-C$_4$alkyl, C$_1$-C$_4$haloalkyl, C$_2$-C$_4$alkenyl, C$_2$-C$_4$alkynyl, —C(O)R$^{14}$, —S(O)R$^{14}$, —S(O)$_2$R$^{14}$, heterocycle, aryl, heteroaryl, cyano, and —C$_1$-C$_3$alkyl-aryl; and wherein the R$^{201}$ group is optionally substituted with 1, 2, or 3 groups independently selected from halogen, C$_1$-C$_3$alkyl, C$_1$-C$_3$haloalkyl, —COOH, cyano, C$_2$-C$_6$alkanoyl, C$_1$-C$_6$alkoxy, —C$_0$-C$_4$alkylNR$^9$R$^{12}$, —C$_0$-C$_4$alkylOR$^{12}$, C$_1$-C$_6$haloalkyl, —SO$_2$R$^{15}$, and C$_1$-C$_6$haloalkoxy;

In one embodiment R$^{201}$ is selected from —(CH$_2$)$_{1-3}$—O-heterocycle, —(CH$_2$)$_{1-3}$—NH-heterocycle, or —(CH$_2$)$_{1-3}$—NR$^9$-heterocycle.

In one embodiment R$^{201}$ is selected from —(CH$_2$)$_{1-3}$—NR$^9$R$^{10}$, —(CH$_2$)$_{1-3}$—OR$^9$, or —(CH$_2$)$_{1-3}$-heterocycle.

In one embodiment R$^{201}$ is selected from —CH$_2$—O-heterocycle, —CH$_2$—NH-heterocycle, or —CH$_2$—NR$^9$-heterocycle.

In one embodiment R$^{201}$ is selected from —CH$_2$—NR$^9$R$^{10}$, —CH$_2$—OR$^9$, or —CH$_2$-heterocycle.

In one embodiment R$^{201}$ is selected from —(CH$_2$)$_{1-3}$—NH$_2$, —(CH$_2$)$_{1-3}$—OH, or —(CH$_2$)$_{1-3}$—OC$_1$-C$_6$alkyl.

In one embodiment (CH$_2$)$_{1-3}$ is —CH$_2$—

In one embodiment (CH$_2$)$_{1-3}$ is —CH$_2$CH$_2$—.

In one embodiment (CH$_2$)$_{1-3}$ is —CH$_2$CH$_2$CH$_2$—.

In the below embodiments m is 1 or 2.

In one embodiment R$^{201}$ is selected from:

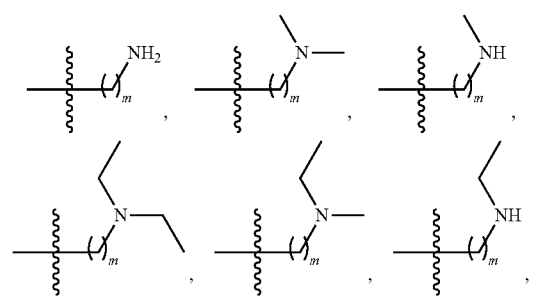

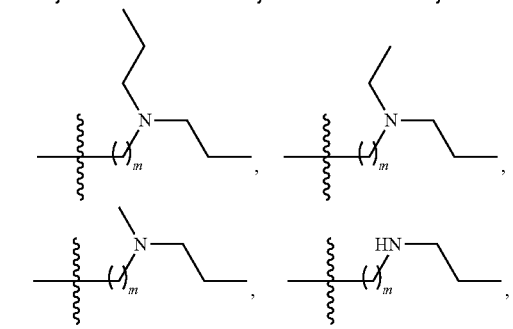

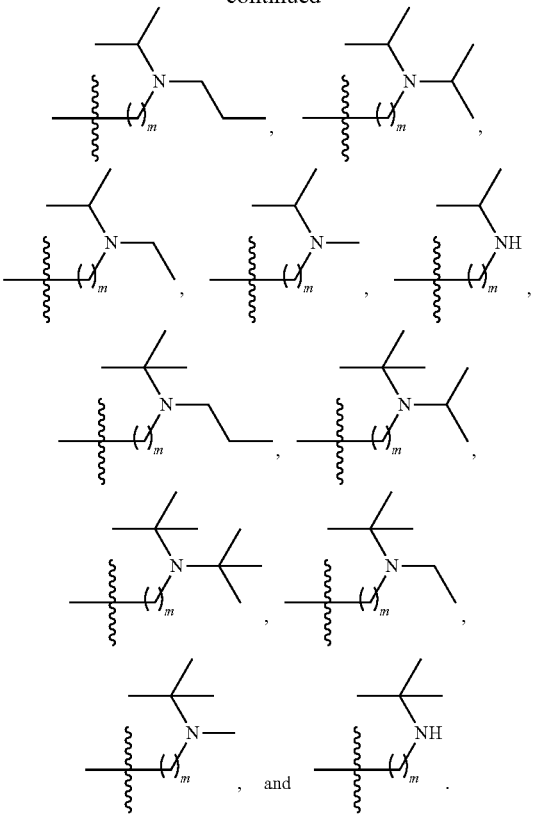

In one embodiment R$^{201}$ is selected from:

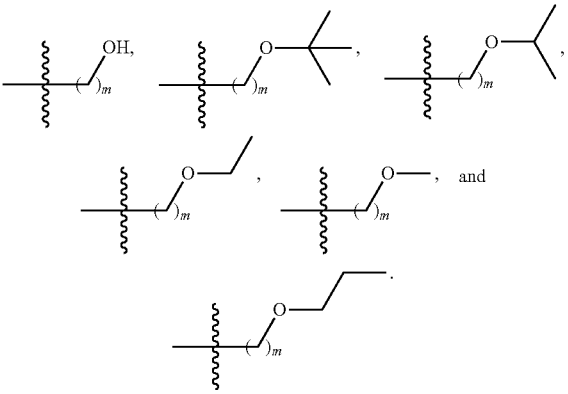

In one embodiment R$^{201}$ is selected from:

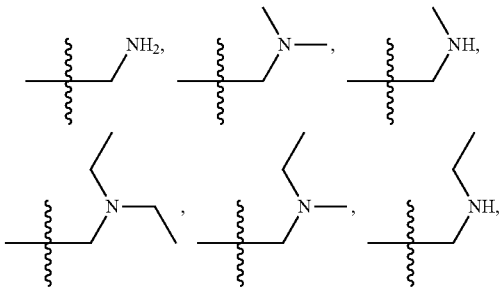

-continued
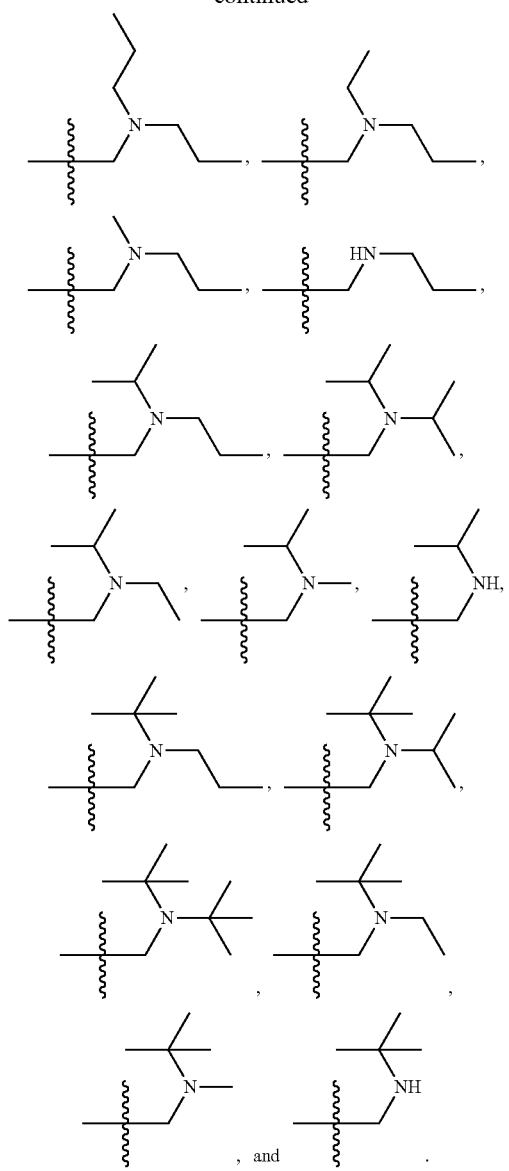
In one embodiment R²⁰¹ is selected from:
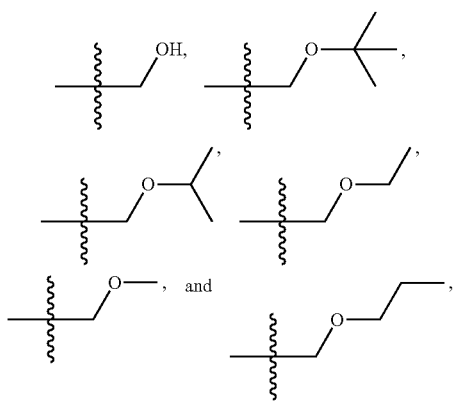
In one embodiment R²⁰¹ is selected from:
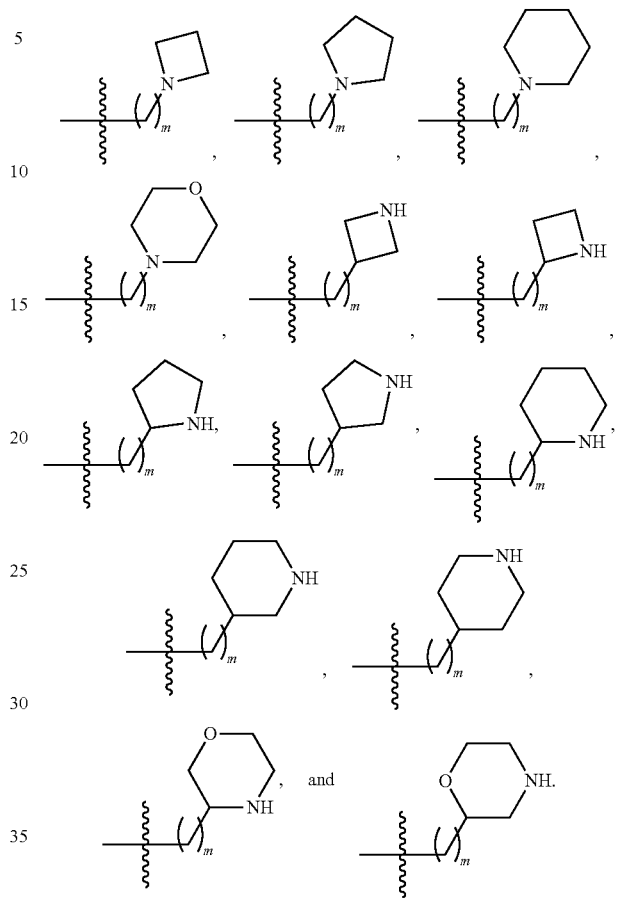
In one embodiment R²⁰¹ is selected from:
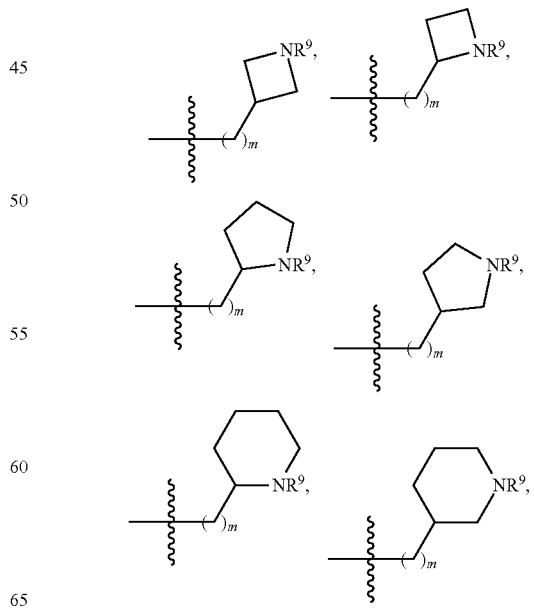

-continued
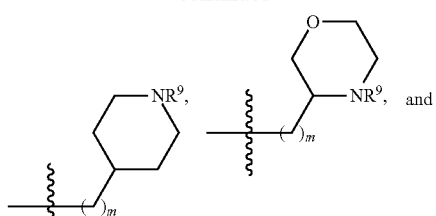
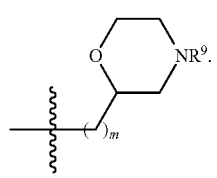
In one embodiment R²⁰¹ is selected from:
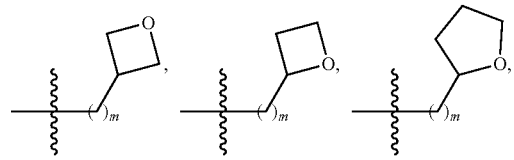
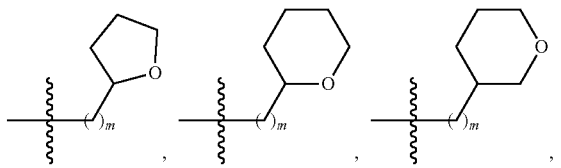
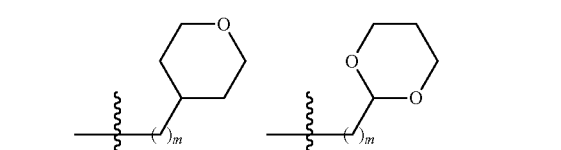
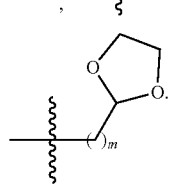
In one embodiment R²⁰¹ is selected from:
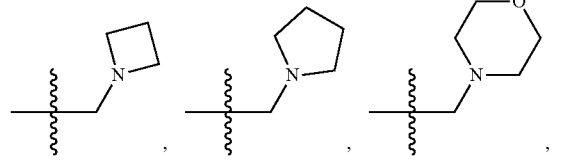
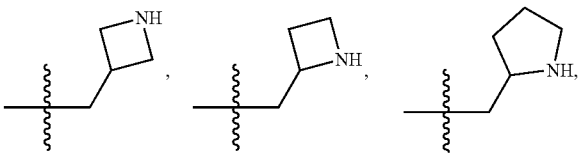
-continued
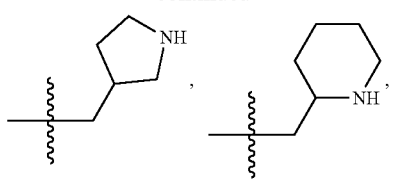
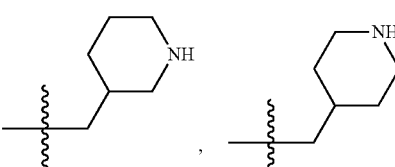
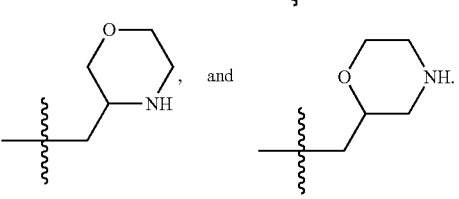
In one embodiment R²⁰¹ is selected from:
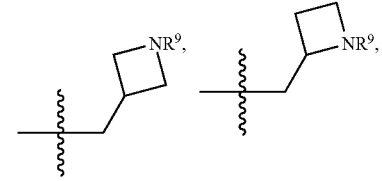
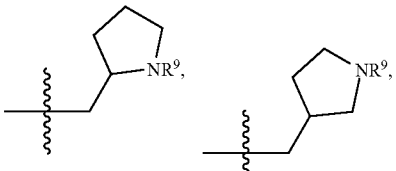
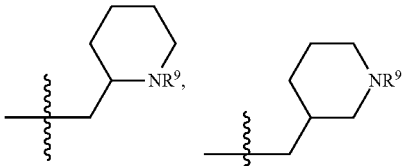
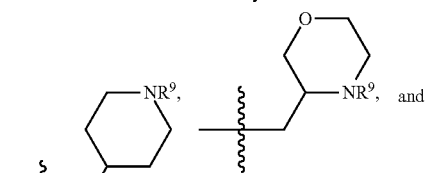
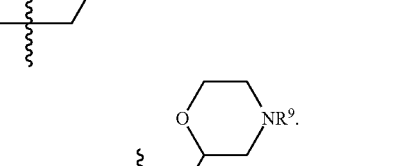

In one embodiment R²⁰¹ is selected from:
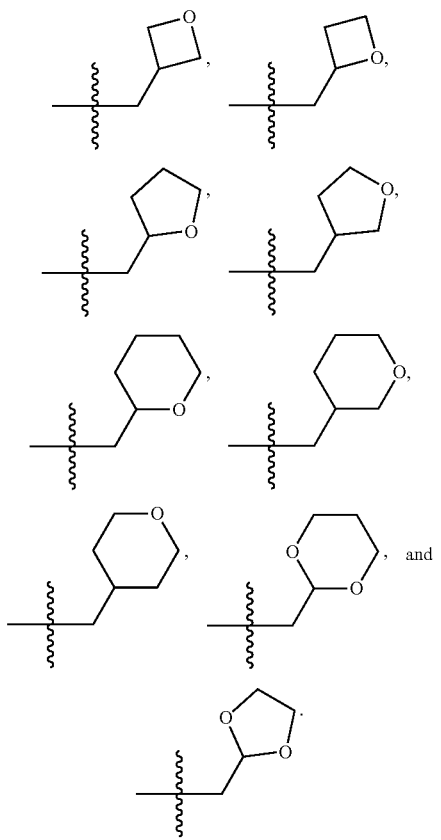
In one embodiment R²⁰¹ is selected from:
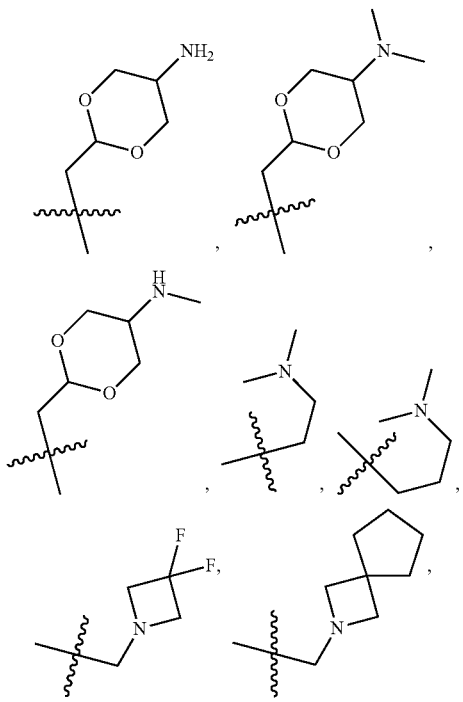
-continued
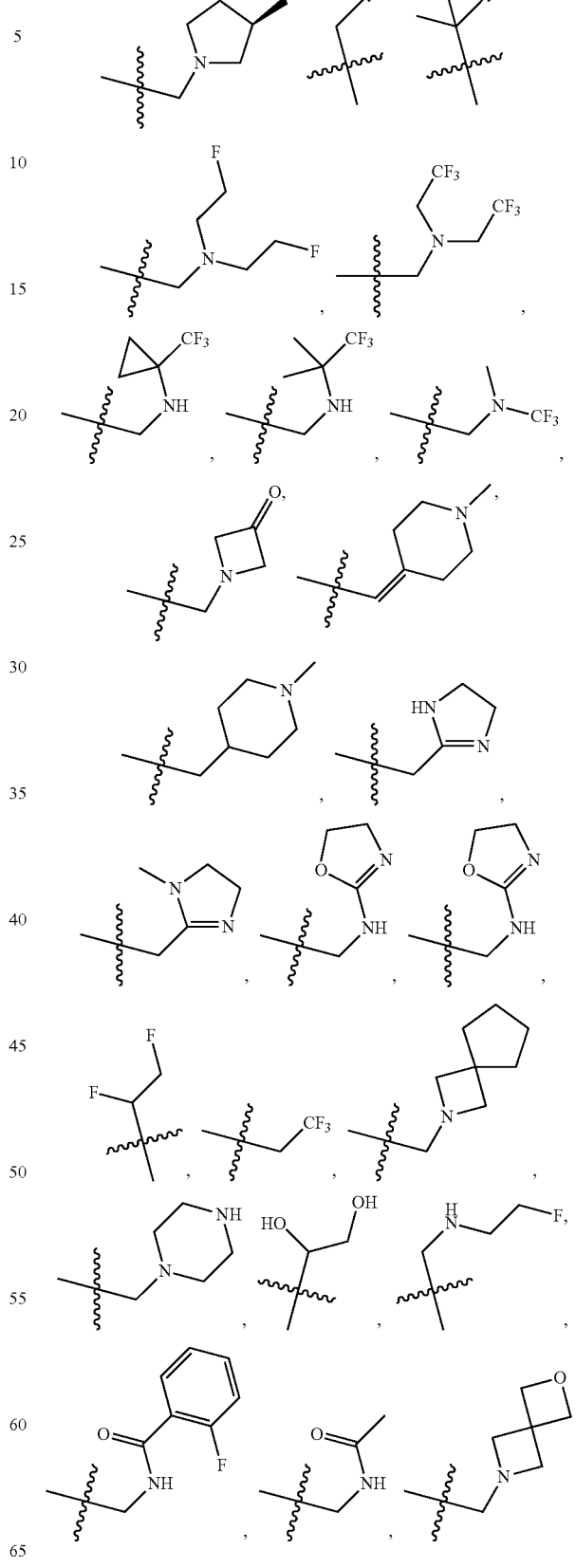

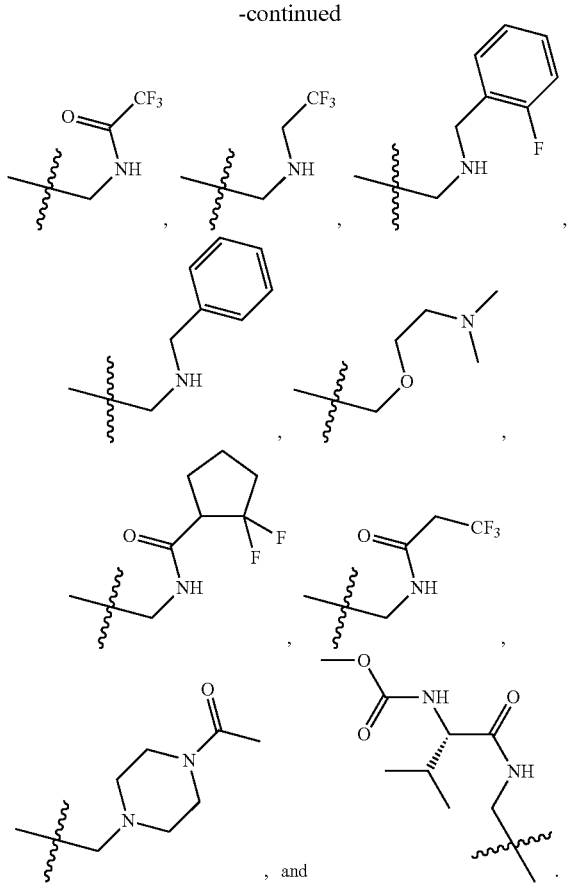

Embodiments of $R^{301}$

In one aspect of the invention, an $R^{301}$ embodiment of an active compound of the invention is provided that exhibits extended half-life or other advantageous pharmacokinetic properties, which may be achieved by albumin stabilization in vivo. In certain embodiments, the acylated analog can include several linking moieties in linear, branched or cyclic manner. In certain embodiments, either one or a series of amino acids is used as a linker to a terminal fatty acid. In one non-limiting example a non-natural amino acid such as one described below, for example 8-amino-3,6-dioxaoctanoic acid (one or several in sequence) is covalently bound to the selected complement D inhibitor of the present invention through a functional group such as a carboxylic acid, sulfonyl, hydroxyl or amino group. See generally Lau, et al., "Discovery of the Once-Weekly Glucagon-Like Peptide-1 (GLP-1) Analogue Semiglutide", *J. Med. Chem.*, 2015, 58, 7370-7380. In this embodiment, the 8-amino-3,6-dioxaoctanoic acid or similar molecule is covalently linked to an aliphatic acid, including but not limited to a $C_{16}$, $C_{18}$, $C_{20}$ aliphatic acid, or a dicarboxylic acid, including but not limited to a $C_8$, $C_{10}$, $C_{12}$, $C_{14}$, $C_{16}$, $C_{18}$ or $C_{20}$ diacid. One or more amino acids can also be used in the selected configuration to add length or functionality. More generally, nonlimiting embodiments include the use of a divalent linker moiety such as a dicarboxylic acid, amino acid, diamine, hydroxycarboxylic acid, hydroxyamine, di-hydroxy compound, or other compound that has at least two functional groups that can link the parent molecule with another linking moiety, and which may be albumin stabilized in vivo. In some embodiments, 2, 3, 4 or 5 linking moieties are covalently bound in sequence, branched or cyclic fashion to the parent compound. In some embodiments, an $R^{301}$ acyl group is located in a position of the active compound that does not significantly adversely affect the complement D inhibition of the molecule, for example, as (i) a substituent on the $R^{32}$ group or (ii) a substituent on a C-ring, such as proline, or as a substituent on a substituent on the C-ring, such as on an $R^1$, $R^2$ or $R^3$ substituent, including for example, on a bridged moiety such as a fused cyclopropyl on the proline ring. In certain embodiments, the acyl group has an aliphatic or heteroaliphatic carbon range of $C_{12}$, $C_{14}$, $C_{16}$, $C_{18}$, $C_{20}$, $C_{22}$ or $C_{24}$.

In one aspect of the present invention a compound of Formula I, Formula II, Formula III, Formula IV, Formula V, Formula VI, Formula VII, Formula VIII, or Formula IX is provided wherein one N—H or O—H bond is replaced with an $R^{301}$ group; wherein $R^{301}$ is selected from the following:

i. The residue of a fatty acid. Examples are short chain fatty acids with 3, 4, or 5 aliphatic carbons, medium-chain fatty acids with aliphatic tails of 6, 7, 8, 9, 10, 11 or 12 carbons, long chain fatty acids, which have aliphatic tails of 13, 14, 15, 16, 17, 18, 19, 20, 21 or 22 carbons, or a very long fatty acid, which has 22, 23, 24, 25, 26 27, or 28 or more aliphatic carbons. The aliphatic chain can be saturated, mono-unsaturated, di-unsaturated, tri-unsaturated, polyunsaturated, or alkynyl. Unsaturated fatty acids can be used in a cis or trans configuration, and include, but are not limited to oleic acid, ω6 fatty acid such as linoleic acid, ω3 fatty acid such as α-linolenic acid, docosahexaenoic acid, stearidonic acid, eicosapentaenoic acid, docosapentaenoic acid, eicosatetraenoic acid, myristoleic acid, palmitoleic acid, sapienic acid, elaidic acid, vaccenic acid, gadoleic acid, eicosenoic acid, nervonic acid, eicosadienoic acid, docasadienoic acid, linolenic acid, t-linolenic acid, pinolenic acid, eleostetic acid, β-eleostearic acid, mead acid, eicosatrienoic acid, linoleic acid, linoelaidic acid, α-linolenic acid, arachidonic acid, erucic acid and docosahexaenoic acid. Nonlimiting examples of saturated fatty acids that can be used to provide the prodrugs of the present invention are caprylic acid, capric acid, lauric acid, myristic acid, palmitic, stearic acid, arachidic acid, behenic acid, lignoceric acid and cerotic acid.

ii. The residue of an amino acid that is naturally occurring or synthetic, and includes for example, α, β γ or δ amino acids. Naturally occurring amino acids include those found in proteins, e.g., glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In some embodiments, the amino acid is in the L-configuration. Alternatively, the amino acid can be used in the D-configuration or in a mixture of L- and D-. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. Additional amino acids include selenocysteine, pyrrolysine, N-formylmethionine, γ-aminobutyric acid (GABA), δ-aminolevulinic acid, aminobenzoic acid (including 4-aminobenzoic acid), aminoisobutyric acid, dehydroalanine, cystathionine, lanthionine, djenkolic acid, diaminopimelic acid, norvaline, alloisoleucine, t-leucine, α-amino-heptanoic acid, pipecolic acid, α,β-diaminopropionic acid, α,γ-diaminobutyric acid, ornithine, glutamic acid, allothreonine, homocysteine, β-aminobutyric acid, α-aminoisobutyric acid, isovaline, sarcosine, N-ethylglycine, N-propylglycine, N-isopropyl glycine, N-methyl alanine, N-ethyl alanine, N-methyl-β-alanine, isoserine, norleucine, homoserine, O-methyl-homoserine, O-ethyl-homoserine, homonorleucine, carboxyglutamic acid, hydroxyproline, hypusine, pyroglutamic acid, and α-hydroxy-γ-aminobutyric acid.

iii. The residue of a non-naturally occurring amino add with an extended length between the amino group and the carboxylic acid, which can be used either alone or as a linker to another prodrug moiety. Examples include amino acids wherein the amino and carboxylic acid are separated by an aliphatic or heteroaliphatic moiety (nonlimiting example is 8-amino-3,6-dioxaoctanoic acid), for example an alkyl, alkenyl, alkynyl, ethylene glycol, propylene glycol, alkylene glycol, or the like, moiety, e.g., with 3, 4, 5, 6, 7, 8, 9, 10, 11 or 12 or more straight, branched or cyclic atoms or moieties (e.g., alkylene glycol moieties), as appropriate to provide the desired properties. In some embodiments, the amino acid has one or more internal amine, carbonyl, carboxy, oxo, thio, phosphate or phosphonate moieties in the heteroaliphatic chain.

iv. The residue of one or a series of amino acids linked to a terminal fatty acid or to an endcap like hydrogen or alkyl. In one non-limiting example, 8-amino-3,6-dioxaoctanoic acid (one or several in sequence) is covalently bound to the selected complement D inhibitor of the present invention through a functional group such as a carboxylic acid, sulfonyl, hydroxyl or amino group. See generally Lau, et al., "Discovery of the Once-Weekly Glucagon-Like Peptide-1 (GLP-1) Analogue Semiglutide", *J. Med. Chem.*, 2015, 58, 7370-7380. The 8-amino-3,6-dioxaoctanoic acid is covalently linked to an aliphatic acid, including but not limited to a C16, C18, C20 aliphatic acid, or a dicarboxylic acid, including but not limited to a C8, C10, C12, C14, C16, C18 or C20 diacid. One or more amino acids can also be used in the selected configuration to add length or functionality.

In one embodiment $R^{301}$ is selected from:

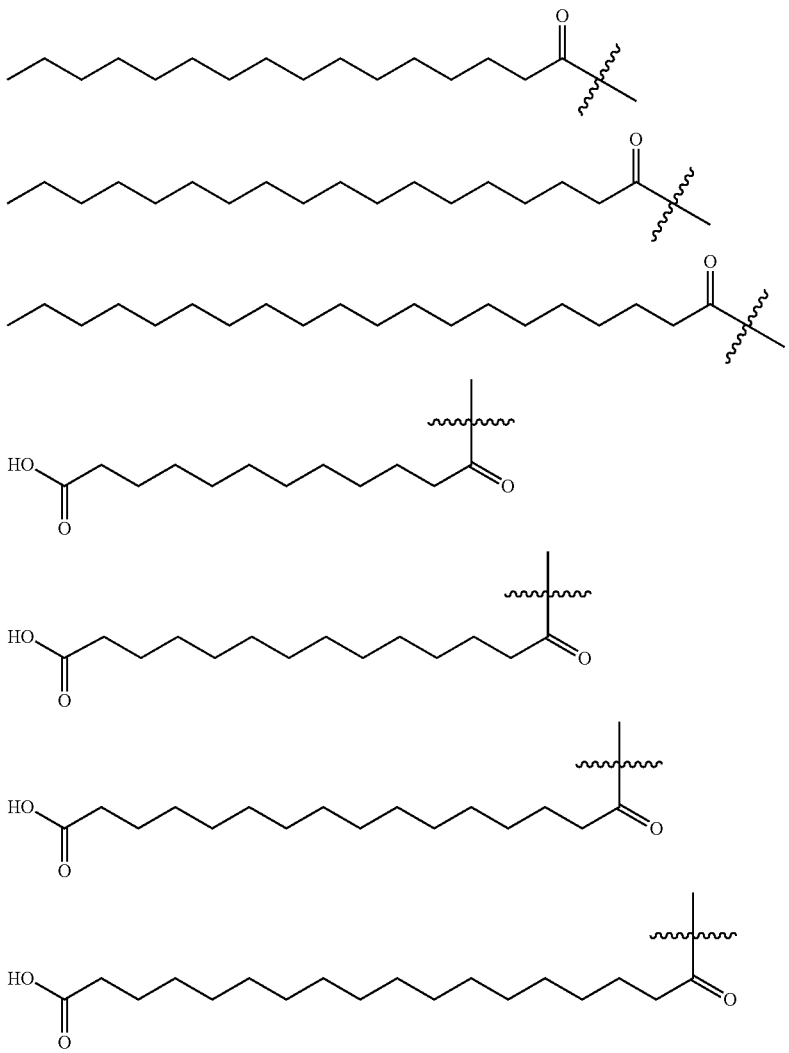

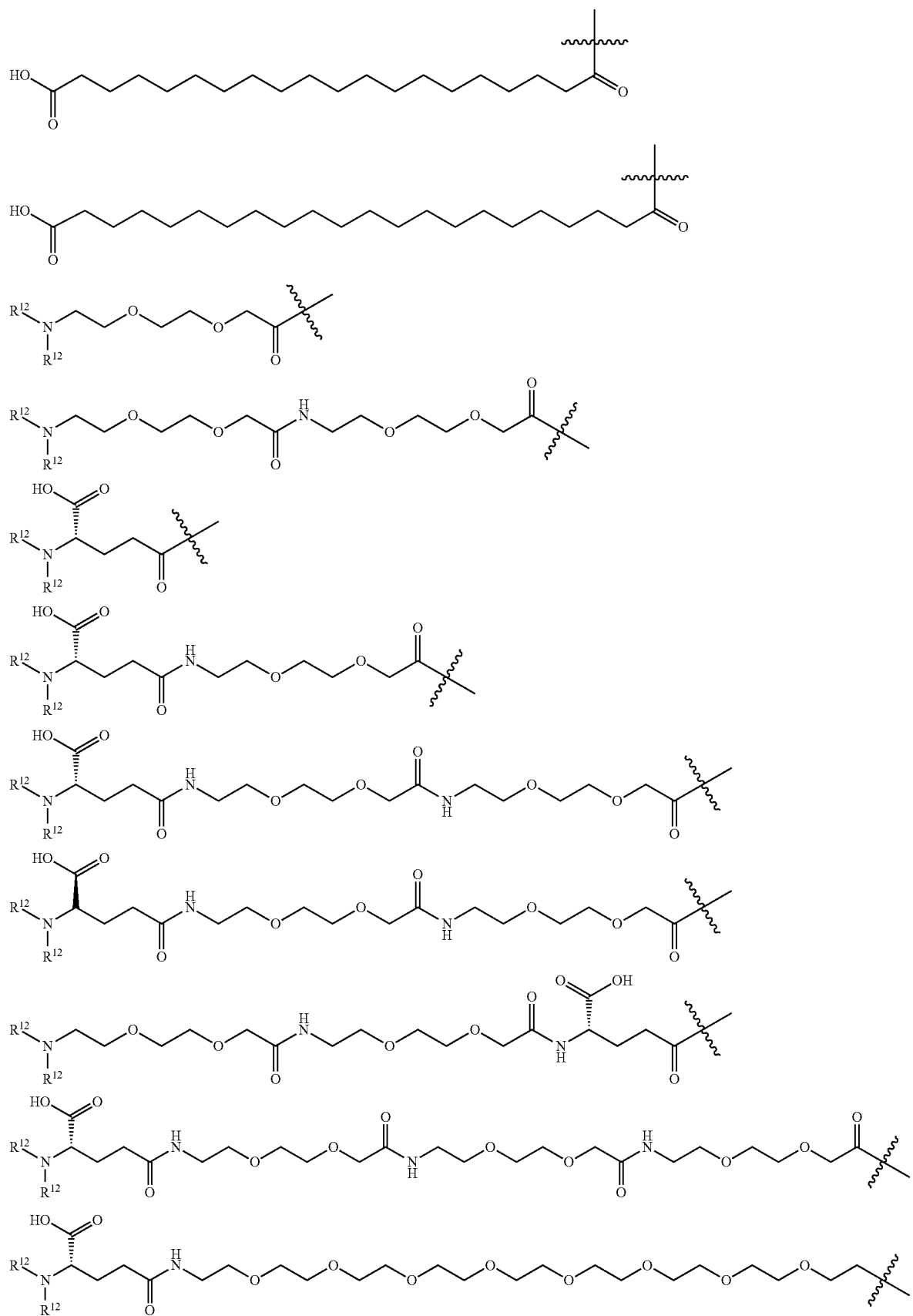

-continued
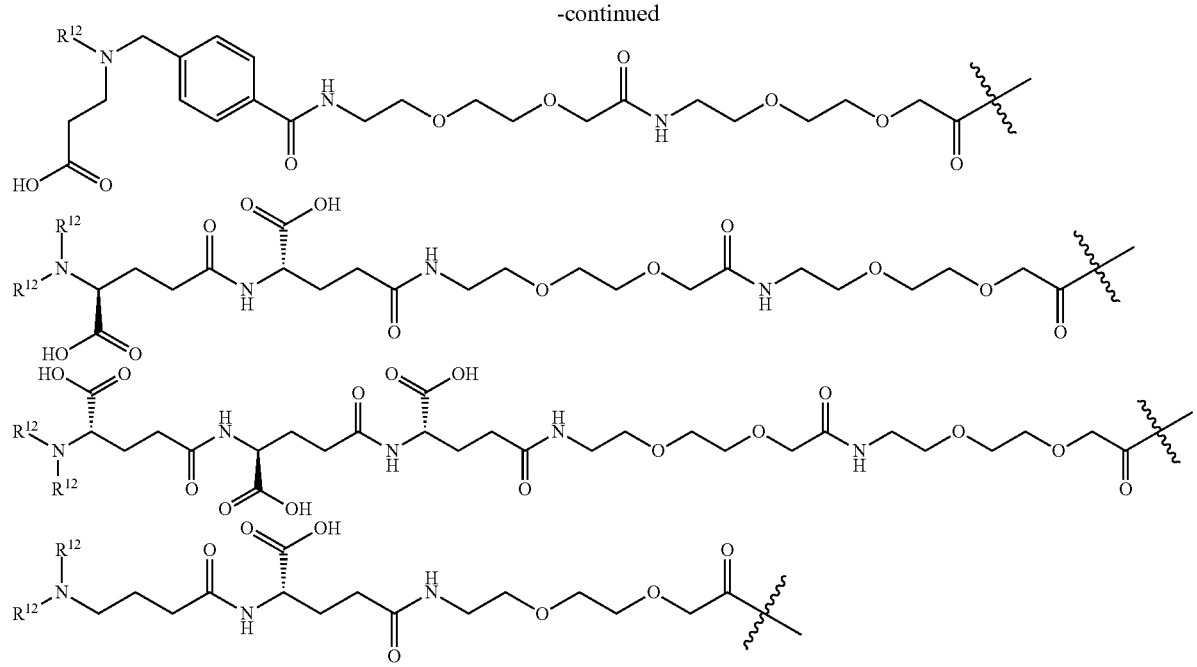
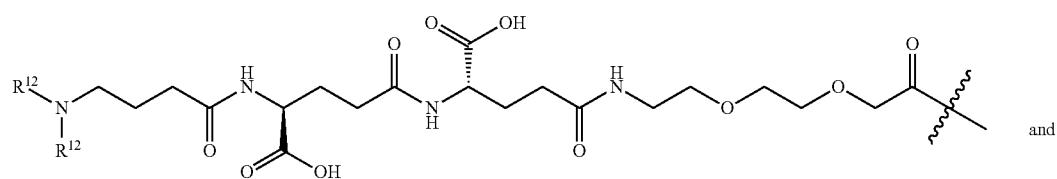
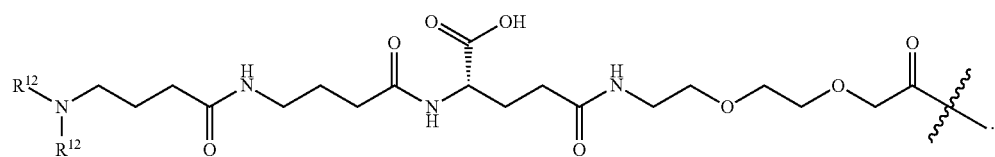
In one embodiment $R^{301}$ is selected from:
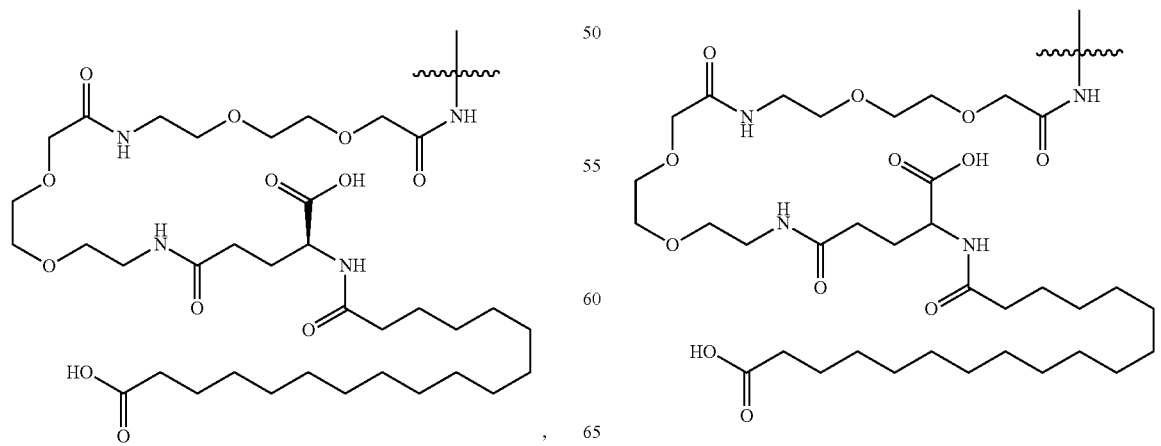

-continued
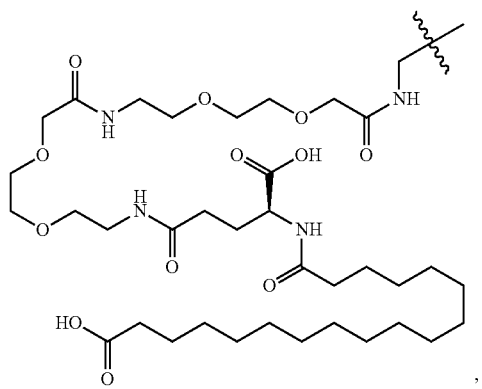
, and
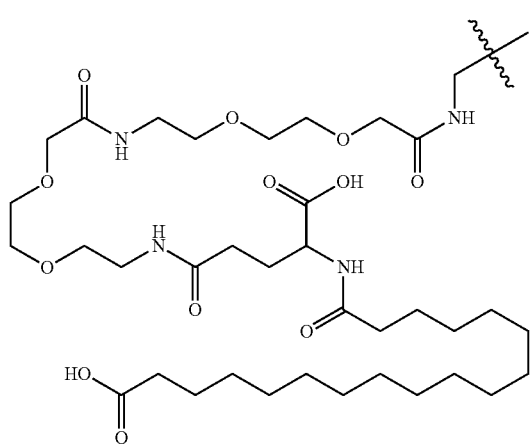
.
In one embodiment $R^{301}$ is
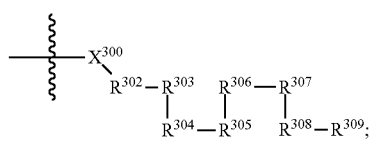
wherein $R^{302}$, $R^{303}$, $R^{304}$, $R^{305}$, $R^{306}$, $R^{307}$, and $R^{308}$ are selected from bond, polyethylene glycol, a natural amino acid, an unnatural amino acid,
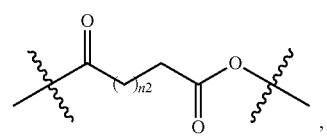
,
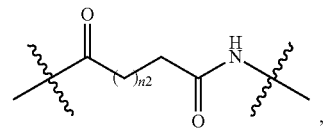
,
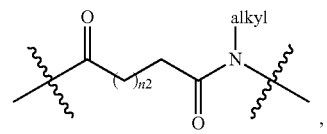
,
-continued
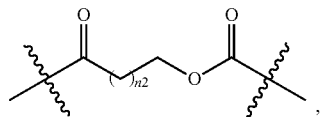
,
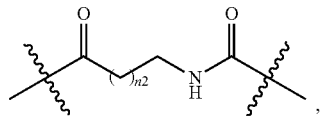
,
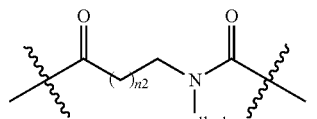
,
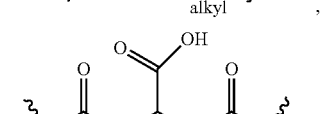
,
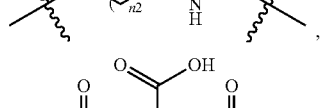
,
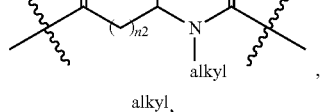
,
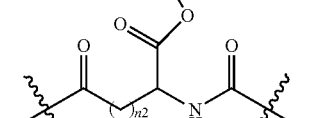
,
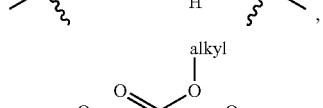
,
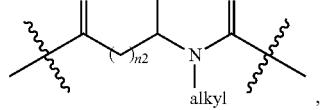
,
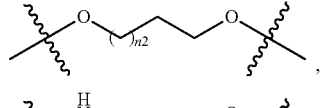
,
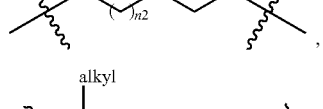
,
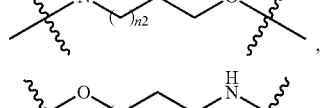
,
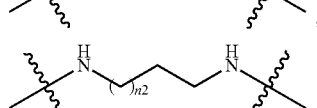
,
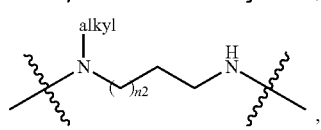
,

401

-continued

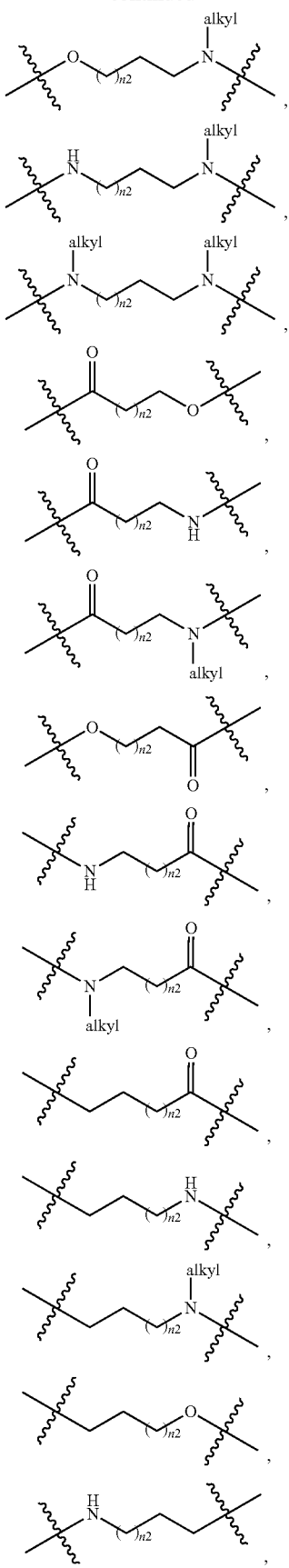

402

-continued

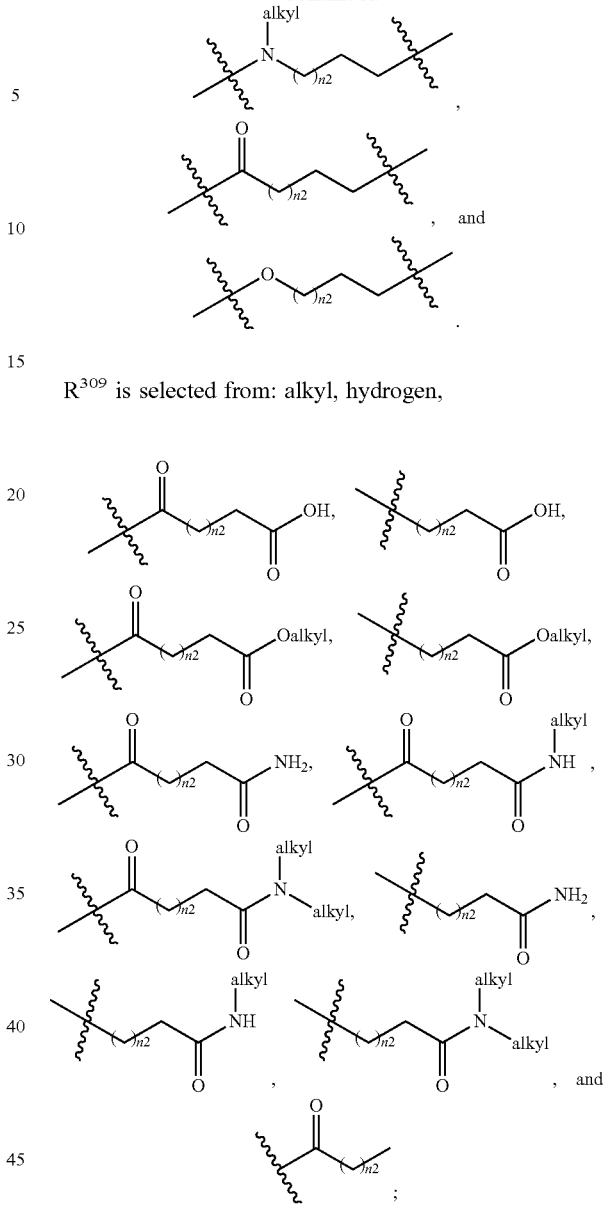

$R^{309}$ is selected from: alkyl, hydrogen,

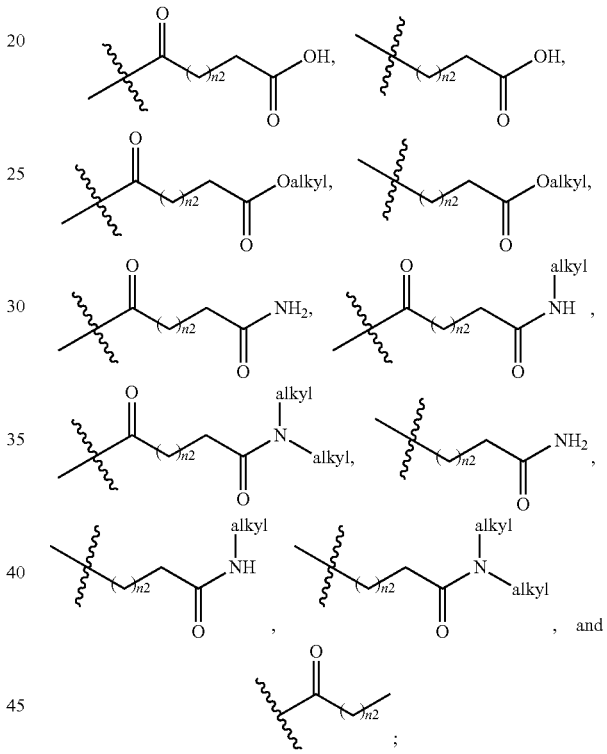

n2 is dependently selected at each instance from 0, 1, 2, 5, 6, 7, 8, 9, 10, 11, 12, 13, 14, 15, 16, 17, 18, 19, and 20; and $X^{300}$ is selected from bond, —NH—, —N(alkyl)-, O, —CH$_2$—O—, —CH$_2$—NH—, and —CH$_2$—N(alkyl).

In one embodiment only 1, 2, 3, 4, or 5 of $R^{302}$, $R^{303}$, $R^{304}$, $R^{305}$, $R^{306}$, $R^{307}$, and $R^{308}$ are selected to be bond.

In one embodiment none of $R^{302}$, $R^{303}$, $R^{304}$, $R^{305}$, $R^{306}$, $R^{307}$, and $R^{308}$ are selected to be bond.

In one embodiment only 1 of $R^{302}$, $R^{303}$, $R^{304}$, $R^{305}$, $R^{306}$, $R^{307}$, and $R^{308}$ are selected to be bond.

In one embodiment only 2 of $R^{302}$, $R^{303}$, $R^{304}$, $R^{305}$, $R^{306}$, $R^{307}$, and $R^{308}$ are selected to be bond.

In one embodiment only 3 of $R^{302}$, $R^{303}$, $R^{304}$, $R^{305}$, $R^{306}$, $R^{307}$, and $R^{308}$ are selected to be bond.

In one embodiment only 4 of $R^{302}$, $R^{303}$, $R^{304}$, $R^{305}$, $R^{306}$, $R^{307}$, and $R^{308}$ are selected to be bond.

In one embodiment only 5 of $R^{302}$, $R^{303}$, $R^{304}$, $R^{305}$, $R^{306}$, $R^{307}$, and $R^{308}$ are selected to be bond.

Non-limiting examples of compounds with an $R^{301}$ and/or substituent of the present invention include:
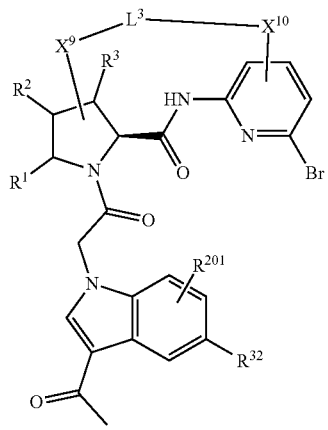
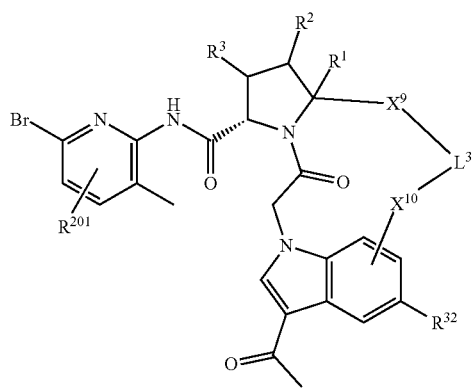
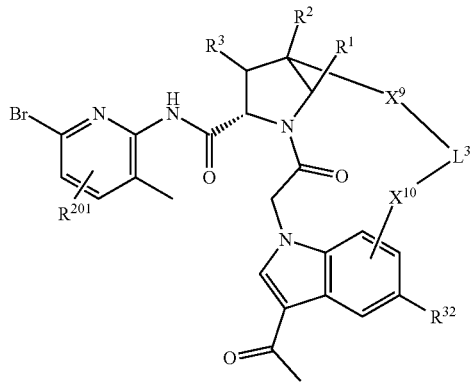
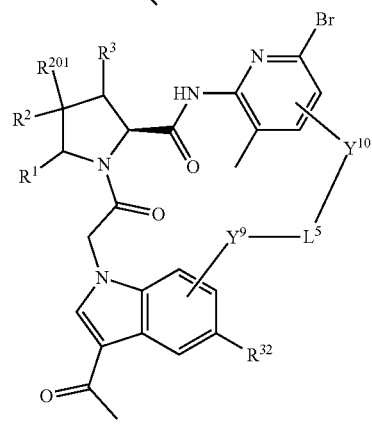
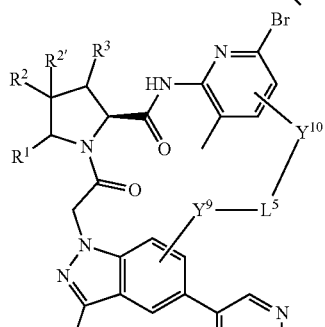
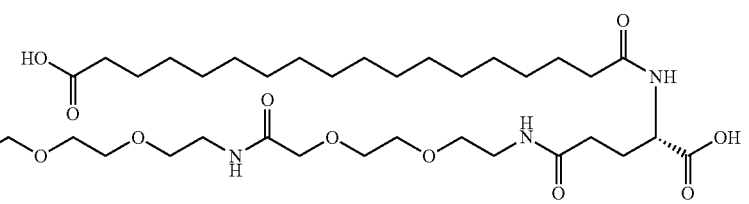
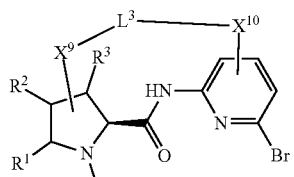
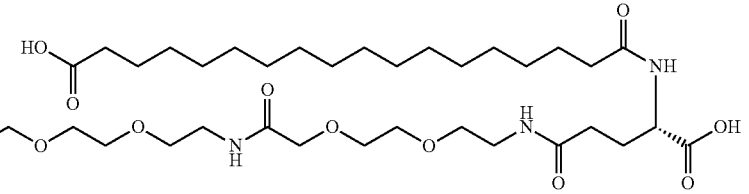

405
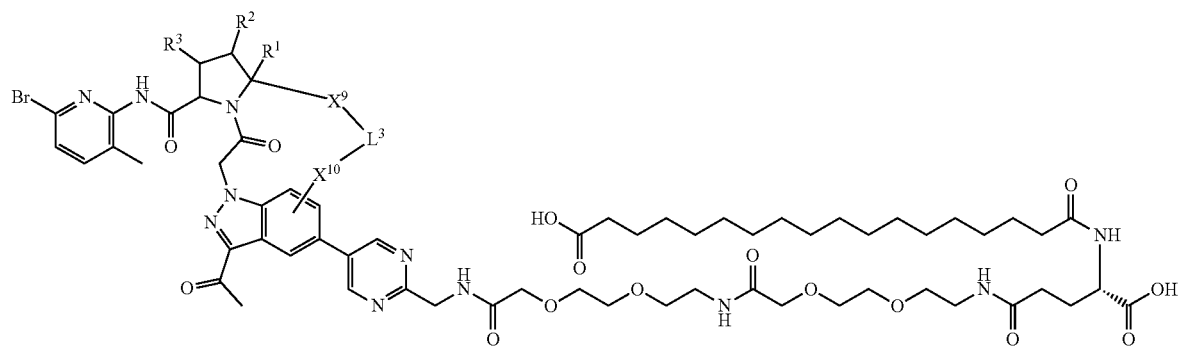
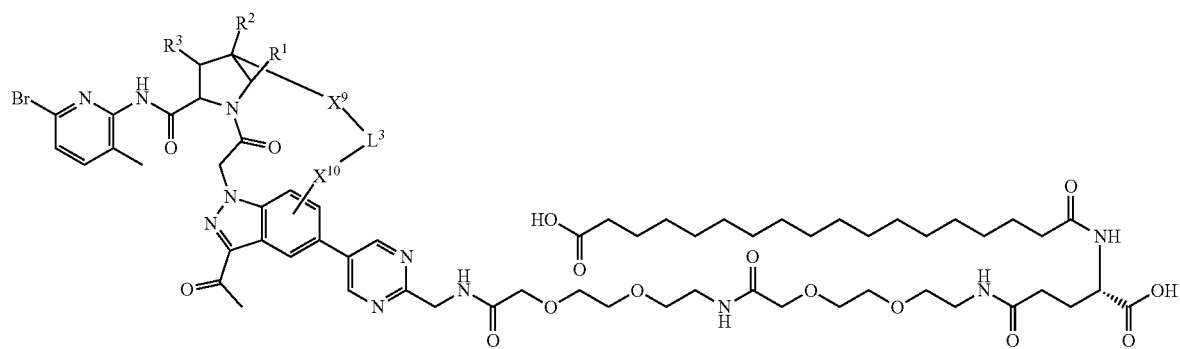
406
-continued
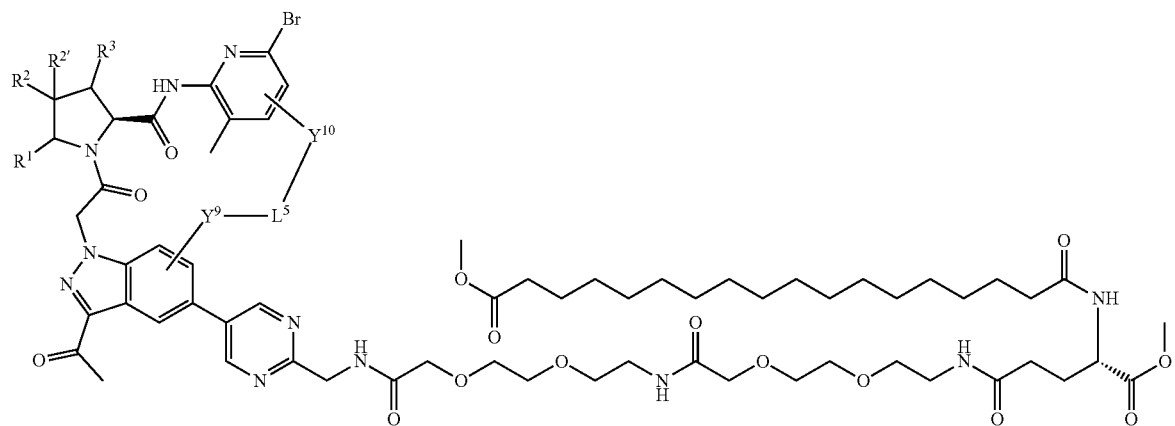
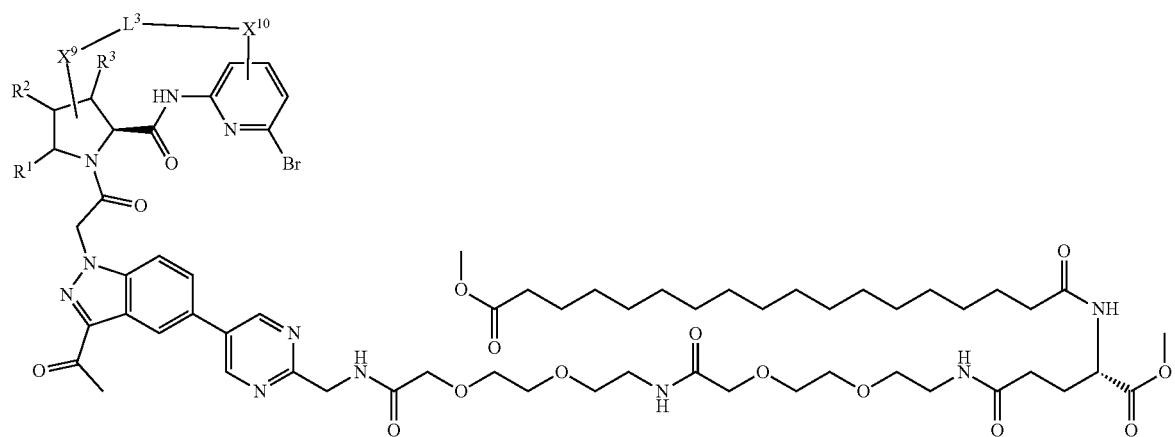

407 408
-continued
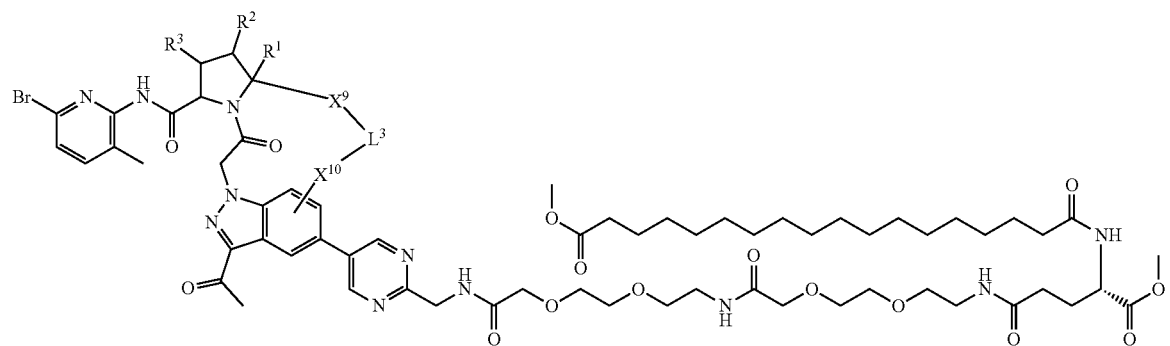
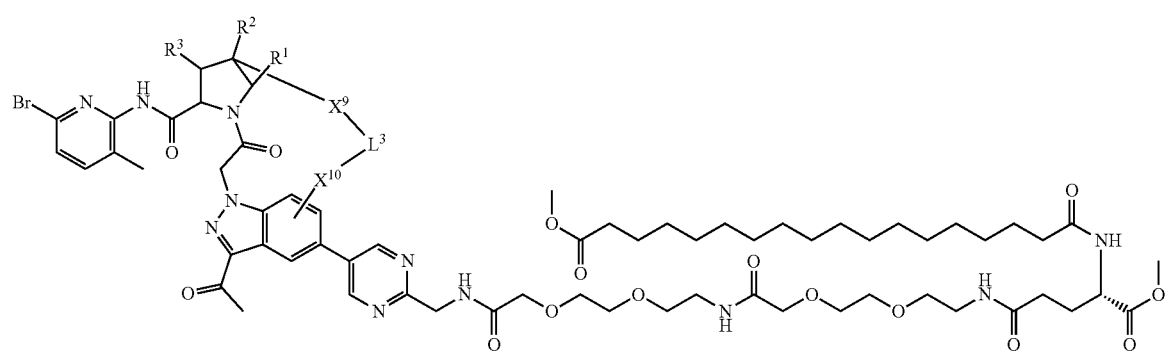
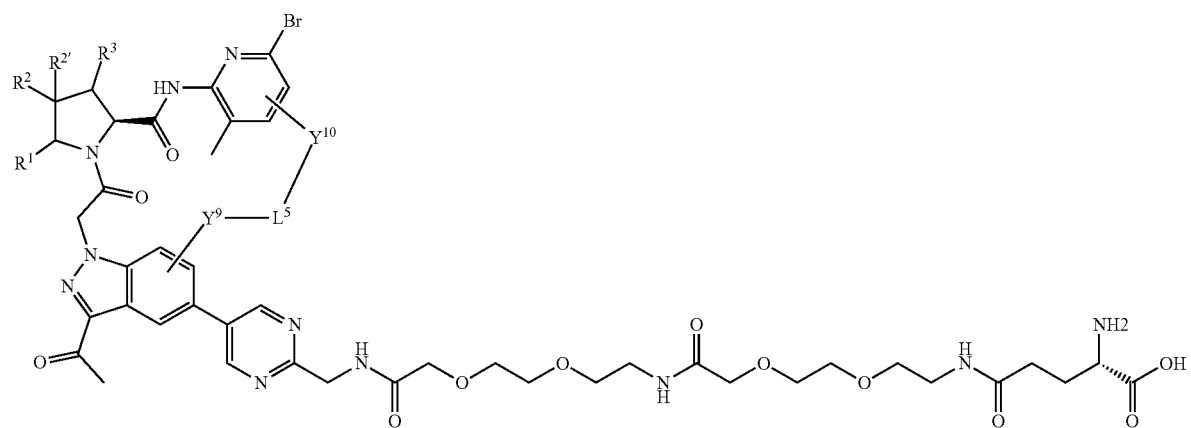
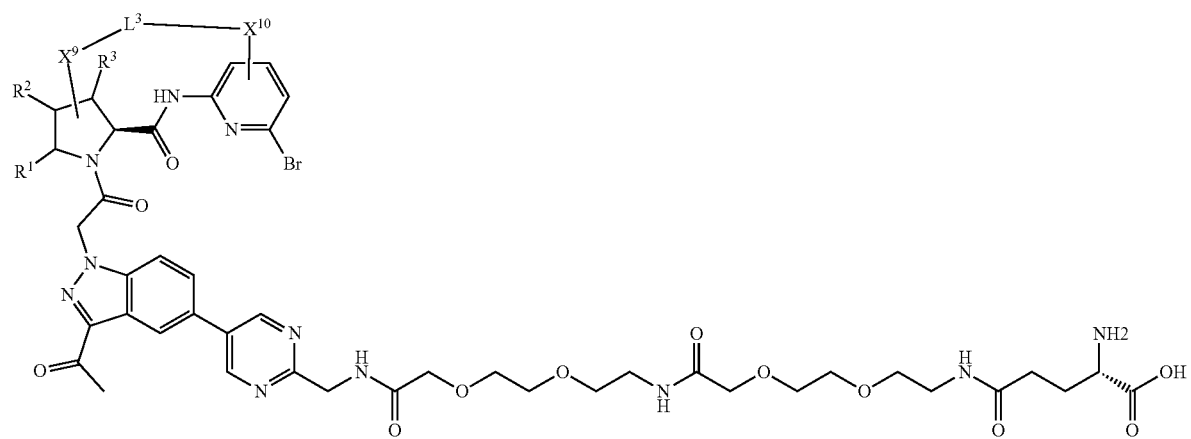

-continued
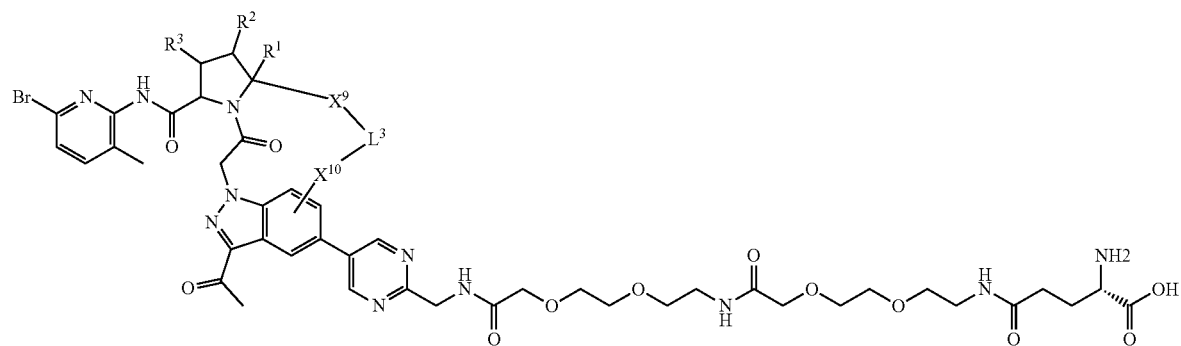
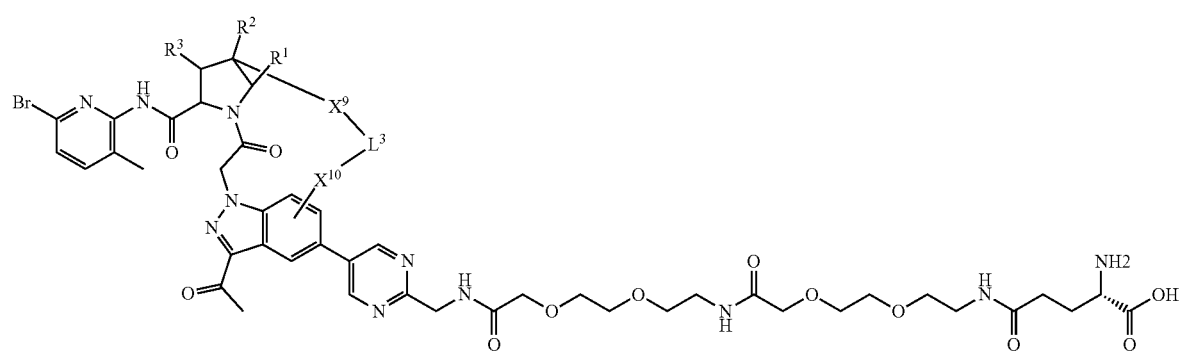
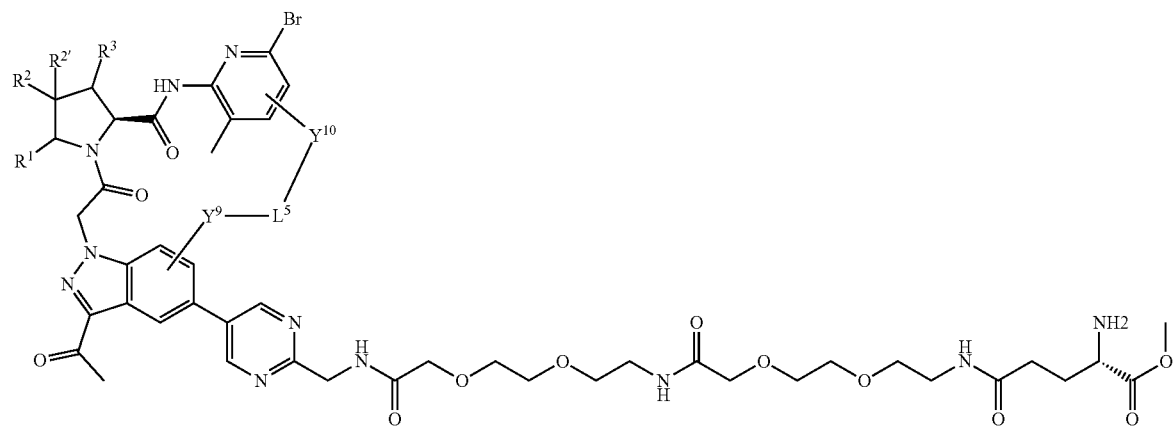
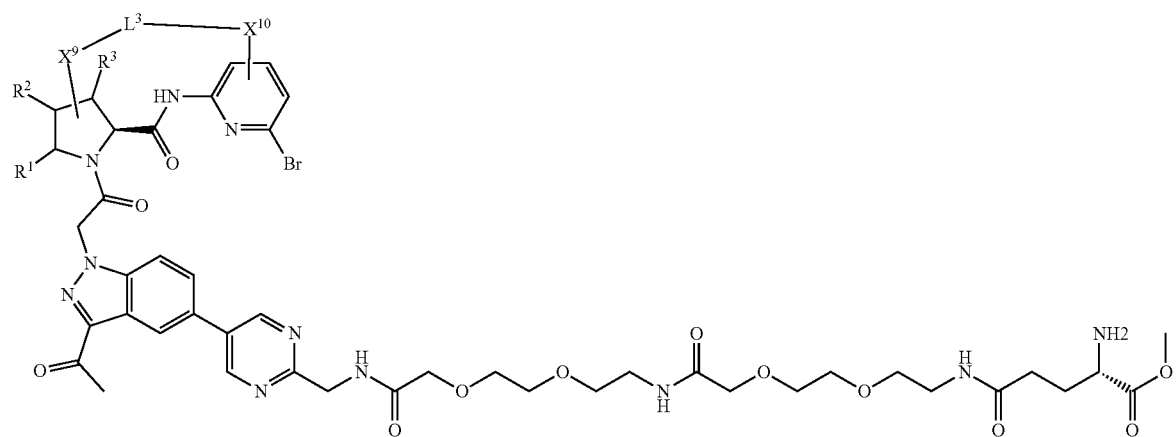

411
412
-continued
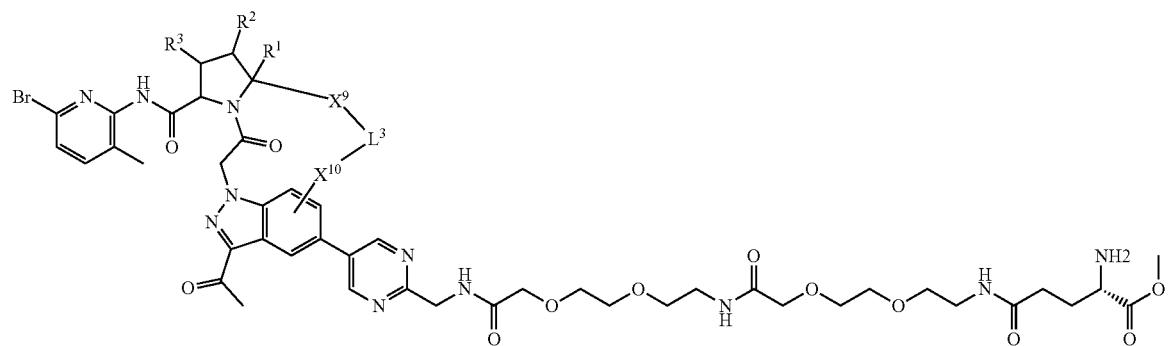
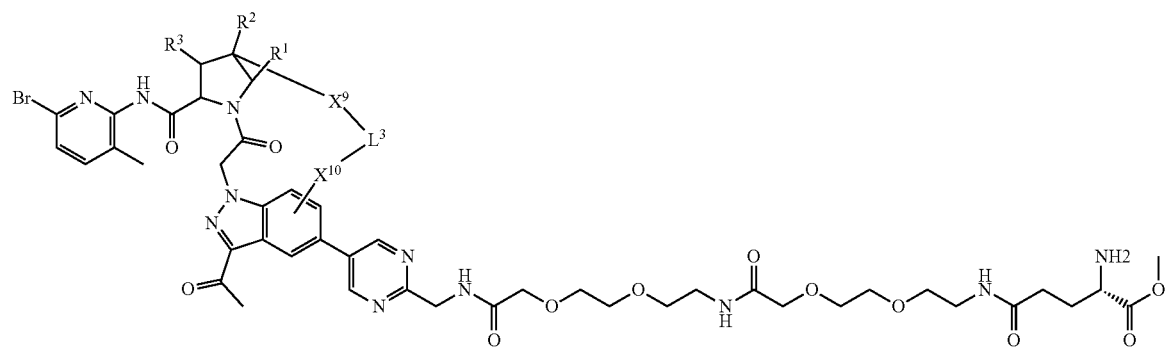
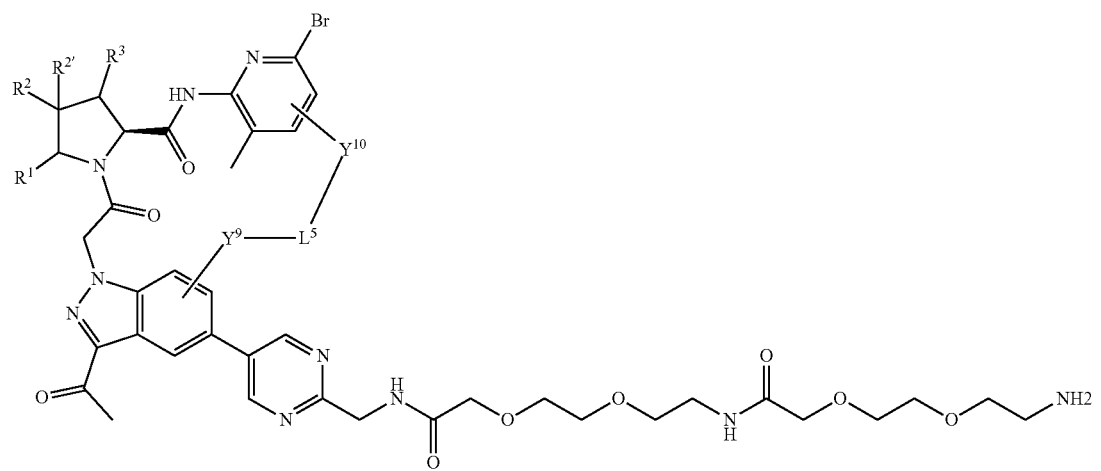
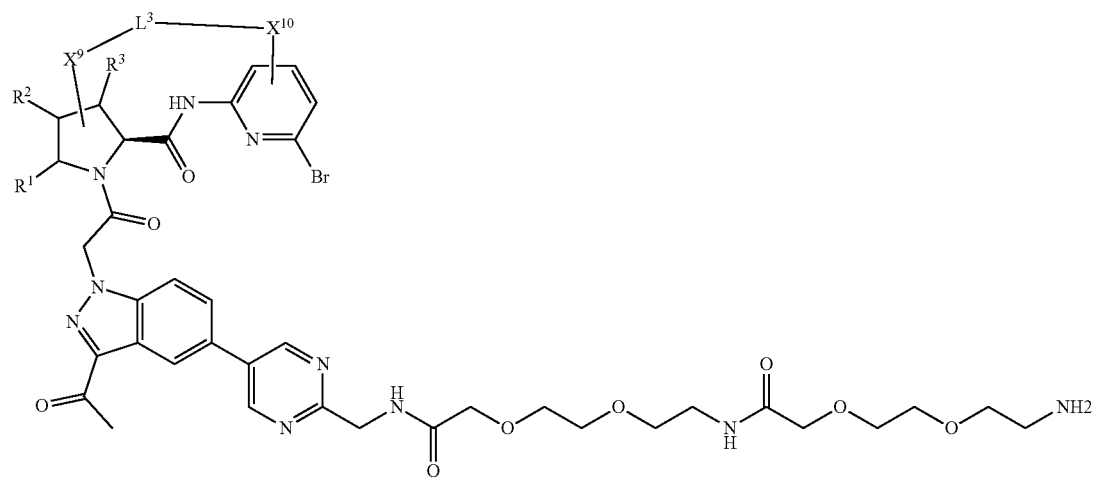

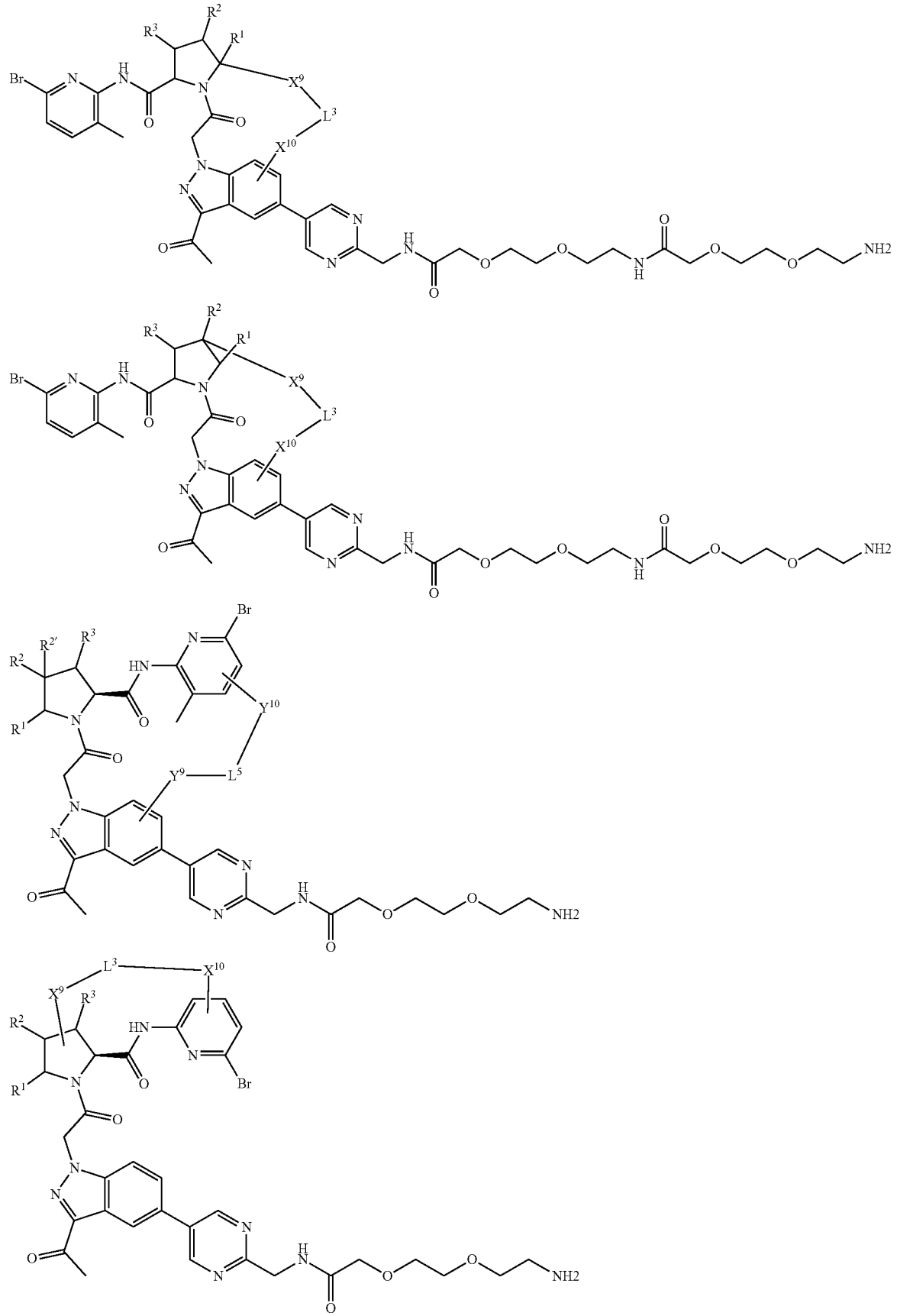
-continued

-continued
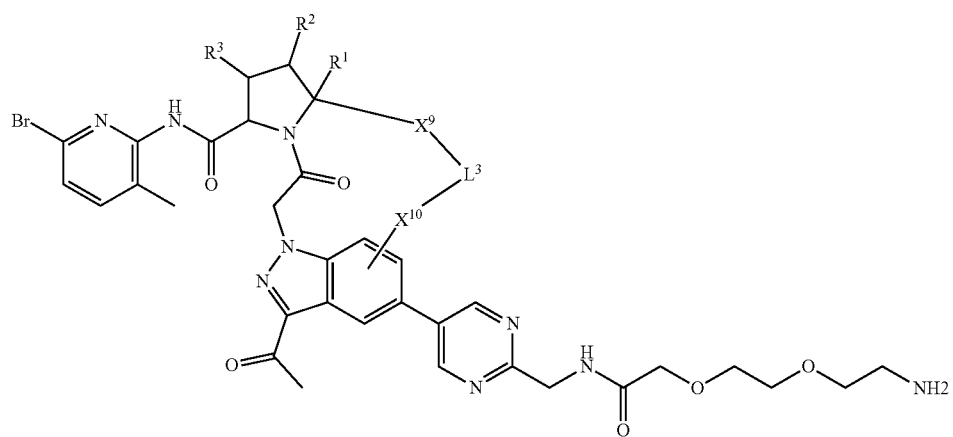
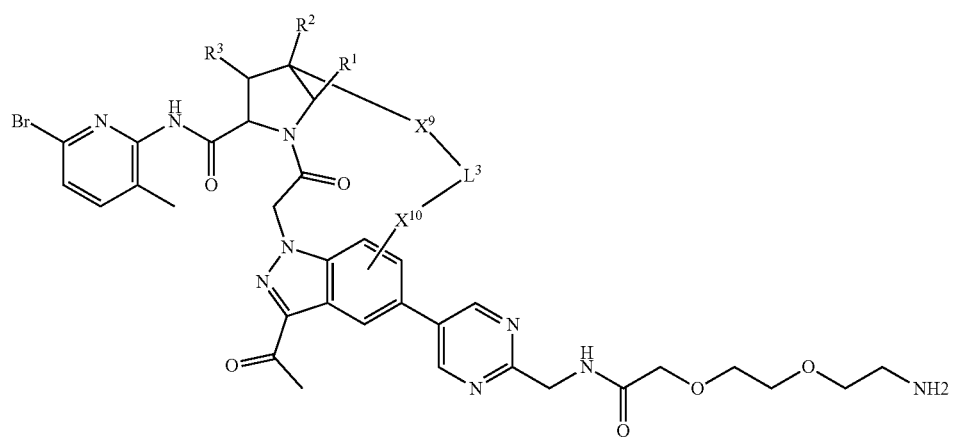
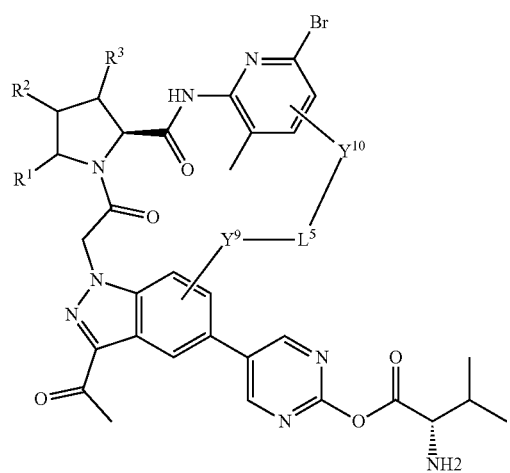
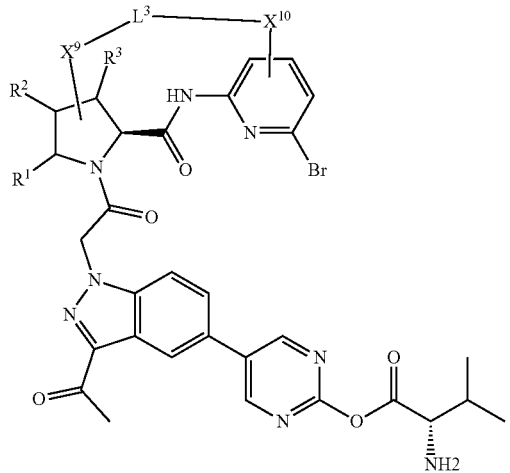

-continued
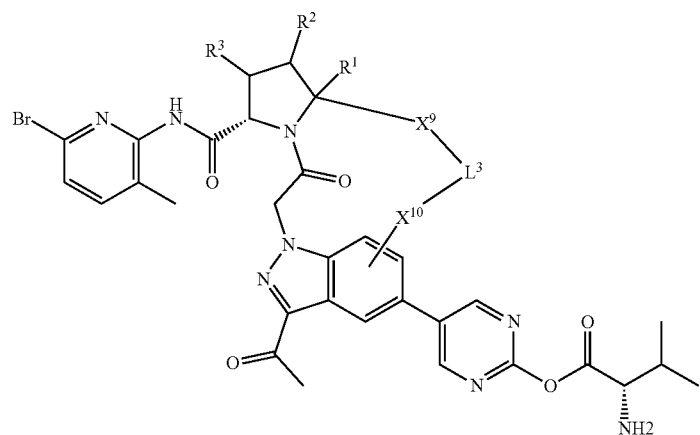
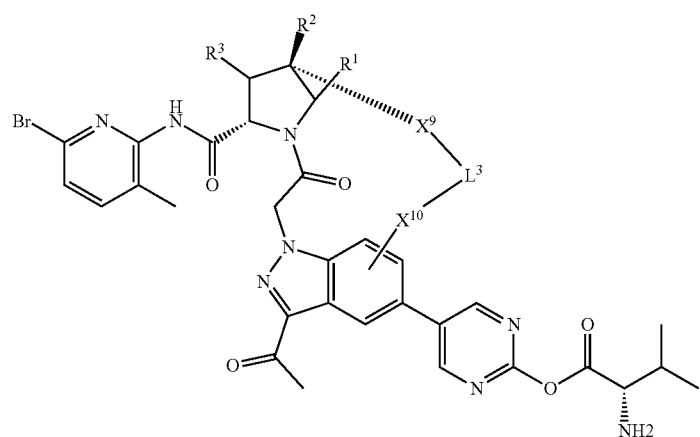
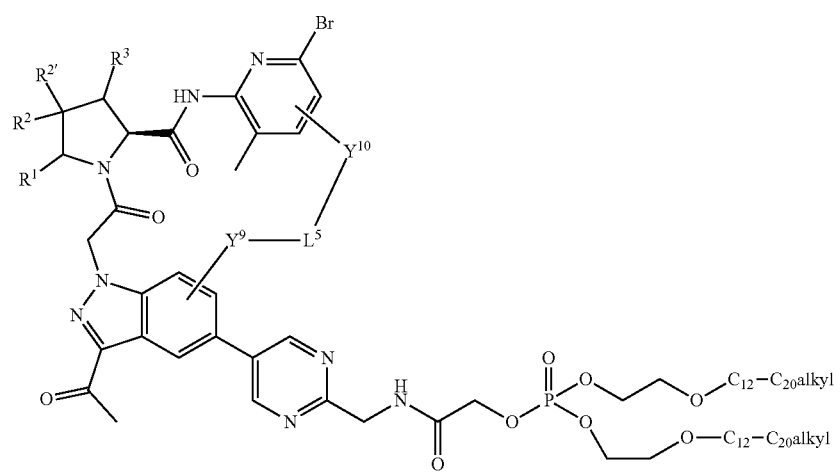

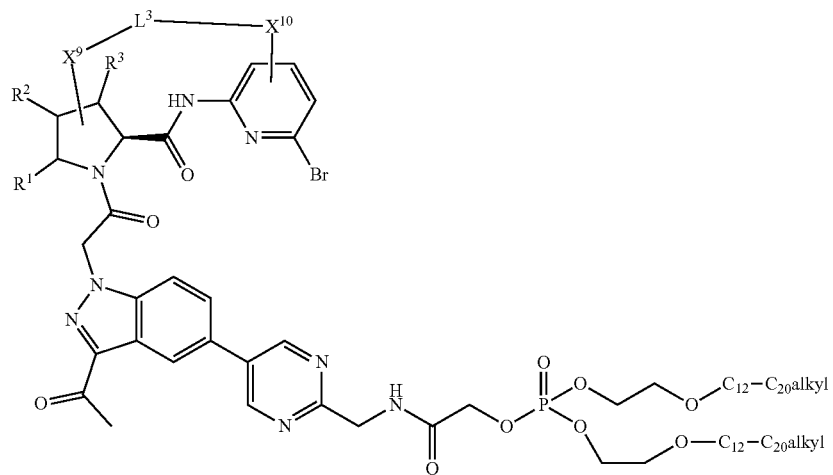
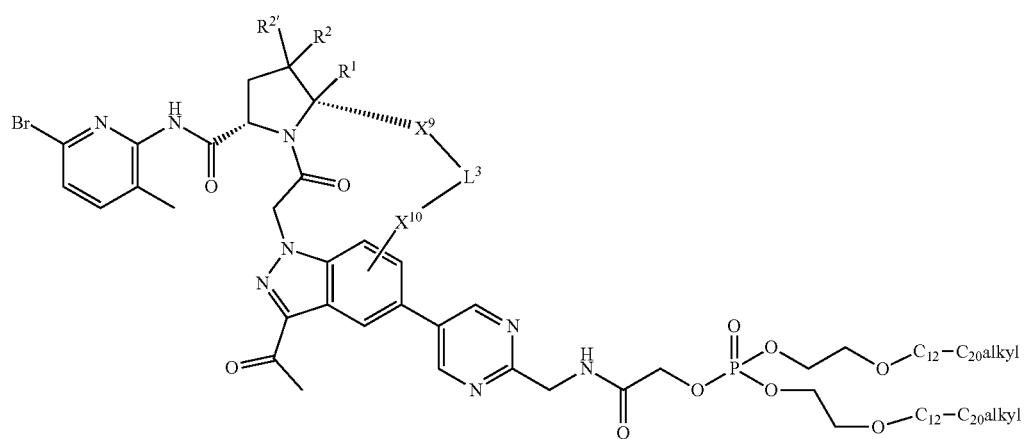
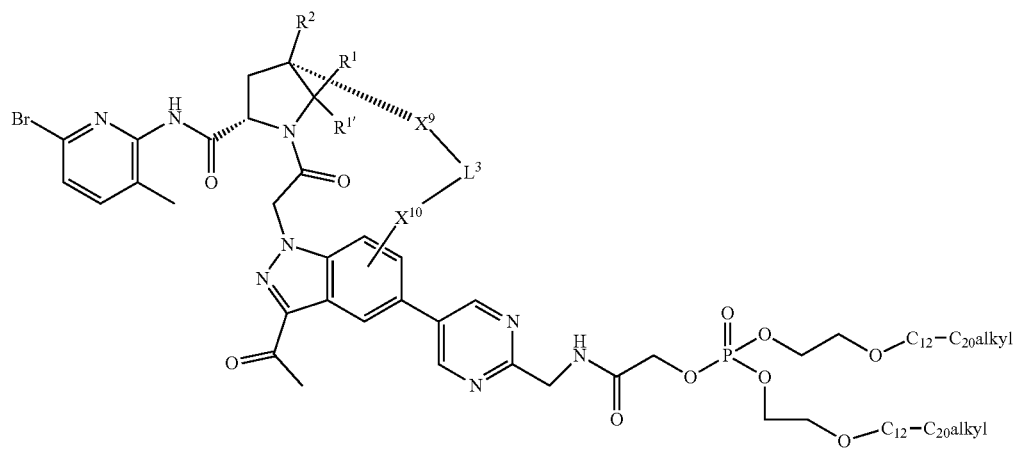

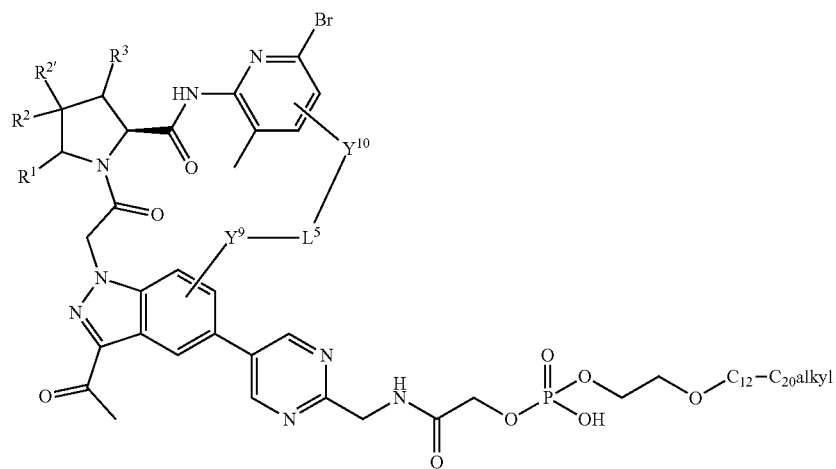
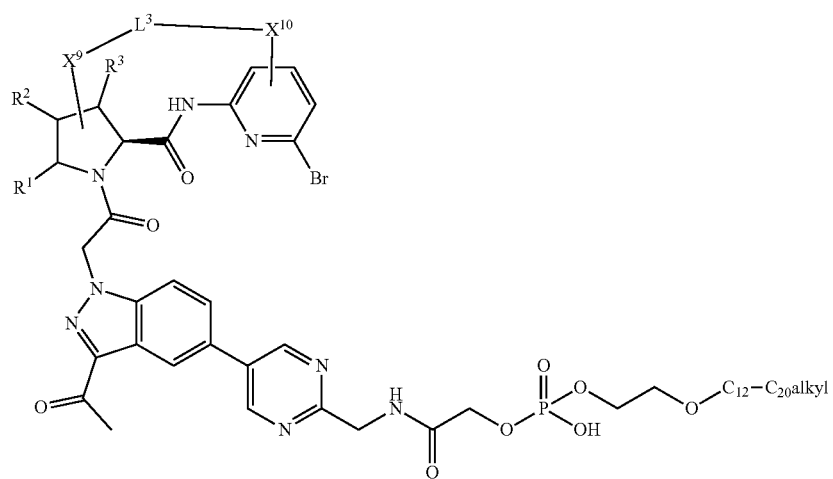
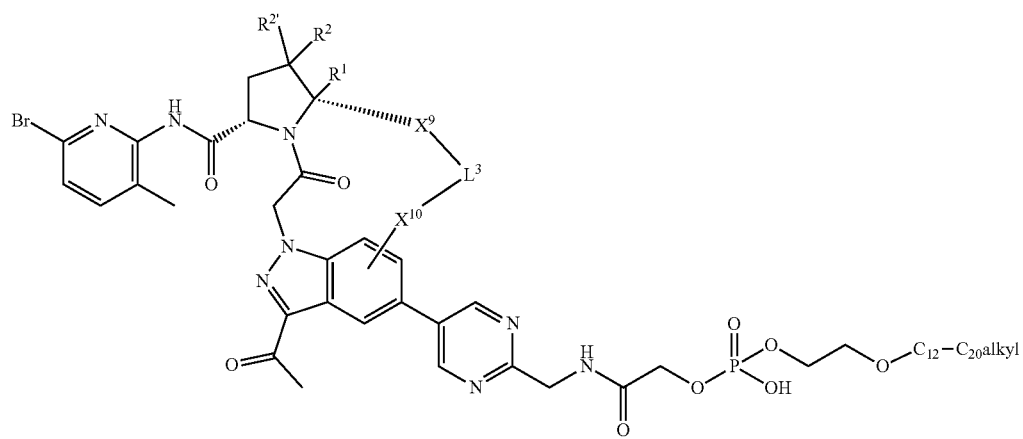
, and

-continued
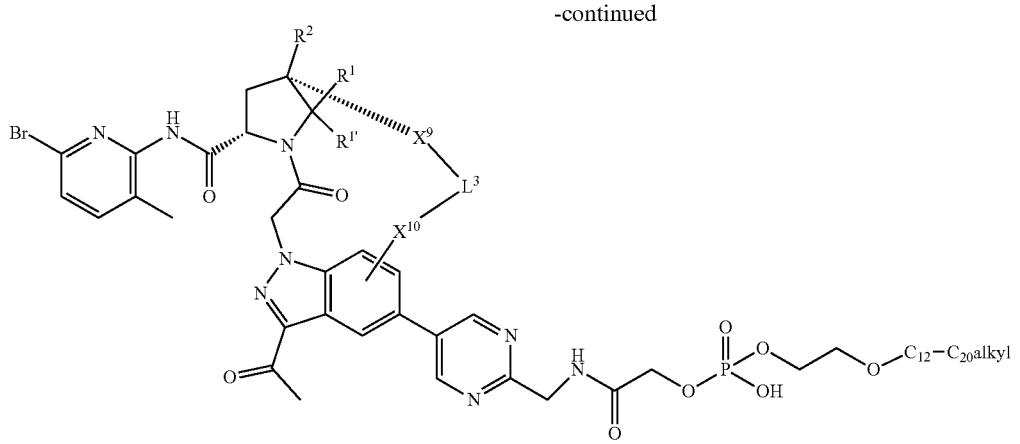
In one embodiment R$^{32}$ is:
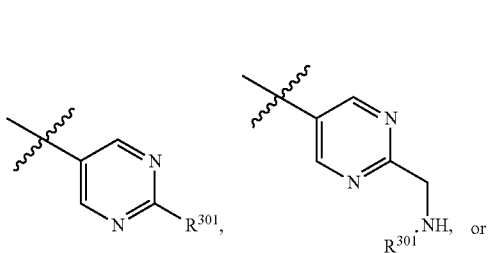
Embodiments of the Central Core
In one embodiment
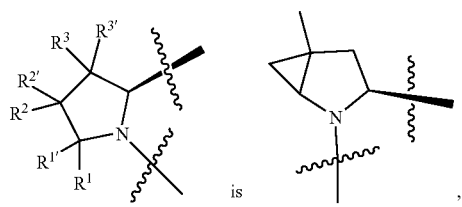
is
In one embodiment
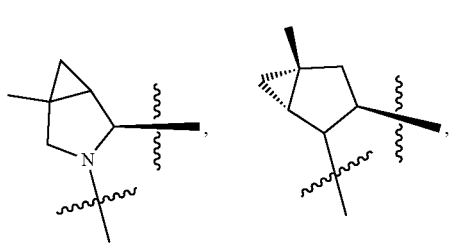
-continued
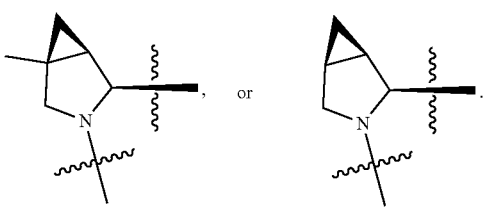
or
In one embodiment
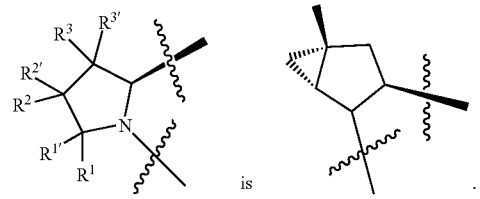
is
In one embodiment
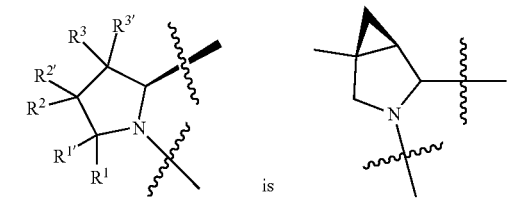
is
In one embodiment
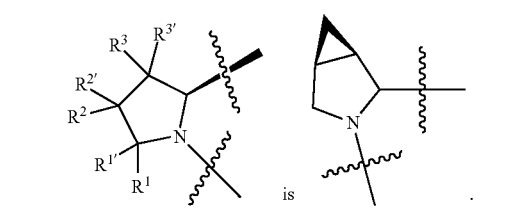
is In another embodiment
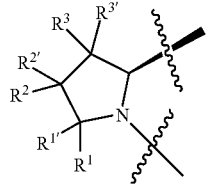
is selected from:
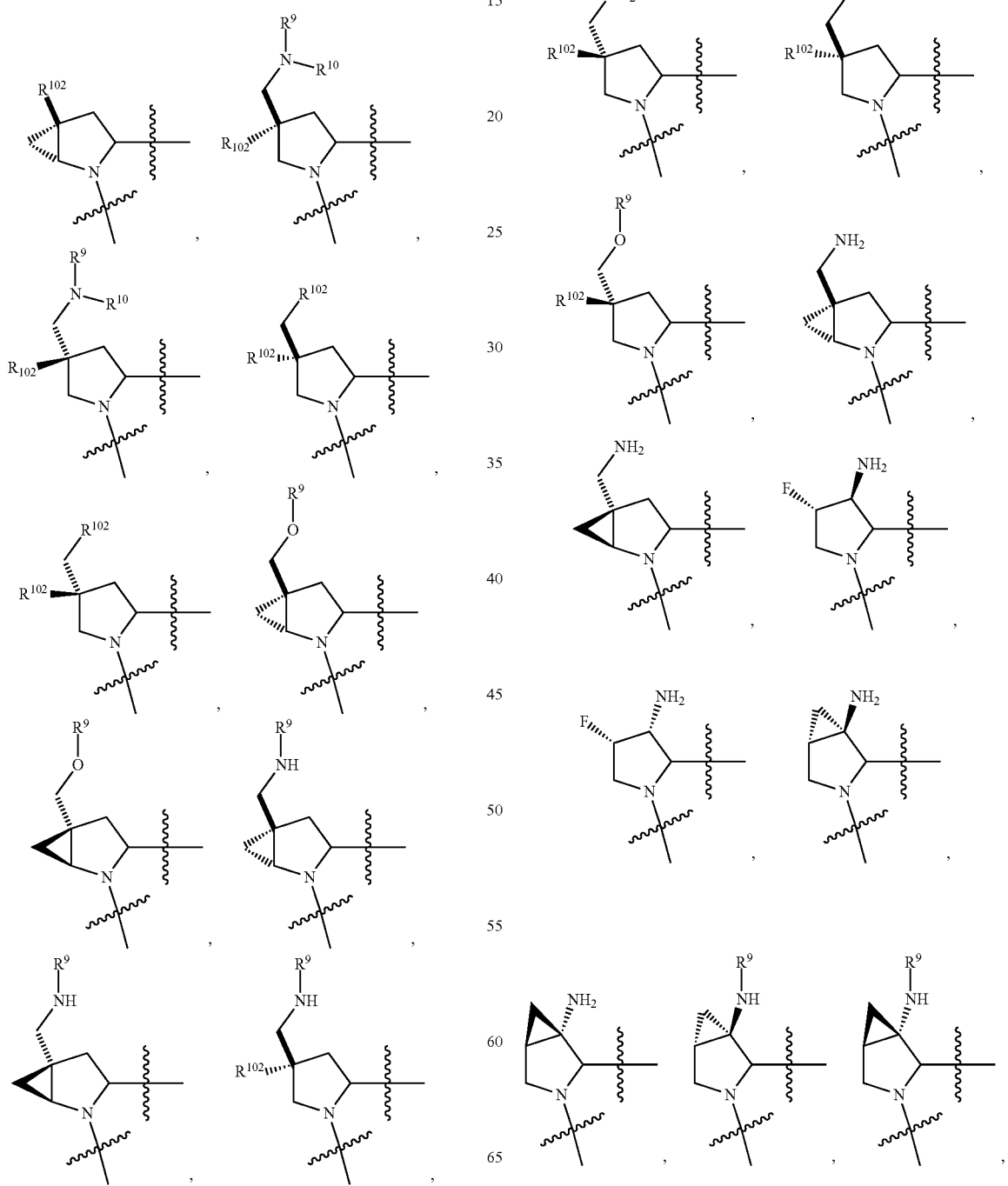

427
-continued
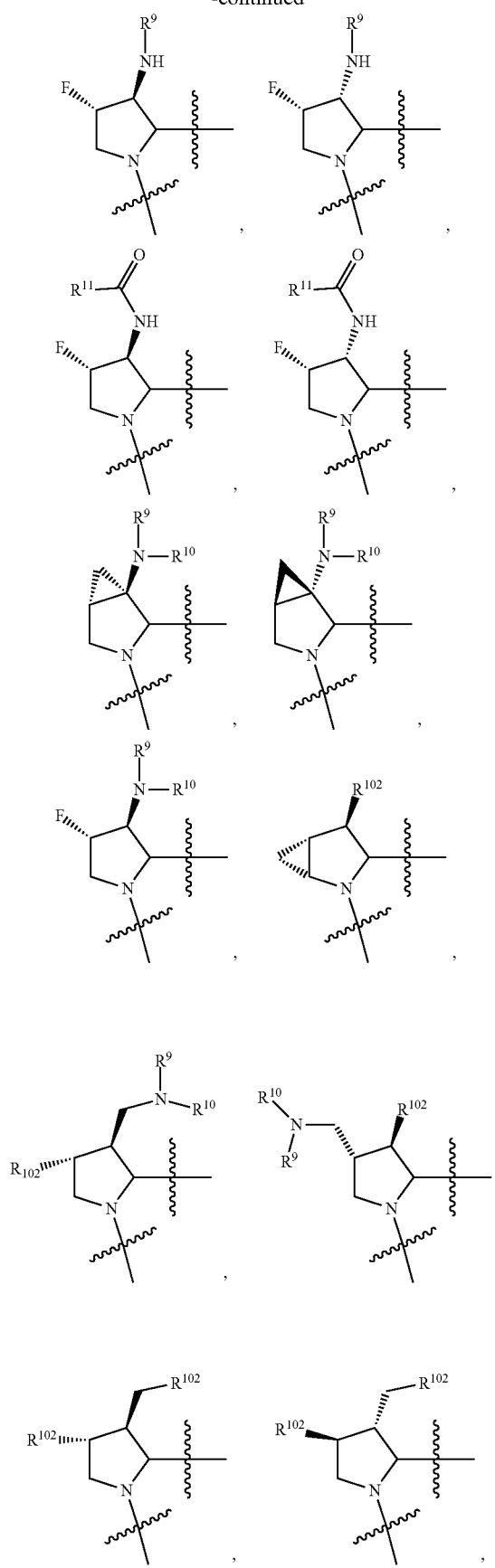
428
-continued
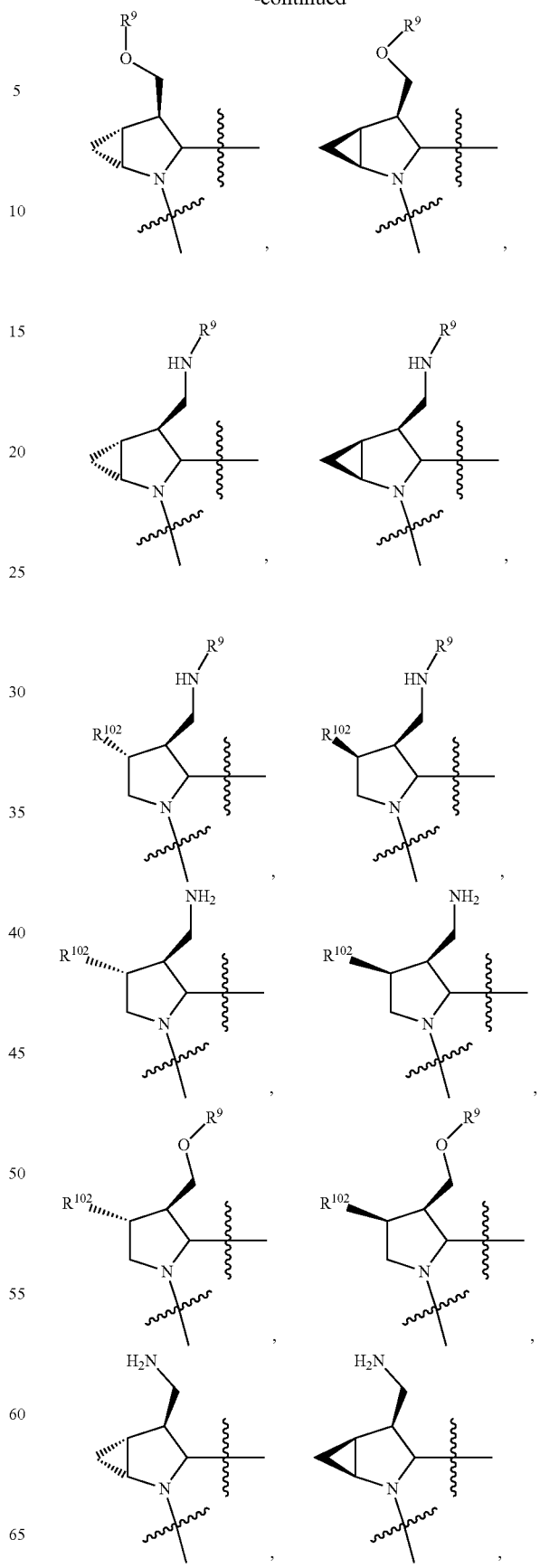

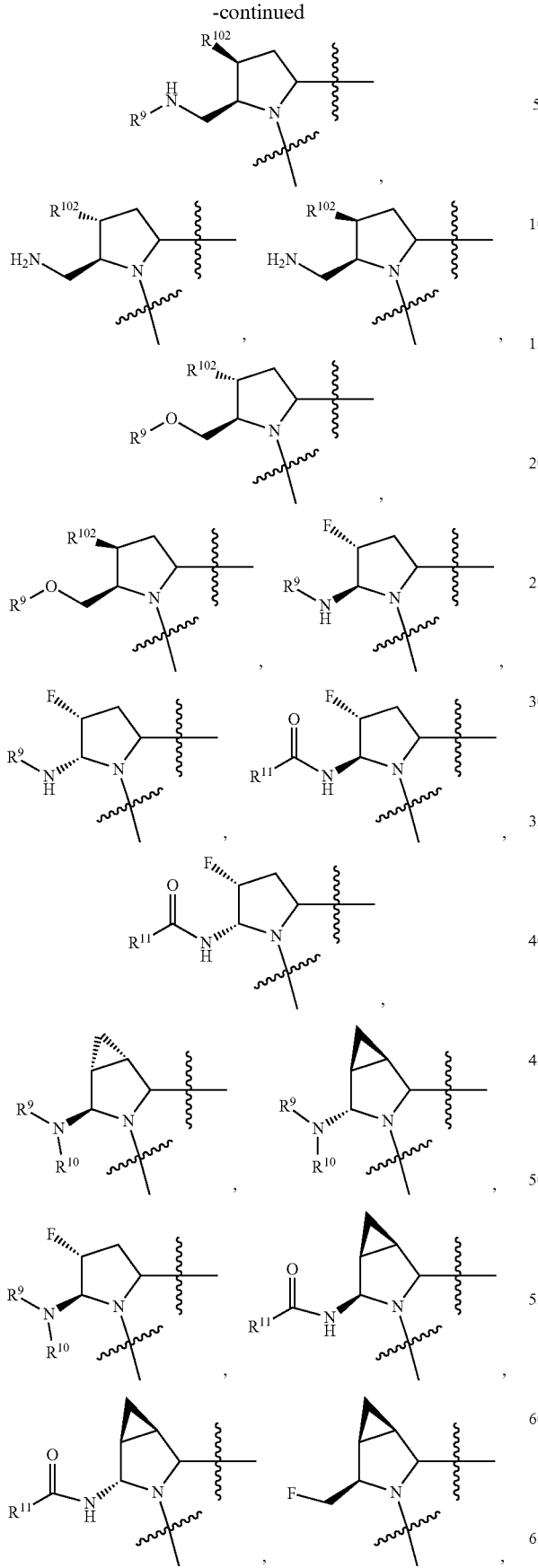
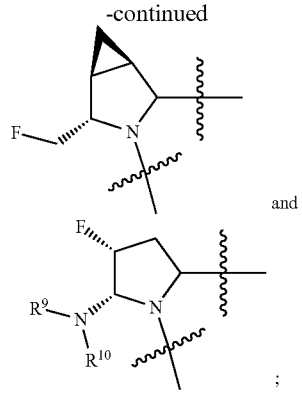
wherein:
$R^{102}$ is $C_1$-$C_4$ alkyl fluorine, chlorine, or bromine.
In one embodiment
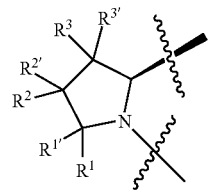
is selected from:
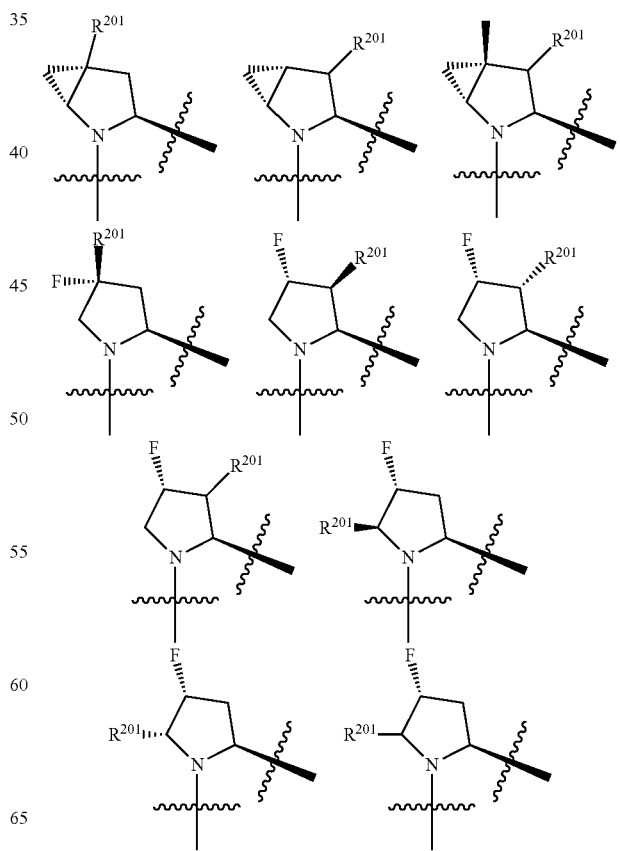

-continued
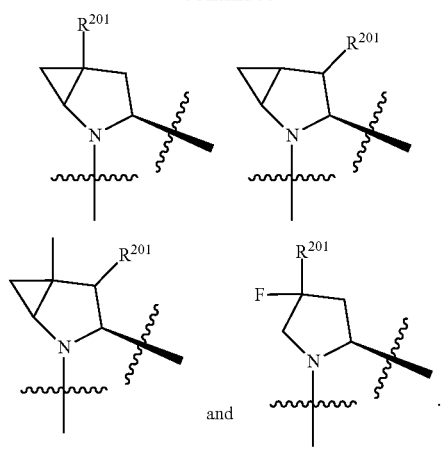
In one embodiment
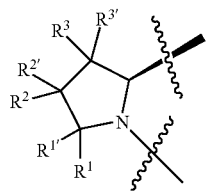
is selected from:
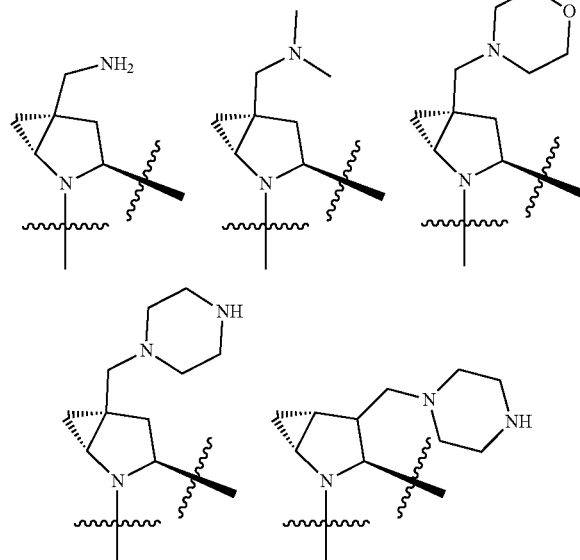
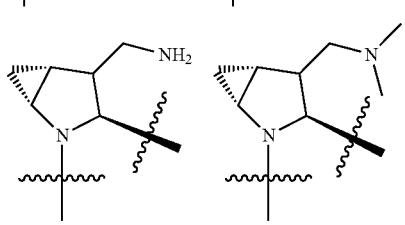
-continued
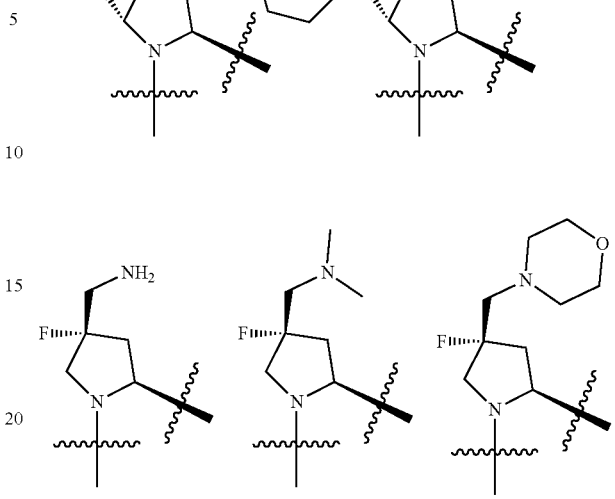
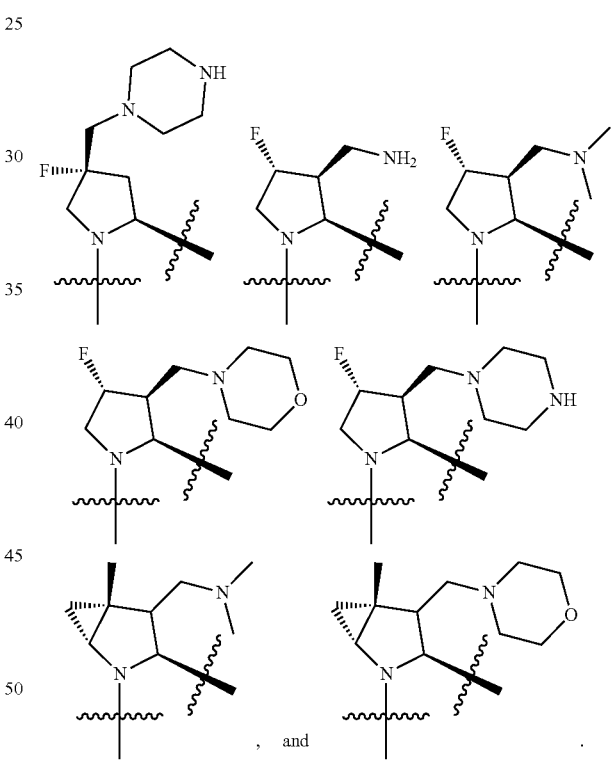
, and .
In one embodiment
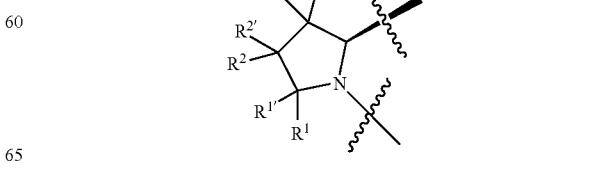

is selected from:
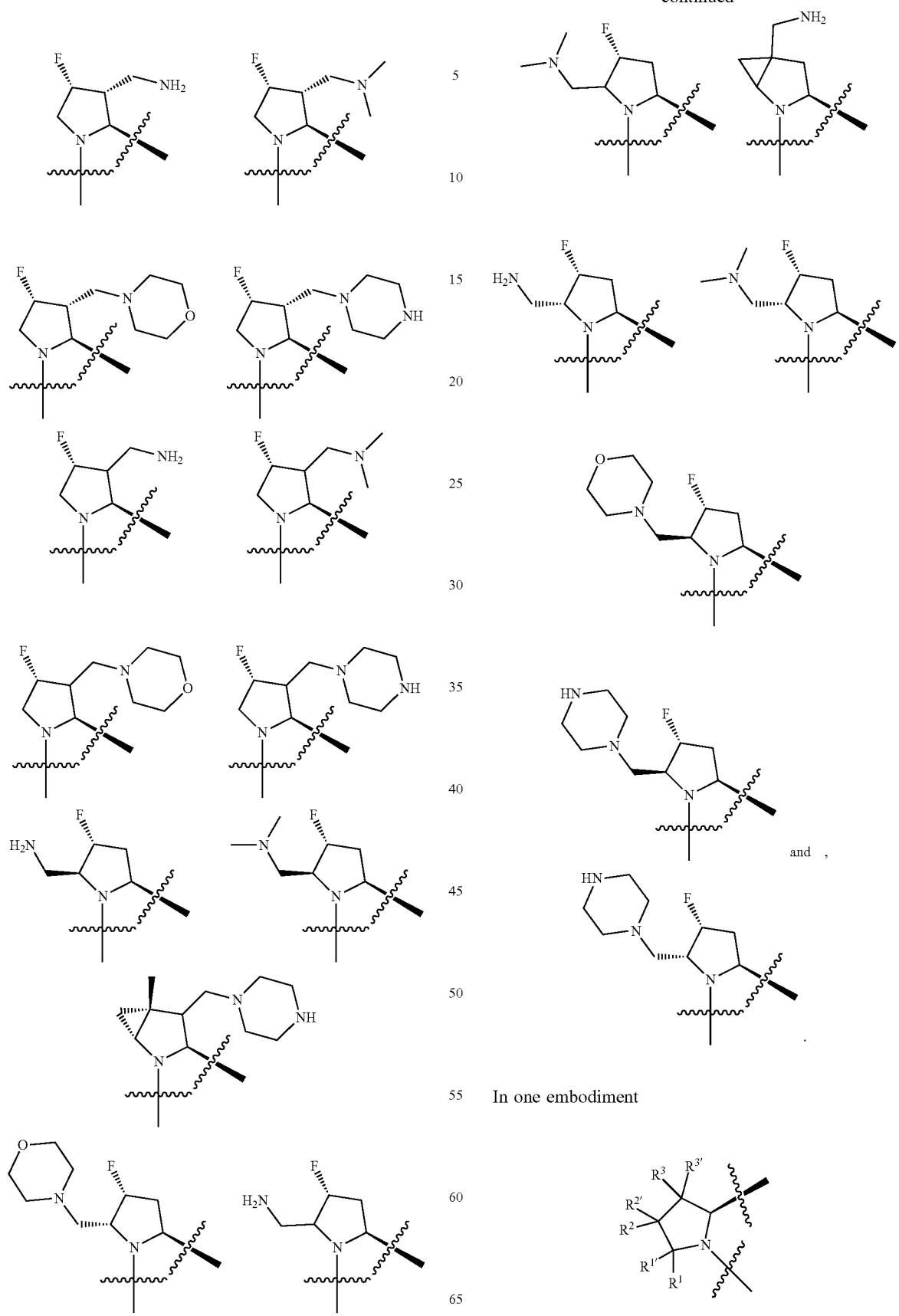
In one embodiment is selected from:

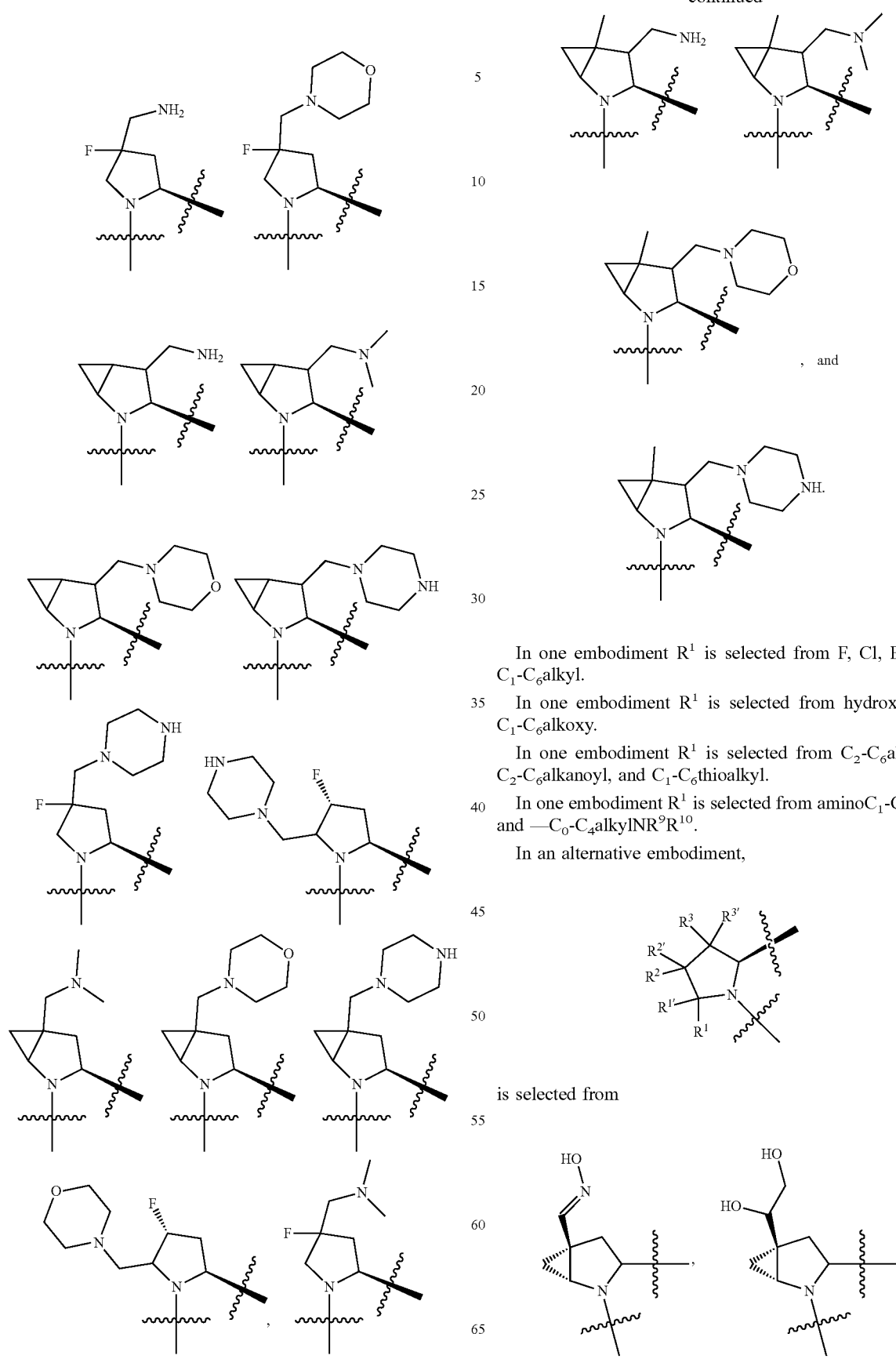

In one embodiment R$^1$ is selected from F, Cl, Br, and C$_1$-C$_6$alkyl.

In one embodiment R$^1$ is selected from hydroxyl and C$_1$-C$_6$alkoxy.

In one embodiment R$^1$ is selected from C$_2$-C$_6$alkynyl, C$_2$-C$_6$alkanoyl, and C$_1$-C$_6$thioalkyl.

In one embodiment R$^1$ is selected from aminoC$_1$-C$_6$alkyl and —C$_0$-C$_4$alkylNR$^9$R$^{10}$.

In an alternative embodiment, is selected from

-continued
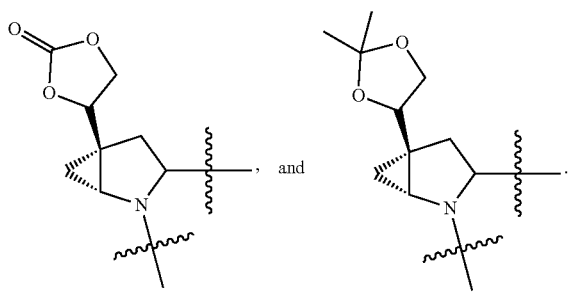
Embodiments of A
Non-limiting examples of A1 include:
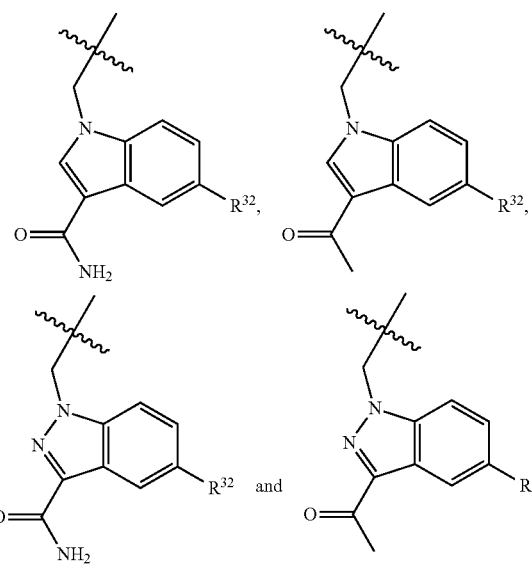
Additional non-limiting examples of A1 include:
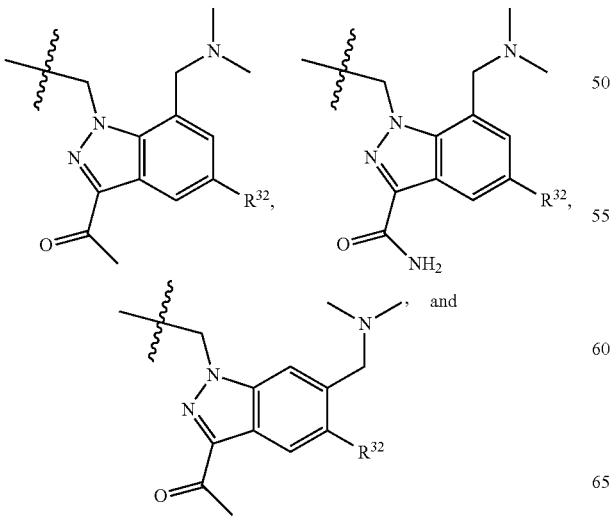
-continued
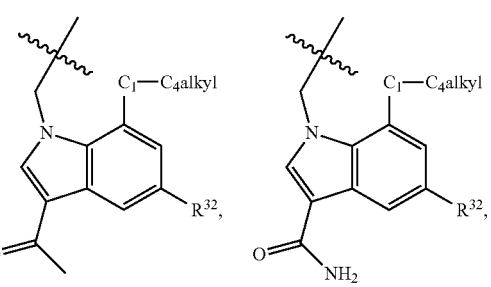
Additional non-limiting examples of A1 include:
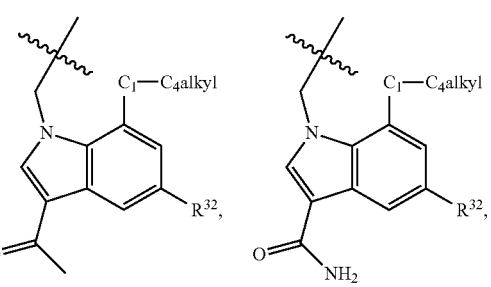
In one embodiment A1 is selected from:

-continued
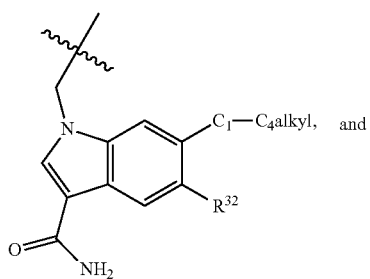
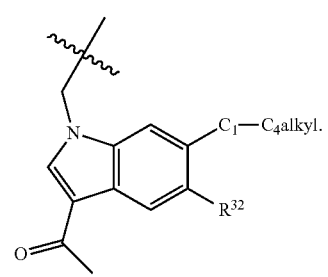
In one embodiment A1 is selected from:
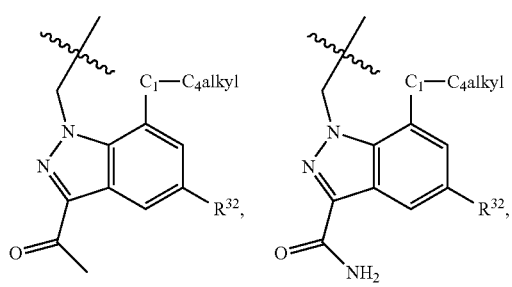
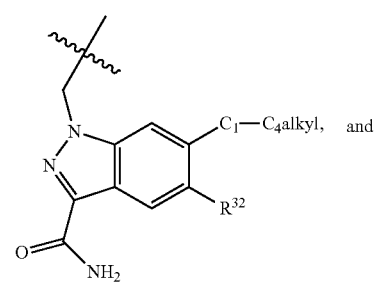
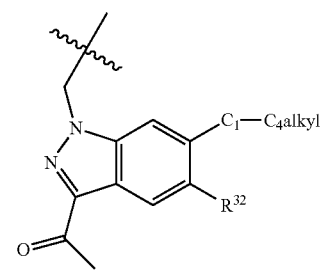
In another embodiment A1 is selected from:
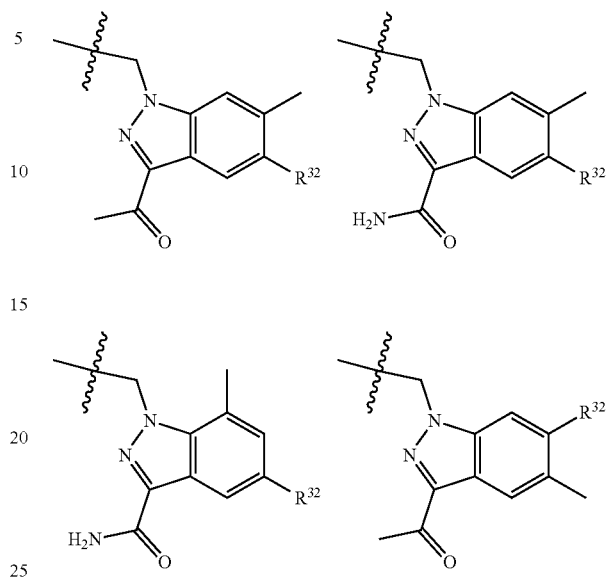
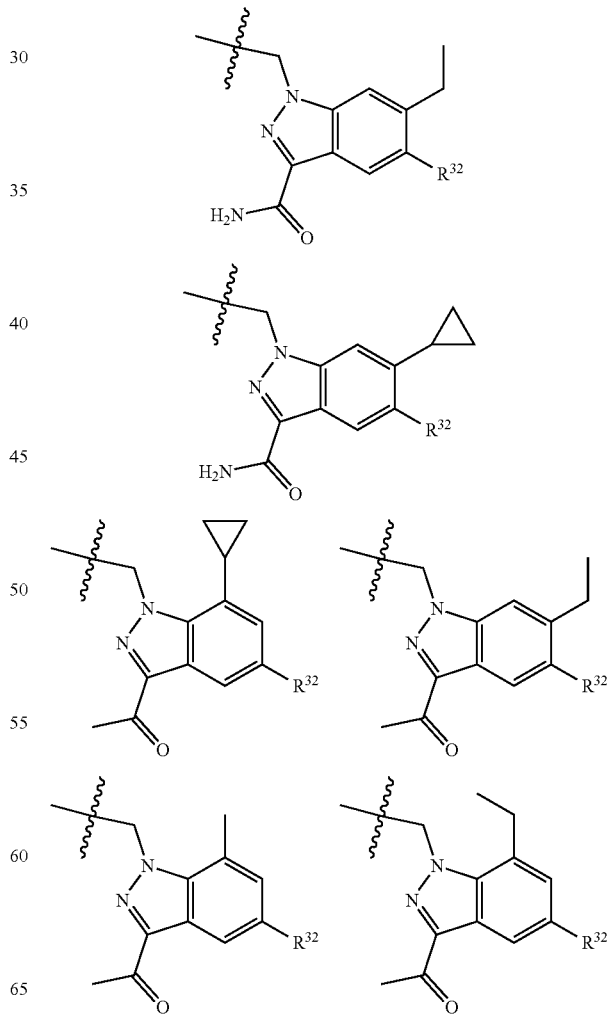

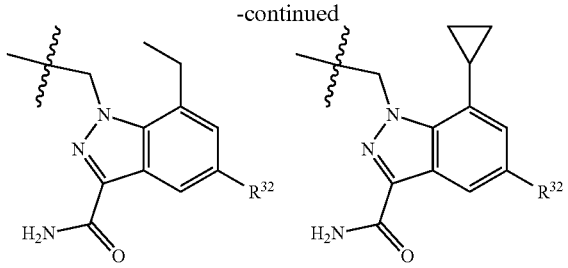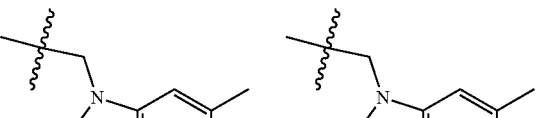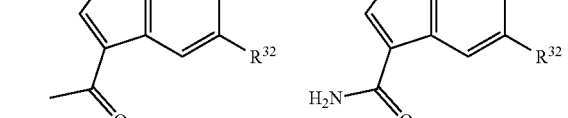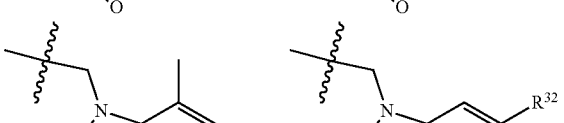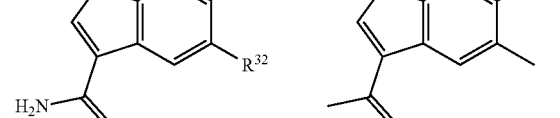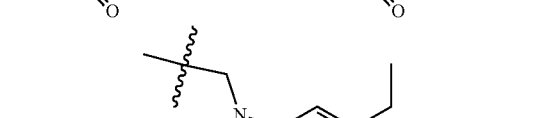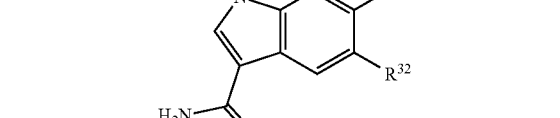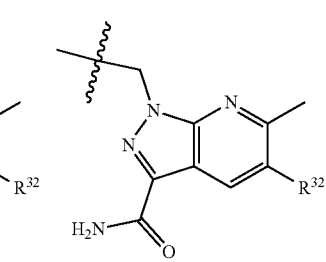
, and
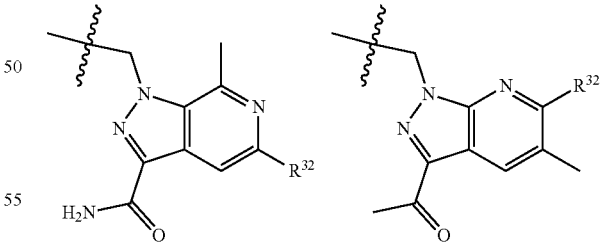
In another embodiment A1 is selected from:
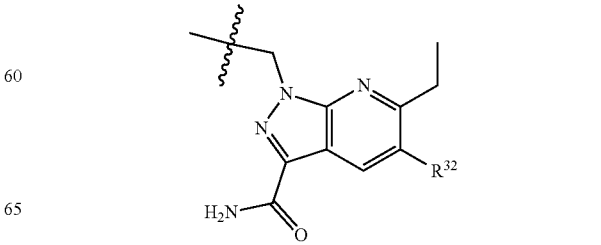

-continued
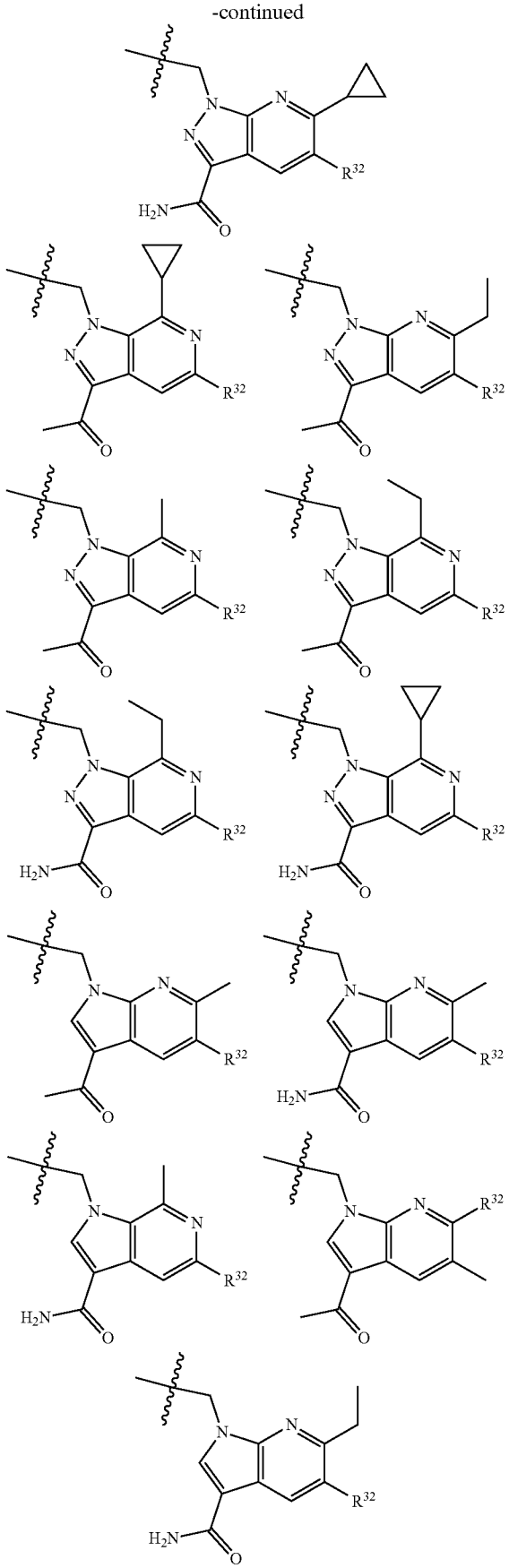
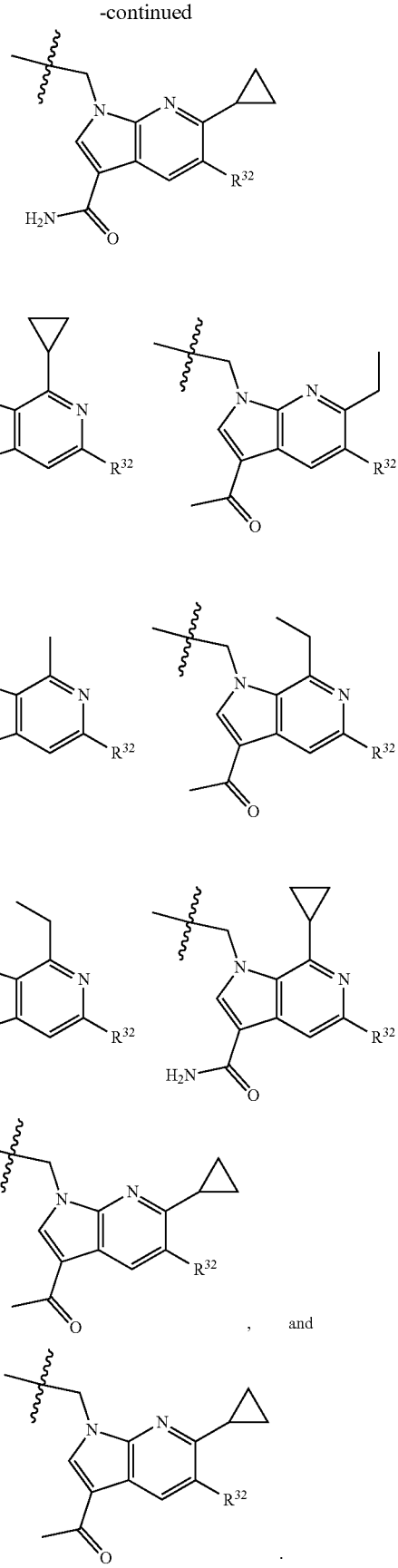

445
Embodiments of B
In one embodiment, B1 is selected from:
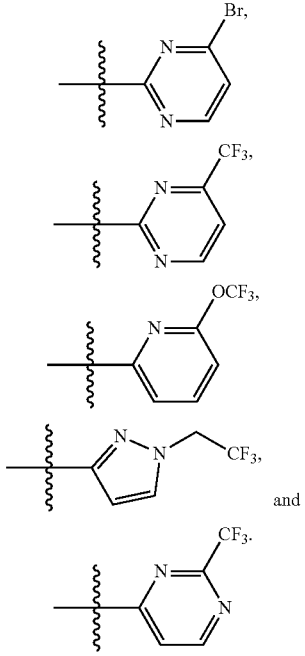
In one embodiment, B1 is selected from:
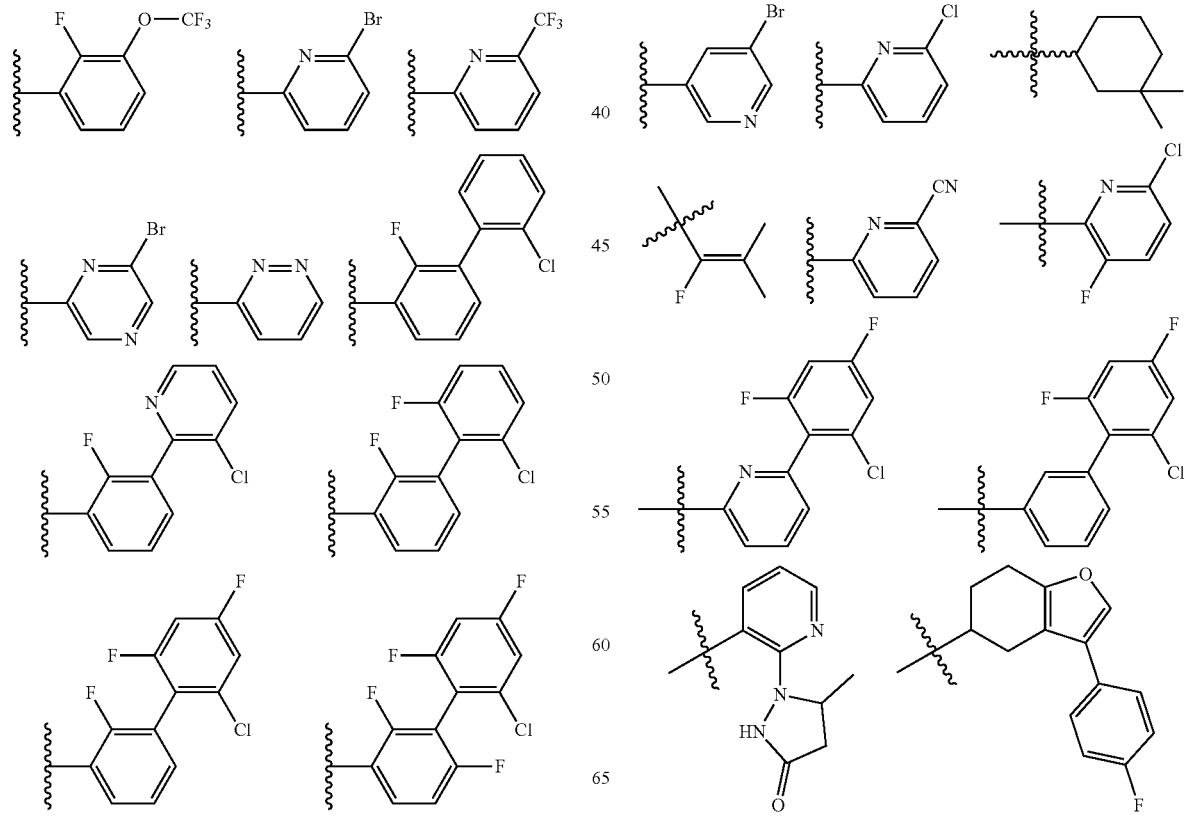
446
-continued
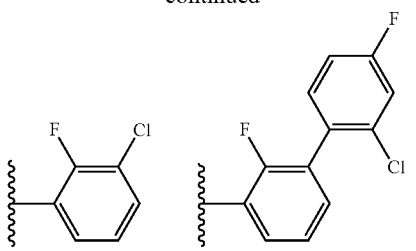
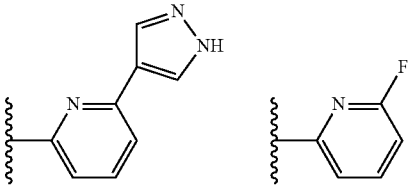
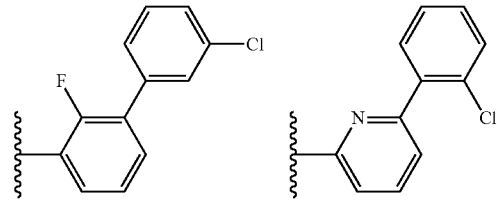
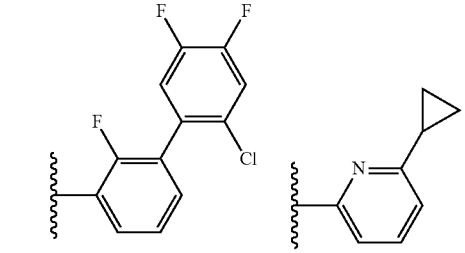
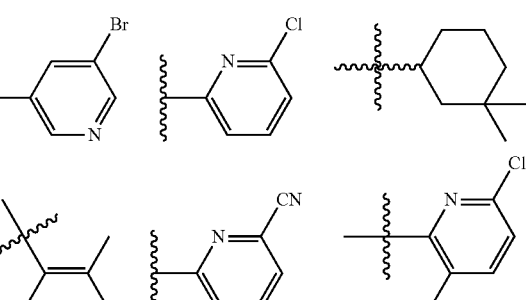
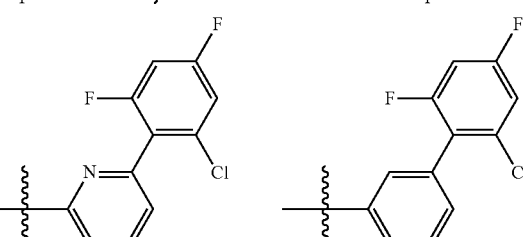
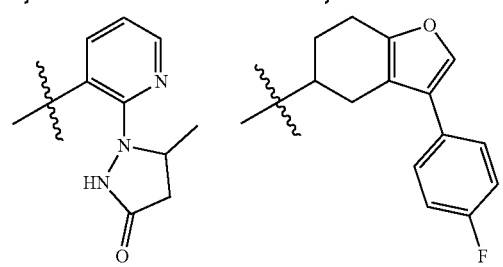

-continued
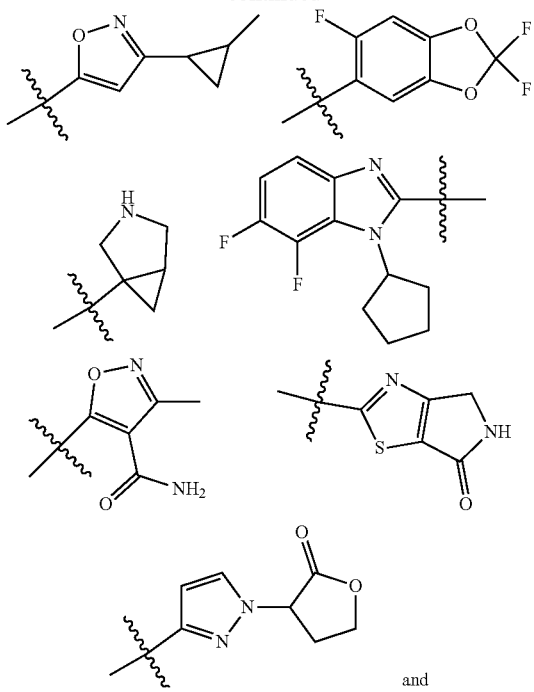
In one embodiment, B1 is selected from:
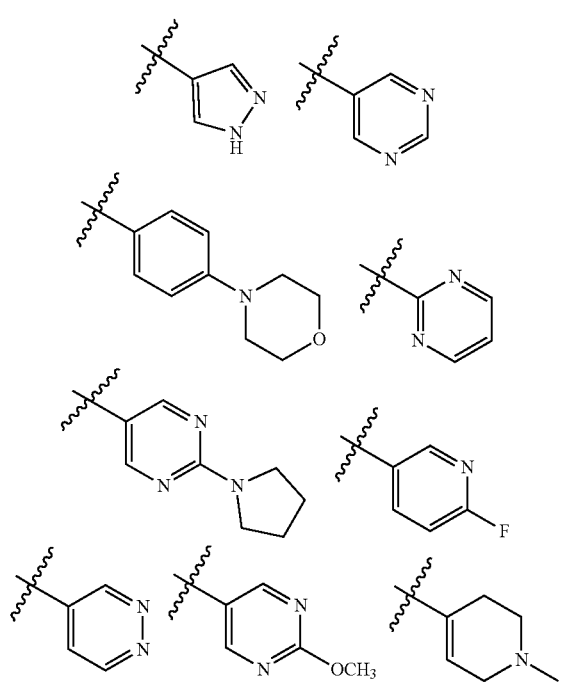
-continued
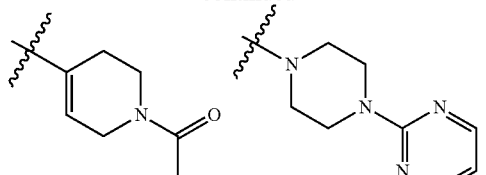
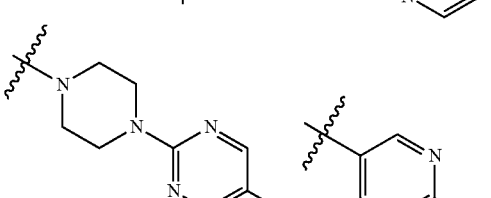
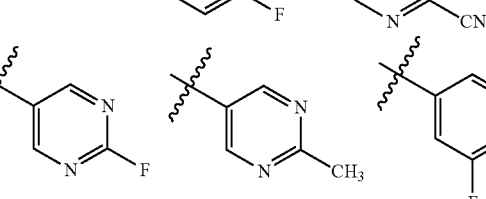
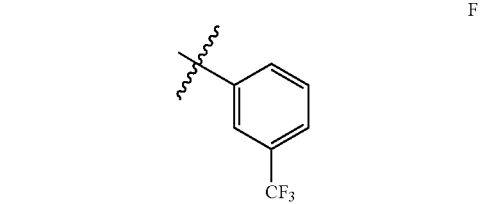
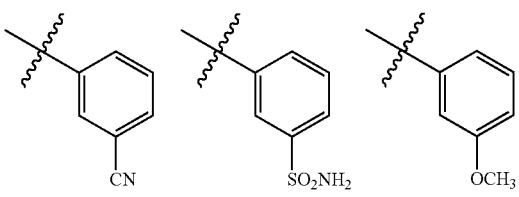
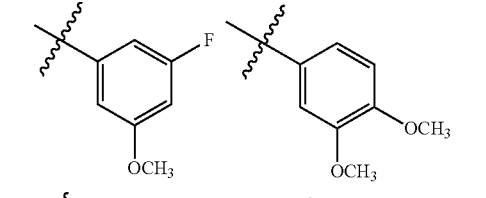
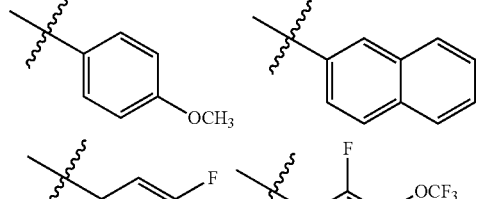
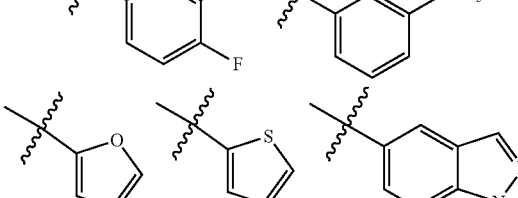
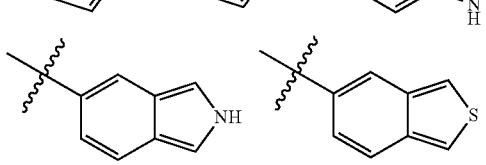

-continued

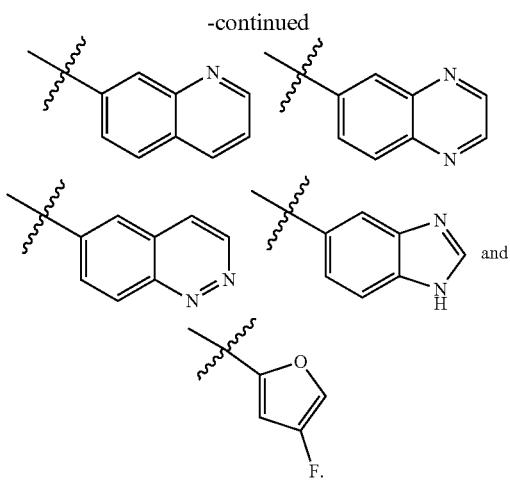

In the below embodiments and throughout the specification $R^{25}$, $R^{26}$, $R^{27}$, $R^{28}$, and $R^{29}$ are independently selected from hydrogen, halogen, $C_1$-$C_3$alkyl, $C_1$-$C_3$haloalkyl, —COOH, cyano, $C_2$-$C_6$alkanoyl, $C_1$-$C_6$alkoxy, —$C_0$-$C_4$alkylNR$^9$R$^{12}$, —$C_0$-$C_4$alkylOR$^{12}$, $C_1$-$C_6$haloalkyl, —SO$_2$R$^{15}$, and $C_1$-$C_6$haloalkoxy.

In one embodiment $R^{25}$, $R^{26}$, $R^{27}$, $R^{28}$, and $R^{29}$ are independently selected from hydrogen, halogen, $C_1$-$C_3$alkyl, and $C_1$-$C_3$haloalkyl.

Examples of B1 moieties include, but are not limited to

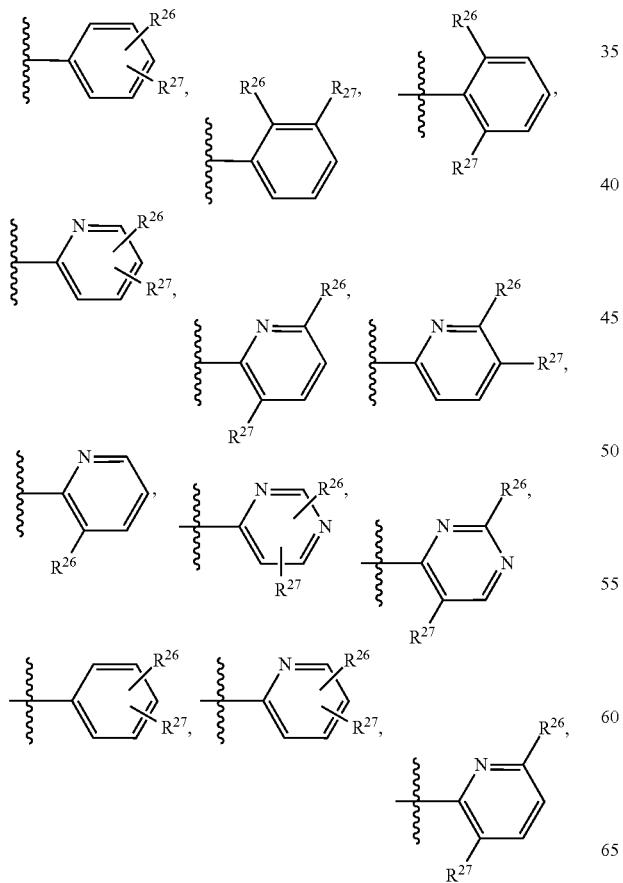

-continued

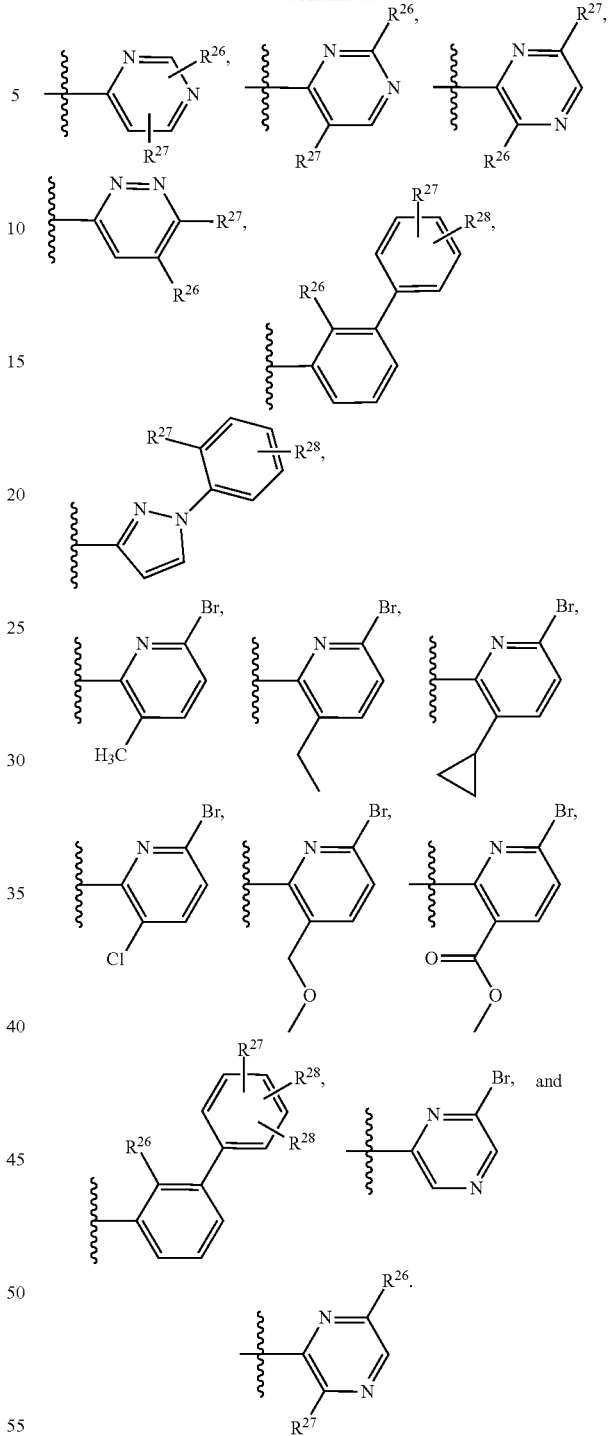

In one embodiment, B1 is selected from:

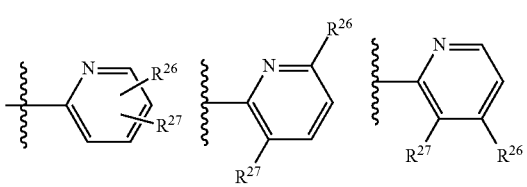

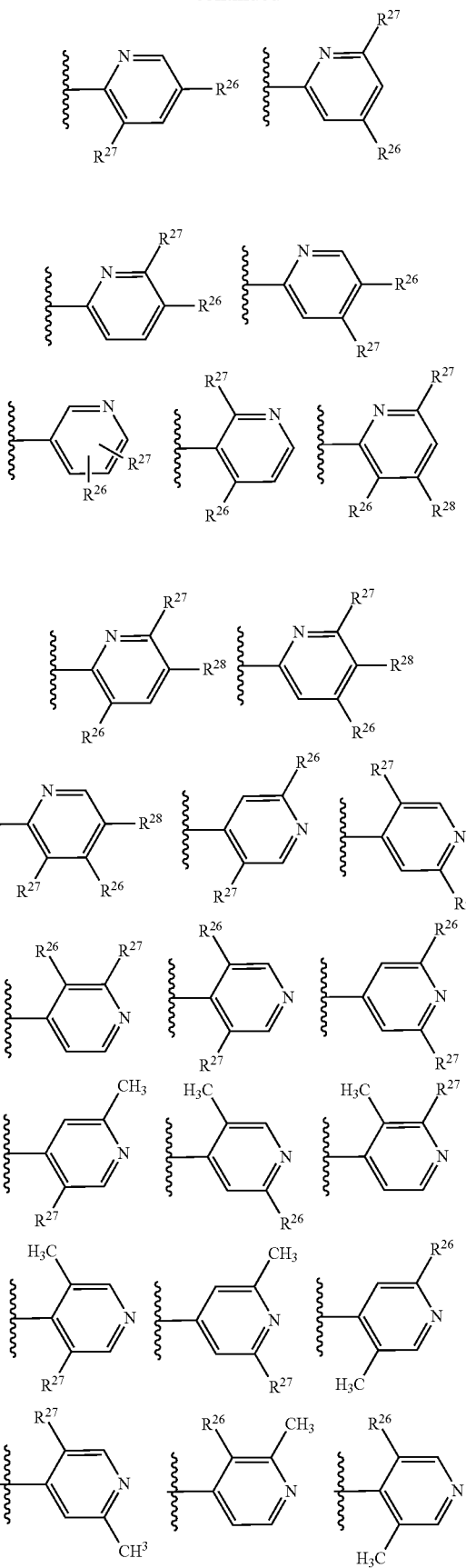
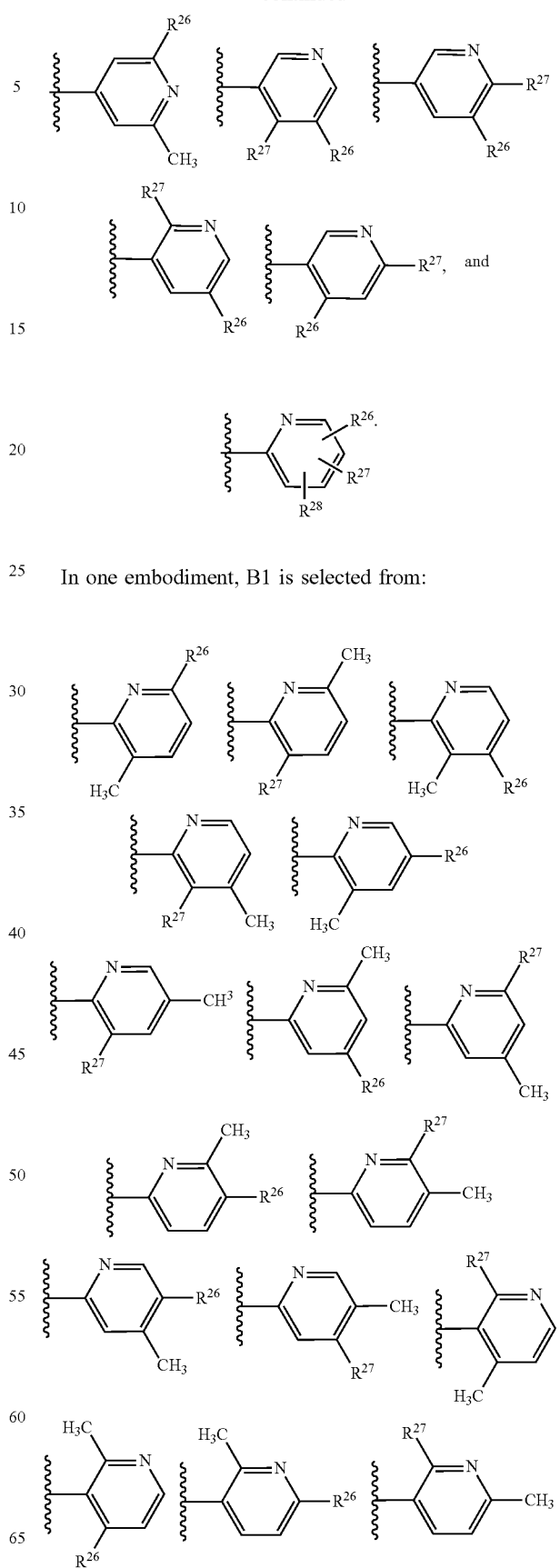
In one embodiment, B1 is selected from:

-continued

In one embodiment, B1 is selected from:

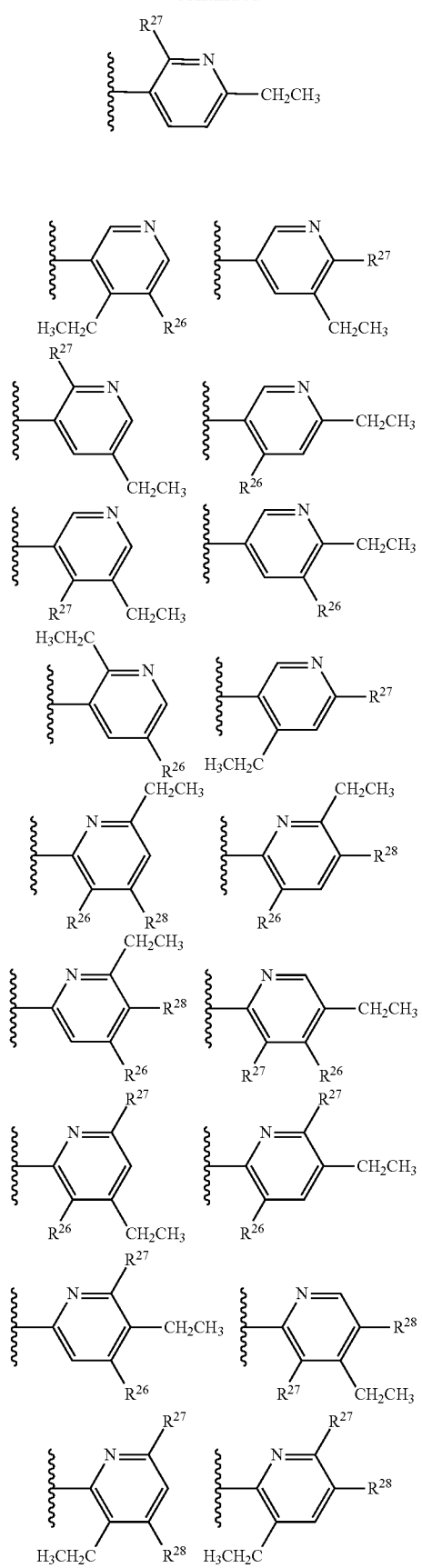
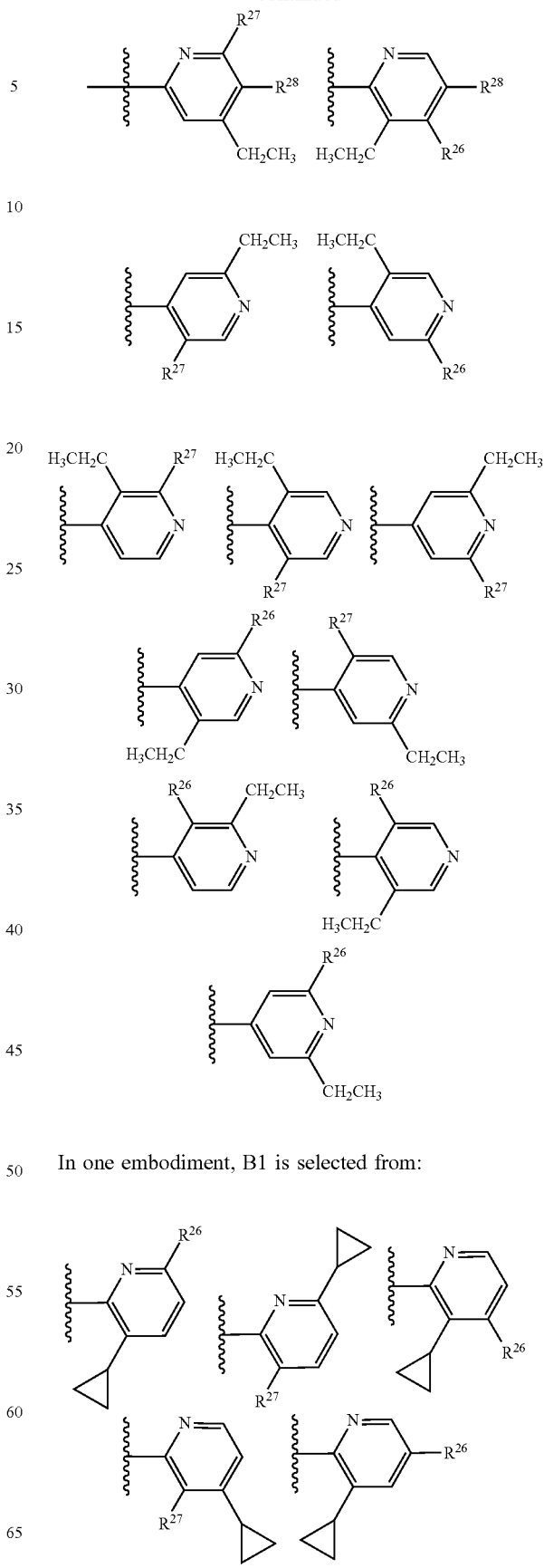
In one embodiment, B1 is selected from:
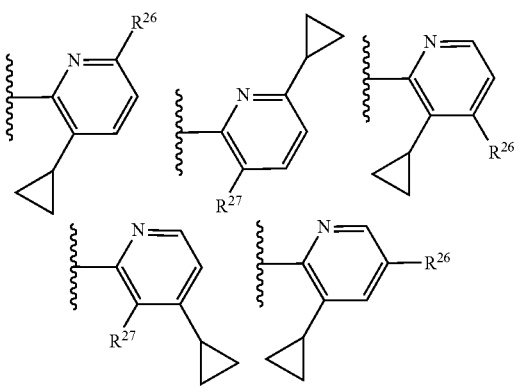

-continued
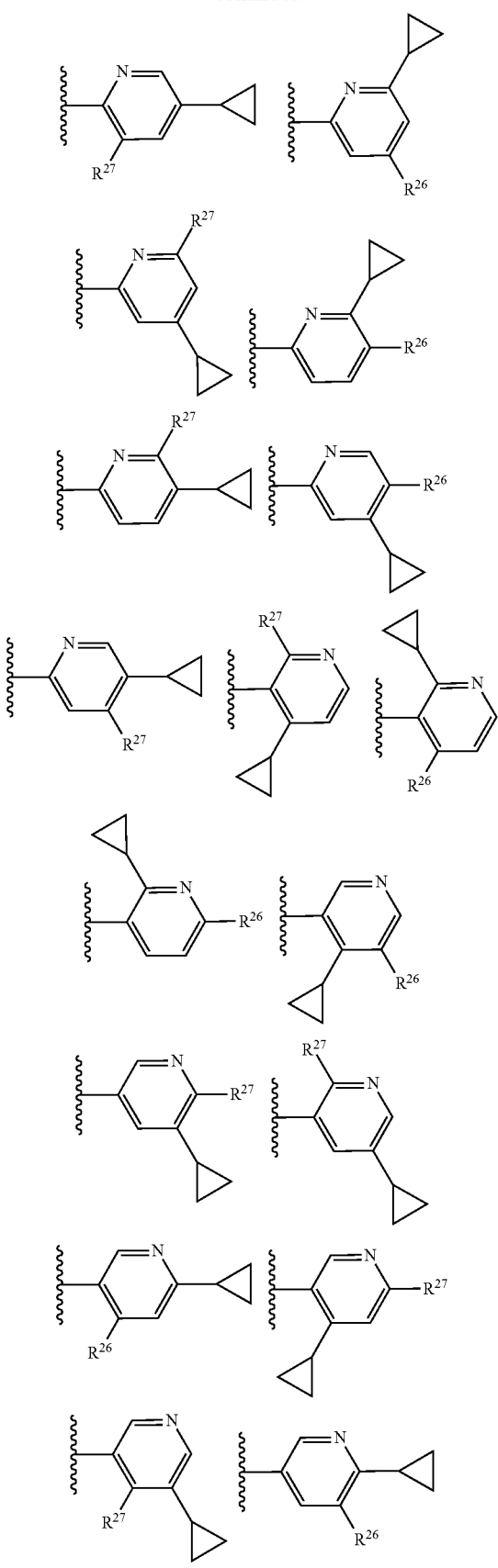
-continued
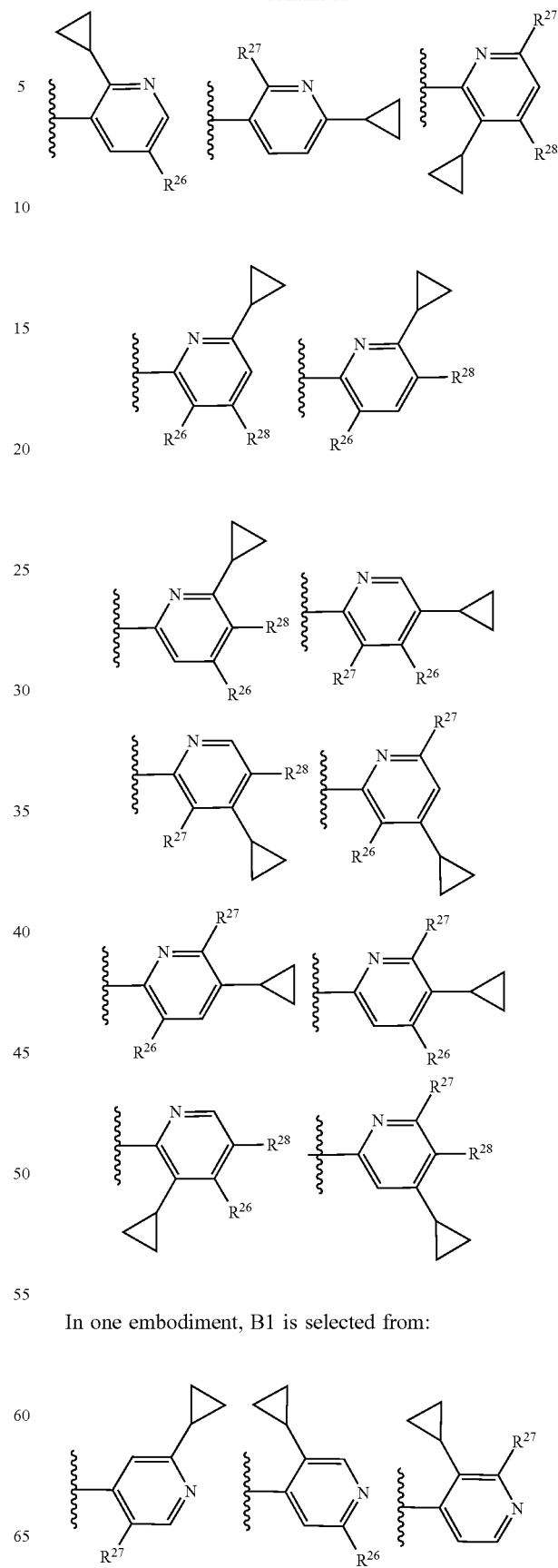
In one embodiment, B1 is selected from:
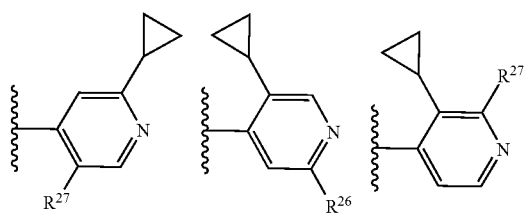

-continued
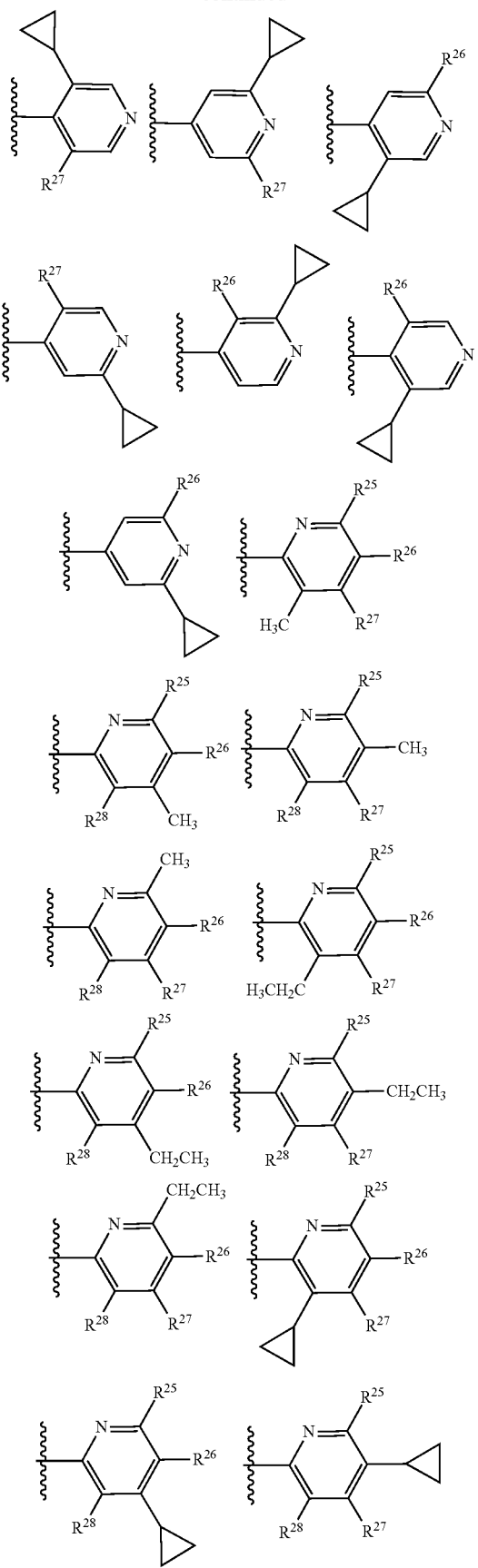
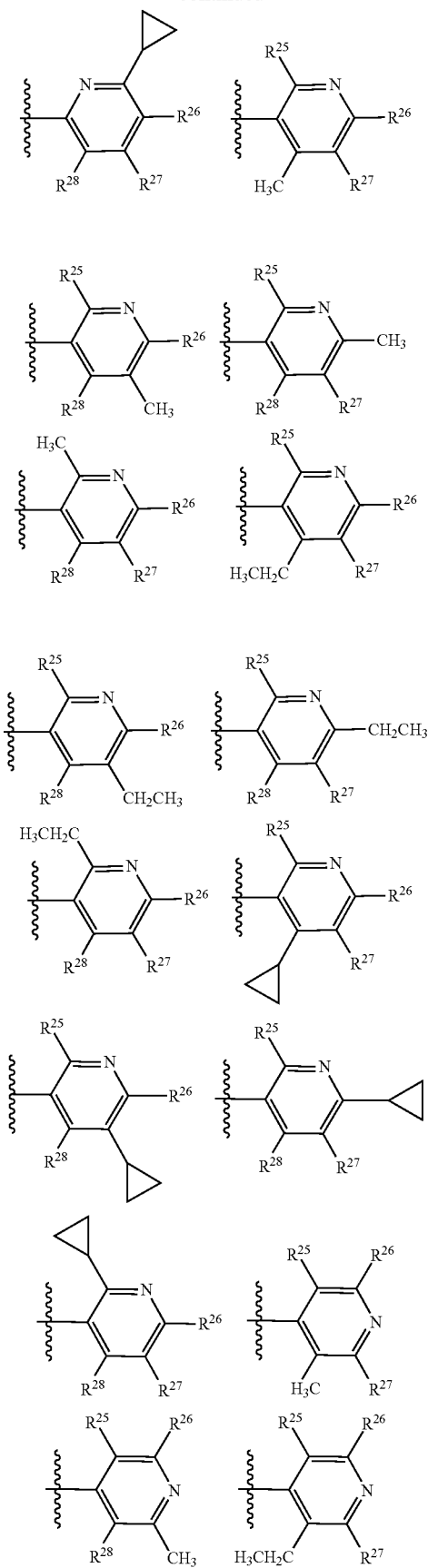

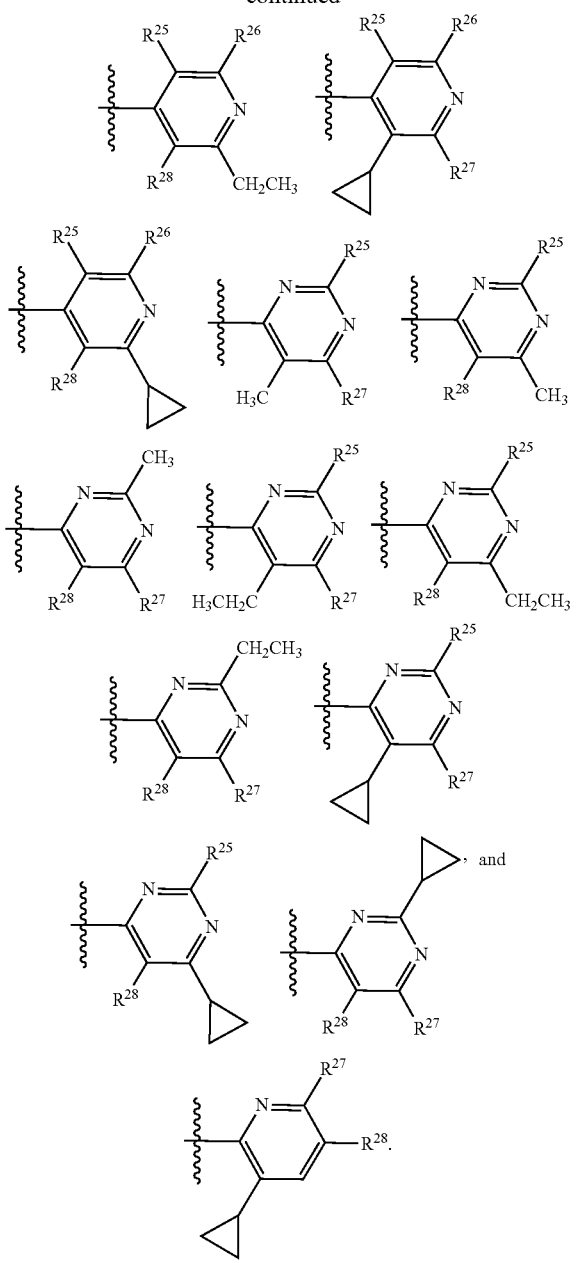
In one embodiment, B1 is selected from:
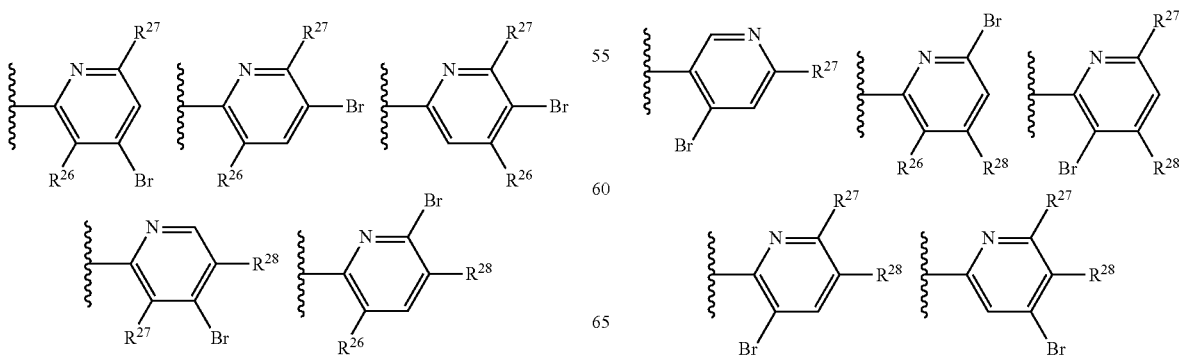

-continued
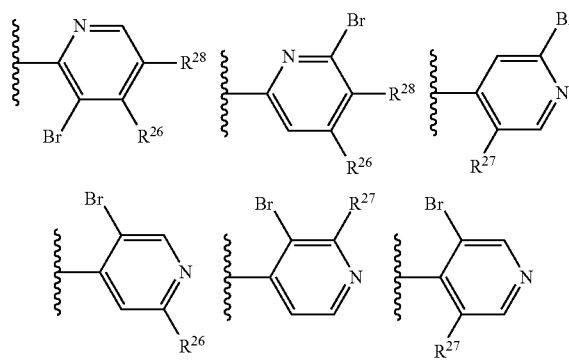
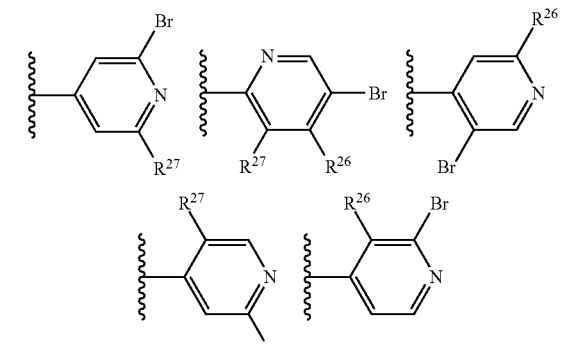
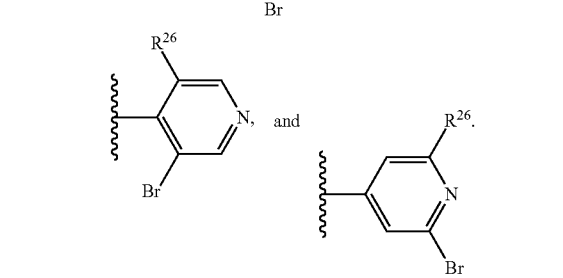
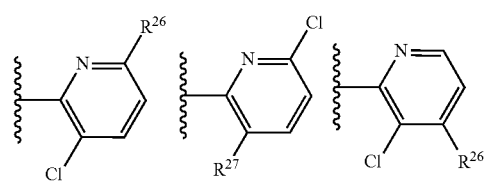
In one embodiment, B1 is selected from:
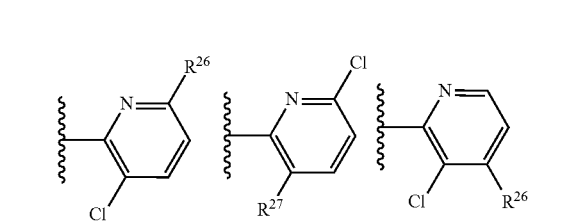
-continued
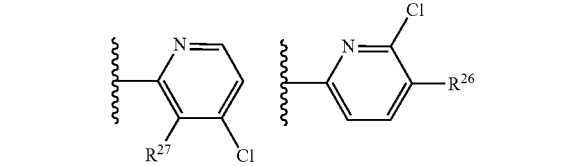
In one embodiment, B1 is selected from:
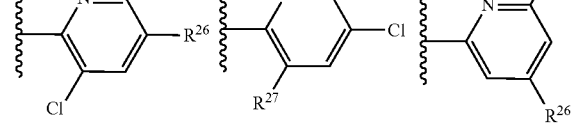

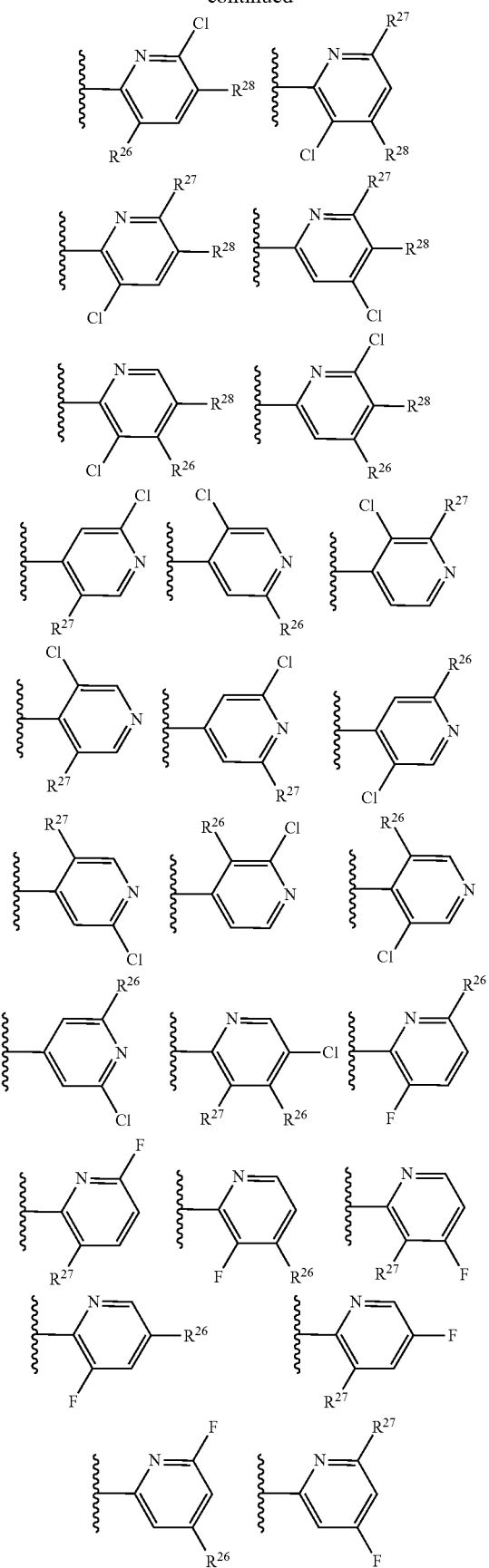
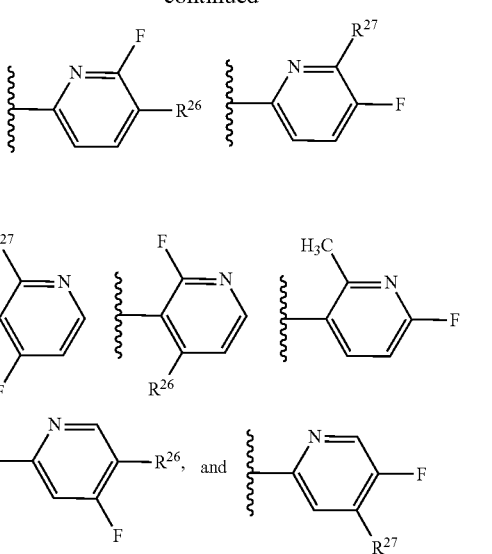
In one embodiment, B1 is selected from:
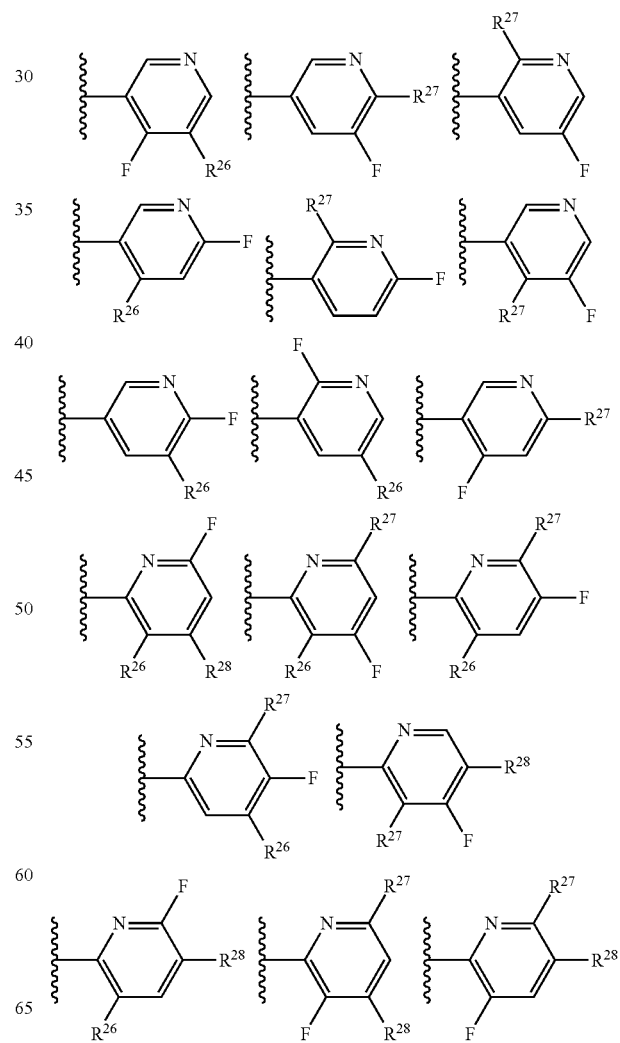

-continued
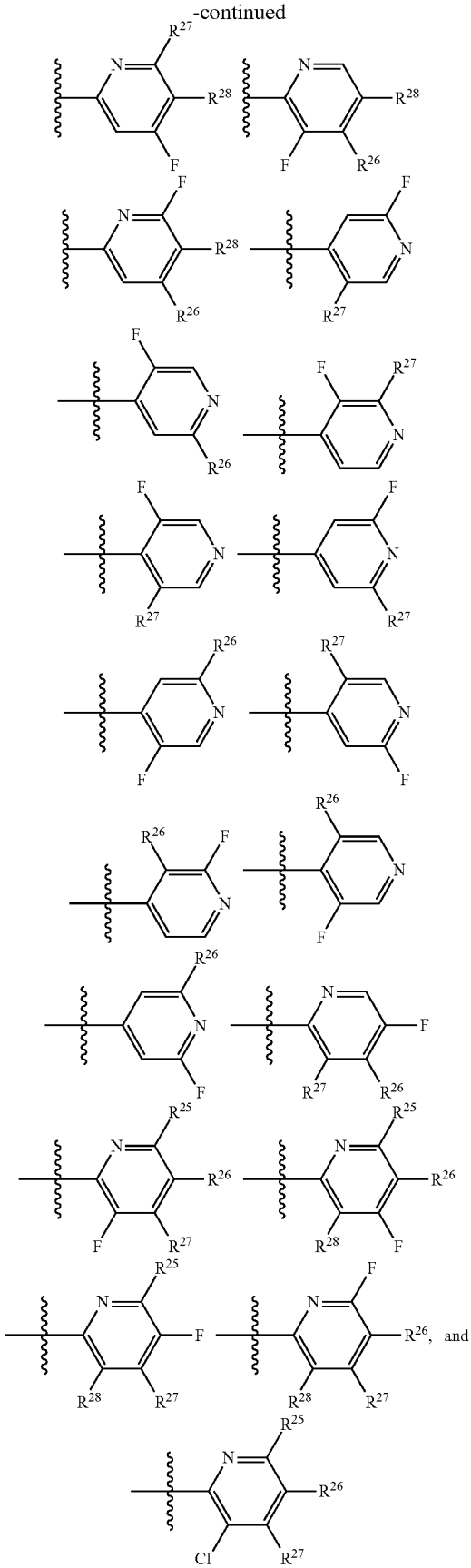
In one embodiment, B1 is selected from:
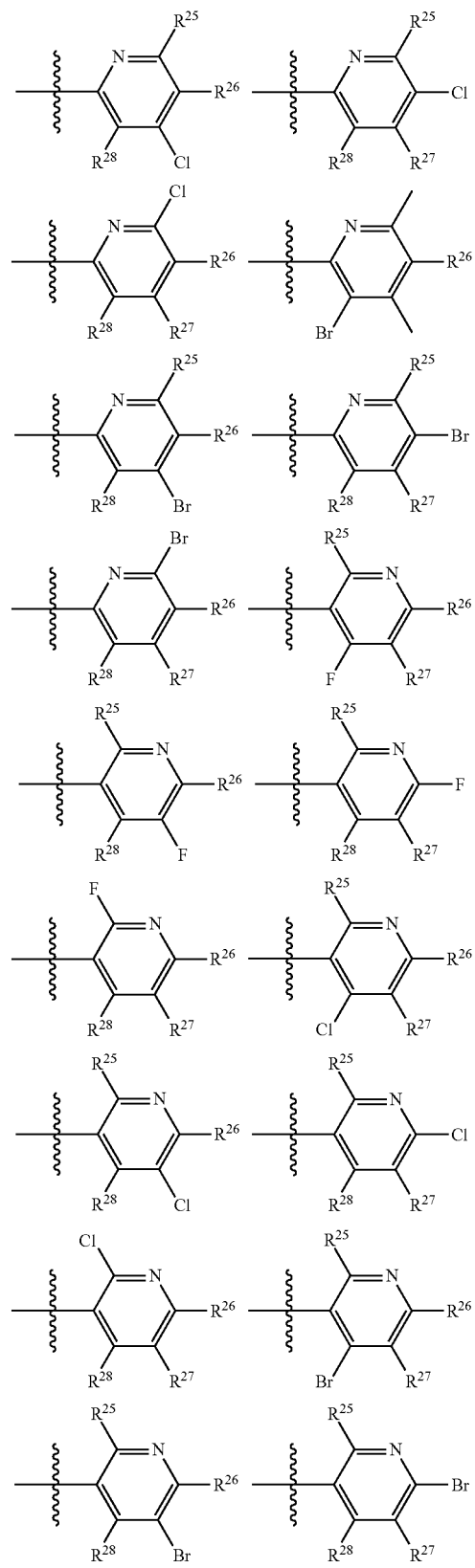

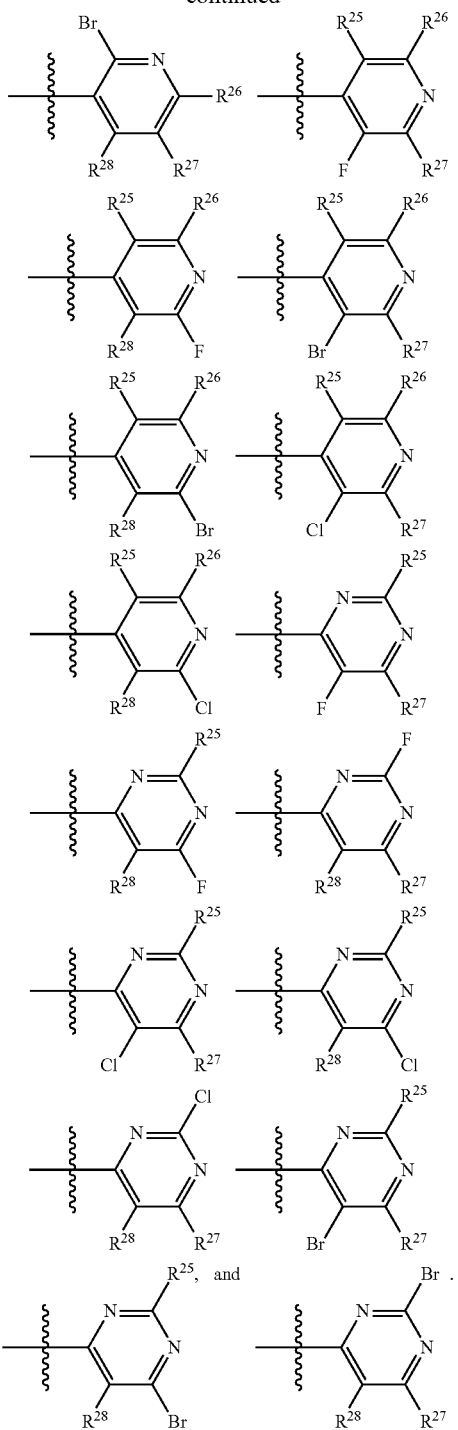
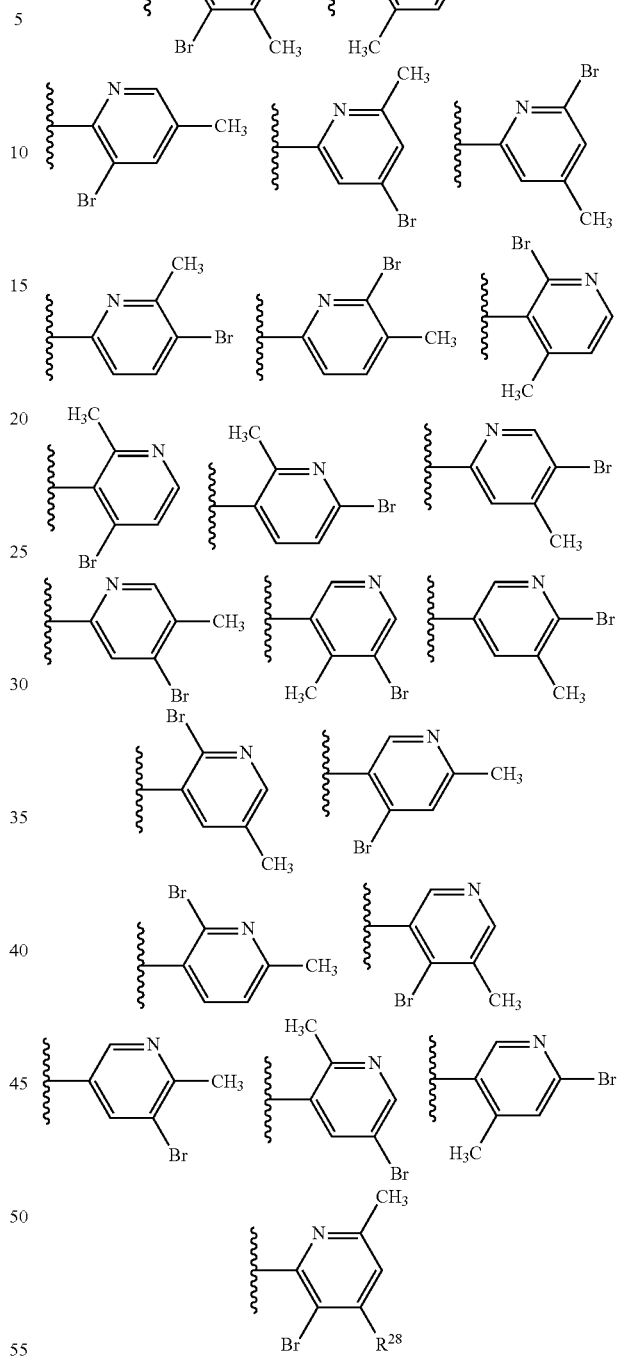
In one embodiment, B1 is selected from:
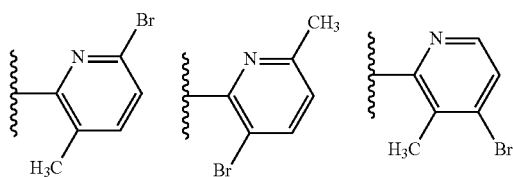
In one embodiment, B1 is selected from:
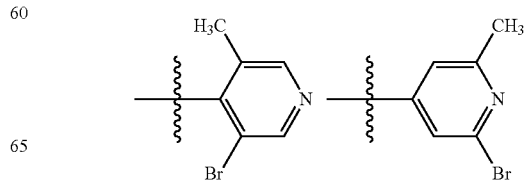

-continued
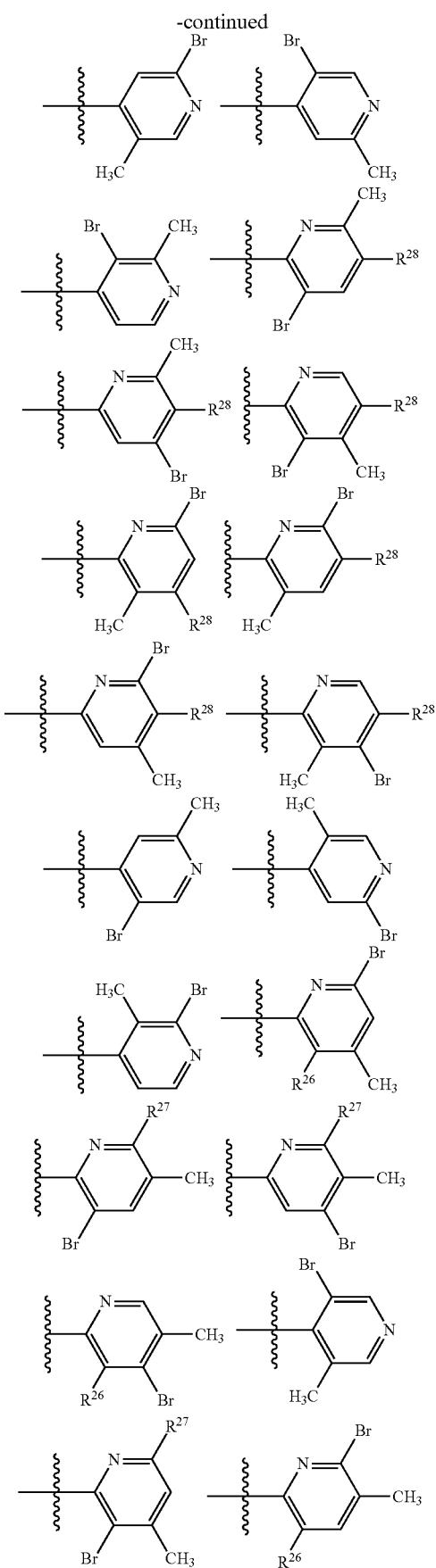
-continued
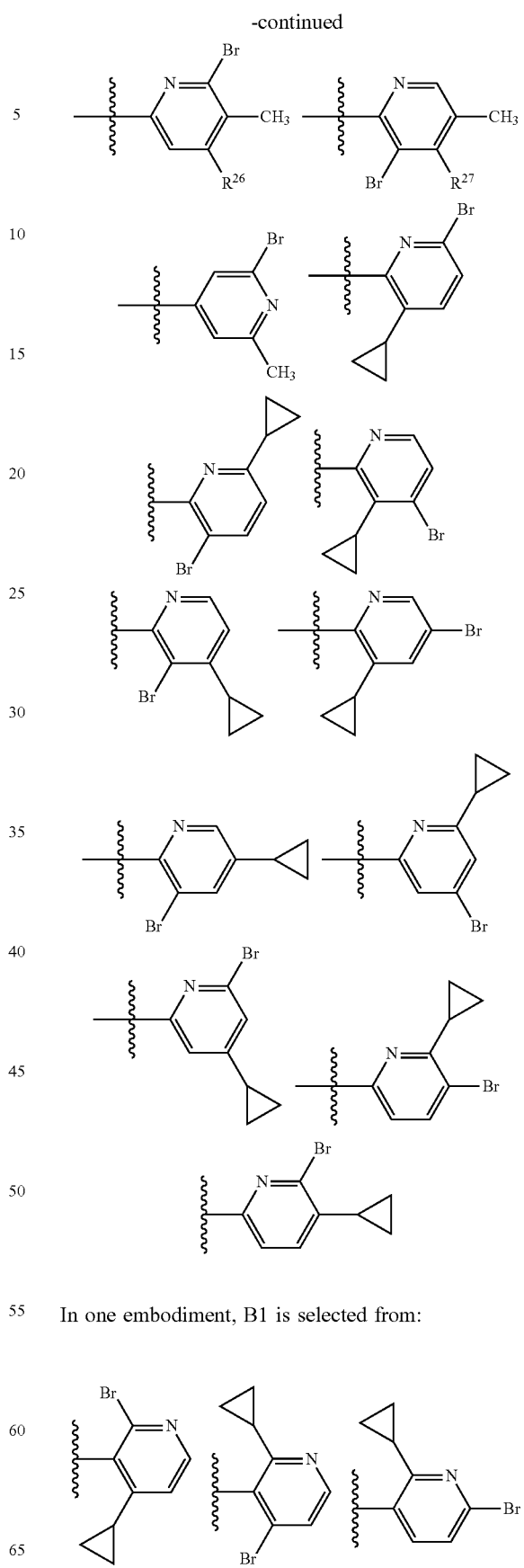
In one embodiment, B1 is selected from:
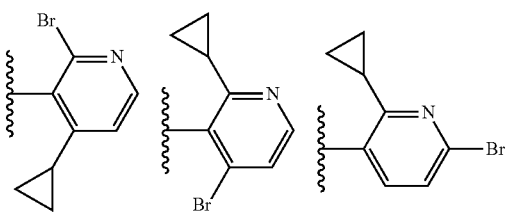

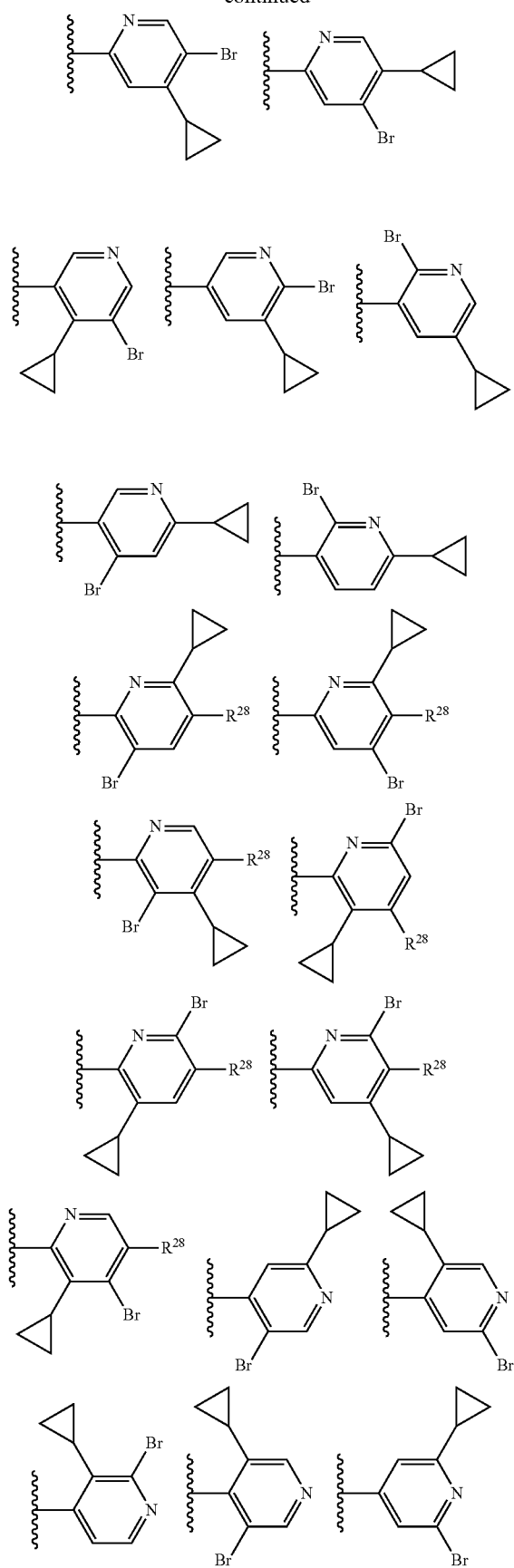
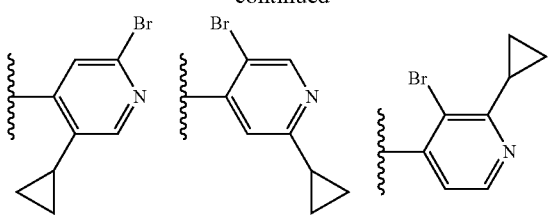
In one embodiment, B1 is selected from:
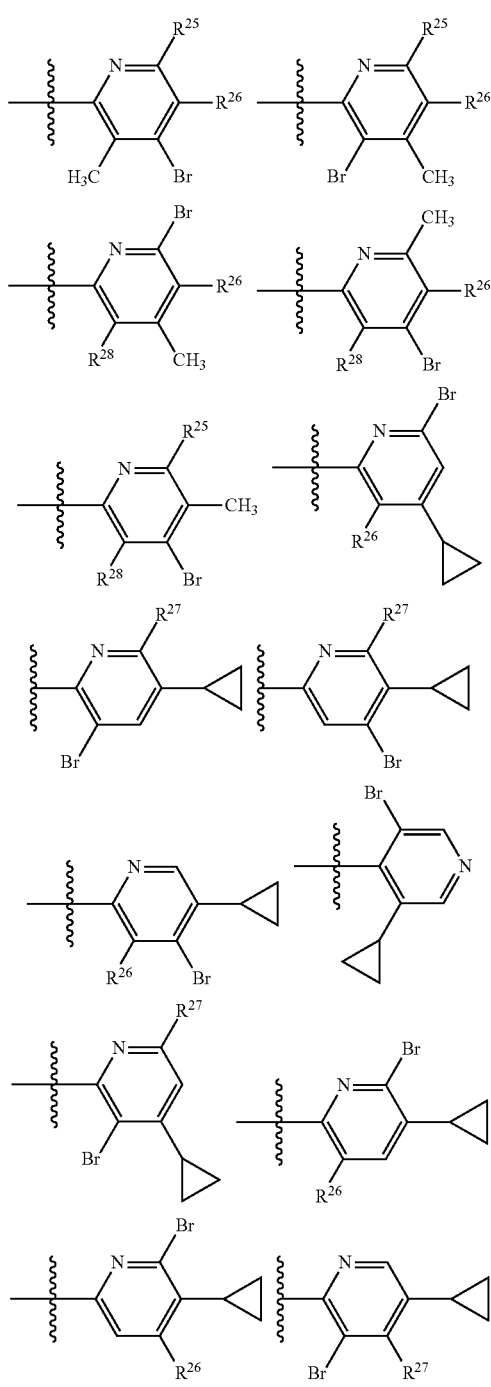

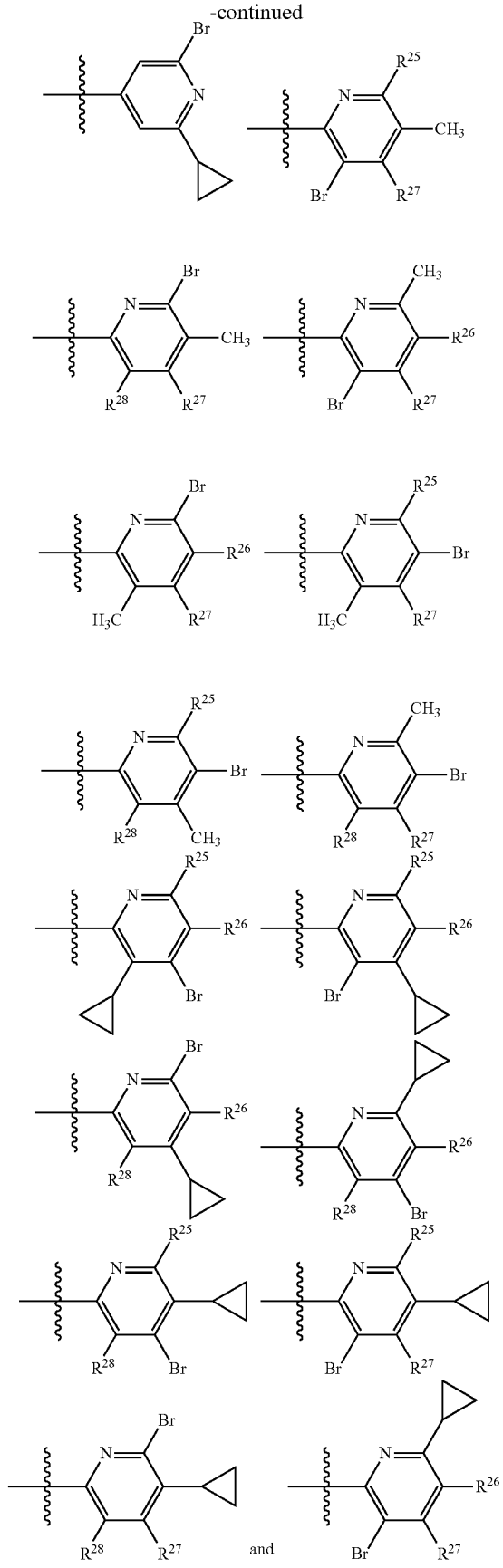
In one embodiment, B1 is selected from:
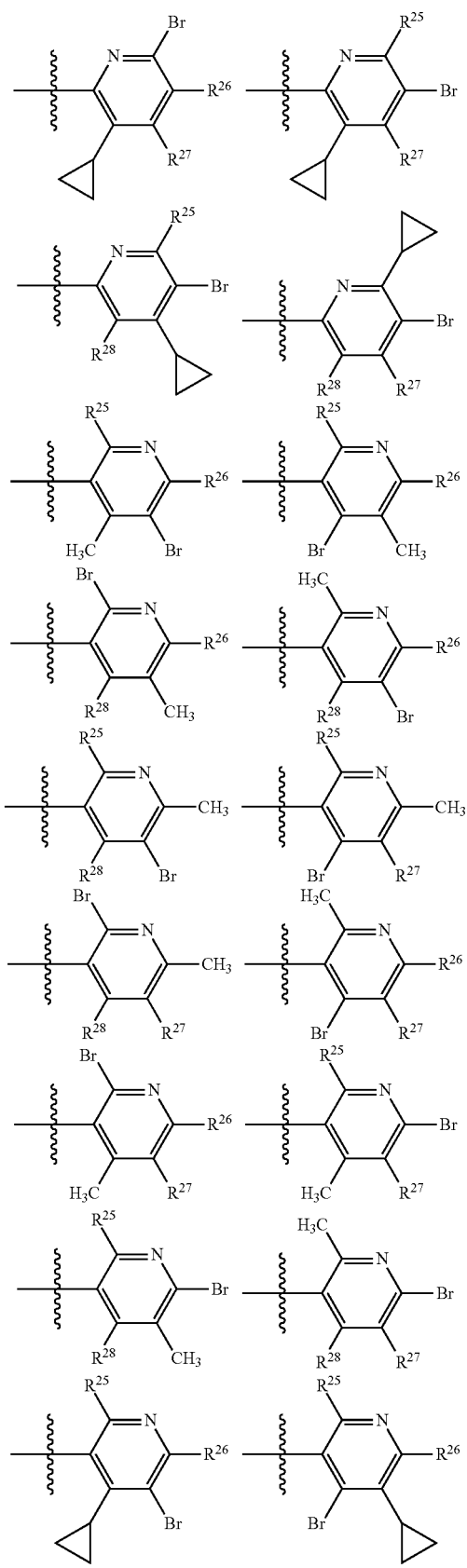

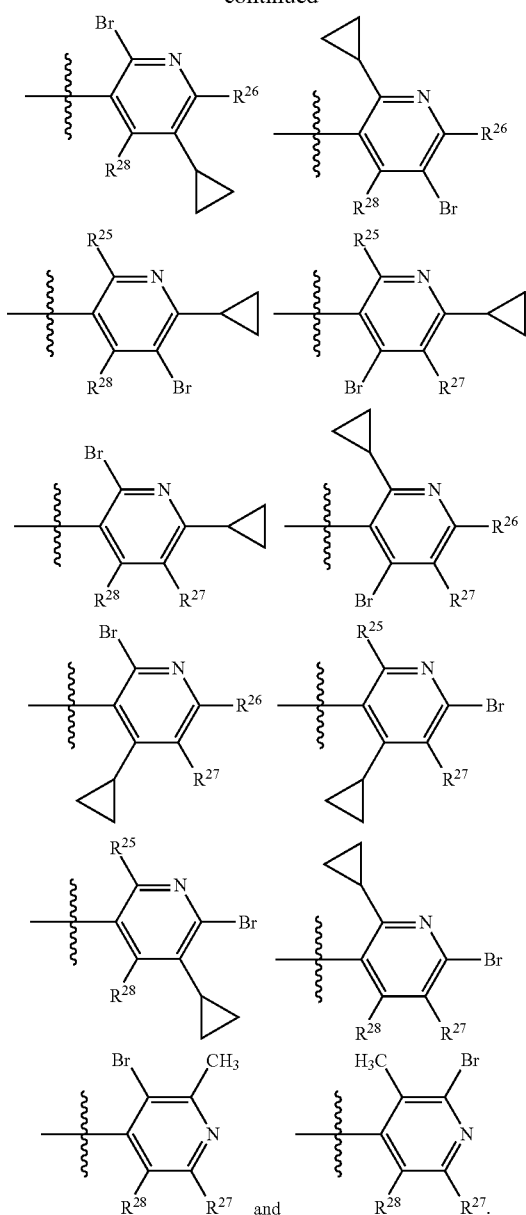
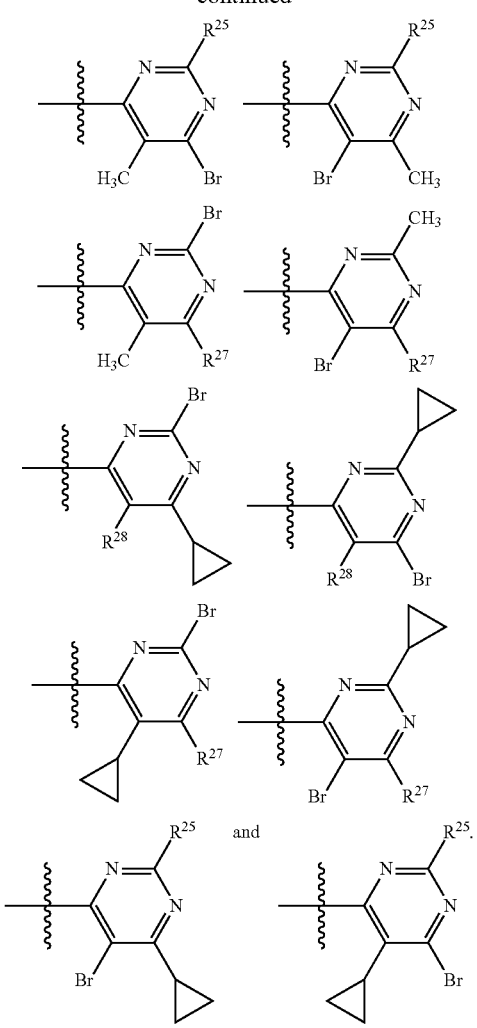
In one embodiment, B1 is selected from:
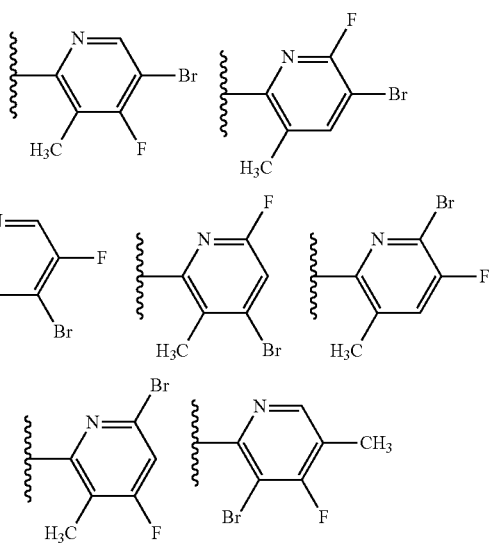
In one embodiment, B1 is selected from:
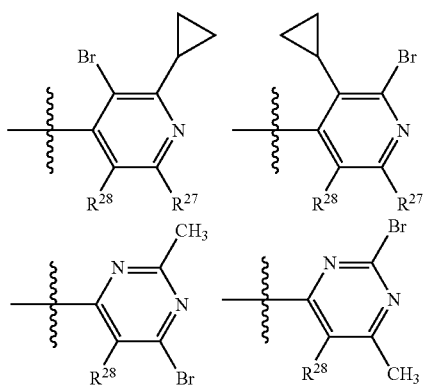

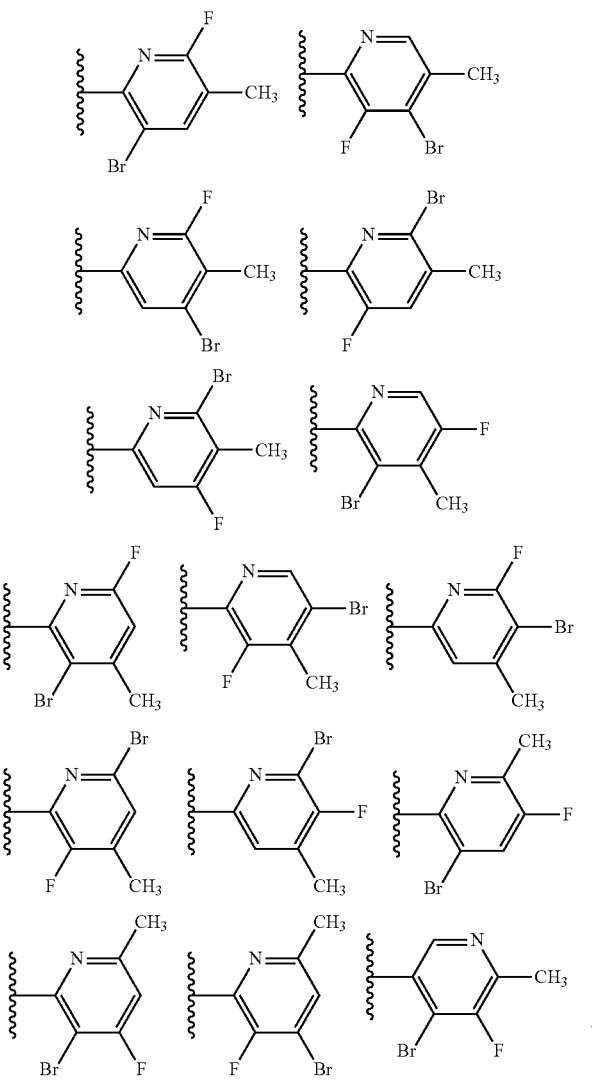
In one embodiment, B1 is selected from:
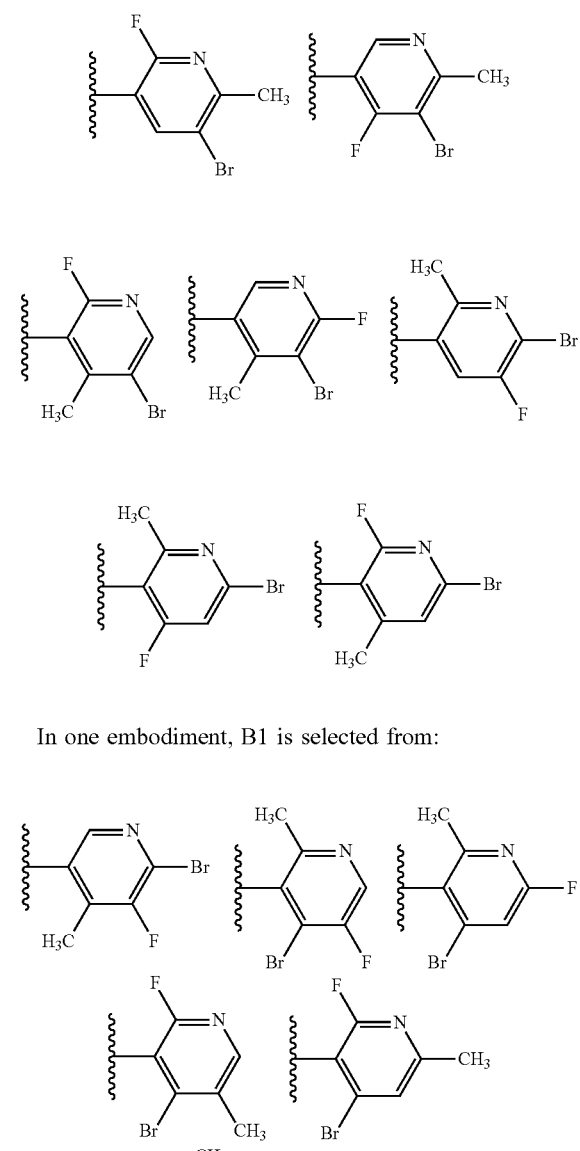
In one embodiment, B1 is selected from:

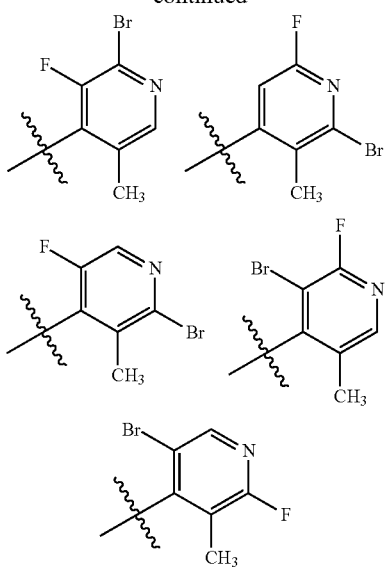
In one embodiment, B1 is selected from:
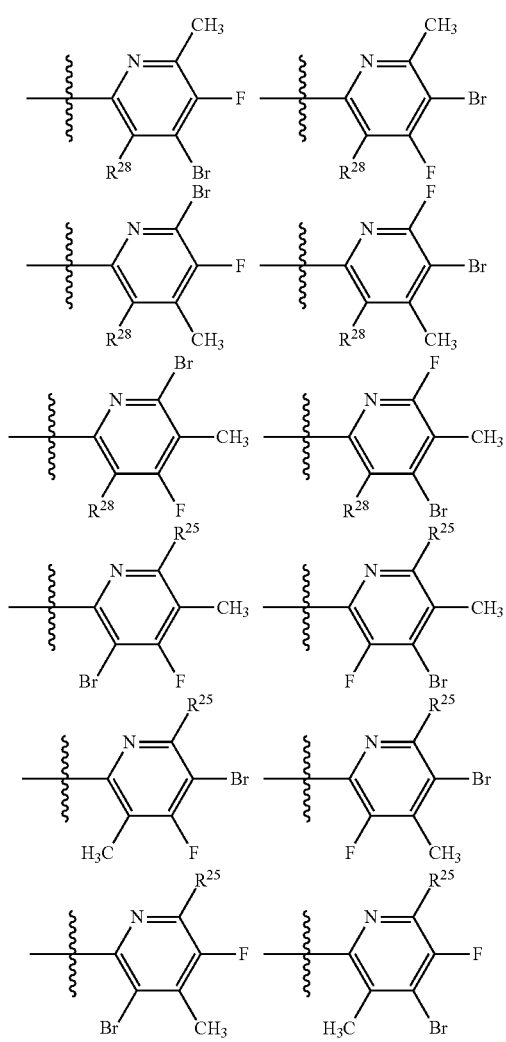
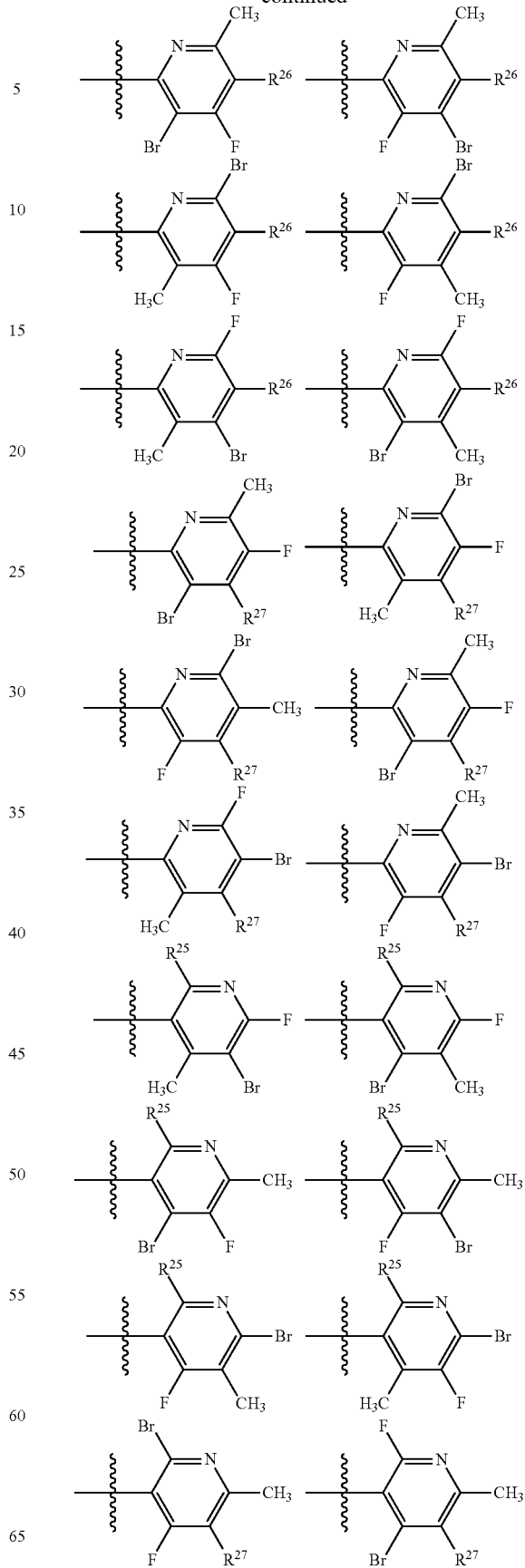

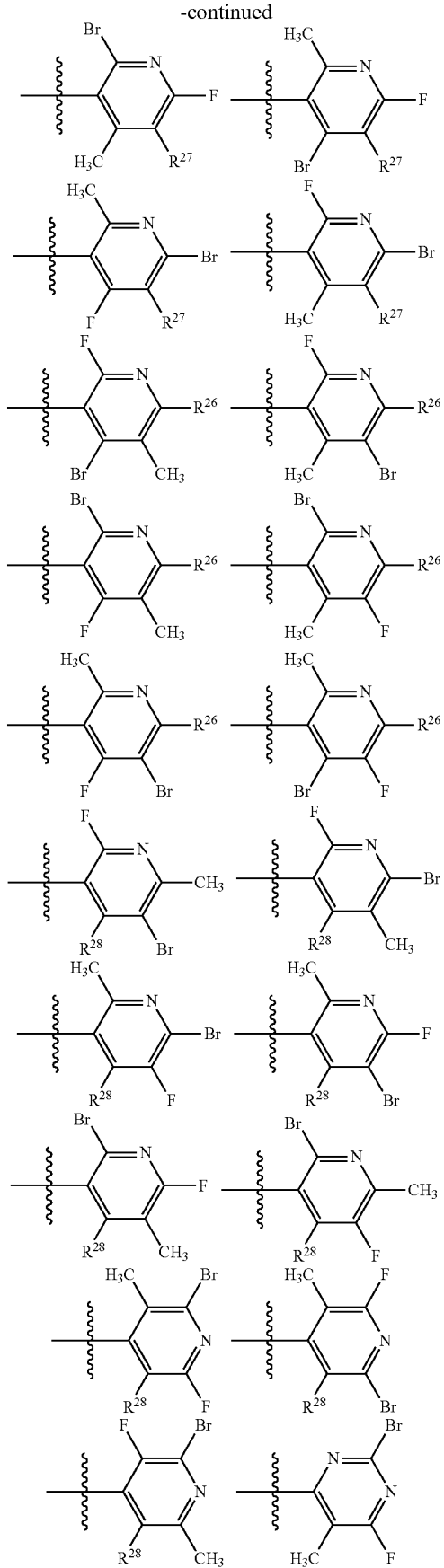
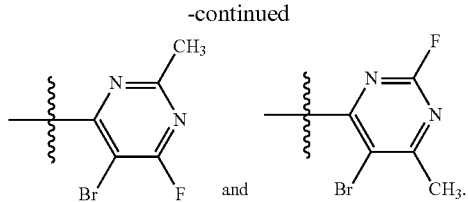
In one embodiment, B1 is selected from:
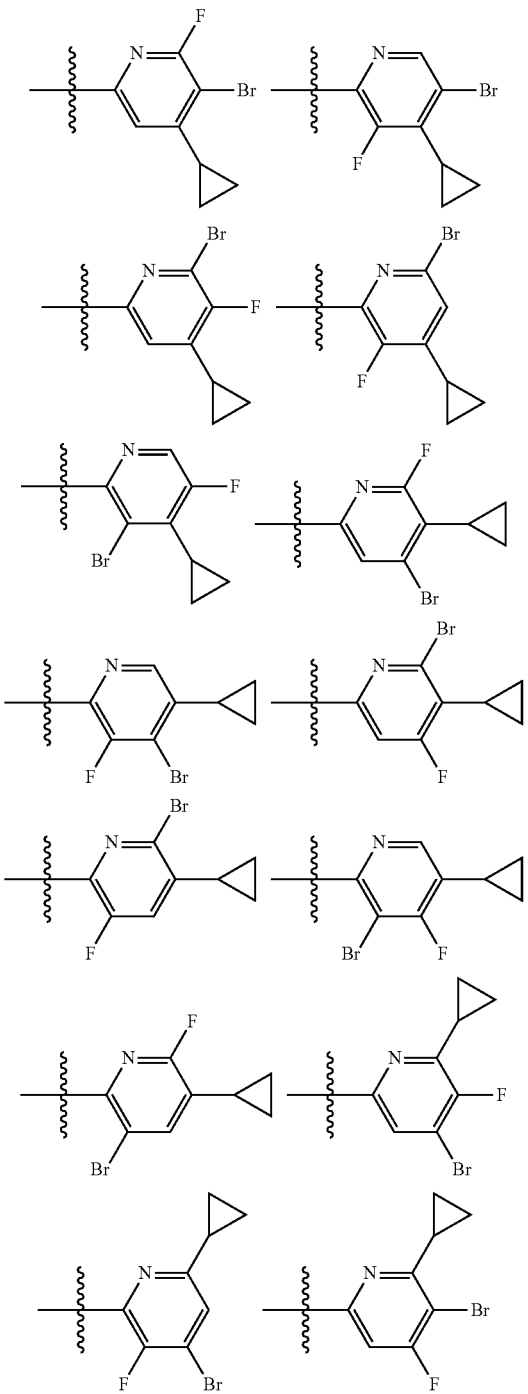

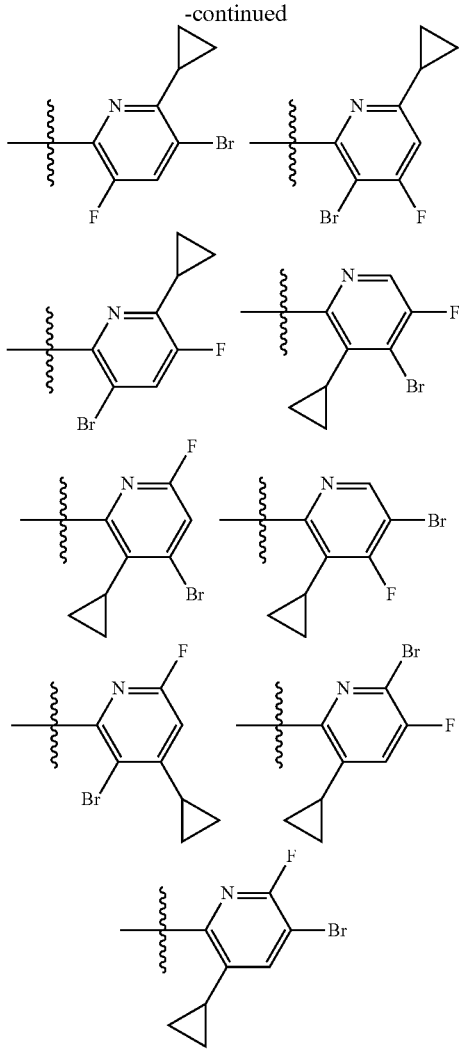
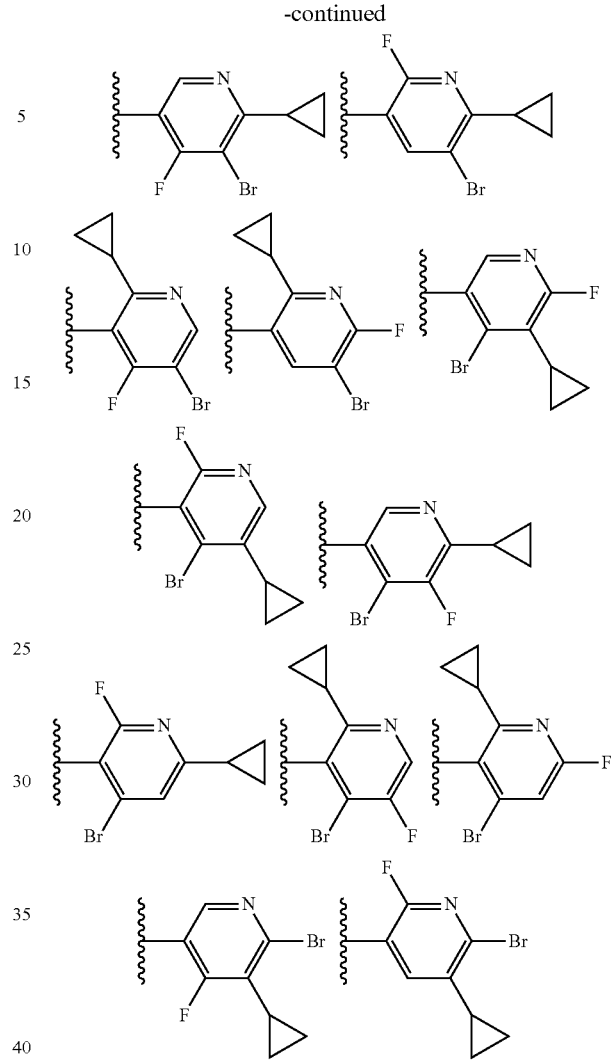
In one embodiment, B1 is selected from:
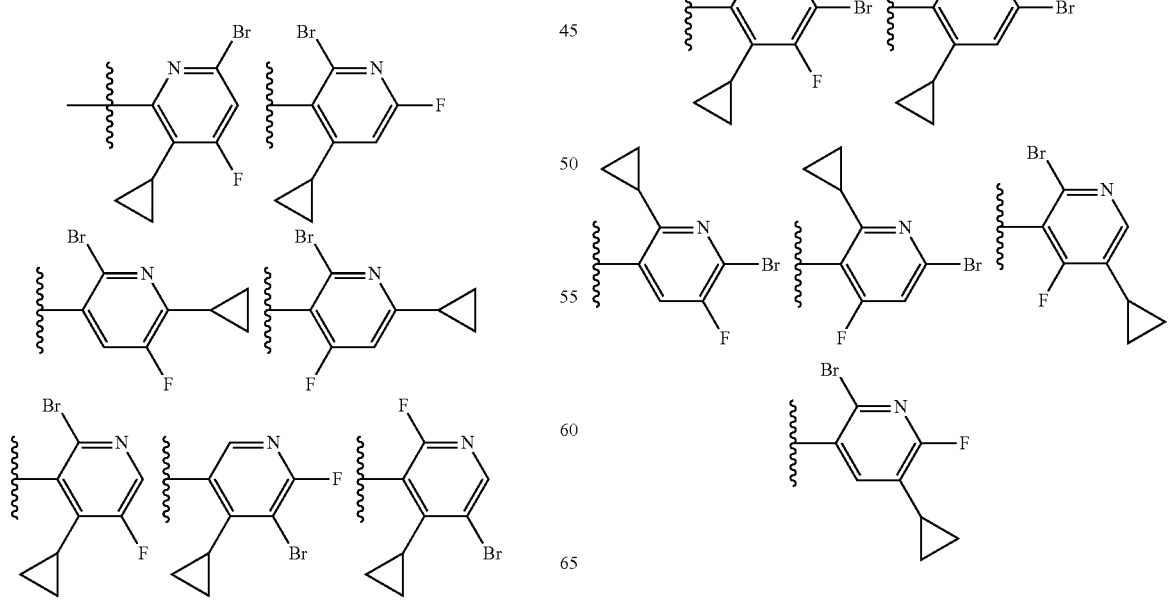

In one embodiment, B1 is selected from:
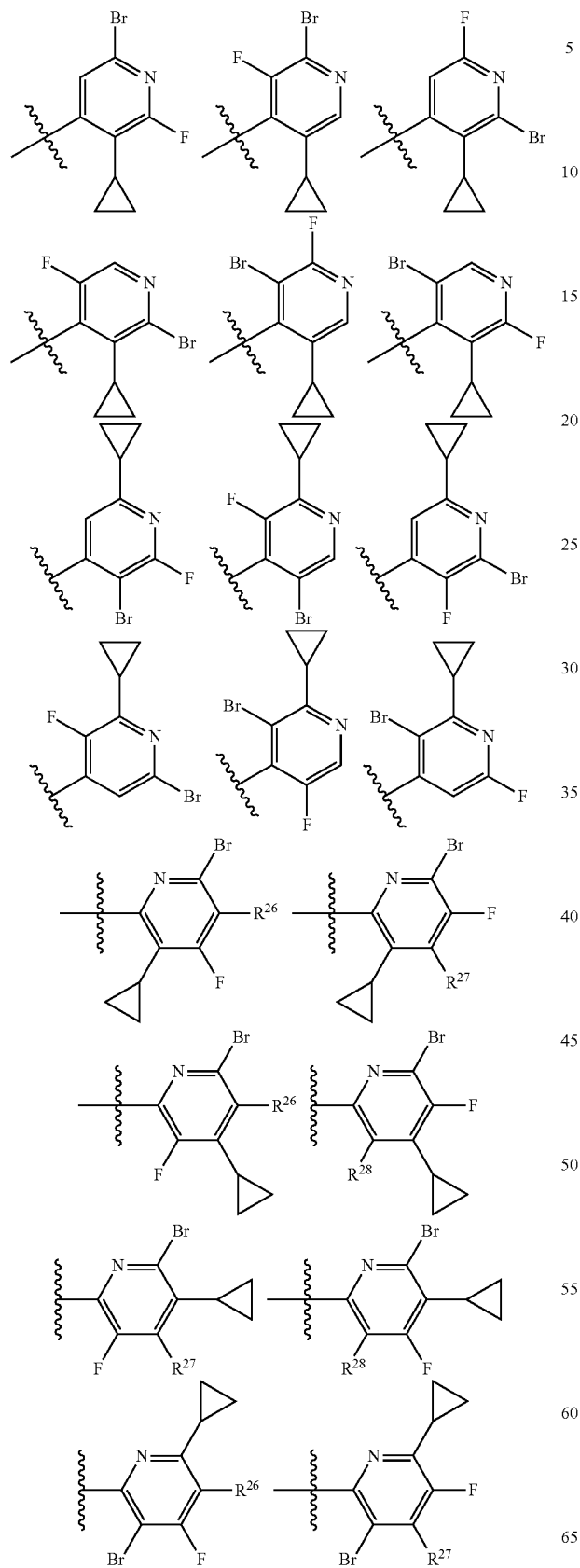
-continued
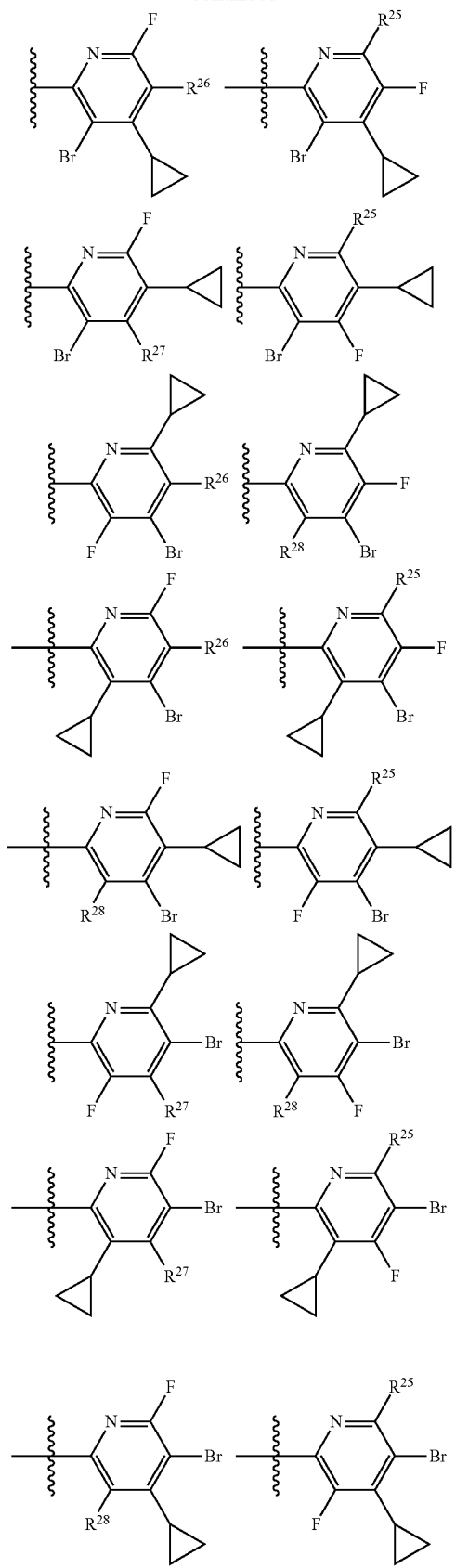

In one embodiment, B1 is selected from:
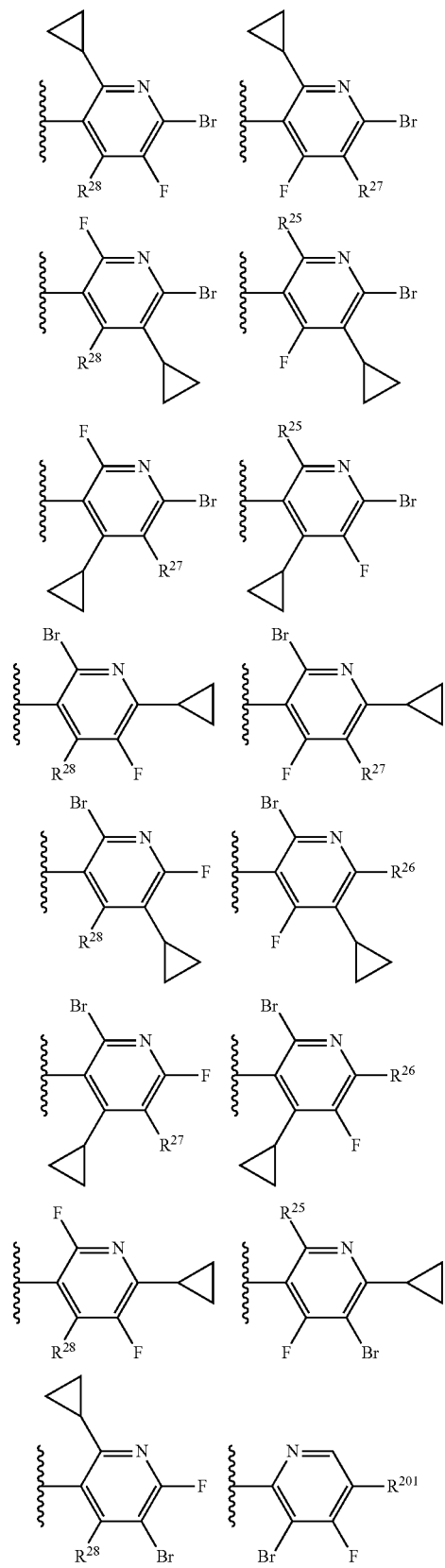
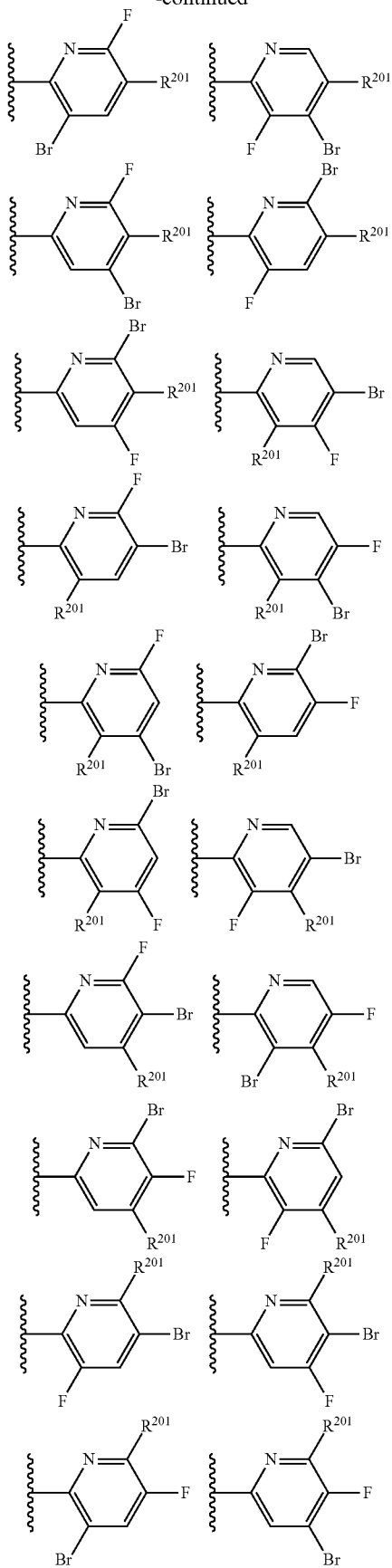

-continued
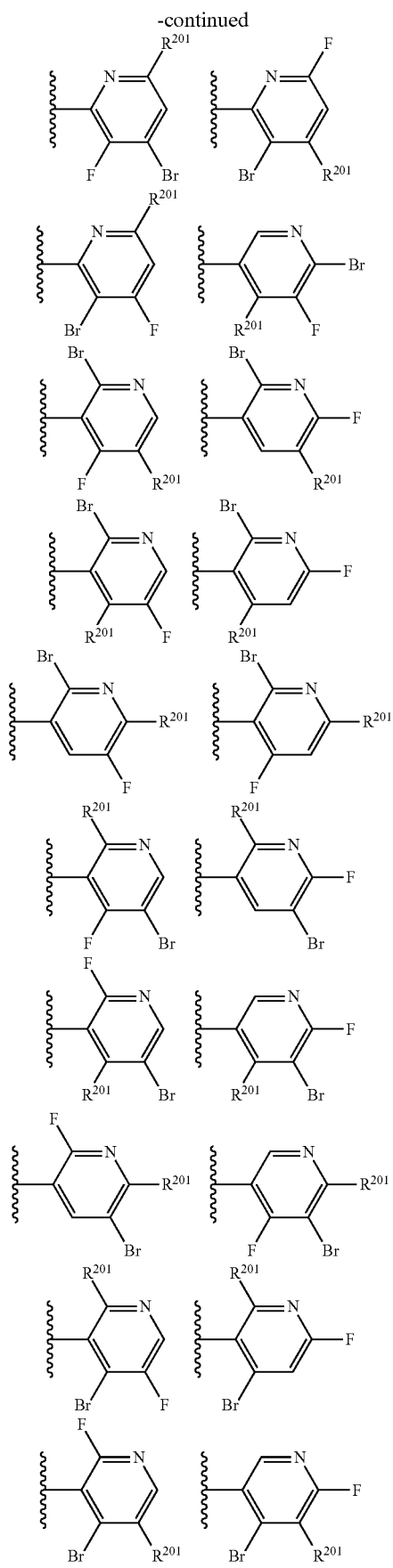
-continued
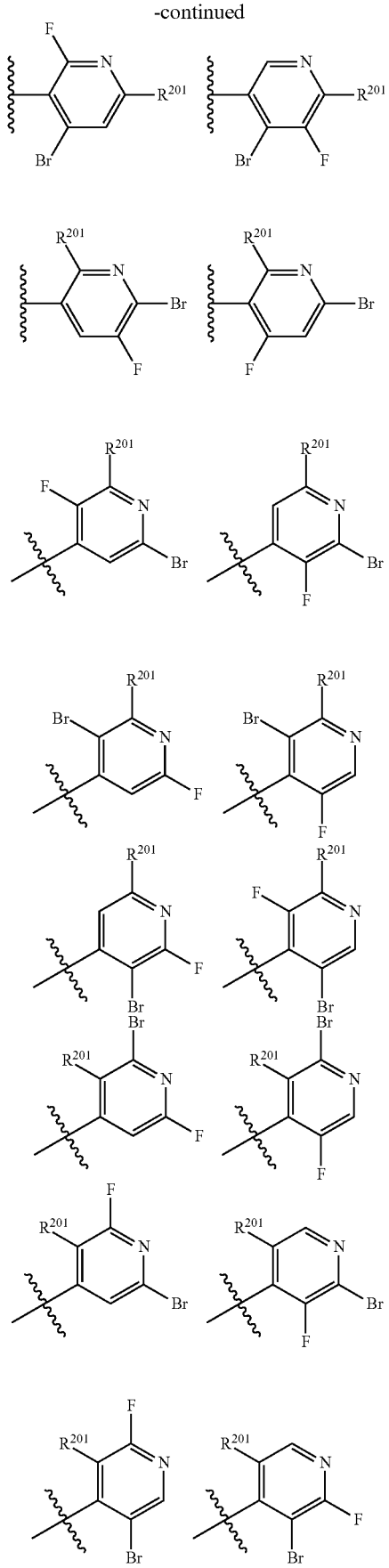

In one embodiment, B1 is selected from:
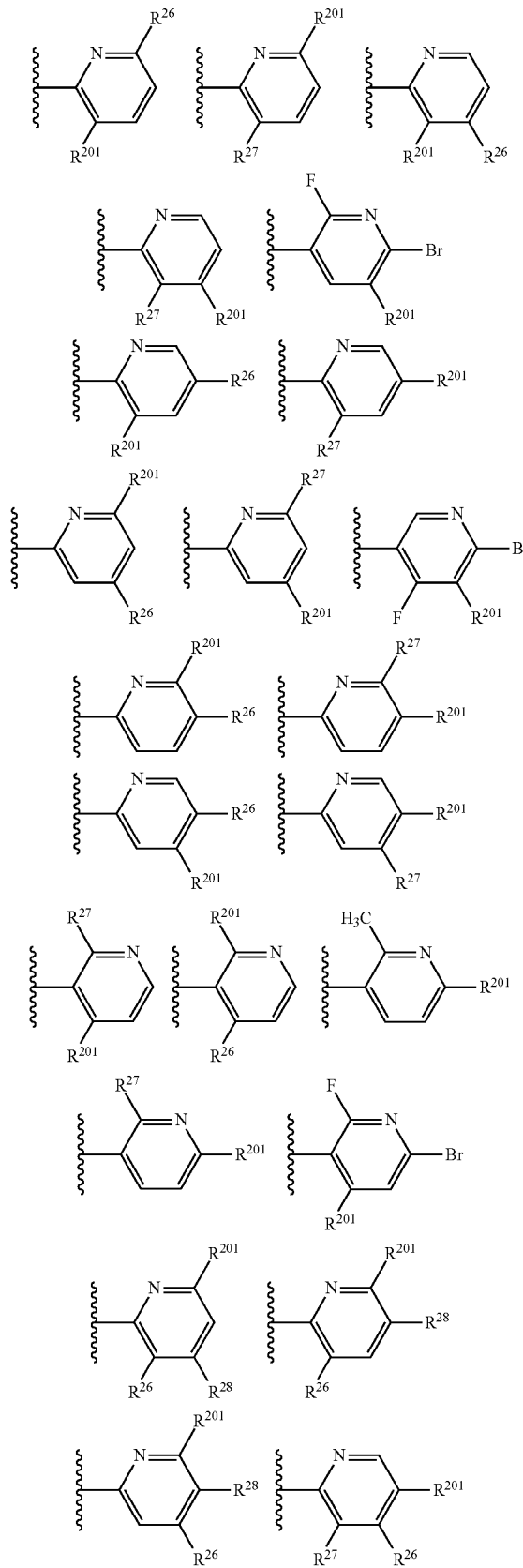
-continued
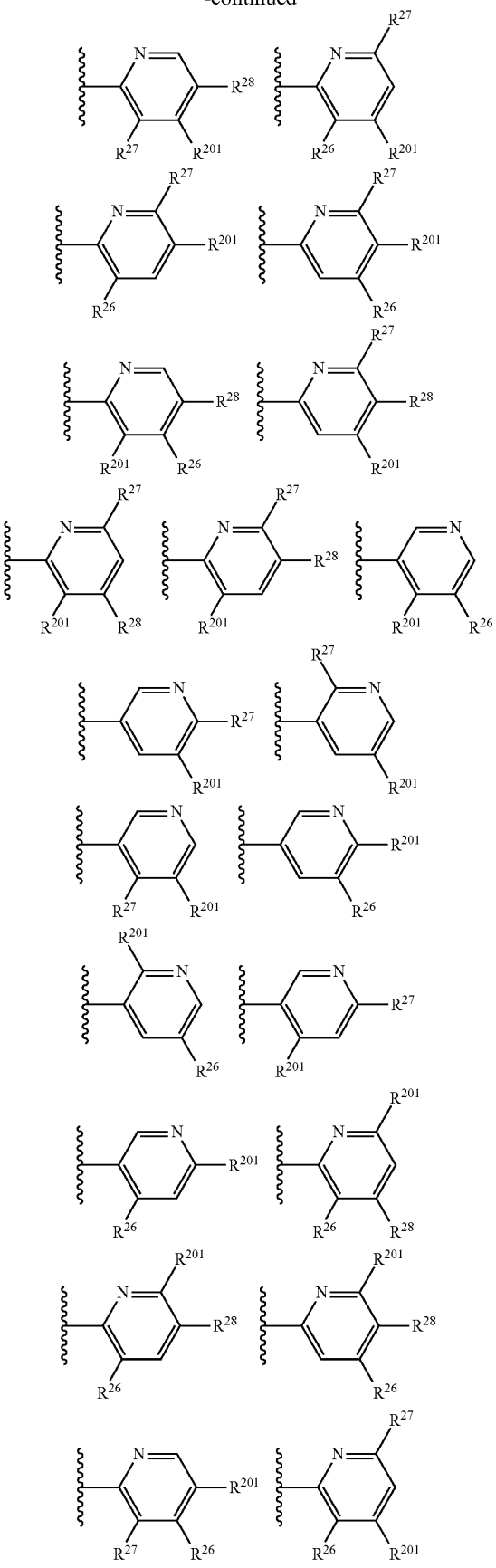

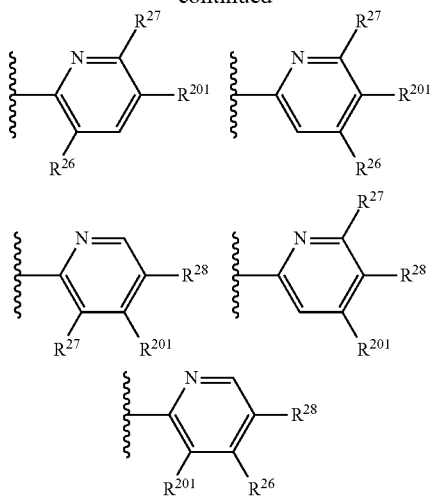
In one embodiment, B1 is selected from:
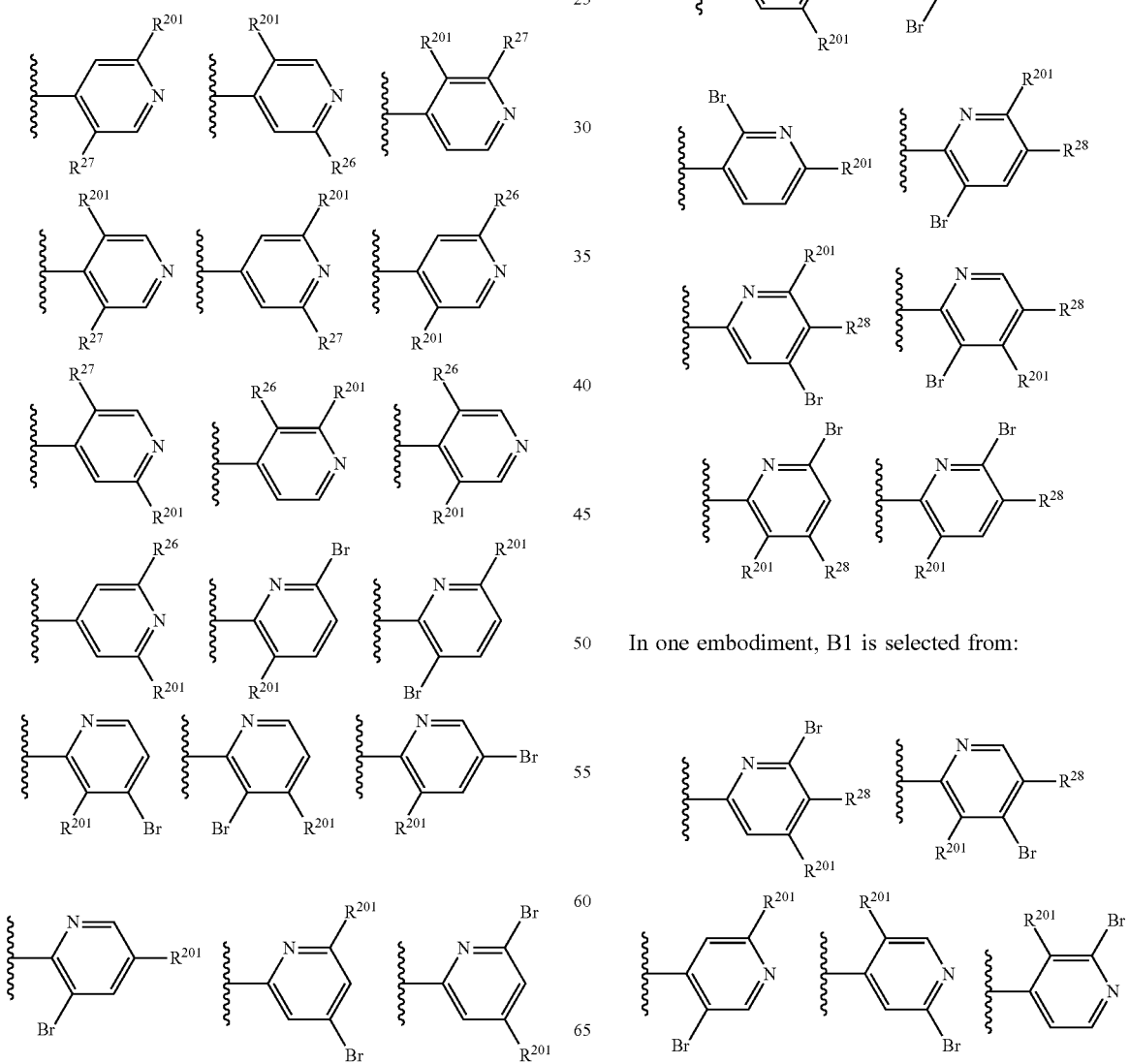
In one embodiment, B1 is selected from:
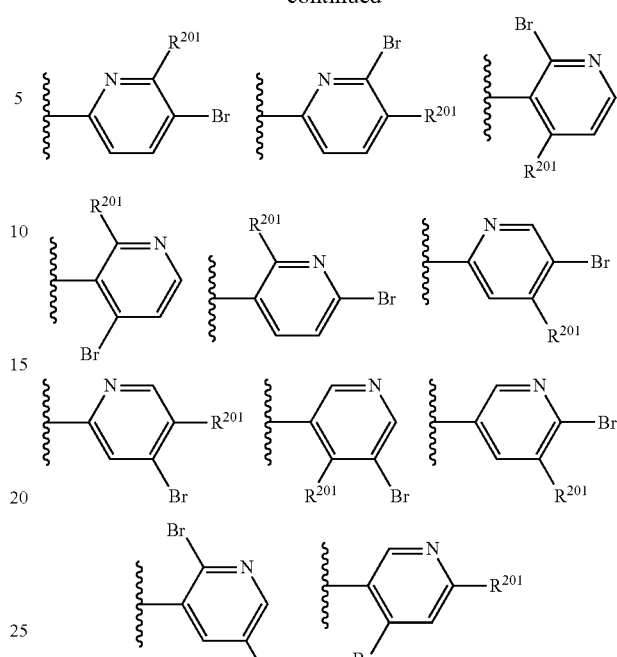

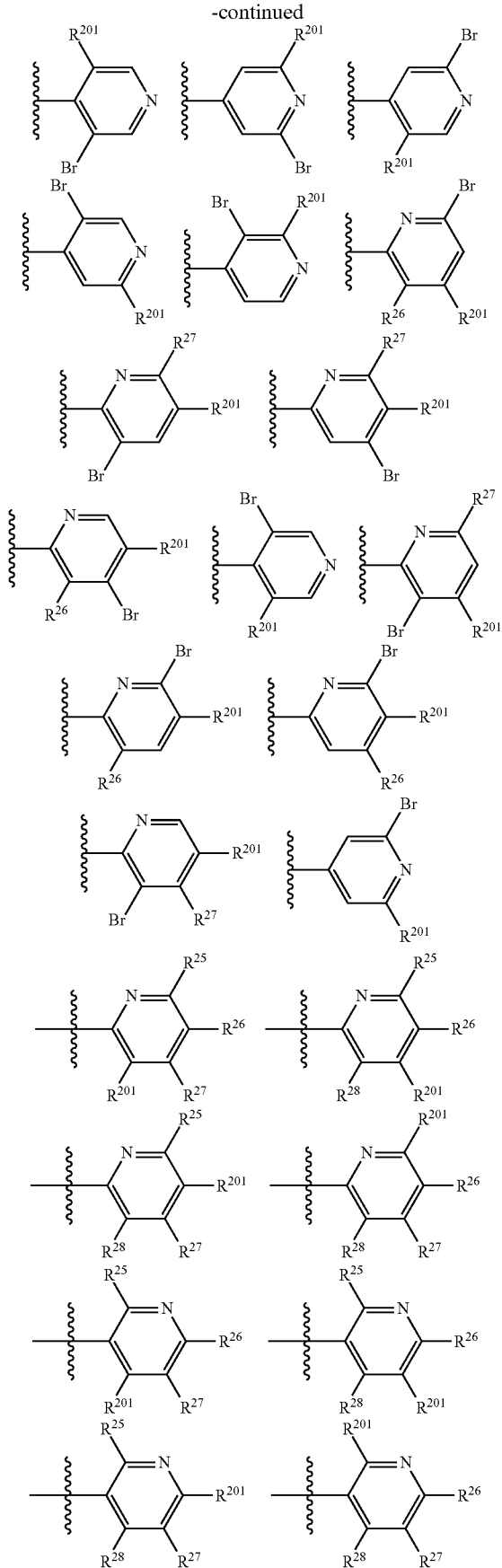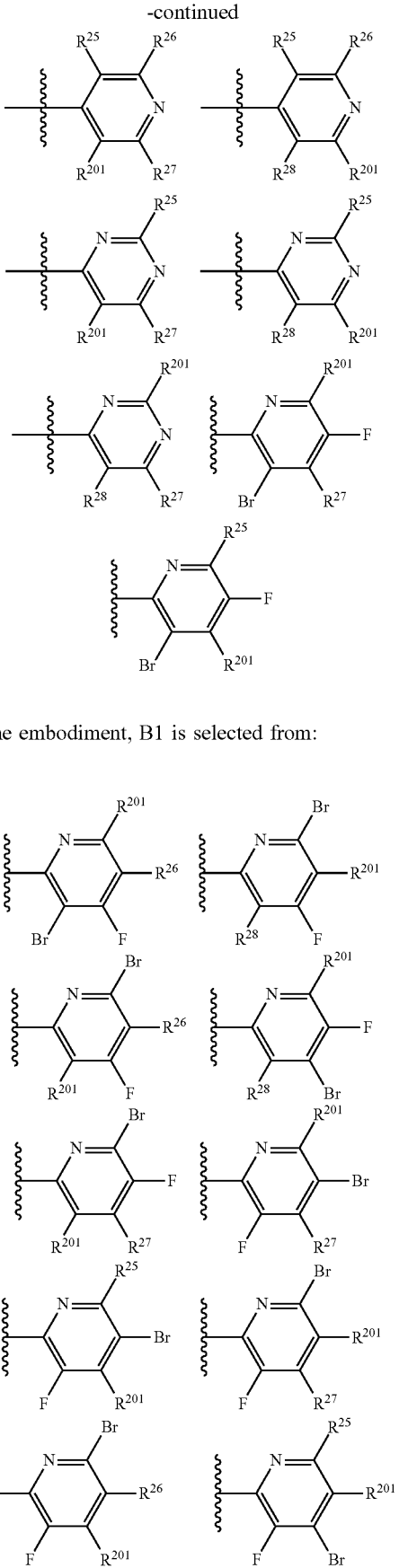
In one embodiment, B1 is selected from:

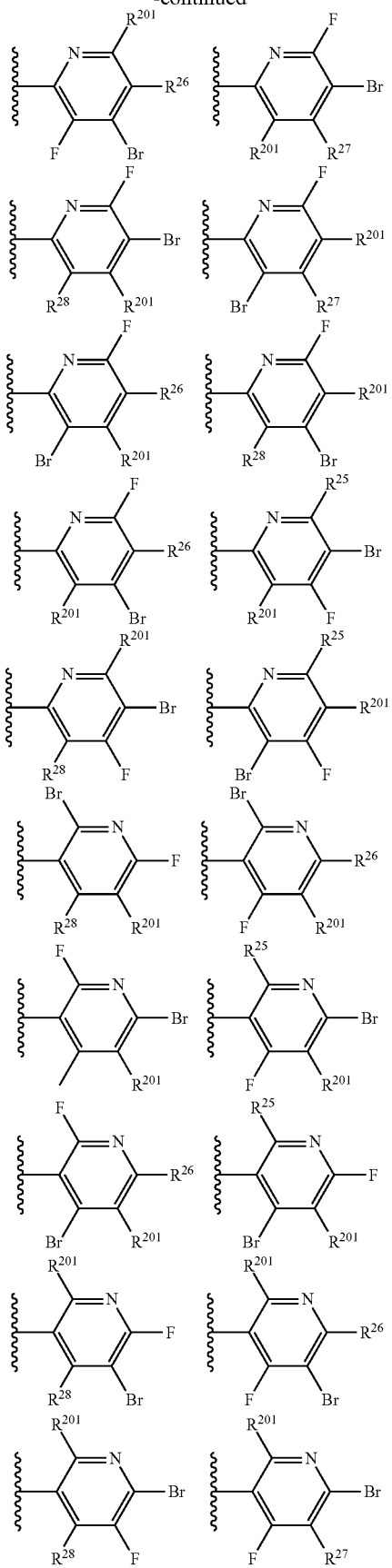
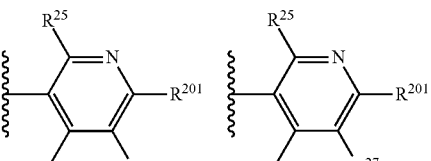
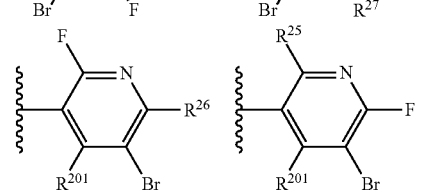
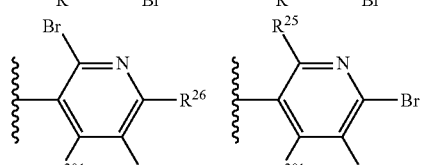
In one embodiment, B1 is selected from:
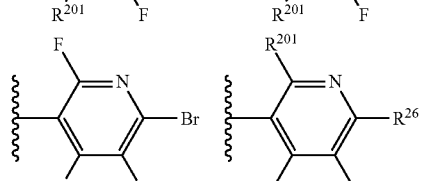
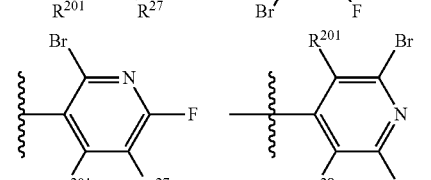
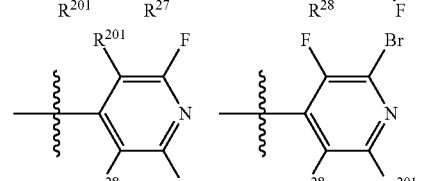

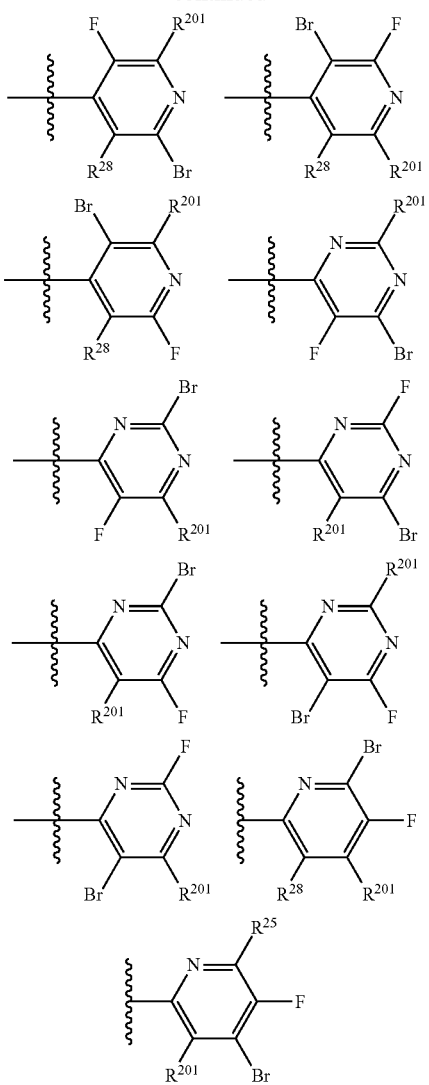
In one embodiment, B1 is selected from:
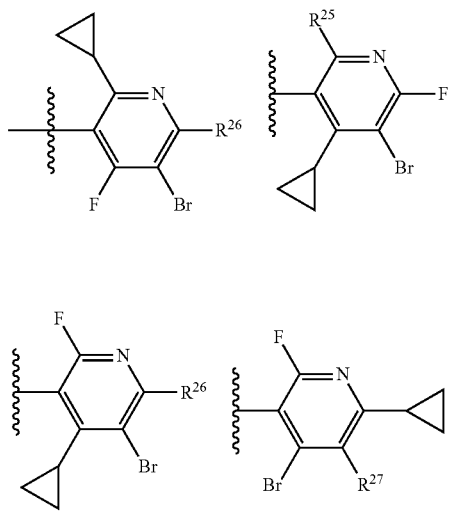
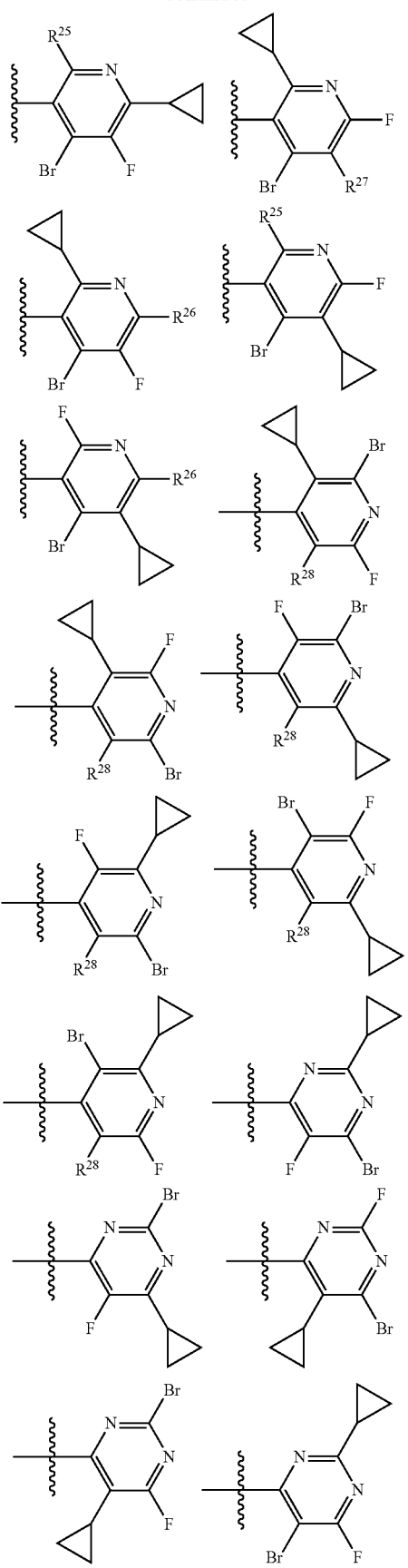

503
-continued
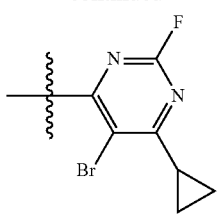
In one embodiment, B1 is selected from:
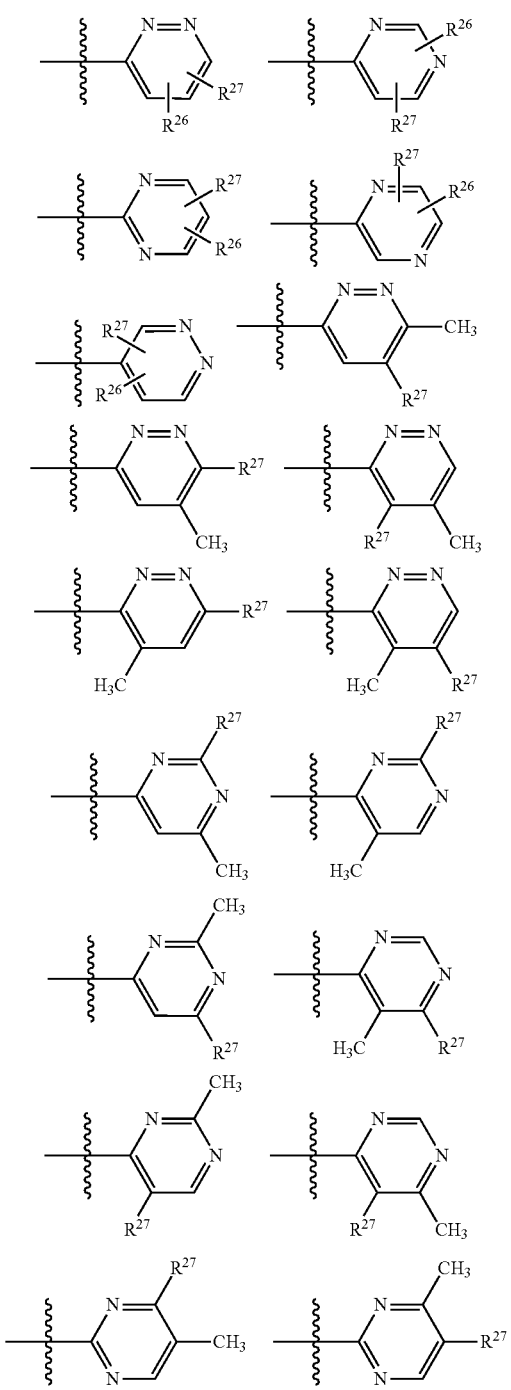
504
-continued
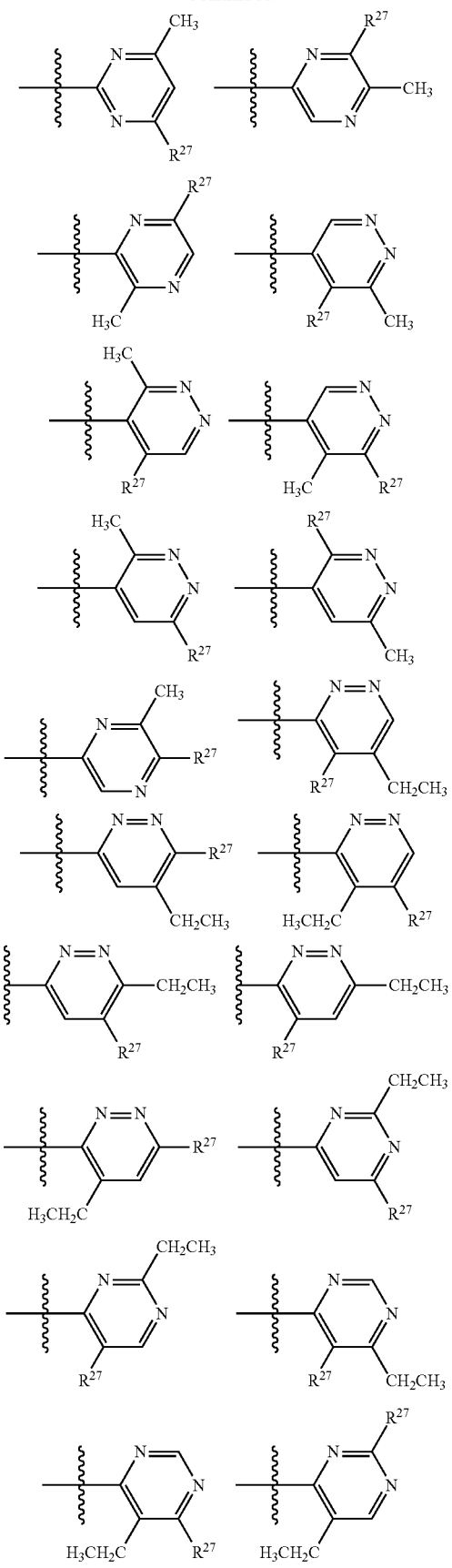

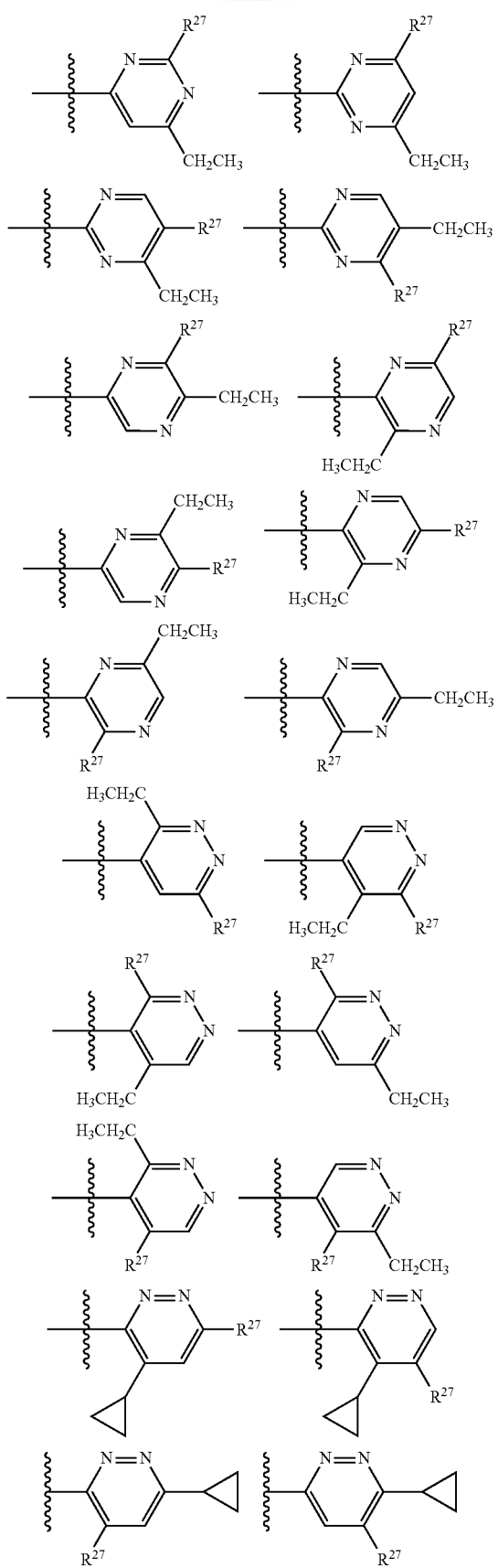
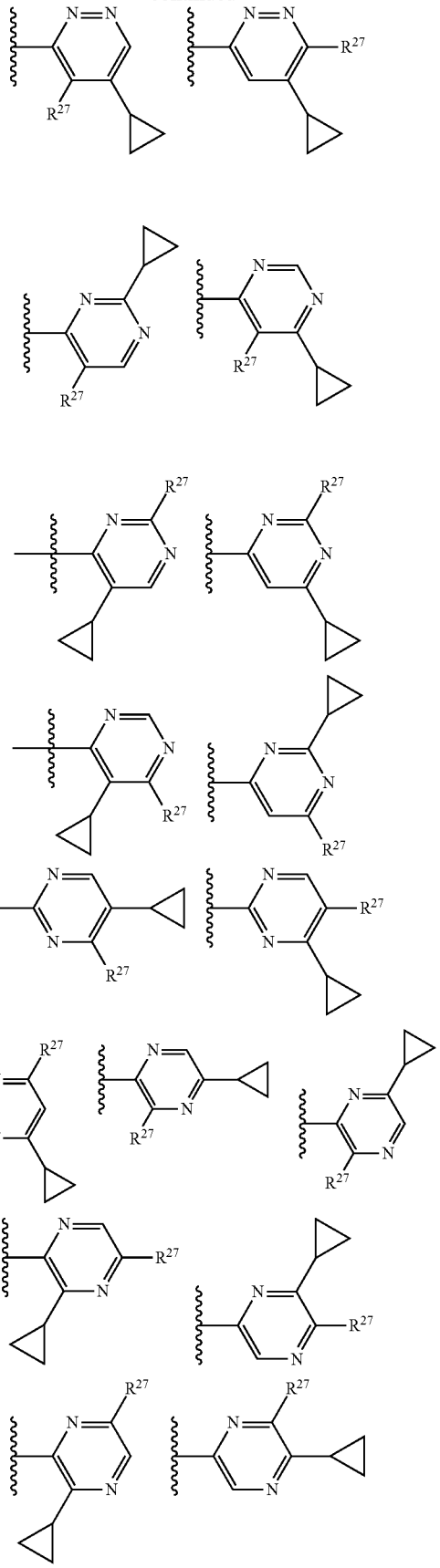

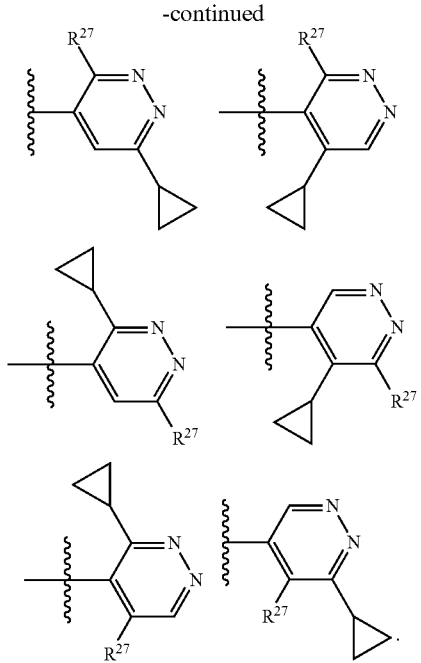
In one embodiment, B1 is selected from:
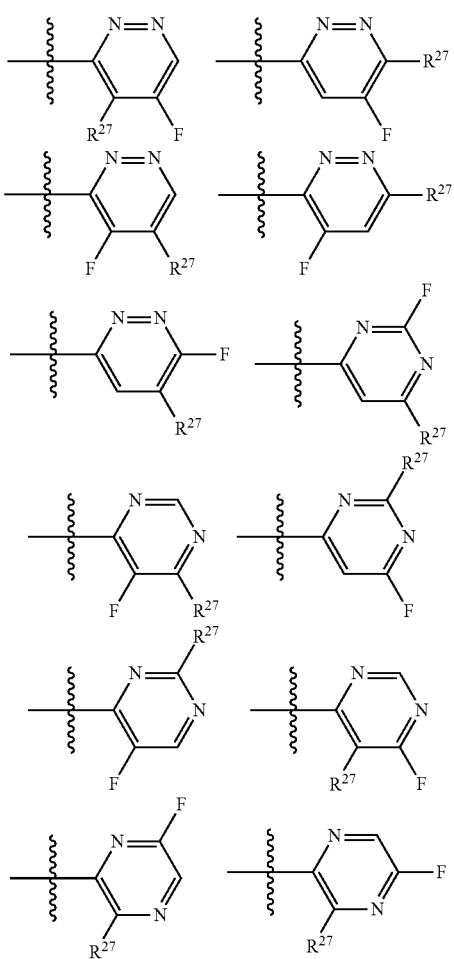
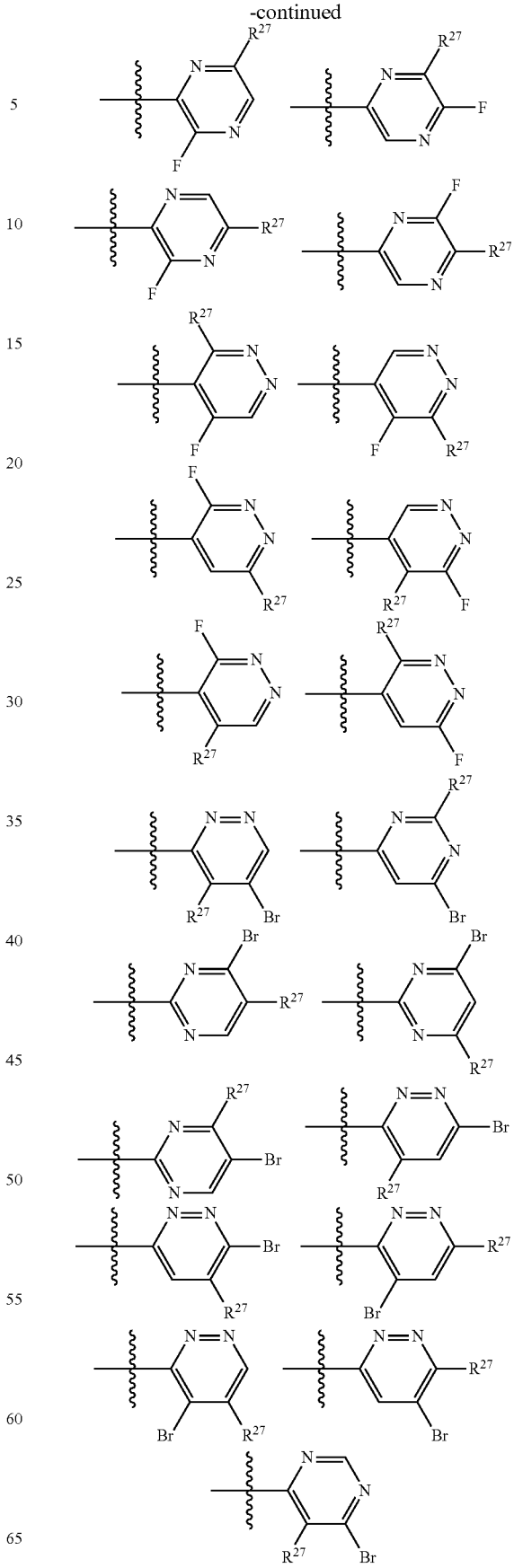

-continued
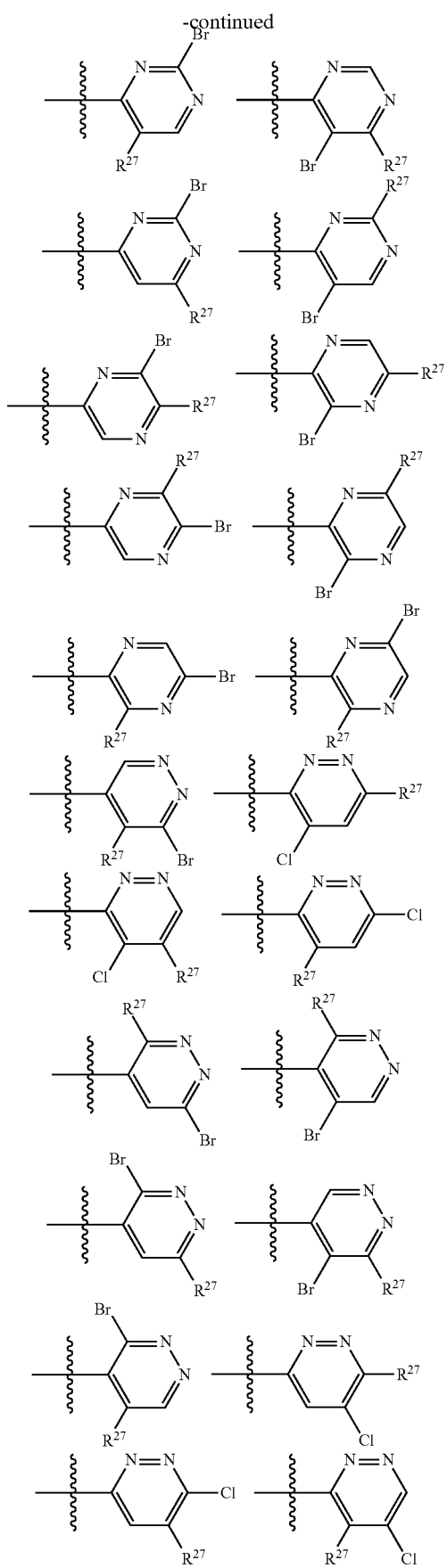
-continued
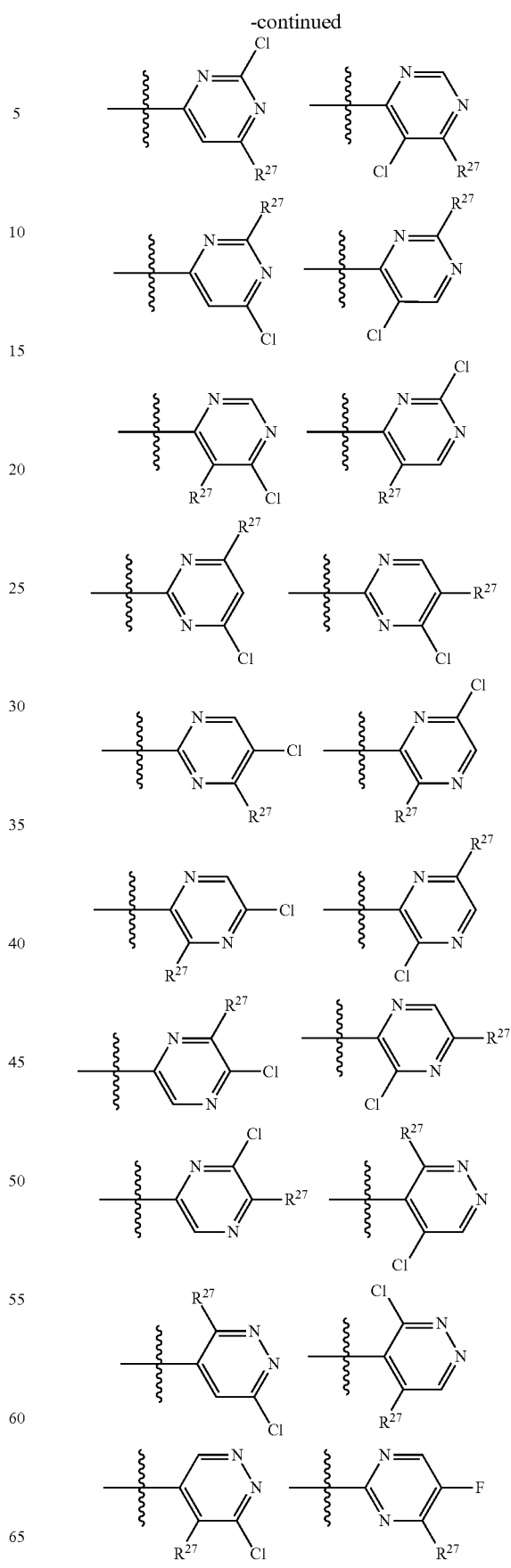

-continued
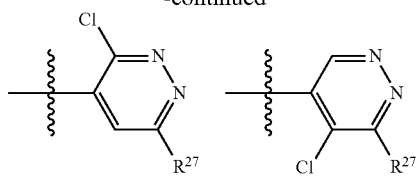
In one embodiment, B1 is selected from:
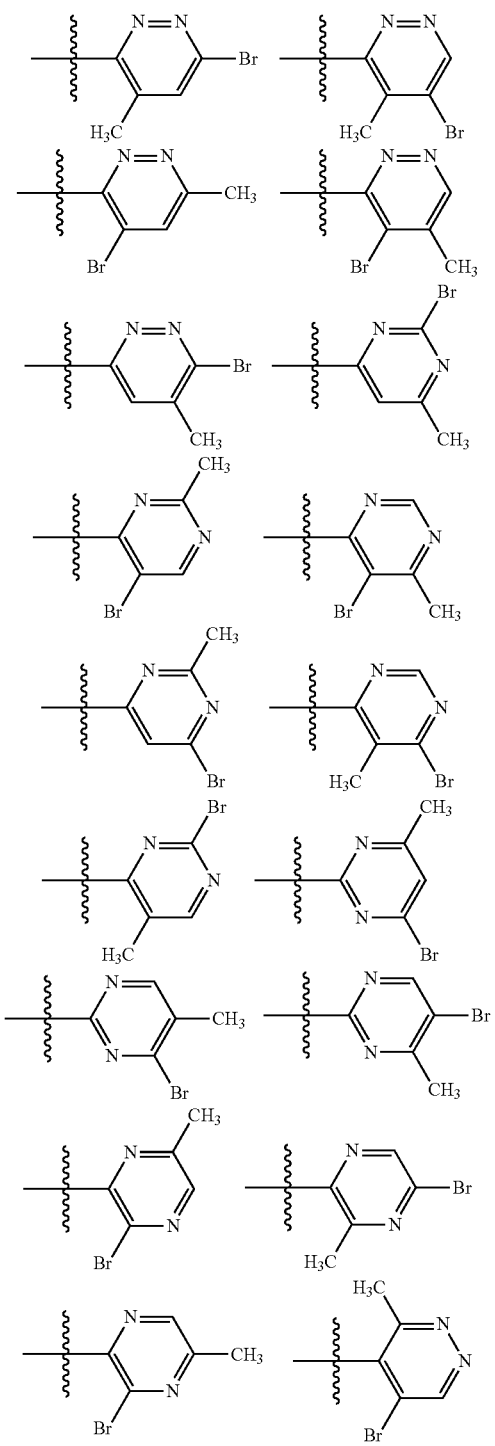
-continued
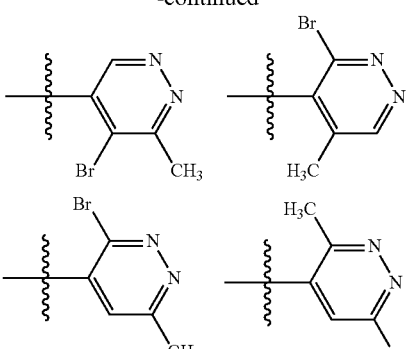
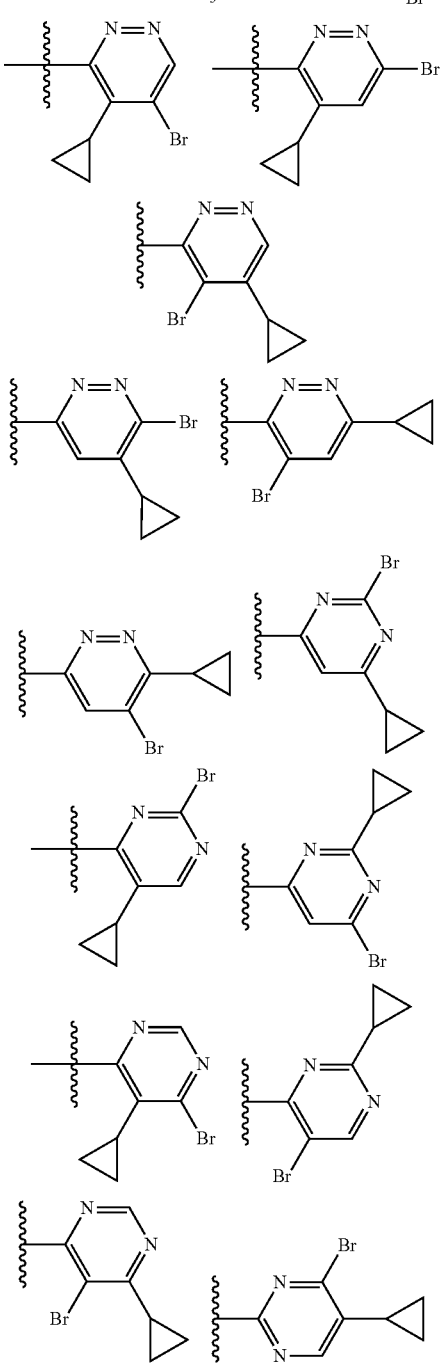

-continued
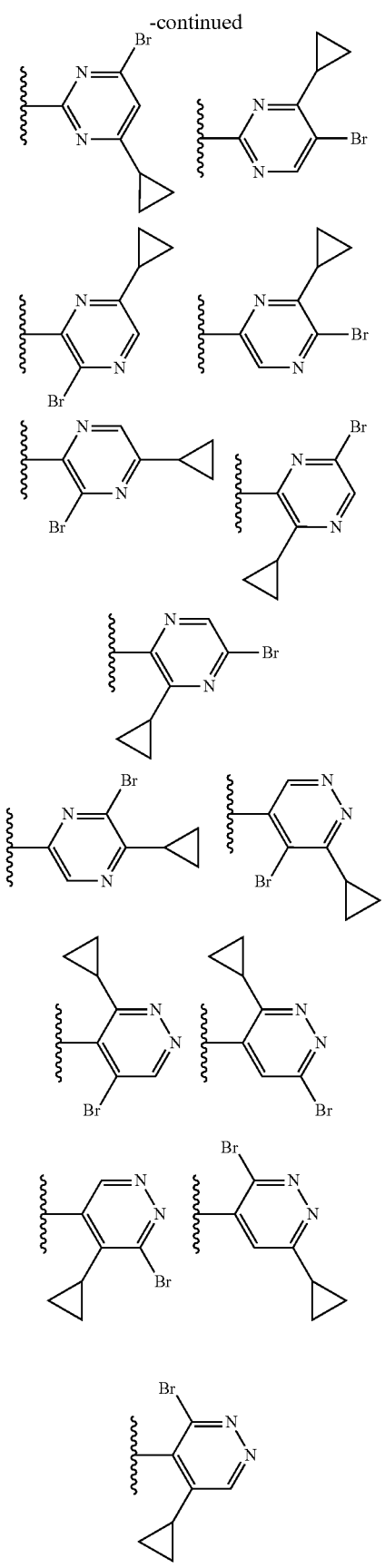
In one embodiment, B1 is selected from:
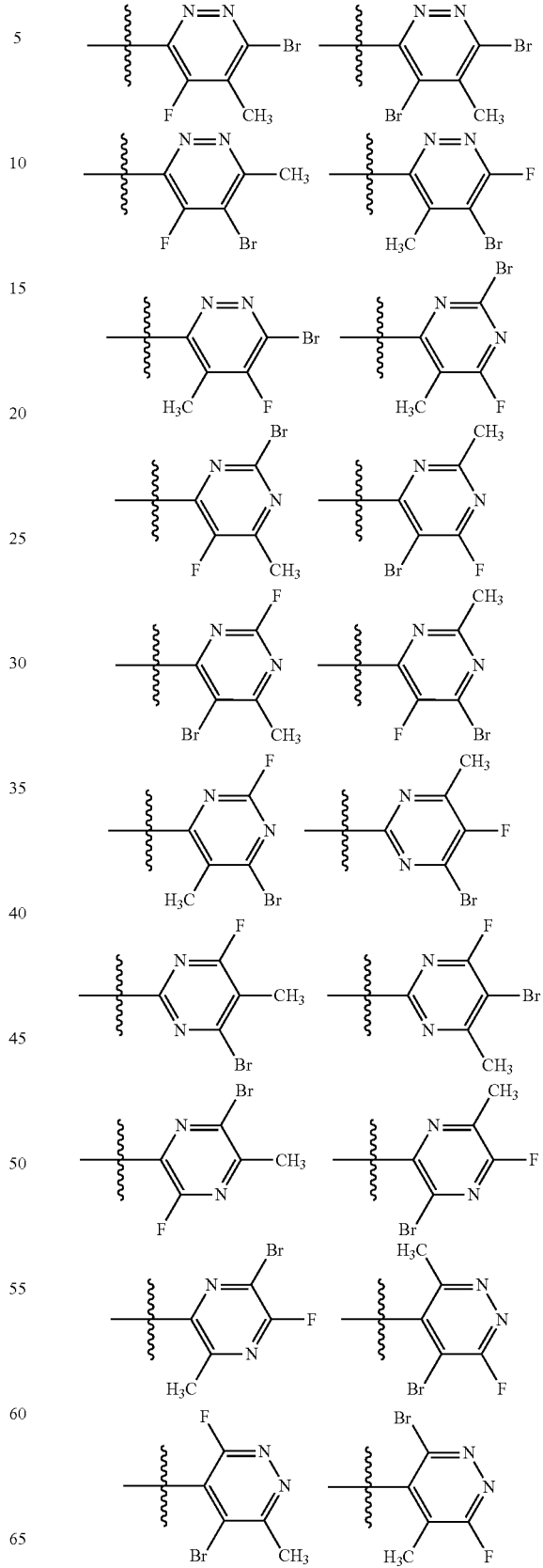

-continued
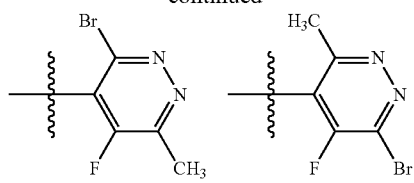
In one embodiment, B1 is selected from:
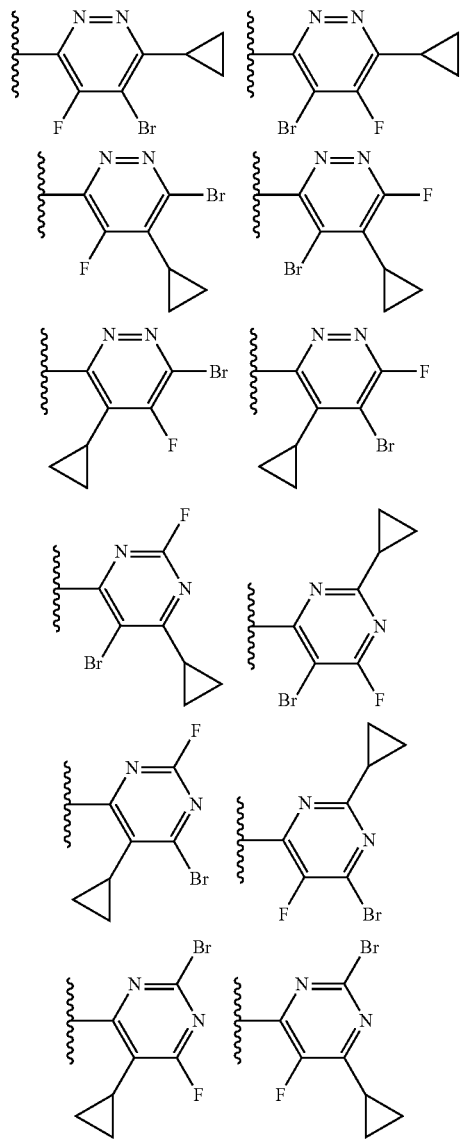
-continued
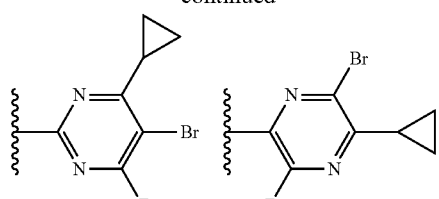
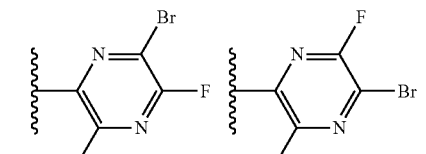
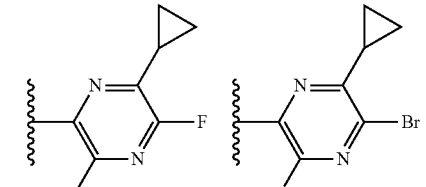
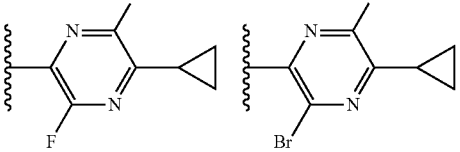
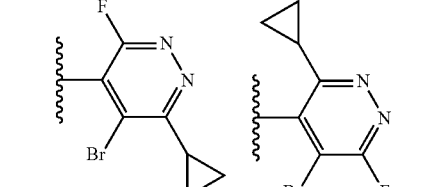
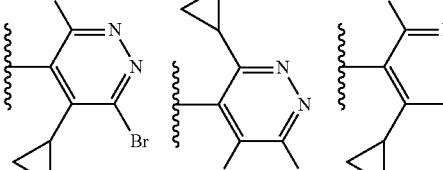
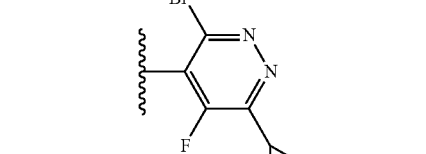
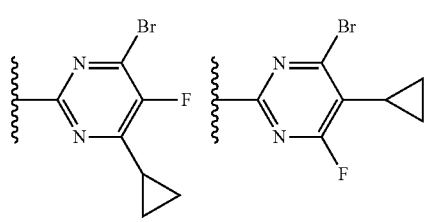
In one embodiment, B1 is selected from:
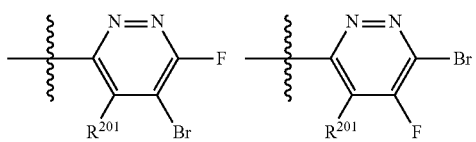

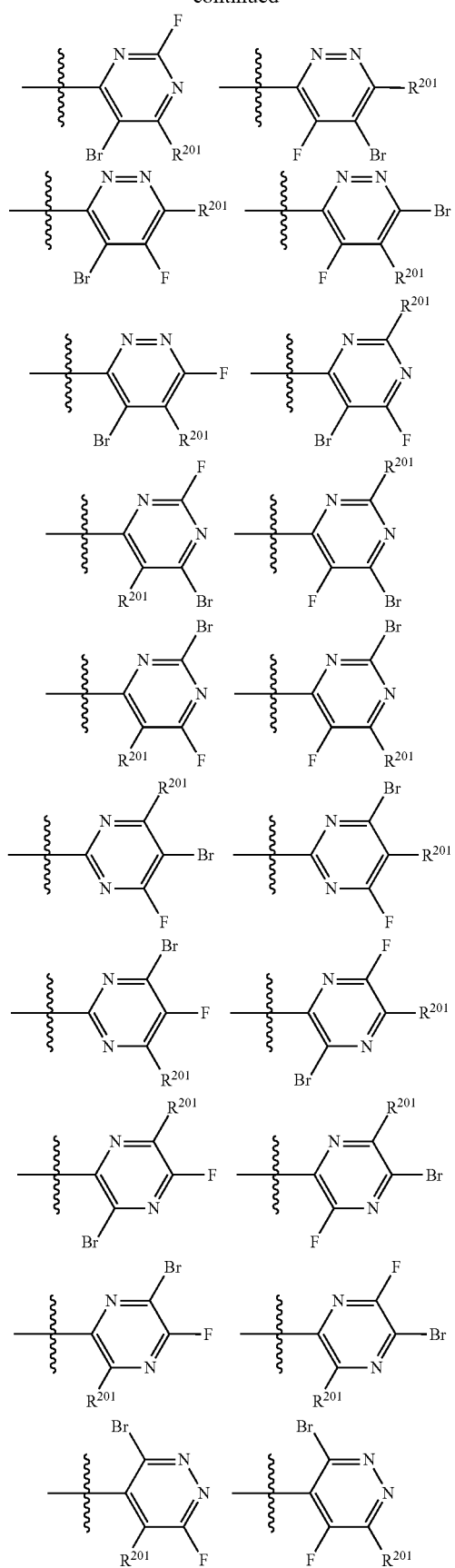
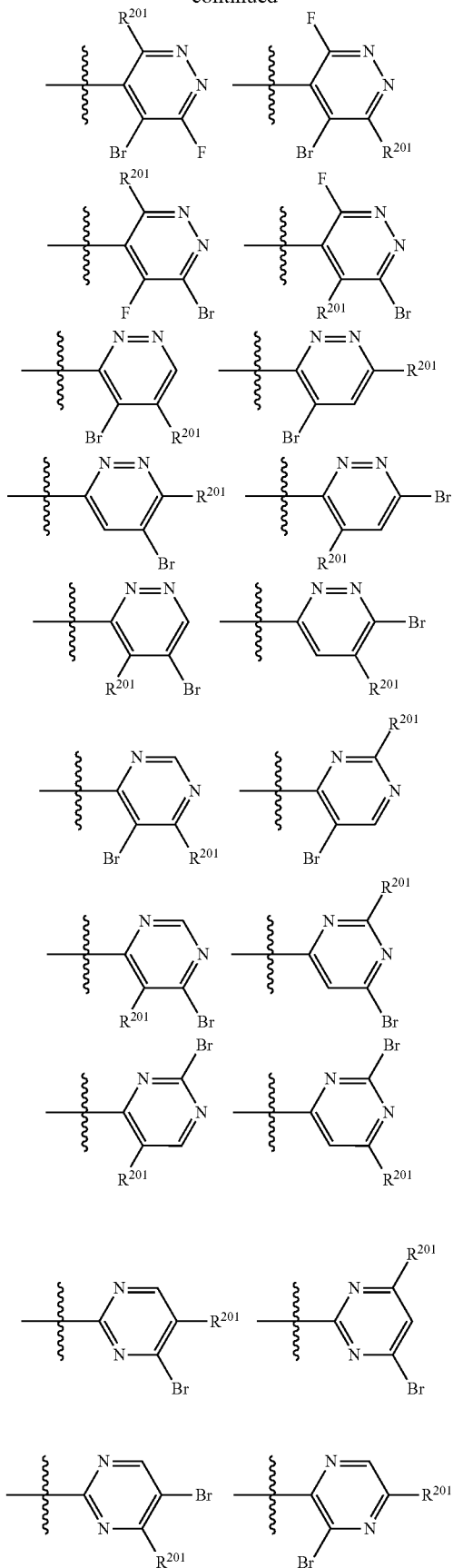

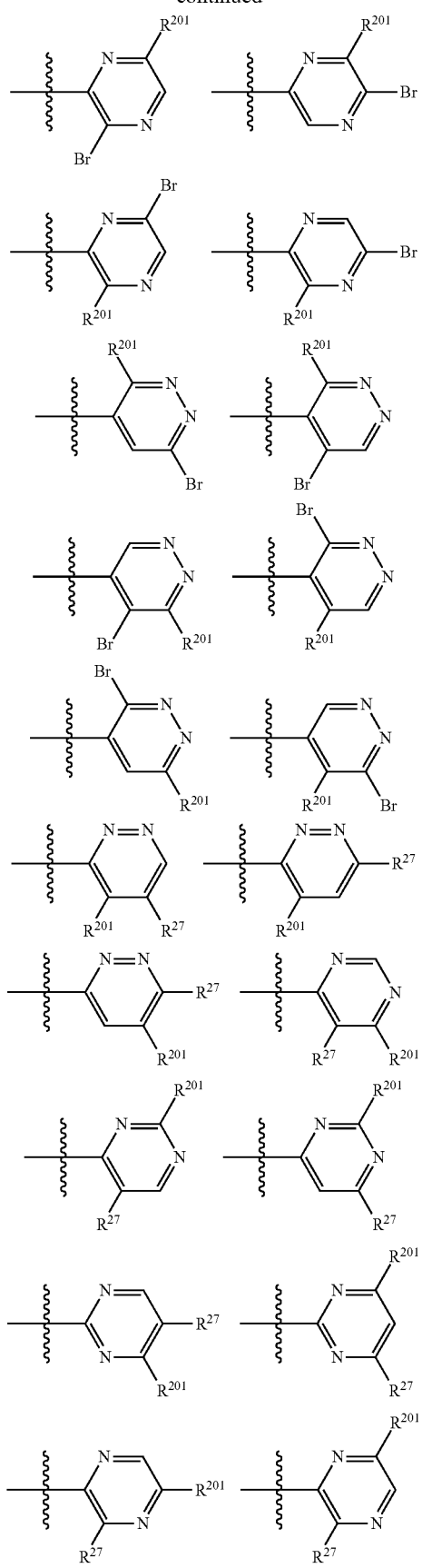
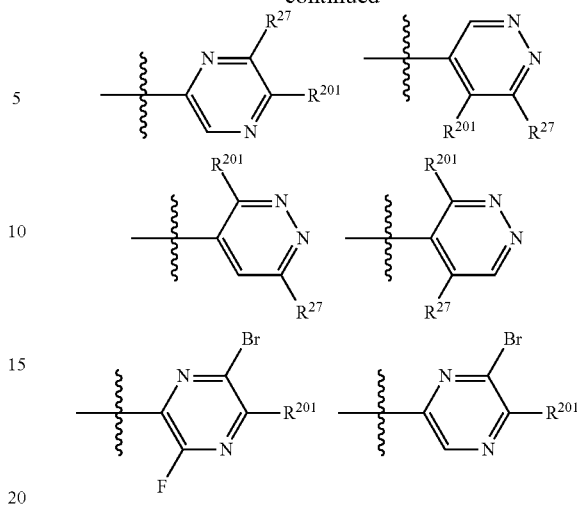
In another embodiment, B1 is selected from:
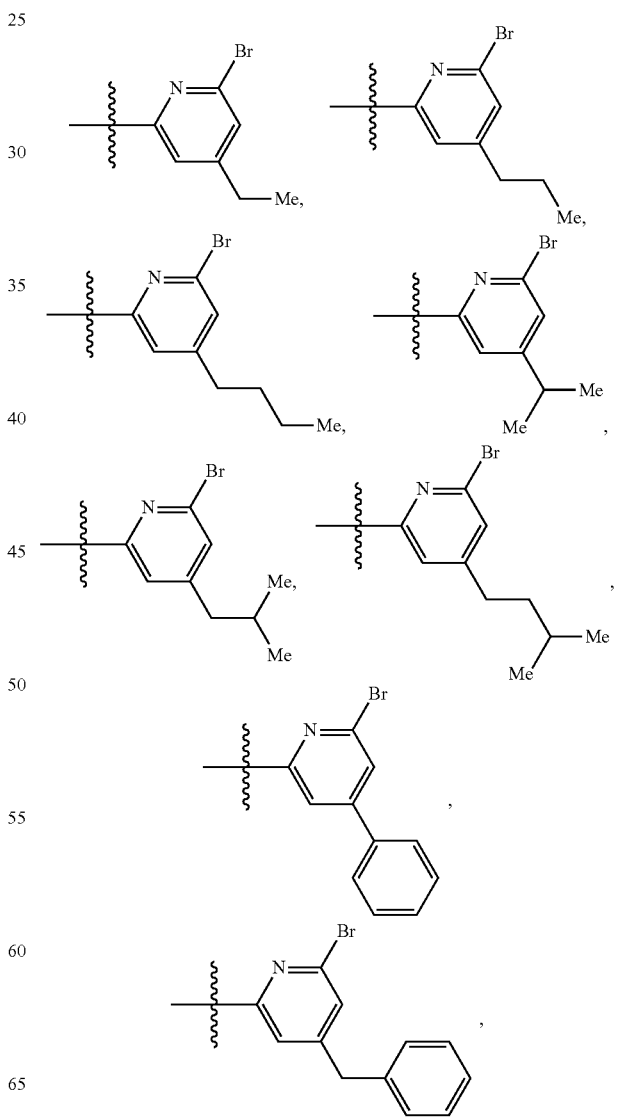

521
-continued
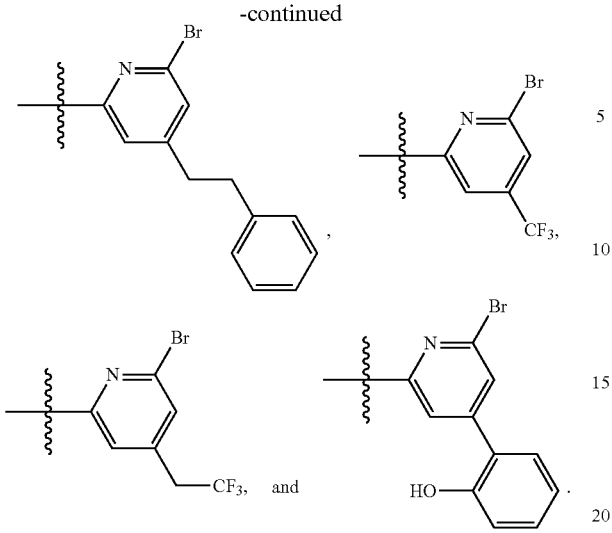
In another embodiment, B1 is selected from:
522
-continued
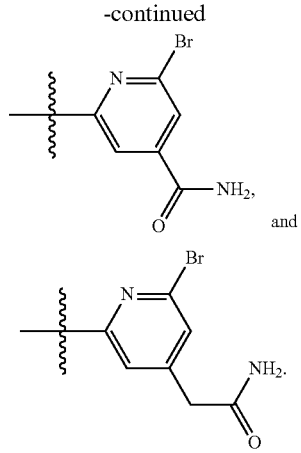
In another embodiment, B1 is selected from:
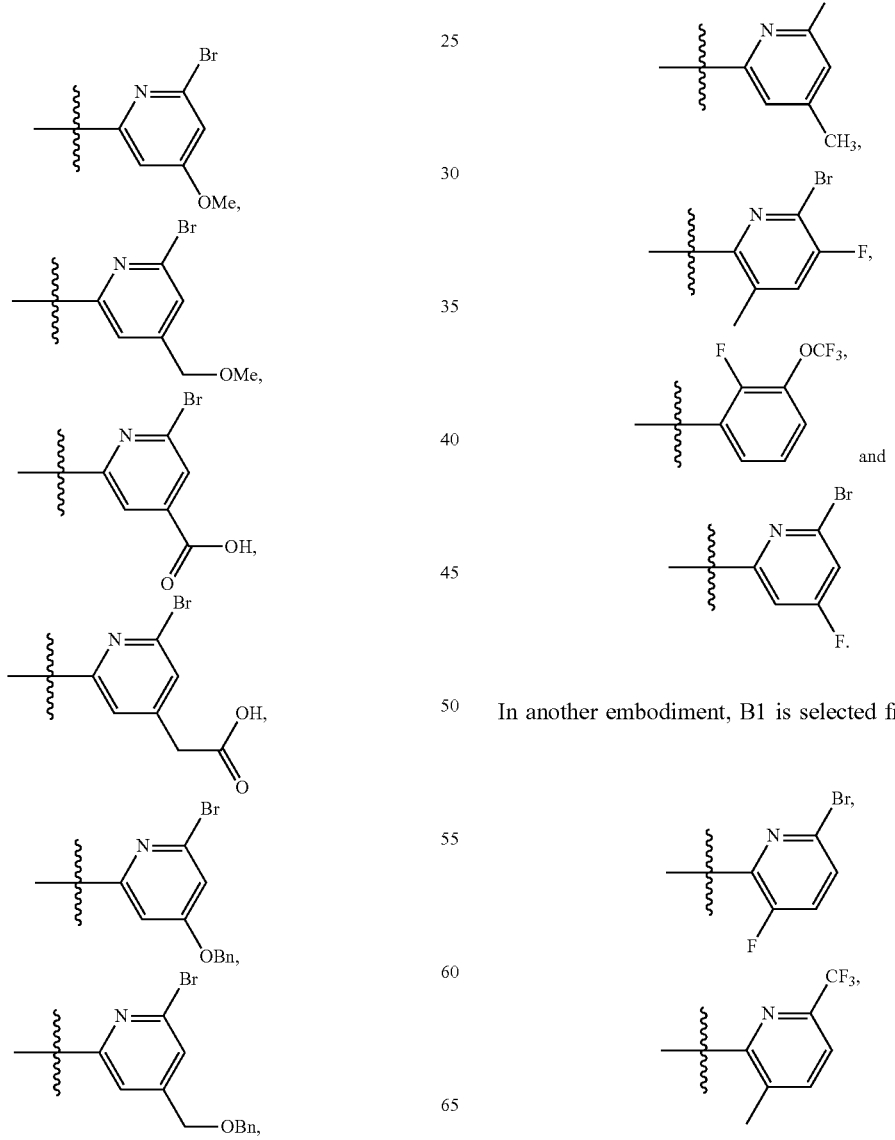
In another embodiment, B1 is selected from:

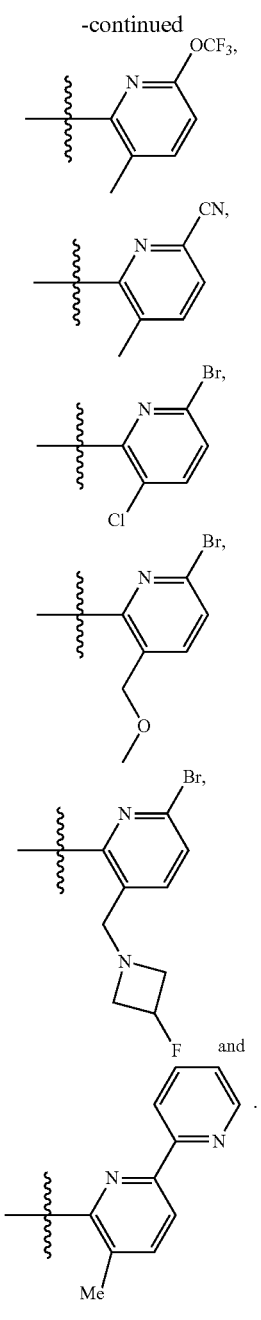
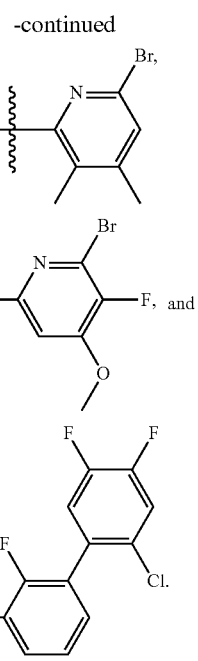
In another embodiment, B1 is selected from:
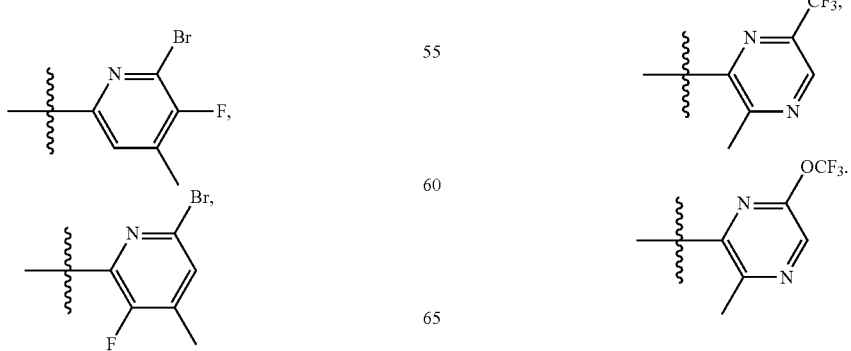
In another embodiment, B1 is selected from:

In an alternative embodiment, B1 is selected from:

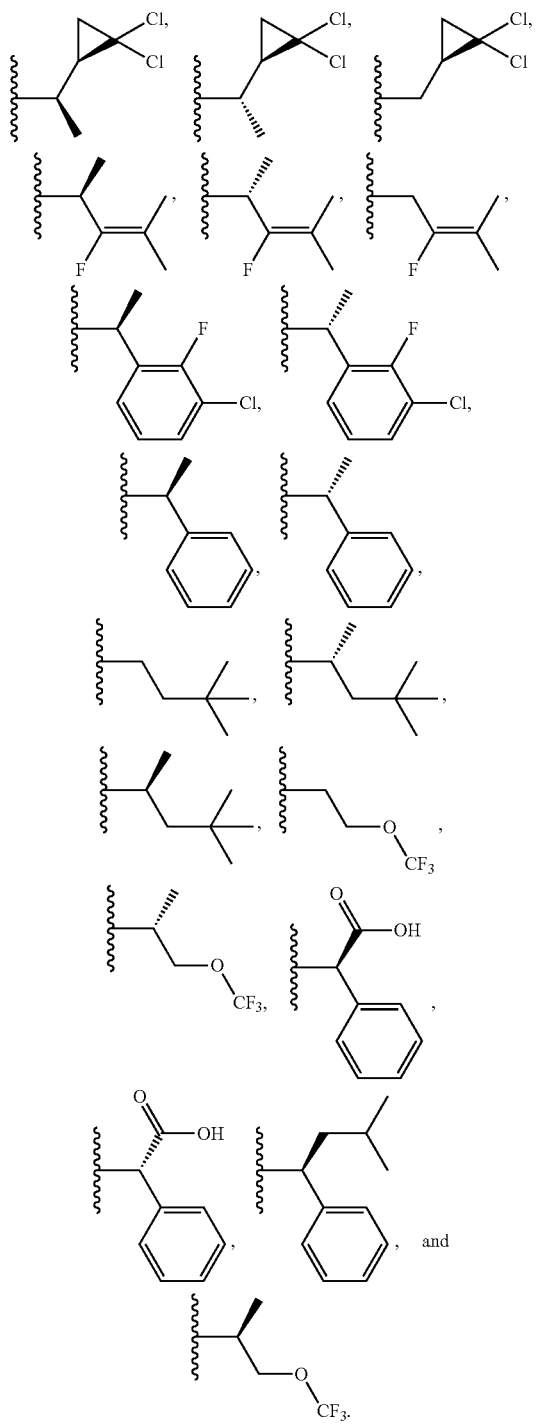

In another alternative embodiment, B1 is selected from:

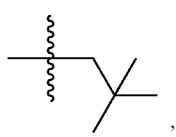

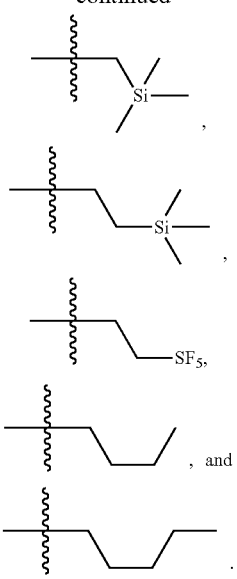

In another alternative embodiment, B1 is -alkyl-Si(alkyl)$_3$ or -alkyl-SF$_5$.

In another alternative embodiment, B1 is a B ring substituted with oxo. In this embodiment if the B ring is a nitrogen containing heteroaryl group then the nitrogen may also be substituted as defined herein. For example:

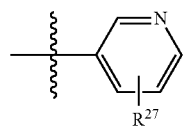

substituted with an oxo can be selected from the following compounds:

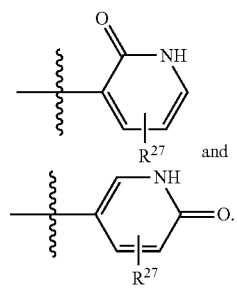

And examples of

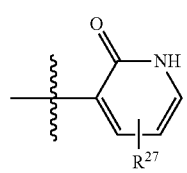

include:

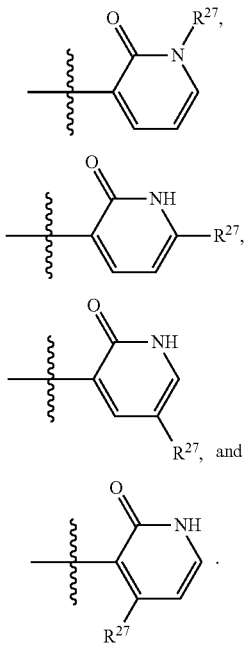

In another alternative embodiment, B1 is selected from:

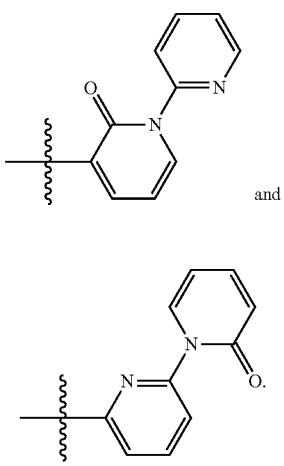

In another alternative embodiment, $R^{32}$ is a heteroaryl ring substituted with oxo as allowed by valence. In this embodiment if the $R^{32}$ ring is a nitrogen containing heteroaryl group then the nitrogen may also be substituted as defined herein. For example:

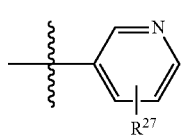

substituted with an oxo can be selected from the following compounds:

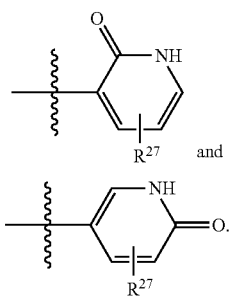

And examples of

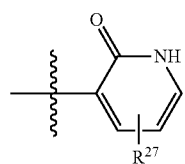

include:

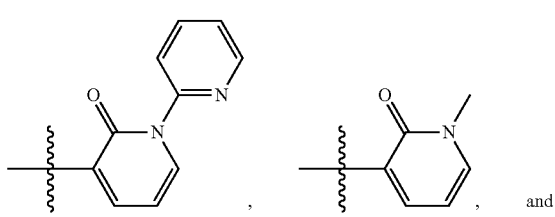

In another alternative embodiment, $R^{32}$ is selected from:

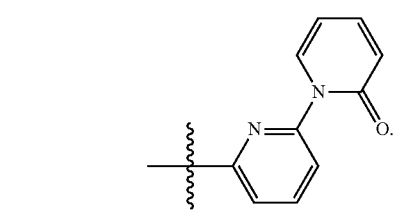

Additional Embodiments
In one embodiment, $R^{32}$ is selected from:
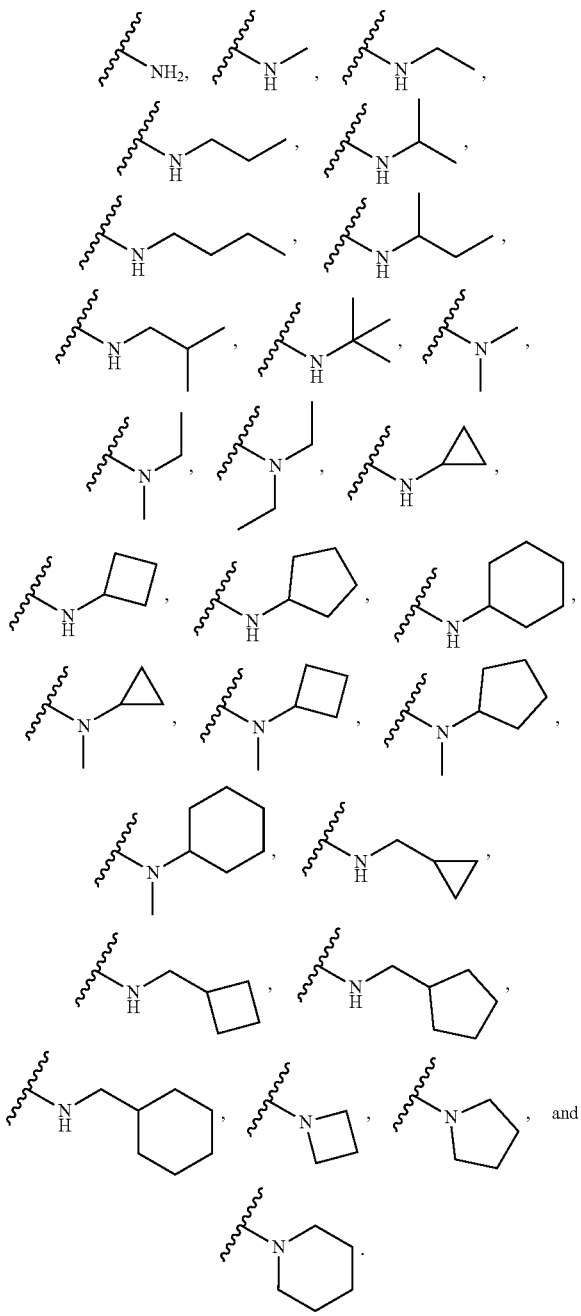
In one embodiment, $R^{32}$ is selected from:
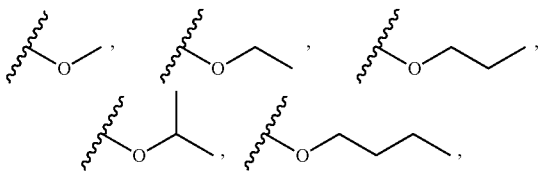
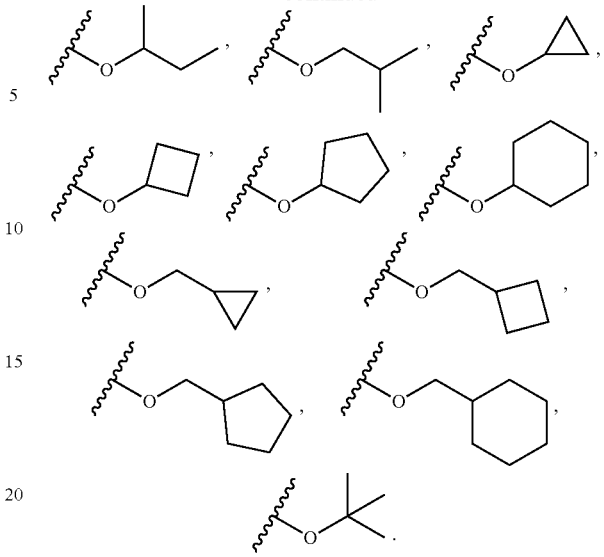
In one embodiment, $R^{32}$ is selected from:
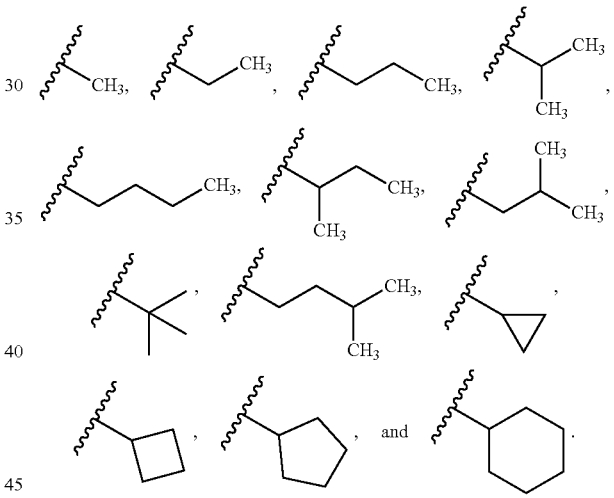
In one embodiment, the compound of Formula II is selected from:
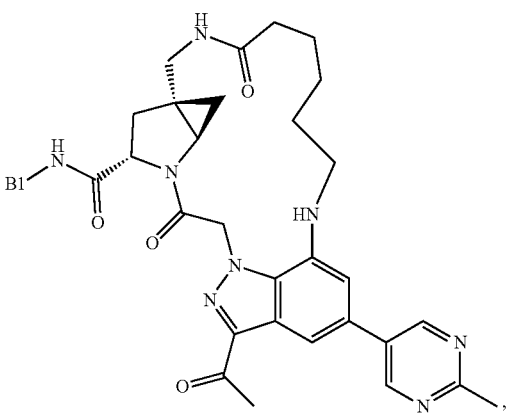

531
-continued
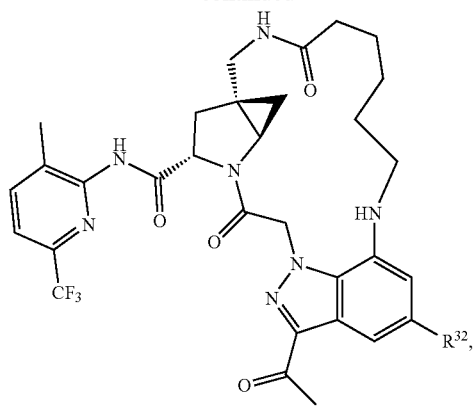
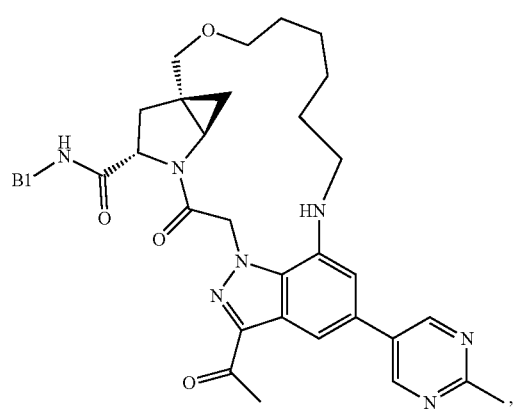
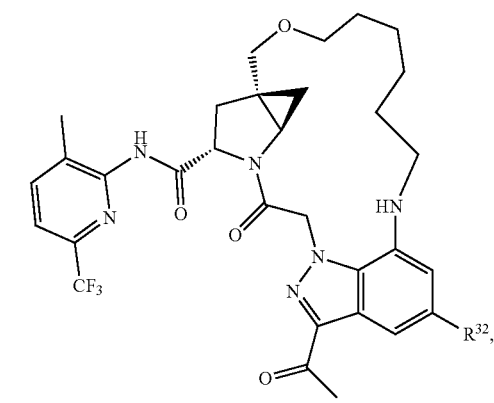
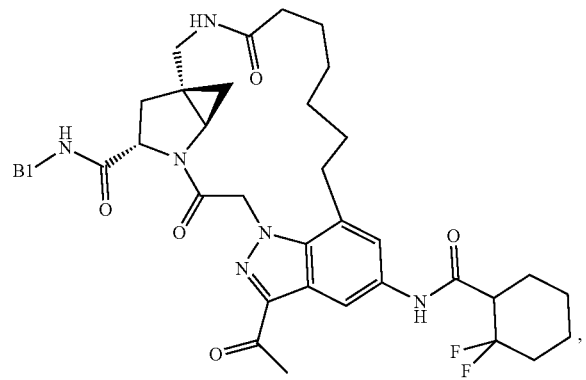
532
-continued
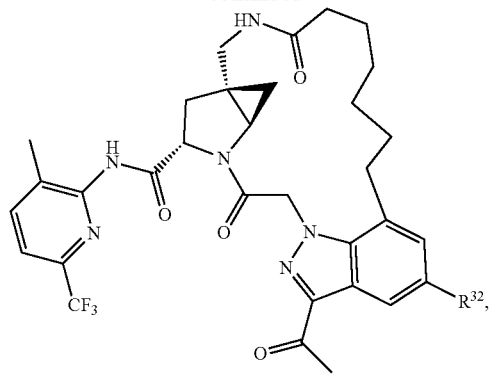
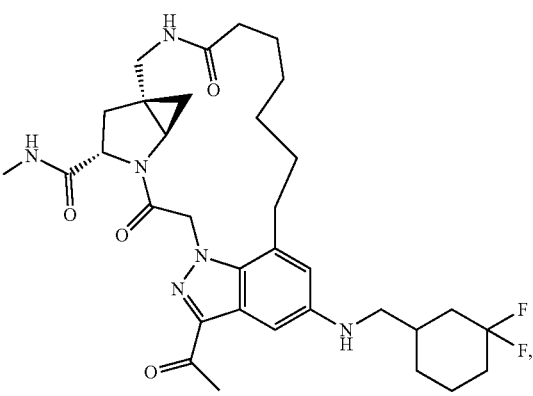
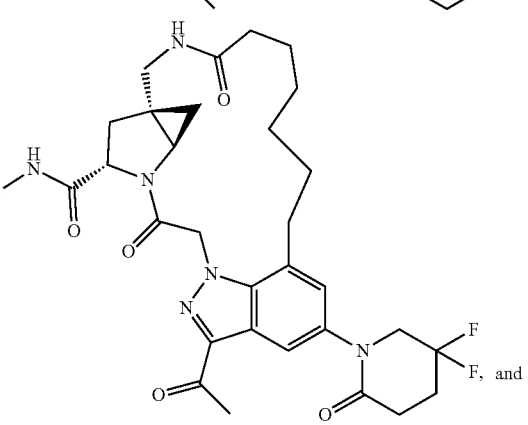
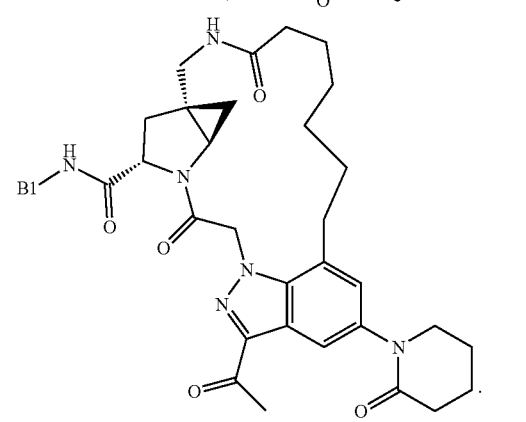
In one embodiment, the compound of Formula II is selected from:

533
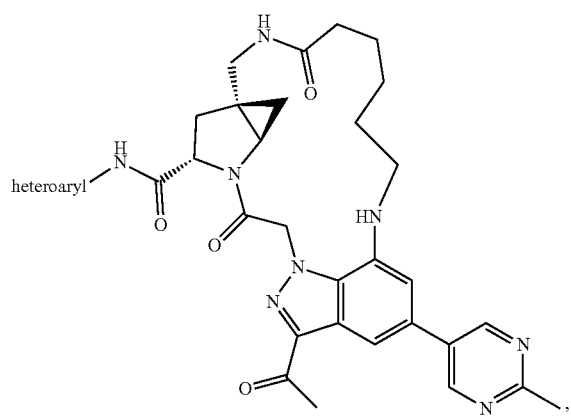
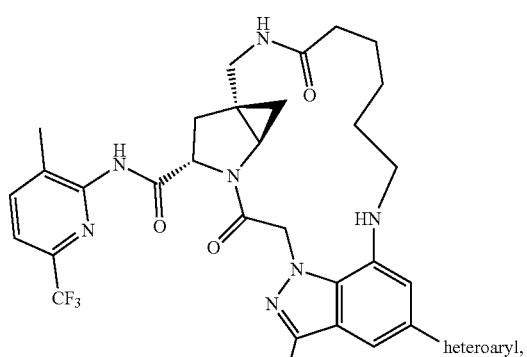
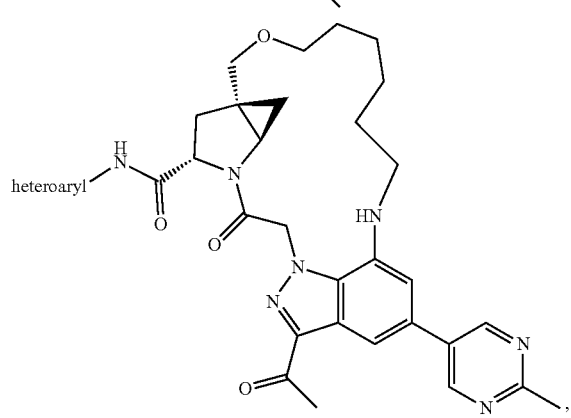
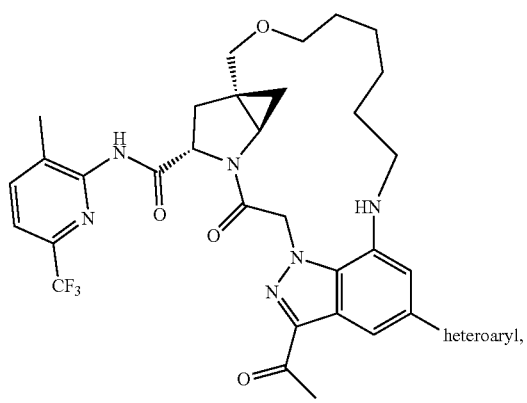
534
-continued
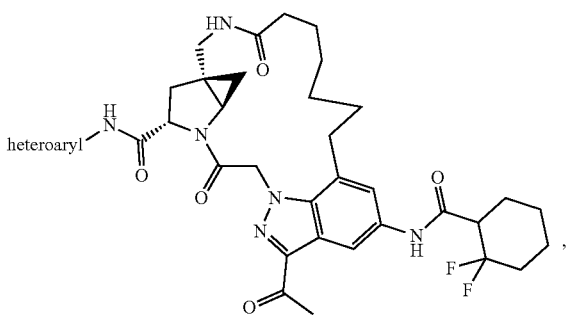
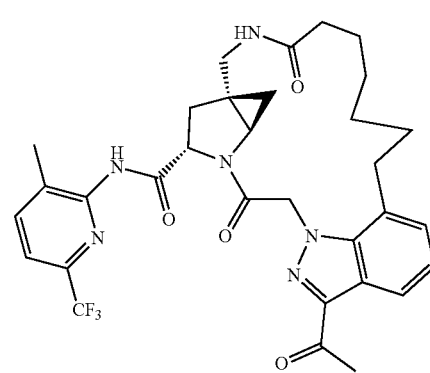
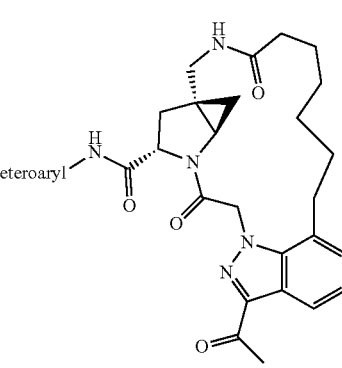
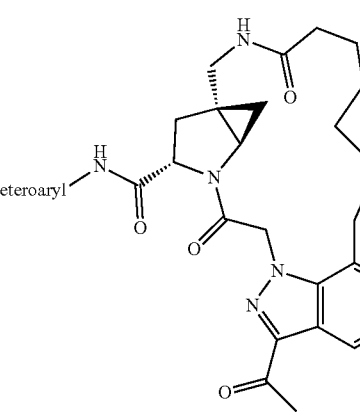

535
-continued
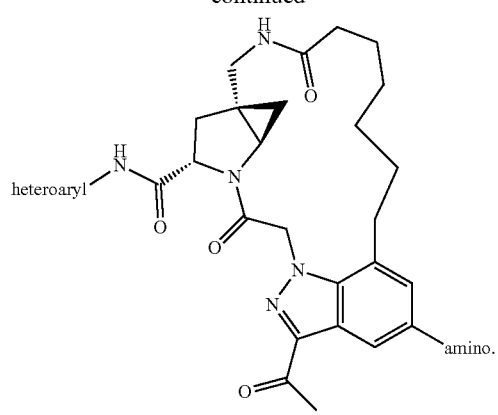
In one embodiment, the compound of Formula II is selected from:
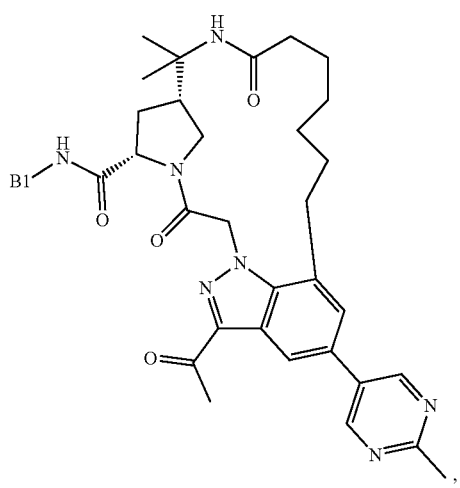
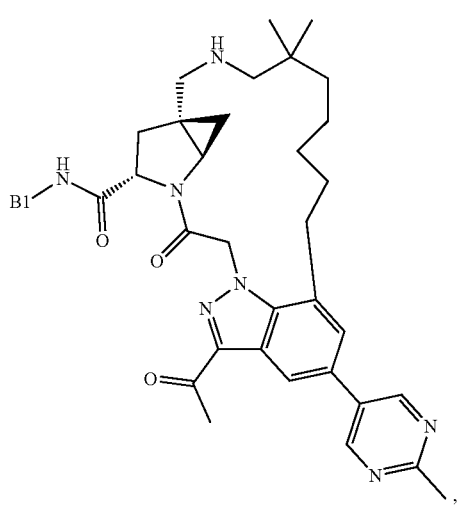
536
-continued
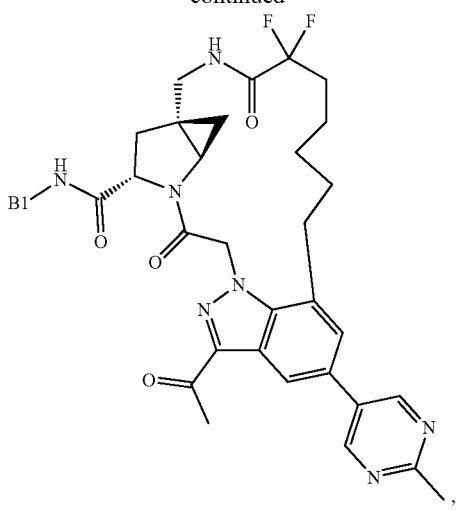
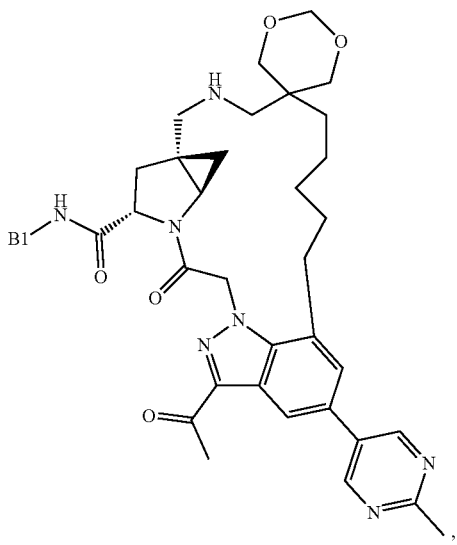
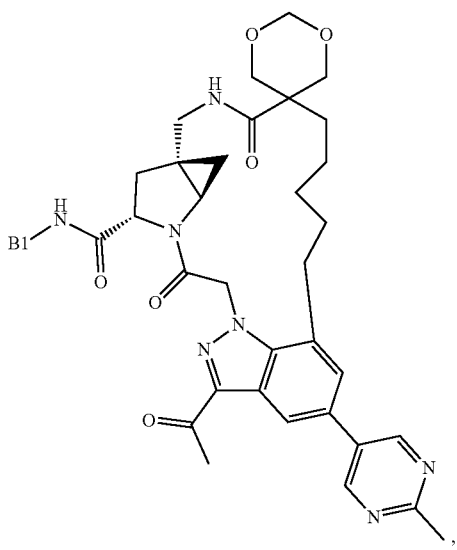

537
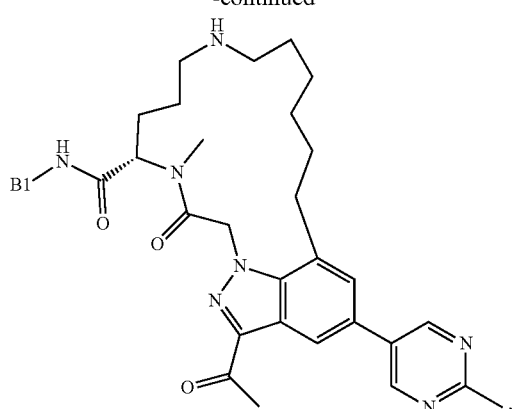
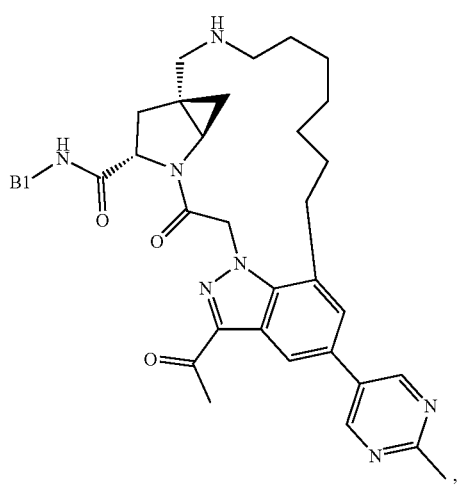
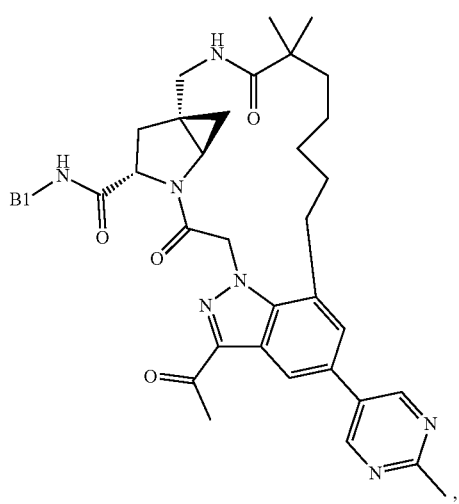
538
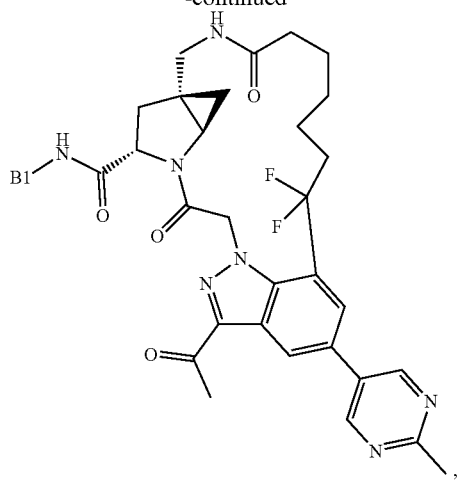
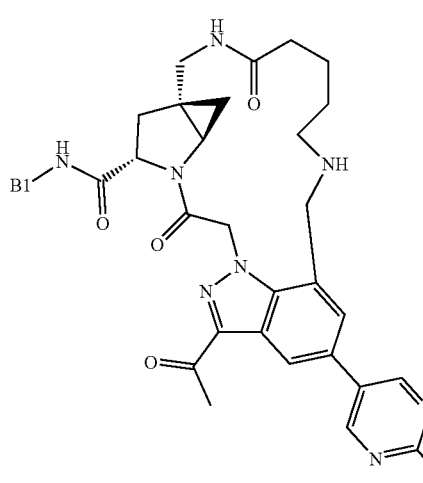
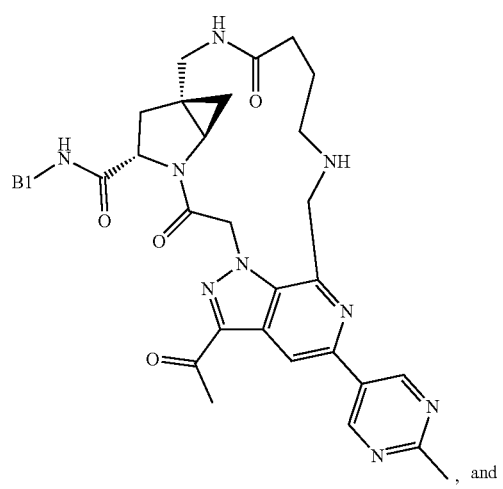
, and

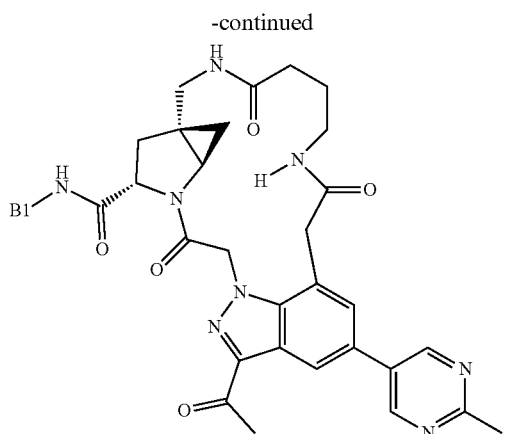
In one embodiment, the compound of Formula II is selected from:
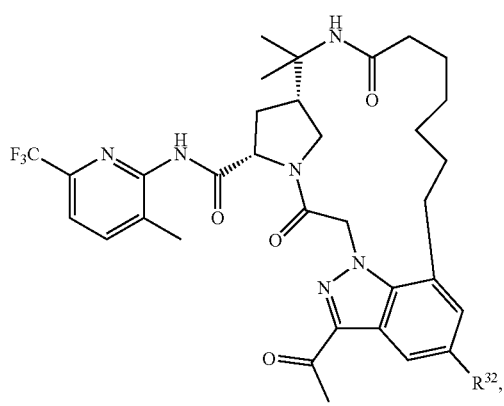
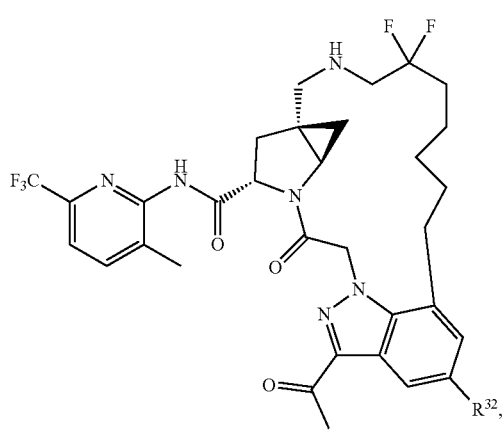
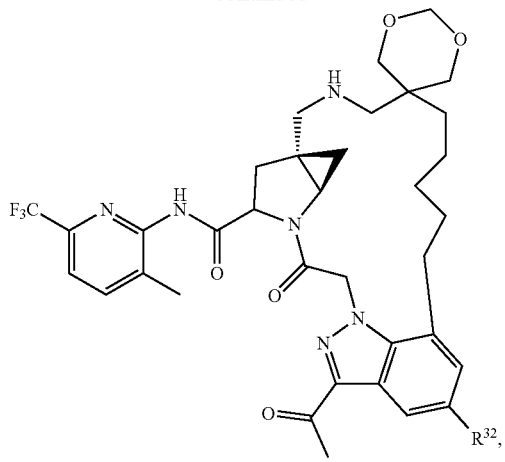
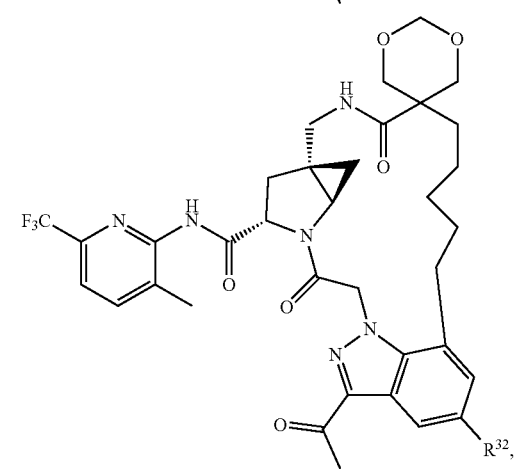
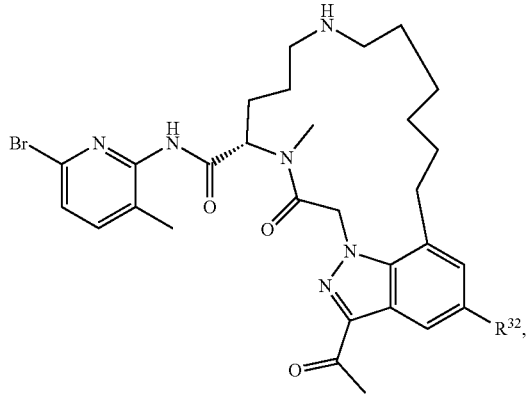
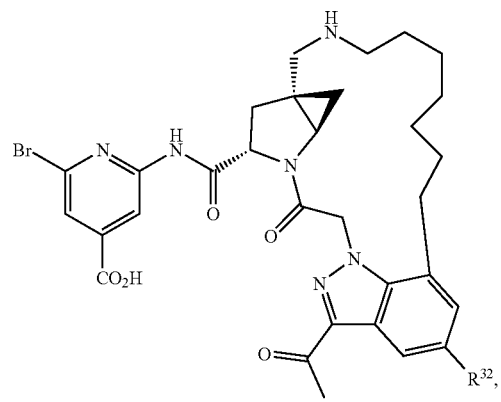

541
-continued
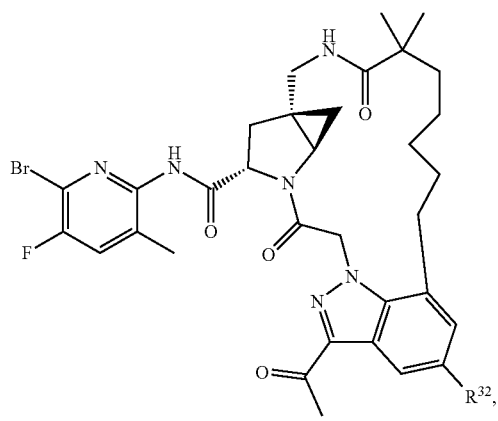
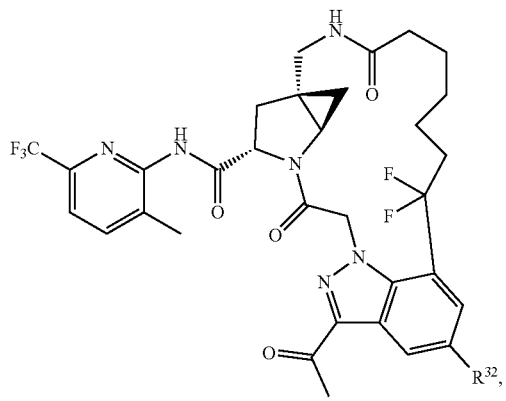
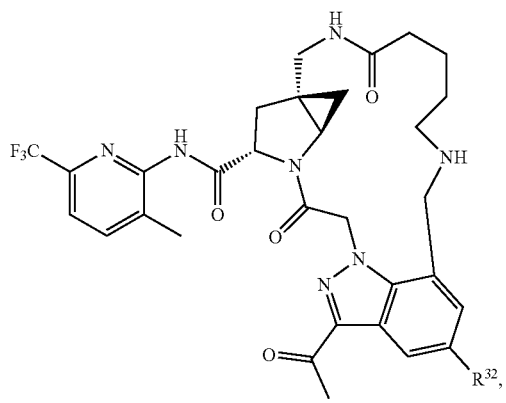
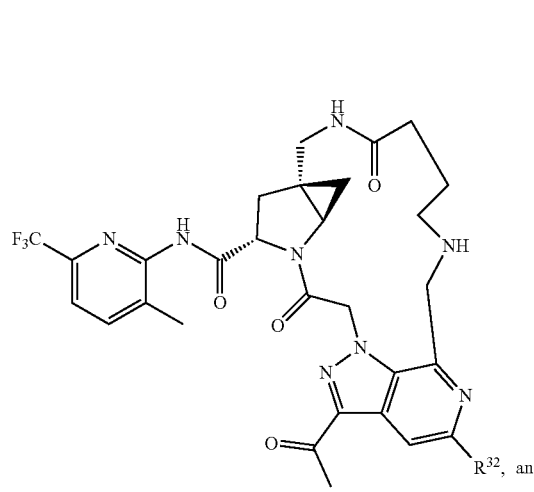
542
-continued
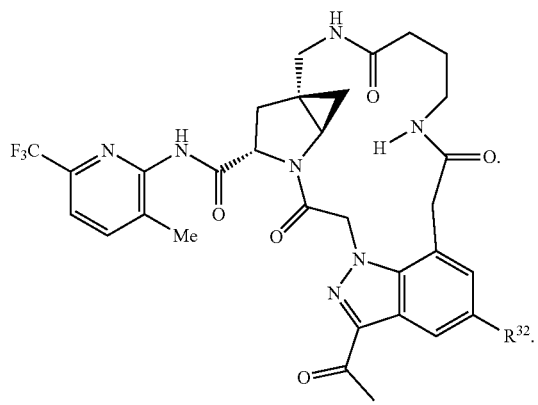
In one embodiment, the compound of Formula II is selected from:
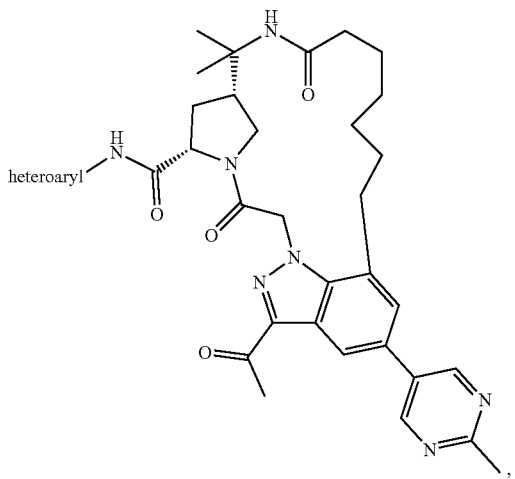
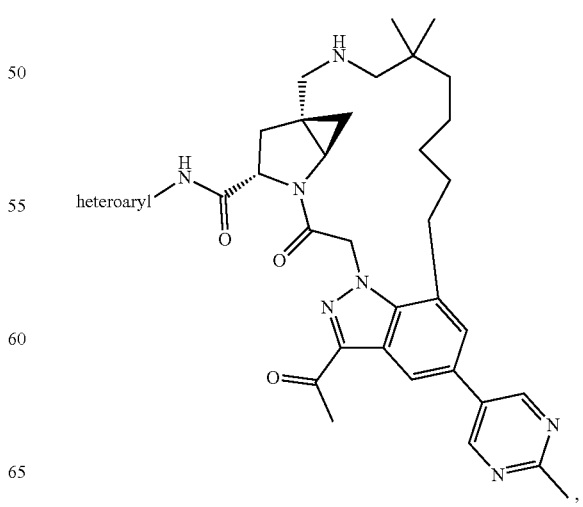

543
-continued
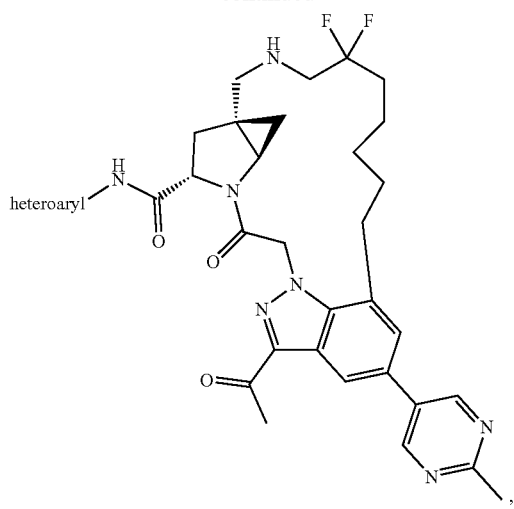
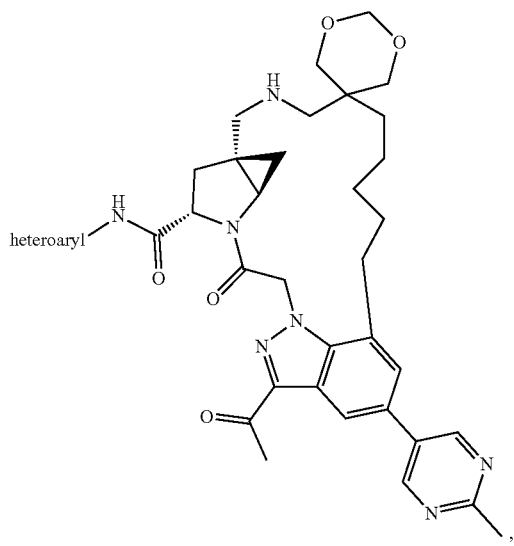
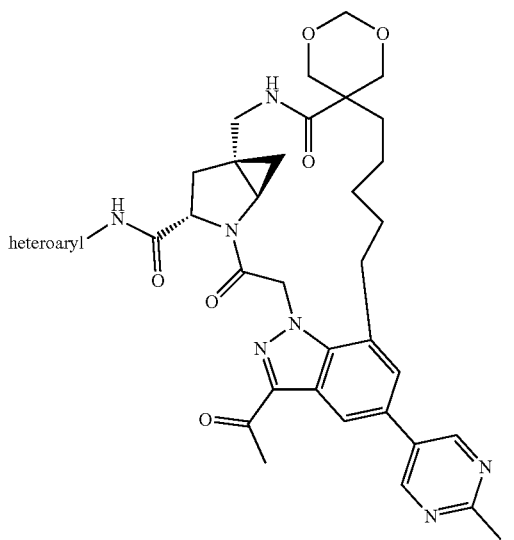
544
-continued
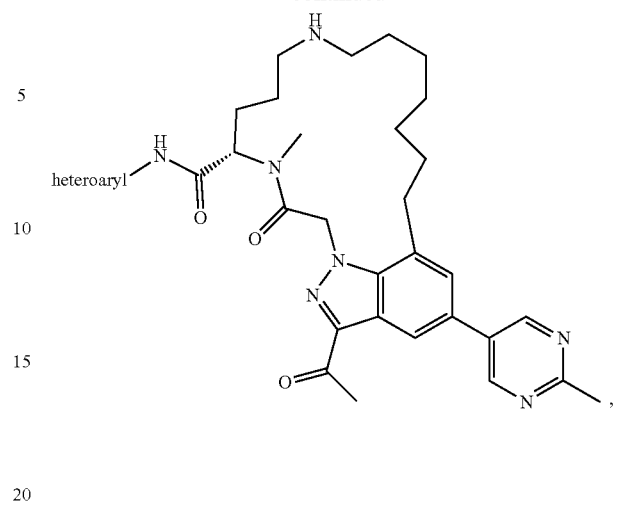
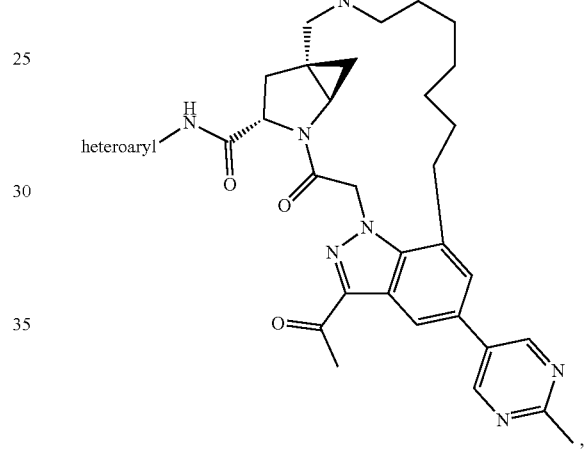
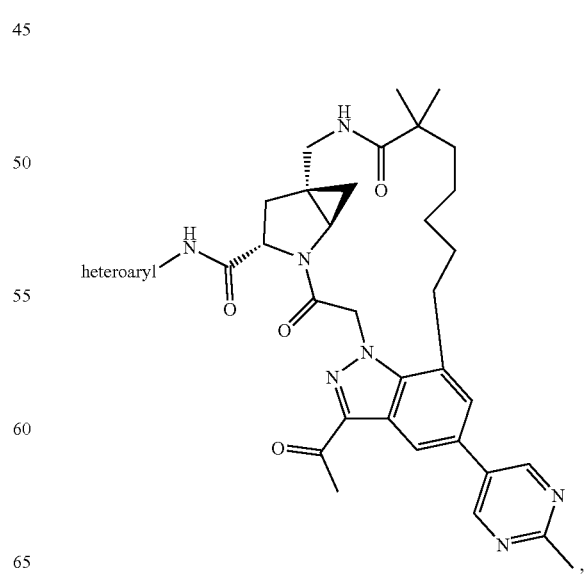

545
-continued
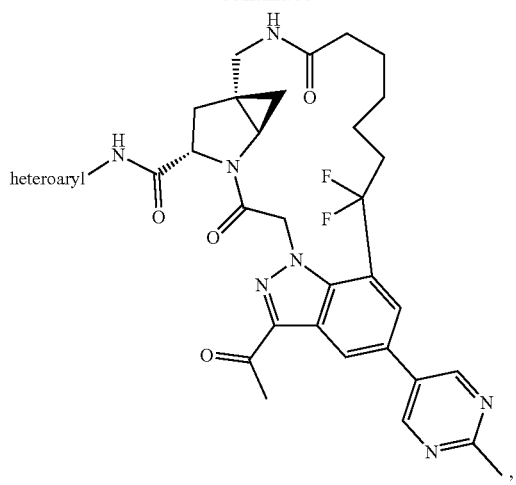
,
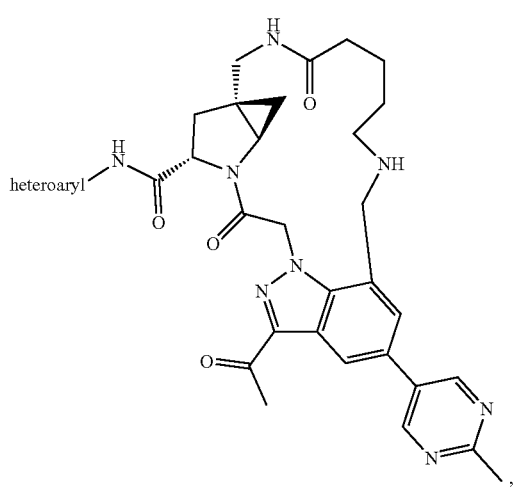
,
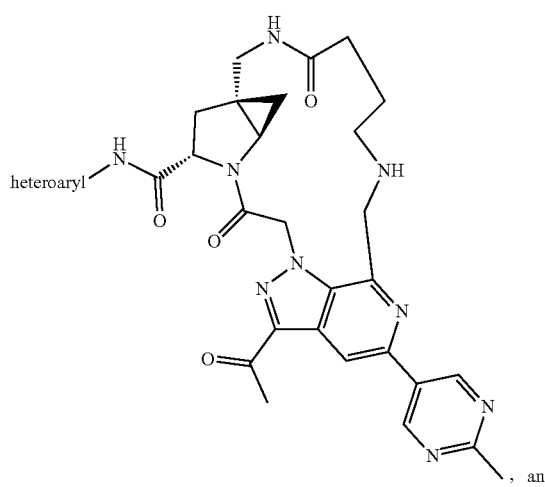
, and
546
-continued
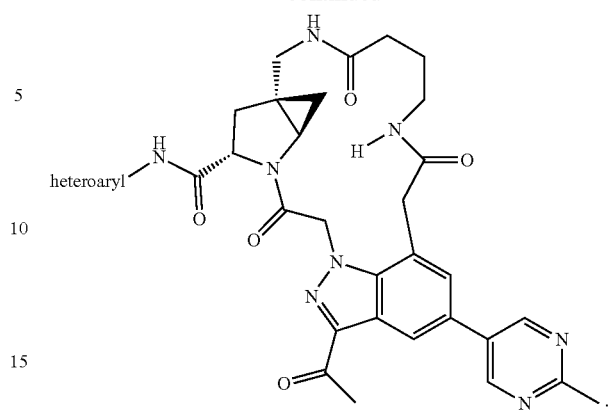
.
In one embodiment, the compound of Formula II is selected from:
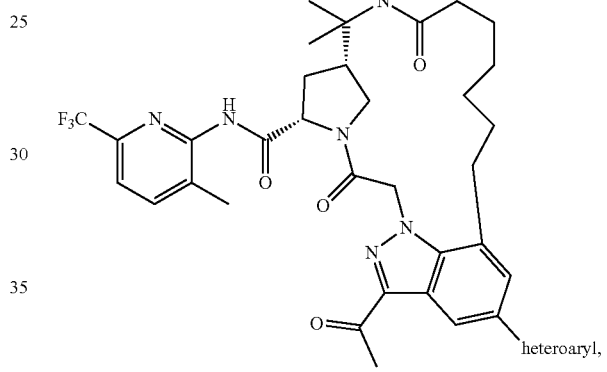
,
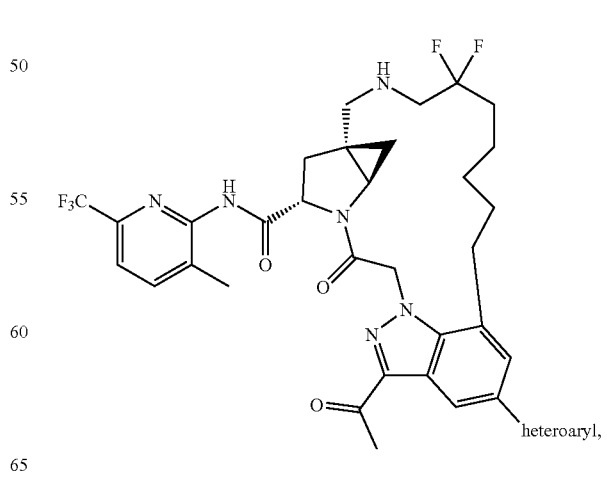
, 547
-continued
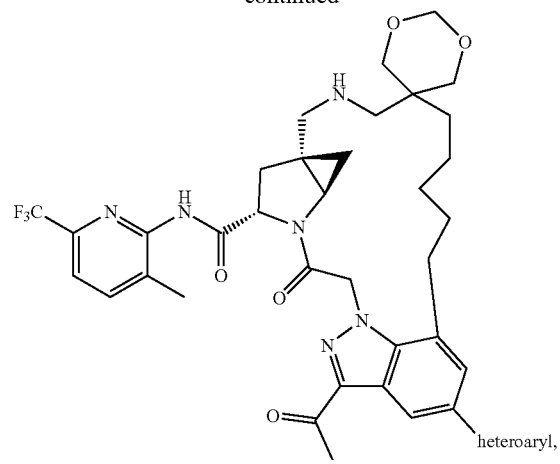
heteroaryl,
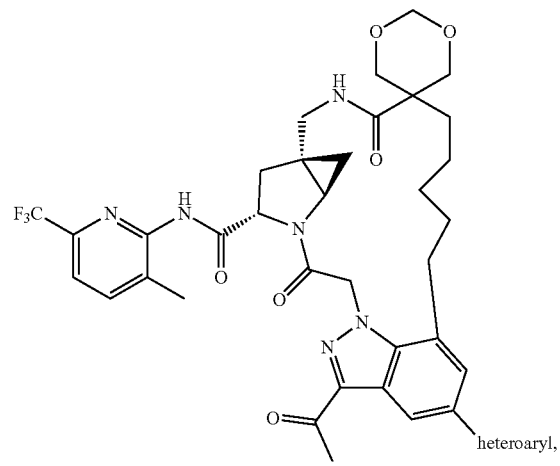
heteroaryl,
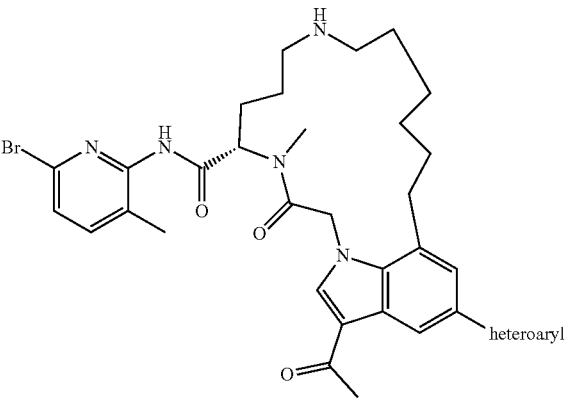
heteroaryl,
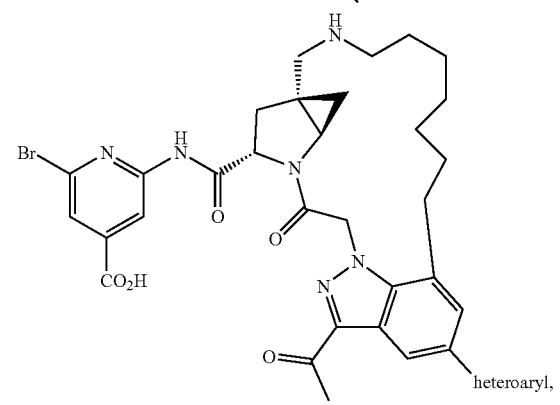
heteroaryl,
548
-continued
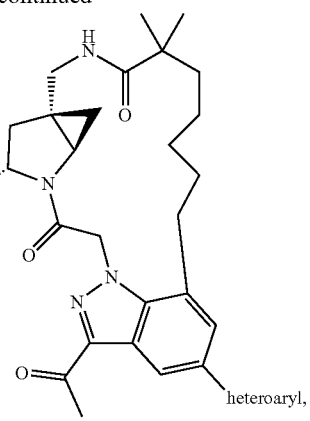
heteroaryl,
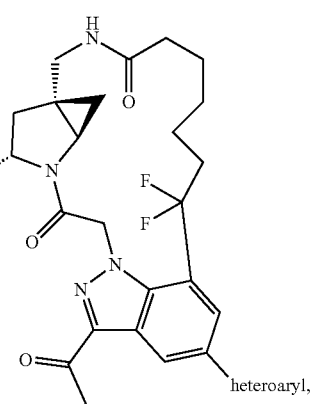
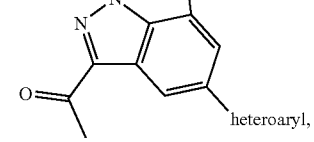
heteroaryl,
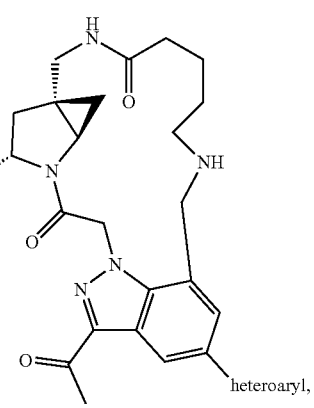
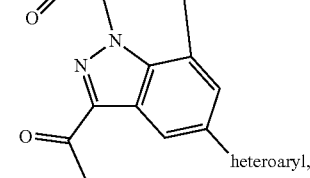
heteroaryl,
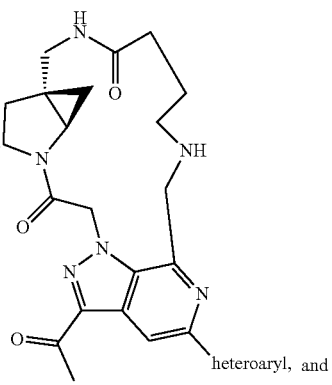
heteroaryl, and

549
-continued
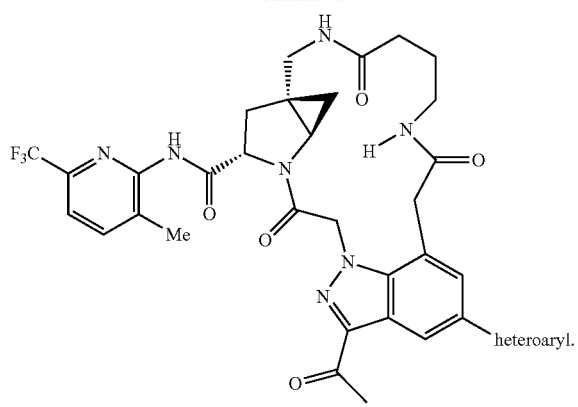
In one embodiment, the compound of Formula II is selected from:
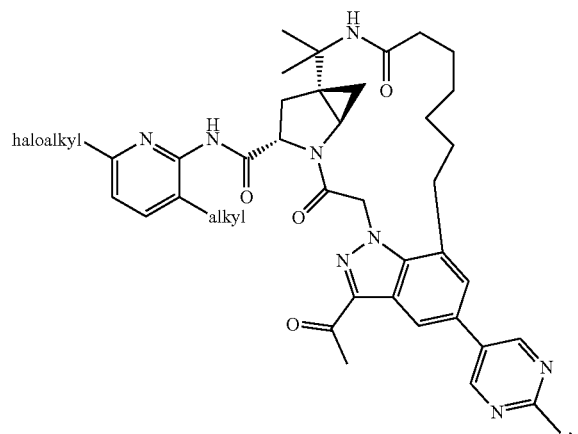
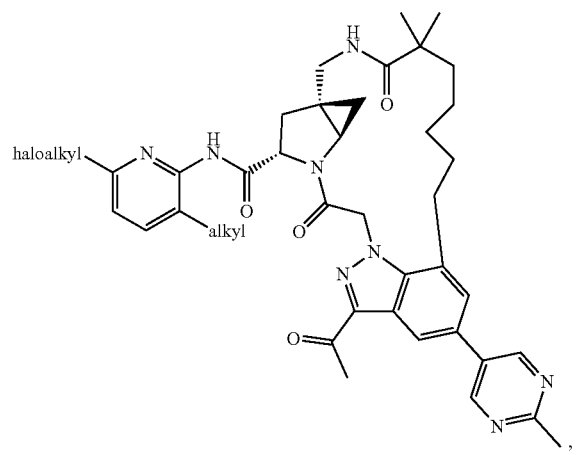
550
-continued
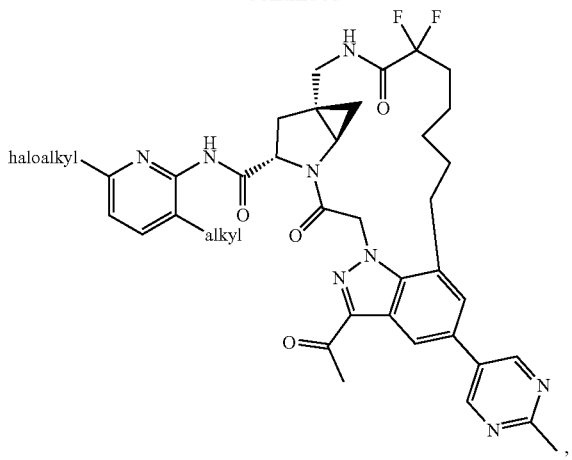
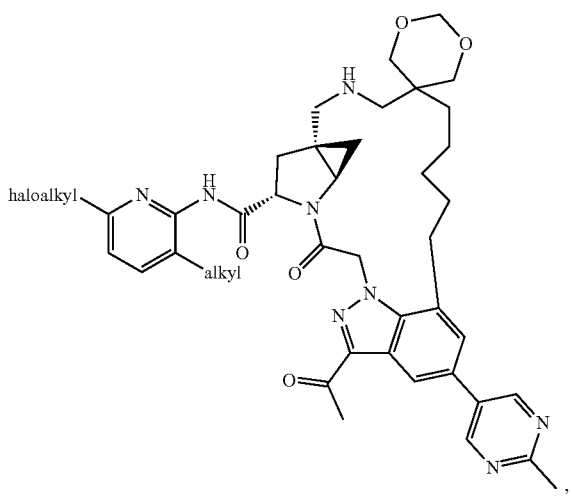
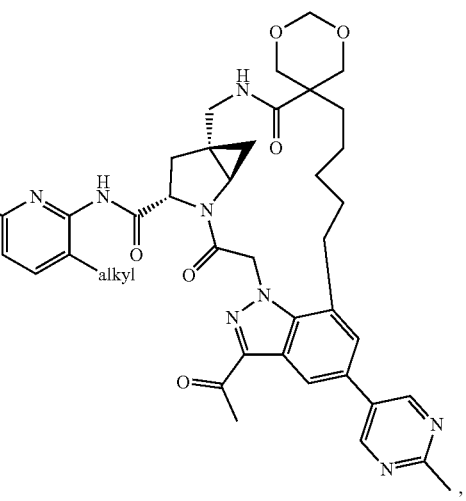

551
-continued
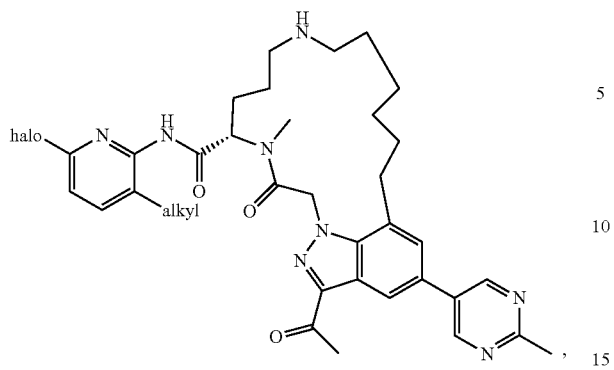
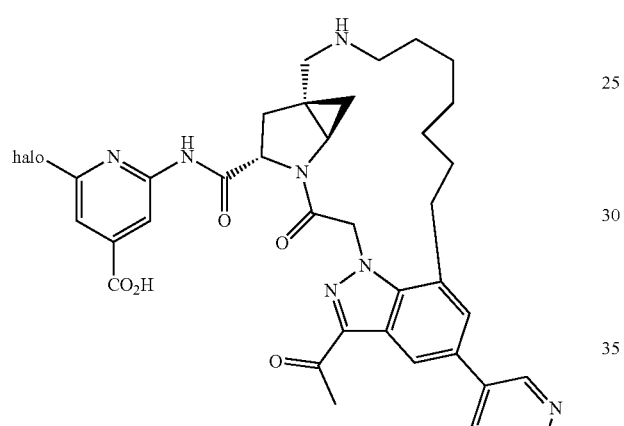
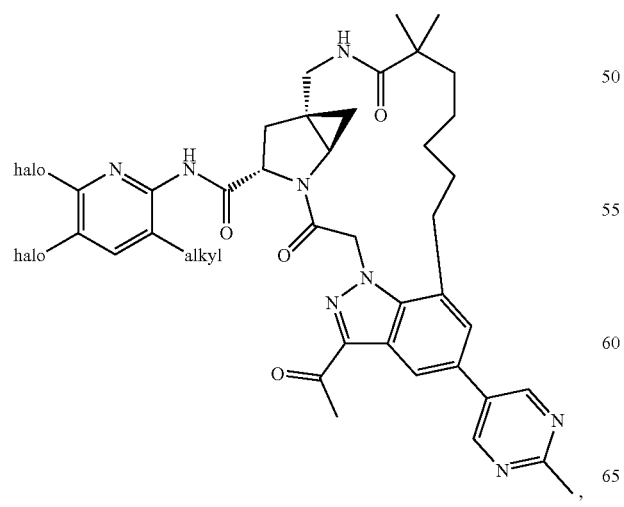
552
-continued
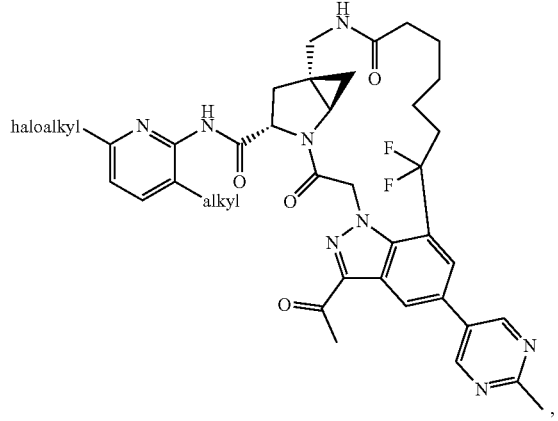
, and
In one embodiment, the compound of Formula II is selected from:

553
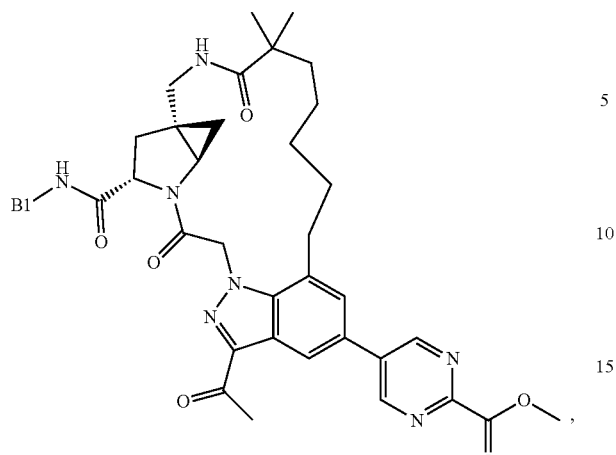
554
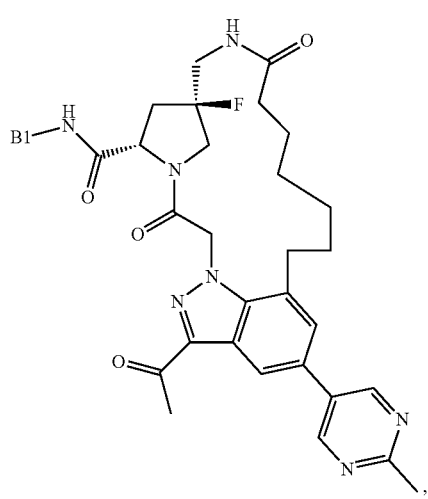
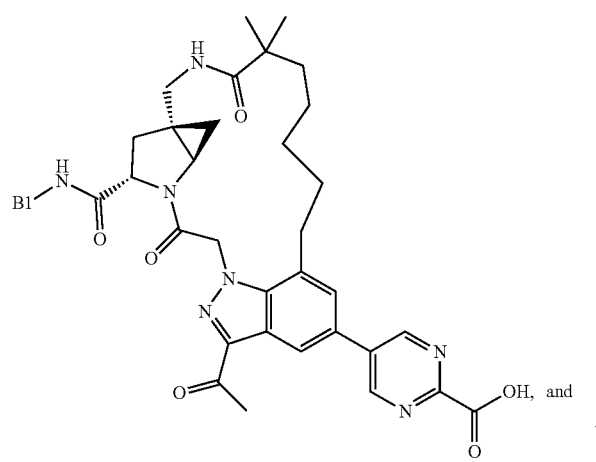
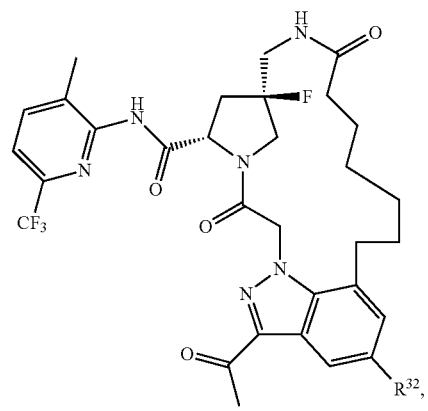
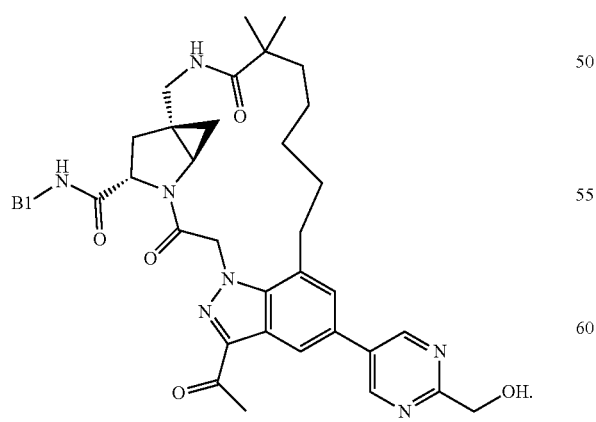
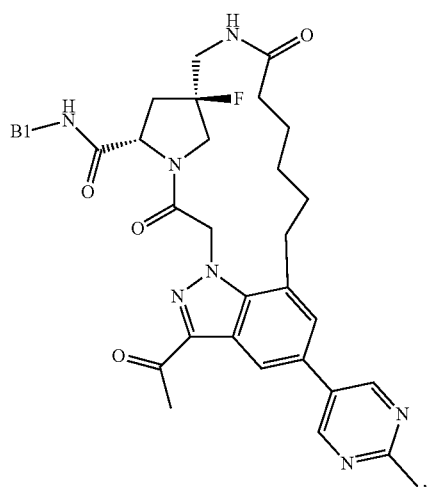
In one embodiment, the compound of Formula II is selected from:

555
-continued
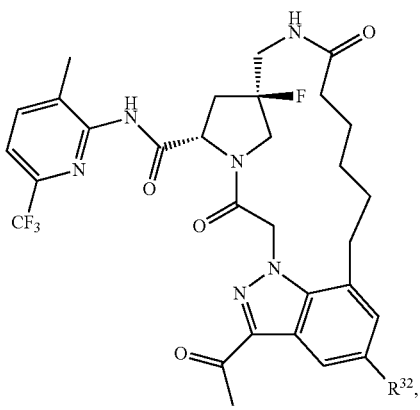
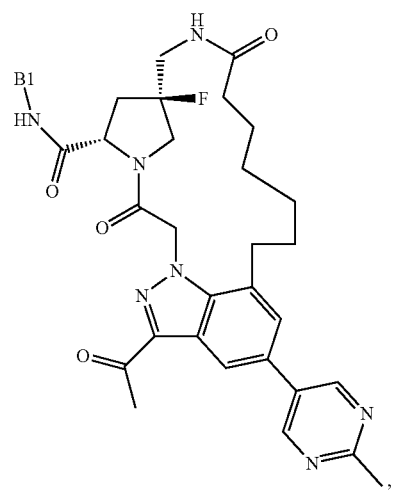
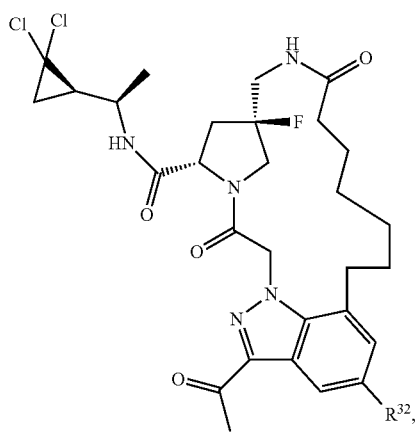
556
-continued
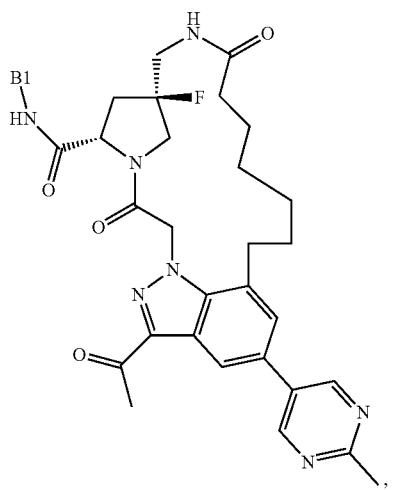
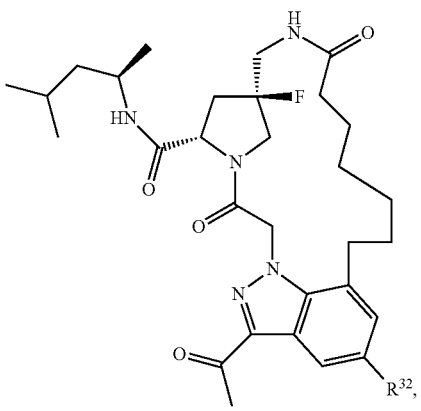
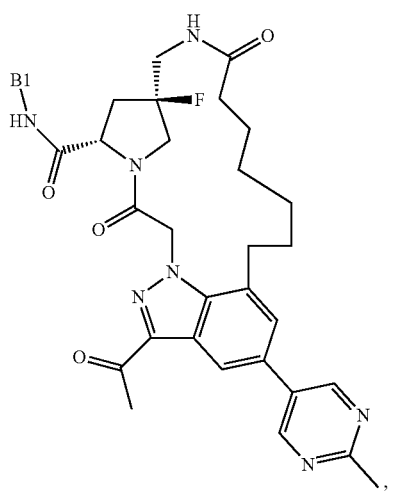

557
-continued
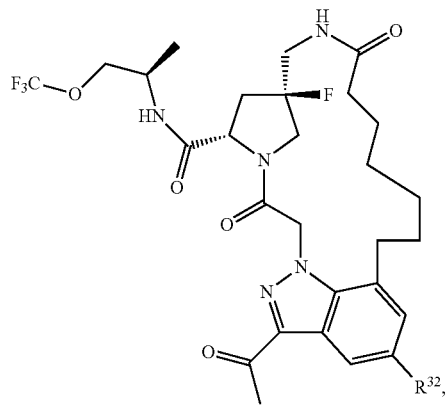
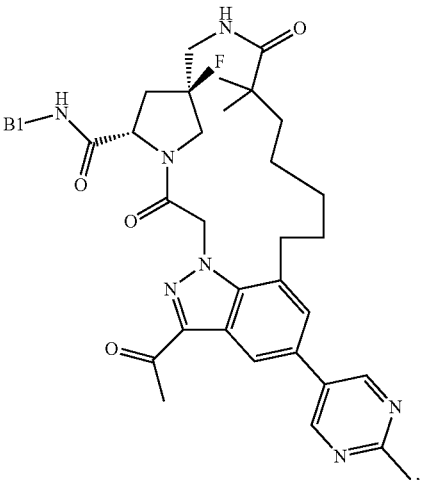
558
-continued
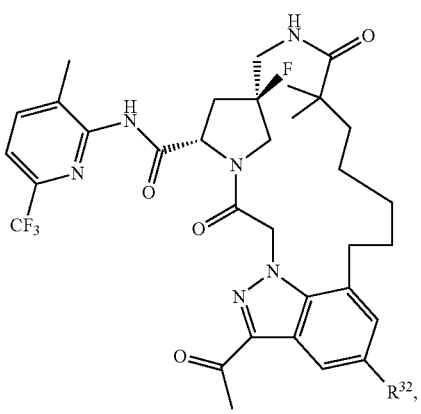
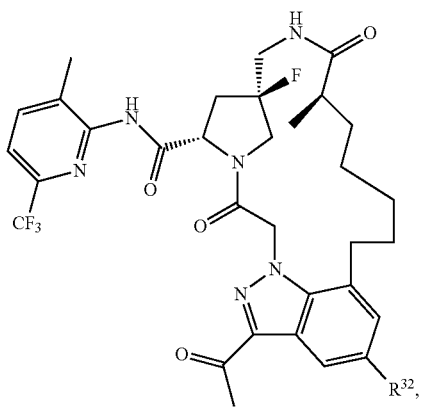

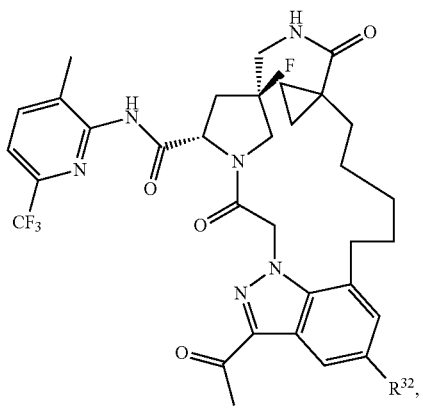
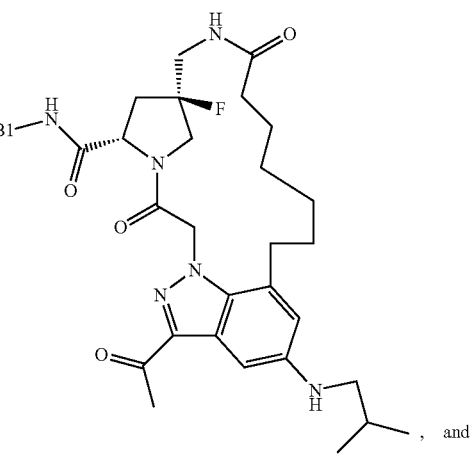
, and
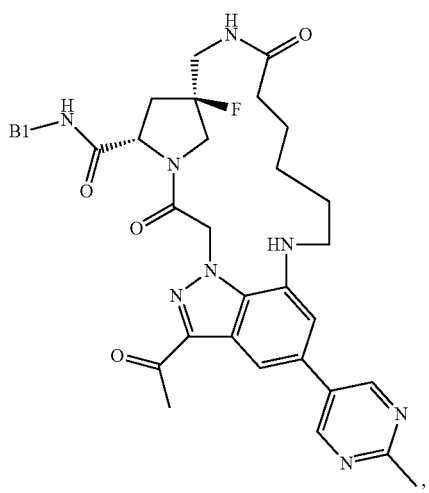
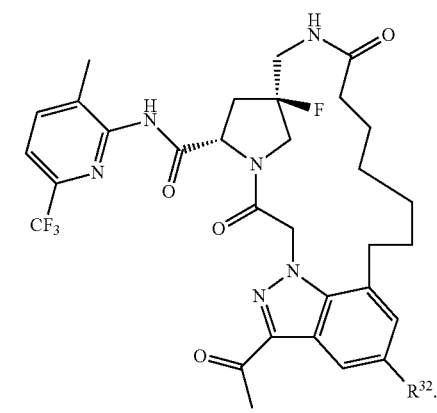
In one embodiment, the compound of Formula II is selected from:
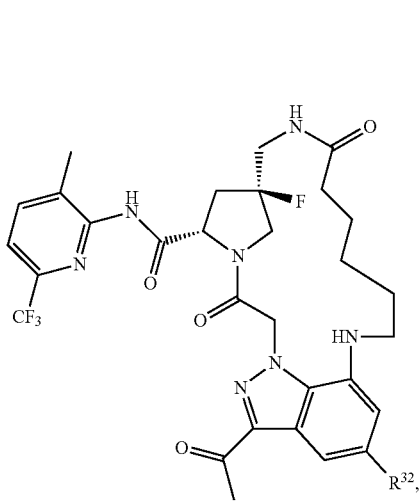
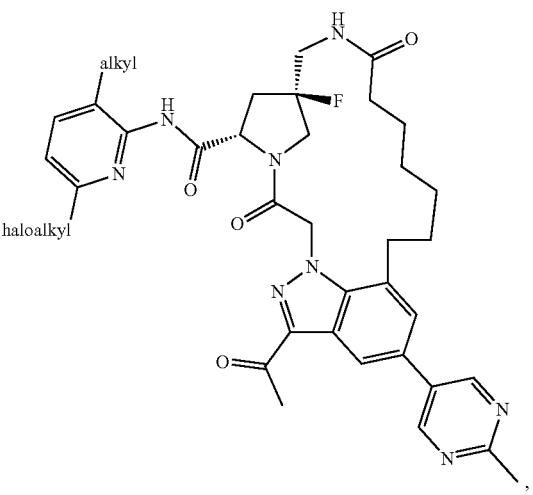

561
-continued
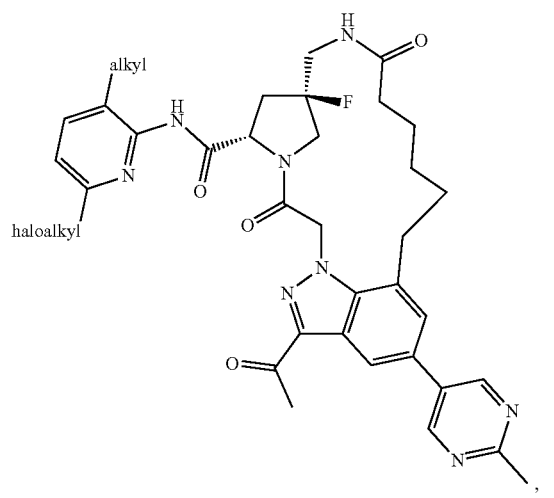
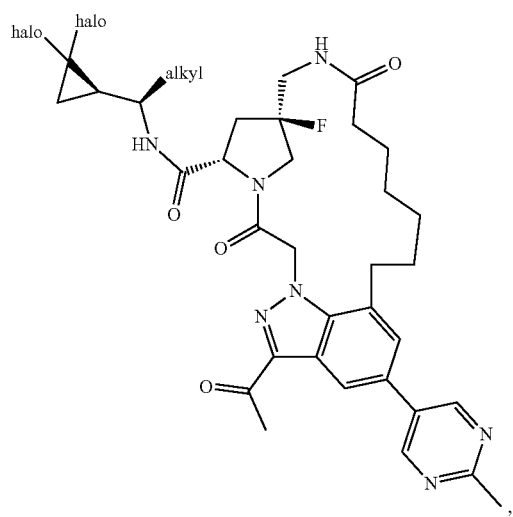
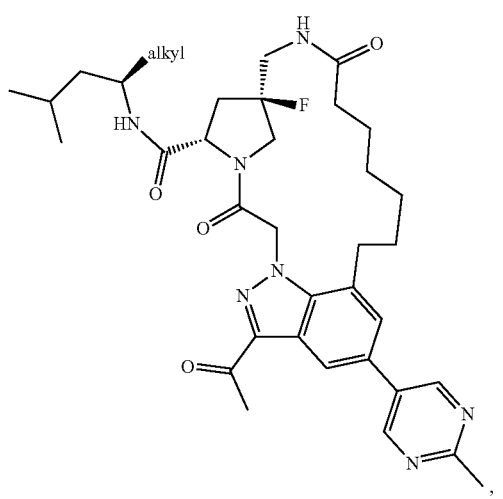
562
-continued
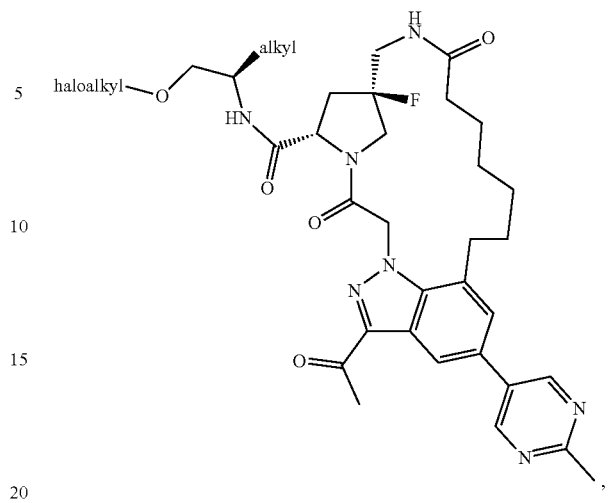
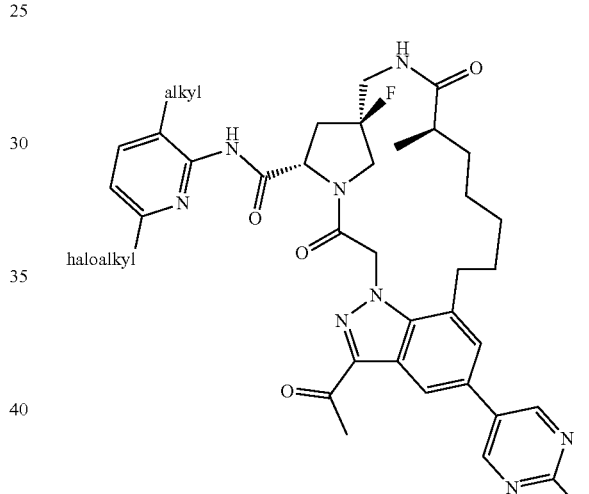
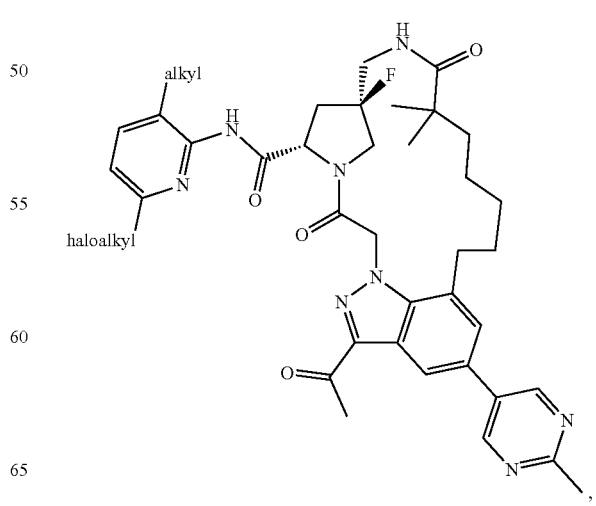

563
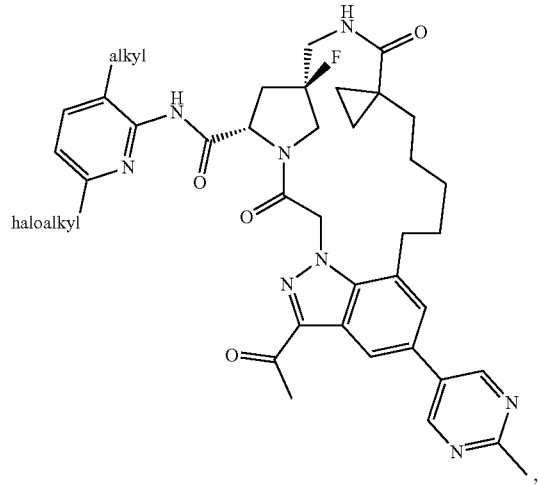
564
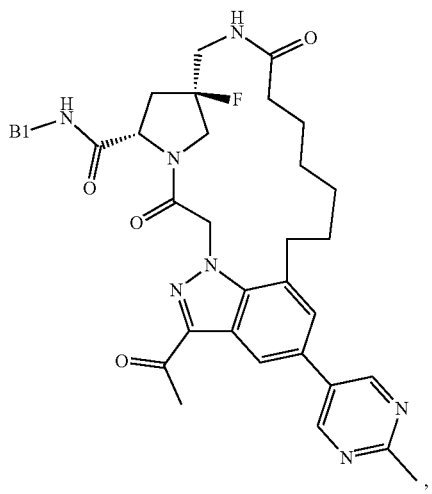
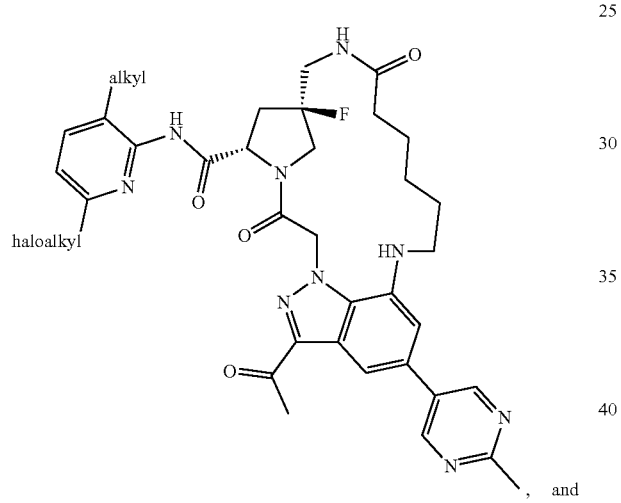, and
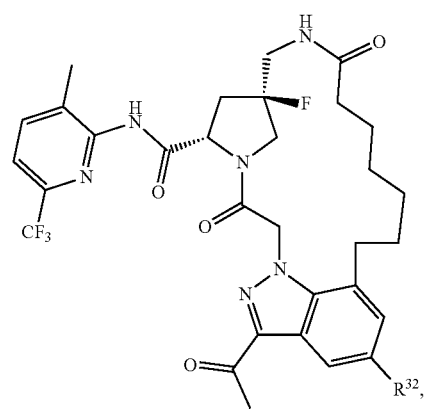
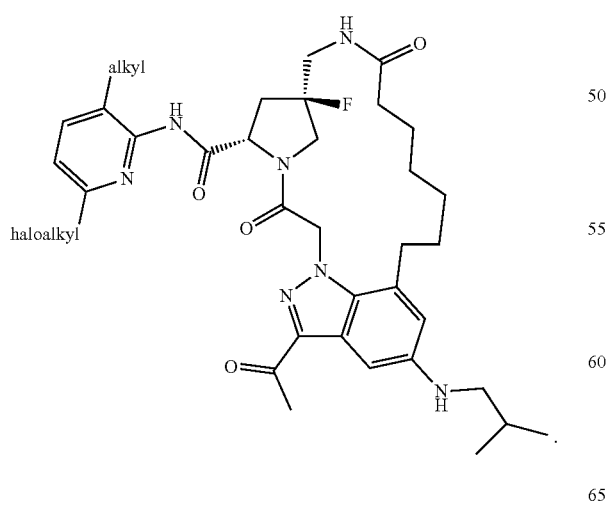
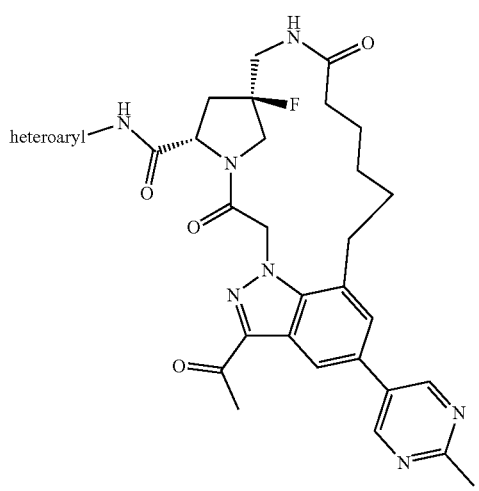
In one embodiment, the compound of Formula II is selected from:

565
-continued
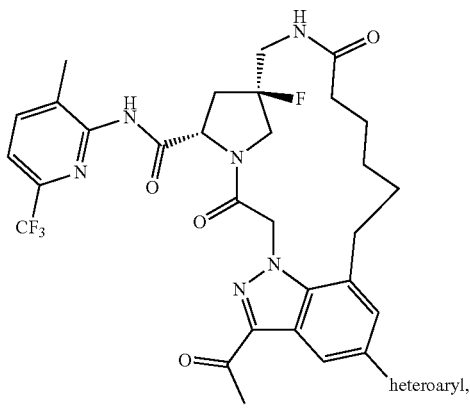
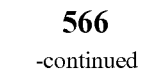
566
-continued
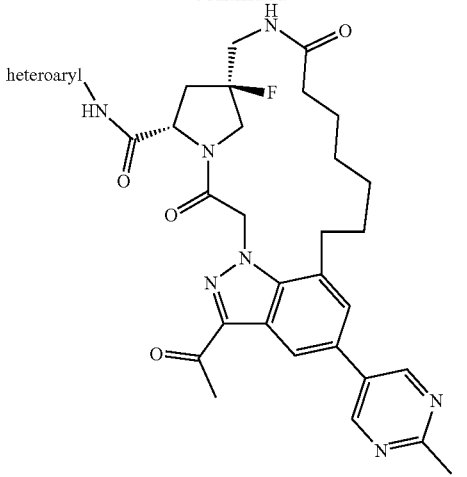
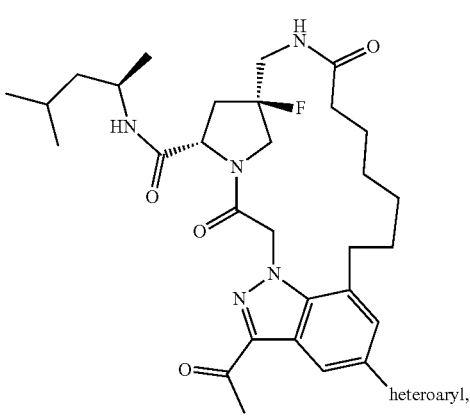
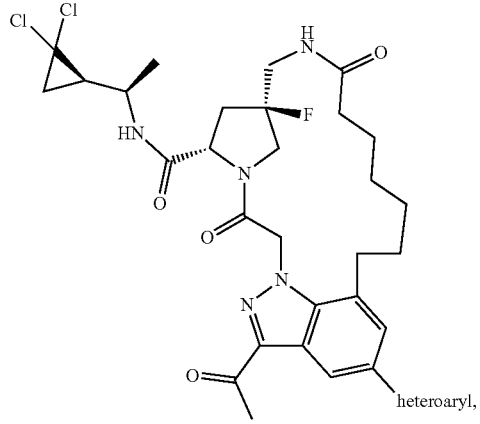
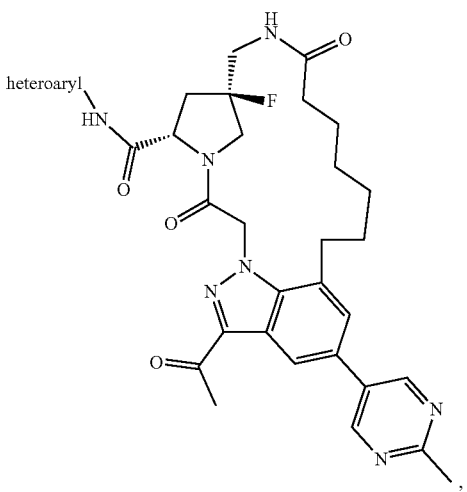

567
-continued
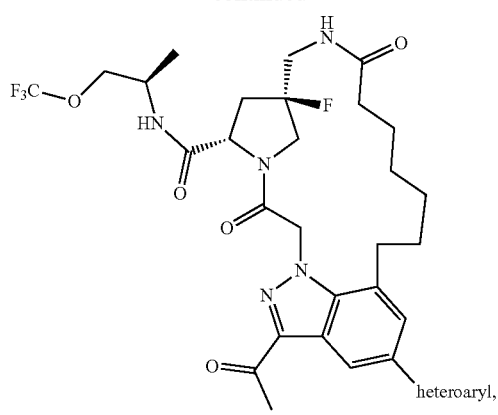
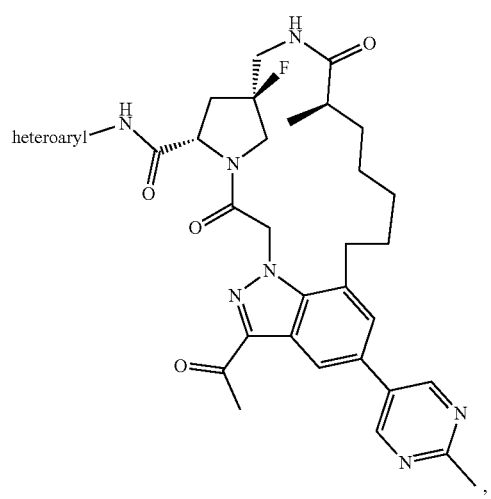
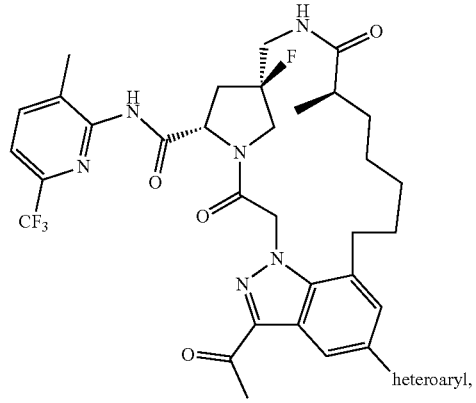
568
-continued
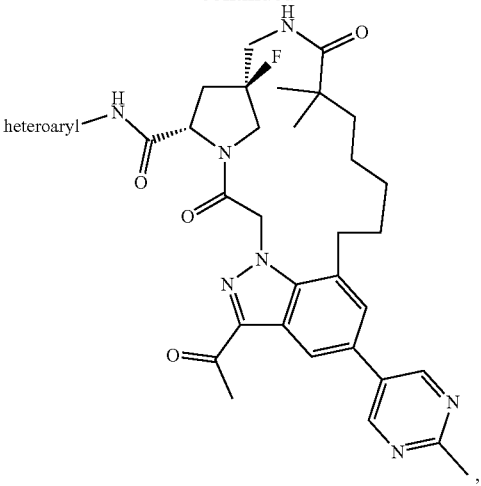
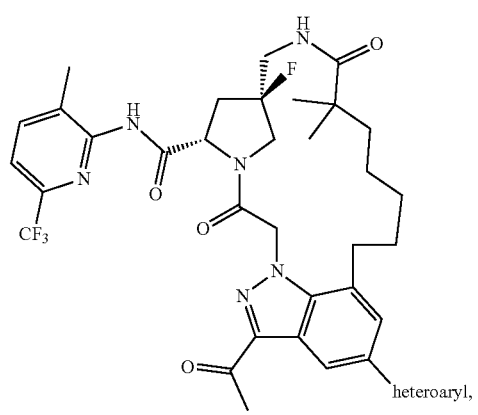
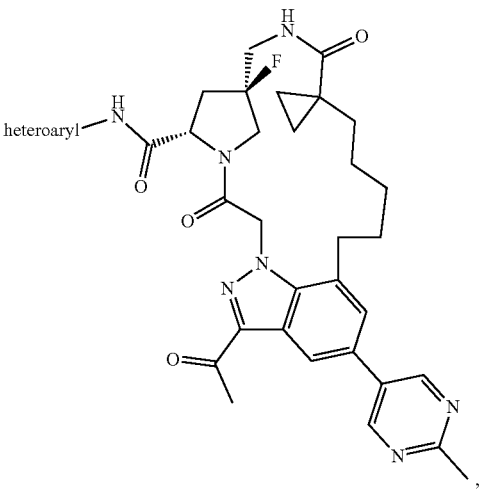

569
-continued
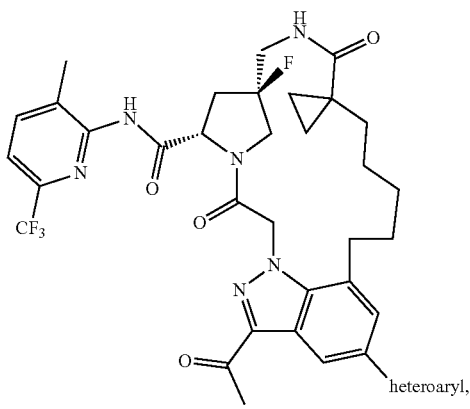
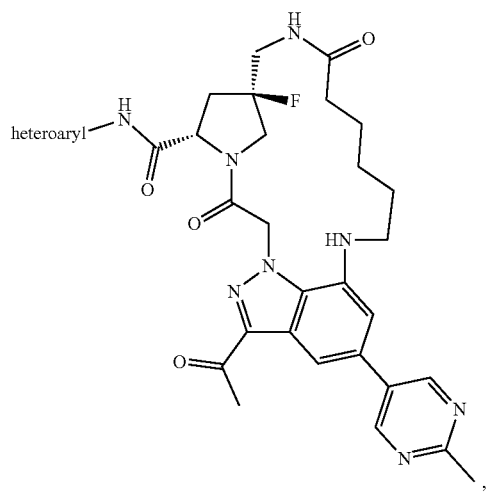
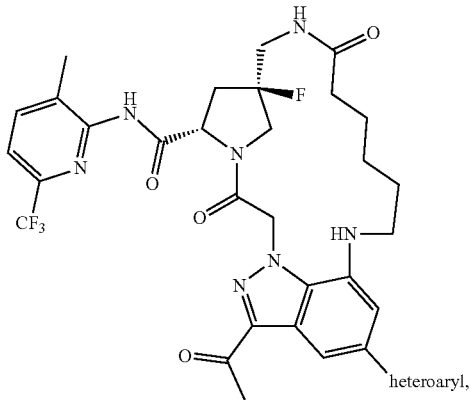
570
-continued
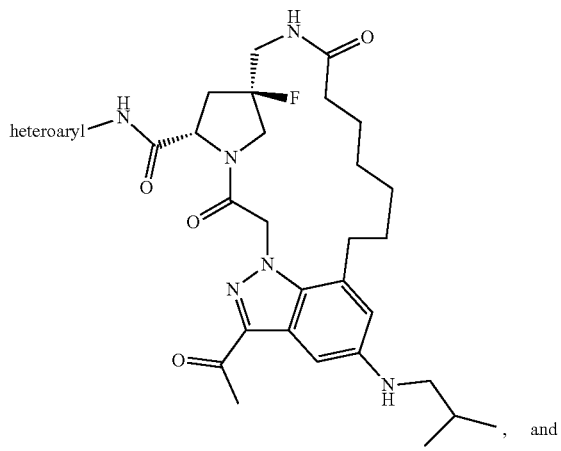
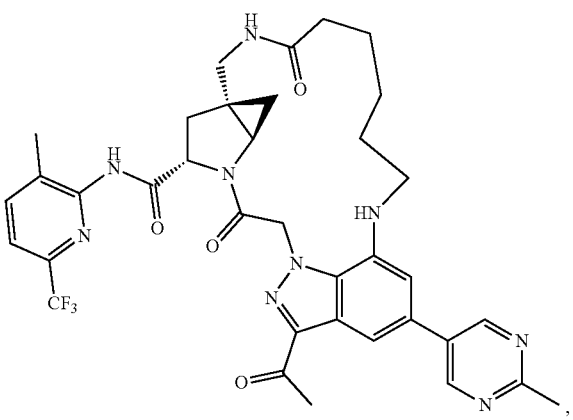
Representative examples of compounds of the present invention include:

571
-continued
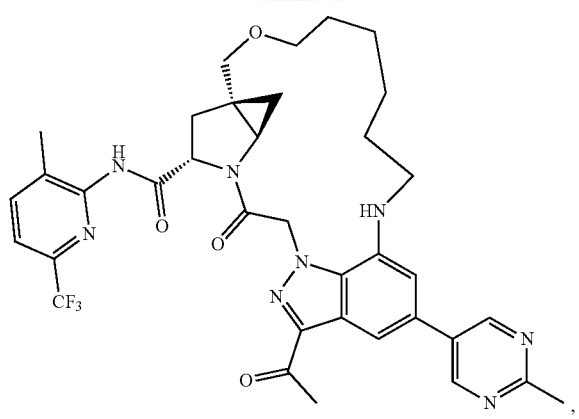
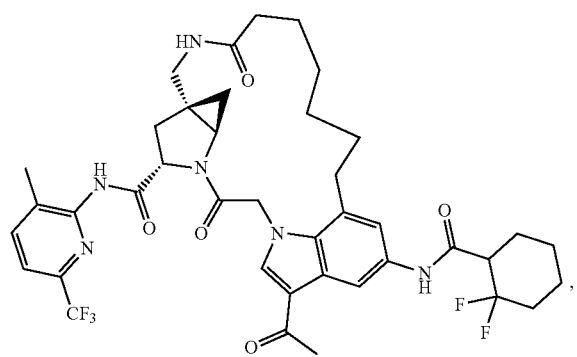
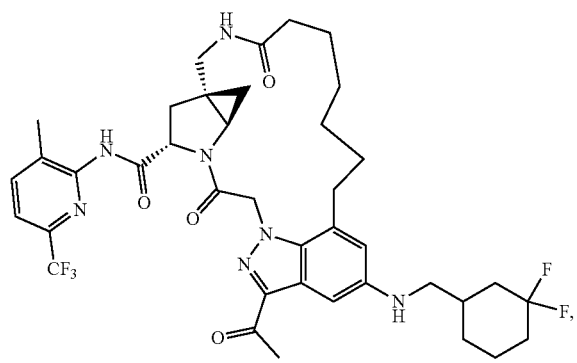
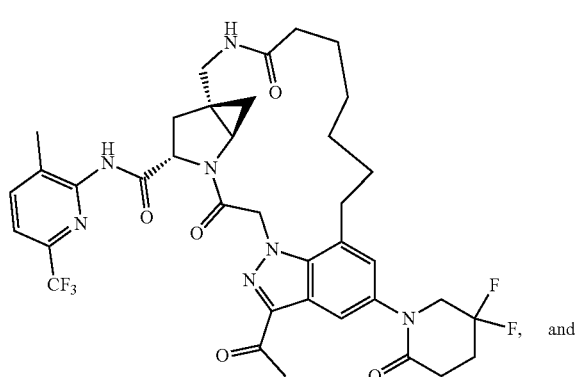, and
572
-continued
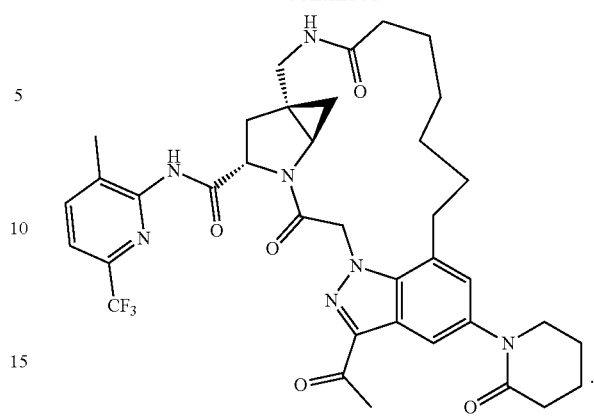.
Additional representative examples of compounds of the present invention include:
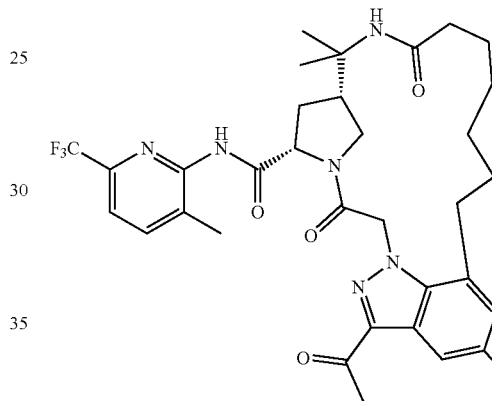,
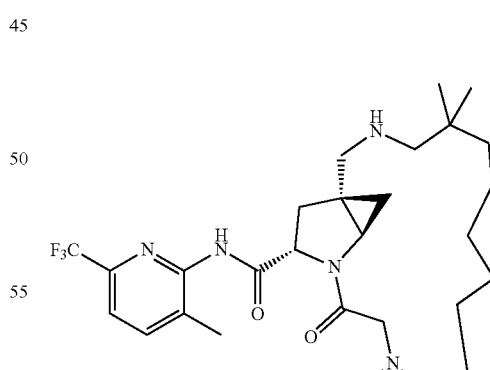, 573
-continued
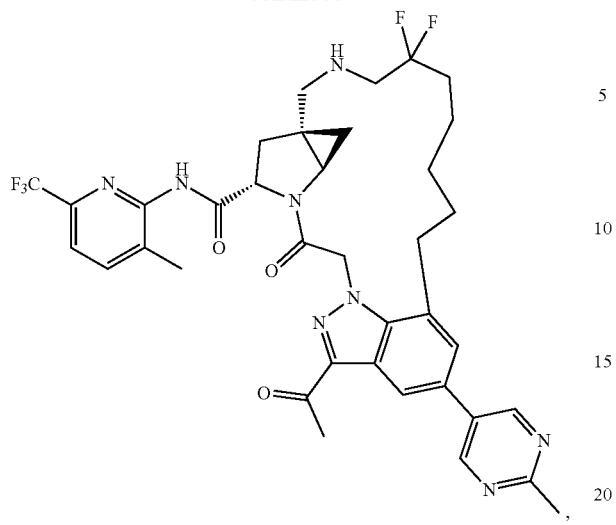
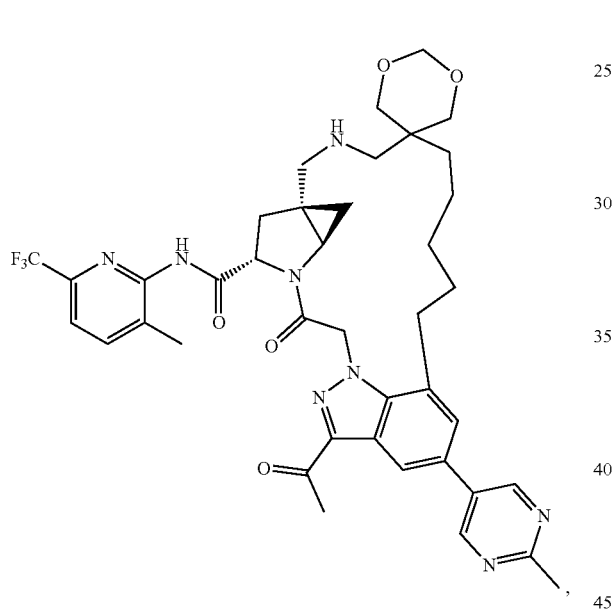
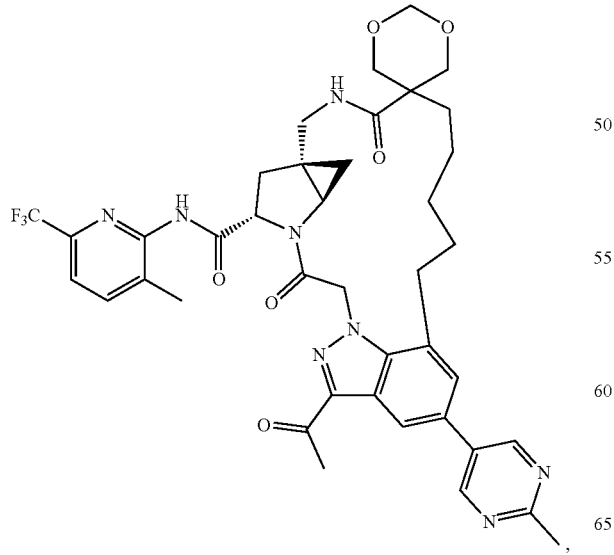
574
-continued
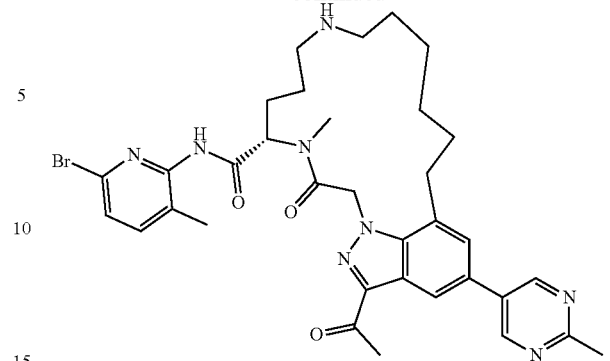
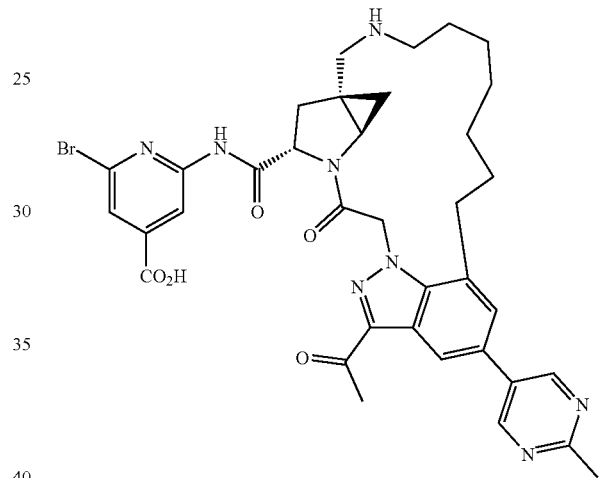
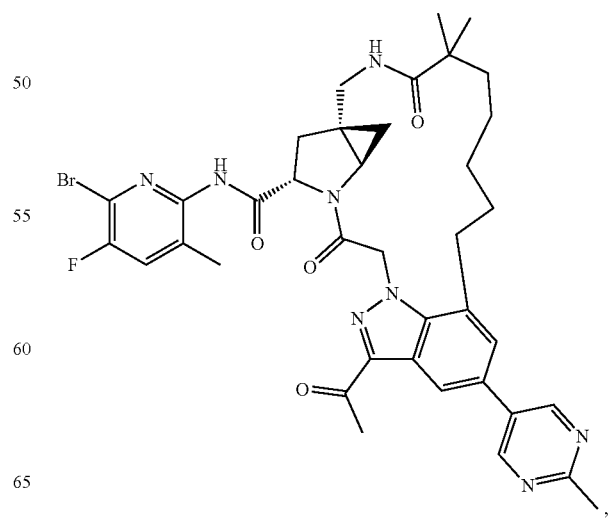

575
-continued
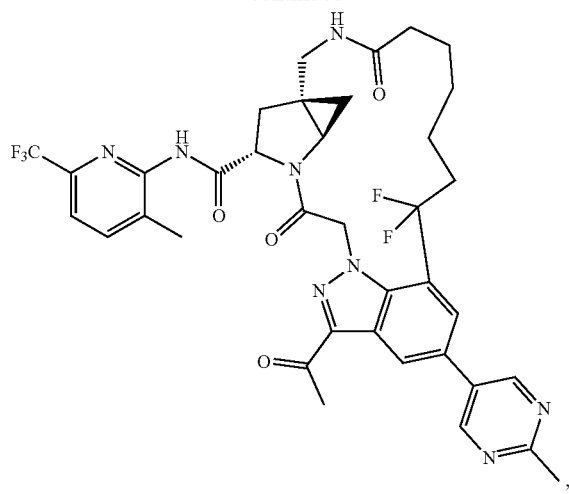
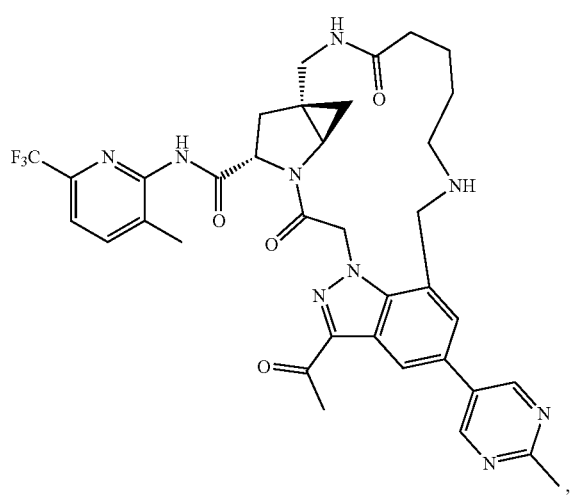
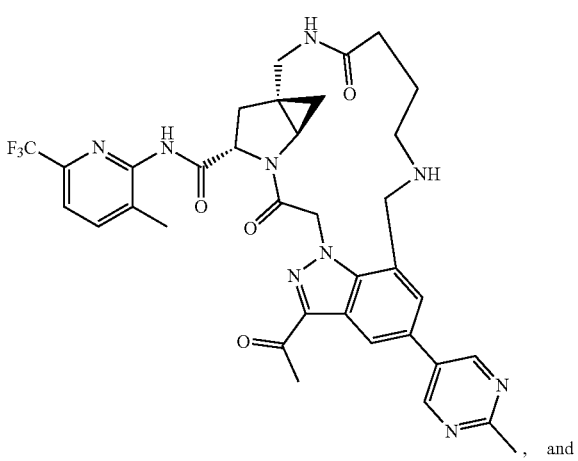
, and
576
-continued
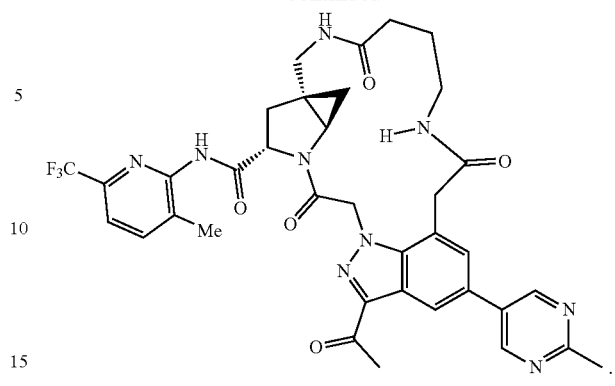
Additional representative compounds of the present invention include:
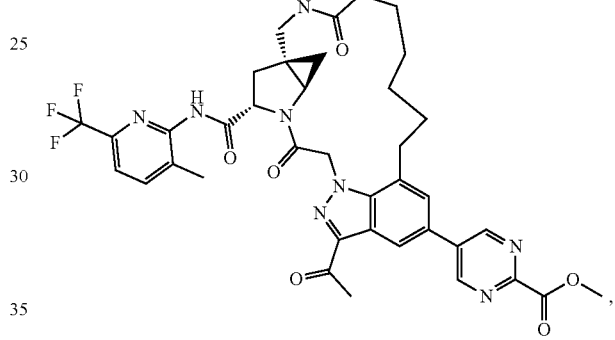
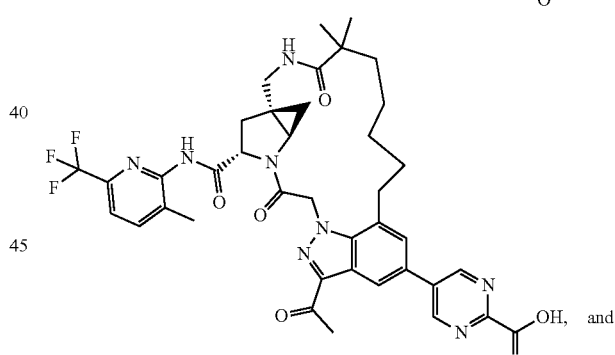
, and
Additional representative compounds of the present invention include:

577
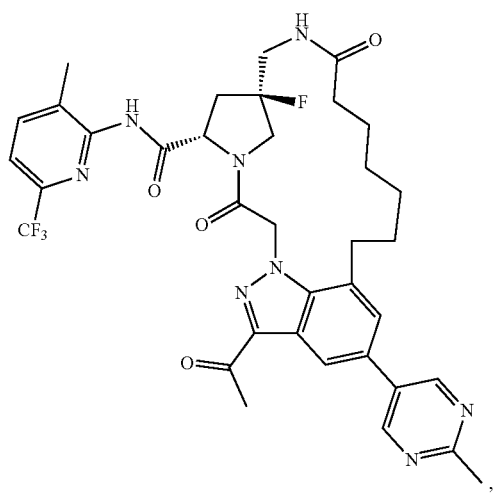
578
-continued
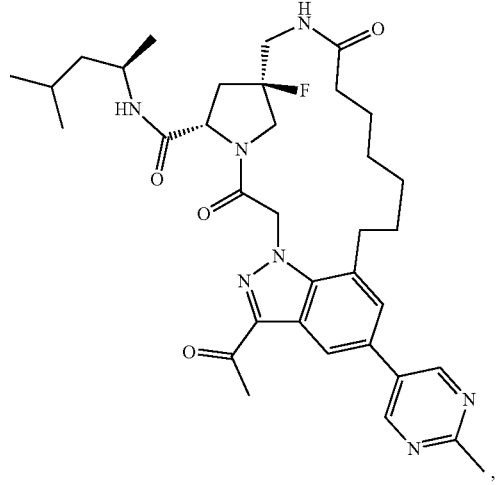
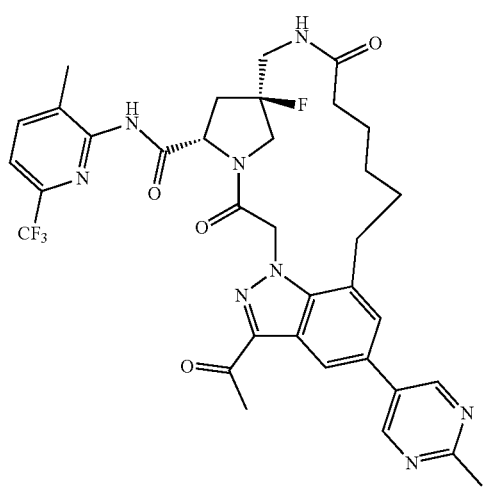
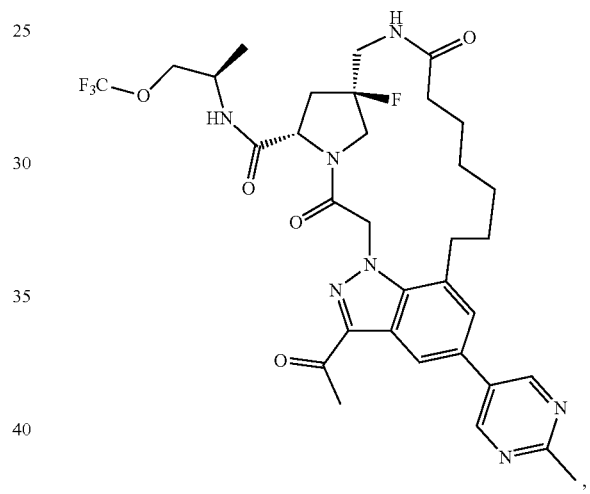
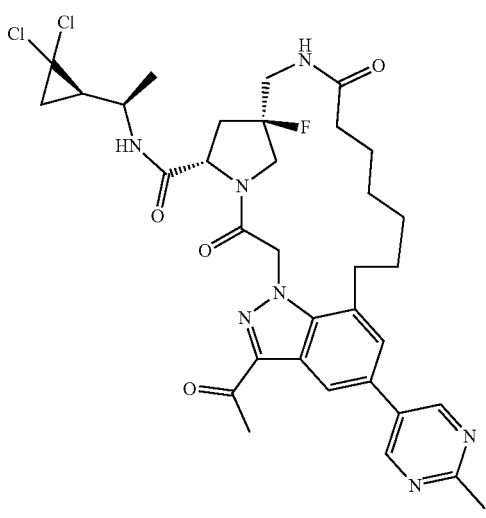
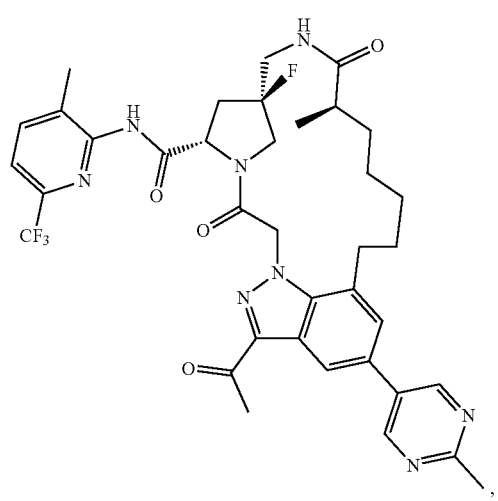

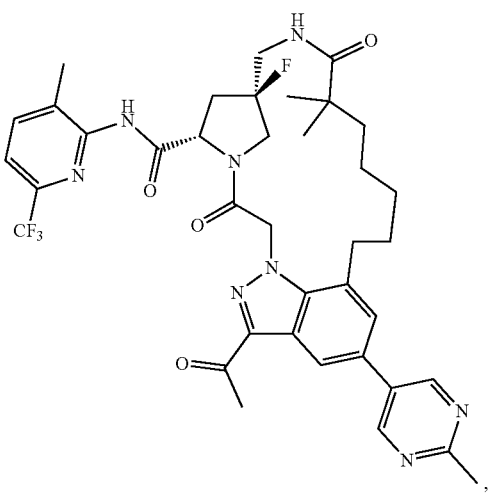
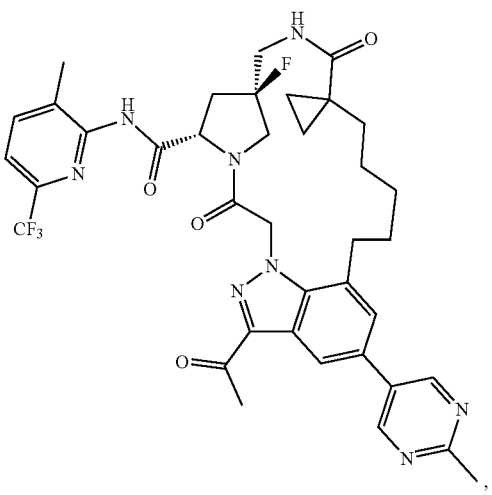
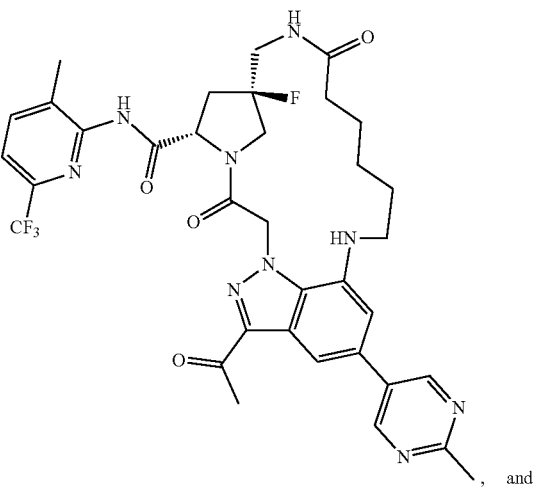
, and
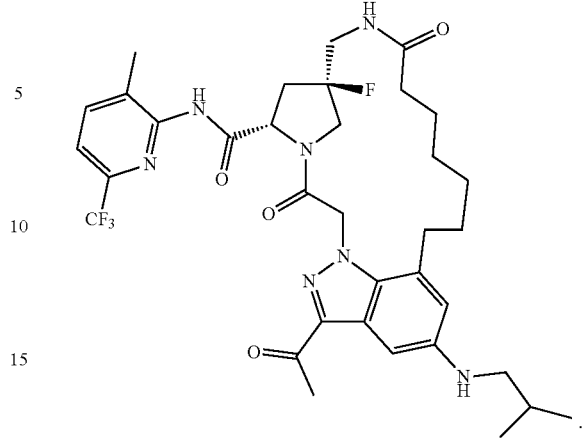
In one embodiment, a compound is provided of the formula:
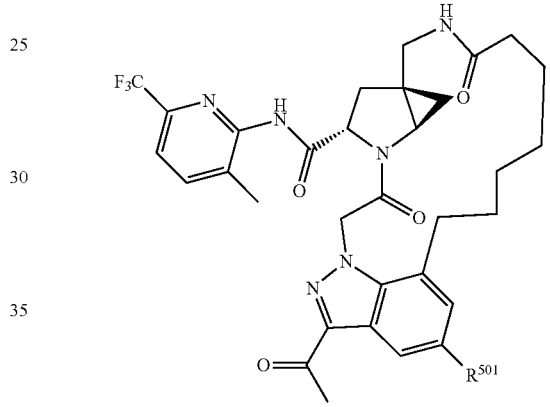
wherein $R^{501}$ is selected from a hetero, heterocycloalkyl, and cycloalkyl group, each of which may be optionally substituted as described herein.
Representative examples of $R^{501}$ include
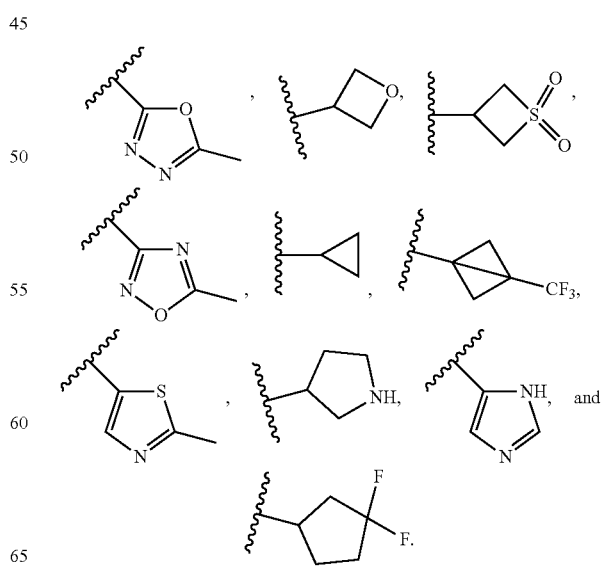

In one embodiment, a compound is provided of the formula:

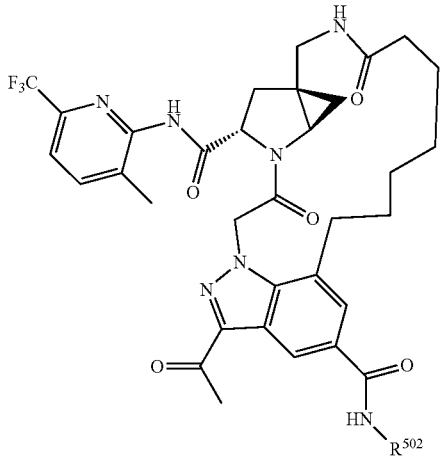

wherein $R^{502}$ is selected from a cycloalkyl, alkyl(cycloalkyl), and alkyl(heteroaryl) group, each of which may be optionally substituted as described herein.

Representative examples of $R^{502}$ include

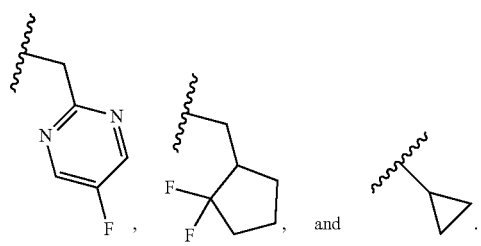

In another embodiment, a compound is provided of the formula:

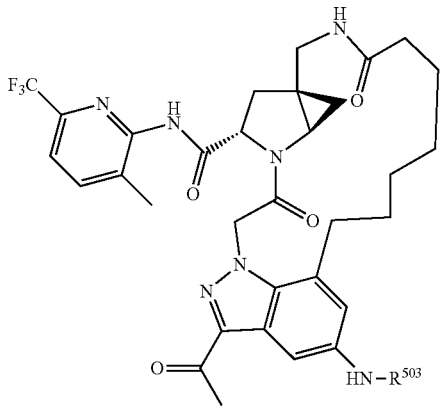

wherein $R^{503}$ is selected from a cycloalkyl, alkyl(cycloalkyl), or alkyl(heteroaryl) group, each of which may be optionally substituted as described herein.

Representative examples of $R^{503}$ include

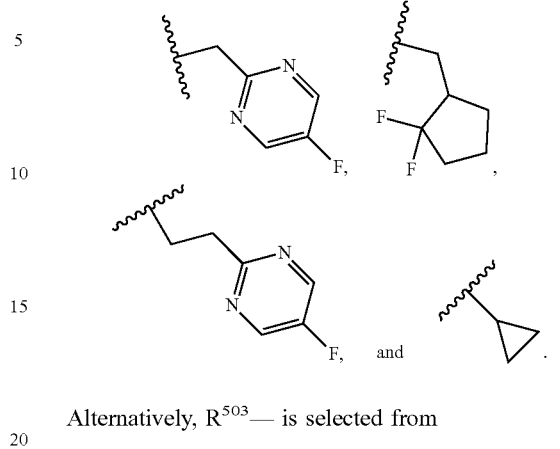

Alternatively, $R^{503}$— is selected from

In another embodiment, a compound is provided of the formula:

wherein $R^{504}$ is selected from a monocyclic and bicyclic heterocycle group, each of which may be optionally substituted as described herein.

Representative examples of $R^{504}$ include

In another embodiment, a compound is provided of the formula:

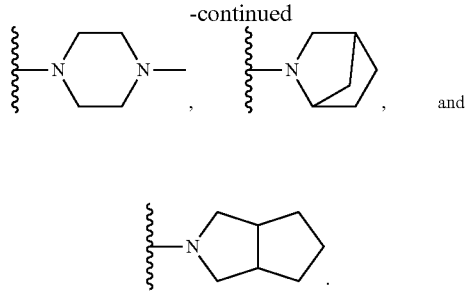

wherein $R^{505}$ is selected from alkyl(dialkylamino), alkyl(heteroaryl), and alkyl(heterocycle), each of which may be optionally substituted as described herein.

Representative examples of $R^{505}$ include

In another embodiment, a compound is provided of the formula:

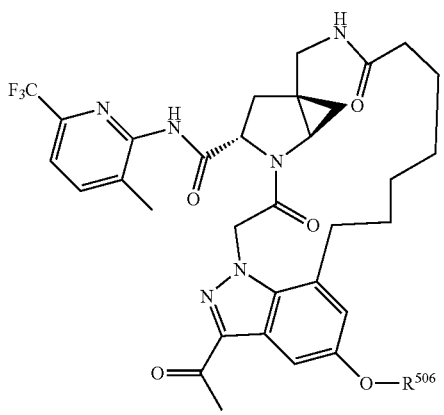

wherein $R^{506}$ is selected from cycloalkyl, haloalkyl, alkyl(heteroaryl), alkyl(dialkylamino), and alkyl(heterocycle), each of which may be optionally substituted as described herein.

Representative examples of $R^{506}$ include

In another embodiment, a compound is provided of the formula:

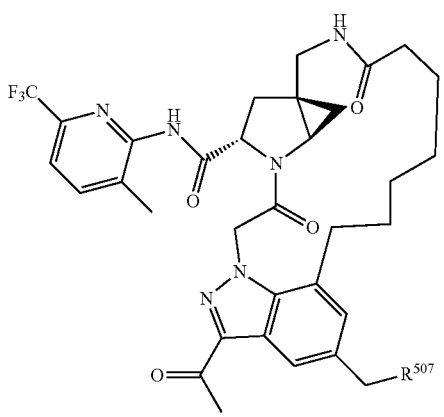

wherein R⁵⁰⁷ is selected from mono or bicyclic heterocycle or heteroaryl, each of which may be optionally substituted as described herein.

Representative examples of R⁵⁰⁷ include

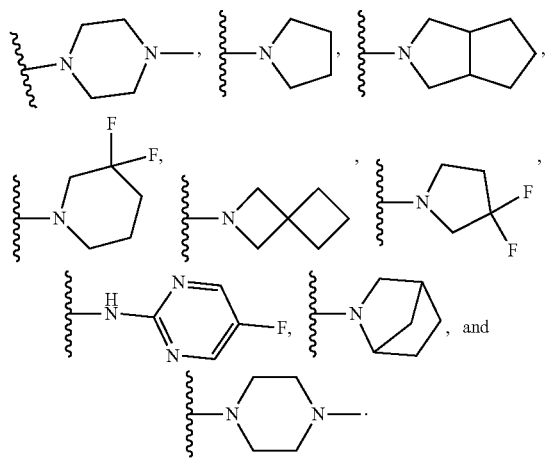

In another embodiment, a compound is provided of the formula:

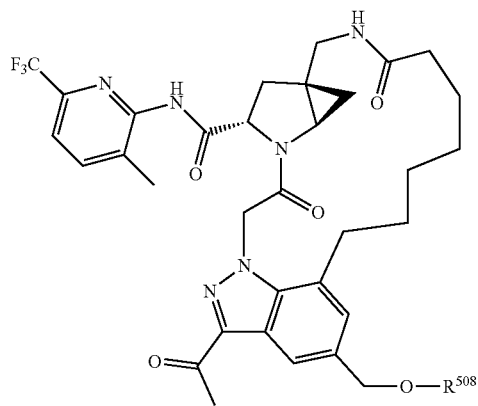

wherein R⁵⁰⁸ is selected from haloalkyl, cycloalkyl, heterocycle, heteroaryl, and alkyl(heteroaryl), each of which may be optionally substituted as described herein.

Representative examples of R⁵⁰⁸ include

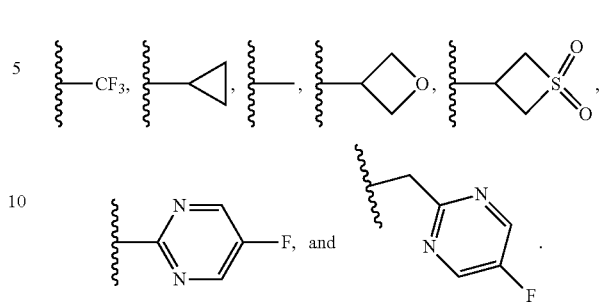

Additional representative examples of compounds of the present invention include:

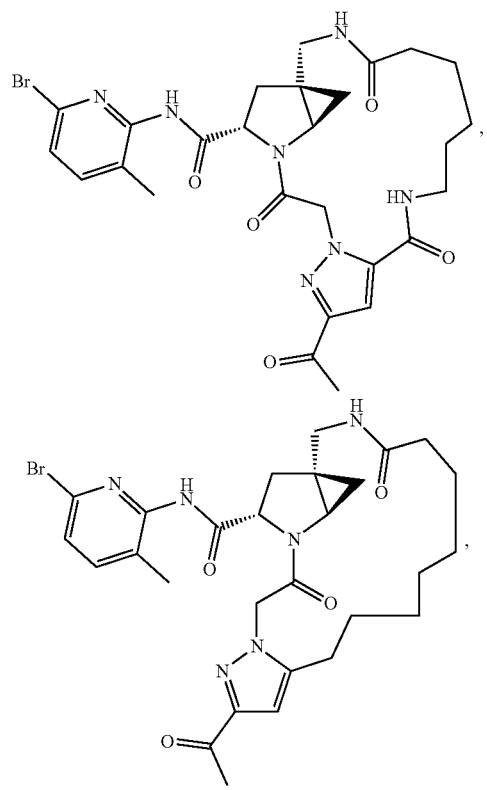

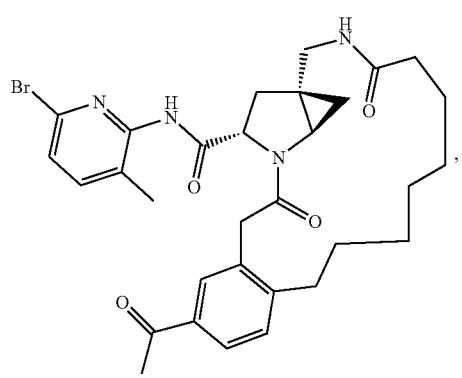

587
-continued
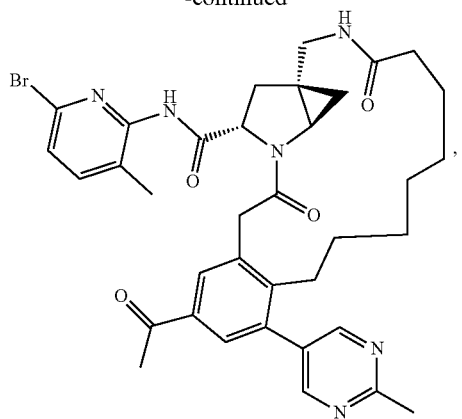
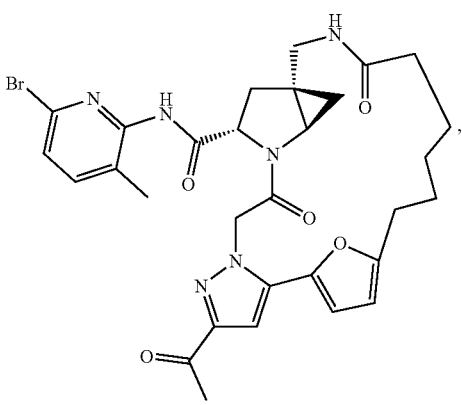
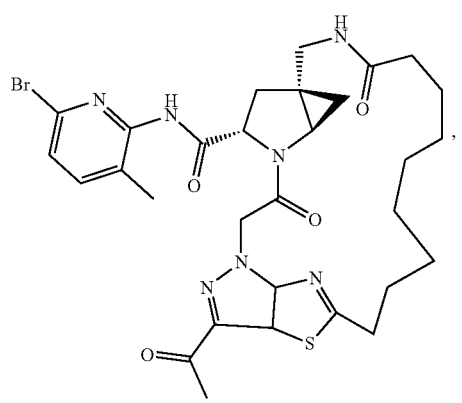
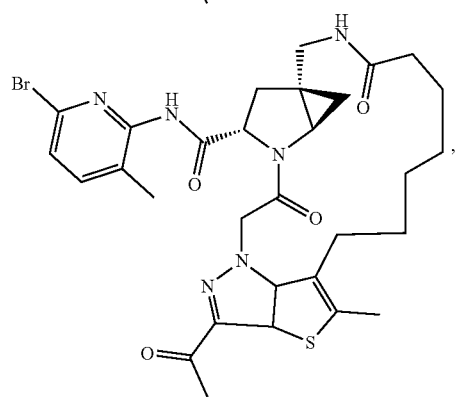
588
-continued
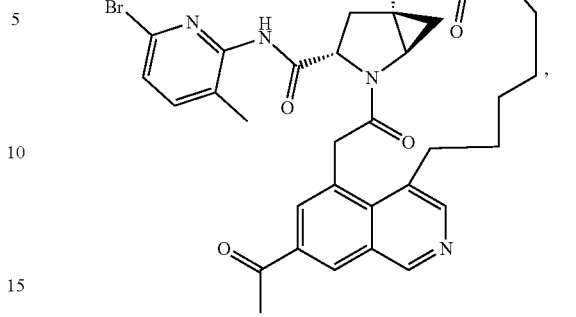
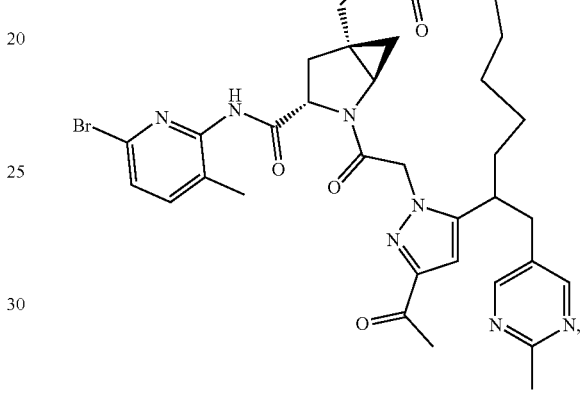
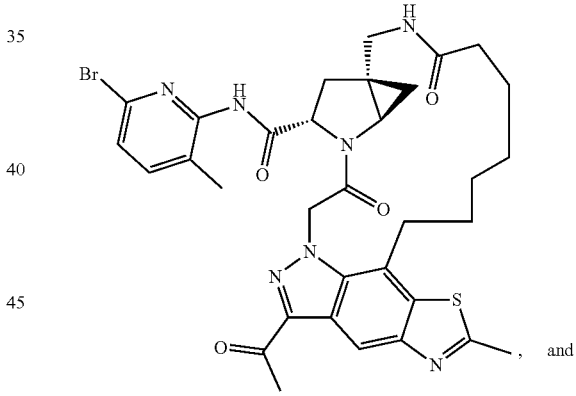
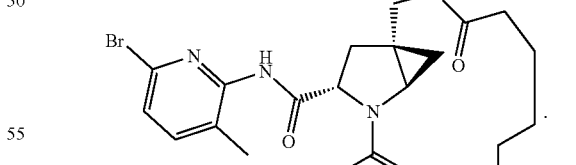, and
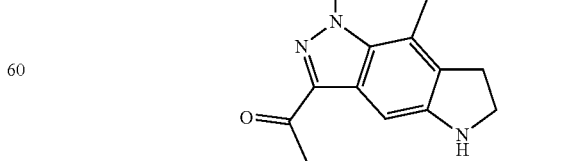
In certain embodiments, the compound of Formula IX is selected from:

589
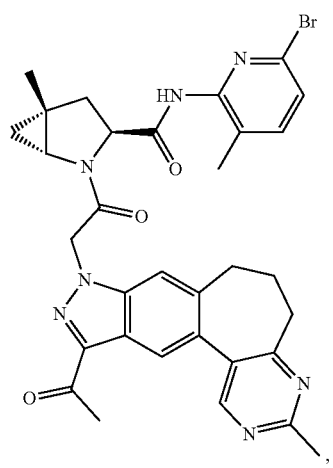
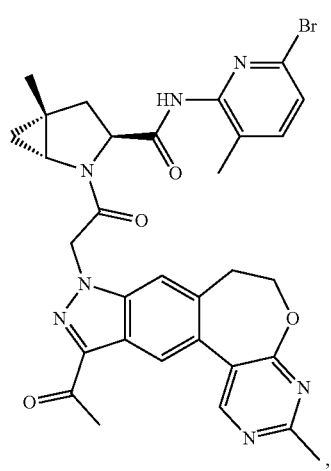
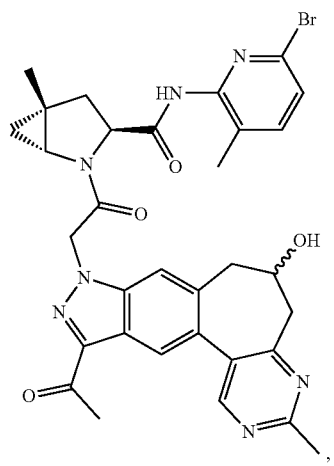
590
-continued
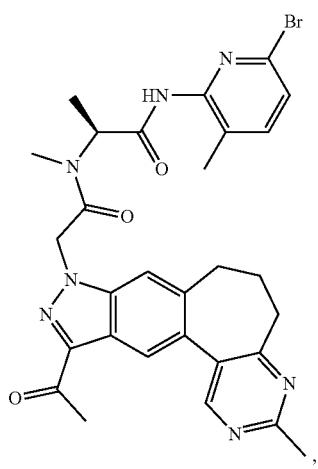
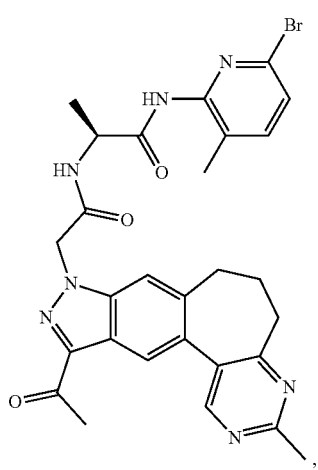
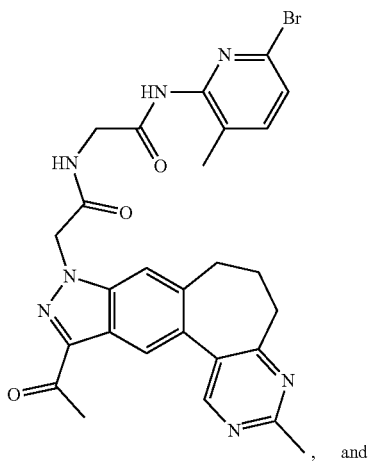
and 591
-continued
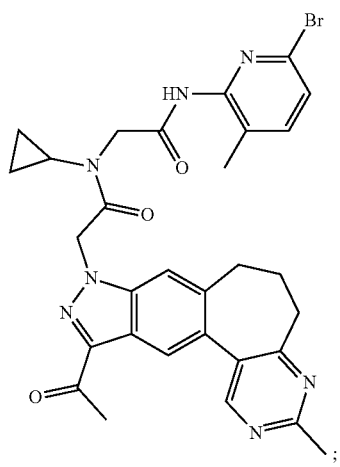 [SMILES: CC(=O)c1nn(CC(=O)N(CC(=O)Nc2nc(Br)ccc2C)C2CC2)c2cc3c(cc12)-c1cnc(C)nc1CCC3]
or a pharmaceutically acceptable salt thereof.
In certain embodiments, the compound of Formula IX is selected from:
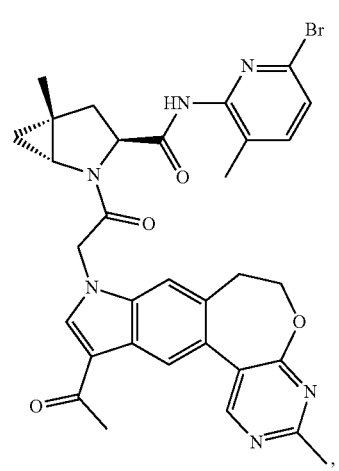
592
-continued
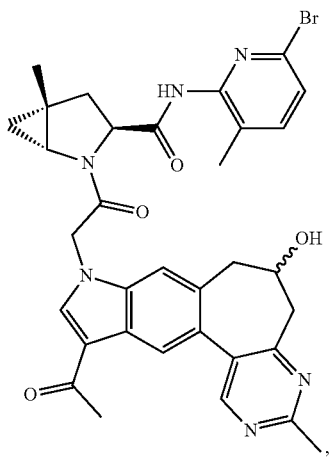
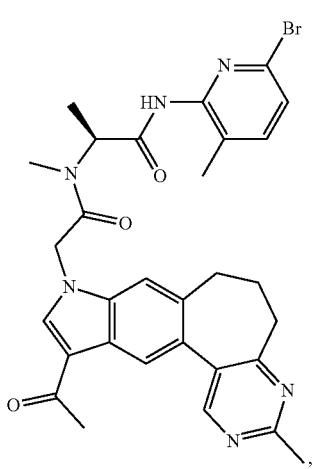
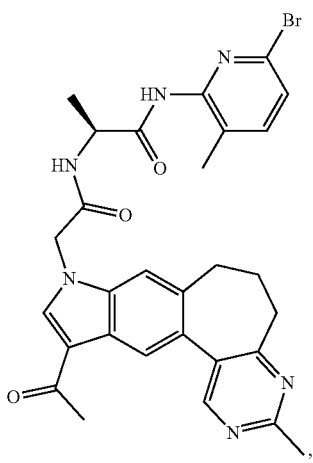

593
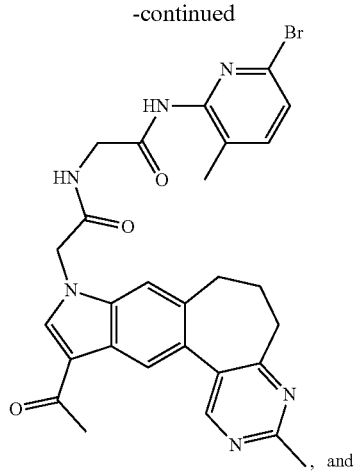
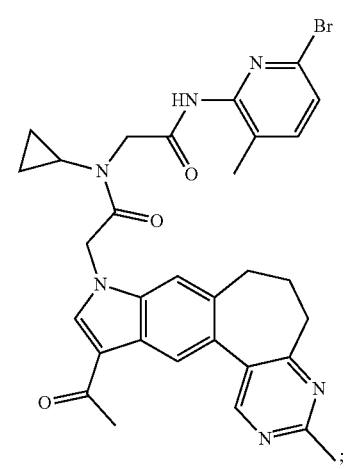
or a pharmaceutically acceptable salt thereof.
In certain embodiments R²⁰ is selected from:
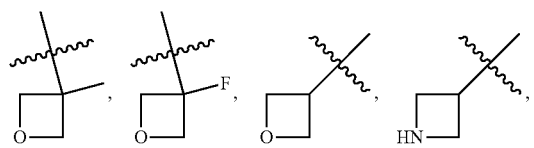
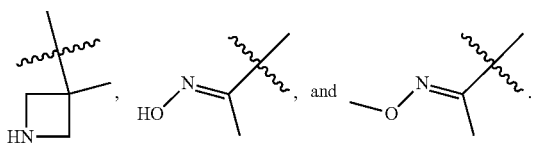
In certain embodiments the compound of Formula IX is selected from:
594
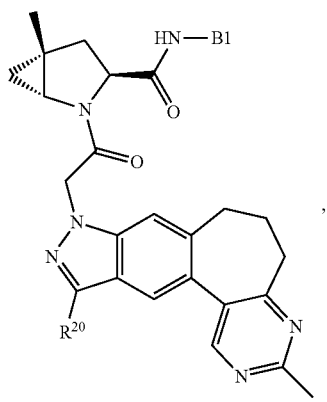

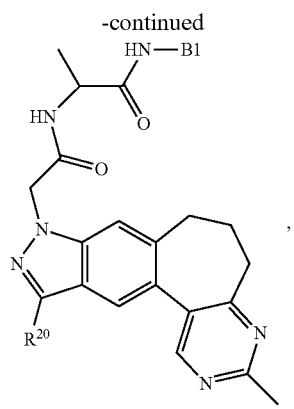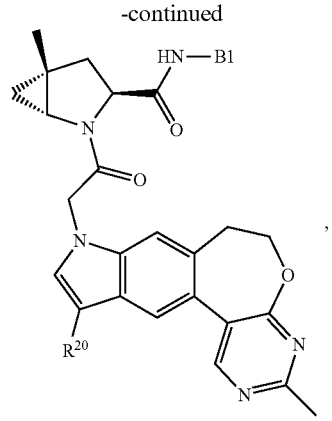

or a pharmaceutically acceptable salt thereof.

In certain embodiments A5 selected from:

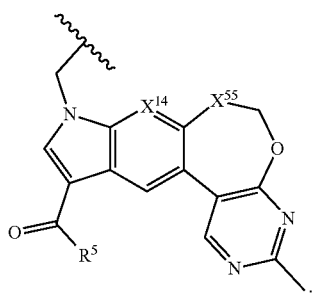
In certain embodiments A1 is selected from:
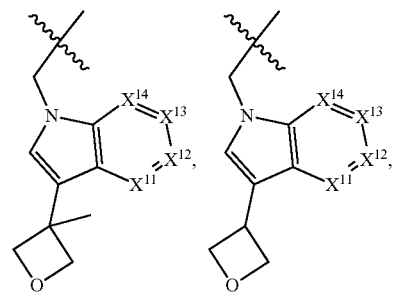
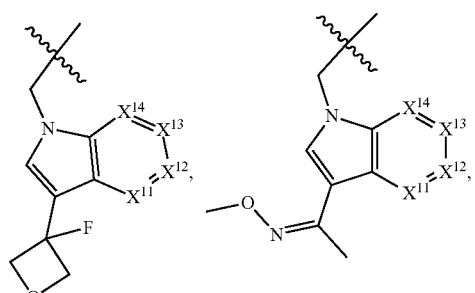
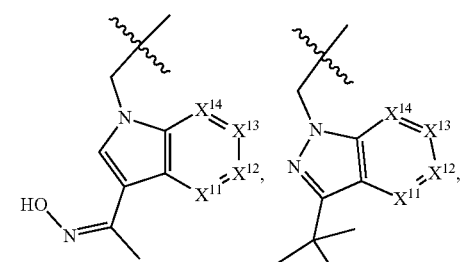
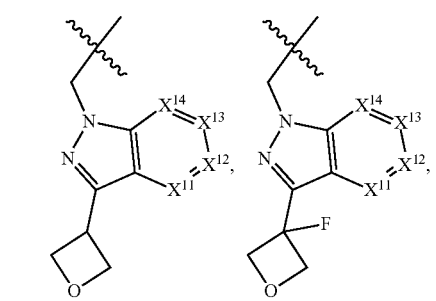
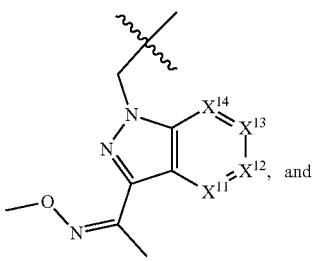
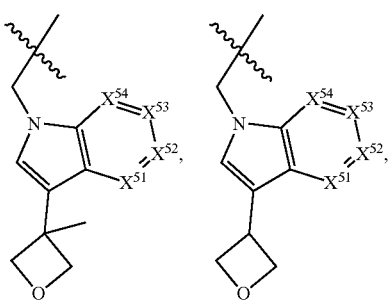
In certain embodiments A2 is selected from:
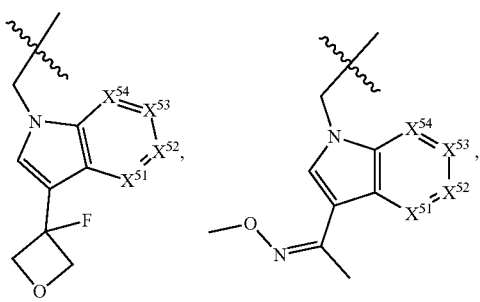
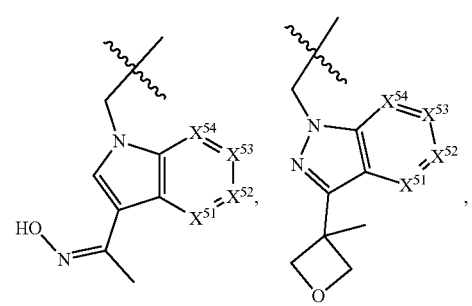

-continued

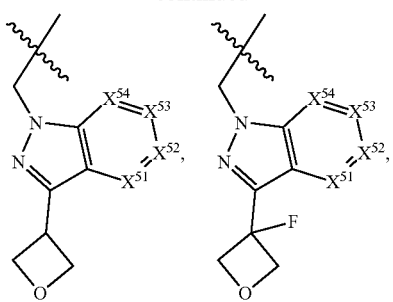

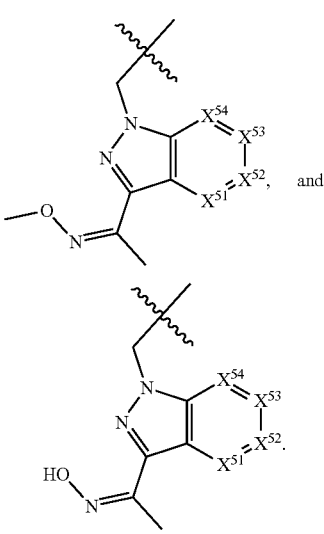

In certain embodiments A3 is selected from:

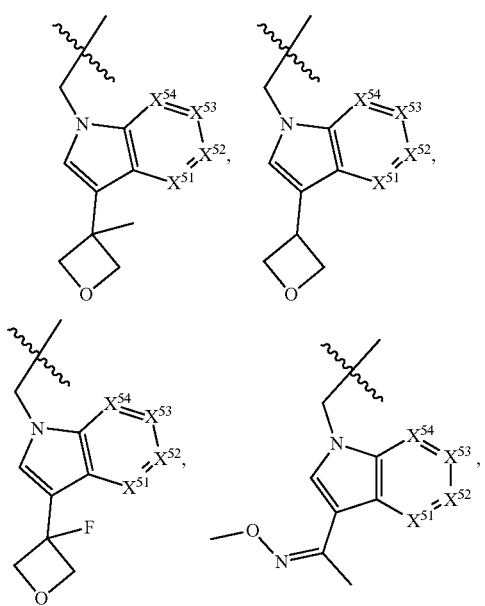

-continued

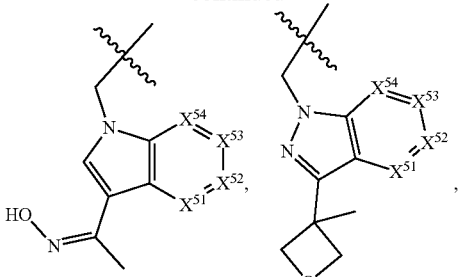

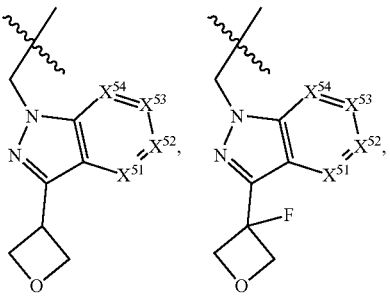

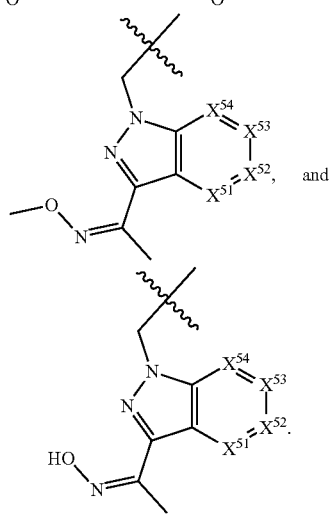

In an alternative embodiment $R^{32}$ is

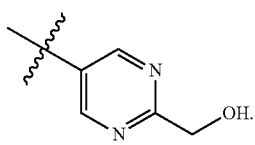 [SMILES: *c1cnc(CO)nc1]

Pharmaceutical Preparations

Active compounds described herein can be administered to a host in need thereof as the neat chemical, but are more typically administered as a pharmaceutical composition that includes an effective amount for a host, typically a human, in need of such treatment of an active compound as described herein or its pharmaceutically acceptable salt, prodrug, isotopic analog, N-oxide, or isolated isomer thereof. Thus, in one embodiment, the disclosure provides pharmaceutical compositions comprising an effective amount of compound or pharmaceutically acceptable salt, prodrug, isotopic analog, N-oxide, or isolated isomer thereof together with at least one pharmaceutically acceptable carrier for any of the uses described herein. The pharmaceutical composition may contain a compound or salt as the only active agent, or, in an alternative embodiment, the compound and at least one additional active agent.

An effective amount of an active compound as described herein, or the active compound described herein in combination or alternation with, or preceded by, concomitant with or followed by another active agent, can be used in an amount sufficient to (a) inhibit the progression of a disorder mediated by the complement pathway, including an inflammatory, immune, including an autoimmune, disorder or complement Factor D related disorder; (b) cause a regression of an inflammatory, immune, including an autoimmune, disorder or complement Factor D related disorder; (c) cause a cure of an inflammatory, immune, including an autoimmune, disorder or complement Factor D related disorder; or inhibit or prevent the development of an inflammatory, immune, including an autoimmune, disorder or complement Factor D related disorder.

Accordingly, an effective amount of an active compound or its salt or composition described herein will provide a sufficient amount of the active agent when administered to a patient to provide a clinical benefit.

The exact amount of the active compound or pharmaceutical composition described herein to be delivered to the host, typically a human, in need thereof, will be determined by the health care provider to achieve the desired clinical benefit.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound, or its salt or prodrug. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound, or its salt. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include a molar ratio of the active compound and an additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent: active compound), or its salt, described herein. In one embodiment, the additional active agent is an anti-inflammatory or immunosuppressing agent.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, sub-tenon, sub-retinal, retro-bulbar, peribulbar, suprachorodial, subchorodial, chorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The pharmaceutical compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Classes of carriers include, but are not limited to binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

In certain embodiments, the pharmaceutical composition for administration further includes a compound or salt of Formula I, Formula II, Formula III, Formula IV, Formula V, Formula VI, Formula VII Formula VIII, or Formula IX and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span® 85) glycocholate; sorbitan monolaurate (Span® 20); polysorbate 20 (Tween® 20); polysorbate 60 (Tween® 60); polysorbate 65 (Tween® 65); polysorbate 80 (Tween® 80); polysorbate 85 (Tween® 85); polyoxyethylene monostearate; surfactin; a poloxamer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetyl phosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethylene-imine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the pharmaceutical preparation may include polymers for controlled delivery of the described compounds, including, but not limited to pluronic polymers, polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates. In some embodiments, polymers may be modified with polyethylene glycol (PEG), with a carbohydrate, and/or with acyclic polyacetals derived from polysaccharides. See, e.g., Papisov, 2001, ACS Symposium Series, 786:301, incorporated by reference herein.

The compounds of the present invention can be formulated as particles. In one embodiment the particles are or include microparticles. In an alternative embodiment the particles are or include nanoparticles.

In an additional alternative embodiment, common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer. Nanoparticles with different sizes and morphologies can be obtained by this method.

Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles from a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment an active compound as described herein is administered to a patient in need thereof as particles formed by solvent removal. In another embodiment the present invention provides particles formed by solvent removal comprising a compound of the present invention and one or more pharmaceutically acceptable excipients as defined herein. In another embodiment the particles formed by solvent removal comprise a compound of the present invention and an additional therapeutic agent. In a further embodiment the particles formed by solvent removal comprise a compound of the present invention, an additional therapeutic agent, and one or more pharmaceutically acceptable excipients. In another embodiment any of the described particles formed by solvent removal can be formulated into a tablet and then coated to form a coated tablet. In an alternative embodiment the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment an active compound as described herein is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional therapeutic agent. In a further embodiment the SDD comprises a compound of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated. Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In one embodiment, an active compound as described herein is administered to a patient in need thereof as particles formed by phase inversion. In another embodiment the present invention provides particles formed by phase inversion comprising a compound of the present invention and one or more pharmaceutically acceptable excipients as defined herein. In another embodiment the particles formed by phase inversion comprise a compound of the present invention and an additional therapeutic agent. In a further embodiment the particles formed by phase inversion comprise a compound of the present invention, an additional therapeutic agent, and one or more pharmaceutically acceptable excipients. In another embodiment any of the described particles formed by phase inversion can be formulated into a tablet and then coated to form a coated tablet. In an alternative embodiment the particles formed by phase inversion are formulated into a tablet but the tablet is uncoated.

Techniques for particle formation using coacervation are known in the art, for example, as described in GB-B-929 406; GB-B-929 40 1; and U.S. Pat. Nos. 3,266,987, 4,794,000, and 4,460,563. Coacervation involves the separation of a compound (or polymer matrix and one or more compounds) solution into two immiscible liquid phases. One phase is a dense coacervate phase, which contains a high concentration of the compound, while the second phase contains a low concentration of the compound. Within the dense coacervate phase, the compound forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment an active compound as described herein is administered to a patient in need thereof as particles formed by coacervation. In another embodiment the present invention provides particles formed by coacervation comprising a compound of the present invention and one or more pharmaceutically acceptable excipients as defined herein. In another embodiment the particles formed by coacervation comprise a compound of the present invention and an additional therapeutic agent. In a further embodiment the particles formed by coacervation comprise a compound of the present invention, an additional therapeutic agent, and one or more pharmaceutically acceptable excipients. In another embodiment any of the described particles formed by coacervation can be formulated into a tablet and then coated to form a coated tablet. In an alternative embodiment the particles formed by coacervation are formulated into a tablet but the tablet is uncoated.

Methods for very low temperature casting of controlled release microspheres are described in U.S. Pat. No. 5,019,400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present invention is administered to a patient in need thereof as particles formed by low temperature casting. In another embodiment the present invention provides particles formed by low temperature casting comprising a compound of the present invention and one or more pharmaceutically acceptable excipients as defined herein. In another embodiment the particles formed by low temperature casting comprise a compound of the present invention and an additional therapeutic agent. In a further embodiment the particles formed by low temperature casting comprise a compound of the present invention, an additional therapeutic agent, and one or more pharmaceutically acceptable excipients. In another embodiment any of the described particles formed by low temperature casting can be formulated into a tablet and then coated to form a coated tablet. In an alternative embodiment the particles formed by low temperature casting are formulated into a tablet but the tablet is uncoated.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

Uses of Active Compounds for Treatment of Selected Disorders

In one aspect, an effective amount of an active compound or its salt or composition as described herein is used to treat a medical disorder which is an inflammatory or immune condition, a disorder mediated by the complement cascade (including a dysfunctional cascade) including a complement-mediated disease or disorder including a complement factor D-related disorder or alternative complement pathway-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

A complement-mediated disease or disorder is a disease or disorder in which the amount or activity of complement is such as to cause disease or disorder in an individual. In some embodiments, the complement-mediated disease or disorder is selected from the group consisting of autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease. In some embodiments, the complement-mediated disease or disorder is an autoimmune disease. In some embodiments, the complement-mediated disease or disorder is cancer. In some embodiments, the complement-mediated disease or disorder is an infectious disease. In some embodiments, the complement-mediated disease or disorder is an inflammatory disease. In some embodiments, the complement-mediated disease or disorder is a hematological disease. In some embodiments, the complement-mediated disease or disorder is an ischemic-reperfusion injury. In some embodiments, the complement-mediated disease or disorder is ocular disease. In some embodiments, the complement-mediated disease or disorder is a renal disease. In some embodiments, the complement-mediated disease or disorder is transplant rejection. In some embodiments, the complement-mediated disease or disorder is antibody-mediated transplant rejection. In some embodiments, the complement-mediated disease or disorder is a vascular disease. In some embodiments, the complement-mediated disease or disorder is a vasculitis disorder. In some embodiments, the complement-mediated disease or disorder is a neurodegenerative disease or disorder. In some embodiments, the complement-mediated disease is a neurodegenerative disease. In some embodiments, the complement-mediated disorder is a neurodegenerative disorder. In some embodiments, the complement-mediated disease or disorder is a tauopathy.

In some embodiments, a method for the treatment of C3 glomerulonephritis (C3G) is provided that includes the administration of an effective amount of a compound to a host of Formula I, Formula II, Formula III, Formula IV, Formula V, Formula VI, Formula VII, Formula VIII, or Formula IX, or a pharmaceutically acceptable salt, prodrug, isotopic analog, N-oxide, or isolated isomer thereof, optionally in a pharmaceutically acceptable composition. In some embodiments, a method for the treatment of paroxysmal nocturnal hemoglobinuria (PNH) is provided that includes the administration of an effective amount of a compound to a host of Formula I, Formula II, Formula III, Formula IV, Formula V, Formula VI, Formula VII, Formula VIII, or Formula IX, or a pharmaceutically acceptable salt, prodrug, isotopic analog, N-oxide, or isolated isomer thereof, optionally in a pharmaceutically acceptable composition. In another embodiment, a method for the treatment of wet or dry age-related macular degeneration (AMD) in a host is provided that includes the administration of an effective amount of a compound of Formula I, Formula II, Formula III, Formula IV, Formula V, Formula VI, Formula VII, Formula VIII, or Formula IX, or a pharmaceutically acceptable salt, prodrug, isotopic analog, N-oxide, or isolated isomer thereof, optionally in a pharmaceutically acceptable composition. In another embodiment, a method for the treatment of rheumatoid arthritis in a host is provided that includes the administration of an effective amount of a compound of Formula I, Formula II, Formula III, Formula IV, Formula V, Formula VI, Formula VII, Formula VIII, or Formula IX, or a pharmaceutically acceptable salt, prodrug, isotopic analog, N-oxide, or isolated isomer thereof, optionally in a pharmaceutically acceptable composition. In another embodiment, a method for the treatment of multiple sclerosis in a host is provided that includes the administration of an effective amount of a compound of Formula I, Formula II, Formula III, Formula IV, Formula V, Formula VI, Formula VII, Formula VIII, or Formula IX, or a pharmaceutically acceptable salt, prodrug, isotopic analog, N-oxide, or isolated isomer thereof, optionally in a pharmaceutically acceptable composition.

The active compound or its pharmaceutically acceptable salt, prodrug, isotopic analog, N-oxide, or isolated isomer thereof, optionally in a pharmaceutically acceptable composition, as disclosed herein is also useful for administration in combination (in the same or a different dosage form) or alternation with a second pharmaceutical agent for use in ameliorating or reducing a side effect of the second pharmaceutical agent. For example, in some embodiments, the active compound may be used in combination with an adoptive cell transfer therapy to reduce an inflammatory response associated with such therapy, for example, a cytokine mediated response such as cytokine response syndrome. In some embodiments, the adoptive cell transfer therapy is a chimeric antigen receptor T-Cell (CAR T) or a dendritic cell used to treat a hematologic or solid tumor, for example, a B-cell related hematologic cancer. In some embodiments, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19. In some embodiments, the associated inflammatory response is a cytokine mediated response.

Another embodiment is provided that includes the administration of an effective amount of an active compound or a pharmaceutically acceptable salt, prodrug, isotopic analog, N-oxide, or isolated isomer thereof, optionally in a pharmaceutically acceptable composition to a host to treat an ocular, pulmonary, gastrointestinal, or other disorder that can benefit from topical or local delivery.

Any of the compounds described herein (e.g. Formula I, Formula II, Formula III, Formula IV, Formula V, Formula VI, Formula VII, Formula VIII, or Formula IX, can be administered to the eye in any desired form of administration, including via intravitreal, intrastromal, intracameral, sub-tenon, sub-retinal, retro-bulbar, peribulbar, suprachoroidal, choroidal, subchoroidal, conjunctival, subconjunctival, episcleral, posterior juxtascleral, scleral, circumcorneal, and tear duct injections, or through a mucus, mucin, or a mucosal barrier, in an immediate or controlled release fashion. In certain embodiments, the active compound includes a lipophilic group, such as a lipophilic acyl group, which is delivered to the eye in a polymeric drug delivery system such as polylactic acid, polylactide-co-glycolide, polyglycolide or other erodible polymer, or a combination thereof, or in another type of lipophilic material for ocular delivery. In some embodiments, the lipophilic active molecule is more soluble in the polymeric or other form of delivery system than in ocular fluid.

In other embodiments of the invention, an active compound provided herein can be used to treat or prevent a disorder in a host mediated by complement factor D, or by an excessive or detrimental amount of the complement-C3 amplification loop of the complement pathway. As examples, the invention includes methods to treat or prevent complement associated disorders that are induced by antibody-antigen interactions, a component of an immune or autoimmune disorder or by ischemic injury. The invention also provides methods to decrease inflammation or an immune response, including an autoimmune response, where mediated or affected by factor D.

In some embodiments, the disorder is selected from fatty liver and conditions stemming from fatty liver, such as nonalcoholic steatohepatitis (NASH), liver inflammation, cirrhosis and liver failure. In some embodiments of the present invention, a method is provided for treating fatty liver disease in a host by administering an effective amount of an active compound or its salt or composition as described herein.

In another embodiment, an active compound or its salt or composition as described herein is used to modulate an immune response prior to or during surgery or other medical procedure. One non-limiting example is use in connection with acute or chronic graft versus host disease, which is a common complication as a result of allogeneic tissue transplant, and can also occur as a result of a blood transfusion.

In some embodiments, the present invention provides a method of treating or preventing dermatomyositis by administering to a subject in need thereof an effective amount of an active compound or its salt or composition as described herein.

In some embodiments, the present invention provides a method of treating or preventing amyotrophic lateral sclerosis by administering to a subject in need thereof an effective amount of an active compound or its salt or composition as described herein.

In some embodiments, the present invention provides a method of treating or preventing abdominal aortic aneurysm, hemodialysis complications, hemolytic anemia, or hemodialysis by administering to a subject in need thereof an effective amount of an active compound or its salt or composition as described herein.

In another embodiment, a method is provided for the treatment or prevention of cytokine or inflammatory reactions in response to the administration of pharmaceutical or biotherapeutic (e.g. CAR T-cell therapy or monoclonal antibody therapy) in a host by administering an effective amount of an active compound or its salt or composition as described herein. Various types of cytokine or inflammatory reactions may occur in response to a number of factors, such as the administrations of biotherapeutics. In some embodiments, the cytokine or inflammatory reaction is cytokine release syndrome. In some embodiments, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as cytokine storm, and can be fatal.

Fatal cytokine storms have been observed in response to infusion with several monoclonal antibody therapeutics. See, Abramowicz D, et al. "Release of tumor necrosis factor, interleukin-2, and gamma-interferon in serum after injection of OKT3 monoclonal antibody in kidney transplant recipients" *Transplantation* (1989) 47(4):606-8; Chatenoud L, et al. "In vivo cell activation following OKT3 administration. Systemic cytokine release and modulation by corticosteroids" *Transplantation* (1990) 49(4):697-702; and Lim L C, Koh L P, and Tan P. "Fatal cytokine release syndrome with chimeric anti-CD20 monoclonal antibody rituximab in a 71-year-old patient with chronic lymphocytic leukemia" *J. Clin Oncol.* (1999) 17(6):1962-3.

Also contemplated herein, is the use of an active compound or its salt or composition as described herein to mediate an adverse immune response in patients receiving bi-specific T-cell engagers (BiTE). A hi-specific T-cell engager directs T-cells to target and bind with a specific antigen on the surface of a cancer cell. For example, Blinatumomab (Amgen), a BiTE has recently been approved as a second line therapy in Philadelphia chromosome-negative relapsed or refractory acute lymphoblastic leukemia. Blinatumomab is given by continuous intravenous infusion in 4-week cycles. The use of BiTE agents has been associated with adverse immune responses, including cytokine release syndrome. The most significantly elevated cytokines in the CRS associated with ACT include IL-10, IL-6, and IFN-γ (Klinger et al., Immunopharmacologic response of patients with B-lineage acute lymphoblastic leukemia to continuous infusion of T cell-engaging CD19/CD3-bispecific BiTE antibody blinatumomab. Blood (2012) 119:6226-6233).

In another embodiment, the disorder is episcleritis, idiopathic episcleritis, anterior episcleritis, or posterior episcleritis. In some embodiments, the disorder is idiopathic anterior uveitis, HLA-B27 related uveitis, herpetic keratouveitis, Posner Schlossman syndrome, Fuch's heterochromic iridocyclitis, or cytomegalovirus anterior uveitis.

In some embodiments, the present invention provides a method of treating or preventing a C3 glomurenopathy by administering to a subject in need thereof an effective amount of an active compound or its salt or composition as described herein. In some embodiments, the disorder is selected from dense deposit disease (DDD) and C3 glomerulonephritis (C3GN).

In some embodiments, the present invention provides a method of treating or preventing a IC-MPGN by administering to a subject in need thereof an effective amount of an active compound or its salt or composition as described herein.

In some embodiments, the present invention provides a method of treating or preventing a delayed graft function (DGF) by administering to a subject in need thereof an effective amount of an active compound or its salt or composition as described herein.

In some embodiments, the present invention provides a method of treating or promoting wound healing by administering to a subject in need thereof an effective amount of an active compound or its salt or composition as described herein In some embodiments, the present invention provides a method of treating or preventing a HSCT-TMA by administering to a subject in need thereof an effective amount of an active compound or its salt or composition as described herein.

In some embodiments, the present invention provides a method of treating or preventing a paroxysmal nocturnal hemoglobinuria (PNH) by administering to a subject in need thereof an effective amount of an active compound or its salt or composition as described herein.

In some embodiments, the present invention provides a method of treating or preventing age-related macular degeneration (AMD) by administering to a subject in need thereof an effective amount of an active compound or its salt or composition as described herein.

In some embodiments, the present invention provides a method of treating or preventing macular dystrophy by administering to a subject in need thereof an effective amount of an active compound or its salt or composition as described herein.

In some embodiments, the present invention provides a method of treating or preventing a Crohn's disease by administering to a subject in need thereof an effective amount of an active compound or its salt or composition as described herein.

In some embodiments, the present invention provides a method of treating or preventing Stargardt's disease (Stargardt macular dystrophy) by administering to a subject in need thereof an effective amount of an active compound or its salt or composition as described herein.

In some embodiments, the present invention provides a method of treating or preventing acute pancreatitis by administering to a subject in need thereof an effective amount of an active compound or its salt or composition as described herein.

In some embodiments, the present invention provides a method of treating or preventing asthma (TH2) or asthma (non-TH2) by administering to a subject in need thereof an effective amount of an active compound or its salt or composition as described herein.

In some embodiments, the present invention provides a method of treating or preventing periodontitis by administering to a subject in need thereof an effective amount of an active compound or its salt or composition as described herein.

In some embodiments, the present invention provides a method of treating or preventing a diabetic retinopathy by administering to a subject in need thereof an effective amount of an active compound or its salt or composition as described herein.

In some embodiments, the present invention provides a method of treating or preventing a hidradenitis suppurativa by administering to a subject in need thereof an effective amount of an active compound or its salt or composition as described herein.

In some embodiments, the present invention provides a method of treating or preventing acute respiratory distress syndrome (ARDS) by administering to a subject in need thereof an effective amount of an active compound or its salt or composition as described herein.

In some embodiments, the present invention provides methods of treating or preventing a nephrology disorder selected from acute kidney injury (AKI), idiopathic membranous nephropathy, IgA nephropathy (IgAN) lupus nephritis (LN), and primary focal segmental glomerulosclerosis by administering to a subject in need thereof an effective amount of an active compound or its salt or composition as described herein.

In some embodiments, the present invention provides methods of treating or preventing preeclampsia by administering to a subject in need thereof an effective amount of an active compound or its salt or composition as described herein.

In some embodiments, the present invention provides a method of treating or preventing rheumatoid arthritis by administering to a subject in need thereof an effective amount of an active compound or its salt or composition as described herein.

In some embodiments, the present invention provides a method of treating or preventing multiple sclerosis by administering to a subject in need thereof an effective amount of an active compound or its salt or composition as described herein.

In some embodiments, the present invention provides a method of treating or preventing myasthenia gravis by administering to a subject in need thereof an effective amount of an active compound or its salt or composition as described herein.

In some embodiments, the present invention provides a method of treating or preventing atypical hemolytic uremic syndrome (aHUS) by administering to a subject in need thereof an effective amount of an active compound or its salt or composition as described herein.

In some embodiments, the present invention provides a method of treating or preventing neuromyelitis optica (NMO) by administering to a subject in need thereof an effective amount of an active compound or its salt or composition as described herein.

In yet another embodiment, the present invention provides a method of treating or preventing a disorder as described below by administering to a subject in need thereof an effective amount of an active compound or its salt or composition as described herein, including: vitritis, sarcoidosis, syphilis, tuberculosis, or Lyme disease; retinal vasculitis, Eales disease, tuberculosis, syphilis, or toxoplasmosis; neuroretinitis, viral retinitis, or acute retinal necrosis; varicella zoster virus, herpes simplex virus, cytomegalovirus, Epstein-Barr virus, lichen planus, or Dengue-associated disease (e.g., hemorraghic Dengue Fever); Masquerade syndrome, contact dermatitis, trauma induced inflammation, UVB induced inflammation, eczema, granuloma annulare, or acne.

In an additional embodiment, the disorder is selected from: acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA); antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy; allergic bronchopulmonary aspergillosis, allergic neuritis, drug allergy, radiation-induced lung injury, eosinophilic pneumonia, radiographic contrast media allergy, bronchiolitis obliterans, or interstitial pneumonia; parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia; Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In some embodiments, the disorder is selected from: transplant-associated thrombotic microangiopathy (TMA); hematopoietic stem cell transplant-associated thrombotic microangiopathy (HSCT-TMA); atopic dermatitis, dermatitis, dermatomyositis bullous pemphigoid, scleroderma, sclerodermatomyositis, psoriatic arthritis, pemphigus vulgaris, Discoid lupus erythematosus, cutaneous lupus, chilblain lupus erythematosus, or lupus erythematosus-lichen planus overlap syndrome; cryoglobulinemic vasculitis, mesenteric/enteric vascular disorder, peripheral vascular disorder, antineutrophil cytoplasm antibody (ANCA)-associated vasculitis (AAV), IL-2 induced vascular leakage syndrome, or immune complex vasculitis; angioedema, low platelets (HELLP) syndrome, sickle cell disease, platelet refractoriness, red cell casts, or typical or infectious hemolytic uremia, syndrome (tHUS); hematuria, hemorrhagic shock, drug-induced thrombocytopenia, autoimmune hemolytic anemia (AIHA), azotemia, blood vessel and/or lymph vessel inflammation, rotational atherectomy, or delayed hemolytic transfusion reaction; British type amyloid angiopathy, Buerger's disease, bullous pemphigoid, C1q nephropathy, cancer, or catastrophic antiphospholipid syndrome.

In another embodiment, the disorder is selected from: wet (exudative) AMD, dry (non-exudative) AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, pathological myopia, or RPE degeneration; pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen; chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita (EBA); essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments; hidradenitis suppurative (HS); hepatitis, hepatitis A, hepatitis B, hepatitis C or human immunodeficiency virus (HIV), a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae; *Neisseria meningitidis*, shiga toxin *E. coli*-related hemolytic uremic syndrome (STEC-HUS), hemolytic uremic syndrome (HUS); *Streptococcus*, or poststreptococcal glomerulonephritis.

In a further embodiment, the disorder is selected from: hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis; inclusion body myositis, intestinal ischemic, iridocyclitis, iritis, juvenile chronic arthritis, Kawasaki's disease (arteritis), or lipiduria; membranoproliferative glomerulonephritis (MPGN) I, microscopic polyangiitis, mixed cryoglobulinemia, molybdenum cofactor deficiency (MoCD) type A, pancreatitis panniculitis, Pick's disease, polyarteritis nodosa (PAN), progressive subcortical gliosis, proteinuria, reduced glomerular filtration rate (GFR), or renovascular disorder; multiple organ failure, multiple system atrophy (MSA), myotonic dystrophy, Niemann-Pick disease type C, chronic demyelinating diseases, or progressive supranuclear palsy; spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thryoiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis; von Hippel-Lindau disease, histoplasmosis of the eye, hard drusen, soft drusen, pigment clumping, or photoreceptor and/or retinal pigmented epithelia (RPE) loss.

In some embodiments, an active compound or its salt or composition as described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Casale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitonial fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, pityriasis lichenoides et varioliformis acuta, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type L autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton mysathenic syndrome, Oshtoran syndrome, pediatric autoimmune neuropsychiatric disorder associated with *Streptococcus* (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis or ischemic-reperfusion injury of the eye.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In a further embodiment, the disorder is selected from glaucoma, diabetic retinopathy, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, diabetic macular edema, Behcet's uveitis, non-infectious uvietis, multifocal choroiditis, Vogt-Koyangi-Harada syndrome, intermediate uveitis, birdshot retina-chorioditis, sympathetic ophthalmia, ocular cicatricial pemphigoid, ocular pemphigus, nonartertic ischemic optic neuropathy, postoperative inflammation, and retinal vein occlusion, or central retinal vein occulusion (CVRO).

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

Disorders that may be treated or prevented by an active compound or its salt or composition as described herein also include, but are not limited to: hereditary angioedema, capillary leak syndrome, hemolytic uremic syndrome (HUS), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome;

inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), lupus nephritides, arthritis, immune complex disorders and autoimmune diseases, systemic lupus, or lupus erythematosus; ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes; Alzheimer's dementia, stroke, schizophrenia, traumatic brain injury, trauma, Parkinson's disease, epilepsy, transplant rejection, prevention of fetal loss, biomaterial reactions (e.g. in hemodialysis, inplants), hyperacute allograft rejection, xenograft rejection, transplantation, psoriasis, burn injury, thermal injury including burns or frostbite, or crush injury; asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In some embodiments, a method for the treatment of sickle cell in a host is provided that includes the administration of an effective amount of an active compound or its salt or composition as described herein. In some embodiments, a method for the treatment of immunothrombocytopenic purpura (ITP), thrombotic thrombocytopenic purpura (TTP), or idiopathic thrombocytopenic purpura (ITP) in a host is provided that includes the administration of an effective amount of an active compound or its salt or composition as described herein. In some embodiments, a method for the treatment of ANCA-vasculitis in a host is provided that includes the administration of an effective amount of an active compound or its salt or composition as described herein, in some embodiments, a method for the treatment of IgA nephropathy in a host is provided that includes the administration of an effective amount of an active compound or its salt or composition as described herein. In some embodiments, a method for the treatment of rapidly progressing glomerulonephritis (RPGN), in a host is provided that includes the administration of an effective amount of an active compound or its salt or composition as described herein. In some embodiments, a method for the treatment of lupus nephritis, in a host is provided that includes the administration of an effective amount of an active compound or its salt or composition as described herein. In some embodiments, a method for the treatment of hemorraghic dengue fever, in a host is provided that includes the administration of an effective amount of an active compound or its salt or composition as described herein.

In an additional alternative embodiment, an active compound or its salt or composition as described herein is used in the treatment of an autoimmune disorder.

The complement pathway enhances the ability of antibodies and phagocytic cells to clear microbes and damaged cells from the body. It is part of the innate immune system and in healthy individuals is an essential process. Inhibiting the complement pathway will decrease the body's immune system response. Therefore, it is an object of the present invention to treat autoimmune disorders by administering an effective does of an active compound or its salt or composition as described herein to a subject in need thereof.

In some embodiments the autoimmune disorder is caused by activity of the complement system. In some embodiments the autoimmune disorder is caused by activity of the alternative complement pathway. In some embodiments the autoimmune disorder is caused by activity of the classical complement pathway. In another embodiment the autoimmune disorder is caused by a mechanism of action that is not directly related to the complement system, such as the over-proliferation of T-lymphocytes or the over-production of cytokines.

Non-limiting examples of autoimmune disorders include: lupus, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In some embodiments, an active compound or its salt or composition as described herein is used in the treatment of lupus. Non-limiting examples of lupus include lupus erythematosus, cutaneous lupus, discoid lupus erythematosus, chilblain lupus erythematosus, or lupus erythematosus-lichen planus overlap syndrome.

Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple Sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in MRI scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In some embodiments an active compound or its salt or composition as described herein is provided at an effective dose to treat a patient with type 1 diabetes. In some embodiments an active compound or its salt or composition as described herein is provided at an effective dose to treat a patient with type 2 diabetes.

Type 1 diabetes is an autoimmune disease. An autoimmune disease results when the body's system for fighting infection (the immune system) attacks a part of the body. In the case of diabetes type 1, the pancreas then produces little or no insulin.

In certain aspects, an effective amount of an active compound described herein, or it pharmaceutically acceptable salt, is used to treat a medical disorder of the central nervous system (CNS) or peripheral nervous system disorders involving complement activation. In embodiments, the CNS disorder is an acquired brain or spinal cord injury, including, but not limited to ischaemic-reperfusion injury or stroke, traumatic brain injury (TBI) and spinal cord injury (SCI). In embodiments, the disorder is a neurodegeneration disorder. In embodiments, the disorder is a neuroinflammation disorder.

In certain aspects, active compound described herein, or it pharmaceutically acceptable salt is used to treat Alzheimer's disease (AD). AD is characterized by two hallmark pathologies; amyloid-β (Aβ) plaques and neurofibrillary tangles comprising hyperphosphorylated tau. Recent studies have implicated complement in AD pathogenesis, including genome wide association studies identifying single nucleotide polymorphisins (SNPs) associated with risk of late-onset AD in genes encoding complement proteins Clusterin (CLU) and CR1 (CR1). See Carpanini et al., Therapeutic Inhibition of the Complement System in Diseases of the Central Nervous System, Front, Immunol., 4 Mar. 2019. Biomarker studies have also identified complement proteins and activation products in plasma and/or CSF that distinguish AD from controls and predict risk of progression to AD. (Id.)

In certain aspects, an effective amount of active compound described herein, or it pharmaceutically acceptable salt is used to treat certain forms of frontotemporal dementia including, but not limited to, Pick's disease, sporadic Frontotemporal dementia and Frontotemporal dementia with Parkinsonism linked to chromosome 17, Progressive supranuclear palsy (PSP), Corticobasal degeneration (CBD), and Subacute sclerosing panencephalitis.

In certain aspects, an effective amount of active compound described herein, or it pharmaceutically acceptable salt is used to treat multiple sclerosis (MS). Multiple sclerosis (MS) is the most common cause of neurological disability in young adults in northern European-Caucasian populations, with an approximate lifetime risk of one in 400. C3 has been shown to be deposited in the brains of MS patients. TCC has been shown to be in association with capillary endothelial cells, predominantly within plaques and adjacent white matter. Localization of C activation to areas of active myelin destruction has also been shown, with TCC deposited exclusively in such areas. C3d has been shown to be deposited in association with short segments of disrupted myelin in plaques with low-grade active demyelination and provides evidence for a C contribution to disease progression as well as acute inflammation. See Ingram et al., Complement in multiple sclerosis: its role in disease and potential as a biomarker. Clin Exp Immunol. 2009 February; 155(2):128-39.

In certain aspects, active compound described herein, or it pharmaceutically acceptable salt is used to treat neuromyelitis optica (NMO). Neuromyelitis optica (NMO) is an inflammatory demyelinating disease affecting predominantly the optic nerves and spinal cord. Traditionally seen as a variant of MS, it has been redefined recently according to new criteria using a combination of phenotypic subtyping along with a newly developed biomarker of disease, NMO-immunoglobulin G (IgG) (reported sensitivity of 58-76% and specificity of 85-99% for NMO). NMO patients have higher levels of C3a and anti-C1q antibodies than healthy controls. C3a levels correlated with disease activity, neurological disability and aquaporin-4 IgG. Nytrova et al., Complement activation in patients with neuromyelitis optica. J Neuroimmunol. 2014 Sep. 15; 274(1-2):185-91.

In certain aspects, active compound described herein, or it pharmaceutically acceptable salt is used to treat amyotrophic lateral sclerosis (ALS). ALS is caused by progressive loss of upper and lower (α) motor neurons resulting in denervation of neuromuscular junctions in the peripheral nervous system, progressive muscle weakness, atrophy, spasticity, respiratory failure, and ultimately paralysis and death. Recent studies have shown increased C1q protein in motor cortex and spinal cord of ALS post-mortem tissue; C3 activation fragments and TCC in areas of pathology; C4d and TCC staining of degenerating neurons and glia in ALS motor cortex and spinal cord, and C5aR1 upregulation in areas of pathology. C3d and C4d have been found on oligodendroglia and degenerating neurites, surrounded by CR4-positive microglia, in spinal cord and motor cortex, and C1q, C3, and TCC have been shown to be present on motor end-plates in intercostal muscles in ALS donors even early in the disease process. See Carpanini et al., Therapeutic Inhibition of the Complement System in Diseases of the Central Nervous System, Front. Immunol., 4 Mar. 2019.

In certain aspects, active compound described herein, or it pharmaceutically acceptable salt is used to treat Parkinson's disease (PD). PD is characterized by loss of dopaminergic neurons in the substantia nigra and deposits of the protein α-synuclein that form the pathological hallmarks of the disease, Lewy bodies. Patients present with resting tremor, bradykinesia, and rigidity. Complement activation has been associated with α-synuclein and Lewy bodies in Parkinson's disease; in vitro studies have demonstrated that the disease-associated splice variant α-synuclein 112, but not the full-length protein, cause activation of complement. In vivo, C3d, C4d, C7 and C9 localization in Lewy bodies has been reported. More recently, deposition of iC3b and C9 in Lewy bodies and melanized neurons has been reported, and iC3b immunoreactivity has been shown to be increased with normal ageing and was further elevated in PD vs. age-matched controls. Furthermore, correlation between the ratios of C3/Aβ42 or FH/Aβ42 in CSF and severity of Parkinson's disease motor and cognitive symptoms has been shown. See Carpanini et al., Therapeutic Inhibition of the Complement System in Diseases of the Central Nervous System, Front. Immunol., 4 Mar. 2019. In some embodiments, the subject to be treated suffers from Parkinson's Disease with dementia (PDD).

In certain aspects, active compound described herein, or it pharmaceutically acceptable salt is used to treat Huntington's disease (HD). HD is an autosomal dominant, inherited neurodegenerative disease characterized by progressive motor symptoms, psychiatric disturbances, and dementia. It is caused by expansion of a three-base-pair (CAG) repeat (39-121 repeats vs, normal range 8-39 repeats) in exon 1 of the HTT gene that translates into a polyglutamine tract at the N-terminus of the protein. This results in a polyglutamine length-dependent misfolding and accumulation of huntingtin protein in the striatum and cortex (layers 3, 5, and 6) followed by neuronal loss in these areas which spreads to the hippocampus. It has been shown that neurons, astrocytes, and myelin sheaths in the HD caudate and striatum were immunoreactive for C1q, C4, C3 and neo-epitopes in iC3b and TCC. Expression of mRNA encoding early complement components C1q (c-chain), C1r, C3, and C4, complement regulators C1INH, Clusterin, MCP, DAF and CD59, a See Carpanini et al., Therapeutic Inhibition of the Complement System in Diseases of the Central Nervous System, Front. Immunol., 4 Mar. 2019.nd complement receptors C3a and C5a has been shown to be upregulated in the HD striatum.

In certain aspects, active compound described herein, or it pharmaceutically acceptable salt is used to treat argyrophilic grain dementia, British type amyloid angiopathy, cerebral amyloid angiopathy, Creutzfeldt-Jakob disease, dementia pugilistica, diffuse neurofibrillary tangles with calcification, Down's syndrome, frontotemporal lobar degeneration, Gerstmann-Straussler-Scheinker disease, Hallervorden-Spatz disease, inclusion body myositis, multiple system atrophy (MSA), myotonic dystrophy, Niemann-Pick disease type C, non-Guamanian motor neuron disease with neurofibrillary tangles, postencephalitic parkinsonism, prion protein cerebral amyloid angiopathy, progressive subcortical gliosis, progressive supranuclear palsy, subacute sclerosing panencephalitis, Tangle only dementia, multi-infarct dementia, ischemic stroke, chronic traumatic encephalopathy (CTE), traumatic brain injury (TBI), and stroke.

In certain aspects active compound described herein, or it pharmaceutically acceptable salt is used to treat a hereditary motor and sensory neuropathy (HMSN). In some embodiments, the hereditary and sensory neuropathy is Charcot-Marie-Tooth (CMT) disease. In some embodiments, the HSMN is Charcot-Marie-Tooth disease type 1A or type 1B. In some embodiments, the HSMN is Charcot-Marie-Tooth disease type 2. In some embodiments, the HSMN is Dejerine-Sottas disease (Charcot-Marie-Tooth type 3). In some embodiments, the HSMN is Refsum disease. In some embodiments, the HSMN is Charcot-Marie-Tooth with pyramidal features. In some embodiments, the HSMN is Charcot-Marie-Tooth type 6. In some embodiments, the HSMN is HMSN+retinitis pigmentosa.

In some embodiments, an active compound as described herein is used to treat Churg-Strauss syndrome.

In some embodiments, an active compound as described herein s used to treat a peripheral artery disease (PAD).

In certain aspects, an effective amount of active compound described herein, or it pharmaceutically acceptable salt to treat myasthenia gravis with CNS involvement.

In certain aspects, an effective amount of active compound described herein, or it pharmaceutically acceptable salt is used to treat dementia with Lewy bodies.

In certain aspects, active compound described herein, or it pharmaceutically acceptable salt is used to treat an individual suffering from prion disease.

In certain aspects, active compound described herein, or it pharmaceutically acceptable salt is used to treat Behcet's Disease.

In certain aspects, active compound described herein, or it pharmaceutically acceptable salt is used to treat congenital myasthenia.

In certain aspects, active compound described herein, or it pharmaceutically acceptable salt is used to treat subacute sclerosing panencephalitis (SSPE).

In certain aspects, active compound described herein, or it pharmaceutically acceptable salt is used to treat Guillain-Barré syndrome.

In certain aspects, the CNS disorder to be treated is a demyelinating disease, including, but not limited to demyelinating myelinoclastic diseases and demyelinating leukostrophic disease.

In certain aspects, the disorder to be treated is a demyelinating myelonoclastic disease including, but not limited to, multiple sclerosis, neuromyelitis optica, neuromyelitis optica spectrum of disorders (NMOSD), idiopathic inflammatory demyelinating diseases (IIDD), anti-NMDA receptor encephalitis, acute disseminated encephalomyelitis, anti-MOG autoimmune encephalomyelitis, chronic relapsing inflammatory optic neuritis (CRION), acute disseminated encephalomyelitis (ADEM), immune-mediated encephalomyelitis, progressive multifocal leukoencephalopathy (PML); McDonalds-positive multiple sclerosis, acute hemorrhagic leukoencephalitis, Rasmussen's Encephalitis, Marburg multiple sclerosis, pseudotumefactive and tumefactive multiple sclerosis, Balo concentric sclerosis, diffuse myelinoclastic sclerosis, solitary sclerosis, multiple sclerosis with cavitary lesions, myelocortical multiple sclerosis (MCMS), atypical optic-spinal multiple sclerosis, pure spinal multiple sclerosis, HLA DRB3*02:02 multiple sclerosis, autoimmune GFAP astrocytopathy, Chronic inflammatory demyelinating polyneuropathy (CIDP), Guillain-Barré syndrome, progressive inflammatory neuropathy, Lewis-Sumner Syndrome, combined central and peripheral demyelination (CCPD), Bickerstaff brainstem encephalitis, Fisher syndrome, trigeminal neuralgia, NMDAR anti-NMDA receptor encephalitis, primary progressive MS (PPMS), OPA1 variant multiple sclerosis, KIR4.1 multiple sclerosis, aquaporine-related multiple sclerosis, chronic cerebrospinal venous insufficiency (CCSVI or CCVI), diffuse sclerosis or Schilder's disease.

In certain aspects, the disorder to be treated is a demyelinating leukostrophic disease including, but not limited to, myelitis, central pontine myelinolysis (CPM), extrapontine myelinolysis, tabes dorsalis, progressive multifocal leukoencephalopathy, leukoencephalopathy with vanishing white matter, leukoencephalopathy with neuroaxonal spheroids, reversible posterior leukoencephalopathy syndrome, megalencephalic leukoencephalopathy with subcortical cysts, megalencephalic leukoencephalopathy with subcortical cysts 1, hypertensive leukoencephalopathy, Metachromatic leukodystrophy, Krabbe disease, Canavan disease, X-linked adrenoleukodystrophy, Alexander disease, cerebrotendineous xanthomatosis, Pelizaeus-Merzbacher disease, Refsum disease.

In some embodiments, an active compound as described herein is used to treat Buerger's disease, also known as thromboangiitis obliterans.

In some embodiments, an active compound as described herein is used to treat giant cell arteritis.

In some embodiments, an active compound as described herein is used to treat Raynaud's disease.

In certain aspects, the disorder to be treated is a demyelinating disease of the peripheral nervous system, including, but not limited to, Guillain-Barré syndrome and its chronic counterpart, chronic inflammatory demyelinating polyneuropathy, anti-MAG peripheral neuropathy, Charcot-Marie-Tooth disease and its counterpart Hereditary neuropathy with liability to pressure palsy, Copper deficiency-associated conditions (peripheral neuropathy, myelopathy, and rarely optic neuropathy), and progressive inflammatory neuropathy.

In certain aspects, the disorder to be treated is a neurological inflammatory disorder. In embodiments, the disorder to be treated is cranial arteritis; giant cell arteritis; Holmes-Adie syndrome; inclusion body myositis (IBM); meningitis; neurologic paraneoplastic syndrome including, but not limited to, Lambert-Eaton myasthenic syndrome, stiff-person syndrome, encephalomyelitis (inflammation of the brain and spinal cord), myasthenia gravis, cerebellar degeneration, limbic and/or brainstem encephalitis, neuromyotonia, and opsoclonus (involving eye movement) and sensory neuropathy; polymyositis; transverse myelitis; vasculitis including temporal arteritis; arachnoiditis; Kinsbourne syndrome or opsoclonus myoclonus syndrome (OMS); or Saint Vitus Dance or sydenham chorea (SD) disease.

In some embodiments, an active compound or its salt or composition as described herein is used to treat transverse myelitis.

In certain aspects, the disorder to be treated is a peripheral neuropathy. In some embodiments, the peripheral neuropathy is a mononeuropathy. In some embodiments, the neuropathy is a polyneuropathy. In some embodiments, the polyneuropathy is distal axonopathy, diabetic neuropathy, a demyelinating polyneuropathy, small fiber peripheral neuropathy, mononeuritis multiplex, polyneuritis multiplex, autonomic neuropathy, or neuritis.

In some embodiments, an active compound or its salt or composition as described herein is used to treat an autoimmune vascular disease. In some embodiments, the autoimmune vascular disease is vasculitis. In some embodiments, the vasculitis includes, but is not limited to, autoimmune inflammatory vasculitis, Cutaneous small-vessel vasculitis, Granulomatosis with polyangiitis, Eosinophilic granulomatosis with polyangiitis, Behçet's disease, Kawasaki disease, Buerger's disease, and "Limited" granulomatosis with polyangiitis vasculitis.

In some embodiments, an active compound or its salt or composition as described herein is used to treat an arteritis. In some embodiments, the arteritis includes, but is not limited to, giant cell arteritis, Takayasu arteritis, temporal arteritis, and polyarteritis nodosa.

In some embodiments, the complement-mediated disease or disorder comprises transplant rejection. In some embodiments, the complement-mediated disease or disorder is antibody-mediated transplant rejection.

In certain aspects, an active compound or its salt or composition as described herein is used to treat a proliferative disorder, including, but not limited to, cancer. Targeted cancers suitable for administration of an active compound or its salt described herein include, but are not limited to, estrogen-receptor positive cancer, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, adenocarcinoma of the colon, adenocarcinoma of the rectum, central nervous system germ cell tumors, teratomas, estrogen receptor-negative breast cancer, estrogen receptor-positive breast cancer, familial testicular germ cell tumors, HER2-negative breast cancer, HER2-positive breast cancer, male breast cancer, ovarian immature teratomas, ovarian mature teratoma, ovarian monodermal and highly specialized teratomas, progesterone receptor-negative breast cancer, progesterone receptor-positive breast cancer, recurrent breast cancer, recurrent colon cancer, recurrent extragonadal germ cell tumors, recurrent extragonadal non-seminomatous germ cell tumor, recurrent extragonadal seminomas, recurrent malignant testicular germ cell tumors, recurrent melanomas, recurrent ovarian germ cell tumors, recurrent rectal cancer, stage III extragonadal non-seminomatous germ cell tumors, stage III extragonadal seminomas, stage III malignant testicular germ cell tumors, stage III ovarian germ cell tumors, stage IV breast cancers, stage IV colon cancers, stage IV extragonadal non-seminomatous germ cell tumors, stage IV extragonadal seminoma, stage IV melanomas, stage IV ovarian germ cell tumors, stage IV rectal cancers, testicular immature teratomas, testicular mature teratomas. In particular embodiments, the targeted cancers included estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, metastatic colorectal cancer, metastatic melanoma with CDK4 mutation or amplification, or cisplatin-refractory, unresectable germ cell tumors, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, fibrosarcoma, myxosarcoma, chondrosarcoma, osteosarcoma, chordoma, malignant fibrous histiocytoma, hemangiosarcoma, angiosarcoma, lymphangiosarcoma, Mesothelioma, leiomyosarcoma, rhabdomyosarcoma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, islet cell carcinoma, malignant carcinoid, malignant paraganglioma, melanoma, Merkel cell neoplasm, cystosarcoma phylloide, salivary cancers, thymic carcinomas, bladder cancer, and Wilms tumor, a blood disorder or a hematologic malignancy, including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others, T-cell or NK-cell lymphoma, for example, but not limited to: peripheral T-cell lymphoma; anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like lymphoma. In some embodiments, the methods described herein can be used to treat a host, for example a human, with a lymphoma or lymphocytic or myelocytic proliferation disorder or abnormality. For example, the methods as described herein can be administered to a host with a Hodgkin Lymphoma or a Non-Hodgkin Lymphoma. For example, the host can have a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia, a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL, a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALX+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma, a leukemia, for example, an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In some embodiments, the patient has an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7), small cell lung cancer, retinoblastoma, HPV positive malignancies like cervical cancer and certain head and neck cancers, MYC amplified tumors such as Burkitts' Lymphoma, and triple negative breast cancer; certain classes of sarcoma, certain classes of non-small cell lung carcinoma, certain classes of melanoma, certain classes of pancreatic cancer, certain classes of leukemia, certain classes of lymphoma, certain classes of brain cancer, certain classes of colon cancer, certain classes of prostate cancer, certain classes of ovarian cancer, certain classes of uterine cancer, certain classes of thyroid and other endocrine tissue cancers, certain classes of salivary cancers, certain classes of thymic carcinomas, certain classes of kidney cancers, certain classes of bladder cancers, and certain classes of testicular cancers.

In certain aspects, an active compound or its salt as described herein can be used to preserve or prevent damage to an organ or blood product. For example, an active compound or its salt described herein can be used to prevent damage to an organ, tissue, cell product, or blood product, that has been harvested for transplantation. In some embodiments, the organ is the heart, kidney, pancreas, lung, liver, or intestine. In some embodiments, the tissue is derived from the cornea, bone, tendon, muscle, heart valve, nerve, artery or vein, or the skin. In some embodiments, the blood product is whole blood, plasma, red blood cells or reticulocytes.

In some embodiments, an active compound or its salt or composition as described herein prevents or delays the onset of at least one symptom of a complement-mediated disease or disorder in an individual in some embodiment, an active compound or its salt or composition as described herein reduces or eliminates at least one symptom of a complement-mediated disease or disorder in an individual. Examples of symptoms include, but are not limited to, symptoms associated with autoimmune disease, cancer, hematological disease, infectious disease, inflammatory disease, ischemia-reperfusion injury, neurodegenerative disease, neurodegenerative disorder, renal disease, transplant rejection, ocular disease, vascular disease, or a vasculitis disorder. The symptom can be a neurological symptom, for example, impaired cognitive function, memory impairment, loss of motor function, etc. The symptom can also be the activity of factor D protein in a cell, tissue, or fluid of an individual. The symptom can also be the extent of complement activation in a cell, tissue, or fluid of an individual.

In some embodiments, administering an active compound or its salt or composition as described herein to an individual modulates complement activation in a cell, tissue, or fluid of an individual. In some embodiments, administration of an active compound or its salt or composition as described herein to an individual inhibits complement activation in a cell, tissue, or fluid of an individual. For example, in some embodiments, an active compound or its salt or composition as described herein, when administered in one or more doses as monotherapy or in combination therapy to an individual having a complement-mediated disease or disorder, inhibits complement activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the compounds described herein.

In some embodiments, an active compound or its salt or composition as described herein reduces C3 deposition onto red blood cells; for example, in some embodiments, an an active compound or its salt or composition as described herein reduces deposition of C3b, iC3b, etc., onto RBCs. In some embodiments, an active compound or its salt or composition as described herein inhibits complement-mediated red blood cell lysis.

In some embodiments, an active compound or its salt or composition as described herein reduces C3 deposition onto platelets; for example, in some embodiments, an active compound or its salt or composition as described herein reduces deposition of C3b, iC3b, etc., onto platelets.

In some embodiments, administering an active compound or its salt or composition as described herein results in an outcome selected from the group consisting of: (a) a reduction in complement activation; (b) an improvement in cognitive function; (c) a reduction in neuron loss; (d) a reduction in phospho-Tau levels in neurons; (e) a reduction in glial cell activation; (f) a reduction in lymphocyte infiltration; (g) a reduction in macrophage infiltration; (h) a reduction in antibody deposition, (i) a reduction in glial cell loss; (j) a reduction in oligodendrocyte loss; (k) a reduction in dendritic cell infiltration; (l) a reduction in neutrophil infiltration; (m) a reduction in red blood cell lysis; (n) a reduction in red blood cell phagocytosis; (o) a reduction in platelet phagocytosis; (p) a reduction in platelet lysis; (q) an improvement in transplant graft survival; (r) a reduction in macrophage mediated phagocytosis; (s) an improvement in vision; (t) an improvement in motor control; (u) an improvement in thrombus formation; (v) an improvement in clotting; (w) an improvement in kidney function; (x) a reduction in antibody mediated complement activation; (y) a reduction in autoantibody mediated complement activation; (z) an improvement in anemia; (aa) reduction of demyelination; (ab) reduction of eosinophilia; (ac) a reduction of C3 deposition on red blood cells (e.g., a reduction of deposition of C3b, iC3b, etc., onto RBCs); and (ad) a reduction in C3 deposition on platelets (e.g., a reduction of deposition of C3b, iC3b, etc., onto platelets); and (ae) a reduction of anaphylatoxin toxin production; (af) a reduction in autoantibody mediated blister formation; (ag) a reduction in autoantibody induced pruritis; (ah) a reduction in autoantibody induced erythematosus; (ai) a reduction in autoantibody mediated skin erosion; (aj) a reduction in red blood cell destruction due to transfusion reactions; (ak) a reduction in red blood cell lysis due to alloantibodies; (al) a reduction in hemolysis due to transfusion reactions; (am) a reduction in allo-antibody mediated platelet lysis; (an) a reduction in platelet lysis due to transfusion reactions; (ao) a reduction in mast cell activation; (ap) a reduction in mast cell histamine release; (aq) a reduction in vascular permeability; (ar) a reduction in edema; (as) a reduction in complement deposition on transplant graft endothelium; (at) a reduction of anaphylatoxin generation in transplant graft endothelium; (au) a reduction in the separation of the dermal-epidermal junction; (av) a reduction in the generation of anaphylatoxins in the dermal epidermal junction; (aw) a reduction in alloantibody mediated complement activation in transplant graft endothelium; (ax) a reduction in antibody mediated loss of the neuromuscular junction; (ay) a reduction in complement activation at the neuromuscular junction; (az) a reduction in anaphylatoxin generation at the neuromuscular junction; (ba) a reduction in complement deposition at the neuromuscular junction; (bb) a reduction in paralysis; (bc) a reduction in numbness; (bd) increased bladder control; (be) increased bowel control; (bf) a reduction in mortality associated with autoantibodies; and (bg) a reduction in morbidity associated with autoantibodies.

In some embodiments, an active compound or its salt or composition as described herein, when administered in one or more doses as monotherapy or in combination therapy to an individual having a complement-mediated disease or disorder, is effect to achieve a reduction of at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: (a) complement activation; (b) decline in cognitive function; (c) neuron loss; (d) phospho-Tau levels in neurons; (e) glial cell activation; (f) lymphocyte infiltration; (g) macrophage infiltration (h) antibody deposition, (i) glial cell loss; (j) oligodendrocyte loss; (k) dendritic cell infiltration; (l) neutrophil infiltration; (m) red blood cell lysis; (n) red blood cell phagocytosis; (o) platelet phagocytosis; (p) platelet lysis; (q) transplant graft rejection; (r) macrophage mediated phagocytosis; (s) vision loss; (t) antibody mediated complement activation; (u) autoantibody mediated complement activation; (v) demyelination; (w) eosinophilia; compared to the level or degree of the outcome in the individual before treatment with the active compound.

In some embodiments, an active compound or its salt or composition as described herein, when administered in one or more doses as monotherapy or in combination therapy to an individual having a complement-mediated disease or disorder, is effect to achieve an improvement of at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: a) cognitive function; b) transplant graft survival; c) vision; d) motor control; e) thrombus formation; f) clotting; g) kidney function; and h) hematocrit (red blood cell count), compared to the level or degree of the outcome in the individual before treatment with the active compound.

In some embodiments, administering an active compound or its salt or composition as described herein to an individual reduces complement activation in the individual. For example, in some embodiments, an active compound or its salt or composition as described herein, when administered in one or more doses as monotherapy or in combination therapy to an individual having a complement-mediated disease or disorder, reduces complement activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the active compound or its salt.

In some embodiments, administering an active compound or its salt or composition as described herein improves cognitive function in the individual. For example, in some embodiments, an active compound described herein, when administered in one or more doses as monotherapy or in combination therapy to an individual having a complement-mediated disease or disorder, improves cognitive function in the individual by at least about 10%, at least about 15%, at least about 20%, at least about 25%, at least about 30?, at least about 40%, at least about 50%, at least about 60%, at least about 70%, at least about 80%, at least about 90%, or more than 90%, compared to the cognitive function in the individual before treatment with the active compound.

In some embodiments, administering an active compound or its salt or composition as described herein reduces the rate of decline in cognitive function in the individual. For example, in some embodiments, an active compound or its salt, when administered in one or more doses as monotherapy or in combination therapy to an individual having a complement-mediated disease or disorder, reduces the rate of decline of cognitive function in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the rate of decline in cognitive function in the individual before treatment with the active compound or its salt.

In some embodiments, administering an active compound or its salt or composition as described herein to an individual reduces neuron loss in the individual. For example, in some embodiments, an active compound or its salt, when administered in one or more doses as monotherapy or in combination therapy to an individual having a complement-mediated disease or disorder, reduces neuron loss in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to neuron loss in the individual before treatment with the active compound.

In some embodiments, administering an active compound or its salt or composition as described herein to an individual reduces phospho-Tau levels in the individual. For example, in some embodiments, an active compound or its salt, when administered in one or more doses as monotherapy or in combination therapy to an individual having a complement-mediated disease or disorder, reduces phospho-Tau in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the phospho-Tau level in the individual before treatment with the active compound or its salt.

In some embodiments, administering an active compound or its salt or composition as described herein to an individual reduces glial cell activation in the individual. For example, in some embodiments, an active compound or its salt, when administered in one or more doses as monotherapy or in combination therapy to an individual having a complement-mediated disease or disorder, reduces glial activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to glial cell activation in the individual before treatment with the active compound or its salt. In some embodiments, the glial cells are astrocytes or microglia.

In some embodiments, administering an active compound or its salt or composition as described herein to an individual reduces lymphocyte infiltration in the individual. For example, in some embodiments, an active compound or its salt, when administered in one or more doses as monotherapy or in combination therapy to an individual having a complement-mediated disease or disorder, reduces lymphocyte infiltration in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to lymphocyte infiltration in the individual before treatment with the active compound or its salt.

In some embodiments, administering an active compound or its salt or composition as described herein to an individual reduces macrophage infiltration in the individual. For example, in some embodiments, an active compound or its salt, when administered in one or more doses as monotherapy or in combination therapy to an individual having a complement-mediated disease or disorder, reduces macrophage infiltration in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to macrophage infiltration in the individual before treatment with the active compound or its salt.

In some embodiments, administering an active compound or its salt or composition as described herein to an individual reduces antibody deposition in the individual. For example, in some embodiments, an active compound or its salt, when administered in one or more doses as monotherapy or in combination therapy to an individual having a complement-mediated disease or disorder, reduces antibody deposition in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to antibody deposition in the individual before treatment with the active compound or its salt.

In some embodiments, administering an active compound or its salt or composition as described herein to an individual reduces anaphylatoxin (e.g., C3a, C4a, C5a) production in an individual. For example, in some embodiments, an active compound or its salt, when administered in one or more doses as monotherapy or in combination therapy to an individual having a complement-mediated disease or disorder, reduces anaphylatoxin production in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the level of anaphylatoxin production in the individual before treatment with the active compound or its salt.

The present disclosure provides for use of an active compound or its salt of the present disclosure or a pharmaceutical composition comprising an active compound or its salt of the present disclosure and a pharmaceutically acceptable excipient to treat an individual having a complement-mediated disease or disorder. In some embodiments, the present disclosure provides for use of an active compound or its salt of the present disclosure to treat an individual having a complement-mediated disease or disorder. In some embodiments, the present disclosure provides for use of a pharmaceutical composition comprising an active compound or its salt of the present disclosure and a pharmaceutically acceptable excipient to treat an individual having a complement-mediated disease or disorder.

Combination Therapy

In some embodiments an active compound or its salt or composition as described herein may be provided in combination or alternation with or preceded by, concomitant with or followed by, an effective amount of at least one additional therapeutic agent, for example, for treatment of a disorder listed herein. Non-limiting examples of second active agents for such combination therapy are provided below.

In some embodiments, an active compound or its salt or composition as described herein may be provided in combination or alternation with at least one additional inhibitor of the complement system or a second active compound with a different biological mechanism of action. In the description below and herein generally, whenever any of the terms referring to an active compound or its salt or composition as described herein are used, it should be understood that pharmaceutically acceptable salts, prodrugs or compositions are considered included, unless otherwise stated or inconsistent with the text.

In non-limiting embodiments, an active compound or its salt or composition as described herein may be provided together with a protease inhibitor, a soluble complement regulator, a therapeutic antibody (monoclonal or polyclonal), complement component inhibitor, receptor agonist, or siRNA.

In other embodiments, an active compound described herein is administered in combination or alternation with an antibody against tumor necrosis factor (TNF), including but not limited to infliximab (Remicade), adalimumab, certolizumab, golimumab, or a receptor fusion protein such as etanercept (Embrel).

In another embodiment, an active compound as described herein can be administered in combination or alternation with an anti-CD20 antibody, including but not limited to rituximab (Rituxan), adalimumab (Humira), ofatumumab (Arzerra), tositumomab (Bexxar), obinutuzumab (Gazyva), or ibritumomab (Zevalin).

In an alternative embodiment, an active compound as described herein can be administered in combination or alternation with an anti-IL6 antibody, including but not limited to tocilizumab (Actemra) and siltuximab (Sylvant).

In an alternative embodiment, an active compound as described herein can be administered in combination or alternation with an IL17 inhibitor, including but not limited to secukibumab (Cosentyx).

In an alternative embodiment, an active compound as described herein can be administered in combination or alternation with a p40 (IL12/IL23) inhibitor, including but not limited to ustekinumab (Stelara).

In an alternative embodiment, an active compound as described herein can be administered in combination or alteration with an IL23 inhibitor, including but not limited to risankizumab.

In an alternative embodiment, an active compound as described herein can be administered in combination or alteration with an anti-interferon α antibody, for example but not limited to sifalimumab.

In an alternative embodiment, an active compound as described herein can be administered in combination or alteration with a kinase inhibitor, for example but not limited to a JAK1/JAK3 inhibitor, for example but not limited to tofacitinib (Xelianz). In an alternative embodiment, an active compound as described herein can be administered in combination or alteration with a JAK1/JAK2 inhibitor, for example but not limited to baracitibib.

In an alternative embodiment, an active compound as described herein can be administered in combination or alteration with an anti-VEGF agent, for example but not limited to: aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids.

In another embodiment, an active compound as described herein can be administered in combination or alternation with an immune checkpoint inhibitor. Non-limiting examples of checkpoint inhibitors include anti-PD-1 or anti-PDL1 antibodies, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc), atezolizumab, durvalumab, and KN035, or anti-CTLA4 antibodies, for example Ipilimumab, Tremelimumab, AGEN1884 and AGEN2041 (Agenus).

Non-limiting examples of active agents that can be used in combination with active compounds described herein are:

Protease inhibitors: plasma-derived C1-INH concentrates, for example Cetor® (Sanquin), Berinert-P® (CSL Behring, Lev Pharma), and Cinryze®; recombinant human C1-inhibitors, for example Rhucin®; ritonavir (Norvir®, Abbvie, Inc.);

Soluble complement regulators: Soluble complement receptor 1 (TP10) (Avant Immunotherapeutics); sCR1-sLe$^x$/

TP-20 (Avant Immunotherapeutics); MLN-2222/CAB-2 (Millenium Pharmaceuticals); Mirococept (Inflazyme Pharmaceuticals); Therapeutic antibodies: Eculizumab/Soliris and Ravulizumab/Ultomiris (Alexion Pharmaceuticals); Pexelizumab (Alexion Pharmaceuticals); ABP959 (Amgen); BOWo8o (Epirus Biopharmaceuticals); SB12 (Samsung Bioepis); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix); 4(1MEW)APL-1, APL-2 (Appelis); CP40/AMY-101, PEG-Cp40 (Amyndas);

PDGF inhibitors: Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; Anti-factor H or anti-factor B agents: Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas);

Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH; Anti-CR3, anti-MASP2, anti C1s, and anti-C1n molecules: Cynryze (ViroPharma/Baxter); TNT003 (True North); OMS721 (Omeros); OMS906 (Omeros); and Imprime PGG (Biothera);

Receptor agonists: PMX-53 (Peptech Ltd.); JPE-137 (Jerini); JSM-7717 (Jerini);

Others: Recombinant human MBL (rhMBL; Enzon Pharmaceuticals); Imides and glutarimide derivatives such as thalidomide, lenalidomide, pomalidomide; Additional non-limiting examples that can be used in combination or alternation with an active compound or its salt or composition as described herein include the following.

| Non-limiting examples for combination therapy | | | |
|---|---|---|---|
| Name | Target | Company | Class of Molecule |
| LFG316 | C5 | Novartis/Morphosys | Monoclonal antibody |
| SB12 | C5 | Samsung Bioepsis | |
| IONIS-FB-LRx | CFB | Ionis | Antisense Inhibitor |
| 4(1MEW)APL-1, APL-2 | C3/C3b | Apellis | Compstatin Family |
| 4(1MeW)POT-4 | C3/C3b | Potentia | Compstatin Family |
| Anti-C5 siRNA | C5 | Alnylam | Si-RNA |
| Anti-FB siRNA | CFB | Alnylam | SiRNA |
| ARC1005 | C5 | Novo Nordisk | Aptamers |
| ATA | C5 | N.A. | Chemical |
| Coversin | C5 | Volution Immuno-Pharmaceuticals | Small animal protein |
| CP40/AMY-101, PEG-Cp40 | C3/C3b | Amyndas | Compstatin Family |
| CRIg/CFH | CAP C3 convertase | NA | CFH-based protein |
| Cynryze | C1n/C1s | ViroPharma/Baxter | Human purified protein |
| FCFD4514S | CFD | Genentech/Roche | Monoclonal antibody |
| H17 | C3 (C3b/iC3b) | EluSys Therapeutics | Monoclonal antibody |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 | C5 | Rapharma | Small molecule |
| sCR1 (CDX-1135) | CAP and CP C3 | Celldex | CR1-based protein |
| SOBI002 | C5 | Swedish Orphan Biovitrum | Affibody |
| SOMAmers | C5 | SomaLogic | Aptamers |
| SOMAmers | CFB and CFD | SomaLogic | Aptamers (SELEX) |
| TA106 | CFB | Alexion Pharmaceuticals | Monoclonal antibody |
| TNT003 | C1s | True North | Monoclonal antibody |
| TT30 (CR2/CFH) | CAP C3 convertase | Alexion | CFH-based protein |
| TT32 (CR2/CR1) | CAP and CCP C3 | Alexion Pharmaceuticals | CR1-based protein |
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-2 | Omeros | Monoclonal antibody |
| Bikaciomab, NM9308 | CFB | Novelmed | Monoclonal antibody |
| NM19401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |

-continued

Non-limiting examples for combination therapy

| Name | Target | Company | Class of Molecule |
| --- | --- | --- | --- |
| rFH | C3-conv, C3b | Optherion | Regulator |
| 5C6, AMY-301 | CFH | Amyndas | Regulator |
| Erdigna | C5 | Adienne Pharma | Antibody |
| ARC1905 | C5 | Opthotech | Monoclonal Antibody |
| MEDI7814 | C5/C5a | MedImmune | Monoclonal Antibody |
| NOX-D19 | C5a | Noxxon | Aptamer (Spiegelmer) |
| IFX-1, CaCP29 | C5a | InflaRx | Monoclonal Antibody |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-C5aR-151, NN8209; Anti-C5aR-215, NN8210 | C5aR | Novo Nordisk | Monoclonal Antibody |
| Imprime PGG | CR3 | Biothera | Soluble beta-glucan |
| ANX005; ANX007 | C1q | Annexon | Monoclonal Antibody |
| Lampalizumab | fD | Roche | Monoclonal Antibody |
| avacincaptad pegol | C5 | Opthotecb | Aptamer |
| regenemab | C6 | Regenesance | Monoclonal Antibody |
| BIVV020 | C1s | Bioverativ | Monoclonal Antibody |
| PRO-02 | C2 | Broteio/Argen-x | Monoclonal Antibody |
| 5C6, compsorbin | fH | Amyndas | Peptide |
| SOBI005 | C5 | Sobi | Protein |
| ISU305 | C5 | ISU ABXIS | Monoclonal Antibody |
| Mubodina | C5 | Adienne | Monoclonal Antibody |
| IFX-2, IFX-3 | C5a | InflaRx | Monoclonal Antibody |
| ALS-205 | C5aR1 | Alsonex | Peptide |
| DF2593A | C5aR1 | Dompé | Small Molecule |
| IPH5401 | C5aR1 | Innate Pharma | Monoclonal Antibody |
| C6-LNA | C6 | Regenesance | Oligonucleotide |
| SKY59 | C5 | Roche | Monoclonal Antibody |
| REGN3918 | C5 | Regeneron | Monoclonal Antibody |
| Aptamers to Factor D | fD | Vitrisa Therapeutics | Aptamer |
| CLG561 | Properdin | Novartis | Monoclonal Antibody |
| Tesidolumab; LFG316 | C5 | Novartis and MorphoSys | Monoclonal Antibody |

In one embodiment the agent for combination therapy is a biosimilar of any agent named in the above table.

In some embodiments, an active compound or its salt or composition as described herein may be provided together with a compound that inhibits an enzyme that metabolizes an administered protease inhibitor. In some embodiments, a compound or salt may be provided together with ritonavir.

In some embodiments, an active compound or its salt or composition as described herein may be provided in combination with a complement C5 inhibitor or C5 convertase inhibitor. In another embodiment, an active compound or its salt or composition as described herein may be provided in combination with eculizumab, a monoclonal antibody directed to the complement factor C5 and manufactured and marketed by Alexion Pharmaceuticals under the tradename Soliris. Eculizumab has been approved by the U.S. FDA for the treatment of PNH, aHUS, and myasthenia gravis. In another embodiment, an active compound or its salt or composition as described herein may be provided in combination with ravulizumab, a monoclonal antibody directed to the complement factor C5 and manufactured and marketed by Alexion Pharmaceuticals under the tradename Ultomiris. In another embodiment, an active compound or its salt or composition as described herein may be provided in combination with ABP959, a monoclonal antibody directed to the complement factor C5 and manufactured and marketed by Amgen. In another embodiment, an active compound or its salt or composition as described herein may be provided in combination with BOWo8o, a monoclonal antibody directed to the complement factor C5 and manufactured and marketed by Epirus Biopharmaceuticals. In another embodiment, an active compound or its salt or composition as described herein may be provided in combination with SB12, a monoclonal antibody directed to the complement factor C5 and manufactured and marketed by Samsung Bioepis.

In some embodiments, an active compound or its salt or composition as described herein may be provided together with a compound that inhibits Complement Factor D. In some embodiments of the invention, an active compound or its salt or composition as described herein as described herein can be used in combination or alternation with a compound described in Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D; Novartis PCT patent publication WO2012/093101 titled "Indole compounds or analogs thereof useful for the treatment of age-related macular degeneration" describes certain Factor D inhibitors; Novartis PCT patent publications WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, WO2015/066241, Bristol-Myers Squibb PCT patent publication WO2004/045518 titled "Open chain prolyl urea-related modulators of androgen receptor function"; Japan Tobacco Inc. PCT patent publication WO1999/048492 titled "Amide derivatives and nociceptin antagonists"; Ferring B. V. and Yamanouchi Pharmaceutical Co. LTD. PCT patent publication WO1993/020099 titled "CCK and/or gastrin receptor ligands"; Alexion Pharmaceuticals PCT patent publication WO1995/029697 titled "Methods and compositions for the treatment of glomerulonephritis and other inflammatory diseases"; or Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

In some embodiments, an active compound or its salt or composition as described herein is administered in combination with an anti-inflammatory drug, antimicrobial agent, anti-angiogenesis agent, immunosuppressant, antibody, steroid, ocular antihypertensive drug or combinations thereof. Examples of such agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogs, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus, anti-PDGFR molecule, and combinations thereof.

In some embodiments of the present invention, an active compound or its salt or composition as described herein can be administered in combination or alternation with at least one immunosuppressive agent. The immunosuppressive agent as non-limiting examples, may be a calcineurin inhibitor, e.g, a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolitnus, zotarolimus, biolitnus-7, biolimus-9, a rapalog, e.g. ridaforolimus, azathioprine, campath 1H, a S1P receptor modulator, e.g. fingolimod or an analog thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, tocilizumab (Actemra), siltuximab (Sylvant), secukibumab (Cosentyx), ustekinumab (Stelara), risankizumab, sifalimumab, aspirin and ibuprofen.

Examples of anti-inflammatory agents include methotrexate, dexamethasone, dexamethasone alcohol, dexamethasone sodium phosphate, fluromethalone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In some embodiments, an active compound or its salt or composition as described herein is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In some embodiments, an active compound or its salt or composition as described herein is administered in combination or alteration with an omega-3 fatty acid or a peroxisome proliferator-activated receptor (PPARs) agonist. Omega-3 fatty acids are known to reduce serum triglycerides by inhibiting DGAT and by stimulating peroxisomal and mitochondrial beta oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark Omacor®. Such a form of omega-3 fatty acid is described, for example, in U.S. Pat. Nos. 5,502,077, 5,656,667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methylpropanoic acid, 1-methylethyl ester, has been known for many years as a medicinally active principle because of its efficacy in lowering blood triglyceride and cholesterol levels.

In some embodiments, the present invention provides a method of treating or preventing age-related macular degeneration (AMD) by administering to a subject in need thereof an effective amount of an active compound or its salt or composition as described herein in combination with an anti-VEGF agent. Non-limiting examples of anti-VEGF agents include, but are not limited to, aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); Cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids, including, but not limited to, triamcinolone acetonide.

In some embodiments, the present invention provides a method of treating or preventing age-related macular degeneration (AMD) by administering to a subject in need thereof an effective amount of an active compound or its salt or composition as described herein in combination with a complement C5 inhibitor, for example, a complement C5 inhibitor described herein and in the table above titled Non-limiting examples of potential therapeutics for combination therapy, including, but not limited to, eculizumab; ravulizumab; ABP959 (Amgen); BOWo8o (Epirus Biopharmaceuticals); SB12 (Samsung Bioepis); LFG316 (Novartis/Morphosys); Anti-C5 siRNA (Alnylam); ARC1005 (Novo Nordisk); Coversin (Volution Immuno-Pharmaceuticals); Mubodine (Adienne Pharma); RA101348 (Ra Pharma); SOBI002 (Swedish Orphan Biovitrum); SOMAmers (SomaLogic); Erdigna (Adienne Pharma); ARC1905 (Opthotech); MEDI7814 (MedImmune); NOX-D19 (Noxxon); IFX-1, CaCP29 (InflaRx); PMX53, PMX205 (Cephalon, Teva); CCX168 (ChemoCentryx); ADC-1004 (Alligator Bioscience); and Anti-C5aR-151, NN8209; Anti-C5aR-215, NN8210 (Novo Nordisk).

In some embodiments, the present invention provides a method of treating or preventing age-related macular degeneration (AMD) by administering to a subject in need thereof an effective amount of an active compound or its salt or composition as described herein in combination with anti-properidin agent, for example, an anti-properidin agent as described above, including but not limited to NM9401 (Novelmed).

In some embodiments, the present invention provides a method of treating or preventing age-related macular degeneration (AMD) by administering to a subject in need thereof an effective amount of an active compound or its salt or composition as described herein in combination with a complement C3 inhibitor for example, a complement C3 inhibitor described above, including, but not limited to, a compstatin or compstatin analog, for example Compstatin/POT-4 (Potentia Pharmaceuticals); ARC1905 (Archemix); 4(1MEW)APL-1, APL-2 (Appelis); CP40/AMY-101, PEG-Cp40 (Amyndas) Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); and CRIg/CFH.

In some embodiments, the present invention provides a method of treating or preventing age-related macular degeneration (AMD) by administering to a subject in need thereof an effective amount of an active compound or its salt or composition as described herein in combination with an anti-factor H or anti-factor B agent selected from Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas).

In some embodiments, the present invention provides a method of treating or preventing age-related macular degeneration (AMD) by administering to a subject in need thereof an effective amount of an active compound or its salt or composition as described herein in combination with an anti-MASP2, anti-C1s or anti-CR3 molecules, for example, but not limited to: Cynryze (ViroPharma/Baxter); TNT003 (True North); OMS721 (Omeros); OMS906 (Omeros); and Imprime PGG (Biothera).

In some embodiments, the present invention provides a method of treating or preventing age-related macular degeneration (AMD) by administering to a subject in need thereof an effective amount of an active compound or its salt or composition as described herein in combination with an PDGF inhibitor, for example as described herein including but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TK1258) Lactate; Sennoside B; Sunitinib; AZD2932; and Trapidil.

In some embodiments, the present invention provides a method of treating or preventing paroxysmal nocturnal hemoglobinuria (PNH) by administering to a subject in need thereof an effective amount of an active compound or its salt or composition as described herein with an additional inhibitor of the complement system or another active compound with a different biological mechanism of action. In another embodiment, the present invention provides a method of treating or preventing paroxysmal nocturnal hemoglobinuria (PNH) by administering to a subject in need thereof an effective amount of an active compound or its salt or composition as described herein in combination or alternation with eculizumab, ravulizumab, ABP959 (Amgen), BOWo8o (Epirus Biopharmaceuticals), or SB12 (Samsung Bioepis). In another embodiment, the present invention provides a method of treating or preventing paroxysmal nocturnal hemoglobinuria (PNH) by administering to a subject in need thereof an effective amount of an active compound or its salt or composition as described herein in combination or alternation with CP40. In some embodiments, the additional agent is PEGylated-CP40. CP40 is a peptide inhibitor that shows a strong binding affinity for C3b and inhibits hemolysis of paroxysmal nocturnal hemoglobinuria (PNH) erythrocytes. In some embodiments, the additional agent is a complement component inhibitor, for example but not limited to Compstatin/POT-4 (Potentia Pharmaceuticals); ARC1905 (Archemix); 4(1MEW)APL-1, APL-2 (Appelis); CP40/AMY-101, PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TM-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera)

In some embodiments, the present invention provides a method of treating or preventing rheumatoid arthritis by administering to a subject in need thereof an effective amount of a composition comprising an active compound or its salt or composition as described herein in combination or alternation with an additional inhibitor of the complement system, or an active agent that functions through a different mechanism of action. In another embodiment, the present invention provides a method of treating or preventing rheumatoid arthritis by administering to a subject in need thereof an effective amount of an active compound or its salt or composition as described herein in combination or alternation with methotrexate. In certain embodiments, an active compound or its salt or composition as described herein is administered in combination or alternation with at least one additional therapeutic agent selected from: salicylates including aspirin (Anacin, Ascriptin, Bayer Aspirin, Ecotrin) and salsalate (Mono-Gesic, Salgesic), nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In some embodiments, the present invention provides a method of treating or preventing multiple sclerosis by administering to a subject in need thereof an effective amount of an active compound or its salt or composition as described herein in combination or alternation with an additional inhibitor of the complement system, or an active agent that functions through a different mechanism of action. In another embodiment, the present invention provides a method of treating or preventing multiple sclerosis by administering to a subject in need thereof an effective amount of an active compound or its salt or composition as described herein in combination or alternation with a corticosteroid. Examples of corticosteroids include, but are not limited to, prednisone, dexamethasone, solumedrol, and methylprednisolone. In some embodiments, an active compound or its salt or composition as described herein is combined with at least one anti-multiple sclerosis drug, for example, selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), Solu-Medrol (methylprednisolone), High-dose oral Deltasone (prednisone), H.P. Acthar Gel (ACTH), or a combination thereof.

In some embodiments, an active compound or its salt or composition as described herein is useful in a combination with another pharmaceutical agent to ameliorate or reduce a side effect of the agent. For example, in some embodiments, an active compound or its salt or composition as described herein may be used in combination with adoptive cell transfer therapies to reduce an associated inflammatory response associated with such therapies, for example, a cytokine mediated response such as cytokine release syndrome. In some embodiments, the adoptive cell transfer therapy includes the use of a chimeric antigen receptor T-Cell (CAR T). In some embodiments, the adoptive cell transfer therapy includes the use of a chimeric antigen receptor T-Cell (CAR T) or a dendritic cell to treat a hematologic or solid tumor, for example, a B-cell related hematologic cancer. In some embodiments, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19.

In an additional alternative embodiment, an active compound or its salt or composition as described herein may be provided in combination with eculizumab, ravulizumab, ABP959 (Amgen), BOWo8o (Epirus Biopharmaceuticals), or SB12 (Samsung Bioepis) for the treatment of PNH, aHUSs, STEC-HUS, ANCA-vasculitis, wet or dry AMD, CAD, diabetic retinopathy, irritable bowl disease (IBD), C3 glomerulopathy, for example DDD or C3GN, chronic hemolysis, neuromyelitis optica, myasthenia gravis, amyotrophic lateral sclerosis (ALS), primary progressive multiple sclerosis (PPMS), or transplantation rejection. In some embodiments, an active compound or its salt or composition as described herein may be provided in combination with compstatin or a compstatin derivative for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In some embodiments, the additional agent is a complement component inhibitor, for example but not limited to Compstatin/POT-4 (Potentia Pharmaceuticals); ARC1905 (Archemix); 4(1MEW)APL-1, APL-2 (Appelis); CP40/AMY-101, PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera).

In some embodiments, an active compound or its salt or composition as described herein may be provided in combination with rituxan for the treatment of a complement mediated disorder. In some embodiments, the complement mediated disorder is, for example, rheumatoid arthritis, Granulomatosis with Polyangiitis (GPA) (Wegener's Granulomatosis), and Microscopic Polyangiitis (MPA). In some embodiments, the disorder is Lupus.

In some embodiments, an active compound or its salt or composition as described herein may be provided in combination with cyclophosphamide for the treatment of a complement mediated disorder. In some embodiments, the disorder is an autoimmune disease. In some embodiments, the complement mediated disorder is, for example, rheumatoid arthritis, Granulomatosis with Polyangiitis (GPA) (Wegener's Granulomatosis), and Microscopic Polyangiitis (MPA). In some embodiments, the disorder is Lupus.

In some embodiments, an active compound or its salt or composition as described herein is dosed in combination with a conventional DLE treatment for the treatment of lupus to a subject in need thereof.

Examples of conventional DLE treatments include topical corticosteroid ointments or creams, such as triamcinolone acetonide, fluocinolone, flurandrenolide, betamethasone valerate, or betamethasone dipropionate. Resistant plaques can be injected with an intradermal corticosteroid. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL).

In some embodiments, an active compound or its salt or composition as described herein may be provided in combination with methotrexate for the treatment of Lupus.

In some embodiments, an active compound or its salt or composition as described herein may be provided in combination with azathioprine for the treatment of Lupus.

In some embodiments, an active compound or its salt or composition as described herein may be provided in combination with a non-steroidal anti-inflammatory drug for the treatment of Lupus.

In some embodiments, an active compound or its salt or composition as described herein may be provided in combination with a corticosteroid for the treatment of Lupus.

In some embodiments, an active compound or its salt or composition as described herein may be provided in combination with a belimumab (Benlysta) for the treatment of Lupus.

In some embodiments, an active compound or its salt or composition as described herein may be provided in combination with hydroxychloroquine (Plaquenil) for the treatment of Lupus.

In some embodiments, an active compound or its salt or composition as described herein may be provided in combination with sifalimumab for the treatment of Lupus.

In some embodiments, an active compound or its salt or composition as described herein may be provided in combination with OMS721 (Omeros) for the treatment of a complement mediated disorder. In some embodiments, an active compound or its salt or composition as described herein may be provided in combination with OMS906 (Omeros) for the treatment of a complement mediated disorder. In some embodiments, the complement mediated disorder is, for example, thrombotic thrombocytopenic purpura (TTP) or aHUS.

In some embodiments, an active compound or its salt or composition as described herein may be provided in combination with an anti-inflammatory agent, immunosuppressive agent, or anti-cytokine agent for the treatment or prevention of cytokine or inflammatory reactions in response to the administration of pharmaceuticals or biotherapeutics (e.g. adoptive T-cell therapy (ACT) such as CAR T-cell therapy, or monoclonal antibody therapy). In some embodiments, an active compound or its salt or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ. In some embodiments, an active compound or its salt or composition as described herein may be provided in combination with an anti-cytokine inhibitor including, but are not limited to, adalimumab, infliximab, etanercept, protopic, efalizumab, alefacept, anakinra, siltuximab, secukibumab, ustekinumab, golimumab, and tocilizumab, or a combination thereof. Additional anti-inflammatory agents that can be used in combination with an active compound or its salt or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline); DAB 486-IL2 and/or DAB 389-IL-2 (IL-2 fusion proteins; Seragen); Anti-Tac (humanized anti-IL-2Rα; Protein Design Labst/Roche); (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibiton); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1β converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 anti-sense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine).

In a specific embodiment, an active compound or its salt or composition as described herein may be provided in combination with a corticosteroid for the treatment or prevention of cytokine or inflammatory reactions in response to the administration of pharmaceuticals or biotherapeutics. In another embodiment, an active compound or its salt or composition as described herein may be provided in combination with etanercept for the treatment or prevention of cytokine or inflammatory reactions in response to the administration of pharmaceuticals or biotherapeutics. In another embodiment, an active compound or its salt or composition as described herein may be provided in combination with tocilizumab for the treatment or prevention of cytokine or inflammatory reactions in response to the administration of pharmaceuticals or biotherapeutics. In another embodiment, an active compound or its salt or composition as described herein may be provided in combination with etarnercept and tocilizumab for the treatment or prevention of cytokine or inflammatory reactions in response to the administration of pharmaceuticals or biotherapeutics. In another embodiment, an active compound or its salt or composition as described herein may be provided in combination with infliximab for the treatment or prevention of cytokine or inflammatory reactions in response to the administration of pharmaceuticals or biotherapeutics. In another embodiment, an active compound or its salt or composition as described herein may be provided in combination with golimumab for the treatment or prevention of cytokine or inflammatory reactions in response to the administration of pharmaceuticals or biotherapeutics.

C5 Inhibitors

Provided herein are methods for treating PNH in a subject comprising administering to the subject an effective amount of a C5 inhibitor in combination or alternation with an effective amount of a CFD inhibitor selected from Formula I, Formula II, Formula III, Formula IV, Formula V, Formula VI, Formula VII, Formula VIII, or Formula IX.

C5 inhibitors are known in the art. In some embodiments, the C5 inhibitor is a monoclonal antibody targeting C5. In some embodiments, the C5 inhibitor is eculizumab (Soliris™ Alexion Pharmaceuticals, New Haven, CT, see, e.g., U.S. Pat. No. 9,352,035). In some embodiments, the C5 inhibitor is ravulizumab (Ultomiris™ Alexion Pharmaceuticals, New Haven, CT, see, e.g., U.S. Pat. Nos. 9,371,377; 9,079,949 and 9,663,574. In some embodiments, the C5 inhibitor is ABP959 (Amgen). In some embodiments, the C5 inhibitor is BOWo8o (Epirus Biopharmaceuticals). In some embodiments, the C5 inhibitor is SB12 (Samsung Bioepis).

In some embodiments, the C5 inhibitor may be, but is not limited to: a recombinant human minibody, for example Mubodina® (monoclonal antibody, Adienne Pharma and Biotech, Bergamo, Italy; see U.S. Pat. No. 7,999,081); coversin (small animal protein, Volution Immuno-pharmaceuticals, Geneva, Switzerland; see e.g. Penabad et al. Lupus, 2012, 23(12):1324-6); LFG316 (monoclonal antibody, Novartis, Basel, Switzerland, and Morphosys, Planegg, Germany; see U.S. Pat. Nos. 8,241,628 and 8,883,158); ARC-1905 (pegylated RNA aptamer, Ophthotech, Princeton, NJ and New York, NY; see Keefe et al., Nature Reviews Drug Discovery, 9, 537-550); RA101348 and RA101495 (macrocyclic peptides, Ra Pharmaceuticals, Cambridge, MA); SOBI002 (affibody, Swedish Orphan Biovitrum, Stockholm, Sweden); ALN-CC5 (Si-RNA, Alnylam Pharmaceuticals, Cambridge, MA); ARC1005 (aptamers, Novo Nordisk, Bagsvaerd, Denmark); SOMAmers (aptamers, SomaLogic, Boulder, Co.); SSL7 (bacterial protein toxin, see, e.g. Laursen et al. Proc. Natl. Acad. Sci. U.S.A., 107(8):3681-6); MEDI7814 (monoclonal antibody, MedImmune, Gaithersburg, MD); aurin tricarboxylic acid; aurin tricarboxylic acid derivatives (Aurin Biotech, Vancouver, BC, see U.S. Patent Appl. Pub. 2013/003592); RG6107 (anti-C5 recycling antibody, Roche Pharmaceuticals, Basel, Switzerland); ALXN1210 and ALXN5500 (monoclonal antibodies, Alexion Pharmaceuticals, New Haven, CT); TT30 (fusion protein, Alexion Pharmaceuticals, New Haven, CT); REGN3918 (monoclonal antibody, Regeneron, Tarrytown, NY); ABP959 (eculizumab biosimilar, Amgen, Thousand Oaks, CA); or combinations thereof.

In some embodiments, the C5 inhibitor is a recombinant human minibody, for example Mubodina®. Mubodina® is a fully human recombinant antibody C5 developed by Adienne Pharma and Biotech. Mubodina® is described in U.S. Pat. No. 7,999,081.

In some embodiments, the C5 inhibitor is coversin. Coversin is a recombinant protein derived from a protein discovered in the saliva of the *Ornithodoros moubata* tick currently developed as a recombinant protein by Akari Therapeutics. Coversin is described in Penabad et al. Lupus 2012, 23(12):1324-6.

In some embodiments, the C5 inhibitor is Tesidolumab/LFG316. Tesidolumab is a monoclonal antibody developed by Novartis and Morphosys. Tesidolumab is described in U.S. Pat. Nos. 8,241,628 and 8,883,158.

In some embodiments, the C5 inhibitor is ARC-1905. ARC-1905 is a pegylated RNA aptamer developed by Ophthotech. ARC-1905 is described in Keefe et al. Nature Reviews Drug Discovery, 9:537-550.

In some embodiments, the C5 inhibitor is RA101348. RA101348 is a macrocyclic peptide developed by Ra Pharmaceuticals.

In some embodiments, the C5 inhibitor is RA101495. RA101495 is a macrocyclic peptide developed by Ra Pharmaceuticals.

In some embodiments, the C5 inhibitor is SOBI002. SOBI002 is an affibody developed by the Swedish Orphan Biovitrum.

In some embodiments, the C5 inhibitor is ARC1005. ARC1005 is an aptamer developed by Novo Nordisk.

In some embodiments, the C5 inhibitor is SOMAmers for C5. SOMAmers are aptamers developed by SomaLogic.

In some embodiments, the C5 inhibitor is SSL7. SSL7 is a bacterial protein toxin described in Laursen et al. Proc. Natl. Acad. Sci. U.S.A., 107(8):3681-6.

In some embodiments, the C5 inhibitor is MEDI7814. MEDI7814 is a monoclonal antibody developed by MedImmune.

In some embodiments, the C5 inhibitor is aurin tricarboxylic acid. In another embodiment, the C5 inhibitor is an aurin tricarboxylic acid derivative. These aurin derivatives were developed by Aurin Biotech and are further described in U.S. Patent Appl. Pub. No. 2013/003592).

In some embodiments, the C5 inhibitor is RG6107/SKY59. RG6107/SKY59 is an anti-C5 recycling antibody developed by Roche Pharmaceuticals.

In some embodiments, the C5 inhibitor is ALXN1210. In another embodiment, the C5 inhibitor is ALXN5500. ALXN1210 and ALXN5500 are monoclonal antibodies developed by Alexion Pharmaceuticals.

In some embodiments, the C5 inhibitor is TT30. TT30 is a fusion protein developed by Alexion Pharmaceuticals.

In some embodiments, the C5 inhibitor is ABP959. ABP959 is an eculizamab biosimilar monoclonal antibody developed by Amgen.

In some embodiments, the C5 inhibitor is Anti-C5 siRNA. Anti-C5 siRNA was developed by Alnylam Pharmaceuticals.

In some embodiments, the C5 inhibitor is Erdigna®. Erdigna® is an antibody developed by Adienne Pharma.

In some embodiments, the C5 inhibitor is avacincaptad pegol/Zimura®. Avacincaptad pegol is in aptamer developed by Opthotech.

In some embodiments, the C5 inhibitor is SOBI005. SOBI005 is a protein in developed by the Swedish Orphan Biovitrum.

In some embodiments, the C5 inhibitor is ISU305. ISU305 is a monoclonal antibody developed by ISU ABXIS.

In some embodiments, the C5 inhibitor is REGN3918. REGN3918 is a monoclonal antibody developed by Regeneron.

C3 Inhibitors

Provided herein are methods for treating PNH in a subject comprising administering to the subject an effective amount of a C3 inhibitor in combination or alternation with an effective amount of a CFD inhibitor selected from Formula I, Formula II, Formula III, Formula IV, Formula V, Formula VI, Formula VII, Formula VIII, or Formula IX.

C3 inhibitors are known in the art. In some embodiments, a compound of the present invention is administered in combination or alternation with compstatin and/or a compstatin analog. Compstatin and compastin analogs are known and are found to be useful inhibitors of C3, see U.S. Pat. Nos. 9,056,076; 8,168,584; 9,421,240; 9,291,622; 8,580,735; 9371365; 9,169,307; 8,946,145; 7,989,589; 7,888,323; 6,319,897; and US Patent Appl. Pub. Nos. 2016/0060297; 2016/0015810; 2016/0215022; 2016/0215020; 2016/0194359; 2014/0371133; 2014/0323407; 2014/0050739; 2013/0324482; and 2015/0158915. In some embodiments, the compstatin analog having the amino acid sequence ICVVQDWGHHCRT (SEQ. ID. NO. 1). In another embodiment, the C3 inhibitor is a compstatin analog. In some embodiments, the compstatin analog is 4(1MeW)/APL-1 of the sequence Ac-ICV(1-mW)QDWGAHRCT (SEQ. ID. NO. 2), wherein Ac is acetyl and 1-mW is 1-methyltryptophan. In another embodiment, the compstatin analog is Cp40/AMY-101, which has an amino acid sequence yICV(1mW)QDW-Sar-AHRC-mI (SEQ. ID. NO. 3), wherein y is D-tyrosine, 1mW is 1-methyltryptophan, Sar is sarcosine, and mI is N-methylisoleucine. In yet another embodiment, the compstatin analog is PEG-Cp40, having the amino acid sequence PEG-yICV(1mW)QDW-Sar-AHRC-mI (SEQ. ID. NO. 4), wherein PEG is polyethyleneglycol (40 kDa), y is D-tyrosine, 1mW is 1-methyltryptophan, Sar is sarcosine, and mI is N-methylisoleucine. In yet another embodiment, the compstatin analog is 4(1MeW)POT-4. 4(1MeW)POT-4 was developed by Potentia. In yet another embodiment, the compstatin analog is AMY-201. AMY-201 was developed by Amyndas Pharmaceuticals.

In some embodiments, a compound of the present invention can be combined with C3 inhibitors that include, but are not limited to: H17 (monoclonal antibody, EluSys Therapeutics, Pine Brook, NJ); mirococept (CR1-based protein); sCR1 (CR1-based protein, Celldex, Hampton, NJ); TT32 (CR-1 based protein, Alexion Pharmaceuticals, New Haven, CT); HC-1496 (recombinant peptide); CB 2782 (enzyme, Catalyst Biosciences, South San Francisco, CA); APL-2 (pegylated synthetic cyclic peptide, Apellis Pharmaceuticals, Crestwood, KY); or combinations thereof.

In some embodiments, the C3 inhibitor is H17. H17 is a humanized monoclonal antibody in development by EluSys Therapeutics. H17 is described in Paixao-Cavalcante et al. J. Immunol. 2014, 192(10):4844-4851.

In some embodiments, the C3 inhibitor is mirococept. Mirococept is a CR1-based protein developed by Inflazyme Pharmaceuticals.

In some embodiments, the C3 inhibitor is sCR1. sCR1 is a soluble form of the CR1 protein developed by Celldex.

In some embodiments, the C3 inhibitor is TT32. TT32 is a CR-1 based protein developed by Alexion Pharmaceuticals.

In some embodiments, the C3 inhibitor is HC-1496. HC-1496 is a recombinant peptide developed by InCode.

In some embodiments, the C3 inhibitor is CB 2782. CB 2782 is novel protease derived from human membrane type serine protease 1 (MTSP-1) that was developed by Catalyst Biosciences.

In some embodiments, the C3 inhibitor is APL-2. APL-2 is a pegylated version of APL-1 developed by Apellis Pharmaceuticals.

Complement Factor B (CFB) Inhibitors

Provided herein are methods for treating PNH comprising administering a CFB inhibitor in combination or alternation with a compound of the present invention. CFB inhibitors are known in the art. In some embodiments, a compound of the present invention can be combined with CFB inhibitors that include, but are not limited to: anti-FB SiRNA (Alnylam Pharmaceuticals, Cambridge, MA); TA106 (monoclonal antibody, Alexion Pharmaceuticals, New Haven, CT); LNP023 (small molecule, Novartis, Basel, Switzerland); SOMAmers (aptamers, SomaLogic, Boulder, CO); bikaciomab (Novelmed Therapeutics, Cleveland, OH); complin (see, Kadam et al., J. Immunol. 2010, DOI:10.409/jimmunol.10000200); (ligand conjugated antisense drug, Ionis Pharmaceuticals, Carlsbad, CA); or a combination thereof. In another embodiment, CFB inhibitors that can be combined with a compound of the present invention include those disclosed in PCT/US17/39557. In another embodiment, CFB inhibitors that can be combined with a compound of the present invention as described herein include those disclosed in PCT/US17/014458. In another embodiment, CFB inhibitors that can be combined with a compound of the present invention as described herein include those disclosed in U.S. Patent Appl. Pub. No. 2016/0024079; PCT Int Appl. WO 2013/192345; PCT Int. Appl. WO 2013/164802; PCT Int. Appl. WO 2015/066241; PCT Int. Appl. WO 2015/009616 (assigned to Novartis AG).

In some embodiments, the CFB inhibitor is

In another embodiment, the CFB inhibitor is

In another embodiment, the CFB inhibitor is

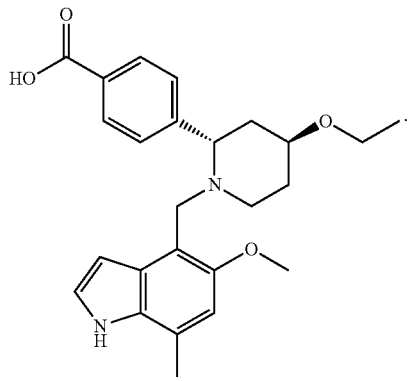 [SMILES: CCO[C@H]1CCN(Cc2c(OC)cc(C)c3[nH]ccc23)[C@H](c2ccc(C(=O)O)cc2)C1]

In some embodiments, the CFB inhibitor is anti-FB siRNA. Anti-FB siRNA was developed by Alnylam Pharmaceuticals.

In some embodiments, the CFB inhibitor is TA106. TA106 is a monoclonal antibody developed by Alexion Pharmaceuticals.

In some embodiments, the CFB inhibitor is LNP023. LNP023 is a small molecule inhibitor of CFB developed by Novartis.

In some embodiments, the CFB inhibitor is complin. Complin is a peptide inhibitor that is described in Kadam et al. J. Immunol. 2010 184(12):7116-24.

In some embodiments, the CFB inhibitor is Ionis-FB-$L_{Rx}$. Ionis-FB-$L_{Rx}$ is a ligand conjugated antisense drug developed by Ionis Pharmaceuticals.

Pan-Inhibitors of Complement Components

Provided herein are methods for treating PNH comprising administering a pan-inhibitor of complement components in combination or alternation with a compound of the present invention. Pan-inhibitors of complement components are known in the art. In some embodiments, the inhibitor is FUT-175.

Combinations for Prophylactic or Concomitant Anti-Bacterial Therapy

In one aspect of the present invention, a method is provided for treating a host in need thereof that comprises administering an effective amount of a prophylactic anti-bacterial vaccine prior to administration of an active compound or its salt or composition for any of the disorders described herein. In another aspect of the present invention, a method is provided for treating a host in need thereof that comprises administering an effective amount of a prophylactic anti-bacterial drug, such as a pharmaceutical drug, prior to administration of an active compound or its salt or composition for any of the disorders described herein. In one aspect of the present invention, a method is provided for treating a host in need thereof that comprises administering an effective amount of an anti-bacterial vaccine after administration of an active compound or its salt or composition for any of the disorders described herein. In another aspect of the present invention, a method is provided for treating a host in need thereof that comprises administering an effective amount of an anti-bacterial drug, such as a pharmaceutical drug, after administration of an active compound or its salt or composition for any of the disorders described herein. In one embodiment, the disorder is PNH, C3G, or aHUS. In one embodiment, the host has received an organ or other tissue or biological fluid transplant. In one embodiment, the host is also administered eculizumab.

In one aspect of the present invention, an active compound or its salt or composition as described herein is administered to a host concomitantly to a subject following the prophylactic administration of a vaccine against a bacterial infection. In one embodiment, the complement mediated disorder is PNH, C3G or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject concomitantly with the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject and, during the administration period of the compound or salt, a vaccine against a bacterial infection is administered to the subject. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, the subject is administered an active compound or its salt or composition as described herein in combination with an antibiotic compound for the duration of Factor D inhibitor administration. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject following the prophylactic administration of a vaccine against a bacterial infection, and in combination with an antibiotic compound for the duration of Factor D inhibitor administration. In one embodiment, the complement mediated disorder is PNH or aHUS. In one embodiment, the subject has received an organ or other tissue or biological fluid transplant. In one embodiment, the subject is also administered eculizumab. In one embodiment, the subject, prior to receiving an active compound or its salt or composition as described herein, is vaccinated against a bacterial infection caused by the bacterium *Neisseria meningitidis*. In one embodiment, the subject is vaccinated against a bacterial infection caused by the bacterium *Haemophilus influenzae*. In one embodiment, the *Haemophilus influenzae* is *Haemophilus influenzae* serotype B (Hib). In one embodiment, the subject is vaccinated against a bacterial infection caused by *Streptococcus pneumoniae*. In one embodiment, the subject is vaccinated against a bacterial infection caused by the bacterium *Nisseria meningitidis, Haemophilus influenzae*, or *Streptococcus pneumoniae*, or a combination of one or more of *Nisseria meningitidis, Haemophilus influenzae*, or *Streptococcus pneumoniae*. In one embodiment, the subject is vaccinated against a bacterial infection caused by the bacterium *Nisseria meningitidis, Haemophilus influenzae*, and *Streptococcus pneumoniae*.

In other embodiments, the subject is vaccinated against a bacterial infection caused by a bacterium selected from a Gram-negative bacterium. In one embodiment, the subject is vaccinated against a bacterial infection caused by a bacterium selected from a Gram-positive bacterium. In one embodiment, the subject is vaccinated against a bacterial infection caused by the bacterium *Nisseria meningitidis, Haemophilus influenzae*, or *Streptococcus pneunemoniae*, or a combination of one or more of *Nisseria meningitidis, Haemophilus influenzae*, or *Streptococcus pneumoniae*, and one or more of, but not limited to, *Bacillus anthracis, Bordetella pertussis, Clostridium tetani, Corynebacterium diphtheria, Coxiella burnetii, Mycobacterium tuberculosis, Salmonella typhi, Vibrio cholerae, Anaplasma phagocytophilum, Ehrlichia ewingii, Ehrlichia chaffeensis, Ehrlichia canis, Neorickettsia sennetsu, Mycobacterium leprae, Borrelia burgdorferi, Borrelia mayonii, Borrelia afzelii, Borrelia garinii, Mycobacterium bovis, Staphylococcus aureus, Streptococcus pyogenes, Treponema pallidum, Francisella tularensis, Yersinia pestis,*

In one embodiment, the subject is vaccinated with one or more vaccines selected from, but not limited to, typhoid vaccine, live (Vivotif Berna Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (prevnar 13, Pfizer), *Haemophilus* b conjugate (prp-t) vaccine (ActHIB, Sanofi; Hibrix, GSK), *Haemophilus* b conjugate (hboc) vaccine (HibTITER, Neuron Biotech), *Haemophilus* b conjugate (prp-omp) vaccine (PedvaxHIB, Merck), *Haemophilus* b conjugate (prp-t) vaccine/meningococcal conjugate vaccine (MenHibrix, GSK), *Haemophilus* b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal Berna, Hendricks Regional Health), *Bacillus* Calmette and Guérin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/polio (Kinrix, GSK; Quadracel, Sanofi), diphtheria and tetanus toxois and pertussis tetanus/hepatitis B/polio (Pediarix, GSK), diphtheria and tetanus toxois and pertussis/polio, *Haemophilus* influenza tybe b (Pentacel, Sanofi), and/or diphtheria, and pertussis (Tdap; Boostrix, GSK; Adacel, Sanofi), or a combination thereof.

As described above, a subject receiving a compound of the present invention to treat a disorder is prophylactically administered an antibiotic compound in addition to a Factor D inhibitor described herein. In one embodiment, the subject is administered an antibiotic compound for the duration of administration of the active compound to reduce the development of a bacterial infection. Antibiotic compounds for concomitant administration with a Factor D inhibitor described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Sumamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen), azlocillin, carbenicillin (Geocillin), cloxacillin (Tegopen), dicloxacillin (Dynapen), flucloxacillin (Cloxapen), mezlocillin (Mezlin), methicillin (Staphcillin), nafcillin (Unipen), oxacillin (Prostaphlin), penicillin G (Pentids), penicillin V (Veetids (Pen-Vee-K), piperacillin (Pipracil), penicillin G (Pfizerpen), temocillin (Negaban), ticarcillin (Ticar), amoxicillin/clavulanate (Augmentin), ampicillin/sulbactam (Unasyn), piperacillin/tazobactam (Zosyn), ticarcillin/clavulanate (Timentin), bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (NegGram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (Micro-Sulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole (Co-trimoxazole) (TMP-SMX) (Bactrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the subject is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenetn, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

Process of Preparation of Compounds of the Present Invention

Abbreviations

ACN Acetonitrile
Ac Acetyl
$Ac_2O$ Acetic anhydride
AcOEt, EtOAc ethyl acetate
AcOH Acetic acid
$Boc_2O$ di-tert-butyl dicarbonate
Bu Butyl
CAN Ceric ammonium nitrate
CBz Carboxybenzyl
CDI Carbonyldiimidazole
$CH_3OH$, MeOH Methanol
CsF Cesium fluoride
CuI Cuprous iodide
DCM, $CH_2Cl_2$ Dichloromethane
DIEA, DIPEA N,N-diisopropylethylamine
DMA N,N-dimethylacetamide
DMAP 4-Dimethylaminopyridine
DMF N,N-dimethylformamide
DMS Dimethyl sulfide
DMSO Dimethylsulfoxide
DPPA Diphenyl phosphoryl azide
EDCI 1-Ethyl-3-(3-dimethylaminopropyl)carbodiimide
EEDQ N-Ethoxycarbonyl-2-ethoxy-1,2-dihydroquinoline
Et Ethyl
$Et_3N$, TEA Triethylamine
EtOAc Ethylacetate
EtOH Ethanol
HATU 1-[Bis(dimethylamino)methylene]-1H-1,2,3-triazolo[4,5-b]pyridinium3-oxide hexafluorophosphate
HCl Hydrochloric acid
HOBT Hydroxybenzotriazole
iBu, i-Bu, isoBu Isobutyl
iPr, i-Pr, isoPr Isopropyl
$^iPr_2NEt$ N,N-diisopropylethylamine
$K_2CO_3$ Potassium carbonate
$K_2CO_3$ Potassium carbonate
LiOH Lithium hydroxide
Me Methyl
MeI Methyl iodide
Ms Mesyl
MSCl Mesylchloride
MTBE Methyl $^t$butylether
$Na_2SO_4$ Sodium sulfate
NaCl Sodium chloride
NaH Sodium hydride
$NaHCO_3$ Sodium bicarbonate
NBS N-bromo succinimide
NCS N-chloro succinimide
$NEt_3$ Trimethylamine
NMP N-Methyl-2-pyrrolidone
PCC Pyridinium chlorochromate
$Pd(OAc)_2$ Palladium acetate
$Pd(dppf)Cl_2$ [1,1'-Bis(diphenylphosphino) ferrocene]dichloropalladium(II)
$Pd(PPh_3)_2Cl_2$ Bis(triphenylphosphine)palladium(II) dichloride
$Pd(PPh_3)_4$ Tetrakis(triphenylphosphine)palladium(0)
Pd/C Palladium on carbon
$Pd_2(dba)_3$ Tris(dibenzylideneacetone)dipalladium(0)

PMB 4-Methoxybenzyl ether
PPh$_3$ Triphenylphosphine
Pr Propyl
Py, py Pyridine
RT Room temperature
T3P Propane phosphonic acid anhydride
TBAF Tetra-n-butylammonium fluoride
TBAT Tetrabutylammonium difluorotriphenylsilicate
tBu, t-Bu tertbutyl
tBuOK Potassium tert-butoxide
TEA Trimethylamine
Tf$_2$O Trifluoromethanesulfonic anhydride
TFA Trifluoroacetic acid
THF Tetrahydrofuran
TMS Trimethylsilane
TMSBr Bromotrimethylsilane
t$_R$ Retention time
Troc 2,2,2-Trichlorethoxycarbonyl chloride
Zn(CN)$_2$ Zinc cyanide General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

LC Method A
  Instrument: Waters Acquity Ultra Performance LC
  Column: ACQUITY UPLC BEH C18 2.1×50 mm, 1.7 μm
  Column Temperature: 40° C.
  Mobile Phase: Solvent A: H$_2$O+0.05% FA; Solvent B: CH$_3$CN+0.05% FA
  Flow Rate: 0.8 mL/min
  Gradient: 0.24 min@15% B, 3.26 min gradient (15-85% B then 0.5 min@85% B.
  Detection: UV (PDA), ELS, and MS (SQ in EI mode)

LC Method B
  Instrument: Shimadzu LC-2010A HT
  Column: Athena, C18-WP, 50×4.6 mm, 5 μm
  Column Temperature: 40° C.
  Mobile Phase: Solvent A: H$_2$O/CH$_3$OH/FA 90/10/0.1; Solvent B: H$_2$O/CH$_3$OH/FA=10/90/0.1
  Flow Rate: 3 mL/min
  Gradient: 0.4 min@30% B, 3.4 min gradient (30-100% B), then 0.8 min@100% B
  Detection: UV (220/254 nm)

LC Method C
  Instrument: Agilent 1100/1200 series LC system with DAD detector
  Column: Atlantis dC18 (250×4.6) mm, 5 μm
  Column Temperature: Ambient
  Mobile Phase A: 0.1% TFA in water, Mobile Phase B: Acetonitrile
  Flow Rate: 1.0 mL/min
  Gradient:

| Time (min) | 0.0 | 15 | 20 | 23 | 30 |
|---|---|---|---|---|---|
| % B | 10 | 100 | 100 | 10 | 10 |

Detection: (210-400 nm)

LC Method D
  Instrument: Shimadzu LC 20AD system with PDA detector
  Column: Phenomenex Gemini NX C18 (150×4.6) mm, 5 μm
  Column Temperature: Ambient
  Mobile Phase A: 10 mM NH$_4$OAC in water, Mobile Phase B: Acetonitrile
  Flow Rate: 1.0 mL/min
  Gradient:

| Time (min) | 0.0 | 15 | 20 | 23 | 30 |
|---|---|---|---|---|---|
| % B | 10 | 100 | 100 | 10 | 10 |

Detection: (210-400 nm)

Example 1. Non-Limiting Synthetic Examples of Compounds of the Present Invention The below schemes are non-limiting examples of methods to make compounds of the present invention. The skilled artisan will recognize that there are various modifications that can be performed to make analogs or prepare compounds in other ways. For example, wherever a Suzuki coupling is used there are other methods known in the art to conduct the coupling such as those described in the literature (Molander, G. A., Trice, S. L. J., & Kennedy, S. M. (2012). Scope of the two-step, one-pot palladium-catalyzed borylation/Suzuki cross-coupling reaction utilizing bis-boronic acid. *Journal of Organic Chemistry*, 77(19), 8678-8688.)

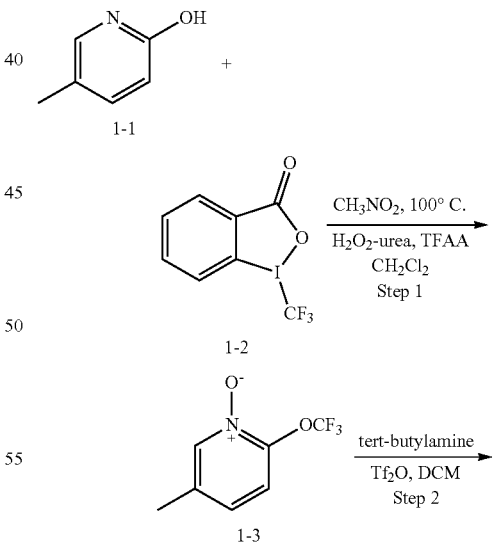

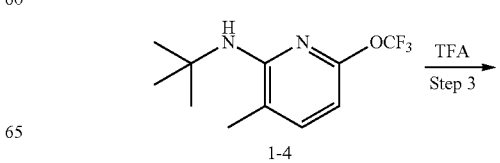

-continued

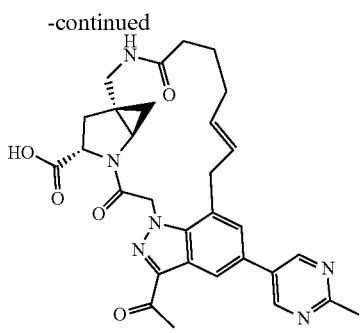

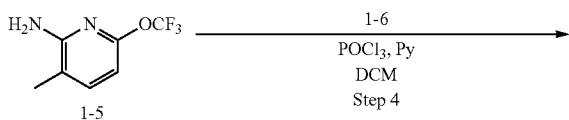

Step 1: 5-Methyl-2-(trifluoromethoxy)pyridine 1-oxide (1-3)

A mixture of 5-methylpyridin-2-ol (1.0 g, 3.16 mmol) and Togni's reagent (1.03 g, 9.48 mmol) in CH₃NO₂ (20 mL) was stirred at 100° C. in presence of air for 16 hours. The mixture was diluted with water and extracted with DCM once. The organic layers were dried over Na₂SO₄ and to the crude solution was added hydrogen peroxide urea complex (1.38 g, 14.68 mmol) followed by the drop-wise addition of TFAA (3.4 mL) at 0° C. The resulting mixture was stirred at room temperature for 16 hours. The mixture was diluted with DCM, washed with water and saturated aqueous sodium metabisulfite solution, dried over anhydrous Na₂SO₄, filtered and concentrated to dryness. The residue was purified by column chromatography on silica gel (eluted with DCM:MeOH=100:1) to afford compound 1-3 (340 mg, yield 55.8%) as a yellow solid. LC/MS (ESI) m/z: 194 (M+H)⁺.

Step 2: N-(tert-Butyl)-3-methyl-6-(trifluoromethoxy)pyridin-2-amine (1-4)

To a solution of compound 1-3 (340 mg, 1.76 mmol) in DCM (5 mL) was added tert-butylamine (450 mg, 6.17 mmoL) followed by the drop-wise addition of trifluoromethanesulfonic anhydride (1.04 g, 3.7 mmol) at −20° C. The mixture was stirred at −20° C. under N₂ atmosphere for 1 hour. The mixture was quenched with ice-water and extracted with DCM twice. The combined organic layers were washed with aqueous K₂CO₃ solution, dried with anhydrous Na₂SO₄, filtered and concentrated to dryness. The residue was purified by chromatography on silica gel (eluted with PE:EtOAc=15:1) to afford compound 1-4 (120 mg, yield 27.5%) as a light yellow oil. LC/MS (ESI) m/z: 249 (M+H)⁺.

Step 3: 3-Methyl-6-(trifluoromethoxy)pyridin-2-amine (2-5)

A solution of compound 1-4 (120 mg, 0.48 mmol) in TFA (7 mL) was stirred at 70° C. for 8 hours. The reaction mixture was concentrated to dryness and the residue was poured into ice-cooled saturated aqueous NaHCO₃ solution. The mixture was extracted with DCM twice and the combined organic layers were washed with brine, dried over anhydrous Na₂SO₄, filtered and concentrated to dryness. The residue was purified by column chromatography on silica gel (eluted with PE:EtOAc=20:1 to 15:1) to afford compound 1-5 (50 mg, yield 53.8%) as a white solid. LC/MS (ESI) m/z: 193 (M+H)⁺.

Step 4: Compound 1-7

To a mixture of compound 1-5 (7 mg, 0.036 mmol) and compound 1-6 (20 mg, 0.036 mmol) in DCM (3 mL) was added pyridine (23 mg, 0.29 mmol) and phosphoryl chloride (11 mg, 0.072 mmol) at 0° C. The mixture was stirred at room temperature for 30 minutes. The reaction mixture was quenched with ice water, extracted with DCM, dried and concentrated to dryness. The residue was purified by column chromatography on silica gel (eluted with DCM:MeOH=40: 1) to afford compound 1-7 (26 mg, yield 98.9%) as a light yellow solid. LC/MS (ESI) m/z: 731 (M+H)⁺.

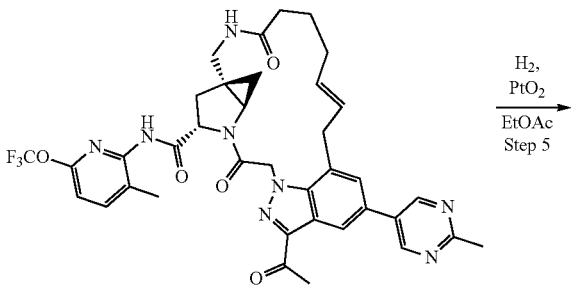

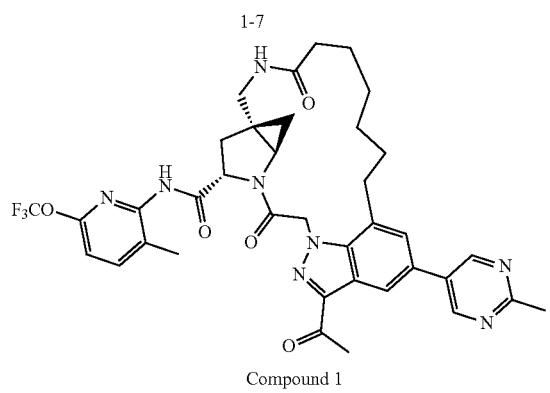
Compound 1

Step 5: Compound 1

To a solution of compound 1-7 (21 mg, 0.029 mmol) in EtOAc (3 mL) was added PtO₂ (7 mg) at 0° C. and the mixture was degassed under N₂ atmosphere three times. The mixture was stirred under a H₂ balloon at room temperature for 2 hours. The mixture was filtered and the filtrate was concentrated to dryness. The residue was purified by preparative HPLC to afford Compound 1 (3 mg, yield 14.2%) as a white solid. ¹H-NMR (400 MHz, CD₃OD) δ 8.99 (s, 2H), 8.42 (d, J=1.6 Hz, 1H), 7.73 (d, J=8.2 Hz, 1H), 7.52 (s, 1H), 6.94 (d, J=8.1 Hz, 1H), 5.95 (d, J=17.8 Hz, 1H), 5.65 (d, J=17.9 Hz, 1H), 4.62 (s, 1H), 4.47 (s, 1H), 3.67-3.64 (m, 1H), 3.51-3.46 (m, 1H), 3.19-3.12 (m, 1H), 2.96-2.90 (m, 1H), 2.74 (s, 3H), 2.68 (s, 3H), 2.63-2.54 (m, 2H), 2.42-2.34 (m, 1H), 2.32-2.26 (m, 1H), 2.05 (s, 3H), 1.87-1.50 (m, 8H), 1.45-1.37 (m, 1H), 1.18-1.13 (m, 1H). LC/MS (ESI) m/z: 733 (M+H)⁺.

Scheme 2. Synthesis of Compound 2

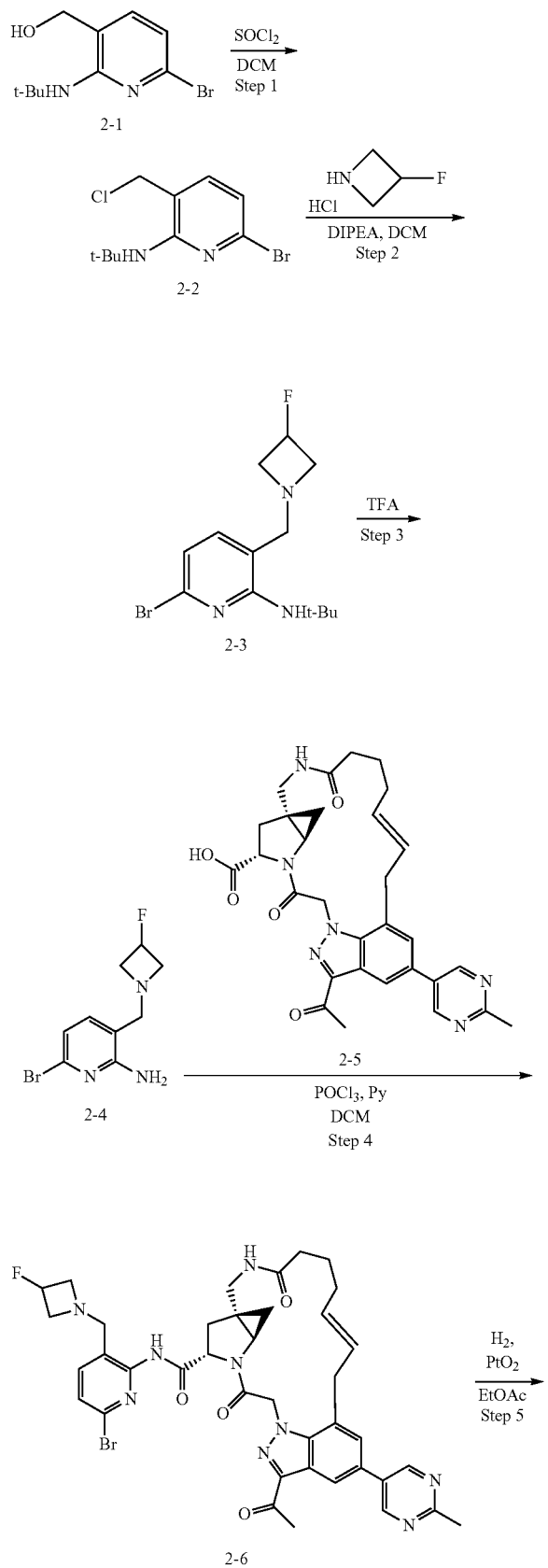

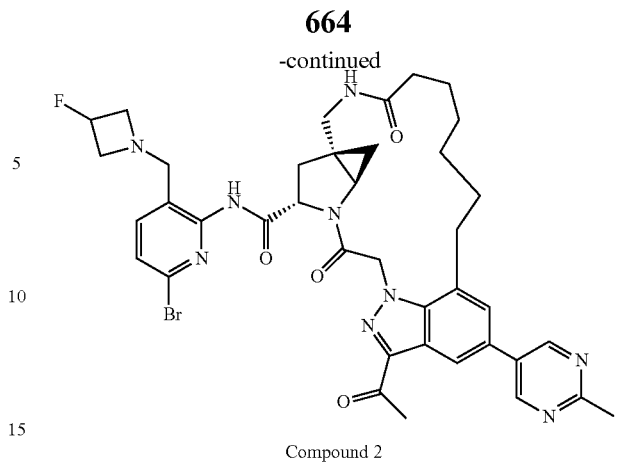

Compound 2

Step 1: 6-Bromo-N-(tert-butyl)-3-(chloromethyl)pyridin-2-amine (2-2)

A solution of compound 2-1 (340 mg, 1.31 mmol) in DCM (6 mL) was added $SOCl_2$ (1 mL) dropwisely at 0° C. and the mixture was stirred at 0° C. to room temperature for 2 hours. The reaction mixture was concentrated to dryness, washed with diethyl ether and dried under vacuum to afford compound 2-2 (360 mg, yield 98.9%) as a yellow solid that was used directly in the next step. LC/MS (ESI) m/z: 277/279 (M+H)$^+$.

Step 2: 6-Bromo-N-(tert-butyl)-3-((3-fluoroazetidin-1-yl)methyl)pyridin-2-amine (2-3)

To a mixture of 3-fluoroazetidine hydrochloride (434 mg, 3.89 mmol) and compound 2-2 (360 mg, 1.30 mmol) in DCM (8 mL) was added DIPEA (838 mg, 6.48 mmol) at 0° C. and the mixture was stirred at room temperature for 1 hour. The mixture was diluted with DCM, washed with brine, dried over anhydrous $Na_2SO_4$, filtered and concentrated to dryness. The residue was purified by chromatography on silica gel (eluted with PE:EtOAc=150:1) to afford compound 2-3 (260 mg, yield 63.4%) as a light yellow oil. LC/MS (ESI) m/z: 316/318 (M+H)$^+$.

Step 3: 6-Bromo-3-((3-fluoroazetidin-1-yl)methyl)pyridin-2-amine (2-4)

A solution of compound 2-3 (260 mg, 0.82 mmol) in TFA (6 mL) was stirred at 70° C. for 1 hour. The reaction mixture was concentrated to dryness and the residue was neutralized with ice-cooled 5% aqueous $NaHCO_3$ solution. The mixture was extracted with DCM twice and the combined organic layers were washed with brine, dried over anhydrous $Na_2SO_4$, filtered and concentrated to dryness. The residue was purified by chromatography on silica gel (eluted with PE:EtOAc=5:1) to afford compound 2-4 (168 mg, yield 78.6%) as a white solid. LC/MS (ESI) m/z: 260/262 (M+H)$^+$.

Step 4: Compound 2-5

To a mixture of compound 2-4 (12 mg, 0.05 mmol) and compound 5 (25 mg, 0.05 mmol) in DCM (3 mL) was added pyridine (18 mg, 0.23 mmol) followed by $POCl_3$ (8 mg, 0.05 mmol) at 0° C. and the mixture was stirred at room temperature under $N_2$ atmosphere for 1 hour. The mixture was poured into ice-water and extracted with DCM twice. The combined organic layers were washed with brine, dried with anhydrous $Na_2SO_4$, filtered and concentrated to dryness. The residue was purified by chromatography on silica gel (eluted with DCM:MeOH=100:1 to 30:1) to afford compound 2-5 (21 mg, yield 58.5%) as a white solid. LC/MS (ESI) m/z: 798/800 (M+H)⁺.

Step 5: Compound 2

To a solution of compound 2-5 (21 mg, 0.026 mmol) in EtOAc (5 mL) was added $PtO_2$ (6 mg) at 0° C. and the mixture was degassed under $N_2$ atmosphere for three times and stirred under a $H_2$ balloon at room temperature for 1 hour. The mixture was filtered and the filtrate was concentrated to dryness. The residue was purified by preparative HPLC to afford Compound 2 (3 mg, yield 14.3%) as a white solid. ¹H-NMR (400 MHz, $CD_3OD$) δ 8.95 (s, 2H), 8.41 (d, J=1.6 Hz, 1H), 7.58 (d, J=8.0 Hz, 1H), 7.51 (d, J=2.0 Hz, 1H), 7.37 (d, J=8.0 Hz, 1H), 5.95 (d, J=17.6 Hz, 1H), 5.66 (d, J=17.6 Hz, 1H), 4.54-4.44 (m, 1H) 3.62 (dd, J=6.0, 6.0 Hz, 1H), 3.51 (d, J=14.4 Hz, 1H), 3.35 (dd, J=14.0, 14.0 Hz, 5H), 3.16-3.09 (m, 1H), 2.99 (s, 1H), 2.90-2.81 (m, 2H), 2.74 (s, 3H), 2.69 (s, 3H), 2.59 (d, J=4.8 Hz, 2H), 2.42-2.28 (m, 2H), 1.88-1.51 (m, 8H), 1.42 (t, J=6.0 Hz, 2H), 1.18 (dd, J=6.0, 6.0 Hz, 1H), LC/MS (ESI) m/z: 800/802 (M+H)⁺.

Scheme 3. Synthesis of Compound 3

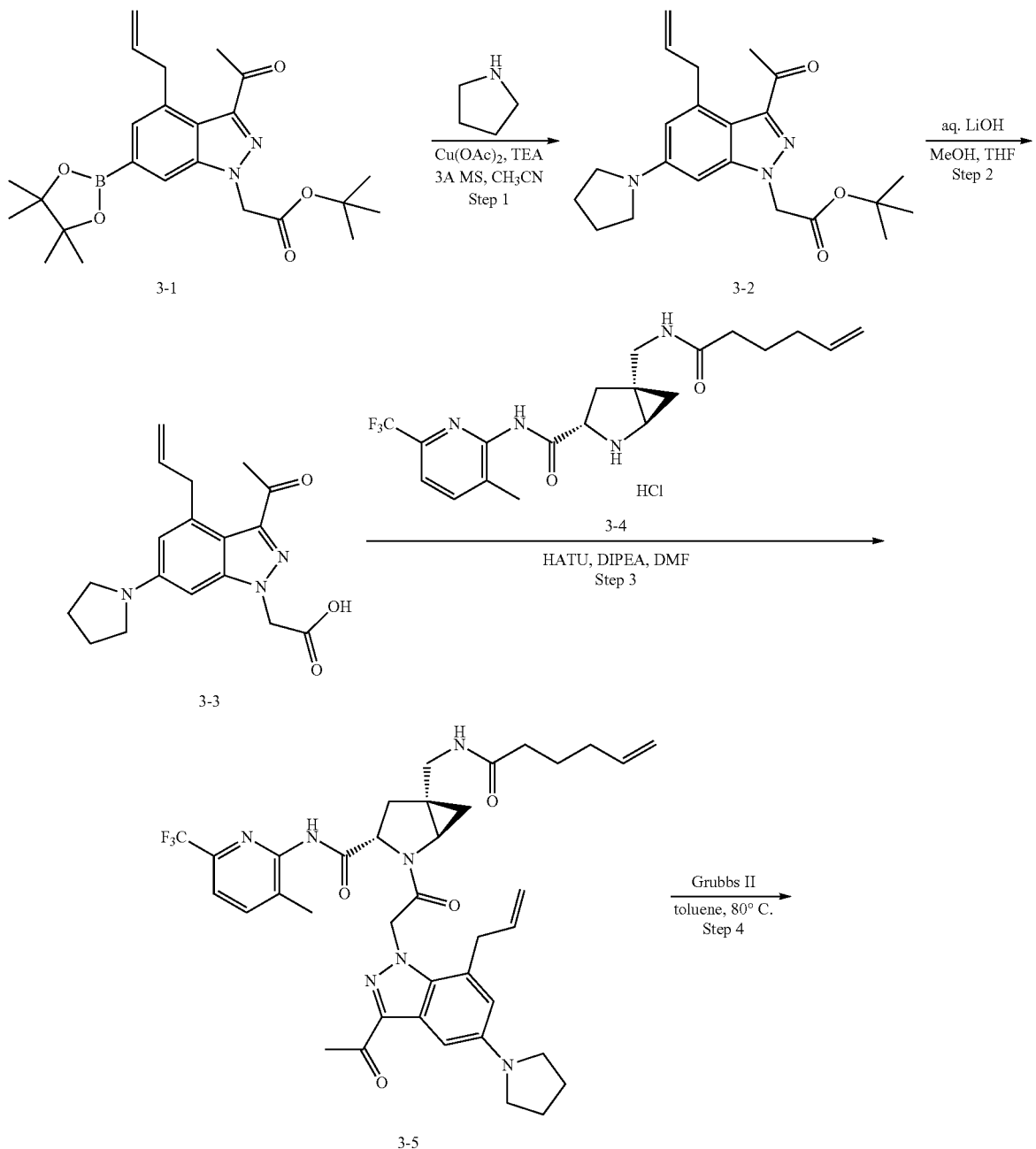

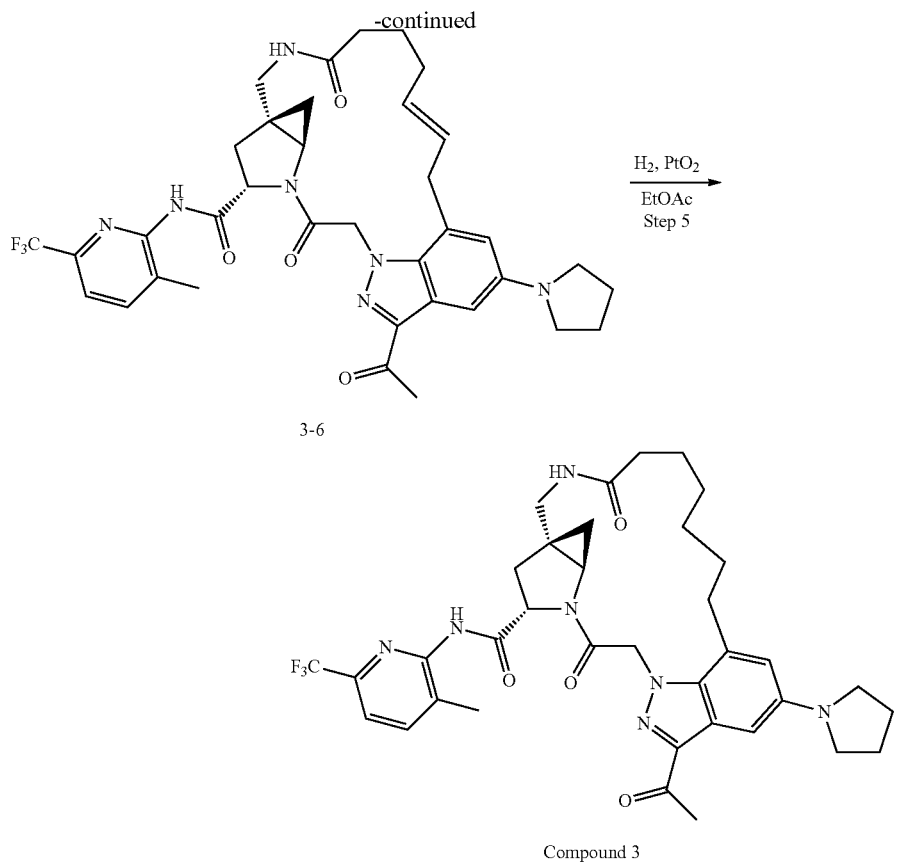

Compound 3

Step 1: tert-Butyl 2-[3-acetyl-4-(prop-2-en-1-yl)-6-(pyrrolidin-1-yl)indazol-1-yl]acetate (3-2)

To a mixture of compound 3-1 (40 mg, 0.09 mmol) and pyrrolidine (10 mg, 0.18 mmol) in MeCN (1 mL) was added TEA (20 mg, 0.18 mmol), Cu(OAc)$_2$ (20 mg, 0.09 mmol) and 3 Å molecular sieve (10 mg) and the mixture was stirred under O$_2$ atmosphere at 80° C. for 24 hours. The reaction mixture was diluted with EtOAc and filtered and the filtrate was concentrated to dryness. The residue was purified by silica gel chromatography (eluted with PE:EtOAc=3:1) to afford compound 3-2 (30 mg, yield 74.6%) as a yellow oil. LC/MS (ESI) m/z: 384 (M+H)$^+$.

Step 2: [3-Acetyl-4-(prop-2-en-1-yl)-6-(pyrrolidin-1-yl)indazol-1-yl]acetic acid (3-3)

To a solution of compound 3-2 (26 mg, 0.07 mmol) in THF (2 mL) and MeOH (1 mL) was added a solution of LiOH (6 mg, 0.14 mmol) in water (1 mL) and the mixture was stirred at room temperature for 2 hours. The mixture was concentrated to dryness and the residue was diluted with water and washed with ether twice. The aqueous layer was acidified with 1N aqueous HCl to a pH of approximately 3 and the mixture was extracted with DCM twice. The combined organic layers were washed with brine, dried over anhydrous Na$_2$SO$_4$, filtered and concentrated to dryness to afford compound 3-3 (20 mg, yield 90.1%) as a colorless oil. LC/MS (ESI) m/z: 328 (M+H)$^+$.

Step 3: (1R,3S,5R)-2-{2-[3-Acetyl-7-(prop-2-en-1-yl)-5-(pyrrolidin-1-yl)indazol-1-yl]acetyl}-5-(hex-5-enamidomethyl)-N-[3-methyl-6-(trifluoromethyl)pyridin-2-yl]-2-azabicyclo[3.1.0]hexane-3-carboxamide (3-5)

To a mixture of compound 3-3 (44 mg, 0.13 mmol) and (1R,3S,5R)-5-(hex-5-enamidomethyl)-N-(3-methyl-6-(trifluoromethyl)pyridin-2-yl)-2-azabicyclo[3.1.0]hexane-3-carboxamide hydrochloride (58 mg, 0.13 mm in DMF (2 mL) was added HATU (102 mg, 0.27 mmol) and DIPEA (52 mg, 0.40 mmol) at 0° C. and the resulting mixture was stirred at room temperature for 4 hours. The mixture was diluted with EtOAc and washed with saturated aqueous NH$_4$Cl solution and brine, dried over anhydrous Na$_2$SO$_4$, filtered and concentrated to dryness. The residue was purified by silica gel chromatography (eluted with PE:EtOAc=10:1 to 3:1) to afford compound 3-5 (36 mg, yield 37.2%) as a white solid. LC/MS (ESI) m/z: 720 (M+H)$^+$.

Step 4: Compound 3-6

To a solution of compound 3-5 (36 mg, 0.05 mmol) in degassed toluene (25 mL) was added Grubbs 2$^{nd}$ catalyst (8 mg, 0.01 mmol) and the reaction mixture was stirred at 80° C. under N$_2$ for 16 hours. The mixture was concentrated to dryness and the residue was purified by silica gel column chromatography (eluted with PE:EtOAc=5:1 to 2:1) to afford compound 3-6 (32 mg, yield 92.5%) as a brown solid. LC/MS (ESI) m/z: 691 (M+H)$^+$.

Step 5: Compound 3

To a solution of compound 3-6 (32 mg, 0.05 mmol) in EtOAc (3 mL) was added PtO$_2$ (53 mg, 0.03 mmol) and the reaction mixture was stirred under a H$_2$ balloon at room temperature for 0.5 hour. The mixture was filtered and the filtrate was concentrated to dryness. The residue was purified by preparative HPLC to afford Compound 3 (2 mg, yield 6.2%) as a white solid. $^1$H-NMR (400 MHz, CD$_3$OD) δ 7.82 (d, J=7.8 Hz, 1H), 7.56 (d, J=7.8 Hz, 1H), 7.14 (d, J=2.0 Hz, 1H), 6.69 (s, 1H), 5.82 (d, J=17.7 Hz, 1H), 5.52 (d, J=17.9 Hz, 1H), 4.53 (d, J=7.0 Hz, 1H), 3.60 (m, 1H), 3.47 (m, 1H), 3.35 (m, 1H), 3.05-2.97 (m, 1H), 2.71 (m, 1H), 2.62 (s, 3H), 2.59 (m, 2H), 2.39-2.15 (m, 4H), 2.15 (s, 3H), 2.03 (m, 4H), 1.66 (m, 8H), 1.42-1.37 (m, 2H), 1.15 (m, 1H), 0.89 (m, 1H). LC/MS (ESI) m/z: 694 (M+H)$^+$.

Scheme 4. Synthesis of Compound 4

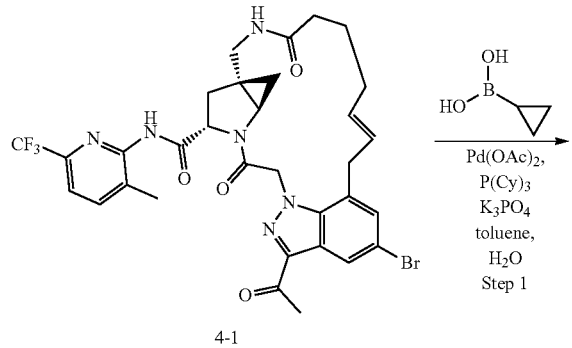

4-1

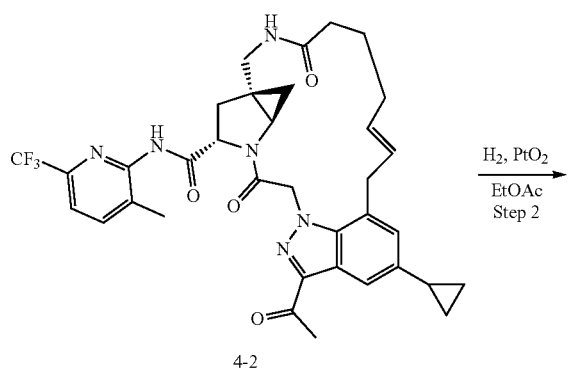

4-2

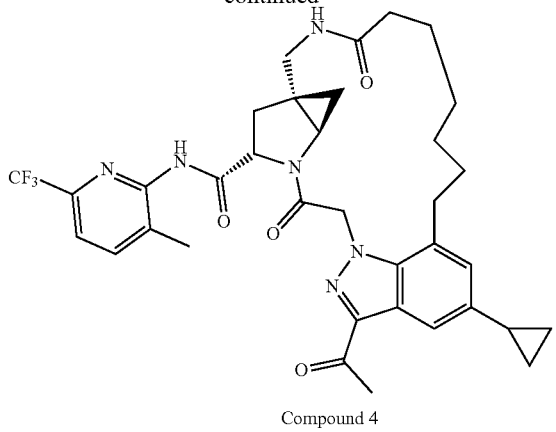

Compound 4

Step 1: Compound 4-2

To a mixture of cyclopropylboronic acid (4 mg, 0.051 mmol) and compound 4-1 (30 mg, 0.043 mmol) in toluene (4 mL) and water (1 mL) was added K$_3$PO$_4$ (23 mg, 0.11 mmol), tricyclohexyl phosphine (2 mg, 0.009 mmol) and Pd(OAc)$_2$ (4 mg, 0.004 mmol). The mixture was degassed under N$_2$ atmosphere three times and stirred at 90° C. under N$_2$ atmosphere for 16 hours. The mixture was diluted with EtOAc and washed with water and brine, dried over anhydrous Na$_2$SO$_4$, filtered and concentrated to dryness. The residue was purified by silica gel chromatography (eluted with DCM:MeOH=30:1) to afford compound 4-2 (28 mg, yield 98.8%) as a yellow solid. LC/MS (ESI) m/z: 663 (M+H)$^+$.

Step 2: Compound 4

To a solution of compound 4-2 (28 mg, 0.042 mmol) in EtOAc (5 mL) was added PtO$_2$ (5 mg) and the mixture was degassed under N$_2$ atmosphere three times and stirred under a H$_2$ balloon at room temperature for 1 hour. The mixture was filtered and the filtrate was concentrated to dryness. The residue product was purified by preparative HPLC to afford Compound 4 (7 mg, yield 24.3%) as a white solid. $^1$H-NMR (400 MHz, DMSO-d$_6$) δ 10.45 (s, 1H), 8.18 (dd, J=8.3, 3.5 Hz, 1H), 7.90 (d, J=7.7 Hz, 1H), 7.72 (s, 1H), 7.65 (d, J=7.7 Hz, 1H), 6.92 (s, 1H), 5.81 (d, J=17.8 Hz, 1H), 5.41 (d, J=17.8 Hz, 1H), 4.32 (m, 1H), 3.54 (m, 1H), 3.28 (d, J=8.9 Hz, 1H), 3.17 (m, 1H), 3.05-2.96 (m, 1H), 2.72 (m, 1H), 2.57 (s, 3H), 2.47-2.40 (m, 2H), 2.20-2.11 (m, 2H), 2.09 (s 3H), 2.06-2.00 (m, 1H), 1.77-1.21 (m, 10H), 1.18 (m, 1H), 1.07 (m, 1H), 0.98-0.91 (m, 2H), 0.69-0.63 (m, 2H). LC/MS (ESI) m/z: 665 (M+H)$^+$.

Scheme 5. Synthesis of Compound 5
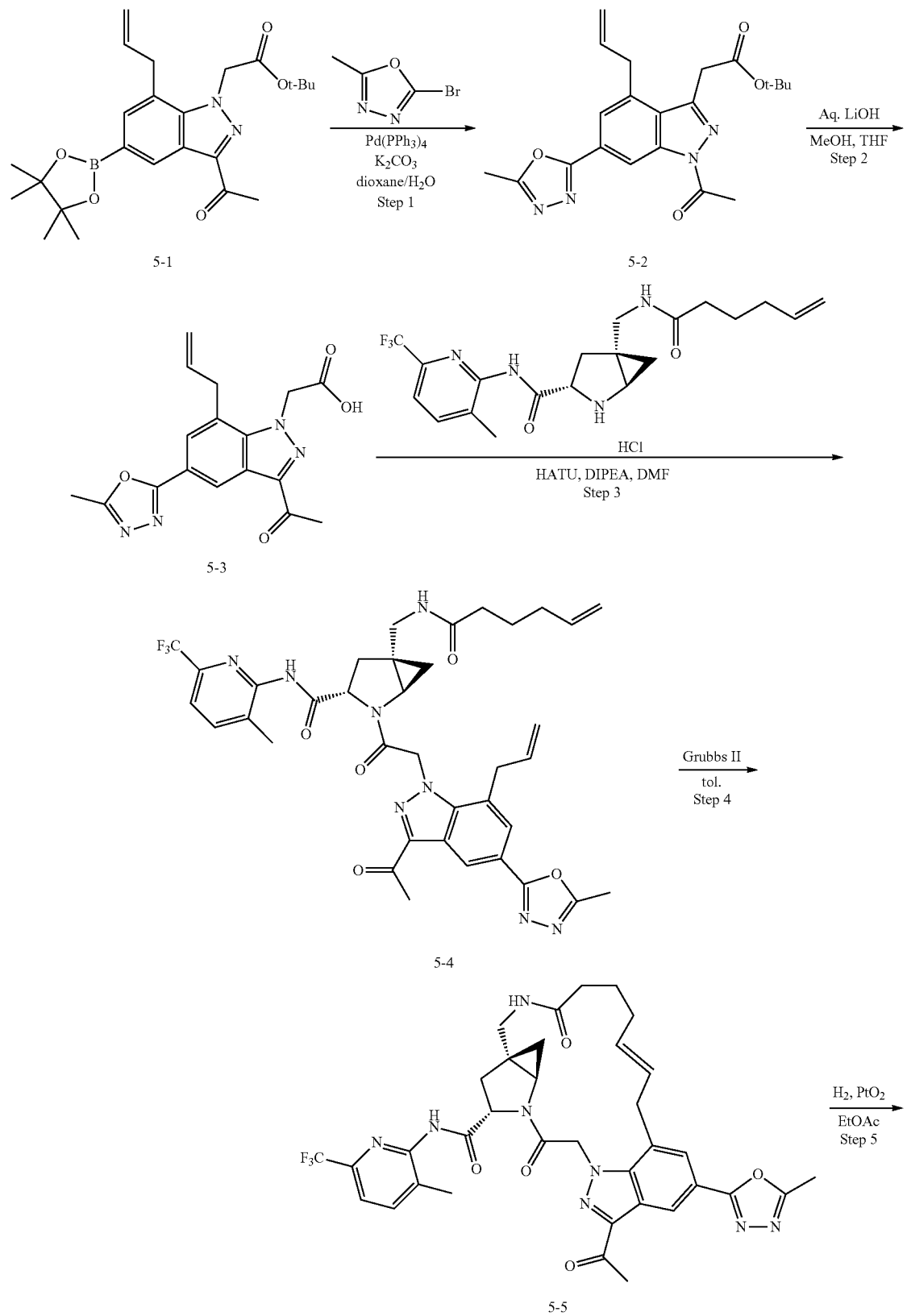

Step 1: tert-Butyl 2-(3-acetyl-7-allyl-5-(5-methyl-1,3,4-oxadiazol-2-yl)-1H-indazol-1-yl)acetate (5-2)

To a solution of 2-bromo-5-methyl-1,3,4-oxadiazole (70 mg, 0.43 mmol) and compound 5-1 (227 mg, 0.52 mmol) in 1,4-dioxane (5 mL) and water (1 mL) was added $K_2CO_3$ (148 mg, 1.07 mmol) and $Pd(PPh_3)_4$ (50 mg, 0.043 mmol). The mixture was degassed under $N_2$ three times and stirred at 90° C. under $N_2$ atmosphere for 16 hours. The mixture was diluted with EtOAc and washed with water and brine, dried over anhydrous $Na_2SO_4$, filtered and concentrated to dryness. The residue was purified by silica gel chromatography (eluted with PE:EtOAc=20:1) to afford compound 5-2 (75 mg, yield 44.1%) as a yellow solid. LC/MS (ESI) m/z: 397 $(M+H)^+$.

Step 2: 2-(3-Acetyl-7-allyl-5-(5-methyl-1,3,4-oxadiazol-2-yl)-1H-indazol-1-yl)acetic acid (5-3)

To a solution of compound 5-2 (75 mg, 0.19 mmol) in THF (1 mL), MeOH (1 mL) and water (0.5 mL) was added LiOH (11 mg, 0.47 mmol) and the mixture was stirred at room temperature for 2 hours. The mixture was concentrated to dryness and diluted with water. The mixture was washed with EtOAc and acidified with 1 N aqueous HCl to a pH of approximately 3 at 0° C. The mixture was extracted with DCM twice and the combined organic layers were washed with brine, dried over anhydrous $Na_2SO_4$, filtered and concentrated to dryness to afford compound 5-3 (65 mg, yield 101%) as a light yellow solid that was directly used to the next reaction without purification. LC/MS (ESI) m/z: 341 $(M+H)^+$.

Step 3: (1R,3S,5R)-2-(2-(3-Acetyl-7-allyl-5-(5-methyl-1,3,4-oxadiazol-2-yl)-1H-indazol-1-yl)acetyl)-5-(hex-5-enamidomethyl)-N-(3-methyl-6-(trifluoromethyl)pyridin-2-yl)-2-azabicyclo[3.1.0]hexane-3-carboxamide (5-4)

To a mixture of compound 5-3 (65 mg, 0.19 mmol) and (1R,3S,5R)-5-(hex-5-enamidomethyl)-N-[3-methyl-6-(trifluoromethyl)pyridin-2-yl]-2-azabicyclo[3.1.0]hexane-3-carboxamide hydrochloride (70 mg, 0.159 mmol) in DMF (3 mL) was added HATU (73 mg, 0.19 mmol) and DIPEA (51 mg, 0.40 mmol) at 0° C. and the reaction mixture was stirred at room temperature for 2 hours. The mixture was diluted with EtOAc, washed with water and brine, dried over $Na_2SO_4$, filtered and concentrated to dryness. The residue was purified by column chromatography via silica gel (eluted with DCM:MeOH=30:1) to afford compound 5-4 (50 mg, yield 42.9%) as a white solid. LC/MS (ESI) m/z: 733 $(M+H)^+$.

Step 4: Compound 5-5

To a solution of compound 5-4 (50 mg, 0.068 mmol) in degassed toluene (50 mL) was added Grubbs $2^{nd}$ catalyst (14 mg) and the mixture was degassed under $N_2$ atmosphere three times and stirred at 80° C. under $N_2$ atmosphere for 16 hours. The mixture was concentrated to dryness and the residue was purified by silica gel chromatography (eluted with DCM:MeOH=30:1) to afford compound 5-5 (40 mg, yield 83.2%) as a light yellow solid, LC/MS (ESI) m/z: 705 $(M+H)^+$.

Step 5: Compound 5

To a solution of compound 5-5 (40 mg, 0.057 mmol) in EtOAc (5 mL) was added $PtO_2$ (14 mg, 0.064 mmol) and the mixture was degassed under $N_2$ three times. The mixture was stirred under a $H_2$ balloon at room temperature for 1 hour. The mixture was filtered and the filtrate was concentrated to dryness. The residue product was purified by preparative HPLC to afford Compound 5 (5 mg, yield 11.1%) as a white solid. $^1$H-NMR (400 MHz, $CD_3OD$) δ 8.78 (d, J=1.3 Hz, 1H), 7.87 (s, 1H), 7.80 (d, J=7.8 Hz, 1H), 7.54 (d, J=7.8 Hz, 1H), 5.99 (d, J=17.9 Hz, 1H), 5.65 (d, J=17.9 Hz, 1H), 4.49 (d, J=6.7 Hz, 1H), 3.67 (dd, J=5.8, 2.7 Hz, 1H), 3.48 (d, J=14.5 Hz, 1H), 3.34 (s, 1H), 3.20-3.10 (m, 1H), 2.98-2.87 (m, 1H), 2.68 (s, 3H), 2.64 (s, 3H), 2.59 (t, J=6.6 Hz, 2H), 2.31 (dd, J=13.0, 6.8 Hz, 2H), 2.11 (s, 3H), 1.89-1.45 (m, 8H), 1.39 (t, J=5.8 Hz, 1H), 1.15 (dd, J=5.7, 2.7 Hz, 1H). LC/MS (ESI) m/z: 707 $(M+H)^+$.

Scheme 6. Synthesis of Compound 6

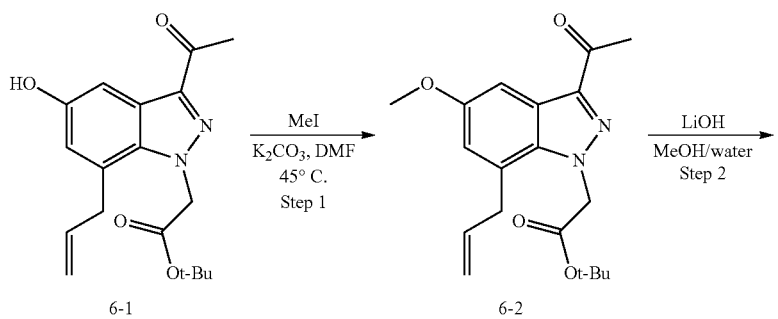

-continued

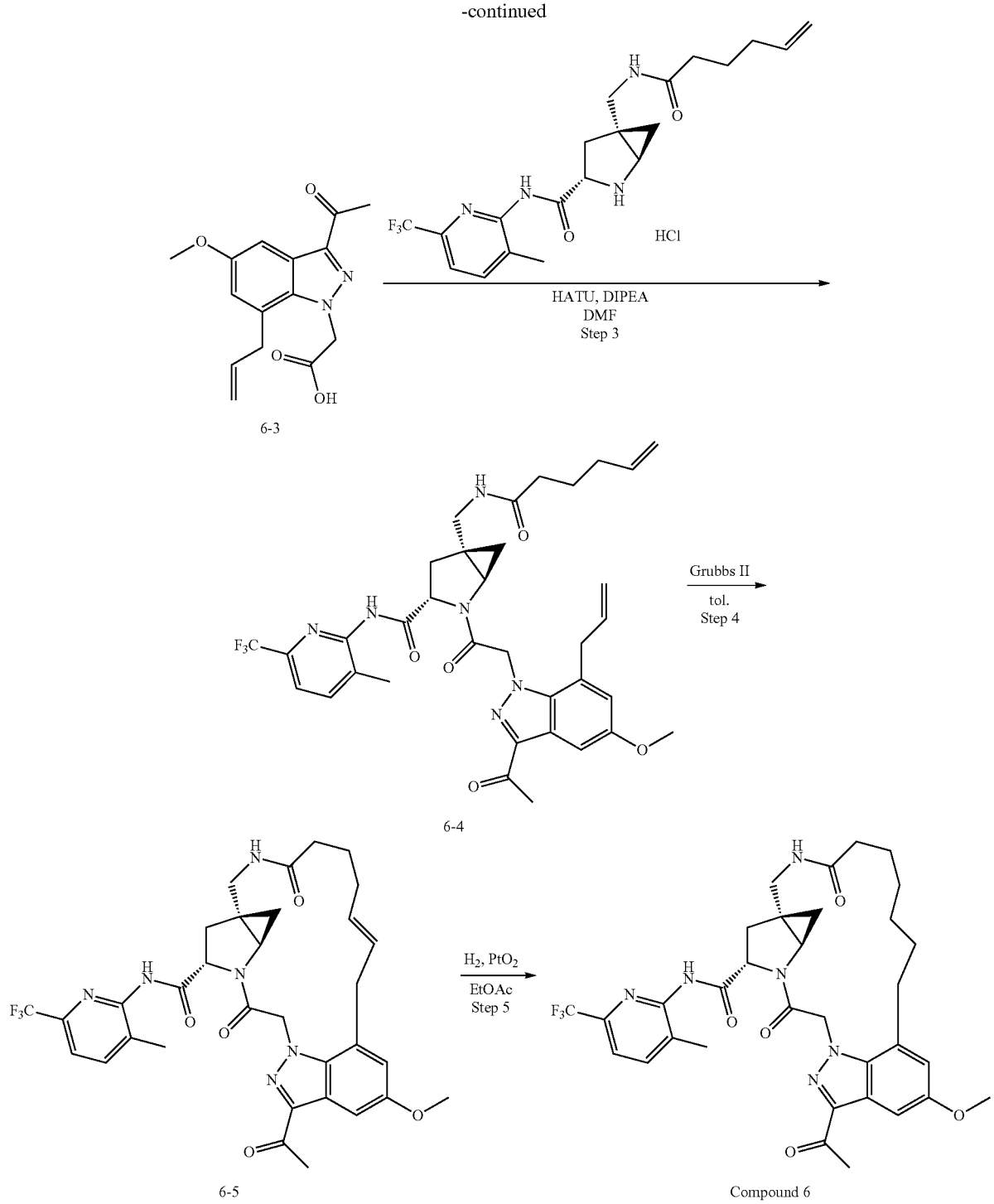

Step 1: tert-Butyl 2-[3-acetyl-5-methoxy-7-(prop-2-en-1-yl)indazol-1-yl]acetate (6-2)

To a solution of tert-butyl 2-[3-acetyl-5-hydroxy-7-(prop-2-en-1-yl)indazol-1-yl]acetate (60 mg, 0.18 mmol) in DMF (1 mL) was added methyl iodide (129 mg, 0.91 mmol) followed by potassium carbonate (50 mg, 0.36 mmol) at 0° C. and the mixture was stirred in a sealed tube at 50° C. for 16 hours. The mixture was diluted with EtOAc and washed with water and brine, dried over anhydrous Na$_2$SO$_4$, filtered and concentrated to dryness. The residue was purified by column chromatography on silica gel (eluted with PE:EtOAc=4:1) to afford compound 6-2 (50 mg, yield 79.9%) as a white solid, LC/MS (ESI) m/z: 345 (M+H)$^+$.

Step 2: [3-Acetyl-5-methoxy-7-(prop-2-en-1-yl)indazol-1-yl]acetic acid (6-3)

To a solution of compound 6-2 (50 mg, 0.145 mmol) in MeOH (3 mL) was added a solution of lithiumol (17 mg, 0.73 mmol) in water (1 mL) and the mixture was stirred at room temperature for 2 hours. The mixture was diluted with water and washed with ether. The aqueous layer was acidified with 1N aqueous HCl solution to a pH of approximately 3 and extracted with DCM. The organic layer was washed with brine, dried over anhydrous $Na_2SO_4$, filtered and concentrated to dryness to afford compound 6-3 (40 mg, yield 95.6%) as a white solid. LC/MS m/z: 289 $(M+H)^+$.

Step 3: (1,R,3S,5R)-2-{2-[3-Acetyl-5-methoxy-7-(prop-2-en-1-yl)indazol-1-yl]acetyl}-5-(hex-5-enamidonaethyl)-N-[3-methyl-6-(trifluoromethyl)pyridin-2-yl]-2-azabicyclo[3.1.0]hexane-3-carboxamide (6-4)

To a mixture of compound 6-3 (40 mg, 0.14 mmol) and (1R,3S,5R)-5-(hex-5-enamidomethyl)-N-[3-methyl-6-(trifluoromethyl)pyridin-2-yl]-2-azabicyclo[3.1.0]hexane-3-carboxamide hydrochloride (63 mg, 0.14 mmol) in DMF (3 mL) was added DIPEA (45 mg, 0.35 mmol) followed by HATU (63 mg, 0.17 mmol) at 0° C. and the mixture was stirred at room temperature for 1 hour. The mixture was diluted with water and extracted with EtOAc twice. The combined organic layers were washed with saturated aqueous $NH_4Cl$ solution and brine, dried over anhydrous $Na_2SO_4$, filtered and concentrated to dryness. The residue was purified by chromatography on silica gel (eluted with PE:EtOAc=1:3) to afford compound 6-4 (43 mg, yield 45.5%) as a colorless oil. LC/MS (ESI) m/z: 681 $(M+H)^+$.

Step 4: Compound 6-5

To a solution of compound 6-4 (39 mg, 0.057 mmol) in degassed toluene (40 mL) was added Grubbs $2^{nd}$ catalyst (10 mg, 0.011 mmol) at 0° C. under $N_2$ atmosphere and the mixture was stirred at 80° C. under $N_2$ atmosphere overnight. The mixture was concentrated to dryness and the residue was purified by chromatography on silica gel (eluted with DCM:MeOH=100:1 to 50:1) to afford compound 6-5 (25 mg, yield 69.1%) as a brown solid. LC/MS (ESI) m/z: 653 $(M+H)^+$.

Step 5: Compound 6

To a solution of compound 6-5 (30 mg, 0.046 mmol) in EtOAc (15 mL) was added platinum dioxide (10 mg) at 0° C. and the mixture was degassed under $N_2$ atmosphere three times and stirred under a $H_2$ balloon at room temperature for 1 hour. The mixture was filtered and the filtrate was concentrated to dryness. The residue was purified by preparative HPLC to afford Compound 6 (5 mg, yield 16.6%) as a white solid. $^1$H-NMR (400 MHz, $CD_3OD$) δ 7.81 (d, J=8.0 Hz, 1H), 7.55 (d, J=7.6 Hz, 1H), 7.53 (d, J=2.4 Hz, 1H), 6.83 (d, J=2.4 Hz, 1H), 5.88 (d, J=18.0 Hz, 1H), 5.54 (d, J=18.0 Hz, 1H), 4.50 (m, 1H), 3.83 (s, 3H), 3.62 (m, 1H), 3.50-3.42 (m, 1H), 3.36-3.33 (m, 1H), 3.09-2.95 (m, 1H), 2.81-2.69 (m, 1H), 2.64 (s, 3H), 2.61-2.54 (m, 2H), 2.40-2.21 (m, 2H), 2.13 (s, 3H), 1.84-1.45 (m, 7H), 1.43-1.33 (m, 2H), 1.16-1.10 (m, 1H). LC/MS (ESI) m/z: 655 $(M+H)^+$.

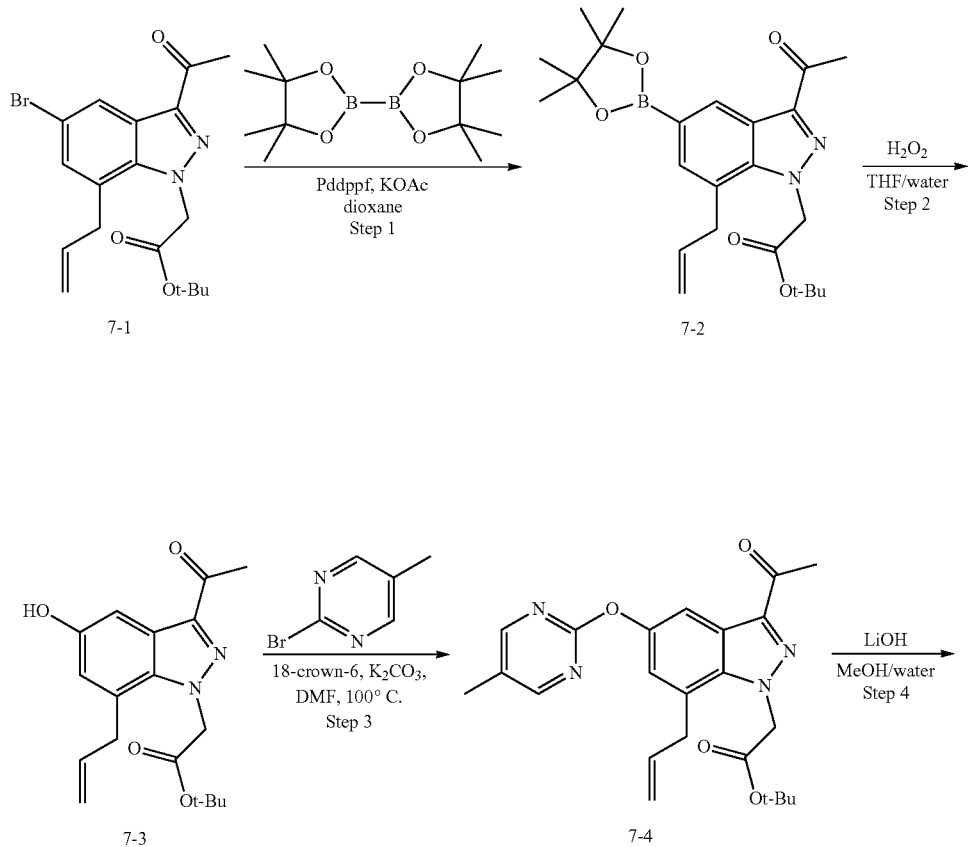

Scheme 7. Synthesis of Compound 7

-continued
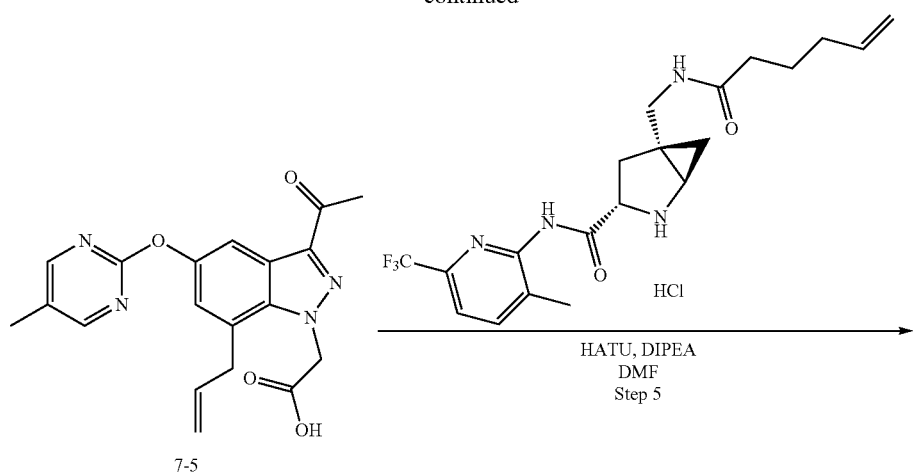
7-5
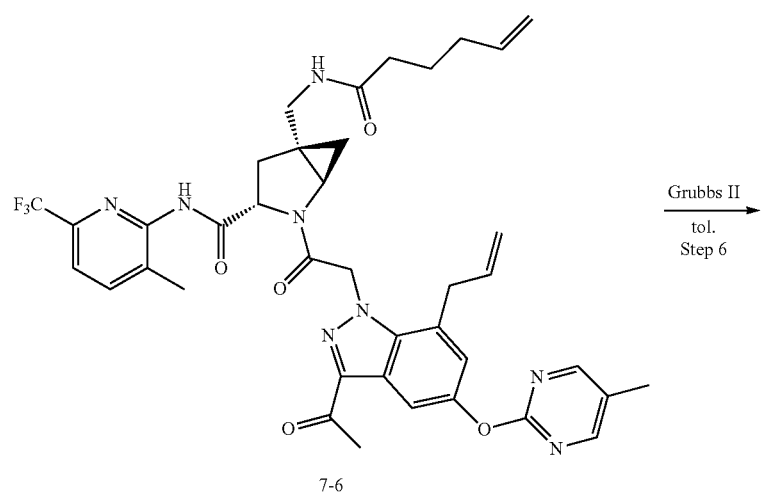
7-6
7-7

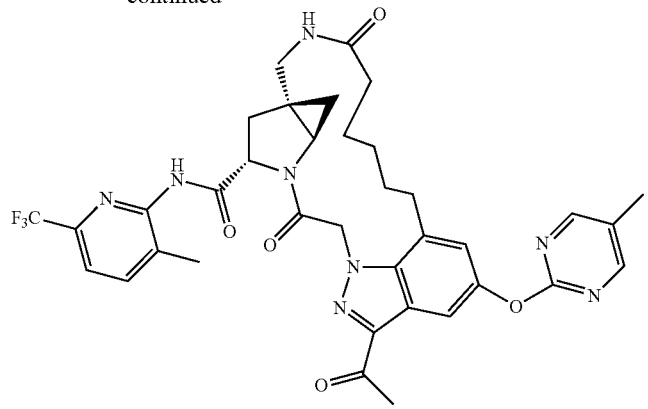

Compound 7

Step 1: tert-Butyl 2-(3-acetyl-7-allyl-5-(4,4,5,5-tetramethyl-1,3,2-dioxaborolan-2-yl)-1H-indazol-1-yl)acetate (7-2)

To a mixture of tert-butyl 2-[3-acetyl-5-bromo-7-(prop-2-en-1-yl)indazol-1-yl]acetate (500 mg, 1.27 mmol) and potassium acetate (374 mg, 3.8 mmol) in 1,4-dioxane (6 mL) was added bis(pinacolato)diboron (355 mg, 1.4 mmol) followed by 1,1'-bis(diphenylphosphino)ferrocene palladium (II)dichloride (93 mg, 0.13 mmol) under $N_2$ atmosphere. The mixture was stirred at 100° C. under $N_2$ atmosphere for 30 hours. The mixture was filtered and the filtrate was concentrated to dryness. The residue was purified by chromatography on silica gel (eluted with PE:EtOAc=50:1 to 20:1) to afford compound 7-2 (290 mg, yield 51.8%) as a yellow solid. LC/MS (ESI) m/z: 441 (M+H)+.

Step 2: tert-Butyl 2-(3-acetyl-7-allyl-5-hydroxy-1H-indazol-1-yl)acetate (7-3)

To a solution of compound 7-2 (150 mg, 0.34 mmol) in THF (3 mL) was added hydrogen peroxide (193 mg, 1.70 mmol, 30% wt) and the mixture was stirred at room temperature for 1 hour. The mixture was diluted with EtOAc and washed with water and brine, dried over anhydrous $Na_2SO_4$, filtered and concentrated to dryness to afford compound 7-3 (105 mg, yield 93.3%) as a white solid. LC/MS (ESI) m/z: 331 (M+H)+.

Step 3: tert-Butyl 2-(3-acetyl-7-allyl-5-((5-methylpyrimidin-2-yl)oxy)-1H-indazol-1-yl)acetate (7-4)

To a mixture of compound 7-3 (80 mg, 0.24 mmol) and 2-bromo-5-methylpyrimidine (46 mg, 0.27 mmol) in DMF (2 mL) was added potassium carbonate (67 mg, 0.48 mmol) and 18-crown-6 (64 mg, 0.24 mmol) and the mixture was stirred at 100° C. for 16 hours. The mixture was diluted with EtOAc and washed with saturated aqueous $NH_4Cl$ solution and brine, dried over anhydrous $Na_2SO_4$, filtered and concentrated to dryness. The residue was purified by chromatography on silica gel (eluted with PE:EtOAc=2:1) to afford compound 7-4 (47 mg, yield 45.9%) as a yellow solid. LC/MS (ESI) m/z: 423 (M+H)+.

Step 4: 2-(3-Acetyl-7-allyl-5-((5-methylpyrimidin-2-yl)oxy)-1H-indazol-1-yl)acetic acid (7-5)

To a solution of compound 7-4 (47 mg, 0.11 mmol) in MeOH (3 mL) was added a solution of lithiumol (14 mg, 0.57 mmol) in water (1 mL) at 0° C., and the mixture was stirred at room temperature for 2 hours. The mixture was diluted with water and washed with diethyl ether. The aqueous layer was acidified with 1N aqueous HCl solution to a pH of approximately 3 and extracted with DCM. The organic layer was washed with brine, dried over anhydrous $Na_2SO_4$, filtered and concentrated to dryness to afford compound 7-5 (40 mg, yield 96.1%) as a white solid. LC/MS (ESI) m/z: 367 (M+H)+.

Step 5: (1R,3S,5R)-2-(2-(3-Acetyl-7-allyl-5-((5-methylpyrimidin-2-yl)oxy)-1H-indazol-1-yl)acetyl)-5-(hex-5-enamidomethyl)-N-(3-methyl-6-(trifluoromethyl)pyridin-2-yl)-2-azabicyclo[3.1.0]hexane-3-carboxamide (7-6)

To a mixture of compound 7-5 (45 mg, 0.11 mmol) and (1R,3S,5R)-5-(hex-5-enamidomethyl)-N-(3-methyl-6-(trifluoromethyl)pyridin-2-yl)-2-azabicyclo[3.1.0]hexane-3-carboxamide hydrochloride (49 mg, 0.11 mmol) in DMF (3 mL) was added DIPEA (53 mg, 0.4 mmol) followed by HATU (50 mg, 0.13 mmol) at 0° C. and the mixture was stirred at room temperature for 1 hour. The mixture was diluted with water and extracted with EtOAc twice. The combined organic layers were washed with saturated aqueous $NH_4Cl$ solution and brine, dried over anhydrous $Na_2SO_4$, filtered and concentrated to dryness. The residue was purified by chromatography on silica gel (eluted with DCM:MeOH=30:1) to afford compound 7-6 (43 mg, yield 51.9%) as a light yellow solid. LC/MS (ESI) m/z: 759 (M+H)+.

Step 6: Compound 7-7

To a solution of compound 7-6 (43 mg, 0.06 mmol) in degassed toluene (40 mL) was added Grubbs $2^{nd}$ Catalyst (10 mg, 0.01 mmol) at 0° C. under $N_2$ atmosphere and the mixture was stirred at 80° C. under $N_2$ atmosphere overnight. The mixture was concentrated to dryness and the residue was purified by chromatography on silica gel (eluted with DCM:MeOH=30:1) to afford compound 7-7 (25 mg, yield 61.5%) as a brown solid. LC/MS (ESI) m/z: 717 (M+H)+.

Step 7: Compound 7

To a solution of compound 7-7 (25 mg, 0.035 mmol) in EtOAc (15 mL) was added platinum dioxide (10 mg) at 0°

C., and the mixture was degassed under N₂ atmosphere three times and stirred under a H₂ balloon at room temperature for 1 hour. The mixture was filtered and the filtrate was concentrated to dryness. The residue was purified by preparative HPLC to afford Compound 7 (1 mg, yield 3.98%) as a white solid. ¹H-NMR (400 MHz, CD₃OD) δ 8.41 (s, 2H), 7.84 (d, J=2.0 Hz, 1H), 7.81 (d, J=8.0 Hz, 1H), 7.55 (d, J=7.6 Hz, 1H), 7.02 (d, J=2.4 Hz, 1H), 5.72 (d, J=17.6 Hz, 1H), 5.90 (d, J=17.6 Hz, 1H), 4.32 (m, 1H), 3.75 (m, 1H), 3.55 (d, J=14.8 Hz, 1H), 3.38-3.31 (m, 1H), 3.08-2.97 (m, 1H), 2.94-2.82 (m, 1H), 2.70-2.60 (m, 1H), 2.65 (s, 3H), 2.54-2.46 (m, 1H), 2.28 (s, 3H), 2.23-2.21 (m, 2H), 2.18 (s, 3H), 1.90-1.51 (m, 6H), 1.37-1.24 (m, 1H), 1.18-1.11 (m, 1H). LC/MS (ESI) m/z: 719 (M+H)⁺.

Scheme 8. Synthesis of Compound 8

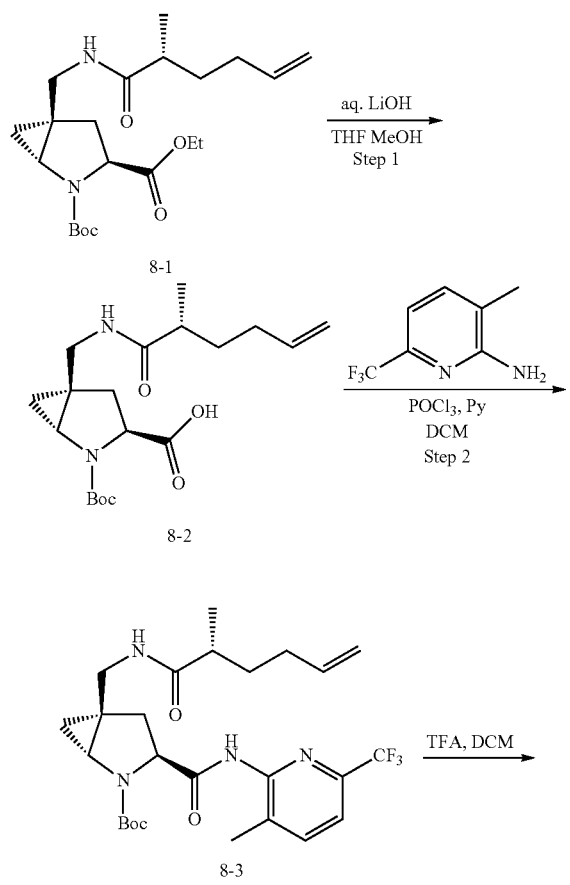

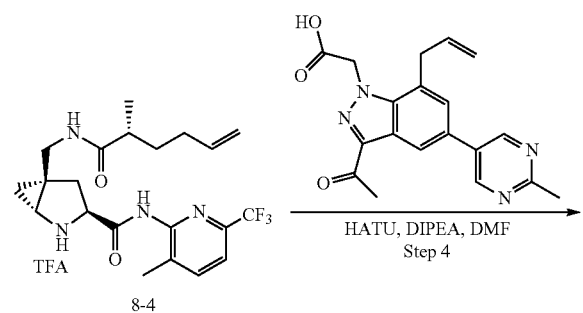

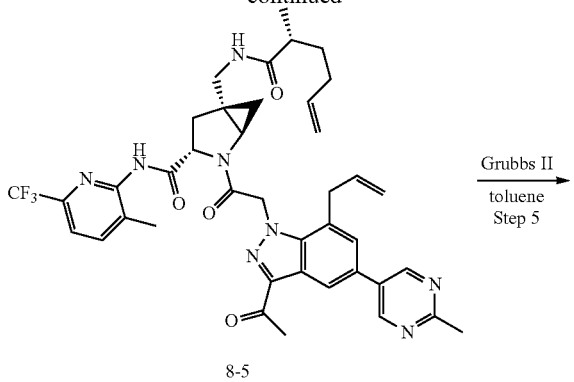

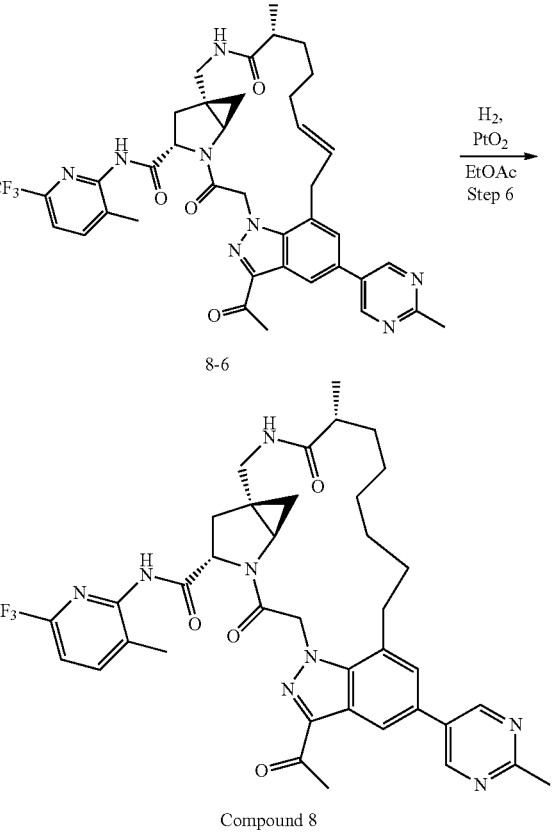

Compound 8

Step 1: (1R,3S,5R)-2-(tert-Butoxycarbonyl)-5-(((R)-2-methylhex-5-enamido)methyl)-2-azabicyclo[3.1.0]hexane-3-carboxylic acid (8-2)

To a solution of compound 8-1 (290 mg, 0.74 mmol) in MeOH (2 mL), THF (2 mL) and water (2 mL) was added LiOH (88 mg, 3.68 mmol) and the mixture was stirred at room temperature for 2 hours. The mixture was concentrated to dryness and the residue was dissolved in water and washed with diethyl ether twice. The aqueous layer was acidified with 1N aqueous HCl to a pH of approximately 4 and extracted with EtOAc twice. The combined organic layers were washed with brine, dried over Na₂SO₄ and concentrated under reduced pressure to afford compound 8-2 (230 mg, yield 85.4%) as a white solid. LC/MS (ESI) m/z: 365 (M+H)⁺.

Step 2: (1R,3S,5R)-tert-Butyl 3-((3-methyl-6-(trifluoromethyl)pyridin-2-yl)carbamoyl)-5-(((R)-2-methylhex-5-enamido)methyl)-2-azabicyclo[3.1.0]hexane-2-carboxylate (8-3)

To a mixture of compound 2 (290 mg, 0.79 mmol) and 3-methyl-6-(trifluoromethyl)pyridin-2-amine (139 mg, 0.79 mmol) in DCM (6 mL) was added pyridine (313 mg, 3.96 mmol) followed by the drop-wise addition of DCM (121 mg, 0.79 mmol) at 0° C. and the mixture was stirred at room temperature for 1 hour. The mixture was diluted with DCM and washed with 1N aqueous HCl solution and brine, dried over Na$_2$SO$_4$, filtered and concentrated to dryness. The residue was purified by silica gel chromatography (eluted with PE:EtOAc=10:1 to 5:1) to afford compound 8-3 (230 mg, yield 55.4%) as a white solid. LC/MS (ESI) m/z: 525 (M+H)$^+$.

Step 3: (1R,3S,5R)-N-(3-Methyl-6-(trifluoromethyl)pyridin-2-yl)-5-(((R)-2-methylhex-5-enamido)methyl)-2-azabicyclo[3.1.0]hexane-3-carboxamide TFA salt (8-4)

To a solution of compound 8-3 (112 mg, 0.21 mmol) in DCM (2 mL) was added TFA (1 mL) at 0° C. and the mixture was stirred at room temperature for 1 hour. Then the mixture was concentrated to dryness to afford compound 8-4 (110 mg, yield 99.3%) as a brown solid that was directly used in the next reaction without further purification, LC/MS (ESI) m/z; 425 (M+H)$^+$.

Step 4: (1R,3S,5R)-2-(2-(3-Acetyl-7-allyl-5-(2-methylpyrimidin-5-yl)-1H-indazol-1-yl)acetyl)-N-(3-methyl-6-(trifluoromethyl)pyridin-2-yl)-5-(((R)-2-methylhex-5-amido)methyl)-2-azabicyclo[3.1.0]hexane-3-carboxamide (8-5)

To a mixture of 2-(3-acetyl-7-allyl-5-(2-methylpyrimidin-5-yl)-1H-indazol-1-yl)acetic acid (74 mg, 0.21 mmol) and compound 4 (110 mg, 0.21 mmol) in DMF (5 mL) was added DIPEA (82 mg, 0.64 mmol) followed by HATU (121 mg, 0.32 mmol) at 0° C. and the mixture was stirred at 25° C. for 1 hour. The mixture was diluted with EtOAc, washed with saturated aqueous NH$_4$Cl solution and brine, dried and concentrated to dryness. The residue was purified by silica gel chromatography (eluted with PE:EtOAc=20:1 to 1:1) to afford compound 8-5 (130 mg, yield 81.0%) as a white solid. LC/MS (ESI) m/z: 757 (M+H)$^+$.

Step 5: Compound 8-6

To a solution of compound 5 (130 mg, 0.172 mmol) in degassed toluene (100 mL) was added Grubbs 2$^{nd}$ catalyst (36 mg, 0.04 mmol) and the mixture was stirred at 80° C. under N$_2$ atmosphere for 16 hours. The mixture was concentrated to dryness and the residue was purified by silica gel chromatography (eluted with PE:EtOAc=20:1 to 1:3) to afford compound 8-6 (60 mg, yield 47.9%) as a brown solid. LC/MS (ESI) m/z: 729 (M+H)$^+$.

Step 6: Compound 8

To a mixture of compound 8-6 (60 mg, 0.082 mmol) in EtOAc (2 mL) was added PtO$_2$ (12 mg) and the mixture was degassed under N$_2$ atmosphere three times and stirred under a H$_2$ balloon at room temperature for 1 hour. The mixture was filtered and the filtrate was concentrated to dryness. The residue was purified by preparative HPLC to afford Compound 8 (10 mg, yield 16.6%) as a white solid. $^1$H-NMR (400 MHz, DMSO-d$_6$) δ 10.52-10.29 (m, 1H), 9.01 (s, 2H), 8.30 (d, J=1.4 Hz, 1H), 7.99 (t, J=6.2 Hz, 1H), 7.89 (d, J=7.8 Hz, 1H), 7.65 (d, J=7.8 Hz, 1H), 7.55 (s, 5.93 (d, J=17.7 Hz, 1H), 5.52 (d, J=17.7 Hz, 1H), 4.27 (t, J=8.2 Hz, 1H), 3.63 (m, 1H), 3.56 (dd, J=14.2, 5.7 Hz, 1H), 3.15-2.94 (m, 3H), 2.68 (s, 2H), 2.64 (s, 2H), 2.49-2.44 (m, 2H), 2.33-2.24 (m, 1H), 2.13 (s, 3H), 1.90-1.75 (m, 1H), 1.73-1.61 (m, 2H), 1.60-1.54 (m, 2H), 1.54-1.46 (m, 1H), 1.43-1.32 (m, 2H), 1.20-1.13 (m, 1H), 1.11-1.03 (m, 4H), LC/MS (ESI) m/z: 731 (M+H)$^+$.

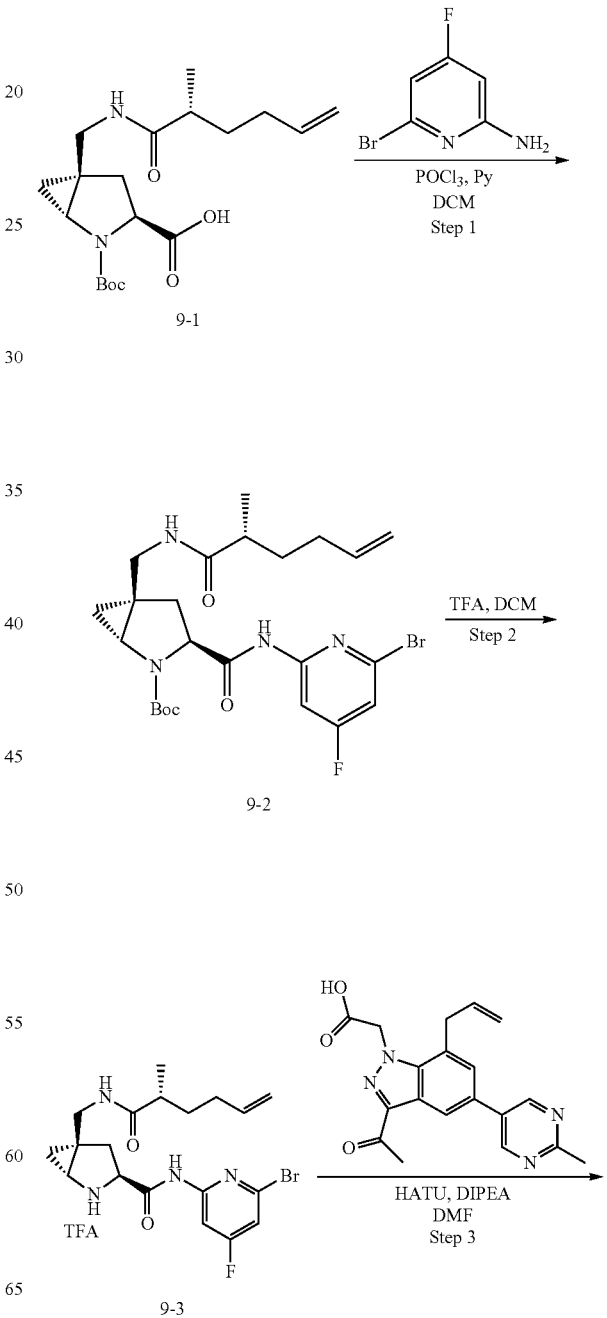

Scheme 9. Synthesis of Compound 9

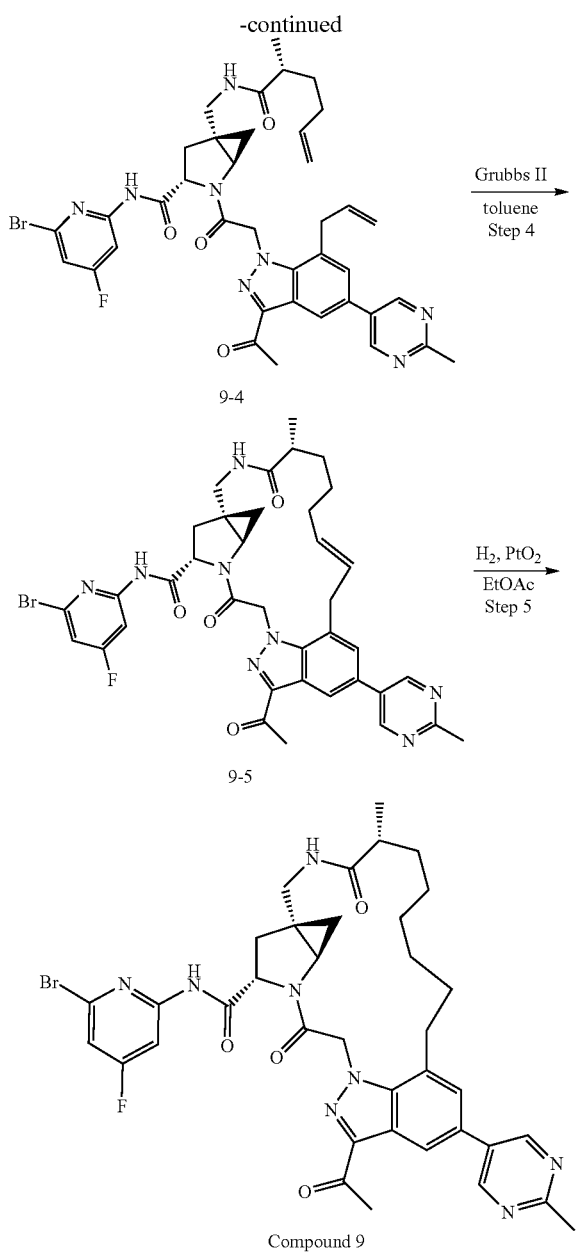

9-4

9-5

Compound 9

Step 1: (1R,3S,5R)-tert-Butyl 3-((6-bromo-4-fluoro-pyridin-2-yl)carbamoyl)-5-(((R)-2-methylhex-5-enamido)methyl)-2-azabicyclo[3.1.0]hexane-2-carboxylate (9-2)

To a mixture of compound 9-1 (50 mg, 0.14 mmol) and 6-bromo-4-fluoropyridin-2-amine (26 mg, 0.14 mmol) in DCM (2 mL) was added pyridine (54 mg, 0.68 mmol) followed by POCl$_3$ (42 mg, 0.28 mmol) at 0° C. and the mixture was stirred at room temperature for 1 hour. The mixture was diluted with DCM and washed with 1N aqueous HCl solution and brine, dried over Na$_2$SO$_4$, filtered and concentrated to dryness. The residue was purified by silica gel chromatography (eluted with PE:EtOAc=10:1) to afford compound 9-2 (37 mg, yield 50.3%) as a white solid. LC/MS (ESI) m/z: 539/541 (M+H)$^+$.

Step 2: (1R,3S,5R)-N-(6-Bromo-4-fluoropyridin-2-yl)-5-(((R)-2-methylhex-5-enamido)methyl)-2-azabicyclo[3.1.0]hexane-3-carboxamide TFA salt (9-3)

To a solution of compound 9-2 (37 mg, 0.069 mmol) in DCM (2 mL) was added TFA (1 mL) at 0° C. and the resulting mixture was stirred at room temperature for 1 hour. Then the mixture was concentrated to dryness to afford compound 9-3 (35 mg, yield 99.6%) as a brown solid that was directly used in the next reaction without further purification. LC/MS (ESI) m/z: 439/441 (M+H)$^+$.

Step 3: (1R,3S,5R)-2-(2-(3-Acetyl-7-allyl-5-(2-methylpyrimidin-5-yl)-1H-indazol-1-yl)acetyl)-N-(6-bromo-4-fluoropyridin-2-yl)-5-(((R)-2-methyl-hex-5-enamido)methyl)-2-azabicyclo[3.1.0]hexane-3-carboxamide (9-4)

To a mixture of 2-(3-acetyl-7-allyl-5-(2-methylpyrimidin-5-yl)-1H-indazol-1-yl)acetic acid (24 mg, 0.068 mmol) and compound 9-3 (35 mg, 0.068 mmol) in DMF (3 mL) was added HATU (39 mg, 0.10 mmol) and DIPEA (26 mg, 0.20 mmol) at 0° C. and the mixture was stirred at 25° C. for 1 hour. The mixture was diluted with EtOAc, washed with saturated aqueous NH$_4$Cl solution and brine, dried and concentrated to dryness. The residue was purified by silica gel chromatography (eluted with PE:EtOAc=20:1 to 1:2) to afford compound 9-4 (50 mg, yield 94.9%) as a white solid. LC/MS (ESI) m/z: 771/773 (M+H)$^+$.

Step 4: Compound 9-5

To a solution of compound 9-4 (50 mg, 0.065 mmol) in degassed toluene (40 mL) was added Grubbs 2$^{nd}$ catalyst (14 mg, 0.016 mmol) and the mixture was stirred at 80° C. under N$_2$ atmosphere for 16 hours. The mixture was concentrated to dryness and the residue was purified by silica gel chromatography (eluted with PE:EtOAc=20:1 to 1:2) to afford compound 9-5 (35 mg, yield 72.6%) as a brown solid. LC/MS (ESI) m/z: 743/745 (M+H)$^+$.

Step 6: Compound 9

To a mixture of compound 9-5 (35 mg, 0.047 mmol) in EtOAc (2 mL) was added PtO$_2$ (7 mg) and the mixture was degassed under N$_2$ atmosphere three times and stirred under a H$_2$ balloon at room temperature for 1 hour. The mixture was filtered and the filtrate was concentrated to dryness. The residue was purified by preparative HPLC to afford Compound 9 (4 mg, yield 11.4%) as white solid. $^1$H-NMR (400 MHz, CD$_3$OD) δ 8.97 (s, 2H), 8.40 (d, J=1.5 Hz, 1H), 7.89 (dd, J=10.9, 1.6 Hz, 1H), 7.54 (s, 1H), 7.09 (dd, J=7.5, 2.0 Hz, 1H), 6.01 (d, J=17.9 Hz, 1H), 5.61 (d, J=17.9 Hz, 1H), 4.58 (m, 1H), 4.30 (t, J=7.9 Hz, 1H), 3.74-3.68 (m, 1H), 3.59 (d, J=14.5 Hz, 1H), 3.28-3.22 (m, 1H), 3.20-3.11 (m, 1H), 3.08-3.00 (m, 1H), 2.73 (s, 3H), 2.67 (s, 3H), 2.61-2.51 (m, 2H), 2.47-2.39 (m, 1H), 2.00-1.90 (m, 1H), 1.84-1.76 (m, 2H), 1.76-1.71 (m, 2H), 1.62-1.53 (m, 1H), 1.51-1.42 (m, 1H), 1.31-1.28 (m, 1H), 1.23-1.17 (m, 3H), 1.16-1.12 (m, 1H). LC/MS (ESI) m/z: 745/747 (M+H)$^+$.

Scheme 10. Synthesis of Compound 10

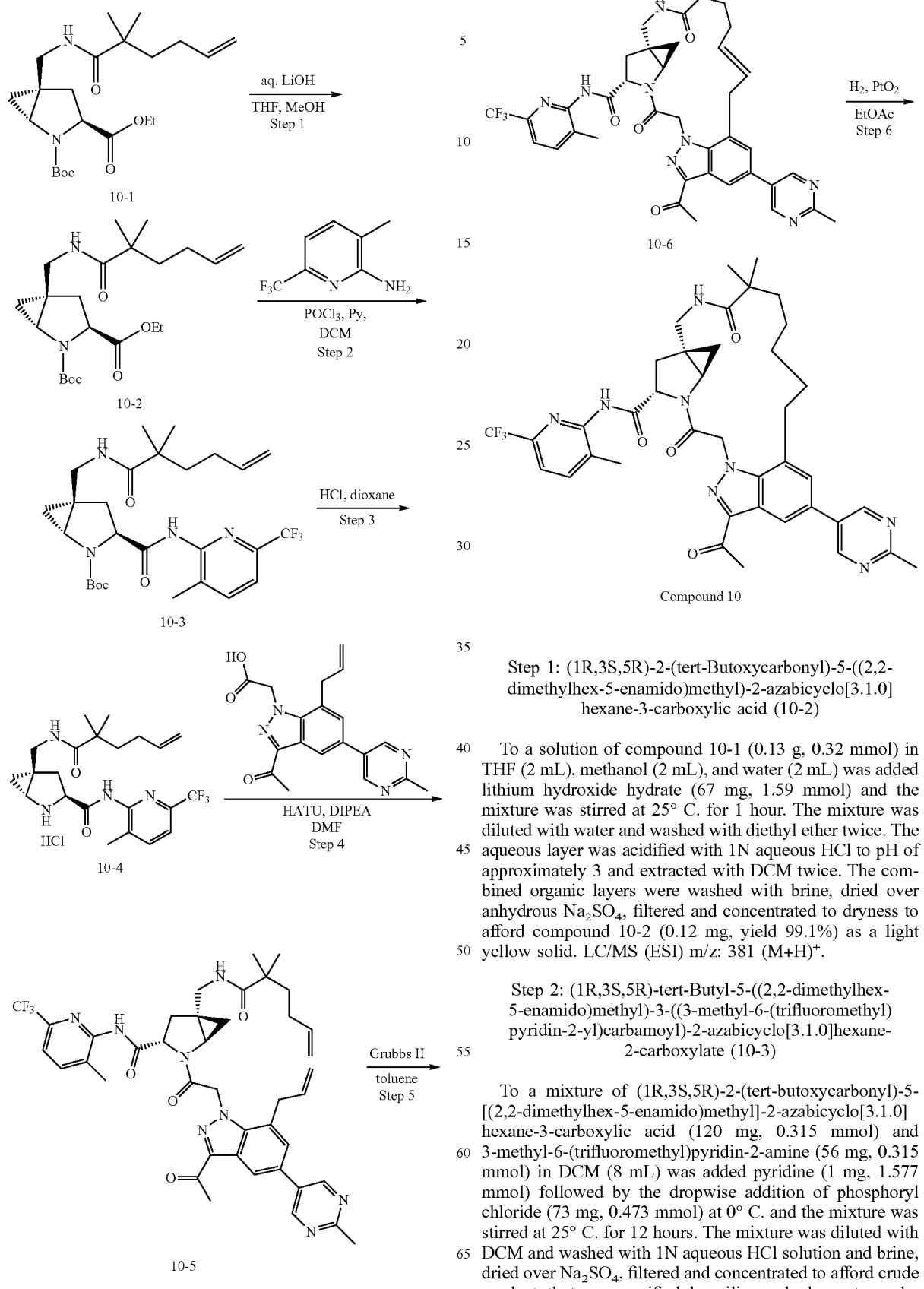

Step 1: (1R,3S,5R)-2-(tert-Butoxycarbonyl)-5-((2,2-dimethylhex-5-enamido)methyl)-2-azabicyclo[3.1.0]hexane-3-carboxylic acid (10-2)

To a solution of compound 10-1 (0.13 g, 0.32 mmol) in THF (2 mL), methanol (2 mL), and water (2 mL) was added lithium hydroxide hydrate (67 mg, 1.59 mmol) and the mixture was stirred at 25° C. for 1 hour. The mixture was diluted with water and washed with diethyl ether twice. The aqueous layer was acidified with 1N aqueous HCl to pH of approximately 3 and extracted with DCM twice. The combined organic layers were washed with brine, dried over anhydrous $Na_2SO_4$, filtered and concentrated to dryness to afford compound 10-2 (0.12 mg, yield 99.1%) as a light yellow solid. LC/MS (ESI) m/z: 381 (M+H)$^+$.

Step 2: (1R,3S,5R)-tert-Butyl-5-((2,2-dimethylhex-5-enamido)methyl)-3-((3-methyl-6-(trifluoromethyl) pyridin-2-yl)carbamoyl)-2-azabicyclo[3.1.0]hexane-2-carboxylate (10-3)

To a mixture of (1R,3S,5R)-2-(tert-butoxycarbonyl)-5-[(2,2-dimethylhex-5-enamido)methyl]-2-azabicyclo[3.1.0]hexane-3-carboxylic acid (120 mg, 0.315 mmol) and 3-methyl-6-(trifluoromethyl)pyridin-2-amine (56 mg, 0.315 mmol) in DCM (8 mL) was added pyridine (1 mg, 1.577 mmol) followed by the dropwise addition of phosphoryl chloride (73 mg, 0.473 mmol) at 0° C. and the mixture was stirred at 25° C. for 12 hours. The mixture was diluted with DCM and washed with 1N aqueous HCl solution and brine, dried over $Na_2SO_4$, filtered and concentrated to afford crude product that was purified by silica gel chromatography (eluted with PE:EtOAc=2:1) to afford compound 10-3 (95 mg, yield 55.9%) as a yellow solid. LC/MS (ESI) m/z: 539 (M+H)+.

Step 3: (1R,3S,5R)-5-((2,2-Dimethylhex-5-enamido)methyl)-N-(3-methyl-6-(trifluoromethyl)pyridin-2-yl)-2-azabicyclo[3.1.0]hexane-3-carboxamide hydrochloride (10-4)

A solution of tert-butyl (1R,3S,5R)-5-[(2,2-dimethylhex-5-enamido)methyl]-3-{[3-methyl-6-(trifluoromethyl)pyridin-2-yl]carbamoyl}-2-azabicyclo[3.1.0]hexane-2-carboxylate (95 mg, 0.176 mmol) in HCl/1,4-dioxane solution (2 mL) was stirred at room temperature for 2 hours. The mixture was concentrated to dryness and the residue was washed with diethyl ether, dried under vacuum to afford compound 10-4 (75 mg, yield 89.7%) as a yellow solid. LC/MS (ESI) m/z: 439 (M+H)+.

Step 4: (1R,3S,5R)-2-(2-(3-Acetyl-7-allyl-5-(2-methylpyrimidin-5-yl)-1H-indazol-1-yl)acetyl)-5-((2,2-dimethylhex-5-enamido)methyl)-N-(3-methyl-6-(trifluoromethyl)pyridin-2-yl)-2-azabicyclo[3.1.0]hexane-3-carboxamide (10-5)

To a mixture of (1R,3S,5R)-5-[(2,2-dimethylhex-5-enamido)methyl]-N-[3-methyl-6-(trifluoromethyl)pyridin-2-yl]-2-azabicyclo[3.1.0]hexane-3-carboxamide hydrochloride (75 mg, 0.16 mmol) and [3-acetyl-5-(2-methylpyrimidin-5-yl)-7-(prop-2-en-1-yl)indazol-1-yl] acetic acid (56 mg, 0.16 mmol) in DMF (5 mL) was added DIPEA (0.11 g, 0.8 mmol) followed by HATU (109 mg, 0.29 mmol) at 0° C. and the mixture was stirred at room temperature for 2 hours. The mixture was diluted with EtOAc and washed with saturated aqueous NH4Cl solution and brine, dried over Na2SO4, filtered and concentrated to afford crude product that was purified by silica gel chromatography (eluted with PE:EtOAc=2:1) to afford compound 10-5 (80 mg, yield 65.0%) as a yellow solid. LC/MS (ESI) m/z: 771 (M+H)+.

Step 5: Compound 10-6

To a solution of compound 10-5 (80 mg, 0.104 mmol) in degassed toluene (65 mL) was added Grubbs 2nd catalyst (22 mg, 0.026 mmol) under N2 atmosphere and the mixture was stirred under N2 atmosphere at 80° C. for 16 hours. The mixture was concentrated to dryness and the residue was purified by silica gel chromatography (eluted with DCM:MeOH=30:1) to afford compound 10-6 (55 mg, yield 71.347%) as a yellow solid. LC/MS (ESI) m/z: 743 (M+H)+.

Step 6: Compound 10

To a solution of compound 10-6 (50 mg, 0.067 mmol) in EtOAc (5 mL) and THF (3 mL) was added PtO2 (15 mg, 0.067 mmol) and the mixture was degassed under N2 atmosphere three times and stirred under a H2 balloon at 25° C. for 1 hour. The mixture was filtered and the filtrate was concentrated to dryness. The residue was purified by preparative HPLC to afford Compound 10 (5.1 mg, yield 10.2%) as a white solid. 1H-NMR (400 MHz, CD3OD) δ 9.01 (s, 2H), 8.44 (s, 1H), 7.58 (s, 1H), 7.38-7.32 (t, J=16 Hz, 1H), 7.25 (t, J=12 Hz, 1H), 7.11 (t, J=16 Hz, 1H), 5.91 (d, J=20 Hz, 1H), 5.61 (d, J=16 Hz, 1H), 5.17 (m, 1H), 4.27 (m, 1H), 3.55 (dd, J=8 Hz, 1H), 3.38 (m, 2H), 3.18-3.09 (m, 1H), 2.93 (m, 1H), 2.75 (s, 3H), 2.69 (s, 3H), 2.43 (m, 1H), 2.27 (m, 3H), 1.77 (m, 8H), 1.34 (m, 4H), 1.15 (m, 1H). LC/MS (ESI) m/z: 745 (M+H)+.

Scheme 11. Syntesis of Compound 11

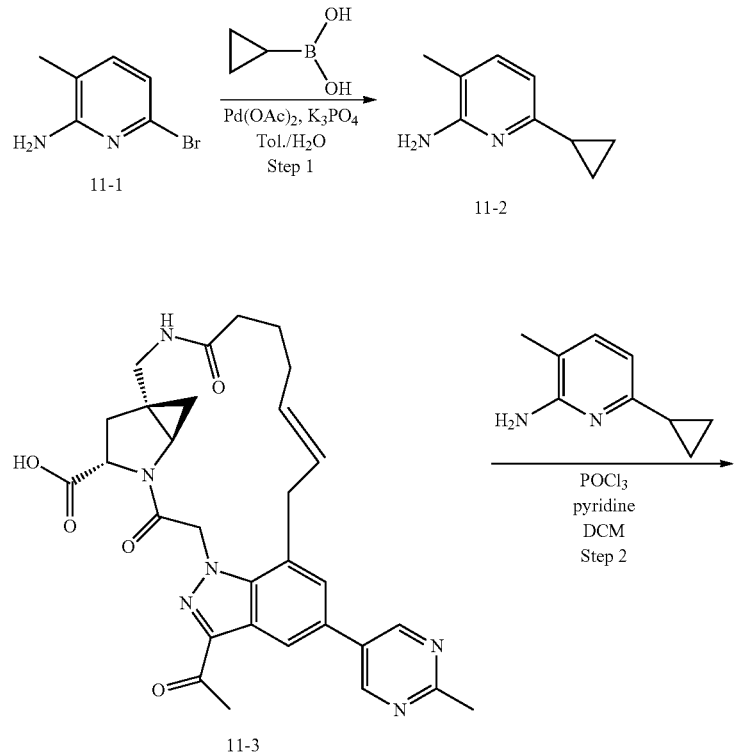

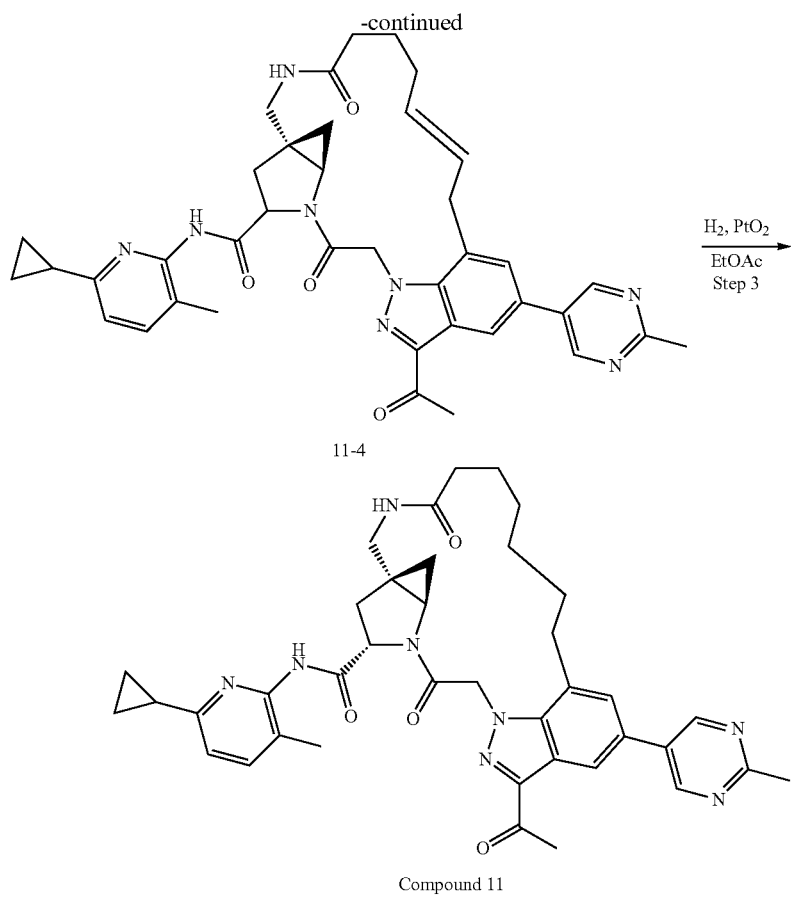

11-4

Compound 11

Step 1: 6-Cyclopropyl-5-methylpyridin-2-amine (11-2)

To a solution of 6-bromo-5-methylpyridin-2-amine (0.15 g, 0.81 mmol) and cyclopropylboronic acid (69 mg, 0.81 mmol) in 1,4-dioxane (4 mL) and water (1 mL) was added $K_3PO_4$ (0.51 g, 2.41 mmol), tri-cyclohexylphosphine (22 mg, 0.08 mmol) and $Pd(OAc)_2$ (9 mg, 0.04 mmol) and the mixture was degassed under $N_2$ atmosphere three times and stirred under $N_2$ atmosphere at 100° C. for 24 hours. The mixture was diluted with EtOAc, washed with brine, dried over anhydrous $Na_2SO_4$, filtered and concentrated to dryness. The residue was purified by column chromatography on silica gel (eluted with DCM:MeOH=100:1) to afford compound 11-2 (42 mg, yield 35.3%) as a yellow solid. LC/MS (ESI) m/z: 149 (M+H)+.

Step 2: Compound 11-4

To a mixture of compound 11-3 (25 mg, 0.045 mmol) and 6-cyclopropyl-3-methylpyridin-2-amine (7 mg, 0.045 mmol) in DCM (3 mL) was added pyridine (28 mg, 0.35 mmol) and phosphorus oxychloride (14 mg, 0.09 mmol) at 0° C. and the mixture was stirred at room temperature for 30 minutes. The mixture was diluted with DCM and washed with 1N aqueous HCl and brine, dried over anhydrous $Na_2SO_4$, filtered and concentrated to dryness. The residue was purified by column chromatography on silica gel (eluted with DCM:MeOH=40:1) to afford compound 11-4 (16 mg, yield 51.8%) as a light yellow solid. LC/MS (ESI) m/z: 687 (M+H)+.

Step 3: Compound 11

To a solution of compound 11-4 (16 mg, 0.023 mmol) in EtOAc (3 mL) was added $PtO_2$ (5 mg) and the mixture was degassed under $N_2$ atmosphere three times and stirred under a $H_2$ balloon at room temperature for 2 hours. The mixture was filtered and the filtrate was concentrated to dryness. The residue was purified by preparative HPLC to afford Compound 11 (3 mg, yield 18.7%) as a white solid, $^1$H-NMR (400 MHz, $CD_3OD$) δ 8.98 (s, 2H), 8.42 (d, 1.6 Hz, 1H), 7.51 (s, 1H), 7.43 (d, J=7.8 Hz, 1H), 6.95 (d, J=7.8 Hz, 1H), 5.92 (d, J=17.8 Hz, 1H), 5.64 (d, J=17.8 Hz, 1H), 4.49-4.58 (m, 4H), 3.63-3.60 (m, 1H), 3.51-3.46 (m, 1H), 3.35 (d, J=14.4 Hz, 1H), 3.19-3.11 (m, 1H), 2.91-2.83 (m, 1H), 2.74 (s, 3H), 2.68 (s, 3H), 2.59 (d, J=7.4 Hz, 2H), 2.39-2.26 (m, 2H), 2.02-1.98 (m, 4H), 1.88-1.50 (m, 8H), 1.46-1.38 (m, 2H), 1.18-1.15 (m, 1H), 0.94-0.86 (m, 4H). LC/MS (ESI) m/z: 689 (M+H)+.

Scheme 12. Synthesis of Compound 12

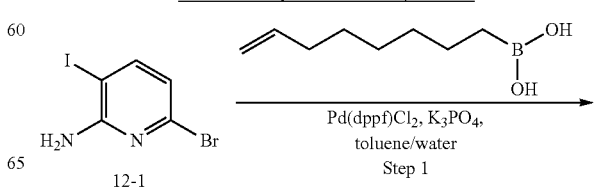

12-1

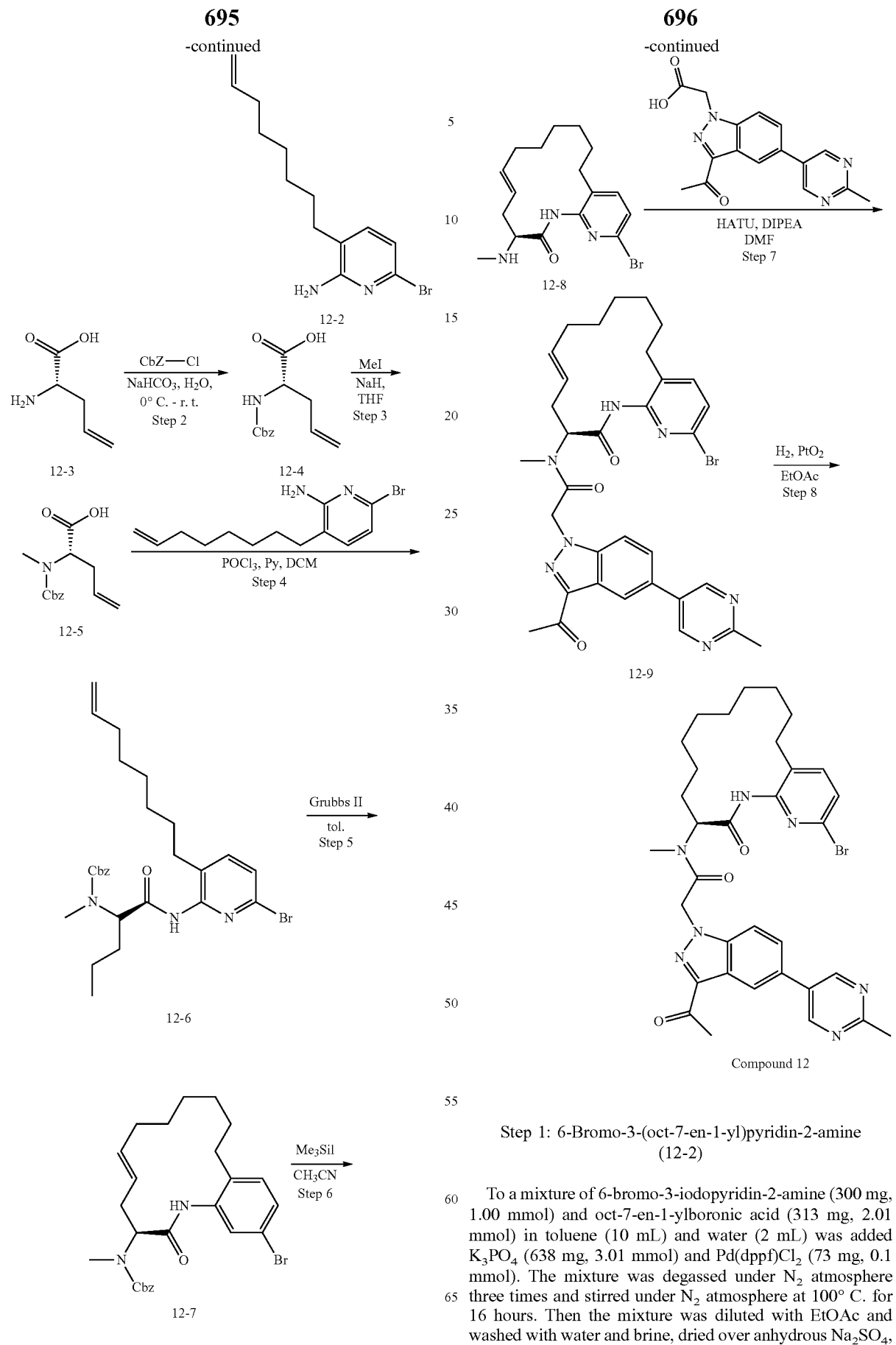

Step 1: 6-Bromo-3-(oct-7-en-1-yl)pyridin-2-amine (12-2)

To a mixture of 6-bromo-3-iodopyridin-2-amine (300 mg, 1.00 mmol) and oct-7-en-1-ylboronic acid (313 mg, 2.01 mmol) in toluene (10 mL) and water (2 mL) was added $K_3PO_4$ (638 mg, 3.01 mmol) and Pd(dppf)$Cl_2$ (73 mg, 0.1 mmol). The mixture was degassed under $N_2$ atmosphere three times and stirred under $N_2$ atmosphere at 100° C. for 16 hours. Then the mixture was diluted with EtOAc and washed with water and brine, dried over anhydrous $Na_2SO_4$, filtered and concentrated to afford crude product that was purified by silica gel chromatography (eluted with PE:EtOAc=60:1) to afford compound 12-2 (95 mg, yield 33.4%) as a light yellow solid. LC/MS (ESI) m/z: 283/285 (M+H)+.

Step 2: (S)-2-(((Benzyloxy)carbonyl)amino)pent-4-enoic acid (12-4)

To a stirring mixture of compound 12-3 (400 mg, 3.47 mmol) and sodium bicarbonate (817 mg, 9.73 mmol) in water (10 mL) was added benzyl chloroformate (1 g, 5.91 mmol) drop-wise at 0° C. and the mixture was stirred at room temperature for 4 hours. The mixture was diluted with water and washed with diethyl ether twice. The aqueous layer was acidified with 10% aqueous citric acid solution and extracted with EtOAc twice. The combined organic layers were washed with brine, dried over anhydrous Na2SO4, filtered and concentrated to dryness to afford compound 12-4 (0.8 g, yield 92.4%) as a viscous oil that was used in the next step without further purification. LC/MS (ESI) m/z: 248 (M−H)−.

Step 3: (S)-2-(((Benzyloxy)carbonyl)(methyl)amino)pent-4-enoic acid (12-5)

To a mixture of compound 12-4 (200 mg, 0.80 mmol) and iodomethane (569 mg, 4.01 mmol) in THF (5 mL) was added sodium hydride (96 mg, 2.41 mmol, 60% dispersion in mineral oil) in portions at 0° C. and the resulting mixture was stirred under N2 atmosphere at room temperature for 5 hours. The reaction was quenched with ice-water and the mixture was concentrated under reduced pressure to remove most of the solvent. The residue was diluted with water and washed with EtOAc twice. The aqueous layer was acidified by adding 10% aqueous citric acid solution and extracted with EtOAc twice. The combined organic layers were dried over anhydrous Na2SO4, filtered and concentrated to dryness. The residue was purified by preparative HPLC to afford compound 12-5 (170 mg, yield 80.5%) as a light yellow oil. LC/MS (ESI) m/z: 262 (M−H).

Step 4: (S)-benzyl (1-((6-Bromo-3-(oct-7-en-1-yl)pyridin-2-yl)amino)-1-oxopent-4-en-2-yl)(methyl)carbamate (12-6)

To a solution of compound 12-5 (50 mg, 0.19 mmol) and compound 2 (54 mg, 0.19 mmol) in DCM (15 mL) was added pyridine (75 mg, 0.95 mmol) and phosphorus oxychloride (44 mg, 0.29 mmol) at 0° C. and the mixture was stirred at 20° C. for 1 hour. The resulting mixture was poured into ice-cooled water and extracted with DCM twice. The combined organic layers were washed with water and brine, dried over anhydrous Na2SO4, filtered and concentrated to dryness. The residue was purified by silica gel chromatography (eluent with PE:EtAOc=5:1) to afford compound 12-6 (65 mg, yield 64.8%) as a gray solid. LC/MS (ESI) m/z: 528/530 (M+H)+.

Step 5: Compound 12-7

To a solution of compound 12-6 (65 mg, 0.12 mmol) in degassed toluene (65 mL) was added Grubbs II (21 mg, 0.025 mmol) and the mixture was stirred under N2 atmosphere at 80° C. for 16 hours. The mixture was concentrated to dryness and the residue was purified by silica gel chromatography (eluent with PE:EtAOc=4:1) to afford compound 12-7 (49 mg, yield 79.6%) as a brown solid. LC/MS (ESI) m/z: 500/502 (M+H)+.

Step 6: Compound 12-8

Iodotrimethylsilane (59 mg, 0.29 mmol) was added to a solution of compound 12-7 (49 mg, 0.10 mmol) in CH3CN (10 mL) at 0° C. and the mixture was stirred at 25° C. for 16 hours. Triethylamine (26 mg, 0.26 mmol) was added and the mixture was stirred at 25° C. for 15 minutes. The mixture was poured into ice-water and extracted with DCM twice. The combined organic layers were washed with saturated aqueous NaHCO3 solution and brine, dried over anhydrous Na2SO4, filtered and concentrated to dryness to afford compound 12-8 (30 mg, yield 83.6%) as a brown oil that was used directly without further purification. (ESI) m/z: 366/368 (M+H)+.

Step 7: Compound 12-9

To a mixture of compound 12-8 (30 mg, 0.08 mmol) and 2-(3-acetyl-5-(2-methylpyrimidin-5-yl)-1H-indazol-1-yl)acetic acid (32 mg, 0.10 mmol) in DMF (5 mL) was added DIPEA (32 mg, 0.25 mmol) and HATU (39 mg, 0.10 mmol) at 0° C. and the resulting mixture was stirred at 25° C. for 24 hours. The mixture was diluted with ethyl acetate, washed with saturated aqueous NH4Cl solution and brine, dried over anhydrous Na2SO4, filtered and concentrated to dryness to afford compound 12-9 (45 mg, yield 85.4%) as a light brown oil that was used directly without further purification. LC/MS (ESI) m/z: 658/660 (M+H)+.

Step 8: Compound 12

To a solution of crude compound 12-9 (45 mg, 0.068 mmol) in EtOAc (5 mL) was added platinum dioxide (15 mg). The mixture was degassed under N2 three times and stirred under a H2 balloon at room temperature for 3 hours. The mixture was filtered and the filtrate was concentrated to dryness. The residue was purified by preparative HPLC to afford Compound 12 (3.1 mg, yield 6.9%) as a white solid. 1H-NMR (400 MHz, DMSO-d6) δ 10.29 (s, 1H), 9.03 (s, 2H), 8.45 (s, 1H), 7.85-7.91 (dd, J=14.8 Hz, 8.4 Hz, 2H), 7.70 (d, J=7.2 Hz, 1H), 7.48 (d, J=6.0 Hz, 1H), 5.65-5.79 (m, 2H), 5.12 (d, J=8.4 Hz, 1H), 3.24 (s, 3H), 2.70 (s, 3H), 2.67 (s, 3H), 2.37-2.62 (m, 2H), 2.04-2.14 (m, 1H), 1.27-1.61 (m, 15H), LC/MS (ESI) m/z: 660/662 (M+H)+.

Scheme 13. Synthesis of Compounds 13 and Compound 14

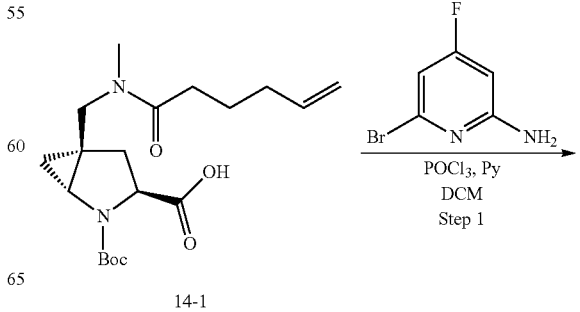

14-1

-continued

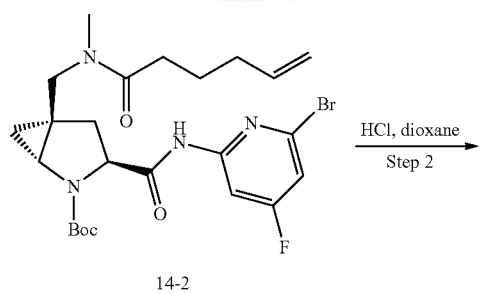

14-2

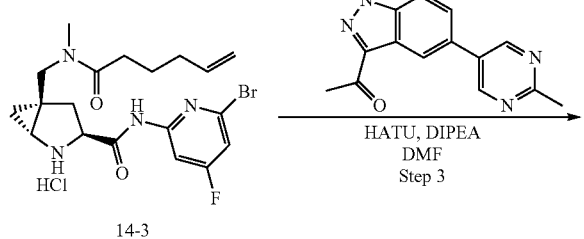

14-3

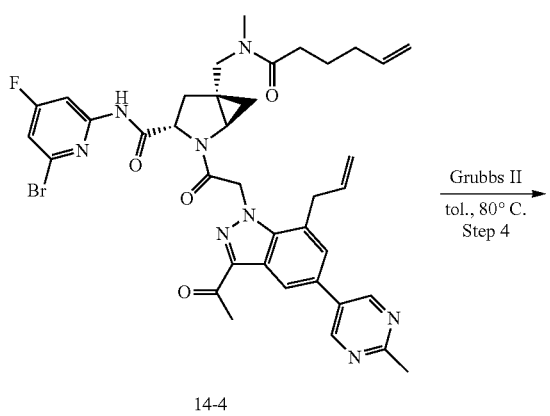

14-4

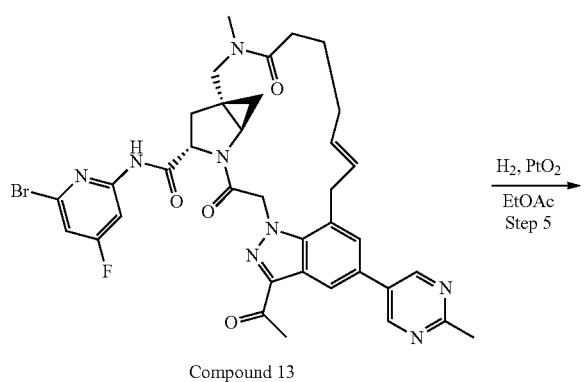

Compound 13

-continued

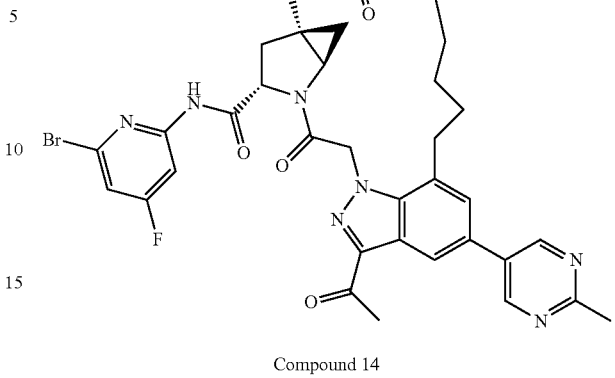

Compound 14

Step 1: (1R,3S,5R)-tert-Butyl 3-((6-bromo-4-fluoro-pyridin-2-yl)carbamoyl)-5-((N-methylhex-5-enamido)methyl)-2-azabicyclo[3.1.0]hexane-2-carboxylate (14-2)

To a mixture of compound 14-1 (120 mg, 0.33 mmol) and 6-bromo-4-fluoropyridin-2-amine (63 mg, 0.33 mmol) in DCM (5 mL) was added pyridine (130 mg, 1.64 mmol) followed by the drop-wise addition of POCl$_3$ (55 mg, 0.36 mmol) at 0° C. and the mixture was stirred at room temperature under N$_2$ atmosphere for 1 hour. The mixture was poured into ice-water and extracted with DCM twice. The combined organic layers were washed with brine, dried with anhydrous Na$_2$SO$_4$, filtered and concentrated to dryness. The residue was purified by chromatography on silica gel (eluted with EtOAc=10:1 to 2:1) to afford compound 14-2 (41 mg, yield 23.2%) as a yellow solid. LC/MS (ESI) m/z: 539/541 (M+H)$^+$.

Step 2: (1R,3S,5R)-N-(6-Bromo-4-fluoropyridin-2-yl)-5-((N-methylhex-5-enamido)methyl)-2-azabicyclo[3.1.0]hexane-3-carboxamide hydrochloride (14-3)

A solution of compound 14-2 (41 mg, 0.076 mmol) in HCl/1,4-dioxane solution (1 mL, 4M) was stirred at 0° C. to room temperature for 1 hour. The reaction mixture was concentrated to dryness, washed with diethyl ether and dried under vacuum to afford compound 14-3 (35 mg, yield 96.8%) as a light yellow solid that was used directly in the next step. LC/MS (ESI) m/z: 439/441 (M+H)$^+$.

Step 3: (1R,3S,5R)-2-(2-(3-Acetyl-7-allyl-5-(2-methylpyrimidin-5-yl)-1H-indazol-1-yl)acetyl)-N-(6-bromo-4-fluoropyridin-2-yl)-5-((N-methylhex-5-enamido)methyl)-2-azabicyclo[3.1.0]hexane-3-carboxamide (14-4)

To a mixture of compound 14-3 (35 mg, 0.075 mmol) and 2-(3-acetyl-7-allyl-5-(2-methylpyrimidin-5-yl)-1H-indazol-1-yl)acetic acid (26 mg, 0.075 mmol) in DMF (1 mL) was added DIPEA (49 mg, 0.38 mmol) followed by HATU (43 mg, 0.11 mmol) at 0° C. and the mixture was stirred at room temperature for 1 hour. The mixture was diluted with EtOAc and washed with saturated aqueous NH$_4$Cl solution and brine, dried over anhydrous Na$_2$SO$_4$, filtered and concentrated to dryness. The residue was purified by chromatography on silica gel (eluted with DCM:MeOH=100:1) to afford compound 14-4 (45 mg, yield 77.6%) as a white solid. LC/MS (ESI) m/z: 771/773 (M+H)⁺.

Step 4: Compound 13

To a solution of compound 14-4 (45 mg, 0.058 mmol) in degassed toluene (45 mL) was added Grubbs 2$^{nd}$ catalyst (12 mg, 0.015 mmol) under $N_2$ atmosphere and the mixture was stirred at 80° C. under $N_2$ atmosphere for 16 hours. The mixture was concentrated to dryness and the residue was purified by chromatography on silica gel (eluted with DCM: MeOH=200:1 to 100:1) to afford Compound 13 (41 mg, yield 94.5%) as a brown solid. ¹H-NMR (400 MHz, CD₃OD) δ 8.99 (s, 2H), 8.46 (d, J=1.6 Hz, 1H), 7.98 (d, J=10.8 Hz, 1H), 7.60-7.55 (m, 1H), 7.16 (dd, J=7.6, 7.6 Hz, 1H), 6.34-6.38 (m, 1H), 6.04-6.08 (d, J=17.6 Hz, 1H), 5.78-5.80 (m, 1H), 5.63-5.68 (d, J=17.8 Hz, 1H), 5.56-5.60 (m, 1H), 4.65-4.67 (m, 1H), 4.20 (d, J=15.6 Hz, 1H), 3.96-3.81 (m, 1H), 3.69 (d, J=17.6 Hz, 1H), 3.51 (d, J=15.6 Hz, 1H), 3.38 (d, J=6.0 Hz, 1H), 3.11-2.98 (m, 1H), 2.93 (s, 3H), 2.74 (s, 3H), 2.67 (s, 3H), 2.59-2.62 (m, 1H), 2.35-2.18 (m, 4H), 1.96-1.90 (m, 1H), 1.83-1.76 (m, 1H), 1.16-1.9 (m, 1H), 1.06-1.11 (m, 1H). LC/MS (ESI) m/z: 743/745 (M+H)⁺.

Step 5: Compound 14

To a solution of Compound 13 (41 mg, 0.055 mmol) in EtOAc (4 mL) was added $PtO_2$ (10 mg) at 0° C. and the mixture was degassed under $N_2$ atmosphere three times and stirred under a $H_2$ balloon at room temperature for 20 minutes. The mixture was filtered and the filtrate was concentrated to dryness. The residue was purified by preparative HPLC to afford Compound 14 (4.6 mg, yield 11.2%) as white solid. ¹H-NMR (400 MHZ, CD₃OD) δ 8.98 (d, J=2.0 Hz, 2H), 8.41 (dd, J=8.4, 1.7 Hz, 1H), 7.92 (d, J=10.6 Hz, 1H), 7.58-7.51 (m, 1H), 7.11-7.16 (m, 1H), 5.97-6.01 (d, J=17.9 Hz, 1H), 5.77-5.61 (m, 1H), 4.45-4.48 (m, 1H), 3.91 (d, J=2.5 Hz, 1H), 3.59-3.46 (m, 1H), 3.24 (s, 3H), 3.20-3.08 (m, 1H), 2.92-2.94 (m, 1H), 2.73 (s, 3H), 2.67 (s, 3H), 2.62-2.50 (m, 2H), 2.35-2.28 (m, 1H), 2.07-1.49 (m, 10H), 1.35-1.38 (m, 1H), 1.06 (dd, J=5.8, 2.8 Hz, 1H). LC/MS (ESI) m/z: 745/747 (M+H)⁺.

Scheme 14. Synthesis of Compound 15

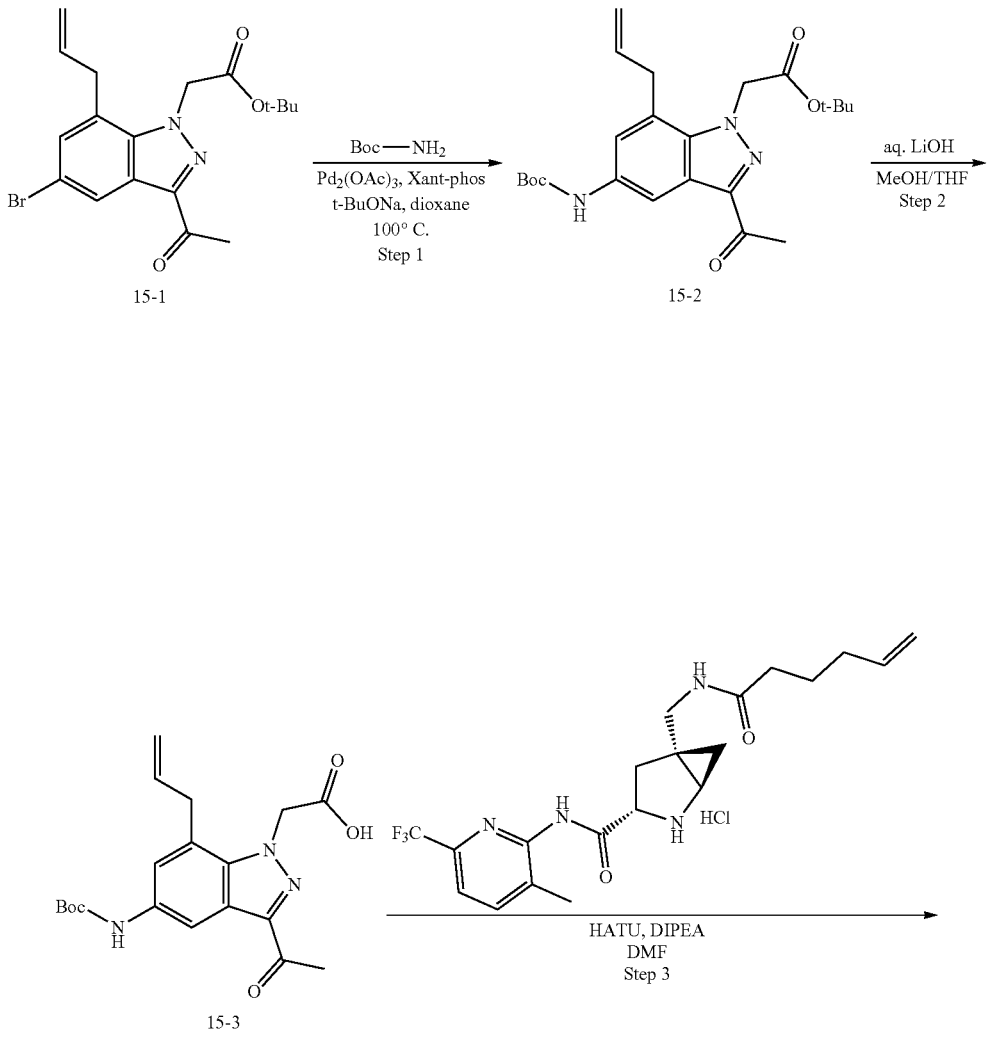

-continued
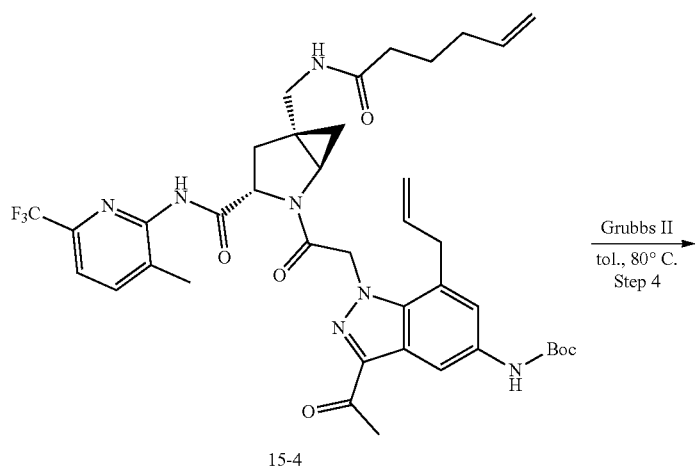
15-4
Grubbs II
tol., 80° C.
Step 4
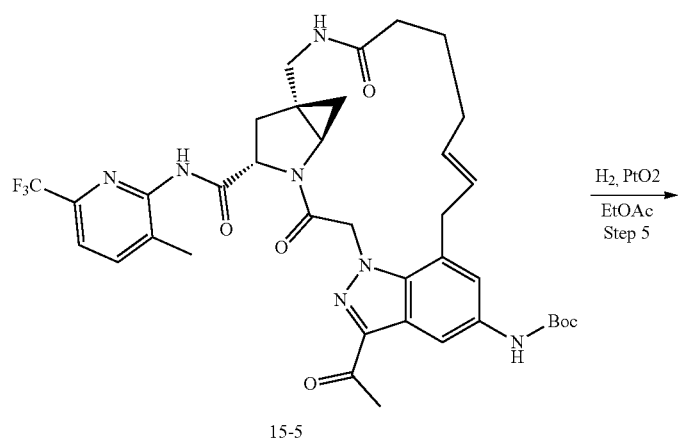
15-5
H₂, PtO2
EtOAc
Step 5
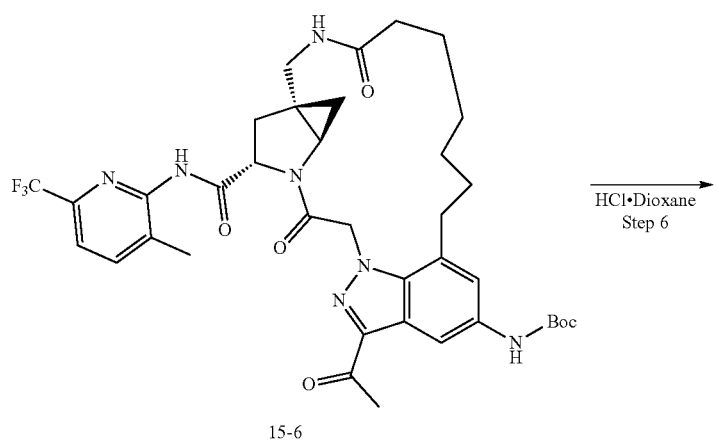
15-6
HCl·Dioxane
Step 6

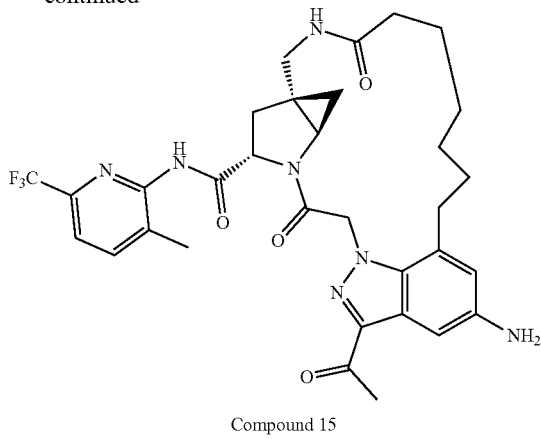

Compound 15

Step 1: tert-Butyl 2-(3-acetyl-7-allyl-5-((tert-butoxycarbonyl)amino)-1H-indazol-1-yl)acetate (15-2)

To a mixture of compound 15-1 (250 mg, 0.64 mmol) and tert-butyl carbamate (223 mg, 1.91 mmol) in 1,4-dioxane were added sodium tert-butoxide (122 mg, 1.27 mmol), Xant-phos (147 mg, 0.25 mmol) and palladium(II) acetate (29 mg, 0.13 mmol) at 0° C. and the mixture was stirred at 100° C. under $N_2$ atmosphere for 4 hours. The mixture was diluted with EtOAc, washed with water and brine, dried over anhydrous $Na_2SO_4$, filtered and concentrated to dryness. The residue was purified by chromatography on silica gel (eluted with PE:EtOAc=20:1) to afford compound 15-2 (115 mg, yield 42.1%) as a white solid. LC/MS (ESI) m/z: 430 $(M+H)^+$.

Step 2: 2-(3-Acetyl-7-allyl-5-((tert-butoxycarbonyl)amino)-1H-indazol-1-yl)acetic acid (15-3)

To a solution of compound 15-2 (50 mg, 0.12 mmol) in methanol (2 mL) and THF (1 mL) was added a solution of LiOH (15 mg, 0.35 mmol) in water (1 mL) at 0° C. and the mixture was stirred at room temperature for 16 hours. The mixture was diluted with water and washed with ether. The aqueous layer was acidified with 1N aqueous HCl solution to a pH of approximately 3 and extracted with DCM twice. The combined organic layers were washed with brine, dried with anhydrous $Na_2SO_4$, filtered and concentrated to dryness to afford compound 15-3 (40 mg, yield 92.0%) as a white solid LC/MS (ESI) m/z: 374 $(M+H)^+$.

Step 3: tert-Butyl (3-acetyl-7-allyl-1-(2-((1R,3S,5R)-5-(hex-5-enamidomethyl)-3-((3-methyl-6-(trifluoromethyl)pyridin-2-yl)carbamoyl)-2-azabicyclo[3.1.0]hexan-2-yl)-2-oxoethyl)-1H-indazol-5-yl)carbamate (15-4)

To a mixture of compound 15-3 (40 mg, 0.11 mmol) and (1R,3S,5R)-5-(hex-5-enamidomethyl)-N-(3-methyl-6-(trifluoromethyl)pyridin-2-yl)-2-azabicyclo[3.1.0]hexane-3-carboxamide hydrochloride (49 mg, 0.11 mmol) in DMF (3 mL) was added DIPEA (69 mg, 0.54 mmol) followed by HATU (61 mg, 0.16 mmol) at 0° C. and the mixture was stirred at room temperature for 1 hour. The mixture was diluted with EtOAc, washed with saturated aqueous $NH_4Cl$ solution and brine, dried over anhydrous $Na_2SO_4$, filtered and concentrated to dryness. The residue was purified by chromatography on silica gel (eluted with DCM:MeOH=80:1) to afford compound 15-4 (50 mg, yield 60.9%) as a yellow solid. LC/MS (ESI) m/z: 766 $(M+H)^+$.

Step 4: Compound 15-5

To a solution of compound 15-4 (50 mg, 0.065 mmol) in degassed toluene (50 mL) was added. Grubbs $2^{nd}$ catalyst (14 mg, 0.016 mmol) under $N_2$ atmosphere and the mixture was stirred at 80° C. under $N_2$ atmosphere for 16 hours. The mixture was concentrated to dryness and the residue was purified by chromatography on silica gel (eluted with DCM:MeOH=200:1 to 80:1) to afford compound 15-5 (38 mg, yield 78.9%) as a brown solid. LC/MS (ESI) m/z: 738 $(M+H)^+$.

Step 5: Compound 15-6

To a solution of compound 15-5 (38 mg, 0.052 mmol) in EtOAc (8 mL) was added $PtO_2$ (10 mg) at 0° C. and the mixture was degassed under $N_2$ atmosphere three times and stirred under a $H_2$ balloon at room temperature for 15 minutes. The mixture was filtered and the filtrate was concentrated to dryness to afford compound 15-6 (38 mg, yield 99.7%) as a brown solid that was used directly in the next step. LC/MS (ESI) m/z: 740 $(M+H)^+$.

Step 6: Compound 15

A solution of compound 15-6 (38 mg, 0.051 mmol) in HCl/1,4-dioxane solution (1 mL, 4M) was stirred at 0° C. to room temperature for 1 hour. The reaction mixture was concentrated to dryness and the residue was purified by preparative HPLC to afford Compound 6 (2 mg, yield 6.1%) as a yellow solid. $^1$H-NMR (400 MHz, DMSO-$d_6$) δ 10.46 (s, 1H), 8.16 (dd, J=8.4, 8.4 Hz, 1H), 7.90 (d, J=8.0 Hz, 1H), 7.65 (d, J=7.6 Hz, 1H), 7.14 (d, 2.0 Hz, 1H), 6.59 (d, J=2.0 Hz, 1H), 5.74 (d, J=17.6 Hz, 1H), 5.31 (d, J=17.6 Hz, 1H), 5.07 (s, 2H), 4.32 (t, J=7.6 Hz, 1H), 3.55-3.50 (m, 1H), 3.30-3.26 (m, 2H), 3.16 (dd, J=14.4, 14.4 Hz, 1H), 2.98-2.90 (m, 1H), 2.46-2.41 (m, 2H), 2.18-2.06 (m, 5H), 1.65-1.32 (m, 8H), 1.17 (t, J=5.6 Hz, 1H), 1.06 (dd, J=5.2, 5.2 Hz, 1H). LC/MS (ESI) m/z: 640 $(M+H)^+$.

Scheme 15. Synthesis of Compound 16

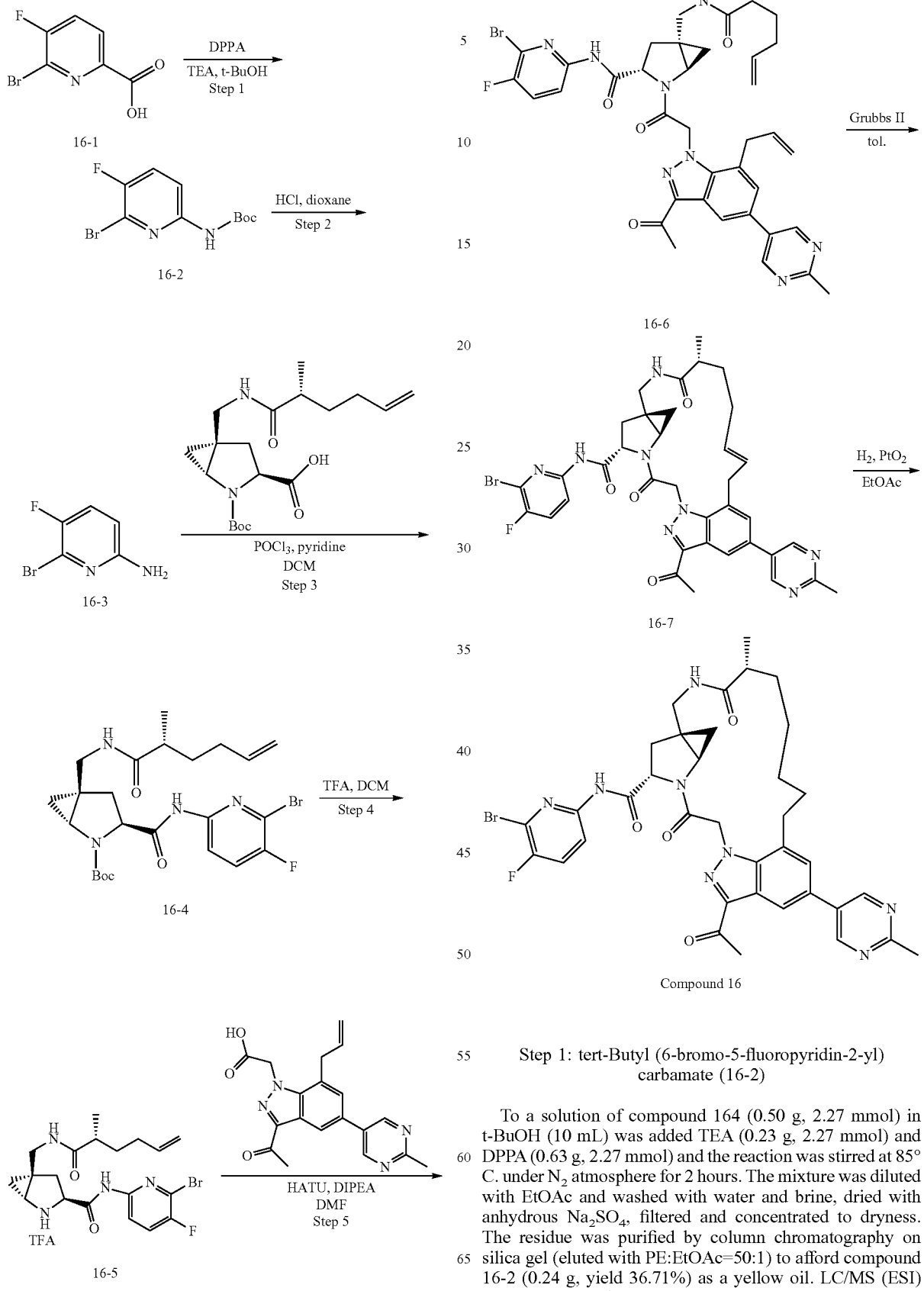

Step 1: tert-Butyl (6-bromo-5-fluoropyridin-2-yl) carbamate (16-2)

To a solution of compound 164 (0.50 g, 2.27 mmol) in t-BuOH (10 mL) was added TEA (0.23 g, 2.27 mmol) and DPPA (0.63 g, 2.27 mmol) and the reaction was stirred at 85° C. under $N_2$ atmosphere for 2 hours. The mixture was diluted with EtOAc and washed with water and brine, dried with anhydrous $Na_2SO_4$, filtered and concentrated to dryness. The residue was purified by column chromatography on silica gel (eluted with PE:EtOAc=50:1) to afford compound 16-2 (0.24 g, yield 36.71%) as a yellow oil. LC/MS (ESI) m/z: 291 (M+H)$^+$.

Step 2: 6-Bromo-5-fluoropyridin-2-amine (16-3)

A solution of compound 16-2 (0.24 g, 0.83 mmol) in HCl/1,4-dioxane solution (3 mL, 4M) was stirred at room temperature for 1 hour. The mixture was concentrated to dryness and the residue was neutralized with saturated aqueous NaHCO$_3$ solution and extracted with EtOAc. The mixture was washed with brine, dried over anhydrous Na$_2$SO$_4$, filtered and concentrated to dryness to afford compound 16-3 (150 mg, yield 94.6%) as a yellow solid. LC/MS (ESI) m/z: 191 (M+H)$^+$.

Step 3: (1R,3S,5R)-tert-Butyl 3-((6-bromo-5-fluoropyridin-2-yl)carbamoyl)-5-(((R)-2-methylhex-5-enamido)methyl)-2-azabicyclo[3.1.0]hexane-2-carboxylate (16-4)

To a mixture of compound 16-3 (30 mg, 0.16 mmol) and (1R,3S,5R)-2-(tert-butoxycarbonyl)-5-(((R)-2-methylhex-5-enamido)methyl)-2-azabicyclo[3.1.0]hexane-3-carboxylic acid (55 mg, 0.16 mmol) in DCM (2 mL) was added pyridine (62 mg, 0.78 mmol) followed by phosphoryl chloride (27 mg, 0.17 mmol) at 0° C. under N$_2$ atmosphere. Then the reaction mixture was stirred at room temperature for 1 hour. The mixture was poured into ice water and extracted with DCM twice. The combined organic layers were washed with brine, dried with Na$_2$SO$_4$ and concentrated. The residue was purified by chromatography on silica gel (eluted with DCM:MeOH=70:1) to afford compound 16-4 (60 mg, yield 70.63%) as a white solid. LC/MS (ESI) m/z: 539 (M+H)$^+$.

Step 4: (1R,3S,5R)-N-(6-Bromo-5-fluoropyridin-2-yl)-5-(((R)-2-methylhex-5-enamido)methyl)-2-azabicyclo[3.1.0]hexane-3-carboxamide (16-5)

To a solution of compound 16-4 (60 mg, 0.11 mmol) in DCM (1 mL) was added. TFA (1 mL) at 0° C. and the reaction was stirred at room temperature for 1 hour. The mixture was concentrated to dryness to afford compound 16-5 (58 mg, yield 100%) as a yellow solid that was directly used in the next reaction without purification. LC/MS (ESI) m/z: 439 (M+H)$^+$.

Step 5: (1R,3S,5R)-2-(2-(3-Acetyl-7-allyl-5-(2-methylpyrimidin-5-yl)-1H-indazol-1-yl)acetyl)-N-(6-bromo-5-fluoropyridin-2-yl)-5-(((R)-2-methylhex-5-enamido)methyl)-2-azabicyclo[3.1.0]hexane-3-carboxamide (16-6)

To a mixture of compound 5 (58 mg, 0.11 mmol) and 2-(3-acetyl-7-allyl-5-(2-methylpyrimidin-5-yl)-1H-indazol-1-yl)acetic acid (39 mg, 0.11 mmol) in DMF (2 mL) was added DIPEA (71 mg, 0.55 mmol) followed by HATU (84 mg, 0.22 mmol) at 0° C. and the reaction was stirred at room temperature for 1 hour. The mixture was diluted with EtOAc and washed with saturated aqueous NH$_4$Cl solution and brine, dried over anhydrous Na$_2$SO$_4$, filtered and concentrated to dryness. The residue was purified by column chromatography on silica gel (eluted with DCM:MeOH=40:1) to afford compound 16-6 (76 mg, yield 90.1%) as a yellow solid. LC/MS (ESI) m/z: 771 (M+H)$^+$.

Step 6: Compound 7

To a solution of compound 16-6 (76 mg, 0.10 mmol) in degassed toluene (60 mL) was added Grubbs 2$^{nd}$ catalyst (21 mg, 0.03 mmol) at 0° C. under N$_2$ atmosphere and the mixture was stirred at 80° C. under N$_2$ atmosphere overnight. The mixture was concentrated to dryness and the residue was purified by chromatography on silica gel (eluted with DCM:MeOH=50:1) to afford compound 16-7 (46 mg, yield 62.8%) as a brown solid. LC/MS (ESI) m/z: 743 (M+H)$^+$.

Step 7: Compound 16

To a solution of compound 16-7 (46 mg, 0.06 mmol) in EtOAc (4 mL) was added PtO$_2$ (12 mg) at 0° C. and the mixture was degassed under N$_2$ atmosphere three times and stirred under a H$_2$ balloon at room temperature for 1.5 hours. The mixture was filtered and the filtrate was concentrated to dryness. The residue was purified by preparative HPLC to afford Compound 16 (3.8 mg, yield 8.50%) as a white solid. $^1$H-NMR (400 MHz, DMSO-d$_6$) δ 10.85 (d, 1H), 9.02 (s, 2H), 8.31 (d, J=5.4 Hz, 1H), 8.06-7.96 (m, 2H), 7.86 (t, 1H), 7.59 (s, 1H), 5.95 (d, J=17.9 Hz, 1H), 5.54 (d, J=17.7 Hz, 1H), 4.24 (t, J=8.3 Hz, 1H), 3.63 (m, 1H), 3.51 (dd, J=14.2, 5.5 Hz, 1H), 3.21-2.96 (m, 4H), 2.68 (s, 3H), 2.63 (s, 3H), 2.40 (d, J=8.3 Hz, 2H), 1.87-1.61 (m, 6H), 1.45 (m, 2H), 1.16 (m, 1H), 1.09 (d, J=6.9 Hz, 3H), 1.06-1.04 (m, 1H). LC/MS (ESI) m/z: 745/747 (M+H)$^+$.

Scheme 16. Synthesis of Compound 17

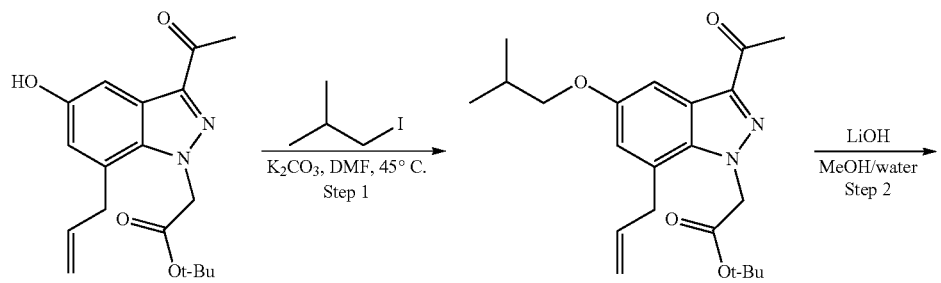

-continued
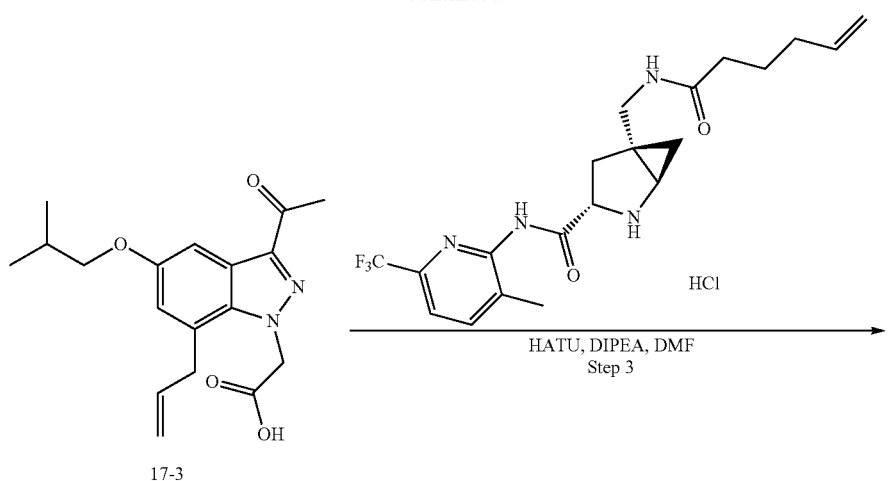
17-3
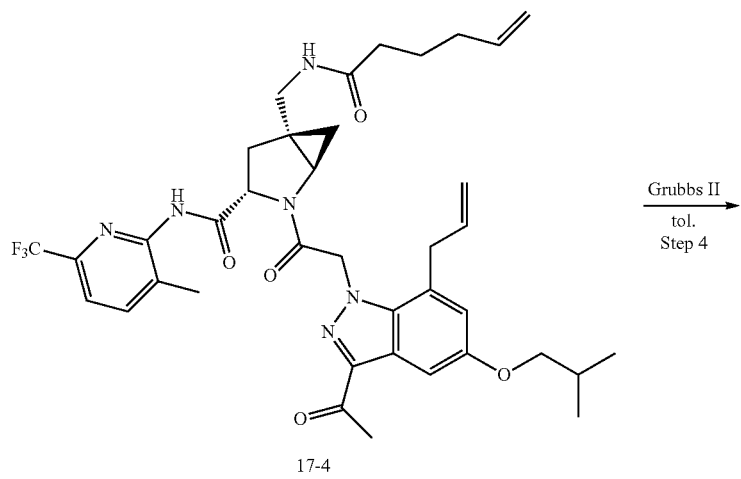
17-4
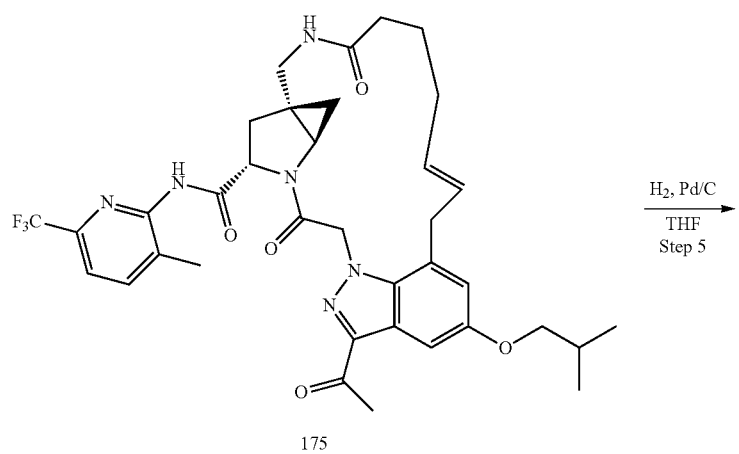
175

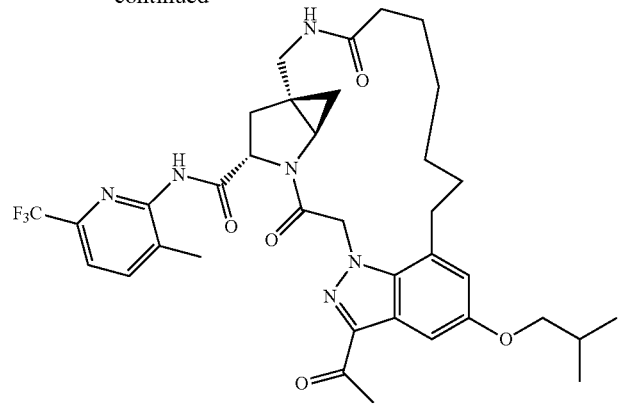

Compound 17

Step 1: tert-Butyl 2-(3-acetyl-7-allyl-5-isobutoxy-1H-indazol-1-yl)acetate (17-2)

To a mixture of compound 17-1 (50 mg, 0.15 mmol) and 1-iodo-2-methylpropane (28 mg, 0.15 mmol) in DMF (2 mL) was added $K_2CO_3$ (52 mg, 0.38 mmol) and the mixture was stirred at 75° C. for 12 hours. The mixture was diluted with EtOAc, washed with water and brine, dried over anhydrous $Na_2SO_4$, filtered and concentrated to dryness. The residue was purified by column chromatography via silica gel (eluted with PE:EtOAc=100:1 to 10:1) to afford compound 17-2 (40 mg, yield 68.4%) as a white solid. LC/MS (ESI) m/z: 387 (M+H)⁺.

Step 2: 2-(3-Acetyl-7-allyl-5-isobutoxy-1H-indazol-1-yl)acetic acid (17-3)

To a solution of compound 17-2 (40 mg, 0.10 mmol) in MeOH (3 mL) was added a solution of lithiumol (6 mg, 0.25 mmol) in water (0.5 mL) and the mixture was stirred at 25° C. for 4 hours. The mixture was diluted with water and washed with diethyl ether twice. The aqueous layer was acidified with 1N aqueous HCl and extracted with DCM twice. The combined organic layers were washed with brine, dried over anhydrous $Na_2SO_4$, filtered and concentrated to dryness to afford compound 17-3 (32 mg, yield 93.6%) as a white solid. LC/MS (ESI) m/z: 331 (M+H)⁺.

Step 3: (1R,3S,5R)-2-(2-(3-Acetyl-7-allyl-5-isobutoxy-1H-indazol-1-yl)acetyl)-5-(hex-5-enamidomethyl)-N-(3-methyl-6-(trifluoromethyl)pyridin-2-yl)-2-azabicyclo[3.1.0]hexane-3-carboxamide (17-4)

To a mixture of compound 17-3 (32 mg, 0.097 mmol) and (1R,3S,5R)-5-(hex-5-enamidomethyl)-N-[3-methyl-6-(trifluoromethyl)pyridin-2-yl]-2-azabicyclo[3.1.0]hexane-3-carboxamide hydrochloride (43 mg, 0.097 mmol) in DMF (2 mL) was added DIPEA (38 mg, 0.29 mmol) followed by added HATU (74 mg, 0.19 mmol) and the mixture was stirred under $N_2$ atmosphere at 25° C. for 12 hours. The mixture was diluted with EtOAc, washed with water, dried over anhydrous $Na_2SO_4$, filtered and concentrated to dryness. The residue was purified by column chromatography via silica gel (eluted with PE:EtOAc=20:1 to 1:3) to afford compound 17-4 (52 mg, yield 74.3%) as a yellow oil. LC/MS (ESI) m/z: 723 (M+H)⁺.

Step 4: Compound 17-5

To a solution of compound 17-4 (52 mg, 0.072 mmol) in toluene (42 mL) was added Grubbs $2^{nd}$ catalyst (13 mg, 0.016 mmol) and the mixture was degassed under $N_2$ atmosphere three times. The mixture was stirred under $N_2$ atmosphere at 80° C. for 16 hours. The mixture was concentrated to dryness and the residue was purified by column chromatography via silica gel (eluted with DCM:MeOH=200:1 to 50:1) to afford compound 17-5 (46 mg, yield 92.0%) as a yellow solid. LC/MS (ESI) m/z: 695 (M+H)⁺.

Step 5: Compound 17

To a solution of compound 17-5 (46 mg, 0.066 mmol) in EtOAc (10 mL) was added $PtO_2$ (9 mg, 0.04 mmol), the mixture was stirred at 25° C. under a $H_2$ balloon for 2 hours. The mixture was filtered and the filtrate was concentrated to dryness. The residue was purified by preparative HPLC to afford Compound 17 (1.2 mg, yield 2.6%) as a white solid. ¹H-NMR (400 MHz, DMSO-$d_6$) δ 10.47 (s, 1H), 8.19 (dd, J=4.7, 3.9 Hz, 1H), 7.90 (d, J=7.8 Hz, 1H), 7.66 (d, J=7.8 Hz, 1H), 7.41 (d, J=2.2 Hz, 1H), 6.83 (d, J=2.1 Hz, 1H), 5.84 (d, J=17.9 Hz, 1H), 5.40 (d, J=17.8 Hz, 1H), 4.32 (t, J=7.8 Hz, 1H), 3.77 (d, J=6.4 Hz, 2H), 3.56 (dd, J=5.6, 2.4 Hz, 1H), 3.28-3.25 (m, 1H), 3.19-3.15 (m, 1H), 3.06-2.99 (m, 1H), 2.78-2.69 (m, 1H), 2.58 (s, 3H), 2.47-2.39 (m, 2.24-2.12 (m, 2H), 2.09 (s, 3H), 2.06-2.00 (m, 1H), 1.72-1.64 (m, 3H), 1.63-1.60 (m, 1H), 1.60-1.54 (m, 1H), 1.51-1.41 (m, 2H), 1.40-1.33 (m, 1H), 1.24 (s, 1H), 1.18 (t, J=5.5 Hz, 1H), 1.09-1.05 (m, 1H), 1.02 (s, 3H), 1.00 (s, 3H). LC/MS (ESI) m/z: 697 (M+H)⁺.

Scheme 17. Synthesis of Compound 18
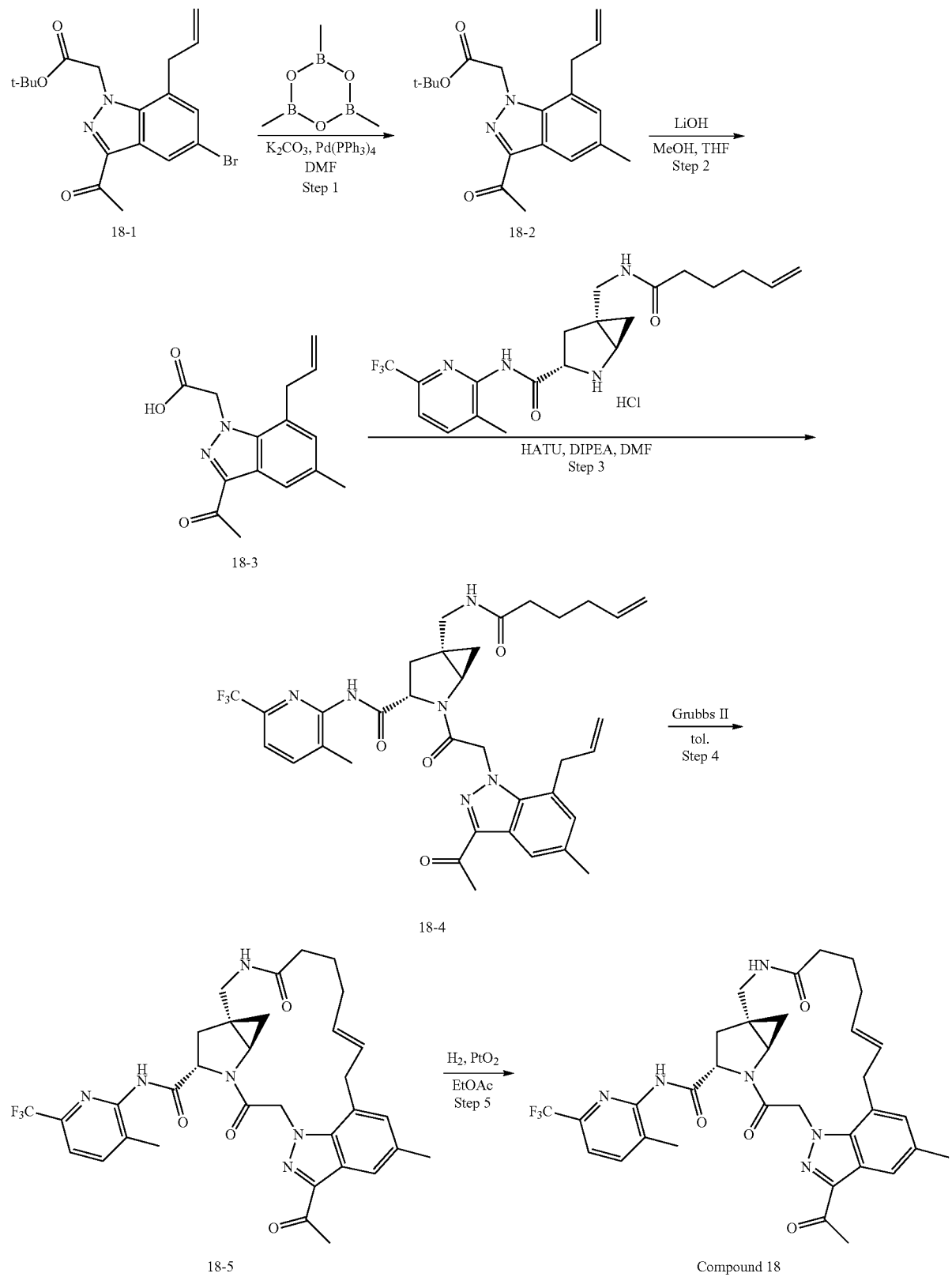

Step 1: tert-Butyl 2-(3-acetyl-7-allyl-5-methyl-1H-indazol-1-yl)acetate (18-2)

To a mixture of compound 18-1 (50 mg, 0.13 mmol) and trimethyl-1,3,5,2,4,6-trioxatriborinane (16 mg, 0.13 mmol) in DMF (2 mL) was added $K_2CO_3$ (35 mg, 0.26 mmol) and $Pd(PPh_3)_4$ (24 mg, 0.02 mmol) and the mixture was stirred at 100° C. under $N_2$ atmosphere for 16 hours. The mixture was diluted with EtOAc, washed with water and brine, dried over anhydrous $Na_2SO_4$, filtered and concentrated to dryness. The residue was purified by column chromatography via silica gel (eluted with PE:EtOAc=50:1 to 5:1) to afford compound 18-2 (35 mg, yield 82%) as a white solid. LC/MS (ESI) m/z: 329 (M+H)$^+$.

Step 2: 2-(3-Acetyl-7-allyl-5-methyl-1H-indazol-1-yl)acetic acid (18-3)

To a solution of compound 18-2 (35 mg, 0.11 mmol) in MeOH (2 mL) was added lithiumol (6 mg, 0.26 mmol) in water (0.5 mL) and the mixture was stirred at 25° C. for 16 hours. The mixture was acidified with 1N aqueous HCl to a pH of approximately 3 and extracted with DCM twice. The combined organic layers were washed with brine, dried over anhydrous $Na_2SO_4$, filtered and concentrated to dryness to afford compound 18-3 (30 mg, yield 98.6%) as a yellow solid. LC/MS (ESI) m/z: 273 (M+H)$^+$.

Step 3: (1R,3S,5R)-2-(2-(3-Acetyl-7-allyl-5-methyl-1H-indazol-1-yl)acetyl)-5-(hex-5-enamidomethyl)-N-(3-methyl-6-(trifluoromethyl)pyridin-2-yl)-2-azabicyclo[3.1.0]hexane-3-carboxamide (18-4)

To a mixture of compound 18-3 (30 mg, 0.11 mmol) and (1R,3S,5R)-5-(hex-5-enamidomethyl)-N-[3-methyl-6-(trifluoromethyl)pyridin-2-yl]-2-azabicyclo[3.1.0]hexane-3-carboxamide hydrochloride (49 mg, 0.11 mmol) in DMF (2 mL) was added DIPEA (43 mg, 0.33 mmol), followed by added HATU (84 mg, 0.22 mmol) and the mixture was stirred at 25° C. for 2 hours. The mixture was diluted with EtOAc, washed with water and brine, dried over anhydrous $Na_2SO_4$, filtered and concentrated to dryness. The residue was purified by column chromatography via silica gel (eluted with DCM:MeOH=200:1 to 75:1) to afford compound 18-4 (40 mg, yield 54.6%) as a yellow oil. LC/MS (ESI) m/z: 665 (M+H)$^+$.

Step 4: Compound 18-5

To a solution of compound 18-4 (40 mg, 0.06 mmol) in degassed toluene (32 mL) was added Grubbs 2$^{nd}$ catalyst (11 mg, 0.013 mmol) under $N_2$ atmosphere and the mixture was stirred at 80° C. under $N_2$ atmosphere for 12 hours. The mixture was concentrated to dryness and the residue was purified by column chromatography via silica gel (eluted with DCM:MeOH=200:1 to 70:1) to afford compound 18-5 (24 mg, yield 62.6%) as a yellow solid. LC/MS (ESI) m/z: 637 (M+H)$^+$.

Step 5: Compound 18

To a solution of compound 18-5 (24 mg, 0.038 mmol) in EtOAc (5 mL) was added $PtO_2$ (5 mg, 0.023 mmol) and the mixture was stirred at 25° C. under a $H_2$ balloon for 2 hours. The mixture was filtered and the filtrate was concentrated to dryness. The residue was purified by preparative HPLC to afford Compound 18 (3.4 mg, yield 14.1%) as a white solid. $^1$H-NMR (400 MHz, DMSO-$d_6$) δ 10.46 (s, 1H), 8.19 (q, J=4.0 Hz, 1H), 7.90 (d, J=7.9 Hz, 1H), 7.83 (s, 1H), 7.66 (d, J=7.8 Hz, 1H), 7.03 (s, 1H), 5.83 (d, J=17.7 Hz, 1H), 5.42 (d, J=17.9 Hz, 1H), 4.33 (t, J=7.8 Hz, 1H), 3.56 (dd, J=5.2, 2.0 Hz, 1H), 3.29-3.26 (m, 1H), 3.20-3.15 (m, 1H), 3.07-2.99 (m, 1H), 2.77-2.68 (m, 1H), 2.58 (s, 3H), 2.47-2.43 (m, 1H), 2.39 (s, 3H), 2.21-2.1 (m, 2H), 2.09 (s, 3H), 1.72-1.64 (m, 3H), 1.63-1.54 (m, 2H), 1.52-1.43 (m, 2H), 1.42-1.35 (m, 1H), 1.24 (m, 1H), 1.19 (m, 1H), 1.10-1.06 (m, 1H). LC/MS (ESI) m/z: 639 (M+H)$^+$.

Scheme 18. Synthesis of Compound 19

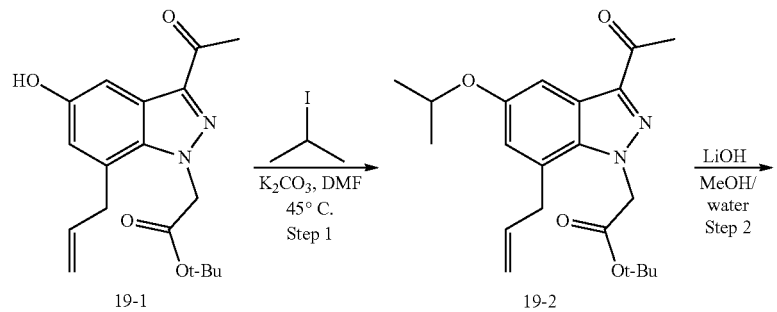

-continued
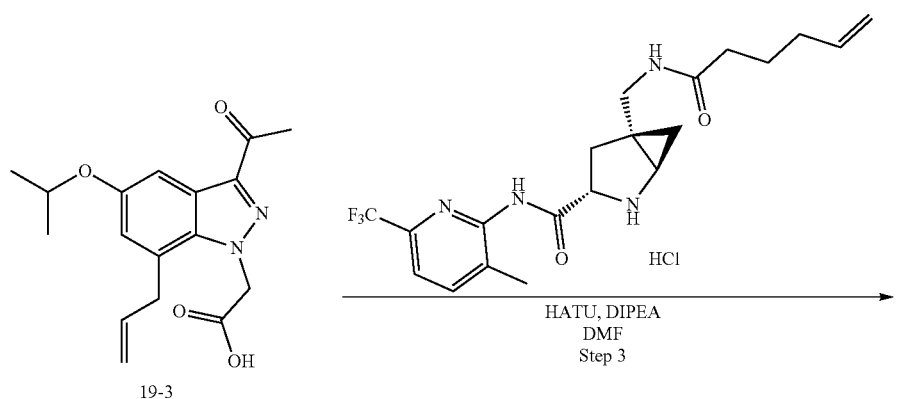
19-3
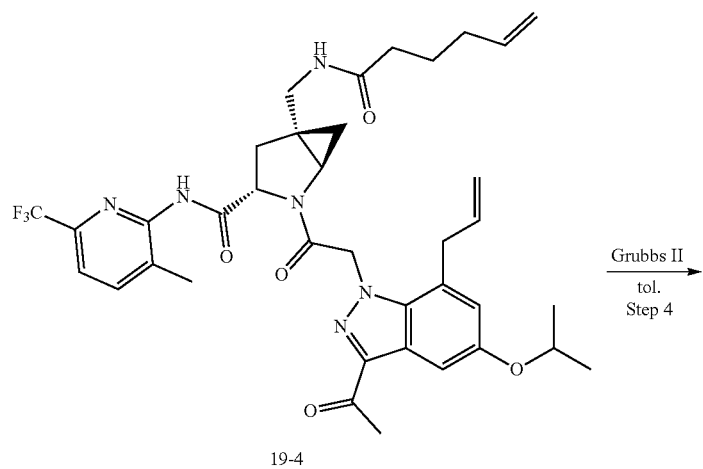
19-4
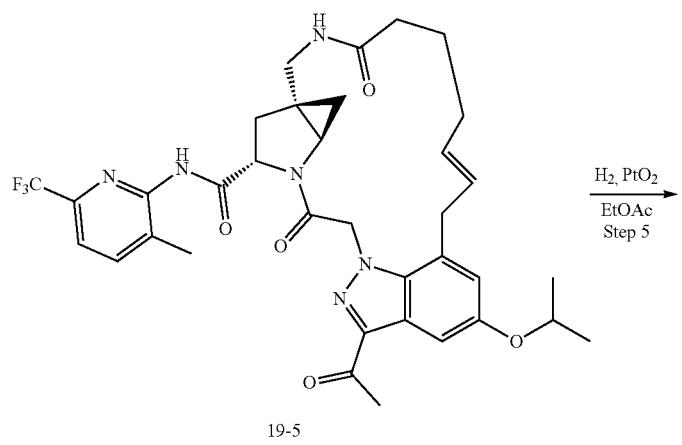
19-5

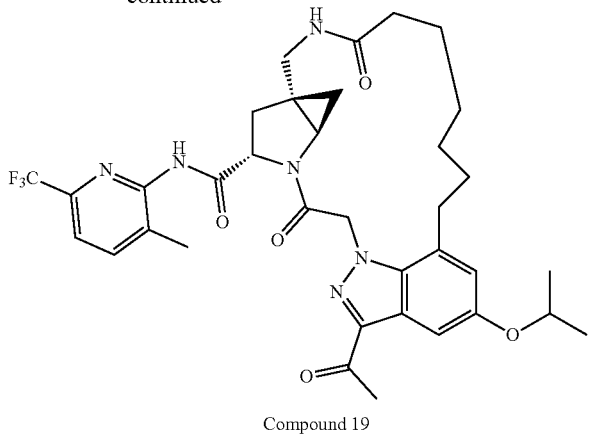

Compound 19

Step 1: tert-Butyl 2-(3-acetyl-7-allyl-5-methyl-1H-indazol-1-yl)acetate (19-2)

To a mixture of compound 19-1 (50 mg, 0.15 mmol) and 2-iodopropane (26 mg, 0.15 mmol) in DMF (2 mL) was added $K_2CO_3$ (52 mg, 0.38 mmol) and the mixture was stirred at 75° C. for 12 hours. The mixture was diluted with EtOAc, washed with water, dried over anhydrous $Na_2SO_4$, filtered and concentrated to dryness. The residue was purified by column chromatography via silica gel (eluted with PE:EtOAc=100:1 to 10:1) to afford compound 19-2 (45 mg, yield 79.8%) as a white solid. LC/MS (ESI) m/z: 373 $(M+H)^+$.

Step 2: 2-(3-Acetyl-7-allyl-5-methyl-1H-indazol-1-yl)acetic acid (19-3)

To a solution of compound 19-2 (43 mg, 0.12 mmol) in MeOH (2 mL) was added a solution of lithiumol (7 mg, 0.29 mmol) in water (0.5 mL) and the mixture was stirred at 25° C. for 4 hours. The mixture was diluted with water and washed with diethyl ether twice. The aqueous layer was acidified with 1N aqueous HCl and extracted with DCM twice. The combined organic layers were washed with brine, dried over anhydrous $Na_2SO_4$, filtered and concentrated to dryness to afford compound 19-3 (37 mg, yield 98.5%) as a yellow solid. LC/MS (ESI) m/z: 317 $(M+H)^+$.

Step 3: (1R,3S,5R)-2-(2-(3-Acetyl-7-allyl-5-methyl-1H-indazol-1-yl)acetyl)-5-(hex-5-enamidomethyl)-N-(3-methyl-6-(trifluoromethyl)pyridin-2-yl)-2-azabicyclo[3.1.0]hexane-3-carboxamide (19-4)

To a mixture of compound 19-3 (37 mg, 0.12 mmol) and (1R,3S,5R)-5-(hex-5-enamidomethyl)-N-[3-methyl-6-(trifluoromethyl)pyridin-2-yl]-2-azabicyclo[3.1.0]hexane-3-carboxamide hydrochloride (51 mg, 0.12 mmol) in DMF (2 mL) was added DIPEA (45 mg, 0.35 mmol), followed by added HATU (90 mg, 0.23 mmol) at 0° C. and the mixture was stirred at 25° C. under $N_2$ atmosphere for 2 hours. The mixture was diluted with EtOAc, washed with saturated aqueous $NH_4Cl$ solution and brine, dried over anhydrous $Na_2SO_4$, filtered and concentrated to dryness. The residue was purified by column chromatography via silica gel (eluted with DCM:MeOH=200:1 to 75:1) to afford compound 19-4 (60 mg, yield 72.4%) as a yellow oil. LC/MS (ESI) m/z: 709 $(M+H)^+$.

Step 4: $(4^1R,4^3S,4^5R,E)$-$1^3$-Acetyl-$1^5$-methyl-N-(3-methyl-6-(trifluoromethyl)pyridin-2-yl)-3,7-dioxo-$1^1H$-$4^2$,6-diaza-1(1,7)-indazola-4(2,5)-bicyclo[3.1.0]hexanacyclotridecaphan-11-ene-$4^3$-carboxamide (19-5)

To a solution of compound 19-4 (60 mg, 0.085 mmol) in toluene (48 mL) was added Grubbs $2^{nd}$ catalyst (16 mg, 0.019 mmol) and the mixture was degassed under $N_2$ atmosphere three times. The mixture was stirred under $N_2$ atmosphere at 80° C. for 16 hours. The mixture was concentrated to dryness and the residue was purified by column chromatography via silica gel (eluted with DCM:MeOH=200:1 to 75:1) to afford compound 19-5 (50 mg, yield 86.7%) as a yellow solid. LC/MS (ESI) m/z: 681 $(M+H)^+$.

Step 5: Compound 19

To a solution of compound 19-5 (50 mg, 0.073 mmol) in EtOAc (10 mL) was added $PtO_2$ (10 mg, 0.044 mmol) and the mixture was stirred at 25° C. under a $H_2$ balloon for 2 hours. The mixture was filtered and the filtrate was concentrated to dryness. The residue was purified by preparative HPLC to afford Compound 19 (3 mg, yield 6.0%) as a white solid. $^1$H-NMR (400 MHz, DMSO-$d_6$) δ 10.47 (s, 1H), 8.19 (dd, J=8.3, 3.7 Hz, 1H), 7.90 (d, J=7.9 Hz, 1H), 7.66 (d, J=7.8 Hz, 1H), 7.43 (d, J=2.2 Hz, 1H), 6.78 (d, J=2.0 Hz, 1H), 5.84 (d, J=17.9 Hz, 1H), 5.39 (d, J=17.8 Hz, 1H), 4.59 (m, 1H), 4.33 (t, J=7.9 Hz, 1H), 3.56 (dd, J=5.5, 2.5 Hz, 1H), 3.31-3.28 (m, 1H), 3.26-3.14 (m, 2H), 3.05-2.97 (m, 1H), 2.77-2.68 (m, 1H), 2.57 (s, 3H), 2.46-2.35 (m, 2H), 2.26-2.12 (m, 2H), 2.09 (s, 3H), 1.72-1.63 (m, 3H), 1.62-1.53 (m, 2H), 1.52-1.42 (m, 2H), 1.40-1.34 (m, 1H), 1.30 (s, 3H), 1.28 (s, 3H), 1.18 (m, 1H), 1.09-1.05 (m, 1H). LC/MS (ESI) m/z: 683 $(M+H)^+$.

Scheme 19. Synthesis of Compound 20
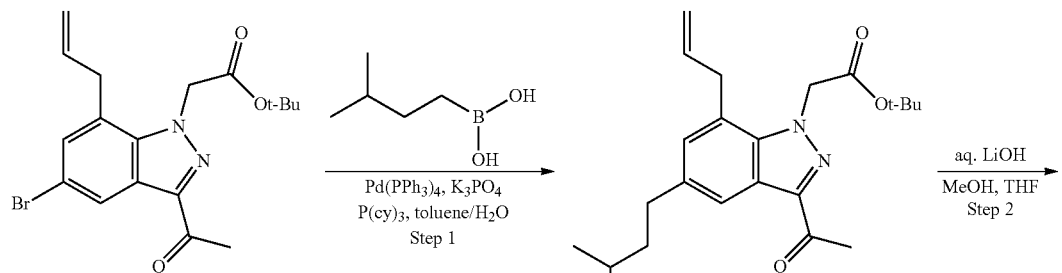
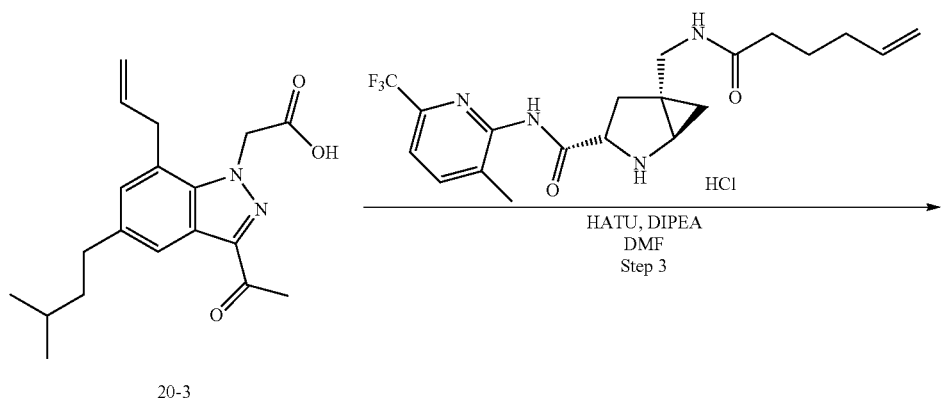
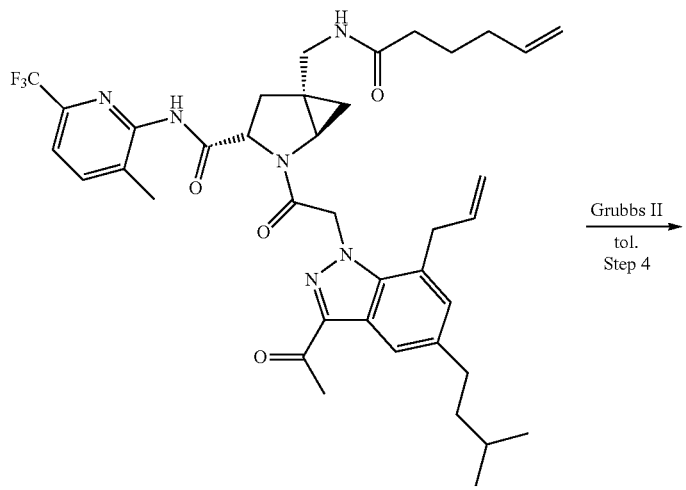

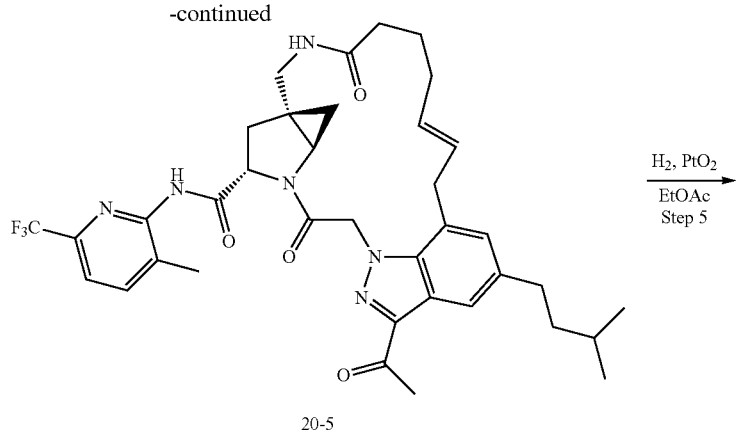

20-5

Step 1: tert-Butyl 2-(3-acetyl-7-allyl-5-isopentyl-1H-indazol-1-yl)acetate (20-2)

To a solution of compound 20-1 (60 mg, 0.15 mmol) and 3-methylbutylboronic acid (21 mg, 0.183 mmol) in toluene (3 mL) and water (0.5 mL) was added $K_3PO_4$ (81 mg, 0.38 mmol), tricyclohexyl phosphine (9 mg, 0.031 mmol) and $Pd(PPh_3)_4$ (18 mg, 0.015 mmol). The mixture was degassed under $N_2$ three times and stirred at 90° C. under $N_2$ atmosphere for 10 hours. The mixture was diluted with EtOAc and washed with water and brine, dried over anhydrous $Na_2SO_4$, filtered and concentrated to dryness. The residue was purified by silica gel chromatography (eluted with PE:EtOAc=20:1) to afford compound 20-2 (50 mg, yield 85.2%) as a yellow oil. LC/MS (ESI) m/z: 385 (M+H)$^+$.

Step 2: 2-(3-Acetyl-7-allyl-5-isopentyl-1H-indazol-1-yl)acetic acid (20-3)

To a solution of compound 20-2 (50 mg, 0.13 mmol) in MeOH (1 mL), THF (1 mL) and water (0.5 mL) was added lithium hydroxide (9 mg, 0.39 mmol) and the mixture was stirred at room temperature for 2 hours. The mixture was concentrated to dryness and diluted with water. The mixture was washed with EtOAc and acidified with 1 N aqueous HCl to a pH of approximately 3 at 0° C. The mixture was extracted with DCM twice and the combined organic layers were washed with brine, dried over anhydrous $Na_2SO_4$, filtered and concentrated to dryness to afford compound 20-3 (45 mg, yield 105.4%) as a light yellow solid that was directly used to the next reaction without purification. LC/MS (ESI) 329 (M+H)$^+$.

Step 3: (1R,3S,5R)-2-(2-(3-Acetyl-7-allyl-5-isopentyl-1H-indazol-1-yl)acetyl)-5-(hex-5-enamidomethyl)-N-(3-methyl-6-(trifluoromethyl)pyridin-2-yl)-2-azabicyclo[3.1.0]hexane-3-carboxamide (20-4)

To a mixture of compound 20-3 (45 mg, 0.13 mmol) and (1R,3S,5R)-5-(hex-5-enamidomethyl)-N-[3-methyl-6-(trifluoromethyl)pyridin-2-yl]-2-azabicyclo[3.1.0]hexane-3-carboxamide hydrochloride (71 mg, 0.16 mmol) in DMF (4 mL) was added HATU (63 mg, 0.16 mmol) followed by DIPEA (44 mg, 0.34 mmol) at 0° C. and the mixture was stirred at room temperature for 2 hours. The mixture was diluted with EtOAc, washed with saturated aqueous $NH_4Cl$ solution and brine, dried over anhydrous $Na_2SO_4$, filtered and concentrated to dryness. The residue was purified by column chromatography via silica gel (eluted with DCM:MeOH=30:1) to afford compound 20-4 (45 mg, yield 45.6%) as a yellow solid. LC/MS (ESI) m/z: 721 (M+H)$^+$.

Step 4: Compound 20-5

To a solution of compound 20-4 (45 mg, 0.062 mmol) in degassed toluene (45 mL) was added Grubbs $2^{nd}$ catalyst (13 mg, 0.016 mmol) and the resulting mixture was degassed again and stirred at 80° C. under $N_2$ atmosphere for 16 hours. The mixture was concentrated to dryness and the residue was purified by silica gel chromatography (eluted with DCM:MeOH=30:1) to afford compound 20-5 (30 mg, yield 27.7%) as a light yellow solid. LC/MS (ESI) m/z: 693 (M+H)$^+$.

Step 5: Compound 20

To a solution of compound 20-5 (30 mg, 0.043 mmol) in EtOAc (3 mL) was added. $PtO_2$ (10 mg, 0.043 mmol) and the mixture was degassed under $N_2$ three times. The mixture was stirred under a $H_2$ balloon at room temperature for 1 hour. The mixture was filtered and the filtrate was concentrated to dryness. The residue product was purified by preparative HPLC to afford Compound 20 (5 mg, yield 16.6%) as a white solid, $^1$H-NMR (400 MHz, $CD_3OD$) δ 7.90 (d, J=10.8 Hz, 1H), 7.81 (d, J=7.6 Hz, 1H), 7.56 (d, J=7.8 Hz, 1H), 7.03 (d, J=11.5 Hz, 1H), 5.87 (d, J=17.8 Hz, 1H), 5.57 (d, J=17.7 Hz, 1H), 4.52 (t, J=6.7 Hz, 1H), 3.62 (d, J=3.0 Hz, 1H), 3.47 (d, J=14.5 Hz, 1H), 3.35 (s, 1H), 3.04 (m, 1H), 2.77 (dd, J=16.9, 5.6 Hz, 1H), 2.73-2.67 (m, 2H), 2.64 (s, 3H), 2.59 (d, J=7.1 Hz, 2H), 2.37-2.24 (m, 2H), 2.13 (s, 3H), 1.86-1.58 (m, 6H), 1.53 (dd, J=14.2, 6.4 Hz, 4H), 1.40 (t, J=5.9 Hz, 2H), 1.15 (m, 1H), 0.95 (d, J=6.3 Hz, 6H). LC/MS (ESI) m/z: 695 (M+H)$^+$.

Scheme 20. Synthesis of Compound 21
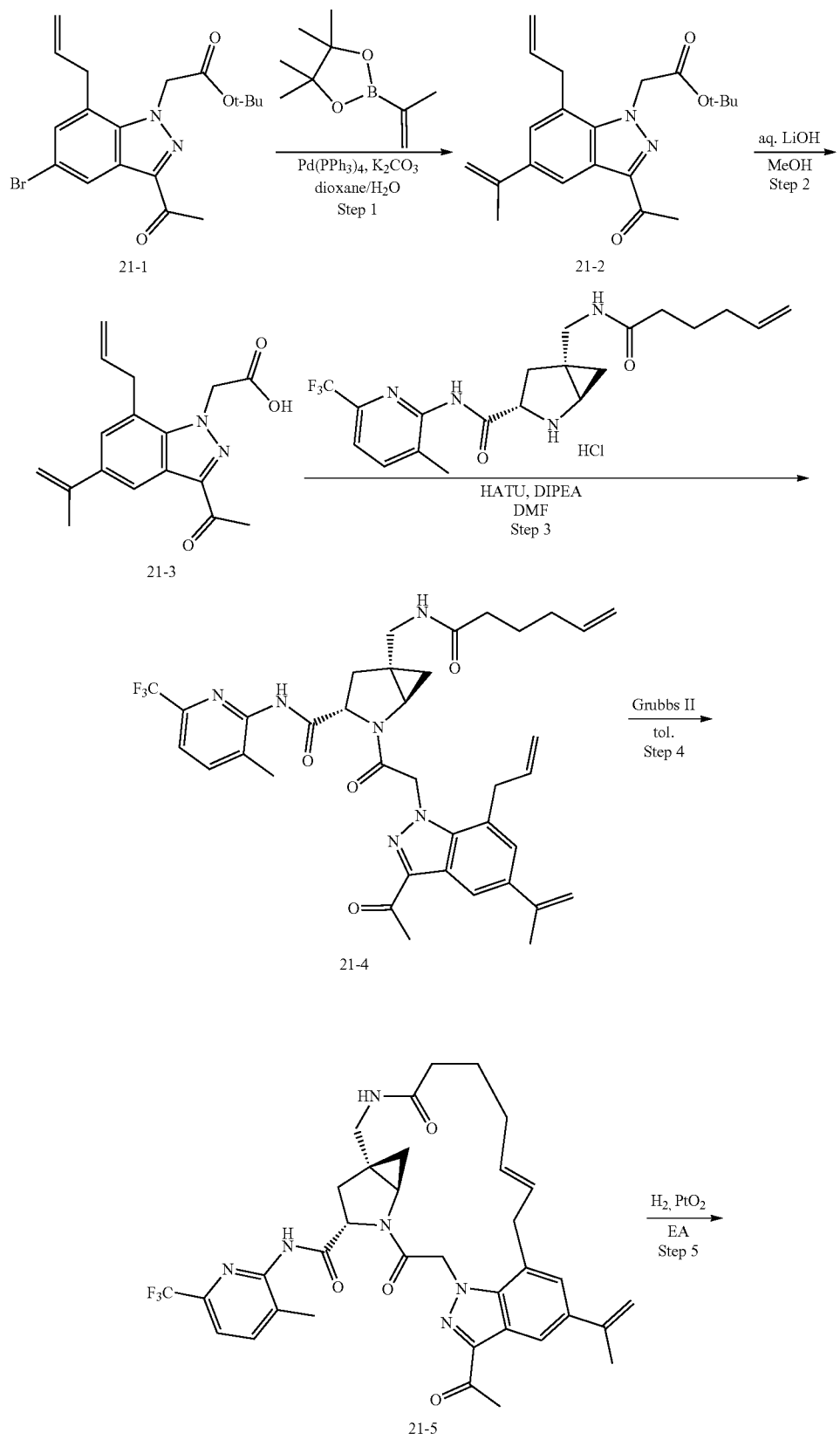

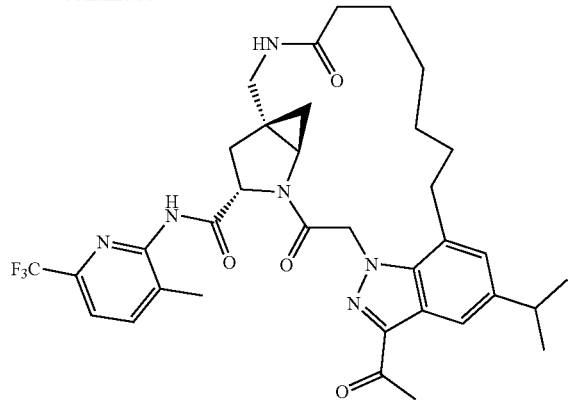

Compound 21

Step 1: tert-Butyl 2-(3-acetyl-7-allyl-5-(prop-1-en-2-yl)-1H-indazol-1-yl)acetate (21-2)

To a solution of compound 21-1 (50 mg, 0.13 mmol) and 4,4,5,5-tetramethyl-2-(prop-1-en-2-yl)-1,3,2-dioxaborolane (18 mg, 0.11 mmol) in 1,4-dioxane (1.5 mL) and water (1 mL) was added K$_2$CO$_3$ (59 mg, 0.42 mmol) and Pd(dppf)Cl$_2$ (13 mg, 0.013 mmol) and the mixture was stirred at 90° C. under N$_2$ atmosphere for 16 hours. The mixture was filtered and the filter cake was washed with ethyl acetate. The combined filtrate was washed with brine, dried over anhydrous Na$_2$SO$_4$, filtered and concentrated to dryness. The residue was purified by silica gel chromatography (eluted with PE:EtOAc=30:1) to afford compound 21-2 (30 mg, yield 64.1%) as a yellow solid. LC/MS (ESI) m/z: 369 (M+H)$^+$.

Step 2: 2-(3-acetyl-7-allyl-5-(prop-1-en-2-yl)-1H-indazol-1-yl)acetic acid (21-3)

To a solution of compound 21-2 (30 mg, 0.085 mmol) in THF (1 mL), MeOH (1 mL) and water (0.5 mL) was added LiOH (5 mg, 0.21 mmol) and the mixture was stirred at room temperature for 2 hours. The mixture was concentrated to dryness and diluted with water. The mixture was washed with EtOAc twice and acidified with 1 N aqueous HCl to a pH of approximately 3 at 0° C. The mixture was extracted with DCM twice and the combined organic layers were washed with brine, dried over anhydrous Na$_2$SO$_4$, filtered and concentrated to dryness to afford compound 21-3 (25 mg, yield 99.0%) as a light yellow solid that was directly used to the next reaction without purification. LC/MS (ESI) m/z: 299 (M+H)$^+$.

Step 3: (1R,3S,5R)-2-(2-(3-Acetyl-7-allyl-5-(prop-1-en-2-yl)-1H-indazol-1yl)acetyl)-5-(hex-5-enamidomethyl)-N-(3-methyl-6-(trifluoromethyl)pyridin-2-yl)-2-azabicyclo[3.1.0]hexane-3-carboxamide (21-4)

To a mixture of compound 21-3 (25 mg, 0.084 mmol) and (1R,3S,5R)-5-(hex-5-enamidomethyl)-N-[3-methyl-6-(trifluoromethyl)pyridin-2-yl]-2-azabicyclo[3.1.0]hexane-3-carboxamide hydrochloride (41 mg, 0.10 mmol) in DMF (3 mL) was added HATU (0.038 g, 0.10 mmol) followed by DIPEA (27 mg, 0.21 mmol) at 0° C. and the mixture was stirred at room temperature for 2 hours. The mixture was diluted with EtOAc, washed with saturated aqueous NH$_4$Cl solution and brine, dried over anhydrous Na$_2$SO$_4$, filtered and concentrated to dryness. The residue was purified by column chromatography via silica gel (DCM:MeOH=30:1) to afford compound 21-4 (30 mg, yield 51.8%) as a yellow solid. LC/MS (ESI) m/z: 691 (M+H)$^+$.

Step 4: (4$^1$R,4$^3$S,4$^5$R,E)-1$^3$-Acetyl-N-(3-methyl-6-(trifluoromethyl)pyridin-2-yl)-3,7-dioxo-1$^5$-(prop-1-en-2-yl)-1$^1$H-4$^2$,6-diaza-1(1,7)-indazola-4(2,5)-bicyclo[3.1.0]hexanacyclotridecaphan-11-ene-4$^3$-carboxamide (21-5)

To a solution of compound 21-4 (30 mg, 0.043 mmol) in degassed toluene (30 mL) was added Grubbs 2$^{nd}$ catalyst (15 mg) and the resulting mixture was degassed again and stirred at 80° C. under N$_2$ atmosphere for 16 hours. The mixture was concentrated to dryness and the residue was purified by silica gel chromatography (eluted with DCM:MeOH=30:1) to afford compound 21-5 (25 mg, yield 21.7%) as a light yellow solid. LC/MS (ESI) m/z: 663 (M+H)$^+$.

Step 5: (4$^1$R,4$^3$S,4$^5$R)-1$^3$-Acetyl-1$^5$-isopropyl-N-(3-methyl-6-(trifluoromethyl)pyridin-2-yl)-3,7-dioxo-1$^1$H-4$^2$,6-diaza-1(1,7)-indazola-4(2,5)-bicyclo[3.1.0]hexanacyclotridecaphane-4$^3$-carboxamide (Compound 21)

To a solution of compound 21-5 (25 mg, 0.038 mmol) in EtOAc (5 mL) was added PtO$_2$ (8 mg) and the mixture was degassed under N$_2$ three times and stirred under a H$_2$ balloon at room temperature for 1 hour. The mixture was filtered and the filtrate was concentrated to dryness. The residue product was purified by preparative HPLC to afford Compound 21 (4 mg, yield 15.9%) as a white solid. $^1$H-NMR (400 MHz, CD$_3$OD) δ 7.96 (s, 1H), 7.81 (d, J=7.8 Hz, 1H), 7.56 (d, J=7.8 Hz, 1H), 7.10 (s, 1H), 5.87 (d, J=17.8 Hz, 1H), 5.57 (d, J=17.8 Hz, 1H), 4.52 (t, J=6.9 Hz, 1H), 3.62 (dd, J=5.8, 2.8 Hz, 1H), 3.47 (d, J=14.5 Hz, 1H), 3.35 (s, 1H), 3.11-3.02 (m, 1H), 2.99 (dd, J=13.7, 6.8 Hz, 1H), 2.77 (dd, J=22.0, 10.7 Hz, 1H), 2.65 (s, 3H), 2.59 (d, J=7.3 Hz, 2H), 2.37-2.25 (m, 2H), 2.13 (s, 3H), 1.64 (m, 8H), 1.40 (t, J=5.8 Hz, 2H), 1.28 (dd, J=6.9, 1.4 Hz, 6H), 1.15 (m, 1H). LC/MS (ESI) m/z: 667 (M+H)$^+$.

Scheme 21. Synthesis of Compound 22
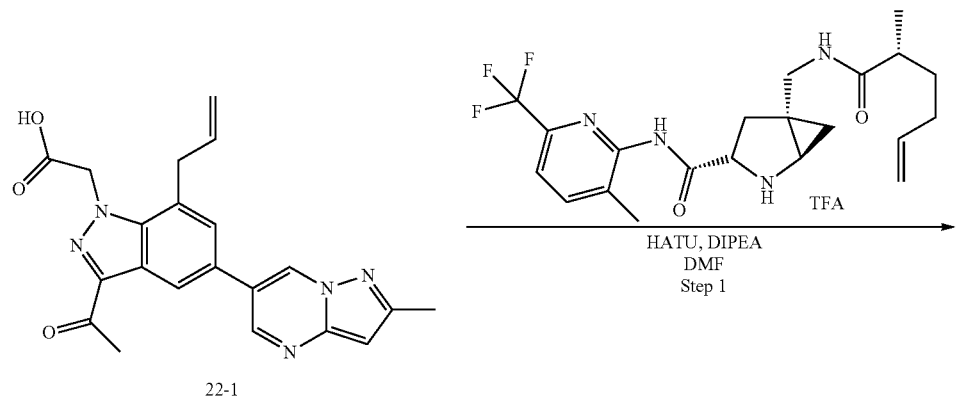
22-1
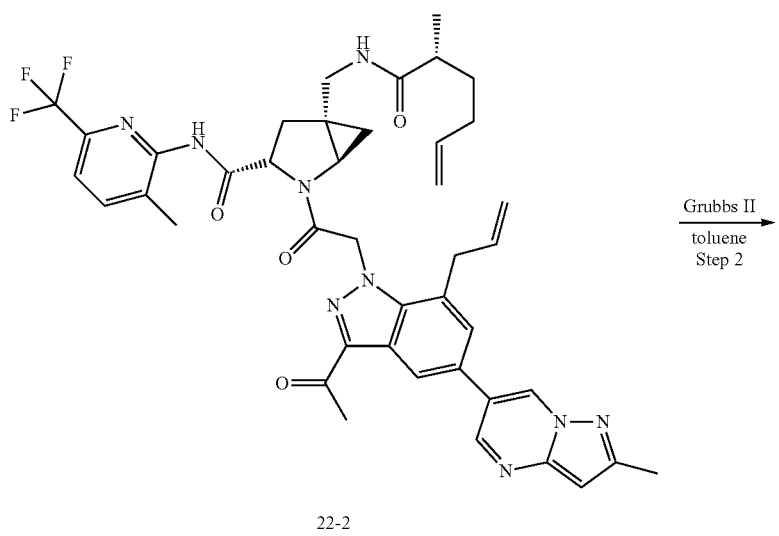
22-2
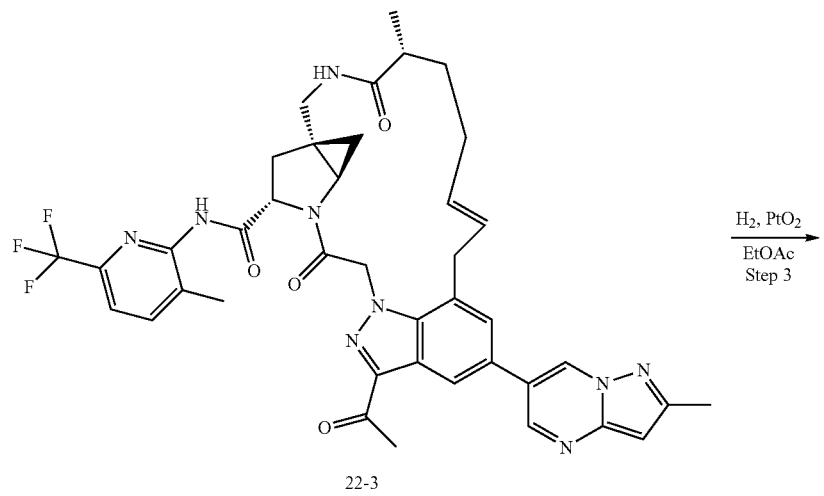
22-3

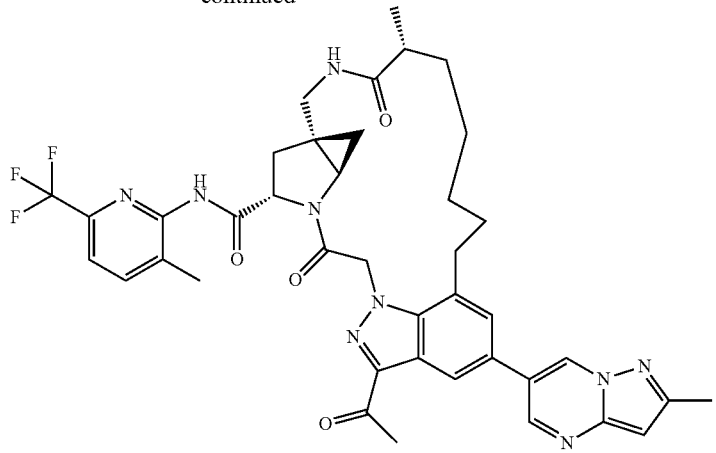

Compound 22

Step 1: (1R,3S,5R)-2-(2-(3-Acetyl-7-allyl-5-(2-methylpyrazolo[1,5-a]pyrimidin-6-yl)-1H-indazol-1-yl)acetyl)-N-(3-methyl-6-(trifluoromethyl)pyridin-2-yl)-5-(((R)-2-methylhex-5-enamido)methyl)-2-azabicyclo[3.1.0]hexane-3-carboxamide (22-2)

To a mixture of compound 22-1 (54 mg, 0.14 mmol) and (1R,3S,5R)-N-(3-methyl-6-(trifluoromethyl)pyridin-2-yl)-5-(((R)-2-methylhex-5-enamido)methyl)-2-azabicyclo[3.1.0]hexane-3-carboxamide TFA salt (73 mg, 0.14 mmol) in DMF (2 mL) was added DIPEA (90 mg, 0.69 mmol) followed by HATU (106 mg, 0.28 mmol) at 0° C. and the reaction was stirred at room temperature for 1 hour. The mixture was diluted with EtOAc and washed with saturated aqueous NH$_4$Cl solution and brine, dried over anhydrous Na$_2$SO$_4$, filtered and concentrated to dryness. The residue was purified by column chromatography on silica gel (eluted with DCM:MeOH=80:1) to afford compound 22-2 (84 mg, yield 76.1%) as a yellow solid. LC/MS (ESI) m/z: 796 (M+H)$^+$.

Step 2: Compound 22-3

To a solution of compound 22-2 (84 mg, 0.11 mmol) in degassed toluene (67 mL) was added Grubbs 2$^{nd}$ catalyst (23 mg, 0.03 mmol) at 0° C. under N$_2$ atmosphere and the mixture was stirred at 80° C. under N$_2$ atmosphere overnight. The mixture was concentrated to dryness and the residue was purified by chromatography on silica gel (eluted with DCM:MeOH=50:1) to afford compound 22-3 (54 mg, yield 66.7%) as a brown solid. LC/MS (ESI) m/z: 768 (M+H)$^+$.

Step 3: Compound 22

To a solution of compound 22-4 (54 mg, 0.07 mmol) in EtOAc (5 mL) was added PtO$_2$ (14 mg) at 0° C. and the mixture was degassed under N$_2$ atmosphere three times and stirred under a H$_2$ balloon at room temperature for 1.5 hours. The mixture was filtered and the filtrate was concentrated to dryness. The residue was purified by preparative HPLC to afford Compound 22 (5.6 mg, yield 10.4%) as a white solid. $^1$H-NMR (400 MHz, DMSO-d$_6$) δ 10.42 (s, 1H), 9.32 (d, J=1.5 Hz, 1H), 8.82 (d, J=2.3 Hz, 1H), 8.33 (d, J=1.6 Hz, 1H), 7.98 (t, J=6.2 Hz, 1H), 7.89 (d, J=7.8 Hz, 1H), 7.69-7.51 (m, 2H), 6.56 (s, 1H), 5.93 (d, J=17.8 Hz, 1H), 5.52 (d, J=17.6 Hz, 1H), 4.27 (t, J=8.2 Hz, 1H), 3.62-3.64 (m, 1H), 3.52-3.57 (dd, J=14.2, 5.7 Hz, 1H), 3.31-3.26 (m, 1H), 3.15-2.93 (m, 3H), 2.64 (s, 3H), 2.47-2.51 (m, 1H), 2.46 (s, 3H), 2.27-2.29 (m, 1H), 2.10 (s, 3H), 1.91-1.50 (m, 6H), 1.38-1.39 (m, 2H), 1.15-1.16 (m, 1H), 1.06-1.08 (d, J=7.2 Hz, 3H), 1.05-1.07 (m, 1H). LC/MS (ESI) m/z: 770 (M+H)$^+$.

Scheme 22. Synthesis of Compound 23

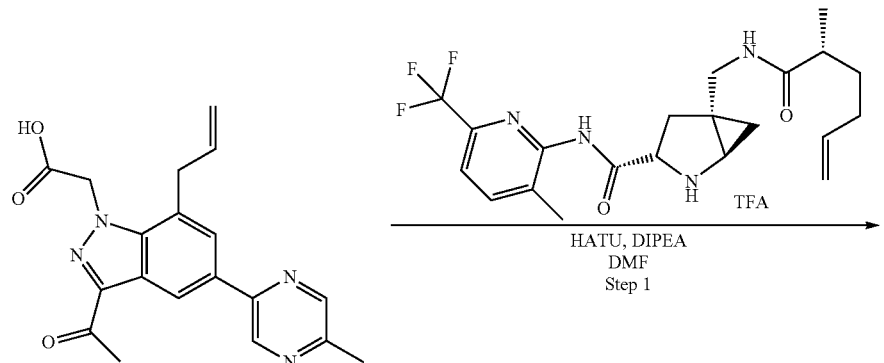

23-1

-continued
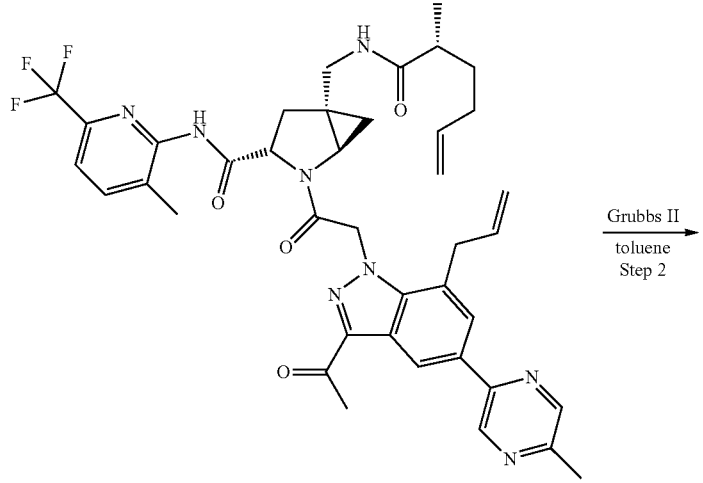
23-2
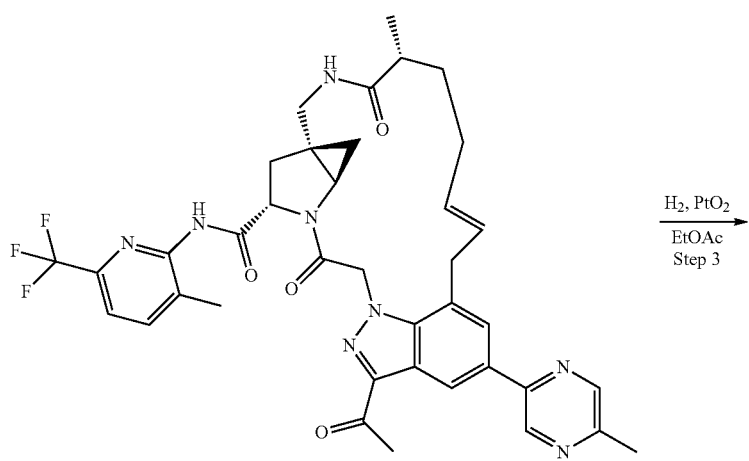
23-3
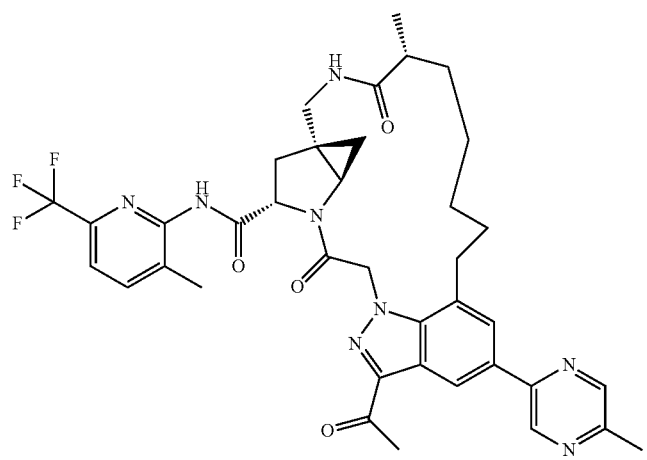
Compound 23

Step 1: (1R,3S,5R)-2-(2-(3-Acetyl-7-allyl-5-(5-methylpyrazin-2-yl)-1H-indazol-1-yl) acetyl)-N-(3-methyl-6-(trifluoromethyl) pyridin-2-yl)-5-(((R)-2-methylhex-5-enamido) methyl)-2-azabicyclo[3.1.0] hexane-3-carboxamide (23-2)

To a mixture of compound 23-1 (40 mg, 0.11 mmol) and (1R,3S,5R)-N-(3-methyl-6-(trifluoromethyl)pyridin-2-yl)-5-(((R)-2-methylhex-5-enamido)methyl)-2-azabicyclo [3.1.0]hexane-3-carboxamide TFA salt (57 mg, 0.11 mmol) in DMF (3 mL) was added DIPEA (74 mg, 0.57 mmol) followed by HATU (65 mg, 0.17 mmol) at 0° C. and the mixture was stirred at room temperature for 2 hours. The mixture was diluted with EtOAc and washed with saturated aqueous NH₄Cl solution and brine, dried over anhydrous Na₂SO₄, filtered and concentrated to dryness. The residue was purified by chromatography on silica gel (eluted with PE:EtOAc=2:1 to 1:2) to afford compound 23-2 (60 mg, yield 69.4%) as a yellow oil. LC/MS (ESI) m/z: 757 (M+H)⁺.

Step 2: Compound 23-3

To a solution of compound 23-2 (60 mg, 0.079 mmol) in degassed toluene (60 mL) was added Grubbs 2ⁿᵈ catalyst (13 mg, 0.016 mmol) at 0° C. under N₂ atmosphere and the mixture was stirred at 80° C. overnight under N₂ atmosphere. The mixture was concentrated to dryness and the residue was purified by chromatography on silica gel (eluted with PE:EtOAc=2:1 to 1:2) to afford compound 23-3 (36 mg, yield 62.1%) as a brown solid. LC/MS (ESI) m/z: 729 (M+H)⁺.

Step 3: Compound 23

To a solution of compound 23-3 (35 mg, 0.048 mmol) in EtOAc (5 mL) was added PtO₂ (15 mg) at 0° C. and the mixture was degassed under N₂ atmosphere three times and stirred under a H₂ balloon at room temperature for 0.5 hour. The mixture was filtered and the filtrate was concentrated to dryness. The residue was purified by preparative HPLC to afford Compound 23 (2.3 mg, yield 6.55%) as a white solid. ¹H-NMR (400 MHz, DMSO-d₆) δ 10.43 (s, 1H), 9.11 (d, J=1.6 Hz, 1H), 8.75 (d, J=1.6 Hz, 1H), 8.62 (s, 1H), 7.98 (t, J=6.4 Hz, 1H), 7.94 (s, 1H), 7.88 (d, J=7.6 Hz, 1H), 7.64 (d, J=7.8 Hz, 1H), 5.93 (d, J=17.6 Hz, 1H), 5.51 (d, J=18.0 Hz, 1H), 4.27 (t, J=8.0 Hz, 1H), 3.63 (dd, J=5.6, 2.4 Hz, 1H), 3.54 (dd, J=14.4, 5.6 Hz, 1H), 3.31-3.26 (m, 1H), 3.14-2.95 (m, 3H), 2.64 (s, 3H), 2.54 (s, 3H), 2.47-2.45 (m, 1H), 2.31-2.22 (m, 1H), 2.11 (s, 3H), 1.89-1.78 (m, 1H), 1.73-1.62 (m, 2H), 1.61-1.49 (m, 3H), 1.44-1.33 (m, 2H), 1.16 (t, J=6.0 Hz, 1H), 1.10-1.04 (m, 4H). LC/MS (ESI) m/z: 731 (M+H)⁺.

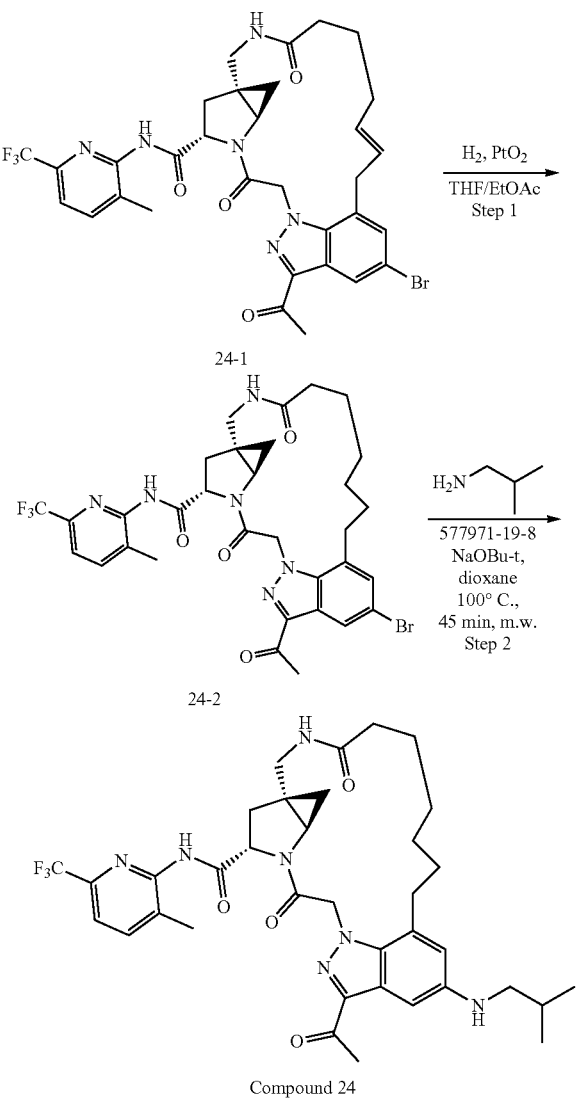

Scheme 23. Synthesis of Compound 24

Step 1: Compound 24-2

To a solution of compound 24-1 (100 mg, 0.14 mmol) in EtOAc (5 mL) and THF (5 mL) was added PtO₂ (20 mg) and the mixture was degassed and stirred under a H₂ balloon at room temperature for 1 hour. The mixture was filtered and the filtrate was concentrated to dryness. The residue was purified by column chromatography on silica gel (eluted with DCM:MeOH=60:1) to afford compound 24-2 (90 mg, yield 90%) as a yellow solid. LC/MS (ESI) m/z: 703 (M+H)⁺.

Step 2: Compound 24

To a mixture of compound 24-2 (30 mg, 0.042 mmol) and 2-methylpropan-1-amine (16 mg, 0.21 mmol) in 1,4-dioxane (1 mL) was added NaOBu-t (12 mg, 0.13 mmol) and 2-(2'-Di-tert-butylphosphine)biphenylpalladium(II) acetate (4 mg 0.008 mmol). The mixture was degassed under N₂ three times and stirred at 100° C. in CEM microwave reactor for 45 minutes. The reaction mixture was diluted with EtOAc, washed with water and brine, dried over anhydrous Na$_2$SO$_4$, filtered and concentrated to dryness. The residue was purified by preparative HPLC to afford Compound 24 (4 mg, yield 13.5%) as a white solid. $^1$H-NMR (400 MHz, CD$_3$OD) δ 7.80-7.82 (d, J=7.6 Hz, 1H), 7.54-7.56 (d, J=7.6 Hz, 1H), 7.15 (s, 1H), 7.69 (s, 1H), 5.79-5.84 (d, J=17.6 Hz, 1H), 5.46-5.50 (d, J=17.6 Hz, 1H), 4.51 (s, 1H), 3.5-3.61 (m, 1H), 3.44-3.48 (m, 2H), 2.91-2.92 (m, 3H), 2.59-2.61 (m, 5H), 2.31-2.34 (m, 2H), 2.14 (s, 3H), 1.74-1.96 (m, 9H), 1.52-1.63 (m, 3H), 0.96-1.09 (m, 6H). LC/MS (ESI) m/z: 696 (M+H)$^+$.

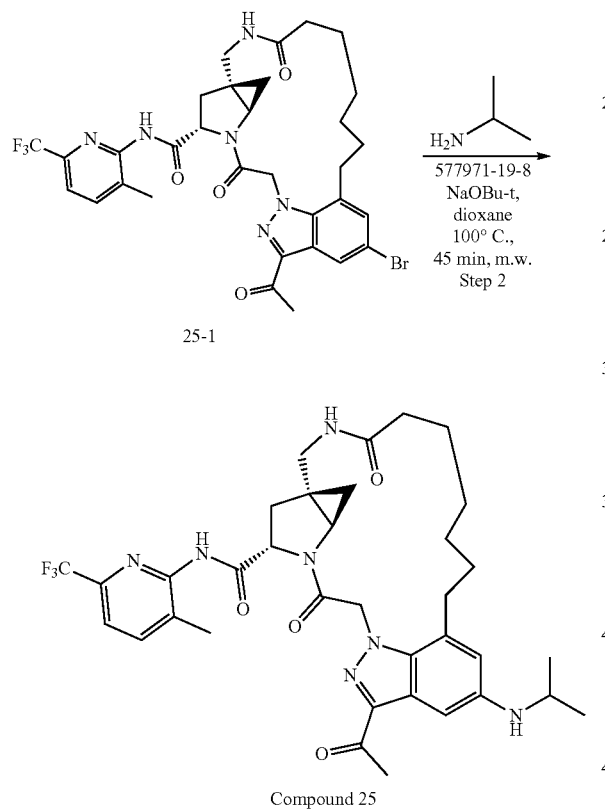

Scheme 24. Synthesis of Compound 25

Compound 25

To a mixture of compound 25-1 (30 mg, 0.042 mmol) and 2-methylpropan-1-amine (13 mg, 0.21 mmol) in 1,4-dioxane (1 mL) was added NaOBu-t (12 mg, 0.13 mmol) and 2-(2'-di-tert-butylphosphine)biphenylpalladium(II) acetate (4 mg 0.008 mmol). The mixture was degassed under N$_2$ three times and stirred at 100° C. in CEM microwave reactor for 45 minutes. The reaction mixture was diluted with EtOAc, washed with water and brine, dried over anhydrous Na$_2$SO$_4$, filtered and concentrated to dryness. The residue was purified by preparative HPLC to afford Compound 25 (3.5 mg, yield 12.0%) as a white solid. $^1$H-NMR (400 MHz, CD$_3$OD): δ 7.80-7.82 (d, J=7.6 Hz, 1H), 7.54-7.56 (d, J=7.6 Hz, 1H), 7.23 (s, 1H), 7.67 (s, 1H), 5.80-5.84 (d, J=17.6 Hz, 1H), 5.47-5.51 (d, J=17.6 Hz, 1H), 4.49-4.79 (m, 2H), 3.59-3.64 (m, 2H), 3.44-3.48 (m, 1H), 2.95-2.97 (m, 1H), 2.57-2.70 (m, 5H), 2.24-2.34 (m, 2H), 2.21 (s, 3H), 1.62-1.78 (m, 9H), 1.15-1.26 (m, 6H), 1.09-1.13 (m, 1H). LC/MS (ESI) m/z: 682 (M+H)$^+$.

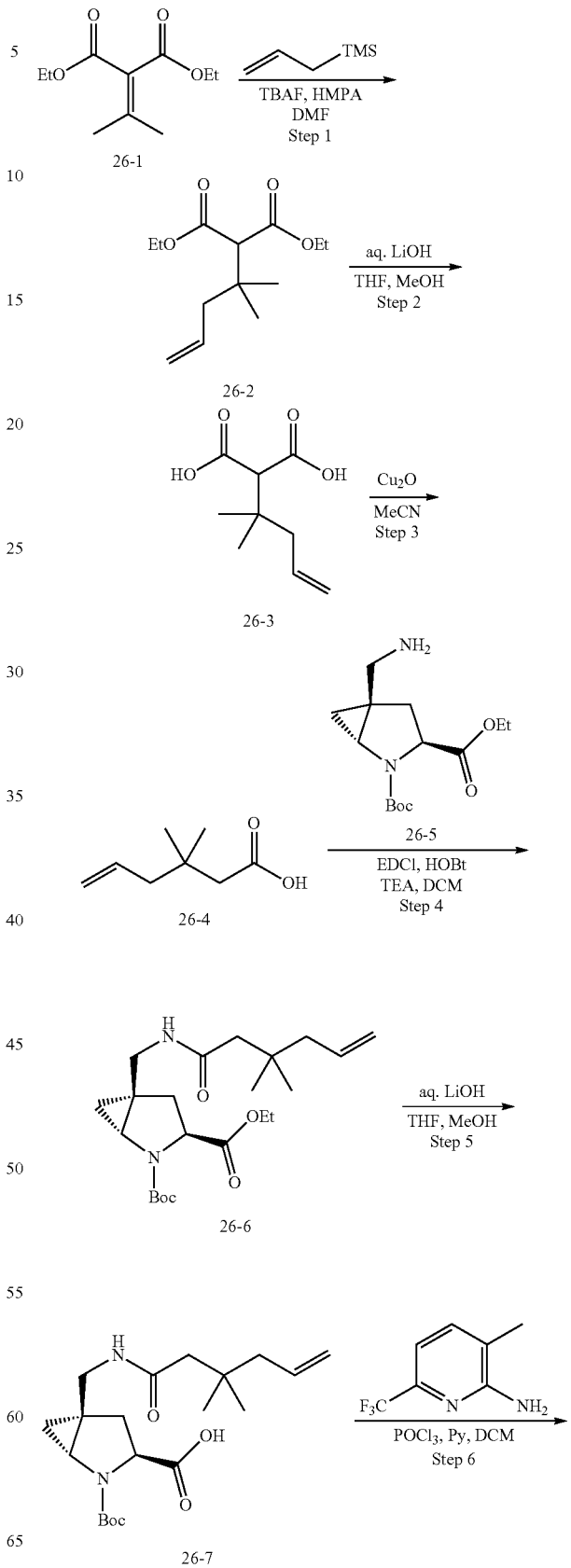

Scheme 25. Synthesis of Compound 26

741
-continued

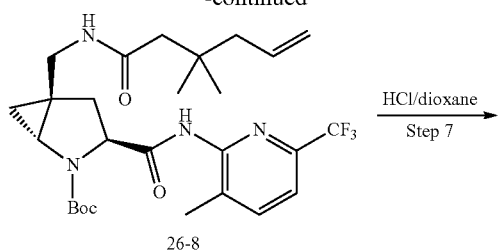

26-8

HCl/dioxane
Step 7

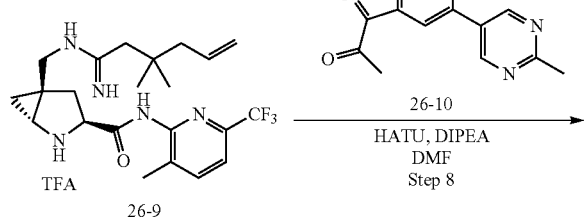

26-9

HATU, DIPEA
DMF
Step 8

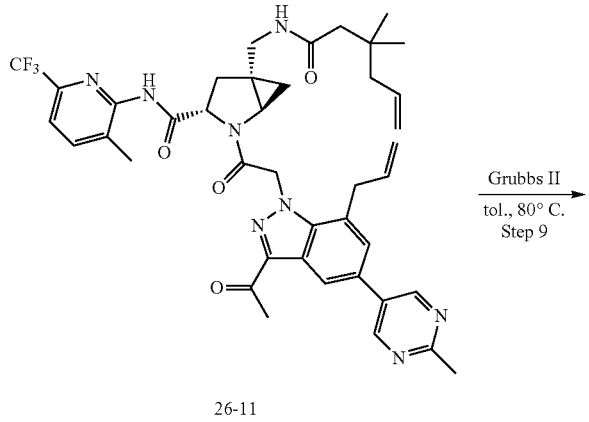

26-11

Grubbs II
tol., 80° C.
Step 9

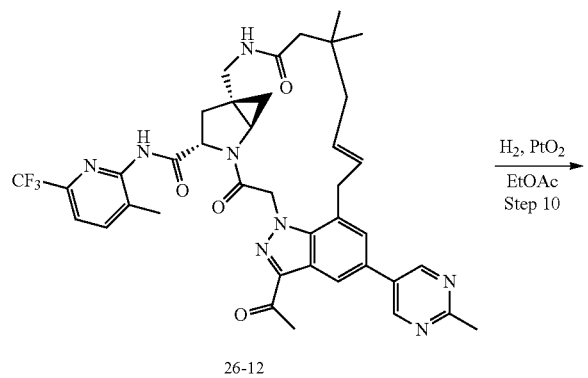

26-12

H₂, PtO₂
EtOAc
Step 10

742
-continued

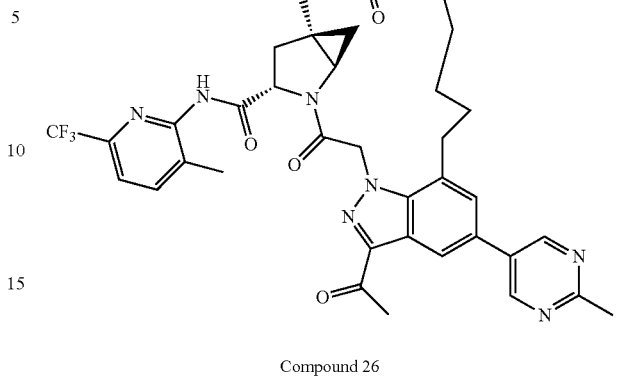

Compound 26

Step 1: Diethyl 2-(2-methylpent-4-en-2-yl)malonate (26-2)

To a solution of compound 26-1 (1 g, 5 mmol) in DMF (10 mL) was added 4 Å molecular sieves (1 g) and TBAF (0.6 mL, 1 M in THF) at 0° C. followed by HMPA (2.69 g, 15 mmol) and allyltrimethylsilane (1.7 g, 15 mmol). After addition, the mixture was stirred at room temperature for 2 hours. The mixture was diluted with EtOAc and washed with saturated aqueous NH4Cl solution and brine, dried with anhydrous Na2SO4, filtered and concentrated to dryness. The residue was purified by chromatography on silica gel (eluted with PE:EtOAc=60:1) to afford compound 26-2 (700 mg, yield 57.9%) as a yellow oil.

Step 2: 2-(2-Methylpent-4-en-2-yl)malonic acid (26-3)

To a solution of compound 26-2 (700 mg, 2.89 mmol) in MeOH (5 mL) and THF (5 mL) was added a solution of LiOH (364 mg, 8.67 mmol) in water (5 mL) at 0° C. After addition, the mixture was stirred at room temperature for 1 hour. The reaction mixture was concentrated to dryness and the residue was dissolved in water. The mixture was washed with tert-butyl methyl ether and acidified by adding 1 N HCl to a pH of approximately 3. The mixture was extracted with DCM twice and the combined organic layers were washed with brine, dried over Na₂SO₄, filtered and concentrated to dryness to afford compound 26-3 (500 mg, yield 93.0%) as a yellow oil. LC/MS (ESI) m/z: 185 (M−H)−.

Step 3: 3,3-Dimethylhex-5-enoic acid (26-4)

To a solution of compound 26-3 (200 mg, 1.08 mmol) in CH₃CN (5 mL) was added CuO (8.35 mg, 0.11 mmol) and the mixture was stirred at 90° C. for 40 hours. The mixture was acidified by adding 3 N aqueous HCl to a pH of approximately 2 and extracted with DCM twice. The combined organic layers were washed with brine, dried over Na₂SO₄, filtered and concentrated to dryness to afford compound 26-4 (150 mg, yield 98.0%) as a yellow oil, LC/MS (ESI) m/z: 141 (M−H)−.

Step 4: (1R,3S,5R)-2-tert-Butyl 3-ethyl 5-((3,3-dimethylhex-5-enamido)methyl)-2-azabicyclo[3.1.0]hexane-2,3-dicarboxylate (26-6)

To a mixture of compound 26-4 (150 mg, 1.06 mmol) and (1R,3S,5R)-2-tert-butyl 3-ethyl 5-(aminomethyl)-2-azabicyclo[3.1.0]hexane-2,3-dicarboxylate (200 mg, 0.71 mmol) in DCM (5 mL) was added HOBt (172 mg, 1.27 mmol) and EDCI (302 mg, 1.59 mmol) followed by triethylamine (428 mg, 4.24 mmol) at 0° C. After addition, the mixture was stirred at 30° C. for 16 hours. The mixture was diluted with EtOAc and washed with saturated aqueous $NH_4Cl$ solution and brine, dried over $Na_2SO_4$, filtered and concentrated to dryness. The residue was purified by silica gel chromatography (eluted with PE:EtOAc=4:1 to 2:1) to afford compound 26-6 (100 mg, yield 23.1%) as a colorless oil. LC/MS (ESI) m/z: 409 (M+H)+.

Step 5: (1R,3S,5R)-2-(tert-Butoxycarbonyl)-5-((3,3-dimethylhex-5-enamido)methyl)-2-azabicyclo[3.1.0]hexane-3-carboxylic acid (26-7)

To a solution of compound 26-6 (100 mg, 0.24 mmol) in MeOH (2 mL) and THF (2 mL) was added a solution of LiOH (30.8 mg, 0.73 mmol) in water (2 mL) at 0° C. After addition, the mixture was stirred at room temperature for 1 hour. The reaction mixture was concentrated to dryness and the residue was dissolved in water. The mixture was washed with tert-butyl methyl ether and acidified by adding 1 N HCl to a pH of approximately 3. The mixture was extracted with DCM twice and the combined organic layers were washed with brine, dried over $Na_2SO_4$, filtered and concentrated to dryness to afford compound 26-7 (80 mg, yield 87.5%) as a yellow oil. LC/MS (ESI) m/z: 381 (M+H)+.

Step 6: (1R,3S,5R)-tert-Butyl 5-((3,3-dimethylhex-5-enamido)methyl)-3-((3-methyl-6-(trifluoromethyl)pyridin-2-yl)carbamoyl)-2-azabicyclo[3.1.0]hexane-2-carboxylate (26-8)

To a mixture of compound 7 (80 mg, 0.21 mmol) and 3-methyl-6-(trifluoromethyl)pyridin-2-amine (37 mg, 0.21 mmol) in DCM (3 mL) was added pyridine (83 mg, 1.05 mmol) followed by POCl3 (48 mg, 0.32 mmol) at 0° C. After addition, the mixture was stirred at room temperature for 1 hour. The mixture was diluted with DCM and washed with 0.5 N HCl and brine successively, dried and concentrated to dryness. The residue was purified by column chromatography on silica gel (eluted with PE:EtOAc=2:1) to afford compound 26-8 (70 mg, yield 62.0%) as a light yellow oil. LC/MS (ESI) m/z: 539 (M+H)$^+$.

Step 7: (1R,3S,5R)-5-((3,3-Dimethylhex-5-enamido)methyl)-N-(3-methyl-6-(trifluoromethyl)pyridin-2-yl)-2-azabicyclo[3.1.0]hexane-3-carboxamide hydrochloride (26-9)

A solution of compound 26-8 (70 mg, 0.13 mmol) in HCl/1,4-dioxane solution (3 mL, 4M) was stirred at room temperature for 1 hour. The mixture was concentrated to dryness to afford compound 26-9 (65 mg, yield 100%) as a white solid that was directly used to the next reaction without purification. LC/MS (ESI) m/z: 439 (M+H)+.

Step 8: (1R,3S,5R)-2-(2-(3-Acetyl-7-allyl-5-(2-methylpyrimidin-5-yl)-1H-indazol-1-yl)acetyl)-5-((3,3-dimethylhex-5-enamido)methyl)-N-(3-methyl-6-(trifluoromethyl)pyridin-2-yl)-2-azabicyclo[3.1.0] hexane-3-carboxamide (26-11)

To a mixture of compound 26-9 (65 mg, 0.13 mmol) and 2-(3-acetyl-7-allyl-5-(2-methylpyrimidin-5-yl)-1H-indazol-1-yl)acetic acid (46 mg, 0.13 mmol) in DMF (3 mL) was added DIPEA (67 mg, 0.52 mmol) followed by HATU (89 mg, 0.23 mmol) at 0° C. After addition, the mixture was stirred at room temperature for 1 hour. The mixture was diluted with water and extracted with EtOAc twice. The combined organic layers were washed with saturated aqueous $NH_4Cl$ solution and brine, dried with anhydrous $Na_2SO_4$, filtered and concentrated to dryness. The residue was purified by chromatography on silica gel (DCM:MeOH=60:1) to afford compound 26-11 (50 mg, yield 50.0%) as a yellow solid. LC/MS (ESI) m/z: 771 (M+H)$^+$.

Step 9: Compound 26-12

To a solution of compound 26-11 (50 mg, 0.06 mmol) in toluene (50 mL) was added Grubbs 2nd catalyst (14 mg, 0.017 mmol) under $N_2$ atmosphere. The mixture was degassed under $N_2$ three times and stirred at 80° C. under $N_2$ atmosphere overnight. The mixture was concentrated to dryness and the residue was purified by column chromatography on silica gel (eluted with DCM:MeOH:=40:1) to afford compound 26-12 (30 mg, yield 67.4%) as a brown solid. LC/MS (ESI) m/z: 743 (M+H)+.

Step 10: Compound 26

To a degassed solution of compound 26-12 (30 mg, 0.04 mmol) in THF (4 mL) and EtOAc (4 mL) was added PtO2 (9.6 mg, 0.04 mmol) and the mixture was degassed under N2 atmosphere three times and stirred under a H2 balloon at 25° C. for 16 hours. The mixture was concentrated to dryness and the residue was purified by preparative HPLC to afford Compound 26 (2 mg, yield 6.7%) as a white solid. 1H-NMR (400 MHz, $CH_3OD$) δ 9.00 (d, J=8.9 Hz, 2H), 8.43 (d, J=1.6 Hz, 1H), 7.82 (d, J=7.9 Hz, 1H), 7.55 (d, J=7.3 Hz, 2H), 5.85 (d, J=17.8 Hz, 1H), 5.65 (d, J=17.7 Hz, 1H), 4.47 (t, J=7.8 Hz, 1H), 3.73-3.76 (m, 1H), 3.35 (d, J=4.2 Hz, 2H), 3.10-3.16 (m, 1H), 2.83-2.93 (m, 1H), 2.74 (s, 3H), 2.69 (s, 3H), 2.61-2.69 (m, 1H), 2.51-2.56 (m, 1H), 2.29 (t, J=14.0 Hz, 1H), 2.18 (s, 3H), 2.10 (d, J=14.7 Hz, 1H), 1.82-1.94 (m, 2H), 1.59-1.75 (m, 3H), 1.33-1.38 (m, 2H), 1.15 (d, J=3.0 Hz, 1H), 1.13 (s, 3H), 0.98 (s, 3H), 0.88-0.92 (m, 1H), LC/MS (ESI) m/z: 745 (M+H)+.

Scheme 26. Snythesis of Compound 27

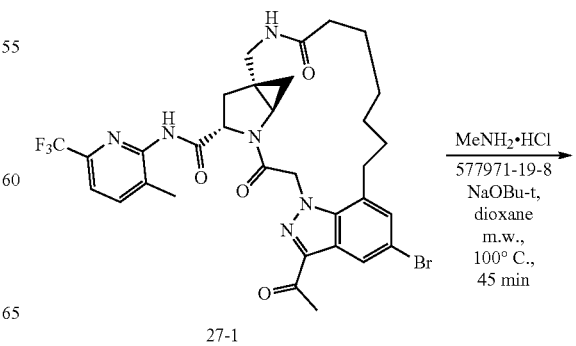

27-1

745

-continued

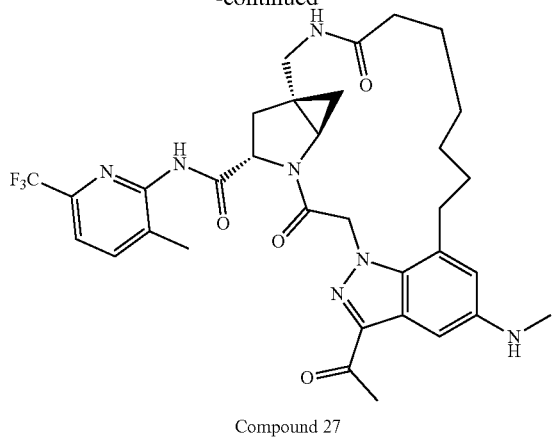

Compound 27

746

To a mixture of compound 27-1 (30 mg, 0.042 mmol) and methyl-amine hydrochloride (13 mg, 0.21 mmol) in 1,4-dioxane (1 mL) was added NaOBu-t (28 mg, 3 mmol) and 2-(2'-Di-tert-butylphosphine)biphenylpalladium(II) acetate (4 mg 0.008 mmol). The mixture was degassed under $N_2$ three times and stirred at 100° C. in CEM microwave reactor for 45 minutes. The reaction mixture was diluted with EtOAc, washed with water and brine, dried over anhydrous $Na_2SO_4$, filtered and concentrated to dryness. The residue was purified by preparative HPLC to afford Compound 27 (3.3 mg, yield 11.8%) as a white solid. $^1$H-NMR (400 MHz, $CH_3OD$) δ 7.82 (d, J=7.9 Hz, 1H), 7.56 (d, J=7.8 Hz, 1H), 7.16 (d, J=2.1 Hz, 1H), 6.67 (d, J=2.2 Hz, 1H), 5.83 (d, J=17.7 Hz, 1H), 5.50 (d, J=17.8 Hz, 1H), 4.53 (d, J=7.3 Hz, 1H), 3.58-3.63 (m, 1H), 3.46 (d, J=14.7 Hz, 1H), 2.93-3.05 (m, 1H), 2.80 (s, 3M), 2.69 (d, J=10.4 Hz, 1M), 2.62 (s, 3H), 2.59 (d, J=7.3 Hz, 2H), 2.24-2.37 (m, 2H), 2.14 (s, 3H), 1.48-1.84 (m, 8H), 1.39 (t, J=5.9 Hz, 2H), 1.28 (m, 2H), 1.01-1.14 (m, 1H). LC/MS (ESI) m/z: 654 (M+H)$^+$.

Scheme 27. Synthesis of Compound 28

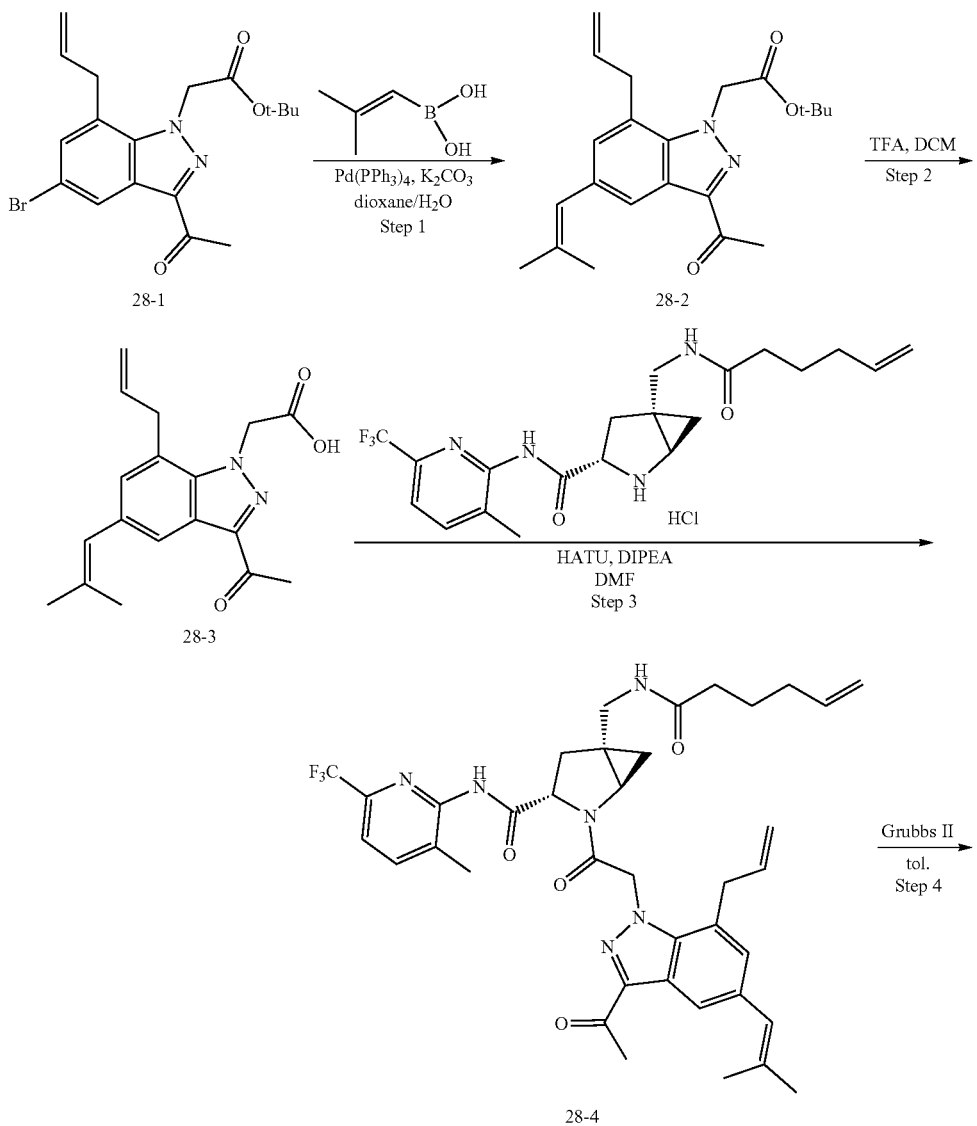

Step 1: tert-Butyl 2-(3-acetyl-7-allyl-5-(2-methyl-prop-1-en-1-yl)-1H-indazol-1-yl)acetate (28-2)

To a solution of compound 28-1 (50 mg, 0.13 mmol) and (2-methylprop-1-en-1-yl)boronic acid (15 mg, 0.15 mmol) in 1,4-dioxane (1.5 mL) and water (1 mL) was added $K_2CO_3$ (44 mg, 0.32 mmol) and $Pd(dppf)Cl_2$ (10 mg, 0.013 mmol) and the mixture was stirred under $N_2$ atmosphere at 90° C. for 16 hours. The mixture was filtered and the filter cake was washed with EtOAc. The combined filtrate was washed with brine, dried over anhydrous $Na_2SO_4$, filtered and concentrated to dryness. The residue was purified by silica gel chromatography (eluted with PE:EtOAc=30:1) to afford compound 28-2 (30 mg, yield 79.9%) as a yellow oil. LC/MS (ESI) m/z: 369 (M+H)+.

Step 2: 2-(3-Acetyl-7-allyl-5-(2-methylprop-1-en-1-yl)-1H-indazol-1-yl)acetic acid (28-3)

A solution of compound 28-2 (30 mg, 0.081 mmol) in TFA (1 mL) and DCM (3 mL) was stirred at room temperature for 2 hours. The mixture was concentrated to dryness to afford compound 28-3 (25 mg, yield 98.3%) as a yellow solid that was directly used to the next reaction without purification. LC/MS (ESI) m/z: 313 (M+H)+.

Step 3: (1R,3S,5R)-2-(2-(3-Acetyl-7-allyl-5-(2-methylprop-1-en-1-yl)-1H-indazol-1-yl)acetyl)-5-(hex-5-enamidomethyl)-N-(3-methyl-6-(trifluoromethyl)pyridin-2-yl)-2-azabicyclo[3.1.0]hexane-3-carboxamide (28-4)

To a mixture of compound 28-3 (25 mg, 0.08 mmol) and (1R,3S,5R)-5-(hex-5-enamidomethyl)-N-[3-methyl-6-(trifluoromethyl)pyridin-2-yl]-2-azabicyclo[3.1.0]hexane-3-carboxamide hydrochloride (29 mg, 0.067 mmol) in DMF (3 mL) was added HATU (30 mg, 0.08 mmol) followed by DIPEA (0.022 g, 0.167 mmol) at 0° C. and the mixture was stirred at room temperature for 2 hours. The mixture was diluted with EtOAc, washed with saturated aqueous $NH_4Cl$ solution and brine, dried over anhydrous $Na_2SO_4$, filtered and concentrated to dryness. The residue was purified by column chromatography via silica gel (eluted with DCM:MeOH=30:1) to afford compound 28-4 (35 mg, yield 62.1%) as a yellow solid. LC/MS (ESI) m/z: 705 (M+H)+.

Step 4: Compound 28-5

To a solution of compound 28-4 (30 mg, 0.05 mmol) in degassed toluene (30 mL) was added Grubbs $2^{nd}$ catalyst (9 mg, 0.011 mmol) and the mixture was degassed again and stirred at 80° C. under $N_2$ atmosphere for 16 hours. The mixture was concentrated to dryness and the residue was purified by silica gel chromatography (eluted with DCM:MeOH=30:1) to afford compound 28-5 (20 yield 69.4%) as a light yellow solid. LC/MS (ESI) m/z: 677 (M+H)+.

Step 5: Compound 28

To a solution of compound 28-5 (20 mg, 0.03 mmol) in EtOAc (2 mL) was added $PtO_2$ (5 mg) and the mixture was degassed under $N_2$ three times and stirred under a $H_2$ balloon at room temperature for 1 hour. The mixture was filtered and the filtrate was concentrated to dryness. The residue product was purified by preparative HPLC to afford Compound 28 (0.5 mg, yield 2.5%) as a white solid. $^1$H-NMR (400 MHz, $CD_3OD$) δ 7.89 (s, 1H), 7.81 (d, J=7.8 Hz, 1H), 7.56 (d, J=7.7 Hz, 1H), 7.02 (s, 1H), 5.88 (d, J=17.9 Hz, 1H), 5.57 (d, J=17.7 Hz, 1H), 4.52 (t, J=6.7 Hz, 1H), 3.62 (d, J=3.6 Hz, 1H), 3.47 (d, 9.2 Hz, 1H), 3.35 (s, 1H), 3.13 (s, 1H), 3.02 (d, J=11.9 Hz, 1H), 2.85-2.78 (m, 1H), 2.65 (s, 3H), 2.60-2.53 (m, 4H), 2.21-2.17 (m, 2H), 2.12 (s, 3H), 1.91-1.86 (m, 1H), 1.72 (s, 4H), 1.60 (s, 6H), 1.15 (dd, J=5.4, 2.8 Hz, 2H). LC/MS (ESI) m/z: 681 (M+H)+.

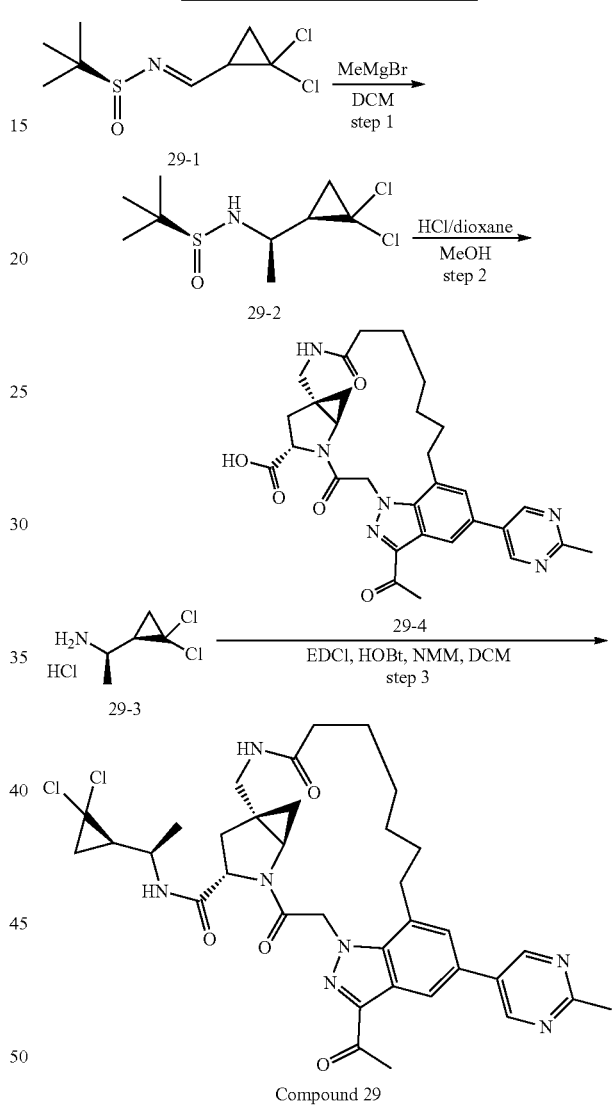

Scheme 28. Synthesis of Compound 29

Compound 29

Step 1: (S)-N-((R)-1-((R)-2,2-Dichlorocyclopropyl)ethyl)-2-methylpropane-2-sulfinamide (29-2)

To a solution of compound 29-1 (230 mg, 0.95 mmol) prepared in the same manner as Scheme 29, Compound 30) in DCM (8 mL) was added methylmagnesium bromide (0.95 mL, 1.91 mmol, 2 M/L in THF) at −78° C. under $N_2$ atmosphere and the resulting mixture was stirred at this temperature for 3.5 hours and at room temperature for 16 hours. The mixture was quenched with saturated aqueous $NH_4Cl$ solution and extracted with DCM twice. The combined organic layers were washed with brine, dried with anhydrous $Na_2SO_4$, filtered and concentrated to dryness.

The residue was purified by chromatography on silica gel (eluted with PE:EtOAc=20:1 to 3:1) to afford compound 29-2 (50 mg, yield 20.4%) as a light yellow oil. LC/MS (ESI) m/z: 258 (M+H)+.

Step 2: (R)-1-((R)-2,2-Dichlorocyclopropyl) ethanamine hydrochloride (29-3)

To a solution of compound 29-2 (30 mg, 0.12 mmol) in MeOH (1 mL) was added HCl/1,4-dioxane solution (0.5 mL) at 0° C. and the mixture was stirred at room temperature overnight. The mixture was concentrated to dryness to afford compound 29-3 (22 mg, yield 100%) as a yellow solid that was used directly in the next step. LC/MS (ESI) m/z: 154 (M+H)+.

Step 3: Compound 29

To a mixture of compound 29-3 (11 mg, 0.072 mmol) and compound 4 (8 mg, 0.048 mmol) in DCM (2 mL) was added NMM (24mg, 0.240 mmol), EDCI (14 mg, 0.072 mmol) and HOBt (8 mg, 0.072 mmol) at 0° C. and the mixture was stirred at room temperature overnight. The mixture was diluted with DCM, washed with water and brine, dried over anhydrous $Na_2SO_4$, filtered and concentrated to dryness. The residue was purified by preparative HPLC to afford Compound 29 (3 mg, yield 9.1%) as a white solid. $^1$H-NMR (400 MHz, $CD_3OD$) δ 8.98 (s, 2H), 8.42 (d, J=1.6 Hz, 1H), 7.53 (s, 1H), 5.90 (d, J=18.0 Hz, 1H), 5.68-5.52 (m, 1H), 4.29 (dd, J=9.2, 4.8 Hz, 1H), 3.73-3.59 (m, 1H), 3.53 (dd, J=5.6, 2.8 Hz, 1H), 3.40 (d, J=6.8 Hz, 1H), 3.22-3.06 (m, 2H), 2.92-2.83 (m, 1H), 2.74 (s, 3H), 2.69 (s, 3H), 2.52-2.40 (m, 2H), 2.39-2.28 (m, 2H), 1.93-1.72 (m, 6H), 1.68-1.58 (m, 2H), 1.56-1.51 (m, 1H), 1.50-1.42 (m, 1H), 1.39 (t, J=6.0 Hz, 1H), 1.36-1.29 (m, 1H), 1.29-1.25 (m, 3H), 1.16 (dd, J=6.0, 3.2 Hz, 1H). LC/MS (ESI) m/z: 694 (M+H)+.

Scheme 29. Synthesis of Compound 30

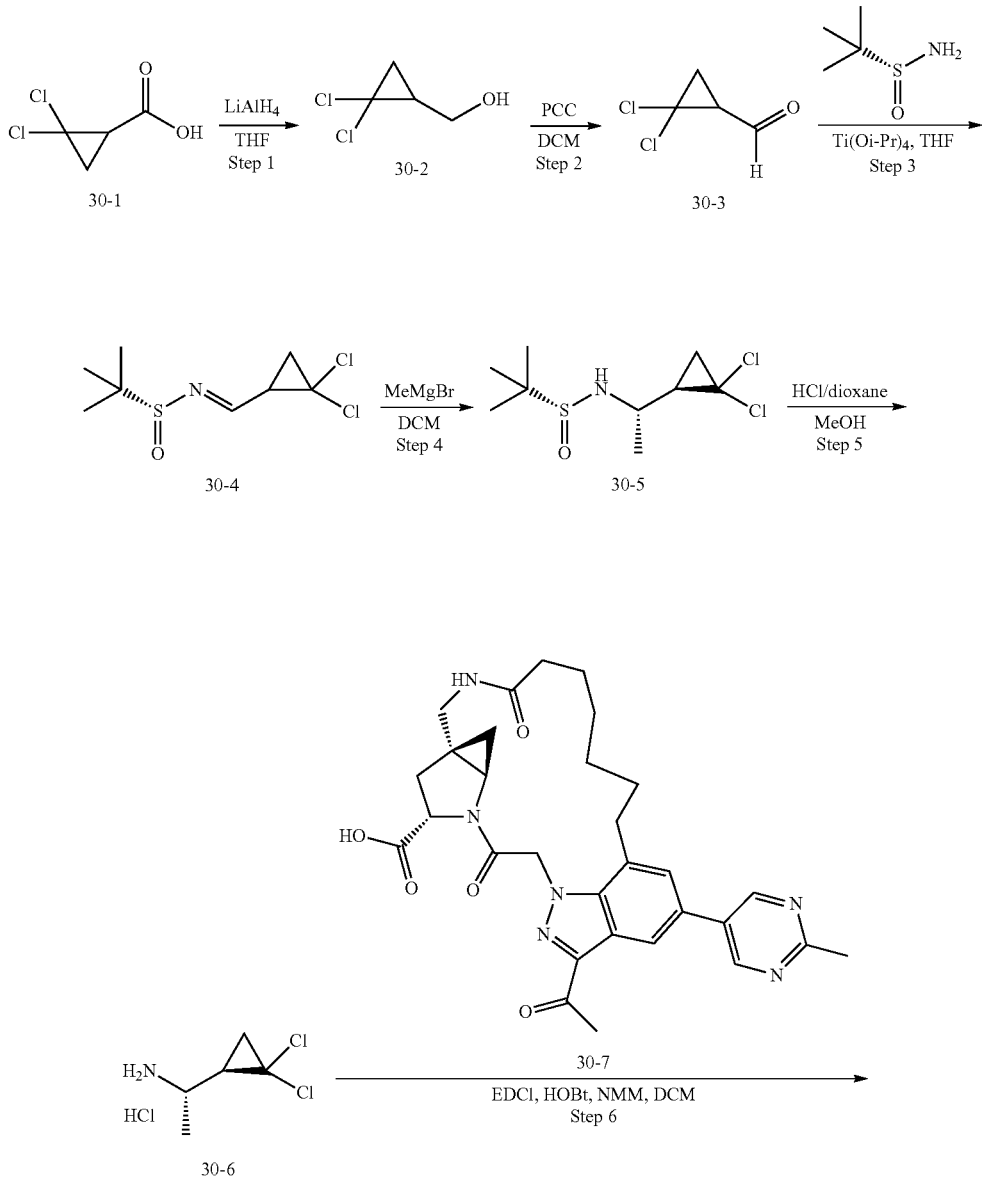

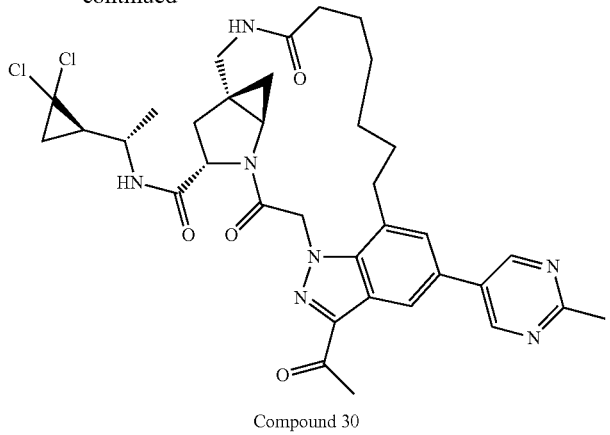

Compound 30

Step 1: (2,2-Dichlorocyclopropyl) methanol (30-2)

To a solution of LiAlH$_4$ (191 mg, 5.03 mmol) in diethyl ether (4 mL) was added a solution of compound 1 (600 mg, 3.87 mmol) in diethyl ether (6 mL) at 0° C. under N$_2$ atmosphere and the resulting mixture was stirred at room temperature for 6 hours. The mixture was quenched with water at 0° C. and extracted with diethyl ether twice. The combined organic layers were washed with brine, dried with anhydrous Na$_2$SO$_4$, filtered and concentrated to dryness. The residue was purified by chromatography on silica gel (eluted with PE:EtOAc=10:1 to 3:1) to afford compound 30-2 (340 mg, yield 62.7%) as a light yellow oil. LC/MS (ESI) m/z: 139 (M−H)⁻.

Step 2: 2,2-Dichlorocyclopropanecarbaldehyde (30-3)

To a solution of compound 30-2 (300 mg, 2.14 mmol) in DCM (6 mL) was added PCC (693 mg, 3.21 mmol) and the resulting mixture was stirred at room temperature for 6 hours. The mixture was diluted with DCM and washed with water and brine, dried over anhydrous Na$_2$SO$_4$, filtered and concentrated to afford compound 30-3 (220 mg, yield 74.4%) as a light yellow oil.

Step 3: (R,E)-N-((2,2-Dichlorocyclopropyl)methylene)-2-methylpropane-2-sulfinamide (30-4)

To a mixture of compound 30-3 (22.0 mg, 1.59 mmol) and (R)-2-methylpropane-2-sulfinamide (212 mg, 1.75 mmol) in THF (6 mL) was added tetraisopropoxytitanium (906 mg, 3.19 mmol) and the resulting mixture was stirred at 60° C. overnight. The mixture was quenched with ice-water and extracted with EtOAc twice. The combined organic layers were washed with brine, dried with anhydrous Na$_2$SO$_4$, filtered and concentrated to dryness. The residue was purified by chromatography on silica gel (eluted with PE:EtOAc=9:1 to 5:1) to afford compound 30-4 (260 mg, yield 67.7%) as a light yellow oil. LC/MS (ESI) m/z: 242 (M−H)⁻.

Step 4: (R)-N-((S)-1-((R)-2,2-Dichlorocyclopropyl)ethyl)-2-methylpropane-2-sulfinamide (30-5)

To a solution of compound 30-4 (200 mg, 0.83 mmol) in DCM (8 mL) was added methylmagnesium bromide (0.83 mL, 1.66 mmol, 2 M/L in THF) at −78° C. under N$_2$ atmosphere and the resulting mixture was stirred at this temperature for 3.5 hours. The reaction was stirred at room temperature overnight under N$_2$ atmosphere. The mixture was quenched with saturated aqueous NH$_4$Cl solution and extracted with DCM twice. The combined organic layers were washed with brine, dried with anhydrous Na$_2$SO$_4$, filtered and concentrated to dryness. The residue was purified by chromatography on silica gel (eluted with PE:EtOAc=20:1 to 3:1) to afford compound 30-5 (98 mg, yield 46.0%) as a light yellow oil. LC/MS (ESI) m/z: 258 (M+H)⁺.

Step 5: (S)-1-((R)-2,2-Dichlorocyclopropyl)ethanamine hydrochloride (30-6)

To a solution of compound 30-5 (45 mg, 0.175 mmol) in MeOH (2 mL) was added HCl/1,4-dioxane (1 mL) at 0° C. and the mixture was stirred at room temperature overnight. The mixture was concentrated to dryness to afford compound 30-6 (33 mg, yield 100%) as a yellow solid that was used directly in the next step. LC/MS (ESI) m/z: 154 (M+H)⁺.

Step 6: Synthesis of Compound 30

To a mixture of compound 30-6 (10 mg, 0.067 mmol) and compound 7 (25 mg, 0.045 mmol) in DCM (2 mL) was added NMM (23mg, 0.224 mmol), EDCI (13 mg, 0.067 mmol) and HOBt (9 mg, 0.067 mmol) at 0° C. and the mixture was stirred at room temperature overnight. The mixture was diluted with DCM and washed with water and brine, dried over anhydrous Na$_2$SO$_4$, filtered and concentrated to dryness. The residue was purified by preparative HPLC to afford Compound 30 (4 mg, yield 12.9%) as a white solid. $^1$H-NMR (400 MHz, CD$_3$OD) δ 9.00 (s, 2H), 8.43 (d, J=1.6 Hz, 1H), 7.56 (s, 1H), 5.90 (d, J=18.0 Hz, 1H), 5.59 (d, J=18.0 Hz, 1H), 4.19 (dd, J=8.8, 5.6 Hz, 1H), 3.71-3.59 (m, 1H), 3.55 (dd, J=6.0, 2.8 Hz, 1H), 3.39 (s, 2H), 3.16-3.07 (m, 1H), 2.95-2.84 (m, 1H), 2.74 (s, 3H), 2.68 (s, 1H), 2.48-2.27 (m, 4H), 1.93-1.73 (m, 4H), 1.71-1.55 (m, 5H), 1.53-1.27 (m, 4H), 1.25 (d, J=6.4 Hz, 1H), 1.14 (dd, J=6.0, 3.2 Hz, 1H). LC/MS (ESI) m/z: 694 (M+H)⁺.

Scheme 30. Synthesis of Compound 31
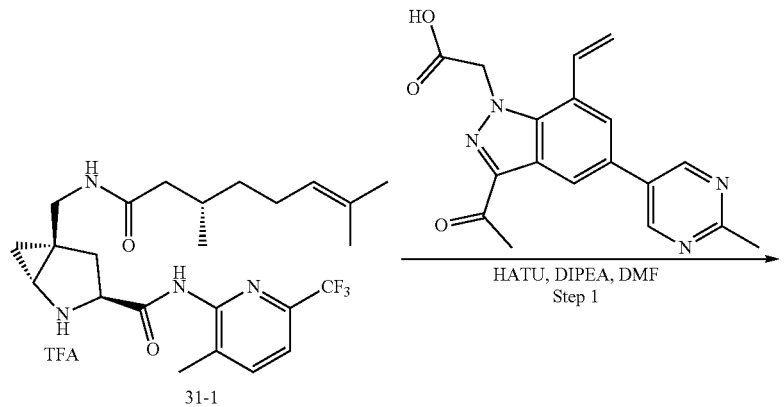
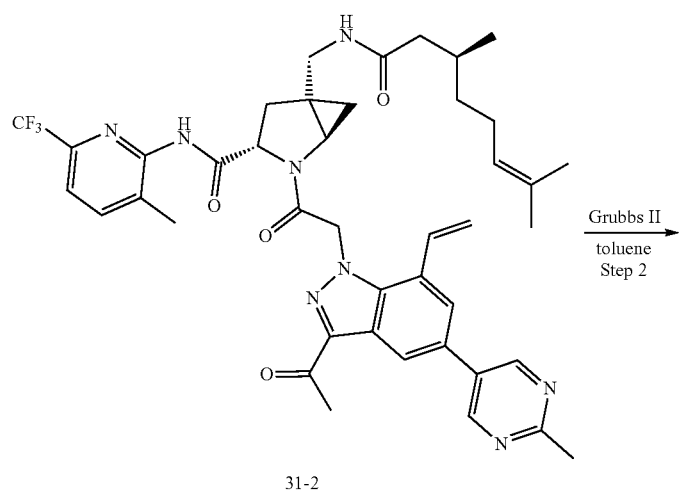
31-2
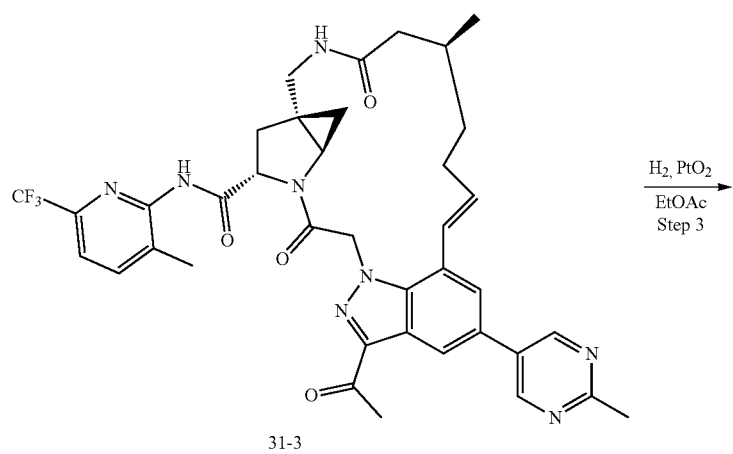
31-3

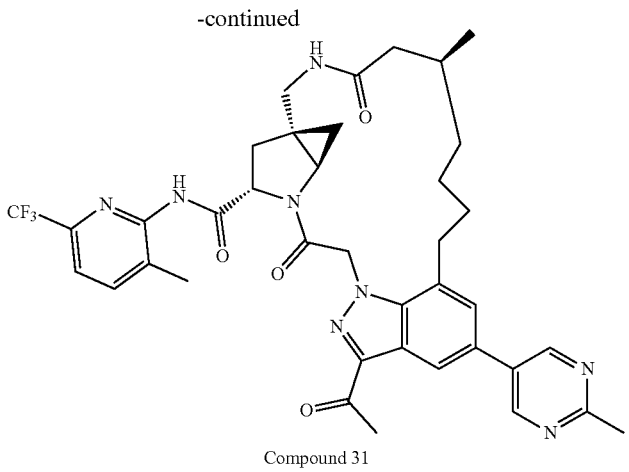

Compound 31

Step 1: (1R,3S,5R)-2-(2-(3-Acetyl-5-(2-methylpyrimidin-5-yl)-7-vinyl-1H-indazol-1-yl)acetyl)-5-(((S)-3,7-dimethyloct-6-enamido)methyl)-N-(3-methyl-6-(trifluoromethyl)pyridin-2-yl)-2-azabicyclo[3.1.0]hexane-3-carboxamide (31-2)

To a mixture of 2-(3-acetyl-5-(2-methylpyrimidin-5-yl)-7-vinyl-1H-indazol-1-yl)acetic acid (63 mg, 0.19 mmol) and compound 31-1 (107 mg, 0.19 mmol, prepared in the same manner as Scheme 33 (Compound 34)) in DMF (3 mL) was added DIPEA (123 mg, 0.95 mmol) followed by HATU (108 mg, 0.29 mmol) at 0° C. and the mixture was stirred at room temperature for 1 hour. The mixture was diluted with EtOAc and washed with saturated aqueous NH$_4$Cl solution and brine, dried over anhydrous Na$_2$SO$_4$, filtered and concentrated to dryness. The residue was purified by chromatography on silica gel (eluted with DCM:MeOH=100:1 to 20:1) to afford compound 31-2 (110 mg, yield 73.8%) as a white solid. LC/MS (ESI) m/z: 785 (M+H)$^+$.

Step 2: Compound 31-3

To a solution of compound 31-2 (40 mg, 0.05 mmol) in degassed DCE (40 mL) was added Grubbs 2$^{nd}$ catalyst (11 mg, 0.013 mmol) at 0° C. under N$_2$ atmosphere and the mixture was stirred at 50° C. under N$_2$ atmosphere overnight. The mixture was concentrated to dryness and the residue was purified by chromatography on silica gel (eluted with DCM:MeOH=20:1) to afford compound 31-3 (20 mg, yield 55.6%) as a brown solid. LC/MS (ESI) m/z: 729 (M+H)$^+$.

Step 3: Compound 31

To a solution of compound 31-3 (20 mg, 0.027 mmol) in EtOAc (3 mL) was added Pd/C (6 mg, 10% wt) at 0° C. and the mixture was degassed under N$_2$ atmosphere three times and stirred under a H$_2$ balloon at room temperature for 20 minutes. The mixture was filtered and the filtrate was concentrated to dryness. The residue was purified by preparative HPLC to afford Compound 31 (0.3 mg, yield 1.6%) as a white solid. $^1$H-NMR (400 MHz, CD$_3$OD) δ 8.99 (s, 2H), 8.42 (s, 1H), 7.80 (d, J=7.6 Hz, 1H), 7.54 (d, J=7.6 Hz, 2H), 6.04 (d, J=18.0 Hz, 1H), 5.60 (d, J=18.0 Hz, 1H), 4.58 (s, 2H), 4.41 (t, J=7.8 Hz, 1H), 3.79 (dd, J=5.6, 5.6 Hz, 1H), 3.50-3.45 (m, 1H), 3.21-3.16 (m, 1H), 3.05-2.99 (m, 1H), 2.75 (s, 3H), 2.69 (s, 3H), 2.63 (dd, J=13.2, 13.2 Hz, 1H), 2.55-2.46 (m, 2H), 2.18 (s, 3H), 1.97-1.88 (m, 3H), 1.80-1.64 (m, 4H), 1.24-1.17 (m, 1H), 1.12 (m, 1H), 1.02 (d, J=6.0 Hz, 3H), LC/MS (ESI) m/z: 731 (M+H)$^+$.

Scheme 31. Synthesis of Compound 32

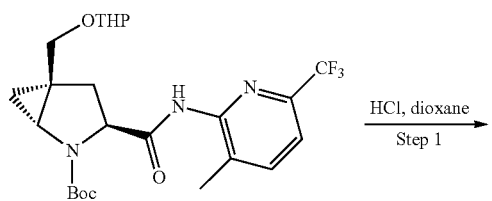

32-1

-continued
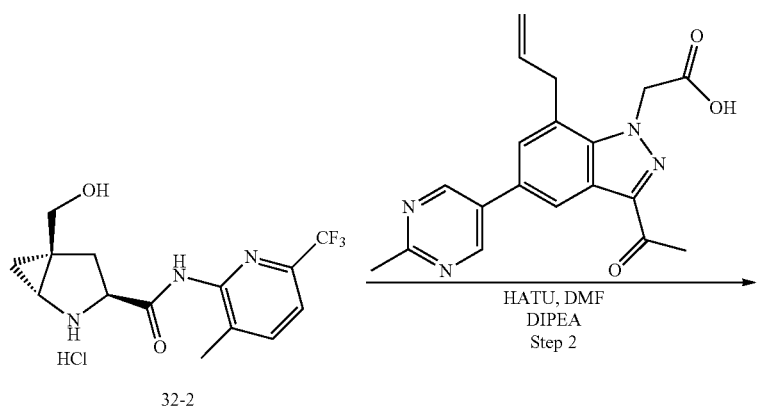
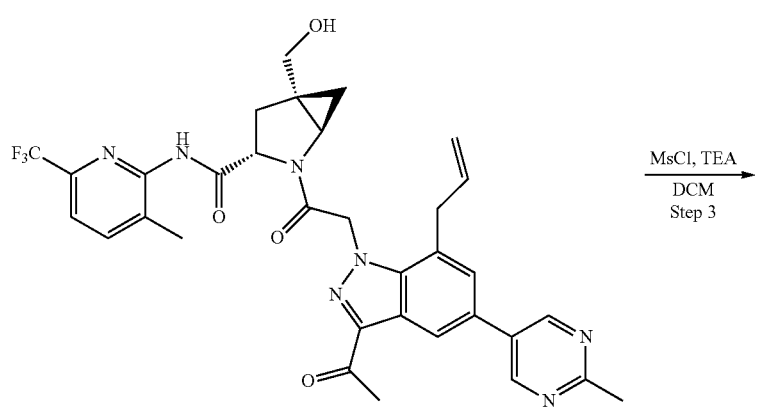
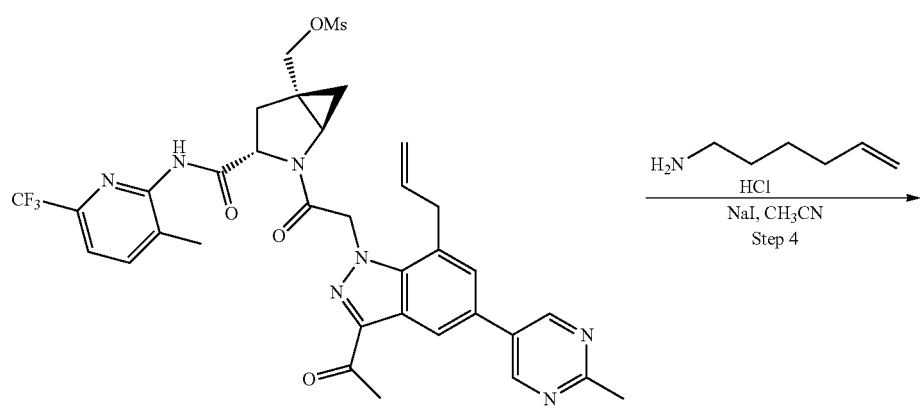

-continued
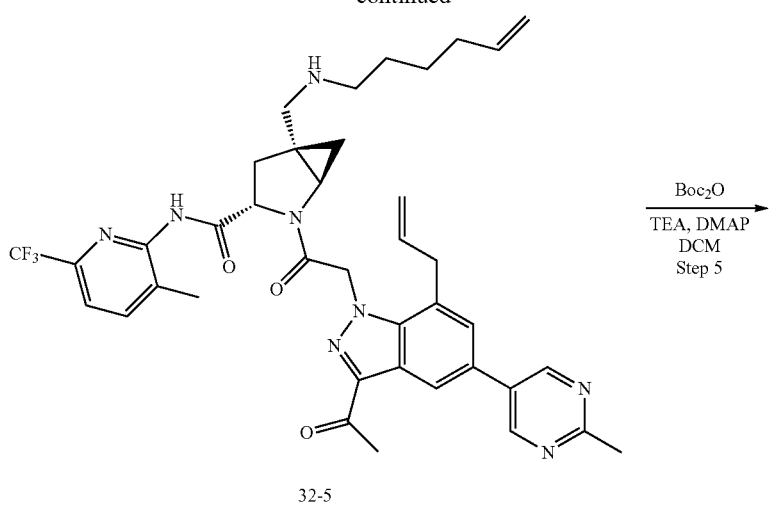
32-5
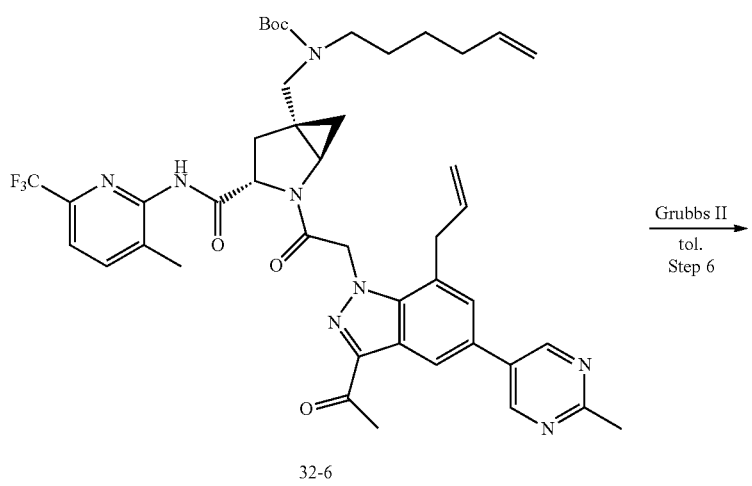
32-6
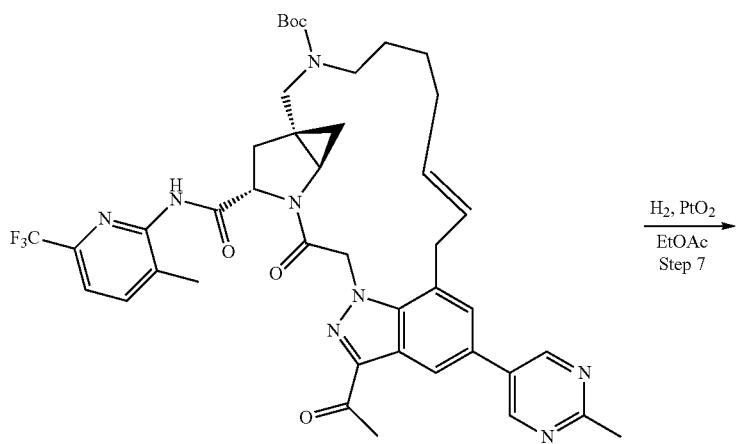
32-7

-continued

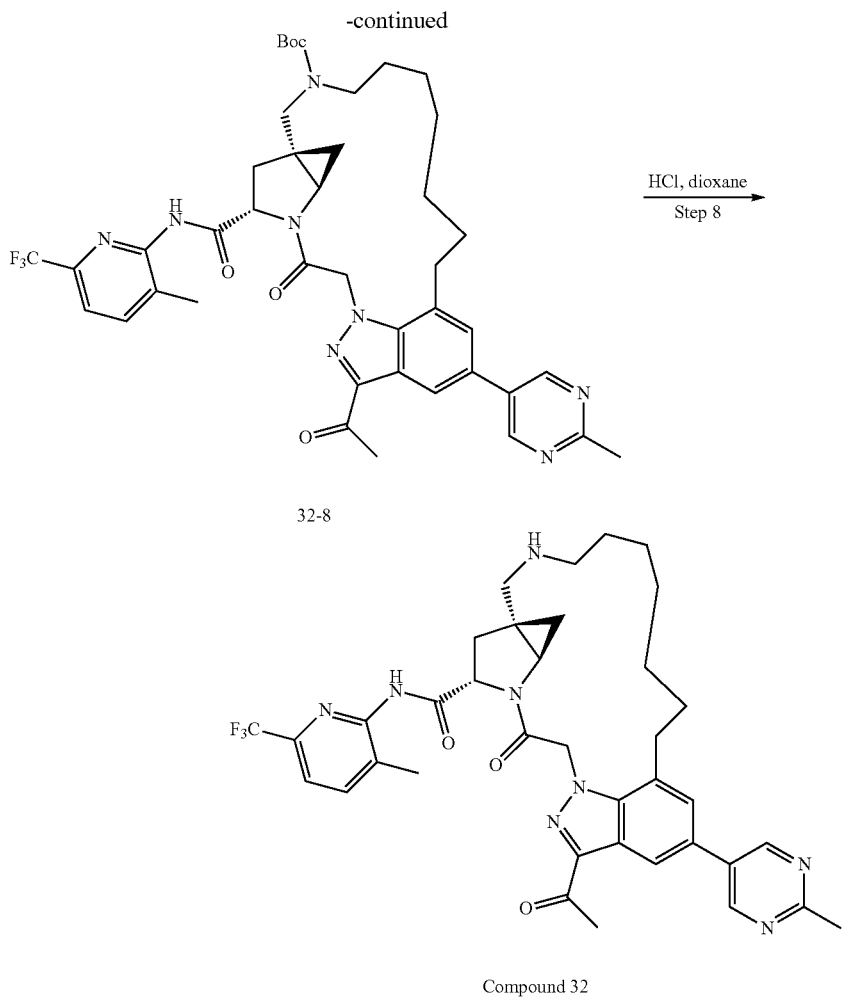

32-8

Compound 32

Step 1: (1S,3S,5R)-5-(Hydroxymethyl)-N-(3-methyl-6-(trifluoromethyl)pyridin-2-yl)-2-azabicyclo[3.1.0]hexane-3-carboxamide hydrochloride (32-2)

A solution of compound 32-1 (280 mg, 0.56 mmol) in HCl/1,4-dioxane solution (4 mL, 4M) was stirred at 0° C. to room temperature for 1 hour. The reaction mixture was concentrated to dryness, washed with ether, and dried under vacuum to afford compound 32-2 (176 mg, yield 89.3%) as a yellow solid. LC/MS (ESI) m/z: 316 (M+H)+.

Step 2: (1R,3S,5S)-2-(2-(3-Acetyl-7-allyl-5-(2-methylpyrimidin-5-yl)-1H-indazol-1-yl)acetyl)-5-(hydroxymethyl)-N-(3-methyl-6-(trifluoromethyl)pyridin-2-yl)-2-azabicyclo[3.1.0]hexane-3-carboxamide (32-3)

To a mixture of compound 32-2 (176 mg, 0.50 mmol) and 2-(3-acetyl-7-allyl-5-(2-methylpyrimidin-5-yl)-1H-indazol-1-yl)acetic acid (196 mg, 0.50 mmol) in DMF (5 mL) was added DIPEA (322 mg, 2.5 mmol) followed by HATU (285 mg, 0.75 mmol) at 0° C. and the mixture was stirred at room temperature for 1 hour. The mixture was diluted with EtOAc, washed with saturated aqueous NH4Cl solution and brine, dried over anhydrous Na2SO4, filtered and concentrated to dryness. The residue was purified by chromatography on silica gel (eluted with DCM:MeOH=60:1) to afford compound 32-3 (204 mg, yield 65.9%) as a white solid, LC/MS (ESI) m/z: 648 (M+H)+.

Step 3: (1R,3S,5S)-2-(2-(3-Acetyl-7-allyl-5-(2-methylpyrimidin-5-yl)-1H-indazol-1-yl)acetyl)-3-((3-methyl-6-(trifluoromethyl)pyridin-2-yl)carbamoyl)-2-azabicyclo[3.1.0]hexan-5-yl)methyl methanesulfonate (32-4)

To a solution of compound 32-3 (200 mg, 0.28 mmol) in DCM (10 mL) was added TEA (85 mg, 0.84 mmol), followed by the drop-wise addition of MsCl (48 mg, 0.42 mmol) at 0° C. The reaction was stirred at room temperature for 1 hour. The mixture was poured into ice-water and extracted with DCM twice. The combined organic layers were washed with brine, dried over anhydrous Na2SO4, filtered and concentrated under reduced pressure to afford compound 32-4 (220 mg, crude) as a yellow solid that was directly used in the next step without further purification, LC/MS (ESI) m/z: 726 (M+H)+.

Step 4: (1R,3S,5R)-2-(2-(3-Acetyl-7-allyl-5-(2-methylpyrimidin-5-yl)-1H-indazol-1-yl)acetyl)-5-((hex-5-en-1-ylamino)methyl)-N-(3-methyl-6-(trifluoromethyl)pyridin-2-yl)-2-azabicyclo[3.1.0]hexane-3-carboxamide (32-5)

To a solution of compound 32-4 (220 mg, 0.42 mmol) in CH3CN (5 mL) was added DIPEA (271 mg, 2.10 mmol), NaI (63 mg, 0.42 mmol) and hex-5-en-1-amine TFA salt (171 mg, 1.26 mmol) and the reaction mixture was stirred at 45° C. for 16 hours. The mixture was diluted with EtOAc, washed with water and brine, dried over $Na_2SO_4$, filtered and concentrated to dryness. The residue was purified by chromatography on silica gel (eluted with DCM:MeOH=30:1 to 15:1) to afford compound 32-5 (268 mg, yield 87.6%) as a yellow solid. LC/MS (ESI) m/z: 729 $(M+H)^+$.

Step 5: tert-Butyl ((((1R,3S,5R)-2-(2-(3-acetyl-7-allyl-5-(2-methylpyrimidin-5-yl)-1H-indazol-1-yl)acetyl)-3-((3-methyl-6-(trifluoromethyl)pyridin-2-yl)carbamoyl)-2-azabicyclo[3.1.0]hexan-5-yl)methyl)(hex-5-en-1-yl)carbamate (32-6)

To a solution of compound 32-5 (268 mg, 0.37 mmol) in DCM (5 mL) was added di-tert-butyl dicarbonate (12.1 mg, 0.56 mmol), DMAP (9 mg, 0.07 mmol) and triethylamine (112 mg, 1.11 mmol) and the mixture was stirred at room temperature for 2 hours. The mixture was diluted with DCM and washed with water and brine, dried and concentrated to dryness. The residue was purified by column chromatography on silica gel (eluted with DCM:MeOH=30:1 to 20:1) to afford compound 32-6 (100 mg, yield 32.6%) as a yellow solid. LC/MS (ESI) m/z: 829 $(M+H)^+$.

Step 6: Compound 32-7

To a solution of compound 32-6 (55 mg, 0.066 mmol) in degassed toluene (55 mL) was added Grubbs II catalyst (11 mg, 0.013 mmol) at 0° C. under $N_2$ atmosphere and the mixture was stirred at 80° C. overnight under $N_2$ atmosphere. The mixture was concentrated to dryness and the residue was purified by chromatography on silica gel (eluted with PE:EtOAc=3:1 to 1:2) to afford compound 32-7 (32 mg, yield 60.38%) as a brown solid. LC/MS (ESI) m/z: 801 $(M+H)^+$.

Step 7: Compound 32-8

To a solution of compound 32-7 (32 mg, 0.04 mmol) in EtOAc (5 mL) was added 10% $PtO_2$ (15 mg) at 0° C. and the mixture was degassed under $N_2$ atmosphere three times and stirred under a $H_2$ balloon at room temperature for 2 hours. The mixture was filtered and the filtrate was concentrated to dryness. The residue was purified by chromatography on silica gel (eluted with PE:EtOAc=2:1 to 1:2) to afford compound 32-8 (30 mg, yield 93.5%) as a yellow solid. LC/MS (ESI) m/z: 803 $(M+H)^+$.

Step 8: Synthesis of Compound 32

To a bottom flask charged with compound 32-8 (30 mg, 0.037 mmol) was added HCl/1,4-dioxane (2 mL) at 0° C. and the mixture was stirred at room temperature for 1 hour. The mixture was concentrated to dryness. The residue was purified by preparative HPLC to afford Compound 32 (4 mg, yield 15.4%) as a white solid. $^1$H-NMR (400 MHz, $CD_3OD$) δ 9.00 (s, 2H), 8.44 (d, J=1.6 Hz, 1H), 7.83 (d, J=7.6 Hz, 1H), 7.64-7.47 (m, 2H), 5.90 (d, J=17.6 Hz, 1H), 5.73 (d, J=17.6 Hz, 1H), 4.58 (s, 1H), 3.97-3.88 (m, 1H), 3.57-3.46 (m, 1H), 3.27-3.17 (m, 2H), 3.06-2.95 (m, 1H), 2.87-2.77 (m, 1H), 2.75 (s, 3H), 2.69 (s, 2H), 2.68-2.61 (m, 1H), 2.60-2.51 (m, 2H), 2.18 (s, 3H), 2.14-2.03 (m, 1H), 1.92 (m, 1H), 1.76-1.55 (m, 6H), 1.43 (m, 2H), 1.15 (t, J=5.6 Hz, 1H), 1.12-1.06 (m, 1H). LC/MS (ESI) m/z: 703 $(M+H)^+$.

Scheme 32. Syntheis of Compound 33

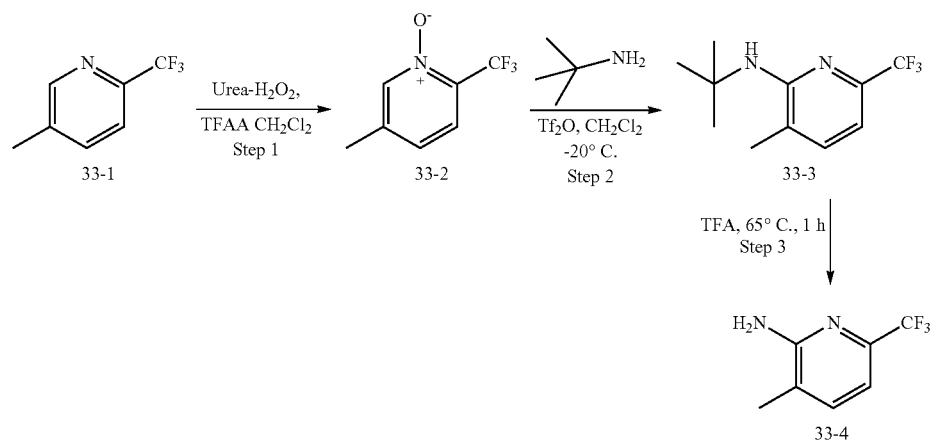

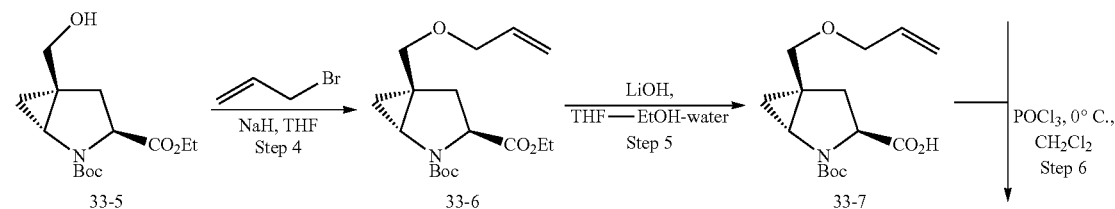

-continued
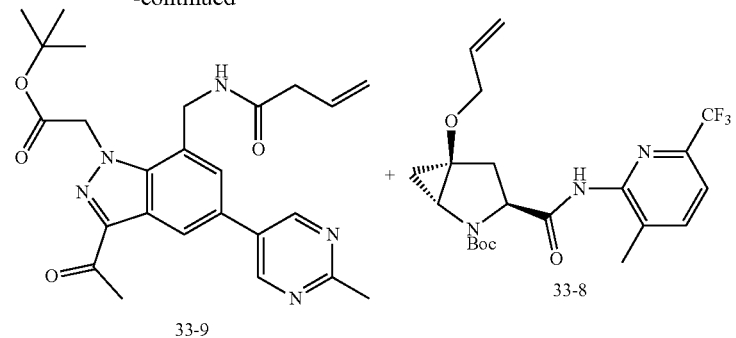
33-9
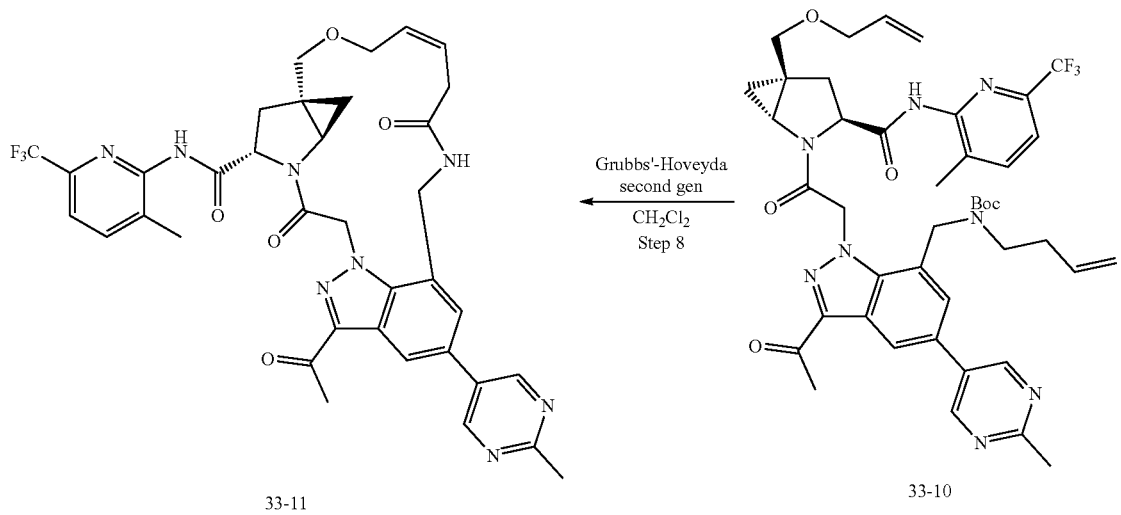
1) TFA, CH$_2$Cl$_2$
2) TBTU, DIPEA, DMF
Step 7
Grubbs'-Hoveyda second gen
CH$_2$Cl$_2$
Step 8
33-11
33-10
PtO$_2$, H$_2$
THF, EtOH
Step 9
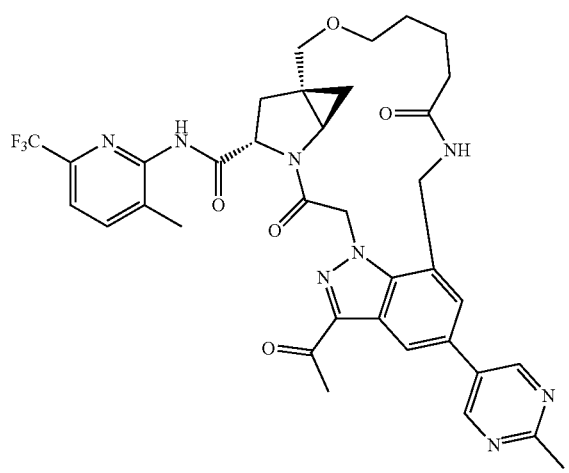
33-12

Step 1: 5-Methyl-2-(trifluoromethyl)pyridine-N-oxide (33-2)

5-Methyl-2-(trifluoromethyl)pyridine (33-1, 1 g, 6.206 mmol, 1 equiv.) was taken up in dichloromethane and the solution was cooled in an ice bath. Powdered urea hydrogen peroxide complex (0.899 g, 9.557 mmol, 1.54 equiv.) was added followed by the dropwise addition of trifluoroacetic anhydride (3.26 g, 2.158 mL, 15.522 mmol, 2.501 equiv.). The cooling bath was removed and the reaction was stirred overnight at room temperature. The reaction was quenched by the careful addition of saturated sodium metabisulfite solution and the reaction was stirred at room temperature for 15 minutes. The solution was diluted with dichloromethane and made basic by the careful addition of saturated aqueous sodium bicarbonate solution. The organic layers was separated and the aqueous layer was extracted with dichloromethane. The combined organic layers were dried and concentrated to afford an orange red oil that was used directly in the next step.

Step 2: N-(tert-Butyl)-3-methyl-6-(trifluoromethyl)pyridin-2-amine (33-3)

To a stirred solution of 5-methyl-2-(trifluoromethyl)pyridine-N-oxide (33-2, 1.05 g, 5.928 mmol, 1 equiv.) in dichloromethane (25 mL) at −20° C. was added tert-butylamine (3.21 mL). Triflic anhydride (3 mL) was added dropwise and the reaction was stirred at −20° C. for 1 hour and quenched by the addition of water. The reaction was stirred at room temperature for 15 minutes. The layers were then separated and the aqueous layer was extracted once with dichloromethane. The combined organic layers was dried and concentrated. The residue was purified by silica gel column chromatography (eluent: hexane) to afford a colorless liquid.

Step 3: 3-Methyl-6-(trifluoromethyl)pyridin-2-amine (33-4)

A solution of N-tert-butyl-3-methyl-6-(trifluoromethyl)pyridin-2-amine (33-3, 0.72 g, 3.1 mmol, 1 equiv.) in TFA was stirred at 65° C. for 1 hour. The reaction was cooled to room temperature and the volatiles were removed under reduced pressure. The residue was taken up in dichloromethane and made basic with saturated aqueous NaHCO₃ solution. The organic layers were separated, dried and concentrated to afford 0.49 g of a white solid that was used as such for the next step.

Step 4. 2-(tert-Butyl) 3-ethyl (1R,3S,5S)-5-((allyloxy)methyl)-2-azabicyclo[3.1.0]hexane-2,3-dicarboxylate (33-6)

To an ice-cold solution of 2-tert-butyl 3-ethyl (1R,3S,5S)-5-(hydroxymethyl)-2-azabicyclo[3.1.0]hexane-2,3-dicarboxylate (33-5, 1.25 g, 4.381 mmol, 1 equiv.) in DMF (15 mL) was added sodium hydride portion-wise. The reaction was stirred at 0° C. for 15 minutes and allyl bromide (1.59 g, 1.137 mL, 13.142 mmol, 3 equiv.) was added dropwise. After the addition was complete, the reaction was stirred overnight at room temperature. The reaction was cooled in an ice-bath and quenched by the careful addition of water. The reaction was then extracted repeatedly with EtOAc. The combined organic layers were dried and concentrated. The residue was purified by silica gel flash column chromatography (eluent: 0-15% EtOAc in hexanes) to afford 0.8 g of a colorless oil.

Step 5. (1R,3S,5S)-5-((Allyloxy)methyl)-2-(tert-butoxycarbonyl)-2-azabicyclo[3.1.0]hexane-3-carboxylic acid (33-7)

2-tert-Butyl 3-ethyl (1R,3S,5S)-5-[(prop-2-en-1-yloxy)methyl]-2-azabicyclo[3.1.0]hexane-2,3-dicarboxylate (33-6, 0.8 g, 2.458 mmol, 1 equiv.) was taken up in THF (4 mL) and EtOH (2 mL). The solution was cooled in an ice bath. LiOH (0.124 g) was dissolved in water (2 mL) and added dropwise to the ice cooled solution. The cooling bath was removed and the reaction was stirred at room temperature for 2 hours. The organic solvents were removed under reduced pressure and 5 mL of water was added. The reaction was once extracted with ether and the organic layers were discarded. The aqueous layer was cooled in an ice bath and acidified with cold 1N aqueous HCl. The acidified aqueous layer was extracted with dichloromethane-MeOH (20:1). The organic layer was dried and concentrated to afford 0.7 g of acid as a white solid.

Step 6. tert-Butyl (1R,3S,5S)-5-(allyloxy)-3-((3-methyl-6-(trifluoromethyl)pyridin-2-yl)carbamoyl)-2-azabicyclo[3.1.0]hexane-2-carboxylate (33-8)

To an ice cold solution of 3-methyl-6-(trifluoromethyl)pyridin-2-amine (0.436 g) and (1R,3S,5S)-5-(allyloxy)-2-(tert-butoxycarbonyl)-2-azabicyclo[3.1.0]hexane-3-carboxylic acid (33-7, 0.7 g) in dichloromethane (15 mL), pyridine (0.9 mL) was added followed by the dropwise addition of POCl₃ (0.21 mL). The stirring was continued at 0° C. for 1 hour before the reaction was quenched by the addition of saturated aqueous NaHCO₃ solution. The cooling bath was removed and the reaction was stirred at room temperature for 15 minutes. The layers were separated and the organic layer was washed with cold 1N aqueous HCl and water. The organic layer was dried and concentrated to afford 0.85 g of a white solid that was used as such for the next step.

Step 7. tert-Butyl ((3-acetyl-1-(2-(((1R,3S,5S)-5-((allyloxy)methyl)-3-((3-methyl-6-(trifluoromethyl)pyridin-2-yl)carbamoyl)-2-azabicyclo[3.1.0]hexan-2-yl)-2-oxoethyl)-5-(2-methylpyrimidin-5-yl)-1H-indazol-7-yl)methyl)(but-3-en-1-yl)carbamate (33-10)

tert-Butyl 2-[3-acetyl-7-(but-3-enamidomethyl)-5-(2-methyl pyrimidin-5-yl)indazol-1-yl]acetate (33-9, 0.03 g, 0.065 mmol, 1 equiv.) was stirred with TFA (1 mL) and dichloromethane (0.5 mL) in a vial for 3 hours at room temperature. In another vial, tert-butyl (1R,3S,5S)-3-{[3-methyl-6-(trifluoromethyl)pyridin-2-yl]carbamoyl}-5-[(prop-2-en-1-yloxy)methyl]-2-azabicyclo[3.1.0]hexane-2-carboxylate (33-8, 0.032 g, 0.071 mmol, 1.1 equiv) was stirred at room temperature with TFA (0.5 mL) and dichloromethane (0.5 mL) for 15 minutes. The contents from both the vials were combined and the volatiles were removed. The residue was taken up in DMF (1 mL) and the vial was cooled in an ice-bath. The solution was made basic with DIPEA (56 μL) and TBTU (0.023 g) was added. The cooling bath was removed and the reaction was stirred at room temperature for 1 hour. DMF was removed under reduced pressure and the residue was dissolved in dichloromethane. The organic layer was washed with saturated aqueous

Step 8. Compound 33-11

To a solution of (1R,3S,5S)-2-{2-[3-acetyl-7-(but-3-enamidomethyl)-5-(2-methylpyrimidin-5-yl)indazol-1-yl]acetyl}-N-[3-methyl-6-(trifluoromethyl)pyridin-2-yl]-5-[(prop-2-en-1-yloxy)methyl]-2-azabicyclo[3.1.0]hexane-3-carboxamide (33-10, 0.03 g, 0.04 mmol, 1 equiv.) in dichloromethane (5 mL) was added solid Hoveyda-Grubbs' 2nd gen catalyst (0.003 g, 0.004 mmol, 0.099 equiv.) and the solution was degassed with argon. The reaction was stirred at room temperature overnight. Additional catalyst (2.5 mg) was added and the reaction was stirred for 2 hours. The solvent was removed under reduced pressure and the residue was purified by silica gel column chromatography (eluent: 0-3% MeOH in dichloromethane) to afford 33-11 mg of a white solid as a mixture of cis and trans isomers.

Step 9. Compound 33

Compound 33-11 (0.011 g, 0.015 mmol, 1 equiv.) was taken up in THF (1 mL)-EtOH (1 mL) and stirred under a hydrogen atmosphere in presence of $PtO_2$ for 90 minutes. The solvent was removed under reduced pressure and the residue was purified by silica gel column chromatography (eluent: 0-3.5% MeOH in dichloromethane) to afford Compound 33 as a white solid. $^1$H NMR (400 MHz, Chloroform-d) δ 1.01 (dd, J=2.9, 5.8 Hz, 1H), 1.25-1.28 (m, 2H), 1.48-1.61 (m, 1H), 1.63-1.74 (m, 1H), 1.92-2.03 (m, 1H), 2.05-2.14 (m, 1H), 2.18-2.29 (m, 1H), 2.22 (s, 3H), 2.43-2.52 (m, 1H), 2.73 (s, 3H), 2.80 (s, 3H), 3.02 (d, J=11.3 Hz, 1H), 3.17 (d, J=13.6 Hz, 1H), 3.34-3.45 (m, 2H), 3.67-3.73 (m, 1H), 4.07 (d, J=11.3 Hz, 1H), 4.48 (d, J=14.8 Hz, 1H), 4.83 (d, J=8.7 Hz, 1H), 5.32-5.42 (m, 1H), 5.53 (d, J=17.5 Hz, 1H), 5.86 (d, J=17.5 Hz, 1H), 7.46-7.54 (m, 2H), 7.67 (brs, 1H), 7.71 (d, J=7.6 Hz, 1H), 8.59 (d, J=1.6 Hz, 1H), 8.87 (s, 2H), 9.61 (s, 1H). $^{19}$F: δ −66.9.

Scheme 33. Synthesis of Compound 34

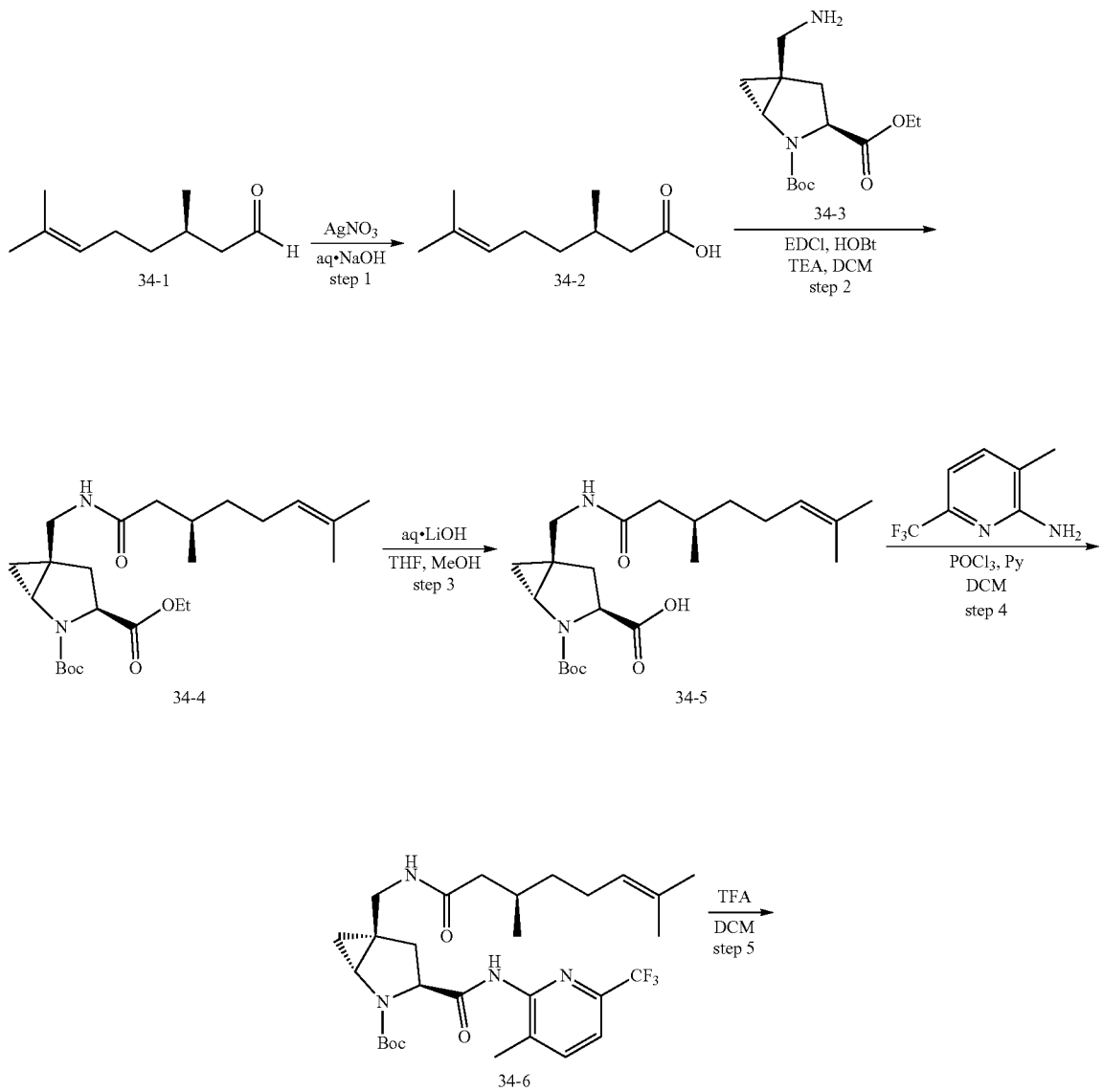

-continued
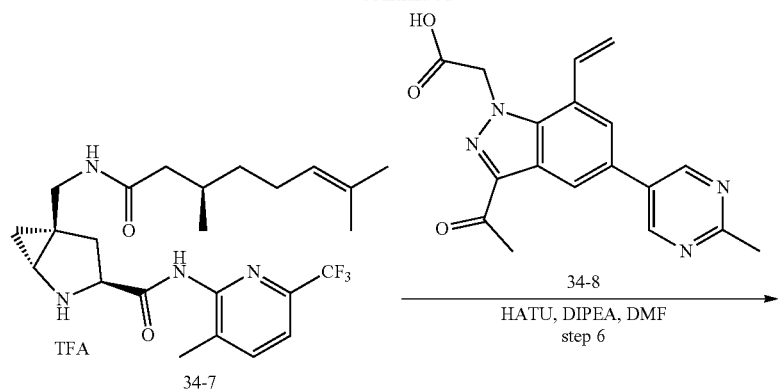
34-7 + 34-8 → HATU, DIPEA, DMF, step 6
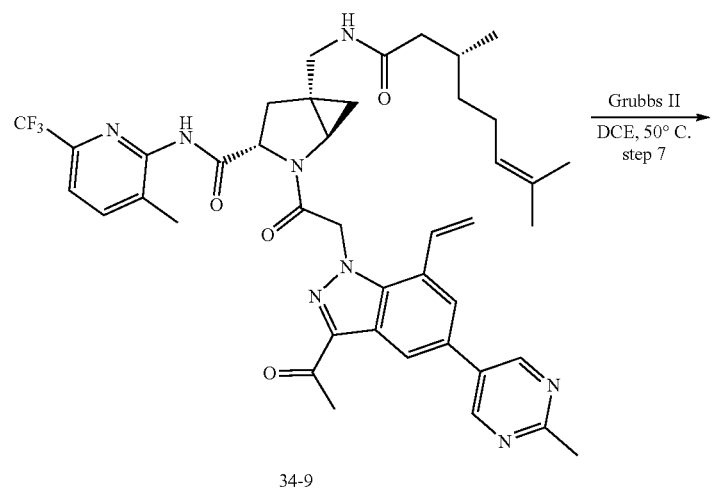
34-9
Grubbs II
DCE, 50° C.
step 7
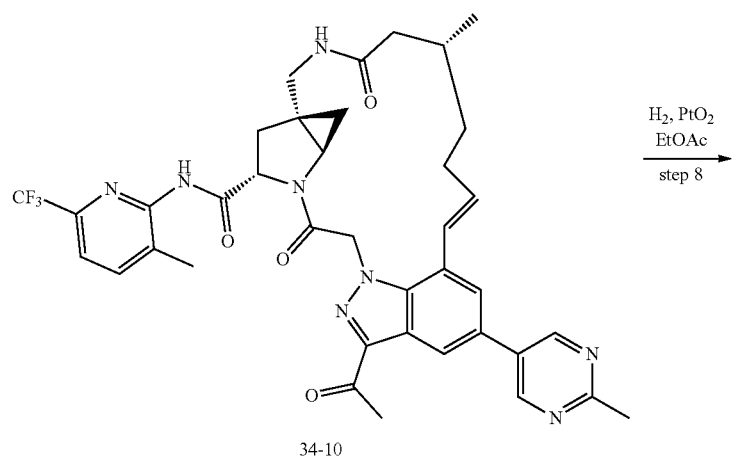
34-10
H₂, PtO₂
EtOAc
step 8

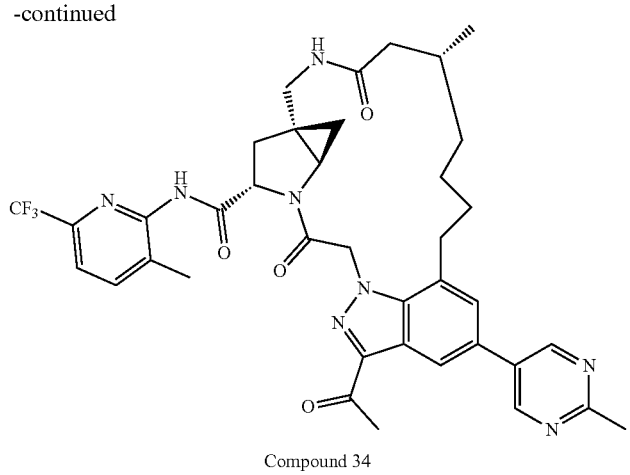

Compound 34

Step 1: (R)-3,7-Dimethyloct-6-enoic acid (34-2)

To a solution of NaOH (1.272 g, 31.82 mmol) in water (2.6 mL) was added a drop-wise addition of a solution of AgNO$_3$ (2.539 g, 14.93 mmol) in water (26 mL) at 0° C. and the mixture was stirred at room temperature for 30 minutes. Compound 34-1 (1.0 g, 6.49 mmol) was added drop-wise and the mixture was stirred at room temperature overnight. The mixture was filtered and the filtrate was acidified with 4 N aqueous HCl solution and extracted with EtOAc twice. The combined organic layers were washed with brine, dried with anhydrous Na$_2$SO$_4$, filtered and concentrated to dryness. The residue was purified by chromatography on silica gel (eluted with PE:EtOAc=10:1 to 8:1) to afford compound 34-2 (880 mg, yield 80.01%) as a yellow oil. LC/MS (ESI) m/z: 171 (M+H)$^+$.

Step 2: (1R,3S,5R)-2-tert-Butyl 3-ethyl 5-(((R)-3,7-dimethyloct-6-enamido) methyl)-2-azabicyclo[3.1.0]hexane-2,3-dicarboxylate (34-4)

To a mixture of compound 34-2 (300 mg, 1.76 mmol) and compound 34-3 (501 mg, 1.76 mmol) in DCM (6 mL) was added TEA (891 mg, 8.82 mmol), EDCI (507 mg, 2.65 mmol) and HOBt (357 mg, 2.65 mmol) at 0° C. and the mixture was stirred at room temperature overnight. The mixture was diluted with water and extracted with EtOAc twice. The combined organic layers were washed with brine, dried with anhydrous Na$_2$SO$_4$, filtered and concentrated to dryness. The residue was purified by chromatography on silica gel (eluted with PE:EtOAc=10:1 to 8:1) to afford compound 34-4 (300 mg, yield 39.01%) as a yellow oil. LC/MS (ESI) m/z: 437 (M+H)$^+$.

Step 3: (1R,3S,5R)-2-(tert-Butoxycarbonyl)-5-(((R)-3,7-dimethyloct-6-enamido) methyl)-2-azabicyclo[3.1.0]hexane-3-carboxylic acid (34-5)

To a solution of compound 34-4 (300 mg, 0.69 mmol) in methanol (1 mL) and THF (1 mL) was added a solution of LiOH (87 mg, 2.06 mmol) in water (1 mL) at 0° C. and the mixture was stirred at room temperature overnight. The mixture was washed with Et$_2$O twice and the aqueous layer was acidified with 0.5 M aqueous HCl solution and extracted with EtOAc twice. The combined organic layers were washed with brine, dried with anhydrous Na$_2$SO$_4$, filtered and concentrated to dryness to afford compound 34-5 (250 mg, yield 89.06%) as a white solid. LC/MS (ESI) m/z: 409 (M+H)$^+$.

Step 4: (1R,3S,5R)-tert-Butyl 5-(((R)-3,7-dimethyloct-6-enamido) methyl)-3-(3-methyl-6-(trifluoromethyl) pyridin-2-ylcarbamoyl)-2-azabicyclo[3.1.0]hexane-2-carboxylate (34-6)

To a mixture of compound 34-5 (232 mg, 0.57 mmol) and 3-methyl-6-(trifluoromethyl)pyridin-2-amine (100 mg, 0.57 mmol) in DCM (6 mL) was added pyridine (224 mg, 2.84 mmol) followed by phosphoryl chloride (96 mg, 0.63 mmol) at 0° C. and the mixture was stirred at room temperature under N$_2$ atmosphere for 1 hour. The mixture was poured into ice-water and extracted with DCM twice. The combined organic layers were washed with brine, dried with anhydrous Na$_2$SO$_4$, filtered and concentrated to dryness. The residue was purified by chromatography on silica gel (eluted with PE:EtOAc=10:1 to 2:1) to afford compound 34-6 (170 mg, yield 52.8%) as a white solid. LC/MS (ESI) m/z: 567 (M+H)$^+$.

Step 5: (1R,3S,5R)-5-(((R)-3,7-Dimethyloct-6-enamido) methyl)-N-(3-methyl-6-(trifluoromethyl) pyridin-2-yl)-2-azabicyclo[3.1.0]hexane-3-carboxamide (34-7)

To a solution of compound 34-6 (0.17 g, 0.30 mmol) in DCM (3 mL) was added TFA (1.5 mL) at 0° C. and the mixture was stirred at room temperature for 2 hours. The reaction mixture was concentrated to dryness, washed with ether and dried under vacuum to afford compound 34-7 (0.13 g, yield 92.8%) as a yellow oil that was used directly in the next step. LC/MS (ESI) m/z: 467 (M+H)$^+$.

Step 6: (1R,3S,5R)-2-(2-(3-Acetyl-5-(2-methylpyrimidin-5-yl)-7-vinyl-1H-indazol-1-yl) acetyl)-5-(((R)-3,7-dimethyloct-6-enamido) methyl)-N-(3-methyl-6-(trifluoromethyl) pyridin-2-yl)-2-azabicyclo[3.1.0]hexane-3-carboxamide (34-9)

To a mixture of compound 34-7 (130 mg, 0.28 mmol) and compound 8 (94 mg, 0.28 mmol) in DMF (2 mL) was added DIPEA (180 mg, 1.40 mmol), followed by HATU (159 mg, 0.42 mmol) at 0° C. and the mixture was stirred at room temperature for 1 hour. The mixture was diluted with water and extracted with EtOAc twice. The combined organic layers were washed with 10% aqueous LiCl solution and brine, dried with anhydrous Na$_2$SO$_4$, filtered and concentrated to dryness. The residue was purified by chromatography on silica gel (eluted with DCM:MeOH=80:1 to 30:1) to afford compound 34-9 (68 mg, yield 31.1%) as a yellow solid. LC/MS (ESI) m/z: 785 (M+H)$^+$.

Step 7: Compound 34-10

To a solution of compound 34-9 (50 mg, 0.064 mmol) in degassed DCE (50 mL) was added Grubbs 2$^{nd}$ catalyst (13 mg, 0.016 mmol) at 0° C. under N$_2$ atmosphere and the mixture was stirred at 70° C. under N$_2$ atmosphere overnight. The mixture was concentrated to dryness and the residue was purified by chromatography on silica gel (eluted with DCM:MeOH=100:1 to 30:1) to afford compound 34-10 (10 mg, yield 21.5) as a brown solid. LC/MS (ESI) m/z: 729 (M+H)$^+$.

Step 8: Compound 34

To a solution of compound 34-10 (10 mg, 0.014 mmol) in EtOAc (3 mL) was added 10% Pd/C (5 mg) at 0° C. and the mixture was degassed under N$_2$ atmosphere three times and stirred under a H$_2$ balloon at room temperature for 0.5 hour. The mixture was filtered and the filtrate was concentrated to dryness. The residue was purified by preparative HPLC to afford Compound 34 (2 mg, yield 19.98%) as a white solid. $^1$H-NMR (400 MHz, DMSO-d$_6$) δ 10.43 (s, 1H), 9.01 (s, 2H), 8.29 (s, 1H), 8.22-8.14 (m, 1H), 7.89 (d, J=7.6 Hz, 1H), 7.64 (d, J=7.6 Hz, 1H), 7.54 (s, 1H), 5.89 (d, J=17.6 Hz, 1H), 5.50 (d, J=17.6 Hz, 1H), 4.54-4.40 (m, 1H), 4.40-4.30 (m, 1H), 3.64-3.53 (m, 1H), 3.14-3.08 (m, 2H) 2.93-2.86 (m, 1H), 2.68 (s, 3H), 2.65-2.61 (m, 3H), 2.28-2.14 (m, 2H), 2.10 (s, 3H), 2.01-1.91 (m, 2H), 1.87-1.80 (m, 1H), 1.74-1.63 (m, 2H), 1.61-1.47 (m, 2H), 1.43-1.34 (m, 2H), 1.22-1.18 (m, 1H), 1.10-1.07 (m, 1H), 0.91 (d, J=6.0 Hz, 3H). LC/MS (ESI) m/z: 731 (M+H)$^+$.

Scheme 34. Synthesis of Compound 35

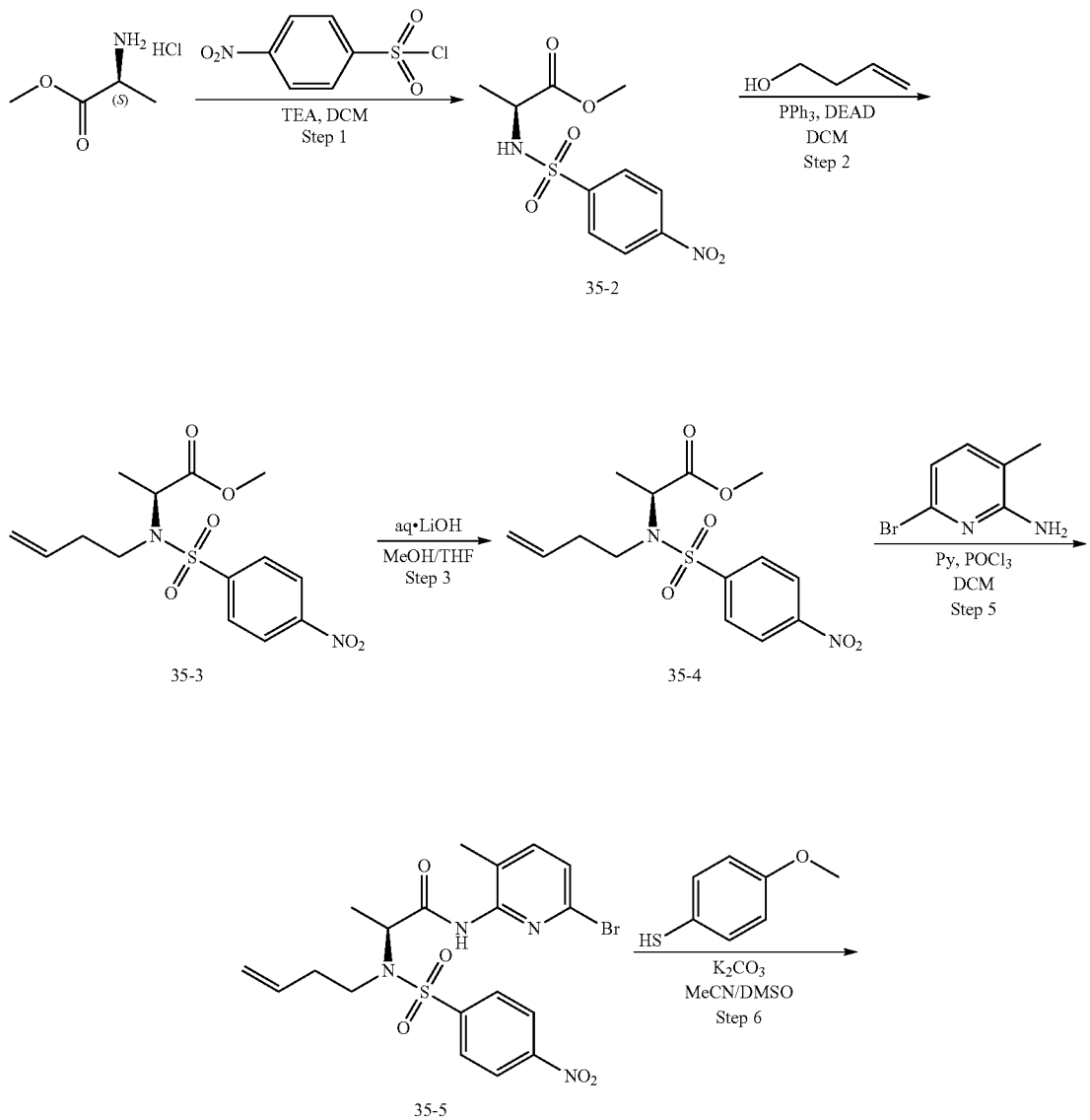

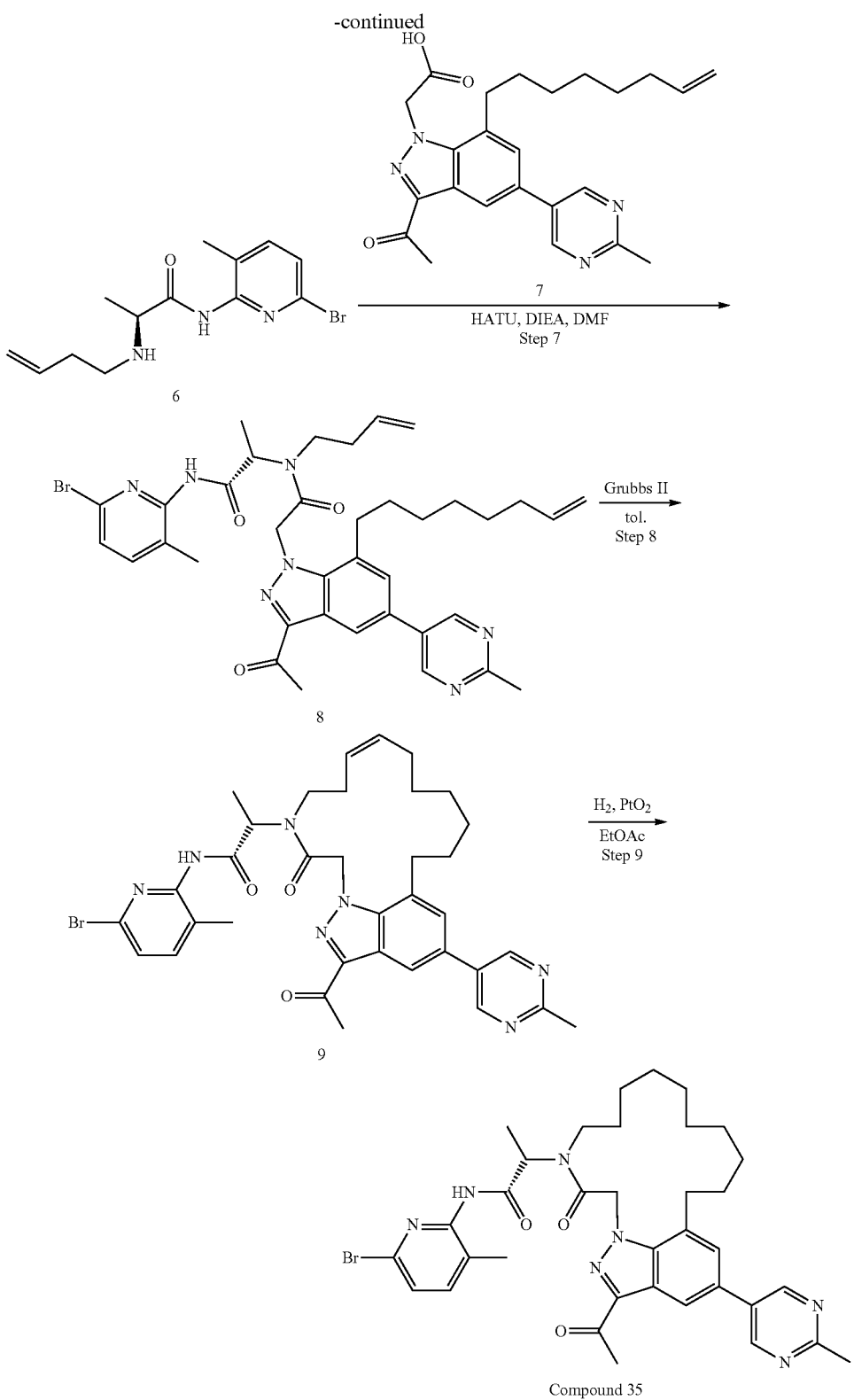

Compound 35

Step 1: (S)-Methyl 2-(1-nitrophenylsulfonamido)propanoate (35-2)

To a solution of compound 354 (580 mg, 4.16 mmol) in DCM (10 mL) was added TEA (1.26 g, 12.48 mmol) followed by 4-nitrobenzene-1-sulfonyl chloride (1.01 g, 4.57 mmol) at 0° C. and the mixture was stirred at room temperature for 16 hours. The mixture was diluted with DCM, washed with brine, dried over anhydrous $Na_2SO_4$, filtered and concentrated to dryness. The residue was purified by flash chromatography (eluted with PE:EtOAc=100:1 to 1:1) to afford compound 35-2 (720 mg, yield 60.1%) as a yellow solid. LC/MS (ESI) m/z: 289 (M+H)+.

Step 2: (S)-Methyl 2-(N-(but-3-en4-yl)-4-nitrophenylsulfonamido)propanoate (35-3)

To a solution of compound 35-2 (680 mg, 2.36 mmol) in DCM (10 mL) was added PPh$_3$ (805 mg, 3.07 mmol) and but-3-en-1-ol (224 mg, 3.07 mmol) followed by the drop-wise addition of DEAD (534 mg, 3.07 mmol) at 0° C. The mixture was stirred at room temperature for 16 hours. The mixture was diluted with DCM and washed with water and brine, dried over anhydrous Na$_2$SO$_4$, filtered and concentrated to dryness. The residue was purified by flash chromatography (eluted with PE:EtOAc=100:1 to 3:1) to afford compound 35-3 (670 mg, yield 83.0%) as a light oil. LC/MS (ESI) m/z: 343 (M+H)+.

Step 3: (S)-2-(N-(But-3-en-1-yl)-4-nitrophenylsulfonamido)propanoic acid (35-4)

To a solution of compound 35-3 (670 mg, 1.96 mmol) in methanol (4 mL) and THF (2 mL) was added a solution of LiOH (247 mg, 5.87 mmol) in water (2 mL) at 0° C. and the mixture was stirred at room temperature for 1 hour. The mixture was diluted with water and washed with ether. The aqueous layer was acidified with 1N aqueous HCl solution to a pH of approximately 3 and extracted with DCM twice. The combined organic layers were washed with brine, dried with anhydrous Na$_2$SO$_4$, filtered and concentrated to dryness to afford compound 35-4 (508 mg, yield 79.0%) as a white solid. LC/MS (ESI) m/z: 329 (M+H)+.

Step 4: (S)-N-(6-Bromo-3-methylpyridin-2-yl)-2-(N-(but-3-en-1-yl)-4-nitrophenylsulfonamido)propanamide (35-5)

To a mixture of compound 35-4 (508 mg, 1.55 mmol) and 6-bromo-3-methylpyridin-2-amine (288 mg, 1.55 mmol) in DCM (8 mL) was added pyridine (612 mg, 7.75 mmol) followed by the drop-wise addition of POCl$_3$ (261 mg, 1.71 mmol) at 0° C. and the mixture was stirred at room temperature under N$_2$ atmosphere for 2 hours. The mixture was poured into ice-water and extracted with DCM twice. The combined organic layers were washed with brine, dried with anhydrous Na$_2$SO$_4$, filtered and concentrated to dryness. The residue was purified by flash chromatography (eluted with PE:EtOAc=50:1 to 1:1) to afford compound 35-5 (560 mg, yield 72.8%) as a white solid. LC/MS (ESI) m/z: 497/499 (M+H)+.

Step 5: (S)-N-(6-Bromo-3-methylpyridin-2-yl)-2-(but-3-en-1-ylamino)propanamide (35-6)

To a solution of compound 35-5 (560 mg, 1.13 mmol) in MeCN/DMSO (10 mL, v/v=49/1) was added K$_2$CO$_3$ (624 mg, 4.52 mmol) followed by 4-methoxybenzenethiol (475 mg, 3.39 mmol) at 0° C. and the mixture was stirred at room temperature for 4 hours. The mixture was diluted with DCM and washed with brine, dried over anhydrous Na$_2$SO$_4$, filtered and concentrated to dryness. The residue was purified by flash chromatography (eluted with PE:EtOAc=10:1 to 1:4) to afford compound 35-6 (284 mg, yield 80.9%) as a light yellow oil. LC/MS (ESI) m/z: 312/314 (M+H)+.

Step 6: (S)-2-(2-(3-Acetyl-5-(2-methylpyrimidin-5-yl)-7-(oct-7-en-1-yl)-1H-indazol-1-yl)-N-(but-3-en-1-yl)acetamido)-N-(6-bromo-3-methylpyridin-2-yl)propanamide (35-8)

To a mixture of compound 35-6 (67 mg, 0.21 mmol) and compound 7 (90 mg, 0.21 mmol) in DMF (5 mL) was added DIPEA (135 mg, 1.05 mmol) followed by HATU (122 mg, 0.32 mmol) at 0° C. and the mixture was stirred at room temperature for 2 hours. The mixture was diluted with EtOAc and washed with saturated aqueous NH$_4$Cl solution and brine, dried over anhydrous Na$_2$SO$_4$, filtered and concentrated to dryness. The residue was purified by flash chromatography (eluted with DCM:MeOH=100:1 to 20:1) to afford compound 35-8 (30 mg, yield 20.1%) as a white solid. LC/MS (ESI) m/z: 714/716 (M+H)+.

Step 7: Compound 35-9

To a solution of compound 35-8 (30 mg, 0.04 mmol) in degassed toluene (30 mL) was added Grubbs 2$^{nd}$ catalyst (9 mg, 0.01 mmol) under N$_2$ atmosphere and the mixture was stirred at 80° C. under N$_2$ atmosphere for 16 hours. The mixture was concentrated to dryness and the residue was purified by flash chromatography (eluted with DCM:MeOH=100:1 to 20:1) to afford compound 35-9 (24 mg, yield 88.9%) as a brown solid. LC/MS (ESI) m/z: 686/688 (M+H)+.

Step 8: Compound 35

To a solution of compound 35-9 (24 mg, 0.035 mmol) in EtOAc (5 mL) was added PtO$_2$ (7 mg) at 0° C. and the mixture was degassed under N$_2$ atmosphere three times and stirred under a H$_2$ balloon at room temperature for 15 minutes. The mixture was filtered and the filtrate was concentrated to dryness. The residue was purified by preparative HPLC to afford Compound 35 (1.9 mg, yield 7.92%) as a white solid. $^1$H-NMR (400 MHz, CD$_3$OD) δ 9.00 (s, 2H), 8.45 (d, J=1.6 Hz, 1H), 7.58 (d, J=2.0 Hz, 1H), 7.55 (d, J=8.0 Hz, 1H), 7.38 (d, J=7.6 Hz, 1H), 5.81 (d, J=17.2 Hz, 1H), 5.70 (d, J=17.2 Hz, 1H), 4.74 (d, J=7.2 Hz, 1H), 3.63 (tt, J=7.6, 4.4 Hz, 2H), 2.95 (q, J=6.6 Hz, 2H), 2.75 (s, 3H), 2.65 (s, 3H), 2.08 (s, 3H), 1.83-1.70 (m, 4H), 1.63 (d, 7.2 Hz, 3H), 1.61-1.39 (m, 12H). LC/MS (ESI) m/z: 688/690 (M+H)+.

Scheme 35. Synthesis of Compound 36
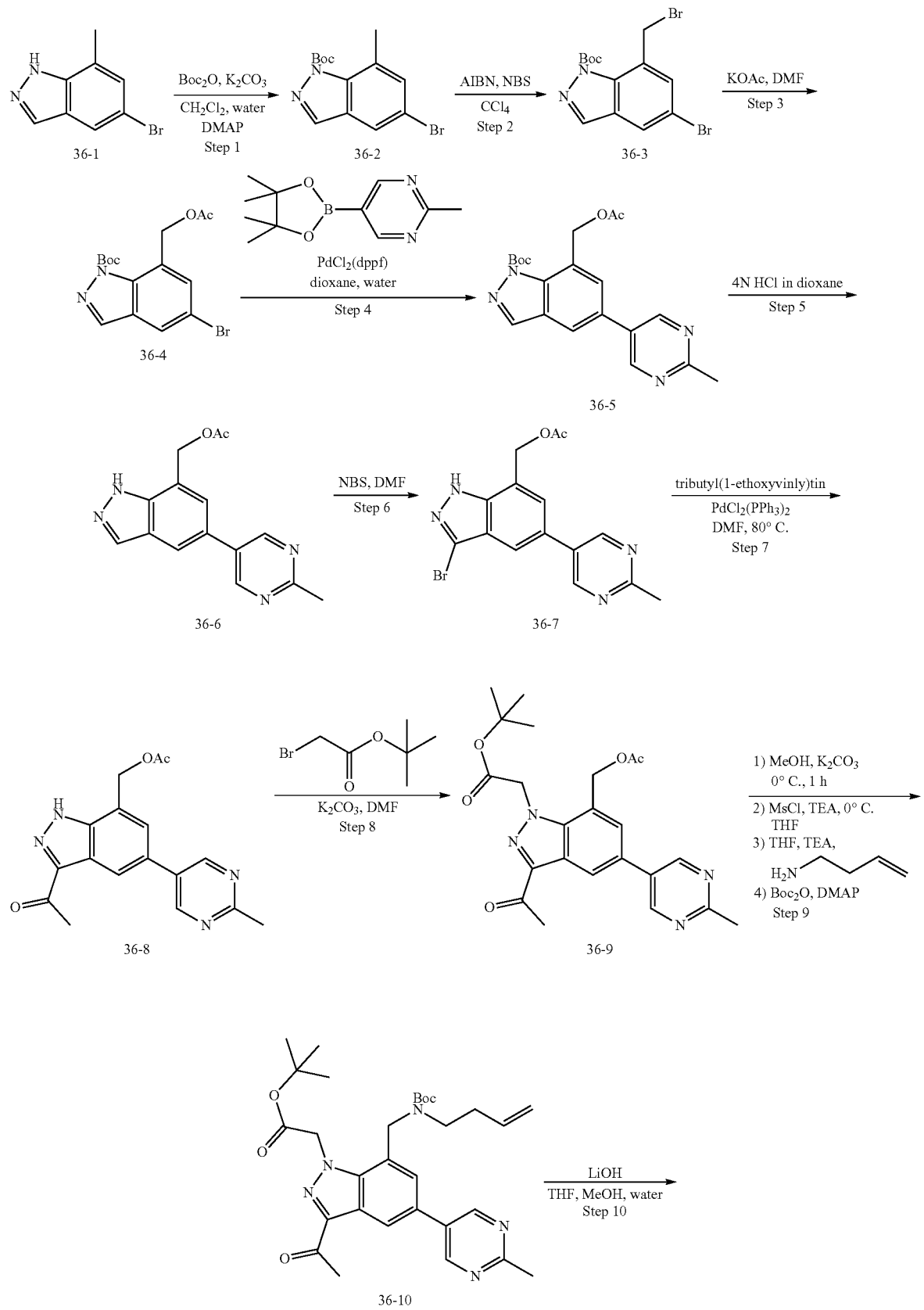

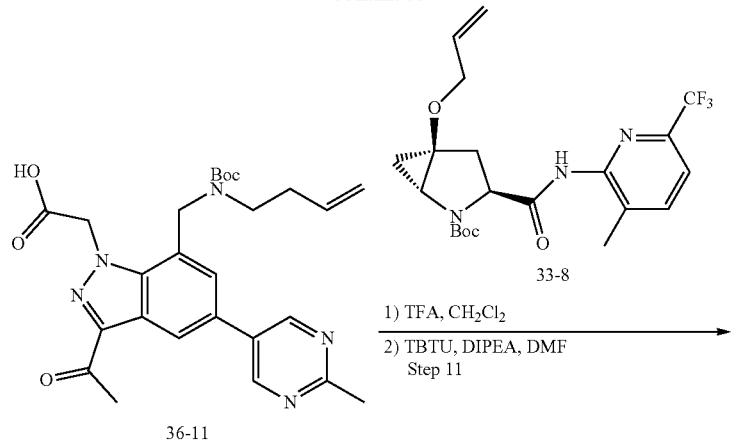
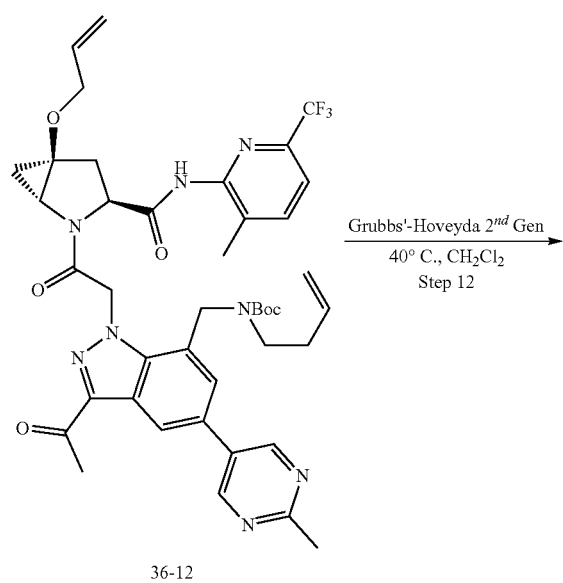
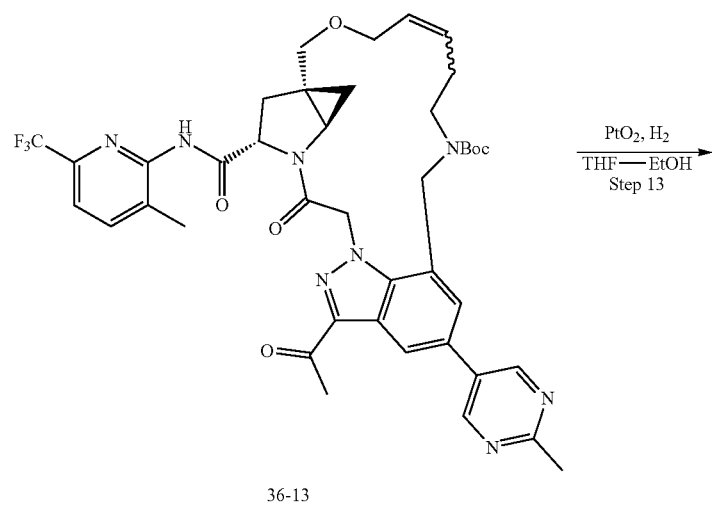

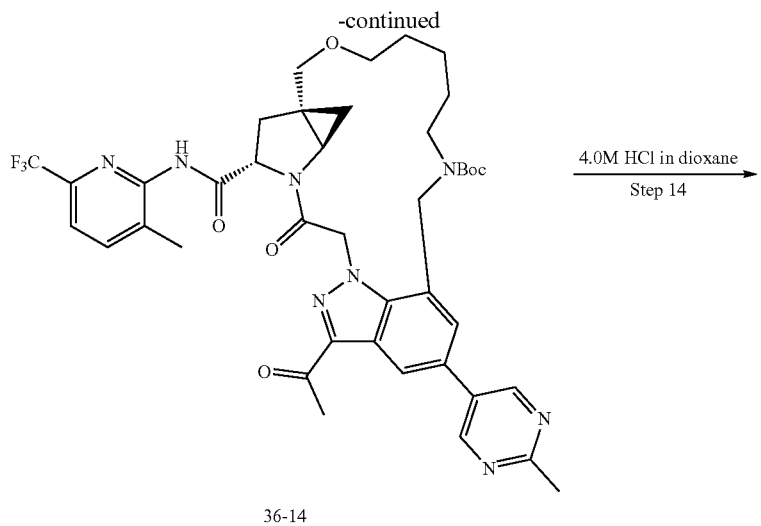

36-14

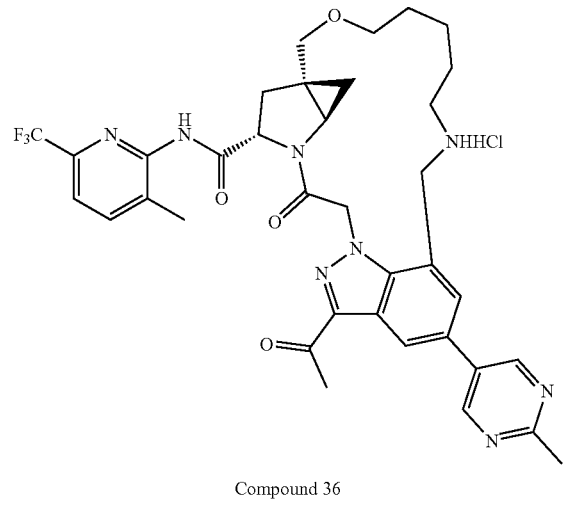

Compound 36

Step 1: tert-Butyl 5-bromo-7-methyl-1H-indazole-1-carboxylate (36-2)

A solution of 5-bromo-7-methyl-1H-indazole (36-1, 45 g), Boc$_2$O (55.8 g), potassium carbonate (5.9 g) and DMAP (0.26 g) in dichloromethane (900 mL) and water (90 mL) was stirred overnight at room temperature. The layers were separated and the organic layer was dried and concentrated. The residue was purified by silica gel column chromatography to afford the title compound.

Step 2: tert-Butyl 5-bromo-7-(bromomethyl)-1H-indazole-1-carboxylate (36-3)

A heterogeneous mixture of tert-butyl 5-bromo-7-methylindazole-1-carboxylate (36-2, 0.2 g, 0.643 mmol, 1 equiv.), NBS (0.114 g, 0.641 mmol, 0.997 equiv.) and AIBN (0.017 g, 0.104 mmol, 0.161 equiv.) in carbon tetrachloride was refluxed for 4 hours. 15% of S2 was remaining and therefore an additional 0.1 equiv of NBS and a crystal of AIBN was added. The reaction was refluxed for 1 hour. The reaction was cooled and diluted with water. Extracted with EtOAc. The organic layer was dried and concentrated. The residue was purified by silica gel column chromatography (eluent: 0-5% EtOAc in hexanes) to afford the product as a white solid. $^1$H-NMR (CDCl$_3$): δ 1.72 (s, 9H), 4.88 (s, 2H), 7.48 (s, 1H), 7.77 (d, J=1.2 Hz, 1H), 8.56 (s, 1H).

Step 3: tert-Butyl 7-(acetoxymethyl)-5-bromo-1H-indazole-1-carboxylate (36-4)

To a solution of tert-butyl 5-bromo-7-(bromomethyl)indazole-1-carboxylate (36-3, 41.43 g, 106.21 mmol, 1 equiv.) in DMF (410 mL) at room temperature was added potassium acetate (31.27 g) and the reaction was stirred at room temperature for 15 minutes. The reaction mixture was placed in a 40° C. bath and stirred for 1.5 hours. The reaction was cooled to room temperature, diluted with EtOAc and washed with water. The organic layer was dried and concentrated. The residue was purified by silica gel column chromatography to afford the title compound (eluent: 0-1% EtOAc in dichloromethane) compound as a yellow solid.

Step 4: tert-Butyl 7-(acetoxymethyl)-5-(2-methylpyrimidin-5-yl)-1H-indazole-1-carboxylate (36-5)

A heterogeneous mixture of 5-bromo-2-methylpyrimidine (23.91 g, 138.198 mmol, 1.501 equiv.), bis(pinacolato)diboron (38.47 g, 152.031 mmol, 1.651 equiv.), potassium acetate (27.13 g, 276.414 mmol, 3.002 equiv.), and dichloro 1,1'-bis(diphenylphosphino) palladium (II) dichloromethane adduct (5.64 g, 6.906 mmol, 0.075 equiv.) in dioxane was degassed with argon and heated at 100° C. overnight. The reaction was cooled to room temperature and charged with tert-butyl 7-[(acetyloxy)methyl]-5-bromoindazole-1-carboxylate (36-4, 34 g, 92.087 mmol, 1 equiv.), potassium carbonate (38.2 g, 276.391 mmol, 3.001 equiv.) and water. The reaction was again degassed and heated at 100° C. for 1.5 hours. The solvent was removed under reduced pressure and the residue was partitioned between dichloromethane and water. The organic layer was separated and washed with water. The combined aqueous layers were extracted with dichloromethane. The combined organic layers were dried and concentrated. The residue was purified by silica gel column chromatography (eluent: 0-5% MeOH in dichloromethane) to afford the title compound as a cream colored solid.

Step 5: (5-(2-Methylpyrimidin-5-yl)-1H-indazol-7-yl)methyl acetate (36-6)

Finely powdered tert-butyl 7-[(acetyloxy)methyl]-5-(2-methylpyrimidin-5-yl)indazole-1-carboxylate (36-5, 20.8 g, 54.39 mmol, 1 equiv.) was suspended in 4N HCl in dioxane (210 mL, 54.39 mmol, 1 equiv.) and stirred at room temperature for 1 hour with frequent sonication. After the reaction was complete, the solid was isolated by filtration. The solid was partitioned between chloroform (1 L) and saturated aqueous sodium bicarbonate. The organic layer was separated, dried and concentrated to afford the title compound as cream colored solid.

Step 6: (3-Bromo-5-(2-methylpyrimidin-5-yl)-1H-indazol-7-yl)methyl acetate (36-7)

[5-(2-Methylpyrimidin-5-yl)-1H-indazol-7-yl]methyl acetate (36-6, 20 g, 70.846 mmol, 1 equiv.) was suspended in DMF (200 mL) and the mixture was warmed until the solution was homogeneous. The solution was allowed to warm to room temperature with stirring. Once the solution was cooled to room temperature, NBS (13.88 g) was added portion-wise at room temperature. The reaction was stirred at room temperature for 30 minutes and then poured into 2 L of water with stirring. The solid was isolated by filtration, washed with 100 mL of saturated aqueous sodium bicarbonate solution, water and dried to afford the title compound as a cream colored solid. $^1$H-NMR (DMSO-d$_6$): δ 2.10 (s, 3H), 2.68 (s, 3H), 5.38 (s, 2H), 7.89 (s, 1H), 7.95 (s, 1H), 9.09 (s, 2H), 13.75 (s, 1H).

Step 7: (3-Acetyl-5-(2-methylpyrimidin-5-yl)-1H-indazol-7-yl)methyl acetate (36-8)

A solution of [3-bromo-5-(2-methylpyrimidin-5-yl)-1H-indazol-7-yl]methyl acetate (36-7, 10 g, 27.686 mmol, 1 equiv.), and trans-dchlorobis(triphenylphosphine)palladium (II) (1.94 g, 2.764 mmol, 0.1 equiv.) in DMF (200 mL) was purged with argon and tributyl(1-ethoxyvinyl)tin (14.99 g, 14.03 mL, 41.506 mmol, 1.499 equiv.) was added while the reaction was continually purged with argon for 5 additional minutes. Then the reaction was heated at 80° C. overnight. The solvent was removed under reduced pressure. Chloroform (200 mL) and cold 2N aqueous HCl (50 mL) was added and the reaction was stirred for 10 minutes in an ice bath. The reaction was made basic by the careful addition of saturated aqueous NaHCO$_3$ solution. The organic layer was separated and the aqueous layer was extracted with chloroform. The combined organic layers were dried and the residue was used as such for the next step.

Step 8: tert-Butyl 2-(7-(acetoxymethyl)-3-acetyl-5-(2-methylpyrimidin-5-yl)-1H-indazol-1-yl)acetate (36-9)

[3-Acetyl-5-(2-methylpyrimidin-5-yl)-1H-indazol-7-yl] methyl acetate (36-8) was taken up in DMF (150 mL) and potassium carbonate (7.65 g, 55.351 mmol, 2 equiv.) was added followed by tert-butyl bromoacetate (6.5 g, 4.921 mL, 33.325 mmol, 1.204 equiv.). The reaction was stirred at room temperature for 1 hour. The reaction was filtered through a fritted funnel and the filtrate was concentrated under reduced pressure. The residue was purified by silica gel column chromatography (0-5% MeOH in dichloromethane) to afford the title compound as a cream colored solid.

Step 9: tert-Butyl 2-(3-acetyl-7-((but-3-en-1-yl(tert-butoxycarbonyl)amino)methyl)-5-(2-methylpyrimidin-5-yl)-1H-indazol-1-yl)acetate (36-10)

An ice-cold mixture of {3-acetyl-1-[2-(tert-butoxy)-2-oxoethyl]-5-(2-methylpyrimidin-5-yl)indazol-7-yl}methyl acetate (36-9, 0.2 g, 0.456 mmol, 1 equiv.) and potassium carbonate (0.032 g, 0.228 mmol, 0.5 equiv.) in MeOH (5 mL) was stirred for 1 hour. The solvent was removed under reduced pressure and the residue was taken up in dichloromethane and washed with water. The organic layer was dried and concentrated. The crude product was used as such for the next step.

To an ice-cold solution of the hydroxy compound from above in THF (3 mL), TEA (0.092 g, 0.127 mL, 0.912 mmol, 2 equiv.) was added followed by the dropwise addition of MsCl (0.063 g, 0.042 mL, 0.547 mmol, 1.2 equiv.). The reaction was stirred for at 0° C. for 3 hours. The solvent was removed under reduced pressure. The residue was dissolved in dichloromethane and washed with water. The organic layer was dried and concentrated. The residue was used as such for the next step.

To an ice-cold solution of mesylate in THF (3 mL), was added TEA (0.127 mL), followed by 3-buten-1-amine (0.039 g, 0.05 mL, 0.547 mmol, 1.2 equiv.). The reaction was stirred overnight at room temperature. The volatiles were removed under reduced pressure. The residue was dissolved in dichloromethane (5 mL). To this solution, Boc$_2$O (0.199 g, 0.912 mmol, 2 equiv.) and a crystal of DMAP were added. The reaction was stirred at room temperature for 24 hours. The solvent was removed under reduced pressure and the residue was purified by silica gel column chromatography (eluent: 0-2% MeOH in dichloromethane) to afford 0.15 g of the product as a cream colored solid.

Step 10: 2-(3-Acetyl-7-((but-3-en-1-yl(tert-butoxycarbonyl)amino)methyl)-5-(2-methylpyrimidin-5-yl)-1H-indazol-1-yl)acetic acid (36-11)

To a solution of tert-butyl 2-(3-acetyl-7-{[but-3-en-1-yl (tert-butoxycarbonyl)amino]methyl}-5-(2-methylpyrimidin-5-yl)indazol-1-yl)acetate (36-10, 0.15 g, 0.273 mmol, 1 equiv.) in THF (1 mL) was added LiOH·H$_2$O (0.023 g, 0.546 mmol, 2 equiv.) in water (1 mL). Methanol (0.5 mL) was added and the reaction was stirred at room temperature for 2 hours. The reaction was diluted with water (3 mL) and the volatiles were removed under reduced pressure. The aqueous solution was extracted once with ether and the organic layer was discarded. The aqueous layer was cooled in an ice-bath and acidified with cold 1N aqueous HCl. The resulting heterogeneous mixture was extracted with chloroform. The chloroform layer was dried and concentrated to afford 130 mg of a cream colored solid that was used as such for the next step.

Step 11: tert-Butyl ((3-acetyl-1-(2-((1R,3S,5S)-5-(allyloxy)-3-((3-methyl-6-(trifluoromethyl)pyridin-2-yl)carbamoyl)-2-azabicyclo[3.1.0]hexan-2-yl)-2-oxoethyl)-5-(2-methylpyrimidin-5-yl)-1H-indazol-7-yl)methyl)(but-3-en-1-yl)carbamate (36-12)

(R2) tert-Butyl (1R,3S,5S)-{3-[3-methyl-6-(trifluoromethyl)pyridin-2-yl]carbamoyl}-5-[(prop-2-en-1-yloxy) methyl]-2-azabicyclo[3.1.0]hexane-2-carboxylate (0.130 g) was stirred at room temperature for 30 minutes in TFA (1 mL)-dichloromethane (1 mL). The volatiles were removed under reduced pressure. The residue was dissolved in DMF (2 mL) and DIPEA (0.23 mL) was added at 0° C. (3-Acetyl-7-{[but-3-en-1-yl(tert-butoxycarbonyl)amino]methyl}-5-(2-methylpyrimidin-5-yl)indazol-1-yl)acetic acid (33-8 from Example 33) was added to the reaction at 0° C. TBTU (0.102 g) was added and the cooling bath was removed. The reaction was stirred at room temperature for 30 minutes. The DMF was removed under reduced pressure. The residue was dissolved in chloroform and washed with saturated sodium bicarbonate solution. The organic layer was dried ($Na_2SO_4$) and concentrated. Crude product was purified by silica gel column chromatography (eluent: 0-2% MeOH in dichloromethane) to afford 170 mg of a colorless solid. $^1$H NMR (400 MHz, Chloroform-d) δ 1.08 (dd, J=2.7, 5.6 Hz, 1H), 1.41 (s, 9H), 1.42-1.45 (m, 1H), 1.92-2.02 (m, 1H), 2.03-2.13 (m, 1H), 2.27 (s, 3H), 2.51 (dd, J=9.4, 13.9 Hz, 1H), 2.64-2.73 (m, 1H), 2.72 (s, 3H), 2.81 (s, 3H), 3.03-3.14 (m, 1H), 3.16-3.26 (m, 1H), 3.52 (d, J=9.9 Hz, 1H), 3.61 (dd, J=2.6, 5.7 Hz, 1H), 3.68 (d, J=9.9 Hz, 1H), 4.03-4.05 (m, 2H), 4.21 (d, J=15.3 Hz, 1H), 4.74-4.86 (m, 3H), 5.17 (d, J=10.4 Hz, 1H), 5.26 (dd, J=17.2, 1.2 Hz, 1H), 5.40-5.52 (m, 2H), 5.66 (d, J=17.4 Hz, 1H), 5.75 (d, J=17.5 Hz, 1H), 5.89 (ddt, J=5.5, 10.7, 16.1 Hz, 1H), 7.38 (d, J=1.8 Hz, 1H), 7.45 (d, J=7.8 Hz, 1H), 7.68 (d, J=7.8 Hz, 1H), 8.62 (d, J=1.6 Hz, 1H), 8.89 (s, 2H), 9.70 (s, 1H). $^{19}$F (376 MHz): δ −67.4.

Step 12: Compound 36-13

To a solution of tert-butyl N-(3-acetyl-1-{2-[(1R,3S,5S)-3-{[3-methyl-6-(trifluoromethyl)pyridin-2-yl]carbamoyl}-5-[(prop-2-en-1-yloxy)methyl]-2-azabicyclo[3.1.0]hexan-2-yl]-2-oxoethyl}-5-(2-methylpyrimidin-5-yl)indazol-7-yl)-N-(pent-4-en-1-yl)carbamate (36-12, 0.1 g, 0.12 mmol, 1 equiv.) in dichloromethane (10 mL) under argon was added the Grubbs'-Hoveyda 2$^{nd}$ generation (8 mg) catalyst and the reaction was stirred overnight at 40° C. Additional catalyst (8 mg) was added and the reaction was stirred at 40° C. for an additional 24 hours. The reaction was adsorbed on silica and purified by silica gel column chromatography (eluent: 0-3% MeOH in dichloromethane) to afford 42 mg of a light brown solid as a cis-trans mixture (10 mg of trans 36-13 was separated).

Step 13: Compound 36-14

A solution of tert-butyl (1S,22R,25S)-16-acetyl-25-{[3-methyl-6-(trifluoromethyl)pyridin-2-yl]carbamoyl}-13-(2-methylpyrimidin-5-yl)-20-oxo-3-oxa-9,17,18,21-tetraazapentacyclo[19.2.2.1$^{11,15}$.0$^{1,22}$.0$^{18,26}$]hexacosa-5,11,13,15 (26),16-pentaene-9-carboxylate (36-12, 0.04 g, 0.05 mmol, 1 equiv.) and platinum oxide in THF (1 mL)-EtOH (1 mL) was stirred under hydrogen for 2 hours at room temperature. The reaction was then adsorbed on silica and purified by silica gel column chromatography (eluent: 0-3% MeOH in dichloromethane) to afford 23 mg of a white solid.

Step 14: Compound 36

A solution of tert-butyl (1S,22R,25S)-16-acetyl-25-{[3-methyl-6-(trifluoromethyl)pyridin-2-yl]carbamoyl}-13-(2-methylpyrimidin-5-yl)-20-oxo-3-oxa-9,17,18,21-tetraazapentacyclo[19.2.2.1$^{11,15}$.0$^{1,22}$.0$^{18,26}$]hexacosa-11,13,15 (26),16-tetraene-9-carboxylate (36-14, 0.02 g, 0.025 mmol, 1 equiv.) in 4.0 M HCl in dioxane was stirred at room temperature for 1 hour. The volatiles were then removed under reduced pressure. The residue was washed with 1:1 mixture of heptane-ether (1 mL). The solid was dried under high vacuum to afford a cream colored solid. $^1$H NMR (400 MHz, DMSO-d$_6$) δ 0.86 (t, J=6.8 Hz, 1H), 1.24-1.28 (m, 1H), 1.51-1.64 (m, 4H), 2.13-2.24 (m, 1H), 2.18 (s, 3H), 2.37-2.49 (m, 2H), 2.65 (s, 3H), 2.69 (s, 3H), 2.97 (d, J=12.2 Hz, 1H), 3.14-3.20 (m, 1H), 3.39-3.56 (m, 2H), 3.63-3.77 (m, 2H), 4.00 (d, J=12.2 Hz, 1H), 4.15 (t, J=4.3 Hz, 1H), 4.40-4.53 (m, 2H), 5.02 (t, J=12.7 Hz, 1H), 5.61 (d, J 18.0 Hz, 1H), 6.65 (d, J=18.1 Hz, 1H), 7.67 (d, J=7.8 Hz, 1H), 7.89-7.96 (m, 2H), 8.51 (d, J=1.4 Hz, 1H), 9.12. (s, 2H), 9.57 (s, 1H), 10.24 (s, 1H), 10.68 (s, 1H). $^{19}$F: δ −66.1.

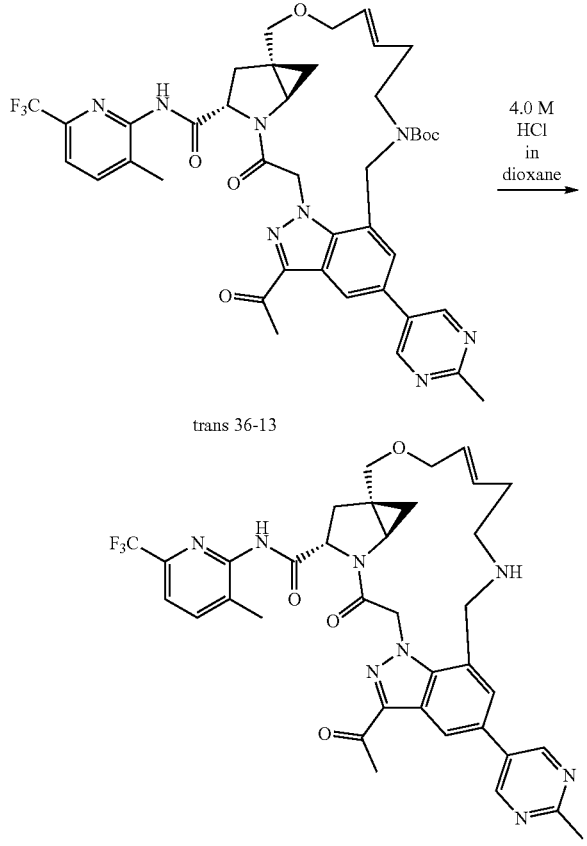

Scheme 36. Synthesis of Compound 37 trans 36-13

4.0 M HCl in dioxane

Compound 37

Compound 37: A solution of trans-36-13 (0.01 g, 0.012 mmol, 1 equiv.) in 4.0 M HCl in dioxane (1 mL) was stirred at room temperature for 2 hours. The solvent was removed under reduced pressure. The residue was dissolved in dichloromethane and 5 drops of TEA and purified by silica gel column chromatography (eluent: 0-4% MeOH in dichloromethane) to afford a white solid. $^1$H NMR (400 MHz, methanol-$d_4$) δ 0.35 (t, J=6.0 Hz, 0.46-0.47 (m, 2.27-2.32 (m, 1H), 2.36 (s, 3H), 2.42-2.54 (m, 3H), 2.68 (s, 3H), 2.74 (s, 3H), 2.94-2.99 (m, 2H), 3.04-3.12 (m, 1H), 3.78-4.01 (m, 4H), 4.19-4.34 (m, 2H), 4.50-4.62 (m, 1H), 5.62-5.69 (m, 1H), 5.91-5.98 (m, 1H), 6.04 (d, J=15.3 Hz, 1H), 6.15 (d, J=15.3 Hz, 1H), 7.58 (d, J=7.8 Hz, 1H), 7.64 (d, J=1.2 Hz, 1H), 7.88 (d, J=7.8 Hz, 1H), 8.52 (d, J=1.6 Hz, 1H), 9.00 (s, 2H). $^{19}$F: δ −69.1.

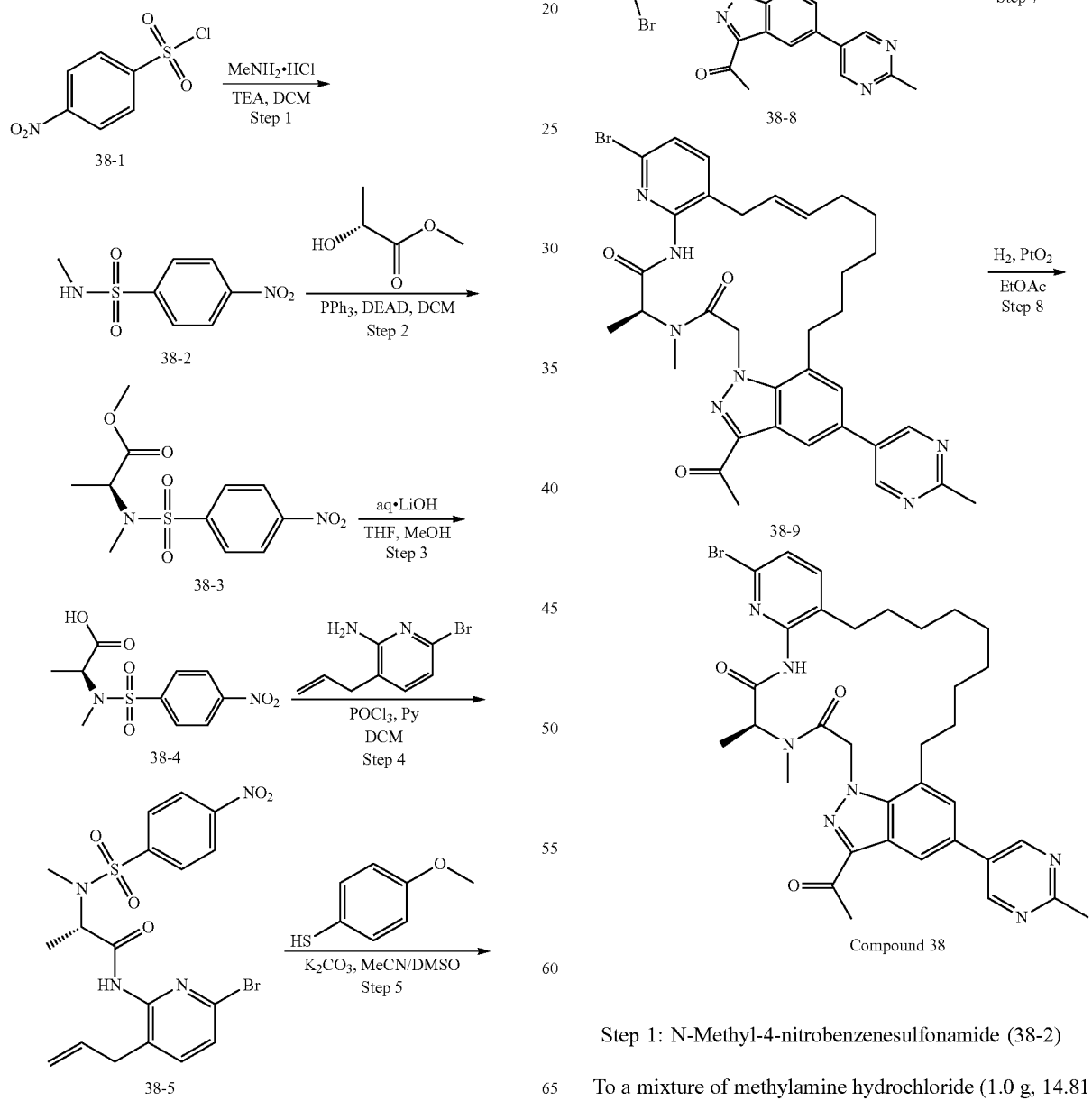

Step 1: N-Methyl-4-nitrobenzenesulfonamide (38-2)

To a mixture of methylamine hydrochloride (1.0 g, 14.81 mmol) and TEA (1.49 g, 44.4 mmol) in DCM (8 mL) was added 4-nitrobenzene-1-sulfonyl chloride (3.61 g, 16.3 mmol) in portions at 0° C. and the mixture was stirred at room temperature overnight. The mixture was diluted DCM and washed with water and brine, dried over anhydrous Na$_2$SO$_4$, filtered and concentrated to dryness. The residue was purified by chromatography on silica gel (eluted with PE:EtOAc=50:1 to 8:1) to afford compound 38-2 (1.34 g, yield 41.8%) as a yellow oil. LC/MS (ESI) m/z: 217 (M+H)$^+$.

Step 2: (S)-Methyl 2-(N-methyl-4-nitrophenylsulfonamido) propanoate (38-3)

To a solution of compound 38-2 (1.3 g, 6.02 mmol) in DCM (15 mL) was added PPh$_3$ (2.37 g, 9.03 mmol) and (R)-methyl 2-hydroxypropanoate (0.94 g, 9.03 mmol) followed by the drop-wise addition of DEAD (1.57 g, 9.03 mmol) at 0° C. The mixture was stirred at room temperature under N$_2$ atmosphere for 16 hours. The mixture was poured into the water and extracted with DCM twice. The combined organic layers were washed with brine, dried over anhydrous Na$_2$SO$_4$, filtered and concentrated to dryness. The residue was purified by chromatography on silica gel (elated with PE:EtOAc=30:1 to 5:1) to afford compound 38-3 (1.3 g, yield 69.4%) as a yellow solid. LC/MS (ESI) m/z: 303 (M+H)$^+$.

Step 3: (S)-2-(N-Methyl-4-nitrophenylsulfonamido) propanoic acid (38-4)

To a solution of compound 38-3 (1.3 g, 4.03 mmol) in methanol (2 mL) and THF (2 mL) was added a solution of LiOH (0.31 g, 12.91 mmol) in water (2 mL) at 0° C. and the mixture was stirred at room temperature overnight. The mixture was diluted with water and washed with Et$_2$O twice. The aqueous layer was acidified with 0.5 M aqueous HCl solution and extracted with DCM twice. The combined organic layers were washed with brine, dried over anhydrous Na$_2$SO$_4$, filtered and concentrated to dryness to afford compound 38-4 (1.1 g, yield 88.78%) as a white solid. LC/MS (ESI) m/z: 289 (M+H)$^+$.

Step 4: (S)-N-(3-Allyl-6-bromopyridin-2-yl)-2-(N-methyl-4-nitrophenylsulfonamido) propanamide (38-5)

To a mixture of compound 38-4 (394 mg, 1.37 mmol) and 3-allyl-6-bromopyridin-2-amine (290 mg, 1.37 mmol) in DCM (8 mL) was added pyridine (540 mg, 6.84 mmol) followed by the drop-wise addition of phosphoryl chloride (230 mg, 1.50 mmol) at 0° C. and the mixture was stirred at room temperature under N$_2$ atmosphere for 1 hour. The mixture was poured into ice-water and extracted with DCM twice. The combined organic layers were washed with brine, dried over anhydrous Na$_2$SO$_4$, filtered and concentrated to dryness. The residue was purified by chromatography on silica gel (eluted with PE:EtOAc=30:1 to 4:1) to afford compound 38-5 (350 mg, yield 53.1%) as a white solid. LC/MS (ESI) m/z: 483 (M+H)$^+$.

Step 5: (S)-N-(3-Allyl-6-bromopyridin-2-yl)-2-(methylamino)propanamide (38-6)

To a solution of compound 38-5 (340 mg, 0.71 mmol) in MeCN/DMSO (10 mL, v/v=49/1) was added K$_2$CO$_3$ (392 mg, 2.84 mmol) followed by 4-methoxybenzenethiol (298 mg, 2.13 mmol) at 0° C. and the mixture was stirred at room temperature for 4 hours. The mixture was diluted with EtOAc and washed with brine, dried over anhydrous Na$_2$SO$_4$, filtered and concentrated to dryness. The residue was purified by flash chromatography (eluted with PE:EtOAc=20:1 to 1:4) to afford compound 38-6 (165 mg, yield 78.2%) as a light yellow oil. LC/MS (ESI) m/z: 298/300 (M+H)$^+$.

Step 6: (S)-2-(2-(3-Acetyl-5-(2-methylpyrimidin-5-yl)-7-(oct-7-en-1-yl)-1H-indazol-1-yl)-N-methylacetamido)-N-(3-allyl-6-bromopyridin-2-yl)propanamide (38-8)

To a mixture of compound 38-6 (90 mg, 0.30 mmol) and 2-(3-acetyl-5-(2-methylpyrimidin-5-yl)-7-(oct-7-en-1-yl)-1H-indazol-1-yl)acetic acid (126 mg, 0.30 mmol) in DMF (5 mL) was added DIPEA (194 mg, 1.5 mmol) followed by HATU (171 mg, 0.45 mmol) at 0° C. and the mixture was stirred at room temperature for 1 hour. The mixture was diluted with EtOAc and washed with saturated aqueous NH$_4$Cl solution and brine, dried over anhydrous Na$_2$SO$_4$, filtered and concentrated to dryness. The residue was purified by flash chromatography (eluted with DCM:MeOH=100:1 to 10:1) to afford compound 38-8 (130 mg, yield 61.9%) as a yellow solid. LC/MS (ESI) m/z: 700/702 (M+H)$^+$.

Step 7: Compound 38-9

To a solution of compound 38-8 (50 mg, 0.07 mmol) in degassed toluene (50 mL) was added Grubbs 2$^{nd}$ catalyst (15 mg, 0.018 mmol) at 0° C. under N$_2$ atmosphere and the mixture was stirred at 80° C. under N$_2$ atmosphere for 16 hours. The mixture was concentrated to dryness and the residue was purified by chromatography on silica gel (eluted with DCM:MeOH=80:1) to afford compound 38-9 (30 mg, yield 63.8%) as a brown solid. LC/MS (ESI) m/z: 672/674 (M+H)$^+$.

Step 8: Compound 38

To a solution of compound 38-9 (30 mg, 0.045 mmol) in EtAOc (3 mL) was added PtO$_2$ (9 mg, 0.04 mmol) at 0° C. and the mixture was degassed under N$_2$ atmosphere three times and stirred under a H$_2$ balloon at room temperature for 30 minutes. The mixture was filtered and the filtrate was concentrated to dryness. The residue was purified by preparative HPLC to afford Compound 38 (0.4 mg, yield 1.3%) as a white solid. $^1$H-NMR (400 MHz, DMSO-d$_6$) δ 10.22 (s, 1H), 9.03 (d, J=3.6 Hz, 2H), 8.34 (d, J=1.6 Hz, 1H), 7.69 (dd, J=16.4, 16.4 Hz, 1H), 7.61 (dd, J=13.6, 13.6 Hz, 1H), 7.56-7.47 (m, 1H), 5.75 (d, J=22.4 Hz, 1H), 5.25 (d, J=7.2 Hz, 1H), 3.19 (s, 3H), 3.02 (t, J=8.0 Hz, 4H), 2.68 (s, 3H), 2.65 (s, 3H), 2.34-2.31 (m, 1H), 2.07-1.94 (m, 2H), 1.83-1.50 (m, 6H), 1.46 (d, J=7.2 Hz, 3H), 1.29-1.25 (m, 4H). LC/MS (ESI) m/z: 674/676 (M+H)$^+$.

Scheme 38. Synthesis of Compound 39

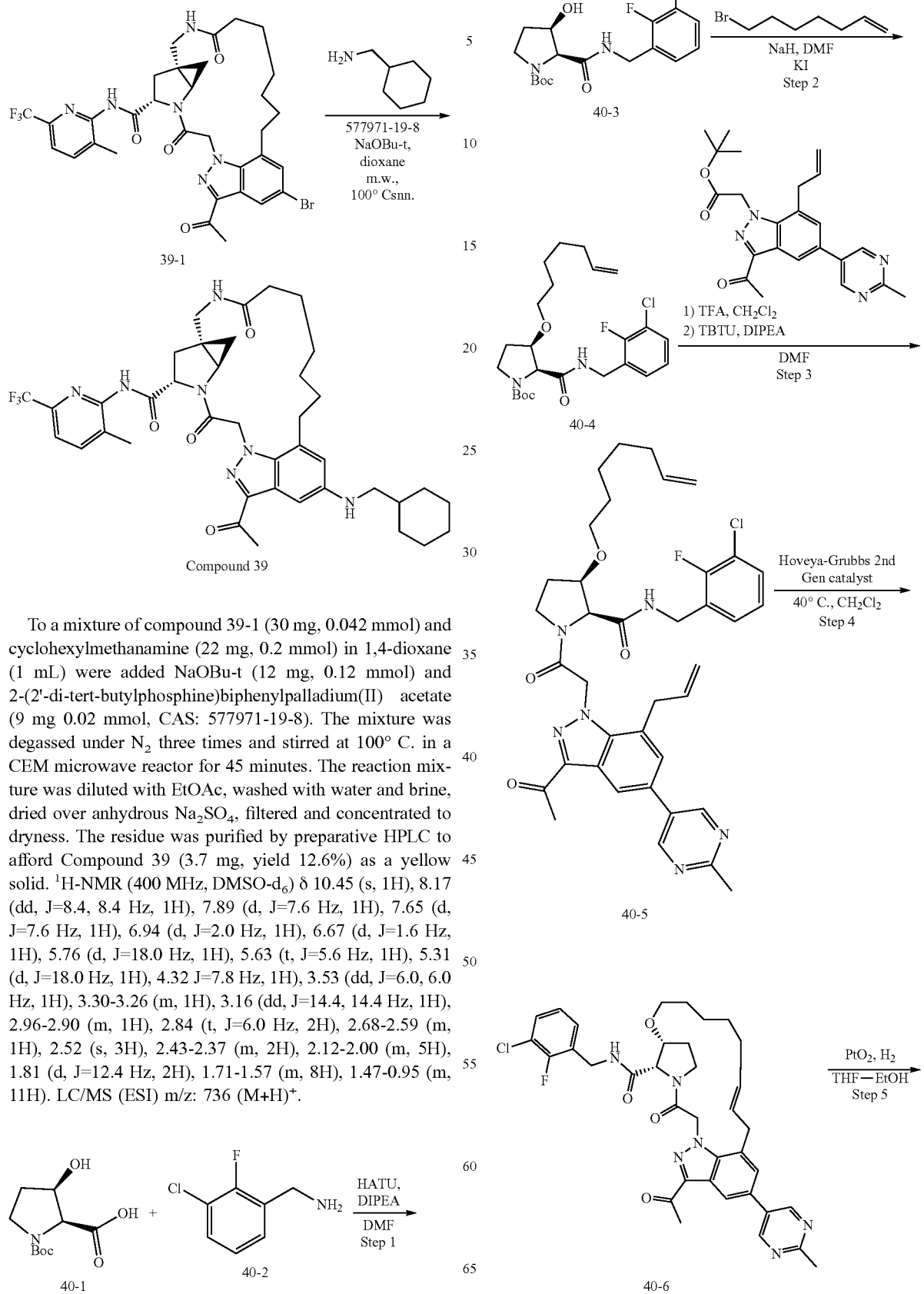

To a mixture of compound 39-1 (30 mg, 0.042 mmol) and cyclohexylmethanamine (22 mg, 0.2 mmol) in 1,4-dioxane (1 mL) were added NaOBu-t (12 mg, 0.12 mmol) and 2-(2'-di-tert-butylphosphine)biphenylpalladium(II) acetate (9 mg 0.02 mmol, CAS: 577971-19-8). The mixture was degassed under $N_2$ three times and stirred at 100° C. in a CEM microwave reactor for 45 minutes. The reaction mixture was diluted with EtOAc, washed with water and brine, dried over anhydrous $Na_2SO_4$, filtered and concentrated to dryness. The residue was purified by preparative HPLC to afford Compound 39 (3.7 mg, yield 12.6%) as a yellow solid. $^1$H-NMR (400 MHz, DMSO-$d_6$) δ 10.45 (s, 1H), 8.17 (dd, J=8.4, 8.4 Hz, 1H), 7.89 (d, J=7.6 Hz, 1H), 7.65 (d, J=7.6 Hz, 1H), 6.94 (d, J=2.0 Hz, 1H), 6.67 (d, J=1.6 Hz, 1H), 5.76 (d, J=18.0 Hz, 1H), 5.63 (t, J=5.6 Hz, 1H), 5.31 (d, J=18.0 Hz, 1H), 4.32 J=7.8 Hz, 1H), 3.53 (dd, J=6.0, 6.0 Hz, 1H), 3.30-3.26 (m, 1H), 3.16 (dd, J=14.4, 14.4 Hz, 1H), 2.96-2.90 (m, 1H), 2.84 (t, J=6.0 Hz, 2H), 2.68-2.59 (m, 1H), 2.52 (s, 3H), 2.43-2.37 (m, 2H), 2.12-2.00 (m, 5H), 1.81 (d, J=12.4 Hz, 2H), 1.71-1.57 (m, 8H), 1.47-0.95 (m, 11H). LC/MS (ESI) m/z: 736 (M+H)$^+$.

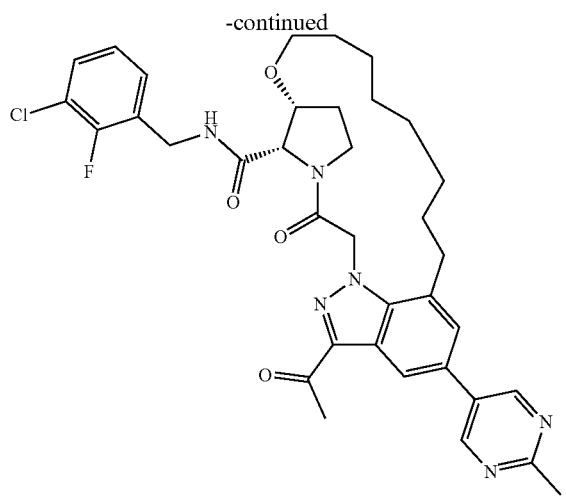

Compound 40

Step 1. tert-Butyl (2S,3R)-2-((3-chloro-2-fluorobenzyl)carbamoyl)-3-hydroxypyrrolidine-1-carboxylate (40-3)

To an ice-cold solution of (2S,3R)-1-(tert-butoxycarbonyl)-3-hydroxypyrrolidine-2-carboxylic acid (40-1, 1 g) in DMF (10 mL) were added HATU (1.97 g) and DIPEA (2.3 mL) followed by (3-chloro-2-fluorophenyl)methanamine (40-2, 0.76 g). The cooling bath was removed and the reaction was stirred overnight at room temperature. The solvent was removed under reduced pressure and the residue was dissolved in chloroform. The resulting solution was washed successively with 1.0 M aqueous citric acid, water, and saturated aqueous NaHCO$_3$ solution. The organic layer was dried with Na$_2$SO$_4$ and concentrated. The crude product was purified by silica gel column chromatography (eluent: 0-2.5% MeOH in dichloromethane) to afford white solid.

Step 2. tert-Butyl (2S,3R)-2-((3-chloro-2-fluorobenzyl)carbamoyl)-3-(hept-6-en-1-yloxy)pyrrolidine-1-carboxylate (40-4)

To an ice-cold solution of tert-butyl (2S,3R)-2-{[(3-chloro-2-fluorophenyl)methyl]carbamoyl}-3-hydroxypyrrolidine-1-carboxylate (1 g) in DMF (10 mL) was added sodium hydride (0.160 g, 60% in mineral oil) portion-wise and the solution was stirred for 30 minutes at 0° C., 7-Bromo-1-heptene (1.43 g) was added dropwise followed by the addition of a crystal of KI. The reaction was stirred at 0° C. for 2 hours and then at room temperature overnight. The solvent was removed under reduced pressure and the residue was diluted with dichloromethane-water. The organic layer was separated and the aqueous layer was extracted once with dichloromethane. The combined organic layers were dried with Na$_2$SO$_4$ and concentrated. The crude product was purified by silica gel column chromatography (eluent: 0-40% EtOAc in hexanes) to afford 0.38 g of a colorless resin.

Step 3. (2S,3R)-1-(2-(3-Acetyl-7-allyl-5-(2-methylpyrimidin-5-yl)-1H-indazol-1-yl)acetyl)-N-(3-chloro-2-fluorobenzyl)-3-(hept-6-en-1-yloxy)pyrrolidine-2-carboxamide (40-5)

tert-Butyl 2-[3-acetyl-5-(2-methylpyrimidin-5-yl)-7-(prop-2-en-1-yl)indazol-1-yl]acetate (0.33 g, 0.812 mmol, 1 equiv.) was stirred in a vial with 3 mL of TFA and 1 mL of CH$_2$Cl$_2$ for 3 hours. In another vial, tert-butyl (2S,3R)-2-{[3-chloro-2-fluorophenyl)methyl]carbamoyl}-3-(hept-6-en-1-yloxy)pyrrolidine-1-carboxylate (0.38 g) was stirred with 2 mL of TFA and 2 mL of CH$_2$Cl$_2$ for 30 minutes. The contents of the two vials were combined and the volatiles were removed under reduced pressure. The residue was dissolved in DMF (3 mL) and cooled in an ice bath. Subsequently, DIPEA (0.71 mL) and TBTU (1.10 g) were added. The cooling bath was removed and the reaction was stirred at room temperature for 30 minutes. The solvent was removed under reduced pressure. The residue was dissolved in dichloromethane and washed with saturated aqueous sodium bicarbonate solution. The organic layer was separated, dried with Na$_2$SO$_4$ and concentrated. The crude product was purified by silica gel column chromatography (0-1.5% MeOH in dichloromethane) to afford 350 mg of a white solid.

Step 4. Compound 40-6

A solution of (2S,3R)-1-{2-[3-acetyl-5-(2-methylpyrimidin-5-yl)-7-(prop-2-en-1-yl)indazol-1-yl]acetyl}-N-[(3-chloro-2-fluorophenyl)methyl]-3-(hept-6-en-1-yloxy)pyrrolidine-2-carboxamide (0.2 g, 0.16 mmol, 1 equiv.) in dichloromethane (34 mL) was degassed with argon. PtO$_2$ (18 mg) was added and the reaction was stirred at 40° C. overnight. Additional catalyst (18 mg) was added and the reaction was stirred for 8 hours at 40° C. The reaction was adsorbed on silica gel and purified by silica gel column chromatography (eluent: 0-3% MeOH in dichloromethane) to afford the desired compound as a brown solid that was a mixture of cis and trans isomers.

Step 5. Compound 40

A solution of Compound 4-6 (5 mg, 0.007 mmol, 1 equiv.) in THF (1 mL)-EtOH (1 mL) was stirred under hydrogen atmosphere for 6 hours in presence of platinum oxide (1 mg). The reaction was filtered through celite and the filtrate was concentrated under reduced pressure. The crude product was purified by preparative TLC (solvent system: 5% MeOH in chloroform) to afford Compound 40 as a colorless solid. $^1$H NMR (400 MHz, Chloroform-d, major rotamer) δ 0.86-0.89 (m, 2H), 1.26-1.63 (m, 8H), 1.71-1.79 (m, 1H), 1.91-1.99 (m, 1H), 2.27-2.37 (m, 2H), 2.72 (s, 3H), 2.87 (s, 3H), 2.87 (t, J=8.5 Hz, 2H), 3.37-3.45 (m, 2H), 3.75 (t, J=8.8 Hz, 1H), 3.92-3.96 (m, 1H), 4.32 (d, J=20.5 Hz, 2H), 4.42 (d, J=5.8 Hz, 2H), 5.41 (d, J=16.8 Hz, 1H), 5.51 (d, J=16.9 Hz, 1H), 6.11-6.15 (m, 1H), 6.64 (t, J=7.8 Hz, 1H), 7.07-7.11 (m, 2H), 7.27 (s, 1H), 8.49 (s, 1H), 8.91 (s, 2H). $^{19}$F NMR (CDCl$_3$) δ −121.1.

Scheme 40. Synthesis of Compound 41

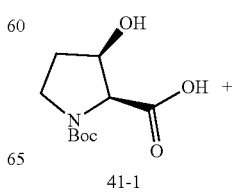

41-1

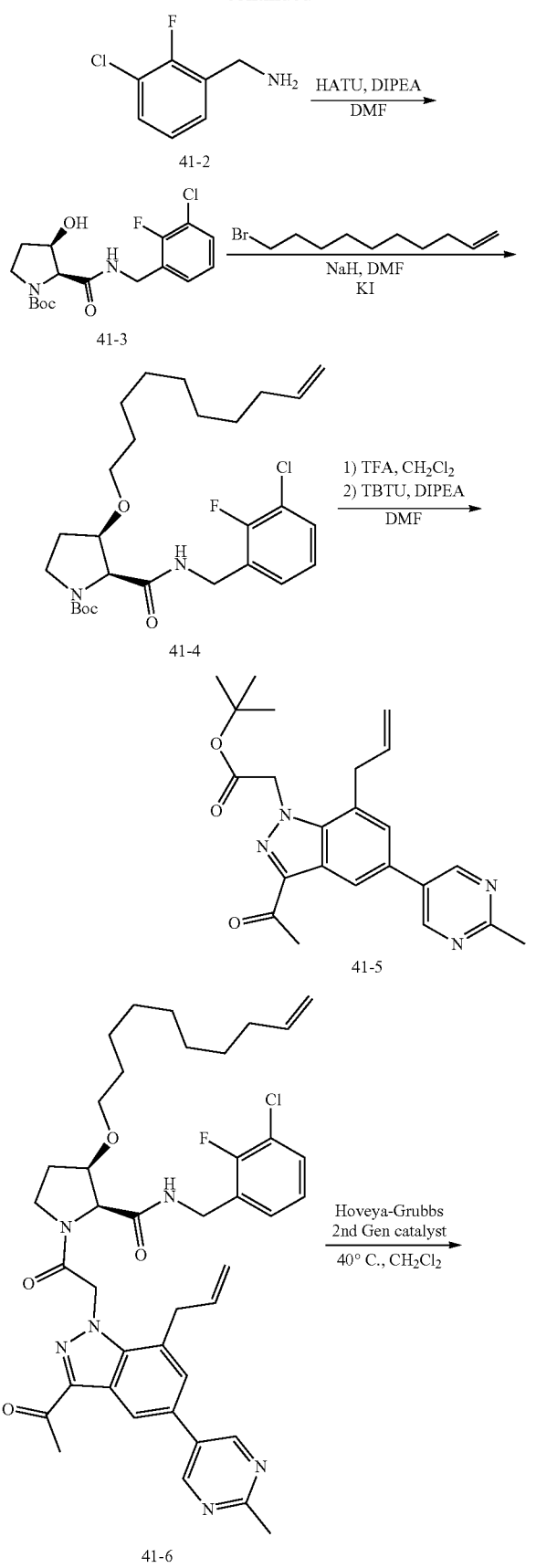
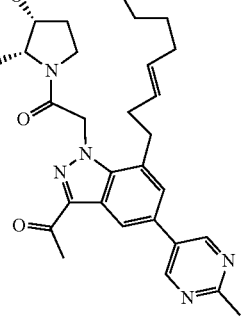

Compound 41

Step 1: tert-Butyl (2S,3R)-2-((3-chloro-2-fluorobenzyl)carbamoyl)-3-hydroxypyrrolidine-1-carboxylate (41-3)

To an ice-cold solution of (2S,3R)-1-(tert-butoxycarbonyl)-3-hydroxypyrrolidine-2-carboxylic acid (1 g) in DMF (10 mL) were added HATU (1.97 g) and DIPEA (2.3 mL) followed by (3-chloro-2-fluorophenyl)methanamine (0.76 g). The cooling bath was removed and the reaction was stirred overnight at room temperature. The solvent was removed under reduced pressure and the residue was dissolved in chloroform. The resulting solution was washed successively with 1.0 M aqueous citric acid, water, and saturated aqueous NaHCO$_3$ solution. The organic layer was dried with Na$_2$SO$_4$ and concentrated. The crude product was purified by silica gel column chromatography (eluent: 0-2.5% MeOH in dichloromethane) to afford a white solid.

Step 2: tert-Butyl (2S,3R)-2-((3-chloro-2-fluorobenzyl)carbamoyl)-3-(dec-9-en-1-yloxy)pyrrolidine-1-carboxylate (41-4)

To a cooled solution of tert-butyl (2S,3R)-2-{[(3-chloro-2-fluorophenyl)methyl]carbamoyl}-3-hydroxypyrrolidine-1-carboxylate (1 g, 2.682 mmol, 0.498 equiv.) in DMF (10 mL) was added sodium hydride (0.16 g, 60% in mineral oil) portion-wise. After the addition of NaH was complete, the reaction was stirred at 0° C. for 30 minutes. 10-Bromodec-1-ene (1.18 g, 5.384 mmol, 1 equiv.) was added dropwise at 0° C. and the reaction was stirred at 0° C. for 2 hours and allowed to warm to room temperature and stir overnight. The reaction was quenched with the careful addition of water and the solvent was removed under reduced pressure. The residue was taken up in dichloromethane and washed with water. The organic layer was separated, dried with Na$_2$SO$_4$, and concentrated. The crude product was purified by silica gel column chromatography (eluent: 0-40% EtOAc in hexanes) to afford 0.28 g of a colorless resin.

Step 3: (2S,3R)-1-(2-(3-Acetyl-7-allyl-5-(2-methylpyrimidin-5-yl)-1H-indazol-1-yl)acetyl)-N-(3-chloro-2-fluorobenzyl)-3-(dec-9-en-1-yloxy)pyrrolidine-2-carboxamide (41-6)

tert-Butyl (2S,3R)-2-{[(3-chloro-2-fluorophenyl)methyl]carbamoyl}-3-(dec-9-en-1-yloxy)pyrrolidine-1-carboxylate (41-4, 0.28 g, 0.548 mmol, 1.012 equiv.) was stirred in a vial with TFA (2 mL) and dichloromethane (2 mL) for 15 minutes. In another vial, tert-butyl 2-[3-acetyl-5-(2-methylpyrimidin-5-yl)-7-(prop-2-en-1-yl)indazol-1-yl]acetate (41-5, 0.22 g, 0.541 mmol, 1 equiv.) was stirred with TFA (2 mL) and dichloromethane (1 mL) for 2 hours at room temperature. The contents of the two vials were combined and the volatiles were removed under reduced pressure. The residue was taken up in DMF (3 mL) and the vial was cooled in an ice-bath. DIPEA (0.477 mL) and TBTU (0.211 g, 0.657 mmol, 1.214 equiv.) were added and the cooling bath was removed. The reaction was stirred for 30 minutes at room temperature. The solvent was removed under reduced pressure. The residue was dissolved in dichloromethane and washed with saturated sodium bicarbonate solution. The organic layer was dried with Na$_2$SO$_4$ and concentrated. The crude product was purified by silica gel column chromatography (eluent: 0-2% MeOH in dichloromethane) to afford the title compound as a cream colored solid.

Step 4: Compound 41-7

A solution of (2S,3R)-1-{2-[3-acetyl-5-(2-methylpyrimidin-5-yl)-7-(prop-2-en-1-yl)indol-1-yl]acetyl}-N-[(3-chloro-2-fluorophenyl)methyl]-3-(dec-9-en-1-yloxy)pyrrolidine-2-carboxamide (0.13 g, 0.175 mmol, 1 equiv.) in dichloromethane (20 mL) was degassed with argon and Hoveyda-Grubbs $2^{nd}$ generation catalyst (10 mg) was added. The reaction mixture was capped and heated at 40° C. overnight. The solvent was reduced by 50% and the reaction was adsorbed on silica and purified by silica gel column chromatography (eluent: 0-1.5% MeOH in dichloromethane) to afford the title compound as a mixture of cis and trans isomers.

Step 5. Compound 41

A mixture of Compound 41-7 (0.02 g, 0.028 mmol, 1 equiv.) and platinum oxide (2 mg) in THF (1 mL)-EtOH 91 mL) was stirred under hydrogen atmosphere overnight at room temperature. The reaction was then adsorbed on silica and purified by silica gel column chromatography (eluent: 0-1.5% MeOH in dichloromethane) to afford the title compound as a white solid. $^1$H NMR (400 MHz, Chloroform-d, major rotamer) δ 1.24-1.27 (m, 18H), 1.99-2.04 (m, 1H), 2.27-2.37 (m, 1H), 2.70 (s, 3H), 2.65-2.81 (m, 1H), 2.78-2.81 (m, 1H), 2.81 (s, 3H), 3.43-3.51 (m, 2H), 3.74-3.92 (m, 2H), 4.29-4.32 (m, 1H), 4.39-4.59 (m, 3H), 5.41 (d, J=17.3 Hz, 1H), 5.56 (d, J=17.1 Hz, 1H), 5.90 (t, J=6.3 Hz, 1H), 6.81 (t, J=7.8 Hz, 1H), 7.17-7.24 (m, 1H), 7.20-7.41 (m, 2H), 8.47 (s, 1H), 8.89 (s, 2H). $^{19}$F δ −121.4.

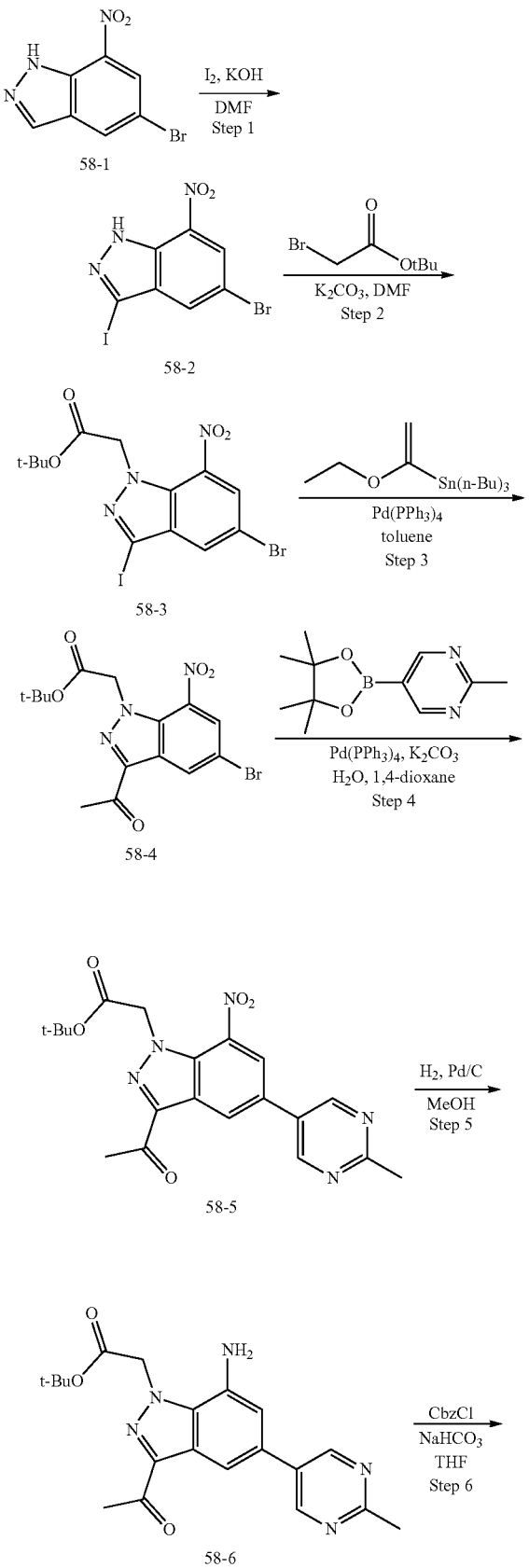

Scheme 41. Synthesis of Compound 58

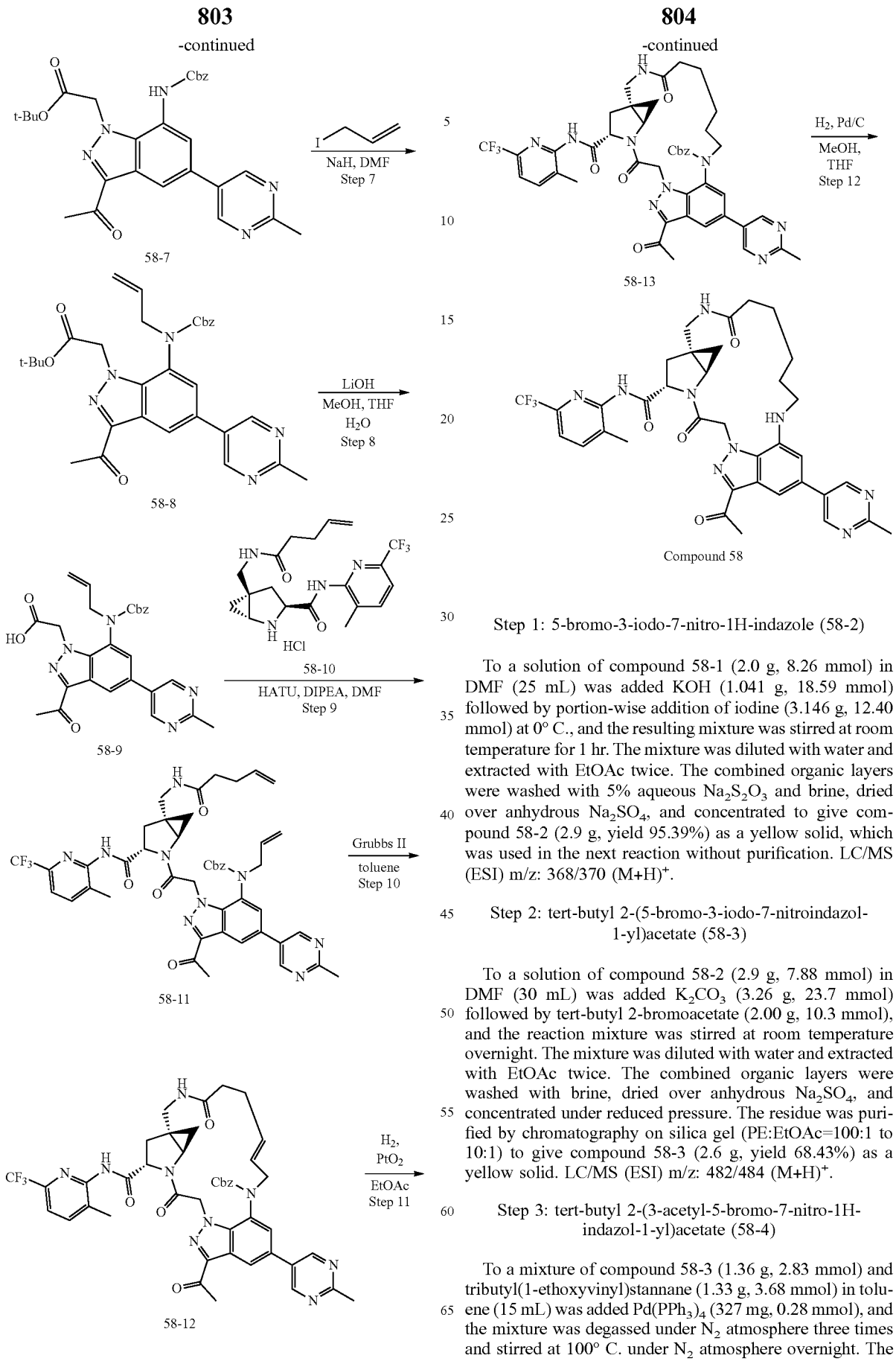

Step 1: 5-bromo-3-iodo-7-nitro-1H-indazole (58-2)

To a solution of compound 58-1 (2.0 g, 8.26 mmol) in DMF (25 mL) was added KOH (1.041 g, 18.59 mmol) followed by portion-wise addition of iodine (3.146 g, 12.40 mmol) at 0° C., and the resulting mixture was stirred at room temperature for 1 hr. The mixture was diluted with water and extracted with EtOAc twice. The combined organic layers were washed with 5% aqueous $Na_2S_2O_3$ and brine, dried over anhydrous $Na_2SO_4$, and concentrated to give compound 58-2 (2.9 g, yield 95.39%) as a yellow solid, which was used in the next reaction without purification. LC/MS (ESI) m/z: 368/370 (M+H)⁺.

Step 2: tert-butyl 2-(5-bromo-3-iodo-7-nitroindazol-1-yl)acetate (58-3)

To a solution of compound 58-2 (2.9 g, 7.88 mmol) in DMF (30 mL) was added $K_2CO_3$ (3.26 g, 23.7 mmol) followed by tert-butyl 2-bromoacetate (2.00 g, 10.3 mmol), and the reaction mixture was stirred at room temperature overnight. The mixture was diluted with water and extracted with EtOAc twice. The combined organic layers were washed with brine, dried over anhydrous $Na_2SO_4$, and concentrated under reduced pressure. The residue was purified by chromatography on silica gel (PE:EtOAc=100:1 to 10:1) to give compound 58-3 (2.6 g, yield 68.43%) as a yellow solid. LC/MS (ESI) m/z: 482/484 (M+H)⁺.

Step 3: tert-butyl 2-(3-acetyl-5-bromo-7-nitro-1H-indazol-1-yl)acetate (58-4)

To a mixture of compound 58-3 (1.36 g, 2.83 mmol) and tributyl(1-ethoxyvinyl)stannane (1.33 g, 3.68 mmol) in toluene (15 mL) was added Pd(PPh₃)₄ (327 mg, 0.28 mmol), and the mixture was degassed under $N_2$ atmosphere three times and stirred at 100° C. under $N_2$ atmosphere overnight. The mixture was concentrated to dryness, and the residue was dissolved in THF (10 mL). 0.5 N aqueous HCl (4 mL) was added to the mixture, and the mixture was stirred at room temperature for 1 hr. The mixture was extracted with EtOAc, washed with brine, dried, and concentrated to dryness. The residue was purified by silica gel chromatography (eluted with PE:EtOAc=100:1) to give compound 58-4 (860 mg, yield 76.6%) as a yellow solid. LC/MS (ESI) m/z: 398/400 (M+H)$^+$.

Step 4: tert-butyl 2-(3-acetyl-5-(2-methylpyrimidin-5-yl)-7-nitro-1H-indazol-1-yl)acetate (58-5)

To a mixture of compound 58-4 (860 mg, 2.02 mmol) and 2-methyl-5-(4,4,5,5-tetramethyl-1,3,2-dioxaborolan-2-yl) pyrimidine (490 mg, 2.23 mmol) in dioxane and water (16 mL, v/v=7:1) was added Pd(PPh$_3$)$_4$ (234 mg, 0.20 mmol) and K$_2$CO$_3$ (697 mg, 5.05 mmol). The mixture was degassed three times and stirred at 90° C. under N$_2$ atmosphere for 2 hrs. The mixture was diluted with water and extracted with EtOAc twice. The combined organic layers were washed with brine, dried over anhydrous Na$_2$SO$_4$, and concentrated under reduced pressure. The residue was purified by chromatography on silica gel (eluted with petroleum ether:ethyl acetate=5:1) to give compound 58-5 (720 mg, yield 86.7%) as a yellow solid, LC/MS (ESI) m/z: 412 (M+H)$^+$.

Step 5: tert-butyl 2-(3-acetyl-7-amino-5-(2-methylpyrimidin-5-yl)-1H-indazol-1-yl)acetate (58-6)

To a solution of compound 58-5 (720 mg, 1.75 mmol) in MeOH and THF (10 mL, v/v=1:1) was added 10% Pd/C (216 mg) at 0° C., and the mixture was degassed under N$_2$ atmosphere three times and stirred under an H$_2$ balloon at room temperature for 30 minutes. The mixture was filtered and the filtrate was concentrated to dryness. The residue was purified by chromatography on silica gel (DCM:MeOH=30:1) to give compound 58-6 (530 mg, yield 79.5%) as a yellow solid. (ESI) m/z: 382 (M+H)$^+$.

Step 6: tert-butyl 2-(3-acetyl-7-(((benzyloxy)carbonyl)amino)-5-(2-methylpyrimidin-5-yl)-1H-indazol-1-yl)acetate (58-7)

To a solution of compound 58-6 (530 mg, 1.39 mmol) in THF (8 mL) was added NaHCO$_3$ (129 mg, 1.53 mmol) in water (4 mL), followed by drop-wise addition of CbzCl (261 mg, 1.53 mmol) at 0° C., and the mixture was stirred at room temperature under N$_2$ atmosphere for 2 hrs. The mixture was quenched with iced-water and extracted with EtOAc twice. The combined organic layers were washed with brine, dried, and concentrated to dryness. The residue was purified by chromatography on silica gel (PE:EtOAc=10:1 to 3:1) to give compound 58-7 (350 mg, yield 48.9%) as a yellow solid. LC/MS (ESI) m/z: 516 (M+H)$^+$.

Step 7: [3-Acetyl-7-(allyl-benzyloxycarbonyl-amino)-5-(2-methyl-pyrimidin-5-yl)-indazol-1-yl]-acetic acid tert-butyl ester (58-8)

To a solution of compound 58-7 (350 mg, 0.68 mmol) in DMF (6 mL) was added NaH (42 mg, 1.02 mmol, 60%) at 0° C. under N$_2$ atmosphere, and the mixture was stirred at 0° C. for 30 minutes. 3-Iodo-propene (228 mg, 1.36 mmol) was added to the above mixture, and the reaction mixture was stirred at room temperature under N$_2$ atmosphere for 1 hr. The mixture was quenched with aqueous NH$_4$Cl at 0° C. and extracted with EtOAc twice. The combined organic layers were washed with brine, dried, and concentrated to dryness. The residue was purified by column chromatography on silica gel (PE:EtOAc=5:1) to give compound 58-8 (350 mg, yield 92.7%) as a light-yellow oil. LC/MS (ESI) m/z: 556 (M+H)$^+$.

Step 8: [3-Acetyl-7-(allyl-benzyloxycarbonyl-amino)-5-(2-methyl-pyrimidin-5-yl)-indazol-1-yl]-acetic acid (58-9)

To a solution of compound 58-8 (350 mg, 0.63 mmol) in MeOH and THF (6 mL, v/v=2/1) was added a solution of LiOH (132 mg, 3.15 mmol) in water (2 mL) at 0° C., and the mixture was stirred at room temperature for 2 hrs. The mixture was concentrated and washed with EtOAc and water, and the aqueous layer was acidified with 0.5 M aqueous HCl and extracted with EtOAc twice. The combined organic layers were washed with brine, dried with anhydrous Na$_2$SO$_4$, filtered, and concentrated to dryness to give compound 58-9 (225 mg, yield 71.6%) as yellow oil. LC/MS (ESI) m/z: 500 (M+H)$^+$.

Step 9: (3-Acetyl-5-(2-methyl-pyrimidin-5-yl)-1-{2-[3-(3-methyl-6-trifluoromethyl-pyridin-2-ylcarbamoyl)-5-(pent-4-enoylamino-methyl)-2-aza-bicyclo [3.1.0]hex-2-yl]-2-oxo-ethyl}-1H-indazol-7-yl)-allyl-carbamic acid benzyl ester (58-11)

To a mixture of compound 58-10 (154 mg, 0.39 mmol) and 58-9 (194 mg, 0.39 mmol) in DMF (6 mL) was added DIPEA (252 mg, 1.95 mmol) followed by HATU (224 mg, 0.59 mmol) at 0° C., and the mixture was stirred at room temperature for 1 hr. The mixture was diluted with EtOAc and washed with saturated aqueous NH$_4$Cl and brine, dried over anhydrous Na$_2$SO$_4$, filtered and concentrated to dryness. The residue was purified by chromatography on silica gel (DCM:MeOH=100:1 to 80:1) to give compound 58-11 (150 mg, yield 43.9%) as a yellow solid. LC/MS (ESI) m/z: 878 (M+H)$^+$.

Step 10: Compound 58-12

To a solution of compound 58-11 (150 mg, 0.17 mmol) in degassed toluene (120 mL) was added Grubbs 2$^{nd}$ generation catalyst (36 mg, 0.04 mmol) at 0° C. under N$_2$ atmosphere, and the mixture was stirred at 80° C. under N$_2$ atmosphere overnight. The mixture was concentrated to dryness, and the residue was purified by chromatography on silica gel (DCM:MeOH=100:1 to 80:1) to give compound 58-12 (130 mg, yield 57.2%) as a brown solid. LC/MS (ESI) m/z: 850 (M+H)$^+$.

Step 11: Compound 58-13

To a solution of compound 58-12 (130 mg, 0.15 mmol) in ethyl acetate (8 mL) was added PtO$_2$ (39 mg) at 0° C., and the mixture was degassed under N$_2$ atmosphere three times and stirred under an H$_2$ balloon at room temperature for 1 hr. The mixture was filtered, and the filtrate was concentrated to dryness. The residue was purified by chromatography on silica gel (DCM:MeOH=100:1 to 80:1) to give compound 58-13 (70 mg, yield 53.8%) as a brown solid. LC/MS (ESI) m/z: 852 (M+H)$^+$.

Step 12: Compound 58

To a solution of compound 58-13 (60 mg, 0.07 mmol) in MeOH and THF (6 mL, v/v=1:1) was added Pd/C (18 mg, 10% wt) at 0° C., and the mixture was degassed under $N_2$ atmosphere three times and stirred under an $H_2$ balloon at room temperature for 30 minutes. The mixture was filtered, and the filtrate was concentrated to dryness. The residue was purified by preparative HPLC to give Compound 58 (2.0 mg, yield 4.0%) as a white solid. $^1$H-NMR (400 MHz, $CD_3OD$) δ 8.93 (s, 2H), 7.96 (s, 1H), 7.78 (d, J=8.0 Hz, 1H), 7.55 (d, J=8.0 Hz, 1H), 6.79 (s, 1H), 6.22 (d, J=17.6 Hz, 1H), 5.54 (d, J=17.6 Hz, 1H), 4.48 (t, J=7.6 Hz, 1H), 3.76-3.72 (m, 1H), 3.49 (d, J=14.4 Hz, 1H), 3.26 (m, 1H), 3.11-3.04 (m, 1H), 3.03-2.94 (m, 1H), 2.74 (s, 3H), 2.67 (s, 3H), 2.64-2.57 (m, 2H), 2.43-2.37 (m, 1H), 2.25 (m, 1H), 2.03 (s, 3H), 1.94-1.83 (m, 2H), 1.71-1.66 (m, 2H), 1.46-1.28 (m, 3H), 1.14-1.09 (m, 1H). LC/MS (ESI) m/z: 718 (M+H)$^+$.

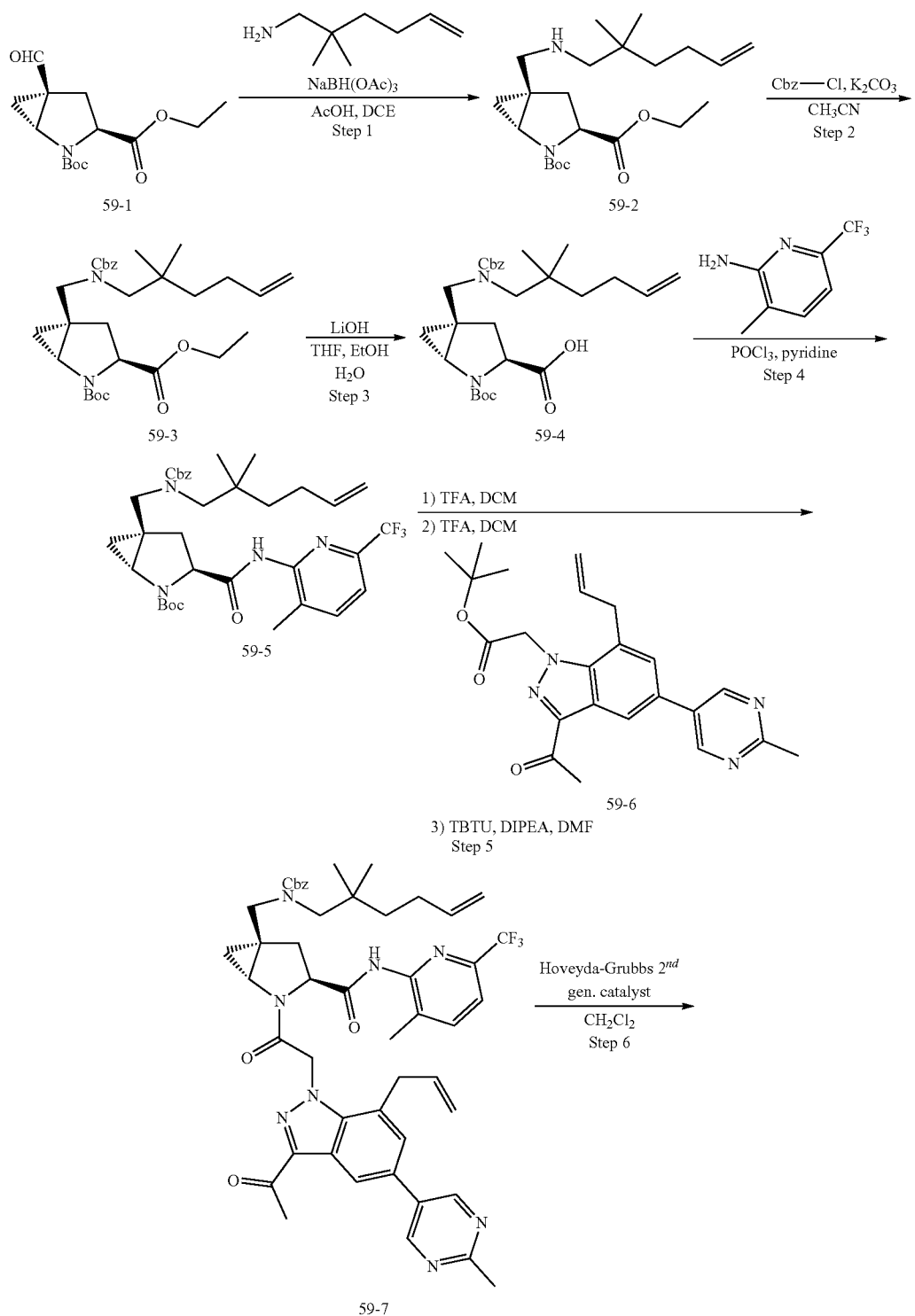

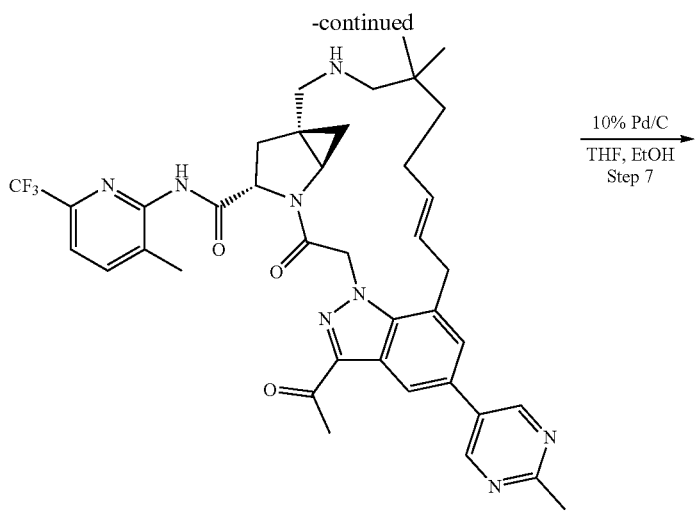

59-8

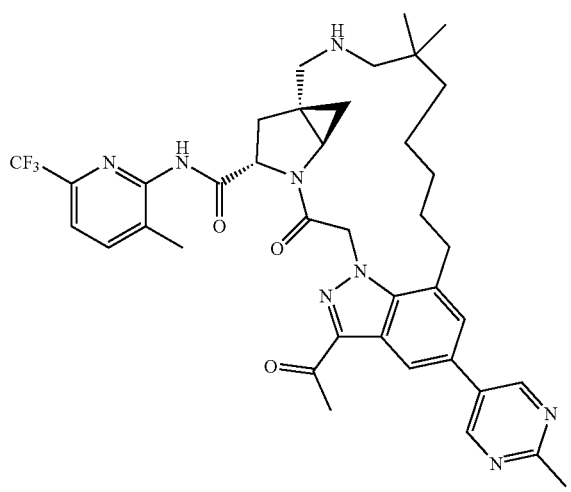

Compound 59

Step 1: 2-(tert-Butyl) 3-ethyl (1R,3S,5R)-5-(((2,2-dimethylhex-5-en-1-yl)amino)methyl)-2-azabicyclo[3.1.0]hexane-2,3-dicarboxylate (59-2)

To an ice-cold solution of compound 59-1 (0.223 g, 0.786 mmol, 1 equiv.) in 1,2-dichloroethane (5 mL), 200 mg of 4 Å molecular sieves and a drop of AcOH were added, followed by the dropwise addition of 2,2-dimethylhex-5-en-1-amine (0.1 g, 0.786 mmol, 1 equiv.) as a solution in dichloroethane (2 mL). The reaction mixture was stirred for 30 min at 0° C., followed by the portion-wise addition of solid sodium triacetoxyborohydride (0.5 g, 2.36 mmol, 3.0 equiv.) at 0° C. The cooling bath was removed and the reaction mixture was stirred at rt overnight. The reaction mixture was quenched by the careful addition of 1M aqueous NaOH solution at 0° C. The organic layer was separated and washed with brine, dried, and concentrated to give a colorless thick oil, which was used without purification in the next step.

Step 2: 2-(tert-Butyl) 3-ethyl (1R,3S,5R)-5-((((benzyloxy)carbonyl)(2,2-dimethylhex-5-en4-yl)amino)methyl)-2-azabicyclo[3.1.0]hexane-2,3-dicarboxylate (59-3)

To an ice-cold solution of compound 59-2 (0.52 g, 1.32 mmol, 1 equiv.) in acetonitrile (6 mL) was added powdered potassium carbonate (0.45 g) followed by Cbz-Cl (0.277 g, 0.23 mL, 1.63 mmol, 1.2 equiv.). The reaction mixture was allowed to come to rt gradually and stirred overnight at rt. The solid was filtered off, and the filtrate was concentrated. The residue was purified by silica gel flash column chromatography (eluent: 0-15% EtOAc in hexane) to give compound 59-3 as colorless resin

Step 3: (1R,3S,5R)-5-(((((Benzyloxy)carbonyl)(2,2-dimethylhex-5-en-1-yl)amino)methyl)-2-(tert-butoxycarbonyl)-2-azabicyclo[3.1.0]hexane-3-carboxylic acid (59-4)

To an ice-cold solution of compound 59-3 (0.6 g, 1.135 mmol, 1 equiv.) in THF (4 mL) and EtOH (2 mL) was added a solution of LiOH (0.072 g, 1.72 mmol, 1.5 equiv.) in water (2 mL). The cooling bath was removed, and the reaction mixture was stirred at rt for 4 h. The reaction mixture was diluted with water (5 mL), and the organic solvents were removed under reduced pressure. The aqueous solution was extracted once with ether and the organic extract was discarded, then the aqueous phase was cooled in an ice-bath and acidified with cold aqueous 1N HCl. This aqueous milky solution was then extracted with EtOAc, and the organic layer was dried (Na$_2$SO$_4$), filtered, and concentrated to get the title compound as a colorless resin, which was used in the next step without further purification.

Step 4: tert-Butyl (1R,3S,5R)-5-((((benzyloxy)carbonyl)(2,2-dimethylhex-5-en-1-yl)amino)methyl)-3-((3-methyl-6-(trifluoromethyl)pyridin-2-yl)carbamoyl)-2-azabicyclo[3.1.0]hexane-2-carboxylate (59-5)

To an ice-cold solution of compound 59-4 (0.26 g, 0.519 mmol, 1 equiv.), 3-methyl-6-(trifluoromethyl)pyridin-2-amine (0.1 g, 0.568 mmol, 1.093 equiv.), and pyridine (0.21 mL, 0.519 mmol, 1 equiv.) in dichloromethane (6 mL) was added phosphorous oxychloride (0.08 g, 0.047 mL, 0.519 mmol, 1 equiv.), and the reaction mixture stirred at 0° C. for 3 h. The reaction mixture was quenched by the careful addition of saturated aqueous sodium bicarbonate solution. The cooling bath was removed and the reaction mixture was stirred at rt for 15 min. The layers were separated, and the aqueous layer was extracted with dichloromethane. The combined organic layers were dried (Na$_2$SO$_4$) and concentrated, and the crude product was purified by silica gel flash column chromatography (eluent: 0-2% MeOH in dichloromethane) to give compound 59-5 as a colorless resin.

Step 5: Benzyl (((1R,3S,5R)-2-(2-(3-acetyl-7-allyl-5-(2-methylpyrimidin-5-yl)-1H-indazol-1-yl)acetyl)-3-((3-methyl-6-(trifluoromethyl)pyridin-2-yl)carbamoyl)-2-azabicyclo[3.1.0]hexan-5-yl)methyl)(2,2-dimethylhex-5-en-1-yl)carbamate (59-7)

Compound 59-6 (0.21 g, 0.516 mmol, 1 equiv.) was stirred with TFA (2 mL) and dichloromethane (1 mL) for 3 h. In another vial, compound 59-5 (0.34 g, 0.516 mmol, 1 equiv.) was stirred with 1 mL of TFA and 1 mL of dichloromethane for 30 min. The contents from both the vials were combined, and the volatiles were removed under reduced pressure. The residue was dissolved in DMF (3 mL) and cooled in an ice-bath. To this cold solution were added successively, DIPEA (0.45 mL, 5 equiv.) and TBTU (0.182 g, 1.1 equiv.), and the cooling bath was removed. The reaction mixture was stirred at rt for 30 min, and the solvent was removed under reduced pressure. The residue was dissolved in dichloromethane and washed with saturated aqueous sodium bicarbonate solution, and the organic layer was dried (Na$_2$SO$_4$), filtered, and concentrated. The crude product was purified by silica gel flash chromatography (eluent: 0-2% MeOH in dichloromethane) to give compound 59-7 as a white solid.

Step 6: (59-8)

A solution of compound 59-7 (0.3 g) and Hoveyda-Grubbs 2$^{nd}$ generation catalyst (0.023 g) in dichloromethane (58 mL) was degassed with argon and stirred at rt overnight. 12 mg of Hoveyda-Grubbs 2$^{nd}$ generation catalyst was added and the reaction mixture was stirred at rt until the reaction was complete. The solvent was removed under reduced pressure and the residue was purified by silica gel flash column chromatography (eluent: 0-2% MeOH in dichloromethane) to give compound 59-8.

Step 7: Compound 59

Compound 59-8 (0.05 g, 0.058 mmol, 1 equiv.) was taken up in THF (2 mL) and EtOH (2 mL) and Pd/C (0.005 g) was added. The reaction mixture was stirred under hydrogen atmosphere overnight. The catalyst was filtered off, Pd/C (0.005 g) was again added and the reaction mixture was stirred under hydrogen atmosphere overnight. The reaction mixture was adsorbed on silica and purified by silica gel flash column chromatography (eluent: 0-9% MeOH in dichloromethane) to give Compound 59 as a cream colored solid. $^1$H NMR (400 MHz, Chloroform-d) δ 0.90 (s, 3H), 0.93 (s, 3H), 0.95-0.98 (m, 1H), 1.09 (t, J=5.9 Hz, 1H), 1.16-1.88 (m, 9H), 2.13 (s, 3H), 2.36 (d, J=13.9 Hz, 1H), 2.43-2.56 (m, 2H), 2.61-2.79 (m, 5H), 2.80 (s, 3H), 2.98-3.13 (m, 2H), 3.44 (d, J=13.7 Hz, 1H), 3.54 (s, 1H), 4.85 (s, 1H), 5.57 (d, J=17.3 Hz, 1H), 5.84 (d, J=17.4 Hz, 1H), 7.35 (d, J=7.6 Hz, 2H), 7.56 (d, J=7.7 Hz, 1H), 8.21 (s, 1H), 8.45 (d, J=1.7 Hz, 1H), 8.88 (s, 2H). $^{19}$F NMR (376 MHz, Chloroform-d) δ −67.6.

Scheme 43. Synthesis of Compound 60

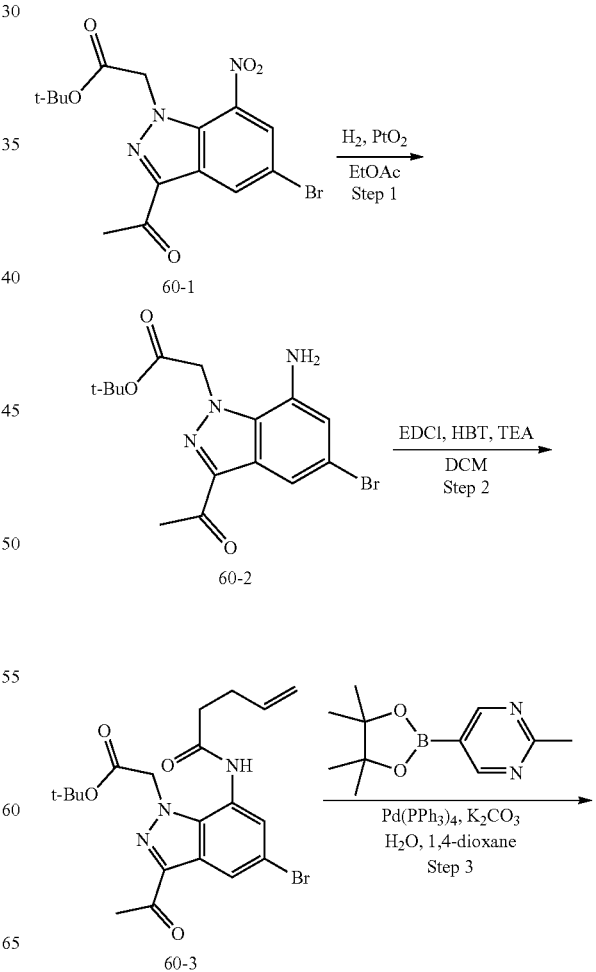

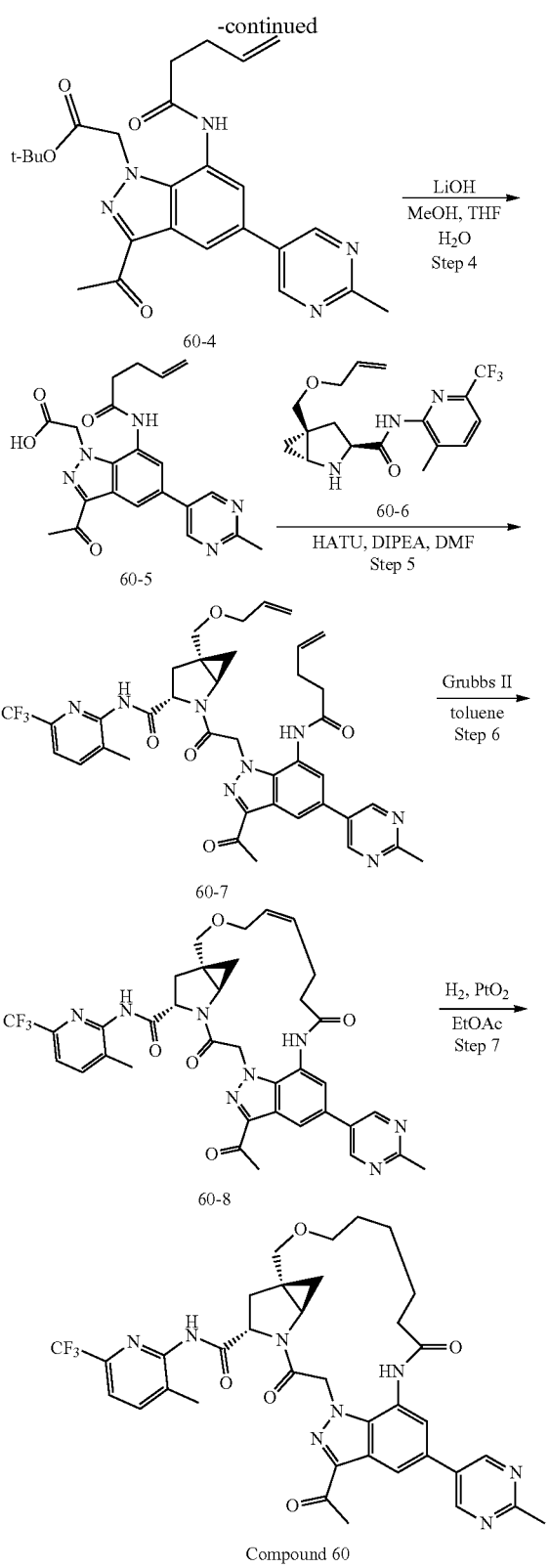

mixture was degassed under N₂ atmosphere three times and stirred under an H₂ balloon at room temperature for 25 minutes. The mixture was filtered, and the filtrate was concentrated to dryness. The residue was purified chromatography on silica gel (PE:EtOAc=15:1) to give compound 60-2 (407 mg, yield 81.5%) as a yellow oil. LC/MS (ESI) m/z: 368/370 (M+H)⁺.

Step 2: (3-Acetyl-5-bromo-7-pent-4-enoylamino-indazol-1-yl)-acetic acid tert-butyl ester (60-3)

To a mixture of compound 60-2 (160 mg, 0.44 mmol) and pent-4-enoic acid (44 mg, 0.44 mmol) in DCM (6 mL) was added pyridine (174 mg, 2.2 mmol) followed by POCl₃ (74 mg, 0.48 mmol) at 0° C., and the mixture was stirred at room temperature under N₂ atmosphere for 2 hrs. The mixture was poured into iced-water and extracted with DCM twice, and the combined organic layers were washed with brine, dried with anhydrous Na₂SO₄, filtered, and concentrated to dryness. The residue was purified by chromatography on silica gel (PE:EtOAc=50:1 to 12:1) to give compound 60-3 (130 mg, yield 66.0%) as a light yellow solid. LC/MS (ESI) m/z: 450/452 (M+H)⁺.

Step 3: [3-Acetyl-5-(2-methyl-pyrimidin-5-yl)-7-pent-4-enoylamino-indazol-1-yl]-acetic acid tert-butyl ester (60-4)

To a mixture of compound 60-3 (130 mg, 0.29 mmol) and 2-methyl-5-(4,4,5,5-tetramethyl-1,3,2-dioxaborolan-2-yl)pyrimidine (70 mg, 0.32 mmol) in dioxane and H₂O (8 mL, v/v=7:1) was added Pd(PPh₃)₄ (34 mg, 0.029 mmol) and K₂CO₃ (100 mg, 0.73 mmol), and the mixture was stirred at 90° C. under N₂ atmosphere for 3 hrs. The mixture was diluted with water and extracted with EtOAc twice, and the combined organic layers were washed with brine, dried over anhydrous Na₂SO₄ and concentrated under reduced pressure. The residue was purified by chromatography on silica gel (PE:EtOAc=20:1 to 5:1) to give compound 60-4 (115 mg, yield 85.6%) as a yellow solid. LC/MS (ESI) m/z: 464 (M+H)⁺.

Step 4: [3-Acetyl-5-(2-methyl-pyrimidin-5-yl)-7-pent-4-enoylamino-indazol-1-yl]-acetic acid (60-5)

To a solution of compound 60-4 (90 mg, 0.19 mmol) in MeOH and THF (6 mL, v/v=2/1) was added a solution of LiOH (41 mg, 97 mmol) in water (2 mL) at 0° C., and the mixture was stirred at room temperature for 2 hrs. The mixture was concentrated to dryness, and the residue was dissolved in water and washed with EtOAc. The aqueous layer was acidified with 0.5 M aqueous HCl and extracted with EtOAc twice. The combined organic layers were washed with brine, dried with anhydrous Na₂SO₄, filtered and concentrated to dryness to give compound 60-5 (50 mg, yield 64.9%) as a white solid. LC/MS (ESI) m/z: 408 (M+H)⁺.

Step 5: 2-{2-[3-Acetyl-5-(2-methyl-pyrimidin-5-yl)-7-pent-4-enoylamino-indazol-1-yl]-acetyl}-5-allyloxymethyl-2-aza-bicyclo[3.1.0]hexane-3-carboxylic acid (3-methyl-6-trifluoromethyl-pyridin-2-yl)-amide (60-7)

To a mixture of compound 60-5 (50 mg, 0.12 mmol) and compound 60-6 (44 mg, 0.12 mmol) in DMF (3 mL) was added DIPEA (77 mg, 0.6 mmol) followed by HATU (68

Step 1: (3-Acetyl-7-amino-5-bromo-indazol-1-yl)-acetic acid tert-butyl ester (60-2)

To a solution of compound 60-2 (540 mg, 1.36 mmol) in EtOAc (10 mL) was added PtO₂ (162 mg) at 0° C., and the mg, 0.18 mmol) at 0° C., and the mixture was stirred at room temperature for 1 hr. The mixture was diluted with EtOAc and washed with saturated aqueous NH₄Cl and brine, dried over anhydrous Na₂SO₄, filtered, and concentrated to dryness. The residue was purified by chromatography on silica gel (DCM:MeOH=100:1 to 60:1) to give compound 60-7 (40 mg, yield 44.9%) as a yellow solid. LC/MS (ESI) m/z: 745 (M+H)⁺.

Step 6: compound 60-8

To a solution of compound 60-7 (40 mg, 0.054 mmol) in degassed toluene (40 mL) was added Grubbs $2^{nd}$ generation catalyst (11 mg, 0.013 mmol) at 0° C. under N₂ atmosphere, and the mixture was stirred at 80° C. under N₂ atmosphere overnight. The mixture was concentrated to dryness, and the residue was purified by chromatography on silica gel (DCM:MeOH=100:1 to 80:1) to give compound 60-8 (25 mg, yield 65.8%) as a brown solid, LC/MS (ESI) m/z: 717 (M+H)⁺.

Step 7: Compound 60

To a solution of compound 60-8 (25 mg, 0.035 mmol) in ethyl acetate (3 mL) was added PtO₂ (7.5 mg) at 0° C., and the mixture was degassed under N₂ atmosphere three times and stirred under an H₂ balloon at room temperature for 15 minutes. The mixture was filtered, and the filtrate was concentrated to dryness. The residue was purified by preparative HPLC to give Compound 60 (2.0 mg, yield 8.0%) as a white solid. ¹H NMR (400 MHz, CD₃OD) δ 8.99 (s, 2H), 8.54 (d, J=1.6 Hz, 1H), 7.85 (d, J=8.0 Hz, 1H), 7.59-7.55 (m, 2H), 5.77 (d, J=17.6 Hz, 1H), 5.61 (d, J=17.6 Hz, 1H), 4.49-4.41 (m, 1H), 4.07 (d, J=11.6 Hz, 1H), 3.85 (dd, J=6.0, 6.0 Hz, 1H), 3.72-3.67 (m, 1H), 3.60-3.54 (m, 1H), 3.18-3.11 (m, 1H), 3.04 (d, J=11.6 Hz, 1H), 2.74 (s, 3H), 2.70 (s, 3H), 2.68-2.61 (m, 2H), 2.40-2.33 (m, 1H), 2.23 (s, 3H), 1.94-1.78 (m, 3H), 1.63-1.59 (m, 2H), 1.17-1.10 (m, 2H), 1.06 (dd, J=6.4, 6.4 Hz, 1H). LC/MS (ESI) m/z: 719 (M+H)⁺.

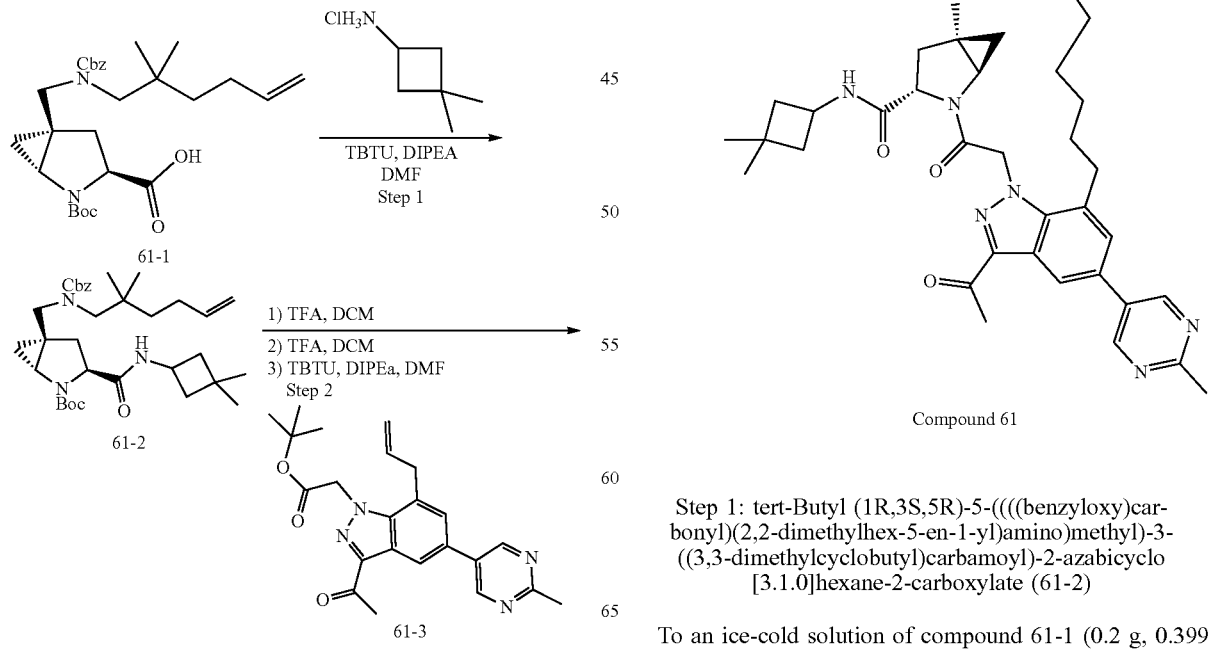

Compound 61

Step 1: tert-Butyl (1R,3S,5R)-5-((((benzyloxy)carbonyl)(2,2-dimethylhex-5-en-1-yl)amino)methyl)-3-((3,3-dimethylcyclobutyl)carbamoyl)-2-azabicyclo[3.1.0]hexane-2-carboxylate (61-2)

To an ice-cold solution of compound 61-1 (0.2 g, 0.399 mmol, 1 equiv.), 3,3-dimethylcyclobutan-1-amine hydrochloride (0.054 g, 0.399 mmol, 1 equiv.) in DMF (2 mL) were added DIPEA (0.258 g, 0.35 mL, 2.00 mmol, 5 equiv.) and TBTU (0.141 g, 0.439 mmol, 1.1 equiv.) successively. The cooling bath was removed, and the reaction mixture was stirred at rt for 30 min. The DMF was removed under reduced pressure, and the residue was dissolved in dichloromethane and washed with saturated aqueous sodium bicarbonate solution and cold 1N aqueous HCl solution. The organic layer was dried ($Na_2SO_4$) and concentrated to give compound 61-2 as a colorless resin, which was used in the next step without further purification.

Step 2: Benzyl (((1R,3S,5R)-2-(2-(3-acetyl-7-allyl-5-(2-methylpyrimidin-5-yl)-1H-indazol-1-yl)acetyl)-3-((3,3-dimethylcyclobutyl)carbamoyl)-2-azabicyclo[3.1.0]hexan-5-yl)methyl)(2,2-dimethylhex-5-en-1-yl)carbamate (61-4)

Compound 61-3 (0.168 g, 0.413 mmol, 1 equiv.) was stirred with TFA (2 mL) and dichloromethane (1 mL) for 3 h. In another vial, compound 61-2 (0.24 g, 0.413 mmol, 1 equiv.) was stirred with 1 mL of TFA and 1 mL of dichloromethane for 30 min. The contents from both the vials were combined and the volatiles were removed under reduced pressure. The residue was dissolved in DMF (2 mL) and cooled in an ice-bath. To this cold solution were added successively, DIPEA (0.267 g, 0.359 mL, 2.06 mmol, 5 equiv.) and TBTU (0.146 g, 0.454 mmol, 1.1 equiv.). The cooling bath was removed, and the reaction mixture was stirred at rt for 30 min. The solvent was removed under reduced pressure, and the residue was dissolved in dichloromethane and washed with saturated aqueous sodium bicarbonate. The organic layer was dried ($Na_2SO_4$), filtered, and concentrated, and the crude product was purified by silica gel flash column chromatography (eluent: 0-2% MeOH in dichloromethane) to give compound 61-4 as a white solid Step 3: (61-5)

A solution of compound 61-4 (0.15 g) and Hoveyda-Grubbs $2^{nd}$ generation catalyst (0.012 g) in dichloromethane (30 mL) was degassed with argon and stirred at rt overnight. 6 mg of Hoveyda-Grubbs $2^{nd}$ generation catalyst was added and the reaction mixture was stirred at rt until the reaction was complete. The solvent was removed under reduced pressure, and the resultant residue was purified by silica gel flash column chromatography (eluent: 0-3% MeOH in dichloromethane) to give the desired product as a brown solid.

Step 4. Compound 61

A solution of compound 61-5 (0.04 g, 0.051 mmol, 1 equiv.) in THF (2 mL) and EtOH (2 mL) was stirred in presence of 10% Pd/C under hydrogen atmosphere (4 mg) at rt overnight. Then the catalyst was filtered off, and a fresh aliquot of 4 mg of the catalyst was added to the reaction mixture, and it was stirred under hydrogen atmosphere overnight. The reaction mixture was adsorbed on silica gel and purified by silica gel flash column chromatography (eluent: 0-20% MeOH in dichloromethane) to give Compound 61 as a light brown solid. $^1$H NMR (400 MHz, Methanol-$d_4$) δ 0.80-1.07 (m, 10H), 1.07 (s, 3H), 1.20-1.30 (m, 2H), 1.41-1.71 (m, 7H), 1.79-2.06 (m, 4H), 2.19-2.38 (m, 3H), 2.40 (d, J=11.3 Hz, 1H), 2.65 (s, 3H), 2.72 (s, 3H), 2.83 (d, J=11.3 Hz, 1H), 2.93-3.06 (m, 1H), 3.12-3.20 (m, 1H), 3.39 (d, J=13.9 Hz, 1H), 3.75 (dd, J=2.6, 5.9 Hz, 1H), 4.07-4.18 (m, 2H), 5.55 (d, J=17.8 Hz, 1H), 5.98 (d, J=17.8 Hz, 1H), 7.52 (s, 1H), 8.38 (d, J=1.6 Hz, 1H), 8.95 (s, 2H).

Example 2. Non-Limiting Examples of Compounds of the Present Invention

Tables 1 and 2 shows illustrative Factor D inhibitors with characterizing data. The assay of Example 3 was used to determine the $IC_{50}$'s of the compounds. Other standard factor D inhibition assays are also available. Three *s are used to denote compounds with an $IC_{50}$ less than 1 micromolar; two s indicate compound with an $IC_{50}$ between 1 micromolar and 10 micromolar, and one * denotes compounds with an $IC_{50}$ greater than 10 micromolar.

TABLE 1

Non-limiting Examples of Compounds of the Present Invention

| Cmp No. | Structure | $IC_{50}$ (Stars) | RT min (Method A,B, C or D) | MS (M + 1) |
|---|---|---|---|---|
| 1 | 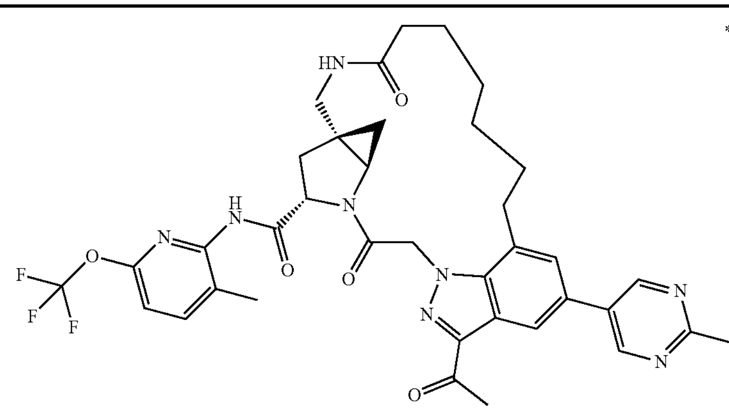 | *** | 3.47 (B) | 733 |

($4^1$R,$4^3$S,$4^5$R)-$1^3$-acetyl-N-(3-methyl-6-(trifluoromethoxy)pyridin-2-yl)-$1^5$-(2-methylpyrimidin-5-yl)-3,7-dioxo-$1^1$H-$4^2$,6-diaza-1(1,7)-indazola-4(2,5)-bicyclo[3.1.0]hexanacyclotridecaphane-$4^3$-carboxamide TABLE 1-continued Non-limiting Examples of Compounds of the Present Invention

| Cmp No. | Structure | IC$_{50}$ (Stars) | RT min (Method A,B, C or D) | MS (M + 1) |
|---|---|---|---|---|
| 2 | (4$^1$R,4$^3$S,4$^5$R)-1$^3$-acetyl-N-(6-bromo-3-((3-fluoroazetidin-1-yl)methyl)pyridin-2-yl)-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | | |
| 3 | (4$^1$R,4$^3$S,4$^5$R)-1$^3$-acetyl-N-(3-methyl-6-(trifluoromethyl)pyridin-2-yl)-3,7-dioxo-1$^5$-(pyrrolidin-1-yl)-1$^1$H-4$^2$,6-diaza-1(1,7)-indazola-4(2,5)-bicyclo[3.1.0]hexanacyclotridecaphane-4$^3$-carboxamide | *** | 3.51 (B) | 694 |
| 4 | (4$^1$R,4$^3$S,4$^5$R)-1$^3$-acetyl-1$^5$-cyclopropyl-N-(3-methyl-6-(trifluoromethyl)pyridin-2-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.8 (B) | 665 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 5 | (4$^1$R,4$^3$S,4$^5$R)-1$^3$-acetyl-1$^5$-(5-methyl-1,3,4-oxadiazol-2-yl)-N-(3-methyl-6-(trifluoromethyl)pyridin-2-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.52 (B) | 707 |
| 6 | (4$^1$R,4$^3$S,4$^5$R)-1$^3$-acetyl-1$^5$-methoxy-N-(3-methyl-6-(trifluoromethyl)pyridin-2-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.81 (B) | 655 |
| 7 | (4$^1$R,4$^3$S,4$^5$R)-1$^3$-acetyl-N-(3-methyl-6-(trifluoromethyl)pyridin-2-yl)-1$^5$-((5-methylpyrimidin-2-yl)oxy)-3,7-dioxo-1$^1$H-4$^2$,6-diaza-1(1,7)-indazola-4(2,5)-bicyclo[3.1.0]hexanacyclododecaphane-4$^3$-carboxamide | *** | 3.01 (B) | 719 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 8 | 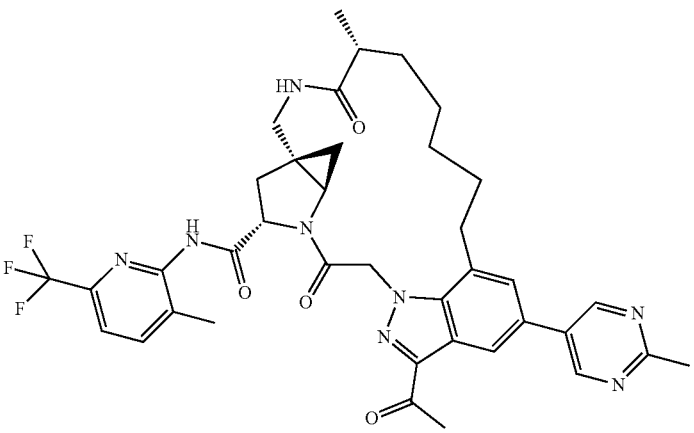 [SMILES: CC(=O)c1nn2c3c(cc(-c4cnc(C)nc4)cc13)CCCCC[C@@H](C)C(=O)NC[C@@]13C[C@@H](C(=O)Nc4nc(C(F)(F)F)ccc4C)N(C(=O)C2)[C@@H]1C3] (4$^1$R,4$^3$S,4$^5$R,8R)-1$^3$-acetyl-8-methyl-N-(3-methyl-6-(trifluoromethyl)pyridin-2-yl)-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.43 (B) | 731 |
| 9 | 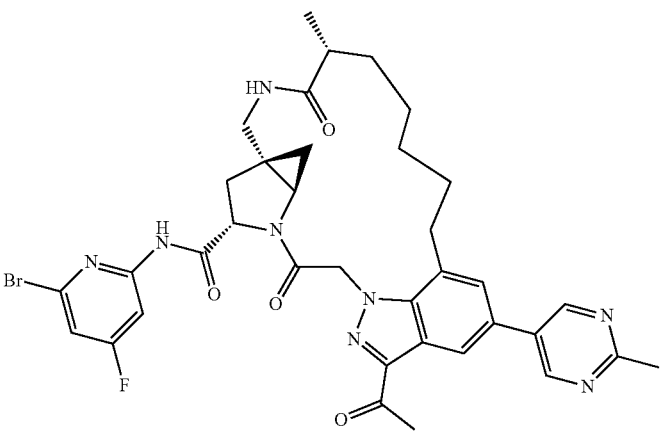 [SMILES: CC(=O)c1nn2c3c(cc(-c4cnc(C)nc4)cc13)CCCCC[C@@H](C)C(=O)NC[C@@]13C[C@@H](C(=O)Nc4cc(F)cc(Br)n4)N(C(=O)C2)[C@@H]1C3] (4$^1$R,4$^3$S,4$^5$R,8R)-1$^3$-acetyl-N-(6-bromo-4-fluoropyridin-2-yl)-8-methyl-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.96 (B) | 745 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 10 | (4$^1$R,4$^3$S,4$^5$R)-1$^3$-acetyl-8,8-dimethyl-N-(3-methyl-6-(trifluoromethyl)pyridin-2-yl)-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 4.04 (B) | 745 |
| 11 | (4$^1$R,4$^3$S,45$^R$)-1$^3$-acetyl-N-(6-cyclopropyl-3-methylpyridin-2-yl)-15-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 2.6 (B) | 689 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 12 | (S)-2-(3-acetyl-5-(2-methylpyrimidin-5-yl)-1H-indazol-1-yl)-N-(2-bromo-15-oxo-5,6,7,8,9,10,11,12,13,14, 15,16-dodecahydropyrido[2,3-b][1]azacyclotetradecin-14-yl)-N-methylacetamide | ** | 4.1 (B) | 660 |
| 13 | (4$^1$R,4$^3$S,4$^5$R,E)-1$^3$-acetyl-N-(6-bromo-4-fluoropyridin-2-yl)-6-methyl-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphan-11-ene-4$^3$-carboxamide | *** | 3.82 (B) | 743 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 14 | (4$^1$R,4$^3$S,4$^5$R)-1$^3$-acetyl-N-(6-bromo-4-fluoropyridin-2-yl)-6-methyl-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.96 (B) | 745 |
| 15 | (4$^1$R,4$^3$S,4$^5$R)-1$^3$-acetyl-1$^5$-amino-N-(3-methyl-6-(trifluoromethyl)pyridin-2-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 2.04 (B) | 640 |
| 16 | (4$^1$R,4$^3$S,4$^5$R,8R)-1$^3$-acetyl-N-(6-bromo-5-fluoropyridin-2-yl)-8-methyl-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.68 (B) | 745 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 17 | ($4^1$R,$4^3$S,$4^5$R)-$1^3$-acetyl-$1^5$-isobutoxy-N-(3-methyl-6-(trifluoromethyl)pyridin-2-yl)-3,7-dioxo-$1^1$H-$4^2$,6-diaza-1(1,7)-indazola-4(2,5)-bicyclo[3.1.0]hexanacyclotridecaphane-$4^3$-carboxamide | *** | 4.49 (B) | 697 |
| 18 | ($4^1$R,$4^3$S,$4^5$R)-$1^3$-acetyl-$1^5$-methyl-N-(3-methyl-6-(trifluoromethyl)pyridin-2-yl)-3,7-dioxo-$1^1$H-$4^2$,6-diaza-1(1,7)-indazola-4(2,5)-bicyclo[3.1.0]hexanacyclotridecaphane-$4^3$-carboxamide | *** | 3.88 (B) | 639 |
| 19 | ($4^1$R,$4^3$S,$4^5$R)-$1^3$-acetyl-$1^5$-isopropoxy-N-(3-methyl-6-(trifluoromethyl)pyridin-2-yl)-3,7-dioxo-$1^1$H-$4^2$,6-diaza-1(1,7)-indazola-4(2,5)-bicyclo[3.1.0]hexanacyclotridecaphane-$4^3$-carboxamide | *** | 4.06 (B) | 683 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 20 | 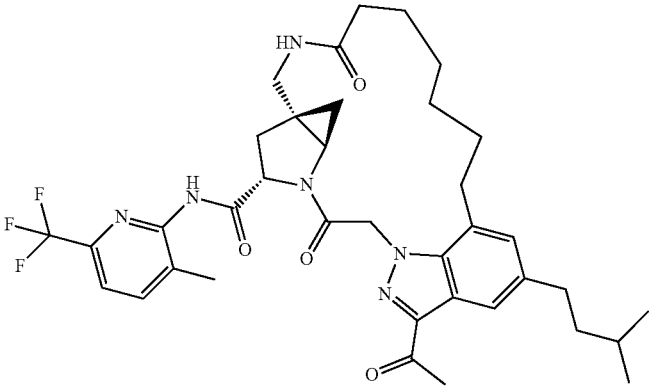 [SMILES: CC(=O)c1nn2c3c(cc(CCC(C)C)cc13)CCCCCCC(=O)NC[C@@]13C[C@@H](C(=O)Nc4nc(C(F)(F)F)ccc4C)N(C(=O)C2)[C@@H]1C3]<br>($4^1$R,$4^3$S,$4^5$R)-$1^3$-acetyl-$1^5$-isopentyl-N-(3-methyl-6-(trifluoromethyl)pyridin-2-yl)-3,7-dioxo-$1^1$H-$4^2$,6-diaza-1(1,7)-indazola-4(2,5)-bicyclo[3.1.0]hexanacyclotridecaphane-$4^3$-carboxamide | *** | 4.55 (B) | 695 |
| 21 | 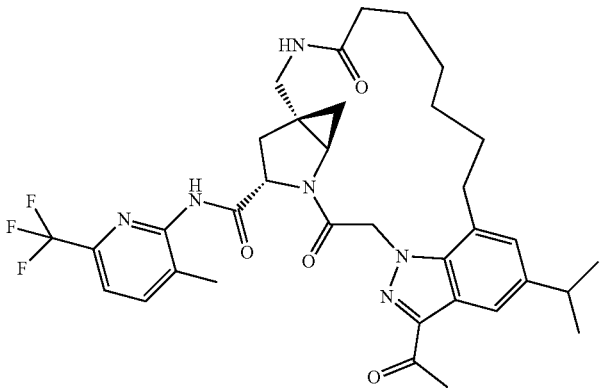 [SMILES: CC(=O)c1nn2c3c(cc(C(C)C)cc13)CCCCCCC(=O)NC[C@@]13C[C@@H](C(=O)Nc4nc(C(F)(F)F)ccc4C)N(C(=O)C2)[C@@H]1C3]<br>($4^1$R,$4^3$S,$4^5$R)-$1^3$-acetyl-$1^5$-isopropyl-N-(3-methyl-6-(trifluoromethyl)pyridin-2-yl)-3,7-dioxo-$1^1$H-$4^2$,6-diaza-1(1,7)-indazola-4(2,5)-bicyclo[3.1.0]hexanacyclotridecaphane-$4^3$-carboxamide | *** | 4.14 (B) | 667 |
| 22 | 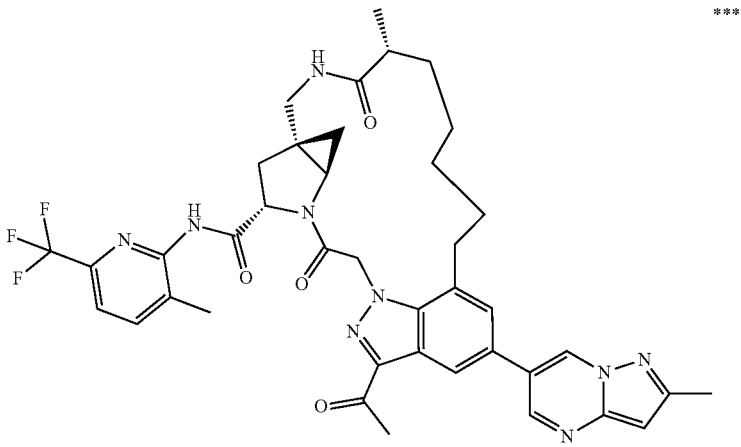<br>($4^1$R,$4^3$S,$4^5$R,8R)-$1^3$-acetyl-8-methyl-N-(3-methyl-6-(trifluoromethyl)pyridin-2-yl)-15-(2-methylpyrazolo[1,5-a]pyrimidin-6-yl)-3,7-dioxo-$1^1$H-$4^2$,6-diaza-1(1,7)-indazola-4(2,5)-bicyclo[3.1.0]hexanacyclotridecaphane-$4^3$-carboxamide | *** | 3.77 (B) | 770 |

TABLE 1-continued

Non-limiting Examples of Compounds of the Present Invention

| Cmp No. | Structure | IC$_{50}$ (Stars) | RT min (Method A,B,C or D) | MS (M + 1) |
|---|---|---|---|---|
| 23 | (4$^1$R,4$^3$S,4$^5$R,8R)-1$^3$-acetyl-8-methyl-N-(3-methyl-6-(trifluoromethyl)pyridin-2-yl)-1$^5$-(5-methylpyrazin-2-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.68 (B) | 731 |
| 24 | (4$^1$R,4$^3$S,4$^5$R)-1$^3$-acetyl-1$^5$-(isobutylamino)-N-(3-methyl-6-(trifluoromethyl)pyridin-2-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 2.72 (B) | 696 |
| 25 | (4$^1$R,4$^3$S,4$^5$R)-1$^3$-acetyl-1$^5$-(isopropylamino)-N-(3-methyl-6-(trifluoromethyl)pyridin-2-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 2.16 (B) | 682 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 26 | (4$^1$R,4$^3$S,4$^5$R)-1$^3$-acetyl-9,9-dimethyl-N-(3-methyl-6-(trifluoromethyl)pyridin-2-yl)-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.85 (B) | 745 |
| 27 | (4$^1$R,4$^3$S,4$^5$R)-1$^3$-acetyl-N-(3-methyl-6-(trifluoromethyl)pyridin-2-yl)-1$^5$-(methylamino)-3,7-dioxo-1$^1$H-4$^2$,6-diaza-1(1,7)-indazola-4(2,5)-bicyclo[3.1.0]hexanacyclotridecaphane-4$^3$-carboxamide | *** | 1.89 (B) | 654 |
| 28 | (4$^1$R,4$^3$S,4$^5$R)-1$^3$-acetyl-1$^5$-isobutyl-N-(3-methyl-6-(trifluoromethyl)pyridin-2-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 4.22 (B) | 681 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 29 | (4$^1$R,4$^3$S,4$^5$R)-1$^3$-acetyl-N-((R)-1-((R)-2,2-dichlorocyclopropyl)ethyl)-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.7 (B) | 694 |
| 30 | (4$^1$R,4$^3$S,4$^5$R)-1$^3$-acetyl-N-((S)-1-((R)-2,2-dichlorocyclopropyl)ethyl)-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.34 (B) | 694 |
| 31 | (4$^1$R,4$^3$S,4$^5$R,9S)-1$^3$-acetyl-9-methyl-N-(3-methyl-6-(trifluoromethyl)pyridin-2-yl)-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.34 (B) | 731 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 32 | 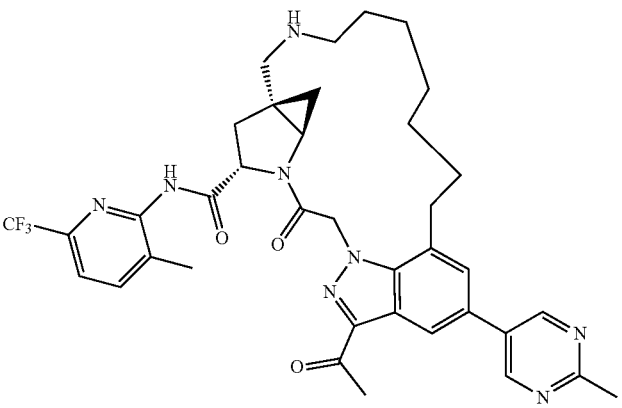 [SMILES: CC(=O)c1nn2c3c(cc(-c4cnc(C)nc4)cc13)CCCCCCCNC[C@@]13C[C@@H](C(=O)Nc4nc(C(F)(F)F)ccc4C)N(C(=O)C2)[C@@H]1C3] (4$^1$R,4$^3$S,4$^5$R)-1$^3$-acetyl-N-(3-methyl-6-(trifluoromethyl)pyridin-2-yl)-1$^5$-(2-methylpyrimidin-5-yl)-3-oxo-1$^1$H-4$^2$,6-diaza-1(1,7)-indazola-4(2,5)-bicyclo[3.1.0]hexanacyclotridecaphane-4$^3$-carboxamide | *** | 3.18 (B) | 703 |
| 33 | 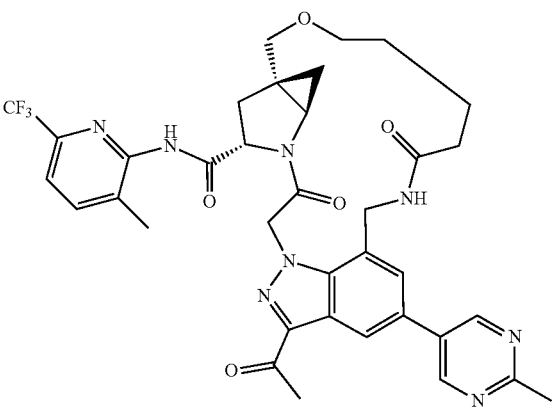 [SMILES: CC(=O)c1nn2c3c(cc(-c4cnc(C)nc4)cc13)CNC(=O)CCCCOC[C@@]13C[C@@H](C(=O)Nc4nc(C(F)(F)F)ccc4C)N(C(=O)C2)[C@@H]1C3] (4$^1$R,4$^3$S,4$^5$S)-1$^3$-acetyl-N-(3-methyl-6-(trifluoromethyl)pyridin-2-yl)-1$^5$-(2-methylpyrimidin-5-yl)-3,11-dioxo-1$^1$H-6-oxa-4$^2$,12-diaza-1(1,7)-indazola-4(2,5)-bicyclo[3.1.0]hexanacyclotridecaphane-4$^3$-carboxamide | *** | 1.75 (A) | 719 |
| 34 | 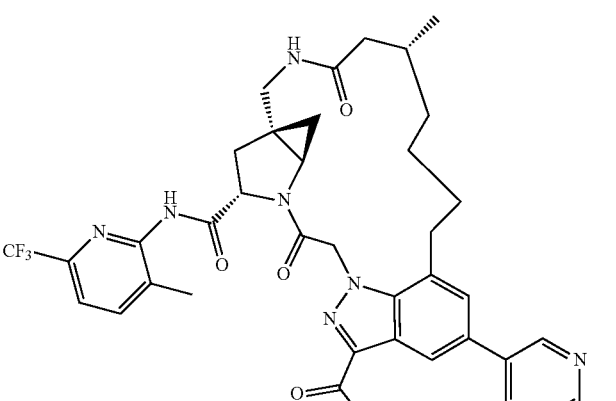 (4$^1$R,4$^3$S,4$^5$R,9R)-1$^3$-acetyl-9-methyl-N-(3-methyl-6-(trifluoromethyl)pyridin-2-yl)-1$^5$-(2-methylpyrimidin-5-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.86 (B) | 731 |

TABLE 1-continued

Non-limiting Examples of Compounds of the Present Invention

| Cmp No. | Structure | IC$_{50}$ (Stars) | RT min (Method A,B,C or D) | MS (M + 1) |
|---|---|---|---|---|
| 35 | (S)-2-(2-acetyl-4-(2-methylpyrimidin-5-yl)-17-oxo-8,9,10,11,12,13,14,15,17,18-decahydro-6H-[1,4]diazacyclohexadecino[15,16,1-hi]indazol-16(7H)-yl)-N-(6-bromo-3-methylpyridin-2-yl)propanamide | ** | 4.01 (B) | 688 |
| 36 | (4$^1$R,4$^3$S,4$^5$S)-1$^3$-acetyl-N-(3-methyl-6-(trifluoromethyl)pyridin-2-yl)-1$^5$-(2-methylpyrimidin-5-yl)-3-oxo-1$^1$H-6-oxa-4$^2$,12-diaza-1(1,7)-indazola-4(2,5)-bicyclo[3.1.0]hexanacyclotridecaphane-4$^3$-carboxamide | *** | 1.59 (A) | 705 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 37 | (4$^1$R,4$^3$S,4$^5$S,E)-1$^3$-acetyl-N-(3-methyl-6-(trifluoromethyl)pyridin-2-yl)-1$^5$-(2-methylpyrimidin-5-yl)-3-oxo-1$^1$H-6-oxa-4$^2$,12-diaza-1(1,7)-indazola-4(2,5)-bicyclo[3.1.0]hexanacyclotridecaphan-8-ene-4$^3$-carboxamide | *** | 1.61 (A) | 703 |
| 38 | (S)-13-acetyl-3-bromo-7,8-dimethyl-15-(2-methylpyrimidin-5-yl)-5,7,8,17,18,19,20,21,22,23,24,25-dodecahydro-6H-pyrido[2',3':8,9][1,4,7]triazacycloicosino[19,20,1-hi]indazole-6,9(10H)-dione | * | 3.81 (B) | 660 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 39 | (4$^1$R,4$^3$S,4$^5$R)-1$^3$-acetyl-1$^5$-((cyclohexylmethyl)amino)-N-(3-methyl-6-(trifluoromethyl)pyridin-2-yl)-3,7-dioxo-1$^1$H-4$^2$,6-diaza-1(1,7)-indazola-4(2,5)-bicyclo[3.1.0]hexanacyclotridecaphane-4$^3$-carboxamide | *** | 3.31 (B) | 736 |
| 40 | (4$^2$S,4$^3$R)-1$^3$-acetyl-N-(3-chloro-2-fluorobenzyl)-1$^5$-(2-methylpyrimidin-5-yl)-3-oxo-1$^1$H-5-oxa-1(1,7)-indazola-4(1,3)-pyrrolidinacyclotridecaphane-4$^2$-carboxamide | *** | 2.97 (A) | 675 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 41 | 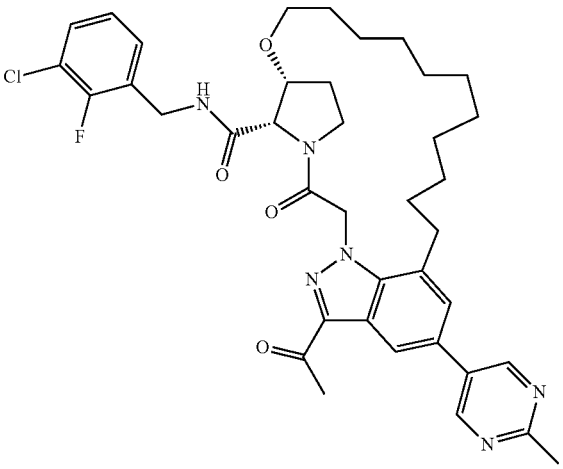 [SMILES: CC(=O)c1nn2c3c(cc(-c4cnc(C)nc4)cc13)CCCCCCCCCCCO[C@@H]1CCN(C(=O)C2)[C@@H]1C(=O)NCc1cccc(Cl)c1F] (42S,43R)-13-acetyl-N-(3-chloro-2-fluorobenzyl)-15-(2-methylpyrimidin-5-yl)-3-oxo-11H-5-oxa-1(1,7)-indazola-4(1,3)-pyrrolidinacyclohexadecaphane-42-carboxamide | | 3.40 (A) | 717 |
| 42 | 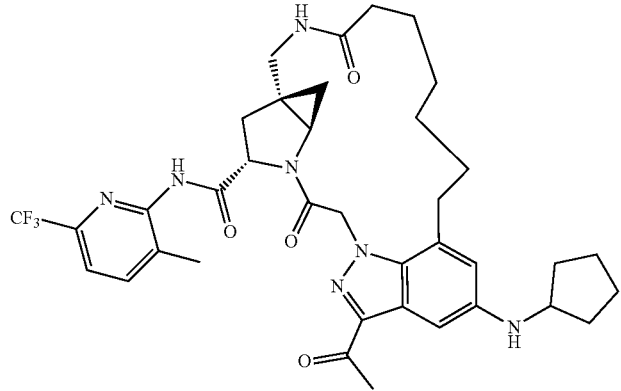 [SMILES: CC(=O)c1nn2c3c(cc(NC4CCCC4)cc13)CCCCCCC(=O)NC[C@@]13C[C@@H](C(=O)Nc4nc(C(F)(F)F)ccc4C)N(C(=O)C2)[C@@H]1C3] (41R,43S,45R)-13-acetyl-15-(cyclopentylamino)-N-(3-methyl-6-(trifluoromethyl)pyridin-2-yl)-3,7-dioxo-11H-42,6-diaza-1(1,7)-indazola-4(2,5)-bicyclo[3.1.0]hexanacyclotridecaphane-43-carboxamide | | 2.8 (B) | 708 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 43 | (S)-2-acetyl-N-(6-bromo-3-methylpyridin-2-yl)-17-methyl-4-(2-methylpyrimidin-5-yl)-18-oxo-6,7,8,9,10,11,12,13,14,15,16,17,18,19-tetradecahydro-[1,4]diazacycloheptadecino[16,17,1-hi]indazole-16-carboxamide | | 3.52 (B) | 688 |
| 44 | (41R,43S,45R)-13-acetyl-15-(cyclopropanecarboxamido)-N-(3-methyl-6-(trifluoromethyl)pyridin-2-yl)-3,7-dioxo-11H-42,6-diaza-1(1,7)-indazola-4(2,5)-bicyclo[3.1.0]hexanacyclotridecaphane-43-carboxamide | | 3.05 (B) | 708 |
| 45 | (20aS,21aR,22aR,E)-26-acetyl-17-bromo-2,21a-dimethyl-8,9,10,11,13,14,20a,21,21a,22,22a,24-dodecahydro-3,13,18,19,22b,24a,25-heptaazabenzo[15,16]cyclopropa[3',4']cyclopenta[1',2':19,20]cyclodocosa[1,2,3-cd]indene-12,20,23(4H,7H,19H)-trione | *** | 1.84 (A) | 676 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 46 | (41R,43S,45R,E)-13-acetyl-N-(6-bromo-3-methylpyridin-2-yl)-3,7-dioxo-11H-42,6-diaza-1(1,7)-indazola-4(2,5)-bicyclo[3.1.0]hexanacyclododecaphan-9-ene-43-carboxamide | *** | 3.28 (B) | 619 |
| 47 | (41R,43S,45R,E)-13-acetyl-N-(6-bromo-3-methylpyridin-2-yl)-3,7-dioxo-11H-42,6-diaza-1(1,7)-indazola-4(2,5)-bicyclo[3.1.0]hexanacyclotridecaphan-10-ene-43-carboxamide | *** | 3.40 (B) | 633 |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 48 | (31R,33S,35R,Z)-32-(2-(3-acetyl-1H-pyrazolo[3,4-c]pyridin-1-yl)acetyl)-66-bromo-11H-8-oxa-32,5-diaza-6(2,3)-pyridina-1(1,4)-triazola-3(5,3)-bicyclo[3.1.0]hexanacyclononaphan-4-one | *** | 0.89 (A) | 608 |
| 49 | 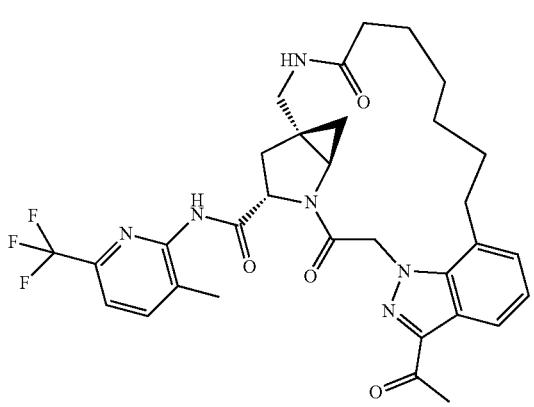 [SMILES: CC(=O)c1nn2c3c(cccc13)CCCCCCC(=O)NC[C@@]13C[C@@H](C(=O)Nc4nc(C(F)(F)F)ccc4C)N(C(=O)C2)[C@@H]1C3] (41R,43S,45R)-13-acetyl-N-(3-methyl-6-(trifluoromethyl)pyridin-2-yl)-3,7-dioxo-11H-42,6-diaza-1(1,7)-indazola-4(2,5)-bicyclo[3.1.0]hexanacyclotridecaphane-43-carboxamide | | | |

TABLE 1-continued

Non-limiting Examples of Compounds of the Present Invention

| Cmp No. | Structure | IC$_{50}$ (Stars) | RT min (Method A,B, C or D) | MS (M + 1) |
|---|---|---|---|---|
| 50 | 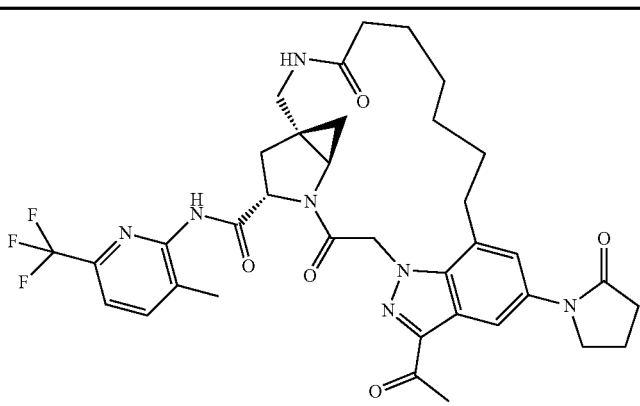<br>(41R,43S,45R)-13-acetyl-N-(3-methyl-6-(trifluoromethyl)pyridin-2-yl)-3,7-dioxo-15-(2-oxopyrrolidin-1-yl)-11H-42,6-diaza-1(1,7)-indazola-4(2,5)-bicyclo[3.1.0]hexanacyclotridecaphane-43-carboxamide | | | |

TABLE 2

Additional Non-limiting Examples of Compounds of the Present Invention

| Cmp No. | Structure | IC$_{50}$ (Stars) | RT min (Method A, B, C or D) | MS (M + 1) |
|---|---|---|---|---|
| 51 | 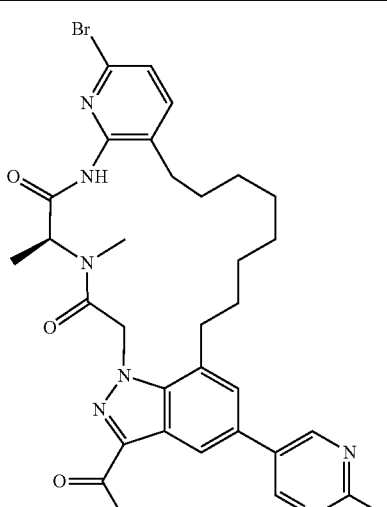<br>(S)-2-acetyl-16-bromo-20,21-dimethyl-4-(2-methylpyrimidin-5-yl)-6,7,8,9,10,11,12,13,20,21-decahydropyrido[2',3':8,9][1,4,7]triazacyclononadecino[18,19,1-hi]indazole-19,22(18H,23H)-dione | * | 3.81 (B) | 660 |

TABLE 2-continued

Additional Non-limiting Examples of Compounds of the Present Invention

| Cmp No. | Structure | IC$_{50}$ (Stars) | RT min (Method A, B, C or D) | MS (M + 1) |
|---|---|---|---|---|
| 52 | (41R,43S,45R)-13-acetyl-15-((cyclohexylmethyl)amino)-N-(3-methyl-6-(trifluoromethyl)pyridin-2-yl)-3,7-dioxo-11H-42,6-diaza-1(1,7)-indazola-4(2,5)-bicyclo[3.1.0]hexanacyclotridecaphane-43-carboxamide | *** | 3.31 (B) | 736 |
| 53 | (42S,43R)-13-acetyl-N-(3-chloro-2-fluorobenzyl)-15-(2-methylpyrimidin-5-yl)-3-oxo-11H-5-oxa-1(1,7)-indazola-4(1,3)-pyrrolidinacyclotridecaphane-42-carboxamide | *** | 2.97 (A) | 675 |

TABLE 2-continued

Additional Non-limiting Examples of Compounds of the Present Invention

| Cmp No. | Structure | IC$_{50}$ (Stars) | RT min (Method A, B, C or D) | MS (M + 1) |
|---|---|---|---|---|
| 54 | 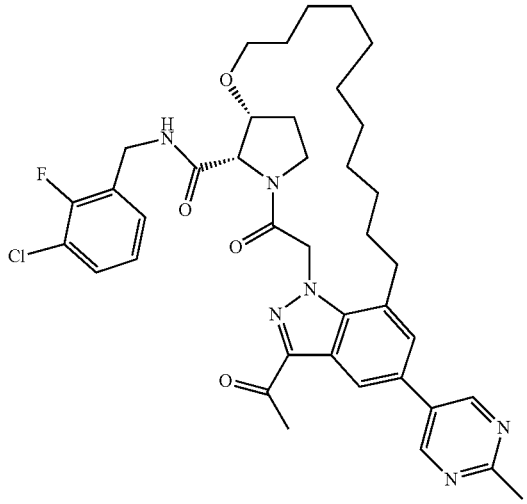 [SMILES: CC(=O)c1nn2c3c(cc(-c4cnc(C)nc4)cc13)CCCCCCCCCCCO[C@@H]1CCN(C(=O)C2)[C@@H]1C(=O)NCc1cccc(Cl)c1F] (42S,43R)-13-acetyl-N-(3-chloro-2-fluorobenzyl)-15-(2-methylpyrimidin-5-yl)-3-oxo-11H-5-oxa-1(1,7)-indazola-4(1,3)-pyrrolidinacyclohexadecaphane-42-carboxamide | *** | 3.40 (A) | 717 |
| 55 | 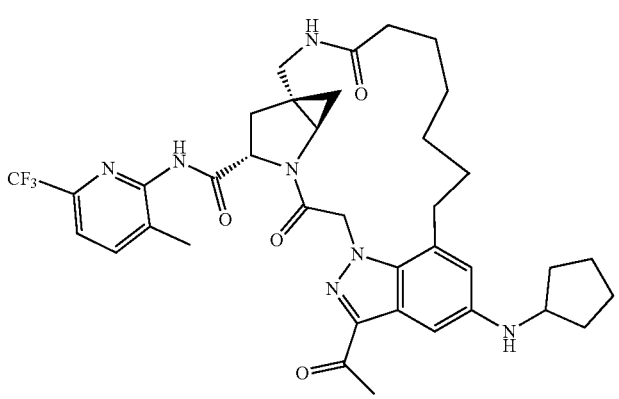 (41R,43S,45R)-13-acetyl-15-(cyclopentylamino)-N-(3-methyl-6-(trifluoromethyl)pyridin-2-yl)-3,7-dioxo-11H-42,6-diaza-1(1,7)-indazola-4(2,5)-bicyclo[3.1.0]hexanacyclotridecaphane-43-carboxamide | *** | 2.8 (B) | 708 |

TABLE 2-continued

Additional Non-limiting Examples of Compounds of the Present Invention

| Cmp No. | Structure | IC$_{50}$ (Stars) | RT min (Method A, B, C or D) | MS (M + 1) |
|---|---|---|---|---|
| 56 | (S)-2-acetyl-N-(6-bromo-3-methylpyridin-2-yl)-17-methyl-4-(2-methylpyrimidin-5-yl)-18-oxo-6,7,8,9,10,11,12,13,14,15,16,17,18,19-tetradecahydro-[1,4]diazacycloheptadecino[16,17,1-hi]indazole-16-carboxamide | * | 3.52 (B) | 688 |
| 57 | (41R,43S,45R)-13-acetyl-15-(cyclopropanecarboxamido)-N-(3-methyl-6-(trifluoromethyl)pyridin-2-yl)-3,7-dioxo-11H-42,6-diaza-1(1,7)-indazola-4(2,5)-bicyclo[3.1.0]hexanacyclotridecaphane-43-carboxamide | *** | 3.05 (B) | 708 |
| 58 | (41R,43S,45R)-13-acetyl-N-(3-methyl-6-(trifluoromethyl)pyridin-2-yl)-15-(2-methylpyrimidin-5-yl)-3,7-dioxo-11H-42,6,13-triaza-1(1,7)-indazola-4(2,5)-bicyclo[3.1.0]hexanacyclotridecaphane-43-carboxamide | *** | 3.3 (B) | 718 |

TABLE 2-continued

Additional Non-limiting Examples of Compounds of the Present Invention

| Cmp No. | Structure | IC$_{50}$ (Stars) | RT min (Method A, B, C or D) | MS (M + 1) |
|---|---|---|---|---|
| 59 | (41R,43S,45R)-13-acetyl-8,8-dimethyl-N-(3-methyl-6-(trifluoromethyl)pyridin-2-yl)-15-(2-methylpyrimidin-5-yl)-3-oxo-11H-42,6-diaza-1(1,7)-indazola-4(2,5)-bicyclo[3.1.0]hexanacyclotridecaphane-43-carboxamide | *** | 1.72 (A) | 731 |
| 60 | (41R,43S,45S)-13-acetyl-N-(3-methyl-6-(trifluoromethyl)pyridin-2-yl)-15-(2-methylpyrimidin-5-yl)-3,12-dioxo-11H-6-oxa-42,13-diaza-1(1,7)-indazola-4(2,5)-bicyclo[3.1.0]hexanacyclotridecaphane-43-carboxamide | *** | 3.39 (B) | 719 |

TABLE 2-continued

Additional Non-limiting Examples of Compounds of the Present Invention

| Cmp No. | Structure | IC$_{50}$ (Stars) | RT min (Method A, B, C or D) | MS (M + 1) |
|---|---|---|---|---|
| 61 | (41R,43S,45R)-13-acetyl-N-(3,3-dimethylcyclobutyl)-8,8-dimethyl-15-(2-methylpyrimidin-5-yl)-3-oxo-11H-42,6-diaza-1(1,7)-indazola-4(2,5)-bicyclo[3.1.0]hexanacyclotridecaphane-43-carboxamide | *** | 1.83 (A) | 654 |

Example 3. Human Factor D Assay

Human Factor D (purified from human serum, Complement Technology, Inc.) at 80 nM final concentration is incubated with test compound at various concentrations for 5 min at room temperature in 50 mM Tris, 1M NaCl, pH 7.5. A synthetic substrate Z-L-Lys-SBzl and DTNB (Ellman's reagent) are added to final concentrations of 100 µM each. Absorbance at 405 nm ($A_{405}$) is recorded at 30 second intervals for 30 min using a microplate spectrophotometer. IC$_{50}$ values are calculated by nonlinear regression of complement Factor D reaction rates as a function of test compound concentration.

Example 4. Hemolysis Assay

The hemolysis assay was previously described by G. Ruiz-Gomez, et al., J. Med. Chem. (2009) 52: 6042-6052. Prior to the assay, the optimum concentration of Normal Human Serum (NHS) needed to achieve 100% lysis of rabbit erythrocytes (RE) is determined by titration. In the assay, NHS (Complement Technology) is diluted in GVB⁰ Buffer (0.1% gelatin, 5 mM Veronal, 145 mM NaCl, 0.025% NaN$_3$, pH 7.3, Complement Technology) plus 10 mM Mg-EGTA and incubated with test compound at various concentrations for 15 min at 37° C. RE (Complement Technology) freshly suspended in GVB⁰ plus 10 mM Mg-EGTA are added to a final concentration of 1×10⁸ cells/mL and reactions are incubated for 30 min at 37° C. Positive control reactions (100% lysis) consist of GVB⁰ plus 10 mM Mg-EGTA with NHS and RE but without test compound; negative control reactions (0% lysis) consist of GVB⁰ plus 10 mM Mg-EGTA with RE only. Samples are centrifuged at 2000 g for 3 min and supernatants collected. Absorbance at 405 nm ($A_{405}$) is recorded using a microplate spectrophotometer. IC$_{50}$ values are calculated by nonlinear regression from the percentage of hemolysis as a function of test compound concentration.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A compound of formula (II):

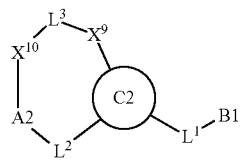

(II)

or a pharmaceutically acceptable salt thereof;
wherein:
A2 is

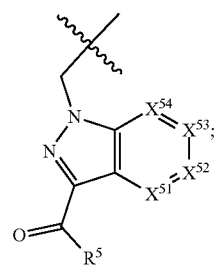

B1 is a pyridinyl, aryl, cyclopropyl or cyclobutyl; each of which B1 is substituted with 1, 2, 3, or 4 substituents independently selected from aryl, heteroaryl, heterocycle, halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{16}$, —$C_0$-$C_4$alkylOR$^{16}$, —$SO_2R^{16}$, $C_1$-$C_6$haloalkyl, and $C_1$-$C_6$haloalkoxy;

C2 is

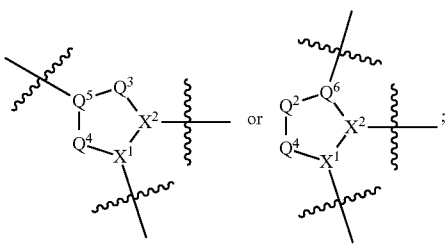

$X^1$ is N, wherein $X^1$ is directly bound to $L^2$;
$X^2$ is CH, wherein $X^2$ is directly bound to $L^1$;
$Q^2$ is $C(R^2R^{2'})$;
$Q^3$ is $C(R^3R^{3'})$;
$Q^4$ is $C(R^1R^{1'})$;
$Q^5$ is $C(R^2)$, wherein $Q^5$ is directly bound to $X^9$;
$Q^6$ is CH, wherein $Q^6$ is directly bound to $X^9$;
$R^1$, $R^{1'}$, $R^2$, $R^{2'}$, $R^3$, and $R^{3'}$ are each hydrogen;
or $R^1$ and $R^2$ are taken together to form a 3-membered carbocyclic ring;
$L^1$ is

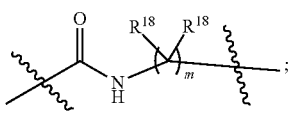

each $R^{18}$ is independently selected from hydrogen and $C_1$-$C_6$alkyl;
m is 0, 1, 2, or 3;
$L^2$ is —C(O)—;
$L^3$ is

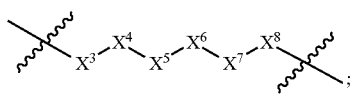

$X^3$, $X^4$, $X^5$, $X^6$, $X^7$, and $X^8$ are each independently selected from bond, —C(R$^{52}$)$_2$—, —C(R$^{52}$)$_2$C(R$^{52}$)$_2$—, —C(R$^{52}$)$_2$C(R$^{52}$)$_2$C(R$^{52}$)$_2$—, —C(O)—, —C(S)—, —P(O)OR$^{16}$—, —S(O)—, —S(O)$_2$—, N=S(O)$_2$(R$^{52}$)—, —S(O)$_2$(R$^{52}$)=N—, —S(O)$_2$-heteroaryl-, -heteroaryl-S(O)$_2$—, —O—, —S—, alkylene, alkenylene, alkynylene, heterocycle, aryl, heteroaryl, cycloalkyl, and —NR$^{16}$—;
$X^9$ and $X^{10}$ are independently selected from alkylene, —C(R$^{52}$)$_2$—, —C(R$^{52}$)$_2$O—, —C(R$^{52}$)$_2$NR$^9$—, —C(R$^{52}$)$_2$OC(O)—, —C(R$^{52}$)$_2$NR$^9$C(O)—, —O—, —S—, —C(O)—, —C(S)—, —P(O)OR$^{16}$—, —S(O)—, —S(O)$_2$—, alkenylene, alkynylene, —CH$_2$O—, —CH$_2$N(H)—, —CH$_2$OC(O)—, —CH$_2$N(H)C(O)—, —CH$_2$N(CH$_3$)—, CH$_2$N(CH$_3$)C(O)—, R$^{32}$ in a divalent state, and —NR$^{16}$—;

$X^{51}$, $X^{52}$, and $X^{53}$ are CR$^{13}$, and $X^{54}$ is a carbon directly bound to $X^{10}$;
$R^5$ is selected from $C_1$-$C_3$alkyl, —$C_1$-$C_3$alkyl-OR$^{16}$, and —NR$^9$R$^{10}$;
each $R^9$ and $R^{10}$ are independently selected from hydrogen, aryl, heteroaryl, and $C_1$-$C_6$alkyl;
$R^{13}$ is selected from hydrogen, $C_1$-$C_6$alkyl, $C_1$-$C_6$alkoxy, —$C_3$-$C_7$cycloalkyl, and R$^{32}$, each $R^{13}$ other than hydrogen is optionally substituted with one or more substituents independently selected from halogen, hydroxyl, nitro, cyano, amino, —COOH, —CONH$_2$, $C_1$-$C_6$haloalkyl, $C_1$-$C_6$haloalkoxy, phenyl, and 4- to 7-membered heterocycle containing 1, 2, or 3 heteroatoms independently selected from N, O, and S;
each $R^{15}$ is independently selected from hydrogen, $C_1$-$C_3$alkyl, —OR$^9$, —NR$^{24}$R$^{25a}$, —NR$^9$R$^{10}$ and

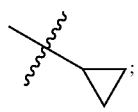

each $R^{16}$ is independently selected from hydrogen, aryl, heteroaryl, $C_1$-$C_3$alkyl, and —C(O)R$^{15}$;
$R^{21}$ and $R^{22}$ are independently selected from hydrogen, hydroxyl, cyano, amino, $C_1$-$C_6$alkyl, $C_1$-$C_6$haloalkyl, $C_1$-$C_6$alkoxy, —$C_0$-$C_4$alkyl-aryl, —$C_0$-$C_4$alkyl-heteroaryl, and —$C_0$-$C_4$alkyl-(4- to 7-membered heterocycle having 1, 2, or 3 heteroatoms independently selected from N, O, and S);
or $R^{21}$ and $R^{22}$ can be taken together to form a carbocyclic or heterocyclic ring;
$R^{24}$ and $R^{25a}$ are taken together with the nitrogen to which they are attached to form a 4- to 7-membered monocyclic heterocycloalkyl group, or a 6- to 10-membered bicyclic heterocyclic group having fused, spiro, or bridged rings;
$R^{32}$ is selected from $C_1$-$C_6$alkyl, saturated heterocycle, and —NR$^9$C(O)R$^{15}$, wherein each $R^{32}$ is optionally substituted with 1, 2, 3, or 4 substituents selected from halogen, —SO$_2$R$^{15}$, $C_1$-$C_6$alkyl, $C_1$-$C_6$haloalkyl, aryl, 5- or 6-membered heterocycle having 1, 2, or 3 heteroatoms independently selected from N, O, and S, 5- or 6-membered heteroaryl, —C(O)R$^{15}$, $C_2$-$C_6$alkanoyl, —B(OH)$_2$, —C(O)(CH$_2$)$_{1-4}$S(O)R$^{21}$, —P(O)(OR$^{21}$)(OR$^{22}$), —P(O)(OR$^{21}$)R$^{22}$, —P(O)R$^{21}$R$^{22}$, —NR$^9$P(O)(NHR$^{21}$)(NHR$^{22}$), —NR$^9$P(O)(OR$^{21}$)(NHR$^{22}$), —NR$^9$P(O)(OR$^{21}$)(OR$^{22}$), —C(S)R$^{21}$, —NR$^{21}$SO$_2$R$^{22}$, —NR$^9$S(O)NR$^{10}$R$^{22}$, —NR$^9$SO$_2$NR$^{10}$R$^{22}$, —SO$_2$NR$^9$COR$^{22}$, —SO$_2$NR$^9$CONR$^{21}$R$^{22}$, —NR$^{21}$SO$_2$R$^{22}$, —C(O)NR$^{21}$SO$_2$R$^{22}$, —C(NH$_2$)NR$^9$R$^{22}$, —C(NH$_2$)NR$^9$S(O)$_2$R$^{22}$, —NR$^9$C(O)OR$^{10}$, —NR$^{21}$OC(O)R$^{22}$, —(CH$^2$)$_{1-4}$C(O)NR$^{21}$R$^{22}$, —C(O)R$^{24}$R$^{25a}$, —NR$^9$C(O)R$^{21}$, —C(O)R$^{21}$, —NR$^9$C(O)NR$^9$R$^{10}$, —NR$^9$C(O)NR$^{24}$R$^{25a}$, and —(CH$_2$)$_{1-4}$OC(O)R$^{21}$; or
$R^{32}$ is

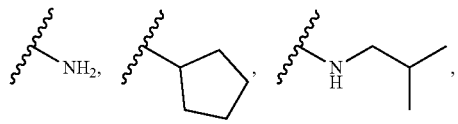

-continued

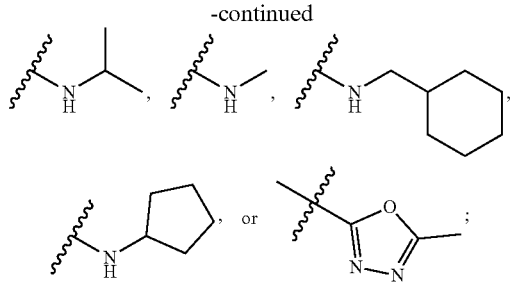

and each $R^{52}$ is independently selected from halogen, hydrogen, $C_1$-$C_6$alkyl, amino, hydroxyl, aminoalkyl, alkenyl, alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), $C_2$-$C_6$alkanoyl, $C_1$-$C_6$alkoxy, $C_1$-$C_6$thioalkyl, —$C_0$-$C_4$alkyl$NR^9R^{16}$, haloalkyl, haloalkoxy, —COOH, $C_2$-$C_6$alkenyloxy, —C(O)$OR^{16}$, —$C_0$-$C_4$alkyl$NR^9R^{10}$, —C(O)$NR^9R^{10}$, —$SO_2R^9$, —$SO_2NR^9R^{10}$, —OC(O)$R^9$, and $N(R^9)C(O)R^{10}$;

or two $R^{52}$ groups can be taken together to form a 3- to 6-membered carbocyclic ring or a 3- to 6-membered heterocyclic spiro ring containing 1 or 2 heteroatoms independently selected from N, O, or S;

or two $R^{52}$ groups on the same carbon can be taken together with the carbon to which they are attached to form an oxo or alkene group.

2. The compound of claim 1, wherein B1 is 2-pyridine substituted with 1, 2, 3, or 4 groups independently selected from halogen, $C_1$-$C_3$alkyl, $C_1$-$C_3$haloalkyl, —COOH, cyano, $C_2$-$C_6$alkanoyl, $C_1$-$C_6$alkoxy, and $C_1$-$C_6$haloalkoxy.

3. The compound of claim 2, wherein B1 is

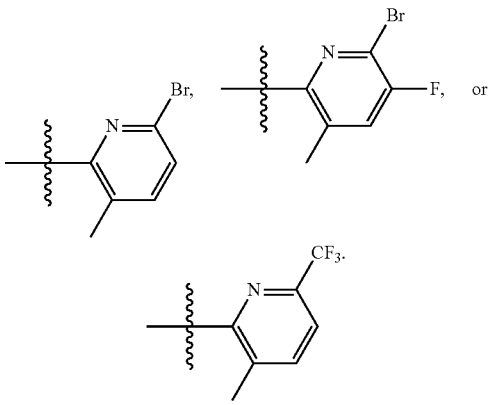

4. The compound of claim 1, wherein $R^1$ and $R^2$ are taken together to form a 3-membered carbocyclic ring.

5. A pharmaceutical composition comprising a compound of claim 1 or a pharmaceutically acceptable salt thereof, and a pharmaceutically acceptable carrier.

6. A method of treating a complement factor D mediated disorder comprising administering to a subject in need thereof a therapeutically effective amount of the compound of claim 1, wherein the disorder is selected from age-related macular degeneration, atypical hemolytic uremic syndrome, C3 glomerulopathy, geographic atrophy, and paroxysmal nocturnal hemoglobinuria (PNH).

7. The method of claim 6, wherein the subject is a human.

8. The method of claim 7, wherein the disorder is C3 glomerulopathy.

9. The method of claim 7, wherein the disorder is geographic atrophy.

10. The method of claim 7, wherein the disorder is age-related macular degeneration (AMD).

11. The method of claim 7, wherein the disorder is paroxysmal nocturnal hemoglobinuria (PNH).

12. The method of claim 8, wherein the disorder is C3 glomerulonephritis.

13. The method of claim 8, wherein the disorder is dense deposit disease.

14. A compound selected from:

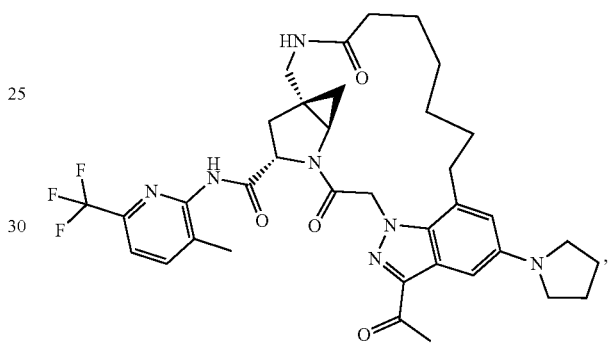

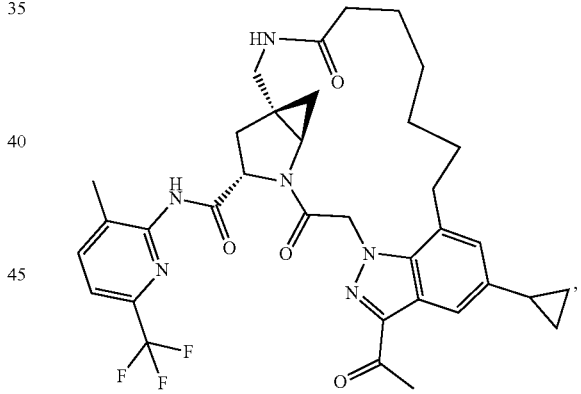

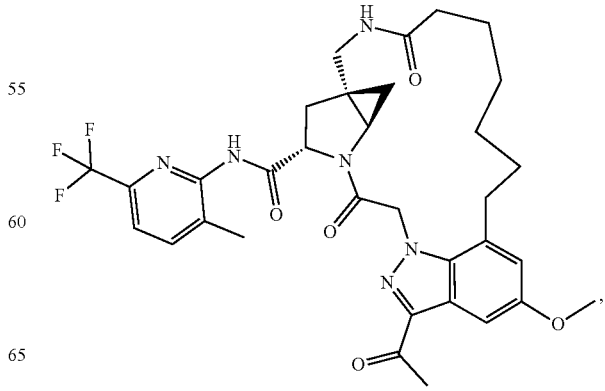

873
-continued
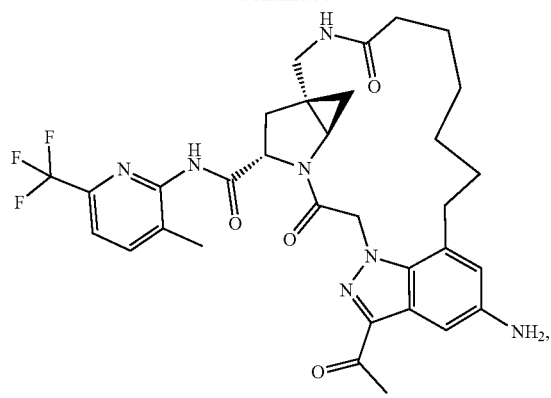
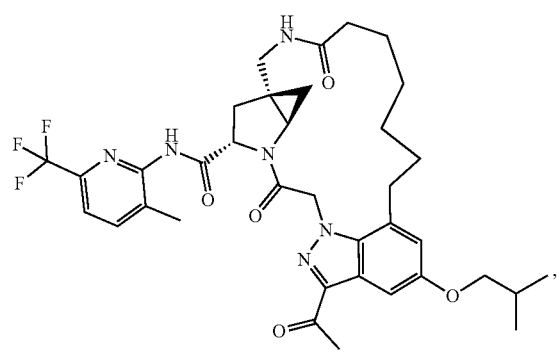
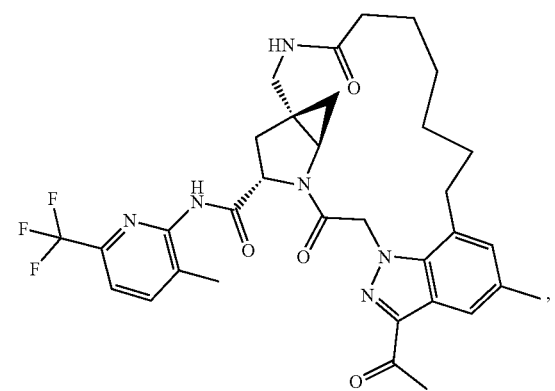
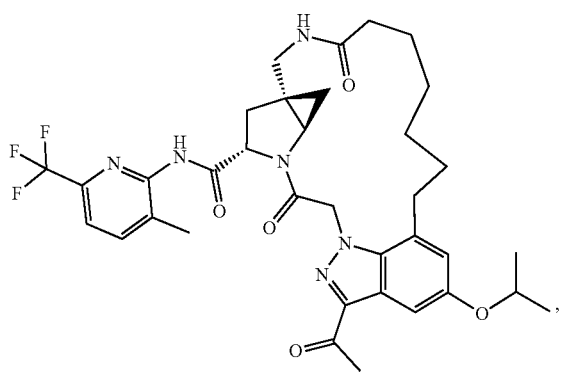
874
-continued
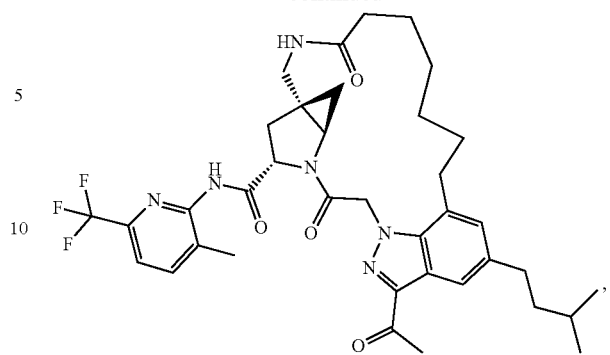
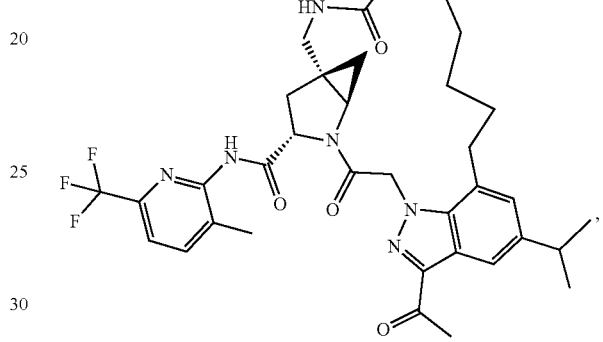
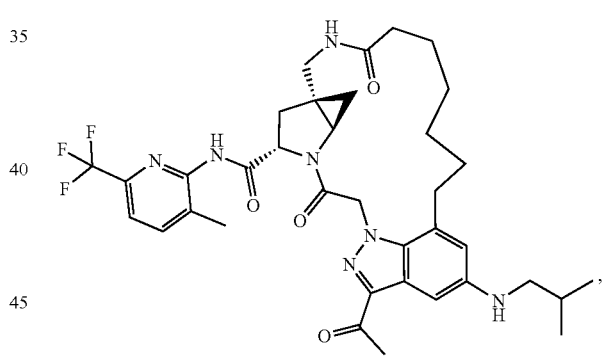
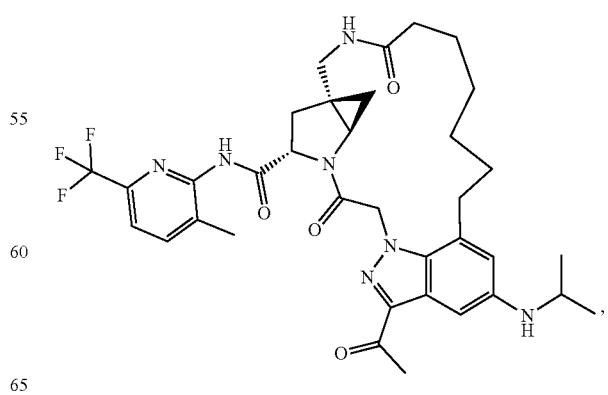

875
-continued
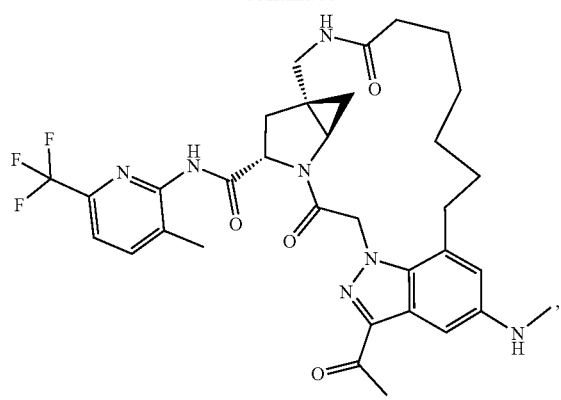
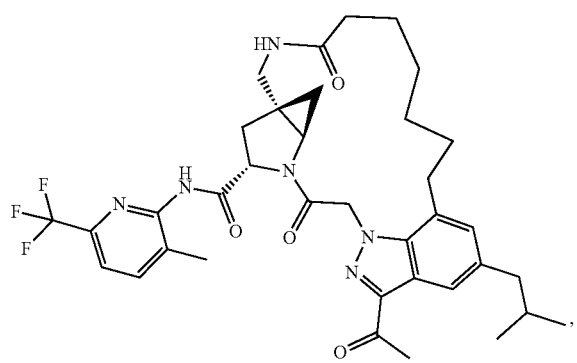
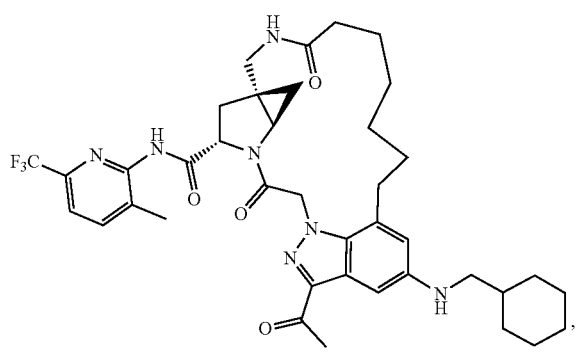
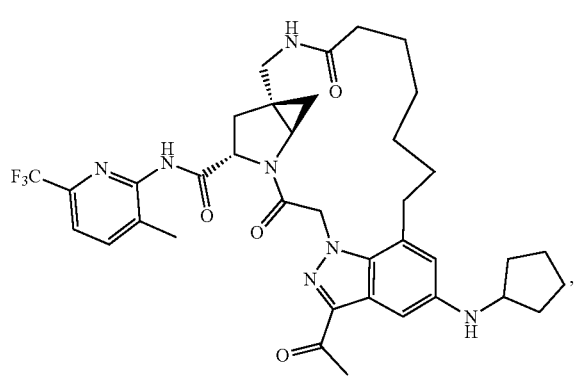
876
-continued
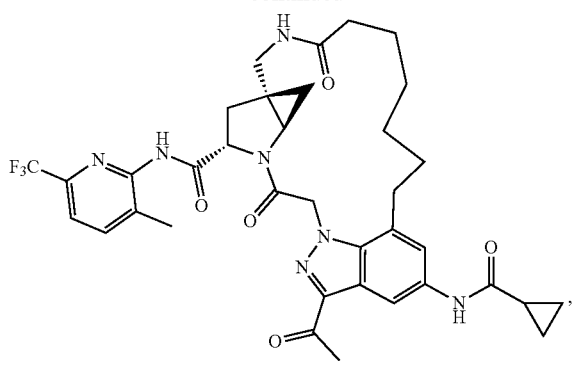
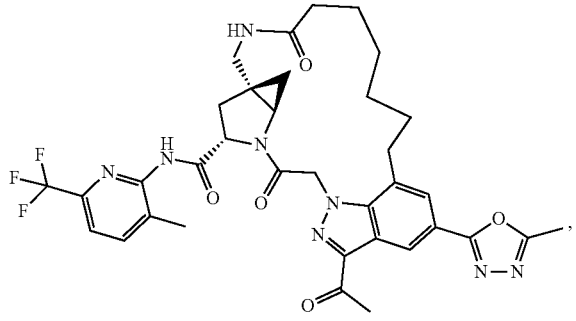
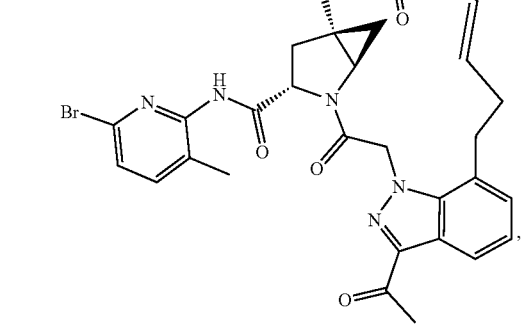
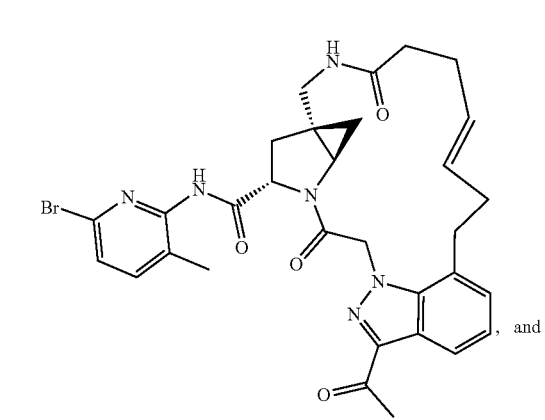
, and 877
-continued

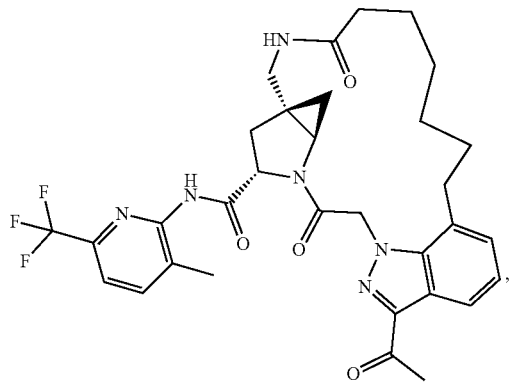

or a pharmaceutically acceptable salt thereof.

15. A pharmaceutical composition comprising a compound of claim 14 or a pharmaceutically acceptable salt thereof, and a pharmaceutically acceptable carrier.

16. A method of treating a complement factor D mediated disorder comprising administering to a subject in need thereof a therapeutically effective amount of the compound of claim 15, wherein the disorder is selected from age-related macular degeneration, atypical hemolytic uremic syndrome, C3 glomerulopathy, geographic atrophy, and paroxysmal nocturnal hemoglobinuria (PNH).

17. A compound selected from:

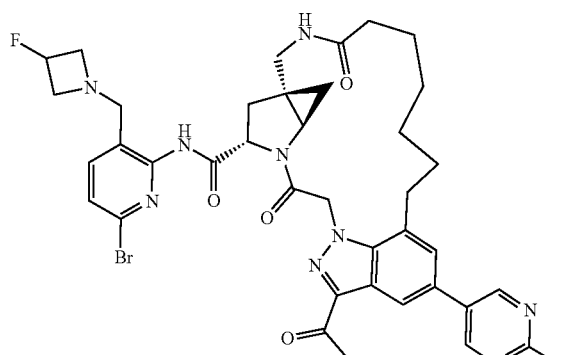

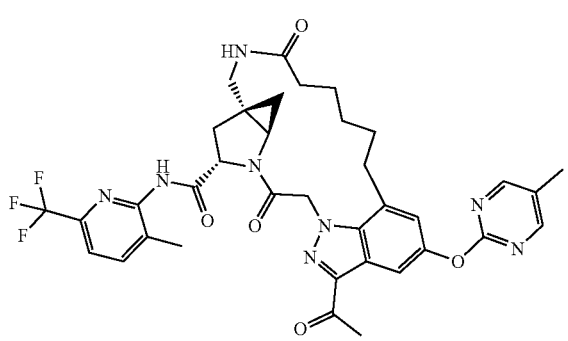

878
-continued

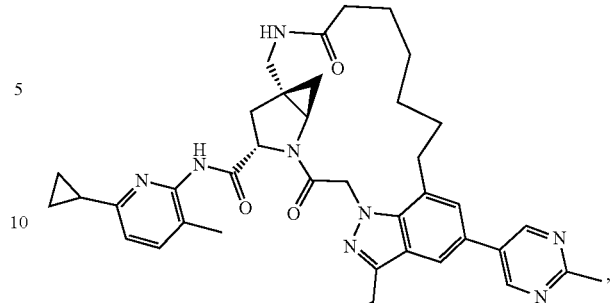

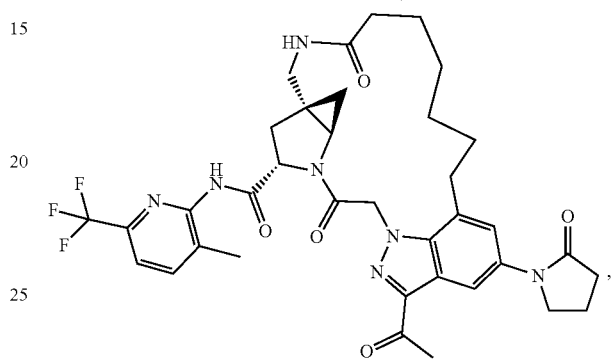

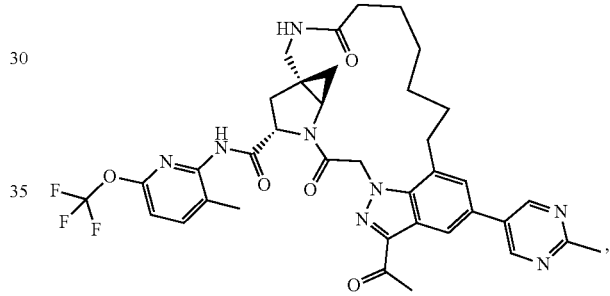

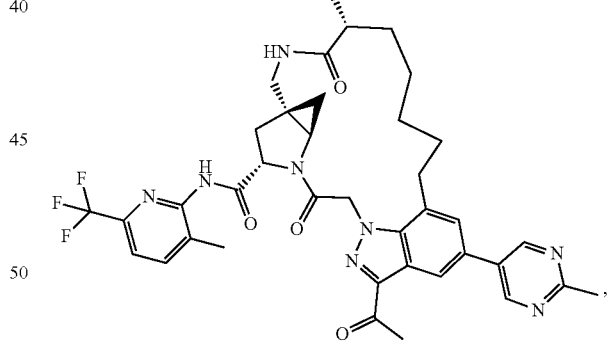

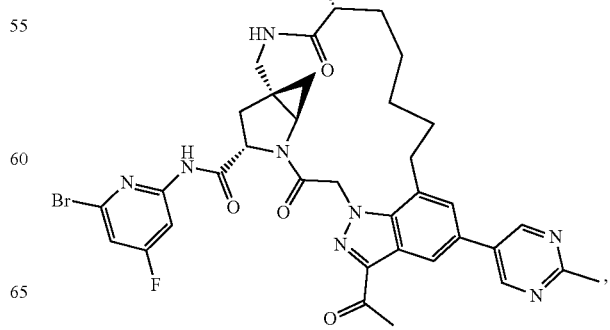

879
-continued
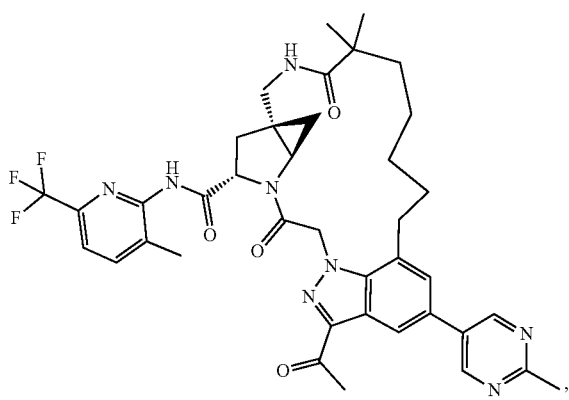
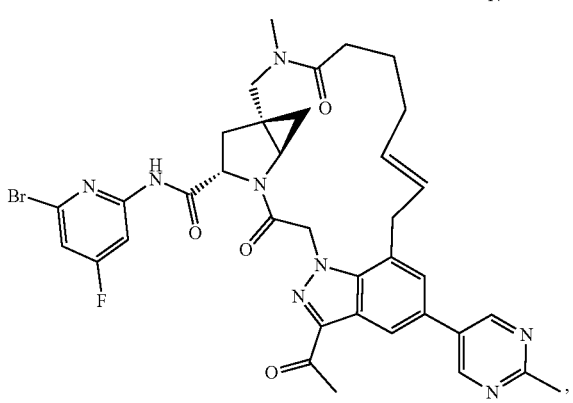
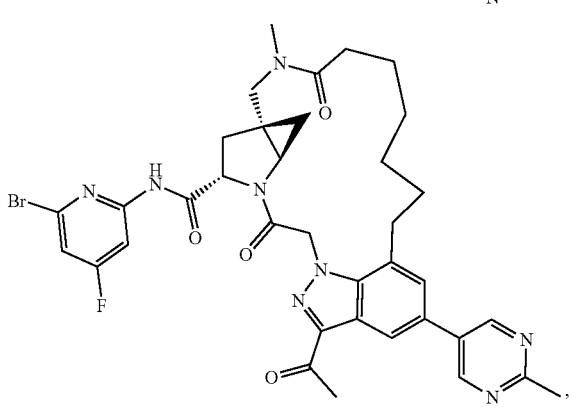
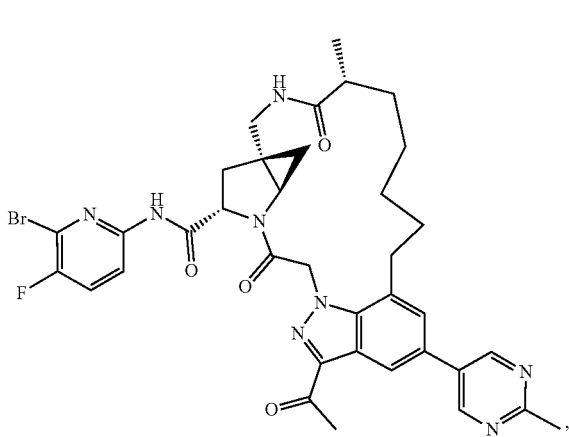
880
-continued
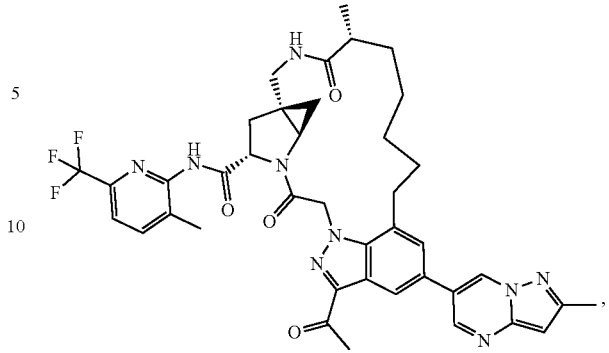
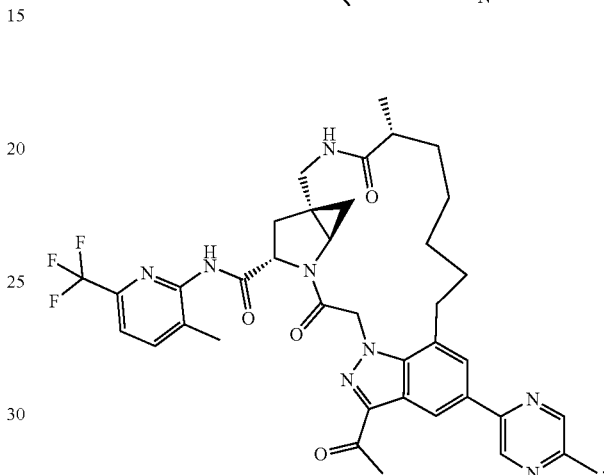
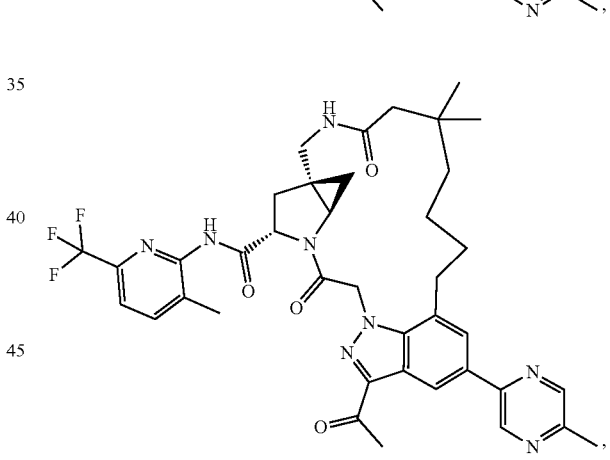
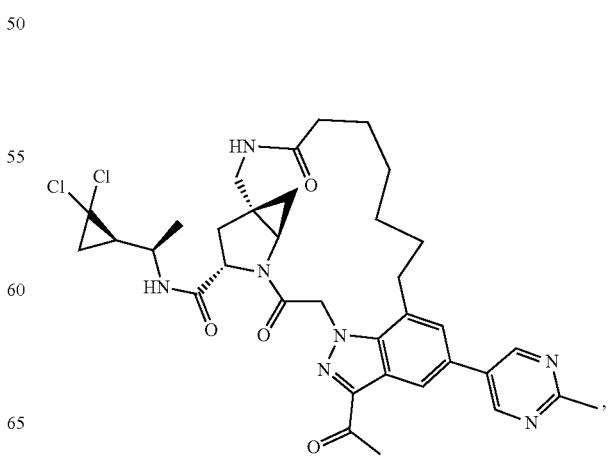

881
-continued
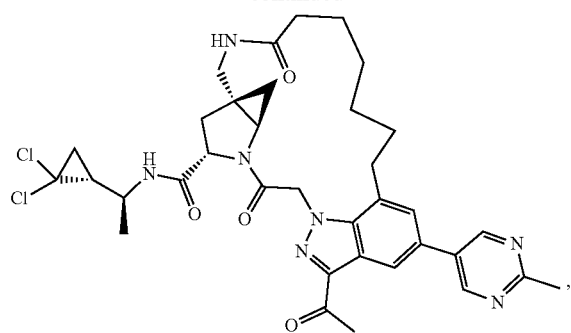
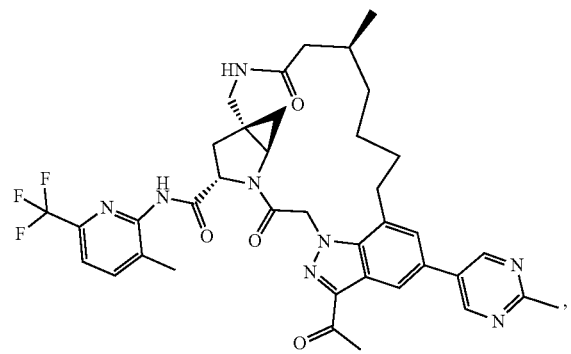
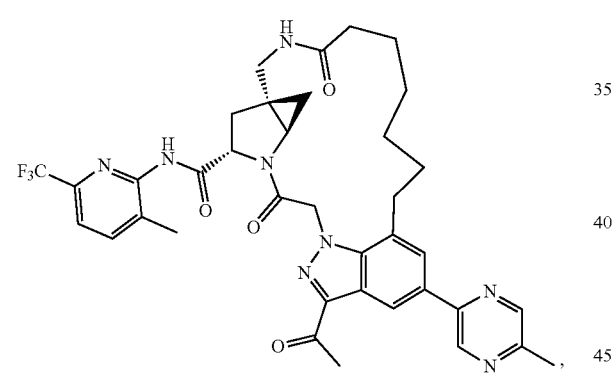
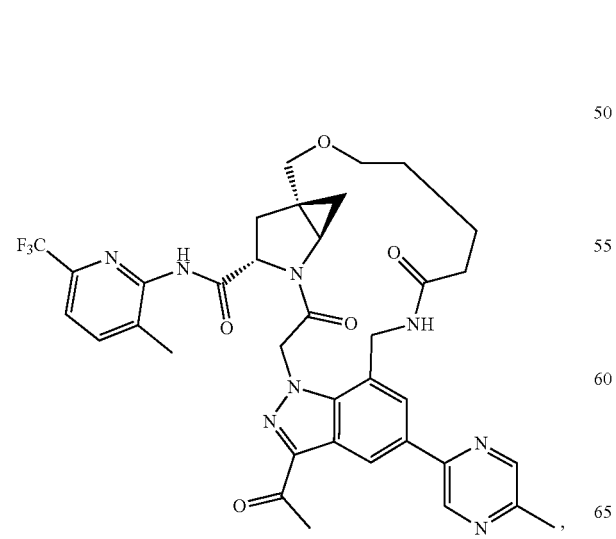
882
-continued
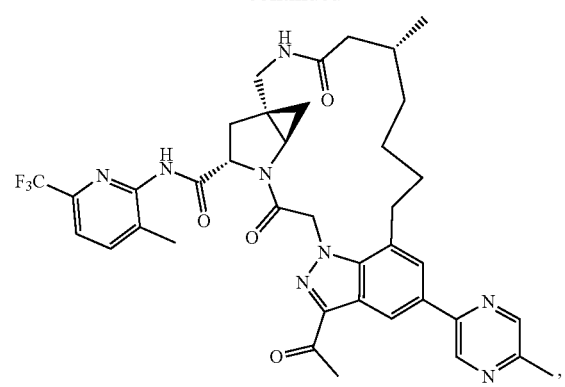
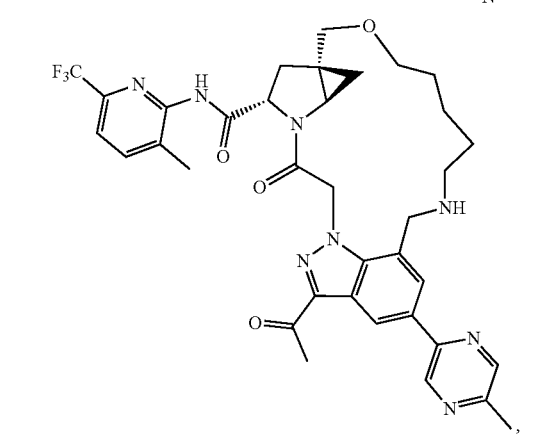
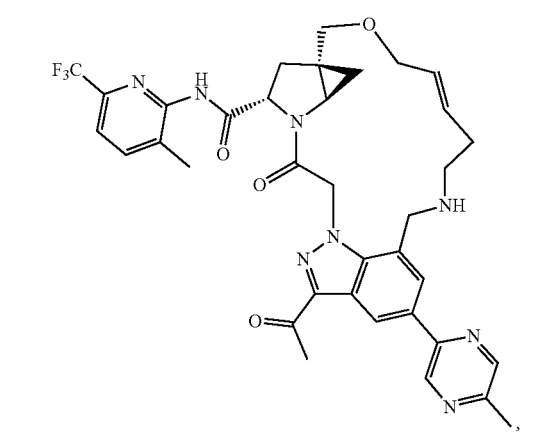
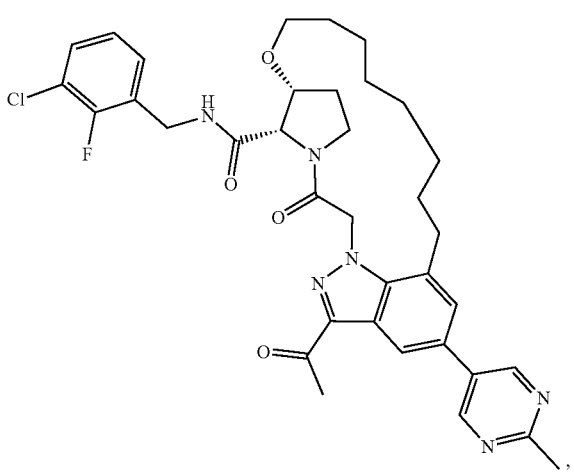

883
-continued
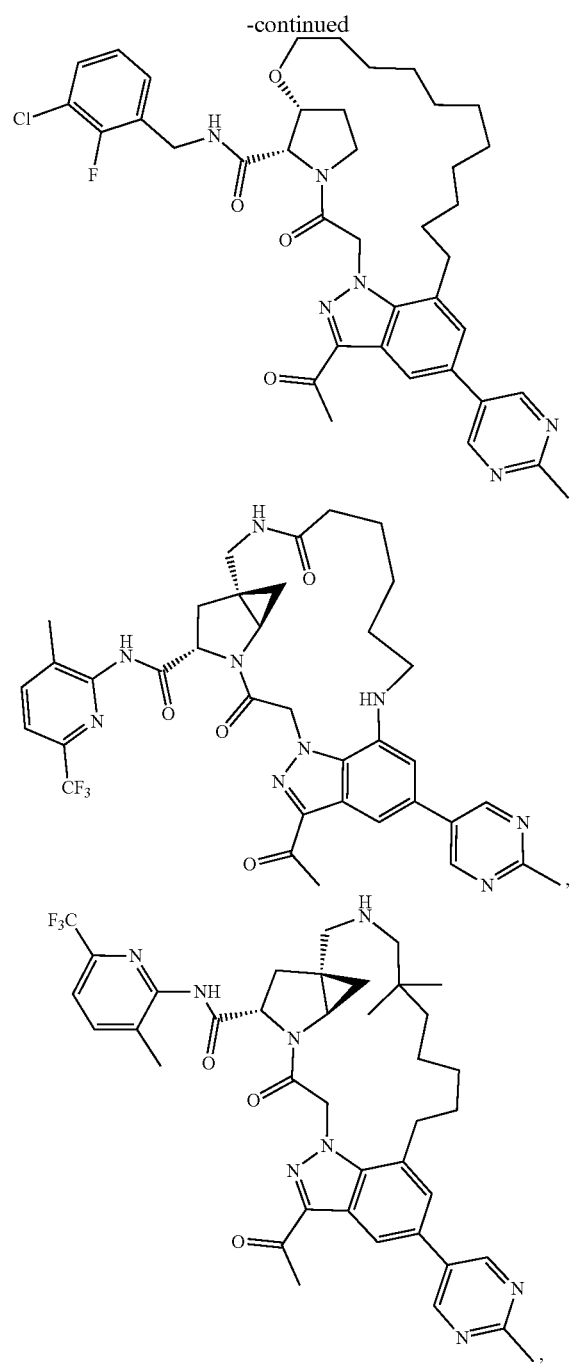
884
-continued
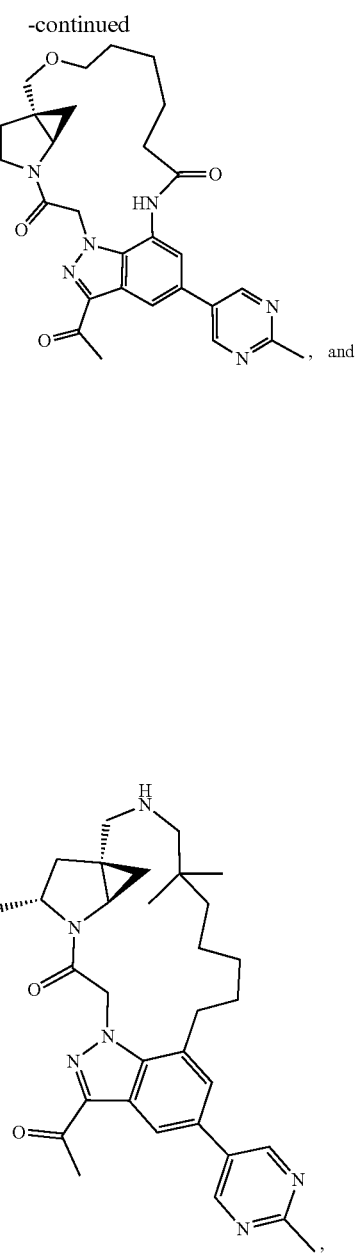
or a pharmaceutically acceptable salt thereof.
* * * * *

UNITED STATES PATENT AND TRADEMARK OFFICE
CERTIFICATE OF CORRECTION

| | |
|---|---|
| PATENT NO. | : 11,814,391 B2 |
| APPLICATION NO. | : 17/272923 |
| DATED | : November 14, 2023 |
| INVENTOR(S) | : Jason Allan Wiles et al. |

It is certified that error appears in the above-identified patent and that said Letters Patent is hereby corrected as shown below:

In the Claims

Column 869, Claim 1, Line 7, replace "-SO$_2$R$^{16}$" with -- -SO$_2$R$^{15}$ --.

Column 870, Claim 1, Line 56, replace "–(CH$^2$)$_{1-4}$" with -- –(CH$_2$)$_{1-4}$ --;

Line 64, replace " 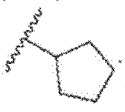 " with -- 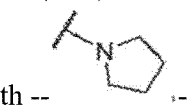 --.

Signed and Sealed this
Eleventh Day of March, 2025

Coke Morgan Stewart
*Acting Director of the United States Patent and Trademark Office*